(12) United States Patent
Gardell et al.

(10) Patent No.: US 11,452,717 B2
(45) Date of Patent: Sep. 27, 2022

(54) SMALL MOLECULE ACTIVATORS OF NICOTINAMIDE PHOSPHORIBOSYLTRANSFERASE (NAMPT) AND USES THEREOF

(71) Applicant: Sanford Burnham Prebys Medical Discovery Institute, La Jolla, CA (US)

(72) Inventors: Stephen Gardell, La Jolla, CA (US); Anthony B. Pinkerton, La Jolla, CA (US); Eduard Sergienko, La Jolla, CA (US); Hampton Sessions, La Jolla, CA (US)

(73) Assignee: SANFORD BURNHAM PREBYS MEDICAL DISCOVERY INSTITUTE, La Jolla, CA (US)

( * ) Notice: Subject to any disclaimer, the term of this patent is extended or adjusted under 35 U.S.C. 154(b) by 0 days.

(21) Appl. No.: 16/475,635

(22) PCT Filed: Jan. 9, 2018

(86) PCT No.: PCT/US2018/012943
§ 371 (c)(1),
(2) Date: Jul. 2, 2019

(87) PCT Pub. No.: WO2018/132372
PCT Pub. Date: Jul. 19, 2018

(65) Prior Publication Data
US 2021/0161873 A1    Jun. 3, 2021

Related U.S. Application Data

(60) Provisional application No. 62/444,557, filed on Jan. 10, 2017.

(51) Int. Cl.
| | |
|---|---|
| A61K 31/4409 | (2006.01) |
| A61K 31/4406 | (2006.01) |
| A61K 31/4402 | (2006.01) |
| A61K 31/44 | (2006.01) |
| C07D 213/40 | (2006.01) |
| C07D 213/73 | (2006.01) |
| C07D 213/643 | (2006.01) |
| A61K 31/505 | (2006.01) |
| C07D 239/26 | (2006.01) |
| C07D 231/12 | (2006.01) |

(Continued)

(52) U.S. Cl.
CPC ........ *A61K 31/4409* (2013.01); *A61K 31/196* (2013.01); *A61K 31/245* (2013.01); *A61K 31/415* (2013.01); *A61K 31/417* (2013.01); *A61K 31/4155* (2013.01); *A61K 31/4192* (2013.01); *A61K 31/42* (2013.01); *A61K 31/422* (2013.01); *A61K 31/426* (2013.01); *A61K 31/427* (2013.01); *A61K 31/437* (2013.01); *A61K 31/4355* (2013.01); *A61K 31/44* (2013.01); *A61K 31/4402* (2013.01); *A61K 31/443* (2013.01); *A61K 31/444* (2013.01); *A61K 31/4406* (2013.01); *A61K 31/4418* (2013.01); *A61K 31/4433* (2013.01); *A61K 31/4436* (2013.01); *A61K 31/4439* (2013.01); *A61K 31/454* (2013.01); *A61K 31/4545* (2013.01); *A61K 31/47* (2013.01); *A61K 31/472* (2013.01); *A61K 31/4725* (2013.01); *A61K 31/497* (2013.01); *A61K 31/50* (2013.01); *A61K 31/505* (2013.01); *A61K 31/5377* (2013.01); *A61K 31/5386* (2013.01); *C07C 275/42* (2013.01); *C07D 213/40* (2013.01); *C07D 213/56* (2013.01); *C07D 213/643* (2013.01); *C07D 213/73* (2013.01); *C07D 213/74* (2013.01); *C07D 231/12* (2013.01); *C07D 233/64* (2013.01); *C07D 237/08* (2013.01); *C07D 239/26* (2013.01); *C07D 249/04* (2013.01); *C07D 261/08* (2013.01); *C07D 263/32* (2013.01); *C07D 277/28* (2013.01); *C07D 401/06* (2013.01); *C07D 401/12* (2013.01); *C07D 403/12* (2013.01); *C07D 405/12* (2013.01); *C07D 405/14* (2013.01); *C07D 409/12* (2013.01); *C07D 413/12* (2013.01); *C07D 413/14* (2013.01); *C07D 417/12* (2013.01); *C07D 471/04* (2013.01); *C07D 498/08* (2013.01)

(58) Field of Classification Search
None
See application file for complete search history.

(56) References Cited

U.S. PATENT DOCUMENTS

| | | |
|---|---|---|
| 3,128,280 A | 4/1964 | Rorig |
| 4,001,256 A | 1/1977 | Callahan et al. |

FOREIGN PATENT DOCUMENTS

| | | |
|---|---|---|
| WO | WO-9724343 A1 | 7/1997 |
| WO | WO-2011109441 A1 | 9/2011 |

(Continued)

OTHER PUBLICATIONS

Wang et al. P7C3 Neuroprotective Chemicals Function by Activating the Rate-Limiting Enzyme in NAD Salvage. Cell 158(6):1324-1334 (2014).

(Continued)

*Primary Examiner* — Kristin A Vajda
(74) *Attorney, Agent, or Firm* — Wilson Sonsini Goodrich & Rosati

(57) ABSTRACT

Provided herein are small molecule activators of Nicotinamide Phosphoribosyltransferase (NAMPT), compositions comprising the compounds, and methods of using the compounds and compositions.

20 Claims, No Drawings

(51) Int. Cl.

| | | |
|---|---|---|
| A61K 31/415 | (2006.01) | |
| A61K 31/50 | (2006.01) | |
| C07D 237/08 | (2006.01) | |
| C07C 275/42 | (2006.01) | |
| A61K 31/245 | (2006.01) | |
| A61K 31/196 | (2006.01) | |
| A61K 31/443 | (2006.01) | |
| C07D 405/12 | (2006.01) | |
| C07D 498/08 | (2006.01) | |
| C07D 401/12 | (2006.01) | |
| A61K 31/5386 | (2006.01) | |
| A61K 31/444 | (2006.01) | |
| A61K 31/4725 | (2006.01) | |
| C07D 413/12 | (2006.01) | |
| C07D 409/12 | (2006.01) | |
| A61K 31/4436 | (2006.01) | |
| A61K 31/4439 | (2006.01) | |
| A61K 31/4433 | (2006.01) | |
| A61K 31/42 | (2006.01) | |
| C07D 261/08 | (2006.01) | |
| C07D 263/32 | (2006.01) | |
| C07D 233/64 | (2006.01) | |
| C07D 249/04 | (2006.01) | |
| A61K 31/417 | (2006.01) | |
| A61K 31/4192 | (2006.01) | |
| C07D 417/12 | (2006.01) | |
| C07D 277/28 | (2006.01) | |
| A61K 31/426 | (2006.01) | |
| C07D 401/06 | (2006.01) | |
| A61K 31/472 | (2006.01) | |
| A61K 31/437 | (2006.01) | |
| A61K 31/4355 | (2006.01) | |
| A61K 31/47 | (2006.01) | |
| C07D 213/74 | (2006.01) | |
| C07D 213/56 | (2006.01) | |
| A61K 31/4418 | (2006.01) | |
| A61K 31/5377 | (2006.01) | |
| A61K 31/4545 | (2006.01) | |
| A61K 31/427 | (2006.01) | |
| C07D 403/12 | (2006.01) | |
| A61K 31/4155 | (2006.01) | |
| A61K 31/422 | (2006.01) | |
| A61K 31/497 | (2006.01) | |
| A61K 31/454 | (2006.01) | |
| C07D 405/14 | (2006.01) | |
| C07D 413/14 | (2006.01) | |
| C07D 471/04 | (2006.01) | |

(56) References Cited

FOREIGN PATENT DOCUMENTS

| WO | WO-2016198698 A2 * | 12/2016 | ............ A61P 35/00 |
|---|---|---|---|
| WO | WO-2018132372 A1 | 7/2018 | |

OTHER PUBLICATIONS

Chemical Abstract compounds, STN express. RN 1178624-49-1 (Entered STN: Sep. 1, 2009).
Chemical Abstract compounds, STN express. RN 1183437-25-3 (Entered STN: Sep. 13, 2009).
Chemical Abstract compounds, STN express. RN 1271453-69-0 (Entered STN: Mar. 28, 2011).
Chemical Abstract compounds, STN express. RN 1271453-76-9 (Entered STN: Mar. 28, 2011).
Chemical Abstract compounds, STN express. RN 1272140-38-1 (Entered STN: Mar. 30, 2011).
Chemical Abstract compounds, STN express. RN 1273721-48-4 (Entered STN: Apr. 3, 2011).
Chemical Abstract compounds, STN express. RN 1273762-09-6 (Entered STN: Apr. 3, 2011).
Chemical Abstract compounds, STN express. RN 1274550-75-2 (Entered STN: Apr. 4, 2011).
Chemical Abstract compounds, STN express. RN 1275953-27-9 (Entered STN: Apr. 6, 2011).
Chemical Abstract compounds, STN express. RN 1293152-85-8 (Entered STN: May 11, 2011).
Chemical Abstract compounds, STN express. RN 1304288-66-1 (Entered STN: Jun. 2, 2011).
Chemical Abstract compounds, STN express. RN 1305713-75-0 (Entered STN: Jun. 5, 2011).
Chemical Abstract compounds, STN express. RN 1308075-89-9 (Entered STN: Jun. 9, 2011).
Chemical Abstract compounds, STN express. RN 1308605-94-8 (Entered STN: Jun. 10, 2011).
Chemical Abstract compounds, STN express. RN 1406753-89-6 (Entered STN: Nov. 26, 2012).
Chemical Abstract compounds, STN express. RN 1479013-07-4 (Entered STN: Nov. 22, 2013).
Chemical Abstract compounds, STN express. RN 1492549-76-4 (Entered STN: Dec. 11, 2013).
Chemical Abstract compounds, STN express. RN 1493376-67-2 (Entered STN: Dec. 12, 2013).
Chemical Abstract compounds, STN express. RN 1553431-46-1 (Entered STN: Feb. 24, 2014).
Cho. Recent Advances in Oral Prodrug Discovery. Annual Reports in Medicinal Chemistry 41:395-407 (2006).
Gleen et al. Urea compounds that increase the biosynthesis of prostaglandins in vivo-in vitro. Agents and actions 7(5-6):517-528 (1977).
Ichihara et al. Development of Self-Indicating Resin. Comb Chern High Throughput Screen 10(4):261-267 (2007).
Nogrady. Chapter 4: Pro Drugs and Soft Drugs. In: Medicinal Chemistry: A Biochemical approach. New York: Oxford Universitry Press, p. 388-392 (1985).
PCT/US2018/012943 International Search Report and Written Opinion dated Jun. 22, 2018.
Rooseboom et al. Enzyme-catalyzed activation of anticancer prodrugs. Pharmacological Reviews 56:53-102 (2004).
Silverman. Chapter 8: Prodrugs and Drug Delivery Systems. The Organic Chemistry of Drug Design and Drug Action, Academic Press, Inc., San Diego (pp. 352-401) (1992).

* cited by examiner

SMALL MOLECULE ACTIVATORS OF NICOTINAMIDE PHOSPHORIBOSYLTRANSFERASE (NAMPT) AND USES THEREOF

CROSS-REFERENCE

This application claims benefit of U.S. Provisional Patent Application No. 62/444,557 filed on Jan. 10, 2017, incorporated herein by reference in its entirety.

FIELD OF THE INVENTION

Nicotinamide phosphoribosyltransferase (NAMPT) is the rate-limiting step in the nicotinamide (NAM) salvage pathway which culminates in NAD+ biosynthesis. NAMPT synthesizes nicotinamide mononucleotide (NMN) and pyrophosphate from NAM and α-D-5-phosphoribosyl-1-pyrophosphate. NAMPT also catalyzes ATP hydrolysis which promotes NMN production via a phosphoenzyme intermediate (His247). Described are small molecule activators of NAMPT and uses of such activators in the treatment of diseases or conditions that would benefit by NAMPT activation.

SUMMARY OF THE INVENTION

Described herein are compounds that are nicotinamide phosphoribosyltransferase (NAMPT) modulators, and compositions, and methods of using these compounds and compositions.

In one aspect, described herein is a compound that has the structure of Formula (I), or a pharmaceutically acceptable salt, or solvate thereof:

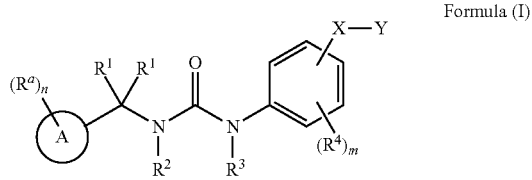

Formula (I)

wherein:
each $R^1$ is independently selected from the group consisting of H, D, $C_1$-$C_4$alkyl and $C_1$-$C_4$deuteroalkyl;
$R^2$ is H, D, substituted or unsubstituted $C_1$-$C_6$alkyl or substituted or unsubstituted $C_1$-$C_6$deuteroalkyl;
$R^3$ is H, D, substituted or unsubstituted $C_1$-$C_6$alkyl or substituted or unsubstituted $C_1$-$C_6$deuteroalkyl;
or $R^2$ and $R^3$ are taken together with the intervening atoms joining $R^2$ and $R^3$ to form a 5- or 6-membered ring;
ring A is a monocyclic ring that is a 6-membered heteroaryl, a 5-membered heteroaryl, or phenyl;
each $R^a$ is independently selected from the group consisting of H, D, halogen, —CN, —OH, —N($R^6$)$_2$, substituted or unsubstituted $C_1$-$C_6$alkyl, substituted or unsubstituted $C_1$-$C_6$deuteroalkyl, substituted or unsubstituted $C_1$-$C_6$alkoxy, substituted or unsubstituted $C_1$-$C_6$fluoroalkyl, substituted or unsubstituted $C_1$-$C_6$fluoroalkoxy, substituted or unsubstituted $C_1$-$C_6$heteroalkyl, substituted or unsubstituted monocyclic carbocycle, and substituted or unsubstituted monocyclic heterocycle;
$R^6$ is H, D, or substituted or unsubstituted $C_1$-$C_6$alkyl;
n is 0, 1, 2, 3, or 4;
each $R^4$ is independently selected from the group consisting of H, D, halogen, —CN, —OH, substituted or unsubstituted $C_1$-$C_6$alkyl, substituted or unsubstituted $C_1$-$C_6$alkoxy, substituted or unsubstituted $C_1$-$C_6$fluoroalkyl, substituted or unsubstituted $C_1$-$C_6$fluoroalkoxy, and substituted or unsubstituted $C_1$-$C_6$heteroalkyl;
m is 0, 1, 2, 3, or 4;
X is absent, —$X^1$-$L^1$- or $L^1$-$X^1$;
$X^1$ is selected from the group consisting of —O—, —S—, —SO$_2$—, —NR$^5$—, —SO$_2$NR$^5$—, —NR$^5$SO$_2$—, —C(=O)NR$^5$—, —NR$^5$C(=O)—, —OC(=O)—, —C(=O)O—, —OC(=O)O—, —C(=O)—, —OC(=O)NR$^5$—, —NR$^5$C(=O)O—, and —NRC(=O)NR$^5$—;
each $R^5$ is independently selected from the group consisting of H, D, substituted or unsubstituted $C_1$-$C_6$alkyl, substituted or unsubstituted $C_1$-$C_6$deuteroalkyl, substituted or unsubstituted $C_1$-$C_6$fluoroalkyl, substituted or unsubstituted $C_3$-$C_6$cycloalkyl, and substituted or unsubstituted benzyl;
$L^1$ is absent or substituted or unsubstituted $C_1$-$C_4$alkylene;
Y is selected from the group consisting of H, D, substituted or unsubstituted $C_1$-$C_6$alkyl, substituted or unsubstituted $C_1$-$C_6$deuteroalkyl, substituted or unsubstituted $C_1$-$C_6$fluoroalkyl, substituted or unsubstituted $C_1$-$C_6$heteroalkyl, substituted or unsubstituted $C_3$-$C_{10}$cycloalkyl, substituted or unsubstituted $C_2$-$C_{10}$heterocycloalkyl, substituted or unsubstituted phenyl, substituted or unsubstituted benzyl, substituted or unsubstituted naphthyl, and substituted or unsubstituted heteroaryl, wherein if Y is substituted then Y is substituted with 1-4 $R^7$ groups;
each $R^7$ is independently selected from the group consisting of D, —CN, —OH, —OR$^9$, —SR$^9$, —S(=O)R$^9$, —S(=O)$_2$R$^9$, —N(R$^8$)S(=O)$_2$R$^9$, —S(=O)$_2$NH$_2$, —S(=O)$_2$NR$^8$R$^9$, —C(=O)R$^9$, —OC(=O)R$^9$, —CO$_2$R$^8$, —OCO$_2$R$^9$, —NH$_2$, —NR$^8$R$^9$, —C(=O)NH$_2$, —C(=O)NR$^8$R$^9$, —OC(=O)NH$_2$, —OC(=O)NR$^8$R$^9$, —NR$^8$C(=O)NH$_2$, —NR$^8$C(=O)NR$^8$R$^9$, —NR$^8$C(=O)R$^9$, —NRC(=O)OR$^9$, a substituted or unsubstituted $C_3$-$C_6$cycloalkyl, a substituted or unsubstituted $C_2$-$C_6$heterocycloalkyl, a substituted or unsubstituted aryl, and a substituted or unsubstituted heteroaryl;
each $R^8$ is independently selected from the group consisting of H, $C_1$-$C_6$alkyl, $C_1$-$C_6$fluoroalkyl, and $C_1$-$C_6$heteroalkyl;
each $R^9$ is independently selected from the group consisting of $C_1$-$C_6$alkyl, $C_1$-$C_6$fluoroalkyl, $C_1$-$C_6$heteroalkyl, a substituted or unsubstituted $C_3$-$C_6$cycloalkyl, a substituted or unsubstituted $C_2$-$C_6$heterocycloalkyl, a substituted or unsubstituted aryl, a substituted or unsubstituted heteroaryl, a substituted or unsubstituted —$C_1$-$C_4$alkylene-$C_3$-$C_{10}$cycloalkyl, a substituted or unsubstituted —$C_1$-$C_4$alkylene-$C_2$-$C_{10}$heterocycloalkyl, a substituted or unsubstituted —$C_1$-$C_4$alkylene-aryl, and a substituted or unsubstituted —$C_1$-$C_4$alkylene-heteroaryl;
or when $R^8$ and $R^9$ are attached to the same N atom then $R^8$ and $R^9$ are taken together with the N atom to which they are attached to form a substituted or unsubstituted $C_2$-$C_{10}$heterocycle;

or when Y and $R^5$ are attached to the same N atom then Y and $R^5$ are taken together with the N atom to which they are attached to form a substituted or unsubstituted $C_2$-$C_{10}$heterocycle.

In some embodiments, the compound of Formula (I) has the structure of Formula (II), or a pharmaceutically acceptable salt, or solvate thereof, wherein:

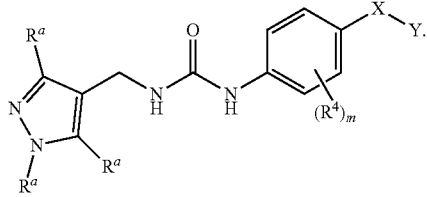

Formula (II)

In some embodiments, the compound of Formula (I) has the structure of Formula (III), or a pharmaceutically acceptable salt, or solvate thereof, wherein:

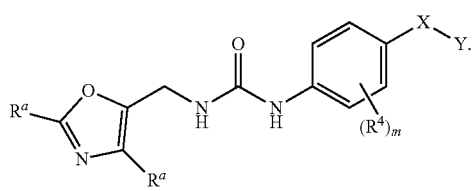

Formula (III)

In some embodiments, the compound of Formula (I) has the structure of Formula (IV), or a pharmaceutically acceptable salt, or solvate thereof, wherein:

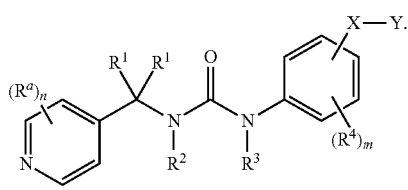

Formula (IV)

In some embodiments, the compound of Formula (IV) has the structure of Formula (V), or a pharmaceutically acceptable salt, or solvate thereof, wherein:

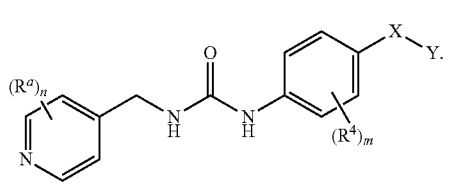

Formula (V)

In some embodiments, compound of Formula (I), or a pharmaceutically acceptable salt, or solvate thereof has the structure of Formula (Ia), or a pharmaceutically acceptable salt, or solvate thereof:

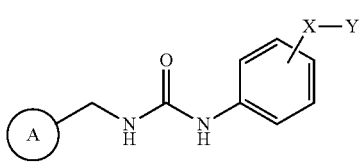

Formula (Ia)

wherein:

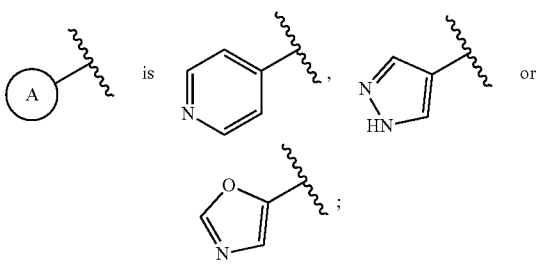

X is absent or -$L^1$-$X^1$-$L^2$-;
$L^1$ is absent or —$CH_2$—
$X^1$ is selected from the group consisting of —O—, —S—, —$SO_2$—, —$NR^5$—, —$SO_2NR^5$—, —$NR^5SO_2$—, —C(=O)$NR^5$—, —$NR^5$C(=O)—, —OC(=O)—, —C(=O)O—, —OC(=O)O—, —C(=O)—, —OC(=O)$NR^5$—, —$NR^5$C(=O)O—, and —$NR^5$C(=O)$NR^5$—;
  each $R^5$ is independently selected from the group consisting of H, D, substituted or unsubstituted $C_1$-$C_6$alkyl, substituted or unsubstituted $C_1$-$C_6$deuteroalkyl, substituted or unsubstituted $C_1$-$C_6$fluoroalkyl, substituted or unsubstituted $C_3$-$C_6$cycloalkyl, and substituted or unsubstituted benzyl;
$L^2$ is absent or substituted or unsubstituted $C_1$-$C_4$alkylene;
Y is selected from the group consisting of H, D, substituted or unsubstituted $C_1$-$C_6$alkyl, substituted or unsubstituted $C_1$-$C_6$deuteroalkyl, substituted or unsubstituted $C_1$-$C_6$fluoroalkyl, substituted or unsubstituted $C_1$-$C_6$heteroalkyl, substituted or unsubstituted $C_3$-$C_{10}$cycloalkyl, substituted or unsubstituted $C_2$-$C_{10}$heterocycloalkyl, substituted or unsubstituted phenyl, substituted or unsubstituted benzyl, substituted or unsubstituted naphthyl, and substituted or unsubstituted heteroaryl, wherein if Y is substituted then Y is substituted with 1-4 $R^7$ groups;
  each $R^7$ is independently selected from the group consisting of D, —CN, F, Cl, Br, I, —OH, —$OR^9$, —$SR^9$, —S(=O)$R^9$, —S(=O)$_2R^9$, —N($R^8$)S(=O)$_2R^9$, —S(=O)$_2NH_2$, —S(=O)$_2NR^8R^9$, —C(=O)$R^9$, —OC(=O)$R^9$, —$CO_2R^8$, —$OCO_2R^9$, —$NH_2$, —$NR^8R^9$, —C(=O)$NH_2$, —C(=O)$NR^8R^9$, —OC(=O)$NH_2$, —OC(=O)$NR^8R^9$, —NRC(=O)$NH_2$, —$NR^8$C(=O)$NR^8R^9$, —$NR^8$C(=O)$R^9$, —$NR^8$C(=O)$OR^9$, substituted or unsubstituted $C_1$-$C_6$alkyl, substituted or unsubstituted $C_1$-$C_6$deuteroalkyl, substituted or unsubstituted $C_1$-$C_6$fluoroalkyl, substituted or unsubstituted $C_1$-$C_6$heteroalkyl, a substituted or unsubstituted $C_3$-$C_6$cycloalkyl, a substituted or unsubstituted $C_2$-$C_6$heterocycloalkyl, a substituted or unsubstituted aryl, or a substituted or unsubstituted heteroaryl, a substituted or unsubstituted —$C_1$-$C_4$alkylene-$C_3$-$C_{10}$cycloalkyl, a substituted or unsubstituted —$C_1$-$C_4$alkylene-$C_2$-$C_{10}$heterocycloalkyl, a substituted or unsubstituted —$C_1$-$C_4$alkylene-aryl, and a substituted or unsubstituted —$C_1$-$C_4$alkylene-heteroaryl;

each $R^8$ is independently selected from the group consisting of H, $C_1$-$C_6$alkyl, $C_1$-$C_6$fluoroalkyl, and $C_1$-$C_6$heteroalkyl;

each $R^9$ is independently selected from the group consisting of $C_1$-$C_6$alkyl, $C_1$-$C_6$fluoroalkyl, $C_1$-$C_6$heteroalkyl, a substituted or unsubstituted $C_3$-$C_6$cycloalkyl, a substituted or unsubstituted $C_2$-$C_6$heterocycloalkyl, a substituted or unsubstituted aryl, a substituted or unsubstituted heteroaryl, a substituted or unsubstituted —$C_1$-$C_4$alkylene-$C_3$-$C_{10}$cycloalkyl, a substituted or unsubstituted —$C_1$-$C_4$alkylene-$C_2$-$C_{10}$heterocycloalkyl, a substituted or unsubstituted —$C_1$-$C_4$alkylene-aryl, and a substituted or unsubstituted —$C_1$-$C_4$alkylene-heteroaryl;

or when $R^8$ and $R^9$ are attached to the same N atom then R and $R^9$ are taken together with the N atom to which they are attached to form a substituted or unsubstituted $C_2$-$C_{10}$heterocycle;

or when Y and $R^5$ are attached to the same N atom then Y and $R^5$ are taken together with the N atom to which they are attached to form a substituted or unsubstituted $C_2$-$C_{10}$heterocycle;

provided that when ring A is pyridin4-yl then —X—Y is not —$SO_2$NHbenzyl, —$SO_2$NH(4-tert-butylphenyl) or —NH$SO_2$(2,5-ditrifluoromethylphenyl).

In some embodiments, the compound of Formula (Ia) has the structure of Formula (IIa), or a pharmaceutically acceptable salt, or solvate thereof, wherein:

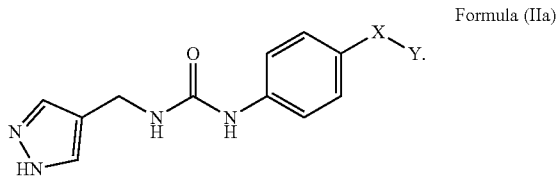

Formula (IIa)

In some embodiments, the compound of Formula (Ia) has the structure of Formula (IIIa), or a pharmaceutically acceptable salt, or solvate thereof, wherein:

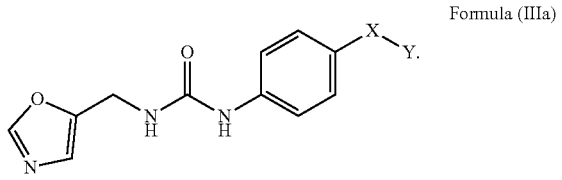

Formula (IIIa)

In some embodiments, the compound of Formula (Ia) has the structure of Formula (IVa), or a pharmaceutically acceptable salt, or solvate thereof, wherein:

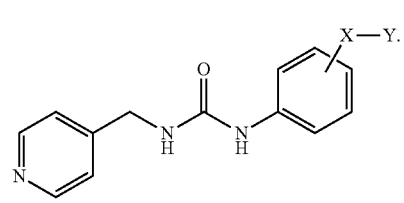

Formula (IVa)

In some embodiments, the compound of Formula (Ia) has the structure of Formula (Va), or a pharmaceutically acceptable salt, or solvate thereof, wherein:

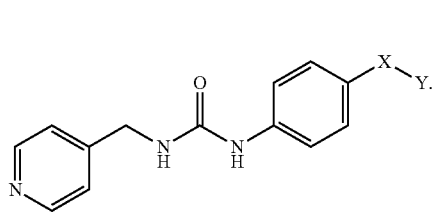

Formula (Va)

Any combination of the groups described above or below for the various variables is contemplated herein. Throughout the specification, groups and substituents thereof are chosen by one skilled in the field to provide stable moieties and compounds.

In one aspect, provided herein is a pharmaceutical composition comprising a compound of Formula (I), (Ia), (II), (IIa), (III), (IIIa), (IV), (IVa), (V) or (Va), or a pharmaceutically acceptable salt thereof, and at least one pharmaceutically acceptable excipient.

In some embodiments, the compound of Formula (I), (Ia), (II), (IIa), (III), (IIIa), (IV), (IVa), (V) or (Va), or a pharmaceutically acceptable salt thereof, is formulated for administration to a mammal by intravenous administration, subcutaneous administration, oral administration, inhalation, nasal administration, dermal administration, or ophthalmic administration. In some embodiments, the compound of Formula (I), (Ia), (II), (Ia), (III), (IIIa), (IV), (IVa), (V) or (Va), or a pharmaceutically acceptable salt thereof, is in the form of a tablet, a pill, a capsule, a liquid, a suspension, a gel, a dispersion, a solution, an emulsion, an ointment, or a lotion.

In one aspect, described herein is a method of treating a disease or condition mediated by nicotinamide phosphoribosyltransferase (NAMPT) activity in a mammal comprising administering a NAMPT activator compound as described herein, or a pharmaceutically acceptable salt, solvate, prodrug, or N-oxide thereof, to the mammal.

In some embodiments, the disease or condition is cancer.

In some embodiments, the disease or condition is hyperproliferative disease or condition.

In some embodiments, the disease or condition is an inflammatory disease or condition.

In some embodiments, the disease or condition is a metabolic disorder.

In some embodiments, the disease or condition is a neurodegenerative disorder.

In some embodiments, the disease or condition is a muscle wasting disorder.

In some embodiments, the disease or condition is a neurodegenerative disease.

In another aspect, described herein is the use of a NAMPT activator compound as described herein, or a pharmaceutically acceptable salt, solvate, prodrug, or N-oxide thereof, in the manufacture of a medicament for the treatment or prevention of a disease or condition that is mediated by NAMPT activity.

In any of the aforementioned aspects are further embodiments in which: (a) the effective amount of the NAMPT activator compound, is systemically administered to the mammal; and/or (b) the effective amount of the NAMPT activator compound is administered orally to the mammal; and/or (c) the effective amount of the compound of the NAMPT activator compound is intravenously administered to the mammal; and/or (d) the effective amount of the NAMPT activator compound is administered by inhalation; and/or (e) the effective amount of the NAMPT activator compound is administered by nasal administration; or and/or (f) the effective amount of the NAMPT activator compound is administered by injection to the mammal; and/or (g) the effective amount of the NAMPT activator compound is administered topically to the mammal; and/or (h) the effective amount of the NAMPT activator compound is administered by ophthalmic administration; and/or (i) the effective amount of the NAMPT activator compound is administered rectally to the mammal; and/or (j) the effective amount is administered non-systemically or locally to the mammal.

In any of the aforementioned aspects are further embodiments comprising single administrations of the effective amount of the NAMPT activator compound, including further embodiments in which (i) the compound is administered once; (ii) the compound is administered to the mammal multiple times over the span of one day; (iii) continually; or (iv) continuously.

In any of the aforementioned aspects are further embodiments comprising multiple administrations of the effective amount of the NAMPT activator compound, including further embodiments in which (i) the compound is administered continuously or intermittently: as in a single dose; (ii) the time between multiple administrations is every 6 hours; (iii) the compound is administered to the mammal every 8 hours; (iv) the compound is administered to the mammal every 12 hours; (v) the compound is administered to the mammal every 24 hours. In further or alternative embodiments, the method comprises a drug holiday, wherein the administration of the compound is temporarily suspended or the dose of the compound being administered is temporarily reduced; at the end of the drug holiday, dosing of the compound is resumed. In one embodiment, the length of the drug holiday varies from 2 days to 1 year.

In any of the aforementioned aspects involving the administration of a compound of Formula (I), (Ia), (II), (IIa), (III), (IIIa), (IV), (IVa), (V) or (Va), or a pharmaceutically acceptable salt thereof, to a subject are further embodiments comprising administering at least one additional agent in addition to the administration of a NAMPT activator compound, or a pharmaceutically acceptable salt thereof. In various embodiments, the NAMPT activator compound and the additional agent are administered in any order, including simultaneously. In some embodiments, the NAMPT activator compound and the additional agent are administered to the subject in the same pharmaceutical composition or in separate pharmaceutical compositions.

In any of the embodiments disclosed herein, the subject is a human.

In some embodiments, compounds and compositions provided herein are administered to a human.

In some embodiments, compounds and compositions provided herein are orally administered.

Articles of manufacture, which include packaging material, a NAMPT activator compound, within the packaging material, and a label that indicates that the compound or composition, or pharmaceutically acceptable salt, tautomers, pharmaceutically acceptable N-oxide, pharmaceutically active metabolite, pharmaceutically acceptable prodrug, or solvate thereof, is used for the treatment of diseases or conditions that would benefit from the activation of NAMPT, are provided.

Other objects, features and advantages of the compounds, methods and compositions described herein will become apparent from the following detailed description. It should be understood, however, that the detailed description and the specific examples, while indicating specific embodiments, are given by way of illustration only, since various changes and modifications within the spirit and scope of the instant disclosure will become apparent to those skilled in the art from this detailed description.

DETAILED DESCRIPTION OF THE INVENTION

Nicotinamide phosphoribosyltransferase (NAMPT) is an essential intracellular enzyme involved in mammalian biosynthetic pathway of nicotinamide adenine dinucleotide (NAD), a coenzyme participating in adenosine triphosphate (ATP) production and redox metabolism. The pathway includes the first rate-limiting step of the NAMPT-catalyzed synthesis of nicotinamide mononucleotide from nicotinamide, and the second step which is a subsequent conversion of nicotinamide mononucleotide to NAD catalyzed by nicotinamide mononucleotide adenyltransferase (NMNAT). It was established that rapid NAD depletion in brain tissue inevitably suppresses ATP generation, which in turn disrupts intracellular energy homeostasis and eventually leads to the cell death and to the brain injuries. Upregulation of NAMPT has been shown as a response to the decreased NAD level in several ischemic stroke models, including several clinical studies.

In addition to its role in intracellular energy production, NAMPT also plays a critical role in sirtuin (SIRT) signaling, which is a key endogenous defense element against various stresses, cell metabolic homeostasis, survival, and aging. NAMPT expression and activity can be regulated by various stimuli, including circadian rhythms, diet, caloric intake restriction, stress, aging, and disease.

Based on importance of NAMPT in regulation of NAD and ATP levels, the compounds which alter NAMPT expression and activity are considered to be useful in treating or preventing the brain injuries which are accompanied by the decreased levels of NAD, including ischemic stroke, hemorrhagic stroke, and traumatic brain injuries. Recently, P7C3 chemicals were found to work as activators of NAMPT in cells and their prolonged administration prevented newborn neuron death and enhanced neurogenesis and preserved cognitive function in aged rodents. In addition to their efficacy in animal models of Alzheimer's disease, P7C3s were found to be effective in other models of neurological disease including Parkinson's disease, amyotrophic lateral sclerosis, traumatic brain injuries, depression, Down syndrome, and neonatal nerve injury.

Brain Injuries

Stroke is among the most common causes of death and the leading cause of disability with high morbidity worldwide. The number of people with first stroke is approximately 17 million per year; almost one-third die and one-third are left permanently disabled. Throughout the world, stroke is responsible for approximately one-tenth of deaths, 33 million people are living with the effects of stroke, and the prevalence of stroke is rising. Stroke refers to an acute cerebrovascular disorder that is manifested by sudden loss or deterioration of brain function due to the disruption in blood supply to the brain. Approximately 78% of strokes are ischemic stroke and others are hemorrhagic stroke. Tissue plasminogen activator (tPA) is the only pharmacological therapy approved for ischemic stroke, and no drug is available for hemorrhagic stroke. Only a small fraction (3-5%) of stroke patients receives tPA treatment. Therefore, there is an urgent need for developing new drugs to treat stroke. Elucidation of the endogenous defense mechanisms against cellular injury is considered key to the development of novel stroke therapies. Furthermore, in addition to salvaging the stroke patients at the acute period, there is the need to provide a solution for stroke rehabilitation during the chronic period. Therefore, an ideal target for stroke treatment could be a multifunctional protein with protection locally and systemically during acute and chronic phases of stroke.

In the animal ischemic stroke model, upregulation of both intracellular NAMPT and extracellular NAMPT has been observed. In humans, several clinical studies provided evidence for the elevation of blood NAMPT level as a response to the decreased NAD level in different ischemic stroke models. In all studies, NAMPT is described to strongly suppress ischemia-induced neuronal death, to inhibit the activation of mitochondrial apoptotic signaling pathways (such as Bax and Caspase-3), and to reduce mitochondrial membrane potential depolarization. It was established that rapid NAD depletion in brain tissue inevitably suppresses ATP generation, which in turn disrupts intracellular energy homeostasis and eventually leads to the cell death and to the brain injuries. Based on importance of NAMPT in regulation of NAD and ATP levels, the compounds which alter NAMPT expression and activity can be used in treating or preventing brain injuries which are accompanied by the decreased levels of NAD, including ischemic stroke, hemorrhagic stroke, and traumatic brain injuries.

Metabolic Disorders

NAMPT has been identified as adipocytokine. It was demonstrated that this protein is expressed in adipocytes and secreted from adipose tissue, in particular from visceral fat. Adipocytokines mediate beneficial and detrimental effects in immunity and inflammation. Many of adipocytokines have a physiological role in metabolism. The uncontrolled secretions of several adipocytokines were associated with the stimulation of inflammatory processes leading to metabolic disorders including obesity, atherosclerosis, insulin resistance, type 2 diabetes, and cardiovascular diseases. Obesity leads to the dysfunction of adipocytes and correlates with the imbalance of adipocytokines levels. Functional balance of both adipocytes and immune cells is important to exert their effects on metabolic disorders. The loss of NAMPT activity was linked to type II diabetes in mice. Several clinical studies showed increased serum NAMPT levels in patients with different metabolic disorders including obese patients and patients with type 2 diabetes. These studies suggest that potential therapies altering NAMPT levels may be translated into the future clinical treatments of chronic endocrine metabolic and inflammatory disorders.

Diabetes mellitus, simply referred to as diabetes, is a syndrome of disordered metabolism with hyperglycemia as a hallmark phenotype. It is usually divided into Type 1 and Type 2 diabetes. Type 1 diabetes is characterized by loss of the insulin producing p cells of the islets of Langerhans in the pancreas, leading to a deficiency of insulin. Type 2 diabetes is characterized differently due to insulin resistance or reduced insulin sensitivity, combined with a reduced insulin secretion. Diabetes is a complex disease.

In some embodiments, NAMPT activation provides improved Glucose tolerance (GTT) along with insulin secretion and sensitivity. The pancreas (0-cell, and islets) which releases insulin responds by improved secretion and response to glucose. In some embodiments, the indices of diabetes are significantly improved with use of NAMPT activators, both short and long term use.

Another major problem with diabetics is cardiac injury with high risk of morbidity and mortality. Major risk factors include myocardial ischemia, diabetic arrhythmogenesis and cardiomyopathy. Co-morbidities include higher atrial fibrillation, ventricular defects, myocardial damage, and scar formation, which can be attenuated by Nampt activator. In some embodiments, NAMPT activators provide for cardioprotection (anti-ischemic) in a mammal with diabetes.

Nicotinamide adenine dinucleotide (NAD+) is an essential coenzyme in all cells and involved cellular metabolism. Nicotinamide phosphoribosyl-transferase (Nampt) is a regulator of intracellular NAD+. Nampt is able to modulate processes involved in diabetes associated cardiovascular disease through modulation of NAD+. In some embodiments, NAD+ levels decrease in diabetic mammals and the use of a Nampt activator increases NAD levels and rescues diabetes. In some embodiments, Nampt activation modulates pyridine nucleotides, altering insulin resistance and insulin release offers cardioprotection.

In some embodiments, a NAMPT activator is used to improve insulin resistance, increases insulin release, insulin secretion, cardiac function, or muscle activity, or a combination thereof, in a mammal with diabetes.

Provided herein are methods for treating metabolic disorders with a NAMPT activator. The NAMPT activator can treat, delay or prevent the onset of a metabolic disorder, wherein such metabolic disorders include, but are not limited to, metabolic syndrome, elevated blood glucose levels, insulin resistance, glucose intolerance, type 2 diabetes, type 1 diabetes, pre-diabetes, non-alcoholic fatty liver disease, nonalcoholic steatohepatitis, and obesity.

Insulin resistance may be detected using a procedure known as the hyperinsulinemic euglycemic clamp, which measures the amount of glucose necessary to compensate for an increased insulin level without causing hypoglycemia. In some embodiments, the methods disclosed herein comprise administering a NAMPT activator to a subject with insulin resistance. In some embodiments, the NAMPT activator improves insulin sensitivity. In some embodiments, the NAMPT activator treats a metabolic disorder. In some embodiments, the NAMPT activator treats a metabolic disorder by improving insulin sensitivity. In some embodiments, the NAMPT activator delays or prevents the onset of the metabolic disorder by improving insulin sensitivity.

In some embodiments, described herein is a method of improving glucose tolerance in an individual comprising administering a NAMPT activator to the subject with impaired glucose tolerance. In some embodiments, the individual has a metabolic disorder and the metabolic disorder is treated by improving glucose tolerance. In some embodiments, the NAMPT activator delays or prevents the onset of a metabolic disorder in an individual by improving glucose tolerance.

In some embodiments, described herein is a method of treatment of a metabolic disorder in a subject that is overweight or obese. In some embodiments, a NAMPT activator is used to treat obesity in a subject. In some embodiments, the NAMPT activator decreases adipose tissue expansion in the subject that is overweight or obese. In some embodiments, the metabolic disorder is treated by decreasing adipose tissue expansion.

In some embodiments, administration of a NAMPT activator to a subject delays or prevents the onset of a metabolic disorder by decreasing adipose tissue expansion. In some embodiments, the subject is at risk for developing a metabolic disorder.

In some embodiments, administration of a NAMPT activator to a subject treats, prevents, or ameliorates the symptoms of drug induced hyperglycemia. In some embodiments, administration of a NAMPT activator to a subject treats, prevents, or ameliorates the symptoms of drug induced hyperglycemia by reducing blood glucose levels. Pharmacological agents can affect glucose homestasis that can result in hyperglycemia. In some embodiments, the hyperglycemia occurs in the absence of a diagnosis of diabetes. If left untreated, the elevated blood glucose levels can lead to a medical emergency. Symptoms include, but are not limited to fatigue, weakness, fruity odor of the breath, confusion, lack of concentration, shortness of breath, nausea, vomiting, dry skin, and flushing of the skin. Common drug categories that are associated with contributing to hyperglycemia include, but are not limited to: antibiotics, such as fluoroquinolones including gatifloxacin; beta-blockers, such as propranolol, metoprolol or atenolol; thiazide, such as hydrochlorothiazide, and thiazide-like diuretics, and thiazide-like drugs (metolazone); second-generation antipsychotics (SGAs) or "atypical antipsychotics" such as olanzapine or clozapine; corticosteroids; calcinuerin inhibitors such as cyclosporine, sirolimus or tarcrolimus; protease inhibitors such as ritonavir.

In some embodiments, administration of a NAMPT activator to a subject treats or prevents or delays the onset of stress induced hyperglycemia. In some embodiments, administration of a NAMPT activator to a subject treats or prevents or delays the onset of stress induced hyperglycemia by reducing blood glucose levels. Stressed induced hyperglycemia (SIH) is a transient increase in plasma glucose levels higher than 200 mg/dL which occurs during an acute illness or injury. In some embodiments, the hyperglycemia occurs in the absence of a diagnosis of diabetes. The SIH results from an excess of glucose production relative glucose clearance. SIH has been associated with conditions including, but not limited to, myocardial infarction, stroke, and trauma. SIH has been associated with increase mortality and a higher incidence of congestive heart failure and cardiogenic shock in patients after myocardial infarction. Stroke victims have higher mortality associated with SIH and worse odds of desirable neurological outcomes as glucose levels increase with SIH. Hyperglycemia was also shown to be a predictor of infectious complications in the form of pneumonia, urinary tract infections, wound infections and bacteria. Overall, published studies have consistently shown higher morbidity and higher mortality rates in those patients that present with SIH.

In certain embodiments, the methods provided herein comprise measuring blood glucose levels. Blood glucose levels may be measured before and/or after administration of a NAMPT activator. Blood glucose levels may be measured in whole blood, or may be measured in plasma. Blood glucose levels may be measured in a clinical laboratory, or may be measured using a blood glucose meter.

In certain embodiments, blood glucose levels are measured in a subject when the subject has fasted for at least 8 hours. In certain embodiments, blood glucose levels are measured at random times, and the measurement is not timed according to the intake of food or drink. In certain embodiments, blood glucose levels are measured in the post-prandial state, i.e. after the subject has eaten a meal. In certain embodiments, blood glucose levels are measured in a subject two hours after the subject has eaten a meal. In certain embodiments, blood glucose levels are measured at timed intervals following administration of glucose to the subject, in order to determine how quickly the subject's body clears glucose from the blood. Any measurements of blood glucose levels may be made in whole blood or in plasma.

In certain embodiments, the subject has elevated blood glucose levels. In certain embodiments, a subject is identified as having elevated blood glucose levels. In certain embodiments, an elevated blood glucose level is a fasting blood glucose level between 100 and 125 mg/dL. In certain embodiments, an elevated blood glucose level is a fasting blood glucose level above 126 mg/dL. In certain embodiments, an elevated blood glucose level is a two-hour postprandial glucose level between 140 and 199 mg/dL. In certain embodiments, an elevated blood glucose level is a two-hour post-prandial glucose level at 200 mg/dL or higher.

In certain embodiments, a subject having elevated blood glucose levels has pre-diabetes. In certain embodiments, a subject is identified as having pre-diabetes. In certain embodiments, a subject having elevated blood glucose levels has diabetes. In certain embodiments, a subject is identified as having diabetes according to the subject's blood glucose levels. In certain embodiments, the methods provided herein comprise monitoring blood glucose levels before administration of a NAMPT activator. In certain embodiments, the methods provided herein comprise measuring blood glucose levels after administration of a NAMPT activator. In certain embodiments, a subject measures blood glucose levels one or more times daily.

In certain embodiments, methods for reducing blood glucose levels comprise reducing a subject's blood glucose levels to blood glucose levels determined as desirable by medical organizations, such as the American Diabetes Association or the World Health Organization. In certain embodiments, blood glucose levels are reduced below 130 mg/dL when measured before a subject has had a meal. In certain embodiments, blood glucose levels are reduced to below 180 mg/dL when measured after a subject has had a meal.

Provided herein are methods for improving insulin sensitivity in a subject comprising administering to the subject a NAMPT activator; and thereby improving insulin sensitivity in the subject. In certain embodiments, the subject has insulin resistance. In some embodiments, the individual with insulin resistance has fasting insulin levels of at least 20 U/mL. In some embodiments, the individual with insulin resistance has fasting insulin levels that exceed 100 U/mL.

Muscle Wasting Disorder

Aging is the accumulation of changes in an organism over time. Aging is a complex process, depending on both genetic compositions and environmental conditions.

Aging is associated with mitochondrial dysfunction due to a specific loss of mitochondrial encoded oxidative phosphorylation subunits throughout the life. Mitochondria are responsible for the generation of cellular energy, in particular NAD and ATP. During aging NAD levels in mitochondria decline which lead to reduction in energy production and reduction of muscle function. As a result, mitochondrial dysfunction leads to muscle wasting disorders. Deleting SIRT1 and NAMPT accelerates decline in nuclear NAD and the accumulation of HIF-1α under normoxic conditions, with parallels to Warburg reprogramming, whereas raising NAD levels in old mice restores mitochondrial function to that of a young mouse in a SIRT1- and NAMPT-dependent manner. The pseudohypoxic state disrupts nuclear-mitochondrial communication contributes to the decline in mitochondrial function with age and leads to subsequent muscle disorders, including skeletal and heart muscle disorders. Specific deletion of NAMPT in adult mice elucidated a critical threshold of NAD required to maintain the exercise performance, as well as the mass and strength of muscle, by directly supporting aerobic ATP synthesis. Importantly, these parameters can be rapidly and uniformly restored by administration of the NAD precursor, nicotinamide riboside. NAMPT activators aiming to increase intracellular NAD levels will potentially reverse the process of muscle wasting disorder.

Axonal degeneration occurs in many neurodegenerative diseases. In some embodiments, NAMPT delays axon degeneration in the presence of nicotinamide. The increased activity of the NAD biosynthetic pathway stemming from nicotinamide promotes axonal protection. Exogenous application of the NAD precursors can also delay axonal degeneration. In some embodiments, stimulation of NAD biosynthetic pathways including NAMPT are useful in preventing or delaying axonal degeneration. In some cases, NAMPT can extend the lifespan of human smooth muscle cells. For example, it has been demonstrated that replicative senescence of smooth muscle cells was preceded by a marked decline in the expression and activity of NAMPT. Furthermore, reducing NAMPT activity with the antagonist FK866 induced premature senescence in smooth muscle cells, assessed by serial quantification of the proportion of cells with senescence-associated beta-galactosidase activity. In contrast, introducing the NAMPT gene into aging human smooth muscle cells delayed senescence and substantially lengthened cell lifespan, together with enhanced resistance to oxidative stress. NAMPT mediated smooth muscle cells lifespan extension was associated with increased activity of the NAD+-dependent longevity enzyme SIRT1 and was abrogated in NAMPT-overexpressing cells transduced with a dominant-negative form of SIRT1 (H363Y). NAMPT overexpression also reduced the fraction of p53 that was acetylated on lysine 382, a target of SIRT1, suppressed an age-related increase in p53 expression, and increased the rate of p53 degradation. Moreover, add-back of p53 with recombinant adenovirus blocked the anti-aging effects of NAMPT. These data indicate that NAMPT is a longevity protein that can add stress-resistant life to human smooth muscle cells by optimizing SIRT1-mediated p53 degradation.

In some embodiments, overexpression of NAMPT increases SIRT1 activity and can protect cells from death due to PARP overexpression, which is consistent with the hypothesis that NAMPT is a functional equivalent of Pnc1 in mammals. Pnc1 is a stress- and calorie-responsive longevity gene that catalyzes the first and rate-limiting step in NAD+ biosynthesis from nicotinamide in yeast.

NAMPT expression and mitochondrial NAD+ levels increase in vivo after fasting.

In some embodiments, a NAMPT activator is used to treat muscle wasting in a mammal. There are many diseases and conditions which cause a decrease in muscle mass, known as atrophy, including: inactivity, as seen when a cast is put on a limb, or upon extended bedrest (which can occur during a prolonged illness); cachexia—which is a syndrome that is a co-morbidity of cancer and congestive heart failure; chronic obstructive pulmonary disease; burns, liver failure, and the wasting Dejerine-Sottas syndrome (HMSN Type III). Glucocorticoids, a class of medications used to treat allergic and other inflammatory conditions can induce muscle atrophy by increasing break-down of muscle proteins. Other syndromes or conditions which can induce skeletal muscle atrophy are liver disease, and starvation.

Examples of diseases affecting the nerves that control muscles include, but are not limited to, Amyotrophic lateral sclerosis (ALS, or Lou Gehrig disease), damage to a single nerve, such as carpal tunnel syndrome, Guillain-Barre syndrome, nerve damage caused by injury, diabetes, toxins, or alcohol, polio (poliomyelitis), spinal cord injury.

Other causes of muscle atrophy may include: burns, long-term corticosteroid therapy, malnutrition, muscular dystrophy, and other diseases of the muscle, osteoarthritis, rheumatoid arthritis.

Amyotrophic lateral sclerosis (ALS) is a debilitating disorder characterized by rapidly progressive motor neuron degeneration, which results into weakness, muscle atrophy and spasticity. Familial ALS (FALS) is caused by mutations of several genes including SOD1 (type-1 superoxide dismutase). Although SOD1 mutations account for only 20% of FALS and about 2% of sporadic ALS, SOD1 mutant mice recapitulate several features of human ALS, and are widely employed as model for ALS. The validity of this model is strengthened by the evidence that SOD1 aggregates are detected in the spinal cord of people with sporadic ALS or with ALS caused by mutations of genes other than SOD1. The mechanisms by which SOD1 misfolding damages motor neurons are only partially elucidated and involve glutamate excitotoxicity, mitochondrial dysfunction, disruption of axonal transport, and abnormalities in astrocytes and microglia. In some embodiments, the NAMPT activators described herein are useful for treating ALS.

Neurodegenerative Disorder

Death of nerve cells is the key mechanism in many highly destructive neurological diseases for which there are limited treatment options exist. Understanding the molecular networks linking these diseases could facilitate the discovery of novel diagnostics and therapeutics. NAD is an essential metabolite for many cellular functions including energy production, protein deacetylation, calcium signaling, and DNA repair. With many different processes dependent on this molecule, the loss of NAD could cause problems in neurons of the brain with age. It was shown that NAMPT levels and therefore NAD levels decline in the brains of mice with age. Supplementation with an NAD precursor was able to restore NAD levels, enhancing regeneration in the brains of aged mice. Compounds that work as activators of NAMPT in cells were found to prevent newborn neuron death and enhanced neurogenesis and preserved cognitive function in aged rodents upon their prolonged administration. In addition to their efficacy in animal models of Alzheimer's disease, NAMPT activators were found to be effective in other models of neurological disorders including Parkinson's disease, amyotrophic lateral sclerosis, depression, Down syndrome, and neonatal nerve injury. Since NAMPT activators elevate NAD levels through activation of NAMPT, it is likely that this pathway is responsible for the protective and regenerative effects of this drug in the brain.

Alzheimer's disease (AD) accounts for 60% to 70% of cases of dementia. It is a chronic neurodegenerative disease that usually starts slowly and gets worse over time. The most common early symptom is difficulty in remembering recent events (short term memory loss). As the disease advances, symptoms can include: problems with language, disorientation (including easily getting lost), mood swings, loss of motivation, not managing self-care, and behavioral issues. As a person's condition declines, she or he often withdraws from family and society. Gradually, bodily functions are lost, ultimately leading to death. Although the speed of progression can vary, the average life expectancy following diagnosis is three to nine years. In some embodiments, the NAMPT activators described herein are useful for treating Alzheimer's disease.

Huntington's disease (HD) is a neurodegenerative genetic disorder that affects muscle coordination and leads to mental decline and behavioral symptoms. Symptoms of the disease can vary between individuals and affected members of the same family, but usually progress predictably. The earliest symptoms are often subtle problems with mood or cognition. A general lack of coordination and an unsteady gait often follows. As the disease advances, uncoordinated, jerky body movements become more apparent, along with a decline in mental abilities and behavioral symptoms. Physical abilities gradually worsen until coordinated movement becomes difficult. Mental abilities generally decline into dementia. Complications such as pneumonia, heart disease, and physical injury from falls reduce life expectancy to around twenty years from the point at which symptoms begin. Physical symptoms can begin at any age from infancy to old age, but usually begin between 35 and 44 years of age. In some embodiments, the NAMPT activators described herein are useful for treating Huntington's disease.

Parkinson's disease (PD) is a chronic movement disorder resulting from a disturbance in the normal functioning of the basal ganglia, a collection of subcortical nuclei that are essential for the initiation and control of motor activity. The underlying pathology of the disease is a progressive degeneration of the dopaminergic nigrostriatal tract that manifests as a range of motor deficits including akinesia or bradykinesia, tremor, rigidity and postural instability. Current therapies for PD are essentially based on dopamine replacement and include levodapa (L-DOPA), a precursor of dopamine, and dopamine receptor agonists. These agents are effective in treating the symptoms of the disease in the early stages, but are less effective as the disease progresses when debilitating side-effects such as "on-off" fluctuations in efficacy and uncontrollable dyskinesias (involuntary muscle movements) ensue. More importantly, dopaminergic treatments do not halt the disease progression. For these reasons, several investigators have started to focus on nondopaminergic interventions as symptomatic and neuroproteceive strategies in PD. In some embodiments, the NAMPT activators described herein are useful for treating Parkinson's disease.

Compounds

In one aspect, described herein is a compound that has the structure of Formula (I), or a pharmaceutically acceptable salt, solvate, prodrug, or N-oxide thereof:

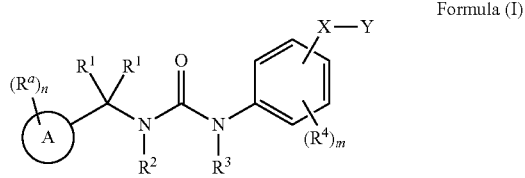

Formula (I)

wherein:
each $R^1$ is independently selected from the group consisting of H, D, $C_1$-$C_4$alkyl and $C_1$-$C_4$deuteroalkyl;

$R^2$ is H, D, substituted or unsubstituted $C_1$-$C_6$alkyl or substituted or unsubstituted $C_1$-$C_6$deuteroalkyl;

$R^3$ is H, D, substituted or unsubstituted $C_1$-$C_6$alkyl or substituted or unsubstituted $C_1$-$C_6$deuteroalkyl;

or $R^2$ and $R^3$ are taken together with the intervening atoms joining $R^2$ and $R^3$ to form a 5- or 6-membered ring;

ring A is a monocyclic ring that is a 6-membered heteroaryl, a 5-membered heteroaryl, or phenyl;

each $R^a$ is independently selected from the group consisting of H, D, halogen, —CN, —OH, —N($R^6$)$_2$, substituted or unsubstituted $C_1$-$C_6$alkyl, substituted or unsubstituted $C_1$-$C_6$deuteroalkyl, substituted or unsubstituted $C_1$-$C_6$alkoxy, substituted or unsubstituted $C_1$-$C_6$fluoroalkyl, substituted or unsubstituted $C_1$-$C_6$fluoroalkoxy, substituted or unsubstituted $C_1$-$C_6$heteroalkyl, substituted or unsubstituted monocyclic carbocycle, and substituted or unsubstituted monocyclic heterocycle;

$R^6$ is H, D, or substituted or unsubstituted $C_1$-$C_6$alkyl;

n is 0, 1, 2, 3, or 4;

each $R^4$ is independently selected from the group consisting of H, D, halogen, —CN, —OH, substituted or unsubstituted $C_1$-$C_6$alkyl, substituted or unsubstituted $C_1$-$C_6$alkoxy, substituted or unsubstituted $C_1$-$C_6$fluoroalkyl, substituted or unsubstituted $C_1$-$C_6$fluoroalkoxy, and substituted or unsubstituted $C_1$-$C_6$heteroalkyl;

m is 0, 1, 2, 3, or 4;

X is absent, —$X^1$-$L^1$- or $L^1$-$X^1$;

$X^1$ is selected from the group consisting of —O—, —S—, —SO$_2$—, —NR$^5$—, —SO$_2$NR$^5$—, —NR$^5$SO$_2$—, —C(=O)NR$^5$—, —NR$^5$C(=O)—, —OC(=O)—, —C(=O)O—, —OC(=O)O—, —C(=O)—, —OC(=O)NR$^5$—, —NR$^5$C(=O)O—, and —NR$^5$C(=O)NR$^5$—;

each $R^5$ is independently selected from the group consisting of H, D, substituted or unsubstituted $C_1$-$C_6$alkyl, substituted or unsubstituted $C_1$-$C_6$deuteroalkyl, substituted or unsubstituted $C_1$-$C_6$fluoroalkyl, substituted or unsubstituted $C_3$-$C_6$cycloalkyl, and substituted or unsubstituted benzyl;

$L^1$ is absent or substituted or unsubstituted $C_1$-$C_4$alkylene;

Y is selected from the group consisting of H, D, substituted or unsubstituted $C_1$-$C_6$alkyl, substituted or unsubstituted $C_1$-$C_6$deuteroalkyl, substituted or unsubstituted $C_1$-$C_6$fluoroalkyl, substituted or unsubstituted $C_1$-$C_6$heteroalkyl, substituted or unsubstituted $C_3$-$C_{10}$cycloalkyl, substituted or unsubstituted $C_2$-$C_{10}$heterocycloalkyl, substituted or unsubstituted phenyl, substituted or unsubstituted benzyl, substituted or unsubstituted naphthyl, and substituted or unsubstituted heteroaryl, wherein if Y is substituted then Y is substituted with 1-4 $R^7$ groups;

each $R^7$ is independently selected from the group consisting of D, —CN, —OH, —OR$^9$, —SR$^9$, —S(=O)R$^9$, —S(=O)$_2$R$^9$, —N(R$^8$)S(=O)$_2$R$^9$, —S(=O)$_2$NH$_2$, —S(=O)$_2$NR$^8$R$^9$, —C(=O)R$^9$, —OC(=O)R$^9$, —CO$_2$R$^8$, —OCO$_2$R$^9$, —NH$_2$, —NR$^8$R$^9$, —C(=O)NH$_2$, —C(=O)NR$^8$R$^9$, —OC(=O)NH$_2$, —OC(=O)NR$^8$R$^9$, —NR$^8$C(=O)NH$_2$, —NR$^8$C(=O)NR$^8$R$^9$, —NR$^8$C(=O)R$^9$, —NR$^8$C(=O)OR$^9$, a substituted or unsubstituted $C_3$-$C_6$cycloalkyl, a substituted or unsubstituted $C_2$-$C_6$heterocycloalkyl, a substituted or unsubstituted aryl, and a substituted or unsubstituted heteroaryl;

each R[8] is independently selected from the group consisting of H, $C_1$-$C_6$alkyl, $C_1$-$C_6$fluoroalkyl, and $C_1$-$C_6$heteroalkyl;

each R[9] is independently selected from the group consisting of $C_1$-$C_6$alkyl, $C_1$-$C_6$fluoroalkyl, $C_1$-$C_6$heteroalkyl, a substituted or unsubstituted $C_3$-$C_6$cycloalkyl, a substituted or unsubstituted $C_2$-$C_6$heterocycloalkyl, a substituted or unsubstituted aryl, a substituted or unsubstituted heteroaryl, a substituted or unsubstituted —$C_1$-$C_4$alkylene-$C_3$-$C_{10}$cycloalkyl, a substituted or unsubstituted —$C_1$-$C_4$alkylene-$C_2$-$C_{10}$heterocycloalkyl, a substituted or unsubstituted —$C_1$-$C_4$alkylene-aryl, or a substituted or unsubstituted —$C_1$-$C_4$alkylene-heteroaryl;

or when R[8] and R[9] are attached to the same N atom then R[8] and R[9] are taken together with the N atom to which they are attached to form a substituted or unsubstituted $C_2$-$C_{10}$heterocycle;

or when Y and R[5] are attached to the same N atom then Y and R[5] are taken together with the N atom to which they are attached to form a substituted or unsubstituted $C_2$-$C_{10}$heterocycle.

For any and all of the embodiments, substituents are selected from among a subset of the listed alternatives. For example, in some embodiments, m is 1 or 2. In other embodiments, m is 0. In some other embodiments, m is 1. In some other embodiments, m is 2.

In some embodiments, each R[1] is H, D, —$CH_3$, or —$CH_2CH_3$; R[2] is H, —$CH_3$, or —$CH_2CH_3$; and R[3] is H, —$CH_3$, or —$CH_2CH_3$.

In some embodiments, R[2] is H; and R[3] is H.

In some embodiments, R[2] and R[3] are taken together with the intervening atoms joining R[2] and R[3] to form an imidazolidin-2-one or a tetrahydropyrimidin-2(1H)-one. In some embodiments, R[2] and R[3] are taken together with the intervening atoms joining R[2] and R[3] to form an imidazolidin-2-one.

In some embodiments, the groups

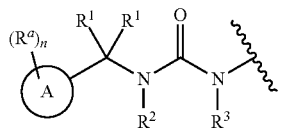

and —X—Y are in a 1,4-relationship on the phenyl or a 1,3-relationship on the phenyl.

In some embodiments, the groups

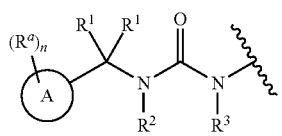

and —X—Y are in a 1,4-relationship on the phenyl.

In some embodiments, ring A is a 6-membered heteroaryl, or a 5-membered heteroaryl.

In some embodiments, ring A is a 6-membered heteroaryl that is selected from pyridinyl, pyrimidinyl, pyrazinyl, pyridazinyl, and triazinyl.

In some embodiments, ring A is a 6-membered heteroaryl that is selected from pyridin-4-yl, pyridin-3-yl, and pyridin-2-yl.

In some embodiments,

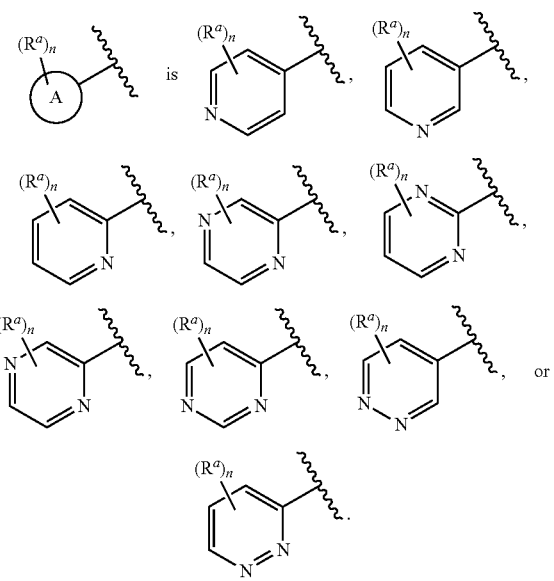

In some embodiments, ring A is a 5-membered heteroaryl containing 1-4 N atoms and 0 or 1 O or S atom, or a monocyclic heterocycle containing 0-4 N atoms and 1 O or S atoms.

In some embodiments, ring A is a 5-membered heteroaryl that is selected from the group consisting of furanyl, pyrrolyl, oxazolyl, thiazolyl, imidazolyl, pyrazolyl, triazolyl, tetrazolyl, isoxazolyl, isothiazolyl, oxadiazolyl, and thiadiazolyl.

In some embodiments,

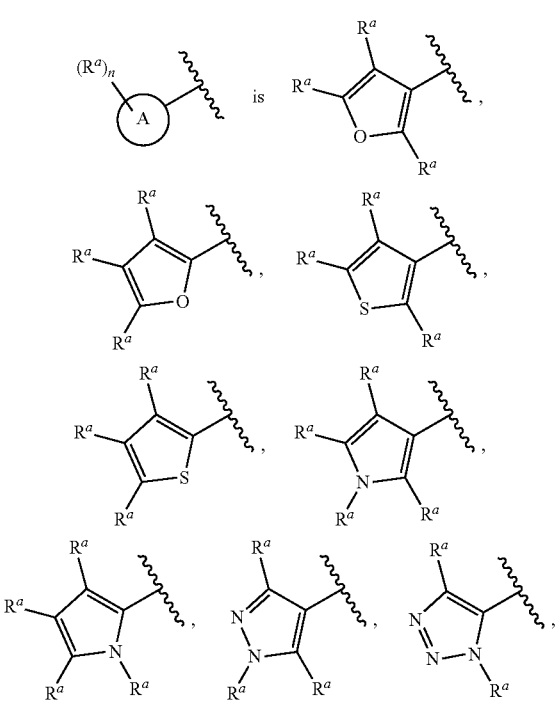

-continued

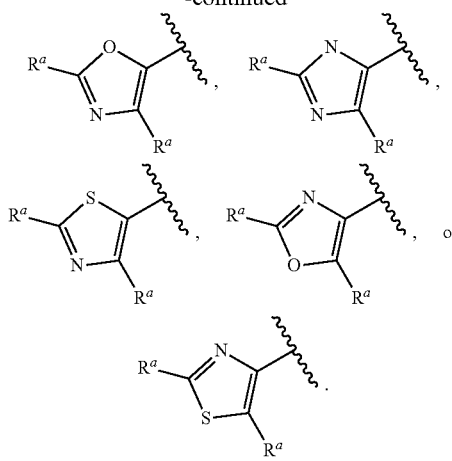

In another aspect, described herein is a compound of Formula (I), or a pharmaceutically acceptable salt, solvate, prodrug, or N-oxide thereof:

Formula (I)

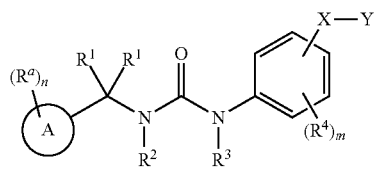

wherein:

each $R^1$ is independently selected from the group consisting of H, D, $C_1$-$C_4$alkyl and $C_1$-$C_4$deuteroalkyl;

$R^2$ is H, D, substituted or unsubstituted $C_1$-$C_6$alkyl or substituted or unsubstituted $C_1$-$C_6$deuteroalkyl;

$R^3$ is H, D, substituted or unsubstituted $C_1$-$C_6$alkyl or substituted or unsubstituted $C_1$-$C_6$deuteroalkyl;

or $R^2$ and $R^3$ are taken together with the intervening atoms joining $R^2$ and $R^3$ to form a 5- or 6-membered ring;

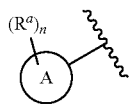

is a monocyclic 5-membered heteroaryl that is

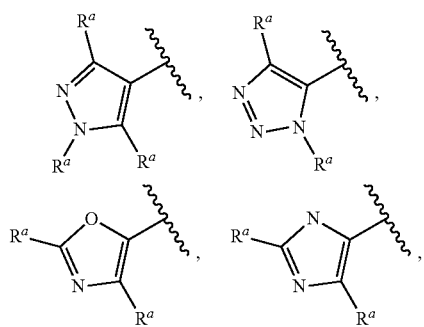

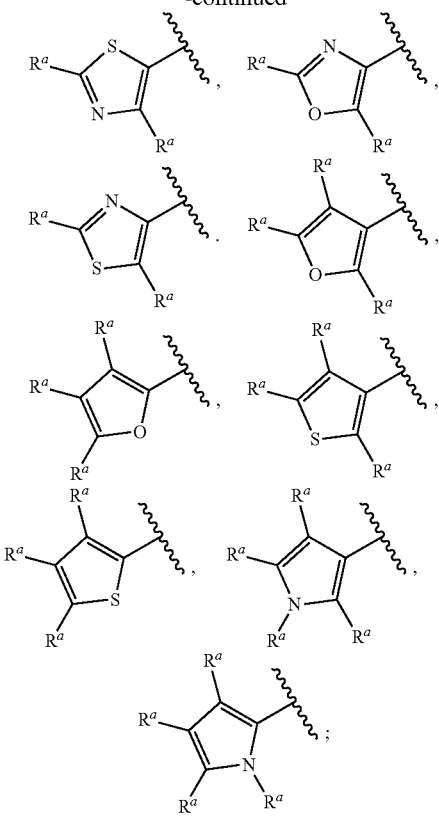

each $R^a$ is independently selected from the group consisting of H, D, halogen, —CN, —OH, —N($R^6$)$_2$, substituted or unsubstituted $C_1$-$C_6$alkyl, substituted or unsubstituted $C_1$-$C_6$deuteroalkyl, substituted or unsubstituted $C_1$-$C_6$alkoxy, substituted or unsubstituted $C_1$-$C_6$fluoroalkyl, substituted or unsubstituted $C_1$-$C_6$fluoroalkoxy, substituted or unsubstituted $C_1$-$C_6$heteroalkyl, substituted or unsubstituted monocyclic carbocycle, and substituted or unsubstituted monocyclic heterocycle;

$R^6$ is H, D, or substituted or unsubstituted $C_1$-$C_6$alkyl;

n is 0, 1, 2, 3, or 4;

or $R^a$ and $R^3$ are taken together with the intervening atoms joining $R^a$ and $R^3$ to form a 5- or 6-membered ring;

each $R^4$ is independently selected from the group consisting of H, D, halogen, —CN, —OH, substituted or unsubstituted $C_1$-$C_6$alkyl, substituted or unsubstituted $C_1$-$C_6$alkoxy, substituted or unsubstituted $C_1$-$C_6$fluoroalkyl, substituted or unsubstituted $C_1$-$C_6$fluoroalkoxy, and substituted or unsubstituted $C_1$-$C_6$heteroalkyl;

m is 0, 1, 2, 3, or 4;

X is absent or -$L^1$-$X^1$-$L^2$-;

$L^1$ is absent or —CH$_2$—;

$X^1$ is selected from the group consisting of —S—, —SO$_2$—, —NR$^5$—, —SO$_2$NR$^5$—, —C(=O)NR$^5$—, —NR$^5$C(=O)—, —OC(=O)—, —C(=O)O—, —OC(=O)O—, —C(=O)—, —OC(=O)NR$^5$—, —NR$^5$C(=O)O—, and —NR$^5$C(=O)NR$^5$—;

each $R^5$ is independently selected from the group consisting of H, D, substituted or unsubstituted $C_1$-$C_6$alkyl, substituted or unsubstituted $C_1$-$C_6$deuteroalkyl, substituted or unsubstituted C$_1$-C$_6$fluoroalkyl, substituted or unsubstituted C$_3$-C$_6$cycloalkyl, and substituted or unsubstituted benzyl;

L$^2$ is absent or substituted or unsubstituted C$_1$-C$_4$alkylene;

Y is selected from the group consisting of H, D, substituted or unsubstituted C$_1$-C$_6$alkyl, substituted or unsubstituted C$_1$-C$_6$deuteroalkyl, substituted or unsubstituted C$_1$-C$_6$fluoroalkyl, substituted or unsubstituted C$_1$-C$_6$heteroalkyl, substituted or unsubstituted C$_3$-C$_{10}$cycloalkyl, substituted or unsubstituted C$_2$-C$_{10}$heterocycloalkyl, substituted or unsubstituted phenyl, substituted or unsubstituted benzyl, substituted or unsubstituted naphthyl, and substituted or unsubstituted heteroaryl, wherein if Y is substituted then Y is substituted with 1-4 R$^7$ groups;

each R$^7$ is independently selected from the group consisting of D, —CN, —OH, —OR$^9$, —SR$^9$, —S(=O)R$^9$, —S(=O)$_2$R$^9$, —N(R$^8$)S(=O)$_2$R$^9$, —S(=O)$_2$NH$_2$, —S(=O)$_2$NR$^8$R$^9$, —C(=O)R$^9$, —OC(=O)R$^9$, —CO$_2$R$^8$, —OCO$_2$R$^9$, —NH$_2$, —NR$^8$R$^9$, —C(=O)NH$_2$, —C(=O)NR$^8$R$^9$, —OC(=O)NH$_2$, —OC(=O)NR$^8$R$^9$, —NR$^8$C(=O)NH$_2$, —NR$^8$C(=O)NR$^8$R$^9$, —NR$^8$C(=O)R$^9$, —NR$^8$C(=O)OR$^9$, substituted or unsubstituted C$_1$-C$_6$alkyl, substituted or unsubstituted C$_1$-C$_6$deuteroalkyl, substituted or unsubstituted C$_1$-C$_6$fluoroalkyl, substituted or unsubstituted C$_1$-C$_6$heteroalkyl, a substituted or unsubstituted C$_3$-C$_6$cycloalkyl, a substituted or unsubstituted C$_2$-C$_6$heterocycloalkyl, a substituted or unsubstituted aryl, and a substituted or unsubstituted heteroaryl;

each R$^8$ is independently selected from the group consisting of H, C$_1$-C$_6$alkyl, C$_1$-C$_6$fluoroalkyl, and C$_1$-C$_6$heteroalkyl;

each R$^9$ is independently selected from the group consisting of C$_1$-C$_6$alkyl, C$_1$-C$_6$fluoroalkyl, C$_1$-C$_6$heteroalkyl, a substituted or unsubstituted C$_3$-C$_6$cycloalkyl, a substituted or unsubstituted C$_2$-C$_6$heterocycloalkyl, a substituted or unsubstituted aryl, a substituted or unsubstituted heteroaryl, a substituted or unsubstituted —C$_1$-C$_4$alkylene-C$_3$-C$_{10}$cycloalkyl, a substituted or unsubstituted —C$_1$-C$_4$alkylene-C$_2$-C$_{10}$heterocycloalkyl, a substituted or unsubstituted —C$_1$-C$_4$alkylene-aryl, and a substituted or unsubstituted —C$_1$-C$_4$alkylene-heteroaryl;

or when R$^8$ and R$^9$ are attached to the same N atom then R$^8$ and R$^9$ are taken together with the N atom to which they are attached to form a substituted or unsubstituted C$_2$-C$_{10}$heterocycle;

or when Y and R$^5$ are attached to the same N atom then Y and R$^5$ are taken together with the N atom to which they are attached to form a substituted or unsubstituted C$_2$-C$_{10}$heterocycle.

In some embodiments, the groups

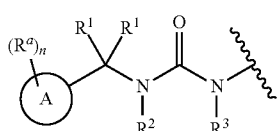

and —X—Y are in a 1,4-relationship on the phenyl or a 1,3-relationship on the phenyl.

In some embodiments, the groups

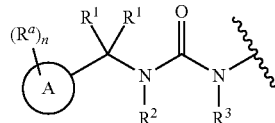

and —X—Y are in a 1,4-relationship on the phenyl.

In some embodiments, each R$^1$ is H, D, —CH$_3$, or —CH$_2$CH$_3$; R$^2$ is H, —CH$_3$, or —CH$_2$CH$_3$; and R$^3$ is H, —CH$_3$, or —CH$_2$CH$_3$.

In some embodiments, R$^2$ is H; and R$^3$ is H.

In some embodiments, the compound of Formula (I) has the structure of Formula (II), or a pharmaceutically acceptable salt, solvate, prodrug, or N-oxide thereof, wherein:

Formula (II)

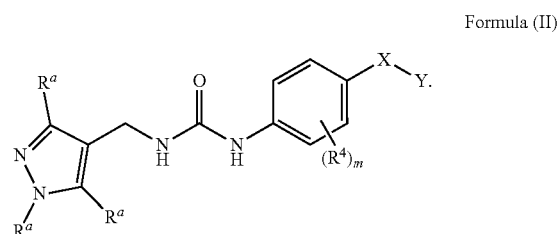

In some embodiments, the compound of Formula (I) has the structure of Formula (III), or a pharmaceutically acceptable salt, solvate, prodrug, or N-oxide thereof, wherein:

Formula (III)

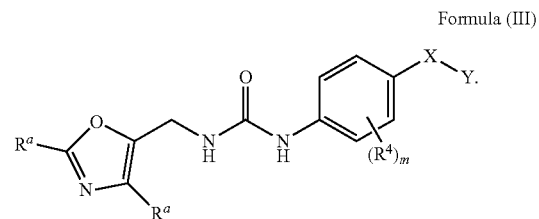

In another aspect, described herein is a compound of Formula (IV), or a pharmaceutically acceptable salt, solvate, prodrug, or N-oxide thereof:

Formula (IV)

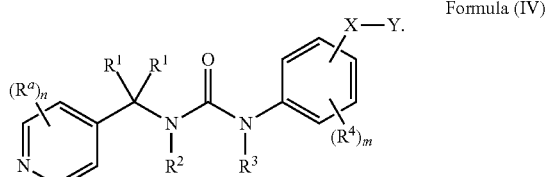

wherein:
each R$^1$ is independently selected from the group consisting of H, D, C$_1$-C$_4$alkyl and C$_1$-C$_4$deuteroalkyl;
R$^2$ is H, D, substituted or unsubstituted C$_1$-C$_6$alkyl or substituted or unsubstituted C$_1$-C$_6$deuteroalkyl;
R$^3$ is H, D, substituted or unsubstituted C$_1$-C$_6$alkyl or substituted or unsubstituted C$_1$-C$_6$deuteroalkyl;
or R$^2$ and R$^3$ are taken together with the intervening atoms joining R$^2$ and R$^3$ to form a 5- or 6-membered ring;

each $R^a$ is independently selected from the group consisting of H, D, halogen, —CN, —OH, —N($R^6$)$_2$, substituted or unsubstituted $C_1$-$C_6$alkyl, substituted or unsubstituted $C_1$-$C_6$deuteroalkyl, substituted or unsubstituted $C_1$-$C_6$alkoxy, substituted or unsubstituted $C_1$-$C_6$fluoroalkyl, substituted or unsubstituted $C_1$-$C_6$fluoroalkoxy, substituted or unsubstituted $C_1$-$C_6$heteroalkyl, substituted or unsubstituted monocyclic carbocycle, and substituted or unsubstituted monocyclic heterocycle;

$R^6$ is H, D, or substituted or unsubstituted $C_1$-$C_6$alkyl;

n is 0, 1, 2, 3, or 4;

or $R^a$ and $R^3$ are taken together with the intervening atoms joining $R^a$ and $R^3$ to form a 5- or 6-membered ring;

each $R^4$ is independently selected from the group consisting of H, D, halogen, —CN, —OH, substituted or unsubstituted $C_1$-$C_6$alkyl, substituted or unsubstituted $C_1$-$C_6$alkoxy, substituted or unsubstituted $C_1$-$C_6$fluoroalkyl, substituted or unsubstituted $C_1$-$C_6$fluoroalkoxy, and substituted or unsubstituted $C_1$-$C_6$heteroalkyl;

m is 0, 1, 2, 3, or 4;

X is absent or -$L^1$-$X^1$-$L^2$-;

$L^1$ is absent or —CH$_2$—;

$X^1$ is selected from the group consisting of —O—, —S—, —SO$_2$—, —NR$^5$—, —SO$_2$NR$^5$—, —C(=O)NR$^5$—, —NR$^5$C(=O)—, —OC(=O)—, —C(=O)O—, —OC(=O)O—, —C(=O)—, —OC(=O)NR$^5$—, —NR$^5$C(=O)O—, and —NR$^5$C(=O)NR$^5$—;

each $R^5$ is independently selected from the group consisting of H, D, substituted or unsubstituted $C_1$-$C_6$alkyl, substituted or unsubstituted $C_1$-$C_6$deuteroalkyl, substituted or unsubstituted $C_1$-$C_6$fluoroalkyl, substituted or unsubstituted $C_3$-$C_6$cycloalkyl, and substituted or unsubstituted benzyl;

$L^2$ is absent or substituted or unsubstituted $C_1$-$C_4$alkylene;

Y is selected from the group consisting of H, D, substituted or unsubstituted $C_1$-$C_6$alkyl, substituted or unsubstituted $C_1$-$C_6$deuteroalkyl, substituted or unsubstituted $C_1$-$C_6$fluoroalkyl, substituted or unsubstituted $C_1$-$C_6$heteroalkyl, substituted or unsubstituted $C_3$-$C_{10}$cycloalkyl, substituted or unsubstituted $C_2$-$C_{10}$heterocycloalkyl, substituted or unsubstituted phenyl, substituted or unsubstituted benzyl, substituted or unsubstituted naphthyl, and substituted or unsubstituted heteroaryl, wherein if Y is substituted then Y is substituted with $R^7$;

$R^7$ is selected from the group consisting of D, —CN, —OH, —OR$^9$, —SR$^9$, —S(=O)R$^9$, —S(=O)$_2$R$^9$, —N(R$^8$)S(=O)$_2$R$^9$, —S(=O)$_2$NH$_2$, —S(=O)$_2$NR$^8$R$^9$, —C(=O)R$^9$, —OC(=O)R$^9$, —CO$_2$R$^8$, —OCO$_2$R$^9$, —NH$_2$, —NR$^8$R$^9$, —C(=O)NH$_2$, —C(=O)NR$^8$R$^9$, —OC(=O)NH$_2$, —OC(=O)NR$^8$R$^9$, —NR$^8$C(=O)NH$_2$, —NR$^8$C(=O)NR$^8$R$^9$, —NR$^8$C(=O)R$^9$, —NR$^8$C(=O)OR$^9$, $C_1$-$C_3$alkyl, $C_1$-$C_6$deuteroalkyl, $C_1$-$C_4$fluoroalkyl, substituted or unsubstituted $C_1$-$C_6$heteroalkyl, a substituted or unsubstituted $C_3$-$C_6$cycloalkyl, a substituted or unsubstituted $C_2$-$C_6$heterocycloalkyl, a substituted or unsubstituted aryl, and a substituted or unsubstituted heteroaryl;

each $R^8$ is independently selected from the group consisting of H, $C_1$-$C_6$alkyl, $C_1$-$C_6$fluoroalkyl, and $C_1$-$C_6$heteroalkyl;

each $R^9$ is independently selected from the group consisting of $C_1$-$C_6$alkyl, $C_1$-$C_6$fluoroalkyl, $C_1$-$C_6$heteroalkyl, a substituted or unsubstituted $C_3$-$C_6$cycloalkyl, a substituted or unsubstituted $C_2$-$C_6$heterocycloalkyl, a substituted or unsubstituted aryl, a substituted or unsubstituted heteroaryl, a substituted or unsubstituted —$C_1$-$C_4$alkylene-$C_3$-$C_{10}$cycloalkyl, a substituted or unsubstituted —$C_1$-$C_4$alkylene-$C_2$-$C_{10}$heterocycloalkyl, a substituted or unsubstituted —$C_1$-$C_4$alkylene-aryl, and a substituted or unsubstituted —$C_1$-$C_4$alkylene-heteroaryl;

or when $R^8$ and $R^9$ are attached to the same N atom then $R^8$ and $R^9$ are taken together with the N atom to which they are attached to form a substituted or unsubstituted $C_2$-$C_{10}$heterocycle;

or when Y and $R^5$ are attached to the same N atom then Y and $R^5$ are taken together with the N atom to which they are attached to form a substituted or unsubstituted $C_2$-$C_{10}$heterocycle;

provided that Y is substituted when $R^5$ is H.

In some embodiments, the groups

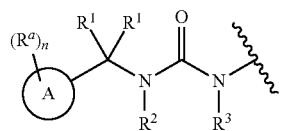

and —X—Y are in a 1,4-relationship on the phenyl or a 1,3-relationship on the phenyl.

In some embodiments, the groups

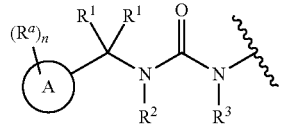

and —X—Y are in a 1,4-relationship on the phenyl.

In some embodiments, each $R^1$ is H, D, —CH$_3$, or —CH$_2$CH$_3$; $R^2$ is H, —CH$_3$, or —CH$_2$CH$_3$; and $R^3$ is H, —CH$_3$, or —CH$_2$CH$_3$.

In some embodiments, $R^2$ is H; and $R^3$ is H.

In some embodiments, the compound of Formula (IV) has the structure of Formula (V), or a pharmaceutically acceptable salt, solvate, prodrug, or N-oxide thereof, wherein:

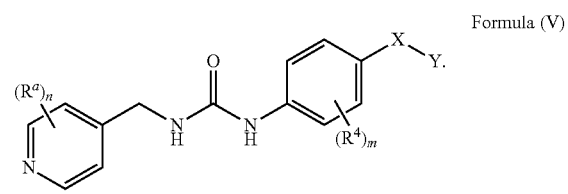

Formula (V)

In some embodiments, each $R^a$ is independently selected from the group consisting of H, D, F, Cl, Br, —CN, —OH, —NH$_2$, —NH(CH$_3$), —N(CH$_3$)$_2$, —CH$_3$, —CH$_2$CH$_3$, —OCH$_3$, —OCH$_2$CH$_3$, —CF$_3$, —CHF$_2$, —CH$_2$F, —CH$_2$CF$_3$, and —OCF$_3$; each $R^4$ is independently selected from the group consisting of H, D, F, Cl, Br, —CN, —OH, —CH$_3$, —CH$_2$CH$_3$, —OCH$_3$, —OCH$_2$CH$_3$, —CF$_3$, —CHF$_2$, —CH$_2$F, —CH$_2$CF$_3$, and —OCF$_3$.

In some embodiments, each $R^a$ is H.

In some embodiments, n is 0, 1, 2, or 3. In some embodiments, n is 0, 1, or 2. In some embodiments, n is 0 or 1.

In some embodiments, n is 0.

In some embodiments, the compound of Formula (Ia) has the structure of Formula (IIa), or a pharmaceutically acceptable salt, or solvate thereof, wherein:

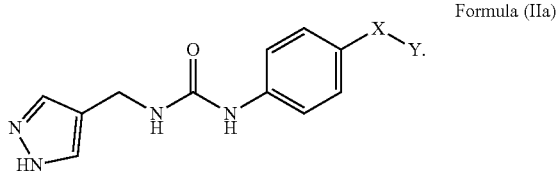

Formula (IIa)

In some embodiments, the compound of Formula (Ia) has the structure of Formula (IIIa), or a pharmaceutically acceptable salt, or solvate thereof, wherein:

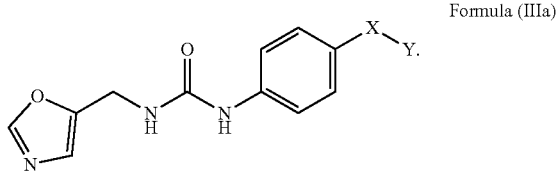

Formula (IIIa)

In some embodiments, the compound of Formula (Ia) has the structure of Formula (Va), or a pharmaceutically acceptable salt, or solvate thereof, wherein:

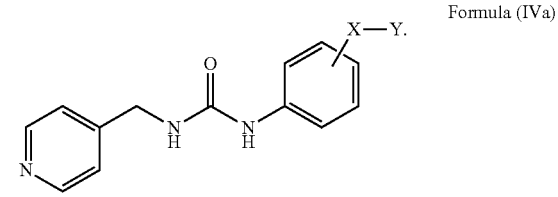

Formula (IVa)

In some embodiments, the compound of Formula (Ia) has the structure of Formula (Va), or a pharmaceutically acceptable salt, or solvate thereof, wherein:

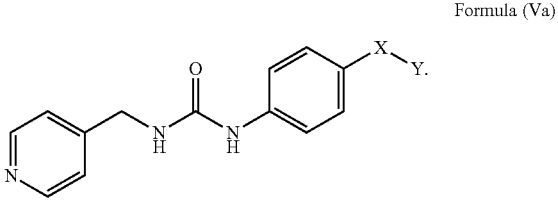

Formula (Va)

In some embodiments, $L^2$ is absent, —$CH_2$—, —$CH_2CH_2$—, —$CH_2CH_2CH_2$—, or —$CH_2CH_2CH_2CH_2$—.

In some embodiments, $L^2$ is absent or —$CH_2$—.

In some embodiments, $L^2$ is absent.

In some embodiments, $X^1$ is selected from the group consisting of —S—, —$SO_2$—, —$NR^5$—, —$SO_2NR^5$—, —C(=O)$NR^5$—, and —C(=O)O—.

In some embodiments, X is —$SO_2$—.

In some embodiments, $L^1$ is absent.

In some embodiments, $X^1$ is selected from the group consisting of —$SO_2$—, —$NR^5$—, —$SO_2NR^5$—, —$NR^5SO_2$—, —C(=O)$NR^5$—, and —$NR^5C(=O)$—.

In some embodiments, each $R^5$ is independently selected from the group consisting of H, $C_1$-$C_4$alkyl, and substituted or unsubstituted benzyl; $L^2$ is absent or —$CH_2$—; or when Y and $R^5$ are attached to the same N atom then Y and $R^5$ are taken together with the N atom to which they are attached to form a substituted or unsubstituted $C_2$-$C_{10}$heterocycle.

In some embodiments, each $R^5$ is H.

In some embodiments, X is absent or -$L^1$-$X^1$-$L^2$-; $L^1$ is absent; $X^1$ is selected from the group consisting of —$SO_2$—, —$NR^5$—, —$SO_2NR^5$—, —$NR^5SO_2$—, —C(=O)$NR^5$—, and —$NR^5C(=O)$—; each $R^5$ is independently selected from the group consisting of H, $C_1$-$C_4$alkyl, and substituted or unsubstituted benzyl; $L^2$ is absent or —$CH_2$—; or when Y and $R^5$ are attached to the same N atom then Y and $R^5$ are taken together with the N atom to which they are attached to form a substituted or unsubstituted $C_2$-$C_{10}$heterocycle.

In some embodiments, X is absent or -$L^1$-$X^1$-$L^2$-; $L^1$ is absent; $X^1$ is selected from the group consisting of —$SO_2$—, —NH—, —$SO_2NH$—, and —$NHSO_2$—; $L^2$ is absent or —$CH_2$—.

In some embodiments, X is absent, —$SO_2$—, —$SO_2CH_2$—, —NH—, —$NHCH_2$—, —$SO_2NH$—, —$SO_2NHCH_2$—, —$NHSO_2$— or —$NHSO_2CH_2$—.

In some embodiments, X is absent, —$SO_2$—, —NH—, —$SO_2NH$—, —$SO_2NHCH_2$—, —$NHSO_2$— or —$NHSO_2CH_2$—.

In some embodiments, X is —$SO_2$—.

In some embodiments, Y is selected from the group consisting of H, D, substituted or unsubstituted $C_1$-$C_6$alkyl, substituted or unsubstituted $C_1$-$C_6$deuteroalkyl, substituted or unsubstituted $C_1$-$C_6$fluoroalkyl, substituted or unsubstituted $C_1$-$C_6$heteroalkyl, substituted or unsubstituted $C_3$-$C_{10}$cycloalkyl, substituted or unsubstituted $C_2$-$C_{10}$heterocycloalkyl, substituted or unsubstituted phenyl, substituted or unsubstituted benzyl, and substituted or unsubstituted monocyclic heteroaryl, wherein if Y is substituted then Y is substituted with $R^7$; or when Y and $R^5$ are attached to the same N atom then Y and $R^5$ are taken together with the N atom to which they are attached to form a substituted or unsubstituted $C_2$-$C_{10}$heterocycle.

In some embodiments, Y is selected from the group consisting of H, D, substituted or unsubstituted $C_1$-$C_6$alkyl, substituted or unsubstituted $C_1$-$C_6$deuteroalkyl, substituted or unsubstituted $C_1$-$C_6$fluoroalkyl, and substituted or unsubstituted $C_1$-$C_6$heteroalkyl, wherein if Y is substituted then Y is substituted with $R^7$.

In some embodiments, Y is selected from the group consisting of substituted or unsubstituted $C_3$-$C_6$cycloalkyl, substituted or unsubstituted $C_2$-$C_6$heterocycloalkyl, substituted or unsubstituted phenyl, substituted or unsubstituted benzyl, and substituted or unsubstituted monocyclic heteroaryl, wherein if Y is substituted then Y is substituted with $R^7$.

In some embodiments, Y is a substituted or unsubstituted phenyl, wherein if Y is substituted then Y is substituted with $R^7$.

In some embodiments, Y is selected from the group consisting of substituted or unsubstituted cyclopropyl, substituted or unsubstituted cyclobutyl, substituted or unsubstituted cyclopentyl, and substituted or unsubstituted cyclohexyl, wherein if Y is substituted then Y is substituted with 1-2 $R^7$ groups.

In some embodiments, Y is a substituted or unsubstituted monocyclic 6-membered heteroaryl containing 1-3 N atoms, wherein if Y is substituted then Y is substituted with 1-2 $R^7$ groups.

In some embodiments, Y is a substituted or unsubstituted monocyclic 5-membered $C_1$-$C_4$heteroaryl, wherein if Y is substituted then Y is substituted with 1-2 $R^7$ groups.

In some embodiments, Y is selected from the group consisting of substituted or unsubstituted furanyl, substituted or unsubstituted thienyl, substituted or unsubstituted pyrrolyl, substituted or unsubstituted oxazolyl, substituted or unsubstituted thiazolyl, substituted or unsubstituted imidazolyl, substituted or unsubstituted pyrazolyl, substituted or unsubstituted triazolylene, substituted or unsubstituted tetrazolyl, substituted or unsubstituted isoxazolyl, substituted or unsubstituted isothiazolyl, substituted or unsubstituted oxadiazolyl, substituted or unsubstituted thiadiazolyl, substituted or unsubstituted pyridinyl, substituted or unsubstituted pyrimidinyl, substituted or unsubstituted pyrazinyl, substituted or unsubstituted pyridazinyl, and substituted or unsubstituted triazinyl, wherein if Y is substituted then Y is substituted with 1-2 $R^7$ groups.

In some embodiments, Y is selected from the group consisting of substituted or unsubstituted pyrrolidinyl, substituted or unsubstituted tetrahydrofuranyl, substituted or unsubstituted dihydrofuranyl, substituted or unsubstituted tetrahydrothienyl, substituted or unsubstituted oxazolidinonyl, substituted or unsubstituted tetrahydropyranyl, substituted or unsubstituted dihydropyranyl, substituted or unsubstituted tetrahydrothiopyranyl, substituted or unsubstituted piperidinyl, substituted or unsubstituted morpholinyl, substituted or unsubstituted thiomorpholinyl, substituted or unsubstituted thioxanyl, substituted or unsubstituted piperazinyl, substituted or unsubstituted aziridinyl, substituted or unsubstituted azetidinyl, substituted or unsubstituted oxetanyl, substituted or unsubstituted thietanyl, substituted or unsubstituted homopiperidinyl, substituted or unsubstituted oxepanyl, substituted or unsubstituted thiepanyl, substituted or unsubstituted oxazepinyl, substituted or unsubstituted diazepinyl, substituted or unsubstituted thiazepinyl, and substituted or unsubstituted 1,2,3,6-tetrahydropyridinyl, wherein if Y is substituted then Y is substituted with 1-2 $R^7$ groups.

In some embodiments, X is absent or -$L^1$-$X^1$-$L^2$-; $L^1$ is absent or —$CH_2$—; $X^1$ is selected from the group consisting of —$NR^5$—, —$SO_2NR^5$—, —$C(=O)NR^5$—, —$OC(=O)NR^5$—, and —$NRC(=O)NR^5$—; each $R^5$ is independently selected from the group consisting of H, D, substituted or unsubstituted $C_1$-$C_6$alkyl, substituted or unsubstituted $C_1$-$C_6$deuteroalkyl, substituted or unsubstituted $C_1$-$C_6$fluoroalkyl, substituted or unsubstituted $C_3$-$C_6$cycloalkyl, and substituted or unsubstituted benzyl; $L^2$ is absent; Y and $R^5$ are taken together with the N atom to which they are attached to form a substituted or unsubstituted $C_2$-$C_{10}$heterocycle.

In some embodiments, Y and $R^5$ are taken together with the N atom to which they are attached to form a substituted or unsubstituted $C_2$-$C_{10}$heterocycle that is a substituted or unsubstituted monocyclic $C_2$-$C_{10}$heterocycle, or a substituted or unsubstituted bicyclic $C_5$-$C_{10}$heterocycle.

In some embodiments, Y and $R^5$ are taken together with the N atom to which they are attached to form a substituted or unsubstituted $C_2$-$C_{10}$heterocycle that is a substituted or unsubstituted monocyclic $C_2$-$C_{10}$heterocycle, substituted or unsubstituted fused bicyclic $C_5$-$C_{10}$heterocycle, substituted or unsubstituted bridged bicyclic $C_5$-$C_{10}$heterocycle, or substituted or unsubstituted spiro bicyclic $C_5$-$C_{10}$heterocycle.

In some embodiments, Y and $R^5$ are taken together with the N atom to which they are attached to form a substituted or unsubstituted $C_2$-$C_{10}$heterocycle that is selected from a substituted or unsubstituted β-lactam, substituted or unsubstituted γ-lactam, substituted or unsubstituted δ-lactam or substituted or unsubstituted ε-lactam.

In some embodiments, Y and $R^5$ are taken together with the N atom to which they are attached to form substituted or unsubstituted aziridinyl, substituted or unsubstituted azetidinyl, substituted or unsubstituted pyrrolidinyl, substituted or unsubstituted piperidinyl, substituted or unsubstituted morpholinyl, substituted or unsubstituted thiomorpholinyl, substituted or unsubstituted piperazinyl, substituted or unsubstituted azepanyl, substituted or unsubstituted indolinyl, substituted or unsubstituted isoindolinyl, substituted or unsubstituted tetrahydroquinolinyl, or substituted or unsubstituted tetrahydroisoquinolinyl, or substituted or unsubstituted 8-oxa-3-azabicyclo[3.2.1]oct-3-yl.

In some embodiments, described herein is a compound that has the following structure:

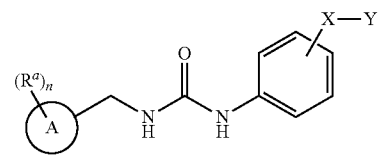

or a pharmaceutically acceptable salt, solvate, prodrug, or N-oxide thereof.

In some embodiments, described herein is a compound that has the following structure:

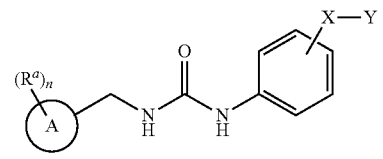

wherein

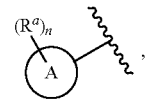

X and Y are as described in Table 1;
or a pharmaceutically acceptable salt, solvate, prodrug, or N-oxide thereof.

In some embodiments, described herein is a compound that has the following structure:

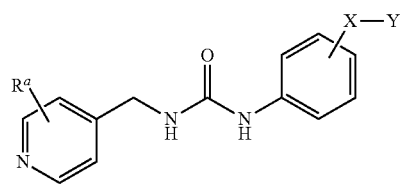

or a pharmaceutically acceptable salt, solvate, prodrug, or N-oxide thereof.

In some embodiments, described herein is a compound that has the following structure:

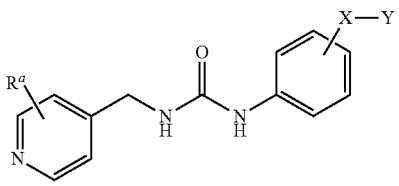

wherein $R^a$, X and Y are as described in Table 2;

or a pharmaceutically acceptable salt, solvate, prodrug, or N-oxide thereof.

In some embodiments, X and Y are as described in Tables 1 to 5.

Any combination of the groups described above for the various variables is contemplated herein. Throughout the specification, groups and substituents thereof are chosen by one skilled in the field to provide stable moieties and compounds.

Exemplary compounds include the compounds described in the following Tables:

TABLE 1

| (R^a)_n / A | X | Y | Compound Name |
|---|---|---|---|
| pyrazol-4-yl (HN) | 4-C(=O)O— | Et | Ethyl 4-(3-((1H-pyrazol-4-yl)methyl)ureido)benzoate |
| oxazol-4-yl | 4-C(=O)O— | Et | Ethyl 4-(3-(oxazol-4-ylmethyl)ureido)benzoate |
| 3,5-dimethylisoxazol-4-yl | 4-C(=O)O— | Et | Ethyl 4-(3-((3,5-dimethylisoxazol-4-yl)methyl)ureido)benzoate |
| 1-methyl-1H-pyrazol-4-yl | 4-C(=O)O— | Et | Ethyl 4-(3-((1-methyl-1H-pyrazol-4-yl)methyl)ureido)benzoate |
| 1H-pyrazol-4-yl | 4-C(=O)NH— | 3-Cl-phenyl | N-(3-Chloro-phenyl)-4-[3-(1H-pyrazol-4-ylmethyl)-ureido]-benzamide |
| 1H-pyrazol-4-yl | 4-C(=O)NH— | 2-OMe-phenyl | 4-(3-((1H-pyrazol-4-yl)methyl)ureido)-N-(2-methoxyphenyl)benzamide |

TABLE 1-continued

| (Rᵃ)ₙ–A– | X | Y | Compound Name |
|---|---|---|---|
| 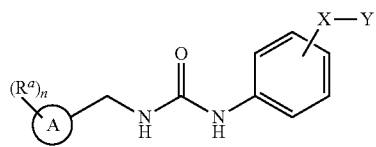 (pyrazol-4-yl) | 4-C(=O)NH— | 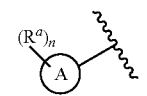 (2-Cl-phenyl) | 4-(3-((1H-pyrazol-4-yl)methyl)ureido)-N-(2-chlorophenyl)benzamide |
|  (pyrazol-4-yl) | 4-C(=O)NH— |  (4-OMe-phenyl) | 4-(3-((1H-pyrazol-4-yl)methyl)ureido)-N-(4-methoxyphenyl)benzamide |
|  (pyrazol-4-yl) | 4-C(=O)NH— |  (4-Cl-phenyl) | 4-(3-((1H-pyrazol-4-yl)methyl)ureido)-N-(4-chlorophenyl)benzamide |
|  (pyrazol-4-yl) | 4-C(=O)NH— |  (3-OMe-phenyl) | 4-(3-((1H-pyrazol-4-yl)methyl)ureido)-N-(3-methoxyphenyl)benzamide |
|  (oxazol-5-yl) | 4-C(=O)O— | Et | Ethyl 4-(3-(oxazol-5-ylmethyl)ureido)benzoate |
|  (3-amino-pyrazol-4-yl) | 4-C(=O)O— | Et | Ethyl 4-(3-((3-amino-1H-pyrazol-4-yl)methyl)ureido)benzoate |
|  (imidazol-5-yl) | 4-C(=O)O— | Et | Ethyl 4-(3-((1H-imidazol-5-yl)methyl)ureido)benzoate |
|  (1-methyl-pyrazol-5-yl) | 4-C(=O)O— | Et | Ethyl 4-(3-((1-methyl-1H-pyrazol-5-yl)methyl)ureido)benzoate |
|  (imidazol-4-yl) | 4-C(=O)O— | Et | Ethyl 4-(3-((1H-imidazol-4-yl)methyl)ureido)benzoate |

TABLE 1-continued

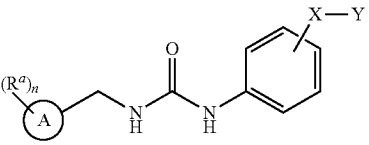

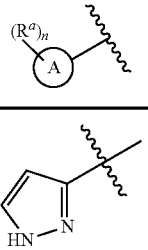

| A (R$^a$)$_n$ | X | Y | Compound Name |
|---|---|---|---|
| 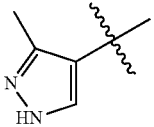 | 4-C(=O)O— | Et | Ethyl 4-(3-((1H-pyrazol-3-yl)methyl)ureido)benzoate |
| 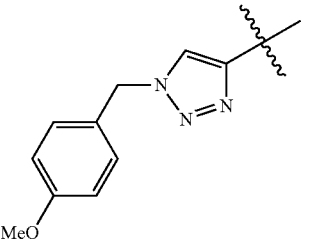 [SMILES: *c1cn(Cc2ccc(OC)cc2)nn1] | 4-C(=O)O— | Et | Ethyl 4-(3-((3-methyl-1H-pyrazol-4-yl)methyl)ureido)benzoate |
| 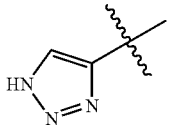 [SMILES: *c1c[nH]nn1] | 4-C(=O)O— | Et | Ethyl 4-(3-((1-(4-methoxybenzyl)-1H-1,2,3-triazol-4-yl)methyl)ureido)benzoate |
| 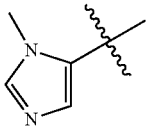 [SMILES: *c1cncn1C] | 4-C(=O)O— | Et | Ethyl 4-(3-((1H-1,2,3-triazol-4-yl)methyl)ureido)benzoate |
| 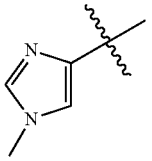 [SMILES: *c1cn(C)cn1] | 4-C(=O)O— | Et | Ethyl 4-(3-((1-methyl-1H-imidazol-5-yl)methyl)ureido)benzoate |
| 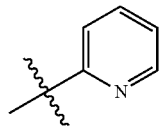 [SMILES: *c1ccccn1] | 4-C(=O)O— | Et | Ethyl 4-(3-((1-methyl-1H-imidazol-4-yl)methyl)ureido)benzoate |
| 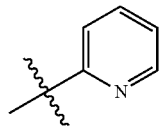 [SMILES: *c1ccccn1] | 4-SO$_2$NH— | 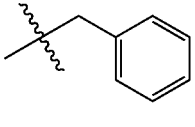 [SMILES: *Cc1ccccc1] | 4-[3-(1H-Pyrazol-4-ylmethyl)-ureido]-N-pyridin-2-yl-benzenesulfonamide |
| 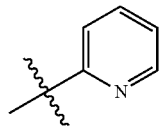 [SMILES: *c1ccccn1] | 4-SO$_2$NH— | 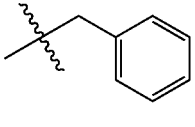 [SMILES: *Cc1ccccc1] | N-Benzyl-4-[3-(1H-pyrazol-4-ylmethyl)-ureido]-benzenesulfonamide |

TABLE 1-continued

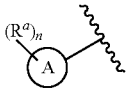

| A (R^a)_n | X | Y | Compound Name |
|---|---|---|---|
| 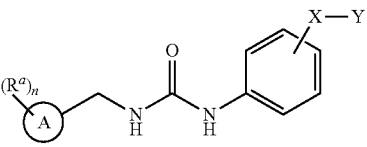 | 4-SO$_2$— | 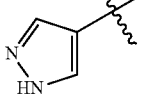 | 1-[4-(3,4-Dihydro-1H-isoquinoline-2-sulfonyl)-phenyl]-3-(1H-pyrazol-4-ylmethyl)-urea |
| 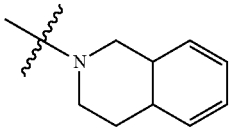 [SMILES: *N1CCC2C=CC=CC2C1] | 4-SO$_2$— | 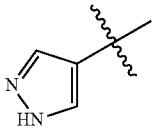 | 1-[4-(8-Oxa-3-aza-bicyclo[3.2.1]octane-3-sulfonyl)-phenyl]-3-(1H-pyrazol-4-ylmethyl)-urea |
| 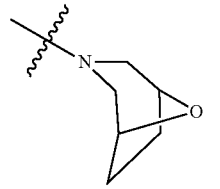 [SMILES: *N1CC2CCC(C1)O2] | 4-SO$_2$NH— | 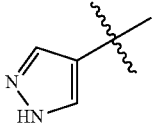 | N-Cyclobutylmethyl-4-[3-(1H-pyrazol-4-ylmethyl)-ureido]-benzenesulfonamide |
| 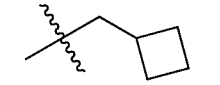 [SMILES: *CC1CCC1] | 4-SO$_2$NH— | Ph | N-Phenyl-4-[3-(1H-pyrazol-4-ylmethyl)-ureido]-benzenesulfonamide |
| 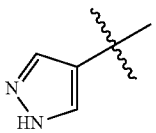 [SMILES: *c1cn[nH]c1] | 4-SO$_2$NMe— | 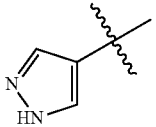 [SMILES: *c1cn[nH]c1] | N-Cyclopentyl-N-methyl-4-[3-(1H-pyrazol-4-ylmethyl)-ureido]-benzenesulfonamide |
| 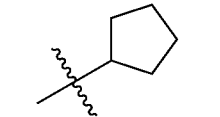 [SMILES: *C1CCCC1] | 4-SO$_2$N$^i$Pr— | 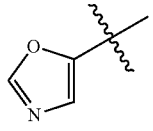 [SMILES: *c1cnco1] | N-Benzyl-N-isopropyl-4-(3-oxazol-5-ylmethyl-ureido)-benzenesulfonamide |
| 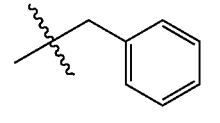 [SMILES: *Cc1ccccc1] | 4-SO$_2$N$^i$Pr— | 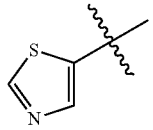 [SMILES: *c1cncs1] | N-Benzyl-N-isopropyl-4-(3-thiazol-5-ylmethyl-ureido)-benzenesulfonamide |
| 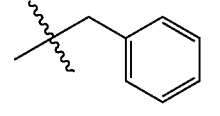 [SMILES: *Cc1ccccc1] | 4-SO$_2$N$^i$Pr— | 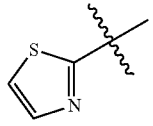 | N-Benzyl-N-isopropyl-4-(3-thiazol-2-ylmethyl-ureido)-benzenesulfonamide |
| 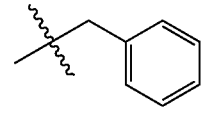 [SMILES: *Cc1ccccc1] | 4-SO$_2$N$^i$Pr— | 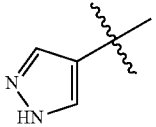 | N-Benzyl-N-isopropyl-4-[3-(1H-pyrazol-4-ylmethyl)-ureido]-benzenesulfonamide |

TABLE 1-continued

| A (Rᵃ)ₙ | X | Y | Compound Name |
|---|---|---|---|
| oxazol-5-yl | 4-SO₂— | 3,4-dihydroisoquinolin-2-yl | 1-[4-(3,4-Dihydro-1H-isoquinoline-2-sulfonyl)-phenyl]-3-oxazol-5-ylmethyl-urea |
| 1H-pyrazol-4-yl | 4-SO₂NH— | 3-methoxybenzyl | N-(3-Methoxy-benzyl)-4-[3-(1H-pyrazol-4-ylmethyl)-ureido]-benzenesulfonamide |
| 1H-pyrazol-4-yl | 4-SO₂NH— | 2-chlorobenzyl | N-(2-Chloro-benzyl)-4-[3-(1H-pyrazol-4-ylmethyl)-ureido]-benzenesulfonamide |
| 1H-pyrazol-4-yl | 4-SO₂NH— | 2-methoxybenzyl | N-(2-Methoxy-benzyl)-4-[3-(1H-pyrazol-4-ylmethyl)-ureido]-benzenesulfonamide |
| 1H-pyrazol-4-yl | 4-SO₂NH— | 4-methoxybenzyl | N-(4-Methoxy-benzyl)-4-[3-(1H-pyrazol-4-ylmethyl)-ureido]-benzenesulfonamide |
| 1H-pyrazol-4-yl | 4-SO₂NH— | 4-chlorobenzyl | N-(4-Chloro-benzyl)-4-[3-(1H-pyrazol-4-ylmethyl)-ureido]-benzenesulfonamide |
| oxazol-5-yl | 4-SO₂NH— | benzyl | N-Benzyl-4-(3-oxazol-5-ylmethyl-ureido)-benzenesulfonamide |
| thiazol-5-yl | 4-SO₂— | 3,4-dihydroisoquinolin-2-yl | 1-[4-(3,4-Dihydro-1H-isoquinoline-2-sulfonyl)-phenyl]-3-thiazol-5-ylmethyl-urea |
| 3,5-dimethylisoxazol-4-yl | 4-SO₂— | 3,4-dihydroisoquinolin-2-yl | 1-[4-(3,4-Dihydro-1H-isoquinoline-2-sulfonyl)-phenyl]-3-(3,5-dimethyl-isoxazol-4-ylmethyl)-urea |

TABLE 1-continued

| A (Rᵃ)ₙ | X | Y | Compound Name |
|---|---|---|---|
| pyrazol-4-yl | 4-SO₂— | 3-chlorophenyl | 1-[4-(3-Chloro-benzenesulfonyl)-phenyl]-3-(1H-pyrazol-4-ylmethyl)-urea |
| pyrazol-4-yl | 4-SO₂— | 2-chlorophenyl | 1-[4-(2-Chloro-benzenesulfonyl)-phenyl]-3-(1H-pyrazol-4-ylmethyl)-urea |
| pyrazol-4-yl | 4-SO₂— | 4-chlorophenyl | 1-[4-(4-Chloro-benzenesulfonyl)-phenyl]-3-(1H-pyrazol-4-ylmethyl)-urea |
| pyrazol-4-yl | 4-SO₂— | 2-methoxyphenyl | 1-[4-(2-Methoxy-benzenesulfonyl)-phenyl]-3-(1H-pyrazol-4-ylmethyl)-urea |
| pyrazol-4-yl | 4-SO₂— | 3-methoxyphenyl | 1-[4-(3-Methoxy-benzenesulfonyl)-phenyl]-3-(1H-pyrazol-4-ylmethyl)-urea |
| oxazol-5-yl | 4-SO₂— | Ph | 1-(4-Benzenesulfonyl-phenyl)-3-oxazol-5-ylmethyl-urea |
| pyrazol-4-yl | 4-SO₂— | Ph | 1-(4-Benzenesulfonyl-phenyl)-3-(1H-pyrazol-4-ylmethyl)-urea |
| pyrazol-4-yl | 4-SO₂— | 4-methoxyphenyl | 1-[4-(4-Methoxy-benzenesulfonyl)-phenyl]-3-(1H-pyrazol-4-ylmethyl)-urea |

TABLE 1-continued

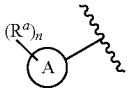

| A (Rᵃ)ₙ | X | Y | Compound Name |
|---|---|---|---|
| 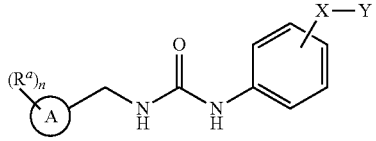 | 4-NHSO₂— | Ph | N-[4-(3-Oxazol-5-ylmethyl-ureido)-phenyl]-benzenesulfonamide |
|  | 4-NHSO₂— | 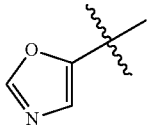 [SMILES: *c1cnco1] | N-Oxazol-5-ylmethyl-2-(4-phenylmethanesulfonylamino-cyclohexa-1,5-dienyl)-acetamide |
| 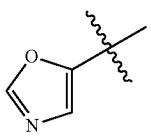 [SMILES: *c1cnco1] | 4-NHSO₂— | Ph | N-{4-[3-(1H-Pyrazol-4-ylmethyl)-ureido]-phenyl}-benzenesulfonamide |
| 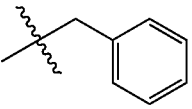 [SMILES: *Cc1ccccc1] | 4-NHSO₂— | 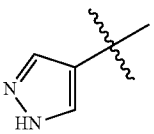 | N-(4-(3-((1H-pyrazol-4-yl)methyl)ureido)phenyl)-1-phenylmethanesulfonamide |
| 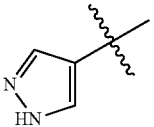 | 4-NHSO₂— | Ph | N-(4-{3-[1-(4-Methoxy-benzyl)-1H-pyrazol-4-ylmethyl]-ureido}-phenyl)-benzenesulfonamide |

In one aspect, provided herein is a pharmaceutically acceptable salt or solvate of a compound described in Table 1.

TABLE 2

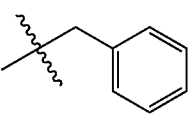 [SMILES: *Cc1ccccc1]

| Rᵃ | X | Y | Compound Name |
|---|---|---|---|
| H | — | 4-F | 1-(4-Fluorophenyl)-3-(pyridin-4-ylmethyl)urea |
| H | — | 4-Cl | 1-(4-Chlorophenyl)-3-(pyridin-4-ylmethyl)urea |
| H | — | 4-Me | 1-(Pyridin-4-ylmethyl)-3-(p-tolyl)urea |
| H | 2-C(=O)O— | Et | Ethyl 2-(3-(pyridin-4-ylmethyl)ureido)benzoate |

TABLE 2-continued

| R$^a$ | X | Y | Compound Name |
|---|---|---|---|
| H | 3-C(=O)O— | Et | Ethyl 3-(3-(pyridin-4-ylmethyl)ureido)benzoate |
| H | — | 4-CF$_3$ | 1-(Pyridin-4-ylmethyl)-3-(4-(trifluoromethyl)phenyl)urea |
| H | — | 4-OCF$_3$ | 1-(Pyridin-4-ylmethyl)-3-(4-(trifluoromethoxy)phenyl)urea |
| H | — | 4-CH$_3$ | 1-(4-Methoxyphenyl)-3-(pyridin-4-ylmethyl)urea |
| H | 4-C(=O)NEt— | Et | N,N-diethyl-4-(3-(pyridin-4-ylmethyl)ureido)benzamide |
| H | 4-C(=O)NH— | p-tolyl | 4-(3-(Pyridin-4-ylmethyl)ureido)-N-(p-tolyl)benzamide |
| H | 4-C(=O)NMe— | p-tolyl | N-methyl-4-(3-(pyridin-4-ylmethyl)ureido)-N-(p-tolyl)benzamide |
| H | 4-C(=O)NH— | Ph | N-phenyl-4-(3-(pyridin-4-ylmethyl)ureido)benzamide |
| H | 4-C(=O)NMe— | Et | N-ethyl-N-methyl-4-(3-(pyridin-4-ylmethyl)ureido)benzamide |
| H | 4-C(=O)NMe— | n-Pr | N-methyl-N-propyl-4-(3-(pyridin-4-ylmethyl)ureido)benzamide |
| H | 4-C(=O)NH— | 2-hydroxyethyl | N-(2-hydroxyethyl)-4-(3-(pyridin-4-ylmethyl)ureido)benzamide |
| H | 4-C(=O)NH— | n-butyl | N-butyl-4-(3-(pyridin-4-ylmethyl)ureido)benzamide |
| H | 4-C(=O)NH— | cyclopentyl | N-cyclopentyl-4-(3-(pyridin-4-ylmethyl)ureido)benzamide |
| H | 4-C(=O)O— | Et | Ethyl 4-(3-(pyridin-4-ylmethyl)ureido)benzoate |
| 2-amino | 4-C(=O)O— | Et | Ethyl 4-(3-((2-aminopyridin-4-yl)methyl)ureido)benzoate |
| 2-methoxy | 4-C(=O)O— | Et | Ethyl 4-(3-((2-methoxypyridin-4-yl)methyl)ureido)benzoate |
| 3-methyl | 4-C(=O)O— | Et | Ethyl 4-(3-((3-methylpyridin-4-yl)methyl)ureido)benzoate |
| 3-amino | 4-C(=O)O— | Et | Ethyl 4-(3-((3-aminopyridin-4-yl)methyl)ureido)benzoate |
| 2-methyl | 4-C(=O)O— | Et | Ethyl 4-(3-((2-methylpyridin-4-yl)methyl)ureido)benzoate |
| 2-chloro | 4-C(=O)O— | Et | Ethyl 4-(3-((2-chloropyridin-4-yl)methyl)ureido)benzoate |
| 3-chloro | 4-C(=O)O— | Et | Ethyl 4-(3-((3-chloropyridin-4-yl)methyl)ureido)benzoate |
| 2-fluoro | 4-C(=O)O— | Et | Ethyl 4-(3-((2-fluoropyridin-4-yl)methyl)ureido)benzoate |
| 3-fluoro | 4-C(=O)O— | Et | Ethyl 4-(3-((3-fluoropyridin-4-yl)methyl)ureido)benzoate |
| H | 4-C(=O)O— | H | 4-(3-(Pyridin-4-ylmethyl)ureido)benzoic acid |
| H | 3-C(=O)O— | H | 3-(3-(Pyridin-4-ylmethyl)ureido)benzoic acid |
| H | 4-C(=O)NH— | H | 4-(3-(Pyridin-4-ylmethyl)ureido)benzamide |
| H | 4-C(=O)NH— | n-propyl | N-propyl-4-(3-(pyridin-4-ylmethyl)ureido)benzamide |
| H | 4-C(=O)NH— | isopropyl | N-Isopropyl-4-(3-(pyridin-4-ylmethyl)ureido)benzamide |
| H | 4-C(=O)NMe— | Me | N,N-dimethyl-4-(3-(pyridin-4-ylmethyl)ureido)benzamide |
| H | 4-C(=O)NH— | 2-morpholinoethyl | N-(2-morpholinoethyl)-4-(3-(pyridin-4-ylmethyl)ureido)benzamide |
| H | 4-C(=O)NH— | cyclohexyl | N-cyclohexyl-4-(3-(pyridin-4-ylmethyl)ureido)benzamide |
| H | 4-C(=O)NH— | 2-(piperidin-1-yl)ethyl | N-(2-(piperidin-1-yl)ethyl)-4-(3-(pyridin-4-ylmethyl)ureido)benzamide |
| H | 4-C(=O)NH— | 2-(pyrrolidin-1-yl)ethyl | 4-(3-(Pyridin-4-ylmethyl)ureido)-N-(2-(pyrrolidin-1-yl)ethyl)benzamide |
| H | 4-C(=O)NH- | isobutyl | N-isobutyl-4-(3-(pyridin-4-ylmethyl)ureido)benzamide |

TABLE 2-continued

| R$^a$ | X | Y | Compound Name |
|---|---|---|---|
| H | 4-C(=O)NH— | cyclobutyl | N-cyclobutyl-4-(3-(pyridin-4-ylmethyl)ureido)benzamide |
| H | 4-C(=O)NH— | cyclopropylmethyl | N-(cyclopropylmethyl)-4-(3-(pyridin-4-ylmethyl)ureido)benzamide |
| H | 4-C(=O)NH— | tetrahydrofuran-3-yl | 4-(3-(pyridin-4-ylmethyl)ureido)-N-(tetrahydrofuran-3-yl)benzamide |
| H | 4-C(=O)NH— | 2-methoxyethyl | N-(2-methoxyethyl)-4-(3-(pyridin-4-ylmethyl)ureido)benzamide |
| H | 4-C(=O)NH— | phenethyl | N-phenethyl-4-(3-(pyridin-4-ylmethyl)ureido)benzamide |
| H | 4-C(=O)— | morpholin-4-yl | 1-(4-(Morpholine-4-carbonyl)phenyl)-3-(pyridin-4-ylmethyl)urea |
| H | 4-C(=O)— | 4-methylpiperazin-1-yl | 1-(4-(4-Methylpiperazine-1-carbonyl)phenyl)-3-(pyriidn-4-ylmethyl)urea |
| H | 4-C(=O)— | piperidin-1-yl | 1-(4-(Piperidine-1-carbonyl)phenyl)-3-(pyridin-4-ylmethyl)urea |
| H | 4-C(=O)— | pyrrolidin-1-yl | 1-(Pyridin-4-ylmethyl)-3-(4-(pyrrolidine-1-carbonyl)phenyl)urea |
| H | 4-C(=O)NH— | cyclopentylmethyl | N-(cyclopentylmethyl)-4-(3-(pyridin-4-ylmethyl)ureido)benzamide |
| H | 4-C(=O)— | 8-oxa-3-azabicyclo[3.2.1]octan-3-yl | 1-(4-(8-Oxa-3-azabicyclo[3.2.1]octane-3-carbonyl)phenyl)-3-(pyridin-4-ylmethyl)urea |
| H | 4-C(=O)NH— | pyridin-4-ylmethyl | N-(pyridin-4-ylmethyl)-4-(3-(pyridin-4-ylmethyl)ureido)benzamide |
| H | 4-C(=O)NH— | 4-methylphenethyl | N-(4-methylphenethyl)-4-(3-(pyridin-4-ylmethyl)ureido)benzamide |
| H | 4-C(=O)NH— | 4-fluorophenethyl | N-(4-fluorophenethyl)-4-(3-(pyridin-4-ylmethyl)ureido)benzamide |
| H | 4-C(=O)NH— | 3-ethoxypropyl | N-(3-ethoxypropyl)-4-(3-(pyridin-4-ylmethyl)ureido)benzamide |
| H | 4-C(=O)NH— | 2-(dimethylamino)ethyl | N-(2-(dimethylamino)ethyl)-4-(3-(pyridin-4-ylmethyl)ureido)benzamide |
| H | 4-C(=O)NH— | 2-chlorobenzyl | N-(2-chlorobenzyl)-4-(3-(pyridin-4-ylmethyl)ureido)benzamide |
| H | 4-C(=O)NH— | 3-chlorobenzyl | N-(3-chlorobenzyl)-4-(3-(pyridin-4-ylmethyl)ureido)benzamide |
| H | 4-C(=O)NH— | 2-methoxybenzyl | N-(2-methoxybenzyl)-4-(3-(pyridin-4-ylmethyl)ureido)benzamide |
| H | 4-C(=O)NH— | 3-methoxybenzyl | N-(3-methoxybenzyl)-4-(3-(pyridin-4-ylmethyl)ureido)benzamide |
| H | 4-C(=O)NH— | 4-methoxybenzyl | N-(4-methoxybenzyl)-4-(3-(pyridin-4-ylmethyl)ureido)benzamide |
| H | 4-C(=O)NH— | 2-fluorobenzyl | N-(2-fluorobenzyl)-4-(3-(pyridin-4-ylmethyl)ureido)benzamide |
| H | 4-C(=O)NH— | 3-fluorobenzyl | N-(3-fluorobenzyl)-4-(3-(pyridin-4-ylmethyl)ureido)benzamide |
| H | 4-C(=O)NH— | 2-methylbenzyl | N-(2-methylbenzyl)-4-(3-(pyridin-4-ylmethyl)ureido)benzamide |
| H | 4-C(=O)NH— | 4-methylbenzyl | N-(4-methylbenzyl)-4-(3-(pyridin-4-ylmethyl)ureido)benzamide |
| H | 4-C(=O)NH— | 3-methylbenzyl | N-(3-methylbenzyl)-4-(3-(pyridin-4-ylmethyl)ureido)benzamide |
| H | 4-C(=O)NH— | 4-chlorobenzyl | N-(4-chlorobenzyl)-4-(3-(pyridin-4-ylmethyl)ureido)benzamide |
| H | 4-C(=O)NH— | 4-fluorobenzyl | N-(4-fluorobenzyl)-4-(3-(pyridin-4-ylmethyl)ureido)benzamide |
| H | 4-C(=O)NMe— | benzyl | N-benzyl-N-methyl-4-(3-(pyridin-4-ylmethyl)ureido)benzamide |
| H | 4-C(=O)— | isoindolin-2-yl | 1-(4-(Isoindoline-2-carbonyl)phenyl)-3-(pyridin-4-ylmethyl)urea |
| H | 4-C(=O)— | 1,2,3,4-tetrahydroisoquinolin-2-yl | 1-(Pyridin-4-ylmethyl)-3-(4-(1,2,3,4-tetrahydroisoquinoline-2-carbonyl)phenyl)urea |
| H | 4-C(=O)NH— | 4-chlorophenyl | N-(4-chlorophenyl)-4-(3-(pyridin-4-ylmethyl)ureido)benzamide |

TABLE 2-continued

| R$^a$ | X | Y | Compound Name |
|---|---|---|---|
| H | 4-C(=O)NH— | 2-chlorophenyl | N-(2-chlorophenyl)-4-(3-(pyridin-4-ylmethyl)ureido)benzamide |
| H | 4-C(=O)NH— | 3-chlorophenyl | N-(3-chlorophenyl)-4-(3-(pyridin-4-ylmethyl)ureido)benzamide |
| H | 4-C(=O)NH— | 2-fluorophenyl | N-(2-fluorophenyl)-4-(3-(pyriidn-4-ylmethyl)ureido)benzamide |
| H | 4-C(=O)NH— | 3-fluorophenyl | N-(3-fluorophenyl)-4-(3-(pyridin-4-ylmethyl)ureido)benzamide |
| H | 4-C(=O)NH— | 4-fluorophenyl | N-(4-fluorophenyl)-4-(3-(pyridin-4-ylmethyl)ureido)benzamide |
| H | 4-C(=O)NH— | o-tolyl | 4-(3-(Pyridin-4-ylmethyl)ureido)-N-(o-tolyl)benzamide |
| H | 4-C(=O)NH— | m-tolyl | 4-(3-(pyridin-4-ylmethyl)ureido)-N-(m-tolyl)benzamide |
| H | 4-C(=O)NH— | 4-(methoxymethyl | N-(4-(methoxymethyl)phenyl)-4-(3-(pyridin-4-ylmethyl)ureido)benzamide |
| H | 4-C(=O)NH— | 2-methoxyphenyl | N-(2-methoxyphenyl)-4-(3-(pyridin-4-ylmethyl)ureido)benzamide |
| H | 4-C(=O)NH— | 3-methoxyphenyl | N-(3-methoxyphenyl-4-(3-(pyridin-4-ylmethyl)ureido)benzamide |
| H | 4-C(=O)NH— | 4-methoxyphenyl | N-(4-methoxyphenyl)-4-(3-(pyridin-4-ylmethyl)ureido)benzamide |
| H | 4-C(=O)NH— | 2-(dimethylamino)phenyl | N-(2-(dimethylamino)phenyl)-4-(3-(pyridin-4-ylmethyl)ureido)benzamide |
| H | 4-C(=O)NH— | 3-(dimethylamino)phenyl | N-(3-(dimethylamino)phenyl)-4-(3-(pyridin-4-ylmethyl)ureido)benzamide |
| H | 4-C(=O)NH— | 4-(dimethylamino)phenyl | N-(4-(dimethylamino)phenyl)-4-(3-(pyridin-4-ylmethyl)ureido)benzamide |
| H | 4-C(=O)NH— | 2-(trifluoromethoxy)phenyl | 4-(3-(Pyridin-4-ylmethyl)ureido)-N-(2-(trifluoromethoxy)phenyl)benzamide |
| H | 4-C(=O)NH— | 3-(trifluoromethoxy)phenyl | 4-(3-(pyridin-4-ylmethyl)ureido)-N-(3-(trifluoromethoxy)phenyl)benzamide |
| H | 4-C(=O)NH— | 4-(trifluoromethoxy)phenyl | 4-(3-(pyridin-4-ylmethyl)ureido)-N-(4-(trifluoromethoxy)phenyl)benzamide |
| H | 4-C(=O)NH— | 4-ethoxyphenyl | N-(4-ethoxyphenyl)-4-(3-(pyridin-4-ylmethyl)ureido)benzamide |
| H | 4-C(=O)NH— | 4-isopropoxyphenyl | N-(4-isopropoxyphenyl)-4-(3-(pyridin-4-ylmethyl)ureido)benzamide |
| H | 4-C(=O)NH— | 4-(methylcarboxy)phenyl | Methyl 4-(4-(3-(pyridin-4-ylmethyl)ureido)benzamido)benzoate |
| H | 4-C(=O)NH— | 4-cyanophenyl | N-(4-cyanophenyl)-4-(3-(pyridin-4-ylmethyl)ureido)benzamide |
| H | 4-C(=O)NH— | 3,4-dimethylphenyl | N-(3,4-dimethylphenyl)-4-(3-(pyridin-4-ylmethyl)ureido)benzamide |
| H | 4-C(=O)NH— | 3,4-dimethoxyphenyl | N-(3,4-dimethoxyphenyl)-4-(3-(pyridin-4-ylmethyl)ureido)benzamide |
| H | 4-C(=O)NH— | benzo[d][1,3]dioxol-5-yl | N-(benzo[d][1,3]dioxol-5-yl)-4-(3-(pyridin-4-ylmethyl)ureido)benzamide |
| H | 4-C(=O)NH— | 4-methoxy-3-methylphenyl | N-(4-methoxy-3-methylphenyl)-4-(3-(pyridin-4-ylmethyl)ureido)benzamide |
| H | 4-C(=O)NH— | 2,3-dihydrobenzo[b][1,4]diox-in-6-yl | N-(2,3-dihydroxybenzo[b][1,4]dioxin-6-yl)-4-(3-(pyridin-4-ylmethyl)ureido)benzamide |
| H | 4-C(=O)NH— | pyridin-2-yl | N-(pyridin-2-yl)-4-(3-(pyridin-4-ylmethyl)ureido)benzamide |
| H | 4-C(=O)NH— | pyridin-3-yl | N-(pyridin-3-yl)-4-(3-(pyridin-4-ylmethyl)ureido)benzamide |
| H | 4-C(=O)NH— | pyrimidin-5-yl | 4-(3-(pyridin-4-ylmethyl)ureido)-N-(pyrimidin-5-yl)benzamide |
| H | 4-C(=O)NH— | 3-methylisoxazol-5-yl | N-(3-methylisoxazol-5-yl)-4-(3-(pyridin-4-ylmethyl)ureido)benzamide |
| H | 4-C(=O)NH— | thiophen-2-yl | 4-(3-(Pyridin-4-ylmethyl)ureido)-N-(thiophen-2-yl)benzamide |
| H | 4-SO$_2$NH— | Cyclohexyl | N-Cyclohexyl-4-(3-pyridin-4-ylmethyl-ureido)-benzenesulfonamide |
| H | 4-SO$_2$NH— | H | N-(4-(3-pyridin-4-ylmethyl-ureido)-benzenesulfonamide |

TABLE 2-continued

| Rᵃ | X | Y | Compound Name |
|---|---|---|---|
| H | 4-SO₂NH— | Methyl | N-Methyl-4-(3-pyridin-4-ylmethyl-ureido)-benzenesulfonamide |
| H | 4-SO₂NH— | Propyl | N-Propyl-4-(3-pyridin-4-ylmethyl-ureido)-benzenesulfonamide |
| H | 4-SO₂NH— | Isopropyl | N-Isopropyl-4-(3-pyridin-4-ylmethyl-ureido)-benzenesulfonamide |
| H | 4-SO₂NH— | Cyclopropyl | N-Cyclopropyl-4-(3-pyridin-4-ylmethyl-ureido)-benzenesulfonamide |
| H | 4-SO₂NH— | Cyclobutyl | N-Cyclobutyl-4-(3-pyridin-4-ylmethyl-ureido)-benzenesulfonamide |
| H | 4-SO₂NH— | cyclopentyl | N-cyclopentyl-4-(3-pyridin-4-ylmethyl-ureido)-benzenesulfonamide |
| H | 4-SO₂NH— | pyrrolidin-3-yl | 4-(3-Pyridin-4-ylmethyl-uerido)-N-pyrrolidin-3-yl-benzenesulfonamide |
| H | 4-SO₂NH— | 1-Methyl-pyrrolidin-3-yl | N-(1-Methyl-pyrrolidin-3-yl)-4-(3-pyridin-4-ylmethyl-ureido)-benzenesulfonamide |
| H | 4-SO₂NH— | tert-butyl | N-(tert-butyl)-4-(3-(pyridin-4-ylmethyl)ureido)benzenesulfonamide |
| H | 4-SO₂NH— | 2-Dimethylamino-ethyl | N-(2-Dimethylamino-ethyl)-4-(3-pyridin-4-ylmethyl-ureido)-benzenesulfonamide |
| H | 4-SO₂NH— | Cyclopropylmethyl | N-Cyclopropylmethyl-4-(3-pyridin-4-ylmethyl-ureido)-benzenesulfonamide |
| H | 4-SO₂NH— | Cyclobutylmethyl | N-(Cyclobutylmethyl-4-(3-pyridin-4-ylmethyl-ureido)-benzenesulfonamide |
| H | 4-SO₂NH— | 2-pyrrolidin-1-yl-ethyl | 4-(3-Pyriidn-4-ylmethyl-ureido)-N-(2-pyrrolidin-1-yl-ethyl)-benzensulfonamide |
| H | 4-SO₂NH— | 2-(4-Methyl-piperazin-1-yl)-ethyl | N-[2-(4-Methyl-piperazin-1-yl)-ethyl]-4-(3-pyridin-4-ylmethyl-ureido)-benzenesulfonamide |
| H | 4-SO₂NH— | 2-Morpholin-4-yl-ethyl | N-(2-Morpholin-4-yl-ethyl)-4-(3-pyridin-4-ylmethyl-ureido)-benzenesulfonamide |
| H | 4-SO₂NH— | 2-Piperidin-1-yl-ethyl | N-(2-Piperidin-1-yl-ethyl)-4-(3-pyridin-4-ylmethyl-ureido)-benzenesulfonamide |
| H | 4-SO₂NH— | 2-Hydroxy-ethyl | N-(2-Hydroxy-ethyl)-4-(3-pyridin-4-ylmethyl-ureido)-benzenesulfonamide |
| H | 4-SO₂NH— | tetrahydro-furan-3-yl | 4-(3-Pyridin-4-ylmethyl-ureido)-N-(tetrahydro-furan-3-yl)-benzenesulfonamide |
| H | 4-SO₂NH- | 2-Methoxy-ethyl | N-(2-Methoxy-ethyl)-4-(3-pyridin-4-ylmethyl-ureido)-benzenesulfonamide |
| H | 4-SO₂NH— | 3-Methoxy-propyl | N-(3-Methoxy-propyl)-4-(3-pyridin-4-ylmethyl-ureido)-benzenesulfonamide |
| H | 4-SO₂NH— | 1-Ethyl-pyrrolidin-2-ylmethyl | N-(1-Ethyl-pyrrolidin-2-ylmethyl)-4-(3-pyridin-4-ylmethyl-ureido)-benzenesulfonamide |
| H | 4-SO₂NH— | neopentyl | N-neopentyl-4-(3-pyridin-4-ylmethyl-ureido)-benzenesulfonamide |
| H | 4-SO₂NH— | 1-Cyclobutyl-ethyl | N-(1-Cyclobutyl-ethyl)-4-(3-pyridin-4-ylmethyl-ureido)-benzenesulfonamide |
| H | 4-SO₂NH— | Benzyl | N-Benzyl-4-(3-pyridin-4-ylmethyl-ureido)-benzenesulfonamide |
| H | 4-SO₂NH— | 2-fluorobenzyl | N-(2-fluorobenzyl)-4-(3-(pyridin-4-ylmethyl)ureido)benzenesulfonamide |
| H | 4-SO₂NH— | 3-fluorobenzyl | N-(3-fluorobenzyl)-4-(3-(pyridin-4-ylmethyl)ureido)benzenesulfonamide |
| H | 4-SO₂NH— | 4-fluorobenzyl | N-(4-fluorobenzyl)-4-(3-(pyridin-4-ylmethyl)ureido)benzenesulfonamide |
| H | 4-SO₂NH— | 2-Chloro-benzyl | N-(2-Chloro-benzyl)-4-(3-pyridin-4-ylmethyl-ureido)-benzenesulfonamide |
| H | 4-SO₂NH— | 3-Chloro-benzyl | N-3-(2-Chloro-benzyl)-4-(3-pyridin-4-ylmethyl-ureido)-benzenesulfonamide |
| H | 4-SO₂NH— | 4-chlorobenzyl | N-(4-chlorobenzyl)-4-(3-(pyridin-4-ylmethyl)ureido)benzenesulfonamide |

TABLE 2-continued

| $R^a$ | X | Y | Compound Name |
|---|---|---|---|
| H | 4-SO$_2$NH— | 2-methoxybenzyl | N-(2-methoxybenzyl)-4-(3-(pyridin-4-ylmethyl)ureido)benzenesulfonamide |
| H | 4-SO$_2$NH— | 3-Methoxy-benzyl | N-(3-Methoxy-benzyl)-4-(3-pyridin-4-ylmethyl-ureido)-benzenesulfonamide |
| H | 4-SO$_2$NH— | 4-methoxybenzyl | N-(4-methoxybenzyl)-4-(3-(pyridin-4-ylmethyl)ureido)benzenesulfonamide |
| H | 4-SO$_2$NH— | 2-Methyl-benzyl | N-(2-Methyl-benzyl)-4-(3-pyridin-4-ylmethyl-ureido)-benzenesulfonamide |
| H | 4-SO$_2$NH— | 3-Methyl-benzyl | N-(3-Methyl-benzyl)-4-(3-pyridin-4-ylmethyl-ureido)-benzenesulfonamide |
| H | 4-SO$_2$NH— | 4-methylbenzyl | N-(4-methylbenzyl)-4-(3-(pyridin-4-ylmethyl)ureido)benzenesulfonamide |
| H | 4-SO$_2$NH— | 2-Cyano-benzyl | N-(2-Cyano-benzyl)-4-(3-pyridin-4-ylmethyl-ureido)-benzenesulfoanmide |
| H | 4-SO$_2$NH— | 3-Cyano-benzyl | N-(3-Cyano-benzyl)-4-(3-pyridin-4-ylmethyl-ureido)-benzenesulfonamide |
| H | 4-SO$_2$NH— | 4-cyanobenzyl | N-(4-cyanobenzyl)-4-(3-(pyridin-4-ylmethyl)ureido)benzenesulfonamide |
| H | 4-SO$_2$NHCH$_2$— | 2-(methylcarboxy)phenyl | 2-{[4-(3-Pyridin-4-ylmethyl-ureido)-benzenesulfonaylamino]-methyl}-benzoic acid methyl ester |
| H | 4-SO$_2$NHCH$_2$— | 3-(methylcarboxy)phenyl | 3-{[4-(3-Pyridin-4-ylmethyl-ureido)-benzenesulfonylamino]-methyl}-benzoic acid methyl ester |
| H | 4-SO$_2$NHCH$_2$— | 4-(methylcarboxy)phenyl | 4-{[4-(3-Pyridin-4-ylmethyl-ureido)-benzenesulfonylamino]-methyl}-benzoic acid methyl ester |
| H | 4-SO$_2$NH— | 3-trifluoromethyl-benzyl | 4-(3-Pyridin-4-ylmethyl-ureido)-N-(3-trifluoromethyl-benzyl)-benzenesulfonamide |
| H | 4-SO$_2$NH— | 2-trifluoromethyl-benzyl | 4-(3-Pyridin-4-ylmethyl-ureido)-N-(2-trifluoromethyl-benzyl)-benzenesulfonamide |
| H | 4-SO$_2$NH— | 4-trifluoromethyl-benzyl | 4-(3-Pyridin-4-ylmethyl-ureido)-N-(4-trifluoromethyl-benzyl)-benzenesulfonamide |
| H | 4-SO$_2$NH— | 2-trifluoromethoxy-benzyl | 4-(3-Pyridin-4-ylmethyl-ureido)-N-(2-trifluoromethoxy-benzyl)-benzenesulfonamide |
| H | 4-SO$_2$NH— | 3-trifluoromethoxy-benzyl | 4-(3-Pyridin-4-ylmethyl-ureido)-N-(3-trifluoromethoxy-benzyl)-benzenesulfonamide |
| H | 4-SO$_2$NH— | 4-trifluoromethoxy-benzyl | 4-(3-Pyridin-4-ylmethyl-ureido)-N-(4-trifluoromethoxy-benzyl)-benzenesulfonamide |
| H | 4-SO$_2$NH— | 2-Dimethylamino-benzyl | N-(2-Dimethylamino-benzyl)-4-(3-pyridin-4-ylmethyl-ureido)-benzenesulfonamide |
| H | 4-SO$_2$NH— | 3-Dimethylamino-benzyl | N-(3-Dimethylamino-benzyl)-4-(3-pyridin-4-ylmethyl-ureido)-benzenesulfonamide |
| H | 4-SO$_2$NH— | 4-Dimethylamino-benzyl | N-(4-Dimethylamino-benzyl)-4-(3-pyridin-4-ylmethyl-ureido)-benzenesulfonamide |
| H | 4-SO$_2$NH— | 4-Methanesulfonyl-benzyl | N-(4-Methanesulfonyl-benzyl)-4-(3-pyridin-4-ylmethyl-ureido)-benzenesulfonamide |
| H | 4-SO$_2$NHCH$_2$— | 4-(SO$_2$N(CH$_3$)$_2$)phenyl | N,N-dimethyl-4-((4-(3-(pyridin-4-ylmethyl)ureido)phenylsulfonamido)methyl)benzenesulfonamide |
| H | 4-SO$_2$NH— | 4-((dimethylamino)methyl)benzyl | N-(4-((dimethylamino)methyl)benzyl)-4-(3-(pyridin-4-ylmethyl)ureido)benzenesulfonamide |
| H | 4-SO$_2$NH— | 4-Methoxymethyl-benzyl | N-(4-Methoxymethyl-benzyl)-4-(3-pyridin-4-ylmethyl-ureido)-benzenesulfonamide |
| H | 4-SO$_2$NH— | 1-phenylethyl | N-(1-phenylethyl)-4-(3-(pyridin-4-ylmethyl)ureido)benzenesulfonamide |

TABLE 2-continued

| Rª | X | Y | Compound Name |
|---|---|---|---|
| H | 4-SO$_2$NH— | Pyridin-4-ylmethyl | N-Pyridin-4-ylmethyl-4-(3-pyridin-4-ylmethyl-ureido)-benzenesulfonamide |
| H | 4-SO$_2$NH— | 1,2,3,4-tetrahydro-naphthalen-1-yl | 4-(3-Pyridin-4-ylmethyl-ureido)-N-(1,2,3,4-tetrahydro-naphthalen-1-yl)-benzenesulfonamide |
| H | 4-SO$_2$NMe— | Me | N,N-Dimethyl-4-(3-pyridin-4-ylmethyl-ureido)-benzenesulfonamide |
| H | 4-SO$_2$NEt— | Et | N,N-Diethyl-4-(3-pyridin-4-ylmethyl-ureido)-benzenesulfonamide |
| H | 4-SO$_2$NMe— | 2-Hydroxy-ethyl | N-(2-Hydroxy-ethyl)-N-methyl-4-(3-pyridin-4-ylmethyl-ureido)-benzenesulfonamide |
| H | 4-SO$_2$NMe— | Cyclopentyl | N-Cyclopentyl-N-methyl-4-(3-pyridin-4-ylmethyl-ureido)-benzenesulfonamide |
| H | 4-SO$_2$NMe— | benzyl | N-benzyl-N-methyl-4-(3-(pyridin-4-ylmethyl)ureido)-benzenesulfonamide |
| H | 4-SO$_2$NMe— | 2-Fluoro-benzyl | N-(2-Fluoro-benzyl)-N-methyl-4-(3-pyridin-4-ylmethyl-ureido)-benzenesulfonamide |
| H | 4-SO$_2$NMe— | 2-Chloro-benzyl | N-(2-Chloro-benzyl)-N-methyl-4-(3-pyridin-4-ylmethyl-ureido)-benzenesulfonamide |
| H | 4-SO$_2$— | piperazin-1-yl | 1-[4-(Piperazine-1-sulfonyl)-phenyl]-3-pyridin-4-ylmethyl-urea |
| H | 4-SO$_2$NMe— | Cyclobutylmethyl | N-Cyclobutylmethyl-N-methyl-4-(3-pyridin-4-ylmethyl-ureido)-benzenesulfonamide |
| H | 4-SO$_2$NMe— | Cyclohexyl | N-Cyclohexyl-N-methyl-4-(3-pyridin-4-ylmethyl-ureido)-benzenesulfonamide |
| H | 4-SO$_2$N(isobutyl)- | Cyclopentyl | N-Cyclopentyl-N-isobutyl-4-(3-pyridin-4-ylmethyl-ureido)-benzenesulfonamide |
| H | 4-SO$_2$NEt— | Cyclopentyl | N-Cyclopentyl-N-ethyl-4-(3-pyridin-4-ylmethyl-ureido)-benzenesulfonamide |
| H | 4-SO$_2$NMe— | 2-(trifluoromethyl)benzyl | N-methyl-4-(3-(pyridin-4-ylmethyl)ureido)-N-(2-(trifluoromethyl)benzyl)benzenesulfonamide |
| H | 4-SO$_2$NMe— | 2-trifluoromethoxy-benzyl | N-Methyl-4-(3-pyridin-4-ylmethyl-ureido)-N-(2-trifluoromethoxy-benzyl)-benzenesulfonamide |
| H | 4-SO$_2$NMe— | 2-Methoxy-benzyl | N-(2-Methoxy-benzyl)-N-methyl-4-(3-pyridin-4-ylmethyl-ureido)-benzenesulfonamide |
| H | 4-SO$_2$N(isopropyl)- | Benzyl | N-Benzyl-N-isopropyl-4-(3-pyridin-4-ylmethyl-ureido)-benzenesulfonamide |
| H | 4-SO$_2$NEt— | Benzyl | N-Benzyl-N-ethyl-4-(3-pyridin-4-ylmethyl-ureido)-benzenesulfonamide |
| H | 4-SO$_2$N(cyclopropyl)- | Benzyl | N-Benzyl-N-cyclopropyl-4-(3-pyridin-4-ylmethyl-ureido)-benzenesulfonamide |
| H | 4-SO$_2$N(propyl)- | Benzyl | N-Benzyl-N-propyl-4-(3-pyridin-4-ylmethyl-ureido)-benzenesulfonamide |
| H | 4-SO$_2$(benzyl)- | benzyl | N,N-Dibenzyl-4-(3-pyridin-4-ylmethyl-ureido)-benzenesulfonamide |
| H | 4-SO$_2$NMe— | 2-methyl-benzyl | N-Methyl-N-(2-methyl-benzyl)-4-(3-pyridin-4-ylmethyl-ureido)-benzenesulfonamide |
| H | 4-SO$_2$N(2,2,2-trifluoro-ethyl)- | Benzyl | N-Benzyl-4-(3-pyridin-4-ylmethyl-ureido)-N-(2,2,2-trifluoro-ethyl)-benzenesulfonamide |
| H | 4-SO$_2$N(benzyl)- | phenyl | N-Benzyl-N-phenyl-4-(3-pyridin-4-ylmethyl-ureido)-benzenesulfonamide |
| H | 4-SO$_2$— | pyrrolidin-1-yl | Pyridin-4-ylmethyl-3-[4-(pyrrolidine-1-sulfonyl)-phenyl]-urea |

TABLE 2-continued

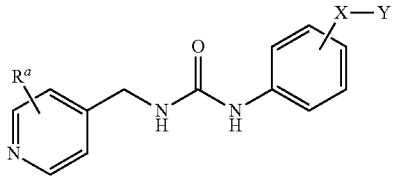

| R$^a$ | X | Y | Compound Name |
|---|---|---|---|
| H | 4-SO$_2$— | Piperidin-1-yl | 1-[4-(Piperidine-1-sulfonyl)-phenyl]-3-pyridin-4-ylmethyl-urea |
| H | 4-SO$_2$— | Morpholin-4-yl | 1-[4-(Morpholine-4-sulfonyl)-phenyl]-3-pyridin-4-ylmethyl-urea |
| H | 4-SO$_2$— | 4-Methyl-piperazin-1-yl | 1-[4-(4-Methyl-piperazine-1-sulfonyl)-phenyl]-3-pyridin-4-ylmethyl-urea |
| H | 4-SO$_2$— | 1,3-Dihydro-isoindol-2-yl | 1-[4-(1,3-Dihydro-isoindole-2-sulfonyl)-phenyl]-3-pyridin-4-ylmethyl-urea |
| H | 4-SO$_2$— | 8-Oxa-3-aza-bicyclo[3.2.1]octane-3-yl | 1-[4-(8-Oxa-3-aza-bicyclo[3.2.1]octane-3-ylsulfonyl)-phenyl]-3-pyridin-4-ylmethyl-urea |
| H | 4-SO$_2$— | 3,4-Dihydro-1H-isoquinolin-2-yl | 1-[4-(3,4-Dihydro-1H-isoquinoline-2-sulfonyl)-phenyl]-3-pyridin-4-ylmethyl-urea |
| H | 4-SO$_2$— | 8-Chloro-3,4-dihydro-1H-isoquinolin-2-yl | 1-[4-(8-Chloro-3,4-dihydro-1H-isoquinoline-2-sulfonyl)-phenyl]-3-pyridin-4-ylmethyl-urea |
| H | 4-SO$_2$— | 8-trifluoromethyl-3,4-dihydro-1H-isoquinolin-2-yl | Pyridin-4-ylmethyl-3-[4-(8-trifluoromethyl-3,4-dihydro-1H-isoquinoline-2-sulfonyl)-phenyl]-urea |
| H | 4-SO$_2$— | 6-trifluoromethyl-3,4-dihydro-1H-isoquinolin-2-yl | Pyridin-4-ylmethyl-3-[4-(6-trifluoromethyl-3,4-dihydro-1H-isoquinoline-2-sulfonyl)-phenyl]-urea |
| H | 4-SO$_2$— | 8-Fluoro-3,4-dihydro-1H-isoquinolin-2-yl | 1-[4-(8-Fluoro-3,4-dihydro-1H-isoquinoline-2-sulfonyl)-phenyl]-3-pyridin-4-ylmethyl-urea |
| H | 4-SO2— | 8-Methyl-3,4-dihydro-1H-isoquinolin-2-yl | 1-[4-(8-Methyl-3,4-dihydro-1H-isoquinoline-2-sulfonyl)-phenyl]-3-pyridin-4-ylmethyl-urea |
| H | 4-SO$_2$— | 3-Methyl-3,4-dihydro-1H-isoquinolin-2-yl | 1-[4-(3-Methyl-3,4-dihydro-1H-isoquinoline-2-sulfonyl)-phenyl]-3-pyridin-4-ylmethyl-urea |
| H | 4-SO$_2$NH— | phenyl | N-Phenyl-4-(3-pyridin-4-ylmethyl-ureido)-benzenesulfonamide |
| H | 4-SO2NH— | 2-Methoxy-phenyl | N-(2-Methoxy-phenyl)-4-(3-pyridin-4-ylmethyl-ureido)-benzenesulfonamide |
| H | 4-SO$_2$NH— | 3-Methoxy-phenyl | N-(3-Methoxy-phenyl)-4-(3-pyridin-4-ylmethyl-ureido)-benzenesulfonamide |
| H | 4-SO$_2$NH– | 4-Methoxy-phenyl | N-(4-Methoxy-phenyl)-4-(3-pyridin-4-ylmethyl-ureido)-benzenesulfonamide |
| H | 4-SO$_2$NH— | o-tolyl | 4-(3-Pyridin-4-ylmethyl-ureido)-N-o-tolyl-benzenesulfonamide |
| H | 4-SO$_2$NH— | m-tolyl | 4-(3-Pyridin-4-ylmethyl-ureido)-N-m-tolyl-benzenesulfonamide |
| H | 4-SO$_2$NH— | p-tolyl | 4-(3-Pyridin-4-ylmethyl-ureido)-N-p-tolyl-benzenesulfonamide |
| H | 4-SO$_2$NH— | thiazol-2-yl | 4-(3-Pyridin-4-ylmethyl-ureido)-N-thiazol-2-yl-benzenesulfonamdie |
| H | 4-SO$_2$NH— | 4,5-Dimethyl-oxazol-2-yl | N-(4,5-Dimethyl-oxazol-2-yl)-4-(3-pyridin-4-ylmethyl-ureido)-benzenesulfonamide |
| H | 4-SO$_2$NH— | 5-Methyl-isoxazol-3-yl | N-(5-Methyl-isoxazol-3-yl)-4-(3-pyridin-4-ylmethyl-ureido)-benzenesulfonamide |
| H | 4-SO$_2$NH— | pyrimidin-2-yl | 4-(3-Pyridin-4-ylmethyl-ureido)-N-pyrimidin-2-yl-benzenesulfonamide |
| H | 4-SO$_2$NH— | 4-Methyl-pyrimidin-2-yl | N-(4-Methyl-pyrimidin-2-yl)-4-(3-pyridin-4-ylmethyl-ureido)-benzenesulfonamide |
| H | 4-SO$_2$NH— | Pyridin-2-yl | N-Pyridin-2-yl-4-(3-pyridin-4-ylmethyl-ureido)-benzenesulfonamide |
| H | 3-SO$_2$NH— | cyclopentyl | N-cyclopentyl-3-(3-(pyridin-4-ylmethyl)ureido)benzenesulfonamide |
| H | 3-SO$_2$NH— | benzyl | N-benzyl-3-(3-(pyridin-4-ylmethyl)ureido)benzenesulfonamide |
| H | 3-SO$_2$— | Morpholin-4-yl | 1-(3-(morpholinosulfonyl)phenyl)-3-(pyridin-4-ylmethyl)urea |

TABLE 2-continued

| $R^a$ | X | Y | Compound Name |
|---|---|---|---|
| H | 3-SO$_2$NH— | cyclobutylmethyl | N-(cyclobutylmethyl)-3-(3-(pyridin-4-ylmethyl)ureido)benzenesulfonamide |
| H | 3-SO$_2$NH— | phenethyl | N-phenethyl-3-(3-(pyridin-4-ylmethyl)ureido)benzenesulfonamide |
| H | 4-SO$_2$NH— | 2-chloro-phenyl | 4-(3-pyridin-4-ylmethyl-ureido)-N-(2-chloro-phenyl)-benzenesuulfonamide |
| H | 4-SO$_2$NH— | 3-chloro-phenyl | 4-(3-pyridin-4-ylmethyl-ureido)-N-(3-chloro-phenyl)-benzenesulfonamide |
| H | 4-SO$_2$NH— | 4-chloro-phenyl | 4-(3-pyridin-4-ylmethyl-ureido)-N-(4-chloro-phenyl)-benzenesulfonamide |
| H | 4-SO$_2$— | 3-Chlorophenyl | 1-[4-(3-Chloro-benzenesulfonyl)-phenyl]-3-pyridin-4-ylmethyl-urea |
| H | 4-SO$_2$— | 4-Chlorophenyl | 1-[4-(4-Chloro-benzenesulfonyl)-phenyl]-3-pyridin-4-ylmethyl-urea |
| H | 4-SO$_2$— | 2-Chlorophenyl | 1-[4-(2-Chloro-benzenesulfonyl)-phenyl]-3-pyridin-4-ylmethyl-urea |
| H | 4-SO$_2$— | 2-Methoxyphenyl | 1-[4-(2-Methoxy-benzenesulfonyl)-phenyl]-3-pyridin-4-ylmethyl-urea |
| H | 4-SO$_2$— | 3-Methoxyphenyl | 1-[4-(3-Methoxy-benzenesulfonyl)-phenyl]-3-pyridin-4-ylmethyl-urea |
| H | 4-SO$_2$— | phenyl | 1-(4-Benzenesulfonyl-phenyl)-3-pyridin-4-ylmethyl-urea |
| H | 4-SO$_2$— | benzyl | 1-(4-Phenylmethanesulfonyl-phenyl)-3-pyridin-4-ylmethyl-urea |
| H | 4-SO$_2$— | 4-methoxyphenyl | 1-[4-(4-Methoxy-benzenesulfonyl)-phenyl]-3-pyridin-4-ylmethyl-urea |
| H | 4-NHSO$_2$— | phenyl | N-[4-(3-Pyridin-4-ylmethyl-ureido)-phenyl]-benzenesulfonamide |
| H | 4-NHSO$_2$— | 2-methoxyphenyl | 2-Methoxy-N-[4-(3-pyridin-4-ylmethyl-ureido)-phenyl]-benzenesulfonamide |
| H | 4-NHSO$_2$— | 3-methoxyphenyl | 3-Methoxy-N-[4-(3-pyridin-4-ylmethyl-ureido)-phenyl]-benzenesulfonamide |
| H | 4-NHSO$_2$— | 4-methoxyphenyl | 4-Methoxy-N-[4-(3-pyridin-4-ylmethyl-ureido)-phenyl]-benzenesulfonamide |
| H | 4-NHSO$_2$— | 2-chlorophenyl | 2-Chloro-N-[4-(3-pyridin-4-ylmethyl-ureido)-phenyl]-benzenesulfonamide |
| H | 4-NHSO$_2$— | 3-chlorophenyl | 3-Chloro-N-[4-(3-pyridin-4-ylmethyl-ureido)-phenyl]-benzenesulfonamide |
| H | 4-NHSO$_2$— | 4-chlorophenyl | 4-Chloro-N-[4-(3-pyridin-4-ylmethyl-ureido)-phenyl]-benzenesulfonamide |
| H | 4-NHSO$_2$— | benzyl | N-[4-(3-Benzyl-ureido)-phenyl]-C-phenyl-methanesulfonamide |
| H | 4-NHSO$_2$— | 2-chlorobenzyl | 1-(2-chlorophenyl)-N-(4-(3-(pyridin-4-ylmethyl)ureido)phenyl)methanesulfonamide |
| H | 4-NHSO$_2$— | 3-chlorobenzyl | 1-(3-chlorophenyl)-N-(4-(3-(pyridin-4-ylmethyl)ureido)phenyl)methanesulfonamide |
| H | 4-NHSO$_2$— | 4-chlorobenzyl | 1-(4-chlorophenyl)-N-(4-(3-(pyridin-4-ylmethyl)ureido)phenyl)methanesulfonamide |
| H | 4-NMeSO$_2$— | benzyl | N-Methyl-C-phenyl-N-[4-(3-pyridin-4-ylmethyl-ureido)-phenyl]-methanesulfonamide |
| H | 4-N(iPr)SO$_2$— | phenyl | N-Isopropyl-N-[4-(3-pyridin-4-ylmethyl-ureido)-phenyl]-benzenesulfonamide |
| H | 4-NMeSO$_2$— | phenyl | N-Methyl-N-[4-(3-pyridin-4-ylmethyl-ureido)-phenyl]-benzenesulfonamide |
| H | 4-N(iPr)SO$_2$— | benzyl | N-Isopropyl-C-phenyl-N-[4-(3-pyridin-4-ylmethyl-ureido)-phenyl]-methanesulfonamide |
| H | 4-CH$_2$SO$_2$NH— | phenyl | N-Phenyl-C-[4-(3-pyridin-4-ylmethyl-ureido)-phenyl]-methanesulfonamide |
| H | 4-CH$_2$SO$_2$NMe— | phenyl | N-Methyl-N-phenyl-C-[4-(3-pyridin-4-ylmethyl-ureido)-phenyl]-methanesulfonamide |

In one aspect, provided herein is a pharmaceutically acceptable salt or solvate of a compound described in Table 2.

TABLE 3

| Compound Structure | Compound Name |
|---|---|
| 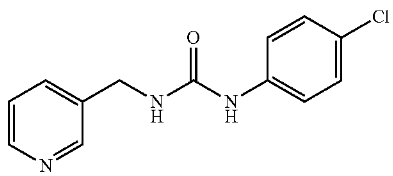 [SMILES: O=C(NCc1cccnc1)Nc1ccc(Cl)cc1] | 1-(4-Chlorophenyl)-3-(pyridin-3-ylmethyl)urea |
| 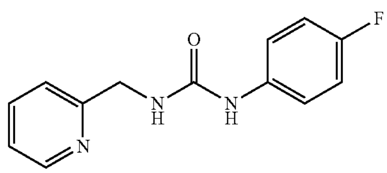 [SMILES: O=C(NCc1ccccn1)Nc1ccc(F)cc1] | 1-(4-Fluorophenyl)-3-(pyridin-2-ylmethyl)urea |
| 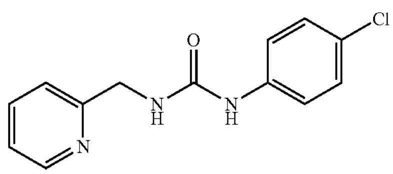 [SMILES: O=C(NCc1ccccn1)Nc1ccc(Cl)cc1] | 1-(4-Chlorophenyl)-3-(pyridin-2-ylmethyl)urea |
| 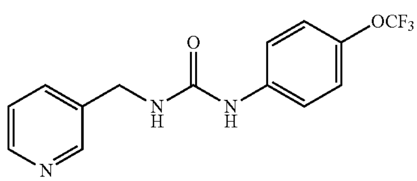 [SMILES: O=C(NCc1cccnc1)Nc1ccc(OC(F)(F)F)cc1] | 1-(Pyridin-3-ylmethyl)-3-(4-(trifluoromethoxy)phenyl)urea |
| 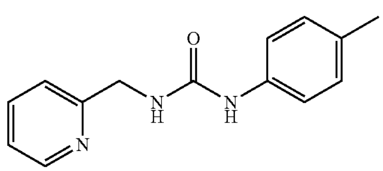 [SMILES: Cc1ccc(NC(=O)NCc2ccccn2)cc1] | 1-(Pyridin-2-ylmethyl)-3-(p-tolyl)urea |
| 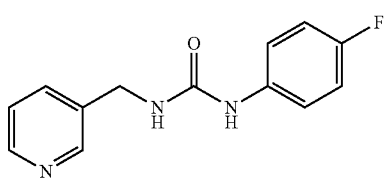 [SMILES: O=C(NCc1cccnc1)Nc1ccc(F)cc1] | 1-(4-Fluorophenyl)-3-(pyriidn-3-ylmethyl)urea |
| 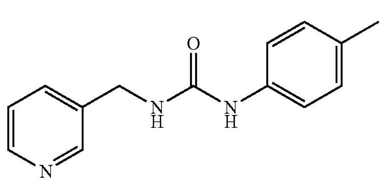 [SMILES: Cc1ccc(NC(=O)NCc2cccnc2)cc1] | 1-(Pyridin-3-ylmethyl)-3-(p-tolyl)urea |

TABLE 3-continued
| Compound Structure | Compound Name |
|---|---|
| 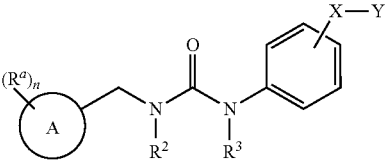 | 1-(Pyridin-3-ylmethyl)-3-(4-(trifluoromethyl)phenyl)urea |
| 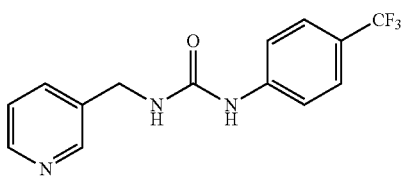 [SMILES: O=C(NCc1cccnc1)Nc1ccc(C(F)(F)F)cc1] | 1-(4-Methoxyphenyl)-3-(pyridin-3-ylmethyl)urea |
| 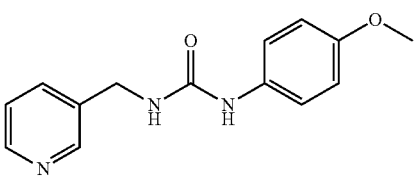 [SMILES: COc1ccc(NC(=O)NCc2cccnc2)cc1] | 1-(Pyridin-2-ylmethyl)-3-(4-(trifluoromethyl)phenyl)urea |
| 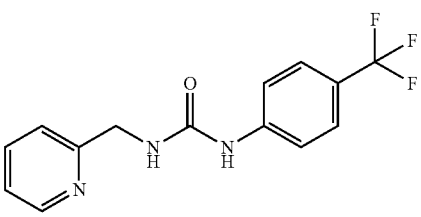 [SMILES: O=C(NCc1ccccn1)Nc1ccc(C(F)(F)F)cc1] | 1-(Pyridin-2-ylmethyl)-3-(4-(trifluoromethoxy)phenyl)urea |
| 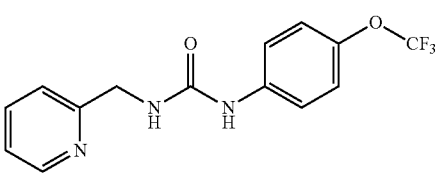 [SMILES: O=C(NCc1ccccn1)Nc1ccc(OC(F)(F)F)cc1] | 1-(4-Methoxyphenyl)-3-(pyridin-2-ylmethyl)urea |
| 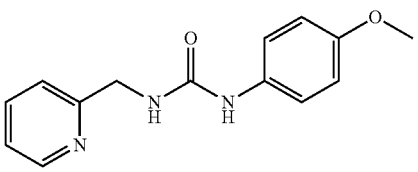 [SMILES: COc1ccc(NC(=O)NCc2ccccn2)cc1] | Ethyl 4-(3-(pyridin-2-ylmethyl)ureido)benzoate |
| 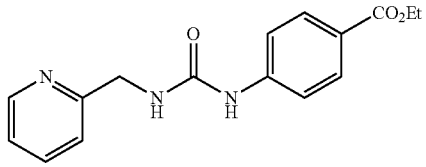 [SMILES: CCOC(=O)c1ccc(NC(=O)NCc2ccccn2)cc1] | Ethyl 4-(3-(pyridin-3-ylmethyl)ureido)benzoate |

TABLE 3-continued

| Compound Structure | Compound Name |
|---|---|
| 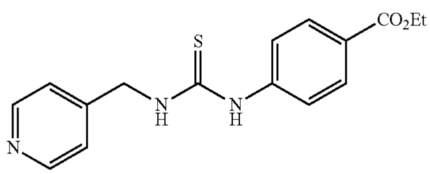 [SMILES: CCOC(=O)c1ccc(NC(=S)NCc2ccncc2)cc1] | Ethyl 4-(3-(pyridin-4-ylmethyl)thioureido)benzoate |
| 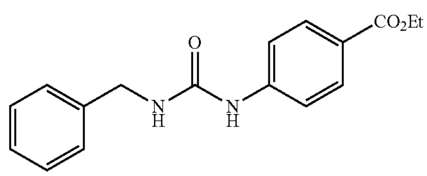 [SMILES: CCOC(=O)c1ccc(NC(=O)NCc2ccccc2)cc1] | Ethyl 4-(3-benzylureido)benzoate |
| 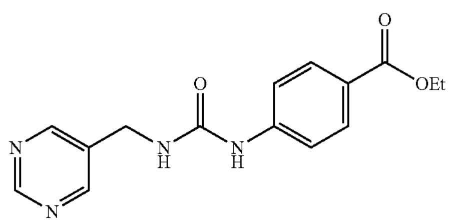 [SMILES: CCOC(=O)c1ccc(NC(=O)NCc2cncnc2)cc1] | Ethyl 4-(3-(pyrimidin-5-ylmethyl)ureido)benzoate |
| 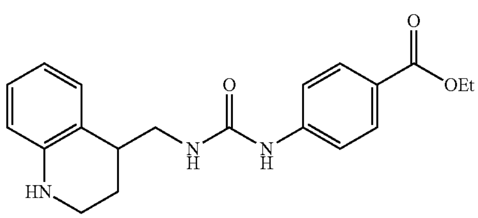 [SMILES: CCOC(=O)c1ccc(NC(=O)NCC2CCNc3ccccc32)cc1] | Ethyl 4-(3-((1,2,3,4-tetrahydroquinolin-4-yl)methyl)ureido)benzoate |
| 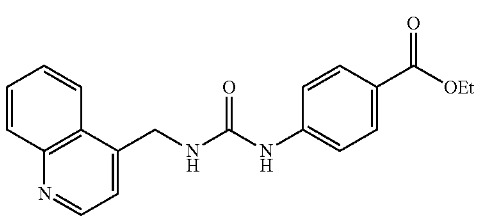 [SMILES: CCOC(=O)c1ccc(NC(=O)NCc2ccnc3ccccc23)cc1] | Ethyl 4-(3-(quinolin-4-ylmethyl)ureido)benzoate |
| 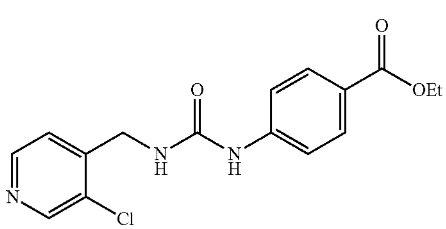 [SMILES: CCOC(=O)c1ccc(NC(=O)NCc2ccncc2Cl)cc1] | Ethyl 4-(3-((3-chloropyridin-4-yl)methyl)ureido)benzoate |

TABLE 3-continued

| Compound Structure | Compound Name |
|---|---|
| 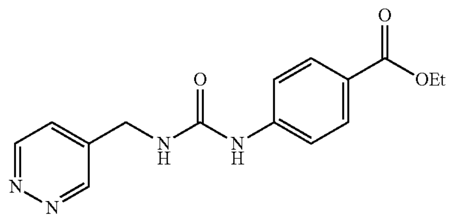 [SMILES: CCOC(=O)c1ccc(NC(=O)NCc2ccnnc2)cc1] | Ethyl 4-(3-(pyridazin-4-ylmethyl)ureido)benzoate |
| 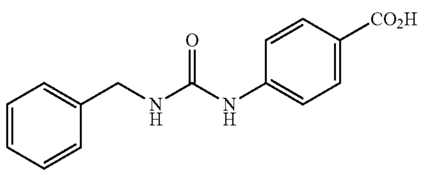 [SMILES: O=C(NCc1ccccc1)Nc1ccc(C(=O)O)cc1] | 3-(3-Benzyl-ureido)-benzoic acid |
| 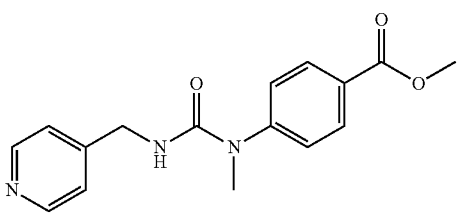 [SMILES: COC(=O)c1ccc(N(C)C(=O)NCc2ccncc2)cc1] | Methyl 4-(1-methyl-3-(pyridin-4-ylmethyl)ureido)benzoate |
| 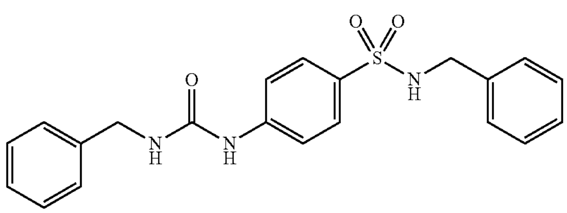 [SMILES: O=C(NCc1ccccc1)Nc1ccc(S(=O)(=O)NCc2ccccc2)cc1] | N-Benzyl-4-(3-benzyl-ureido)-benzenesulfonamide |
| 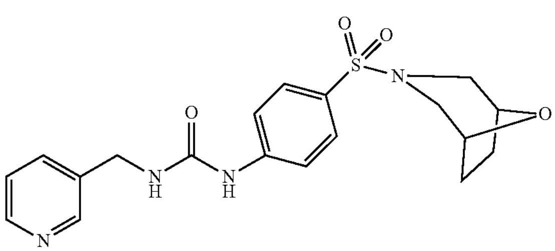 [SMILES: O=C(NCc1cccnc1)Nc1ccc(S(=O)(=O)N2CC3CCC(C2)O3)cc1] | 1-[4-(8-Oxa-3-aza-bicyclo[3.2.1]octane-3-sulfonyl)-phenyl]-3-pyridin-3-ylmethyl-urea |
| 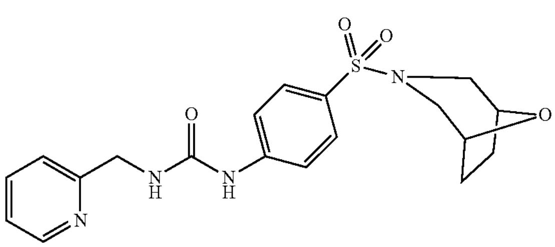 [SMILES: O=C(NCc1ccccn1)Nc1ccc(S(=O)(=O)N2CC3CCC(C2)O3)cc1] | 1-[4-(8-Oxa-3-aza-bicyclo[3.2.1]octane-3-sulfonyl)-phenyl]-3-pyridin-2-ylmethyl-urea |

TABLE 3-continued

| Compound Structure | Compound Name |
|---|---|
| | Ethyl 6-(3-(pyridin-4-ylmethyl)ureido)nicotinate |
| | Ethyl 5-(3-(pyridin-4-ylmethyl)ureido)picolinate |
| 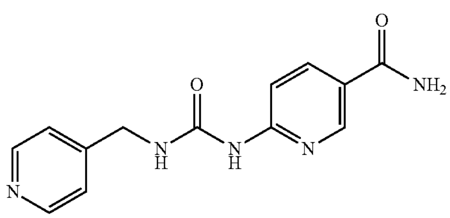 [SMILES: NC(=O)c1ccc(NC(=O)NCc2ccncc2)nc1] | 6-(3-Pyridin-4-ylmethyl-ureido)-nicotinamide |
| 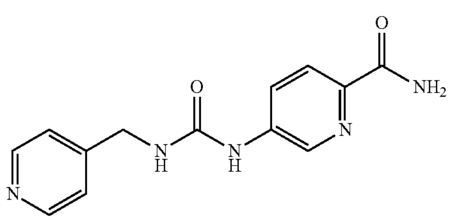 [SMILES: NC(=O)c1ccc(NC(=O)NCc2ccncc2)cn1] | 5-(3-(pyridin-4-ylmethyl)ureido)picolinamide |
| | Ethyl 6-(3-(pyridin-4-ylmethyl)ureido)nicotinate |
| | Ethyl 5-(3-(pyridin-4-ylmethyl)ureido)picolinate |

TABLE 3-continued

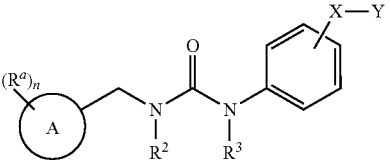

| Compound Structure | Compound Name |
|---|---|
| 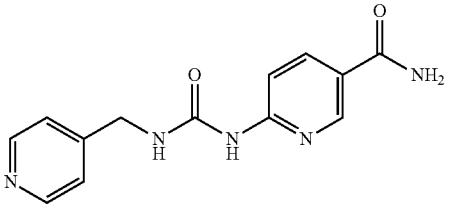 [SMILES: NC(=O)c1ccc(NC(=O)NCc2ccncc2)nc1] | 6-(3-Pyridin-4-ylmethyl-ureido)-nicotinamide |
| 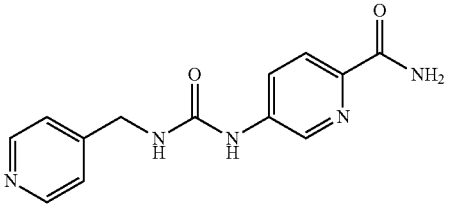 [SMILES: NC(=O)c1ccc(NC(=O)NCc2ccncc2)cn1] | 5-(3-(pyridin-4-ylmethyl)ureido)picolinamide |
| 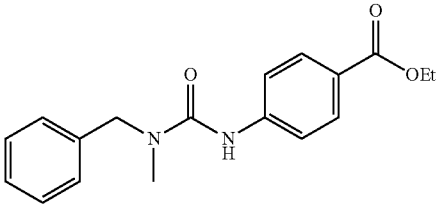 [SMILES: CCOC(=O)c1ccc(NC(=O)N(C)Cc2ccccc2)cc1] | 4-(3-Benzyl-3-methyl-ureido)-benzoic acid ethyl ester |
| 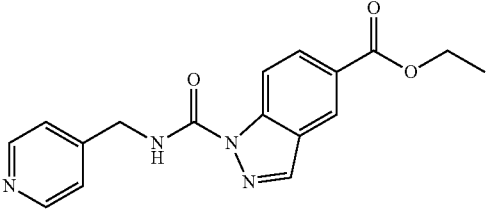 [SMILES: CCOC(=O)c1ccc2c(cnn2C(=O)NCc2ccncc2)c1] | 1-[(Pyridin-4-ylmethyl)-carbamoyl]-1H-indazole-5-carboxylic acid ethyl ester |
| 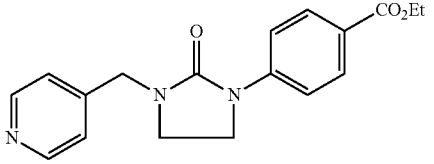 [SMILES: CCOC(=O)c1ccc(N2CCN(Cc3ccncc3)C2=O)cc1] | 4-(2-Oxo-3-pyridin-4-ylmethyl-imidazolidin-1-yl)-benzoic acid ethy lester |
| 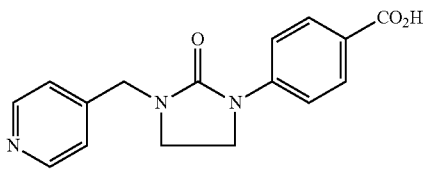 [SMILES: O=C(O)c1ccc(N2CCN(Cc3ccncc3)C2=O)cc1] | 4-(2-oxo-3-pyridin-4-ylmethyl-imidazolidin-1-yl)-benzoic acid |

In one aspect, provided herein is a pharmaceutically acceptable salt or solvate of a compound described in Table 3.

TABLE 4

[Structure: general formula with X—Y substituted phenyl connected via urea to (1H-pyrazol-4-yl)methyl]

| Compound Structure | Compound Name |
|---|---|
| [structure] | 1-((1H-Pyrazol-4-yl)methyl)-3-(4-((4-(trifluoromethyl)phenyl)sulfonyl)phenyl)urea |
| [structure] | 1-((1H-Pyrazol-4-yl)methyl)-3-(4-(pyridin-2-ylsulfonyl)phenyl)urea |
| [structure] | 1-[4-(5-Methyl-pyridine-2-sulfonyl-phenyl]-3-(1H-pyrazol-4-ylmethyl)-urea |
| [structure] | 1-((1H-Pyrazol-4-yl)methyl)-3-(4-((2-fluorophenyl)sulfonyl)phenyl)urea |
| [structure] | 1-((1H-Pyrazol-4-yl)methyl)-3-(4-((3-fluorophenyl)sulfonyl)phenyl)urea |
| [structure] | 1-((1H-Pyrazol-4-yl)methyl)-3-(4-((4-fluorophenyl)sulfonyl)phenyl)urea |

TABLE 4-continued

| Compound Structure | Compound Name |
|---|---|
| 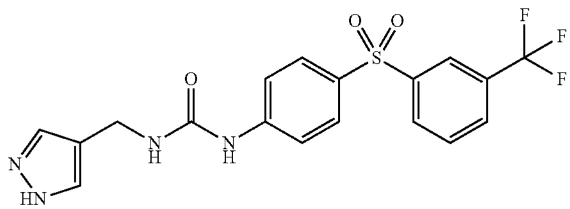 [SMILES: O=C(NCc1cn[nH]c1)Nc1ccc(S(=O)(=O)c2cccc(C(F)(F)F)c2)cc1] | 1-((1H-Pyrazol-4-yl)methyl)-3-(4-((3-(trifluoromethyl)phenyl)sulfonyl)phenyl)urea |
| 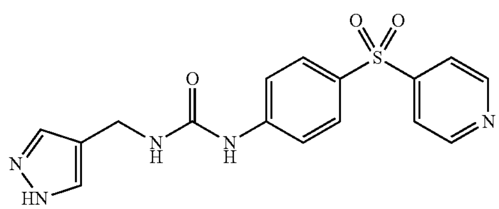 [SMILES: O=C(NCc1cn[nH]c1)Nc1ccc(S(=O)(=O)c2ccncc2)cc1] | 1-((1H-Pyrazol-4-yl)methyl)-3-(4-(pyridin-4-ylsulfonyl)phenyl)urea |
| 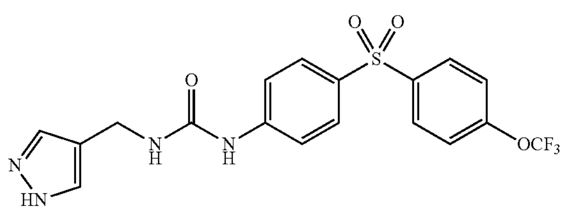 [SMILES: O=C(NCc1cn[nH]c1)Nc1ccc(S(=O)(=O)c2ccc(OC(F)(F)F)cc2)cc1] | 1-(1H-Pyrazol-4-ylmethyl)-3-[4-(4-trifluoromethoxy-benzenesulfonyl)-phenyl]-urea |
| 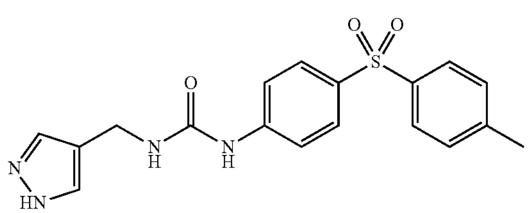 [SMILES: Cc1ccc(S(=O)(=O)c2ccc(NC(=O)NCc3cn[nH]c3)cc2)cc1] | 1-(1H-Pyrazol-4-ylmethyl)-3-[4-(toluene-4-sulfonyl)-phenyl]-urea |
| 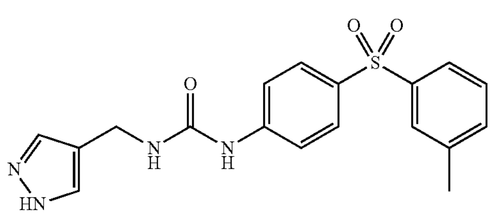 [SMILES: Cc1cccc(S(=O)(=O)c2ccc(NC(=O)NCc3cn[nH]c3)cc2)c1] | 1-(1H-Pyrazol-4-ylmethyl)-3-[4-(toluene-3-sulfonyl)-phenyl]-urea |
| 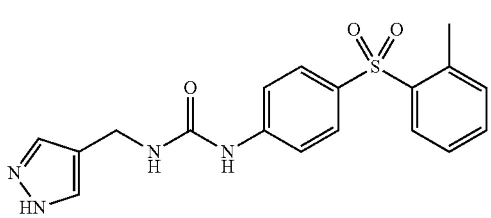 [SMILES: Cc1ccccc1S(=O)(=O)c1ccc(NC(=O)NCc2cn[nH]c2)cc1] | 1-(1H-Pyrazol-4-ylmethyl)-3-[4-(toluene-2-sulfonyl)-phenyl]-urea |

TABLE 4-continued

| Compound Structure | Compound Name |
|---|---|
| 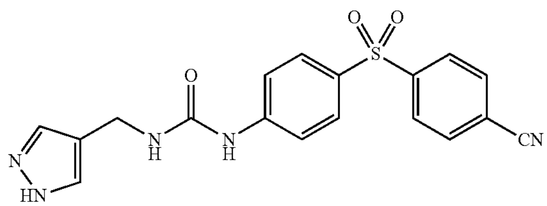 [SMILES: N#Cc1ccc(S(=O)(=O)c2ccc(NC(=O)NCc3cn[nH]c3)cc2)cc1] | 1-[4-(4-Cyano-benzenesulfonyl)-phenyl]-3-(1H-pyrazol-4-ylmethyl)-urea |
| 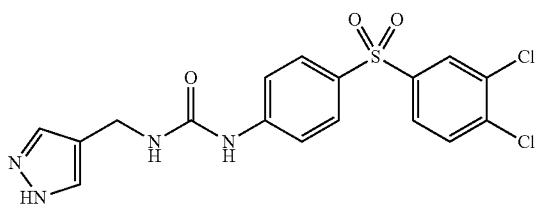 [SMILES: O=C(NCc1cn[nH]c1)Nc1ccc(S(=O)(=O)c2ccc(Cl)c(Cl)c2)cc1] | 1-[4-(3,4-Dichloro-benzenesulfonyl)-phenyl]-3-(1H-pyrazol-4-ylmethyl)-urea |
| 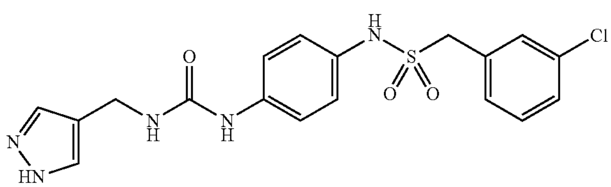 [SMILES: O=C(NCc1cn[nH]c1)Nc1ccc(NS(=O)(=O)Cc2cccc(Cl)c2)cc1] | C-(3-Chloro-phenyl)-N-{4-[3-(1H-pyrazol-4-ylmethyl)-ureido]-phenyl}-methanesulfonamide |
| 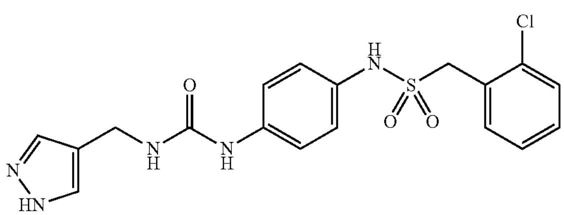 [SMILES: O=C(NCc1cn[nH]c1)Nc1ccc(NS(=O)(=O)Cc2ccccc2Cl)cc1] | C-(2-Chloro-phenyl)-N-{4-[3-(1H-pyrazol-4-ylmethyl)-ureido]-phenyl}-methanesulfonamide |
| 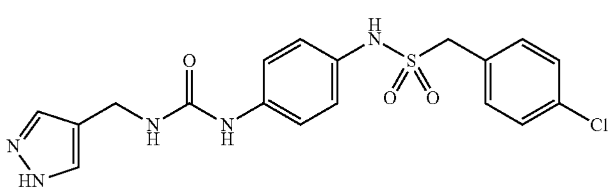 [SMILES: O=C(NCc1cn[nH]c1)Nc1ccc(NS(=O)(=O)Cc2ccc(Cl)cc2)cc1] | C-(4-Chloro-phenyl)-N-{4-[3-(1H-pyrazol-4-ylmethyl)-ureido]-phenyl}-methanesulfonamide |
| 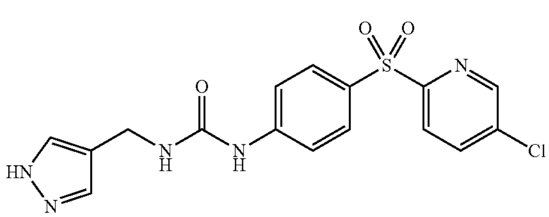 [SMILES: O=C(NCc1cn[nH]c1)Nc1ccc(S(=O)(=O)c2ccc(Cl)cn2)cc1] | 1-[4-(5-Chloro-pyridin-2-sulfonyl)-phenyl]-3-(1H-pyrazol-4-ylmethyl)-urea |

TABLE 4-continued

[General structure: pyrazol-4-ylmethyl-urea-phenyl-X—Y]

| Compound Structure | Compound Name |
|---|---|
| [structure] | 1-(1H-Pyrazol-4-ylmethyl)-3-[4-(2-trifluoromethyl-benzenesulfonyl)-phenyl]-urea |
| [structure] | C-(3,4-Dichloro-phenyl)-N-{4-[3-(1H-pyrazol-4-ylmethyl)-ureido]-phenyl}-methanesulfonamide |
| [structure] | N-(3-Fluoro-benzyl)-4-[3-(1H-pyrazol-4-ylmethyl)-ureido]-benzenesulfonamide |
| [structure] | 1-[4-(6-Methyl-pyridine-3-sulfonyl)-phenyl]-3-(1H-pyrazol-4-ylmethyl)-urea |
| [structure] | 1-(((1H-Pyrazol-4-yl)methyl)-3-(4-(pyrimidin-5-ylsulfonyl)phenyl)urea |
| [structure] | 1-(4-Cyclohexanesulfonyl-phenyl)-3-(1H-pyrazol-4-ylmethyl)-urea |

TABLE 4-continued

| Compound Structure | Compound Name |
|---|---|
| 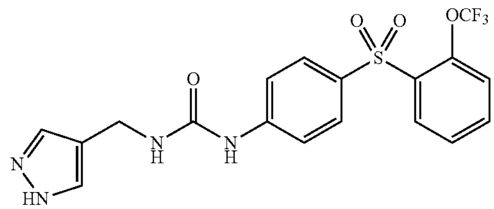 [SMILES: O=C(NCc1cn[nH]c1)Nc1ccc(S(=O)(=O)c2ccccc2OC(F)(F)F)cc1] | 1-(1H-Pyrazol-4-ylmethyl)-3-[4-(2-trifluoromethoxy-benzenesulfonyl)-phenyl]-urea |
| 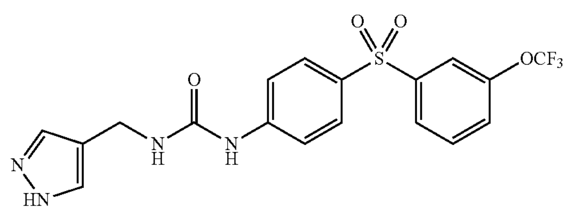 [SMILES: O=C(NCc1cn[nH]c1)Nc1ccc(S(=O)(=O)c2cccc(OC(F)(F)F)c2)cc1] | 1-(1H-Pyrazol-4-ylmethyl)-3-[4-(3-trifluoromethoxy-benzenesulfonyl)-phenyl]-urea |
| 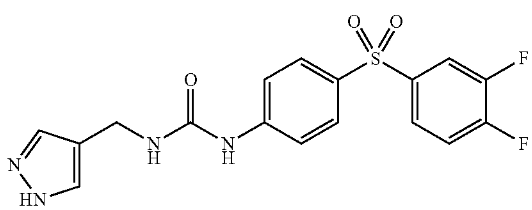 [SMILES: O=C(NCc1cn[nH]c1)Nc1ccc(S(=O)(=O)c2ccc(F)c(F)c2)cc1] | 1-[4-[3,4-Difluoro-benzenesulfonyl)-phenyl]-3-(1H-pyrazol-4-ylmethyl)-urea |
| 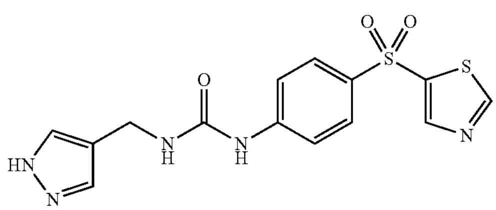 [SMILES: O=C(NCc1cn[nH]c1)Nc1ccc(S(=O)(=O)c2cncs2)cc1] | 1-(1H-Pyrazol-4-ylmethyl)-3-[4-(thiazole-2-sulfonyl)-phenyl]-urea |
| 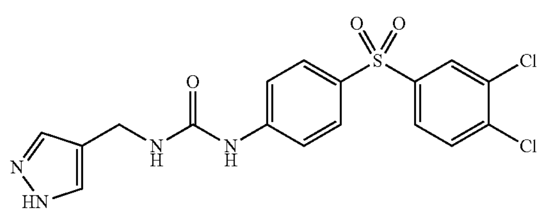 [SMILES: O=C(NCc1cn[nH]c1)Nc1ccc(S(=O)(=O)c2ccc(Cl)c(Cl)c2)cc1] | 1-[4-(3,4-Dichloro-benzenesulfonyl)-phenyl]-3-(1H-pyrazol-4-ylmethyl)-urea |
| 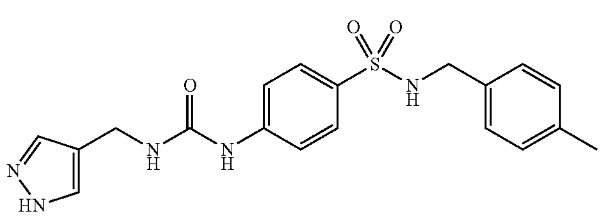 [SMILES: Cc1ccc(CNS(=O)(=O)c2ccc(NC(=O)NCc3cn[nH]c3)cc2)cc1] | N-(4-Methyl-benzyl)-4-[3-(1H-pyrazol-4-ylmethyl)-ureido]-benzenesulfonamide |

TABLE 4-continued

| Compound Structure | Compound Name |
|---|---|
| 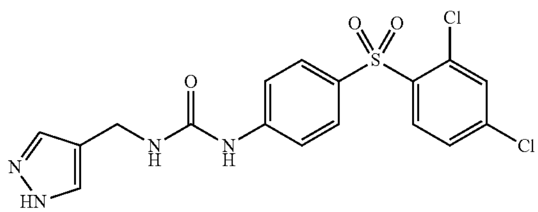 [SMILES: O=C(NCc1cn[nH]c1)Nc1ccc(S(=O)(=O)c2ccc(Cl)cc2Cl)cc1] | 1-[4-(2,4-Dichloro-benzenesulfonyl)-phenyl]-3-(1H-pyrazol-4-ylmethyl)-urea |
| 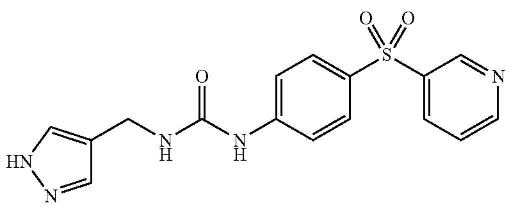 [SMILES: O=C(NCc1cn[nH]c1)Nc1ccc(S(=O)(=O)c2cccnc2)cc1] | 1-(1H-Pyrazol-4-ylmethyl)-3-[4-(pyridine-3-sulfonyl)-phenyl]-urea |
| 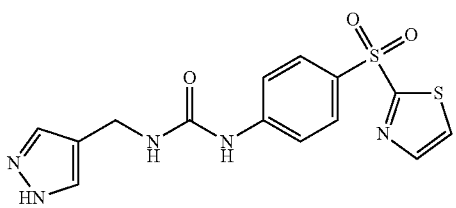 [SMILES: O=C(NCc1cn[nH]c1)Nc1ccc(S(=O)(=O)c2nccs2)cc1] | 1-(1H-Pyrazol-4-ylmethyl)-3-[4-(thiazole-2-sulfonyl)-phenyl]-urea |
| 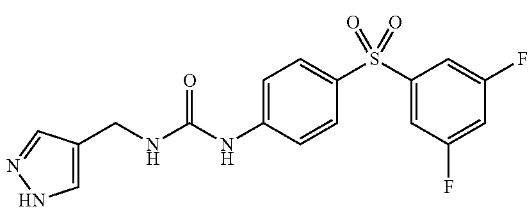 [SMILES: O=C(NCc1cn[nH]c1)Nc1ccc(S(=O)(=O)c2cc(F)cc(F)c2)cc1] | 1-[4-(3,5-Difluoro-benzenesulfonyl)-phenyl]-3-(1H-pyrazol-4-ylmethyl)-urea |
| 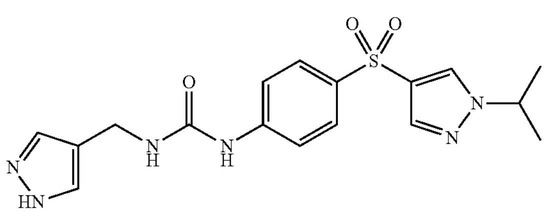 [SMILES: CC(C)n1cc(S(=O)(=O)c2ccc(NC(=O)NCc3cn[nH]c3)cc2)cn1] | of 1-[4-(1-Isopropyl-1H-pyrazole-4-sulfonyl)-phenyl]-3-(1H-pyrazol-4-ylmethyl)-urea |
| 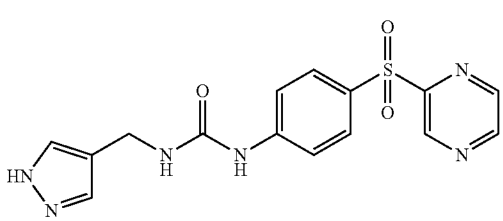 [SMILES: O=C(NCc1cn[nH]c1)Nc1ccc(S(=O)(=O)c2cnccn2)cc1] | 1-[4-(Pyrazine-2-sulfonyl)-phenyl]-3-(1H-pyrazol-4-ylmethyl)-urea |

TABLE 4-continued

| Compound Structure | Compound Name |
|---|---|
| 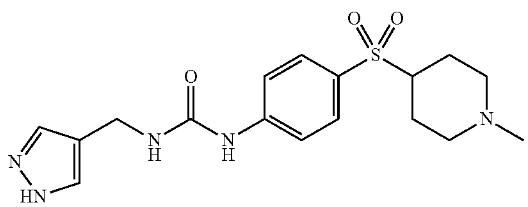 [SMILES: CN1CCC(S(=O)(=O)c2ccc(NC(=O)NCc3cn[nH]c3)cc2)CC1] | 1-[4-(1-Methyl-piperidine-4-sulfonyl)-phenyl]-3-(1H-pyrazol-4-ylmethyl)-urea |
| 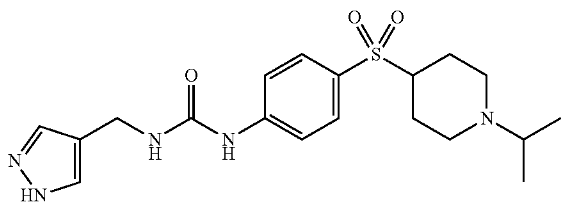 [SMILES: CC(C)N1CCC(S(=O)(=O)c2ccc(NC(=O)NCc3cn[nH]c3)cc2)CC1] | 1-[4-(1-Isopropyl-piperidine-4-sulfonyl)-phenyl]-3-(1H-pyrazol-4-ylmethyl)-urea |
| 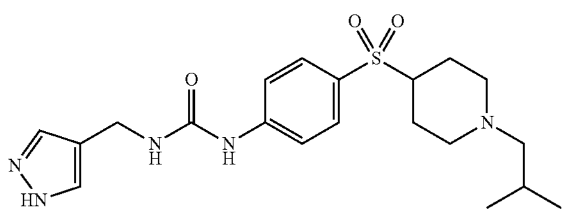 [SMILES: CC(C)CN1CCC(S(=O)(=O)c2ccc(NC(=O)NCc3cn[nH]c3)cc2)CC1] | 1-[4-(1-Isobutyl-piperidine-4-sulfonyl)-phenyl]-3-(1H-pyrazol-4-ylmethyl)-urea |
| 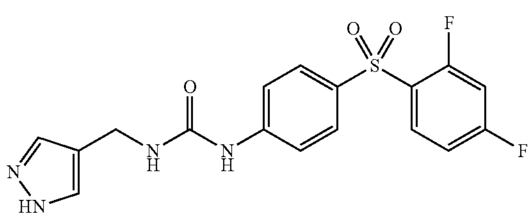 [SMILES: O=C(NCc1cn[nH]c1)Nc1ccc(S(=O)(=O)c2ccc(F)cc2F)cc1] | of 1-[4-(2,4-Difluoro-benzenesulfonyl)-phenyl]-3-(1H-pyrazol-4-ylmethyl)-urea |
| 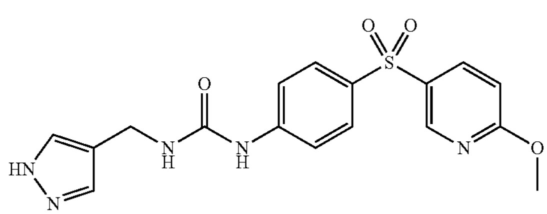 [SMILES: COc1ccc(S(=O)(=O)c2ccc(NC(=O)NCc3cn[nH]c3)cc2)cn1] | 1-[4-(6-Methyl-pyridine-3-sulfonyl)-phenyl]-3-(1H-pyrazol-4-ylmethyl)-urea |
| 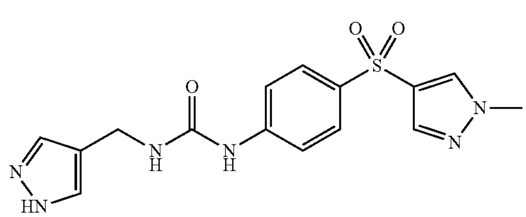 [SMILES: Cn1cc(S(=O)(=O)c2ccc(NC(=O)NCc3cn[nH]c3)cc2)cn1] | 1-[4-(1-Methyl-1H-pyrazole-4-sulfonyl-phenyl]-3-(1H-pyrazol-4-ylmethyl)-urea |

TABLE 4-continued

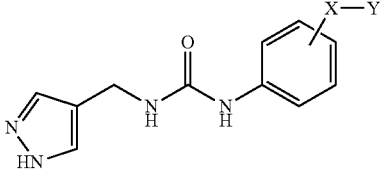

| Compound Structure | Compound Name |
|---|---|
| 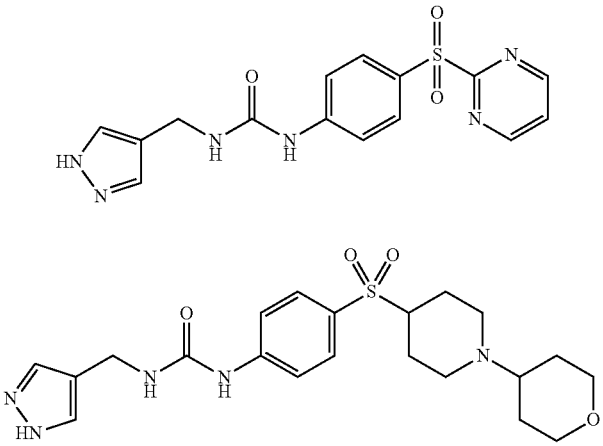 | 1-(1H-Pyrazol-4-ylmethyl)-3-[4-(pyrimidine-2-sulfonyl)-phenyl]-urea |
| 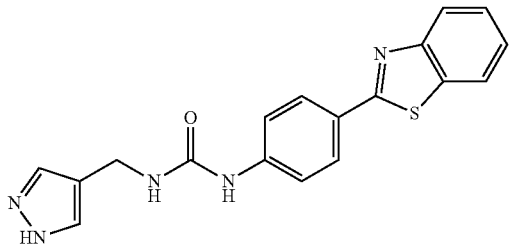 [SMILES: O=C(NCc1cn[nH]c1)Nc1ccc(-c2nc3ccccc3s2)cc1] | 1-(1H-Pyrazol-4-ylmethyl)-3-{4-[1-(tetrahydro-pyran-4-yl)-piperidine-4-sulfonyl]-phenyl}-urea |
| 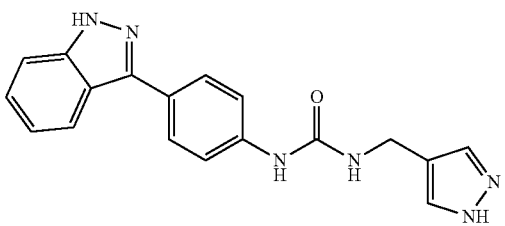 [SMILES: O=C(NCc1cn[nH]c1)Nc1ccc(-c2n[nH]c3ccccc23)cc1] | 1-((1H-Pyrazol-4-yl)methyl)-3-(4-(benzo[d]thiazol-2-yl)phenyl)urea |
| 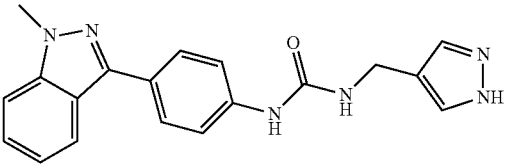 [SMILES: Cn1nc(-c2ccc(NC(=O)NCc3cn[nH]c3)cc2)c2ccccc21] | 1-[4-(1H-Indazol-3-yl)-phenyl]-3-(1H-pyrazol-4-ylmethyl)-urea |
| 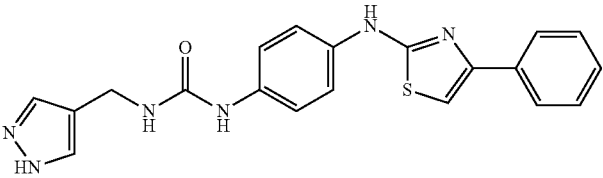 | 1-[4-(1-Methyl-1H-indazol-3-yl)-phenyl]-3-(1H-pyrazol-4-ylmethyl)-urea |
| 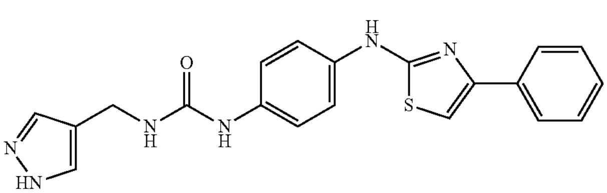 [SMILES: O=C(NCc1cn[nH]c1)Nc1ccc(Nc2nc(-c3ccccc3)cs2)cc1] | 1-((1H-Pyrazol-4-yl)methyl)-3-(4-((4-phenylthiazol-2-yl)amino)phenyl)urea |

TABLE 4-continued

| Compound Structure | Compound Name |
|---|---|
| 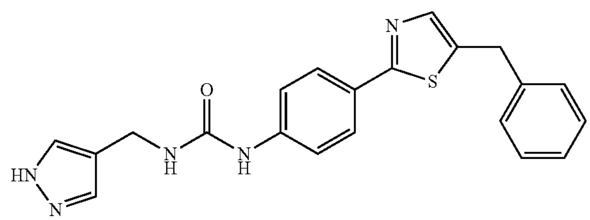 [SMILES: O=C(NCc1cn[nH]c1)Nc1ccc(-c2ncc(Cc3ccccc3)s2)cc1] | 1-((1H-Pyrazol-4-yl)methyl)-3-(4-(5-benzylthiazol-2-yl)phenyl)urea |
| 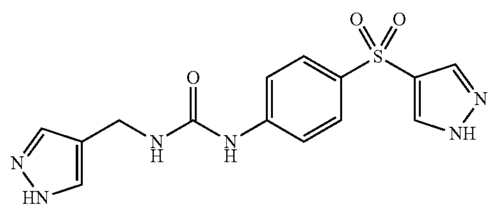 [SMILES: O=C(NCc1cn[nH]c1)Nc1ccc(S(=O)(=O)c2cn[nH]c2)cc1] | 1-((1H-Pyrazol-4-yl)methyl)-3-(4-((1H-pyrazol-4-yl)sulfonyl)phenyl)urea |
| 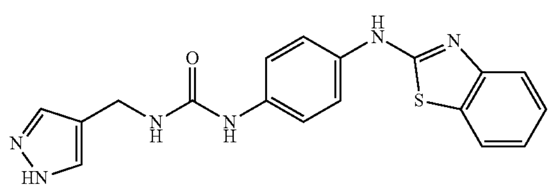 [SMILES: O=C(NCc1cn[nH]c1)Nc1ccc(Nc2nc3ccccc3s2)cc1] | 1-((1H-Pyrazol-4-yl)methyl)-3-(4-(benzo[d]thiazol-2-ylamino)phenyl)urea |
| 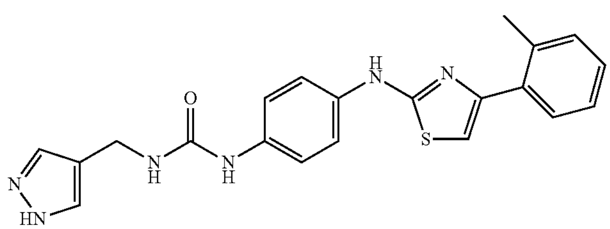 [SMILES: Cc1ccccc1-c1csc(Nc2ccc(NC(=O)NCc3cn[nH]c3)cc2)n1] | 1-(1H-Pyrazol-4-ylmethyl)-3-[4-(4-o-tolyl-thiazol-2-ylamino)-phenyl]-urea |
| 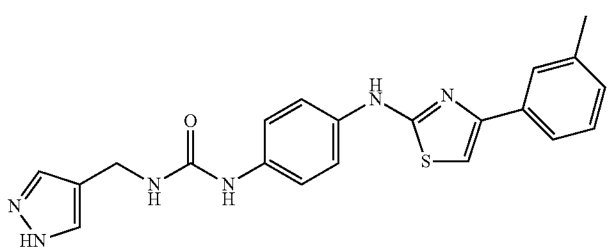 [SMILES: Cc1cccc(-c2csc(Nc3ccc(NC(=O)NCc4cn[nH]c4)cc3)n2)c1] | 1-(1H-Pyrazol-4-ylmethyl)-3-[4-(4-m-tolyl-thiazol-2-ylamino)-phenyl]-urea |
| 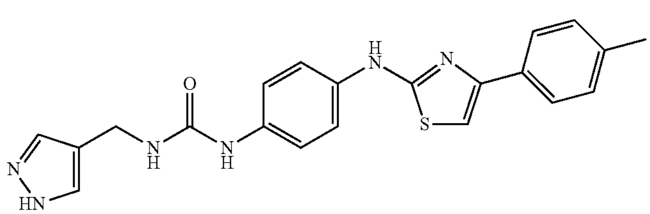 [SMILES: Cc1ccc(-c2csc(Nc3ccc(NC(=O)NCc4cn[nH]c4)cc3)n2)cc1] | 1-(1H-Pyrazol-4-ylmethyl)-3-[4-(4-p-tolyl-thiazol-2-ylamino)-phenyl]-urea |

TABLE 4-continued

| Compound Structure | Compound Name |
|---|---|
| 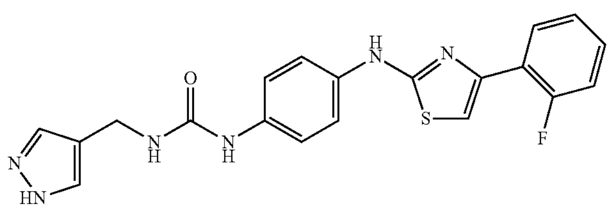 [SMILES: O=C(NCc1cn[nH]c1)Nc1ccc(Nc2nc(-c3ccccc3F)cs2)cc1] | 1-{4-[4-(2-Fluoro-phenyl)-thiazol-2-ylamino]-phenyl}-3-(1H-pyrazol-4-ylmethyl)-urea |
| 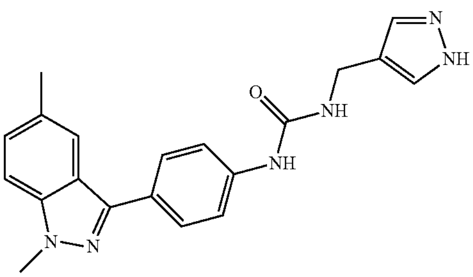 [SMILES: Cc1ccc2c(c1)c(-c1ccc(NC(=O)NCc3cn[nH]c3)cc1)nn2C] | 1-((1H-Pyrazol-4-yl)methyl)-3-(4-(1,5-dimethyl-1H-indazol-3-yl)phenyl)urea |
| 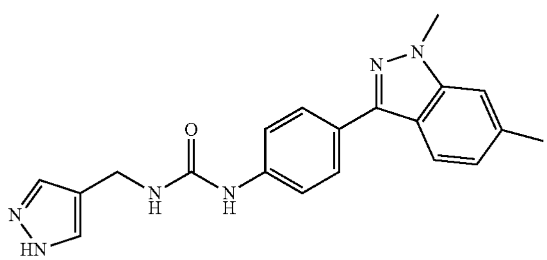 [SMILES: Cc1ccc2c(-c3ccc(NC(=O)NCc4cn[nH]c4)cc3)nn(C)c2c1] | 1-[4-(1,6-Dimethyl-1H-indazol-3-yl)-phenyl]-3-(1H-pyrazol-4-ylmethyl)-urea |
| 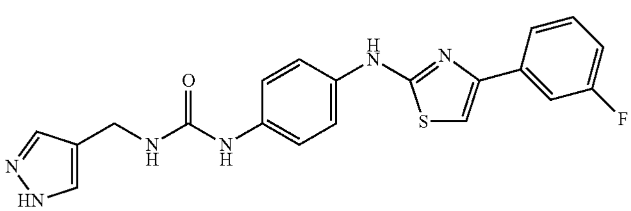 [SMILES: O=C(NCc1cn[nH]c1)Nc1ccc(Nc2nc(-c3cccc(F)c3)cs2)cc1] | 1-{4-[4-(3-Fluoro-phenyl)-thiazol-2-ylamino]-phenyl}-3-(1H-pyrazol-4-ylmethyl)-urea |
| 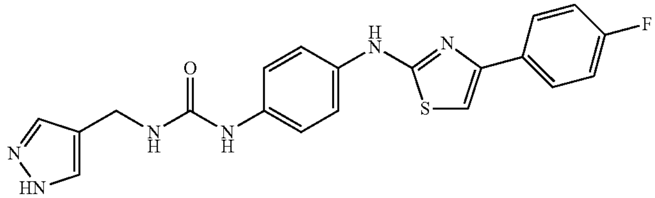 [SMILES: O=C(NCc1cn[nH]c1)Nc1ccc(Nc2nc(-c3ccc(F)cc3)cs2)cc1] | 1-{4-[4-(4-Fluoro-phenyl)-thiazol-2-ylamino]-phenyl}-3-(1H-pyrazol-4-ylmethyl)-urea |

TABLE 4-continued
| Compound Structure | Compound Name |
|---|---|
| 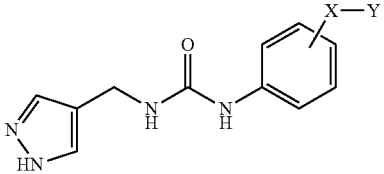 | 1-((1H-Pyrazol-4-yl)methyl)-3-(4-((4-(2-methoxyphenyl)thiazol-2-yl)amino)phenyl)urea |
| 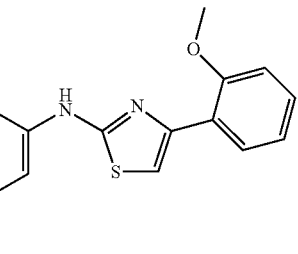 | 1-((1H-Pyrazol-4-yl)methyl)-3-(4-((4-(3-methoxyphenyl)thiazol-2-yl)amino)phenyl)urea |
| 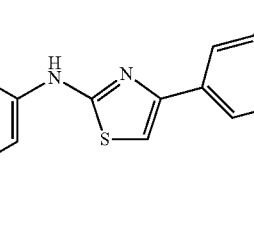 | 1-(4-Benzothiazol-4-yl-phenyl)-3-(1H-pyrazol-4-ylmethyl)-urea |
| 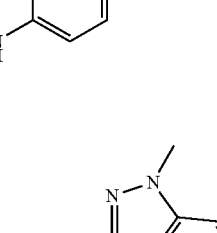 | 1-((1H-Pyrazol-4-yl)methyl)-3-(4-(1,7-dimethyl-1H-indazol-3-yl)phenyl)urea |
| 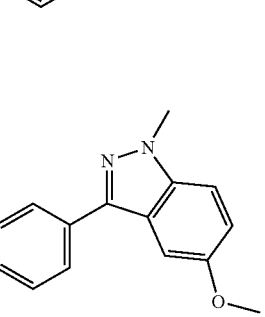 | 1-[4-(5-Methoxy-1-methyl-1H-indazol-3-yl)-phenyl]-3-(1H-pyrazol-4-ylmethyl)-urea |

TABLE 4-continued

| Compound Structure | Compound Name |
|---|---|
| 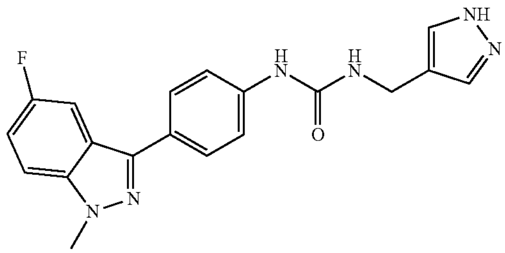 [SMILES: Cn1nc(-c2ccc(NC(=O)NCc3cn[nH]c3)cc2)c2cc(F)ccc21] | 1-[4-(5-Fluoro-1-methyl-1H-indazol-3-yl)-phenyl]-3-(1H-pyrazol-4-ylmethyl)-urea |
| 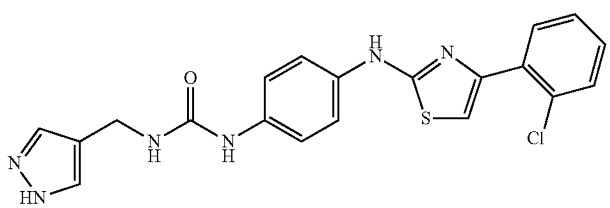 [SMILES: O=C(NCc1cn[nH]c1)Nc1ccc(Nc2nc(-c3ccccc3Cl)cs2)cc1] | 1-{4-[4-(2-Chloro-phenyl)-thiazol-2-ylamino]-phenyl}-3-(1H-pyrazol-4-ylmethyl)-urea |
| 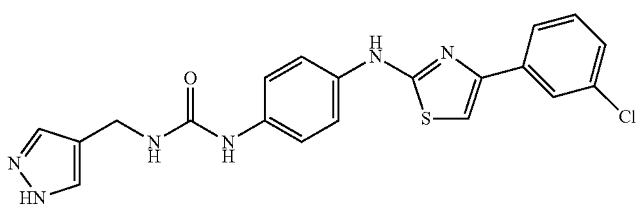 [SMILES: O=C(NCc1cn[nH]c1)Nc1ccc(Nc2nc(-c3cccc(Cl)c3)cs2)cc1] | 1-{4-[4-(3-Chloro-phenyl)-thiazol-2-ylamino]-phenyl}-3-(1H-pyrazol-4-ylmethyl)-urea |
| 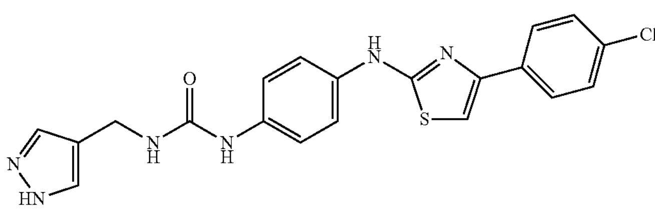 [SMILES: O=C(NCc1cn[nH]c1)Nc1ccc(Nc2nc(-c3ccc(Cl)cc3)cs2)cc1] | 1-{4-[4-(4-Chloro-phenyl)-thiazol-2-ylamino]-phenyl}-3-(1H-pyrazol-4-ylmethyl)-urea |
| 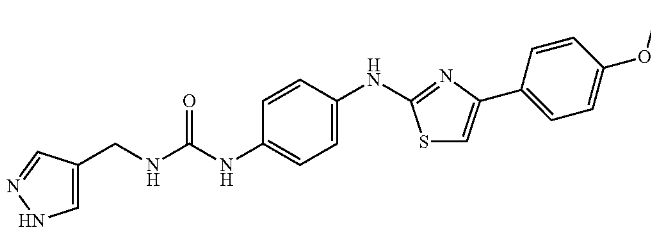 | 1-((1H-Pyrazol-4-yl)methyl)-3-(4-((4-(4-methoxyphenyl)thiazol-2-yl)amino)phenyl)urea |
| 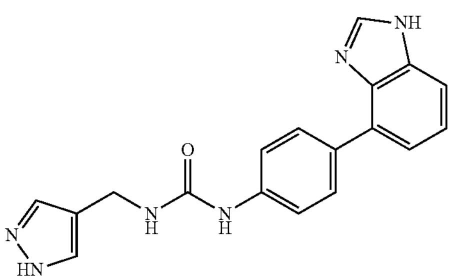 [SMILES: O=C(NCc1cn[nH]c1)Nc1ccc(-c2cccc3[nH]cnc23)cc1] | 1-[4-(1H-Benzoimidazol-4-yl)-phenyl]-3-(1H-pyrazol-4-ylmethyl)-urea |

TABLE 4-continued

| Compound Structure | Compound Name |
|---|---|
| 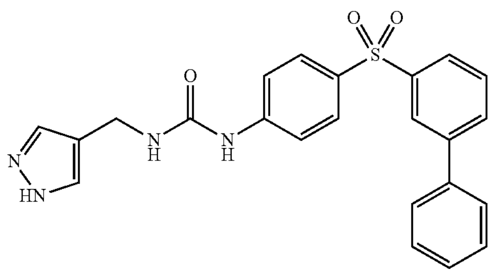 [SMILES: O=C(NCc1cn[nH]c1)Nc1ccc(S(=O)(=O)c2cccc(-c3ccccc3)c2)cc1] | 1-((1H-Pyrazol-4-yl)methyl)-3-(4-([1,1'-biphenyl]-3-ylsulfonyl)phenyl)urea |
| 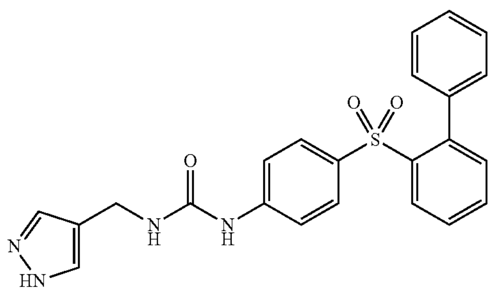 [SMILES: O=C(NCc1cn[nH]c1)Nc1ccc(S(=O)(=O)c2ccccc2-c2ccccc2)cc1] | 1-((1H-Pyrazol-4-yl)methyl)-3-(4-([1,1'-biphenyl]-2-ylsulfonyl)phenyl)urea |
| 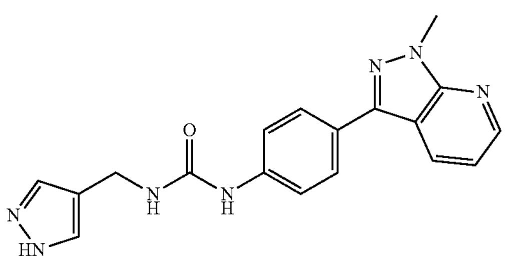 [SMILES: Cn1nc(-c2ccc(NC(=O)NCc3cn[nH]c3)cc2)c2cccnc21] | 1-[4-(1-Methyl-1H-pyrazolo[3,4-b]pyridin-3-yl)-phenyl]-3-(1H-pyrazol-4-ylmethyl)-urea |
| 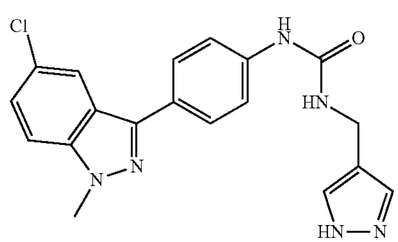 [SMILES: Cn1nc(-c2ccc(NC(=O)NCc3cn[nH]c3)cc2)c2cc(Cl)ccc21] | 1-((1H-Pyrazol-4-yl)methyl)-3-(4-(5-chloro-1-methyl-1H-indazol-3-yl)phenyl)urea |
| 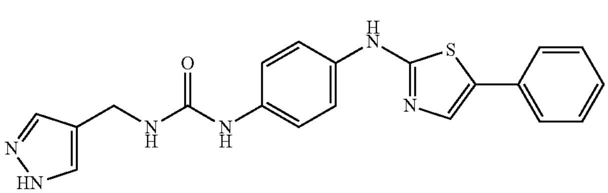 | 1-((1H-Pyrazol-4-yl)methyl)-3-(4-((5-phenylthiazol-2-yl)amino)phenyl)urea |

TABLE 4-continued
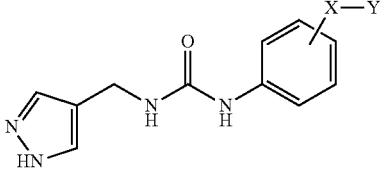
| Compound Structure | Compound Name |
| --- | --- |
| 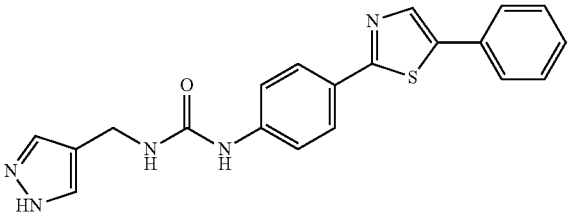 [SMILES: O=C(NCc1cn[nH]c1)Nc1ccc(-c2ncc(-c3ccccc3)s2)cc1] | 1-((1H-Pyrazol-4-yl)methyl)-3-(4-(5-phenylthiazol-2-yl)phenyl)urea |
| 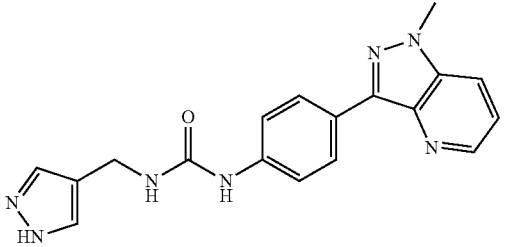 [SMILES: Cn1nc(-c2ccc(NC(=O)NCc3cn[nH]c3)cc2)c2ncccc21] | 1-[4-(1-Methyl-1H-pyrazolo[4,3-b]pyridin-3-yl)-phenyl]-3-(1H-pyrazol-4-ylmethyl)-urea |
| 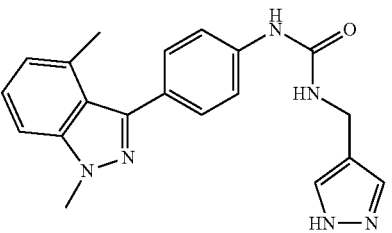 [SMILES: Cc1cccc2c1c(-c1ccc(NC(=O)NCc3cn[nH]c3)cc1)nn2C] | 1-((1H-Pyrazol-4-yl)methyl)-3-(4-(1-methyl-1H-pyrazolo[3,4-c]pyridin-3-yl)phenyl)urea |
| 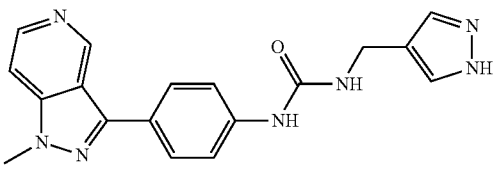 [SMILES: Cn1nc(-c2ccc(NC(=O)NCc3cn[nH]c3)cc2)c2cnccc21] | 1-((1H-Pyrazol-4-yl)methyl)-3-(4-(1,4-dimethyl-1H-indazol-3-yl)phenyl)urea |
| 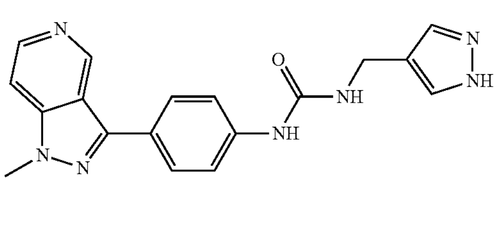 | 1-[4-(1-Methyl-1H-pyrazolo[4,3-c]pyridin-3-yl)-phenyl]-3-(1H-pyrazol-4-ylmethyl)-urea |

TABLE 4-continued

[Structure: pyrazolylmethyl-urea-phenyl-X-Y core scaffold]

| Compound Structure | Compound Name |
|---|---|
| 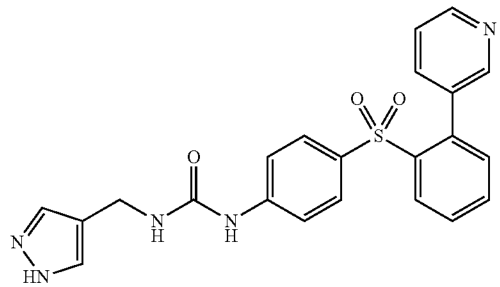 [SMILES: O=C(NCc1cn[nH]c1)Nc1ccc(S(=O)(=O)c2ccccc2-c2cccnc2)cc1] | 1-(1H-Pyrazol-4-ylmethyl)-3-[4-(1-pyridin-3-yl-benzenesulfonyl)-phenyl]-urea |
| 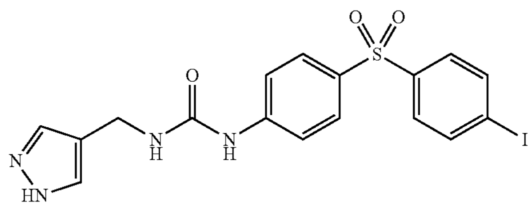 [SMILES: O=C(NCc1cn[nH]c1)Nc1ccc(S(=O)(=O)c2ccc(I)cc2)cc1] | 1-[4-(3-Iodo-benzenesulfonyl)-phenyl]-3-(1H-pyrazol-4-ylmethyl)-urea |
| 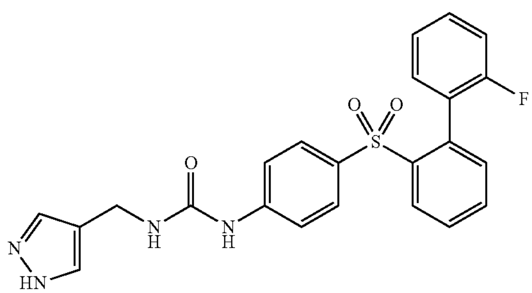 [SMILES: O=C(NCc1cn[nH]c1)Nc1ccc(S(=O)(=O)c2ccccc2-c2ccccc2F)cc1] | 1-[4-(2'-Fluoro-biphenyl-2-sulfonyl)-phenyl]-3-(1H-pyrazol-4-ylmethyl)-urea |
| 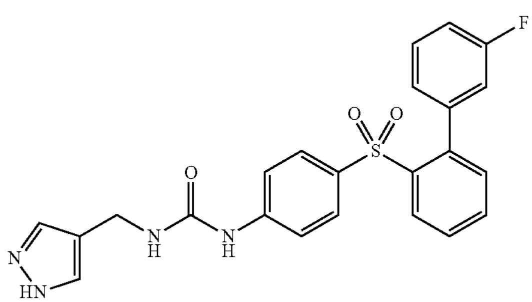 [SMILES: O=C(NCc1cn[nH]c1)Nc1ccc(S(=O)(=O)c2ccccc2-c2cccc(F)c2)cc1] | 1-[4-(3'-Fluoro-biphenyl-2-sulfonyl)-phenyl]-3-(1H-pyrazol-4-ylmethyl)-urea |
| 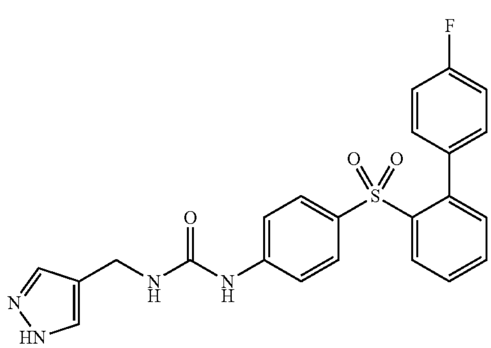 [SMILES: O=C(NCc1cn[nH]c1)Nc1ccc(S(=O)(=O)c2ccccc2-c2ccc(F)cc2)cc1] | 1-[4-(4'-Fluoro-biphenyl-2-sulfonyl)-phenyl]-3-(1H-pyrazol-4-ylmethyl)-urea |

TABLE 4-continued

| Compound Structure | Compound Name |
|---|---|
| 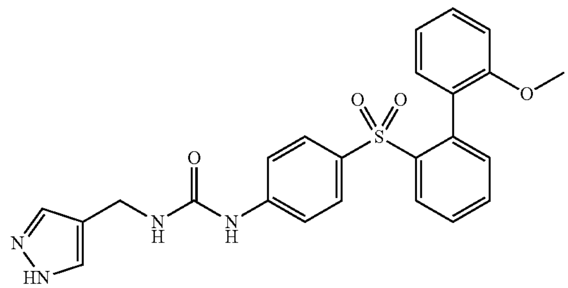 [SMILES: COc1ccccc1-c1ccccc1S(=O)(=O)c1ccc(NC(=O)NCc2cn[nH]c2)cc1] | 1-[4-(2'-Methoxy-biphenyl-2-sulfonyl)-phenyl]-3-(1H-pyrazol-4-ylmethyl)-urea |
| 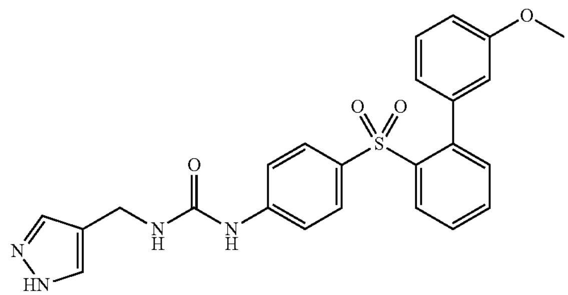 [SMILES: COc1cccc(-c2ccccc2S(=O)(=O)c2ccc(NC(=O)NCc3cn[nH]c3)cc2)c1] | 1-[4-(3'-Methoxy-biphenyl-2-sulfonyl)-phenyl]-3-(1H-pyrazol-4-ylmethyl)-urea |
| 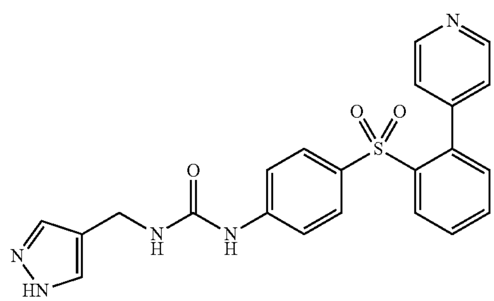 [SMILES: O=C(NCc1cn[nH]c1)Nc1ccc(S(=O)(=O)c2ccccc2-c2ccncc2)cc1] | 1-(1H-Pyrazol-4-ylmethyl)-3-[4-(2-pyridin-4-yl-benzenesulfonyl)-phenyl]-urea |
| 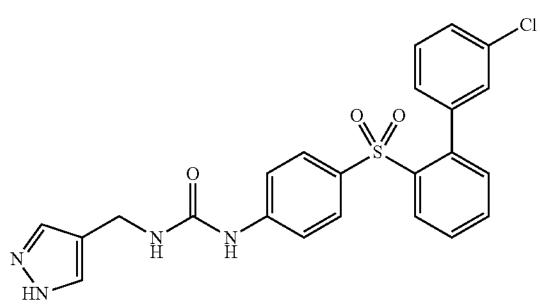 [SMILES: O=C(NCc1cn[nH]c1)Nc1ccc(S(=O)(=O)c2ccccc2-c2cccc(Cl)c2)cc1] | 1-[4-(3'-Chloro-biphenyl-2-sulfonyl)-phenyl]-3-(1H-pyrazol-4-ylmethyl)-urea |

TABLE 4-continued

| Compound Structure | Compound Name |
|---|---|
| 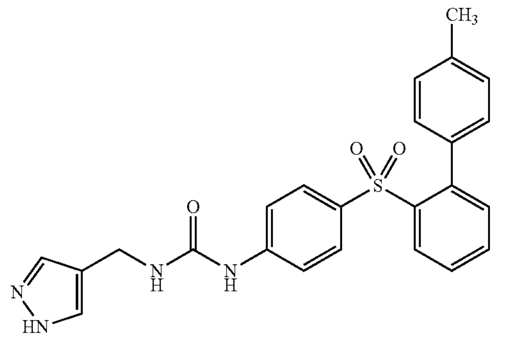 [SMILES: Cc1ccc(-c2ccccc2S(=O)(=O)c2ccc(NC(=O)NCc3cn[nH]c3)cc2)cc1] | 1-[4-(4'-Methyl-biphenyl-2-sulfonyl)-phenyl]-3-(1H-pyrazol-4-ylmethyl)-urea |
| 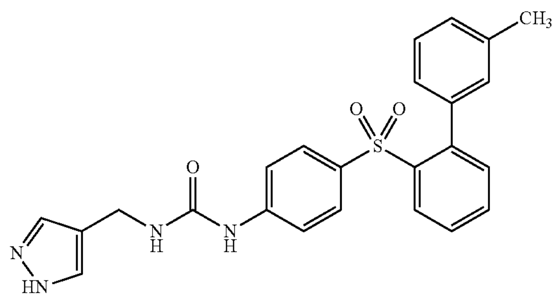 [SMILES: Cc1cccc(-c2ccccc2S(=O)(=O)c2ccc(NC(=O)NCc3cn[nH]c3)cc2)c1] | 1-[4-(3'-Methyl-biphenyl-2-sulfonyl)-phenyl]-3-(1H-pyrazol-4-ylmethyl)-urea |
| 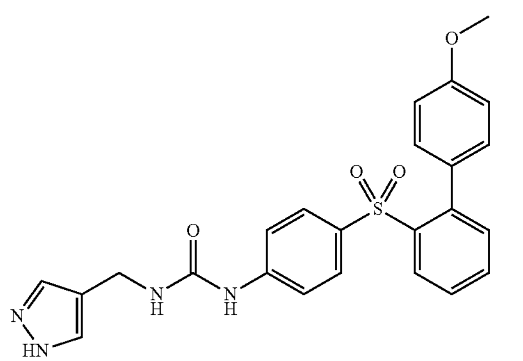 [SMILES: COc1ccc(-c2ccccc2S(=O)(=O)c2ccc(NC(=O)NCc3cn[nH]c3)cc2)cc1] | 1-[4-(4'-Methoxy-biphenyl-2-sulfonyl)-phenyl]-3-(1H-pyrazol-4-ylmethyl)-urea |
| 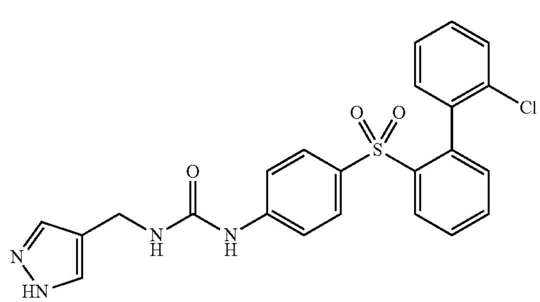 [SMILES: O=C(NCc1cn[nH]c1)Nc1ccc(S(=O)(=O)c2ccccc2-c2ccccc2Cl)cc1] | 1-((1H-Pyrazol-4-yl)methyl)-3-(4-((2'-chloro-[1,1'-biphenyl]-2-yl)sulfonyl)phenyl)urea |

TABLE 4-continued

| Compound Structure | Compound Name |
|---|---|
| 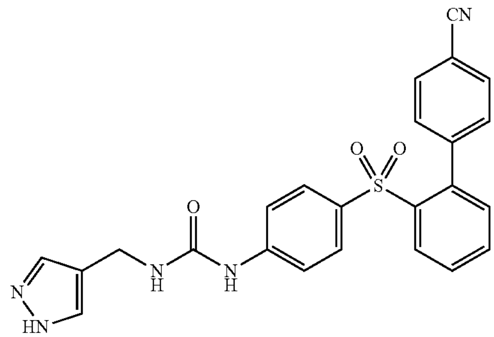 [SMILES: N#Cc1ccc(-c2ccccc2S(=O)(=O)c2ccc(NC(=O)NCc3cn[nH]c3)cc2)cc1] | 1-((1H-Pyrazol-4-yl)methyl)-3-(4-((4'-cyano-[1,1'-biphenyl]-2-yl)sulfonyl)phenyl)urea |
| 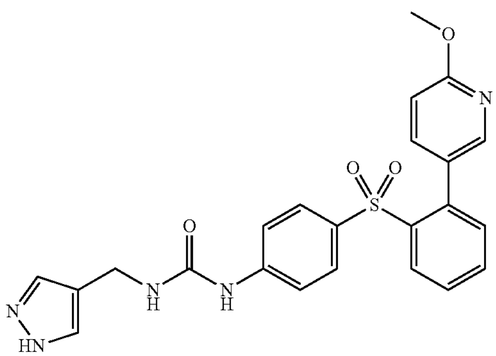 [SMILES: COc1ccc(-c2ccccc2S(=O)(=O)c2ccc(NC(=O)NCc3cn[nH]c3)cc2)cn1] | 1-((1H-Pyrazol-4-yl)methyl)-3-(4-((2-(6-methoxypyridin-3-yl)phenyl)sulfonyl)phenyl)urea |
| 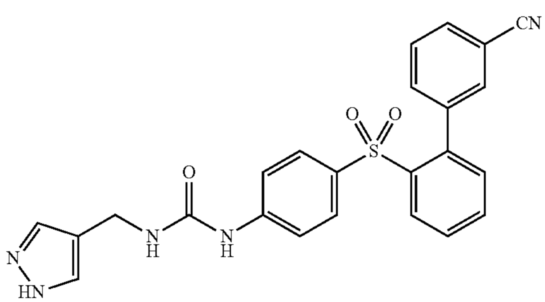 [SMILES: N#Cc1cccc(-c2ccccc2S(=O)(=O)c2ccc(NC(=O)NCc3cn[nH]c3)cc2)c1] | 1-((1H-Pyrazol-4-yl)methyl)-3-(4-((3'-cyano-[1,1'-biphenyl]-2-yl)sulfonyl)phenyl)urea |
| 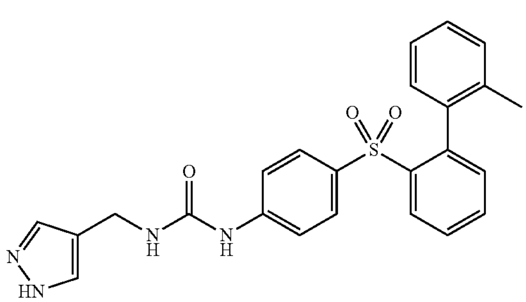 [SMILES: Cc1ccccc1-c1ccccc1S(=O)(=O)c1ccc(NC(=O)NCc2cn[nH]c2)cc1] | 1-((1H-Pyrazol-4-yl)methyl)-3-(4-((2'-methyl-[1,1'-biphenyl]-2-yl)sulfonyl)phenyl)urea |

TABLE 4-continued

| Compound Structure | Compound Name |
|---|---|
| (structure: 1H-pyrazol-4-ylmethyl-urea with phenyl-sulfonyl-pyridin-2-ol) | 1-[4-(6-Hydroxy-pyridine-3-sulfonyl)-phenyl]-3-(1H-pyrazol-4-ylmethyl)-urea |

In one aspect, provided herein is a pharmaceutically acceptable salt or solvate of a compound described in Table 4.

TABLE 5

| Compound Structure | Compound Name |
|---|---|
| (structure with OCF₃) | 1-Oxazol-5-ylmethyl-3-[4-(4-trifluoromethoxy-benzenesulfonyl)-phenyl]-urea |
| (structure with CN) | 1-[4-(4-Cyano-benzenesulfonyl)-phenyl]-3-oxazol-5-ylmethyl-urea |
| (structure with 3-Cl) | 1-(3-Chlorophenyl)-N-(4-(3-(oxazol-5-ylmethyl)ureido)phenyl)methanesulfonamide |
| (structure with 4-Cl) | 1-(4-Chlorophenyl)-N-(4-(3-(oxazol-5-ylmethyl)ureido)phenyl)methanesulfonamide |

TABLE 5-continued

| Compound Structure | Compound Name |
|---|---|
| 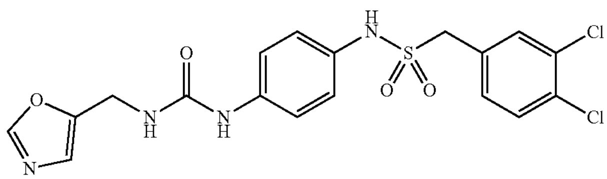 [SMILES: O=C(NCc1cnco1)Nc1ccc(NS(=O)(=O)Cc2ccc(Cl)c(Cl)c2)cc1] | 1-(3,4-Dichlorophenyl)-N-(4-(3-(oxazol-5-ylmethyl)ureido)phenyl)methanesulfonamide |
| 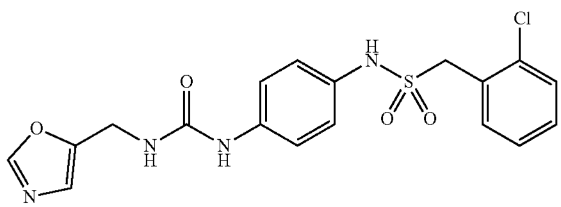 [SMILES: O=C(NCc1cnco1)Nc1ccc(NS(=O)(=O)Cc2ccccc2Cl)cc1] | 1-(2-Chlorophenyl)-N-(4-(3-(oxazol-5-ylmethyl)ureido)phenyl)methanesulfonamide |
| 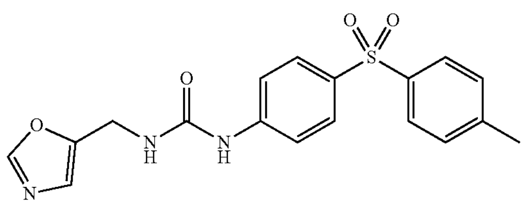 [SMILES: Cc1ccc(S(=O)(=O)c2ccc(NC(=O)NCc3cnco3)cc2)cc1] | 1-Oxazol-5-ylmethyl-3-[4-(toluene-4-sulfonyl)-phenyl]-urea |
| 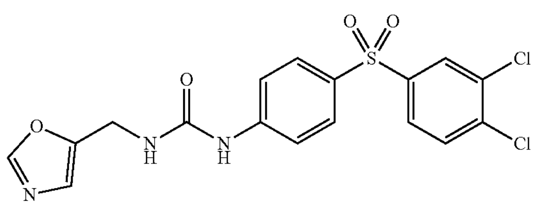 [SMILES: O=C(NCc1cnco1)Nc1ccc(S(=O)(=O)c2ccc(Cl)c(Cl)c2)cc1] | 1-[4-(3,4-Dichloro-benzenesulfonyl)-phenyl]-3-oxazol-5-ylmethyl-urea |
| 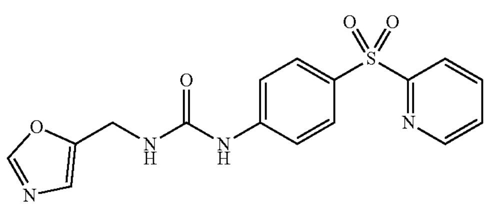 [SMILES: O=C(NCc1cnco1)Nc1ccc(S(=O)(=O)c2ccccn2)cc1] | 1-(Oxazol-5-ylmethyl)-3-(4-(pyridin-2-ylsulfonyl)phenyl)urea |
| 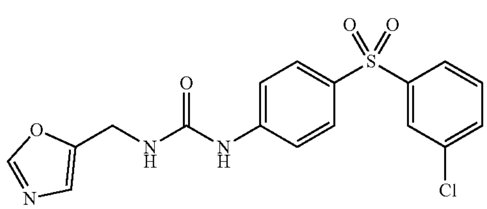 [SMILES: O=C(NCc1cnco1)Nc1ccc(S(=O)(=O)c2cccc(Cl)c2)cc1] | 1-(4-((3-Chlorophenyl)sulfonyl)phenyl)-3-(oxazol-5-ylmethypurea |
| 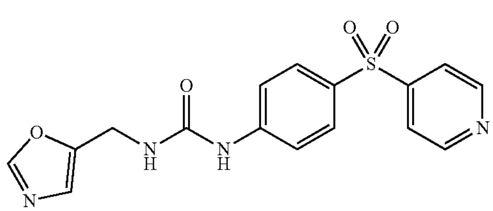 [SMILES: O=C(NCc1cnco1)Nc1ccc(S(=O)(=O)c2ccncc2)cc1] | 1-(Oxazol-5-ylmethyl)-3-(4-(pyridin-4-ylsulfonyl)phenyl)urea |

TABLE 5-continued

| Compound Structure | Compound Name |
|---|---|
| | 1-(4-((2-Methoxyphenyl)sulfonyl)phenyl)-3-(oxazol-5-ylmethyl)urea |
| 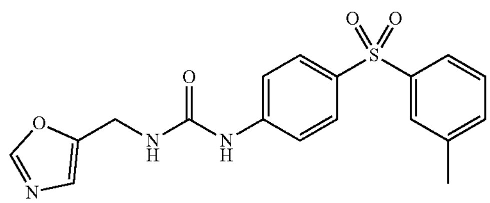 [SMILES: Cc1cccc(S(=O)(=O)c2ccc(NC(=O)NCc3cnco3)cc2)c1] | 1-Oxazol-5-ylmethyl-3-[4-(toluene-3-sulfonyl)-phenyl]-urea |
| 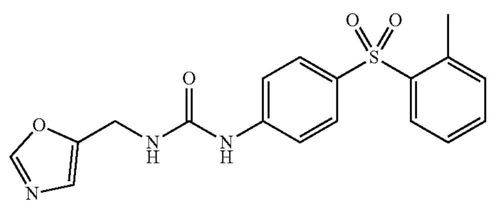 [SMILES: Cc1ccccc1S(=O)(=O)c1ccc(NC(=O)NCc2cnco2)cc1] | 1-Oxazol-5-ylmethyl-3-[4-(toluene-2-sulfonyl)-phenyl]-urea |
| 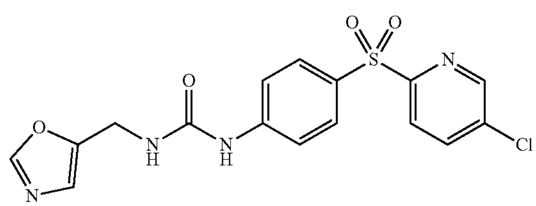 [SMILES: O=C(NCc1cnco1)Nc1ccc(S(=O)(=O)c2ccc(Cl)cn2)cc1] | 1-[4-(5-Chloro-pyridine-2-sulfonyl)-phenyl]-3-oxazol-5-ylmethyl-urea |
| 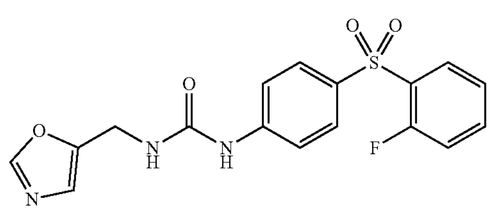 [SMILES: O=C(NCc1cnco1)Nc1ccc(S(=O)(=O)c2ccccc2F)cc1] | 1-(4-((2-Fluorophenyl)sulfonyl)phenyl)-3-(oxazol-5-ylmethyl)urea |
| 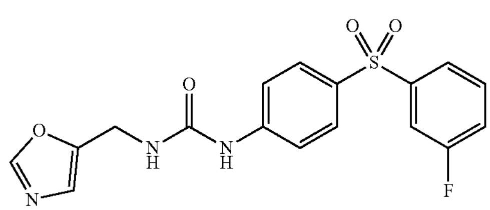 | 1-(4-((3-Fluorophenyl)sulfonyl)phenyl)-3-(oxazol-5-ylmethyl)urea |

TABLE 5-continued

| Compound Structure | Compound Name |
|---|---|
| 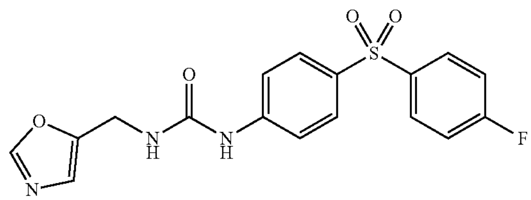 [SMILES: O=C(NCc1cnco1)Nc1ccc(S(=O)(=O)c2ccc(F)cc2)cc1] | 1-(4-((4-Fluorophenyl)sulfonyl)phenyl)-3-(oxazol-5-ylmethyl)urea |
| 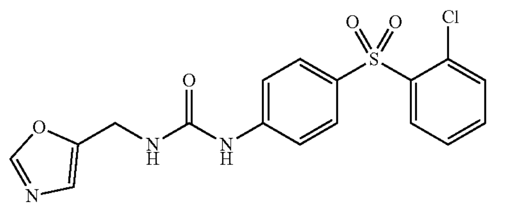 [SMILES: O=C(NCc1cnco1)Nc1ccc(S(=O)(=O)c2ccccc2Cl)cc1] | 1-[4-(2-Chloro-benzenesulfonyl)-phenyl]-3-oxazol-5-ylmethyl-urea |
| 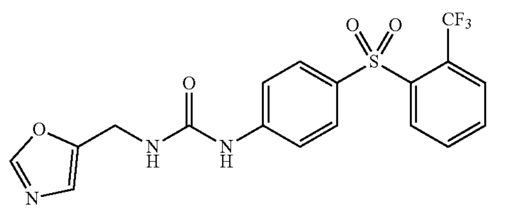 [SMILES: O=C(NCc1cnco1)Nc1ccc(S(=O)(=O)c2ccccc2C(F)(F)F)cc1] | 1-Oxazol-5-ylmethyl-3-[4-(2-trifluoromethyl-benzenesulfonyl)-phenyl]-urea |
| 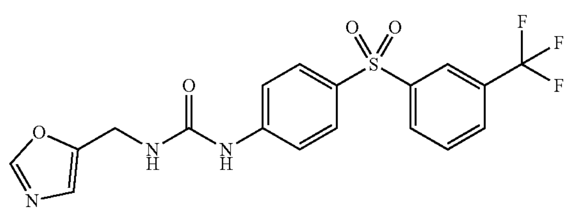 [SMILES: O=C(NCc1cnco1)Nc1ccc(S(=O)(=O)c2cccc(C(F)(F)F)c2)cc1] | 1-(Oxazol-5-ylmethyl)-3-(4-((3-(trifluoromethyl)phenyl)sulfonyl)phenyl)urea |
| 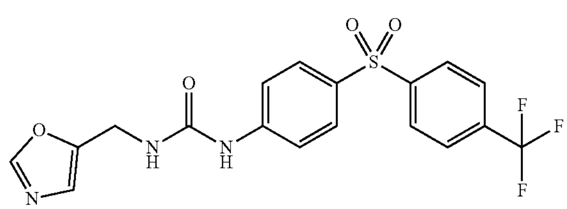 [SMILES: O=C(NCc1cnco1)Nc1ccc(S(=O)(=O)c2ccc(C(F)(F)F)cc2)cc1] | 1-(Oxazol-5-ylmethyl)-3-(4-((4-(trifluoromethyl)phenyl)sulfonyl)phenyl)urea |
| 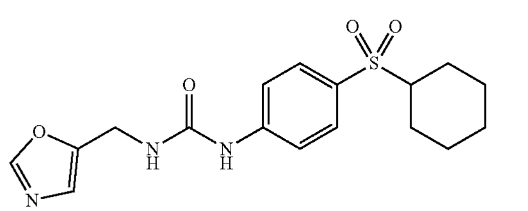 [SMILES: O=C(NCc1cnco1)Nc1ccc(S(=O)(=O)C2CCCCC2)cc1] | 1-(4-Cyclohexanesulfonyl-phenyl)-3-oxazol-5-ylmethyl-urea |

TABLE 5-continued

| Compound Structure | Compound Name |
|---|---|
| 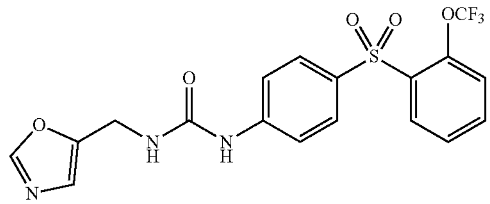 [SMILES: O=C(NCc1cnco1)Nc1ccc(S(=O)(=O)c2ccccc2OC(F)(F)F)cc1] | 1-Oxazol-5-ylmethyl-3-[4-(4-trifluoromethoxy-benzenesulfonyl)-phenyl]-urea |
| 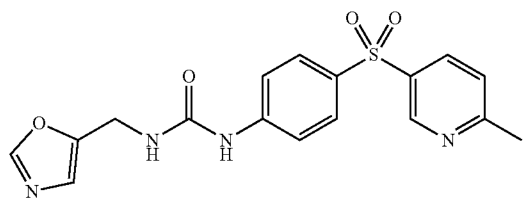 | 1-[4-(6-Methyl-pyridine-3-sulfonyl)-phenyl]-3-oxazol-5-ylmethyl-urea |
| 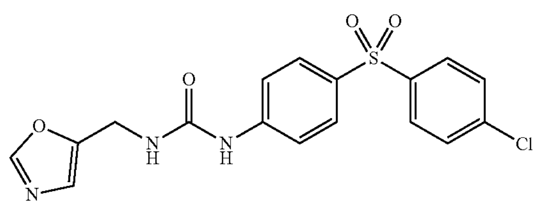 [SMILES: O=C(NCc1cnco1)Nc1ccc(S(=O)(=O)c2ccc(Cl)cc2)cc1] | 1-(4-((4-Chlorophenyl)sulfonyl)phenyl)-3-(oxazol-5-ylmethyl)urea |
| 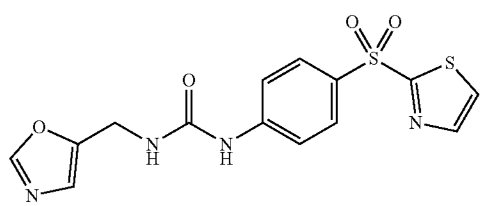 [SMILES: O=C(NCc1cnco1)Nc1ccc(S(=O)(=O)c2nccs2)cc1] | 1-Oxazol-5-ylmethyl-3-[4-(thiazole-2-sulfonyl)-phenyl]-urea |
| 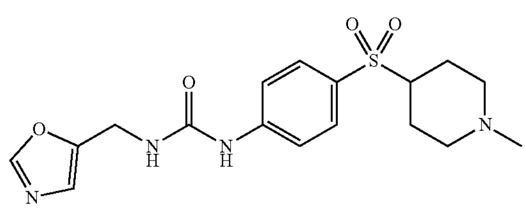 [SMILES: CN1CCC(S(=O)(=O)c2ccc(NC(=O)NCc3cnco3)cc2)CC1] | 1-[4-(1-Methyl-piperidine-4-sulfonyl)-phenyl]-3-oxazol-5-ylmethyl-urea |
| 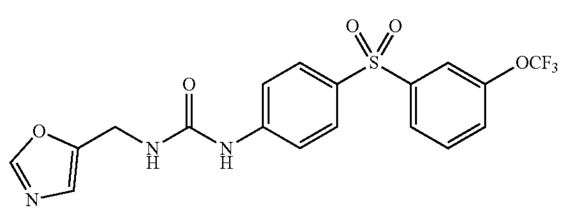 [SMILES: O=C(NCc1cnco1)Nc1ccc(S(=O)(=O)c2cccc(OC(F)(F)F)c2)cc1] | 1-Oxazol-5-ylmethyl-3-[4-(3-trifluoromethoxy-benzenesulfonyl)-phenyl]-urea |

TABLE 5-continued

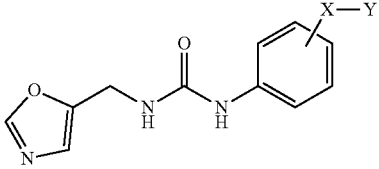

| Compound Structure | Compound Name |
| --- | --- |
| 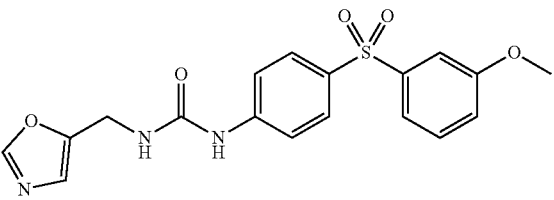 [SMILES: COc1cccc(S(=O)(=O)c2ccc(NC(=O)NCc3cnco3)cc2)c1] | 1-[4-(3-Methoxy-benzenesulfonyl)-phenyl]-3-oxazol-5-ylmethyl-urea |
| 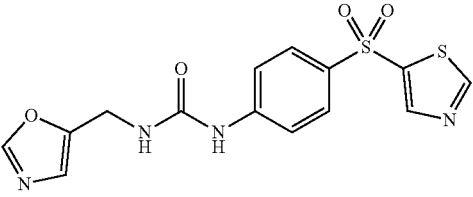 [SMILES: O=C(NCc1cnco1)Nc1ccc(S(=O)(=O)c2cncs2)cc1] | 1-[4-(3,4-Difluoro-benzenesulfonyl)-phenyl]-3-oxazol-5-ylmethyl-urea |
| 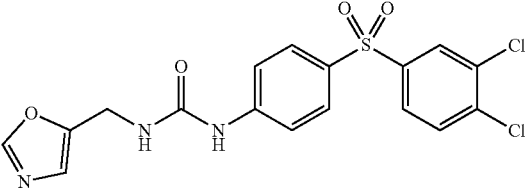 [SMILES: O=C(NCc1cnco1)Nc1ccc(S(=O)(=O)c2ccc(Cl)c(Cl)c2)cc1] | 1-Oxazol-5-ylmethyl-3-[4-(thiazole-2-sulfonyl)-phenyl]-urea |
| 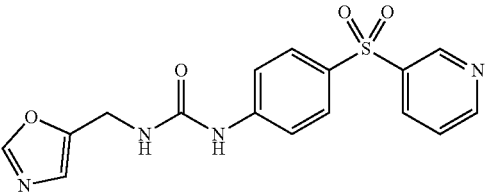 [SMILES: O=C(NCc1cnco1)Nc1ccc(S(=O)(=O)c2cccnc2)cc1] | 1-[4-(3,4-Dichloro-benzenesulfonyl)-phenyl]-3-oxazol-5-ylmethyl-urea |
| 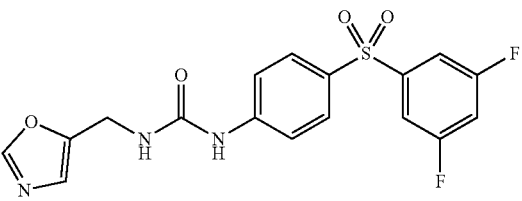 | 1-Oxazol-5-ylmethyl-3-[4-(pyridine-3-sulfonyl)-phenyl]-urea |
| 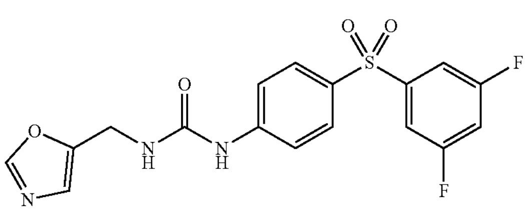 [SMILES: O=C(NCc1cnco1)Nc1ccc(S(=O)(=O)c2cc(F)cc(F)c2)cc1] | 1-[4-(3,5-Difluoro-benzenesulfonyl)-phenyl]-3-oxazol-5-ylmethyl-urea |

TABLE 5-continued

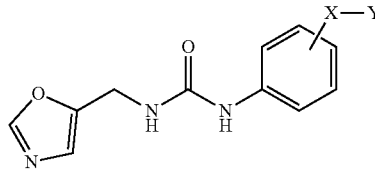

| Compound Structure | Compound Name |
|---|---|
| 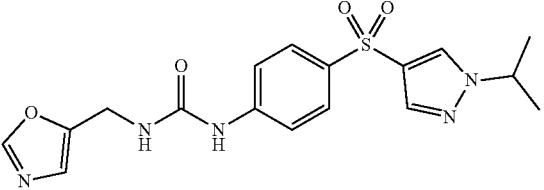 [SMILES: CC(C)n1cc(S(=O)(=O)c2ccc(NC(=O)NCc3cnco3)cc2)cn1] | 1-[4-(1-Isopropyl-1H-pyrazole-4-sulfonyl)-phenyl]-3-oxazol-5-ylmethyl-urea |
| 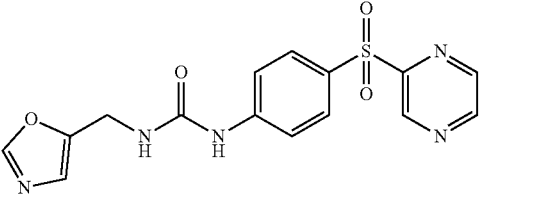 [SMILES: O=C(NCc1cnco1)Nc1ccc(S(=O)(=O)c2cnccn2)cc1] | 1-Oxazol-5-ylmethyl-3-[4-(pyrazine-2-sulfonyl)-phenyl]-urea |
| 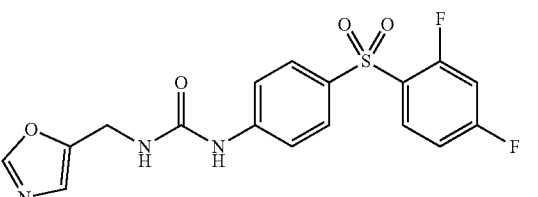 | 1-[4-(2,4-Difluoro-benzenesulfonyl)-phenyl]-3-oxazol-5-ylmethyl-urea |
| 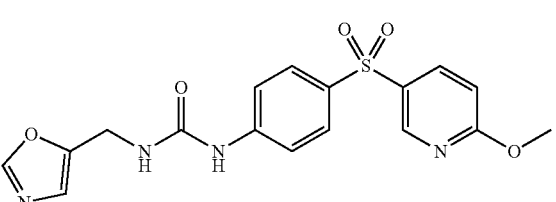 | 1-[4-(6-Methoxy-pyridine-3-sulfonyl)-phenyl]-3-oxazol-5-ylmethyl-urea |
| 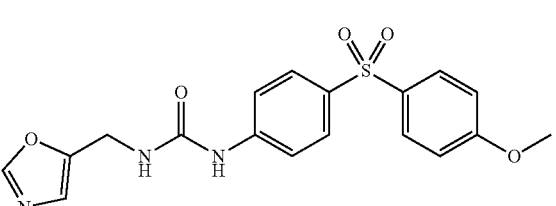 | 1-[4-(4-Methoxy-benzenesulfonyl)-phenyl]-3-oxazol-5-ylmethyl-urea |
| 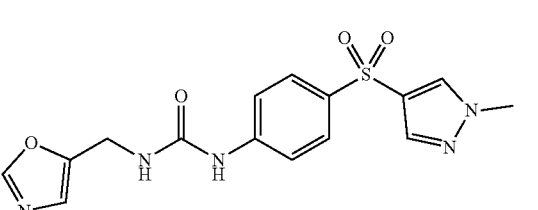 | 1-[4-(1-Methyl-1H-pyrazole-4-sulfonyl)-phenyl]-3-oxazol-5-ylmethyl-urea |

TABLE 5-continued

| Compound Structure | Compound Name |
|---|---|
| 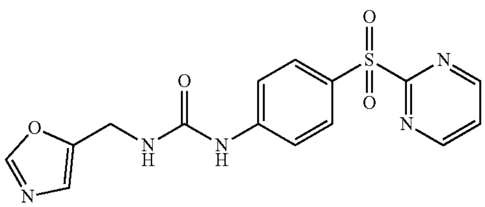 [SMILES: O=C(NCc1cnco1)Nc1ccc(S(=O)(=O)c2ncccn2)cc1] | 1-Oxazol-5-ylmethyl-3-[4-(pyrimidine-2-sulfonyl)-phenyl]-urea |
| 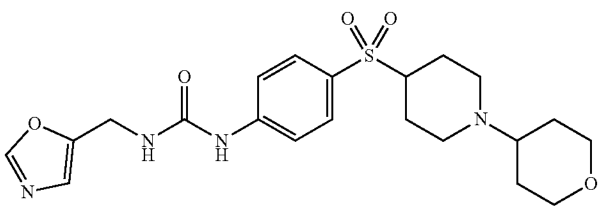 [SMILES: O=C(NCc1cnco1)Nc1ccc(S(=O)(=O)C2CCN(C3CCOCC3)CC2)cc1] | 1-Oxazol-5-ylmethyl-3-{4-[1-(tetrahydro-pyran-4-yl)-piperidine-4-sulfonyl]-phenyl}-urea |
| 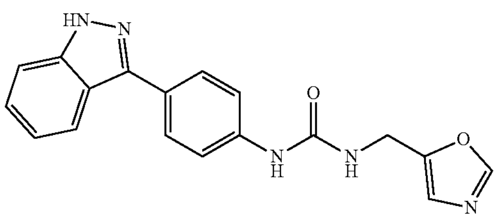 [SMILES: O=C(NCc1cnco1)Nc1ccc(-c2n[nH]c3ccccc23)cc1] | 1-[4-(1H-Indazol-3-yl)-phenyl]-3-oxazol-5-ylmethyl-urea |
| 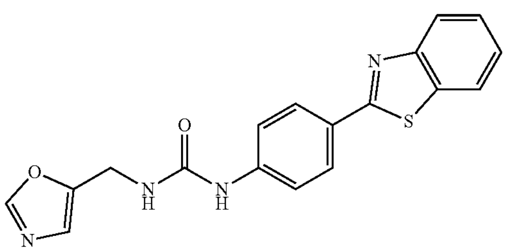 [SMILES: O=C(NCc1cnco1)Nc1ccc(-c2nc3ccccc3s2)cc1] | 1-(4-(Benzo[d]thiazol-2-yl)phenyl)-3-(oxazol-5-ylmethyl)urea |
| 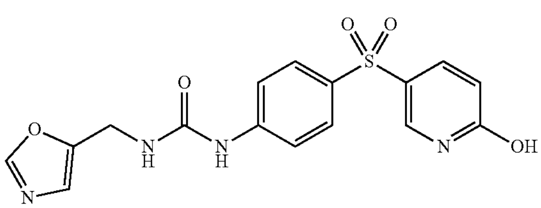 [SMILES: O=C(NCc1cnco1)Nc1ccc(S(=O)(=O)c2ccc(O)nc2)cc1] | 1-[4-(6-Hydroxy-pyridine-3-sulfonyl)-phenyl]-3-oxazol-5-ylmethyl-urea |
| 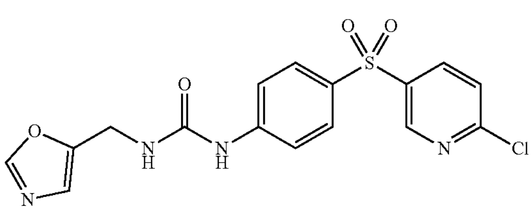 [SMILES: O=C(NCc1cnco1)Nc1ccc(S(=O)(=O)c2ccc(Cl)nc2)cc1] | 1-[4-(6-Chloro-pyridine-3-sulfonyl)-phenyl]-3-oxazol-5-ylmethyl-urea |

TABLE 5-continued

| Compound Structure | Compound Name |
|---|---|
| 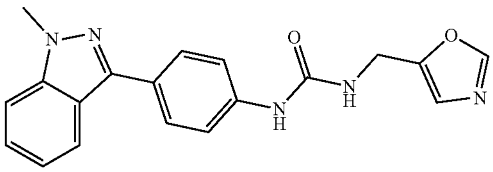 [SMILES: Cn1nc(-c2ccc(NC(=O)NCc3cnco3)cc2)c2ccccc21] | 1-[4-(1-Methyl-1H-indazol-3-yl)-phenyl]-3-oxazol-5-ylmethyl-urea |
| 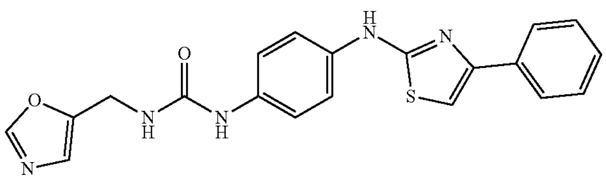 [SMILES: O=C(NCc1cnco1)Nc1ccc(Nc2nc(-c3ccccc3)cs2)cc1] | 1-(Oxazol-5-ylmethyl)-3-(4-((4-phenylthiazol-2-yl)amino)phenyl)urea |
| 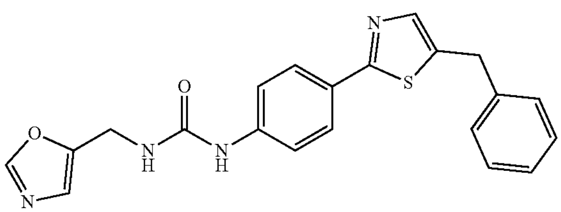 [SMILES: O=C(NCc1cnco1)Nc1ccc(-c2ncc(Cc3ccccc3)s2)cc1] | 1-(4-(5-Benzylthiazol-2-yl)phenyl)-3-(oxazol-5-ylmethyl)urea |
| 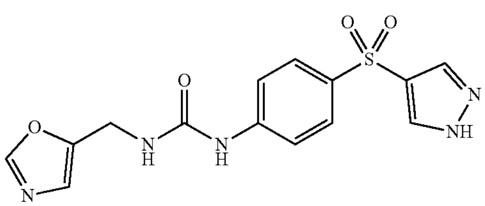 [SMILES: O=C(NCc1cnco1)Nc1ccc(S(=O)(=O)c2cn[nH]c2)cc1] | 1-(4-((1H-pyrazol-4-yl)sulfonyl)phenyl)-3-(oxazol-5-ylmethyl)urea |
| 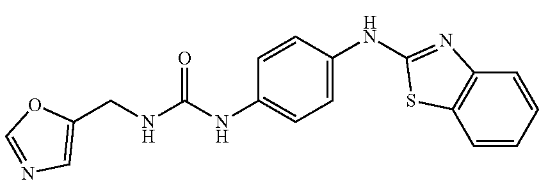 [SMILES: O=C(NCc1cnco1)Nc1ccc(Nc2nc3ccccc3s2)cc1] | 1-(4-(Benzo[d]thiazol-2-ylamino)phenyl)-3-(oxazol-5-ylmethyl)urea |
| 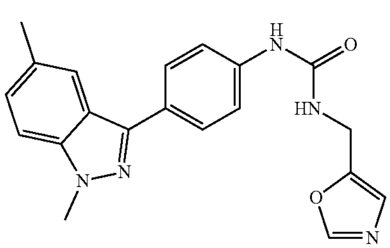 [SMILES: Cc1ccc2c(c1)c(-c1ccc(NC(=O)NCc3cnco3)cc1)nn2C] | 1-(4-(1,5-Dimethyl-1H-indazol-3-yl)phenyl)-3-(oxazol-5-ylmethyl)urea |

TABLE 5-continued
| Compound Structure | Compound Name |
|---|---|
| 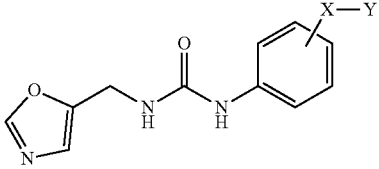 | 1-[4-(1,6-Dimethyl-1H-indazol-3-yl)-phenyl]-3-oxazol-5-ylmethyl-urea |
| 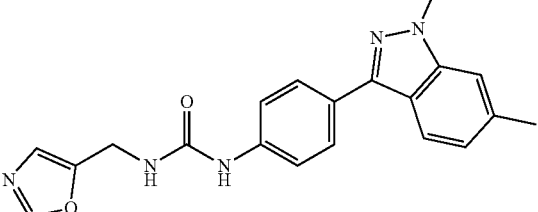 | 1-(4-(1,7-Dimethyl-1H-indazol-3-yl)phenyl)-3-(oxazol-5-ylmethyl)urea |
| 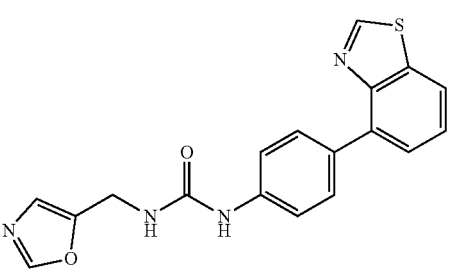 [SMILES: O=C(NCc1cnco1)Nc1ccc(-c2cccc3scnc23)cc1] | 1-(4-Benzothiazol-4-yl-phenyl)-3-oxazol-5-ylmethyl-urea |
| 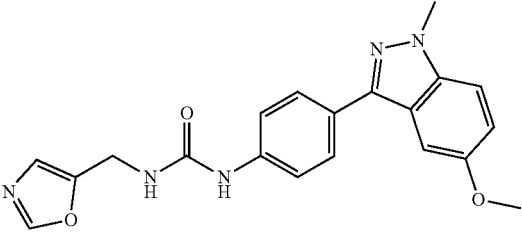 [SMILES: COc1ccc2c(c1)c(-c1ccc(NC(=O)NCc3cnco3)cc1)nn2C] | 1-[4-(5-Methoxy-1-methyl-1H-indazol-3-yl)-phenyl]-3-oxazol-5-ylmethyl-urea |
| 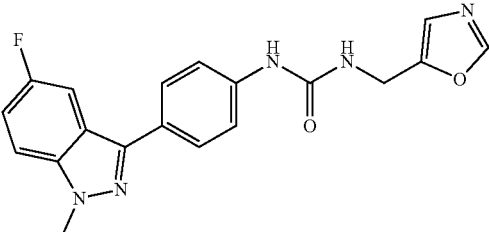 | 1-[4-(5-Fluoro-1-methyl-1H-indazol-3-yl)-phenyl]-3-oxazol-5-ylmethyl-urea |

TABLE 5-continued

| Compound Structure | Compound Name |
|---|---|
| 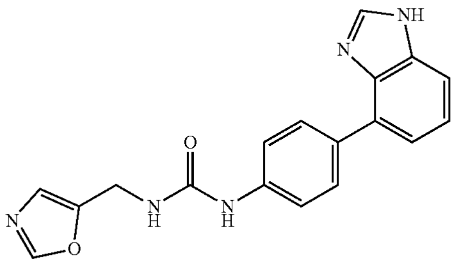 [SMILES: O=C(NCc1cnco1)Nc1ccc(-c2cccc3[nH]cnc23)cc1] | 1-[4-(1H-Benzoimidazol-4-yl)-phenyl]-3-oxazol-5-ylmethyl-urea |
| 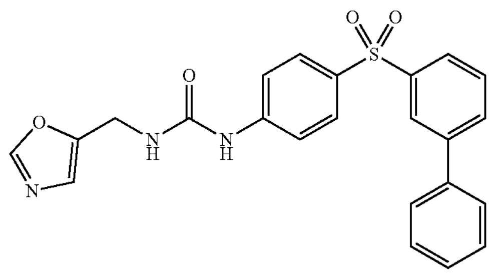 [SMILES: O=C(NCc1cnco1)Nc1ccc(S(=O)(=O)c2cccc(-c3ccccc3)c2)cc1] | 1-(4-([1,1'-Biphenyl]-3-ylsulfonyl)phenyl)-3-(oxazol-5-ylmethyl)urea |
| 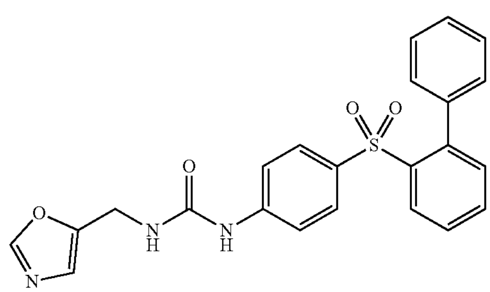 [SMILES: O=C(NCc1cnco1)Nc1ccc(S(=O)(=O)c2ccccc2-c2ccccc2)cc1] | 1-(4-([1,1'-Biphenyl]-2-ylsulfonyl)phenyl)-3-(oxazol-5-ylmethyl)urea |
| 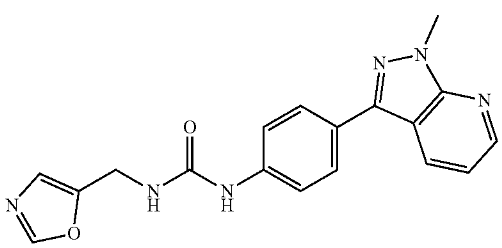 [SMILES: Cn1nc(-c2ccc(NC(=O)NCc3cnco3)cc2)c2cccnc21] | 1-[4-(1-Methyl-1H-pyrazolo[3,4-b]pyridin-3-yl)-phenyl]-3-oxazol-5-ylmethyl-urea |
| 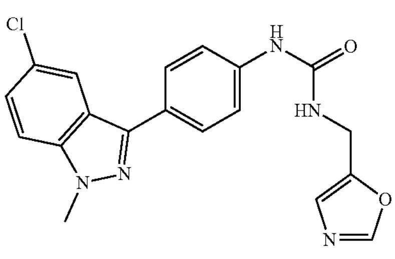 [SMILES: Cn1nc(-c2ccc(NC(=O)NCc3cnco3)cc2)c2cc(Cl)ccc21] | 1-(4-(5-Chloro-1-methyl-1H-indazol-3-yl)phenyl)-3-(oxazol-5-ylmethyl)urea |

TABLE 5-continued

| Compound Structure | Compound Name |
|---|---|
| 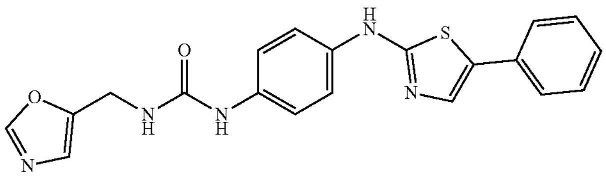 [SMILES: O=C(NCc1cnco1)Nc1ccc(Nc2ncc(-c3ccccc3)s2)cc1] | 1-(Oxazol-5-ylmethyl)-3-(4-((5-phenylthiazol-2-yl)amino)phenyl)urea |
| 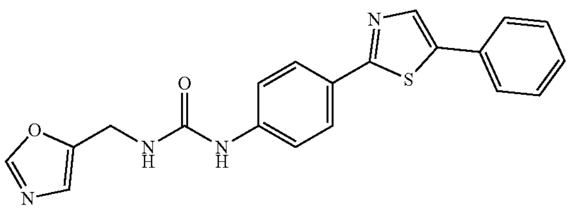 [SMILES: O=C(NCc1cnco1)Nc1ccc(-c2ncc(-c3ccccc3)s2)cc1] | 1-(Oxazol-5-ylmethyl)-3-(4-((5-phenylthiazol-2-yl)phenyl)urea |
| 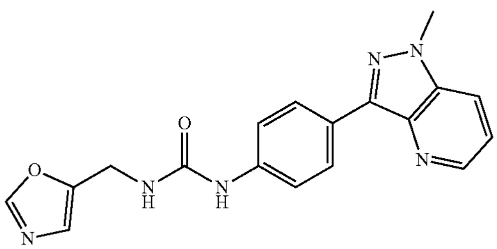 [SMILES: Cn1nc(-c2ccc(NC(=O)NCc3cnco3)cc2)c2ncccc21] | 1-[4-(1-Methyl-1H-pyrazolo[4,3-b]pyridin-3-yl)-phenyl]-3-oxazol-5-ylmethyl-urea |
| 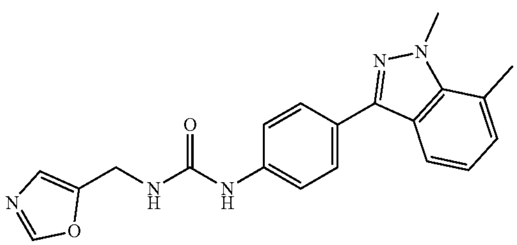 [SMILES: Cc1cccc2c(-c3ccc(NC(=O)NCc4cnco4)cc3)nn(C)c12] | 1-(4-(1,7-Dimethyl-1H-indazol-3-yl)phenyl)-3-(oxazol-5-ylmethyl)urea |
| 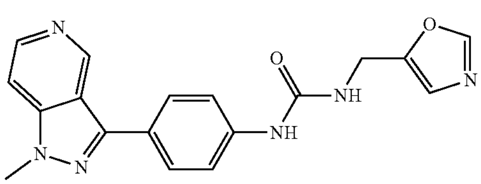 [SMILES: Cn1nc(-c2ccc(NC(=O)NCc3cnco3)cc2)c2cnccc21] | 1-[4-(1-Methyl-1H-pyrazolo[4,3-c]pyridin-3-yl)-phenyl]-3-oxazol-5-ylmethyl-urea |

In one aspect, provided herein is a pharmaceutically acceptable salt or solvate of a compound described in Table 5.

TABLE 6

| Compound Structure | Compound Name |
|---|---|
| 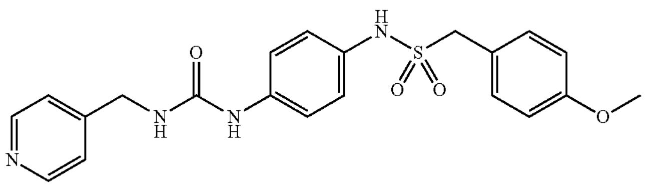 [SMILES: COc1ccc(CS(=O)(=O)Nc2ccc(NC(=O)NCc3ccncc3)cc2)cc1] | C-(4-Methoxy-phenyl)-N-[4-(3-pyridin-4-ylmethyl-ureido)-phenyl]-methanesulfonamide |
| 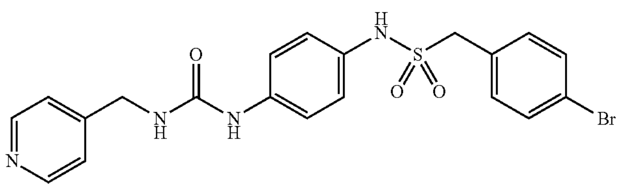 [SMILES: O=C(NCc1ccncc1)Nc1ccc(NS(=O)(=O)Cc2ccc(Br)cc2)cc1] | C-(4-Bromo-phenyl)-N-[4-(3-pyridin-4-ylmethyl-ureido)-phenyl]-methanesulfonamide |
| 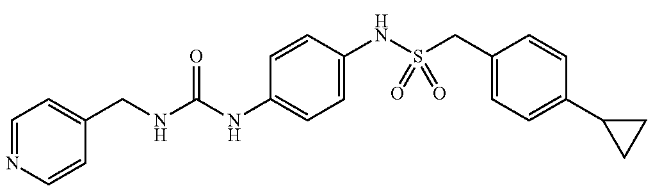 [SMILES: O=C(NCc1ccncc1)Nc1ccc(NS(=O)(=O)Cc2ccc(C3CC3)cc2)cc1] | C-(4-Cyclopropyl-phenyl)-N-[4-(3-pyridin-4-ylmethyl-ureido)-phenyl]-methanesulfonamide |
| 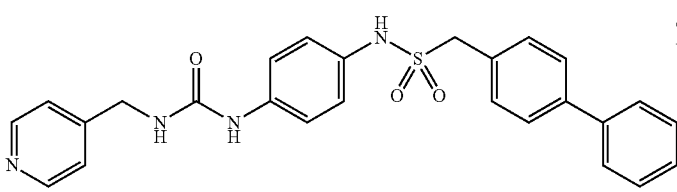 [SMILES: O=C(NCc1ccncc1)Nc1ccc(NS(=O)(=O)Cc2ccc(-c3ccccc3)cc2)cc1] | C-Biphenyl-4-yl-N-[4-(3-pyridin-4-ylmethyl-ureido)-phenyl]-methanesulfonamide |
| 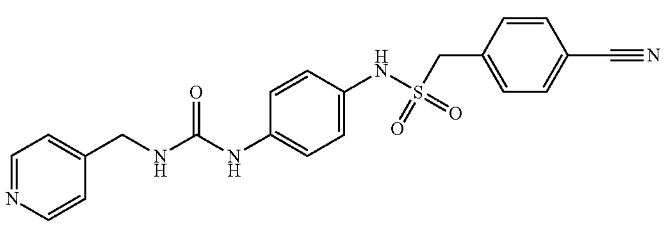 [SMILES: N#Cc1ccc(CS(=O)(=O)Nc2ccc(NC(=O)NCc3ccncc3)cc2)cc1] | C-(4-Cyano-phenyl)-N-[4-(3-pyridin-4-ylmethyl-ureido)-phenyl]-methanesulfonamide |
| 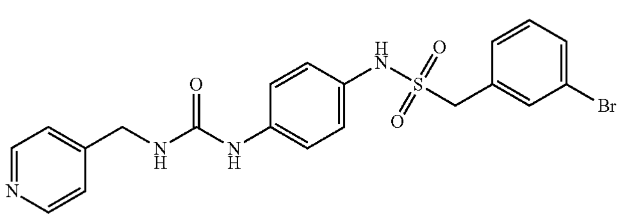 [SMILES: O=C(NCc1ccncc1)Nc1ccc(NS(=O)(=O)Cc2cccc(Br)c2)cc1] | 1-[4-(3-Bromo-benzylsulfanylamino)-phenyl]-3-pyridin-4-ylmethyl-urea |

TABLE 6-continued

| Compound Structure | Compound Name |
|---|---|
| 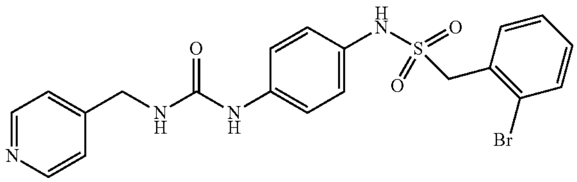 [SMILES: O=C(NCc1ccncc1)Nc1ccc(NS(=O)(=O)Cc2ccccc2Br)cc1] | C-(2-Bromo-phenyl)-N-[4-(3-pyridin-4-ylmethyl-ureido)-phenyl]-methanesulfonamide |
| 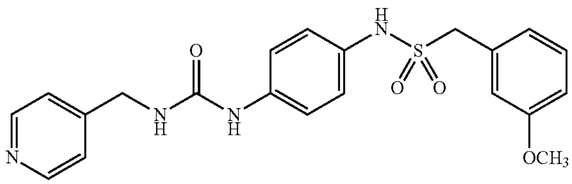 [SMILES: COc1cccc(CS(=O)(=O)Nc2ccc(NC(=O)NCc3ccncc3)cc2)c1] | C-(3-Methoxy-phenyl)-N-[4-(3-pyridin-4-ylmethyl-ureido)-phenyl]-methanesulfonamide |
| 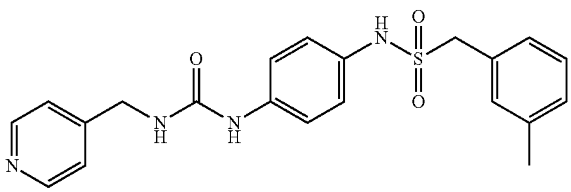 [SMILES: Cc1cccc(CS(=O)(=O)Nc2ccc(NC(=O)NCc3ccncc3)cc2)c1] | N-[4-(3-Pyridin-4-ylmethyl-ureido)-phenyl]-C-m-tolyl-methanesulfonamide |
| 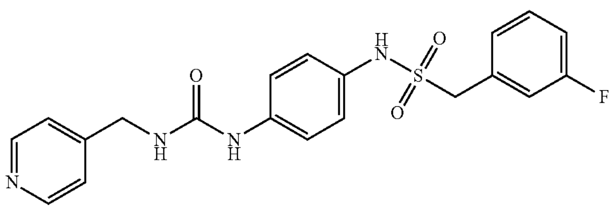 [SMILES: O=C(NCc1ccncc1)Nc1ccc(NS(=O)(=O)Cc2cccc(F)c2)cc1] | C-(3-Fluoro-phenyl)-N-[4-(3-pyridin-4-ylmethyl-ureido)-phenyl]-methanesulfonamide |
| 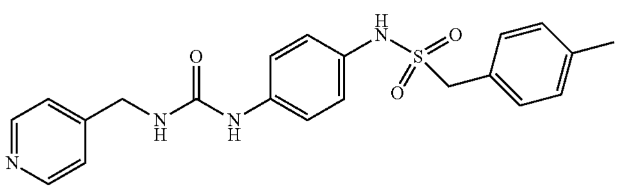 [SMILES: Cc1ccc(CS(=O)(=O)Nc2ccc(NC(=O)NCc3ccncc3)cc2)cc1] | N-[4-(3-Pyridin-4-ylmethyl-ureido)-phenyl]-C-p-tolyl-methanesulfonamide |
| 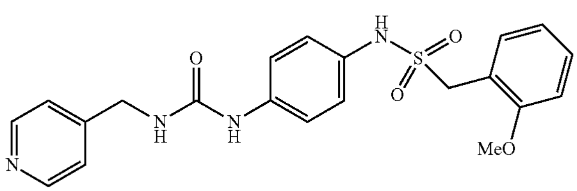 [SMILES: COc1ccccc1CS(=O)(=O)Nc1ccc(NC(=O)NCc2ccncc2)cc1] | C-(2-Methoxy-phenyl)-N-[4-(3-pyridin-4-ylmethyl-ureido)-phenyl]-methanesulfonamide |
| 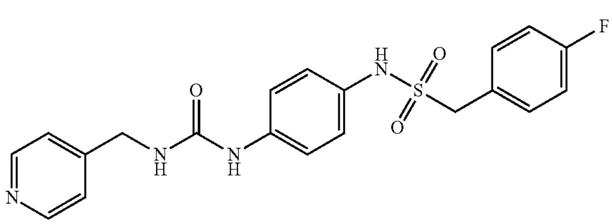 [SMILES: O=C(NCc1ccncc1)Nc1ccc(NS(=O)(=O)Cc2ccc(F)cc2)cc1] | 1-[4-(4-Fluoro-phenylmethanesulfonyl)-phenyl]-3-(1H-pyrazol-4-yl)-urea |

TABLE 6-continued

| Compound Structure | Compound Name |
|---|---|
| 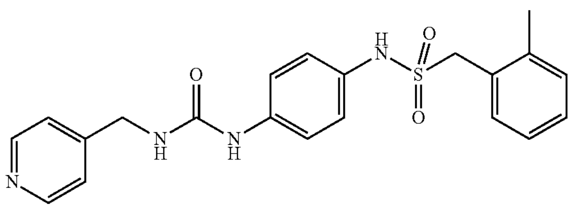 [SMILES: Cc1ccccc1CS(=O)(=O)Nc1ccc(NC(=O)NCc2ccncc2)cc1] | 1-[4-(2-Methyl-benzylsulfanylamino)-phenyl]-3-pyridin-4-ylmethyl-urea |
| 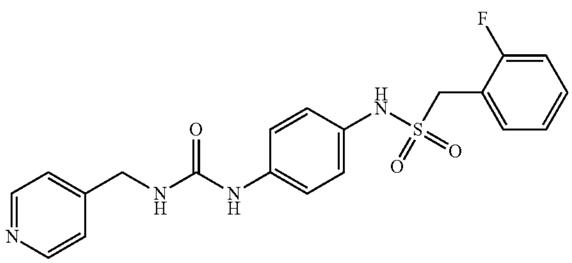 [SMILES: O=C(NCc1ccncc1)Nc1ccc(NS(=O)(=O)Cc2ccccc2F)cc1] | C-(2-Fluoro-phenyl)-N-[4-(3-pyridin-4-ylmethyl-ureido)-phenyl]-methanesulfonamide |
| 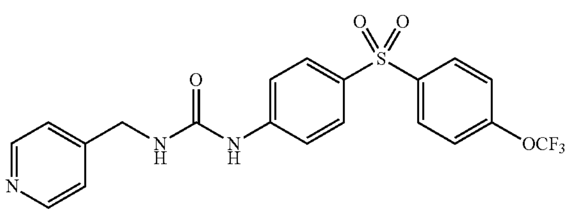 [SMILES: O=C(NCc1ccncc1)Nc1ccc(S(=O)(=O)c2ccc(OC(F)(F)F)cc2)cc1] | 1-Pyridin-4-ylmethyl-3-[4-(4-trifluoromethoxy-benzenesulfonyl)-phenyl]-urea |
| 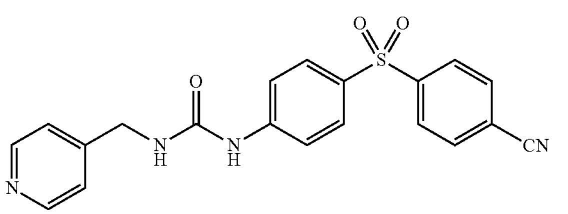 [SMILES: N#Cc1ccc(S(=O)(=O)c2ccc(NC(=O)NCc3ccncc3)cc2)cc1] | 1-[4-(4-Cyano-benzenesulfonyl)-phenyl]-3-pyridin-4-ylmethyl-urea |
| 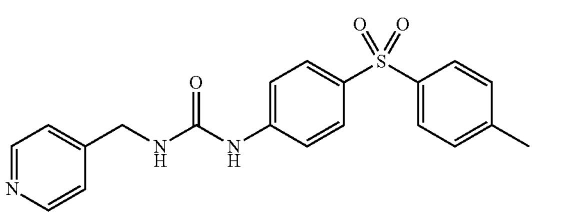 | 1-Pyridin-4-ylmethyl-3-[4-(toluene-4-sulfonyl)-phenyl]-urea |
| 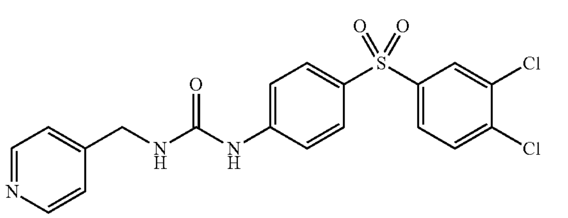 [SMILES: O=C(NCc1ccncc1)Nc1ccc(S(=O)(=O)c2ccc(Cl)c(Cl)c2)cc1] | 1-[4-(3,4-Dichloro-benzenesulfonyl)-phenyl]-3-pyridin-4-ylmethyl-urea |

TABLE 6-continued

| Compound Structure | Compound Name |
|---|---|
| 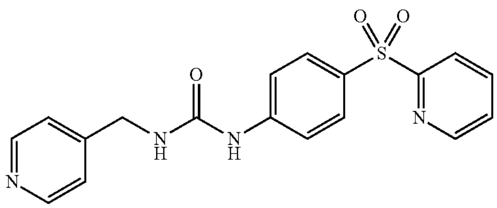 [SMILES: O=C(NCc1ccncc1)Nc1ccc(S(=O)(=O)c2ccccn2)cc1] | 1-(4-(Pyridin-2-ylsulfonyl)phenyl)-3-(pyridin-4-ylmethyl)urea |
| 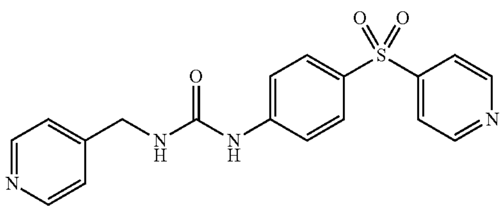 [SMILES: O=C(NCc1ccncc1)Nc1ccc(S(=O)(=O)c2ccncc2)cc1] | 1-(Pyridin-4-ylmethyl)-3-(4-(pyridin-4-ylsulfonyl)phenyl)urea |
| 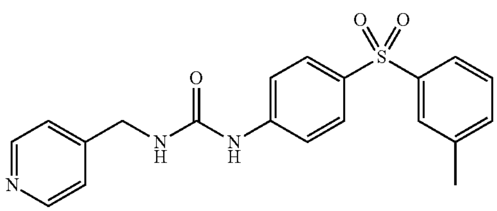 [SMILES: Cc1cccc(S(=O)(=O)c2ccc(NC(=O)NCc3ccncc3)cc2)c1] | 1-Pyridin-4-ylmethyl-3-[4-(toluene-3-sulfonyl)-phenyl]-urea |
| 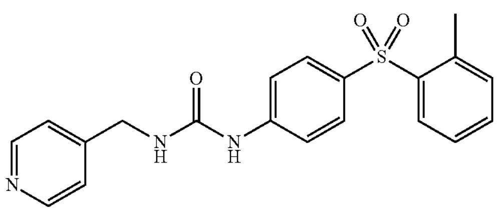 [SMILES: Cc1ccccc1S(=O)(=O)c1ccc(NC(=O)NCc2ccncc2)cc1] | 1-Pyridin-4-ylmethyl-3-[4-(toluene-2-sulfonyl)-phenyl]-urea |
| 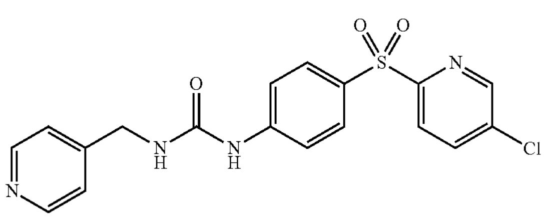 | 1-[4-(5-Chloro-pyridine-2-sulfonyl)-phenyl]-3-pyridin-4-ylmethyl-urea |
| 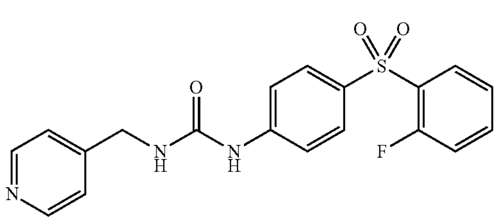 [SMILES: O=C(NCc1ccncc1)Nc1ccc(S(=O)(=O)c2ccccc2F)cc1] | 1-(4-((2-Fluorophenyl)sulfonyl)phenyl)-3-(pyridin-4-ylmethyl)urea |

TABLE 6-continued

| Compound Structure | Compound Name |
|---|---|
| 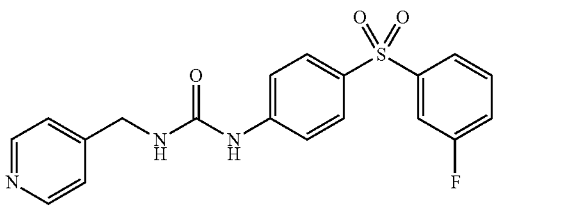 | 1-(4-((3-Fluorophenyl)sulfonyl)phenyl)-3-(pyridin-4-ylmethyl)urea |
| 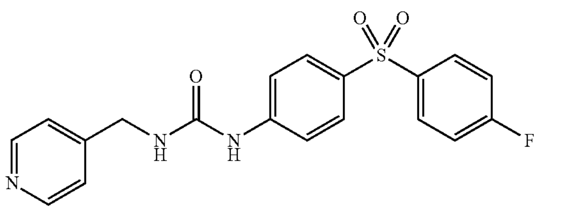 [SMILES: O=C(NCc1ccncc1)Nc1ccc(S(=O)(=O)c2ccc(F)cc2)cc1] | 1-(4-((4-Fluorophenyl)sulfonyl)phenyl)-3-(pyridin-4-ylmethyl)urea |
| 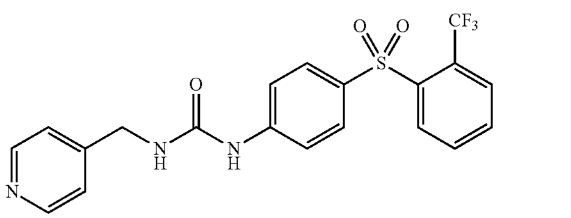 [SMILES: O=C(NCc1ccncc1)Nc1ccc(S(=O)(=O)c2ccccc2C(F)(F)F)cc1] | 1-Pyridin-4-ylmethyl-3-[4-(2-trifluoromethyl-benzenesulfonyl)-phenyl]-urea |
| 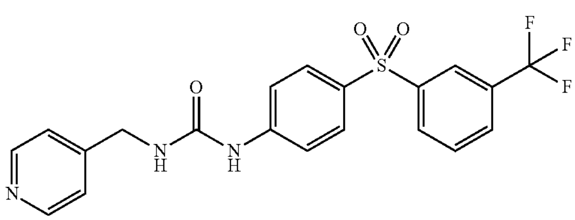 [SMILES: O=C(NCc1ccncc1)Nc1ccc(S(=O)(=O)c2cccc(C(F)(F)F)c2)cc1] | 1-(Pyridin-4-ylmethyl)-3-(4-((3-(trifluoromethyl)phenyl)sulfonyl)phenyl)urea |
| 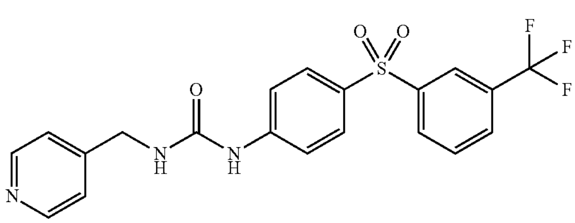 [SMILES: O=C(NCc1ccncc1)Nc1ccc(S(=O)(=O)c2cccc(C(F)(F)F)c2)cc1] | 1-((1H-Pyrazol-4-yl)methyl)-3-(4-((3-(trifluoromethyl)phenyl)sulfonyl)phenyl)urea |
| 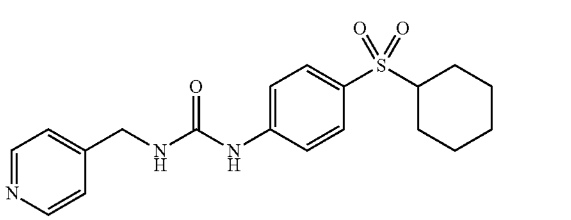 [SMILES: O=C(NCc1ccncc1)Nc1ccc(S(=O)(=O)C2CCCCC2)cc1] | 1-(4-Cyclohexanesulfonyl-phenyl)-3-pyridin-4-ylmethyl-urea |

TABLE 6-continued

| Compound Structure | Compound Name |
|---|---|
| 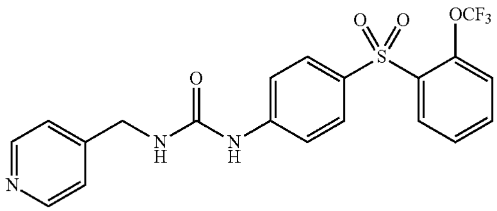 [SMILES: O=C(NCc1ccncc1)Nc1ccc(S(=O)(=O)c2ccccc2OC(F)(F)F)cc1] | 1-Pyridin-4-ylmethyl-3-[4-(2-trifluoromethoxy-benzenesulfonyl)-phenyl]-urea |
| 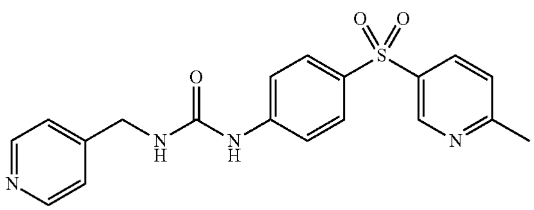 [SMILES: Cc1ccc(S(=O)(=O)c2ccc(NC(=O)NCc3ccncc3)cc2)cn1] | 1-[4-(6-Methyl-pyridine-3-sulfonyl)-phenyl]-3-pyridin-4-ylmethyl-urea |
| 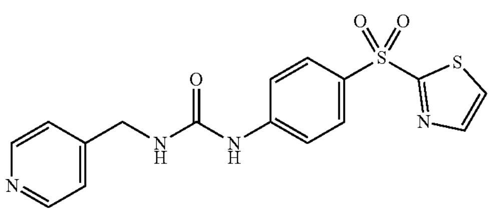 [SMILES: O=C(NCc1ccncc1)Nc1ccc(S(=O)(=O)c2nccs2)cc1] | Pyridin-4-ylmethyl-3-[4-(thiazole-2-sulfonyl)-phenyl]-urea |
| 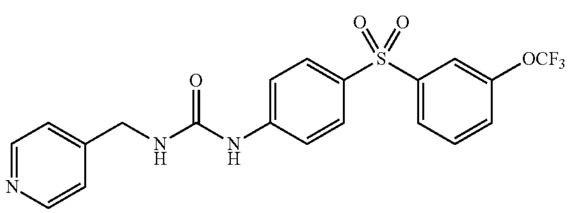 [SMILES: O=C(NCc1ccncc1)Nc1ccc(S(=O)(=O)c2cccc(OC(F)(F)F)c2)cc1] | 1-Pyridin-4-ylmethyl-3-[4-(3-trifluoromethoxy-benzenesulfonyl)-phenyl]-urea |
| 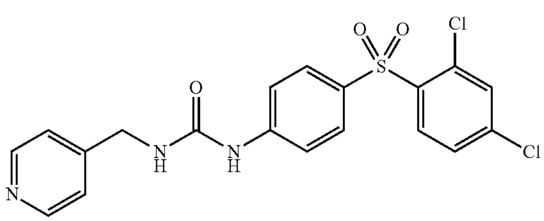 [SMILES: O=C(NCc1ccncc1)Nc1ccc(S(=O)(=O)c2ccc(Cl)cc2Cl)cc1] | 1-[4-(2,4-Dichloro-benzenesulfonyl)-phenyl]-3-pyridin-4-ylmethyl-urea |
| 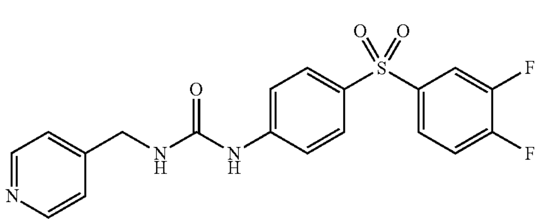 [SMILES: O=C(NCc1ccncc1)Nc1ccc(S(=O)(=O)c2ccc(F)c(F)c2)cc1] | of 1-[4-(3,4-Difluoro-benzenesulfonyl)-phenyl]-3-pyridin-4-ylmethyl-urea |

TABLE 6-continued

| Compound Structure | Compound Name |
|---|---|
| 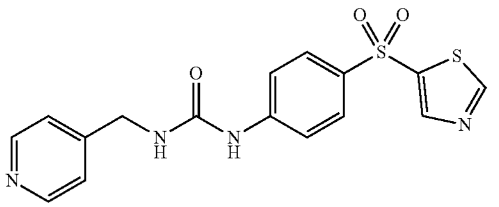 [SMILES: O=C(NCc1ccncc1)Nc1ccc(S(=O)(=O)c2cncs2)cc1] | 1-Pyridin-4-ylmethyl)-3-(4-(thiazol-5-ylsulfonyl)phenyl)urea |
| 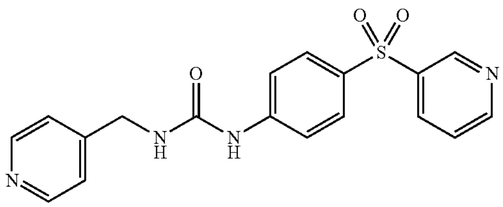 [SMILES: O=C(NCc1ccncc1)Nc1ccc(S(=O)(=O)c2cccnc2)cc1] | 1-[4-(Pyridine-3-sulfonyl)-phenyl]-3-pyridin-4-ylmethyl-urea |
| 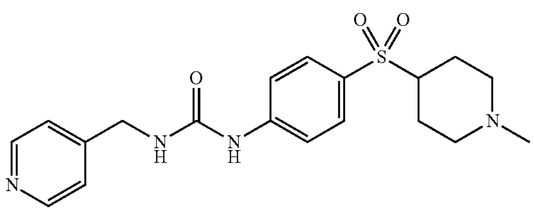 [SMILES: CN1CCC(S(=O)(=O)c2ccc(NC(=O)NCc3ccncc3)cc2)CC1] | 1-[4-(1-Methyl-piperidine-4-sulfonyl)-phenyl]-3-pyridin-4-ylmethyl-urea |
| 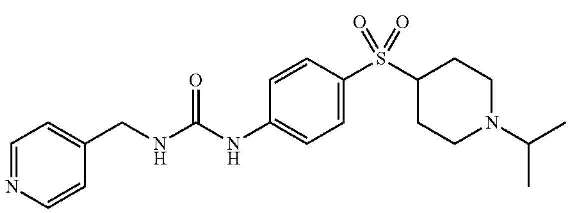 [SMILES: CC(C)N1CCC(S(=O)(=O)c2ccc(NC(=O)NCc3ccncc3)cc2)CC1] | 1-[4-(1-Isopropyl-piperidine-4-sulfonyl)-phenyl]-3-pyridin-4-ylmethyl-urea |
| 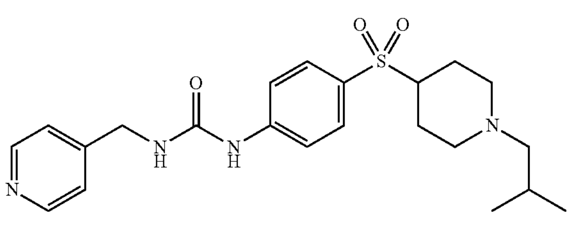 [SMILES: CC(C)CN1CCC(S(=O)(=O)c2ccc(NC(=O)NCc3ccncc3)cc2)CC1] | 1-[4-(1-Isobutyl-piperidine-4-sulfonyl)-phenyl]-3-pyridin-4-ylmethyl-urea |
| 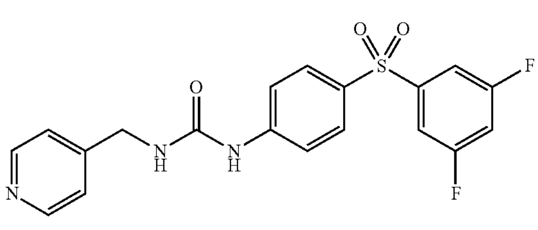 [SMILES: O=C(NCc1ccncc1)Nc1ccc(S(=O)(=O)c2cc(F)cc(F)c2)cc1] | 1-[4-(3,5-Difluoro-benzenesulfonyl)-phenyl]-3-pyridin-4-ylmethyl-urea |

TABLE 6-continued

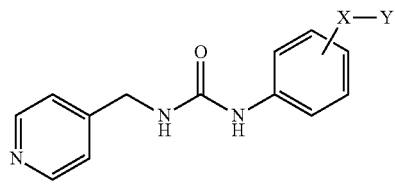

| Compound Structure | Compound Name |
| --- | --- |
| 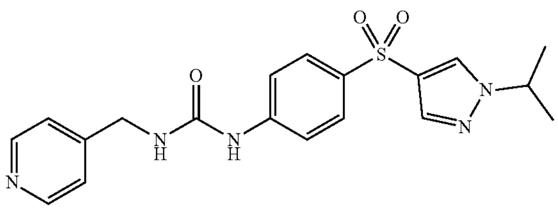 [SMILES: CC(C)n1cc(S(=O)(=O)c2ccc(NC(=O)NCc3ccncc3)cc2)cn1] | 1-[4-(1-Isopropyl-1H-pyrazole-4-sulfonyl)-phenyl]-3-pyridin-4-ylmethyl-urea |
| 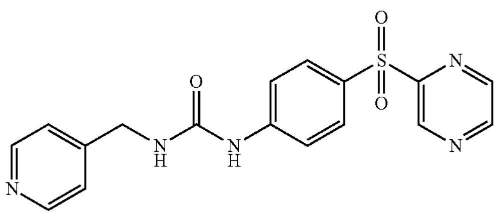 [SMILES: O=C(NCc1ccncc1)Nc1ccc(S(=O)(=O)c2cnccn2)cc1] | 1-[4-(Pyrazine-2-sulfonyl)-phenyl]-3-pyridin-4-ylmethyl-urea |
| 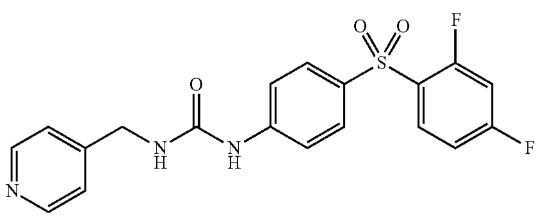 [SMILES: O=C(NCc1ccncc1)Nc1ccc(S(=O)(=O)c2ccc(F)cc2F)cc1] | 1-[4-(2,4-Difluoro-benzenesulfonyl)-phenyl]-3-pyridin-4-ylmethyl-urea |
| 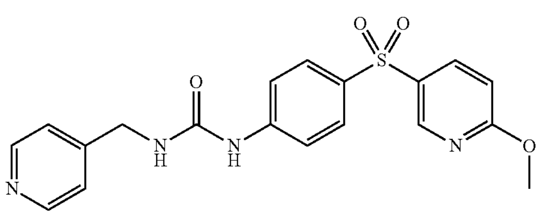 [SMILES: COc1ccc(S(=O)(=O)c2ccc(NC(=O)NCc3ccncc3)cc2)cn1] | 1-[4-(6-Methoxy-pyridine-3-sulfonyl)-phenyl]-3-pyridin-4-ylmethyl-urea |
| 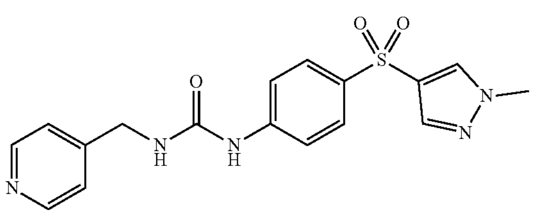 [SMILES: Cn1cc(S(=O)(=O)c2ccc(NC(=O)NCc3ccncc3)cc2)cn1] | 1-[4-(1-Methyl-1H-pyrazole-4-sulfonyl)-phenyl]-3-pyridin-4-ylmethyl-urea |
| 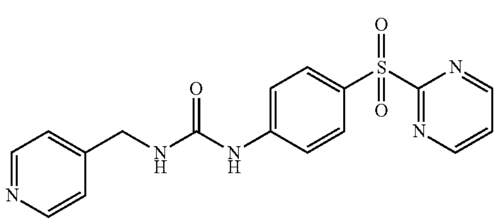 [SMILES: O=C(NCc1ccncc1)Nc1ccc(S(=O)(=O)c2ncccn2)cc1] | 1-Pyridin-4-ylmethyl-3-[4-(pyrimidine-2-sulfonyl)-phenyl]-urea |

TABLE 6-continued

| Compound Structure | Compound Name |
|---|---|
| 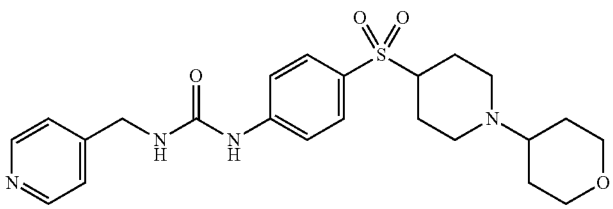 [SMILES: O=C(NCc1ccncc1)Nc1ccc(S(=O)(=O)C2CCN(C3CCOCC3)CC2)cc1] | 1-(1H-Pyrazol-4-ylmethyl)-3-{4-[1-(tetrahydro-pyran-4-yl)-piperidine-4-sulfonyl]-phenyl}-urea |
| 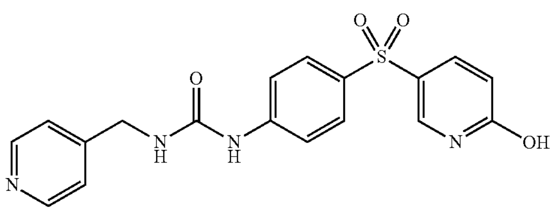 [SMILES: O=C(NCc1ccncc1)Nc1ccc(S(=O)(=O)c2ccc(O)nc2)cc1] | 1-[4-(6-Hydroxy-pyridine-3-sulfonyl)-phenyl]-3-pyridin-4-ylmethyl-urea |
| 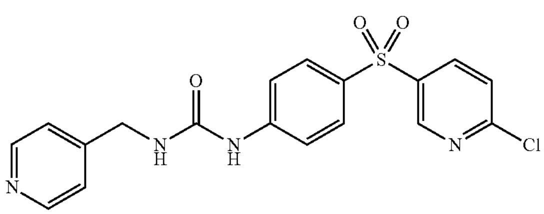 [SMILES: O=C(NCc1ccncc1)Nc1ccc(S(=O)(=O)c2ccc(Cl)nc2)cc1] | 1-[4-(6-Chloro-pyridine-3-sulfonyl)-phenyl]-3-pyridin-4-ylmethyl-urea |
| 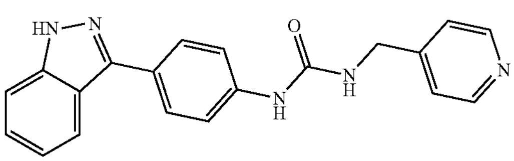 [SMILES: O=C(NCc1ccncc1)Nc1ccc(-c2n[nH]c3ccccc23)cc1] | 1-[4-(1H-Indazol-3-yl)-phenyl]-3-pyridin-4-ylmethyl-urea |
| 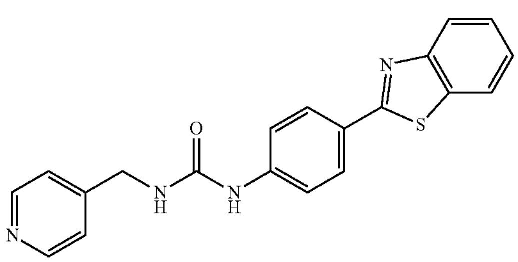 [SMILES: O=C(NCc1ccncc1)Nc1ccc(-c2nc3ccccc3s2)cc1] | 1-(4-(Benzo[d]thiazol-2-yl)phenyl)-3-(pyridin-4-ylmethyl)urea |
| 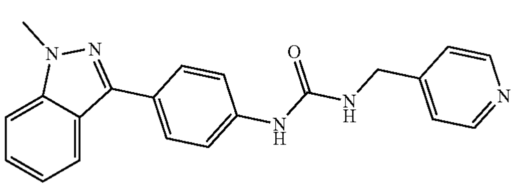 [SMILES: Cn1nc(-c2ccc(NC(=O)NCc3ccncc3)cc2)c2ccccc21] | 1-[4-(1-Methyl-1H-indazol-3-yl)-phenyl]-3-pyridin-4-ylmethyl-urea |

TABLE 6-continued

| Compound Structure | Compound Name |
|---|---|
| 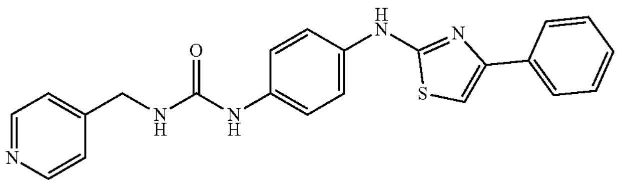 [SMILES: O=C(NCc1ccncc1)Nc1ccc(Nc2nc(-c3ccccc3)cs2)cc1] | 1-(4-((4-Phenylthiazol-2-yl)amino)phenyl)-3-(pyridin-4-ylmethyl)urea |
| 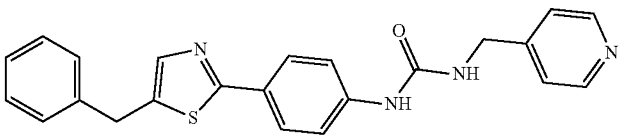 [SMILES: O=C(NCc1ccncc1)Nc1ccc(-c2ncc(Cc3ccccc3)s2)cc1] | 1-(4-(5-Benzylthiazol-2-yl)phenyl)-3-(pyridin-4-ylmethyl)urea |
| 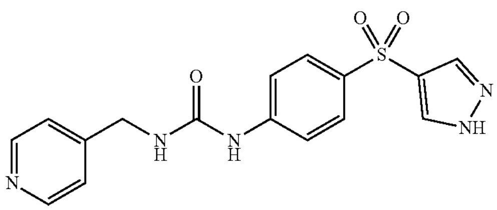 [SMILES: O=C(NCc1ccncc1)Nc1ccc(S(=O)(=O)c2cn[nH]c2)cc1] | 1-(4-((1H-pyrazol-4-yl)sulfonyl)phenyl)-3-(pyridin-4-ylmethyl)urea |
| 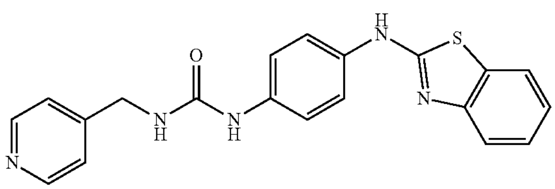 [SMILES: O=C(NCc1ccncc1)Nc1ccc(Nc2nc3ccccc3s2)cc1] | 1-[4-(Benzothiazol-2-ylamino)-phenyl]-3-pyridin-4-ylmethyl-urea |
| 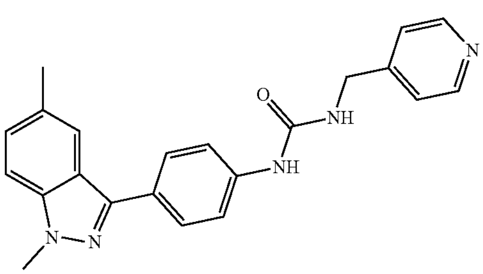 [SMILES: Cc1ccc2c(c1)c(-c1ccc(NC(=O)NCc3ccncc3)cc1)nn2C] | 1-(4-(1,5-Dimethyl-1H-indazol-3-yl)phenyl)-3-(pyridin-4-ylmethyl)urea |
| 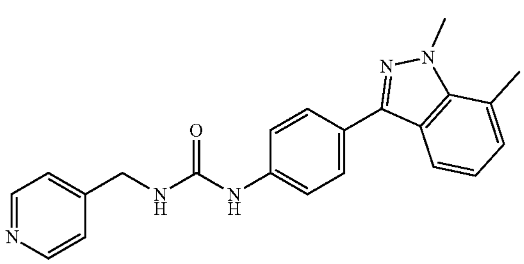 [SMILES: Cc1cccc2c(-c3ccc(NC(=O)NCc4ccncc4)cc3)nn(C)c12] | 1-(4-(1,7-Dimethyl-1H-indazol-3-yl)phenyl)-3-(pyridin-4-ylmethyl)urea |

TABLE 6-continued

| Compound Structure | Compound Name |
|---|---|
| 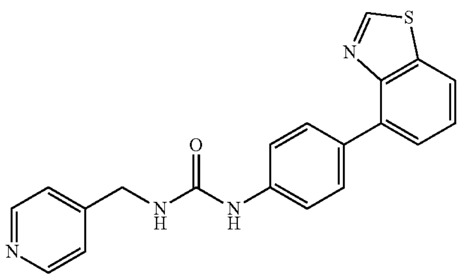 [SMILES: O=C(NCc1ccncc1)Nc1ccc(-c2cccc3scnc23)cc1] | 1-(4-Benzothiazol-4-yl-phenyl)-3-pyridin-4-ylmethyl-urea |
| 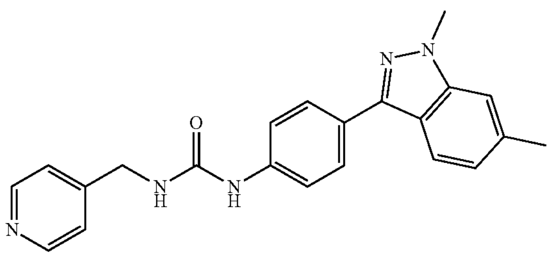 [SMILES: Cc1ccc2c(-c3ccc(NC(=O)NCc4ccncc4)cc3)nn(C)c2c1] | 1-[4-(1,6-Dimethyl-1H-indazol-3-yl)-phenyl]-3-pyridin-4-ylmethyl-urea |
| 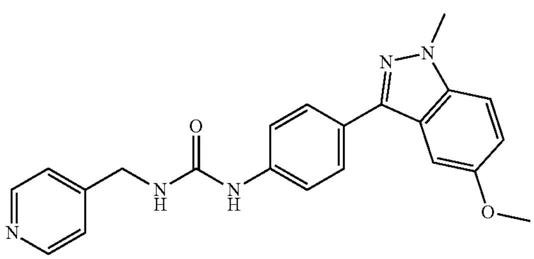 [SMILES: COc1ccc2c(c1)c(-c1ccc(NC(=O)NCc3ccncc3)cc1)nn2C] | 1-[4-(5-Methoxy-1-methyl-1H-indazol-3-yl)-phenyl]-3-pyridin-4-ylmethyl-urea |
| 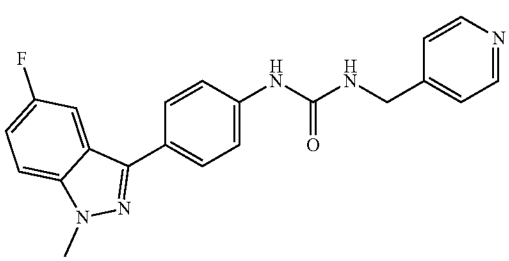 [SMILES: Cn1nc(-c2ccc(NC(=O)NCc3ccncc3)cc2)c2cc(F)ccc21] | 1-[4-(5-Fluoro-1-methyl-1H-indazol-3-yl)-phenyl]-3-pyridin-4-ylmethyl-urea |
| 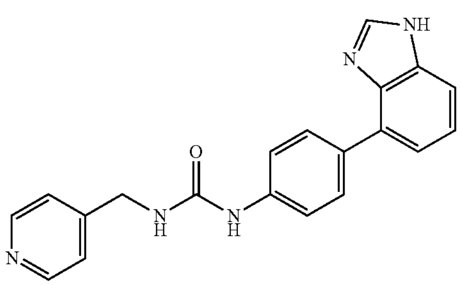 [SMILES: O=C(NCc1ccncc1)Nc1ccc(-c2cccc3[nH]cnc23)cc1] | 1-[4-(1H-Benzoimidazol-4-yl)-phenyl]-3-pyridin-4-ylmethyl-urea |

TABLE 6-continued

| Compound Structure | Compound Name |
|---|---|
| | 1-(4-([1,1'-Biphenyl]-2-ylsulfonyl)phenyl)-3-(pyridin-4-ylmethyl)urea |
| | 1-(4-([1,1'-Biphenyl]-2-ylsulfonyl)phenyl)-3-(pyridin-4-ylmethyl)urea |
| 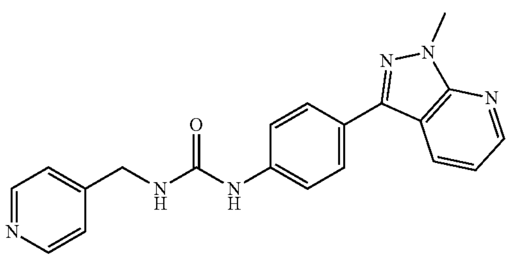 [SMILES: Cn1nc(-c2ccc(NC(=O)NCc3ccncc3)cc2)c2cccnc21] | 1-[4-(1-Methyl-1H-pyrazolo[3,4-b]pyridin-3-yl)-phenyl]-3-pyridin-4-ylmethyl-urea |
| 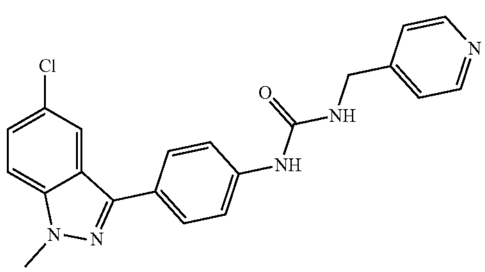 [SMILES: Cn1nc(-c2ccc(NC(=O)NCc3ccncc3)cc2)c2cc(Cl)ccc21] | 1-(4-(5-Chloro-1-methyl-1H-indazol-3-yl)phenyl)-3-(pyridin-4-ylmethyl)urea |
| 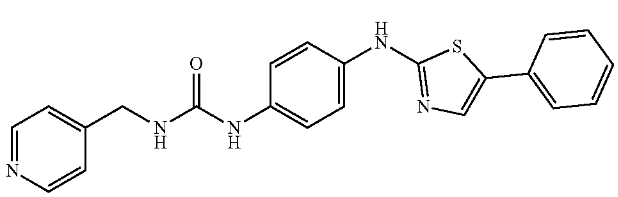 [SMILES: O=C(NCc1ccncc1)Nc1ccc(Nc2ncc(-c3ccccc3)s2)cc1] | 1-(4-((5-Phenylthiazol-2-yl)amino)phenyl)-3-(pyridin-4-ylmethyl)urea |

TABLE 6-continued

| Compound Structure | Compound Name |
|---|---|
| 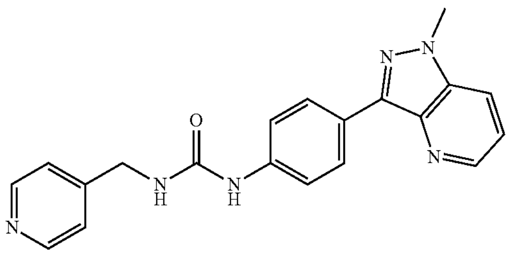 [SMILES: Cn1nc(-c2ccc(NC(=O)NCc3ccncc3)cc2)c2ncccc21] | 1-[4-(1-Methyl-1H-pyrazolo[4,3-b]pyridin-3-yl)-phenyl]-3-pyridin-4-ylmethyl-urea |
| 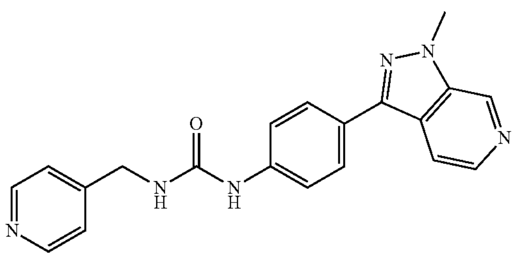 [SMILES: Cn1nc(-c2ccc(NC(=O)NCc3ccncc3)cc2)c2ccncc21] | 1-(4-(1-Methyl-1H-pyrazolo[3,4-c]pyridin-3-yl)phenyl)-3-(pyridin-4-ylmethyl)urea |
| 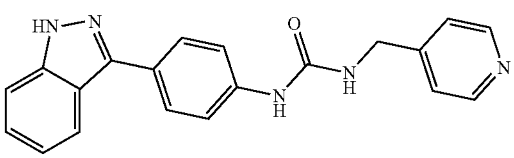 [SMILES: O=C(NCc1ccncc1)Nc1ccc(-c2n[nH]c3ccccc23)cc1] | 1-[4-(1H-Indazol-3-yl)-phenyl]-3-pyridin-4-ylmethyl-urea |
| 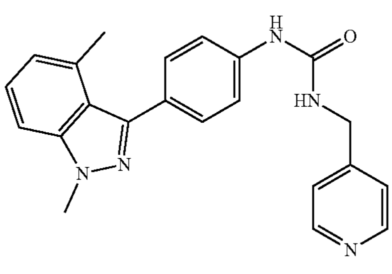 [SMILES: Cc1cccc2c1c(-c1ccc(NC(=O)NCc3ccncc3)cc1)nn2C] | 1-(4-(1,4-Dimethyl-1H-indazol-3-yl)phenyl)-3-(pyridin-4-ylmethyl)urea |
| 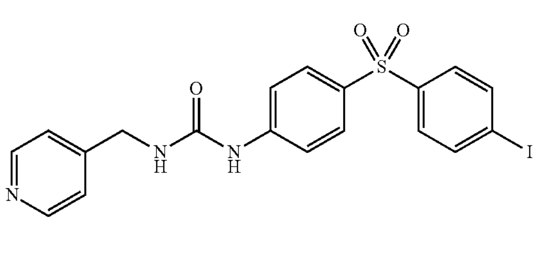 [SMILES: O=C(NCc1ccncc1)Nc1ccc(S(=O)(=O)c2ccc(I)cc2)cc1] | 1-[4-(3-Iodo-benzenesulfonyl)-phenyl]-3-pyridin-4-ylmethyl-urea |

TABLE 6-continued

| Compound Structure | Compound Name |
|---|---|
| 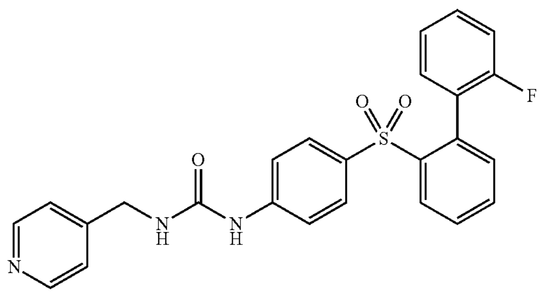 [SMILES: O=C(NCc1ccncc1)Nc1ccc(S(=O)(=O)c2ccccc2-c2ccccc2F)cc1] | 1-[4-(2'-Fluoro-biphenyl-2-sulfonyl)-phenyl]-3-pyridin-4-ylmethyl-urea |
| 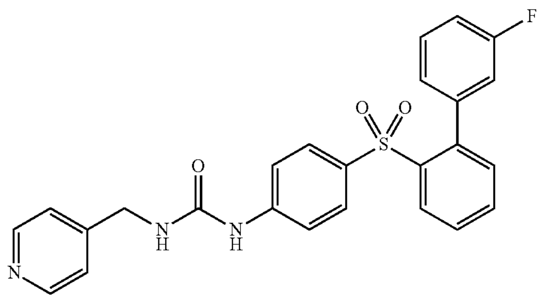 [SMILES: O=C(NCc1ccncc1)Nc1ccc(S(=O)(=O)c2ccccc2-c2cccc(F)c2)cc1] | 1-[4-(3'-Fluoro-biphenyl-2-sulfonyl)-phenyl]-3-pyridin-4-ylmethyl-urea |
| 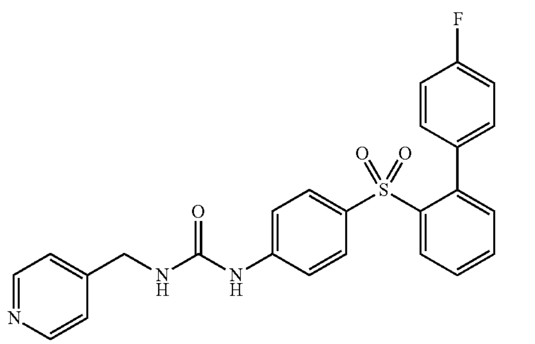 [SMILES: O=C(NCc1ccncc1)Nc1ccc(S(=O)(=O)c2ccccc2-c2ccc(F)cc2)cc1] | 1-[4-(4'-Fluoro-biphenyl-2-sulfonyl)-phenyl]-3-pyridin-4-ylmethyl-urea |
| 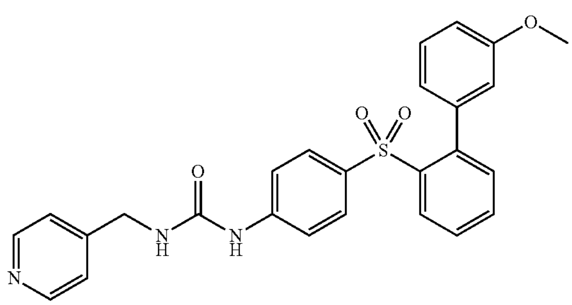 [SMILES: COc1cccc(-c2ccccc2S(=O)(=O)c2ccc(NC(=O)NCc3ccncc3)cc2)c1] | 1-[4-(3'-Methoxy-biphenyl-2-sulfonyl)-phenyl]-3-pyridin-4-ylmethyl-urea |

TABLE 6-continued

| Compound Structure | Compound Name |
|---|---|
| 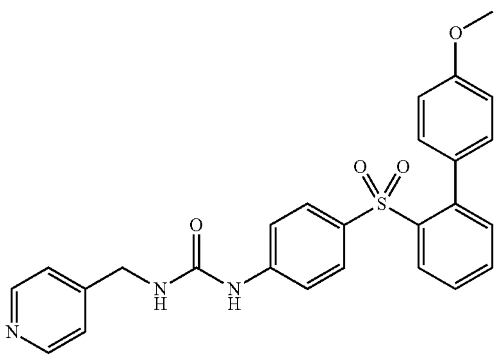 [SMILES: COc1ccc(-c2ccccc2S(=O)(=O)c2ccc(NC(=O)NCc3ccncc3)cc2)cc1] | 1-[4-(4'-Methoxy-biphenyl-2-sulfonyl)-phenyl]-3-pyridin-4-ylmethyl-urea |
| 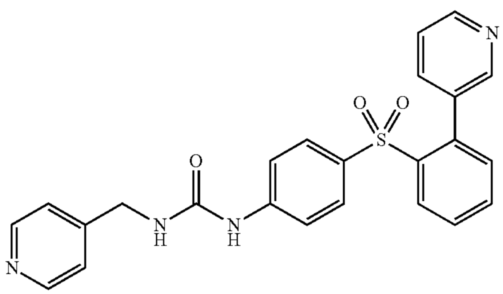 [SMILES: O=C(NCc1ccncc1)Nc1ccc(S(=O)(=O)c2ccccc2-c2cccnc2)cc1] | 1-[4-(2-Pyridin-3-yl-benzenesulfonyl)-phenyl]-3-pyridin-4-ylmethyl-urea |
| 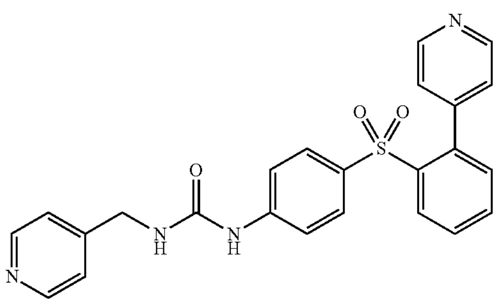 [SMILES: O=C(NCc1ccncc1)Nc1ccc(S(=O)(=O)c2ccccc2-c2ccncc2)cc1] | 1-[4-(2-Pyridin-4-yl-benzenesulfonyl)-phenyl]-3-pyridin-4-ylmethyl-urea |
| 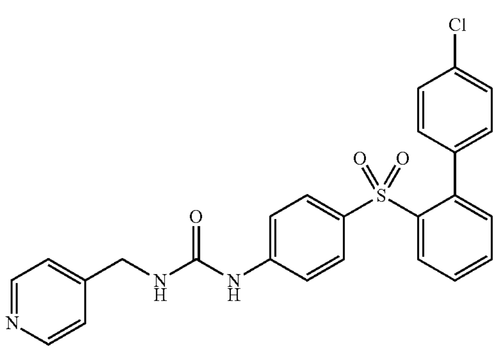 | 1-[4-(4'-Chloro-biphenyl-2-sulfonyl)-phenyl]-3-pyridin-4-ylmethyl-urea |

TABLE 6-continued

| Compound Structure | Compound Name |
|---|---|
| 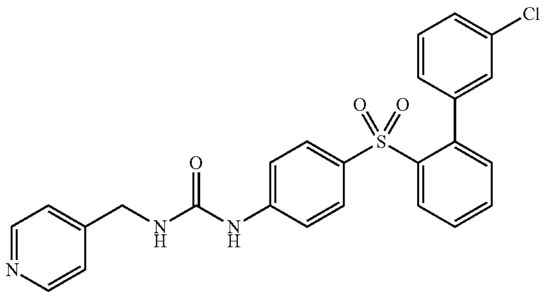 [SMILES: O=C(NCc1ccncc1)Nc1ccc(S(=O)(=O)c2ccccc2-c2cccc(Cl)c2)cc1] | 1-[4-(3'-Chloro-biphenyl-2-sulfonyl)-phenyl]-3-pyridin-4-ylmethyl-urea |
| 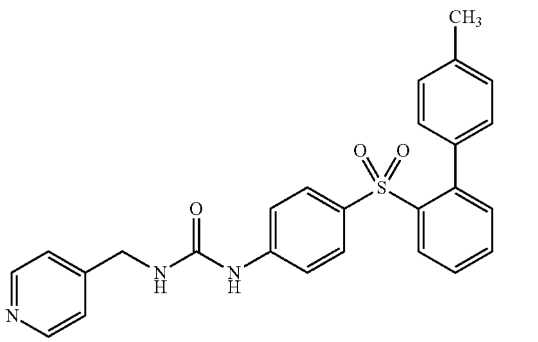 [SMILES: Cc1ccc(-c2ccccc2S(=O)(=O)c2ccc(NC(=O)NCc3ccncc3)cc2)cc1] | 1-[4-(4'-Methyl-biphenyl-2-sulfonyl)-phenyl]-3-pyridin-4-ylmethyl-urea |
| 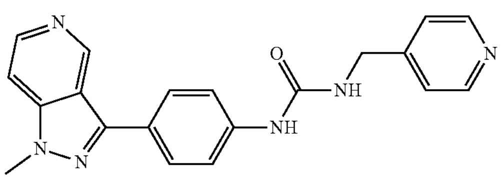 [SMILES: Cn1nc(-c2ccc(NC(=O)NCc3ccncc3)cc2)c2cnccc21] | 1-[4-(1-Methyl-1H-pyrazolo[4,3-c]pyridin-3-yl)-phenyl]-3-pyridin-4-ylmethyl-urea |
| 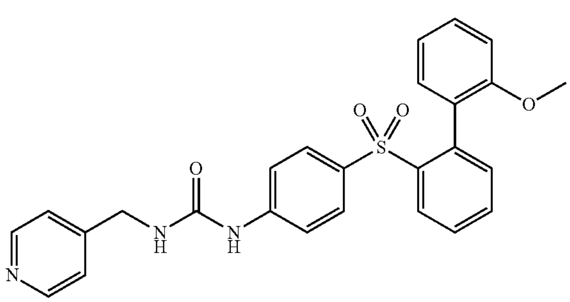 [SMILES: COc1ccccc1-c1ccccc1S(=O)(=O)c1ccc(NC(=O)NCc2ccncc2)cc1] | 1-[4-(2'-Methoxy-biphenyl-2-sulfonyl)-phenyl]-3-pyridin-4-ylmethyl-urea |

TABLE 6-continued

| Compound Structure | Compound Name |
|---|---|
| 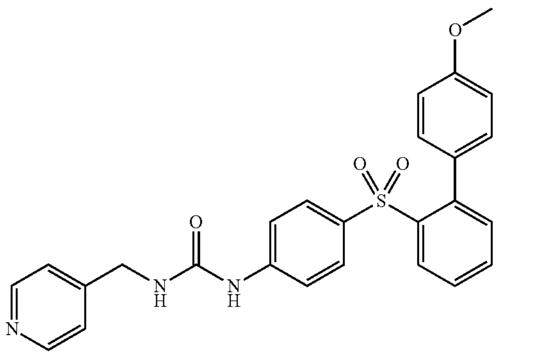 [SMILES: COc1ccc(-c2ccccc2S(=O)(=O)c2ccc(NC(=O)NCc3ccncc3)cc2)cc1] | 1-[4-(4'-Methoxy-biphenyl-2-sulfonyl)-phenyl]-3-pyridin-4-ylmethyl-urea |
| 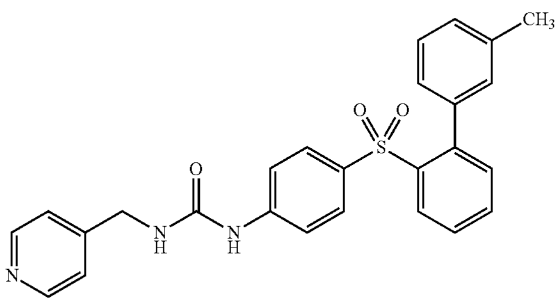 [SMILES: Cc1cccc(-c2ccccc2S(=O)(=O)c2ccc(NC(=O)NCc3ccncc3)cc2)c1] | 1-[4-(3'-Methyl-biphenyl-2-sulfonyl)-phenyl]-3-pyridin-4-ylmethyl-urea |
| 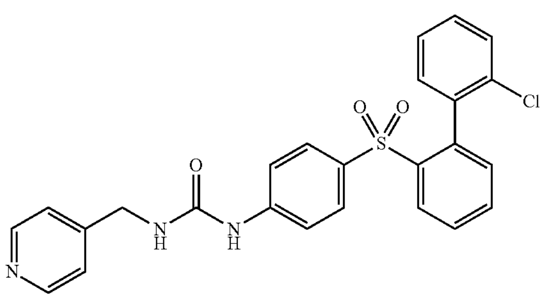 [SMILES: O=C(NCc1ccncc1)Nc1ccc(S(=O)(=O)c2ccccc2-c2ccccc2Cl)cc1] | 1-(4-((2'-Chloro-[1,1'-biphenyl]-2-yl)sulfonyl)phenyl)-3-(pyridin-4-ylmethyl)urea |
| 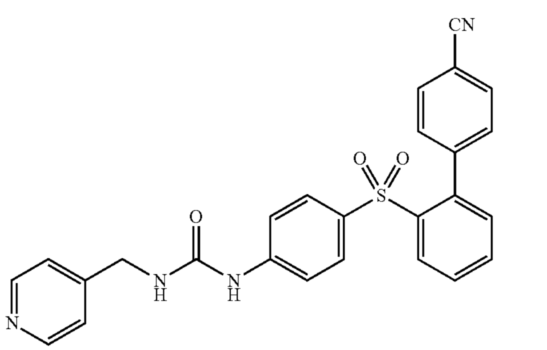 [SMILES: N#Cc1ccc(-c2ccccc2S(=O)(=O)c2ccc(NC(=O)NCc3ccncc3)cc2)cc1] | 1-(4-((4'-Cyano-[1,1'-biphenyl]-2-yl)sulfonyl)phenyl)-3-(pyridin-4-ylmethyl)urea |

TABLE 6-continued

| Compound Structure | Compound Name |
|---|---|
| 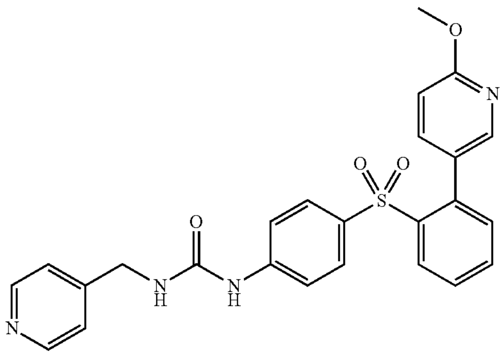 [SMILES: COc1ccc(-c2ccccc2S(=O)(=O)c2ccc(NC(=O)NCc3ccncc3)cc2)cn1] | 1-(4-((2-(6-Methoxypyridin-3-yl)phenyl)sulfonyl)phenyl)-3-(pyridin-4-ylmethyl)urea |
| 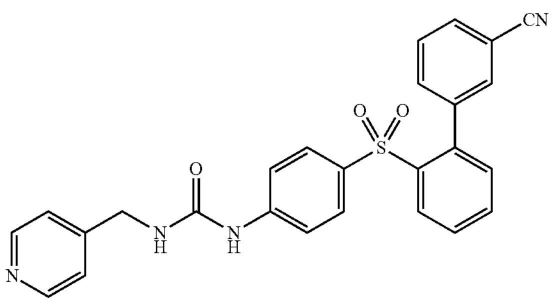 [SMILES: N#Cc1cccc(-c2ccccc2S(=O)(=O)c2ccc(NC(=O)NCc3ccncc3)cc2)c1] | 1-(4-((3'-Cyano-[1,1'-biphenyl]-2-yl)sulfonyl)phenyl)-3-(pyridin-4-ylmethyl)urea |
| 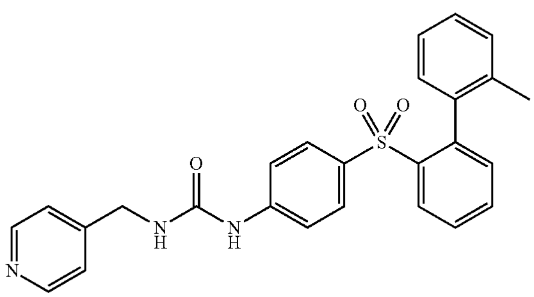 [SMILES: Cc1ccccc1-c1ccccc1S(=O)(=O)c1ccc(NC(=O)NCc2ccncc2)cc1] | 1-(4-((2'-Methyl-[1,1'-biphenyl]-2-yl)sulfonyl)phenyl)-3-(pyridin-4-ylmethyl)urea |
| 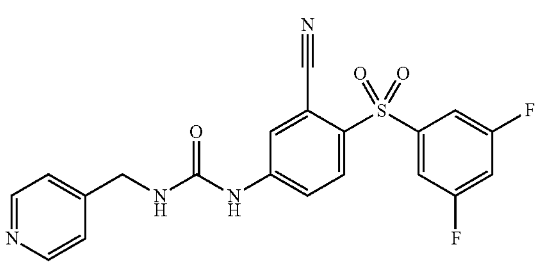 [SMILES: N#Cc1cc(NC(=O)NCc2ccncc2)ccc1S(=O)(=O)c1cc(F)cc(F)c1] | 1-(3-Cyano-4-((3,5-difluorophenyl)sulfonyl)phenyl)-3-(pyridin-4-ylmethyl)urea |
| 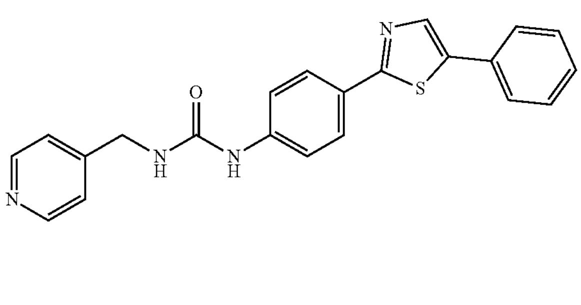 [SMILES: O=C(NCc1ccncc1)Nc1ccc(-c2ncc(-c3ccccc3)s2)cc1] | 1-(4-(5-phenylthiazol-2-yl)phenyl)-3-(pyridin-4-ylmethyl)urea |

TABLE 6-continued

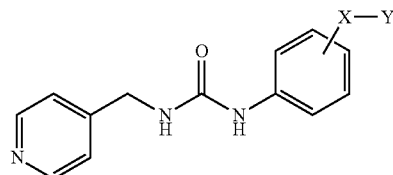

| Compound Structure | Compound Name |
|---|---|
| 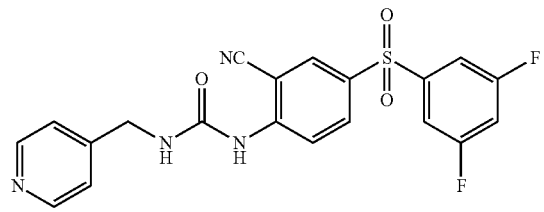 [SMILES: N#Cc1cc(S(=O)(=O)c2cc(F)cc(F)c2)ccc1NC(=O)NCc1ccncc1] | 1-(2-Cyano-4-((3,5-difluorophenyl)sulfonyl)phenyl)-3-(pyridin-4-ylmethyl)urea |

In one aspect, provided herein is a pharmaceutically acceptable salt or solvate of a compound described in Table 6.

Any combination of the groups described above for the various variables is contemplated herein. Throughout the specification, groups and substituents thereof are chosen by one skilled in the field to provide stable moieties and compounds.

Further Forms of Compounds

In one aspect, the compound of Formula (I), (Ia), (II), (IIa), (III), (IIIa), (IV), (IVa), (V) or (Va), possesses one or more stereocenters and each stereocenter exists independently in either the R or S configuration. The compounds presented herein include all diastereomeric, enantiomeric, and epimeric forms as well as the appropriate mixtures thereof. The compounds and methods provided herein include all cis, trans, syn, anti, entgegen (E), and zusammen (Z) isomers as well as the appropriate mixtures thereof. In certain embodiments, compounds described herein are prepared as their individual stereoisomers by reacting a racemic mixture of the compound with an optically active resolving agent to form a pair of diastereoisomeric compounds/salts, separating the diastereomers and recovering the optically pure enantiomers. In some embodiments, resolution of enantiomers is carried out using covalent diastereomeric derivatives of the compounds described herein. In another embodiment, diastereomers are separated by separation/resolution techniques based upon differences in solubility. In other embodiments, separation of stereoisomers is performed by chromatography or by the forming diastereomeric salts and separation by recrystallization, or chromatography, or any combination thereof. Jean Jacques, Andre Collet, Samuel H. Wilen, "Enantiomers, Racemates and Resolutions", John Wiley And Sons, Inc., 1981. In one aspect, stereoisomers are obtained by stereoselective synthesis.

In some embodiments, compounds described herein are prepared as prodrugs. A "prodrug" refers to an agent that is converted into the parent drug in vivo. Prodrugs are often useful because, in some situations, they may be easier to administer than the parent drug. They may, for instance, be bioavailable by oral administration whereas the parent is not. The prodrug may also have improved solubility in pharmaceutical compositions over the parent drug. In some embodiments, the design of a prodrug increases the effective water solubility. An example, without limitation, of a prodrug is a compound described herein, which is administered as an ester (the "prodrug") to facilitate transmittal across a cell membrane where water solubility is detrimental to mobility but which then is metabolically hydrolyzed to the carboxylic acid, the active entity, once inside the cell where water-solubility is beneficial. A further example of a prodrug might be a short peptide (polyaminoacid) bonded to an acid group where the peptide is metabolized to reveal the active moiety. In certain embodiments, upon in vivo administration, a prodrug is chemically converted to the biologically, pharmaceutically or therapeutically active form of the compound. In certain embodiments, a prodrug is enzymatically metabolized by one or more steps or processes to the biologically, pharmaceutically or therapeutically active form of the compound.

In one aspect, prodrugs are designed to alter the metabolic stability or the transport characteristics of a drug, to mask side effects or toxicity, to improve the flavor of a drug or to alter other characteristics or properties of a drug. By virtue of knowledge of pharmacokinetic, pharmacodynamic processes and drug metabolism in vivo, once a pharmaceutically active compound is known, the design of prodrugs of the compound is possible. (see, for example, Nogrady (1985) Medicinal Chemistry A Biochemical Approach, Oxford University Press, New York, pages 388-392; Silverman (1992), The Organic Chemistry of Drug Design and Drug Action, Academic Press, Inc., San Diego, pages 352-401, Rooseboom et al., Pharmacological Reviews, 56:53-102, 2004; Aesop Cho, "Recent Advances in Oral Prodrug Discovery", Annual Reports in Medicinal Chemistry, Vol. 41, 395-407, 2006; T. Higuchi and V. Stella, Pro-drugs as Novel Delivery Systems, Vol. 14 of the A.C.S. Symposium Series).

In some cases, some of the herein-described compounds may be a prodrug for another derivative or active compound.

In some embodiments, sites on the aromatic ring portion of compounds described herein are susceptible to various metabolic reactions Therefore incorporation of appropriate substituents on the aromatic ring structures will reduce, minimize or eliminate this metabolic pathway. In specific embodiments, the appropriate substituent to decrease or eliminate the susceptibility of the aromatic ring to metabolic reactions is, by way of example only, a halogen, or an alkyl group.

In another embodiment, the compounds described herein are labeled isotopically (e.g. with a radioisotope) or by another other means, including, but not limited to, the use of chromophores or fluorescent moieties, bioluminescent labels, or chemiluminescent labels.

Compounds described herein include isotopically-labeled compounds, which are identical to those recited in the various formulae and structures presented herein, but for the fact that one or more atoms are replaced by an atom having an atomic mass or mass number different from the atomic mass or mass number usually found in nature. Examples of isotopes that can be incorporated into the present compounds include isotopes of hydrogen, carbon, nitrogen, oxygen, sulfur, fluorine and chlorine, such as, for example, $^{2}H$, $^{3}H$, $^{13}C$, $^{14}C$, $^{15}N$, $^{18}O$, $^{17}O$, $^{35}S$, $^{18}F$, $^{36}Cl$. In one aspect, isotopically-labeled compounds described herein, for example those into which radioactive isotopes such as $^{3}H$ and $^{14}C$ are incorporated, are useful in drug and/or substrate tissue distribution assays. In one aspect, substitution with isotopes such as deuterium affords certain therapeutic advantages resulting from greater metabolic stability, such as, for example, increased in vivo half-life or reduced dosage requirements.

In additional or further embodiments, the compounds described herein are metabolized upon administration to an organism in need to produce a metabolite that is then used to produce a desired effect, including a desired therapeutic effect.

"Pharmaceutically acceptable" as used herein, refers a material, such as a carrier or diluent, which does not abrogate the biological activity or properties of the compound, and is relatively nontoxic, i.e., the material may be administered to an individual without causing undesirable biological effects or interacting in a deleterious manner with any of the components of the composition in which it is contained.

The term "pharmaceutically acceptable salt" refers to a formulation of a compound that does not cause significant irritation to an organism to which it is administered and does not abrogate the biological activity and properties of the compound. In some embodiments, pharmaceutically acceptable salts are obtained by reacting a compound of Formula (I), (Ia), (II), (IIa), (III), (IIIa), (IV), (IVa), (V) or (Va) with acids. Pharmaceutically acceptable salts are also obtained by reacting a compound of Formula (I), (Ia), (II), (Ia), (III), (IIIa), (IV), (IVa), (V) or (Va) with a base to form a salt.

Compounds described herein may be formed as, and/or used as, pharmaceutically acceptable salts. The type of pharmaceutical acceptable salts, include, but are not limited to: (1) acid addition salts, formed by reacting the free base form of the compound with a pharmaceutically acceptable: inorganic acid, such as, for example, hydrochloric acid, hydrobromic acid, sulfuric acid, phosphoric acid, metaphosphoric acid, and the like; or with an organic acid, such as, for example, acetic acid, propionic acid, hexanoic acid, cyclopentanepropionic acid, glycolic acid, pyruvic acid, lactic acid, malonic acid, succinic acid, malic acid, maleic acid, fumaric acid, trifluoroacetic acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, toluenesulfonic acid, 2-naphthalenesulfonic acid, 4-methylbicyclo-[2.2.2]oct-2-ene-1-carboxylic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, butyric acid, phenylacetic acid, phenylbutyric acid, valproic acid, and the like; (2) salts formed when an acidic proton present in the parent compound is replaced by a metal ion, e.g., an alkali metal ion (e.g. lithium, sodium, potassium), an alkaline earth ion (e.g. magnesium, or calcium), or an aluminum ion. In some cases, compounds described herein may coordinate with an organic base, such as, but not limited to, ethanolamine, diethanolamine, triethanolamine, tromethamine, N-methylglucamine, dicyclohexylamine, tris(hydroxymethyl)methylamine. In other cases, compounds described herein may form salts with amino acids such as, but not limited to, arginine, lysine, and the like. Acceptable inorganic bases used to form salts with compounds that include an acidic proton, include, but are not limited to, aluminum hydroxide, calcium hydroxide, potassium hydroxide, sodium carbonate, sodium hydroxide, and the like.

It should be understood that a reference to a pharmaceutically acceptable salt includes the solvent addition forms, particularly solvates. Solvates contain either stoichiometric or non-stoichiometric amounts of a solvent, and may be formed during the process of crystallization with pharmaceutically acceptable solvents such as water, ethanol, and the like. Hydrates are formed when the solvent is water, or alcoholates are formed when the solvent is alcohol. Solvates of compounds described herein can be conveniently prepared or formed during the processes described herein. In addition, the compounds provided herein can exist in unsolvated as well as solvated forms. In general, the solvated forms are considered equivalent to the unsolvated forms for the purposes of the compounds and methods provided herein.

Synthesis of Compounds

In some embodiments, the synthesis of compounds described herein are accomplished using means described in the chemical literature, using the methods described herein, or by a combination thereof. In addition, solvents, temperatures and other reaction conditions presented herein may vary.

In other embodiments, the starting materials and reagents used for the synthesis of the compounds described herein are synthesized or are obtained from commercial sources, such as, but not limited to, Sigma-Aldrich, Fisher Scientific (Fisher Chemicals), and Acros Organics.

In further embodiments, the compounds described herein, and other related compounds having different substituents are synthesized using techniques and materials described herein as well as those that are recognized in the field, such as described, for example, in Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991), Larock's Comprehensive Organic Transformations (VCH Publishers Inc., 1989), March, Advanced Organic Chemistry $4^{th}$ Ed., (Wiley 1992); Carey and Sundberg, Advanced Organic Chemistry $4^{th}$ Ed., Vols. A and B (Plenum 2000, 2001), and Green and Wuts, Protective Groups in Organic Synthesis $3^{rd}$ Ed., (Wiley 1999) (all of which are incorporated by reference for such disclosure). General methods for the preparation of compounds as disclosed herein may be derived from reactions and the reactions may be modified by the use of appropriate reagents and conditions, for the introduction of the various moieties found in the formulae as provided herein. As a guide the following synthetic methods may be utilized.

In the reactions described, it may be necessary to protect reactive functional groups, for example hydroxy, amino, imino, thio or carboxy groups, where these are desired in the final product, in order to avoid their unwanted participation in reactions. A detailed description of techniques applicable to the creation of protecting groups and their removal are described in Greene and Wuts, Protective Groups in Organic Synthesis, 3rd Ed., John Wiley & Sons, New York, N.Y., 1999, and Kocienski, Protective Groups, Thieme Verlag, New York, N.Y., 1994, which are incorporated herein by reference for such disclosure).

In one aspect, compounds are synthesized as described in the Examples section.

Definitions

In the following description, certain specific details are set forth in order to provide a thorough understanding of various embodiments. However, one skilled in the art will understand that the invention may be practiced without these details. In other instances, well-known structures have not been shown or described in detail to avoid unnecessarily obscuring descriptions of the embodiments. Unless the context requires otherwise, throughout the specification and claims which follow, the word "comprise" and variations thereof, such as, "comprises" and "comprising" are to be construed in an open, inclusive sense, that is, as "including, but not limited to." Further, headings provided herein are for convenience only and do not interpret the scope or meaning of the claimed invention.

As used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

The terms below, as used herein, have the following meanings, unless indicated otherwise:

"Oxo" refers to the =O substituent.

"Thioxo" refers to the =S substituent.

"Alkyl" refers to a straight or branched hydrocarbon chain radical, having from one to twenty carbon atoms, and which is attached to the rest of the molecule by a single bond. An alkyl comprising up to 10 carbon atoms is referred to as a $C_1$-$C_{10}$ alkyl, likewise, for example, an alkyl comprising up to 6 carbon atoms is a $C_1$-$C_6$ alkyl. Alkyls (and other moieties defined herein) comprising other numbers of carbon atoms are represented similarly. Alkyl groups include, but are not limited to, $C_1$-$C_{10}$ alkyl, $C_1$-$C_9$ alkyl, $C_1$-$C_8$ alkyl, $C_1$-$C_7$ alkyl, $C_1$-$C_6$ alkyl, $C_1$-$C_5$ alkyl, $C_1$-$C_4$ alkyl, $C_1$-$C_3$ alkyl, $C_1$-$C_2$ alkyl, $C_2$-$C_8$ alkyl, $C_3$-$C_8$ alkyl and $C_4$-$C_8$ alkyl. Representative alkyl groups include, but are not limited to, methyl, ethyl, n-propyl, 1-methylethyl (i-propyl), n-butyl, i-butyl, s-butyl, n-pentyl, 1,1-dimethylethyl (t-butyl), 3-methylhexyl, 2-methylhexyl, 1-ethyl-propyl, and the like. In some embodiments, the alkyl is methyl or ethyl. In some embodiments, the alkyl is —CH(CH$_3$)$_2$ or —C(CH$_3$)$_3$. Unless stated otherwise specifically in the specification, an alkyl group may be optionally substituted as described below. "Alkylene" or "alkylene chain" refers to a straight or branched divalent hydrocarbon chain linking the rest of the molecule to a radical group. In some embodiments, the alkylene is —CH$_2$—, —CH$_2$CH$_2$—, or —CH$_2$CH$_2$CH$_2$—. In some embodiments, the alkylene is —CH$_2$—. In some embodiments, the alkylene is —CH$_2$CH$_2$—. In some embodiments, the alkylene is —CH$_2$CH$_2$CH$_2$—.

"Alkoxy" refers to a radical of the formula —OR where R is an alkyl radical as defined. Unless stated otherwise specifically in the specification, an alkoxy group may be optionally substituted as described below. Representative alkoxy groups include, but are not limited to, methoxy, ethoxy, propoxy, butoxy, pentoxy. In some embodiments, the alkoxy is methoxy. In some embodiments, the alkoxy is ethoxy.

"Heteroalkylene" refers to an alkyl radical as described above where one or more carbon atoms of the alkyl is replaced with a O, N or S atom. "Heteroalkylene" or "heteroalkylene chain" refers to a straight or branched divalent heteroalkyl chain linking the rest of the molecule to a radical group. Unless stated otherwise specifically in the specification, the heteroalkyl or heteroalkylene group may be optionally substituted as described below. Representative heteroalkyl groups include, but are not limited to —OCH$_2$OMe, —OCH$_2$CH$_2$OMe, or —OCH$_2$CH$_2$OCH$_2$CH$_2$NH$_2$. Representative heteroalkylene groups include, but are not limited to —OCH$_2$CH$_2$O—, —OCH$_2$CH$_2$OCH$_2$CH$_2$O—, or —OCH$_2$CH$_2$OCH$_2$CH$_2$OCH$_2$CH$_2$O—.

"Alkylamino" refers to a radical of the formula —NHR or —NRR where each R is, independently, an alkyl radical as defined above. Unless stated otherwise specifically in the specification, an alkylamino group may be optionally substituted as described below.

The term "aromatic" refers to a planar ring having a delocalized π-electron system containing 4n+2 π electrons, where n is an integer. Aromatics can be optionally substituted. The term "aromatic" includes both aryl groups (e.g., phenyl, naphthalenyl) and heteroaryl groups (e.g., pyridinyl, quinolinyl).

"Aryl" refers to an aromatic ring wherein each of the atoms forming the ring is a carbon atom. Aryl groups can be optionally substituted. Examples of aryl groups include, but are not limited to phenyl, and naphthyl. In some embodiments, the aryl is phenyl. Depending on the structure, an aryl group can be a monoradical or a diradical (i.e., an arylene group). Unless stated otherwise specifically in the specification, the term "aryl" or the prefix "ar-" (such as in "aralkyl") is meant to include aryl radicals that are optionally substituted.

"Carboxy" refers to —CO$_2$H. In some embodiments, carboxy moieties may be replaced with a "carboxylic acid bioisostere", which refers to a functional group or moiety that exhibits similar physical and/or chemical properties as a carboxylic acid moiety. A carboxylic acid bioisostere has similar biological properties to that of a carboxylic acid group. A compound with a carboxylic acid moiety can have the carboxylic acid moiety exchanged with a carboxylic acid bioisostere and have similar physical and/or biological properties when compared to the carboxylic acid-containing compound. For example, in one embodiment, a carboxylic acid bioisostere would ionize at physiological pH to roughly the same extent as a carboxylic acid group. Examples of bioisosteres of a carboxylic acid include, but are not limited to:

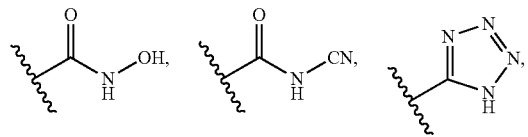

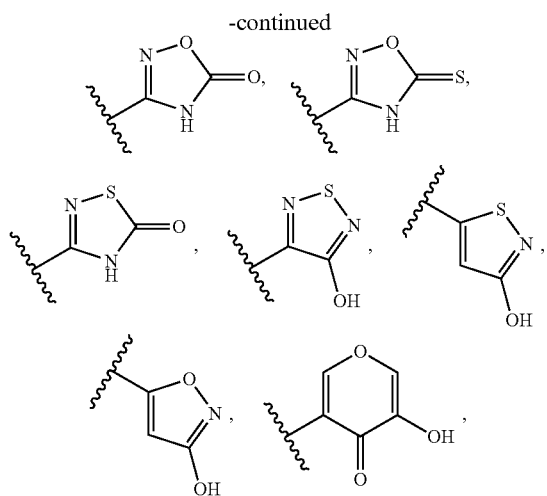

and the like.

"Cycloalkyl" refers to a monocyclic or polycyclic non-aromatic radical, wherein each of the atoms forming the ring (i.e. skeletal atoms) is a carbon atom. Cycloalkyls may be saturated, or partially unsaturated. Cycloalkyls may be fused with an aromatic ring (in which case the cycloalkyl is bonded through a non-aromatic ring carbon atom). Cycloalkyl groups include groups having from 3 to 10 ring atoms. Representative cycloalkyls include, but are not limited to, cycloalkyls having from three to ten carbon atoms, from three to eight carbon atoms, from three to six carbon atoms, or from three to five carbon atoms. Monocyclic cyclcoalkyl radicals include, for example, cyclopropyl, cyclobutyl, cyclopentyl, cyclohexyl, cycloheptyl, and cyclooctyl. In some embodiments, the monocyclic cyclcoalkyl is cyclopropyl, cyclobutyl, cyclopentyl or cyclohexyl. In some embodiments, the monocyclic cyclcoalkyl is cyclopentyl. Polycyclic radicals include, for example, adamantyl, norbornyl, decalinyl, and 3,4-dihydronaphthalen-1(2H)-one. Unless otherwise stated specifically in the specification, a cycloalkyl group may be optionally substituted.

"Fused" refers to any ring structure described herein which is fused to an existing ring structure. When the fused ring is a heterocyclyl ring or a heteroaryl ring, any carbon atom on the existing ring structure which becomes part of the fused heterocyclyl ring or the fused heteroaryl ring may be replaced with a nitrogen atom.

"Halo" or "halogen" refers to bromo, chloro, fluoro or iodo.

"Haloalkyl" refers to an alkyl radical, as defined above, that is substituted by one or more halo radicals, as defined above, e.g., trifluoromethyl, difluoromethyl, fluoromethyl, trichloromethyl, 2,2,2-trifluoroethyl, 1,2-difluoroethyl, 3-bromo-2-fluoropropyl, 1,2-dibromoethyl, and the like. Unless stated otherwise specifically in the specification, a haloalkyl group may be optionally substituted.

"Haloalkoxy" refers to an alkoxy radical, as defined above, that is substituted by one or more halo radicals, as defined above, e.g., trifluoromethoxy, difluoromethoxy, fluoromethoxy, trichloromethoxy, 2,2,2-trifluoroethoxy, 1,2-difluoroethoxy, 3-bromo-2-fluoropropoxy, 1,2-dibromoethoxy, and the like. Unless stated otherwise specifically in the specification, a haloalkoxy group may be optionally substituted.

"Heterocycloalkyl" or "heterocyclyl" or "heterocyclic ring" refers to a stable 3- to 14-membered non-aromatic ring radical comprising 2 to 10 carbon atoms and from one to 4 heteroatoms selected from the group consisting of nitrogen, oxygen, and sulfur. Unless stated otherwise specifically in the specification, the heterocycloalkyl radical may be a monocyclic, or bicyclic ring system, which may include fused (when fused with an aryl or a heteroaryl ring, the heterocycloalkyl is bonded through a non-aromatic ring atom) or bridged ring systems. The nitrogen, carbon or sulfur atoms in the heterocyclyl radical may be optionally oxidized. The nitrogen atom may be optionally quaternized. The heterocycloalkyl radical is partially or fully saturated. Examples of such heterocycloalkyl radicals include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, 1,1-dioxo-thiomorpholinyl. The term heterocycloalkyl also includes all ring forms of carbohydrates, including but not limited to monosaccharides, disaccharides and oligosaccharides. Unless otherwise noted, heterocycloalkyls have from 2 to 10 carbons in the ring. In some embodiments, heterocycloalkyls have from 2 to 8 carbons in the ring. In some embodiments, heterocycloalkyls have from 2 to 8 carbons in the ring and 1 or 2 N atoms. In some embodiments, heterocycloalkyls have from 2 to 10 carbons, 0-2 N atoms, 0-2 O atoms, and 0-1 S atoms in the ring. In some embodiments, heterocycloalkyls have from 2 to 10 carbons, 1-2 N atoms, 0-1 O atoms, and 0-1 S atoms in the ring. It is understood that when referring to the number of carbon atoms in a heterocycloalkyl, the number of carbon atoms in the heterocycloalkyl is not the same as the total number of atoms (including the heteroatoms) that make up the heterocycloalkyl (i.e. skeletal atoms of the heterocycloalkyl ring). Unless stated otherwise specifically in the specification, a heterocycloalkyl group may be optionally substituted.

"Heteroaryl" refers to an aryl group that includes one or more ring heteroatoms selected from nitrogen, oxygen and sulfur. The heteroaryl is monocyclic or bicyclic. Illustrative examples of monocyclic heteroaryls include pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, pyridazinyl, triazinyl, oxadiazolyl, thiadiazolyl, furazanyl, indolizine, indole, benzofuran, benzothiophene, indazole, benzimidazole, purine, quinolizine, quinoline, isoquinoline, cinnoline, phthalazine, quinazoline, quinoxaline, 1,8-naphthyridine, and pteridine. Illustrative examples of monocyclic heteroaryls include pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, pyridazinyl, triazinyl, oxadiazolyl, thiadiazolyl, and furazanyl. Illustrative examples of bicyclic heteroaryls include indolizine, indole, benzofuran, benzothiophene, indazole, benzimidazole, purine, quinolizine, quinoline, isoquinoline, cinnoline, phthalazine, quinazoline, quinoxaline, 1,8-naphthyridine, and pteridine. In some embodiments, heteroaryl is pyridinyl, pyrazinyl, pyrimidinyl, thiazolyl, thienyl, thiadiazolyl or furyl. In some embodiments, a heteroaryl contains 0-4 N atoms in the ring. In some embodiments, a heteroaryl contains 1-4 N atoms in the ring. In some embodiments, a heteroaryl contains 0-4 N atoms, 0-1 O atoms, and 0-1 S atoms in the ring. In some embodiments, a heteroaryl contains 1-4 N atoms, 0-1 O atoms, and 0-1 S atoms in the ring. In some embodiments, heteroaryl is a $C_1$-$C_9$heteroaryl. In some embodiments, monocyclic heteroaryl is a $C_1$-$C_5$heteroaryl. In some embodiments, monocyclic heteroaryl is a 5-membered or 6-membered heteroaryl. In some embodiments, a bicyclic heteroaryl is a $C_6$-$C_9$heteroaryl.

The term "optionally substituted" or "substituted" means that the referenced group may be substituted with one or more additional group(s) individually and independently selected from alkyl, haloalkyl, cycloalkyl, aryl, heteroaryl, heterocycloalkyl, —OH, alkoxy, aryloxy, alkylthio, arylthio, alkylsulfoxide, arylsulfoxide, alkylsulfone, arylsulfone, —CN, alkyne, $C_1$-$C_6$alkylalkyne, halogen, acyl, acyloxy, —$CO_2H$, —$CO_2$alkyl, nitro, and amino, including mono- and di-substituted amino groups (e.g. —$NH_2$, —NHR, —$N(R)_2$), and the protected derivatives thereof. In some embodiments, optional substituents are independently selected from alkyl, alkoxy, haloalkyl, cycloalkyl, halogen, —CN, —$NH_2$, —$NH(CH_3)$, —$N(CH_3)_2$, —OH, —$CO_2H$, and —$CO_2$alkyl. In some embodiments, optional substituents are independently selected from fluoro, chloro, bromo, iodo, —$CH_3$, —$CH_2CH_3$, —$CF_3$, —$OCH_3$, and —$OCF_3$. In some embodiments, substituted groups are substituted with one or two of the preceding groups. In some embodiments, an optional substituent on an aliphatic carbon atom (acyclic or cyclic, saturated or unsaturated carbon atoms, excluding aromatic carbon atoms) includes oxo (=O).

The terms "co-administration" or the like, as used herein, are meant to encompass administration of the selected therapeutic agents to a single patient, and are intended to include treatment regimens in which the agents are administered by the same or different route of administration or at the same or different time.

The terms "effective amount" or "therapeutically effective amount," as used herein, refer to a sufficient amount of an agent or a compound being administered which will relieve to some extent one or more of the symptoms of the disease or condition being treated. The result can be reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in disease symptoms. An appropriate "effective" amount in any individual case may be determined using techniques, such as a dose escalation study.

The term "pharmaceutical combination" as used herein, means a product that results from the mixing or combining of more than one active ingredient and includes both fixed and non-fixed combinations of the active ingredients. The term "fixed combination" means that the active ingredients, e.g. a compound of Formula (I), (Ia), (II), (IIa), (III), (IIIa), (IV), (IVa), (V) or (Va) and a co-agent, are both administered to a patient simultaneously in the form of a single entity or dosage. The term "non-fixed combination" means that the active ingredients, e.g. a compound of Formula (I), (Ia), (II), (IIa), (III), (IIIa), (IV), (IVa), (V) or (Va) and a co-agent, are administered to a patient as separate entities either simultaneously, concurrently or sequentially with no specific intervening time limits, wherein such administration provides effective levels of the two compounds in the body of the patient. The latter also applies to cocktail therapy, e.g. the administration of three or more active ingredients.

The term "subject" or "patient" encompasses mammals. Examples of mammals include, but are not limited to, humans. In one embodiment, the mammal is a human.

The terms "treat," "treating" or "treatment," as used herein, include alleviating, abating or ameliorating at least one symptom of a disease or condition, preventing additional symptoms, inhibiting the disease or condition, e.g., arresting the development of the disease or condition, relieving the disease or condition, causing regression of the disease or condition, relieving a condition caused by the disease or condition, or stopping the symptoms of the disease or condition either prophylactically and/or therapeutically.

A "tautomer" refers to a proton shift from one atom of a molecule to another atom of the same molecule. The compounds presented herein may exist as tautomers. Tautomers are compounds that are interconvertible by migration of a hydrogen atom, accompanied by a switch of a single bond and adjacent double bond. In bonding arrangements where tautomerization is possible, a chemical equilibrium of the tautomers will exist. All tautomeric forms of the compounds disclosed herein are contemplated. The exact ratio of the tautomers depends on several factors, including temperature, solvent, and pH. Some examples of tautomeric interconversions include:

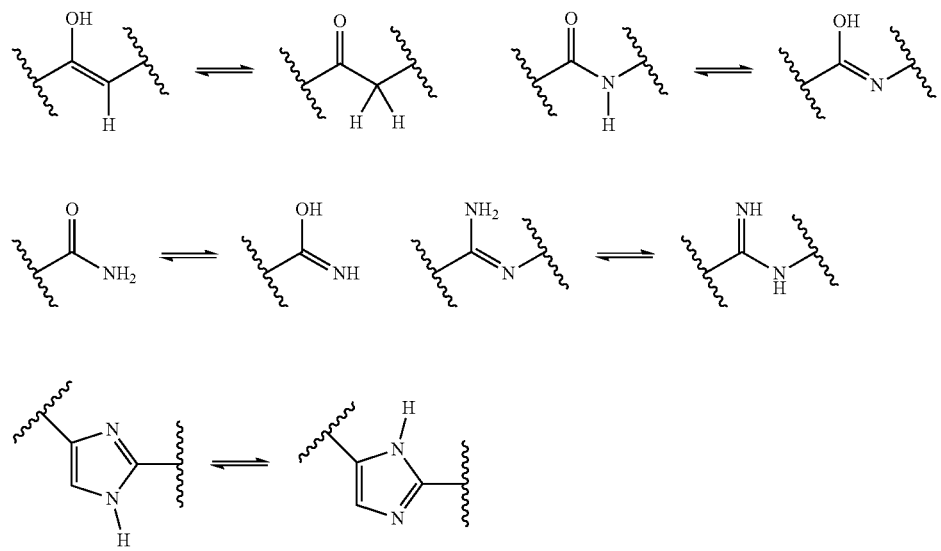

-continued

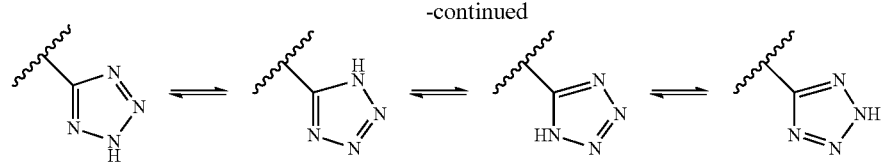

Administration and Pharmaceutical Composition

In some embodiments, the compounds described herein are formulated into pharmaceutical compositions. Pharmaceutical compositions are formulated in a conventional manner using one or more pharmaceutically acceptable inactive ingredients that facilitate processing of the active compounds into preparations that can be used pharmaceutically. Proper formulation is dependent upon the route of administration chosen. A summary of pharmaceutical compositions described herein can be found, for example, in Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pa. 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins 1999), herein incorporated by reference for such disclosure.

A pharmaceutical composition, as used herein, refers to a mixture of a compound of Formula (I), (Ia), (II), (IIa), (III), (IIIa), (IV), (IVa), (V) or (Va) with other chemical components (i.e. pharmaceutically acceptable inactive ingredients), such as carriers, excipients, binders, filling agents, suspending agents, flavoring agents, sweetening agents, disintegrating agents, dispersing agents, surfactants, lubricants, colorants, diluents, solubilizers, moistening agents, plasticizers, stabilizers, penetration enhancers, wetting agents, antifoaming agents, antioxidants, preservatives, or one or more combination thereof. The pharmaceutical composition facilitates administration of the compound to an organism.

Pharmaceutical formulations described herein are administrable to a subject in a variety of ways by multiple administration routes, including but not limited to, oral, parenteral (e.g., intravenous, subcutaneous, intramuscular, intramedullary injections, intrathecal, direct intraventricular, intraperitoneal, intralymphatic, intranasal injections), intranasal, buccal, topical or transdermal administration routes. The pharmaceutical formulations described herein include, but are not limited to, aqueous liquid dispersions, self-emulsifying dispersions, solid solutions, liposomal dispersions, aerosols, solid dosage forms, powders, immediate release formulations, controlled release formulations, fast melt formulations, tablets, capsules, pills, delayed release formulations, extended release formulations, pulsatile release formulations, multiparticulate formulations, and mixed immediate and controlled release formulations.

In some embodiments, the compounds of Formula (I), (Ia), (II), (IIa), (III), (IIIa), (IV), (IVa), (V) or (Va) are administered orally.

In some embodiments, the compounds of Formula (I), (Ia), (II), (IIa), (III), (IIIa), (IV), (IVa), (V) or (Va) are administered topically. In such embodiments, the compound of Formula (I), (Ia), (II), (IIa), (III), (IIIa), (IV), (IVa), (V) or (Va) is formulated into a variety of topically administrable compositions, such as solutions, suspensions, lotions, gels, pastes, shampoos, scrubs, rubs, smears, medicated sticks, medicated bandages, balms, creams or ointments. In one aspect, the compounds of Formula (I), (Ia), (II), (IIa), (III), (IIIa), (IV), (IVa), (V) or (Va) are administered topically to the skin.

In another aspect, the compounds of Formula (I), (Ia), (II), (IIa), (III), (IIIa), (IV), (IVa), (V) or (Va) are administered by inhalation.

In another aspect, the compounds of Formula (I), (Ia), (II), (IIa), (III), (IIIa), (IV), (IVa), (V) or (Va) are formulated for intranasal administration. Such formulations include nasal sprays, nasal mists, and the like.

In another aspect, the compounds of Formula (I), (Ia), (II), (IIa), (III), (IIIa), (IV), (IVa), (V) or (Va) are formulated as eye drops.

In any of the aforementioned aspects are further embodiments in which the effective amount of the compound of Formula (I), (Ia), (II), (IIa), (III), (IIIa), (IV), (IVa), (V) or (Va) is: (a) systemically administered to the mammal; and/or (b) administered orally to the mammal; and/or (c) intravenously administered to the mammal; and/or (d) administered by inhalation to the mammal; and/or (e) administered by nasal administration to the mammal; or and/or (f) administered by injection to the mammal; and/or (g) administered topically to the mammal; and/or (h) administered by ophthalmic administration; and/or (i) administered rectally to the mammal; and/or (j) administered non-systemically or locally to the mammal.

In any of the aforementioned aspects are further embodiments comprising single administrations of the effective amount of the compound of Formula (I), (Ia), (II), (IIa), (III), (IIIa), (IV), (IVa), (V) or (Va), including further embodiments in which (i) the compound is administered once; (ii) the compound is administered to the mammal multiple times over the span of one day; (iii) continually; or (iv) continuously.

In any of the aforementioned aspects are further embodiments comprising multiple administrations of the effective amount of the compound of Formula (I), (Ia), (II), (IIa), (III), (IIIa), (IV), (IVa), (V) or (Va), including further embodiments in which (i) the compound is administered continuously or intermittently: as in a single dose; (ii) the time between multiple administrations is every 6 hours; (iii) the compound is administered to the mammal every 8 hours; (iv) the compound is administered to the mammal every 12 hours; (v) the compound is administered to the mammal every 24 hours. In further or alternative embodiments, the method comprises a drug holiday, wherein the administration of the compound of Formula (I), (Ia), (II), (IIa), (III), (IIIa), (IV), (IVa), (V) or (Va) is temporarily suspended or the dose of the compound being administered is temporarily reduced; at the end of the drug holiday, dosing of the compound is resumed. In one embodiment, the length of the drug holiday varies from 2 days to 1 year.

In certain embodiments, the compound of Formula (I), (Ia), (II), (IIa), (III), (IIIa), (IV), (IVa), (V) or (Va) is administered in a local rather than systemic manner.

In some embodiments, the compound of Formula (I), (Ia), (II), (IIa), (III), (IIIa), (IV), (IVa), (V) or (Va) is administered topically. In some embodiments, the compound of Formula (I), (Ia), (II), (IIa), (III), (IIIa), (IV), (IVa), (V) or (Va) is administered systemically.

In some embodiments, the pharmaceutical formulation is in the form of a tablet. In other embodiments, pharmaceutical formulations of the compounds of Formula (I), (Ia), (II), (IIa), (III), (IIIa), (IV), (IVa), (V) or (Va) are in the form of a capsule.

In one aspect, liquid formulation dosage forms for oral administration are in the form of aqueous suspensions or solutions selected from the group including, but not limited to, aqueous oral dispersions, emulsions, solutions, elixirs, gels, and syrups.

For administration by inhalation, a compound of Formula (I), (Ia), (II), (IIa), (III), (IIIa), (IV), (IVa), (V) or (Va) is formulated for use as an aerosol, a mist or a powder.

For buccal or sublingual administration, the compositions may take the form of tablets, lozenges, or gels formulated in a conventional manner.

In some embodiments, compounds of Formula (I), (Ia), (II), (IIa), (III), (IIIa), (IV), (IVa), (V) or (Va) are prepared as transdermal dosage forms.

In one aspect, a compound of Formula (I), (Ia), (II), (IIa), (III), (IIIa), (IV), (IVa), (V) or (Va) is formulated into a pharmaceutical composition suitable for intramuscular, subcutaneous, or intravenous injection.

In some embodiments, the compound of Formula (I), (Ia), (II), (IIa), (III), (IIIa), (IV), (IVa), (V) or (Va) is be administered topically and can be formulated into a variety of topically administrable compositions, such as solutions, suspensions, lotions, gels, pastes, medicated sticks, balms, creams or ointments.

In some embodiments, the compounds of Formula (I), (Ia), (II), (IIa), (III), (IIIa), (IV), (IVa), (V) or (Va) are formulated in rectal compositions such as enemas, rectal gels, rectal foams, rectal aerosols, suppositories, jelly suppositories, or retention enemas.

Methods of Dosing and Treatment Regimens

In one embodiment, the compounds of Formula (I), (Ia), (II), (IIa), (III), (IIIa), (IV), (IVa), (V) or (Va) are used in the preparation of medicaments for the treatment of diseases or conditions described herein. In addition, a method for treating any of the diseases or conditions described herein in a subject in need of such treatment, involves administration of pharmaceutical compositions that include at least one compound of Formula (I), (Ia), (II), (IIa), (III), (IIIa), (IV), (IVa), (V) or (Va) or a pharmaceutically acceptable salt, active metabolite, prodrug, or solvate thereof, in therapeutically effective amounts to said subject.

In certain embodiments, the compositions containing the compound of Formula (I), (Ia), (II), (IIa), (III), (IIIa), (IV), (IVa), (V) or (Va) are administered for prophylactic and/or therapeutic treatments. In certain therapeutic applications, the compositions are administered to a patient already suffering from a disease or condition, in an amount sufficient to cure or at least partially arrest at least one of the symptoms of the disease or condition. Amounts effective for this use depend on the severity and course of the disease or condition, previous therapy, the patient's health status, weight, and response to the drugs, and the judgment of the treating physician. Therapeutically effective amounts are optionally determined by methods including, but not limited to, a dose escalation clinical trial.

In prophylactic applications, compositions containing the compounds of Formula (I), (Ia), (II), (IIa), (III), (IIIa), (IV), (IVa), (V) or (Va) are administered to a patient susceptible to or otherwise at risk of a particular disease, disorder or condition.

In certain embodiments, the dose of drug being administered may be temporarily reduced or temporarily suspended for a certain length of time (i.e., a "drug holiday").

Doses employed for adult human treatment are typically in the range of 0.01 mg-5000 mg per day or from about 1 mg to about 1000 mg per day. In one embodiment, the desired dose is conveniently presented in a single dose or in divided doses.

Combination Treatments

In certain instances, it is appropriate to administer at least one compound of Formula (I), (Ia), (II), (IIa), (III), (IIIa), (IV), (IVa), (V) or (Va) in combination with another therapeutic agent.

In one specific embodiment, a compound of Formula (I), (Ia), (II), (IIa), (III), (IIIa), (IV), (IVa), (V) or (Va) is co-administered with a second therapeutic agent, wherein the compound of Formula (I), (Ia), (II), (IIa), (III), (IIIa), (IV), (IVa), (V) or (Va) and the second therapeutic agent modulate different aspects of the disease, disorder or condition being treated, thereby providing a greater overall benefit than administration of either therapeutic agent alone.

For combination therapies described herein, dosages of the co-administered compounds vary depending on the type of co-drug(s) employed, on the specific drug(s) employed, on the disease or condition being treated and so forth. In additional embodiments, when co-administered with one or more other therapeutic agents, the compound provided herein is administered either simultaneously with the one or more other therapeutic agents, or sequentially.

If administration is simultaneous, the multiple therapeutic agents are, by way of example only, provided in a single, unified form, or in multiple forms.

In some embodiments, the one or more agents used in the treatment of a metabolic disorder include, but are not limited to, a statin, an insulin sensitizing drug, (such as sitagliptin, vildagliptin, saxagliptin, linagliptin, anagliptin, teneligliptin, alogliptin, gemigliptin, or dutoglpitin), meglitinide, sulfonylurea, peroxisome proliferator-activated receptor (alpha-glucosidase inhibitor, amylin agonist, dipeptidyl-peptidase 4 (DPP-4) inhibitor PPAR)-gamma agonist (e.g., a thiazolidinedione (TZD) [such as ioglitazone, rosiglitazone, rivoglitazone, or troglitazone], aleglitazar, farglitazar, muraglitazar, or tesaglitazar), a glucagon-like peptide (GLP) agonist, anti-inflammatory agent (e.g., oral corticosteroid), or a combination thereof. In some embodiments, the one or more agents used in the treatment of a metabolic disorder include, but are not limited to, a statin, HMG-CoA reductase inhibitor, fish oil, fibrate, niacin or other treatment for dyslipidemia. In some embodiments retinoic acid is also administered. In one example, nicotinamide ribonucleoside and/or nicotinamide ribonucleoside analogs are also administered. Nicotinamide ribonucleoside and its analogs promote NAD+ production of which is a substrate for many enzymatic reactions such as p450s.

In some embodiments, the therapy that is used in conjunction with a NAMPT activator includes administration of one or more additional compounds or therapies, such as an anti-obesity and/or an anti-diabetes therapy. For example, in some embodiments the disclosed therapies described herein is provided with a meglitinide, e.g., to stimulate the release of insulin. Exemplary meglitinides are repaglinide (Prandin) and nateglinide (Starlix). In some embodiments, a therapy described herein is provided with a sulfonylurea, e.g., to stimulate the release of insulin. Exemplary sulfonylureas are glipizide (Glucotrol), glimepiride (Amaryl), and glyburide (DiaBeta, Glynase). In some embodiments, a therapy described herein is provided with a dipeptidyl peptidase-4 (DPP-4) inhibitor, e.g., to stimulate the release of insulin and/or to inhibit the release of glucose from the liver. Exemplary dipeptidyl peptidase-4 (DPP-4) inhibitors are saxagliptin (Onglyza), sitagliptin (Januvia), and linagliptin (Tradjenta). In some embodiments, a therapy described herein is provided with a biguanide, e.g., to inhibit the release of glucose from the liver and/or to improve sensitivity to insulin. An exemplary biguanide is metformin (Fortamet, Glucophage). In some embodiments, a therapy described herein is provided with a thiazolidinedione, e.g., to improve sensitivity to insulin and/or to inhibit the release of glucose from the liver. Exemplary thiazolidinediones include but are not limited to rosiglitazone (Avandia) and pioglitazone (Actos). In some embodiments a therapy described herein is provided with an alpha-glucosidase inhibitor, e.g., to slow the breakdown of starches and some sugars. Exemplary alpha-glucosidase inhibitors include acarbose (Precose) and miglitol (Glyset). In some embodiments, a therapy as described herein is provided with an injectable medication such as an amylin mimetic or an incretin memetic, e.g., to stimulate the release of insulin. An exemplary amylin mimetic is pramlintide (Symlin); exemplary incretin mimetics include exenatide (Byetta) and liraglutide (Victoza). In some embodiments a therapy described herein is provided with insulin. The technology is not limited to any particular form of insulin, but encompasses providing the compounds described with any form of insulin. In some embodiments, the therapy described is used with an insulin injection. In some embodiments, a therapy described herein is provided with more than one additional therapy (e.g., drug or other biologically active composition or compound), e.g., two, three, four or more compounds.

In some embodiments, a NAMPT activator described herein is used in conjunction with therapy used to treat muscle atrophy. Therapies used to treat muscle atrophy include, but are not limited to, physical therapy programs, medication, surgery and electrical stimulation. Muscle atrophy treatment medications include, but are not limited to, anti-inflammatory medication, anabolic steroids, amino acid therapy, selective adrenergic receptor modulators (SARM).

In some embodiments, a NAMPT activator is used in combination with donepezil, galantamine, rivastigmine, memantine, latrepirdine, idalopridine, or cerlapirdine.

In some embodiments, a NAMPT activator is used in combination with levodopa. In some embodiments, a NAMPT activator is used in combination with carbidopa-levodopa. In some embodiments, a NAMPT activator is used in combination with a dopamine agonist, such as ropinirole, pramipexole, or rotigotine. In some embodiments, a NAMPT activator is used in combination with a MAO-B inhibitor such as selegiline or rasagiline. In some embodiments, a NAMPT activator is used in combination with an anticholinergic such as benztropine or trihexyphenidyl. In some embodiments, the additional therapeutic agent is amantadine.

In some embodiments, a NAMPT activator is used in combination with tetrabenazine, haloperidol, chlorpromazine, risperidone, olanzapine, quetiapine, amantadine, levetiracetam, clonazepam, citalopram, fluoxetine, sertraline, valproate, carbamazepine, or lamotrigine.

In some embodiments, a NAMPT activator is used in combination with riluzole, baclofen, diazepam, trihexyphenidyl or amitriptyline.

In some embodiments, a NAMPT activator is used in combination with aripiprazole, asenapine, clozapine, iloperidone, lurasidone, olanzapine, paliperidone, quetiapine, risperidone, ziprasidone, chlorpromazine, fluphenazine, haloperidol, perphenazine, escitalopram, duloxetine, venlafaxine, or paroxetine, buspirone, or a benzodiazepine, such as alprazolam, chlordiazepoxide, diazepam, or lorazepam.

In some embodiments, a NAMPT activator is used in combination with an anti-cancer therapy. In some embodiments, a NAMPT activator is used in combination with conventional chemotherapy, radiotherapy, hormonal therapy, and/or immunotherapy. In some embodiments, a NAMPT activator is used in combination with conventional chemotherapeutic agents including alkylating agents (e.g., temozolomide, cyclophosphamide, ifosfamide, chlorambucil, busulfan, melphalan, mechlorethamine, uramustine, thiotepa, nitrosoureas, etc.), anti-metabolites (e.g., 5-fluorouracil, azathioprine, methotrexate, leucovorin, capecitabine, cytarabine, floxuridine, fludarabine, gemcitabine, pemetrexed, raltitrexed, etc.), plant alkaloids (e.g., vincristine, vinblastine, vinorelbine, vindesine, podophyllotoxin, paclitaxel, docetaxel, etc.), topoisomerase inhibitors (e.g., irinotecan, topotecan, amsacrine, etoposide (VP16), etoposide phosphate, teniposide, etc.), antitumor antibiotics (e.g., doxorubicin, adriamycin, daunorubicin, epirubicin, actinomycin, bleomycin, mitomycin, mitoxantrone, plicamycin, etc.), platinum-based compounds (e.g. cisplatin, oxaloplatin, carboplatin, etc.), EGFR inhibitors (e.g., gefitinib, erlotinib, etc.), and the like.

EXAMPLES

The following examples are intended to illustrate but not limit the disclosed embodiments.

Example 1: Synthesis of
1-(4-Chlorophenyl)-3-(pyridin-3-ylmethyl)urea

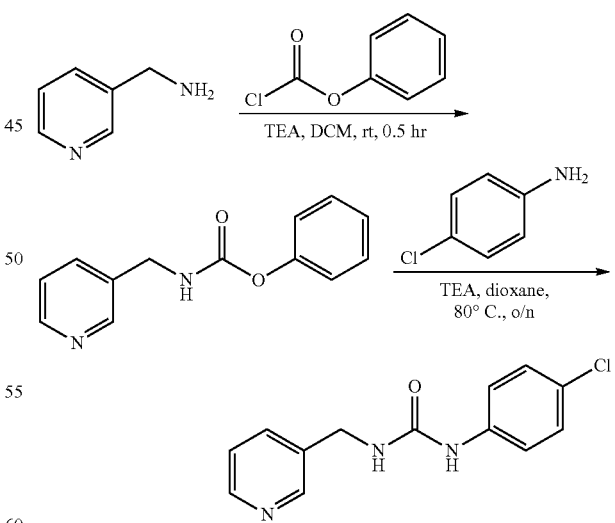

Step 1: To a solution of pyridin-3-ylmethanamine (5.0 g, 46.2 mmol) in dry DCM (200 mL) was added phenyl chloroformate (8.7 g, 55.4 mmol), followed by triethylamine (5.6 g, 55.4 mmol). The resulting mixture was stirred at room temperature for 0.5 hr. The reaction was monitored by TLC. Then DCM was removed in vacuum to give a residue, which was purified by a silica gel column eluting with DCM/MeOH=50/1 to afford phenyl (pyridin-3-ylmethyl)carbamate (9.82 g, yield: 93%) as a yellow solid. $^1$H NMR (400 MHz, DMSO-$d_6$): δ=8.60 (s, 1H), 8.56 (d, J=4.4 Hz, 1H), 7.71 (d, J=7.6 Hz, 1H), 7.40-7.33 (m, 2H), 7.32-7.27 (m, 1H), 7.24-7.18 (m, 1H), 7.17-7.10 (m, 2H), 5.53 (brs, 1H), 4.47 (d, J=6.0 Hz, 2H).

Step 2: To a solution of phenyl (pyridin-3-ylmethyl) carbamate (100 mg, 0.438 mmol) in dioxane (10 mL) was added 4-chloro-phenylamine (62 mg, 0.482 mmol), followed by triethyl-amine (133 mg, 1.31 mmol). The resulting mixture was stirred at 80° C. overnight. The reaction was monitored by TLC. Then the reaction mixture was allowed to cool to room temperature and concentrated in vacuum to give a residue, which was purified by prep-TLC (DCM/MeOH=20/1) to afford 1-(4-chlorophenyl)-3-(pyridin-3-ylmethyl)urea (55.4 mg, yield: 48%) as a white solid. $^1$H NMR (400 MHz, DMSO-$d_6$): δ=8.77 (brs, 1H), 8.52 (d, J=2.0 Hz, 1H), 8.45 (dd, J=4.8, 1.6 Hz, 1H), 7.74-7.68 (m, 1H), 7.46-7.40 (m, 2H), 7.36 (dd, J=8.0, 4.8 Hz, 1H), 7.29-7.23 (m, 2H), 6.75 (t, J=5.6 Hz, 1H), 4.31 (d, J=6.0 Hz, 2H). MS: m/z 262.0 (M+H$^+$).

Example 2: Synthesis of 1-(4-Fluorophenyl)-3-(pyridin-4-ylmethyl)urea

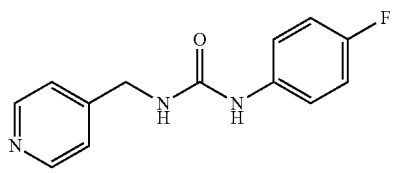 [SMILES: O=C(NCc1ccncc1)Nc1ccc(F)cc1]

The title compound was prepared as described in example 1-(4-chlorophenyl)-3-(pyridin-3-ylmethyl)urea. $^1$H NMR (400 MHz, DMSO-$d_6$): δ=8.72 (brs, 1H), 8.50 (dd, J=4.8, 1.6 Hz, 2H), 7.44-7.38 (m, 2H), 7.28 (d, J=5.6 Hz, 2H), 7.10-7.02 (m, 2H), 6.72 (t, J=6.0 Hz, 1H), 4.32 (d, J=6.0 Hz, 2H). MS: m/z 246.1 (M+H$^+$).

Example 3: Synthesis of 1-(4-Chlorophenyl)-3-(pyridin-4-ylmethyl)urea

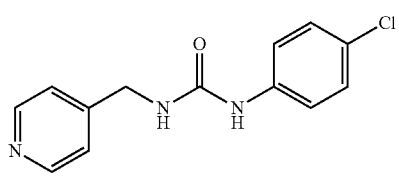 [SMILES: O=C(NCc1ccncc1)Nc1ccc(Cl)cc1]

The title compound was prepared as described in example 1-(4-chlorophenyl)-3-(pyridin-3-ylmethyl)urea. $^1$H NMR (400 MHz, DMSO-$d_6$): δ=8.85 (brs, 1H), 8.50 (d, J=6.0 Hz, 2H), 7.44 (d, J=8.8 Hz, 1H), 7.33-7.21 (m, 4H), 6.78 (t, J=6.0 Hz, 1H), 4.32 (d, J=6.0 Hz, 2H). MS: m/z 262.0 (M+H$^+$).

Example 4: Synthesis of 1-(Pyridin-4-ylmethyl)-3-(p-tolyl)urea

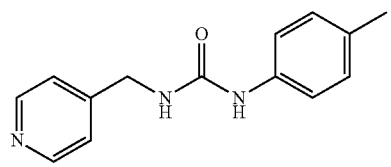 [SMILES: Cc1ccc(NC(=O)NCc2ccncc2)cc1]

The title compound was prepared as described in example 1-(4-chlorophenyl)-3-(pyridin-3-ylmethyl)urea. $^1$H NMR (400 MHz, DMSO-$d_6$): δ=8.55 (brs, 1H), 8.50 (dd, J=4.8, 1.6 Hz, 2H), 7.28 (d, J=7.6 Hz, 4H), 7.03 (d, J=8.0 Hz, 2H), 6.60 (t, J=6.0 Hz, 1H), 4.31 (d, J=6.0 Hz, 2H), 2.21 (s, 3H). MS: m/z 242.1 (M+H$^+$).

Example 5: Synthesis of 1-(4-Fluorophenyl)-3-(pyridin-2-ylmethyl)urea

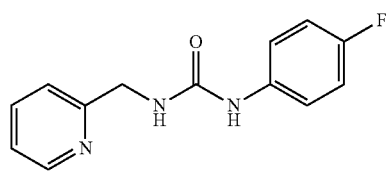 [SMILES: O=C(NCc1ccccn1)Nc1ccc(F)cc1]

The title compound was prepared as described in example 1-(4-chlorophenyl)-3-(pyridin-3-ylmethyl)urea. $^1$H NMR (400 MHz, DMSO-$d_6$): δ=8.80 (brs, 1H), 8.52 (d, J=5.2 Hz, 1H), 7.81-7.74 (m, 1H), 7.45-7.38 (m, 2H), 7.34 (d, J=7.6 Hz, 1H), 7.27 (dd, J=6.8, 5.2 Hz, 1H), 7.10-7.02 (m, 2H), 6.73 (t, J=5.6 Hz, 1H), 4.40 (d, J=5.6 Hz, 2H). MS: m/z 245.9 (M+H$^+$).

Example 6: Synthesis of 1-(4-Chlorophenyl)-3-(pyridin-2-ylmethyl)urea

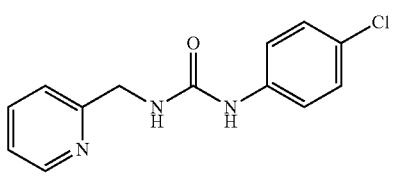 [SMILES: O=C(NCc1ccccn1)Nc1ccc(Cl)cc1]

The title compound was prepared as described in example 1-(4-chlorophenyl)-3-(pyridin-3-ylmethyl)urea. $^1$H NMR (400 MHz, DMSO-$d_6$): δ=8.92 (brs, 1H), 8.52 (d, J=5.2 Hz, 1H), 7.80-7.74 (m, 1H), 7.48-7.40 (m, 2H), 7.34 (d, J=8.0 Hz, 1H), 7.30-7.23 (m, 3H), 6.79 (t, J=5.6 Hz, 1H), 4.40 (d, J=5.6 Hz, 2H). MS: m/z 262.0 (M+H$^+$).

Example 7: Synthesis of 1-(Pyridin-2-ylmethyl)-3-(p-tolyl)urea

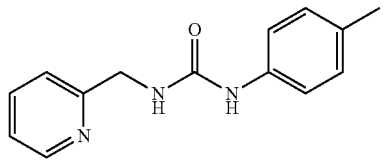 [SMILES: Cc1ccc(NC(=O)NCc2ccccn2)cc1]

The title compound was prepared as described in example 1-(4-chlorophenyl)-3-(pyridin-3-ylmethyl)urea. $^1$H NMR (400 MHz, DMSO-d$_6$): δ=8.63 (brs, 1H), 8.52 (d, J=4.8, 1H), 7.76 (dt, J=7.2, 1.6 Hz, 1H), 7.34 (d, J=8.0 Hz, 1H), 7.31-7.24 (m, 3H), 7.02 (d, J=8.8 Hz, 2H), 6.68 (t, J=5.6 Hz, 1H), 4.39 (d, J=5.6 Hz, 2H), 2.21 (s, 3H). MS: m/z 242.1 (M+H$^+$).

Example 8: Synthesis of 1-(4-Fluorophenyl)-3-(pyridin-3-ylmethyl)urea

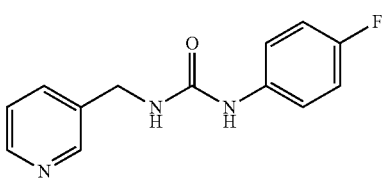 [SMILES: O=C(NCc1cccnc1)Nc1ccc(F)cc1]

The title compound was prepared as described in example 1-(4-chlorophenyl)-3-(pyridin-3-ylmethyl)urea. $^1$H NMR (400 MHz, DMSO-d$_6$): δ=8.63 (brs, 1H), 8.52 (d, J=2.0 Hz, 1H), 8.45 (dd, J=4.8, 1.6 Hz, 1H), 7.74-7.68 (m, 1H), 7.44-7.32 (m, 3H), 7.09-7.01 (m, 2H), 6.68 (t, J=6.0 Hz, 1H), 4.31 (d, J=6.0 Hz, 2H). MS: m/z 246.0 (M+H$^+$).

Example 9: Synthesis of 1-(Pyridin-3-ylmethyl)-3-(p-tolyl)urea

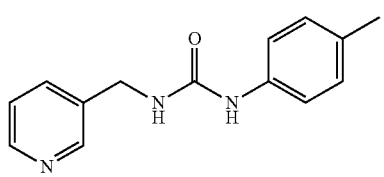 [SMILES: Cc1ccc(NC(=O)NCc2cccnc2)cc1]

The title compound was prepared as described in example 1-(4-chlorophenyl)-3-(pyridin-3-ylmethyl)urea. $^1$H NMR (400 MHz, DMSO-d$_6$): δ=8.52 (d, J=2.0 Hz, 1H), 8.47 (brs, 1H), 8.45 (dd, J=4.8, 1.6 Hz, 1H), 7.74-7.68 (m, 1H), 7.35 (dd, J=8.0, 4.8 Hz, 1H), 7.31-7.24 (m, 2H), 7.06-6.99 (m, 2H), 6.62 (t, J=6.0 Hz, 1H), 4.30 (d, J=6.0 Hz, 2H), 2.21 (s, 3H). MS: m/z 242.1 (M+H$^+$).

Example 10: Synthesis of 1-(Pyridin-3-ylmethyl)-3-(4-(trifluoromethyl)phenyl)urea

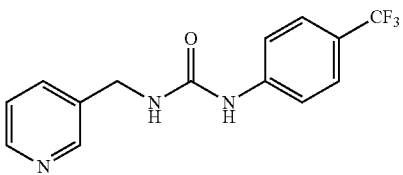 [SMILES: O=C(NCc1cccnc1)Nc1ccc(C(F)(F)F)cc1]

The title compound was prepared as described in example 1-(4-chlorophenyl)-3-(pyridin-3-ylmethyl)urea. $^1$H NMR (400 MHz, DMSO-d$_6$): δ=9.07 (brs, 1H), 8.53 (d, J=2.4 Hz, 1H), 8.46 (dd, J=4.8, 1.6 Hz, 1H), 7.75-7.69 (m, 1H), 7.64-7.54 (m, 4H), 7.36 (dd, J=8.0, 4.8 Hz, 1H), 6.87 (t, J=6.0 Hz, 1H), 4.32 (d, J=6.0 Hz, 2H). MS: m/z 296.0 (M+H$^+$).

Example 11: Synthesis of 1-(Pyridin-3-ylmethyl)-3-(4-(trifluoromethoxy)phenyl)urea

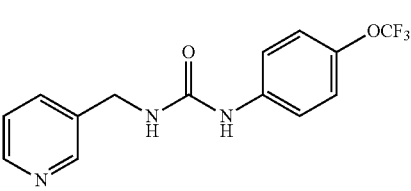 [SMILES: O=C(NCc1cccnc1)Nc1ccc(OC(F)(F)F)cc1]

The title compound was prepared as described in example 1-(4-chlorophenyl)-3-(pyridin-3-ylmethyl)urea. $^1$H NMR (400 MHz, DMSO-d$_6$): δ=8.84 (brs, 1H), 8.53 (d, J=2.0 Hz, 1H), 8.45 (dd, J=4.8, 1.6 Hz, 1H), 7.75-7.68 (m, 1H), 7.55-7.47 (m, 2H), 7.36 (dd, J=8.0, 4.0 Hz, 1H), 7.26-7.19 (m, 2H), 6.77 (t, J=6.0 Hz, 1H), 4.32 (d, J=6.0 Hz, 2H). MS: m/z 312.0 (M+H$^+$).

Example 12: Synthesis of 1-(4-Methoxyphenyl)-3-(Pyridin-3-ylmethyl)urea

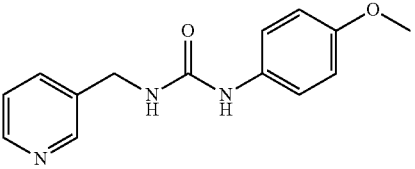 [SMILES: COc1ccc(NC(=O)NCc2cccnc2)cc1]

The title compound was prepared as described in example 1-(4-chlorophenyl)-3-(pyridin-3-ylmethyl)urea. $^1$H NMR (400 MHz, DMSO-d$_6$): δ=8.51 (d, J=2.0 Hz, 1H), 8.45 (dd, J=4.8, 1.6 Hz, 1H), 8.38 (brs, 1H), 7.73-7.67 (m, 1H), 7.35 (dd, J=7.6, 4.4 Hz, 1H), 7.32-7.26 (m, 2H), 6.84-6.78 (m, 2H), 6.58 (t, J=6.0 Hz, 1H), 4.30 (d, J=6.0 Hz, 2H), 3.69 (s, 3H). MS: m/z 258.1 (M+H$^+$).

Example 13: Synthesis of Ethyl 2-(3-(pyridin-4-ylmethyl)ureido)benzoate

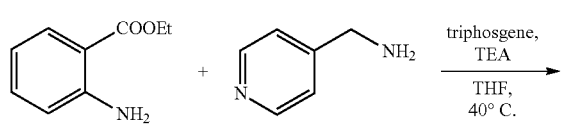

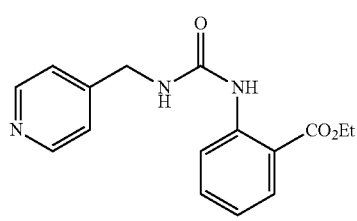

To a solution of 2-amino-benzoic acid ethyl ester (158 mg, 0.96 mmol) in THF (10 mL) was added triethylamine (316.0 mg, 3.13 mmol) and triphosgene (118 mg, 0.40 mmol). The mixture was stirred at 40° C. for 1 hr. Then 4-(aminomethyl)pyridine (126 mg, 1.17 mmol) was added and the mixture was stirred at 40° C. for 4 hrs. After that, the solution was partitioned between water (10 mL) and EA (10 mL). The aqueous phase was extracted with EA (20 mL×3). The organic layer was washed with water (20 mL×2), dried over $Na_2SO_4$, and concentrated under reduced pressure. The residue was purified by silica gel column chromatography (PE/EA=1/1) to give ethyl 2-(3-(pyridin-4-ylmethyl)ureido)benzoate (239 mg, yield: 83%) as a white solid. $^1$H NMR (400 MHz, DMSO-$d_6$): δ=9.98 (s, 1H), 8.51 (dd, J=4.8, 1.2 Hz, 2H), 8.35 (d, J=8.8 Hz, 1H), 8.11 (t, J=6.0 Hz, 1H), 7.92 (dd, J=8.0, 1.2 Hz, 1H), 7.53-7.49 (m, 1H), 7.31-7.29 (m, 2H), 7.03-6.99 (m, 1H), 4.33 (q, J=7.2 Hz, 4H), 1.34 (t, J=7.2 Hz, 3H). MS: m/z 299.9 (M+H$^+$).

Example 14: Synthesis of Ethyl 3-(3-(pyridin-4-ylmethyl)ureido)benzoate

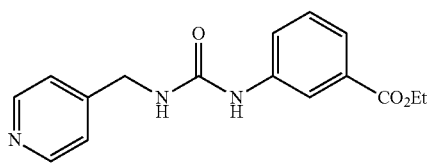 [SMILES: CCOC(=O)c1cccc(NC(=O)NCc2ccncc2)c1]

The title compound was prepared as described in example ethyl 2-(3-(pyridin-4-ylmethyl)ureido)benzoate. $^1$H NMR (400 MHz, DMSO-$d_6$): δ=9.02 (s, 1H), 8.51 (d, J=5.6 Hz, 2H), 8.11 (s, 1H), 7.65 (d, J=8.0 Hz, 1H), 7.51 (d, J=7.2 Hz, 1H), 7.38 (t, J=8.0 Hz, 1H), 7.31 (d, J=7.2 Hz, 2H), 6.81 (t, J=6.0 Hz, 1H), 4.36-4.28 (m, 4H). 1.32 (t, J=7.2 Hz, 3H). MS: m/z 300.1 (M+H$^+$).

Example 15: Synthesis of 1-(Pyridin-2-ylmethyl)-3-(4-(trifluoromethyl)phenyl)urea

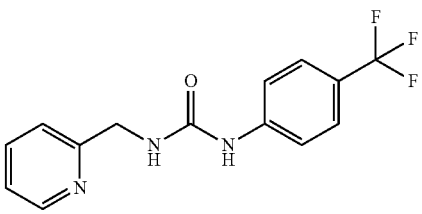 [SMILES: O=C(NCc1ccccn1)Nc1ccc(C(F)(F)F)cc1]

The title compound was prepared as described in example ethyl 2-(3-(pyridin-4-ylmethyl)ureido)benzoate. $^1$H NMR (400 MHz, DMSO-$d_6$): δ=9.22 (s, 1H), 8.52 (d, J=4.0 Hz, 1H), 7.77 (td, J=7.6, 1.6 Hz, 1H), 7.61 (d, J=8.8 Hz, 2H), 7.57 (d, J=8.8 Hz, 2H), 7.35 (d, J=8.0 Hz, 1H), 7.28 (dd, J=7.2, 4.8 Hz, 1H), 6.93 (d, J=5.2 Hz, 1H), 4.43 (d, J=5.6 Hz, 2H). MS: m/z 295.9 (M+H$^+$).

Example 16: Synthesis of 1-(Pyridin-4-ylmethyl)-3-(4-(trifluoromethyl)phenyl)urea

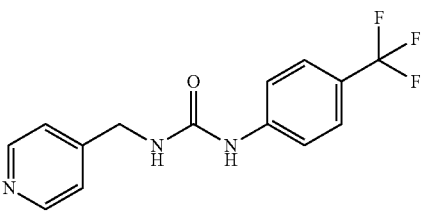 [SMILES: O=C(NCc1ccncc1)Nc1ccc(C(F)(F)F)cc1]

The title compound was prepared as described in example ethyl 2-(3-(pyridin-4-ylmethyl)ureido)benzoate. $^1$H NMR (400 MHz, DMSO-$d_6$): δ=9.15 (s, 1H), 8.50 (dd, J=8.8, 1.6 Hz, 2H), 7.61 (d, J=8.4 Hz, 2H), 7.57 (d, J=8.8 Hz, 2H), 7.29 (d, J=8.8 Hz, 2H), 6.89 (t, J=6.0 Hz, 1H), 4.34 (d, J=6.0 Hz, 2H). MS: m/z 295.8 (M+H$^+$).

Example 17: Synthesis of 1-(Pyridin-2-ylmethyl)-3-(4-(trifluoromethoxy)phenyl)urea

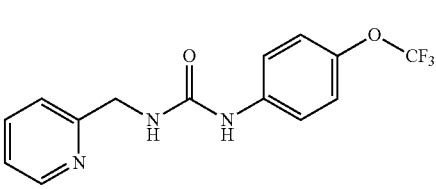 [SMILES: O=C(NCc1ccccn1)Nc1ccc(OC(F)(F)F)cc1]

The title compound was prepare as described in example ethyl 2-(3-(pyridin-4-ylmethyl)ureido)benzoate. $^1$H NMR (400 MHz, DMSO-$d_6$): δ=9.03 (s, 1H), 8.51 (d, J=8.8 Hz, 1H), 7.77 (d, J=6.0 Hz, 1H), 7.50 (d, J=8.8 Hz, 2H), 7.34 (d, J=7.6 Hz, 1H), 7.30-7.20 (m, 3H), 6.83 (t, J=5.6 Hz, 1H), 4.40 (d, J=5.6 Hz, 2H). MS: m/z 311.8 (M+H$^+$).

Example 18: Synthesis of 1-(Pyridin-4-ylmethyl)-3-(4-(trifluoromethoxy)phenyl)urea

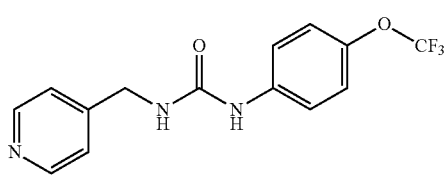 [SMILES: O=C(NCc1ccncc1)Nc1ccc(OC(F)(F)F)cc1]

The title compound was prepared as described in example ethyl 2-(3-(pyridin-4-ylmethyl)ureido)benzoate. $^1$H NMR (400 MHz, DMSO-d$_6$): δ=8.94 (s, 1H), 8.50 (d, J=5.6 Hz, 2H), 7.50 (d, J=8.8 Hz, 2H), 7.28 (d, J=8.8 Hz, 2H), 7.22 (d, J=8.8 Hz, 2H), 6.81 (t, J=6.0 Hz, 1H), 4.40 (d, J=6.0 Hz, 2H). MS: m/z 311.8 (M+H$^+$).

Example 19: Synthesis of 1-(4-Methoxyphenyl)-3-(pyridin-2-ylmethyl)urea

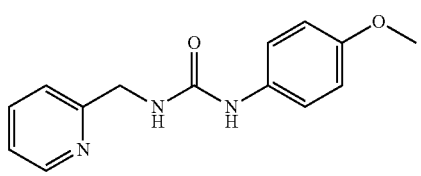 [SMILES: COc1ccc(NC(=O)NCc2ccccn2)cc1]

The title compound was prepared as described in example ethyl 2-(3-(pyridin-4-ylmethyl)ureido)benzoate. $^1$H NMR (400 MHz, DMSO-d$_6$): δ=8.55-8.50 (m, 2H), 7.79-7.75 (m, 1H), 7.36-7.25 (m, 4H), 6.81 (dd, J=8.2, 2.8 Hz, 2H), 6.64 (t, J=7.6 Hz, 1H), 4.40 (d, J=7.6 Hz, 2H), 3.69 (s, 3H). MS: m/z 258.1 (M+H$^+$).

Example 20: Synthesis of 1-(4-Methoxyphenyl)-3-(pyridin-4-ylmethyl)urea

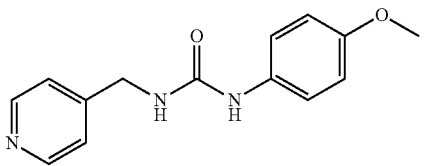 [SMILES: COc1ccc(NC(=O)NCc2ccncc2)cc1]

The title compound was prepared as described in example ethyl 2-(3-(pyridin-4-ylmethyl)ureido)benzoate. $^1$H NMR (400 MHz, DMSO-d$_6$): δ=8.51-8.46 (m, 3H), 7.32-7.26 (m, 4H), 6.81 (d, J=9.2 Hz, 2H), 6.35 (t, J=6.0 Hz, 1H), 4.31 (d, J=6.0 Hz, 2H), 3.69 (s, 3H). MS: m/z 257.9 (M+H$^+$).

Example 21: Synthesis of N,N-diethyl-4-(3-(pyridin-4-ylmethyl)ureido)benzamide

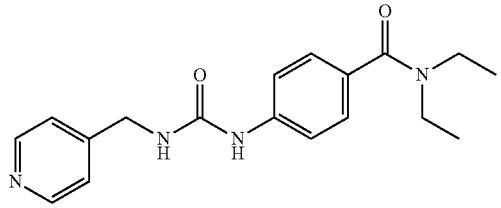 [SMILES: CCN(CC)C(=O)c1ccc(NC(=O)NCc2ccncc2)cc1]

The title compound was prepared as described in example 2-(3-pyridin-4-ylmethyl-ureido)-benzoic acid ethyl ester. $^1$H NMR (400 MHz, DMSO-d$_6$): δ=9.23 (brs, 1H), 8.48 (d, J=8.0 Hz, 2H), 7.47-7.42 (m, 2H), 7.29 (d, J=7.6 Hz, 2H), 7.22 (d, J=8.0 Hz, 2H), 7.05 (brs, 1H), 4.33 (d, J=8.0 Hz, 2H), 3.30-3.25 (4H, m), 1.02 (t, J=7.2 Hz, 6H). MS: m/z 326.9 (M+H$^+$).

Example 22: Synthesis of 4-(3-(Pyridin-4-ylmethyl)ureido)-N-(p-tolyl)benzamide

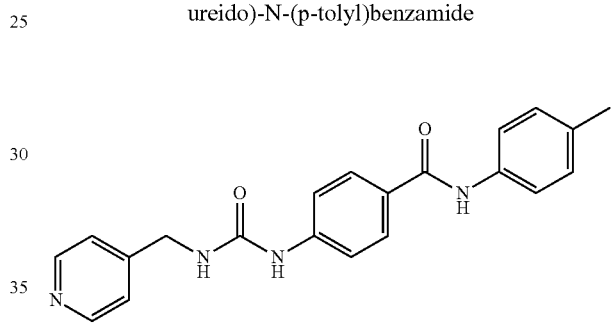

The title compound was prepared as described in example ethyl 2-(3-(pyridin-4-ylmethyl)ureido)benzoate. $^1$H NMR (400 MHz, DMSO-d$_6$): δ=9.96 (d, J=3.2 Hz, 1H), 9.13 (s, 1H), 8.55 (d, J=8.0 Hz, 2H), 7.88 (d, J=8.0 Hz, 2H), 7.54 (d, J=8.0 Hz, 2H), 7.52 (d, J=8.0 Hz, 2H), 7.15 (d, J=8.0 Hz, 2H), 7.10 (d, J=8.0 Hz, 2H), 6.90 (t, J=6.0 Hz, 1H), 4.37 (t, J=6.0 Hz, 2H), 2.44 (s, 3H). MS: m/z 360.9 (M+H$^+$).

Example 23: Synthesis of N-methyl-4-(3-(pyridin-4-ylmethyl)ureido)-N-(p-tolyl)benzamide

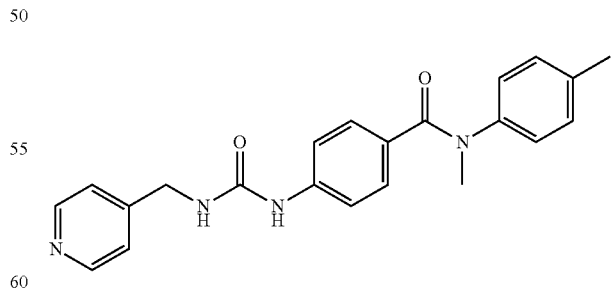

The title compound was prepared as described in example ethyl 2-(3-(pyridin-4-ylmethyl)ureido)benzoate. $^1$H NMR (400 MHz, DMSO-d$_6$): δ=8.88 (brs, 1H), 8.48 (dd, J=6.4, 2.0 Hz, 2H), 7.27-7.19 (m, 4H), 7.13-6.97 (m, 6H), 6.83 (t, J=7.2 Hz, 1H), 4.28 (t, J=7.2 Hz, 2H), 3.31 (s, 3H), 2.23 (s, 3H). MS: m/z 375.1 (M+H$^+$).

Example 24: Synthesis of N-phenyl-4-(3-(pyridin-4-ylmethyl)ureido)benzamide

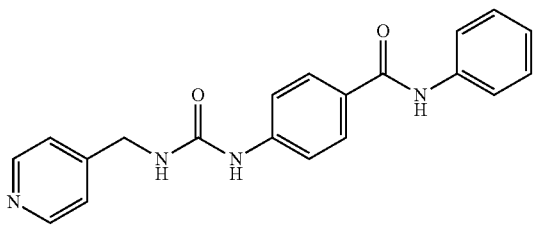 [SMILES: O=C(NCc1ccncc1)Nc1ccc(C(=O)Nc2ccccc2)cc1]

The title compound was prepared as described in example ethyl 2-(3-(pyridin-4-ylmethyl)ureido)benzoate. $^1$H NMR (400 MHz, DMSO-$d_6$): δ=10.04 (brs, 1H), 9.17 (brs, 1H), 8.52 (d, J=6.0 Hz, 2H), 7.88 (d, J=8.8 Hz, 2H), 7.76 (d, J=7.6 Hz, 2H), 7.55 (d, J=8.8 Hz, 2H), 7.36-7.30 (m, 4H), 7.07 (t, J=7.6 Hz, 1H), 7.00-6.92 (m, 1H), 4.36 (t, J=6.0 Hz, 2H). MS: m/z 346.9 (M+H$^+$).

Example 25: Synthesis of N-ethyl-N-methyl-4-(3-(pyridin-4-ylmethyl)ureido)benzamide

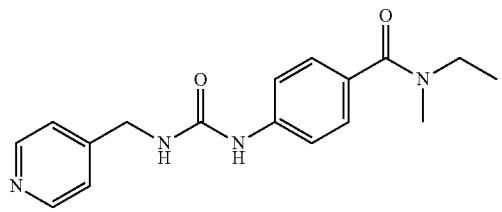 [SMILES: CCN(C)C(=O)c1ccc(NC(=O)NCc2ccncc2)cc1]

The title compound was prepared as described in example ethyl 2-(3-(pyridin-4-ylmethyl)ureido)benzoate. $^1$H NMR (400 MHz, DMSO-$d_6$): δ=8.94 (brs, 1H), 8.54 (d, J=4.4 Hz, 2H), 7.45 (d, J=8.8 Hz, 2H), 7.35 (d, J=5.6 Hz, 2H), 7.30-7.24 (m, 2H), 6.85-6.82 (m, 1H), 4.36 (t, J=6.0 Hz, 2H), 3.37-3.30 (m, 2H), 2.91 (s, 3H), 1.11-1.07 (m, 3H). MS: m/z 312.9 (M+H$^+$).

Example 26: Synthesis of N-methyl-N-propyl-4-(3-(pyridin-4-ylmethyl)ureido)benzamide

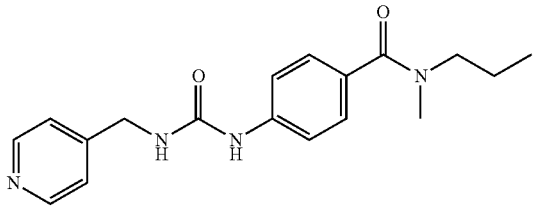 [SMILES: CCCN(C)C(=O)c1ccc(NC(=O)NCc2ccncc2)cc1]

The title compound was prepared as described in example ethyl 2-(3-(pyridin-4-ylmethyl)ureido)benzoate. $^1$H NMR (400 MHz, DMSO-$d_6$): δ=8.93 (brs, 1H), 8.50 (d, J=5.6 Hz, 2H), 7.45 (d, J=8.4 Hz, 2H), 7.31-7.24 (m, 4H), 6.82 (t, J=6.0 Hz, 1H), 4.34 (t, J=6.0 Hz, 2H), 3.28-3.15 (m, 2H), 2.91 (s, 3H), 1.60-1.48 (m, 2H), 0.92-0.72 (m, 3H). MS: m/z 326.9 (M+H$^+$).

Example 27: Synthesis of N-(2-hydroxyethyl)-4-(3-(pyridin-4-ylmethyl)ureido)benzamide

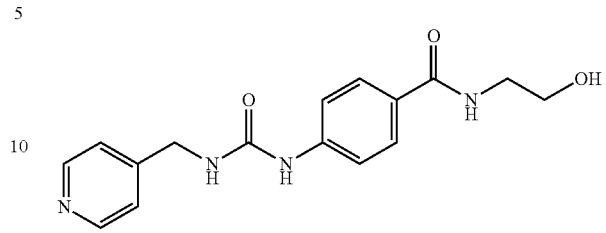

The title compound was prepared as described in example ethyl 2-(3-(pyridin-4-ylmethyl)ureido)benzoate. $^1$H NMR (400 MHz, DMSO-$d_6$): δ=8.99 (brs, 1H), 8.50 (d, J=8.8 Hz, 2H), 8.23 (t, J=6.4 Hz, 1H), 7.74 (d, J=9.2 Hz, 2H), 7.46 (d, J=8.8 Hz, 2H), 7.29 (d, J=9.2 Hz, 2H), 6.85 (t, J=6.4 Hz, 1H), 4.71 (t, J=5.6 Hz, 1H), 4.33 (t, J=6.0 Hz, 2H), 3.51-3.45 (m, 2H), 3.35-3.25 (m, 2H). MS: m/z 314.9 (M+H$^+$).

Example 28: Synthesis of N-butyl-4-(3-(pyridin-4-ylmethyl)ureido)benzamide

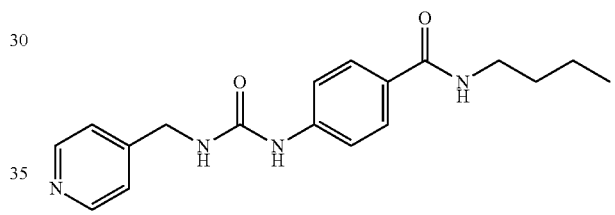

The title compound was prepared as described in example ethyl 2-(3-(pyridin-4-ylmethyl)ureido)benzoate. $^1$H NMR (400 MHz, CD$_3$OD): δ=8.47-8.46 (m, 2H), 7.74-7.72 (m, 2H), 7.49-7.47 (m, 2H), 7.40-7.39 (m, 2H), 4.46 (s, 2H), 3.37-3.35 (m, 1H), 3.31-3.29 (m, 2H), 1.60-1.57 (m, 2H), 1.43-1.39 (m, 2H), 0.98-0.94 (m, 2H). MS: m/z 326.9 (M+H$^+$).

Example 29: Synthesis of N-cyclopentyl-4-(3-(pyridin-4-ylmethyl)ureido)benzamide

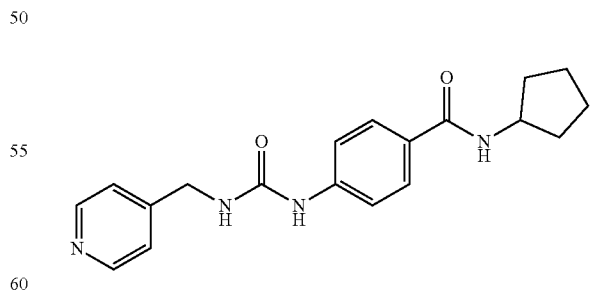

The title compound was prepared as described in example ethyl 2-(3-(pyridin-4-ylmethyl)ureido)benzoate. $^1$H NMR (400 MHz, CD$_3$OD): δ=8.47-8.46 (m, 2H), 7.74-7.72 (m, 2H), 7.49-7.46 (m, 2H), 7.40-7.38 (m, 2H), 4.86 (s, 2H), 4.45-4.26 (m, 1H), 2.03-1.99 (m, 2H), 1.78-1.75 (m, 2H), 1.65-1.56 (m, 4H). MS: m/z 338.9 (M+H$^+$).

Example 30: Synthesis of Ethyl 4-(3-(pyridin-2-ylmethyl)ureido)benzoate

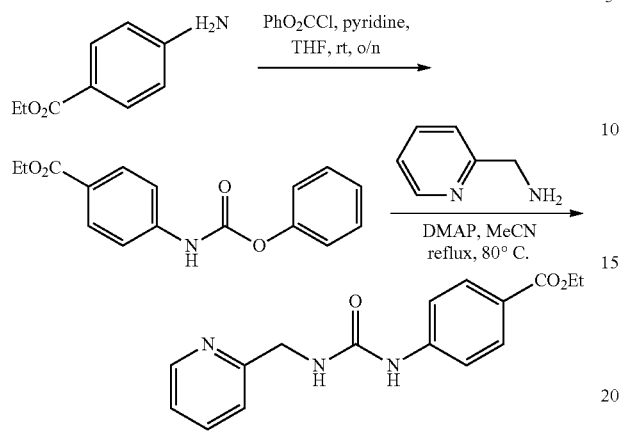

Step 1: The solution of phenyl chroloformate (6.88 g, 43.9 mmol) and pyridine (6.42 g, 81.3 mmol) in THF (100 mL) was degassed and purged with $N_2$. The mixture was stirred at 0° C. for a while. Then 4-amino-benzoic acid ethyl ester (6.60 g, 40.0 mmol) was added and the mixture was stirred at room temperature for overnight. After that, the solution was partitioned between water (100 mL) and EA (100 mL). The aqueous phase was extracted with EA (100 mL×3). The organic layer was washed with water (100 mL×2), dried over $Na_2SO_4$, and concentrated under reduced pressure to give ethyl 4-((phenoxycarbonyl)amino)benzoate (14.27 g, crude) as a white solid. MS: m/z 285.9 (M+H$^+$).

Step 2: To a solution of 4-phenoxycarbonylamino-benzoic acid ethyl ester (576 mg, 2.02 mmol) in MeCN (8 mL), was added DMAP (242 mg, 1.95 mmol) and 2-(aminomethyl)pyridine (230 mg, 2.13 mmol). The mixture was refluxed at 80° C. for overnight. After that, the solution was partitioned between water (20 mL) and EA (20 mL). The aqueous phase was extracted with EA (20 mL×3). The organic layer was washed with water (20 mL×2), dried over $Na_2SO_4$, and concentrated under reduced pressure. The residue was purified by silica gel column chromatography (EA) to give ethyl 4-(3-(pyridin-2-ylmethyl)ureido)benzoate (42 mg, yield: 10%) as a white solid. $^1$H NMR (400 MHz, DMSO-$d_6$): δ=9.23 (s, 1H), 8.53 (d, J=4.0 Hz, 1H), 7.83 (d, J=8.8 Hz, 2H), 7.77 (d, J=1.6 Hz, 1H), 7.54 (d, J=8.4 Hz, 1H), 7.35 (d, J=8.0 Hz, 1H), 6.93 (s, 1H), 4.42 (d, J=5.6 Hz, 2H), 4.26 (d, J=7.2 Hz, 4H), 1.30 (t, J=7.2 Hz, 3H). MS: m/z 299.9 (M+H$^+$).

Example 31: Synthesis of Ethyl 4-(3-(pyridin-3-ylmethyl)ureido)benzoate

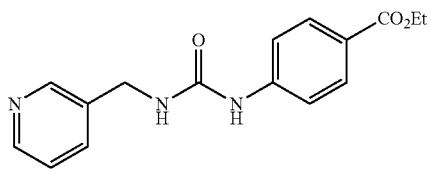 [SMILES: CCOC(=O)c1ccc(NC(=O)NCc2cccnc2)cc1]

The title compound was prepared as described in example ethyl 4-(3-(pyridin-2-ylmethyl)ureido)benzoate. $^1$H NMR (400 MHz, DMSO-$d_6$): δ=9.07 (s, 1H), 8.54 (d, J=1.2 Hz, 1H), 8.46 (dd, J=4.8, 1.2 Hz, 1H), 7.84 (d, J=8.8 Hz, 2H), 7.71 (d, J=8.0 Hz, 1H), 7.53 (d, J=8.8 Hz, 2H), 7.38-7.35 (m, 1H), 6.87 (s, 1H), 4.34 (d, J=5.6 Hz, 2H), 4.26 (q, J=7.2 Hz, 2H). 1.30 (t, J=7.2 Hz, 3H). MS: m/z 299.9 (M+H$^+$).

Example 32: Synthesis of Ethyl 4-(3-(pyridin-4-ylmethyl)ureido)benzoate

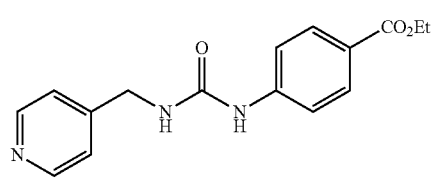 [SMILES: CCOC(=O)c1ccc(NC(=O)NCc2ccncc2)cc1]

The title compound was prepared as described in example ethyl 4-(3-(pyridin-2-ylmethyl)ureido)benzoate. $^1$H NMR (400 MHz, DMSO-$d_6$): δ=9.16 (s, 1H), 8.51 (d, J=6.0 Hz, 2H), 7.84 (d, J=8.4 Hz, 2H), 7.53 (d, J=8.8 Hz, 2H), 7.29 (d, J=5.2 Hz, 2H), 6.90 (s, 1H), 4.34 (d, J=5.2 Hz, 2H), 4.28 (q, J=6.8 Hz, 2H), 1.30 (t, J=7.2 Hz, 3H). MS: m/z 299.9 (M+H$^+$).

Example 33: Synthesis of Ethyl 4-(3-(pyridin-4-ylmethyl)thioureido)benzoate

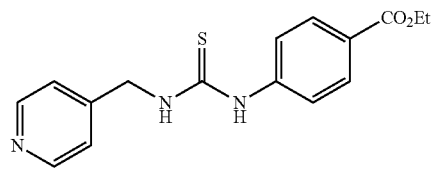 [SMILES: CCOC(=O)c1ccc(NC(=S)NCc2ccncc2)cc1]

The title compound was prepared as described in example 4-(3-pyridin-2-ylmethyl-ureido)-benzoic acid ethyl ester. $^1$H NMR (400 MHz, DMSO-$d_6$): δ=10.32 (s, 1H), 8.69 (s, 1H), 8.51 (d, J=6.0 Hz, 2H), 7.90 (d, J=8.8 Hz, 2H), 7.71 (d, J=8.4 Hz, 2H), 7.31 (d, J=6.0 Hz, 2H), 4.79 (d, J=5.6 Hz, 2H), 4.28 (q, J=6.8 Hz, 2H), 1.30 (t, J=7.2 Hz, 3H). MS: m/z 316.0 (M+H$^+$).

Example 34: Synthesis of Ethyl 4-(3-benzylureido)benzoate

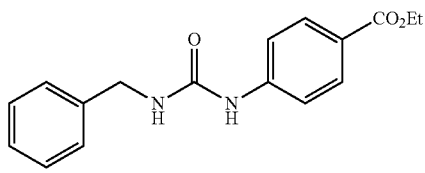 [SMILES: CCOC(=O)c1ccc(NC(=O)NCc2ccccc2)cc1]

The title compound was prepared as described in example ethyl 4-(3-(pyridin-2-ylmethyl)ureido)benzoate. $^1$H NMR (400 MHz, DMSO-$d_6$): δ=9.01 (s, 1H), 7.83 (d, J=8.8 Hz, 2H), 7.53 (d, J=8.8 Hz, 2H), 7.32 (t, J=7.2 Hz, 4H), 7.29 (s, 1H), 6.78 (s, 1H), 4.31 (d, J=6.0 Hz, 2H), 4.26 (q, J=7.2 Hz, 2H), 1.30 (t, J=7.2 Hz, 3H). MS: m/z 299.1 (M+H$^+$).

Example 35: Synthesis of Ethyl 4-(3-((2-aminopyridin-4-yl)methyl)ureido)benzoate

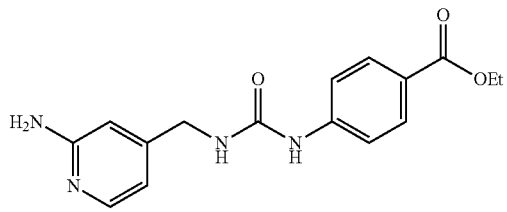 [SMILES: CCOC(=O)c1ccc(NC(=O)NCc2ccnc(N)c2)cc1]

The title compound was prepared as described in example ethyl 4-(3-(pyridin-2-ylmethyl)ureido)benzoate. ¹H NMR (400 MHz, DMSO-d$_6$): δ=9.10 (brs, 1H), 7.84 (dd, J=8.8 Hz, 2H), 7.81 (d, J=5.2 Hz, 1H), 7.54 (d, J=8.8 Hz, 2H), 6.75 (t, J=5.6 Hz, 1H), 6.39 (dd, J=5.2, 1.2 Hz, 1H), 6.33 (s, 1H), 5.87 (brs, 2H), 4.26 (q, J=7.2 Hz, 2H), 4.16 (d, J=6.4 Hz, 2H), 1.30 (t, J=7.2 Hz, 3H). MS: m/z 315.1 (M+H$^+$).

Example 36: Synthesis of Ethyl 4-(3-((2-methoxypyridin-4-yl)methyl)ureido)benzoate

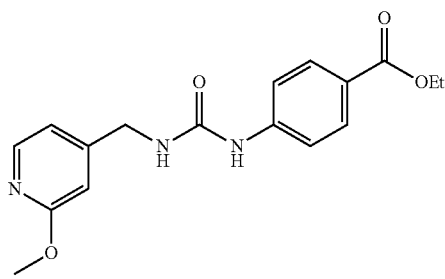 [SMILES: CCOC(=O)c1ccc(NC(=O)NCc2ccnc(OC)c2)cc1]

The title compound was prepared as described in example ethyl 4-(3-(pyridin-2-ylmethyl)ureido)benzoate. ¹H NMR (400 MHz, DMSO-d$_6$): δ=9.15 (brs, 1H), 8.09 (dd, J=5.2 Hz, 1H), 7.84 (dd, J=8.8 Hz, 2H), 7.54 (d, J=8.8 Hz, 2H), 6.91 (dd, J=5.6, 0.8 Hz, 1H), 6.88 (t, J=6.0 Hz, 1H), 6.69 (s, 1H), 4.29 (d, J=5.6 Hz, 2H), 4.26 (q, J=7.2 Hz, 2H), 3.83 (s, 3H), 1.30 (t, J=7.2 Hz, 3H). MS: m/z 330.1 (M+H$^+$).

Example 37: Synthesis of Ethyl 4-(3-(pyrimidin-5-ylmethyl)ureido)benzoate

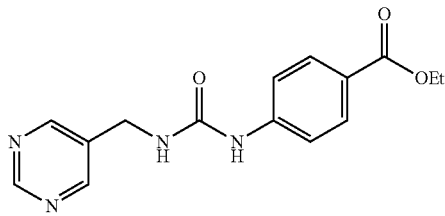 [SMILES: CCOC(=O)c1ccc(NC(=O)NCc2cncnc2)cc1]

The title compound was prepared as described in example ethyl 4-(3-(pyridin-2-ylmethyl)ureido)benzoate. ¹H NMR (400 MHz, DMSO-d$_6$): δ=9.36 (brs, 1H), 9.12 (d, J=1.2 Hz, 1H), 8.74 (d, J=5.2 Hz, 1H), 7.84 (d, J=8.8 Hz, 2H), 7.54 (d, J=9.2 Hz, 2H), 7.46 (d, J=5.2 Hz, 1H), 6.99 (t, J=6.0 Hz, 1H), 4.42 (d, J=5.6 Hz, 2H), 4.26 (q, J=7.2 Hz, 2H), 1.30 (t, J=6.8 Hz, 3H). MS: m/z 301.0 (M+H$^+$).

Example 38: Synthesis of Ethyl 4-(3-((3-methylpyridin-4-yl)methyl)ureido)benzoate

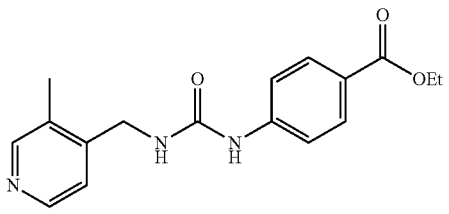 [SMILES: CCOC(=O)c1ccc(NC(=O)NCc2ccncc2C)cc1]

The title compound was prepared as described in example ethyl 4-(3-(pyridin-2-ylmethyl)ureido)benzoate. ¹H NMR (400 MHz, DMSO-d$_6$): δ=9.17 (brs, 1H), 8.36 (d, J=4.8 Hz, 1H), 8.33 (s, 1H), 7.84 (d, J=8.8 Hz, 2H), 7.54 (d, J=8.8 Hz, 2H), 7.21 (d, J=5.2 Hz, 1H), 6.86 (t, J=6.0 Hz, 1H), 4.31 (d, J=5.6 Hz, 2H), 4.26 (q, J=7.2 Hz, 2H), 2.28 (s, 3H), 1.30 (t, J=7.2 Hz, 3H). MS: m/z 314.0 (M+H$^+$).

Example 39: Synthesis of Ehyl 4-(3-((3-aminopyridin-4-yl)methyl)ureido)benzoate

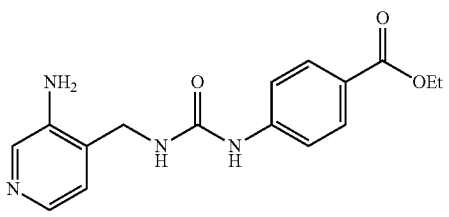 [SMILES: CCOC(=O)c1ccc(NC(=O)NCc2ccncc2N)cc1]

The title compound was prepared as described in example ethyl 4-(3-(pyridin-2-ylmethyl)ureido)benzoate. ¹H NMR (400 MHz, DMSO-d$_6$): δ=9.22 (brs, 1H), 7.94 (s, 1H), 7.84 (d, J=8.8 Hz, 2H), 7.74 (d, J=4.8 Hz, 1H), 7.54 (d, J=8.8 Hz, 2H), 6.99 (d, J=4.8 Hz, 1H), 6.79 (t, J=6.0 Hz, 1H), 5.31 (brs, 2H), 4.26 (q, J=7.2 Hz, 2H), 4.16 (d, J=6.0 Hz, 2H), 1.30 (t, J=7.2 Hz, 3H). MS: m/z 315.0 (M+H$^+$).

Example 40: Synthesis of Ethyl 4-(3-((2-methylpyridin-4-yl)methyl)ureido)benzoate

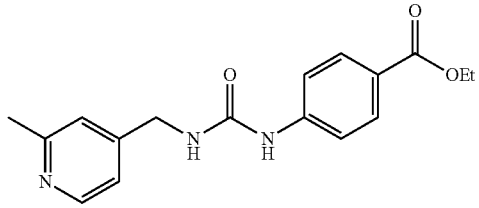 [SMILES: CCOC(=O)c1ccc(NC(=O)NCc2ccnc(C)c2)cc1]

The title compound was prepared as described in example ethyl 4-(3-(pyridin-2-ylmethyl)ureido)benzoate. ¹H NMR (400 MHz, DMSO-d$_6$): δ=9.16 (brs, 1H), 8.36 (d, J=4.8 Hz, 1H), 7.84 (dd, J=7.2, 2.0 Hz, 2H), 7.54 (dd, J=7.2, 2.0 Hz, 2H), 7.15 (s, 1H), 7.09 (d, J=4.8 Hz, 1H), 6.89 (t, J=6.0 Hz, 1H), 4.30 (d, J=6.0 Hz, 2H), 4.26 (q, J=7.2 Hz, 2H), 2.44 (s, 3H), 1.30 (t, J=7.2 Hz, 3H). MS: m/z 314.0 (M+H⁺).

Example 41: Synthesis of Ethyl 4-(3-((2-chloropyridin-4-yl)methyl)ureido)benzoate

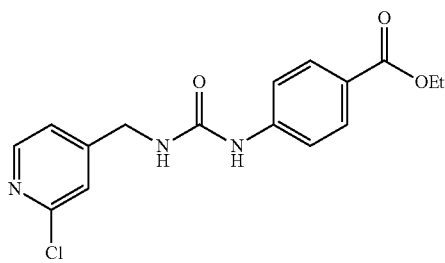

The title compound was prepared as described in example ethyl 4-(3-(pyridin-2-ylmethyl)ureido)benzoate. ¹H NMR (400 MHz, DMSO-d₆): δ=9.29 (brs, 1H), 8.35 (d, J=5.2 Hz, 1H), 7.84 (d, J=8.8 Hz, 2H), 7.54 (d, J=8.8 Hz, 2H), 7.40 (s, 1H), 7.33 (d, J=5.2 Hz, 1H), 7.00 (t, J=5.6 Hz, 1H), 4.36 (d, J=6.0 Hz, 2H), 4.26 (q, J=7.2 Hz, 2H), 1.30 (t, J=7.2 Hz, 3H). MS: m/z 333.9 (M+H⁺).

Example 42: Synthesis of Ethyl 4-(3-((1H-pyrazol-4-yl)methyl)ureido)benzoate

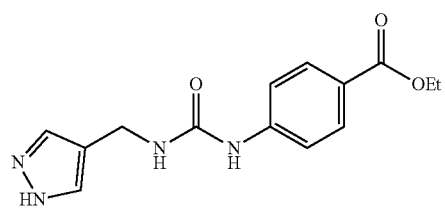 [SMILES: CCOC(=O)c1ccc(NC(=O)NCc2cn[nH]c2)cc1]

The title compound was prepared as described in example ethyl 4-(3-(pyridin-2-ylmethyl)ureido)benzoate. ¹H NMR (400 MHz, DMSO-d₆): δ=12.67 (brs, 1H), 8.98 (brs, 1H), 7.83 (d, J=8.8 Hz, 2H), 7.65-7.44 (m, 4H), 6.57 (t, J=5.6 Hz, 1H), 4.26 (q, J=7.2 Hz, 2H), 4.16 (d, J=5.6 Hz, 2H), 1.30 (t, J=7.2 Hz, 3H). MS: m/z 289.0 (M+H⁺).

Example 43: Synthesis of Ethyl 4-(3-((3-chloropyridin-4-yl)methyl)ureido)benzoate

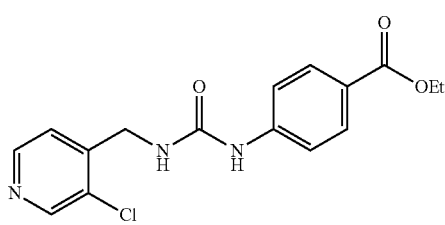 [SMILES: CCOC(=O)c1ccc(NC(=O)NCc2ccncc2Cl)cc1]

The title compound was prepared as described in example ethyl 4-(3-(pyridin-2-ylmethyl)ureido)benzoate. ¹H NMR (400 MHz, DMSO-d₆): δ=9.32 (brs, 1H), 8.59 (s, 1H), 8.50 (d, J=1.2 Hz, 1H), 7.84 (d, J=8.8 Hz, 2H), 7.54 (d, J=8.8 Hz, 2H), 7.37 (d, J=5.2 Hz, 1H), 6.96 (t, J=6.0 Hz, 1H), 4.40 (d, J=6.0 Hz, 2H), 4.26 (q, J=7.2 Hz, 2H), 1.30 (t, J=7.2 Hz, 3H). MS: m/z 334.0 (M+H⁺).

Example 44: Synthesis of Ethyl 4-(3-((2-fluoropyridin-4-yl)methyl)ureido)benzoate

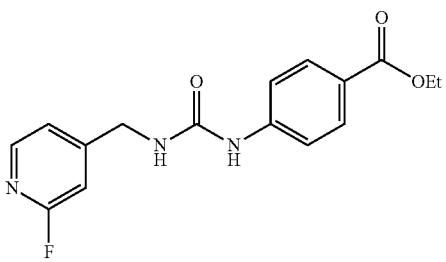 [SMILES: CCOC(=O)c1ccc(NC(=O)NCc2ccnc(F)c2)cc1]

The title compound was prepared as described in example ethyl 4-(3-(pyridin-2-ylmethyl)ureido)benzoate. ¹H NMR (400 MHz, DMSO-d₆): δ=9.29 (brs, 1H), 8.18 (d, J=5.2 Hz, 1H), 7.84 (d, J=8.8 Hz, 2H), 7.54 (d, J=8.8 Hz, 2H), 7.28 (d, J=4.8 Hz, 1H), 7.05 (s, 1H), 7.01 (t, J=6.0 Hz, 1H), 4.39 (d, J=6.0 Hz, 2H), 4.26 (q, J=7.2 Hz, 2H), 1.30 (t, J=7.2 Hz, 3H). MS: m/z 318.0 (M+H⁺).

Example 45: Synthesis of Ethyl 4-(3-((3-fluoropyridin-4-yl)methyl)ureido)benzoate

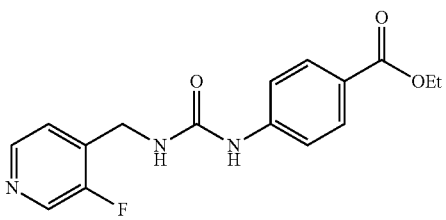

The title compound was prepared as described in example ethyl 4-(3-(pyridin-2-ylmethyl)ureido)benzoate. ¹H NMR (400 MHz, DMSO-d₆): δ=9.26 (brs, 1H), 8.51 (d, J=5.6 Hz, 1H), 8.40 (d, J=4.4 Hz, 1H), 7.84 (d, J=8.8 Hz, 2H), 7.54 (d, J=8.8 Hz, 2H), 7.39 (t, J=6.0 Hz, 1H), 6.94 (t, J=6.0 Hz, 1H), 4.41 (d, J=6.0 Hz, 2H), 4.26 (q, J=7.2 Hz, 2H), 1.30 (t, J=7.2 Hz, 3H). MS: m/z 318.0 (M+H⁺).

Example 46: Synthesis of Ethyl 4-(3-(pyridazin-4-ylmethyl)ureido)benzoate

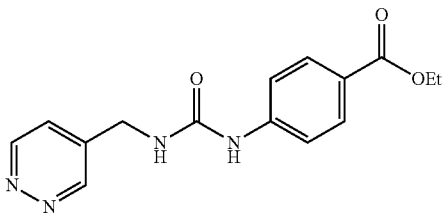 [SMILES: CCOC(=O)c1ccc(NC(=O)NCc2ccnnc2)cc1]

The title compound was prepared as described in example ethyl 4-(3-(pyridin-2-ylmethyl)ureido)benzoate. ¹H NMR (400 MHz, DMSO-d₆): δ=9.25 (brs, 1H), 9.18 (s, 1H), 9.15

(dd, J=5.2, 0.8 Hz, 1H), 7.84 (d, J=8.8 Hz, 2H), 7.59-7.50 (m, 3H), 6.96 (t, J=6.0 Hz, 1H), 4.38 (d, J=6.0 Hz, 2H), 4.26 (q, J=7.2 Hz, 2H), 1.30 (t, J=7.2 Hz, 3H). MS: m/z 300.9 (M+H⁺).

Example 47: Synthesis of 4-(3-(Pyridin-4-ylmethyl)ureido)benzoic acid

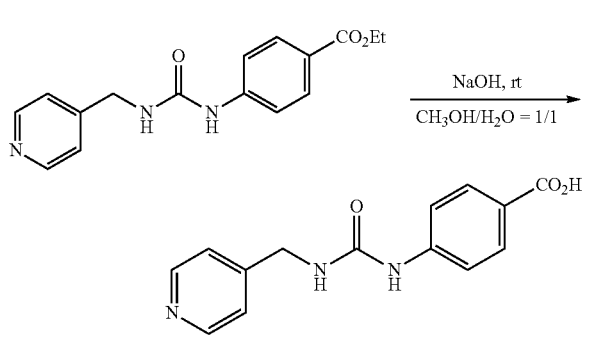

To a solution of ethyl 4-(3-(pyridin-4-ylmethyl)ureido) benzoate (200 mg, 0.67 mmol) in CH₃OH (10 mL) was added a solution of NaOH (116 mg, 2.9 mmol) in H₂O (10 mL). The resulting mixture was stirred overnight at room temperature. The mixture was concentrated under reduced pressure. Then HCl (4 M) was dropped into the mixture until pH=5-6. Much solid was separated out and filtered to give 4-(3-(pyridin-4-ylmethyl)ureido)benzoic acid (117 mg, yield: 64%). ¹H NMR (400 MHz, CF₃CO₂D): δ=8.80 (s, 2H), 8.25-8.19 (m, 4H), 7.55 (s, 2H), 4.98 (s, 2H), MS: m/z 271.8 (M+H⁺).

Example 48: Synthesis of 3-(3-(Pyridin-4-ylmethyl)ureido)benzoic acid

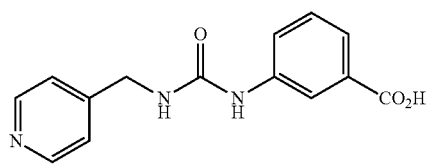 [SMILES: O=C(NCc1ccncc1)Nc1cccc(C(=O)O)c1]

The title compound was prepare as described in example 4-(3-(pyridin-4-ylmethyl)ureido)benzoic acid. ¹H NMR (400 MHz, CF₃CO₂D): δ=8.90 (d, J=6.8 Hz, 2H), 8.29-8.23 (m, 4H), 7.79 (d, J=7.6 Hz, 1H), 7.73 (t, J=7.6 Hz, 1H), 5.06 (s, 2H). MS: m/z 271.9 (M+H⁺).

Example 49: Synthesis of 3-(3-Benzyl-ureido)-benzoic acid

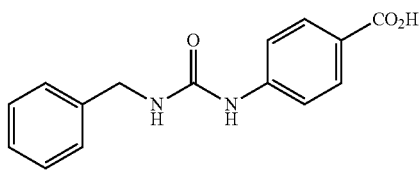 [SMILES: O=C(NCc1ccccc1)Nc1ccc(C(=O)O)cc1]

The title compound was prepared as described in example 4-(3-(Pyridin-4-ylmethyl)ureido)benzoic acid. ¹H NMR (400 MHz, DMSO-d₆): δ=8.94 (s, 1H), 7.81 (d, J=9.2 Hz, 2H), 7.51-7.49 (m, 2H), 7.34-7.30 (m, 4H), 7.24 (s, 1H), 6.76 (s, 1H), 4.31 (d, J=6.0 Hz, 2H). MS: m/z 271.0 (M+H⁺).

Example 50: Synthesis of 4-(3-(Pyridin-4-ylmethyl)ureido)benzamide

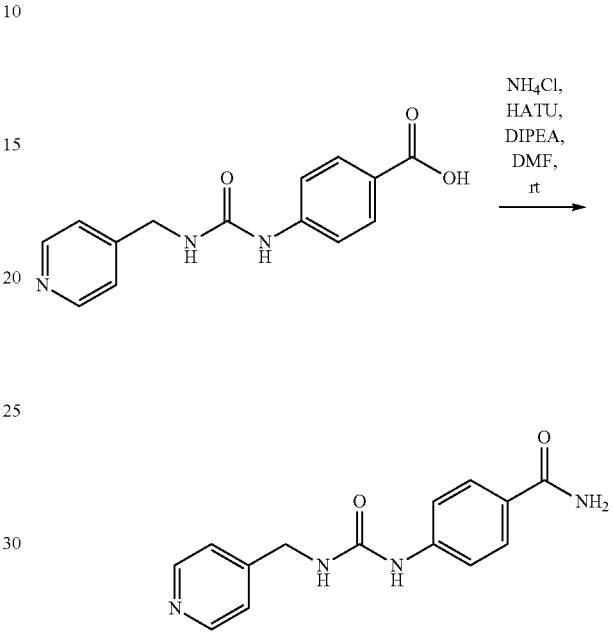

To a solution of 4-(3-(pyridin-4-ylmethyl)ureido)benzoic acid (55 mg, 0.20 mmol) in DMF (3 mL) was added HATU (116 mg, 0.31 mmol), DIPEA (131.00 mg, 1.01 mmol), and the mixture was stirred for 1 hr at room temperature. Then NH₄Cl (21.8 mg, 0.41 mmol) was added. The mixture was stirred overnight at room temperature. The mixture was concentrated under reduced pressure. The target (17 mg, yield: 31%) was obtained by prep-HPLC as a white solid. ¹H NMR (400 MHz, CD₃OD): δ=8.47 (d, J=5.2 Hz, 2H), 7.80 (d, J=8.8 Hz, 2H), 7.49 (d, J=9.6 Hz, 2H), 7.40 (d, J=5.2 Hz, 2H), 4.46 (s, 2H). MS: m/z 271.3 (M+H⁺).

Example 51: Synthesis of Methyl 4-(1-methyl-3-(pyridin-4-ylmethyl)ureido)benzoate

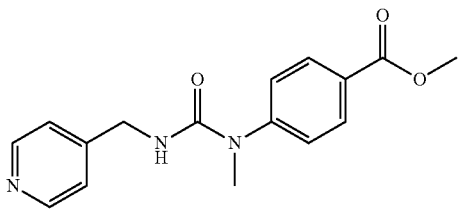 [SMILES: COC(=O)c1ccc(N(C)C(=O)NCc2ccncc2)cc1]

The title compound was prepared as described in example ethyl 4-(3-(pyridin-2-ylmethyl)ureido)benzoate. ¹H NMR (400 MHz, CD3OD): δ=8.44-8.43 (m, 2H), 8.07-8.05 (m, 2H), 7.45-7.43 (m, 2H), 7.34-7.32 (m, 2H), 4.36 (s, 2H), 3.89 (s, 3H), 3.31-3.29 (s, 3H). MS: m/z 300.0 (M+H⁺).

Example 52: Synthesis of N-propyl-4-(3-(pyridin-4-ylmethyl)ureido)benzamide

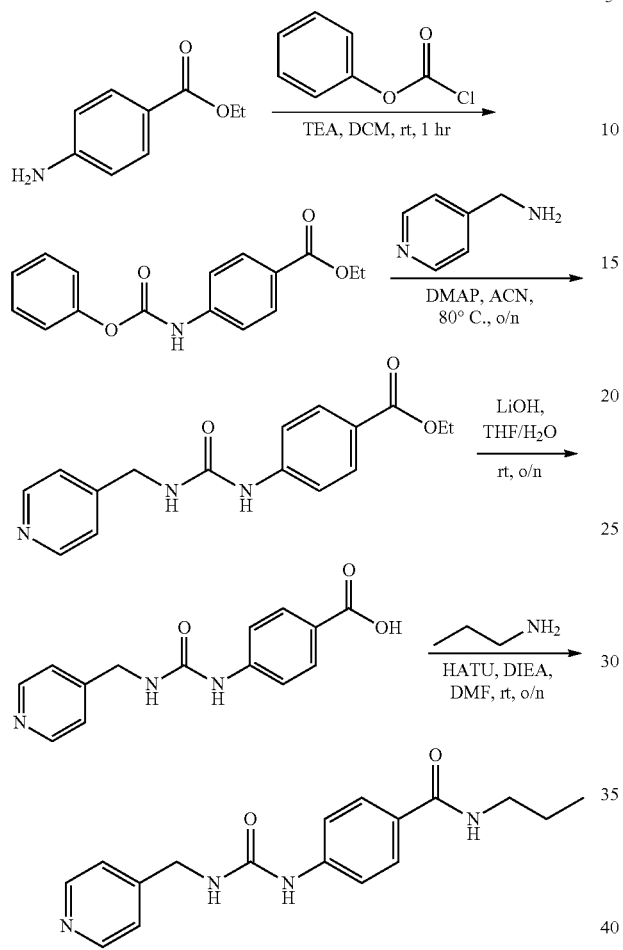

Step 1: To a solution of 4-amino-benzoic acid ethyl ester (500 mg, 3.03 mmol) in DCM (10 mL) was added phenyl carbonchloridate (570 mg, 3.63 mmol), followed by TEA (926 mg, 9.09 mmol). The resulting mixture was stirred at room temperature for 1 hour. The reaction was monitored by TLC. Then the mixture was concentrated in vacuum to give a residue, which was purified by a silica gel column eluting with DCM to afford ethyl 4-((phenoxycarbonyl)amino)benzoate (826 mg, yield: 96%) as a white solid.

Step 2: To a solution of ethyl 4-((phenoxycarbonyl)amino)benzoate (826 mg, 2.89 mmol) in ACN (40 mL) was added c-Pyridin-3-yl-methylamine (376 mg, 3.47 mmol), followed by DMAP (424 mg, 3.47 mmol). The resulting mixture was stirred at 80° C. overnight. The reaction was monitored by LC-MS. Then the mixture was concentrated in vacuum to give a residue, which was purified by a reversed-phase column (5-95% CAN in H₂O) to afford ethyl 4-(3-(pyridin-4-ylmethyl)ureido)benzoate (786 mg, yield: 91%) as a white solid. ¹H NMR (400 MHz, DMSO-d₆): δ=9.18 (brs, 1H), 8.51 (dd, J=4.4, 1.6 Hz, 2H), 7.84 (dd, J=7.2, 1.6 Hz, 2H), 7.54 (dd, J=7.2, 1.6 Hz, 2H), 7.29 (dd, J=4.0, 1.6 Hz, 2H), 6.90 (t, J=6.0 Hz, 1H), 4.34 (d, J=6.0 Hz, 2H), 4.26 (q, J=7.2 Hz, 2H), 1.30 (t, J=7.2 Hz, 3H).

Step 3: To a solution of ethyl 4-(3-(pyridin-4-ylmethyl)ureido)benzoate (12.76 g, 42.6 mmol) in THF/H2O (100 mL+30 mL) was added LiOH (5.37 g, 127.8 mmol). The resulting mixture was stirred at room temperature overnight. The reaction was monitored by TLC. Then THF was removed in vacuum to give an aqueous residue, which was acidified to pH=4~5 with conc. HCl. The solid precipitated from the mixture was filtered. The cake was washed with H2O (50 mL×3) and dried in air to afford 4-(3-(pyridin-4-ylmethyl)ureido)benzoic acid (10.2 g, yield: 88%) as white solid.

Step 4: To a solution of 4-(3-(pyridin-4-ylmethyl)ureido) benzoic acid (100 mg, 0.369 mmol) in DMF (8 mL) was added HATU (154 mg, 0.406 mmol) and DIEA (143 mg, 1.107 mmol). The mixture was stirred at room temperature for 30 mins. Then propylamine (24 mg, 0.406 mmol) was added into the reaction mixture. The resulting reaction mixture was stirred at room temperature overnight. The reaction was monitored by LC-MS. Then the mixture was concentrated in vacuum to give a residue, which was purified by a reversed-phase column (5-95% ACN in H2O) to afford N-propyl-4-(3-(pyridin-4-ylmethyl)ureido)benzamide (90.4 mg, yield: 78%) as a white solid. ¹H NMR (400 MHz, DMSO-d6): δ=8.98 (brs, 1H), 8.50 (dd, J=4.4, 1.6 Hz, 2H), 8.25 (t, J=5.6 Hz, 1H), 7.74 (d, J=9.2 Hz, 2H), 7.46 (d, J=8.8 Hz, 2H), 7.29 (d, J=6.0 Hz, 2H), 6.85 (t, J=6.0 Hz, 1H), 4.34 (d, J=6.4 Hz, 2H), 3.24-3.14 (m, 2H), 1.57-1.45 (m, 2H), 0.88 (t, J=7.6 Hz, 3H). MS: m/z 312.9 (M+H⁺).

Example 53: Synthesis of N-Isopropyl-4-(3-(pyridin-4-ylmethyl)ureido)benzamide

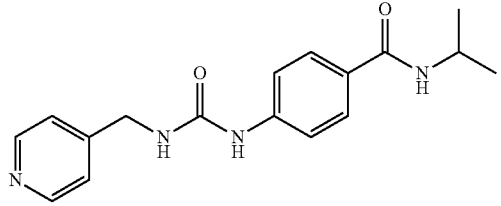 [SMILES: CC(C)NC(=O)c1ccc(NC(=O)NCc2ccncc2)cc1]

The title compound was prepared as described in example N-propyl-4-(3-(pyridin-4-ylmethyl)ureido)benzamide. ¹H NMR (400 MHz, CD₃OD): δ=8.48-8.46 (m, 2H), 7.74 (d, J=6.8 Hz, 2H), 7.48 (d, J=6.8 Hz, 2H), 7.39 (d, J=5.6 Hz, 2H), 4.46 (s, 2H), 4.20-4.16 (m, 1H), 1.23 (d, J=6.4 Hz, 6H). MS: m/z 313.1 (M+H⁺).

Example 54: Synthesis of N,N-dimethyl-4-(3-(pyridin-4-ylmethyl)ureido)benzamide

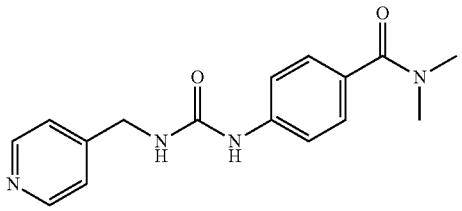 [SMILES: CN(C)C(=O)c1ccc(NC(=O)NCc2ccncc2)cc1]

The title compound was prepared as described in example N-propyl-4-(3-(pyridin-4-ylmethyl)ureido)benzamide. ¹H NMR (400 MHz, DMSO-d₆): δ=8.94 (brs, 1H), 8.51 (d, J=3.2 Hz, 2H), 7.46 (d, J=8.0 Hz, 2H), 7.37-7.25 (m, 4H), 6.88-6.77 (m, 1H), 4.35 (d, J=5.6 Hz, 2H), 2.95 (s, 6H). MS: m/z 298.9 (M+H⁺).

Example 55: Synthesis of N-(2-morpholinoethyl)-4-(3-(pyridin-4-ylmethyl)ureido)benzamide

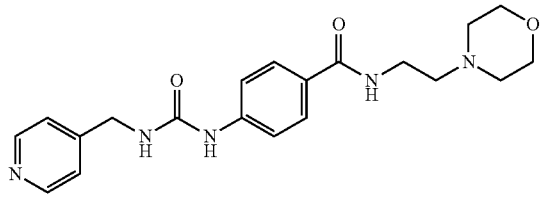 [SMILES: O=C(NCc1ccncc1)Nc1ccc(C(=O)NCCN2CCOCC2)cc1]

The title compound was prepared as described in example N-propyl-4-(3-(pyridin-4-ylmethyl)ureido)benzamide. ¹H NMR (400 MHz, DMSO-d₆): δ=9.02 (brs, 1H), 8.50 (dd, J=4.4, 1.6 Hz, 2H), 8.20 (t, J=5.6 Hz, 1H), 7.73 (d, J=8.4 Hz, 2H), 7.47 (d, J=8.8 Hz, 2H), 7.29 (d, J=5.6 Hz, 2H), 6.88 (t, J=6.0 Hz, 1H), 4.33 (d, J=6.0 Hz, 2H), 3.63-3.52 (m, 4H), 3.40-3.29 (m, 2H), 2.47-2.42 (m, 2H), 2.41-2.36 (m, 4H). MS: m/z 384.1 (M+H⁺).

Example 56: Synthesis of N-cyclohexyl-4-(3-(pyridin-4-ylmethyl)ureido)benzamide

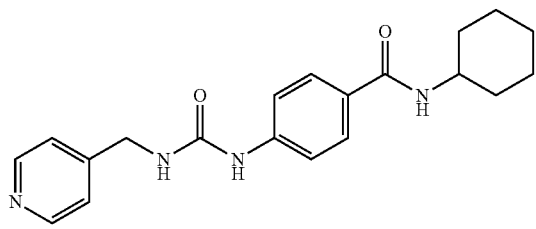 [SMILES: O=C(NCc1ccncc1)Nc1ccc(C(=O)NC2CCCCC2)cc1]

The title compound was prepared as described in example N-propyl-4-(3-(pyridin-4-ylmethyl)ureido)benzamide. ¹H NMR (400 MHz, DMSO-d₆): δ=8.98 (brs, 1H), 8.51 (dd, J=4.4, 1.6 Hz, 2H), 7.98 (d, J=8.0 Hz, 1H), 7.74 (d, J=8.8 Hz, 2H), 7.45 (d, J=8.8 Hz, 2H), 7.29 (d, J=6.0 Hz, 2H), 6.83 (t, J=6.0 Hz, 1H), 4.33 (d, J=6.0 Hz, 2H), 3.80-3.66 (m, 1H), 1.86-1.67 (m, 4H), 1.65-1.55 (m, 1H), 1.34-1.22 (m, 4H), 1.18-1.05 (m, 1H). MS: m/z 353.1 (M+H⁺).

Example 57: Synthesis of N-(2-(piperidin-1-yl)ethyl)-4-(3-(pyridin-4-ylmethyl)ureido)benzamide

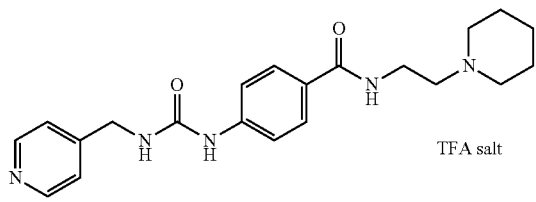 [SMILES: O=C(NCc1ccncc1)Nc1ccc(C(=O)NCCN2CCCCC2)cc1]

The title compound was prepared as described in example N-propyl-4-(3-(pyridin-4-ylmethyl)ureido)benzamide. ¹H NMR (400 MHz, DMSO-d₆): δ=9.48 (brs, 1H), 9.26 (brs, 1H), 8.80 (d, J=6.8 Hz, 2H), 8.57 (t, J=5.2 Hz, 1H), 7.82 (d, J=6.8 Hz, 2H), 7.77 (d, J=8.8 Hz, 2H), 7.52 (d, J=8.8 Hz, 2H), 7.40 (t, J=6.0 Hz, 1H), 4.54 (d, J=5.6 Hz, 2H), 3.64-3.57 (m, 2H), 3.57-3.48 (m, 2H), 3.27-3.16 (m, 2H), 3.00-2.85 (m, 2H), 1.88-1.76 (m, 2H), 1.74-1.58 (m, 3H), 1.45-1.34 (m, 1H). MS: m/z 382.2 (M+H⁺).

Example 58: Synthesis of 4-(3-(Pyridin-4-ylmethyl)ureido)-N-(2-(Pyrrolidin-1-yl)ethyl)benzamide

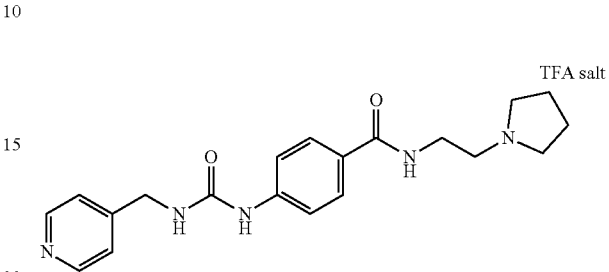

The title compound was prepared as described in example N-propyl-4-(3-(pyridin-4-ylmethyl)ureido)benzamide. ¹H NMR (400 MHz, DMSO-d₆): δ=9.59 (brs, 1H), 9.42 (brs, 1H), 8.77 (d, J=6.8 Hz, 2H), 8.54 (t, J=5.6 Hz, 1H), 7.83-7.73 (m, 4H), 7.52 (d, J=9.2 Hz, 2H), 7.32 (t, J=5.6 Hz, 1H), 4.52 (d, J=6.0 Hz, 2H), 3.69-3.60 (m, 2H), 3.59-3.52 (m, 2H), 3.36-3.28 (m, 2H), 3.11-2.98 (m, 2H), 2.09-1.95 (m, 2H), 1.92-1.79 (m, 2H). MS: m/z 368.1 (M+H⁺).

Example 59: Synthesis of N-isobutyl-4-(3-(pyridin-4-ylmethyl)ureido)benzamide

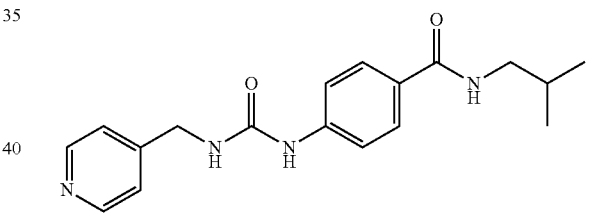

The title compound was prepared as described in example N-propyl-4-(3-(pyridin-4-ylmethyl)ureido)benzamide. ¹H NMR (400 MHz, DMSO-d₆): δ=8.98 (brs, 1H), 8.50 (dd, J=4.4, 1.6 Hz, 2H), 8.26 (t, J=6.0 Hz, 1H), 7.75 (d, J=8.8 Hz, 2H), 7.47 (d, J=8.8 Hz, 2H), 7.29 (d, J=6.0 Hz, 2H), 6.84 (t, J=6.0 Hz, 1H), 4.34 (d, J=6.0 Hz, 2H), 3.05 (t, J=6.4 Hz, 2H), 1.88-1.76 (m, 1H), 0.87 (d, J=6.8 Hz, 6H). MS: m/z 326.9 (M+H⁺).

Example 60: Synthesis of N-cyclobutyl-4-(3-(Pyridin-4-ylmethyl)ureido)benzamide

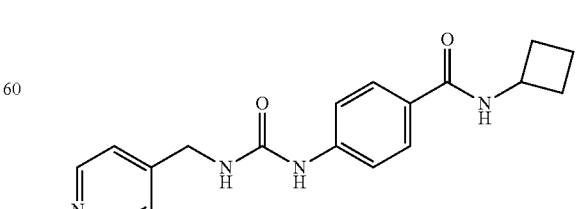

The title compound was prepared as described in example N-propyl-4-(3-(pyridin-4-ylmethyl)ureido)benzamide. $^1$H NMR (400 MHz, DMSO-d$_6$): δ=9.00 (brs, 1H), 8.50 (dd, J=4.4, 1.6 Hz, 2H), 8.40 (d, J=8.0 Hz, 1H), 7.74 (d, J=8.8 Hz, 2H), 7.46 (d, J=8.4 Hz, 2H), 7.29 (d, J=6.0 Hz, 2H), 6.85 (t, J=6.0 Hz, 1H), 4.46-4.36 (m, 1H), 4.34 (d, J=6.0 Hz, 2H), 2.25-2.13 (m, 2H), 2.11-1.98 (m, 2H), 1.71-1.58 (m, 2H). MS: m/z 324.9 (M+H$^+$).

Example 61: Synthesis of N-(cyclopropylmethyl)-4-(3-(Pyridin-4-ylmethyl)ureido)benzamide

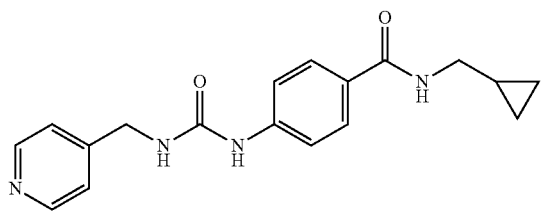 [SMILES: O=C(NCc1ccncc1)Nc1ccc(C(=O)NCC2CC2)cc1]

The title compound was prepared as described in example N-propyl-4-(3-(pyridin-4-ylmethyl)ureido)benzamide. $^1$H NMR (400 MHz, DMSO-d$_6$): δ=9.00 (brs, 1H), 8.50 (dd, J=4.0, 1.6 Hz, 2H), 8.36 (t, J=5.2 Hz, 1H), 7.75 (d, J=8.8 Hz, 2H), 7.47 (d, J=8.8 Hz, 2H), 7.30 (dd, J=4.8, 1.6 Hz, 2H), 6.85 (t, J=6.0 Hz, 1H), 4.34 (d, J=6.0 Hz, 2H), 3.11 (t, J=6.0 Hz, 2H), 1.07-0.96 (m, 1H), 0.45-0.38 (m, 2H), 0.24-0.18 (m, 2H). MS: m/z 324.9 (M+H$^+$).

Example 62: Synthesis of 4-(3-(pyridin-4-ylmethyl)ureido)-N-(tetrahydrofuran-3-yl)benzamide

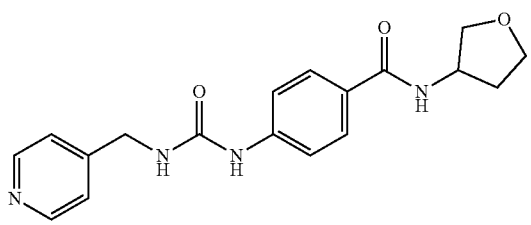 [SMILES: O=C(NCc1ccncc1)Nc1ccc(C(=O)NC2CCOC2)cc1]

The title compound was prepared as described in example N-propyl-4-(3-(pyridin-4-ylmethyl)ureido)benzamide. $^1$H NMR (400 MHz, DMSO-d$_6$): δ=9.01 (brs, 1H), 8.50 (dd, J=4.4, 1.6 Hz, 2H), 8.31 (d, J=6.4 Hz, 1H), 7.77 (d, J=8.8 Hz, 2H), 7.47 (d, J=9.2 Hz, 2H), 7.30 (d, J=6.0 Hz, 2H), 6.85 (t, J=6.0 Hz, 1H), 4.48-4.38 (m, 1H), 4.34 (d, J=6.0 Hz, 2H), 3.88-3.80 (m, 2H), 3.74-3.66 (m, 2H), 3.58-3.52 (m, 1H), 2.18-2.07 (m, 1H), 1.95-1.86 (m, 1H). MS: m/z 340.9 (M+H$^+$).

Example 63: Synthesis of N-(2-methoxyethyl)-4-(3-(pyridin-4-ylmethyl)ureido)benzamide


The title compound was prepared as described in example N-propyl-4-(3-(pyridin-4-ylmethyl)ureido)benzamide. $^1$H NMR (400 MHz, DMSO-d$_6$): δ=9.01 (brs, 1H), 8.50 (dd, J=4.4, 1.6 Hz, 2H), 8.31 (t, J=5.2 Hz, 1H), 7.75 (d, J=8.8 Hz, 2H), 7.47 (d, J=8.8 Hz, 2H), 7.29 (d, J=5.6 Hz, 2H), 6.87 (t, J=6.0 Hz, 1H), 4.34 (d, J=6.0 Hz, 2H), 3.46-3.42 (m, 2H), 3.41-3.37 (m, 2H), 3.26 (s, 3H). MS: m/z 329.1 (M+H$^+$).

Example 64: Synthesis of N-phenethyl-4-(3-(pyridin-4-ylmethyl)ureido)benzamide


The title compound was prepared as described in example N-propyl-4-(3-(pyridin-4-ylmethyl)ureido)benzamide. $^1$H NMR (400 MHz, DMSO-d$_6$): δ=8.99 (brs, 1H), 8.50 (dd, J=4.4, 1.6 Hz, 2H), 8.38 (t, J=6.0 Hz, 1H), 7.72 (d, J=9.2 Hz, 2H), 7.46 (d, J=8.8 Hz, 2H), 7.33-7.26 (m, 4H), 7.26-7.17 (m, 3H), 6.85 (t, J=6.0 Hz, 1H), 4.33 (d, J=6.0 Hz, 2H), 3.49-3.41 (m, 2H), 2.82 (t, J=7.6 Hz, 2H). MS: m/z 374.8 (M+H$^+$).

Example 65: Synthesis of 1-(4-(Morpholine-4-carbonyl)phenyl)-3-(pyridin-4-ylmethyl)urea

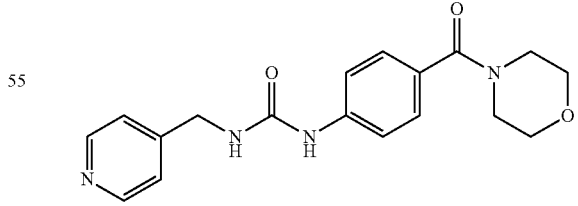

The title compound was prepared as described in example N-propyl-4-(3-pyridin-4-ylmethyl)ureido)benzamide. $^1$H NMR (400 MHz, DMSO-d$_6$): δ=8.98 (brs, 1H), 8.50 (d, J=6.0 Hz, 2H), 7.47 (d, J=8.8 Hz, 2H), 7.38-7.24 (m, 4H), 6.85 (t, J=6.0 Hz, 1H), 4.33 (d, J=6.0 Hz, 2H), 3.68-3.38 (m, 8H). MS: m/z 341.1 (M+H$^+$).

Example 66: Synthesis of 1-(4-(4-Methylpiperazine-1-carbonyl)phenyl)-3-(pyridin-4-ylmethyl)urea

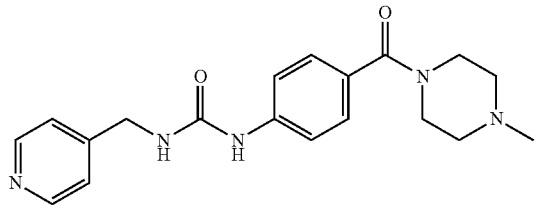 [SMILES: CN1CCN(C(=O)c2ccc(NC(=O)NCc3ccncc3)cc2)CC1]

The title compound was prepared as described in example N-propyl-4-(3-(pyridin-4-ylmethyl)ureido)benzamide. $^1$H NMR (400 MHz, DMSO-d$_6$): δ=8.98 (brs, 1H), 8.50 (d, J=4.4 Hz, 2H), 7.47 (d, J=8.0 Hz, 2H), 7.37-7.20 (m, 4H), 6.85 (t, J=6.0 Hz, 1H), 4.33 (d, J=5.6 Hz, 2H), 3.67-3.36 (m, 4H), 2.37-2.22 (m, 4H), 2.18 (s, 3H). MS: m/z 354.1 (M+H$^+$).

Example 67: Synthesis of 1-(4-(Piperidine-1-carbonyl)phenyl)-3-(pyridin-4-ylmethyl)urea

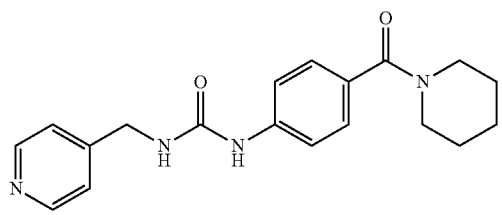 [SMILES: O=C(NCc1ccncc1)Nc1ccc(C(=O)N2CCCCC2)cc1]

The title compound was prepared as described in example N-propyl-4-(3-(pyridin-4-ylmethyl)ureido)benzamide. $^1$H NMR (400 MHz, DMSO-d$_6$): δ=8.98 (brs, 1H), 8.64-8.36 (m, 2H), 7.46 (d, J=6.4 Hz, 2H), 7.38-7.15 (m, 4H), 6.98-6.76 (m, 1H), 4.46-4.21 (m, 2H), 3.68-3.33 (m, 4H), 1.72-1.55 (m, 2H), 1.54-1.36 (m, 4H). MS: m/z 339.1 (M+H$^+$).

Example 68: Synthesis of 1-(Pyridin-4-ylmethyl)-3-(4-(pyrrolidine-1-carbonyl)phenyl)urea

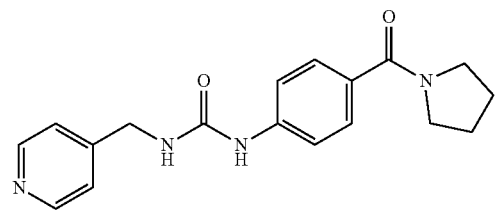 [SMILES: O=C(NCc1ccncc1)Nc1ccc(C(=O)N2CCCC2)cc1]

The title compound was prepared as described in example N-propyl-4-(3-(pyridin-4-ylmethyl)ureido)benzamide. $^1$H NMR (400 MHz, DMSO-d$_6$): δ=8.97 (brs, 1H), 8.50 (dd, J=4.8, 1.2 Hz, 2H), 7.50-7.40 (m, 4H), 7.29 (d, J=7.2 Hz, 2H), 6.86 (t, J=6.0 Hz, 1H), 4.33 (d, J=6.0 Hz, 2H), 3.49-3.39 (m, 4H), 1.92-1.74 (m, 4H). MS: m/z 325.1 (M+H$^+$).

Example 69: Synthesis of N-(cyclopentylmethyl)-4-(3-(pyridin-4-ylmethyl)ureido)benzamide

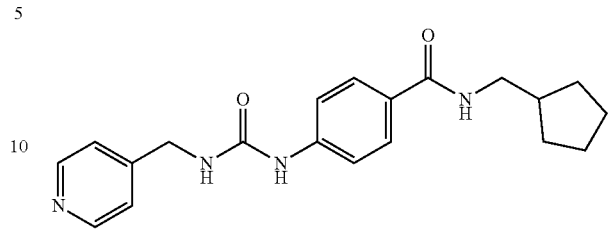

The title compound was prepared as described in example N-propyl-4-(3-(pyridin-4-ylmethyl)ureido)benzamide. $^1$H NMR (400 MHz, DMSO-d$_6$): δ=9.02 (brs, 1H), 8.61-8.39 (m, 2H), 7.58-7.38 (m, 2H), 7.37-7.15 (m, 5H), 7.00-6.82 (m, 1H), 4.48-4.20 (m, 2H), 2.92-2.71 (m, 3H), 1.83-1.55 (m, 6H), 1.53-1.36 (m, 2H). MS: m/z 353.1 (M+H$^+$).

Example 70: Synthesis of 1-(4-(8-Oxa-3-azabicyclo[3.2.1]octane-3-carbonyl)phenyl)-3-(pyridin-4-ylmethyl)urea

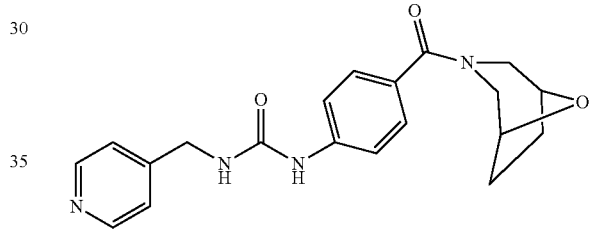

The title compound was prepared as described in example N-propyl-4-(3-(pyridin-4-ylmethyl)ureido)benzamide. $^1$H NMR (400 MHz, CD$_3$OD): δ=8.47 (dd, J=4.8, 1.6 Hz, 2H), 7.50 (dd, J=6.4, 1.6 Hz, 2H), 7.39 (d, J=6.0 Hz, 2H), 7.34 (dd, J=6.4, 2.0 Hz, 2H), 4.46 (s, 2H), 4.40-4.16 (m, 3H), 3.59-3.36 (m, 2H), 3.19-3.00 (m, 1H), 1.99-1.79 (m, 3H), 1.77-1.55 (m, 1H). MS: m/z 367.1 (M+H$^+$).

Example 71: Synthesis of N-(pyridin-4-ylmethyl)-4-(3-(pyridin-4-ylmethyl)ureido)benzamide

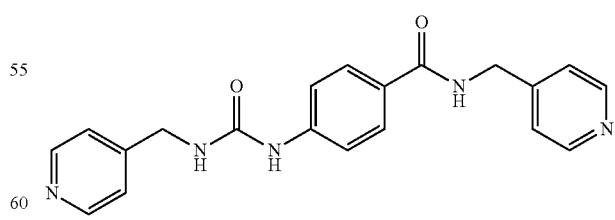

The title compound was prepared as described in example N-propyl-4-(3-(pyridin-4-ylmethyl)ureido)benzamide. $^1$H NMR (400 MHz, CD$_3$OD): δ=8.47-8.45 (m, 4H), 7.82 (d, J=8.8 Hz, 2H), 7.53 (d, J=8.8 Hz, 2H), 7.41-7.39 (m, 4H), 4.60 (s, 2H), 4.47 (s, 2H). MS: m/z 362.1 (M+H$^+$).

Example 72: Synthesis of N-(4-methylphenethyl)-4-(3-(pyridin-4-ylmethyl)ureido)benzamide

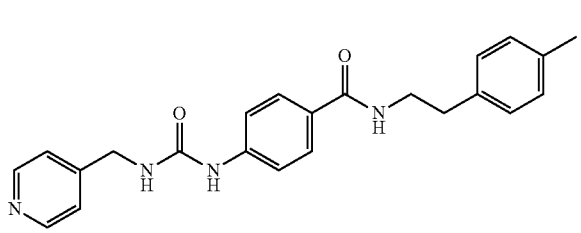 [SMILES: Cc1ccc(CCNC(=O)c2ccc(NC(=O)NCc3ccncc3)cc2)cc1]

The title compound was prepared as described in example N-propyl-4-(3-(pyridin-4-ylmethyl)ureido)benzamide. $^1$H NMR (400 MHz, CD$_3$OD): δ=8.52-8.50 (m, 2H), 7.76-7.74 (m, 2H), 7.53-7.50 (m, 2H), 7.44-7.43 (m, 2H), 7.18-7.12 (m, 4H), 4.50 (s, 2H), 3.60-3.56 (m, J=8.0 HZ 2H), 2.91-2.87 (m, J=8.0 HZ, 2H), 2.33 (s, 3H). MS: m/z 388.9 (M+H$^+$).

Example 73: Synthesis of N-(4-fluorophenethyl)-4-(3-(pyridin-4-ylmethyl)ureido)benzamide

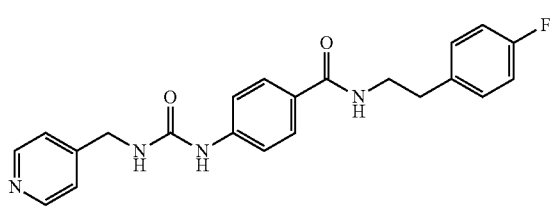 [SMILES: O=C(NCc1ccncc1)Nc1ccc(C(=O)NCCc2ccc(F)cc2)cc1]

The title compound was prepared as described in example N-propyl-4-(3-(pyridin-4-ylmethyl)ureido)benzamide. $^1$H NMR (400 MHz, CD$_3$OD): δ=8.49 (s, 2H), 7.71-7.69 (m, 2H), 7.50-7.43 (m, 4H), 7.27-7.23 (m, 2H), 7.02-3.97 (m, 2H), 4.46 (s, 2H), 3.57-3.53 (m, J=8.0 HZ 2H), 2.90-2.86 (m, J=8.0 HZ 2H), MS: m/z 392.8 (M+H$^+$).

Example 74: Synthesis of N-(3-ethoxypropyl)-4-(3-(pyridin-4-ylmethyl)ureido)benzamide

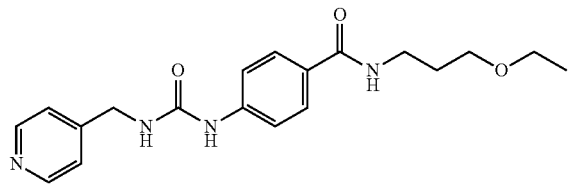 [SMILES: CCOCCCNC(=O)c1ccc(NC(=O)NCc2ccncc2)cc1]

The title compound was prepared as described in example N-propyl-4-(3-(pyridin-4-ylmethyl)ureido)benzamide. $^1$H NMR (400 MHz, CD$_3$OD): δ=8.47-8.46 (m, 2H), 7.74-7.72 (m, 2H), 7.49-7.47 (m, 2H), 7.40-7.39 (m, 2H), 4.46 (s, 2H), 3.54-3.42 (m, 6H), 1.87-1.84 (q' 2H), 1.20-1.16 (m, J=8.0 HZ, 2H). MS: m/z 356.9 (M+H$^+$).

Example 75: Synthesis of N-(2-(dimethylamino)ethyl)-4-(3-(pyridin-4-ylmethyl)ureido)benzamide The title compound was prepared as described in example N-propyl-4-(3-(pyridin-4-ylmethyl)ureido)benzamide. $^1$H NMR (400 MHz, CD$_3$OD): δ=8.53 (d, J=6.0 Hz, 2H), 7.81 (d, J=8.8 Hz, 2H), 7.53-7.51 (m, 4H), 4.51 (s, 2H), 3.73 (t, J=6.0 Hz, 2H). 3.40-3.35 (m, 2H), 2.98 (s, 6H) MS: m/z 342.1 (M+H$^+$).

Example 76: Synthesis of N-(2-chlorobenzyl)-4-(3-(pyridin-4-ylmethyl)ureido)benzamide The title compound was prepared as described in example N-propyl-4-(3-(pyridin-4-ylmethyl)ureido)benzamide. $^1$H NMR (400 MHz, DMSO-d$_6$): δ=9.90 (s, 1H), 8.88-8.85 (m, 1H), 8.51-8.50 (m, 2H), 7.83-781 (m, 2H), 7.51-7.43 (m, 3H), 7.33-7.29 (m, 5H), 6.91-6.88 (m, 1H), 4.52-4.50 (s, 2H), 4.35-4.33 (s, 2H). MS: m/z 394.9 (M+H$^+$).

Example 77: Synthesis of N-(3-chlorobenzyl)-4-(3-(pyridin-4-ylmethyl)ureido)benzamide

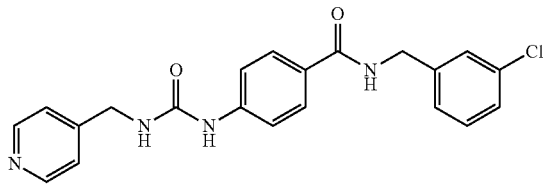 [SMILES: O=C(NCc1ccncc1)Nc1ccc(C(=O)NCc2cccc(Cl)c2)cc1]

The title compound was prepared as described in example N-propyl-4-(3-(pyridin-4-ylmethyl)ureido)benzamide. $^1$H NMR (400 MHz, DMSO-d$_6$): δ=9.17 (s, 1H), 8.92-8.88 (m, 1H), 8.62-8.60 (m, 2H), 7.81-7.78 (m, 2H), 7.51-7.48 (m, 4H), 7.38-7.25 (m, 4H), 7.03-7.00 (m, 1H), 4.45-4.40 (s, 4H). MS: m/z 394.9 (M+H$^+$).

Example 78: Synthesis of N-(2-methoxybenzyl)-4-(3-(pyridin-4-ylmethyl)ureido)benzamide

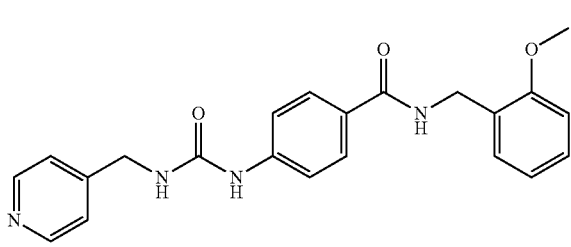 [SMILES: COc1ccccc1CNC(=O)c1ccc(NC(=O)NCc2ccncc2)cc1]

The title compound was prepared as described in example N-propyl-4-(3-(pyridin-4-ylmethyl)ureido)benzamide. $^1$H NMR (400 MHz, DMSO-d$_6$): δ=9.03 (s, 1H), 8.68-8.65 (m, 1H), 8.51-8.50 (m, 2H), 7.82-7.80 (m, 2H), 7.50-7.48 (m, 2H), 7.30-7.29 (m, 2H), 7.24-7.20 (m, 1H), 7.16-7.14 (m, 1H), 6.99-6.91 (m, 1H), 6.89-6.86 (m, 2H), 4.42-4.41 (s, 2H), 4.34-4.33 (s, 2H), 3.82 (s, 3H). MS: m/z 391.0 (M+H$^+$).

Example 79: Synthesis of N-(3-methoxybenzyl)-4-(3-(pyridin-4-ylmethyl)ureido)benzamide

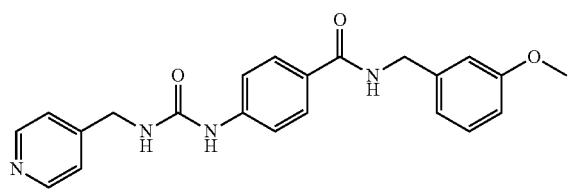 [SMILES: COc1cccc(CNC(=O)c2ccc(NC(=O)NCc3ccncc3)cc2)c1]

The title compound was prepared as described in example N-propyl-4-(3-(pyridin-4-ylmethyl)ureido)benzamide. $^1$H NMR (400 MHz, DMSO-d$_6$): δ=9.03 (s, 1H), 8.68-8.65 (m, 1H), 8.51-8.50 (m, 2H), 7.82-7.80 (m, 2H), 7.50-7.48 (m, 2H), 7.30-7.29 (m, 2H), 7.24-7.20 (m, 1H), 7.16-7.14 (m, 1H), 6.99-6.91 (m, 1H), 6.89-6.86 (m, 2H), 4.42-4.41 (s, 2H), 4.34-4.33 (s, 2H), 3.82 (s, 3H). MS: m/z 391.0 (M+H$^+$).

Example 80: Synthesis of N-(4-methoxybenzyl)-4-(3-(pyridin-4-ylmethyl)ureido)benzamide

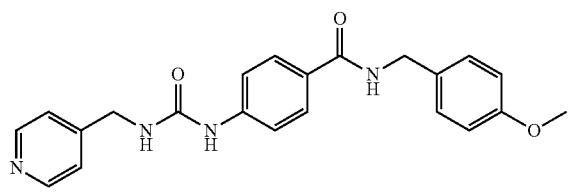 [SMILES: COc1ccc(CNC(=O)c2ccc(NC(=O)NCc3ccncc3)cc2)cc1]

The title compound was prepared as described in example N-propyl-4-(3-(pyridin-4-ylmethyl)ureido)benzamide. $^1$H NMR (400 MHz, DMSO-d$_6$): δ=9.07 (s, 1H), 8.78-8.75 (m, 1H), 8.50-8.49 (m, 2H), 7.78-7.76 (m, 2H), 7.49-7.46 (m, 2H), 7.29-7.28 (m, 2H), 7.24-7.21 (m, 2H), 6.96-6.93 (m, 1H), 6.88-6.86 (m, 2H), 4.38-4.36 (s, 2H), 4.33-4.32 (s, 2H), 3.71 (s, 3H). MS: m/z 391.0 (M+H$^+$).

Example 81: Synthesis of N-(2-fluorobenzyl)-4-(3-(pyridin-4-ylmethyl)ureido)benzamide

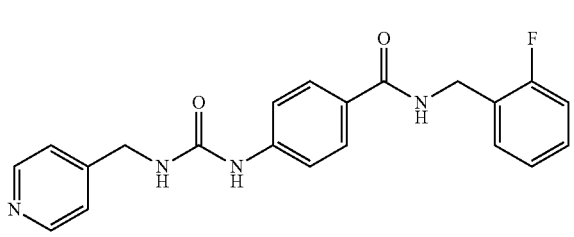

The title compound was prepared as described in example N-propyl-4-(3-(pyridin-4-ylmethyl)ureido)benzamide. $^1$H NMR (400 MHz, DMSO-d$_6$): δ=9.04 (s, 1H), 8.84-8.81 (m, 1H), 8.51-8.49 (m, 2H), 7.81-7.79 (m, 2H), 7.50-7.48 (m, 2H), 7.36-7.32 (m, 4H), 7.30-7.14 (m, 2H), 6.90-6.87 (m, 1H), 4.49-4.48 (s, 2H), 4.34-4.33 (s, 2H). MS: m/z 379.0 (M+H$^+$).

Example 82: Synthesis of N-(3-fluorobenzyl)-4-(3-(pyridin-4-ylmethyl)ureido)benzamide

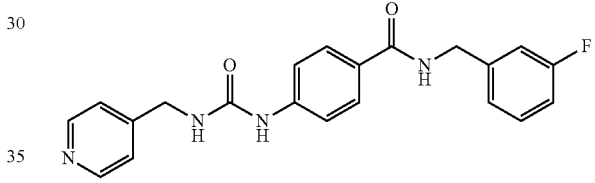

The title compound was prepared as described in example N-propyl-4-(3-(pyridin-4-ylmethyl)ureido)benzamide. $^1$H NMR (400 MHz, DMSO-d$_6$): δ=9.05 (s, 1H), 8.90-8.87 (m, 1H), 8.51-8.49 (m, 2H), 7.80-7.78 (m, 2H), 7.50-7.48 (m, 2H), 7.39-7.33 (m, 2H), 7.30-7.11 (m, 1H), 7.09-7.04 (m, 3H), 6.91-6.88 (m, 1H), 4.46-4.45 (s, 2H), 4.34-4.33 (s, 2H). MS: m/z 379.0 (M+H$^+$).

Example 83: Synthesis of N-(2-methylbenzyl)-4-(3-(pyridin-4-ylmethyl)ureido)benzamide

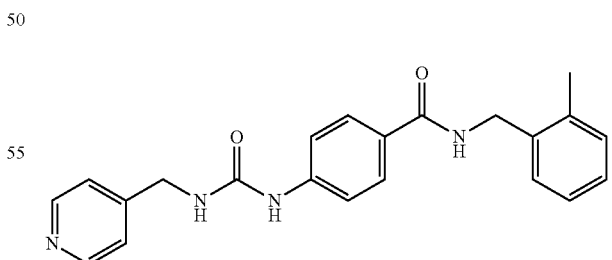

The title compound was prepared as described in example N-propyl-4-(3-(pyridin-4-ylmethyl)ureido)benzamide. $^1$H NMR (400 MHz, CD3OD): δ=8.37-8.35 (m, 2H), 7.69-7.67 (m, 2H), 7.40-7.38 (m, 2H), 7.29-7.28 (m, 2H), 7.17-7.14 (m, 1H), 7.05-7.04 (m, 3H), 4.77 (s, 2H), 4.45-4.35 (s, 2H), 2.25 (s, 3H). MS: m/z 375.0 (M+H$^+$).

Example 84: Synthesis of N-(4-methylbenzyl)-4-(3-(pyridin-4-ylmethyl)ureido)benzamide

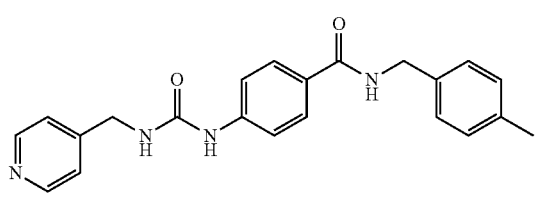 [SMILES: Cc1ccc(CNC(=O)c2ccc(NC(=O)NCc3ccncc3)cc2)cc1]

The title compound was prepared as described in example N-propyl-4-(3-(pyridin-4-ylmethyl)ureido)benzamide. $^1$H NMR (400 MHz, DMSO-d$_6$): δ=9.03 (s, 1H), 8.81-8.78 (m, 1H), 8.51-8.49 (m, 2H), 7.79-7.77 (m, 2H), 7.49-7.47 (m, 2H), 7.30-7.28 (m, 2H), 7.19-7.12 (m, 2H), 7.12-7.10 (m, 2H), 6.90-6.87 (m, 1H), 4.40-4.39 (m, 2H), 4.34-4.32 (m, 2H), 2.26 (s, 3H). MS: m/z 375.0 (M+H$^+$).

Example 85: Synthesis of N-(3-methylbenzyl)-4-(3-(pyridin-4-ylmethyl)ureido)benzamide

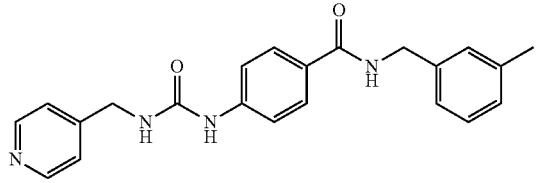 [SMILES: Cc1cccc(CNC(=O)c2ccc(NC(=O)NCc3ccncc3)cc2)c1]

The title compound was prepared as described in example N-propyl-4-(3-(pyridin-4-ylmethyl)ureido)benzamide. $^1$H NMR (400 MHz, DMSO-d$_6$): δ=9.02 (s, 1H), 8.83-8.80 (s, 1H), 8.51-8.50 (m, 2H), 7.81-7.78 (m, 2H), 7.49-7.47 (m, 2H), 7.30-7.28 (m, 2H), 7.21-7.18 (m, 1H), 7.08-7.03 (m, 3H), 6.88-6.85 (m, 1H), 4.42-4.40 (s, 2H), 4.34-4.33 (s, 2H), 2.27 (s, 3H). MS: m/z 375.0 (M+H$^+$).

Example 86: Synthesis of N-(4-chlorobenzyl)-4-(3-(pyridin-4-ylmethyl)ureido)benzamide

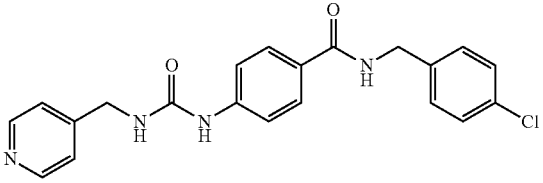 [SMILES: O=C(NCc1ccncc1)Nc1ccc(C(=O)NCc2ccc(Cl)cc2)cc1]

The title compound was prepared as described in example N-propyl-4-(3-(pyridin-4-ylmethyl)ureido)benzamide. $^1$H NMR (400 MHz, CD3OD): δ=8.46 (s, 2H), 7.79-7.77 (m, 2H), 7.50-7.49 (m, 2H), 7.39 (m, 2H), 7.31 (m, 4H), 4.52 (s, 2H), 4.45 (s, 2H). MS: m/z 395.0 (M+H$^+$).

Example 87: Synthesis of N-(4-fluorobenzyl)-4-(3-(pyridin-4-ylmethyl)ureido)benzamide

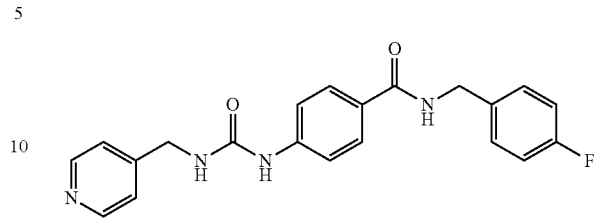

The title compound was prepared as described in example N-propyl-4-(3-(pyridin-4-ylmethyl)ureido)benzamide. $^1$H NMR (400 MHz, DMSO-d$_6$): δ=9.02 (s, 1H), 8.87-8.84 (s, 1H), 8.51-8.50 (m, 2H), 7.80-7.78 (m, 2H), 7.49-7.47 (m, 2H), 7.35-7.28 (s, 4H), 7.16-7.12 (s, 2H), 6.88-6.85 (m, 1H), 4.43-4.42 (s, 2H), 4.34-4.33 (s, 2H). MS: m/z 379.0 (M+H$^+$).

Example 88: Synthesis of N-benzyl-N-methyl-4-(3-(pyridin-4-ylmethyl)ureido)benzamide

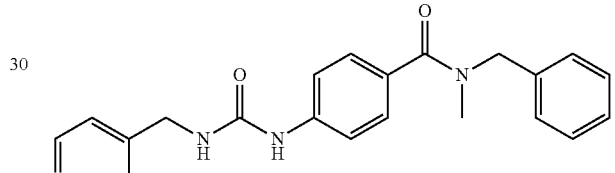

The title compound was prepared as described in example N-propyl-4-(3-(pyridin-4-ylmethyl)ureido)benzamide. $^1$H NMR (400 MHz, DMSO-d$_6$): δ=8.96 (s, 1H), 8.50-8.49 (m, 2H), 7.47-7.27 (m, 11H), 6.85-6.82 (m, 1H), 4.60-4.59 (s, 2H), 4.33-4.32 (s, 2H), 2.86 (s, 3H). MS: m/z 375.0 (M+H$^+$).

Example 89: Synthesis of 1-(4-(Isoindoline-2-carbonyl)phenyl)-3-(pyridin-4-ylmethyl)urea

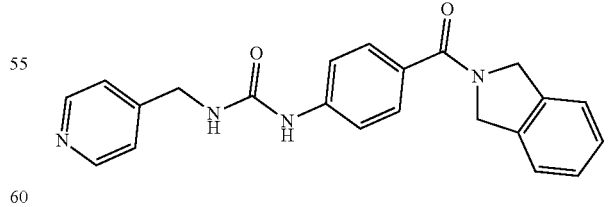

The title compound was prepared as described in example N-propyl-4-(3-(pyridin-4-ylmethyl)ureido)benzamide. $^1$H NMR (400 MHz, DMSO-d$_6$): δ=8.97 (s, 1H), 8.52-8.50 (m, 2H), 7.55-7.49 (m, 4H), 7.39-7.38 (m, 1H), 7.30-7.27 (m, 5H), 6.86-6.83 (m, 1H), 4.85-4.83 (s, 4H), 4.36-4.34 (s, 2H). MS: m/z 373.0 (M+H$^+$).

Example 90: Synthesis of 1-(Pyridin-4-ylmethyl)-3-(4-(1,2,3,4-tetrahydroisoquinoline-2-carbonyl)phenyl)urea

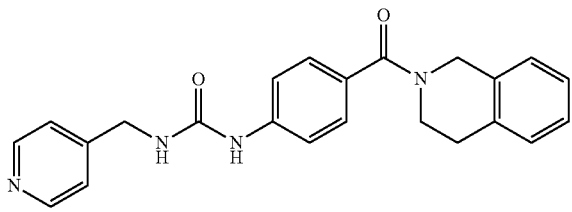 [SMILES: O=C(NCc1ccncc1)Nc1ccc(C(=O)N2CCc3ccccc3C2)cc1]

The title compound was prepared as described in example N-propyl-4-(3-(pyridin-4-ylmethyl)ureido)benzamide. $^1$H NMR (400 MHz, DMSO-d$_6$): δ=8.97 (s, 1H), 8.51-8.50 (m, 2H), 7.50-7.48 (m, 2H), 7.36-7.34 (m, 2H), 7.30-7.29 (m, 2H), 7.17 (m, 4H), 6.85-6.82 (m, 1H), 4.67 (s, 2H), 4.35-4.33 (s, 2H), 3.67 (s, 2H), 2.87-2.84 (m, 2H). MS: m/z 387.0 (M+H$^+$).

Example 91: Synthesis of N-(4-chlorophenyl)-4-(3-(pyridin-4-ylmethyl)ureido)benzamide

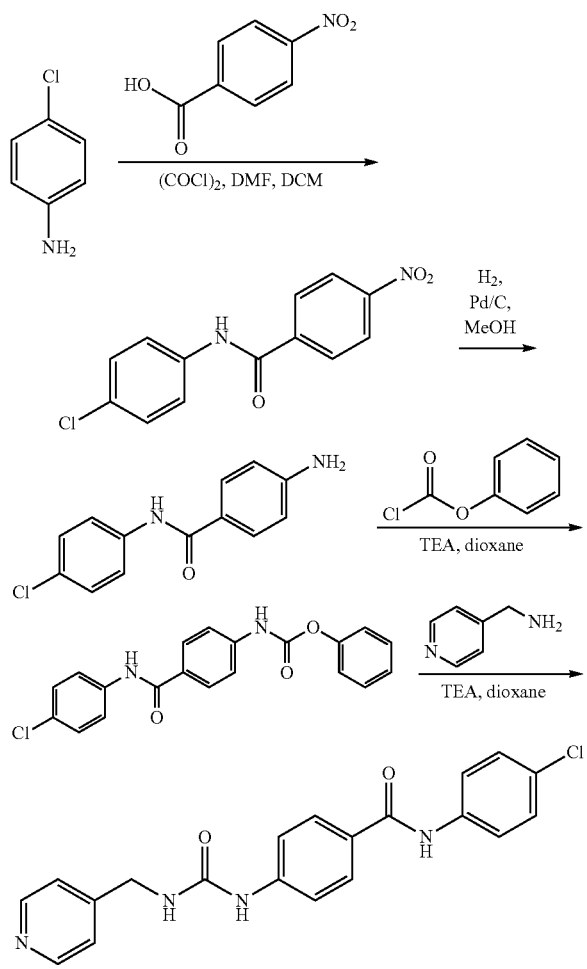

Step 1: A mixture of 4-nitrobenzoic acid (4.0 g, 24 mmol), (COCl)$_2$ (3.3 g, 26 mmol) and DMF (2 drops) in DCM (50 mL) was stirred until the mixture became clear. The mixture was concentrated in vacuum. The residue was added to a mixture of 4-chloroaniline (2.7 g, 22 mmol) and TEA (4.4 g, 44 mmol) and was stirred at room temperature for 16 hrs. The mixture was filtered and the filter cake was dried in vacuum to give crude N-(4-chlorophenyl)-4-nitrobenzamide (2.8 g, yield: 46%) as a yellow solid, which was used in next step without further purification.

Step 2: A mixture of N-(4-chlorophenyl)-4-nitrobenzamide (2.5 g, 9 mmol) and wet 10% Pd/C (50 mg) in MeOH (50 mL) was stirred at room temperature under H2 balloon atmosphere for 2 hrs. The mixture was filtered and the filtrate was concentrated in vacuum to give crude product (2.0 g, yield: 90%) as a white solid, which was used in next step without further purification.

Step 3: A mixture of 4-amino-N-(4-chlorophenyl)benzamide (1.1 g, 4.5 mmol), phenyl carbonochloridate (840 mg. 5.4 mmol) and TEA (700 mg, 6.8 mmol) in DCM (20 mL) was stirred at room temperature for 1 hr. The mixture was filtered and the filter cake was dried in vacuum to give crude product (1.1 g, yield: 68%) as a white solid, which was used in next step without further purification.

Step 4: A mixture of phenyl (4-((4-chlorophenyl)carbamoyl)phenyl)carbamate (100 mg, 0.27 mmol), pyridin-4-ylmethanamine (40 mg. 0.37 mmol) and TEA (54 mg, 0.54 mmol) in dioxane (5 mL) was stirred at 90° C. for 16 hrs. The mixture was concentrated in vacuum and the residue was purified by flash chromatography to give N-(4-chlorophenyl)-4-(3-(pyridin-4-ylmethyl)ureido)benzamide (25 mg, yield: 25%) as a white solid. $^1$H NMR (400 MHz, CD$_3$OD): δ=8.47 (d, J=5.6 Hz, 2H), 7.87 (d, J=8.8 Hz, 2H), 7.68 (d, J=8.8 Hz, 2H), 7.55 (d, J=8.4 Hz, 2H), 7.40 (d, J=5.6 Hz, 2H), 7.33 (d, J=8.8 Hz, 2H), 4.47 (s, 2H). MS: m/z 380.9 (M+H$^+$).

Example 92: Synthesis of N-(2-chlorophenyl)-4-(3-(pyridin-4-ylmethyl)ureido)benzamide

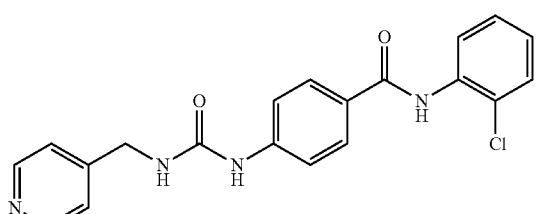

The title compound was prepared as described in example N-(4-chlorophenyl)-4-(3-(pyridin-4-ylmethyl)ureido)benzamide. $^1$H NMR (400 MHz, DMSO-d$_6$): δ=9.82 (s, 1H), 9.13 (s, 1H), 8.52-8.51 (m, 2H), 7.91-7.89 (m, 2H), 7.60-7.53 (m, 4H), 7.39-7.25 (m, 4H), 6.93-6.90 (s, 1H), 4.36-4.35 (m, 2H). MS: m/z 380.9 (M+H$^+$).

Example 93: Synthesis of N-(3-chlorophenyl)-4-(3-(pyridin-4-ylmethyl)ureido)benzamide

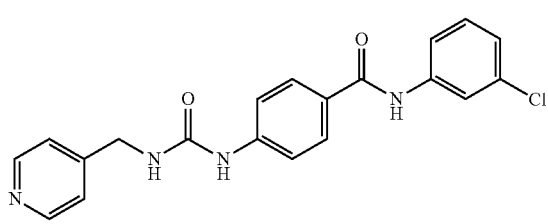 [SMILES: O=C(NCc1ccncc1)Nc1ccc(C(=O)Nc2cccc(Cl)c2)cc1]

The title compound was prepared as described in example N-(4-chlorophenyl)-4-(3-(pyridin-4-ylmethyl)ureido)benzamide. ¹H NMR (400 MHz, DMSO-d₆): δ=10.2 (s, 1H), 9.33 (s, 1H), 8.51 (s, 2H), 7.98-7.88 (m, 3H), 7.71-7.70 (m, 3H), 7.37-7.34 (m, 3H), 7.14-7.08 (m, 2H), 4.35 (s, 2H). MS: m/z 380.9 (M+H⁺).

Example 94: Synthesis of N-(2-fluorophenyl)-4-(3-(pyridin-4-ylmethyl)ureido)benzamide

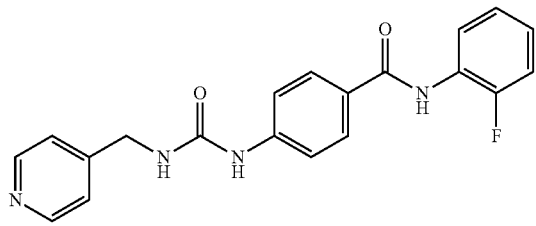 [SMILES: O=C(NCc1ccncc1)Nc1ccc(C(=O)Nc2ccccc2F)cc1]

The title compound was prepared as described in example N-(4-chlorophenyl)-4-(3-(pyridin-4-ylmethyl)ureido)benzamide. ¹H NMR (400 MHz, CD3OD): δ=8.48-8.47 (m, 2H), 7.90-7.88 (m, 2H), 7.73-7.71 (m, 1H), 7.69 (m, 2H), 7.57-7.40 (m, 2H), 7.24-7.17 (m, 3H), 4.47 (s, 2H). MS: m/z 365.0 (M+H⁺).

Example 95: Synthesis of N-(3-fluorophenyl)-4-(3-(pyridin-4-ylmethyl)ureido)benzamide

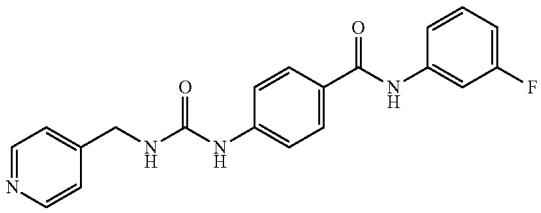 [SMILES: O=C(NCc1ccncc1)Nc1ccc(C(=O)Nc2cccc(F)c2)cc1]

The title compound was prepared as described in example N-(4-chlorophenyl)-4-(3-(pyridin-4-ylmethyl)ureido)benzamide. ¹H NMR (400 MHz, CD3OD): δ=8.48-8.47 (m, 2H), 7.8-7.86 (m, 2H), 7.66-7.62 (m, 1H), 7.56-7.54 (m, 2H), 7.43-7.40 (m, 3H), 7.35-7.32 (m, 1H), 6.85-6.84 (m, 1H), 4.47 (s, 2H). MS: m/z 365.0 (M+H⁺).

Example 96: Synthesis of N-(4-fluorophenyl)-4-(3-(pyridin-4-ylmethyl)ureido)benzamide

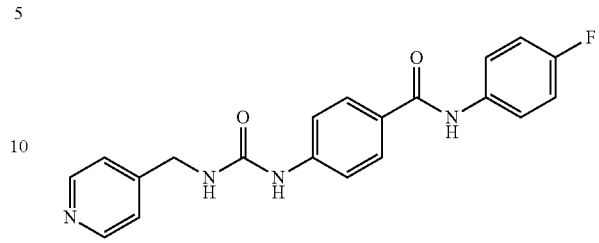

The title compound was prepared as described in example N-(4-chlorophenyl)-4-(3-(pyridin-4-ylmethyl)ureido)benzamide. H NMR (400 MHz, DMSO-d₆): δ=10.1 (s, 1H), 9.10 (s, 1H), 8.52-8.50 (m, 2H), 7.89-7.87 (m, 2H), 7.79-7.76 (m, 2H), 7.56-7.54 (m, 2H), 7.31-7.30 (m, 2H), 7.20-7.15 (m, 2H), 6.90 (s, 1H), 4.36-4.34 (m, 2H). MS: m/z 365.0 (M+H⁺).

Example 97: Synthesis of 4-(3-(Pyridin-4-ylmethyl)ureido)-N-(o-tolyl)benzamide

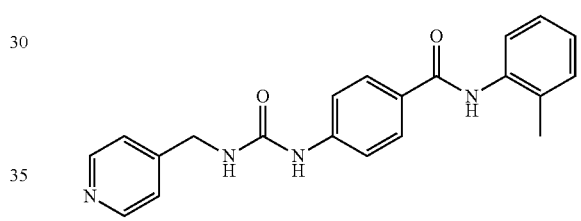

The title compound was prepared as described in example N-(4-chlorophenyl)-4-(3-(pyridin-4-ylmethyl)ureido)benzamide. ¹H NMR (400 MHz, CD3OD): δ=8.48-8.47 (m, 2H), 7.91-7.89 (m, 2H), 7.56-7.54 (m, 2H), 7.41-7.40 (m, 2H), 7.32-7.26 (m, 2H), 7.22-7.18 (m, 2H), 4.47 (s, 2H), 2.28 (s, 3H). MS: m/z 361.0 (M+H⁺).

Example 98: Synthesis of 4-(3-(Pyridin-4-ylmethyl)ureido)-N-(m-tolyl)benzamide

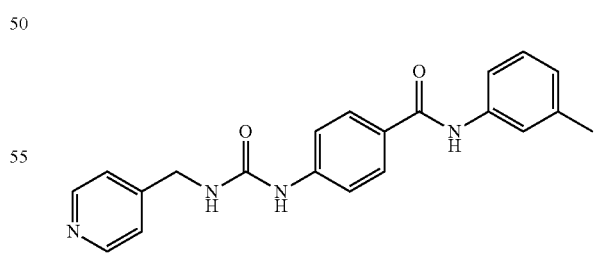

The title compound was prepared as described in example N-(4-chlorophenyl)-4-(3-(pyridin-4-ylmethyl)ureido)benzamide. ¹H NMR (400 MHz, DMSO-d₆): δ=9.96 (s, 1H), 9.12 (s, 1H), 8.52-8.50 (m, 2H), 7.88-7.86 (m, 2H), 7.60 (m, 1H), 7.55-7.53 (m, 3H), 7.31-7.29 (m, 2H), 7.22-7.19 (m, 1H), 6.92-6.88 (m, 2H), 4.36-4.34 (s, 2H), 2.30 (s, 3H). MS: m/z 361.0 (M+H⁺).

Example 99: Synthesis of N-(4-(methoxymethyl)phenyl)-4-(3-(pyridin-4-ylmethyl)ureido)benzamide

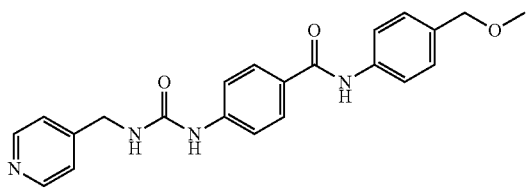 [SMILES: COCc1ccc(NC(=O)c2ccc(NC(=O)NCc3ccncc3)cc2)cc1]

The title compound was prepared as described in example N-(4-chlorophenyl)-4-(3-(pyridin-4-ylmethyl)ureido)benzamide. $^1$H NMR (400 MHz, DMSO-$d_6$): δ=10.07 (brs, 1H), 9.32 (brs, 1H), 8.68 (d, J=5.6 Hz, 2H), 7.89 (d, J=8.4 Hz, 2H), 7.75 (d, J=8.4 Hz, 2H), 7.60 (d, J=6.0 Hz, 2H), 7.56 (d, J=8.8 Hz, 2H), 7.28 (d, J=8.8 Hz, 2H), 7.15-7.12 (brs, 1H), 4.46 (d, J=5.6 Hz, 2H), 4.36 (s, 2H), 3.27 (s, 3H). MS: m/z 391.0 (M+H$^+$)

Example 100: Synthesis of N-(2-methoxyphenyl)-4-(3-(pyridin-4-ylmethyl)ureido)benzamide

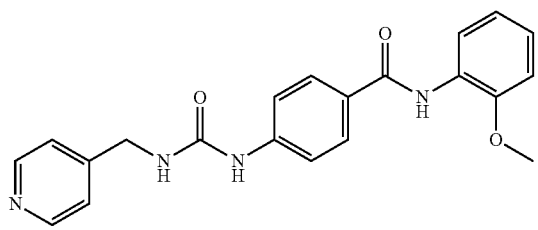 [SMILES: COc1ccccc1NC(=O)c1ccc(NC(=O)NCc2ccncc2)cc1]

The title compound was prepared as described in example N-(4-chlorophenyl)-4-(3-(pyridin-4-ylmethyl)ureido)benzamide. $^1$H NMR (400 MHz, CD3OD): δ=8.48-8.46 (m, 2H), 8.00-7.97 (m, 1H), 7.87-7.84 (m, 2H), 7.57-7.54 (m, 2H), 7.41-7.40 (m, 2H), 7.17-7.13 (m, 1H), 7.06-7.04 (m, 1H), 6.98-9.94 (m, 1H), 4.47 (s, 2H), 3.91 (s, 3H). MS: m/z 377.0 (M+H$^+$).

Example 101: Synthesis of N-(3-methoxyphenyl)-4-(3-(pyridin-4-ylmethyl)ureido)benzamide

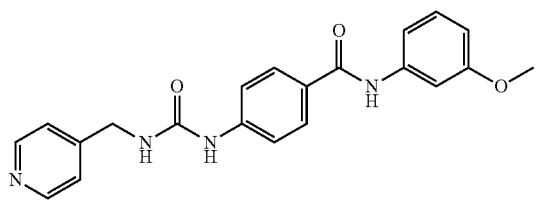 [SMILES: COc1cccc(NC(=O)c2ccc(NC(=O)NCc3ccncc3)cc2)c1]

The title compound was prepared as described in example N-(4-chlorophenyl)-4-(3-(pyridin-4-ylmethyl)ureido)benzamide. $^1$H NMR (400 MHz, CD$_3$OD): δ=8.48-8.46 (m, 2H), 7.88-7.85 (m, 2H), 7.55-7.53 (m, 2H), 7.41-7.38 (m, 3H), 7.23-7.21 (m, 2H), 6.71-6.68 (m, 1H), 4.47 (s, 2H), 3.80-3.29 (s, 3H). MS: m/z 376.8 (M+H$^+$).

Example 102: Synthesis of N-(4-methoxyphenyl)-4-(3-(pyridin-4-ylmethyl)ureido)benzamide

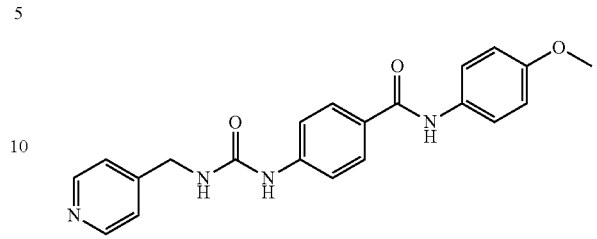

The title compound was prepared as described in example N-(4-chlorophenyl)-4-(3-(pyridin-4-ylmethyl)ureido)benzamide. $^1$H NMR (400 MHz, CD$_3$OD): δ=8.48-8.47 (m, 2H), 7.87-7.85 (m, 2H), 7.55-7.52 (m, 4H), 7.41-7.40 (m, 2H), 6.92-6.90 (m, 2H), 4.47 (s, 2H), 3.79 (s, 3H). MS: m/z 376.9 (M+H$^+$).

Example 103: Synthesis of N-(2-(dimethylamino)phenyl)-4-(3-(pyridin-4-ylmethyl)ureido)benzamide

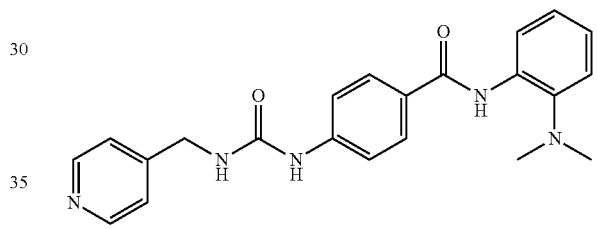

The title compound was prepared as described in example N-(4-chlorophenyl)-4-(3-(pyridin-4-ylmethyl)ureido)benzamide. $^1$H NMR (400 MHz, CD3OD): δ=8.48-8.47 (m, 2H), 8.16-8.14 (m, 1H), 7.87-7.85 (m, 2H), 7.59-7.57 (m, 2H), 7.41-7.40 (m, 2H), 7.26 (m, 1H), 7.13-7.11 (m, 2H), 4.47 (s, 2H), 2.71 (m, 6H). MS: m/z 390.0 (M+H$^+$).

Example 104: Synthesis of N-(3-(dimethylamino)phenyl)-4-(3-(pyridin-4-ylmethyl)ureido)benzamide

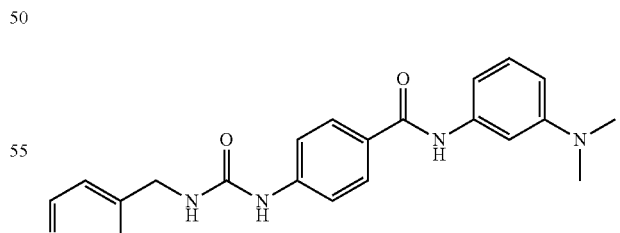

The title compound was prepared as described in example N-(4-chlorophenyl)-4-(3-(pyridin-4-ylmethyl)ureido)benzamide. $^1$H NMR (400 MHz, CD3OD): δ=8.48-8.46 (m, 2H), 7.87-7.85 (m, 2H), 7.54-7.52 (m, 2H), 7.41-7.39 (m, 2H), 7.18-7.14 (m, 2H), 7.01-7.00 (m, 1H), 6.99-6.56 (m, 1H), 4.47 (s, 2H), 3.03-2.93 (s, 6H). MS: m/z 390.0 (M+H$^+$).

Example 105: Synthesis of N-(3-(dimethylamino)phenyl)-4-(3-(pyridin-4-ylmethyl)ureido)benzamide

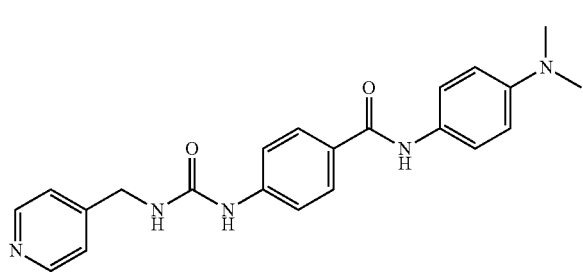 [SMILES: CN(C)c1ccc(NC(=O)c2ccc(NC(=O)NCc3ccncc3)cc2)cc1]

The title compound was prepared as described in example N-(4-chlorophenyl)-4-(3-(pyridin-4-ylmethyl)ureido)benzamide. $^1$H NMR (400 MHz, DMSO-$d_6$): δ=9.77 (s, 1H), 9.14 (s, 1H), 8.51-8.50 (m, 2H), 7.88-7.84 (m, 2H), 7.56-7.51 (m, 4H), 7.30-7.29 (m, 2H), 6.99-6.96 (m, 1H), 6.72-6.70 (m, 2H), 4.35-4.33 (s, 2H), 2.86 (s, 6H). MS: m/z 390.0 (M+H$^+$).

Example 106: Synthesis of 4-(3-(Pyridin-4-ylmethyl)ureido)-N-(2-(trifluoromethoxy)phenyl)benzamide

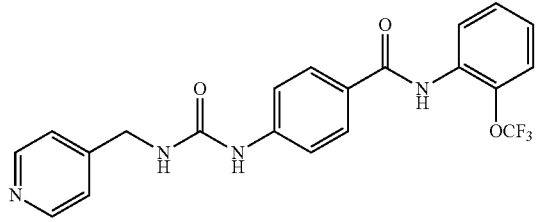

The title compound was prepared as described in example N-(4-chlorophenyl)-4-(3-(pyridin-4-ylmethyl)ureido)benzamide. $^1$H NMR (400 MHz, CD3OD): δ=8.75-8.74 (m, 2H), 7.99-7.97 (m, 2H), 7.89-7.87 (m, 2H), 7.77-7.75 (m, 1H), 7.58-7.56 (m, 2H), 7.39-7.33 (m, 3H), 4.68 (s, 2H). MS: m/z 431.0 (M+H$^+$).

Example 107: Synthesis of 4-(3-(pyridin-4-ylmethyl)ureido)-N-(3-(trifluoromethoxy)phenyl)benzamide

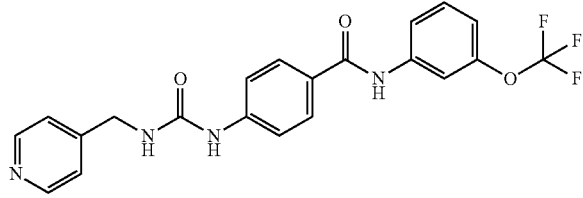 [SMILES: O=C(NCc1ccncc1)Nc1ccc(C(=O)Nc2cccc(OC(F)(F)F)c2)cc1]

The title compound was prepared as described in example N-(4-chlorophenyl)-4-(3-(pyridin-4-ylmethyl)ureido)benzamide. $^1$H NMR (400 MHz, CD3OD): δ=8.48-8.47 (m, 2H), 7.86-7.83 (m, 3H), 7.65-7.62 (m, 1H), 7.57-7.54 (m, 2H), 7.44-7.40 (m, 3H), 7.03-7.01 (m, 1H), 4.47 (s, 2H). MS: m/z 430.9 (M+H$^+$).

Example 108: Synthesis of 4-(3-(pyridin-4-ylmethyl)ureido)-N-(4-(trifluoromethoxy)phenyl)benzamide

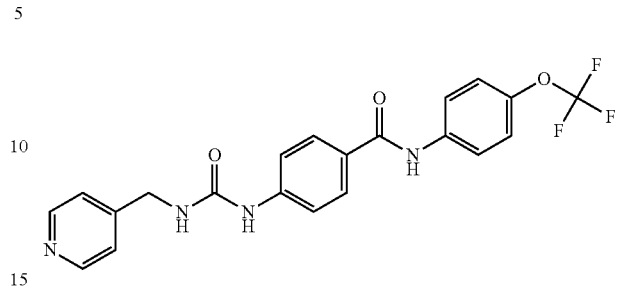

The title compound was prepared as described in example N-(4-chlorophenyl)-4-(3-(pyridin-4-ylmethyl)ureido)benzamide. $^1$H NMR (400 MHz, CD3OD): δ=8.48-8.47 (m, 2H), 7.89-7.83 (m, 2H), 7.79-7.77 (m, 2H), 7.56-7.54 (m, 2H), 7.41-7.40 (m, 2H), 7.27-7.25 (m, 2H), 4.47 (s, 2H). MS: m/z 431.0 (M+H$^+$).

Example 109: Synthesis of N-(4-ethoxyphenyl)-4-(3-(pyridin-4-ylmethyl)ureido)benzamide

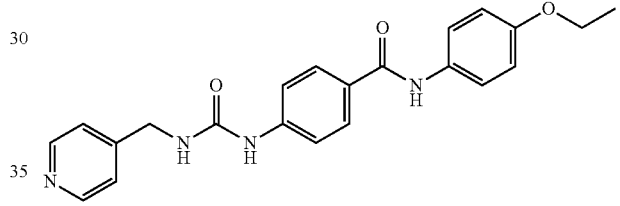

The title compound was prepared as described in example N-(4-chlorophenyl)-4-(3-(pyridin-4-ylmethyl)ureido)benzamide. $^1$H NMR (400 MHz, DMSO-$d_6$): δ=9.92 (s, 1H), 9.09 (s, 1H), 8.52-8.50 (m, 2H), 7.87-7.85 (m, 2H), 7.65-7.62 (m, 2H), 7.54-7.52 (m, 2H), 7.31-7.29 (m, 2H), 6.91-6.88 (m, 3H), 4.35-4.34 (s, 2H), 4.02-3.97 (q, 2H), 1.31-1.30 (t, 3H). MS: m/z 391.0 (M+H$^+$).

Example 110: Synthesis of N-(4-isopropoxyphenyl)-4-(3-(pyridin-4-ylmethyl)ureido)benzamide

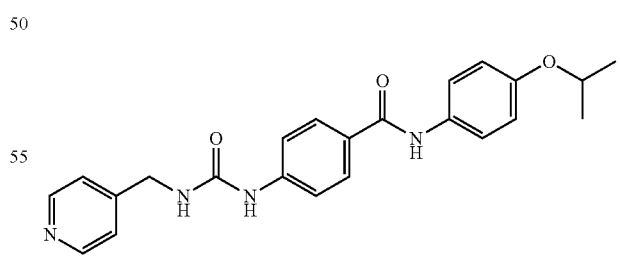

The title compound was prepare as described in example N-(4-chlorophenyl)-4-(3-(pyridin-4-ylmethyl)ureido)benzamide. $^1$H NMR (400 MHz, DMSO-$d_6$): δ=9.91 (s, 1H), 9.07 (s, 1H), 8.52-8.50 (m, 2H), 7.87-7.85 (m, 2H), 7.63-7.61 (m, 2H), 7.54-7.52 (m, 2H), 7.31-7.29 (m, 2H), 6.89-6.87 (m, 3H), 4.57-4.54 (m, 1H), 4.35-4.34 (s, 2H), 1.25-1.24 (s, 6H). MS: m/z 405.0 (M+H$^+$).

Example 111: Synthesis of Methyl 4-(4-(3-(pyridin-4-ylmethyl)ureido)benzamido)benzoate

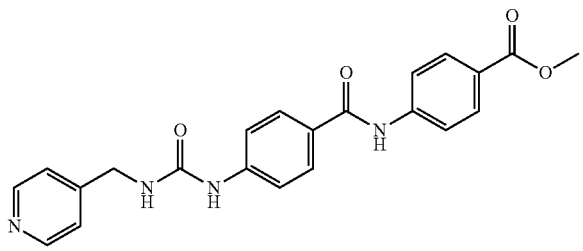 [SMILES: COC(=O)c1ccc(NC(=O)c2ccc(NC(=O)NCc3ccncc3)cc2)cc1]

The title compound was prepared as described in example N-(4-chlorophenyl)-4-(3-(pyridin-4-ylmethyl)ureido)benzamide. $^1$H NMR (400 MHz, DMSO-$d_6$): δ=10.3 (s, 1H), 9.14 (s, 1H), 8.52-8.50 (m, 2H), 7.94-7.89 (m, 6H), 7.57-7.55 (m, 2H), 7.31-7.30 (m, 2H), 6.93-6.90 (m, 1H), 4.36-4.34 (s, 2H), 3.83 (s, 3H). MS: m/z 405.0 (M+H$^+$).

Example 112: Synthesis of N-(4-cyanophenyl)-4-(3-(pyridin-4-ylmethyl)ureido)benzamide stirred at room temperature for another 1 hour. The reaction was monitored by TLC. Then the mixture was concentrated in vacuum to give a residue, which was purified by a silica gel column (DCM as eluent) to afford N-(4-cyanophenyl)-4-nitrobenzamide (726 mg, yield: 55%) as a yellow solid. $^1$H NMR (400 MHz, DMSO-$d_6$): δ=10.94 (brs, 1H), 8.39 (dd, J=7.2, 2.0 Hz, 2H), 8.19 (dd, J=7.2, 2.0 Hz, 2H), 7.99 (d, J=8.8 Hz, 2H), 7.86 (d, J=8.8 Hz, 2H).

Step 3: To a solution of N-(4-cyanophenyl)-4-nitrobenzamide (726 mg, 2.72 mmol) in EtOH/H$_2$O (v/v=40 mL/10 mL) was added powder iron (760 mg, 13.58 mmol) and NH$_4$Cl (727 mg, 13.58 mmol). The resulting mixture was stirred at 80° C. overnight. The reaction was monitored by LC-MS. Then powder iron was filtered off. The filtrate was concentrated in vacuum to afford 4-amino-N-(4-cyano-phenyl)-benzamide (588 mg, yield: 91%) as a yellow solid. $^1$H NMR (400 MHz, DMSO-$d_6$): δ=10.14 (brs, 1H), 7.96 (d, J=8.8 Hz, 2H), 7.81-7.69 (m, 4H), 6.61 (d, J=8.8 Hz, 2H), 5.86 (s, 2H).

Step 4: To a solution of 4-amino-N-(4-cyano-phenyl)-benzamide (588 mg, 2.48 mmol) in DCM (20 mL) was added phenyl carbonchloridate (776 mg, 4.96 mmol), followed by TEA (753 mg, 7.44 mmol). The resulting mixture was stirred at room temperature for 1 hour. The reaction was monitored by TLC. Then the mixture was concentrated in

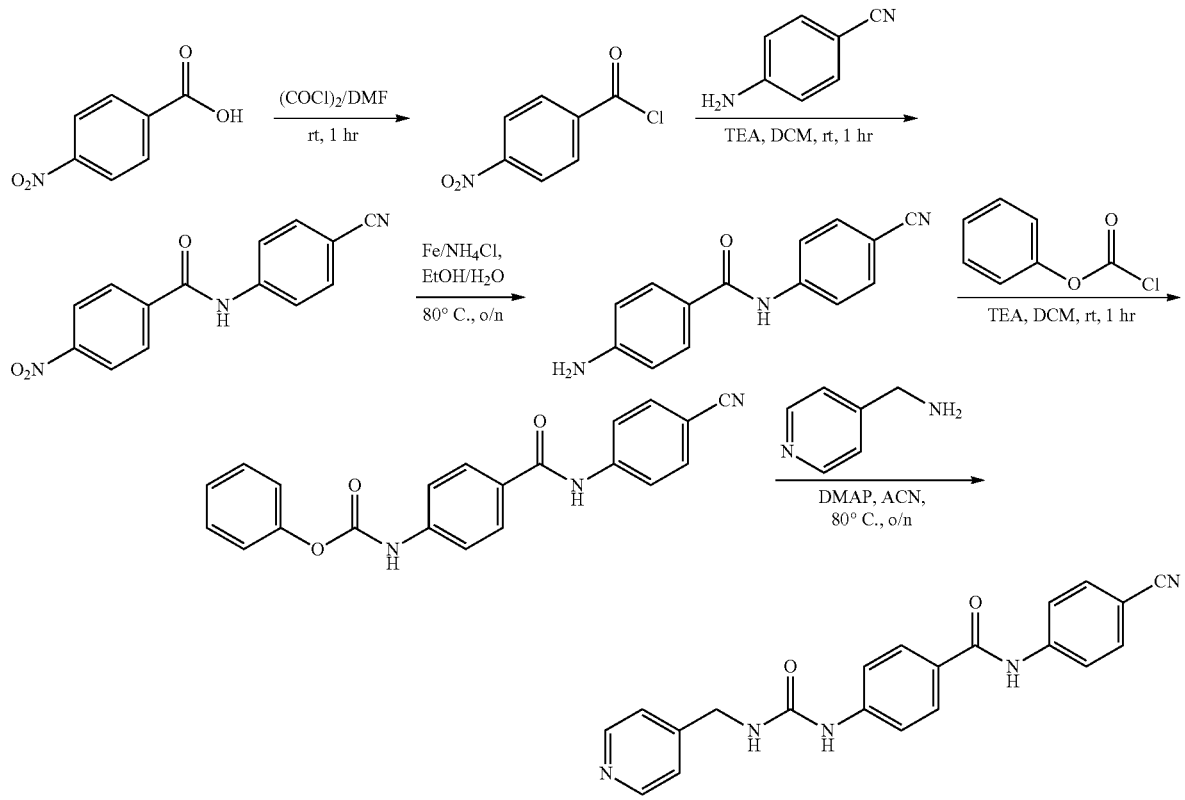

Step 1, 2: To a solution of 4-nitro-benzoic acid (836 mg, 5.0 mmol) in (COCl)$_2$ (5 mL) was added a drop of dry DMF. The reaction was stirred at room temperature for 1 hour. Then the mixture was concentrated in vacuum to give 4-nitro-benzoyl chloride as a yellow solid, which was dissolved in dry DCM (40 mL). Then 4-amino-benzonitrile (1.184 g, 10.0 mmol) was added into the mixture, followed by TEA (1.518 g, 15.0 mmol). The resulting mixture was vacuum to give a residue, which was purified by a silica gel column eluting with DCM to afford phenyl (4-((4-cyanophenyl)carbamoyl)phenyl)carbamate (496 mg, yield: 56%) as a white solid. $^1$H NMR (400 MHz, DMSO-$d_6$): δ=10.59 (brs, 1H), 10.51 (brs, 1H), 8.02-7.93 (m, 4H), 7.81 (d, J=8.8 Hz, 2H), 767 (d, J=9.2 Hz, 2H), 7.45 (d, J=8.0 Hz, 2H), 7.32-7.23 (m, 3H).

Step 5: To a solution of phenyl (4-((4-cyanophenyl)carbamoyl)phenyl)carbamate (150 mg, 0.42 mmol) in ACN (20 mL) was added c-pyridin-4-yl-methylamine (54 mg, 0.50 mmol), followed by TEA (127 mg, 1.26 mmol). The resulting mixture was stirred at 80° C. for 3 hours. The reaction was monitored by LC-MS. Then the mixture was concentrated in vacuum to give a residue, which was purified by a prep-HPLC with NH$_4$OH as additive to afford N-(4-cyanophenyl)-4-(3-(pyridin-4-ylmethyl)ureido)benzamide (66.6 mg, yield: 43%) as a white solid. $^1$H NMR (400 MHz, DMSO-d$_6$): δ=10.42 (brs, 1H), 9.13 (s, 1H), 8.51 (dd, J=4.4, 1.6 Hz, 2H), 7.98 (dd, J=7.2, 2.0 Hz, 2H), 7.90 (d, J=8.8 Hz, 2H), 7.80 (dd, J=7.2, 2.0 Hz, 2H), 7.57 (d, J=8.8 Hz, 2H), 7.30 (d, J=5.6 Hz, 2H), 6.90 (t, J=6.0 Hz, 1H), 4.35 (d, J=6.0 Hz, 2H). MS: m/z 372.1 (M+H$^+$).

Example 113: Synthesis of N-(3,4-dimethylphenyl)-4-(3-(pyridin-4-ylmethyl)ureido)benzamide

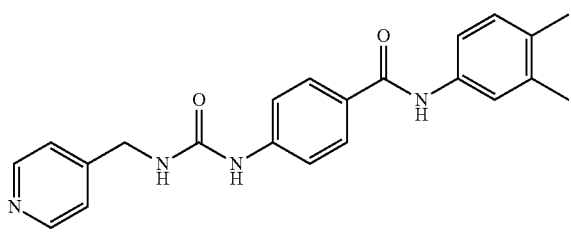 [SMILES: Cc1ccc(NC(=O)c2ccc(NC(=O)NCc3ccncc3)cc2)cc1C]

The title compound was prepared as described in example N-(4-cyanophenyl)-4-(3-(pyridin-4-ylmethyl)ureido)benzamide. $^1$H NMR (400 MHz, CD3OD): δ=8.48-8.47 (m, 2H), 7.87-7.84 (m, 2H), 7.54-7.52 (m, 2H), 7.41-7.35 (m, 4H), 7.10-7.08 (m, 1H), 4.47 (s, 2H), 2.26-2.24 (s, 6H). MS: m/z 375.0 (M+H$^+$).

Example 114: Synthesis of N-(3,4-dimethoxyphenyl)-4-(3-(pyridin-4-ylmethyl)ureido)benzamide

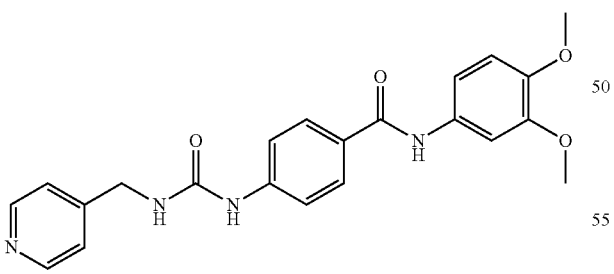

The title compound was prepared as described in example N-(4-cyanophenyl)-4-(3-(pyridin-4-ylmethyl)ureido)benzamide. $^1$H NMR (400 MHz, CD3OD): δ=8.48-8.46 (m, 2H), 7.87-7.85 (m, 2H), 7.55-7.53 (m, 2H), 7.41-7.40 (m, 3H), 7.10-7.08 (m, 1H), 6.94-6.92 (m, 1H), 4.47 (s, 2H), 2.26-2.24 (s, 6H). MS: m/z 407.0 (M+H$^+$).

Example 115: Synthesis of N-(benzo[d][1,3]dioxol-5-yl)-4-(3-(pyridin-4-ylmethyl)ureido)benzamide

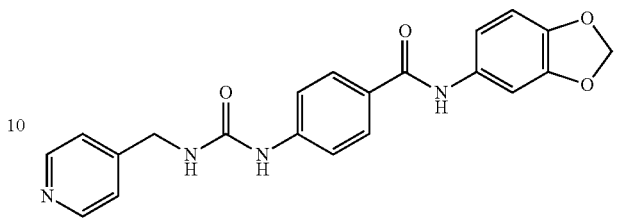

The title compound was prepared as described in example N-(4-cyanophenyl)-4-(3-(pyridin-4-ylmethyl)ureido)benzamide. $^1$H NMR (400 MHz, CD3OD): δ=8.48-8.46 (m, 2H), 7.85-7.83 (m, 2H), 7.54-7.52 (m, 2H), 7.41-7.39 (m, 2H), 7.28 (m, 1H), 7.04-7.02 (m, 1H), 6.80-6.78 (m, 1H), 5.94 (s, 2H), 4.47 (s, 2H). MS: m/z 391.0 (M+H$^+$).

Example 116: Synthesis of N-(4-methoxy-3-methylphenyl)-4-(3-(pyridin-4-ylmethyl)ureido)benzamide

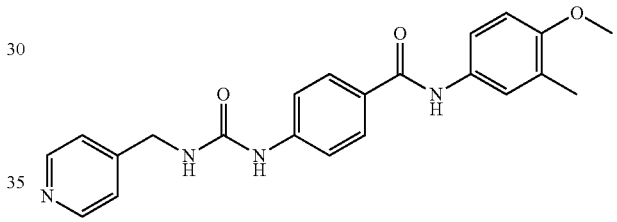

The title compound was prepared as described in example N-(4-cyanophenyl)-4-(3-(pyridin-4-ylmethyl)ureido)benzamide. $^1$H NMR (400 MHz, CD3OD): δ=8.48-8.46 (m, 2H), 7.86-7.84 (m, 2H), 7.54-7.51 (m, 2H), 7.41-7.36 (m, 4H), 6.88-6.86 (m, 1H), 4.46 (s, 2H), 3.81 (s, 3H), 2.19 (s, 3H). MS: m/z 391.0 (M+H$^+$).

Example 117: Synthesis of N-(2,3-dihydrobenzo[b][1,4]dioxin-6-yl)-4-(3-(pyridin-4-ylmethyl)ureido)benzamide

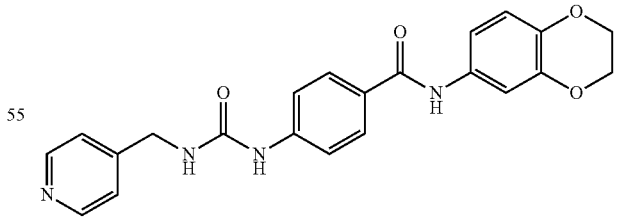

The title compound was prepared as described in example N-(4-cyanophenyl)-4-(3-(pyridin-4-ylmethyl)ureido)benzamide. $^1$H NMR (400 MHz, DMSO-d$_6$): δ=9.87 (s, 1H), 9.10 (s, 1H), 8.51-8.50 (m, 2H), 7.86-7.83 (m, 2H), 7.54-7.52 (m, 2H), 7.37 (m, 1H), 7.30-7.29 (m, 2H), 7.19-7.16 (m, 1H), 6.92-6.89 (m, 1H), 6.89-6.79 (m, 1H), 4.35-4.34 (s, 2H), 4.22-4.21 (m, 4H). MS: m/z 405.0 (M+H$^+$).

Example 118: Synthesis of N-(pyridin-2-yl)-4-(3-(pyridin-4-ylmethyl)ureido)benzamide

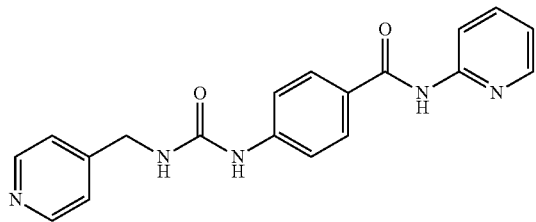

The title compound was prepared as described in example N-(4-cyanophenyl)-4-(3-(pyridin-4-ylmethyl)ureido)benzamide. $^1$H NMR (400 MHz, CD$_3$OD): δ=8.48-8.47 (s, 2H), 8.34-8.33 (m, 1H), 8.20-8.18 (m, 1H), 7.93-7.91 (m, 2H), 7.84-7.80 (m, 1H), 7.58-7.55 (m, 2H), 7.41-7.40 (m, 2H), 7.14-7.13 (m, 1H), 4.47 (s, 2H). MS: m/z 348.0 (M+H$^+$).

Example 119: Synthesis of N-(pyridin-3-yl)-4-(3-(pyridin-4-ylmethyl)ureido)benzamide

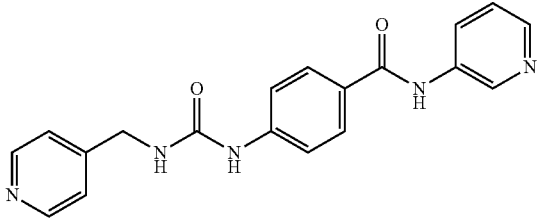 [SMILES: O=C(NCc1ccncc1)Nc1ccc(C(=O)Nc2cccnc2)cc1]

The title compound was prepared as described in example N-(4-cyanophenyl)-4-(3-(pyridin-4-ylmethyl)ureido)benzamide. $^1$H NMR (400 MHz, CD$_3$OD): δ=8.78-8.77 (s, 1H), 8.38-8.37 (m, 2H), 8.19-8.13 (m, 2H), 7.82-7.80 (m, 2H), 7.48-7.46 (m, 2H), 7.34-7.30 (m, 3H), 4.38 (s, 2H). MS: m/z 347.9 (M+H$^+$).

Example 120: Synthesis of 4-(3-(pyridin-4-ylmethyl)ureido)-N-(pyrimidin-5-yl)benzamide

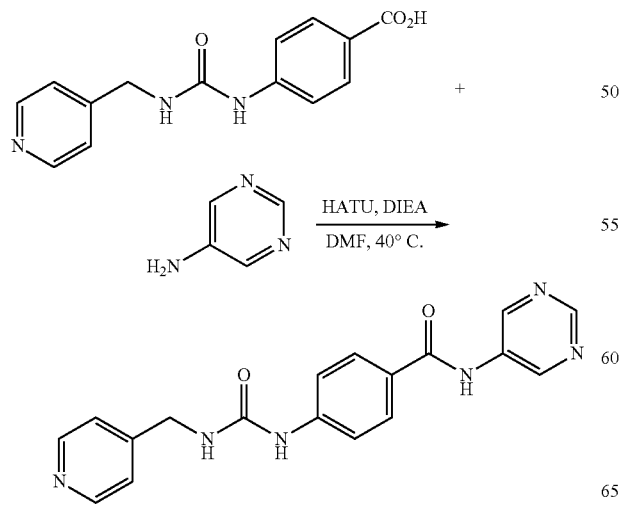

To a stirred mixture of 4-(3-(pyridin-4-ylmethyl)ureido)benzoic acid (50 mg, 0.18 mmol), pyrimidin-5-ylamine (21 mg, 0.22 mmol) and DIEA (71 mg, 0.55 mmol) in DMF (5 mL) was added HATU (105 mg, 0.28 mmol). The mixture was stirred at 40° C. for 3 days. The mixture was diluted with water (20 mL), and the aqueous phase was extracted with EtOAc (30 mL*3). The combined organic layer was washed with brine (20 mL), dried over Na$_2$SO$_4$ and filtered. The filtrate was concentrated to dryness in vacuum and the residue was purified by preparative TLC (DCM/MeOH=10/1) to afford 4-(3-(pyridin-4-ylmethyl)ureido)-N-(pyrimidin-5-yl)benzamide (4 mg, yield: 6%) as a white solid. $^1$H NMR (400 MHz, CD$_3$OD): δ=9.19 (s, 2H), 8.89 (s, 1H), 8.48 (d, J=5.2 Hz, 2H), 7.93 (d, J=8.8 Hz, 2H), 7.58 (d, J=8.4 Hz, 2H), 7.41 (d, J=5.6 Hz, 2H), 4.48 (s, 2H). MS: m/z 349.1 (M+H$^+$).

Example 121: Synthesis of N-(3-methylisoxazol-5-yl)-4-(3-(pyridin-4-ylmethyl)ureido)benzamide

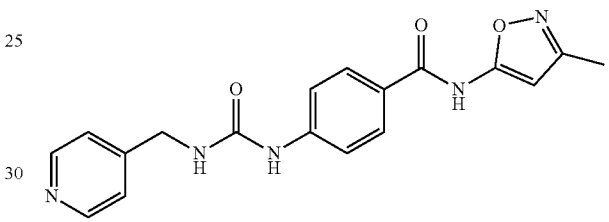

The title compound was prepare as described in example 4-(3-(pyridin-4-ylmethyl)ureido)-N-(pyrimidin-5-yl)benzamide. $^1$H NMR (300 MHz, DMSO-d$_6$): δ=11.68 (s, 1H), 9.22 (s, 1H), 8.51 (d, J=4.8 Hz, 2H), 7.93 (d, J=7.8 Hz, 2H), 7.55 (d, J=7.8 Hz, 2H), 7.30 (d, J=4.5 Hz, 2H), 6.98-6.95 (m, 1H), 6.28 (s, 1H), 4.34 (d, J=5.4 Hz, 2H), 2.20 (s, 3H). MS: m/z 352.1 (M+H$^+$).

Example 122: Synthesis of 4-(3-(Pyridin-4-ylmethyl)ureido)-N-(thiophen-2-yl)benzamide

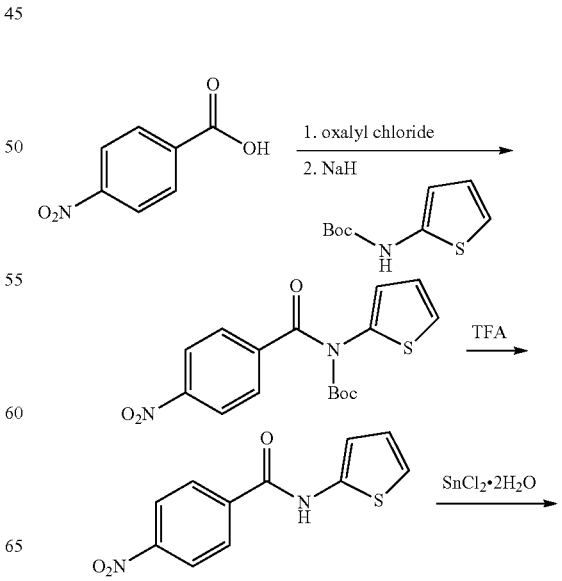

-continued

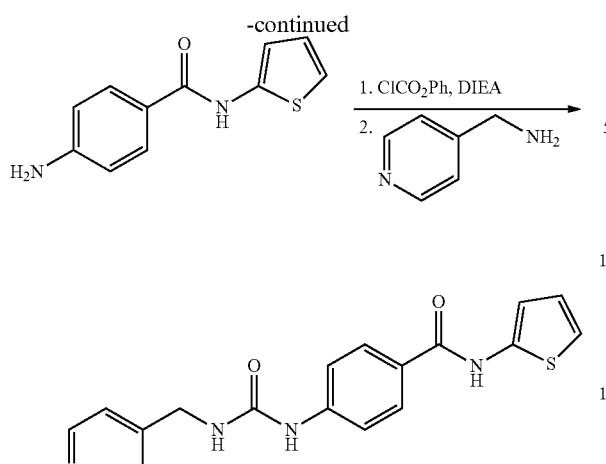

Step 1: To a solution of 4-nitrobenzoic acid (400 mg, 2.39 mmol) in DCM (50 mL) was added oxalyl chloride (395 mg, 3.11 mmol) and DMF (1 drop). The mixture was stirred at room temperature for 1 hr. The solution was concentrated to afford the intermediate acyl chloride. It was then dropped to a suspension of thiophen-2-yl-carbamic acid tert-butyl ester (523 mg, 2.63 mmol) and NaH (143 mg, 3.59 mmol) in anhydrous THF (30 mL) and the mixture was stirred at room temperature overnight. Resultant was quenched with MeOH (3 mL), concentrated and purified by combi-flash (EA in PE: 0 to 30%) to afford tert-butyl (4-nitrobenzoyl)(thiophen-2-yl)carbamate (410 mg, yield: 49%) as a white solid.

Step 2: To a solution of (4-nitro-benzoyl)-thiophen-2-yl-carbamic acid tert-butyl ester (410 mg, 1.18 mmol) in DCM (50 mL) was added TFA (2 mL). The mixture was stirred at room temperature for 2 hrs. The reactant was concentrated and diluted with EA (50 mL). The mixture was washed with aq. $K_2CO_3$ and the organic layer was dried over $Na_2SO_4$. The solution was concentrated to afford 4-nitro-N-(thiophen-2-yl)benzamide (400 mg, crude) without further purification.

Step 3: To a solution of 4-nitro-N-(thiophen-2-yl)benzamide (400 mg, 1.16 mmol) in EtOH (30 mL) was added $SnCl_2.2H_2O$ (2.1 g, 8.1 mmol), it was then heated at reflux for 2 hrs. After cooled to room temperature, the reaction was quenched by $NH_3.H_2O$ (2 mL). The white precipitate was filtrated through celite. The filtrate was concentrated and purified by combi-flash (EA in PE: 0 to 50%) to afford 4-amino-N-(thiophen-2-yl)benzamide (170 mg, yield: 48%) as a white solid. MS: m/z 219.1 (M+H$^+$).

Step 4: To a solution of 4-amino-N-(thiophen-2-yl)benzamide (170 mg, 0.78 mmol) in DCM (20 mL) was added phenyl chloroformate (140 mg, 0.47 mmol) and DIEA (0.5 mL), it was stirred at room temperature over 30 min before the addition of pyridin-4-ylmethanamine (101 mg, 0.94 mmol). The mixture was then stirred at room temperature overnight. Resultant was concentrated and the residue was purified by prep-HPLC to afford 4-(3-(pyridin-4-ylmethyl)ureido)-N-(thiophen-2-yl)benzamide (82 mg, yield: 27%) as a white solid. $^1$H NMR (400 MHz, DMSO-d$_6$): δ=11.33 (s, 1H), 9.14 (s, 1H), 8.51 (d, J=5.6 Hz, 2H), 7.91 (d, J=8.4 Hz, 2H), 7.56 (d, J=8.4 Hz, 2H), 7.30 (d, J=4.8 Hz, 2H), 6.97-6.89 (m, 4H), 4.35 (d, J=5.6 Hz, 2H). MS: m/z 353.1 (M+H$^+$).

Example 123: Synthesis of Ethyl 4-(3-(oxazol-4-ylmethyl)ureido)benzoate

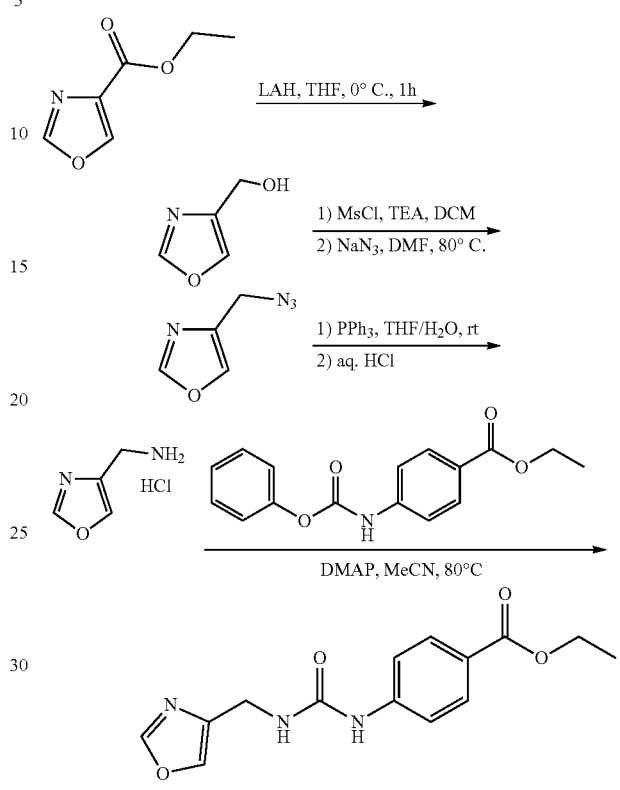

Step 1: To a solution of ethyl oxazole-4-carboxylate (1.0 g, 7.1 mmol) in THF (20 mL) was added LAH (330 mg, 8.5 mmol) portion wise at 0° C. After stirring at 0° C. for 30 min, $H_2O$ (0.3 mL), 15% NaOH (0.3 mL) and $H_2O$ (0.9 mL) were then added dropwise at 0° C. The mixture was stirred at room temperature for another 20 min, dried over $MgSO_4$ and filtered. The filtrate was concentrated to give oxazol-4-ylmethanol (390 mg, yield: 56%) as yellow oil. $^1$H NMR (300 MHz, CDCl$_3$): δ=7.90 (s, 1H), 7.64 (d, J=0.3 Hz, 1H), 4.63 (s, 2H).

Step 2: To a solution of oxazol-4-ylmethanol (375 mg, 3.8 mmol) and Et$_3$N (0.8 mL, 5.7 mmol) in DCM (10 mL) was added MsCl (520 mg, 4.5 mmol) dropwise at 0° C. After stirring at room temperature for 20 min, the reaction mixture was diluted with DCM (50 mL) and washed with water (30 mL). The DCM solution was dried over $Na_2SO_4$ and concentrated. The residue was dissolved in DMF (20 mL) and NaN$_3$ (320 mg, 4.9 mmol) was added. After stirring at 80° C. for 16 hrs, the reaction mixture was poured to water (60 mL) and extracted with EA (50 mL×3). The combined organic layer was washed with brine (40 mL×3), dried over $Na_2SO_4$ and concentrated. The residue was purified by silica gel column (PE/EA=10/1) to give 4-(azidomethyl)oxazole (180 mg, yield: 38%) as colorless oil. $^1$H NMR (400 MHz, CDCl$_3$): δ=7.91 (s, 1H), 7.68 (d, J=1.2 Hz, 1H), 4.32 (s, 2H).

Step 3: To a solution of 4-azidomethyl-oxazole (140 mg, 1.1 mmol) in THF/H$_2$O (4 mL/0.5 mL) was added PPh$_3$ (440 mg, 1.7 mmol). After stirring at room temperature for 16 hrs, the reaction mixture was poured to aq.HCl (2 N, 5 mL) and extracted with DCM (20 mL*2). The acidic layer was concentrated and co-evaporated with toluene (10 mL*2) to give oxazol-4-ylmethanamine.HCl (crude) as a white solid.

Step 4: A mixture of C-oxazol-4-yl-methylamine.HCl (crude), 4-phenoxycarbonylamino-benzoic acid ethyl ester (320 mg, 1.1 mmol) and DMAP (280 mg, 2.3 mmol) in MeCN (6 mL) was stirred at 80° C. for 10 min and then concentrated. The residue was diluted by DCM (40 mL), washed by aq.HCl (1 N, 20 mL), dried over $Na_2SO_4$ and concentrated. The residue was purified by Prep-HPLC ($NH_4HCO_3$) to give ethyl 4-(3-(oxazol-4-ylmethyl)ureido) benzoate (90 mg, yield: 28%) as a white solid. $^1$H NMR (400 MHz, DMSO-$d_6$): δ=8.99 (s, 1H), 8.34 (s, 1H), 7.96 (d, J=0.8 Hz, 1H), 7.83 (d, J=8.8 Hz, 2H), 7.51 (d, J=8.8 Hz, 2H), 6.66 (t, J=5.6 Hz, 1H), 4.26 (q, J=7.2 Hz, 2H), 4.22 (d, J=5.2 Hz, 2H), 1.30 (t, J=7.2 Hz, 3H). MS: m/z 290.0 (M+H$^+$).

Example 124: Synthesis of Ethyl 4-(3-((3,5-dimethylisoxazol-4-yl)methyl)ureido)benzoate

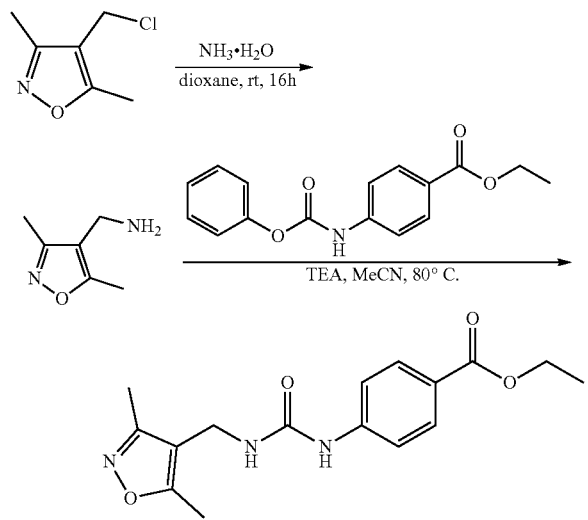

Step 1: To a solution of 4-chloromethyl-3,5-dimethyl-isoxazole (1.0 g, 6.9 mmol) in dioxane (10 mL) was added $NH_3.H_2O$ (10 mL). After stirring at room temperature for 16 hrs, the reaction mixture was concentrated and washed with MeCN (20 mL) to give (3,5-dimethylisoxazol-4-yl)methanamine (800 mg, yield: 92%) as a white solid. $^1$H NMR (400 MHz, DMSO-$d_6$): δ=8.52 (brs, 2H), 3.81 (s, 2H), 2.45 (s, 3H), 2.30 (s, 3H).

Step 2: A mixture of (3,5-dimethylisoxazol-4-yl)methanamine (70 mg, 0.6 mmol), 4-phenoxycarbonylamino-benzoic acid ethyl ester (150 mg, 0.5 mmol) and TEA (0.2 mL, 1.6 mmol) in MeCN (8 mL) was stirred at 80° C. for 1 h and then concentrated. The residue was diluted with DCM (40 mL), washed with aq.HCl (1 N, 20 mL) and Sat..NaHCO$_3$ (20 mL). The DCM solution was dried over Na$_2$SO$_4$, concentrated and purified by Prep-HPLC (NH$_3$.H$_2$O) to give ethyl 4-(3-((3,5-dimethylisoxazol-4-yl)methyl)ureido)benzoate (50 mg, yield: 30%) as a white solid. $^1$H NMR (400 MHz, DMSO-$d_6$): δ=8.85 (s, 1H), 7.82 (d, J=8.8 Hz, 2H), 7.50 (d, J=8.8 Hz, 2H), 6.64 (t, J=5.6 Hz, 1H), 4.26 (q, J=7.2 Hz, 2H), 4.06 (d, J=5.6 Hz, 2H), 2.38 (s, 3H), 2.21 (s, 3H), 1.29 (t, J=7.2 Hz, 3H). MS: m/z 318.0 (M+H$^+$).

Example 125: Synthesis of Ethyl 4-(3-((1-methyl-1H-pyrazol-4-yl)methyl)ureido)benzoate

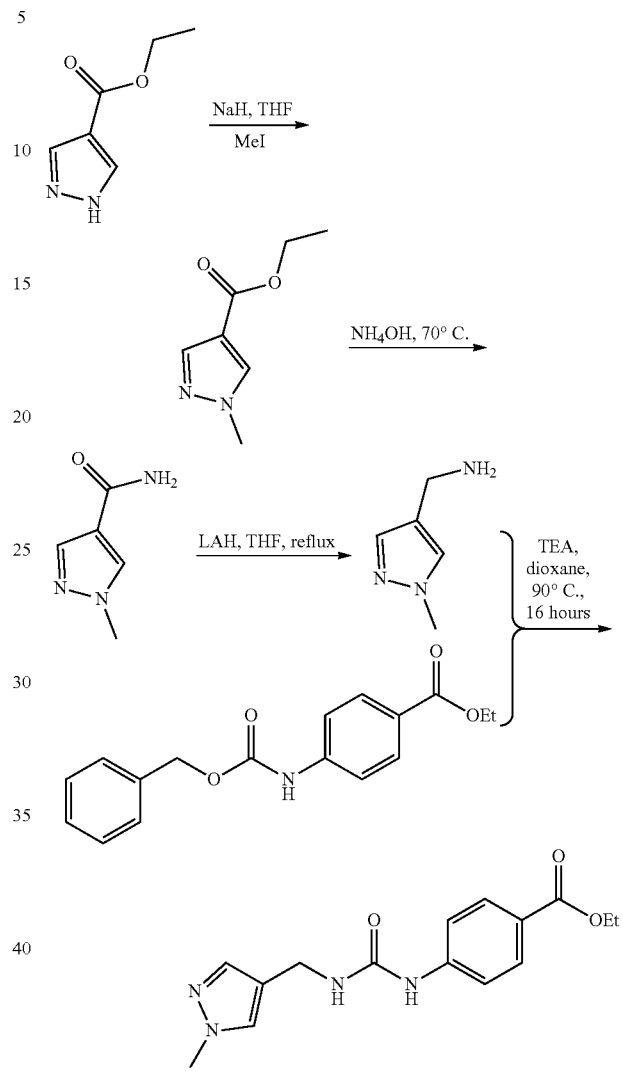

Step 1: The solution of ethyl 1H-pyrazole-4-carboxylate (2.5 g, 17.9 mmol), and iodomethane (3.1 g, 21.5 mmol) in DMF (10 mL) was added K$_2$CO$_3$ (5.0 g, 35.8 mmol) and then the reaction mixture was stirred at room temperature for 16 hrs. Water (50 mL) was added to the mixture and then extracted by EA (50 mL×2). The organic layer was washed with brine (40 mL), dried over Na$_2$SO$_4$, and concentrated under reduced pressure. The residue was purified by silica gel column (PE/EA=8/1) to give the ethyl 1-methyl-1H-pyrazole-4-carboxylate (214 mg, yield: 85%) as a colorless oil. $^1$H NMR (300 MHz, DMSO-$d_6$): δ=8.28 (s, 1H), 7.82 (s, 1H), 4.26 (q, J=6.9 Hz, 2H), 3.87 (s, 3H), 1.25 (t, J=6.9 Hz, 3H). MS: m/z 155.3 (M+H$^+$).

Step 2: The solution of ethyl 1-methyl-1H-pyrazole-4-carboxylate (0.52 g, 3.4 mmol) in EtOH (10 mL) was added NH$_4$OH (20 mL) and the reaction mixture was stirred at 80° C. for 16 hrs. Then the reaction mixture was concentrated under reduced pressure to give the 1-methyl-1H-pyrazole-4-carboxamide (0.61 g, yield: quantitative) as a colorless oil. MS: m/z 127.3 (M+H$^+$).

Step 3: The solution of 1-methyl-1H-pyrazole-4-carboxamide (0.61 g, 3.4 mmol) in THF (10 mL) was added LAH (0.40 g, 10.2 mmol) and the mixture was stirred at 70° C. for 2 hrs. H$_2$O (0.5 mL), 15% NaOH (0.5 mL) and H$_2$O (1.5 mL) were then added dropwise at 0° C. The mixture was stirred at room temperature for another 20 min, dried over MgSO$_4$ and filtered. The filtrate was concentrated under reduced pressure to give the C-(1-methyl-1H-pyrazol-4-yl)-methylamine (0.58 g, yield: quantitative) as colorless oil.

Step 4: This step was similar to the procedure of ethyl 4-(3-((3,5-dimethylisoxazol-4-yl)methyl)ureido)benzoate. $^1$H NMR (400 MHz, DMSO-d$_6$): δ=8.86 (s, 1H), 7.82 (d, J=8.4 Hz, 2H), 7.59 (s, 1H), 7.51 (d, J=8.0 Hz, 2H), 7.34 (s, 1H), 6.51 (s, 1H), 4.26 (q, J=6.8 Hz, 2H), 4.11 (d, J=4.8 Hz, 2H), 3.78 (s, 3H), 1.29 (t, J=6.8 Hz, 3H). MS: m/z 303.0 (M+H$^+$).

Example 126: Synthesis of N-(3-Chloro-phenyl)-4-[3-(1H-pyrazol-4-ylmethyl)-ureido]-benzamide

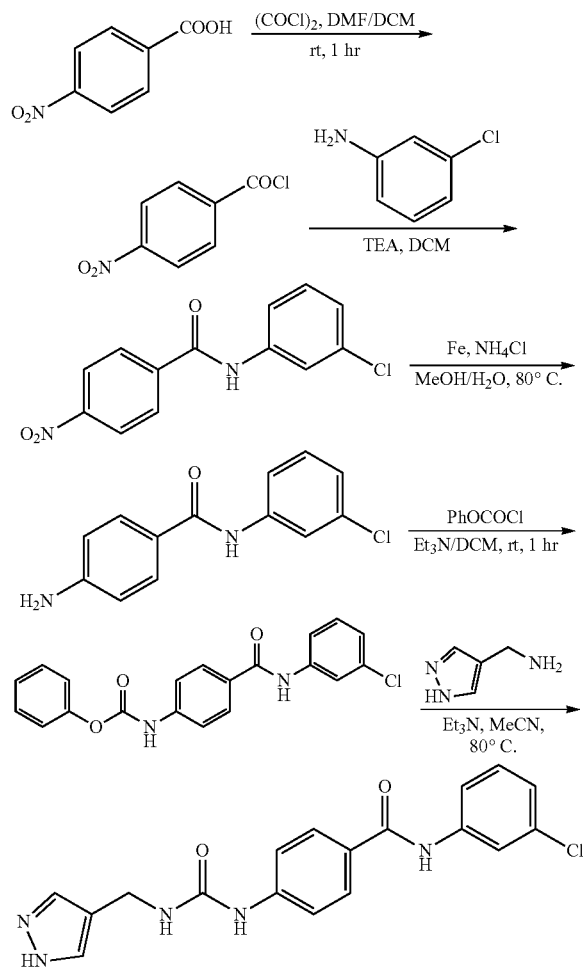

Step 1: To a solution of 4-nitro-benzoic acid (2.1 g, 12.6 mmol) in DCM (20 mL) was added (COCl)$_2$ (8.0 g, 62.9 mmol) at 0° C. then one drop of DMF was added. The reaction mixture was stirred for 1 hr at room temperature. The white solid was got by filtration and washed by DCM (10 mL) to get the 4-nitro-benzoyl chloride (3.0 g, yield: quantitative) as a white solid.

Step 2: The solution of 4-nitro-benzoyl chloride (3.0 g, 12.6 mmol) and TEA (2.5 g, 25.2 mmol) in DCM (10 mL) was added 3-chloro-phenylamine (1.6 g, 12.6 mmol) and the reaction mixture was stirred at room temperature for 2 hrs. The reaction was concentrated under reduced pressure and the residue was purified by silica gel column (PE/EA=5/1) to give the N-(3-chloro-phenyl)-4-nitro-benzamide (1.8 g, yield: 51%) as a yellow solid.

Step 3: To a solution of N-(3-chloro-phenyl)-4-nitro-benzamide (1.8 g, 6.5 mmol) and Fe (3.6 g, 65.0 mmol) in MeOH (10 mL) was added a solution of NH$_4$Cl (7.0 g, 130.0 mmol) in water (10 mL). The reaction was stirred at 80° C. for 4 hrs. Then the reaction mixture was filtered. The filtrate was added to water (10 ml) and then extracted by EA (20 mL×2). The organic layer was washed with brine (40 mL), dried over Na$_2$SO$_4$, and concentrated under reduced pressure to give the 4-amino-N-(3-chloro-phenyl)-benzamide (0.9 g, yield: 56%) as a yellow solid. MS: m/z 247.4 (M+H$^+$)

Step 4: The solution of 4-amino-N-(3-chloro-phenyl)-benzamide (501 mg, 2.0 mmol) and TEA (404 mg, 4.0 mmol) in DCM (20 mL) was degassed and purged with N$_2$. The mixture was stirred at 0° C. for a while. Then phenyl chroloformate (376 mg, 2.4 mmol) was added and the mixture was stirred at room temperature for 1 hr. After that, the solution was concentrated under reduced pressure. The residue was washed by PE/EA=2/1 (10 mL) to give the [4-(3-chloro-phenylcarbamoyl)-phenyl]-carbamic acid phenyl ester (130 mg, yield: 18%) as a white solid.

Step 5: To a solution of [4-(3-chloro-phenylcarbamoyl)-phenyl]-carbamic acid phenyl ester (130 mg, 0.35 mmol) and TEA (71 mg, 0.70 mmol) in MeCN (20 mL) was added C-(1H-pyrazol-4-yl)-methylamine (34 mg, 0.35 mmol). The mixture was refluxed at 80° C. for overnight. After that, the solution was concentrated under reduced pressure. The residue was purified by prep-HPLC to give N-(3-chloro-phenyl)-4-[3-(1H-pyrazol-4-ylmethyl)-ureido]-benzamide (35 mg, yield: 27%) as a white solid. $^1$H NMR (300 MHz, DMSO-d6): δ=12.67 (s, 1H), 10.17 (s, 1H), 8.79 (s, 1H), 7.96 (s, 1H), 7.88 (d, J=3.0 Hz, 2H), 7.71 (d, J=8.7 Hz, 1H), 7.58 (d, J=8.7 Hz, 4H), 7.35 (t, J=8.7 Hz, 1H), 7.11 (d, J=7.8 Hz, 1H), 6.47 (t, J=3.9 Hz, 1H), 4.17 (d, J=5.7 Hz, 2H). MS: m/z 369.9 (M+H$^+$).

Example 127: Synthesis of 4-(3-((1H-pyrazol-4-yl)methyl)ureido)-N-(2-methoxyphenyl)benzamide

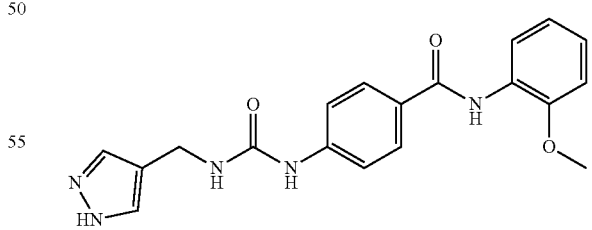

The title compound was prepared as described in example 4-(3-((1H-pyrazol-4-yl)methyl)ureido)-N-(3-chlorophenyl)benzamide. $^1$H NMR (400 MHz, DMSO-d6): δ=12.64 (s, 1H), 9.17 (s, 1H), 8.78 (s, 1H), 7.87-7.81 (m, 3H), 7.53-7.51 (m, 4H), 7.17-7.14 (m, 1H), 7.09 (d, J=8.4 Hz, 1H), 6.96 (t, J=7.6 Hz, 1H), 6.46 (t, J=6.0 Hz, 1H), 4.17 (d, J=5.2 Hz, 2H), 3.32 (s, 3H). MS: m/z 365.9 (M+H$^+$).

Example 128: Synthesis of 4-(3-((1H-pyrazol-4-yl)methyl)ureido)-N-(2-chlorophenyl)benzamide

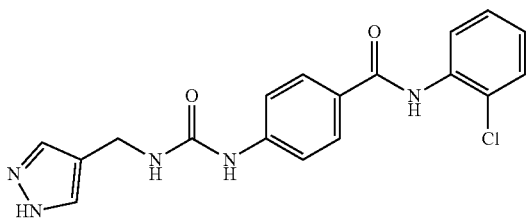 [SMILES: O=C(NCc1cn[nH]c1)Nc1ccc(C(=O)Nc2ccccc2Cl)cc1]

The title compound was prepared as described in example 4-(3-((1H-pyrazol-4-yl)methyl)ureido)-N-(3-chlorophenyl)benzamide. $^1$H NMR (300 MHz, DMSO-d$_6$): δ=12.62 (s, 1H), 9.78 (s, 1H), 8.78 (s, 1H), 7.91 (d, J=9.3 Hz, 2H), 7.62-7.51 (m, 6H), 7.37 (t, J=9.0 Hz, 1H), 7.26 (t, J=9.3 Hz, 1H), 6.47 (t, J=6.9 Hz, 1H), 4.17 (d, J=5.4 Hz, 2H). MS: m/z 369.9 (M+H$^+$).

Example 129: Synthesis of 4-(3-((1H-pyrazol-4-yl)methyl)ureido)-N-(4-methoxyphenyl)benzamide

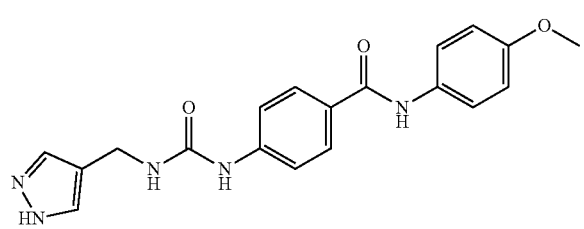 [SMILES: COc1ccc(NC(=O)c2ccc(NC(=O)NCc3cn[nH]c3)cc2)cc1]

The title compound was prepared as described in example 4-(3-((1H-pyrazol-4-yl)methyl)ureido)-N-(3-chlorophenyl)benzamide. $^1$H NMR (400 MHz, DMSO-d$_6$): δ=12.64 (s, 1H), 9.89 (s, 1H), 8.77 (s, 1H), 7.85 (d, J=8.4 Hz, 2H), 7.67-7.50 (m, 6H), 6.90 (d, J=8.8 Hz, 2H), 6.47 (t, J=4.8 Hz, 1H), 7.08 (d, J=4.8 Hz, 2H), 3.74 (s, 3H). MS: m/z 364.0 (M−H$^+$).

Example 130: Synthesis of 4-(3-((1H-pyrazol-4-yl)methyl)ureido)-N-(4-chlorophenyl)benzamide

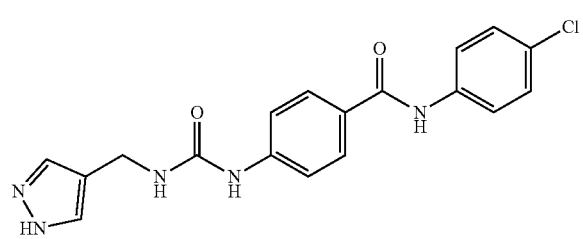 [SMILES: O=C(NCc1cn[nH]c1)Nc1ccc(C(=O)Nc2ccc(Cl)cc2)cc1]

The title compound was prepared as described in example 4-(3-((1H-pyrazol-4-yl)methyl)ureido)-N-(3-chlorophenyl)benzamide. $^1$H NMR (300 MHz, DMSO-d$_6$): δ=12.62 (s, 1H), 10.13 (s, 1H), 8.78 (s, 1H), 7.87-7.78 (m, 4H), 7.54 (d, J=8.7 Hz, 4H), 7.39 (d, J=8.7 Hz, 2H), 6.47 (t, J=6.9 Hz, 1H), 4.16 (d, J=4.8 Hz, 2H). MS: m/z 370.0 (M+H$^+$).

Example 131: Synthesis of 4-(3-((1H-pyrazol-4-yl)methyl)ureido)-N-(3-methoxyphenyl)benzamide

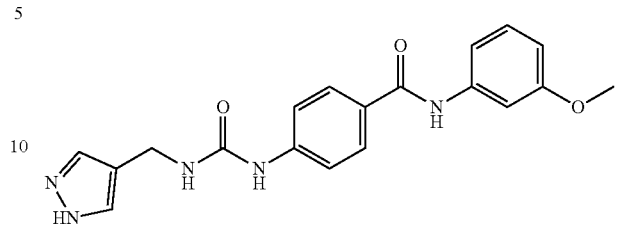

The title compound was prepared as described in example 4-(3-((1H-pyrazol-4-yl)methyl)ureido)-N-(3-chlorophenyl)benzamide. $^1$H NMR (400 MHz, DMSO-d$_6$): δ=12.61 (s, 1H), 9.98 (s, 1H), 8.86 (s, 1H), 7.86 (d, J=8.8 Hz, 2H), 7.53-7.51 (m, 4H), 7.46 (t, J=2.4 Hz, 1H), 7.36 (d, J=8.0 Hz, 1H), 7.22 (t, J=8.0 Hz, 1H), 6.67-6.64 (m, 1H), 6.53 (t, J=5.2 Hz, 1H), 4.17 (d, J=4.8 Hz, 2H), 3.75 (s, 3H). MS: m/z 366.0 (M+H$^+$).

Example 132: Synthesis of Ethyl 4-(3-(oxazol-5-ylmethyl)ureido)benzoate

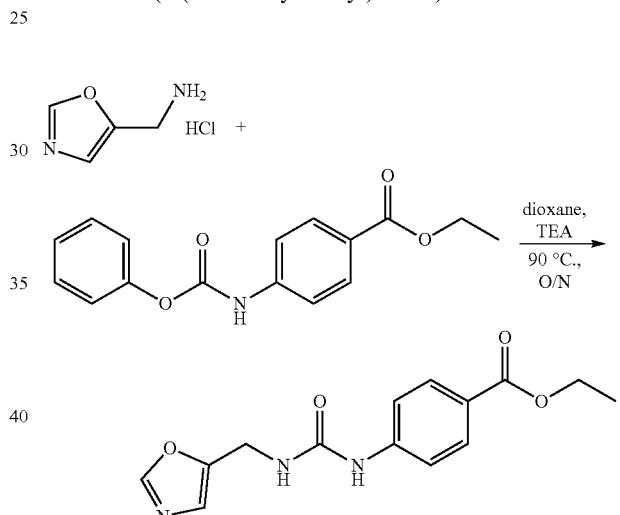

Step 1: To a solution of C-oxazol-5-yl-methylamine hydrochloride (47.2 mg, 0.35 mmol) in dioxane (20 mL) was added 4-phenoxycarbonylamino-benzoic acid ethyl ester (100 mg, 0.35 mmol) and TEA (70.9 mg, 0.7 mmol). After stirred at 90° C. overnight, the reaction mixture was concentrated in vacuum. The residue was purified by pre-HPLC to afford ethyl 4-(3-(oxazol-5-ylmethyl)ureido)benzoate (22 mg, 22%) as a white solid. $^1$H NMR (400 MHz, CD$_3$OD): δ=8.18 (s, 1H), 7.94 (d, J=8.8 Hz, 2H), 7.52 (d, J=8.8 Hz, 2H), 7.07 (s, 1H), 4.51 (s, 2H), 4.35 (q, J=7.2 Hz, 2H), 1.40 (t, J=7.2 Hz, 3H). MS: m/z 290.0 (M+H)+.

Example 133: Synthesis of Ethyl 4-(3-((3-amino-1H-pyrazol-4-yl)methyl)ureido)benzoate

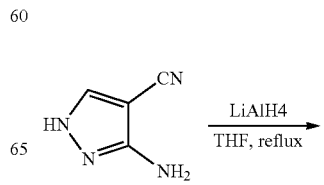

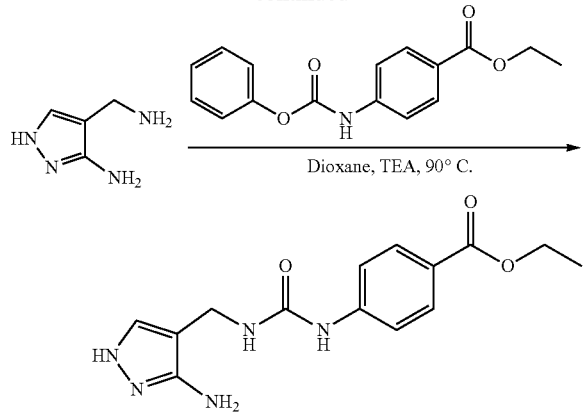

Step 1: To a solution of 3-amino-1H-pyrazole-4-carbonitrile (300 mg, 2.78 mmol) in THF (100 mL) was added LiAlH₄ (316 mg, 8.34 mmol). After stirred at reflux overnight, the reaction mixture was quenched by H₂O (2 mL). And the mixture was dried over anhydrous Na₂SO₄ and filtered. The filtrate was evaporated in vacuum. The residue was used for next step without further purification.

Step 2: To a solution of 4-aminomethyl-1H-pyrazol-3-ylamine (78.5 mg, 0.7 mmol) in dioxane (30 mL) was added 4-phenoxycarbonylamino-benzoic acid ethyl ester (200 mg, 0.7 mmol) and TEA (142 mg, 1.4 mmol). After stirred at 90° C. overnight, the reaction mixture was concentrated in vacuum. The residue was purified by pre-HPLC to afford ethyl 4-(3-((3-amino-1H-pyrazol-4-yl)methyl)ureido)benzoate (28 mg, 13%) as a yellow solid. ¹H NMR (400 MHz, CD₃OD): δ=7.91 (d, J=8.8 Hz, 2H), 7.76 (s, 1H), 7.50 (d, J=8.8 Hz, 2H), 4.31 (q, J=7.2 Hz, 2H), 4.19 (s, 2H), 1.37 (t, J=7.2 Hz, 3H). MS: m/z 304.1 (M+H)+.

Example 134: Synthesis of Ethyl 4-(3-((1H-imidazol-5-yl)methyl)ureido)benzoate

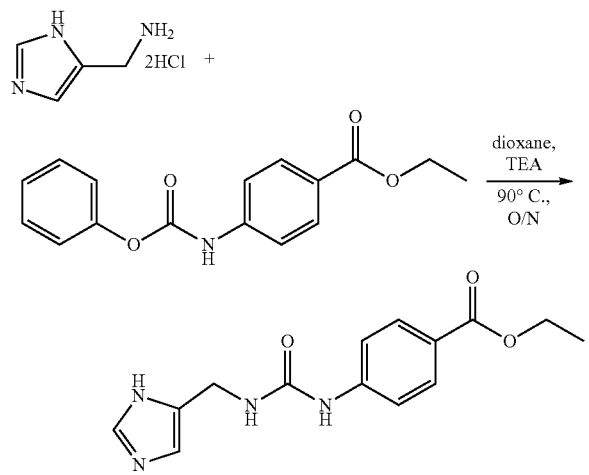

Step 1: To a solution of C-(3H-imidazol-4-yl)-methylamine hydrochloride (119 mg, 0.7 mmol) in dioxane (30 mL) was added 4-phenoxycarbonylamino-benzoic acid ethyl ester (200 mg, 0.7 mmol) and TEA (213 mg, 2.1 mmol). After stirred at 90° C. overnight, the reaction mixture was concentrated in vacuum. The residue was purified by pre-HPLC to afford ethyl 4-(3-((1H-imidazol-5-yl)methyl)ureido)benzoate (35 mg, 17%) as a white solid. ¹H NMR (400 MHz, CD₃OD): δ=8.81 (d, J=1.2 Hz, 1H), 7.92 (d, J=8.8 Hz, 2H), 7.53 (d, J=8.8 Hz, 2H), 7.46 (s, 1H), 4.48 (s, 2H), 4.33 (q, J=7.2 Hz, 2H), 1.38 (t, J=7.2 Hz, 3H). MS: m/z 289.1 (M+H)+.

Example 135: Synthesis of Ethyl 4-(3-((1-methyl-1H-pyrazol-5-yl)methyl)ureido)benzoate

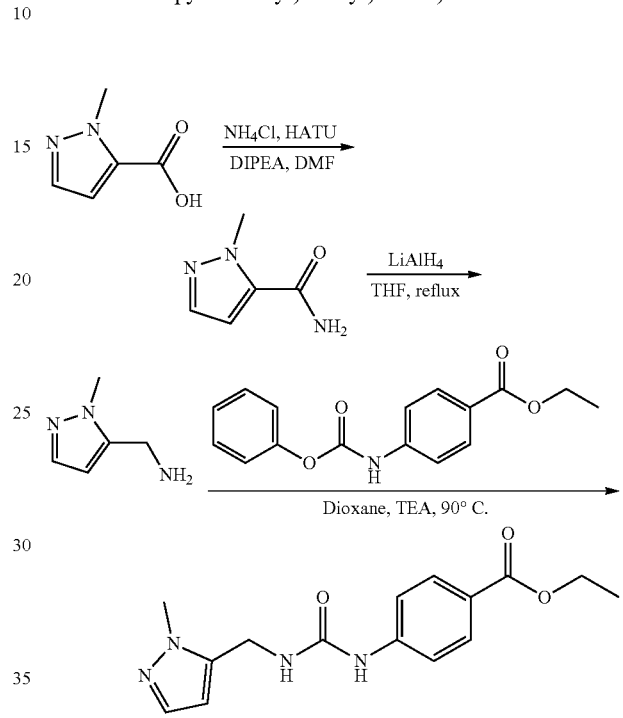

Step 1: To a solution of 2-methyl-2H-pyrazole-3-carboxylic acid (500 mg, 3.97 mmol) in DMF (20 mL) was added NH₄Cl (318 mg, 6.0 mmol), HATU (1.8 g, 4.8 mmol), and DIPEA (1.03 g, 8 mmol). After stirred at room temperature overnight, the reaction mixture was evaporated in vacuum. The residue was partitioned in a mixture of H₂O (30 mL) and EA (30 mL). Organic phase was collected, dried over anhydrous Na₂SO₄, and evaporated in vacuum. The residue was used for next step without further purification.

Step 2: To a solution of 2-methyl-2H-pyrazole-3-carboxylic acid amide (crude, 3.97 mmol) in THF (50 mL) was added LiAlH₄ (453 mg, 11.9 mmol). After stirred at reflux overnight, the reaction mixture was quenched by H₂O (2 mL). And the mixture was then dried over anhydrous Na₂SO₄ and filtered. The filtrate was evaporated in vacuum. The residue was used for next step without further purification.

Step 3: To a solution of C-(2-methyl-2H-pyrazol-3-yl)-methylamine (78 mg, 0.7 mmol) in dioxane (30 mL) was added 4-phenoxycarbonylamino-benzoic acid ethyl ester (200 mg, 0.7 mmol) and TEA (213 mg, 2.1 mmol). After stirred at 90° C. overnight, the reaction mixture was concentrated in vacuum. The residue was purified by pre-HPLC to afford ethyl 4-(3-((1-methyl-1H-pyrazol-5-yl)methyl)ureido)benzoate (45 mg, 21%) as a white solid. ¹H NMR (400 MHz, CD₃OD): δ=7.91 (d, J=8.8 Hz, 2H), 7.49 (d, J=8.4 Hz, 2H), 7.36 (d, J=1.6 Hz, 1H), 6.24 (d, J=1.6 Hz, 1H), 4.47 (s, 2H), 4.32 (q, J=7.2 Hz, 2H), 3.87 (s, 3H), 1.37 (t, J=7.2 Hz, 3H). MS: m/z 303.0 (M+H)+.

Example 136: Synthesis of Ethyl 4-(3-((1H-imidazol-4-yl)methyl)ureido)benzoate

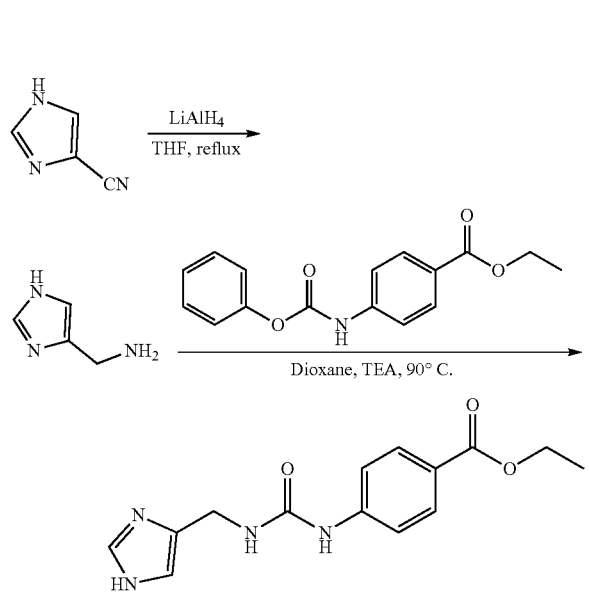

Step 1: To a solution of 1H-imidazole-4-carbonitrile (300 mg, 3.2 mmol) in THF (50 mL) was added LiAlH₄ (365 mg, 9.6 mmol). After stirred at reflux overnight, the reaction mixture was quenched by H₂O (2 mL). And the mixture was dried over anhydrous Na₂SO₄ and filtered. The filtrate was evaporated in vacuum. The residue was used for next step without further purification.

Step 2: To a solution of C-(1H-imidazol-4-yl)-methylamine (81.6 mg, 0.84 mmol) in dioxane (30 mL) was added 4-phenoxycarbonylamino-benzoic acid ethyl ester (200 mg, 0.7 mmol) and TEA (213 mg, 2.1 mmol). After stirred at 90° C. overnight, the reaction mixture was concentrated in vacuum. The residue was purified by pre-HPLC to afford ethyl 4-(3-((1H-imidazol-4-yl)methyl)ureido)benzoate (30 mg, 15%) as a white solid. $^1$H NMR (400 MHz, DMSO-d₆): δ=11.93 (s, 1H), 8.98 (s, 1H), 7.83 (d, J=8.8 Hz, 2H), 7.59 (s, 1H), 7.51 (d, J=8.4 Hz, 2H), 6.95 (s, 1H), 6.51 (t, J=4.8 Hz, 1H), 4.26 (q, J=7.2 Hz, 2H), 4.19 (d, J=4.8 Hz, 2H), 1.29 (t, J=7.2 Hz, 3H). MS: m/z 289.0 (M+H)⁺.

Example 137: Synthesis of Ethyl 4-(3-((1H-pyrazol-3-Yl)methyl)ureido)benzoate

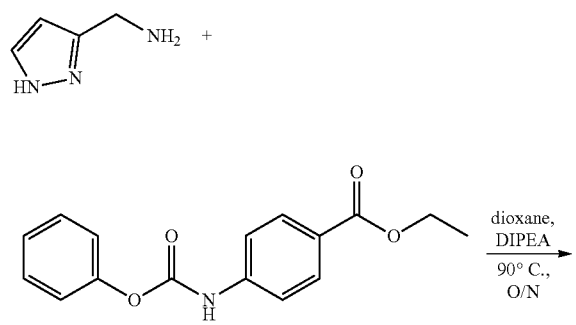

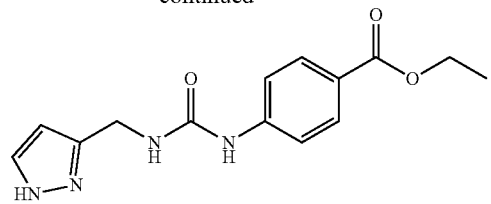

Step 1: To a solution of C-(1H-pyrazol-3-yl)-methylamine (81.5 mg, 0.84 mmol) in dioxane (30 mL) was added 4-phenoxycarbonylamino-benzoic acid ethyl ester (200 mg, 0.7 mmol) and DIPEA (181 mg, 1.4 mmol). After stirred at 90° C. overnight, the reaction mixture was concentrated in vacuum. The residue was purified by pre-HPLC to afford ethyl 4-(3-((1H-pyrazol-3-yl)methyl)ureido)benzoate (25 mg, 12%) as a white solid. $^1$H NMR (400 MHz, CD₃OD): δ=7.91 (d, J=8.8 Hz, 2H), 7.57 (s, 1H), 7.49 (d, J=8.4 Hz, 2H), 6.29 (s, 1H), 4.43 (s, 2H), 4.32 (q, J=7.2 Hz, 2H), 1.37 (t, J=7.2 Hz, 3H). MS: m/z 289.0 (M+H)⁺.

Example 138: Synthesis of Ethyl 4-(3-((3-methyl-1H-pyrazol-4-Yl)methyl)ureido)benzoate

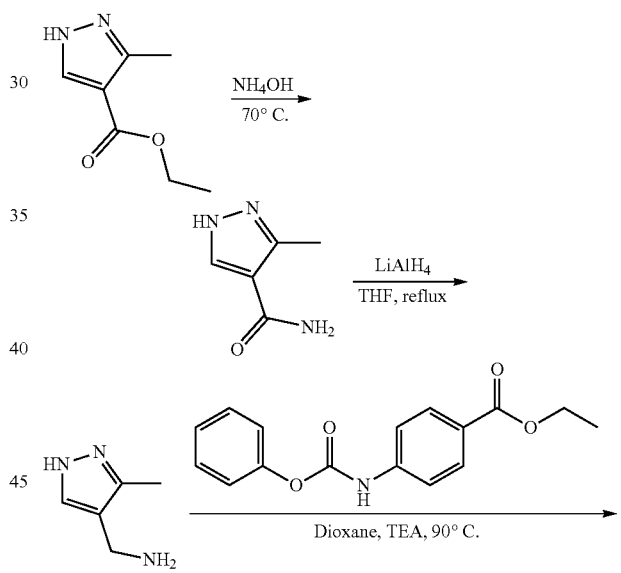

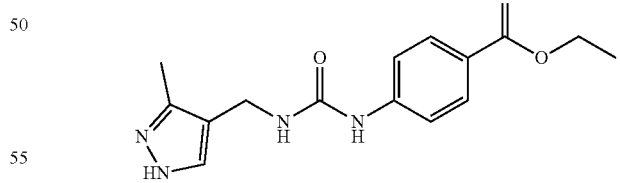

Step 1: 3-Methyl-1H-pyrazole-4-carboxylic acid ethyl ester (500 mg, 3.24 mmol) was dissolved in NH₄OH (30 mL). After stirred at 70° C. overnight, the mixture was evaporated in vacuum to afford crude 3-methyl-1H-pyrazole-4-carboxylic acid amide as a yellow solid which was used for next step without further purification.

Step 2: To a solution of 3-methyl-1H-pyrazole-4-carboxylic acid amide (crude, 3.24 mmol) in THF (30 mL) was added LiAlH₄ (492 mg, 13 mmol). After stirred at reflux overnight, the reaction was quenched by H₂O (2 mL). Then the mixture was dried over anhydrous Na₂SO₄ and filtered. The filtrate was evaporated in vacuum to afford C-(3-methyl-1H-pyrazol-4-yl)-methylamine as a crude product which was used for next step without further purification.

Step 3: To a solution of C-(3-methyl-1H-pyrazol-4-yl)-methylamine (93.3 mg, 0.84 mmol) in dioxane (20 mL) was added 4-phenoxycarbonylamino-benzoic acid ethyl ester (200 mg, 0.7 mmol) and DIPEA (181 mg, 1.4 mmol). After stirred at 90° C. overnight, the reaction mixture was concentrated in vacuum. The residue was purified by pre-HPLC to afford ethyl 4-(3-((3-methyl-1H-pyrazol-4-yl)methyl)ureido)benzoate (27 mg, 13%) as a white solid. ¹H NMR (400 MHz, DMSO-d₆): δ=12.3 (s, 1H), 8.84 (s, 1H), 7.82 (d, J=8.8 Hz, 2H), 7.50 (d, J=8.8 Hz, 2H), 7.41 (s, 1H), 6.42 (s, 1H), 4.26 (q, J=7.2 Hz, 2H), 4.09 (d, J=4.8 Hz, 2H), 2.18 (s, 3H), 1.29 (t, J=7.2 Hz, 3H). MS: m/z 303.0 (M+H)⁺.

Example 139: Synthesis of Ethyl 4-(3-((1-(4-methoxybenzyl)-1H-1,2,3-triazol-4-yl)methyl)ureido)benzoate

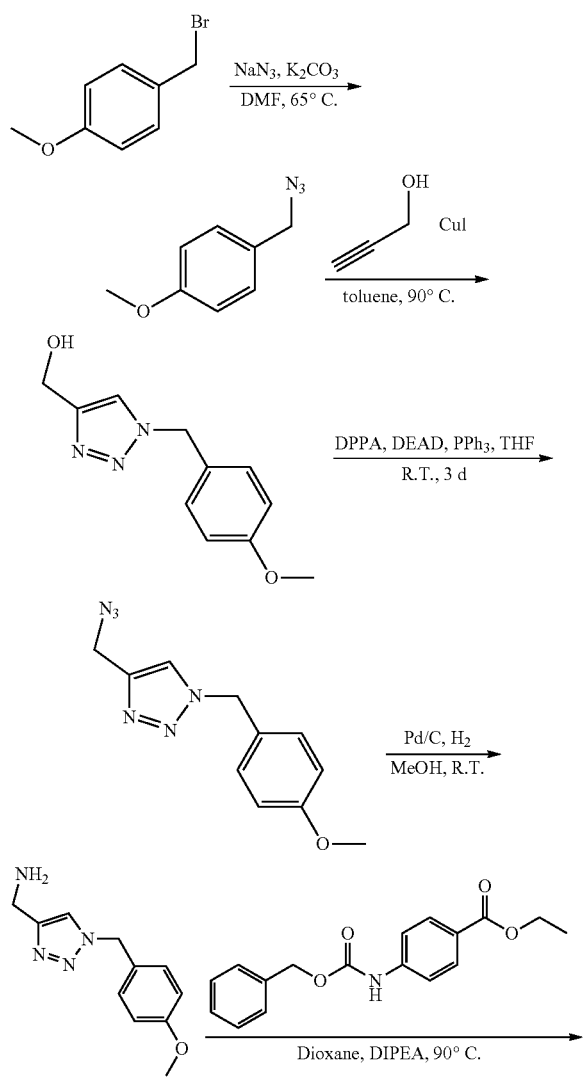

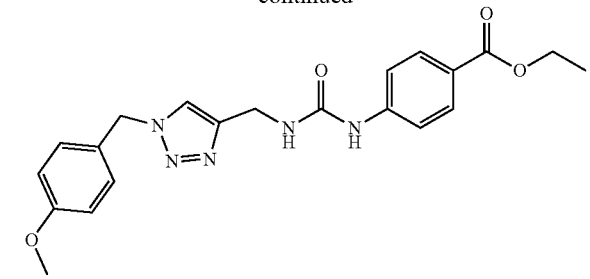

Step 1: To a solution of 1-bromomethyl-4-methoxy-benzene (2 g, 10 mmol) in DMF (20 mL) was added NaN₃ (720 mg, 11 mmol) and K₂CO₃ (2.07 g, 15 mmol). After stirred at 65° C. overnight, the mixture was evaporated in vacuum. The residue was purified by silica gel column chromatograph (PE/EA=5/1) to afford 1-azidomethyl-4-methoxy-benzene (1.6 g, 98%) as a colorless oil.

Step 2: To a solution of 1-azidomethyl-4-methoxy-benzene (1.6 g, 10 mmol) in toluene (50 mL) was added prop-2-yn-1-ol (616 mg, 11 mmol) and CuI (95 mg, 0.5 mmol). After stirred at 90° C. overnight, the reaction mixture was filtered. The filtrate was evaporated in vacuum. The residue was purified by flash column (ACN in water, 10% to 95%) to afford [1-(4-methoxy-benzyl)-1H-[1,2,3]triazol-4-yl]-methanol (1.3 g, 70%) as a yellow solid. ¹H NMR (400 MHz, DMSO-d₆) δ=7.95 (s, 1H), 7.29 (d, J=8.8 Hz, 2H), 6.92 (d, J=8.4 Hz, 2H), 5.47 (s, 2H), 5.15 (s, 1H), 4.48 (s, 2H), 3.73 (s, 3H).

Step 3: To a solution of [1-(4-methoxy-benzyl)-1H-[1,2,3]triazol-4-yl]-methanol (500 mg, 2.64 mmol) in a mixture of toluene (9 mL) and DMF (1 mL) was added DPPA (1.45 g, 5.28 mmol) and DBU (803 mg, 5.28 mmol). Then the reaction mixture was heated to 50° C. for 36 hrs. Then the mixture was diluted in H₂O (50 mL), and extracted by EA (50 mL×3). Organic phase was combined, dried over anhydrous Na₂SO₄, and evaporated in vacuum. The residue was purified by silica gel column chromatograph (PE:EA=2:1) to afford 4-azidomethyl-1-(4-methoxy-benzyl)-1H-[1,2,3]triazole (401 mg, 72%). ¹H NMR (400 MHz, DMSO-d₆): δ=8.16 (s, 1H), 7.29 (d, J=8.8 Hz, 2H), 6.92 (d, J=8.8 Hz, 2H), 5.53 (s, 2H), 4.48 (s, 2H), 3.74 (s, 3H).

Step 4: To a solution of 4-azidomethyl-1-(4-methoxy-benzyl)-1H-[1,2,3]triazole (400 mg, 1.64 mmol) in MeOH (20 mL) was added 10% Pd/C (174 mg, 0.16 mmol). After stirred at room temperature overnight under balloon hydrogen atmosphere, the reaction mixture was filtered. The filtrate was evaporated in vacuum to afford C-[1-(4-methoxy-benzyl)-1H-[1,2,3]triazol-4-yl]-methylamine as a crude product which was used for next step without further purification.

Step 5: To a solution of C-[1-(4-methoxy-benzyl)-1H-[1,2,3]triazol-4-yl]-methylamine (358 mg, 1.64 mmol) in dioxane (20 mL) was added 4-phenoxycarbonylamino-benzoic acid ethyl ester (468 mg, 1.64 mmol) and DIPEA (424 mg, 3.28 mmol). After stirred at 90° C. overnight, the reaction mixture was concentrated in vacuum. The residue was purified by silica gel column chromatograph (DCM/MeOH=10/1) to afford ethyl 4-(3-((1-(4-methoxybenzyl)-1H-1,2,3-triazol-4-yl)methyl)ureido)benzoate (350 mg, 52%) as a white solid. ¹H NMR (400 MHz, DMSO-d₆): δ=8.99 (s, 1H), 7.96 (s, 1H), 7.82 (d, J=8.8 Hz, 2H), 7.51 (d, J=8.4 Hz, 2H), 7.29 (d, J=8.4 Hz, 2H), 6.92 (d, J=8.4 Hz, 2H), 6.74 (s, 1H), 5.48 (s, 2H), 4.32 (d, J=5.2 Hz, 2H), 4.25 (q, J=7.2 Hz, 2H), 3.73 (s, 3H), 1.29 (t, J=7.2 Hz, 3H). MS: m/z 410.0 (M+H)⁺.

Example 140: Synthesis of Ethyl 4-(3-((1H-1,2,3-triazol-4-yl)methyl)ureido)benzoate

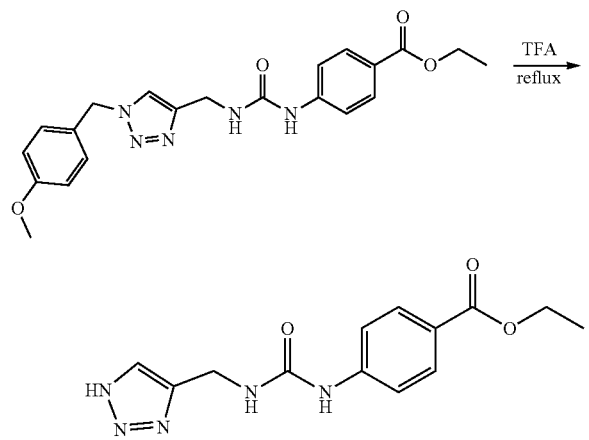 [SMILES: CCOC(=O)c1ccc(NC(=O)NCc2cn(Cc3ccc(OC)cc3)nn2)cc1 ; CCOC(=O)c1ccc(NC(=O)NCc2c[nH]nn2)cc1]

Ethyl 4-(3-((1-(4-methoxybenzyl)-1H-1,2,3-triazol-4-yl)methyl)ureido)benzoate (100 mg, 0.24 mmol) was dissolved in TFA (20 mL) and heated to reflux overnight. Then the solvent was removed in vacuum. The residue was purified by pre-HPLC to afford ethyl 4-(3-((1H-1,2,3-triazol-4-yl)methyl)ureido)benzoate (42 mg, 60%) as a white solid. ¹H NMR (400 MHz, DMSO-d₆): δ=15.01 (s, 0.35H), 14.71 (s, 0.65H), 9.01 (s, 1H), 7.95 (s, 0.35H), 7.83 (d, J=8.8 Hz, 2H), 7.65 (s, 0.65H), 7.52 (d, J=8.8 Hz, 2H), 6.74 (t, J=4.8 Hz, 1H), 4.38 (d, J=5.6 Hz, 2H), 4.26 (q, J=6.8 Hz, 2H), 1.30 (t, J=6.8 Hz, 3H). MS: m/z 290.0 (M+H)⁺.

Example 141: Synthesis of Ethyl 4-(3-((1-methyl-1H-imidazol-5-yl)methyl)ureido)benzoate

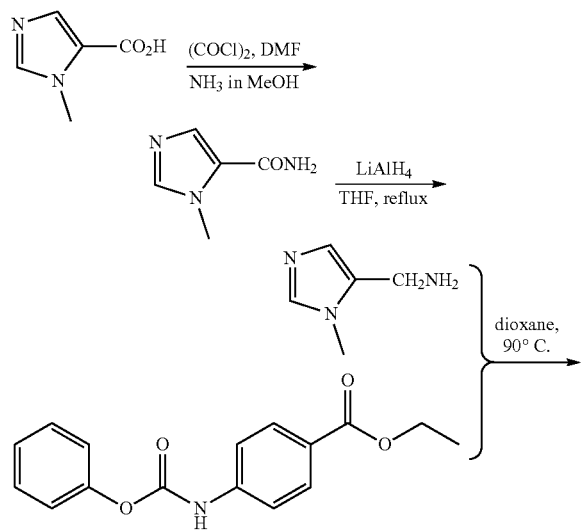

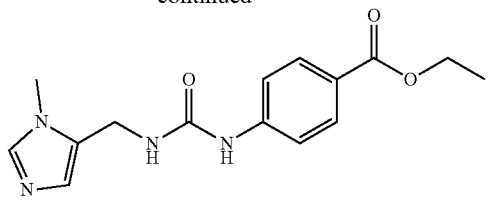

Step 1: To a solution of 3-methyl-3H-imidazole-4-carboxylic acid (200 mg, 1.58 mmol) in DCM (10 mL) was added (COCl)₂ (400 mg, 3.16 mmol) and DMF (2 drops). After stirred at room temperature overnight, the reaction mixture was evaporated in vacuum. The residue was then dissolved in 7 N NH₃ in MeOH (10 mL). After stirred at room temperature overnight, the reaction mixture was evaporated in vacuum to afford 3-methyl-3H-imidazole-4-carboxylic acid amide as a crude product which was used for next step without further purification.

Step 2: To a solution of 3-methyl-3H-imidazole-4-carboxylic acid amide (188 mg, 1.5 mmol) in THF (20 mL) was added LiAlH₄ (228 mg, 6 mmol). After stirred at reflux overnight, the reaction was quenched by H₂O (2 mL). Then the mixture was dried over anhydrous Na₂SO₄ and filtered. The filtrate was evaporated in vacuum to afford C-(3-methyl-3H-imidazol-4-yl)-methylamine as a crude product which was used for next step without further purification.

Step 3: To a solution of C-(3-methyl-3H-imidazol-4-yl)-methylamine (89 mg, 0.80 mmol) in dioxane (10 mL) was added 4-phenoxycarbonylamino-benzoic acid ethyl ester (150 mg, 0.53 mmol) and DIPEA (137 mg, 1.06 mmol). After stirred at 90° C. overnight, the reaction mixture was concentrated in vacuum. The residue was purified by pre-HPLC to afford ethyl 4-(3-((1-methyl-1H-imidazol-5-yl)methyl)ureido)benzoate (20 mg, 13%) as a white solid. ¹H NMR (400 MHz, CD₃OD): δ=7.91 (d, J=8.4 Hz, 2H), 7.64 (s, 1H), 7.49 (d, J=8.4 Hz, 2H), 6.95 (s, 1H), 4.44 (s, 2H), 4.32 (q, J=7.2 Hz, 2H), 3.71 (s, 3H), 1.37 (t, J=7.2 Hz, 3H). MS: m/z 303.0 (M+H)⁺.

Example 142: Synthesis of Ethyl 4-(3-((1-methyl-1H-imidazol-4-yl)methyl)ureido)benzoate

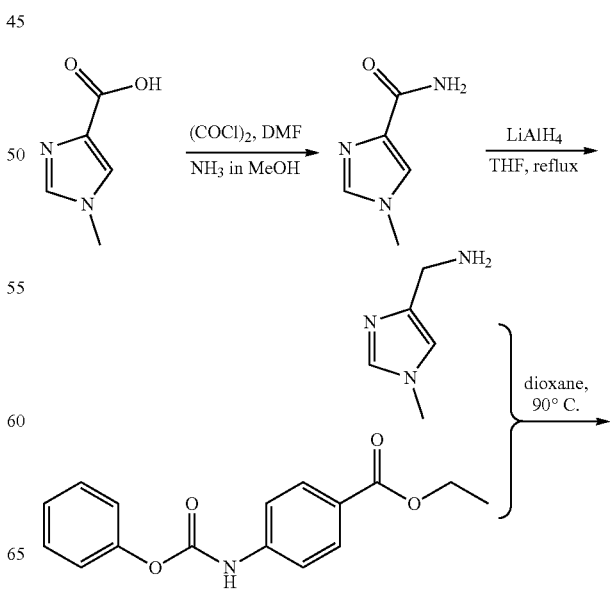

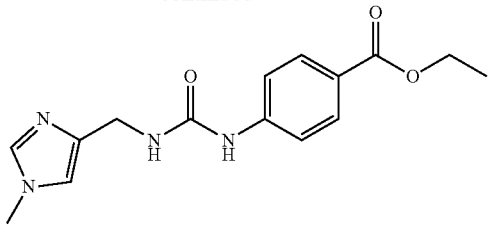

Step 1: To a solution of 1-methyl-1H-imidazole-4-carboxylic acid (1 g, 7.94 mmol) in DCM (10 mL) was added (COCl)$_2$ (2 g, 15.9 mmol) and DMF (2 drops). After stirred at room temperature for 5 hrs, the reaction mixture was evaporated in vacuum. The residue was then dissolved in 7 N NH$_3$ in MeOH (10 mL). After stirred at room temperature overnight, the reaction mixture was evaporated in vacuum. The residue was purified by flash column chromatograph (ACN in water, 5% to 60%) to afford 1-methyl-1H-imidazole-4-carboxylic acid amide (480 mg, 48%) as a white solid. $^1$H NMR (400 MHz, DMSO-d$_6$): δ=7.62 (d, J=11.6 Hz, 2H), 7.24 (s, 1H), 7.03 (s, 1H), 3.68 (s, 3H).

Step 2: To a solution of 1-methyl-1H-imidazole-4-carboxylic acid amide (480 mg, 3.84 mmol) in THF (30 mL) was added LiAlH$_4$ (584 mg, 15.4 mmol). After stirred at reflux overnight, the reaction was quenched by H$_2$O (2 mL). Then the mixture was dried over anhydrous Na$_2$SO$_4$ and filtered. The filtrate was evaporated in vacuum to afford C-(1-methyl-1H-imidazol-4-yl)-methylamine as a crude product which was used for next step without further purification.

Step 3: To a solution of C-(1-methyl-1H-imidazol-4-yl)-methylamine (110 mg, 1.06 mmol) in dioxane (5 mL) was added 4-phenoxycarbonylamino-benzoic acid ethyl ester (150 mg, 0.53 mmol) and DIPEA (137 mg, 1.06 mmol). After stirred at 90° C. overnight, the reaction mixture was concentrated in vacuum. The residue was purified by pre-HPLC to afford ethyl 4-(3-((1-methyl-1H-imidazol-4-yl)methyl)ureido)benzoate (45 mg, 28%) as a yellow solid. $^1$H NMR (400 MHz, DMSO-d$_6$): δ=8.96 (s, 1H), 7.82 (d, J=7.2 Hz, 2H), 7.51-7.49 (m, 3H), 6.97 (s, 1H), 6.50 (t, J=6.0 Hz, 1H), 4.25 (q, J=7.2 Hz, 2H), 4.13 (d, J=4.8 Hz, 2H), 3.60 (s, 3H), 1.37 (t, J=7.2 Hz, 3H). MS: m/z 303.0 (M+H)$^+$.

Example 143: Synthesis of N-Cyclohexyl-4-(3-pyridin-4-ylmethyl-ureido)-benzenesulfonamide

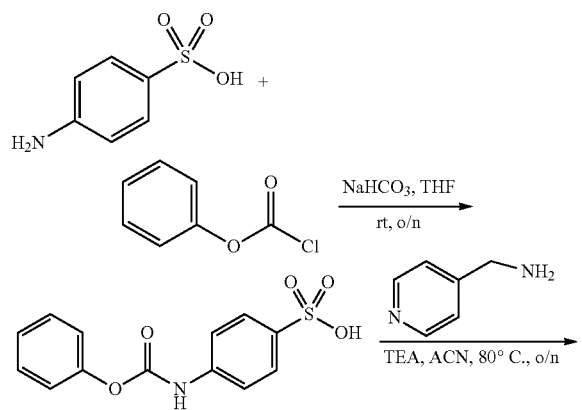

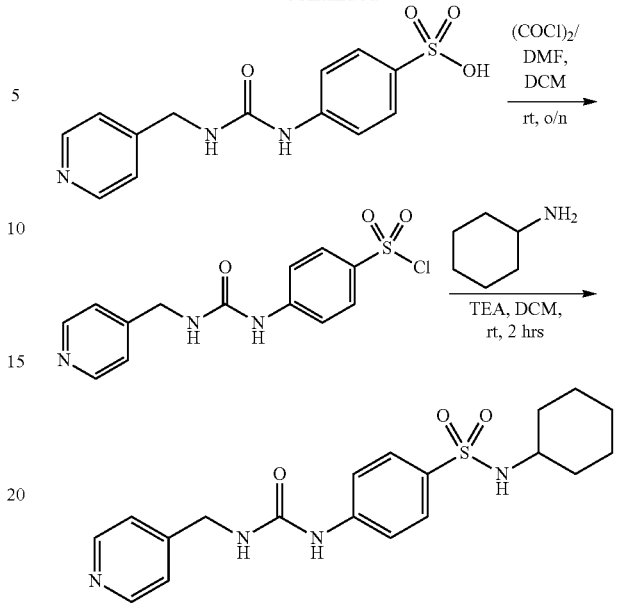

Step 1: To a solution of 4-amino-benzenesulfonic acid (346.4 mg, 2.00 mmol) in THF (30 mL) was added phenyl chloroformate (376 mg, 2.40 mmol) and followed by NaHCO$_3$ (504 mg, 6.00 mmol). The resulting mixture was stirred at room temperature overnight. The reaction was monitored by LC-MS. Then THF was removed in vacuum to give a residue which was mixed with H$_2$O (20 mL) and acidified to adjust pH=1-2 with conc.HCl. The precipitate formed from the mixture was filtered. The cake was washed with H$_2$O (20 mL*3) and air-dried to afford 4-phenoxycarbonylamino-benzenesulfonic acid (524 mg, yield: 89%) as a white solid. $^1$H NMR (400 MHz, DMSO-d$_6$): δ=10.33 (brs, 1H), 7.56 (d, J=8.4 Hz, 2H), 7.49-7.40 (m, 4H), 7.30-7.21 (m, 3H).

Step 2: To a stirring suspension of 4-phenoxycarbonylamino-benzenesulfonic acid (524 mg, 1.78 mmol) in dioxane (30 mL) was added c-pyridin-4-yl-methylamine (232 mg, 2.14 mmol) and followed by TEA (542 mg, 5.36 mmol). The resulting mixture was stirred at 80° C. overnight. The reaction was monitored by LC-MS. Then the mixture was concentrated in vacuum to give a residue which was mixed with H$_2$O (20 mL) and acidified to adjust pH=5-6 with conc.HCl. The precipitate formed from the mixture was filtered. The cake was washed with H$_2$O (20 mL*3) and air-dried to afford 4-(3-pyridin-4-ylmethyl-ureido)-benzenesulfonic acid (526 mg, yield: 96%) as a white solid.

Step 3, 4: To a solution of 4-(3-pyridin-4-ylmethyl-ureido)-benzenesulfonic acid (70 mg, 0.228 mmol) in (COCl)$_2$ (4 mL) was added a drop of dry DMF. The reaction was stirred at room temperature for 1 hour. Then the mixture was concentrated in vacuum to give 4-(3-Pyridin-4-ylmethyl-ureido)-benzenesulfonyl chloride as a yellow solid which was dissolved in dry DCM (20 mL). Then cyclohexylamine (27.2 mg, 0.273 mmol) was added into the mixture and followed by TEA (69.2 mg, 0.684 mmol). The resulting mixture was stirred at room temperature for another 1 hour. The reaction was monitored by LC-MS. Then the mixture was concentrated in vacuum to give a residue which was purified by a reverse-phase column (5-95% ACN in H$_2$O) to afford N-cyclohexyl-4-(3-pyridin-4-ylmethyl-ureido)-benzenesulfonamide (82.7 mg, yield: 93%) as a brown solid. $^1$H NMR (400 MHz, DMSO-d$_6$): δ=9.23 (brs, 1H), 8.50 (dd, J=4.4, 1.6 Hz, 2H), 7.65 (d, J=8.8 Hz, 2H), 7.57 (d, J=8.8 Hz, 2H), 7.42 (d, J=7.2 Hz, 1H), 7.29 (d, J=6.0 Hz, 2H), 6.97 (t, J=5.6 Hz, 1H), 4.34 (d, J=6.4 Hz, 2H), 2.92-2.79 (m, 1H), 1.65-1.49 (m, 4H), 1.47-1.38 (m, 1H), 1.17-0.95 (m, 5H). MS: m/z 389.1 (M+H$^+$).

Example 144: Synthesis of N-4-(3-pyridin-4-ylmethyl-ureido)-benzenesulfonamide

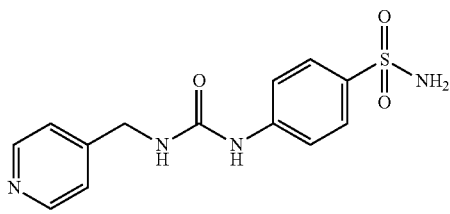 [SMILES: NS(=O)(=O)c1ccc(NC(=O)NCc2ccncc2)cc1]

The title compound was prepared as described in example N-cyclohexyl-4-(3-pyridin-4-ylmethyl-ureido)-benzenesulfonamide. $^1$H NMR (400 MHz, DMSO-d$_6$): δ=9.15 (brs, 1H), 8.52-8.50 (d, J=1.2 Hz, 2H), 7.67 (d, J=7.2 Hz, 2H), 7.56 (d, J=8.8 Hz, 2H), 7.29 (d, J=6.0 Hz, 2H), 7.18 (s, 2H), 6.89 (brs, 1H), 4.34 (d, J=6.0 Hz, 2H). MS: m/z 307.0 (M+H$^+$)

Example 145: Synthesis of N-Methyl-4-(3-pyridin-4-ylmethyl-ureido)-benzenesulfonamide

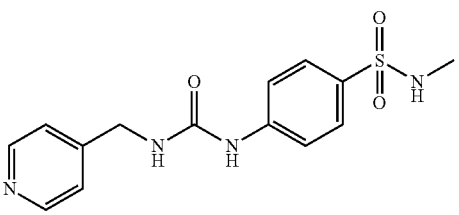 [SMILES: CNS(=O)(=O)c1ccc(NC(=O)NCc2ccncc2)cc1]

The title compound was prepared as described in example N-cyclohexyl-4-(3-pyridin-4-ylmethyl-ureido)-benzenesulfonamide. $^1$H NMR (400 MHz, CD$_3$OD): δ=8.48 (d, J=6.0 Hz, 2H), 7.72 (d, J=8.8 Hz, 2H), 7.61 (d, J=8.8 Hz, 2H), 7.41 (d, J=5.6 Hz, 2H), 4.47 (s, 2H), 2.49 (s, 3H). MS: m/z 320.9 (M+H$^+$).

Example 146: Synthesis of N-Propyl-4-(3-pyridin-4-ylmethyl-ureido)-benzenesulfonamide

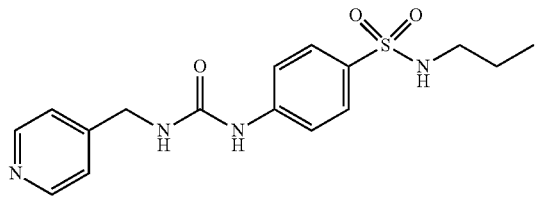 [SMILES: CCCNS(=O)(=O)c1ccc(NC(=O)NCc2ccncc2)cc1]

The title compound was prepared as described in example N-cyclohexyl-4-(3-pyridin-4-ylmethyl-ureido)-benzenesulfonamide. $^1$H NMR (400 MHz, DMSO-d$_6$): δ=9.21 (brs, 1H), 8.51 (d, J=5.6 Hz, 2H), 7.65 (d, J=8.8 Hz, 2H), 7.60 (d, J=9.2 Hz, 2H), 7.38 (t, J=6.0 Hz, 1H), 7.30 (d, J=6.0 Hz, 2H), 6.94 (t, J=6.0 Hz, 1H), 4.35 (d, J=6.0 Hz, 2H), 2.71-2.60 (m, 2H), 1.42-1.30 (m, 2H), 0.79 (t, J=7.2 Hz, 3H). MS: m/z 349.0 (M+H$^+$).

Example 147: Synthesis of N-Isopropyl-4-(3-pyridin-4-ylmethyl-ureido)-benzenesulfonamide

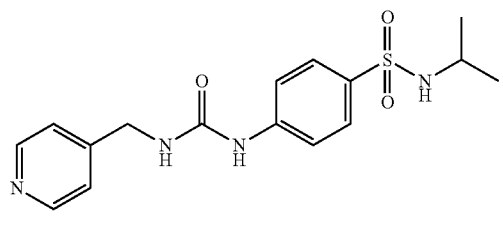 [SMILES: CC(C)NS(=O)(=O)c1ccc(NC(=O)NCc2ccncc2)cc1]

The title compound was prepared as described in example N-cyclohexyl-4-(3-pyridin-4-ylmethyl-ureido)-benzenesulfonamide. $^1$H NMR (400 MHz, DMSO-d$_6$): δ=9.24 (brs, 1H), 8.51 (s, 2H), 7.61 (d, J=28.8 Hz, 4H), 7.37 (brs, 1H), 7.30 (s, 2H), 6.91 (brs, 1H), 4.34 (s, 2H), 3.16 (s, 1H). 0.92 (s, 6H). MS: m/z 349.0 (M+H$^+$)

Example 148: Synthesis of N-Cyclopropyl-4-(3-pyridin-4-ylmethyl-ureido)-benzenesulfonamide

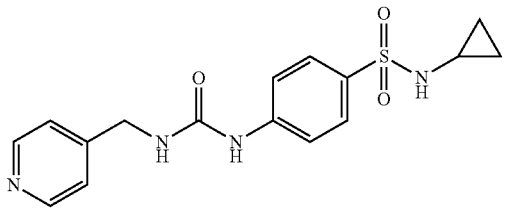 [SMILES: O=C(NCc1ccncc1)Nc1ccc(S(=O)(=O)NC2CC2)cc1]

The title compound was prepared as described in example N-cyclohexyl-4-(3-pyridin-4-ylmethyl-ureido)-benzenesulfonamide. $^1$H NMR (400 MHz, DMSO-d$_6$): δ=9.22 (brs, 1H), 8.52-8.50 (dd, J=1.6 Hz, 2H), 7.69 (brs, 1H), 7.66 (d, J=8.8 Hz, 2H), 7.60 (d, J=9.2 Hz, 2H), 7.30 (d, J=6.0 Hz, 2H), 6.95-6.92 (brs, 1H), 4.35 (d, J=6.0 Hz, 2H). 2.07-2.05 (m, 1H), 0.48-0.43 (m, 2H), 0.36-0.32 (m, 2H). MS: m/z 346.9 (M+H$^+$)

Example 149: Synthesis of N-Cyclobutyl-4-(3-pyridin-4-ylmethyl-ureido)-benzenesulfonamide

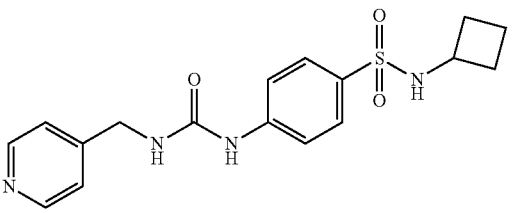 [SMILES: O=C(NCc1ccncc1)Nc1ccc(S(=O)(=O)NC2CCC2)cc1]

The title compound was prepared as described in example N-cyclohexyl-4-(3-pyridin-4-ylmethyl-ureido)-benzenesulfonamide. $^1$H NMR (400 MHz, CD$_3$OD): δ=8.48 (d, J=6.0 Hz, 2H), 7.72 (d, J=8.8 Hz, 2H), 7.58 (d, J=8.8 Hz, 2H), 7.40 (d, J=5.2 Hz, 2H), 4.47 (s, 2H), 3.71-3.67 (m, 1H), 2.03-1.96 (m, 2H), 1.83-1.71 (m, 2H), 1.61-1.50 (m, 2H). MS: m/z 361.0 (M+H$^+$).

Example 150: Synthesis of N-cyclopentyl-4-(3-pyridin-4-ylmethyl-ureido)-benzenesulfonamide

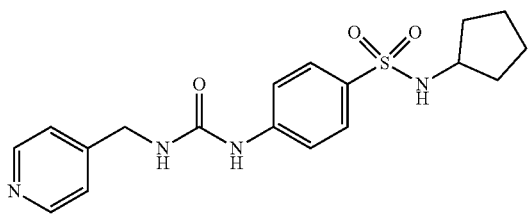 [SMILES: O=C(NCc1ccncc1)Nc1ccc(S(=O)(=O)NC2CCCC2)cc1]

The title compound was prepared as described in example N-cyclohexyl-4-(3-pyridin-4-ylmethyl-ureido)-benzene-sulfonamide. $^1$H NMR (400 MHz, DMSO-d$_6$): δ=9.23 (brs, 1H), 8.51 (d, J=6.0 Hz, 2H), 7.65 (d, J=8.8 Hz, 2H), 7.58 (d, J=8.8 Hz, 2H), 7.43 (d, J=6.8 Hz, 1H), 7.30 (d, J=5.6 Hz, 2H), 6.95 (t, J=6.0 Hz, 1H), 4.34 (d, J=6.0 Hz, 2H), 3.36-3.28 (m, 1H), 1.63-1.46 (m, 4H), 1.42-1.32 (m, 2H), 1.31-1.18 (m, 2H). MS: m/z 375.0 (M+H$^+$).

Example 151: Synthesis of 4-(3-Pyridin-4-ylmethyl-ureido)-N-pyrrolidin-3-yl-benzenesulfonamide

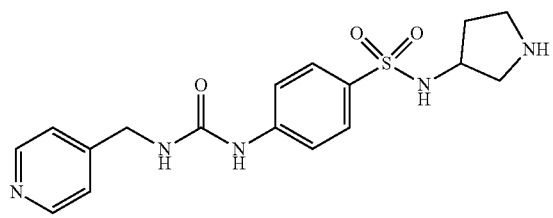 [SMILES: O=C(NCc1ccncc1)Nc1ccc(S(=O)(=O)NC2CCNC2)cc1]

The title compound was prepared as described in example N-cyclohexyl-4-(3-pyridin-4-ylmethyl-ureido)-benzene-sulfonamide. $^1$H NMR (400 MHz, DMSO-d$_6$): δ=9.41 (brs, 1H), 8.49 (dd, J=4.4, 1.6 Hz, 2H), 7.70-7.56 (m, 4H), 7.29 (d, J=5.6 Hz, 2H), 7.14 (t, J=5.6 Hz, 1H), 4.33 (d, J=5.6 Hz, 2H), 3.50-3.42 (m, 1H), 2.81-2.60 (m, 3H), 2.46-2.38 (m, 1H), 1.74-1.61 (m, 1H), 1.44-1.34 (m, 1H). MS: m/z 376.0 (M+H$^+$).

Example 152: Synthesis of N-(1-Methyl-pyrrolidin-3-yl)-4-(3-pyridin-4-ylmethyl-ureido)-benzenesulfonamide

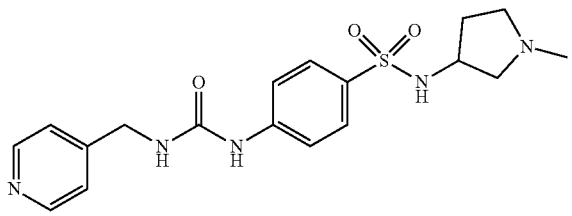 [SMILES: CN1CCC(NS(=O)(=O)c2ccc(NC(=O)NCc3ccncc3)cc2)C1]

The title compound was prepared as described in example N-cyclohexyl-4-(3-pyridin-4-ylmethyl-ureido)-benzene-sulfonamide. $^1$H NMR (400 MHz, DMSO-d$_6$): δ=9.24 (brs, 1H), 8.50 (d, J=6.0 Hz, 2H), 7.70-7.62 (m, 3H), 7.58 (d, J=9.2 Hz, 2H), 7.30 (d, J=5.2 Hz, 2H), 6.97 (t, J=5.6 Hz, 1H), 4.34 (d, J=5.6 Hz, 2H), 3.61-3.50 (m, 1H), 2.49-2.45 (m, 1H), 2.40-2.28 (m, 2H), 2.14 (s, 3H), 2.13-2.09 (m, 1H), 1.90-1.78 (m, 1H), 1.47-1.36 (m, 1H). MS: m/z 390.0 (M+H$^+$).

Example 153: Synthesis of N-(tert-butyl)-4-(3-(pyridin-4-ylmethyl)ureido)benzenesulfonamide

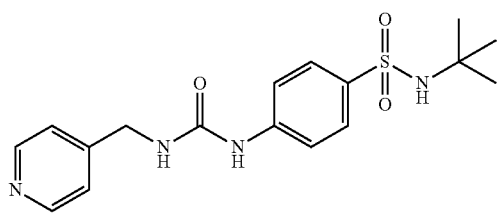 [SMILES: CC(C)(C)NS(=O)(=O)c1ccc(NC(=O)NCc2ccncc2)cc1]

The title compound was prepared as described in example N-cyclohexyl-4-(3-pyridin-4-ylmethyl-ureido)-benzene-sulfonamide. $^1$H NMR (400 MHz, DMSO-d$_6$): δ=9.15 (s, 1H), 8.51-8.49 (m, 2H), 7.68-7.65 (m, 2H), 7.57-7.54 (m, 2H), 7.30-7.28 (m, 3H), 6.94-6.90 (m, 1H), 4.35-4.33 (s, 2H), 1.07 (s, 9H). MS: m/z 363.0 (M+H$^+$).

Example 154: Synthesis of N-(2-Dimethylamino-ethyl)-4-(3-pyridin-4-ylmethyl-ureido)-benzene-sulfonamide

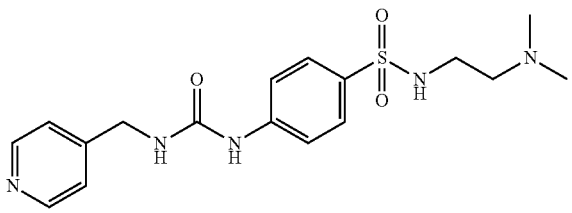 [SMILES: CN(C)CCNS(=O)(=O)c1ccc(NC(=O)NCc2ccncc2)cc1]

The title compound was prepared as described in example N-cyclohexyl-4-(3-pyridin-4-ylmethyl-ureido)-benzene-sulfonamide. $^1$H NMR (400 MHz, CD$_3$OD): 8.48 (d, J=6.0 Hz, 2H), 7.76 (d, J=8.8 Hz, 2H), 8.8 (d, J=8.8 Hz, 2H), 7.41 (d, J=6.0 Hz, 2H), 4.47 (s, 2H), 3.00-2.97 (t, J=6.4 Hz, 2H), 2.63-2.60 (t, J=6.0 Hz, 2H). 2.37 (s, 6H). MS: m/z 378.0 (M+H$^+$)

Example 155: Synthesis of N-Cyclopropylmethyl-4-(3-pyridin-4-ylmethyl-ureido)-benzenesulfonamide

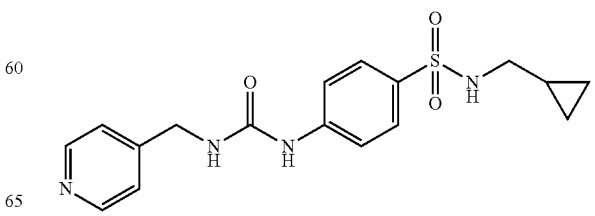

The title compound was prepared as described in example N-cyclohexyl-4-(3-pyridin-4-ylmethyl-ureido)-benzenesulfonamide. $^1$H NMR (400 MHz, DMSO-d$_6$): δ=9.18 (brs, 1H), 8.52 (d, J=4.4 Hz, 2H), 7.65 (d, J=8.4 Hz, 2H), 7.58 (d, J=8.8 Hz, 2H), 7.52 (brs, 1H), 7.31 (d, J=5.2 Hz, 2H), 6.93 (brs, 1H), 4.35 (t, J=6.0 Hz, 2H), 2.61 (t, J=6.4 Hz, 2H). 0.79-0.76 (t, J=7.6 Hz, 1H), 0.36-0.32 (m, 2H), 0.07-0.04 (in, 2H). MS: m/z 361.0 (M+H$^+$)

Example 156: Synthesis of N-Cyclobutylmethyl-4-(3-pyridin-4-ylmethyl-ureido)-benzenesulfonamide

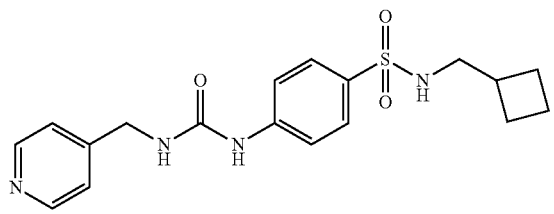 [SMILES: O=C(NCc1ccncc1)Nc1ccc(S(=O)(=O)NCC2CCC2)cc1]

The title compound was prepare as described in example N-cyclohexyl-4-(3-pyridin-4-ylmethyl-ureido)-benzenesulfonamide. $^1$H NMR (400 MHz, DMSO-d$_6$): δ=9.20 (brs, 1H), 8.52 (d, J=4.8 Hz, 2H), 7.65-7.57 (m, 4H), 7.39 (brs, 1H), 7.31 (d, J=5.2 Hz, 2H), 6.95 (brs, 1H), 4.35 (d, J=6.0 Hz, 2H), 2.71-2.68 (t, J=6.4 Hz, 2H). 2.32.28 (m, 1H), 1.90-1.86 (m, 2H), 1.77-1.71 (m, 2H), 1.58-1.54 (m, 2H). MS: m/z 375.0 (M+H$^+$)

Example 157: Synthesis of 4-(3-Pyridin-4-ylmethyl-ureido)-N-(2-pyrrolidin-1-yl-ethyl)-benzensulfonamide

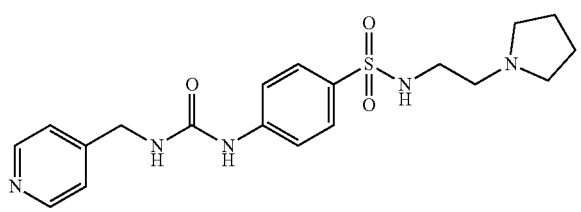 [SMILES: O=C(NCc1ccncc1)Nc1ccc(S(=O)(=O)NCCN2CCCC2)cc1]

The title compound was prepared as described in example N-cyclohexyl-4-(3-pyridin-4-ylmethyl-ureido)-benzenesulfonamide. $^1$H NMR (400 MHz, DMSO-d$_6$): δ=9.25 (brs, 1H), 8.51 (d, J=4.8 Hz, 2H), 7.67-7.58 (dd, J=8.4 Hz, 4H), 7.30 (d, J=4.8 Hz, 3H), 7.00-6.97 (brs, 1H), 4.35 (d, J=5.6, 2H), 2.82-2.78 (t, J=6.8 Hz, 2H), 2.45-2.42 (t, J=6.8 Hz, 2H), 2.37 (s, 4H). 1.63 (s, 4H). MS: m/z 404.0 (M+H$^+$)

Example 158: Synthesis of N-[2-(4-Methyl-piperazin-1-yl)-ethyl]-4-(3-pyridin-4-ylmethyl-ureido)-benzenesulfonamide

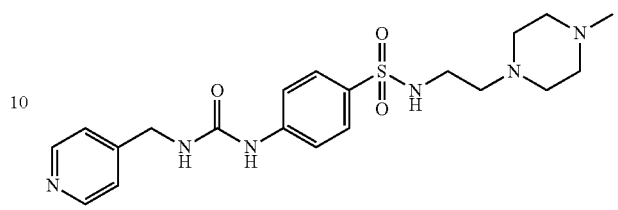

The title compound was prepared as described in example N-cyclohexyl-4-(3-pyridin-4-ylmethyl-ureido)-benzenesulfonamide. $^1$H NMR (400 MHz, DMSO-d$_6$): δ=9.21 (brs, 1H), 8.51-8.50 (d, J=6.0 Hz, 2H), 7.66-7.57 (dd, J=8.4 Hz, 4H), 7.30-7.28 (d, J=5.6 Hz, 2H), 6.94 (brs, 1H), 4.35-4.33 (d, J=6.0 Hz, 2H), 2.80-2.78 (m, 2H), 2.29-2.26 (t, 9H). 2.12 (s, 4H). MS: m/z 433.0 (M+H$^+$)

Example 159: Synthesis of N-(2-Morpholin-4-yl-ethyl)-4-(3-pyridin-4-ylmethyl-ureido)-benzenesulfonamide

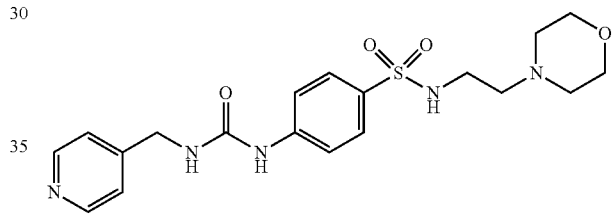

The title compound was prepared as described in example N-cyclohexyl-4-(3-pyridin-4-ylmethyl-ureido)-benzenesulfonamide. $^1$H NMR (400 MHz, DMSO-d$_6$): δ=9.23 (brs, 1H), 8.51 (dd, J=4.4, 1.2 Hz, 2H), 7.66 (d, J=8.8 Hz, 2H), 7.59 (d, J=8.8 Hz, 2H), 7.33 (t, J=5.6 Hz, 1H), 7.29 (d, J=5.6 Hz, 2H), 6.95 (t, J=6.0 Hz, 1H), 4.34 (d, J=6.0 Hz, 2H), 3.56-3.46 (m, 4H), 2.86-2.77 (m, 2H), 2.37-2.19 (m, 6H). MS: m/z 420.2 (M+H$^+$).

Example 160: Synthesis of N-(2-Piperidin-1-yl-ethyl)-4-(3-pyridin-4-ylmethyl-ureido)-benzenesulfonamide

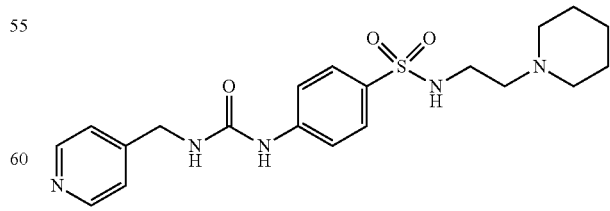

The title compound was prepared as described in example N-cyclohexyl-4-(3-pyridin-4-ylmethyl-ureido)-benzenesulfonamide. $^1$H NMR (400 MHz, DMSO-d$_6$): δ=9.21 (brs, 1H), 8.51 (dd, J=4.4, 1.2 Hz, 2H), 7.65 (d, J=8.8 Hz, 2H), 7.59 (d, J=9.2 Hz, 2H), 7.29 (d, J=6.0 Hz, 2H), 7.25 (brs, 1H), 6.94 (t, J=6.0 Hz, 1H), 4.34 (d, J=6.0 Hz, 2H), 2.83-2.74 (m, 2H), 2.30-2.15 (m, 6H), 1.49-1.38 (m, 4H), 1.37-1.28 (m, 2H). MS: m/z 418.2 (M+H⁺).

Example 161: Synthesis of N-(2-Hydroxy-ethyl)-4-(3-pyridin-4-ylmethyl-ureido)-benzenesulfonamide

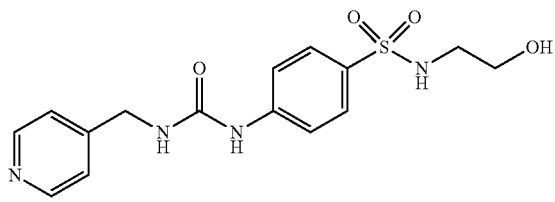 [SMILES: O=C(NCc1ccncc1)Nc1ccc(S(=O)(=O)NCCO)cc1]

The title compound was prepared as described in example N-cyclohexyl-4-(3-pyridin-4-ylmethyl-ureido)-benzenesulfonamide. ¹H NMR (400 MHz, DMSO-d₆): δ=9.22 (brs, 1H), 8.51 (d, J=5.6 Hz, 2H), 7.65 (d, J=8.8 Hz, 2H), 7.59 (d, J=8.8 Hz, 2H), 7.38 (t, J=6.0 Hz, 1H), 7.30 (d, J=6.0 Hz, 2H), 6.95 (t, J=6.0 Hz, 1H), 4.67 (brs, 1H), 4.35 (d, J=5.6 Hz, 2H), 3.48-3.28 (m, 2H), 2.81-2.69 (m, 2H). MS: m/z 350.9 (M+H⁺).

Example 162: Synthesis of 4-(3-Pyridin-4-ylmethyl-ureido)-N-(tetrahydro-furan-3-yl)-benzenesulfonamide

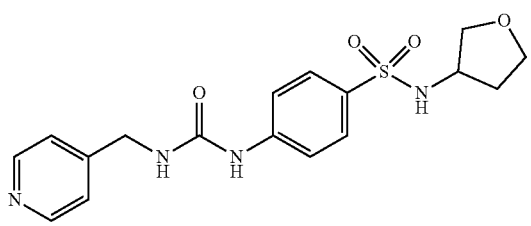 [SMILES: O=C(NCc1ccncc1)Nc1ccc(S(=O)(=O)NC2CCOC2)cc1]

The title compound was prepared as described in example N-cyclohexyl-4-(3-pyridin-4-ylmethyl-ureido)-benzenesulfonamide. ¹H NMR (400 MHz, DMSO-d₆): δ=9.25 (brs, 1H), 8.50 (dd, J=4.4, 1.6 Hz, 2H), 7.71 (d, J=6.4 Hz, 1H), 7.67 (d, J=9.2 Hz, 2H), 7.60 (d, J=9.2 Hz, 2H), 7.29 (d, J=6.0 Hz, 2H), 6.96 (t, J=6.0 Hz, 1H), 4.34 (d, J=6.0 Hz, 2H), 3.72-3.52 (m, 4H), 3.32-3.39 (m, 1H), 1.91-1.81 (m, 1H), 1.63-1.54 (m, 1H). MS: m/z 377.0 (M+H⁺).

Example 163: Synthesis of N-(2-Methoxy-ethyl)-4-(3-pyridin-4-ylmethyl-ureido)-benzenesulfonamide

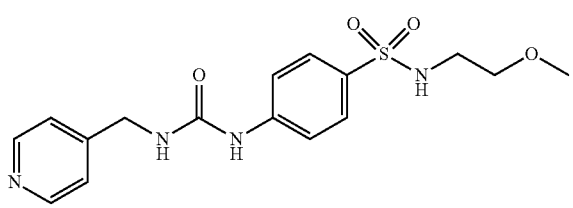 [SMILES: COCCNS(=O)(=O)c1ccc(NC(=O)NCc2ccncc2)cc1]

The title compound was prepared as described in example N-cyclohexyl-4-(3-pyridin-4-ylmethyl-ureido)-benzenesulfonamide. ¹H NMR (400 MHz, DMSO-d₆): δ=9.21 (brs, 1H), 8.51 (dd, J=4.8, 1.6 Hz, 2H), 7.65 (d, J=8.8 Hz, 2H), 7.58 (d, J=9.2 Hz, 2H), 7.51 (t, J=6.0 Hz, 1H), 7.30 (d, J=6.0 Hz, 2H), 6.93 (t, J=6.0 Hz, 1H), 4.34 (d, J=6.4 Hz, 2H), 3.31-3.26 (m, 2H), 3.16 (s, 3H), 2.88-2.81 (m, 2H). MS: m/z 365.1 (M+H⁺).

Example 164: Synthesis of N-(3-Methoxy-propyl)-4-(3-pyridin-4-ylmethyl-ureido)-benzenesulfonamide

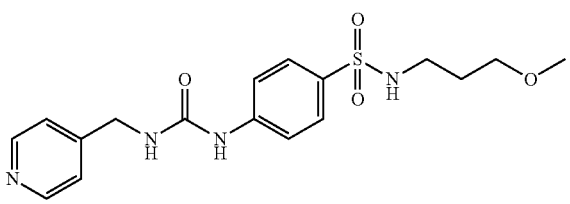 [SMILES: COCCCNS(=O)(=O)c1ccc(NC(=O)NCc2ccncc2)cc1]

The title compound was prepared as described in example N-cyclohexyl-4-(3-pyridin-4-ylmethyl-ureido)-benzenesulfonamide. ¹H NMR (400 MHz, DMSO-d₆): δ=9.21 (brs, 1H), 8.51 (d, J=4.8 Hz, 2H), 7.65-7.58 (dd, J=8.8 Hz, 4H), 7.39-7.36 (brs, 1H), 7.30 (d, J=4.8 Hz, 2H), 6.95-6.92 (brs, 1H), 4.35 (d, J=5.6 Hz, 2H), 3.28-3.24 (t, 2H), 3.15 (s, 3H), 2.75-2.70 (dd, J=6.4 Hz, 2H), 1.60-1.53 (m, 2H). MS: m/z 397.0 (M+H⁺)

Example 165: Synthesis of N-(1-Ethyl-pyrrolidin-2-ylmethyl)-4-(3-pyridin-4-ylmethyl-ureido)-benzenesulfonamide

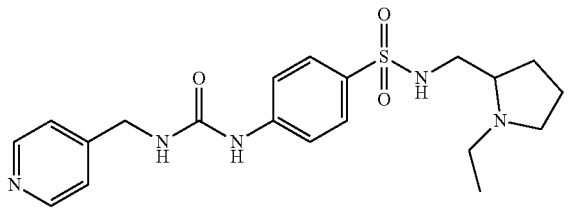 [SMILES: CCN1CCCC1CNS(=O)(=O)c1ccc(NC(=O)NCc2ccncc2)cc1]

The title compound was prepared as described in example N-cyclohexyl-4-(3-pyridin-4-ylmethyl-ureido)-benzenesulfonamide. ¹H NMR (400 MHz, DMSO-d₆): δ=9.22 (brs, 1H), 8.51-8.50 (dd, J=1.2 Hz, 2H), 7.66-7.30 (dd, J=9.2 Hz, 4H), 7.28 (d, J=5.6 Hz, 3H), 6.96-6.93 (brs, 1H), 4.34 (d, J=6.0 Hz, 2H), 2.97-2.93 (brs, 1H), 2.76 (d, J=11.6 Hz, 1H). 2.57-2.33 (m, 2H), 2.17-2.01 (m, 2H), 1.77-1.61 (m, 1H), 1.75-1.23 (m, 4H), 0.96-0.92 (t, J=0.7.2 Hz, 3H). MS: m/z 418.0 (M+H⁺)

Example 166: Synthesis of N-neopentyl-4-(3-pyridin-4-ylmethyl-ureido)-benzenesulfonamide

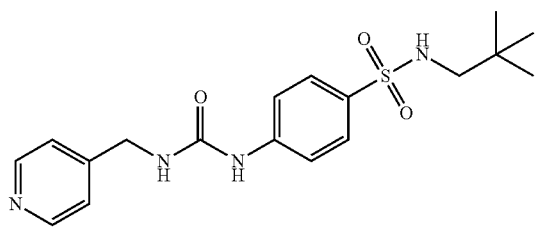 [SMILES: CC(C)(C)CNS(=O)(=O)c1ccc(NC(=O)NCc2ccncc2)cc1]

The title compound was prepared as described in example N-cyclohexyl-4-(3-pyridin-4-ylmethyl-ureido)-benzenesulfonamide. $^1$H NMR (400 MHz, CD$_3$OD): δ=8.48 (d, J=4.8 Hz, 2H), 7.72 (d, J=8.4 Hz, 2H), 7.57 (d, J=8.8 Hz, 2H), 7.41 (d, J=5.6 Hz, 2H), 4.47 (s, 2H), 2.55 (s, 2H), 0.87 (s, 9H). MS: m/z 377.0 (M+H)$^+$.

Example 167: Synthesis of N-(1-Cyclobutyl-ethyl)-4-(3-pyridin-4-ylmethyl-ureido)-benzenesulfonamide

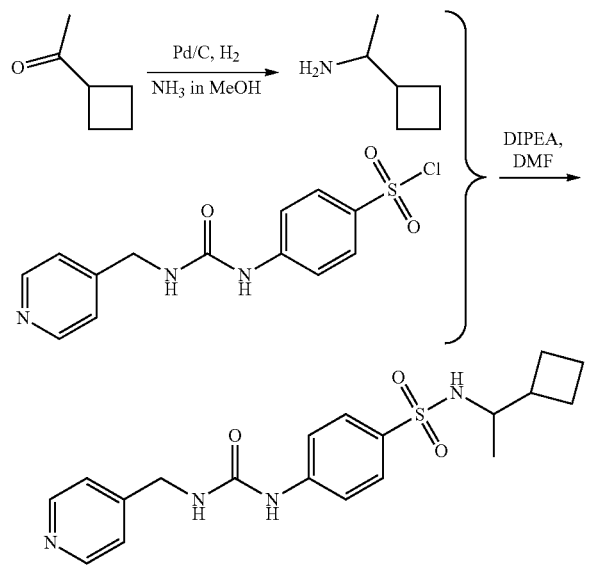

Step 1: To a solution of 1-cyclobutyl-ethanone (500 mg, 5.1 mmol) in 7 N NH$_3$ in MeOH (10 mL) was added 10% Pd/C (270 mg, 0.26 mmol). After stirred at room temperature under balloon hydrogen atmosphere overnight, the reaction mixture was filtered. The filtrate was evaporated in vacuum to afford 1-cyclobutyl-ethylamine as a crude product which was used for next step without further purification.

Step 2: To a solution of 4-(3-pyridin-4-ylmethyl-ureido)-benzenesulfonic acid (150 mg, 0.49 mmol) in DCM (15 mL) was added (COCl)$_2$ (124 mg, 0.98 mmol) and DMF (2 drops). After stirred at room temperature for 5 hrs, the reaction mixture was evaporated in vacuum. The residue was dissolved in DMF (5 mL), and then 1-cyclobutyl-ethylamine (73 mg, 0.74 mmol) and DIPEA (190 mg, 1.47 mmol) were added. After stirred at room temperature overnight, the residue was purified by pre-HPLC to afford N-(1-cyclobutyl-ethyl)-4-(3-pyridin-4-ylmethyl-ureido)-benzenesulfonamide (30 mg, 16%) as a white solid. $^1$H NMR (400 MHz, DMSO-d$_6$): δ=9.15 (s, 1H), 8.50 (d, J=4.4 Hz, 2H), 7.65 (d, J=8.4 Hz, 2H), 7.57 (d, J=8.8 Hz, 2H), 7.29 (d, J=4.4 Hz, 2H), 7.23 (d, J=8.4 Hz, 1H), 6.91 (t, J=4.8 Hz, 1H), 4.34 (d, J=5.2 Hz, 2H), 3.01-2.96 (m, 1H), 2.16-2.10 (m, 1H), 1.81-1.46 (m, 6H), 0.72 (d, J=6.4 Hz, 3H). MS: m/z 389.0 (M+H)$^+$.

Example 168: Synthesis of N-Benzyl-4-(3-pyridin-4-ylmethyl-ureido)-benzenesulfonamide

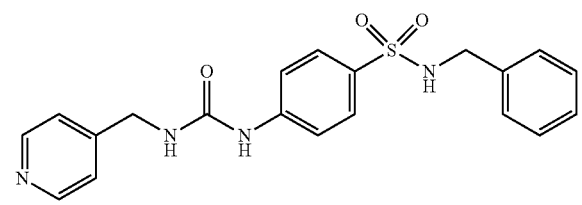 [SMILES: O=C(NCc1ccncc1)Nc1ccc(S(=O)(=O)NCc2ccccc2)cc1]

The title compound was prepared as described in example N-cyclohexyl-4-(3-pyridin-4-ylmethyl-ureido)-benzenesulfonamide. $^1$H NMR (400 MHz, DMSO-d$_6$): δ=9.18 (brs, 1H), 8.51 (dd, J=4.4, 1.6 Hz, 2H), 7.92 (t, J=6.4 Hz, 1H), 7.67 (d, J=8.8 Hz, 2H), 7.58 (d, J=9.2 Hz, 2H), 7.32-7.26 (m, 4H), 7.26-7.20 (m, 3H), 6.92 (t, J=6.0 Hz, 1H), 4.35 (d, J=6.0 Hz, 2H), 3.92 (d, J=6.4 Hz, 2H). MS: m/z 396.9 (M+H$^+$).

Example 169: Synthesis of N-Benzyl-4-(3-benzyl-ureido)-benzenesulfonamide

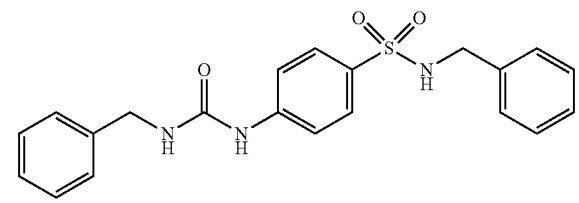 [SMILES: O=C(NCc1ccccc1)Nc1ccc(S(=O)(=O)NCc2ccccc2)cc1]

The title compound was prepare as described in example N-cyclohexyl-4-(3-pyridin-4-ylmethyl-ureido)-benzenesulfonamide. $^1$H NMR (400 MHz, DMSO-d$_6$): δ=9.04 (brs, 1H), 7.91 (t, J=6.4 Hz, 1H), 7.66 (d, J=8.8 Hz, 2H), 7.57 (d, J=9.2 Hz, 2H), 7.38-7.19 (m, 10H), 6.81 (t, J=6.0 Hz, 1H), 4.32 (d, J=6.0 Hz, 2H), 3.92 (d, J=6.4 Hz, 2H). MS: m/z 395.9 (M+H$^+$).

Example 170: Synthesis of N-(2-fluorobenzyl)-4-(3-(pyridin-4-ylmethyl)ureido)benzenesulfonamide

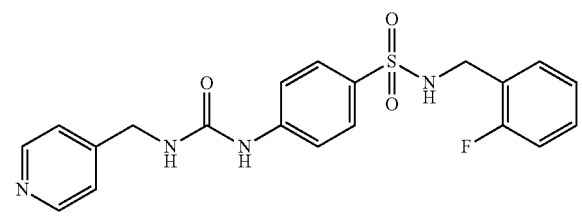 [SMILES: O=C(NCc1ccncc1)Nc1ccc(S(=O)(=O)NCc2ccccc2F)cc1]

The title compound was prepared as described in example N-cyclohexyl-4-(3-pyridin-4-ylmethyl-ureido)-benzenesulfonamide. ¹H NMR (400 MHz, CD3OD): δ=8.48-8.47 (m, 2H), 7.70-7.68 (m, 2H), 7.54-7.52 (m, 2H), 7.41-7.39 (m, 2H), 7.31-7.20 (m, 2H), 7.07-7.04 (m, 1H), 6.99-6.94 (m, 1H), 4.46 (s, 2H), 4.40 (s, 2H). MS: m/z 414.9 (M+H⁺).

Example 171: Synthesis of N-(3-fluorobenzyl)-4-(3-(pyridin-4-ylmethyl)ureido)benzenesulfonamide

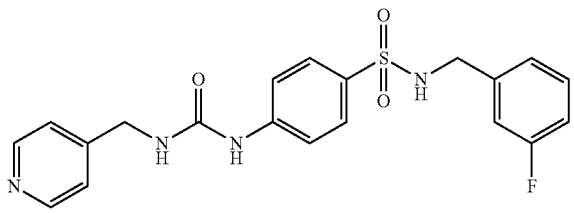 [SMILES: O=C(NCc1ccncc1)Nc1ccc(S(=O)(=O)NCc2cccc(F)c2)cc1]

The title compound was prepared as described in example N-cyclohexyl-(3-pyridin-4-ylmethyl-ureido)-benzenesulfonamide. ¹H NMR (400 MHz, CD3OD): δ=8.50-8.48 (m, 2H), 7.77-7.71 (m, 2H), 7.58-7.55 (m, 2H), 7.42-7.40 (m, 2H), 7.30-7.23 (m, 1H), 7.06-6.91 (m, 3H), 4.48 (s, 2H), 4.05 (s, 2H). MS: m/z 414.9 (M+H⁺).

Example 172: Synthesis of N-(4-fluorobenzyl)-4-(3-(pyridin-4-ylmethyl)ureido)benzenesulfonamide

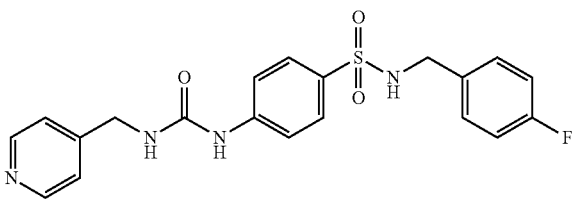 [SMILES: O=C(NCc1ccncc1)Nc1ccc(S(=O)(=O)NCc2ccc(F)cc2)cc1]

The title compound was prepared as described in example N-cyclohexyl-4-(3-pyridin-4-ylmethyl-ureido)-benzenesulfonamide. ¹H NMR (400 MHz, CD3OD): δ=7.70-7.68 (m, 2H), 7.55-7.53 (m, 2H), 7.36-733 (m, 2H), 7.24-7.20 (m, 2H), 7.07-7.03 (m, 2H), 6.99-6.94 (m, 2H), 4.37 (s, 2H), 4.00 (s, 2H). MS: m/z 411.0 (M+H⁺).

Example 173: Synthesis of N-(2-Chloro-benzyl)-4-(3-pyridin-4-ylmethyl-ureido)-benzenesulfonamide

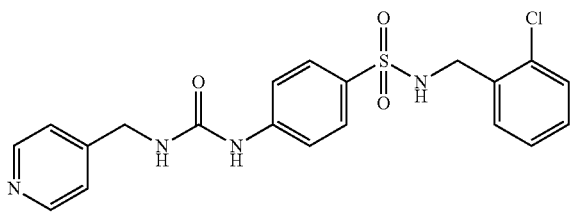 [SMILES: O=C(NCc1ccncc1)Nc1ccc(S(=O)(=O)NCc2ccccc2Cl)cc1]

The title compound was prepared as described in example N-cyclohexyl-4-(3-pyridin-4-ylmethyl-ureido)-benzenesulfonamide. ¹H NMR (400 MHz, DMSO-d6): δ=9.22 (brs, 1H), 8.51 (d, J=5.6 Hz, 2H), 8.04-8.00 (brs, 1H), 7.68 (d, J=8.8 Hz, 2H), 7.59 (d, J=8.4 Hz, 2H), 7.45-7.43 (t, 1H), 7.40-7.38 (t, 1H), 7.33-7.28 (m, 4H), 6.95-6.92 (brs, 1H), 4.35 (d, J=6.0 Hz, 2H), 4.01 (d, J=6.0 Hz, 2H). MS: m/z 430.9 (M+H⁺)

Example 174: Synthesis of N-(3-Chloro-benzyl)-4-(3-pyridin-4-ylmethyl-ureido)-benzenesulfonamide

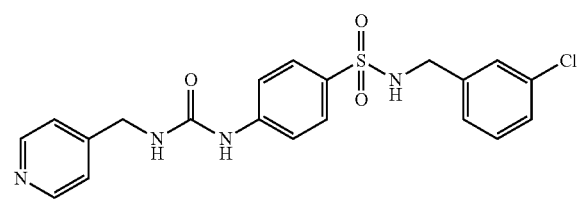 [SMILES: O=C(NCc1ccncc1)Nc1ccc(S(=O)(=O)NCc2cccc(Cl)c2)cc1]

The title compound was prepare as described in example N-cyclohexyl-4-(3-pyridin-4-ylmethyl-ureido)-benzenesulfonamide. ¹H NMR (400 MHz, DMSO-d₆): δ=9.28 (brs, 1H), 8.51 (dd, J=4.8, 1.6 Hz, 2H), 8.00 (brs, 1H), 7.65 (d, J=8.8 Hz, 2H), 7.59 (d, J=8.8 Hz, 2H), 7.32-7.27 (m, 5H), 7.21 (d, J=7.2 Hz, 1H), 6.98 (brs, 1H), 4.35 (d, J=6.0 Hz, 2H), 3.96 (d, J=6.4 Hz, 2H). MS: m/z 430.9 (M+H⁺)

Example 175: Synthesis of N-(4-chlorobenzyl)-4-(3-(pyridin-4-ylmethyl)ureido)benzenesulfonamide

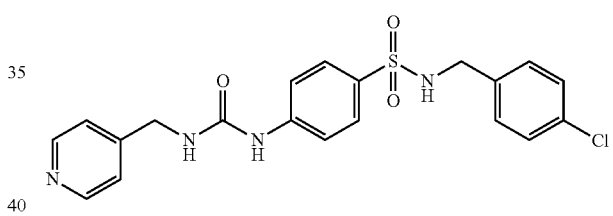

The title compound was prepared as described in example N-cyclohexyl-4-(3-pyridin-4-ylmethyl-ureido)-benzenesulfonamide. ¹H NMR (400 MHz, CD₃OD): δ=8.48-8.46 (s, 2H), 7.70-7.68 (m, 2H), 7.55-7.53 (m, 2H), 7.41-7.39 (m, 2H), 7.24-7.18 (m, 4H), 4.47 (s, 2H), 4.01 (s, 2H). MS: m/z 428.9 (M+H⁺).

Example 176: Synthesis of N-(2-methoxybenzyl)-4-(3-(pyridin-4-ylmethyl)ureido)benzenesulfonamide

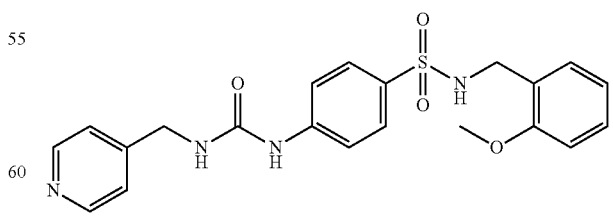

The title compound was prepared as described in example N-cyclohexyl-4-(3-pyridin-4-ylmethyl-ureido)-benzenesulfonamide. ¹H NMR (400 MHz, CD₃OD): δ=8.48 (m, 2H), 7.66-7.64 (m, 2H), 7.51-7.49 (m, 2H), 7.40-7.39 (m, 2H), 7.19-7.15 (m, 2H), 6.83-6.79 (m, 2H), 4.46 (s, 2H), 4.04 (s, 2H), 3.71 (s, 3H). MS: m/z 427.0 (M+H⁺).

Example 177: Synthesis of N-(3-Methoxy-benzyl)-4-(3-pyridin-4-ylmethyl-ureido)-benzenesulfonamide

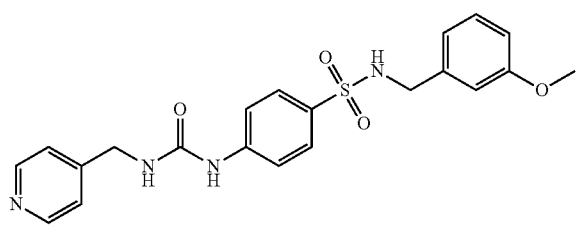 [SMILES: COc1cccc(CNS(=O)(=O)c2ccc(NC(=O)NCc3ccncc3)cc2)c1]

The title compound was prepared as described in example N-cyclohexyl-4-(3-pyridin-4-ylmethyl-ureido)-benzenesulfonamide. ¹H NMR (300 MHz, DMSO-d₆): δ=9.19 (s, 1H), 8.51 (d, J=5.7 Hz, 2H), 7.93-7.91 (m, 1H), 7.82-7.79 (m, 2H), 7.89-7.56 (m, 4H), 7.29 (d, J=5.7 Hz, 2H), 7.22-7.16 (m, 1H), 6.94-6.82 (m, 1H), 6.79-7.76 (m, 3H), 4.34 (d, J=6.0 Hz, 2H), 3.91 (d, J=6.0 Hz, 2H), 3.69 (s, 3H). MS: m/z 427.1 (M+H⁺).

Example 178: Synthesis of N-(4-methoxybenzyl)-4-(3-(pyridin-4-ylmethyl)ureido)benzenesulfonamide

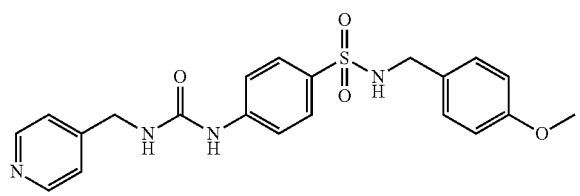 [SMILES: COc1ccc(CNS(=O)(=O)c2ccc(NC(=O)NCc3ccncc3)cc2)cc1]

The title compound was prepare as described in example N-cyclohexyl-4-(3-pyridin-4-ylmethyl-ureido)-benzenesulfonamide. ¹H NMR (400 MHz, DMSO-d₆): δ=9.25 (brs, 1H), 8.51 (dd, J=6.0 Hz, 2H), 7.83 (t, J=5.6 Hz, 1H), 7.64 (d, J=8.8 Hz, 2H), 7.57 (d, J=8.8 Hz, 2H), 7.29 (d, J=5.6 Hz, 2H), 7.13 (d, J=8.8 Hz, 2H), 6.96 (t, J=6.8 Hz, 1H), 6.83 (d, J=8.8 Hz, 2H), 4.34 (d, J=6.4 Hz, 2H), 3.85 (d, J=4.8 Hz, 2H), 3.71 (s, 3H). MS: m/z 427.0 (M+H⁺).

Example 179: Synthesis of N-(2-Methyl-benzyl)-4-(3-pyridin-4-ylmethyl-ureido)-benzenesulfonamide

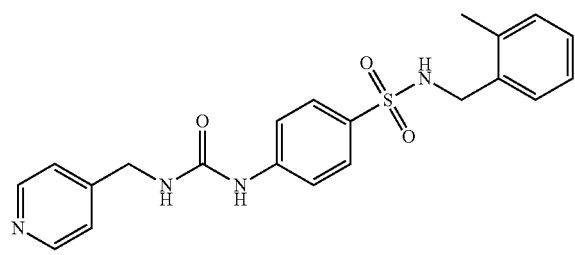 [SMILES: Cc1ccccc1CNS(=O)(=O)c1ccc(NC(=O)NCc2ccncc2)cc1]

The title compound was prepared as described in example N-cyclohexyl-4-(3-pyridin-4-ylmethyl-ureido)-benzenesulfonamide. ¹H NMR (300 MHz, DMSO-d6): δ=9.20 (s, 1H), 8.51 (d, J=6.0 Hz, 2H), 7.75-7.58 (m, 5H), 7.30 (d, J=5.1 Hz, 2H), 7.20-7.13 (m, 4H), 6.96-6.92 (m, 1H), 4.35 (d, J=5.7 Hz, 2H), 3.87 (d, J=6.3 Hz, 2H), 2.20 (s, 3H). MS: m/z 411.1 (M+H⁺).

Example 180: Synthesis of N-(3-Methyl-benzyl)-4-(3-pyridin-4-ylmethyl-ureido)-benzenesulfonamide

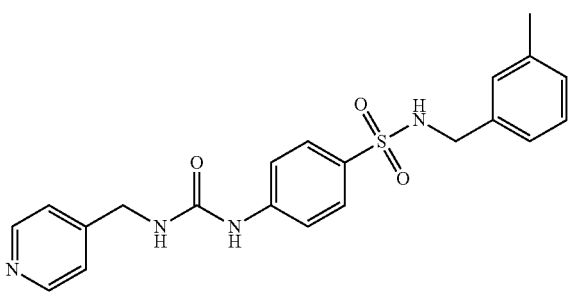 [SMILES: Cc1cccc(CNS(=O)(=O)c2ccc(NC(=O)NCc3ccncc3)cc2)c1]

The title compound was prepared as described in example N-cyclohexyl-4-(3-pyridin-4-ylmethyl-ureido)-benzenesulfonamide. ¹H NMR (400 MHz, DMSO-d₆): δ=9.53 (s, 1H), 8.75 (d, J=6.8 Hz, 2H), 7.89-7.86 (m, 1H), 7.74 (d, J=6.4 Hz, 2H), 7.67 (d, J=8.8 Hz, 2H), 7.58 (d, J=9.2 Hz, 2H), 7.33-7.30 (m, 1H), 7.17-7.14 (m, 1H), 7.03-7.00 (m, 3H), 4.52 (d, J=6.0 Hz, 2H), 4.89 (d, J=6.0 Hz, 2H), 2.23 (s, 3H). MS: m/z 411.1 (M+H⁺).

Example 181: Synthesis of N-(4-methylbenzyl)-4-(3-(pyridin-4-ylmethyl)ureido)benzenesulfonamide

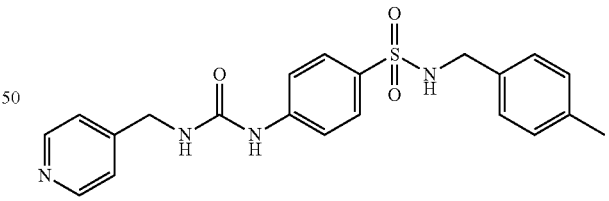

The title compound was prepared as described in example N-cyclohexyl-4-(3-pyridin-4-ylmethyl-ureido)-benzenesulfonamide. ¹H NMR (400 MHz, DMSO-d₆): δ=9.19 (s, 1H), 8.51-8.49 (m, 2H), 7.87-7.82 (m, 1H), 7.67-7.62 (m, 2H), 7.59-7.56 (m, 2H), 7.30-7.28 (m, 2H), 7.13-7.06 (m, 4H), 6.95-6.91 (m, 1H), 4.37-4.33 (s, 2H), 3.87-3.86 (s, 2H), 2.25 (s, 3H). MS: m/z 411.0 (M+H⁺).

Example 182: Synthesis of N-(2-Cyano-benzyl)-4-(3-pyridin-4-ylmethyl-ureido)-benzenesulfonamide

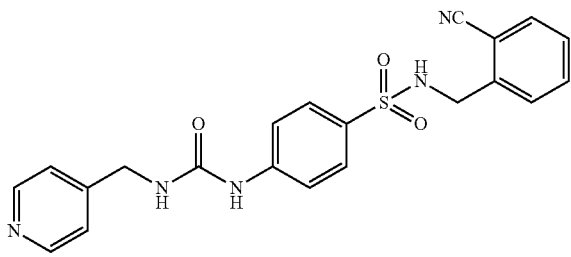 [SMILES: N#Cc1ccccc1CNS(=O)(=O)c1ccc(NC(=O)NCc2ccncc2)cc1]

The title compound was prepared as described in example N-cyclohexyl-4-(3-pyridin-4-ylmethyl-ureido)-benzenesulfonamide. $^1$H NMR (400 MHz, DMSO-$d_6$): δ=9.35-9.26 (m, 1H), 8.70 (s, 1H), 8.48 (d, J=4.8 Hz, 1H), 7.88-7.85 (m, 2H), 7.72-7.46 (m, 6H), 7.26 (d, J=5.2 Hz, 2H), 6.95 (brs, 1H), 5.00-4.88 (m, 2H), 4.32 (d, J=6.0 Hz, 2H). MS: m/z 422.1 (M+H$^+$).

Example 183: Synthesis of N-(3-Cyano-benzyl)-4-(3-pyridin-4-ylmethyl-ureido)-benzenesulfonamide

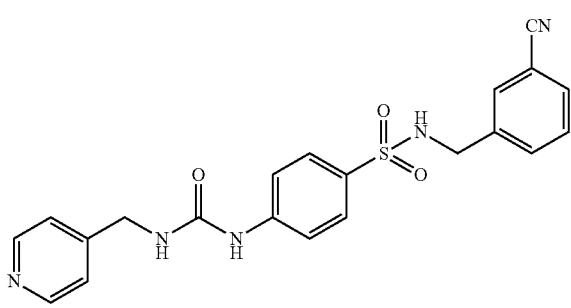 [SMILES: N#Cc1cccc(CNS(=O)(=O)c2ccc(NC(=O)NCc3ccncc3)cc2)c1]

The title compound was prepared as described in example N-cyclohexyl-4-(3-pyridin-4-ylmethyl-ureido)-benzenesulfonamide. $^1$H NMR (400 MHz, DMSO-$d_6$): δ=9.19 (s, 1H), 8.51 (d, J=6.0 Hz, 2H), 8.06 (t, J=6.4 Hz, 1H), 7.69-7.48 (m, 7H), 7.29 (d, J=6.0 Hz, 2H), 6.92 (t, J=6.4 Hz, 1H), 4.34 (d, J=6.0 Hz, 2H), 4.02 (d, J=6.0 Hz, 2H). MS: m/z 422.1 (M+H$^+$).

Example 184: Synthesis of N-(4-cyanobenzyl)-4-(3-(pyridin-4-ylmethyl)ureido)benzenesulfonamide

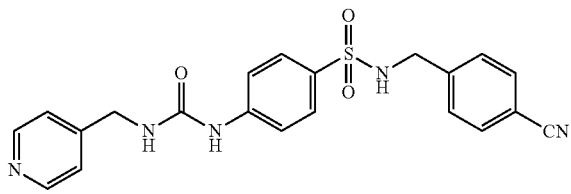 [SMILES: N#Cc1ccc(CNS(=O)(=O)c2ccc(NC(=O)NCc3ccncc3)cc2)cc1]

The title compound was prepare as described in example N-cyclohexyl-4-(3-pyridin-4-ylmethyl-ureido)-benzenesulfonamide. $^1$H NMR (400 MHz, CD$_3$OD): δ=8.79-8.77 (m, 2H), 8.07-8.06 (m, 2H), 7.66-7.64 (m, 2H), 7.58-7.51 (m, 4H), 7.38-7.36 (m, 2H), 4.71 (s, 2H), 4.14 (s, 2H). MS: m/z 421.9 (M+H$^+$).

Example 185: Synthesis of 2-{[4-(3-Pyridin-4-ylmethyl-ureido)-benzenesulfonylamino]-methyl}-benzoic acid methyl ester

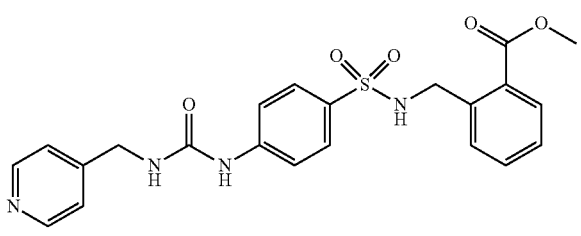 [SMILES: COC(=O)c1ccccc1CNS(=O)(=O)c1ccc(NC(=O)NCc2ccncc2)cc1]

The title compound was prepared as described in example N-cyclohexyl-4-(3-pyridin-4-ylmethyl-ureido)-benzenesulfonamide. $^1$H NMR (400 MHz, DMSO-$d_6$): δ=9.21 (brs, 1H), 8.52 (d, J=4.0 Hz, 2H), 7.91-7.79 (m, 2H), 7.72-7.64 (m, 2H), 7.64-7.50 (m, 4H), 7.44-7.35 (m, 1H), 7.36-7.25 (m, 2H), 6.95 (t, J=5.6 Hz, 1H), 4.36 (d, J=5.6 Hz, 2H), 4.29 (d, J=6.0 Hz, 2H), 3.80 (s, 3H). MS: m/z 454.9 (M+H$^+$).

Example 186: Synthesis of 3-{[4-(3-Pyridin-4-ylmethyl-ureido)-benzenesulfonylamino]-methyl}-benzoic acid methyl ester

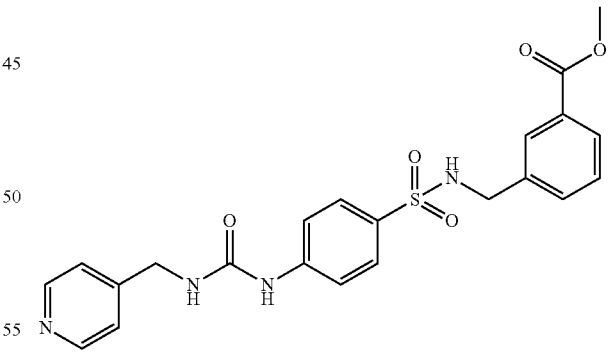

The title compound was prepared as described in example N-cyclohexyl-4-(3-pyridin-4-ylmethyl-ureido)-benzenesulfonamide. $^1$H NMR (300 MHz, DMSO-$d_6$): δ=9.19 (s, 1H), 8.51 (d, J=4.5 Hz, 2H), 8.04 (t, J=6.6 Hz, 1H), 7.82-7.79 (m, 2H), 7.65-7.43 (m, 6H), 7.29 (d, J=5.1 Hz, 2H), 6.93 (t, J=6.9 Hz, 1H), 4.34 (d, J=6.0 Hz, 2H), 4.02 (d, J=6.0 Hz, 2H), 3.84 (s, 3H). MS: m/z 455.1 (M+H$^+$).

Example 187: Synthesis of 4-{[4-(3-Pyridin-4-ylmethyl-ureido)-benzenesulfonylamino]-methyl}-benzoic acid methyl ester

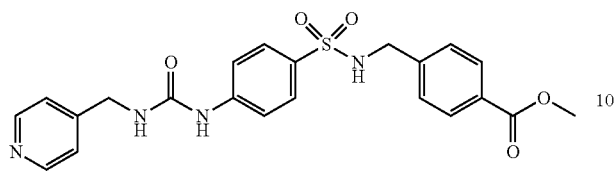

The title compound was prepared as described in example N-cyclohexyl-4-(3-pyridin-4-ylmethyl-ureido)-benzenesulfonamide. $^1$H NMR (400 MHz, DMSO-$d_6$): δ=9.18 (brs, 1H), 8.52 (d, J=6.0 Hz, 2H), 8.04 (t, J=6.4 Hz, 1H), 7.88 (d, J=8.4 Hz, 2H), 7.66 (d, J=9.2 Hz, 2H), 7.57 (d, J=9.2 Hz, 2H), 7.40 (d, J=6.0 Hz, 2H), 7.31 (d, J=6.0 Hz, 2H), 6.92 (t, J=6.0 Hz, 1H), 4.35 (d, J=5.6 Hz, 2H), 4.02 (d, J=6.4 Hz, 2H), 3.83 (s, 3H). MS: m/z 454.9 (M+H$^+$).

Example 188: Synthesis of 4-(3-Pyridin-4-ylmethyl-ureido)-N-(2-trifluoromethyl-benzyl)-benzenesulfonamide

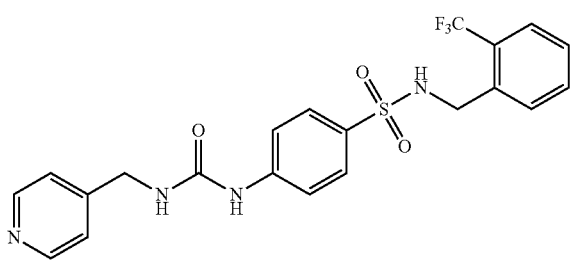 [SMILES: O=C(NCc1ccncc1)Nc1ccc(S(=O)(=O)NCc2ccccc2C(F)(F)F)cc1]

The title compound was prepared as described in example N-cyclohexyl-4-(3-pyridin-4-ylmethyl-ureido)-benzenesulfonamide. $^1$H NMR (300 MHz, DMSO-$d_6$): δ=9.20 (s, 1H), 8.52 (d, J=4.5 Hz, 2H), 8.12-8.08 (m, 1H), 7.68-7.44 (m, 8H), 7.32 (d, J=5.7 Hz, 2H), 6.95-6.91 (m, 1H), 4.35 (d, J=5.4 Hz, 2H), 4.09 (d, J=6.3 Hz, 2H). MS: m/z 465.1 (M+H$^+$).

Example 189: Synthesis of 4-(3-Pyridin-4-ylmethyl-ureido)-N-(3-trifluoromethyl-benzyl)-benzenesulfonamide

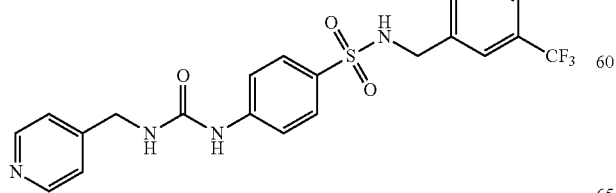

The title compound was prepared as described in example N-cyclohexyl-4-(3-pyridin-4-ylmethyl-ureido)-benzenesulfonamide. $^1$H NMR (300 MHz, DMSO-$d_6$): δ=9.19 (s, 1H), 8.51 (d, J=6.0 Hz, 2H), 8.08-8.04 (m, 1H), 7.65-7.54 (m, 8H), 7.29 (d, J=6.0 Hz, 2H), 6.95-6.89 (m, 1H), 4.35 (d, J=6.0 Hz, 2H), 4.06 (d, J=6.0 Hz, 2H). MS: m/z 464.9 (M+H$^+$).

Example 190: Synthesis of 4-(3-Pyridin-4-ylmethyl-ureido)-N-(4-trifluoromethyl-benzyl)-benzenesulfonamide

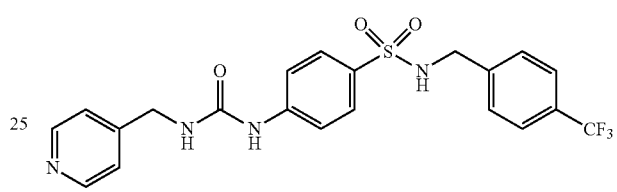

The title compound was prepared as described in example N-(2-Dimethylamino-ethyl)-4-(3-pyridin-4-ylmethyl-ureido)-benzenesulfonamide. $^1$H NMR (400 MHz, DMSO-$d_6$): δ=9.18 (s, 1H), 8.52 (d, J=6.4 Hz, 2H), 8.06 (t, J=6.6 Hz, 1H), 7.66-7.63 (m, 4H), 7.56 (d, J=8.8 Hz, 2H), 7.47 (d, J=8.0 Hz, 2H), 7.29 (d, J=4.8 Hz, 2H), 6.92 (t, J=5.6 Hz, 1H), 4.35 (d, J=6.0 Hz, 2H), 4.04 (d, J=6.8 Hz, 2H). MS: m/z 464.9 (M+H$^+$).

Example 191: Synthesis of 4-(3-Pyridin-4-ylmethyl-ureido)-N-(2-trifluoromethoxy-benzyl)-benzenesulfonamide

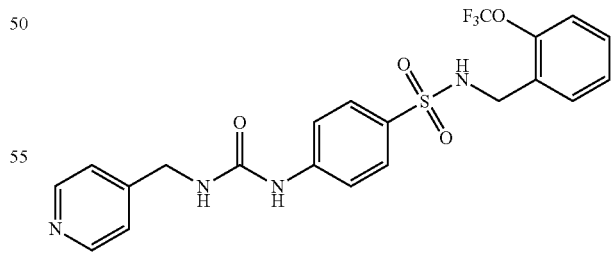

The title compound was prepared as described in example N-cyclohexyl-4-(3-pyridin-4-ylmethyl-ureido)-benzenesulfonamide. $^1$H NMR (400 MHz, DMSO-$d_6$): δ=9.20 (s, 1H), 8.51 (d, J=4.4 Hz, 2H), 8.01-7.98 (m, 1H), 7.65 (d, J=8.0 Hz, 2H), 7.58 (d, J=8.0 Hz, 2H), 7.49 (d, J=7.6 Hz, 1H), 7.41-7.29 (m, 5H), 6.94-6.91 (m, 1H), 4.35 (d, J=5.2 Hz, 2H), 3.99 (d, J=6.0 Hz, 2H). MS: m/z 481.1 (M+H$^+$)

Example 192: Synthesis of 4-(3-Pyridin-4-ylmethyl-ureido)-N-(3-trifluoromethoxy-benzyl)-benzene-sulfonamide

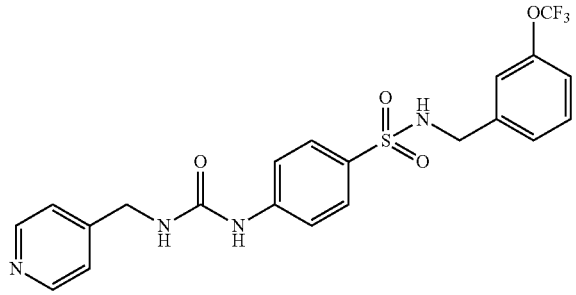 [SMILES: O=C(NCc1ccncc1)Nc1ccc(S(=O)(=O)NCc2cccc(OC(F)(F)F)c2)cc1]

The title compound was prepared as described in example N-cyclohexyl-4-(3-pyridin-4-ylmethyl-ureido)-benzene-sulfonamide. $^1$H NMR (400 MHz, DMSO-d$_6$): δ=9.21 (s, 1H), 8.51 (d, J=4.8 Hz, 2H), 8.05 (t, J=6.0 Hz, 1H), 7.64 (d, J=8.4 Hz, 2H), 7.56 (d, J=8.8 Hz, 2H), 7.42 (t, J=8.0 Hz, 1H), 7.30-7.20 (m, 5H), 6.95-6.92 (m, 1H), 4.34 (d, J=6.0 Hz, 2H), 4.01 (d, J=6.4 Hz, 2H). MS: m/z 481.1 (M+H$^+$).

Example 193: Synthesis of 4-(3-Pyridin-4-ylmethyl-ureido)-N-(4-trifluoromethoxy-benzyl)-benzene-sulfonamide The title compound was prepared as described in example N-cyclohexyl-4-(3-pyridin-4-ylmethyl-ureido)-benzene-sulfonamide. $^1$H NMR (300 MHz, DMSO-d$_6$): δ=9.21 (s, 1H), 8.51 (d, J=5.7 Hz, 2H), 8.01-7.97 (m, 1H), 7.66-7.55 (m, 4H), 7.37-7.25 (m, 6H), 6.96-6.92 (m, 1H), 4.35 (d, J=6.3 Hz, 2H), 3.97 (d, J=6.6 Hz, 2H). MS: m/z 481.1 (M+H$^+$).

Example 194: Synthesis of N-(2-Dimethylamino-benzyl)-4-(3-pyridin-4-ylmethyl-ureido)-benzene-sulfonamide

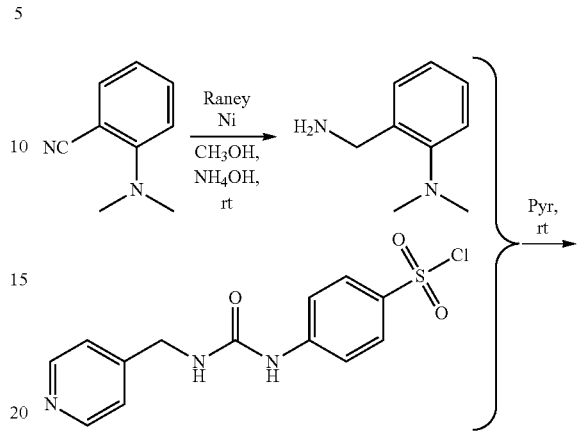

Step 1: To a solution of 2-dimethylamino-benzonitrile (300 mg, 2.1 mmol) in CH$_3$OH (5 mL) and NH$_4$OH (1 mL) was added Raney-Ni (100 mg). The reaction mixture was stirred at room temperature overnight under H$_2$ balloon atmosphere. The suspension was filtered and the filter cake was washed with CH$_3$OH (20 mL). The combined filtrate were concentrated to dryness to give the (2-aminomethyl-phenyl)-dimethyl-amine (200 mg, yield: quantitative) as colorless oil.

Step 2: Step 2 was prepared as described in example N-Methyl-4-(3-pyridin-4-ylmethyl-ureido)-N-(2-trifluoromethyl-benzyl)-benzenesulfonamide. $^1$H NMR (400 MHz, DMSO-d$_6$): δ=9.18 (s, 1H), 8.53 (s, 2H), 7.75 (t, J=6.4 Hz, 1H), 7.69 (d, J=2.8 Hz, 2H), 7.67 (d, J=2.4 Hz, 2H), 7.35-7.30 (m, 3H), 7.21-7.17 (m, 1H), 7.07 (d, J=6.8 Hz, 1H), 6.70 (t, J=6.6 Hz, 1H), 6.93 (t, J=6.4 Hz, 1H), 4.35 (d, J=6.0 Hz, 1H), 3.99 (d, J=6.4 Hz, 1H), 2.50 (s, 6H). MS: m/z 439.9 (M+H$^+$).

Example 195: Synthesis of N-(3-Dimethylamino-benzyl)-4-(3-pyridin-4-ylmethyl-ureido)-benzene-sulfonamide

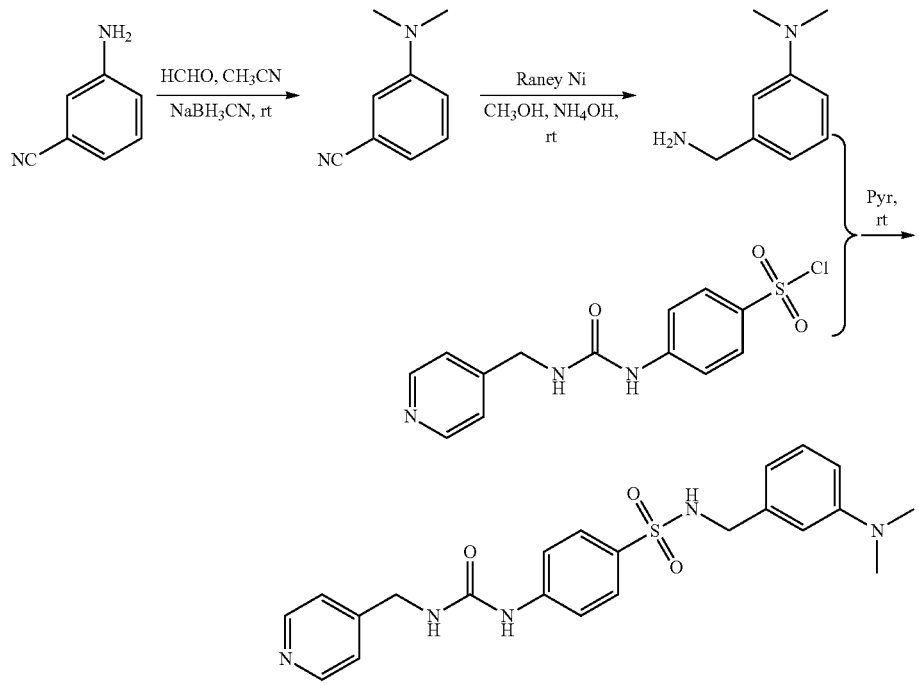

Step 1: To a solution of 3-amino-benzonitrile (1.0 g, 8.5 mmol) and HCHO (2.1 g, 69.0 mmol) in CH₃CN (20 mL) was added NaBH₃CN (2.7 g, 42.5 mmol). The reaction was stirred at room temperature for 2 hrs. HAc (100 mL) was added to adjust pH to 7. The resulting reaction mixture was stirred for 2 hrs. KOH (1 N, 100 mL) was added and the mixture was extracted with EtOAc (100 mL*2). The organic layer was washed with and brine (80 mL), dried over Na₂SO₄ and concentrated. The residue was purified by silica gel column eluting with PE/EtOAc (10:1) to give the 3-dimethylamino-benzonitrile (1.3 g, 100%) as colorless oil. MS: m/z 147.3 (M+H⁺).

Step 2, 3: Step 2 and 3 was prepared as described in example N-(2-dimethylamino-benzyl)-4-(3-pyridin-4-ylmethyl-ureido)-benzenesulfonamide. ¹H NMR (400 MHz, DMSO-d₆) δ=9.16 (s, 1H), 8.51 (d, J=4.8 Hz, 2H), 7.82 (t, J=6.0 Hz, 1H), 7.65 (d, J=8.8 Hz, 2H), 7.57 (d, J=8.8 Hz, 2H), 7.29 (d, J=5.6 Hz, 2H), 7.07 (t, J=8.0 Hz, 1H), 6.91 (t, J=2.0 Hz, 1H), 6.58-6.51 (m, 3H), 4.34 (d, J=6.0 Hz, 2H), 3.86 (d, J=6.0 Hz, 2H), 2.82 (s, 6H). MS: m/z 440.0 (M+H⁺).

Example 196: Synthesis of N-(4-Dimethylamino-benzyl)-4-(3-pyridin-4-ylmethyl-ureido)-benzene-sulfonamide

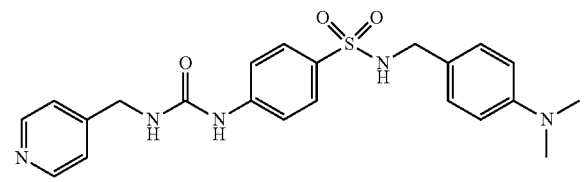 [SMILES: CN(C)c1ccc(CNS(=O)(=O)c2ccc(NC(=O)NCc3ccncc3)cc2)cc1]

The title compound was prepared as described in example N-cyclohexyl-4-(3-pyridin-4-ylmethyl-ureido)-benzene-sulfonamide. ¹H NMR (300 MHz, DMSO-d₆): δ=9.16 (s, 1H), 8.51 (d, J=6.0 Hz, 2H), 7.71-7.55 (m, 5H), 7.29 (d, J=5.1 Hz, 2H), 7.01 (d, J=8.4 Hz, 2H), 6.92-6.90 (m, 1H), 6.62 (d, J=8.1 Hz, 2H), 4.35 (d, J=6.0 Hz, 2H), 3.78 (d, J=6.0 Hz, 2H), 2.84 (s, 6H). MS: m/z 440.1 (M+H⁺).

Example 197: Synthesis of N-(4-Methanesulfonyl-benzyl)-4-(3-pyridin-4-ylmethyl-ureido)-benzene-sulfonamide

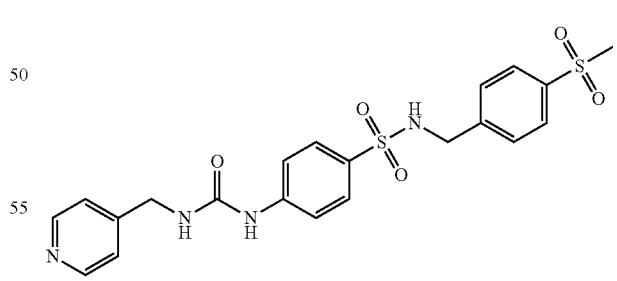

The title compound was prepared as described in example N-cyclohexyl-4-(3-pyridin-4-ylmethyl-ureido)-benzene-sulfonamide. ¹H NMR (400 MHz, DMSO-d₆): δ=9.19 (s, 1H), 8.52 (s, 2H), 8.10 (t, J=6.0 Hz, 1H), 7.82 (d, J=8.0 Hz, 2H), 7.64 (d, J=8.8 Hz, 2H), 7.56 (d, J=8.8 Hz, 2H), 7.50 (d, J=8.0 Hz, 2H), 7.30 (d, J=3.6 Hz, 2H), 6.91 (t, J=4.8 Hz, 1H), 4.34 (d, J=5.6 Hz, 2H), 4.06 (d, J=6.0 Hz, 2H), 3.15 (s, 3H). MS: m/z 474.9 (M+H⁺).

Example 198: Synthesis of N,N-dimethyl-4-((4-(3-(pyridin-4-ylmethyl)ureido)phenylsulfonamido)methyl)benzenesulfonamide

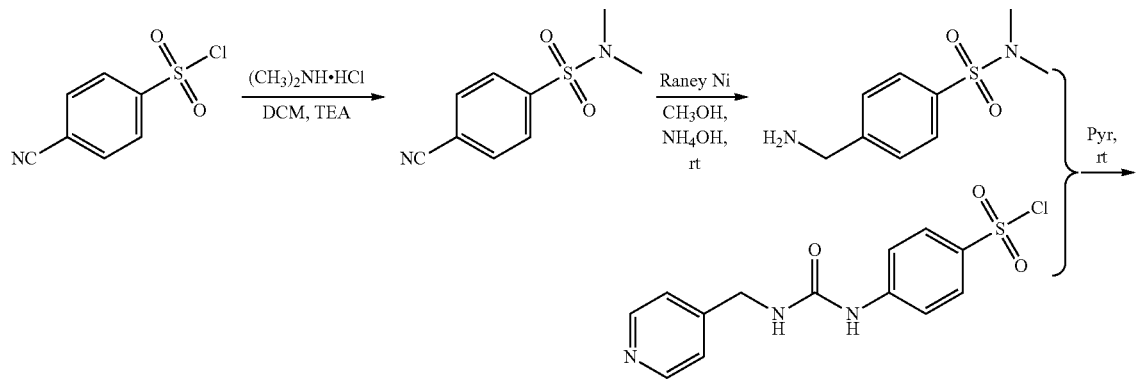

Step 1: To a solution of 4-cyano-benzenesulfonyl chloride (1.0 g, 5.0 mmol) in DCM (20 mL) was added TEA (1.5 g, 15.0 mmol) at 0° C. The reaction was stirred for 1 hr at room temperature. The reaction was concentrated to dryness in vacuum and the residue was purified by silica gel column eluting with PE/EtOAc (10:1) to give the 4-cyano-N,N-dimethyl-benzenesulfonamide (720 mg, 65%) as a white solid.

Step 2, 3: Step 2 and 3 was prepared as described in example N-(2-dimethylamino-benzyl)-4-(3-pyridin-4-ylmethyl-ureido)-benzenesulfonamide. $^1$H NMR (300 MHz, DMSO-$d_6$) δ=9.17 (s, 1H), 8.50 (d, J=5.4 Hz, 2H), 8.12 (t, J=6.6 Hz, 1H), 4.34 (d, J=8.7 Hz, 4H), 7.55-7.48 (m, 4H), 7.28 (d, J=5.4 Hz, 2H), 6.91 (t, J=6.0 Hz, 1H), 4.33 (d, J=5.7 Hz, 2H), 4.08 (d, J=6.3 Hz, 2H), 2.49 (s, 6H). MS: m/z 503.9 (M+H$^+$).

Example 199: Synthesis of N-(4-((dimethylamino)methyl)benzyl)-4-(3-(pyridin-4-ylmethyl)ureido)benzenesulfonamide

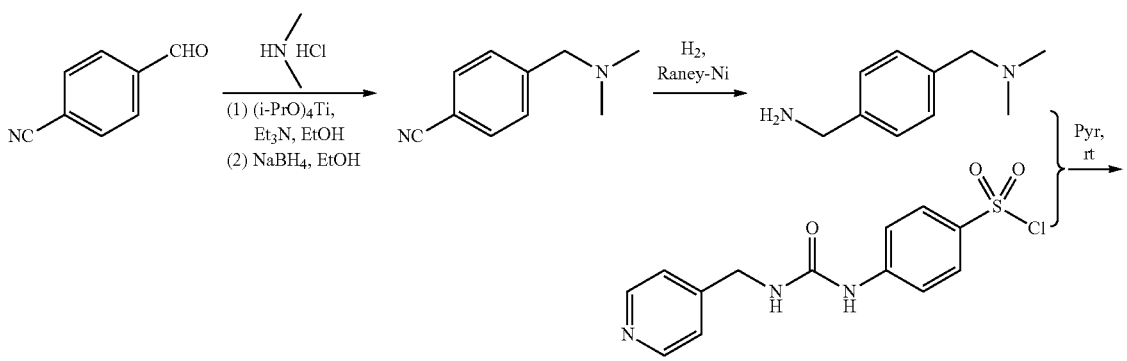

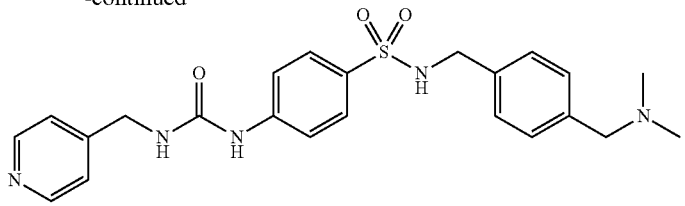

Step 1: To a solution of 4-formyl-benzonitrile (1.30 g, 10 mmoL), dimethylamine.HCl (1.63 g, 20 mmoL) and Et$_3$N (3 mL, 20 mmoL) in EtOH (15 mL) was added (i-PrO)$_4$Ti (6 mL, 20 mmoL) dropwise at room temperature. Then the mixture was stirred at room temperature for 19 hrs. The reaction mixture was poured into aqueous ammonia (30 mL, 30%). The resulting inorganic precipitate was filtered. The filtrate was extracted with DCM (50 mL*2). The extracts were dried over Na$_2$SO$_4$ and concentrated to dryness in vacuum. The residue was purified by silica gel column eluting with DCM/MeOH (100:1) to give 4-dimethylaminomethyl-benzonitrile (500 mg, yield: 31%) as white oil. $^1$H NMR (300 MHz, DMSO-d$_6$): δ=7.77 (d, J=7.2 Hz, 2H), 7.49 (d, J=7.5 Hz, 2H), 3.45 (s, 2H), 2.14 (s, 6H). MS: m/z 161.4 (M+H$^+$).

Step 2: To a solution of 4-dimethylaminomethyl-benzonitrile (240 mg, 1.5 mmoL) in MeOH (5 mL) was added Raney-Ni (40 mg) under H$_2$ atmosphere (balloon) at room temperature. Then the mixture was stirred at room temperature for 2 hrs. The reaction mixture was filtered to remove the catalyst and the filtrate was concentrated to give 4-dimethylaminomethyl-benzylamine (crude) as colorless oil. MS: m/z 165.1 (M+H$^+$).

Step 3: To a solution of 4-dimethylaminomethyl-benzylamine (220 mg, 1.3 mmoL) in pyridine (5 mL) was added 4-(3-pyridin-4-ylmethyl-ureido)-benzenesulfonyl chloride (524 mg, 1.6 mmoL) at room temperature. Then the mixture was stirred at room temperature for 2 hrs. The reaction mixture was concentrated to dryness in vacuum. The residue was purified by silica gel column eluting with DCM/MeOH (2:1) to give the crude product. Then the crude product was purified by Prep-HPLC to give N-(4-dimethylaminomethyl-benzyl)-4-(3-pyridin-4-ylmethyl-ureido)-benzenesulfonamide (23 mg, yield: 4%) as a white solid. $^1$H NMR (400 MHz, DMSO-d$_6$): δ=9.16 (s, 1H), 8.51 (d, J=6.4 Hz, 2H), 7.90 (t, J=6.4 Hz, 1H), 7.64 (d, J=8.8 Hz, 2H), 7.56 (d, J=8.8 Hz, 2H), 7.29 (d, J=6.0 Hz, 2H), 7.18-7.16 (m, 4H), 6.92 (t, J=5.6 Hz, 1H), 4.34 (d, J=6 Hz, 2H), 3.92 (d, J=6.4 Hz, 2H), 3.33 (overlap, 2H), 2.10 (s, 6H). MS: m/z 454.0 (M+H$^+$).

Example 200: Synthesis of N-(4-Methoxymethyl-benzyl)-4-(3-pyridin-4-ylmethyl-ureido)-benzene-sulfonamide

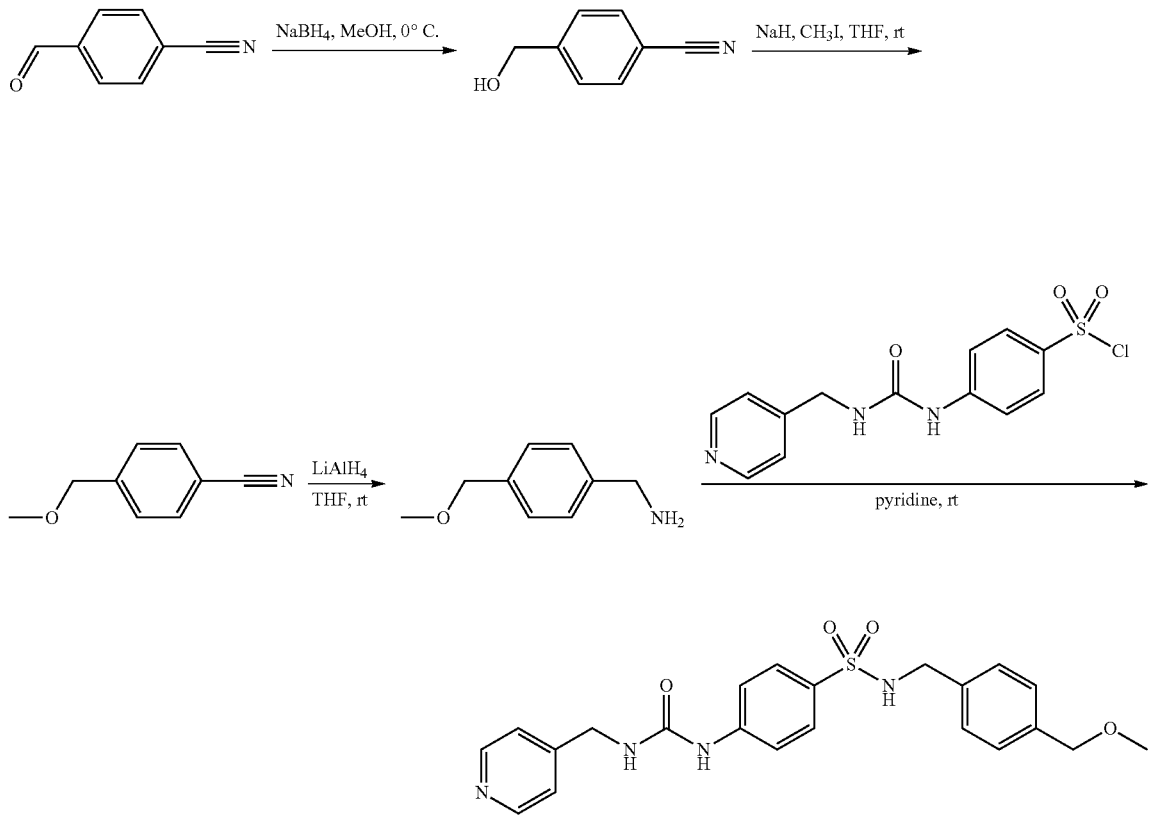

Step 1: To a solution of 4-formyl-benzonitrile (1.51 g, 11.5 mmoL) in MeOH (15 mL) was added NaBH₄ (0.51 g, 13.4 mmoL) at 0° C. Then the mixture was stirred at this temperature for 1.5 hrs. The reaction was quenched with H₂O (7.5 mL) and the resulting mixture was concentrated to remove most of the MeOH. Then the residue was poured into H₂O (20 mL) and extracted with EtOAc (30 mL*2). The combined EtOAc extracts were washed with brine (20 mL), dried over Na₂SO₄ and concentrated to give 4-hydroxymethyl-benzonitrile (1.26 g, yield: 82%) as colorless oil.

Step 2: To a solution of 4-hydroxymethyl-benzonitrile (1.26 g, 9.5 mmoL) in THF (10 mL) was added NaH (0.76 g, 19 mmoL) at −10° C., and the suspension was stirred at this temperature for 0.5 hrs and followed by the addition of MeI (2.7 g, 19 mmol). Then the mixture was stirred at this temperature for 2 hrs. The reaction was quenched with H₂O (50 mL). The mixture was extracted with EtOAc (25 mL*3). The combined EtOAc extracts were dried over Na₂SO₄ and concentrated to give 4-methoxymethyl-benzonitrile (crude) as yellow oil.

Step 3: To a suspension of LiAlH₄ (1.1 g, 28.9 mmoL) in THF (15 mL) was added dropwise a solution of 4-methoxymethyl-benzonitrile (1.4 g, 9.5 mmoL) in THF (15 mL) at 0° C. Then the mixture was stirred at room temperature for 19 hrs. The reaction was quenched with the dropwise addition of H₂O (1.2 mL) at 0° C. and followed by an aqueous NaOH (15%, 1.2 mL) and H₂O (3.6 mL). The mixture was stirred at room temperature for 30 min and the precipitate was filtered and the pad was washed with EtOAc (10 mL). The filtrate was concentrated to give 4-methoxymethyl-benzylamine (1.3 g, yield: 90%) as yellow oil.

Step 4: To a solution of 4-methoxymethyl-benzylamine (251 mg, 1.7 mmoL) in pyridine (5 mL) was added 4-(3-pyridin-4-ylmethyl-ureido)-benzenesulfonyl chloride (650 mg, 2.0 mmoL) at 0° C. and the mixture was stirred overnight at room temperature. The reaction mixture was concentrated to dryness in vacuum. The residue was purified by silica gel column eluting with DCM/MeOH (5:1) to give the yellow crude product. Then the crude was purified by Prep-HPLC to give N-(4-methoxymethyl-benzyl)-4-(3-pyridin-4-ylmethyl-ureido)-benzenesulfonamide (111 mg, yield: 15%) as a white solid. ¹H NMR (400 MHz, DMSO-d₆): δ=9.18 (s, 1H), 8.51 (d, J=6 Hz, 2H), 7.91 (t, J=6.4 Hz, 1H), 7.65 (d, J=8.8 Hz, 2H), 7.57 (d, J=8.8 Hz, 2H), 7.29 (d, J=6 Hz, 2H), 7.23-7.19 (m, 4H), 6.92 (t, J=5.6 Hz, 1H), 4.35 (d, J=6.8 Hz, 4H), 3.92 (d, J=6.4 Hz, 2H), 3.24 (s, 3H). MS: m/z 440.9 (M+H⁺).

Example 201: Synthesis of N-(1-phenylethyl)-4-(3-(pyridin-4-ylmethyl)ureido)benzenesulfonamide

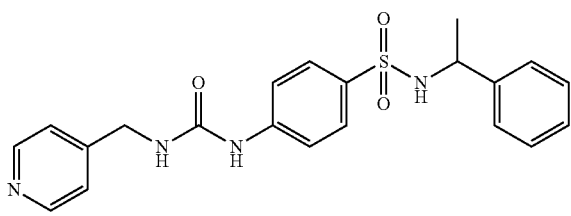 [SMILES: CC(NS(=O)(=O)c1ccc(NC(=O)NCc2ccncc2)cc1)c1ccccc1]

The title compound was prepared as described in example N-cyclohexyl-4-(3-pyridin-4-ylmethyl-ureido)-benzene-sulfonamide. ¹H NMR (400 MHz, CD₃OD): δ=8.78-8.76 (m, 2H), 8.05-8.04 (m, 2H), 7.57-7.54 (m, 2H), 7.45-7.43 (m, 2H), 7.17-7.11 (m, 5H), 4.69 (s, 2H), 4.39-4.35 (m, 1H), 1.30 (d, J=8.0 Hz, 3H). MS: m/z 410.9 (M+H⁺).

Example 202: Synthesis of N-Pyridin-4-ylmethyl-4-(3-pyridin-4-ylmethyl-ureido)-benzenesulfonamide

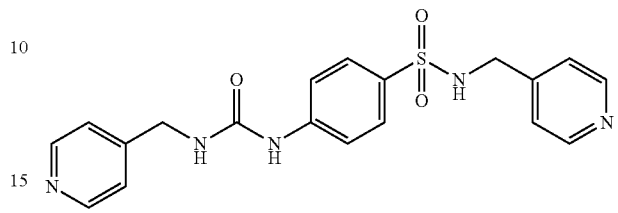

The title compound was prepared as described in example N-cyclohexyl-4-(3-pyridin-4-ylmethyl-ureido)-benzene-sulfonamide. ¹H NMR (400 MHz, DMSO-d₆): δ=9.26 (brs, 1H), 8.52-8.46 (dd, J=4.4 Hz, 4H), 8.11 (brs, 1H), 7.67-7.57 (dd, J=8.4 Hz, 4H), 7.30-7.26 (dd, J=4.8 Hz, 4H), 6.95 (brs, 1H), 4.35 (d, J=6.0 Hz, 2H), 3.98 (d, J=6.0 Hz, 2H). MS: m/z 397.9 (M+H⁺)

Example 203: Synthesis of 4-(3-Pyridin-4-ylmethyl-ureido)-N-(1,2,3,4-tetrahydro-naphthalen-1-yl)-benzenesulfonamide

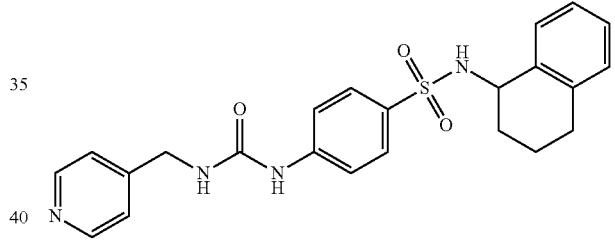

The title compound was prepared as described in example N-cyclohexyl-4-(3-pyridin-4-ylmethyl-ureido)-benzene-sulfonamide. ¹H NMR (400 MHz, DMSO-d₆): δ=9.23 (s, 1H), 8.50 (d, J=5.4 Hz, 2H), 7.84 (d, J=8.2 Hz, 1H), 7.73 (d, J=5.4 Hz, 2H), 7.61 (d, J=8.8 Hz, 2H), 7.32 (d, J=5.6 Hz, 2H), 7.15-7.07 (m, 3H), 7.03 (d, J=7.6 Hz, 1H), 6.95 (t, J=5.6 Hz, 1H), 4.36 (d, J=5.6 Hz, 3H), 2.63 (overlap, 2H), 1.77 (s, 1H), 1.55 (d, J=6.0 Hz, 3H). MS: m/z 436.9 (M+H⁺).

Example 204: Synthesis of N,N-Dimethyl-4-(3-pyridin-4-ylmethyl-ureido)-benzenesulfonamide

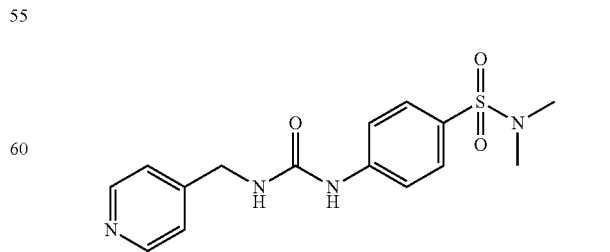

The title compound was prepared as described in example N-cyclohexyl-4-(3-pyridin-4-ylmethyl-ureido)-benzenesulfonamide. ¹H NMR (400 MHz, CD₃OD): δ=8.48 (d, J=5.2 Hz, 2H), 7.68-7.62 (m, 4H), 7.41 (d, J=4.8 Hz, 2H), 4.47 (s, 2H), 2.65 (s, 6H). MS: m/z 335.0 (M+H⁺).

Example 205: Synthesis of N,N-Diethyl-4-(3-pyridin-4-ylmethyl-ureido)-benzenesulfonamide

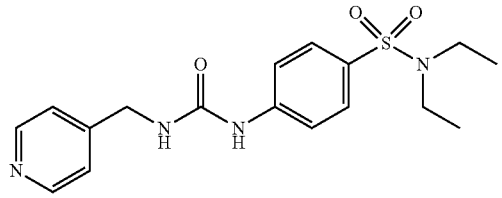 [SMILES: CCN(CC)S(=O)(=O)c1ccc(NC(=O)NCc2ccncc2)cc1]

The title compound was prepared as described in example N-cyclohexyl-4-(3-pyridin-4-ylmethyl-ureido)-benzenesulfonamide. ¹H NMR (400 MHz, DMSO-d₆): δ=9.22 (brs, 1H), 8.50 (dd, J=4.4, 1.6 Hz, 2H), 7.66-7.56 (m, 4H), 7.29 (d, J=6.0 Hz, 2H), 6.92 (t, J=6.0 Hz, 1H), 4.34 (d, J=6.4 Hz, 2H), 3.11 (q, J=7.2 Hz, 4H), 1.02 (t, J=7.2 Hz, 6H). MS: m/z 363.0 (M+H⁺).

Example 206: Synthesis of N-(2-Hydroxy-ethyl)-N-methyl-4-(3-pyridin-4-ylmethyl-ureido)-benzenesulfonamide

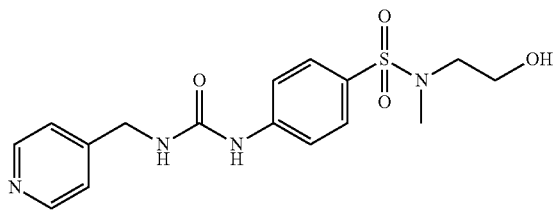 [SMILES: CN(CCO)S(=O)(=O)c1ccc(NC(=O)NCc2ccncc2)cc1]

The title compound was prepared as described in example N-cyclohexyl-4-(3-pyridin-4-ylmethyl-ureido)-benzenesulfonamide. ¹H NMR (400 MHz, DMSO-d₆): δ=9.27 (brs, 1H), 8.50 (d, J=6.0 Hz, 2H), 7.62 (s, 4H), 7.29 (d, J=5.6 Hz, 2H), 6.95-6.93 (brs, 1H), 4.79-4.77 (brs, 1H), 4.35 (d, J=5.6 Hz, 2H), 3.50 (dd, J=11.6, 6.0 Hz, 2H), 2.95-2.92 (t, 2H), 2.67 (s, 3H). MS: m/z 364.9 (M+H⁺)

Example 207: Synthesis of N-Cyclopentyl-N-methyl-4-(3-pyridin-4-ylmethyl-ureido)-benzenesulfonamide

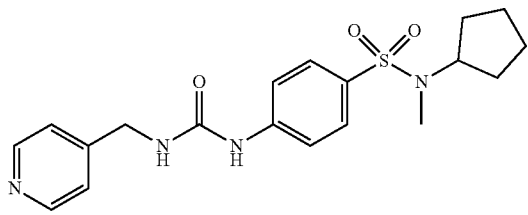 [SMILES: CN(C1CCCC1)S(=O)(=O)c1ccc(NC(=O)NCc2ccncc2)cc1]

The title compound was prepared as described in example N-cyclohexyl-4-(3-pyridin-4-ylmethyl-ureido)-benzenesulfonamide. ¹H NMR (400 MHz, DMSO-d₆): δ=9.25 (brs, 1H), 8.51 (dd, J=4.8, 1.6 Hz, 2H), 7.67-7.57 (m, 4H), 7.29 (d, J=6.0 Hz, 2H), 6.94 (t, J=6.0 Hz, 1H), 4.34 (d, J=6.0 Hz, 2H), 4.22-4.11 (m, 1H), 2.59 (s, 3H), 1.55-1.43 (m, 4H), 1.42-1.34 (m, 2H), 1.32-1.20 (m, 2H). MS: m/z 389.1 (M+H⁺).

Example 208: Synthesis of N-benzyl-N-methyl-4-(3-(pyridin-4-ylmethyl)ureido)benzenesulfonamide

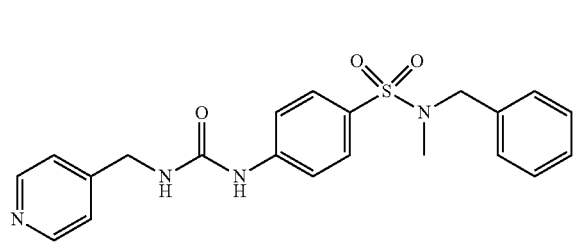 [SMILES: CN(Cc1ccccc1)S(=O)(=O)c1ccc(NC(=O)NCc2ccncc2)cc1]

The title compound was prepared as described in example N-cyclohexyl-4-(3-pyridin-4-ylmethyl-ureido)-benzenesulfonamide. ¹H NMR (400 MHz, CD₃OD): δ=8.50-8.48 (m, 2H), 7.77-7.74 (m, 2H), 7.69-7.65 (m, 2H), 7.43-7.41 (m, 2H), 7.35-7.31 (m, 5H), 4.49 (s, 2H), 4.12 (s, 2H), 2.56 (s, 3H). MS: m/z 411.0 (M+H⁺).

Example 209: Synthesis of N-(2-Fluoro-benzyl)-N-methyl-4-(3-pyridin-4-ylmethyl-ureido)-benzenesulfonamide

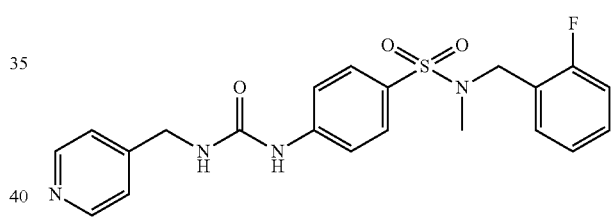

The title compound was prepared as described in example N-cyclohexyl-4-(3-pyridin-4-ylmethyl-ureido)-benzenesulfonamide. ¹H NMR (400 MHz, DMSO-d₆): δ=9.29 (s, 1H), 8.49 (d, J=7.5 Hz, 2H), 7.72-7.65 (m, 4H), 7.41-7.39 (m, 2H), 7.30 (d, J=5.6 Hz, 2H), 7.24-7.20 (m, 2H), 6.96 (t, J=6.0 Hz, 1H), 4.36 (d, J=6.0 Hz, 2H), 4.13 (s, 2H), 2.53-2.49 (m, 3H). MS: m/z 428.9 (M+H⁺)

Example 210: Synthesis of N-(2-Chloro-benzyl)-N-methyl-4-(3-pyridin-4-ylmethyl-ureido)-benzenesulfonamide

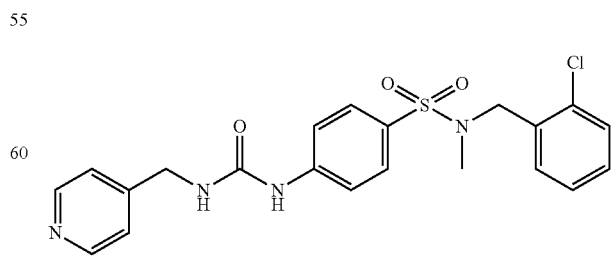

The title compound was prepared as described in example N-cyclohexyl-4-(3-pyridin-4-ylmethyl-ureido)-benzenesulfonamide. ¹H NMR (400 MHz, DMSO-d₆): δ=9.32 (s, 1H), 8.52 (d, J=6.0 Hz, 2H), 7.74-7.66 (m, 4H), 7.47 (d, J=4.8 Hz, 2H), 7.39-7.30 (m, 4H), 6.97 (t, J=6.0 Hz, 1H), 4.36 (d, J=6.4 Hz, 2H), 4.19 (s, 2H), 2.55-2.49 (m, 3H). MS: m/z 444.9 (M+H⁺)

Example 211: Synthesis of 1-[4-(Piperazine-1-sulfonyl)-phenyl]-3-pyridin-4-ylmethyl-urea

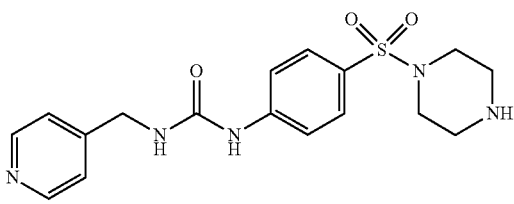 [SMILES: O=C(NCc1ccncc1)Nc1ccc(S(=O)(=O)N2CCNCC2)cc1]

The title compound was prepared as described in example N-cyclohexyl-4-(3-pyridin-4-ylmethyl-ureido)-benzenesulfonamide. ¹H NMR (400 MHz, DMSO-d₆): δ=9.42 (brs, 1H), 8.50 (dd, J=4.4, 1.6 Hz, 2H), 7.66 (d, J=8.8 Hz, 2H), 7.56 (d, J=8.8 Hz, 2H), 7.29 (d, J=6.0 Hz, 2H), 7.08 (t, J=6.0 Hz, 1H), 4.34 (d, J=6.0 Hz, 2H), 2.80-2.64 (m, 8H). MS: m/z 376.0 (M+H⁺).

Example 212: Synthesis of N-Cyclobutylmethyl-N-methyl-4-(3-pyridin-4-ylmethyl-ureido)-benzenesulfonamide Step 1: To a solution of C-cyclobutyl-methylamine hydrochloride (1.0 g, 8.2 mmol) in THF (50 mL) was added Boc₂O (1.97 g, 9.0 mmol) and TEA (1.7 g, 16.4 mmol). After stirring at room temperature overnight, the reaction mixture was evaporated in vacuum. The residue was purified by silica gel column chromatograph eluting with PE/EtOAc (10:1) to afford cyclobutylmethyl-carbamic acid tert-butyl ester (1.25 g, 82%) as colorless oil. ¹H NMR (400 MHz, CD₃Cl): δ=4.48 (s, 1H), 3.14 (t, J=6.4 Hz, 2H), 2.46-2.39 (m, 1H), 2.07-2.00 (m, 2H), 1.93-1.84 (m, 2H), 1.71-1.64 (m, 2H), 1.44 (s, 9H).

Step 2: To a solution of cyclobutylmethyl-carbamic acid tert-butyl ester (1.25 g, 6.75 mmol) in THF (50 mL) was added LiAlH₄ (1.28 g, 33.8 mmol). After stirring at reflux overnight, the reaction was quenched with H₂O (2 mL). Then the mixture was dried over anhydrous Na₂SO₄ and filtered. The filtrate was evaporated in vacuum to afford cyclobutylmethyl-methyl-amine as a crude product which was used for next step without further purification.

Step 3: To a solution of 4-(3-pyridin-4-ylmethyl-ureido)-benzenesulfonic acid (200 mg, 0.65 mmol) in DCM (15 mL) was added (COCl)₂ (165 mg, 1.3 mmol) and DMF (2 drops). After stirring at room temperature for 5 hrs, the reaction mixture was evaporated in vacuum. The residue was dissolved in DMF (5 mL) and then cyclobutylmethyl-methyl-amine (97 mg, 0.98 mmol) and DIPEA (252 mg, 1.95 mmol) were added. After stirring at room temperature overnight, the residue was purified by pre-HPLC to afford N-cyclobutylmethyl-N-methyl-4-(3-pyridin-4-ylmethyl-ureido)-benzenesulfonamide (21 mg, 8%) as a yellow solid. ¹H NMR (400 MHz, CD₃OD): δ=8.47 (dd, J=4.8, 1.6 Hz, 2H), 7.67 (d, J=9.2 Hz, 2H), 7.61 (d, J=8.8 Hz, 2H), 7.41 (d, J=6.0 Hz, 2H), 4.47 (s, 2H), 2.97 (d, J=7.2 Hz, 2H), 2.65 (s, 3H), 2.59-2.51 (m, 1H), 2.08-2.01 (m, 2H), 1.95-1.82 (m, 2H), 1.78-1.71 (m, 2H). MS: m/z 388.9 (M+H⁺).

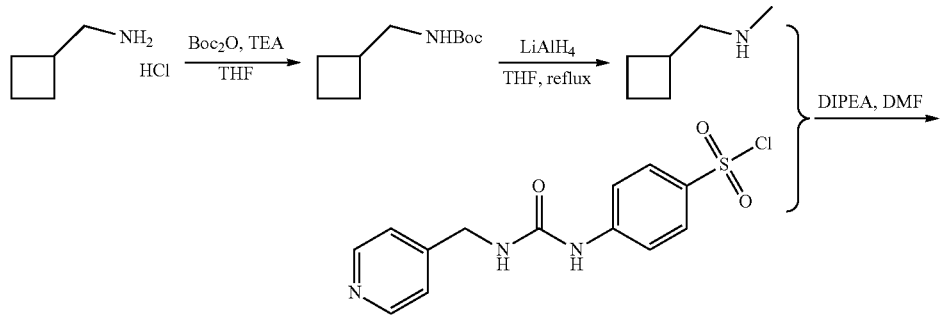

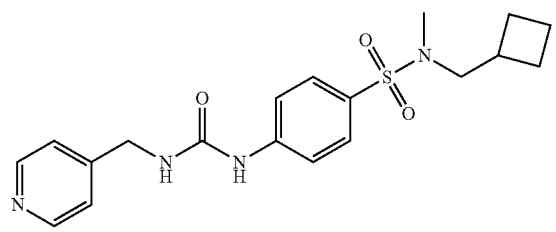

Example 213: Synthesis of N-Cyclohexyl-N-methyl-4-(3-pyridin-4-ylmethyl-ureido)-benzene-sulfonamide

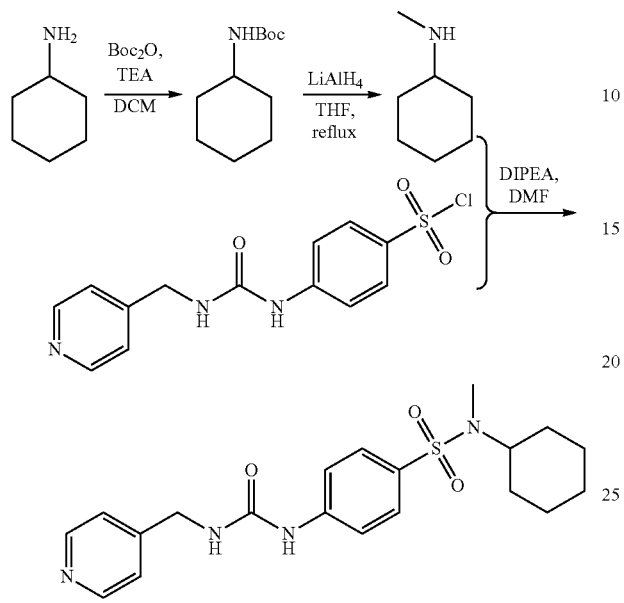

Example 214: Synthesis of N-Cyclopentyl-N-isobutyl-4-(3-pyridin-4-ylmethyl-ureido)-benzene-sulfonamide

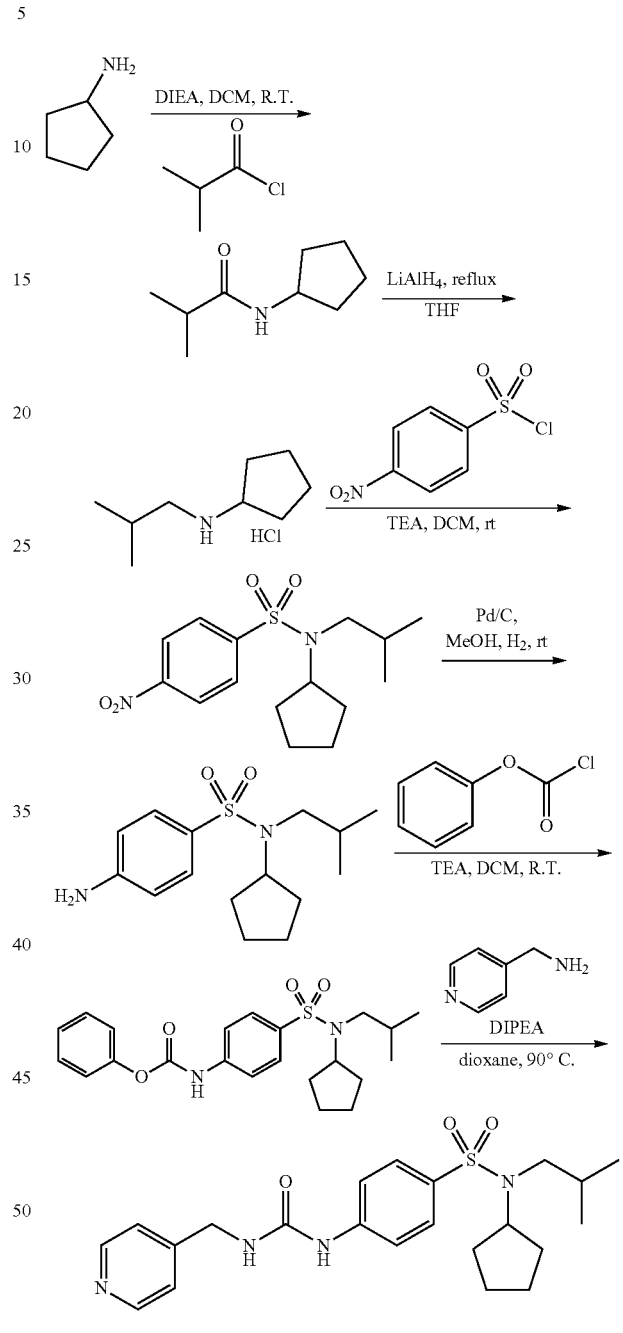

Step 1: To a solution of cyclohexylamine (1.0 g, 10.1 mmol) in DCM (50 mL) was added Boc$_2$O (2.2 g, 10.1 mmol) and TEA (2.04 g, 20.2 mmol). After stirring at room temperature overnight, the reaction mixture was evaporated in vacuum. The residue was purified by silica gel column chromatograph eluting with PE/EtOAc (10:1) to afford cyclohexyl-carbamic acid tert-butyl ester (1.93 g, 97%) as a white solid.

Step 2: To a solution of cyclohexyl-carbamic acid tert-butyl ester (1.0 g, 5 mmol) in THF (30 mL) was added LiAlH$_4$ (760 mg, 20 mmol). After stirring at reflux overnight, the reaction was quenched with H$_2$O (2 mL). Then the mixture was dried over anhydrous Na$_2$SO$_4$ and filtered. The filtrate was evaporated in vacuum to afford cyclohexyl-methyl-amine as a crude product which was used for next step without further purification.

Step 3: To a solution of 4-(3-pyridin-4-ylmethyl-ureido)-benzenesulfonic acid (150 mg, 0.49 mmol) in DCM (15 mL) was added (COCl)$_2$ (124 mg, 0.98 mmol) and DMF (2 drops). After stirring at room temperature for 5 hrs, the reaction mixture was evaporated in vacuum. The residue was dissolved in DMF (5 mL) and then cyclohexyl-methyl-amine (83 mg, 0.74 mmol) and DIPEA (190 mg, 1.47 mmol) were added. After stirring at room temperature overnight, the residue was purified by pre-HPLC to afford N-cyclohexyl-N-methyl-4-(3-pyridin-4-ylmethyl-ureido)-benzene-sulfonamide (21 mg, 11%) as a white solid. $^1$H NMR (400 MHz, DMSO-d$_6$): δ=9.31 (s, 1H), 8.50 (d, J=5.6 Hz, 2H), 7.65-7.58 (m, 4H), 7.29 (d, J=4.8 Hz, 2H), 7.00 (s, 1H), 4.34 (d, J=6.0 Hz, 2H), 3.62-3.54 (m, 1H), 2.63 (s, 3H), 1.67-1.64 (m, 2H), 1.53-1.50 (m, 1H), 1.32-1.19 (m, 7H). MS: m/z 403.0 (M+H)$^+$.

Step 1: To a solution of cyclopentylamine (500 mg, 5.9 mmol) in DCM (10 mL) was added isobutyryl chloride (629 mg, 5.9 mmol) and DIPEA (1.1 g, 8.6 mmol). After stirring at room temperature overnight, the reaction mixture was evaporated in vacuum. The residue was purified by silica gel column chromatograph eluting with PE/EtOAc (3:1) to afford N-cyclopentyl-isobutyramide (878 mg, 96%) as a yellow solid.

Step 2: To a solution of N-cyclopentyl-isobutyramide (300 mg, 1.9 mmol) in THF (20 mL) was added LiAlH$_4$ (289 mg, 7.6 mmol). After stirring at reflux overnight, the reaction was quenched with H$_2$O (1 mL). Then the mixture was dried over anhydrous Na₂SO₄ and filtered. The filtrate was adjusted to pH=3 with conc. HCl and evaporated in vacuum to afford cyclopentyl-isobutyl-amine hydrochloride as a crude product which was used for next step without further purification.

Step 3: To a solution of cyclopentyl-isobutyl-amine hydrochloride (340 mg, 1.9 mmol) in DCM (10 mL) was added 4-nitro-benzenesulfonyl chloride (463 mg, 2.1 mmol) and TEA (384 mg, 3.8 mmol). After stirring at room temperature overnight, the reaction mixture was evaporated in vacuum. The residue was purified by silica gel column chromatograph eluting with PE/EtOAc (10:1) to afford N-cyclopentyl-N-isobutyl-4-nitro-benzenesulfonamide (110 mg, 18%) as yellow oil. ¹H NMR (400 MHz, CD₃OD): δ=8.40 (d, J=9.2 Hz, 2H), 8.07 (d, J=8.8 Hz, 2H), 4.16-4.09 (m, 1H), 2.98 (d, J=7.6 Hz, 2H), 2.09-2.03 (m, 1H), 1.64-1.60 (m, 4H), 1.50-1.41 (m, 4H), 0.95 (d, J=6.8 Hz, 6H).

Step 4: To a solution of N-cyclopentyl-N-isobutyl-4-nitro-benzenesulfonamide (110 mg, 0.37 mmol) in MeOH (10 mL) was added 10% Pd/C (39 mg, 0.04 mmol). After stirring at room temperature under balloon hydrogen atmosphere overnight, the reaction mixture was filtered. The filtrate was evaporated in vacuum to afford 4-amino-N-cyclopentyl-N-isobutyl-benzenesulfonamide as a crude product which was used for next step without further purification.

Step 5: To a solution of 4-amino-N-cyclopentyl-N-isobutyl-benzenesulfonamide in DCM (5 mL) was added phenyl chloroformate (116 mg, 0.74 mmol) and DIPEA (95.6 mg, 0.74 mmol). After stirring at room temperature overnight, the reaction mixture was evaporated in vacuum. The residue was purified by silica gel column chromatograph eluting with PE/EtOAc (3:1) to afford [4-(cyclopentyl-isobutyl-sulfamoyl)-phenyl]-carbamic acid phenyl ester as the crude product.

Step 6: To a solution of [4-(cyclopentyl-isobutyl-sulfamoyl)-phenyl]-carbamic acid phenyl ester (crude, 0.35 mmol) in dioxane (10 mL) was added C-pyridin-4-yl-methylamine (56.8 mg, 0.53 mmol) and DIPEA (90.5 mg, 0.7 mmol). After stirring at 90° C. for 5 hrs, the reaction mixture was concentrated in vacuum. The residue was purified by pre-HPLC to afford N-cyclopentyl-N-isobutyl-4-(3-pyridin-4-ylmethyl-ureido)-benzenesulfonamide (40 mg, 27%) as a white solid. ¹H NMR (400 MHz, DMSO-d₆): δ=9.21 (s, 1H), 8.50 (dd, J=4.8, 1.6 Hz, 2H), 7.65 (d, J=9.2 Hz, 2H), 7.58 (d, J=8.8 Hz, 2H), 7.29 (d, J=5.6 Hz, 2H), 6.92 (t, J=6.0 Hz, 1H), 4.34 (d, J=6.0 Hz, 2H), 4.00-3.96 (m, 1H), 2.77 (d, J=7.2 Hz, 2H), 2.00-1.94 (m, 1H), 1.51-1.26 (m, 8H), 0.88 (d, J=6.8 Hz, 6H). MS: m/z 431.0 (M+H)⁺.

Example 215: Synthesis of N-Cyclopentyl-N-ethyl-4-(3-pyridin-4-ylmethyl-ureido)-benzenesulfonamide

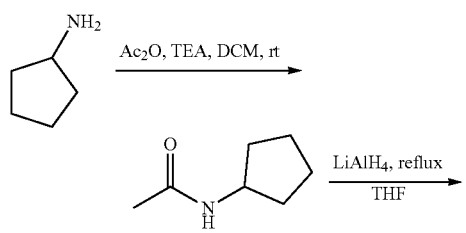

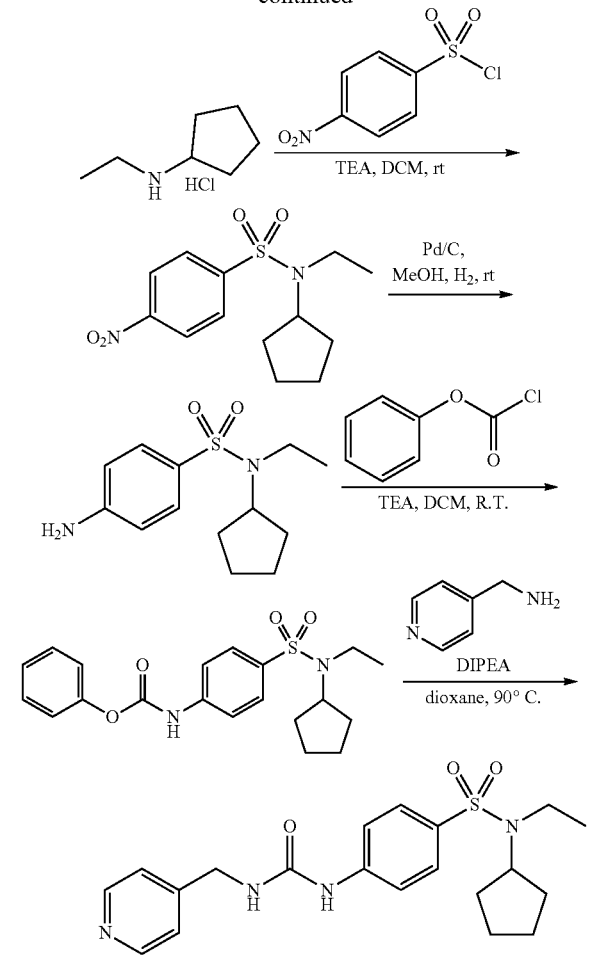

Step 1: To a solution of cyclopentylamine (1.0 g, 11.7 mmol) in DCM (50 mL) was added Ac₂O (1.32 g, 12.9 mmol) and TEA (2.37 g, 23.4 mmol). After stirring at room temperature overnight, the reaction mixture was evaporated in vacuum. The residue was purified by silica gel column chromatograph eluting with PE/EtOAc (1:1) to afford N-cyclopentyl-acetamide (1.24 g, 83%) as colorless oil. ¹H NMR (400 MHz, CDCl₃): δ=5.62 (s, 1H), 4.24-4.15 (m, 1H), 2.02-1.96 (m, 5H), 1.69-1.53 (m, 4H), 1.41-1.33 (m, 2H).

Step 2: To a solution of N-cyclopentyl-acetamide (1.35 g, 10.6 mmol) in THF (30 mL) was added LiAlH₄ (1.6 g, 42.4 mmol). After stirring at reflux overnight, the reaction was quenched with H₂O (2 mL). Then the mixture was dried over anhydrous MgSO₄ and filtered. The filtrate was adjusted to pH=3 with conc.HCl and evaporated in vacuum to afford cyclopentyl-ethyl-amine hydrochloride as a crude product which was used for next step without further purification.

Step 3: To a solution of cyclopentyl-ethyl-amine hydrochloride (820 mg, 3.6 mmol) in DCM (15 mL) was added 4-nitro-benzenesulfonyl chloride (600 mg, 3.6 mmol) and TEA (729 mg, 7.2 mmol). After stirring at room temperature overnight, the reaction mixture was evaporated in vacuum. The residue was purified by silica gel column chromatograph eluting with PE/EtOAc (10:1) to afford N-cyclopentyl-N-ethyl-4-nitro-benzenesulfonamide (600 mg, 56%) as a yellow solid. ¹H NMR (400 MHz, DMSO-d₆): δ=8.38 (d, J=8.8 Hz, 2H), 8.10 (d, J=8.4 Hz, 2H), 4.19-4.11 (m, 1H), 3.15 (q, J=6.8 Hz, 2H), 1.65-1.52 (m, 4H), 1.46-1.39 (m, 2H), 1.35-1.28 (m, 2H), 1.19 (t, J=6.8 Hz, 3H).

Step 4: To a solution of N-cyclopentyl-N-ethyl-4-nitro-benzenesulfonamide (250 mg, 0.84 mmol) in EtOH (15 mL) was added 10% Pd/C (89 mg, 0.08 mmol). After stirring overnight at room temperature under balloon hydrogen atmosphere, the reaction mixture was filtered. The filtrate was evaporated in vacuum to afford 4-amino-N-cyclopentyl-N-ethyl-benzenesulfonamide as a crude product which was used for next step without further purification.

Step 5: To a solution of 4-amino-N-cyclopentyl-N-ethyl-benzenesulfonamide (226 mg, 0.84 mmol) in DCM (10 mL) was added phenyl chloroformate (263 mg, 1.68 mmol) and DIPEA (217 mg, 1.68 mmol). After stirring at room temperature overnight, the reaction mixture was evaporated in vacuum. The residue was purified by silica gel column chromatograph eluting with PE/EtOAc (4:1) to afford [4-(cyclopentyl-ethyl-sulfamoyl)-phenyl]-carbamic acid phenyl ester (210 mg, 64%) as yellow oil.

Step 6: To a solution of [4-(cyclopentyl-ethyl-sulfamoyl)-phenyl]-carbamic acid phenyl ester (150 mg, 0.38 mmol) in dioxane (10 mL) was added C-pyridin-4-yl-methylamine (61.6 mg, 0.57 mmol) and DIPEA (98 mg, 0.76 mmol). After stirring at 90° C. overnight, the reaction mixture was concentrated in vacuum. The residue was purified by pre-HPLC to afford N-Cyclopentyl-N-ethyl-4-(3-pyridin-4-ylmethyl-ureido)-benzenesulfonamide (30 mg, 19%) as a yellow solid. $^1$H NMR (400 MHz, DMSO-$d_6$): δ=9.19 (s, 1H), 8.50 (dd, J=4.4, 1.2 Hz, 2H), 7.65 (d, J=9.2 Hz, 2H), 7.58 (d, J=9.2 Hz, 2H), 7.29 (d, J=6.0 Hz, 2H), 6.91 (t, J=6.0 Hz, 1H), 4.34 (d, J=5.6 Hz, 2H), 4.09-4.01 (m, 1H), 3.04 (q, J=7.2 Hz, 2H), 1.58-1.51 (m, 4H), 1.43-1.37 (m, 2H), 1.29-1.18 (m, 2H), 1.16 (t, J=7.2 Hz, 3H). MS: m/z 403.0 (M+H)$^+$.

Example 216: Synthesis of N-methyl-4-(3-(pyridin-4-ylmethyl)ureido)-N-(2-(trifluoromethyl)benzyl)benzenesulfonamide

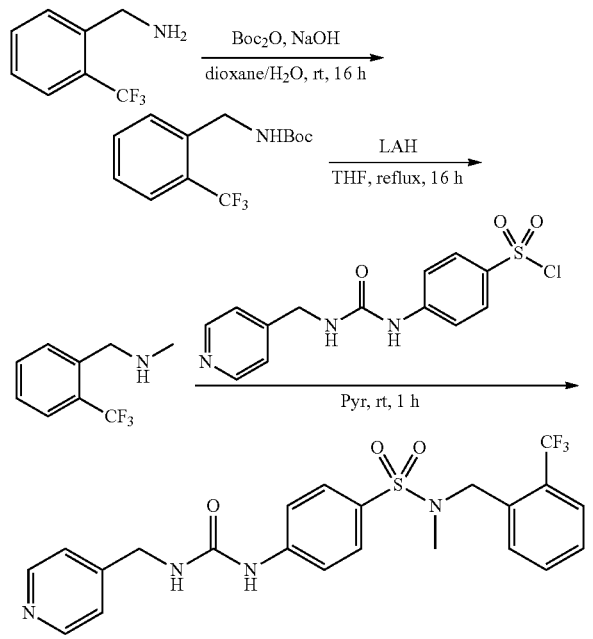

Step 1: To a stirring solution of 2-trifluoromethyl-benzylamine (2.5 g, 14.3 mmol) in dioxane/H$_2$O (80 mL/40 mL) was added NaOH (2.3 g, 57.1 mmol) and Boc$_2$O (3.8 g, 17.1 mmol). After stirring at room temperature for 16 hrs, the reaction mixture was poured to water (100 mL) and extracted with EtOAc (50 mL*2). The combined organic layer was washed with brine (50 mL), dried over Na$_2$SO$_4$ and concentrated. The residue was purified by silica gel column eluting with PE/EtOAc (40:1) to give (2-trifluoromethyl-benzyl)-carbamic acid tert-butyl ester (2.0 g, yield: 51%) as a white solid. $^1$H NMR (400 MHz, CDCl$_3$): δ=7.63 (d, J=7.6 Hz, 1H), 7.59-7.51 (m, 2H), 7.37 (t, J=7.8 Hz, 1H), 4.94 (brs, 1H), 4.50 (d, J=6.0 Hz, 2H), 1.46 (s, 9H).

Step 2: To a solution of (2-trifluoromethyl-benzyl)-carbamic acid tert-butyl ester (2.0 g, 7.3 mmol) in THF (20 mL) was added LAH (830 mg, 21.8 mmol) portionwise at 0° C. After stirring at 70° C. for 16 hrs, H$_2$O (0.8 mL), 15% NaOH (0.8 mL) and H$_2$O (2.5 mL) were then added dropwise at 0° C. The mixture was stirred at room temperature for another 20 min, dried over MgSO$_4$ and filtered. The filtrate was concentrated and purified by silica gel column eluting with DCM/MeOH (30:1) to give methyl-(2-trifluoromethyl-benzyl)-amine (900 mg, yield: 66%) as yellow oil. $^1$H NMR (400 MHz, CDCl$_3$): δ=7.63 (t, J=8.0 Hz, 2H), 7.52 (t, J=7.6 Hz, 1H), 7.35 (t, J=7.6 Hz, 1H), 3.91 (s, 2H), 2.48 (s, 3H).

Step 3: This step was similar to general procedure of N-(2-methoxy-benzyl)-N-methyl-4-(3-pyridin-4-ylmethyl-ureido)-benzenesulfonamide. $^1$H NMR (400 MHz, DMSO-$d_6$): δ=9.32 (s, 1H), 8.51 (dd, J=4.8, 1.6 Hz, 2H), 7.78-7.67 (m, 7H), 7.54 (t, J=7.4 Hz, 1H), 7.31 (d, J=6.0 Hz, 2H), 6.98 (t, J=5.6 Hz, 1H), 4.37 (d, J=5.6 Hz, 2H), 4.26 (s, 2H), 2.56 (s, 3H). MS: m/z 478.9 (M+H$^+$).

Example 217: Synthesis of N-Methyl-4-(3-pyridin-4-ylmethyl-ureido)-N-(2-trifluoromethoxy-benzyl)-benzenesulfonamide

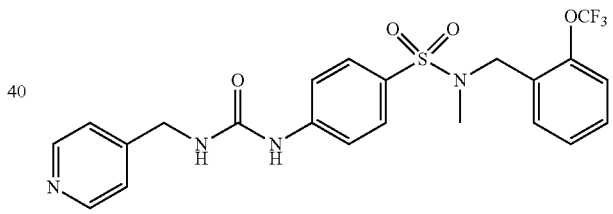

The title compound was prepared as described in example N-methyl-4-(3-pyridin-4-ylmethyl-ureido)-N-(2-trifluoromethyl-benzyl)-benzenesulfonamide. $^1$H NMR (400 MHz, DMSO-$d_6$): δ=9.30 (s, 1H), 8.51 (dd, J=4.4, 1.6 Hz, 2H), 7.73-7.66 (m, 4H), 7.55-7.37 (m, 4H), 7.30 (d, J=6.0 Hz, 2H), 6.96 (t, J=5.6 Hz, 1H), 4.36 (d, J=5.6 Hz, 2H), 4.16 (s, 2H), 2.53-2.49 (m, 3H). MS: m/z 494.9 (M+H$^+$).

Example 218: Synthesis of N-(2-Methoxy-benzyl)-N-methyl-4-(3-pyridin-4-ylmethyl-ureido)-benzenesulfonamide

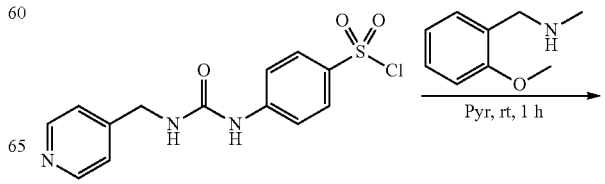

-continued

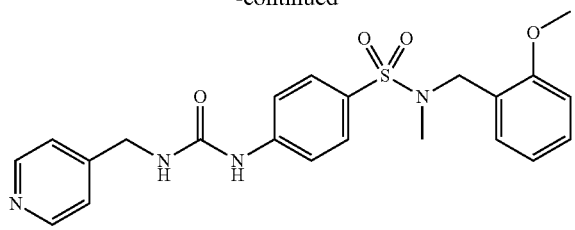

To a stirring solution of 4-(3-pyridin-4-ylmethyl-ureido)-benzenesulfonyl chloride (500 mg, 1.5 mmol) in pyridine (5 mL) was added (2-methoxy-benzyl)-methyl-amine (230 mg, 1.5 mmol). After stirring at room temperature for 1 h, the reaction mixture was concentrated. The residue was purified by silica gel column eluting with DCM/MeOH (10:1) and Prep-HPLC (NH$_4$HCO$_3$) to give N-(2-methoxy-benzyl)-N-methyl-4-(3-pyridin-4-ylmethyl-ureido)-benzenesulfonamide (15 mg, yield: 2%) as a white solid. $^1$H NMR (400 MHz, DMSO-d$_6$): δ=9.27 (s, 1H), 8.51 (dd, J=4.4, 1.2 Hz, 2H), 7.71-7.64 (m, 4H), 7.31-7.27 (m, 4H), 7.01-6.93 (m, 3H), 4.36 (d, J=6.0 Hz, 2H), 4.05 (s, 2H), 3.74 (s, 3H), 2.53 (s, 3H). MS: m/z 440.9 (M+H$^+$).

Example 219: Synthesis of N-Benzyl-N-isopropyl-4-(3-pyridin-4-ylmethyl-ureido)-benzenesulfonamide

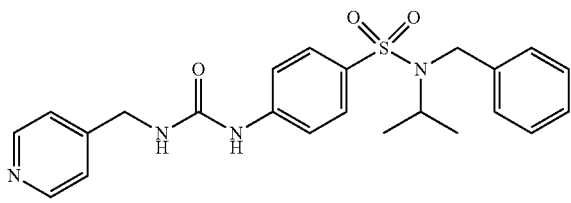 [SMILES: CC(C)N(Cc1ccccc1)S(=O)(=O)c1ccc(NC(=O)NCc2ccncc2)cc1]

The title compound was prepared as described in example N-cyclohexyl-4-(3-pyridin-4-ylmethyl-ureido)-benzenesulfonamide. $^1$H NMR (400 MHz, DMSO-d$_6$): δ=9.35 (brs, 1H), 8.51 (d, J=6.0 Hz, 2H), 7.70 (d, J=8.4 Hz, 2H), 7.61 (d, J=8.8 Hz, 2H), 7.41 (d, J=7.2 Hz, 2H), 7.37-7.28 (m, 4H), 7.24 (t, J=7.2 Hz, 1H), 7.01 (t, J=6.0 Hz, 1H), 4.39-4.31 (m, 4H), 4.05-3.96 (m, 1H), 0.83 (d, J=6.8 Hz, 6H). MS: m/z 439.0 (M+H$^+$).

Example 220: Synthesis of N-Benzyl-N-ethyl-4-(3-pyridin-4-ylmethyl-ureido)-benzenesulfonamide

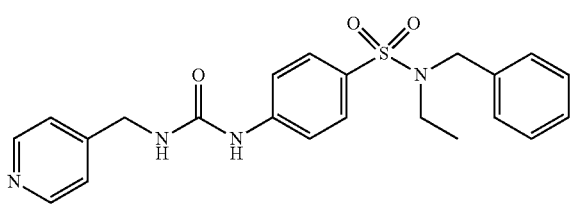 [SMILES: CCN(Cc1ccccc1)S(=O)(=O)c1ccc(NC(=O)NCc2ccncc2)cc1]

The title compound was prepared as described in example N-cyclohexyl-4-(3-pyridin-4-ylmethyl-ureido)-benzenesulfonamide. $^1$H NMR (400 MHz, DMSO-d$_6$): δ=9.29 (brs, 1H), 8.51 (dd, J=4.4, 1.6 Hz, 2H), 7.69 (d, J=9.2 Hz, 2H), 7.64 (d, J=8.8 Hz, 2H), 7.39-7.25 (m, 7H), 6.97 (t, J=6.0 Hz, 1H), 4.35 (d, J=6.0 Hz, 2H), 4.27 (s, 2H), 3.07 (q, J=7.2 Hz, 2H), 0.82 (t, J=7.2 Hz, 3H). MS: m/z 425.0 (M+H$^+$).

Example 221: Synthesis of N-Benzyl-N-cyclopropyl-4-(3-pyridin-4-ylmethyl-ureido)-benzenesulfonamide

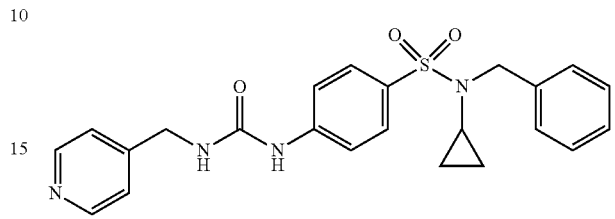

The title compound was prepared as described in example N-cyclohexyl-4-(3-pyridin-4-ylmethyl-ureido)-benzenesulfonamide. $^1$H NMR (400 MHz, DMSO-d$_6$): δ=9.33 (brs, 1H), 8.51 (d, J=5.6 Hz, 2H), 7.72 (d, J=9.2 Hz, 2H), 7.63 (d, J=9.2 Hz, 2H), 7.37-7.23 (m, 7H), 6.98 (t, J=6.0 Hz, 1H), 4.35 (d, J=6.0 Hz, 2H), 4.28 (s, 2H), 2.04-1.96 (m, 1H), 0.56-0.50 (m, 2H), 0.50-0.44 (m, 2H). MS: m/z 436.9 (M+H$^+$).

Example 222: Synthesis of N-Benzyl-N-propyl-4-(3-pyridin-4-ylmethyl-ureido)-benzenesulfonamide

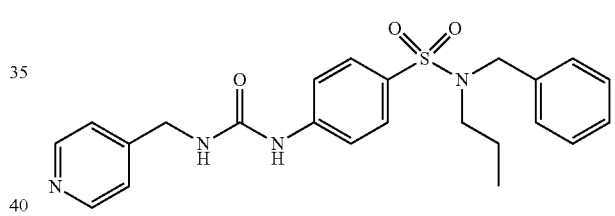

The title compound was prepared as described in example N-cyclohexyl-4-(3-pyridin-4-ylmethyl-ureido)-benzenesulfonamide. $^1$H NMR (400 MHz, DMSO-d$_6$): δ=9.35 (brs, 1H), 8.51 (dd, J=4.4, 1.2 Hz, 2H), 7.71 (d, J=9.2 Hz, 2H), 7.63 (d, J=9.2 Hz, 2H), 7.38-7.24 (m, 7H), 7.01 (t, J=6.0 Hz, 1H), 4.35 (d, J=6.4 Hz, 2H), 4.25 (s, 2H), 2.96 (t, J=7.6 Hz, 2H), 1.30-1.16 (m, 2H), 0.62 (t, J=7.2 Hz, 3H). MS: m/z 439.0 (M+H$^+$).

Example 223: Synthesis of N,N-Dibenzyl-4-(3-pyridin-4-ylmethyl-ureido)-benzenesulfonamide

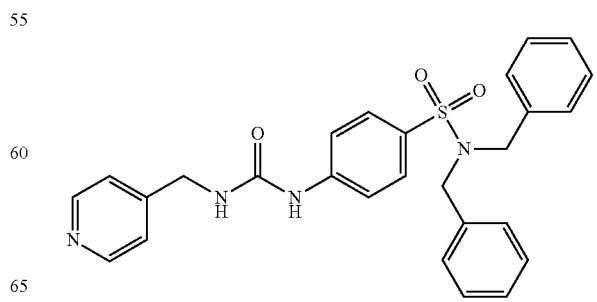

The title compound was prepared as described in example N-cyclohexyl-4-(3-pyridin-4-ylmethyl-ureido)-benzenesulfonamide. ¹H NMR (400 MHz, DMSO-d₆): δ=9.27 (brs, 1H), 8.52 (d, J=5.6 Hz, 2H), 7.74 (d, J=8.8 Hz, 2H), 7.63 (d, J=8.8 Hz, 2H), 7.31 (d, J=6.0 Hz, 2H), 7.25-7.15 (m, 6H), 7.12-7.04 (m, 4H), 6.95 (t, J=6.0 Hz, 1H), 4.36 (d, J=5.6 Hz, 2H), 4.24 (s, 4H). MS: m/z 486.9 (M+H⁺).

Example 224: Synthesis of N-Methyl-N-(2-methyl-benzyl)-4-(3-pyridin-4-ylmethyl-ureido)-benzenesulfonamide

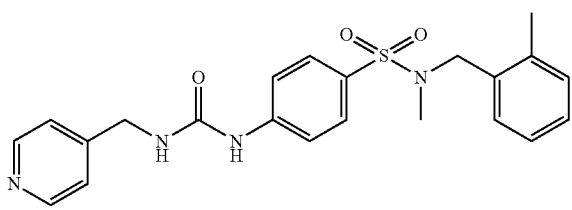 [SMILES: Cc1ccccc1CN(C)S(=O)(=O)c1ccc(NC(=O)NCc2ccncc2)cc1]

The title compound was prepared as described in example N-cyclohexyl-4-(3-pyridin-4-ylmethyl-ureido)-benzenesulfonamide. ¹H NMR (400 MHz, DMSO-d₆): δ=9.29 (s, 1H), 8.51 (d, J=6.0 Hz, 2H), 7.74-7.66 (m, 4H), 7.30 (d, J=5.6 Hz, 2H), 7.22-7.18 (m, 4H), 6.96 (t, J=6.8 Hz, 1H), 4.36 (d, J=6.0 Hz, 2H), 4.04 (s, 2H), 2.41 (s, 3H), 2.32 (s, 3H). MS: m/z 425.0 (M+H⁺).

Example 225: Synthesis of N-Benzyl-4-(3-pyridin-4-ylmethyl-ureido)-N-(2,2,2-trifluoro-ethyl)-benzenesulfonamide

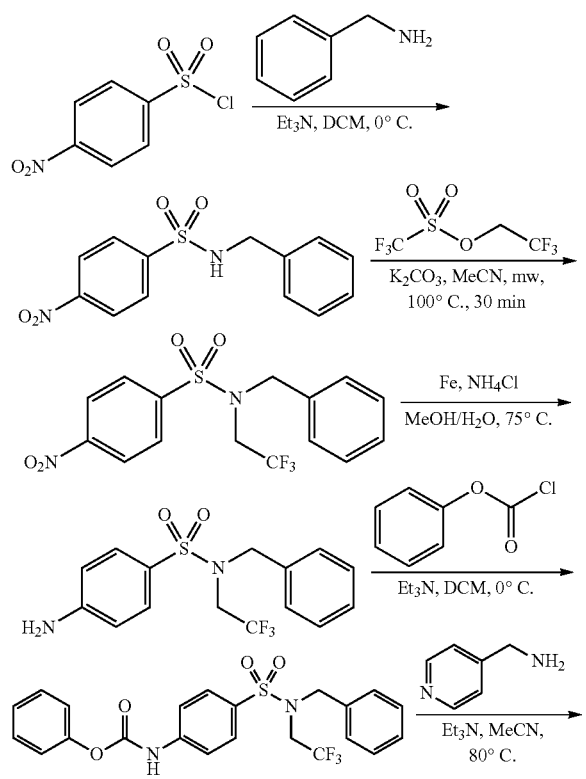

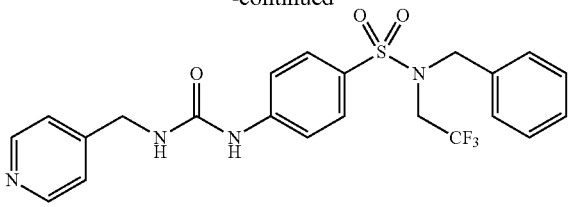

Step 1: To a solution of 4-nitro-benzenesulfonyl chloride (2.2 g, 10.0 mmol) and Et₃N (2.9 mL, 20.0 mmol) in DCM (30 mL) was added benzylamine (1.4 g, 13.0 mmol) at 0° C. After stirring at room temperature for 1 h, the reaction mixture was diluted with DCM (30 mL) and washed with aq.HCl (1 N, 30 mL) and Sat.NaHCO₃ (20 mL). The organic layer was dried over Na₂SO₄ and concentrated. The residue was washed with PE/EtOAc (4:1, 20 mL) to give N-benzyl-4-nitro-benzenesulfonamide (1.4 g, yield: 48%) as a yellow solid. ¹H NMR (400 MHz, CDCl₃): δ=8.32-8.28 (m, 2H), 8.01-7.96 (m, 2H), 7.28-7.24 (m, 3H), 7.18-7.15 (m, 2H), 4.50 (t, J=5.6 Hz, 1H), 4.23 (d, J=6.0 Hz, 2H).

Step 2: A mixture of N-benzyl-4-nitro-benzenesulfonamide (600 mg, 3.9 mmol), trifluoro-methanesulfonic acid 2,2,2-trifluoro-ethyl ester (950 mg, 4.1 mmol) and K₂CO₃ (850 mg, 6.2 mmol) in MeCN (10 mL) was sealed in a tube and heated in microwave at 100° C. for 30 min. The reaction mixture was poured to water (20 mL) and extracted with EtOAc (20 mL*2). The combined organic layer was washed with brine (20 mL), dried over Na₂SO₄ and concentrated. The residue was purified by silica gel column eluting with PE/EtOAc (20:1) to give N-benzyl-4-nitro-N-(2,2,2-trifluoro-ethyl)-benzenesulfonamide (740 mg, yield: 96%) as a white solid. ¹H NMR (400 MHz, CDCl₃): δ=8.38-8.34 (m, 2H), 8.03 (d, J=8.8 Hz, 2H), 7.40-7.27 (m, 5H), 4.58 (s, 2H), 3.85 (q, J=9.2 Hz, 2H).

Step 3: To a solution of N-benzyl-4-nitro-N-(2,2,2-trifluoro-ethyl)-benzenesulfonamide (740 mg, 2.0 mmol) in MeOH/H₂O (30 mL/8 mL) was added Fe (550 mg, 10.0 mmol) and NH₄C (1.1 g, 20.0 mmol). After stirring at 75° C. for 2 hrs, the reaction mixture was concentrated, diluted with EtOAc/H₂O (50 mL/50 mL) and filtered. The organic layer was separated, washed with brine (20 mL), dried over Na₂SO₄ and concentrated to give 4-amino-N-benzyl-N-(2,2,2-trifluoro-ethyl)-benzenesulfonamide (650 mg, yield: 96%) as a white solid which was used to the next step without further purification.

Step 4: To a solution of 4-amino-N-benzyl-N-(2,2,2-trifluoro-ethyl)-benzenesulfonamide (250 mg, 0.7 mmol) and TEA (0.3 mL, 2.2 mmol) in DCM (20 mL) was added phenyl chloroformate (150 mg, 0.9 mmol) dropwise at 0° C. After stirring at this temperature for 30 min, the reaction mixture was diluted with DCM (20 mL) and washed with aq.HCl (1 N, 20 mL) and Sat.NaHCO₃ (20 mL). The DCM solution was dried over Na₂SO₄ and concentrated to give {4-[benzyl-(2,2,2-trifluoro-ethyl)-sulfamoyl]-phenyl}-carbamic acid phenyl ester (crude) as colorless oil.

Step 5: A mixture of {4-[benzyl-(2,2,2-trifluoro-ethyl)-sulfamoyl]-phenyl}-carbamic acid phenyl ester (crude), C-pyridin-4-yl-methylamine (70 mg, 0.6 mmol) and TEA (0.2 mL, 1.4 mmol) in MeCN (15 mL) was stirred at 80° C. for 16 hrs and then concentrated. The residue was purified by silica flash column eluting with DCM/MeOH (DCM to 10:1) to give N-benzyl-4-(3-pyridin-4-ylmethyl-ureido)-N-(2,2,2-trifluoro-ethyl)-benzenesulfonamide (70 mg, yield: 20% for two steps) as a white solid. ¹H NMR (400 MHz, DMSO-d₆):

δ=9.31 (s, 1H), 8.51 (dd, J=4.4, 1.6 Hz, 2H), 7.79 (d, J=8.8 Hz, 2H), 7.64 (d, J=8.8 Hz, 2H), 7.35-7.27 (m, 5H), 7.23-7.20 (m, 2H), 6.97 (t, J=6.0 Hz, 1H), 4.37-4.34 (m, 4H), 3.98 (q, J=9.2 Hz, 2H). MS: m/z 478.9 (M+H$^+$).

Example 226: Synthesis of N-Benzyl-N-phenyl-4-(3-pyridin-4-ylmethyl-ureido)-benzenesulfonamide

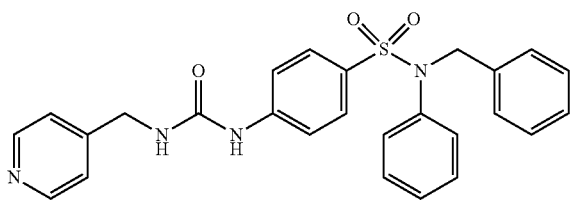 [SMILES: O=C(NCc1ccncc1)Nc1ccc(S(=O)(=O)N(Cc2ccccc2)c2ccccc2)cc1]

The title compound was prepared as described in example N-cyclohexyl-4-(3-pyridin-4-ylmethyl-ureido)-benzene-sulfonamide. $^1$H NMR (400 MHz, DMSO-d$_6$): δ=9.29 (brs, 1H), 8.51 (d, J=5.6 Hz, 2H), 7.61 (d, J=8.8 Hz, 2H), 7.49 (d, J=8.8 Hz, 2H), 7.30 (d, J=5.2 Hz, 2H), 7.27-7.21 (m, 6H), 7.21-7.14 (m, 2H), 7.05 (d, J=5.2 Hz, 2H), 6.96 (t, J=6.0 Hz, 1H), 4.76 (s, 2H), 4.35 (d, J=6.0 Hz, 2H). MS: m/z 472.9 (M+H$^+$).

Example 227: Synthesis of Pyridin-4-ylmethyl-3-[4-(pyrrolidine-1-sulfonyl)-phenyl]-urea

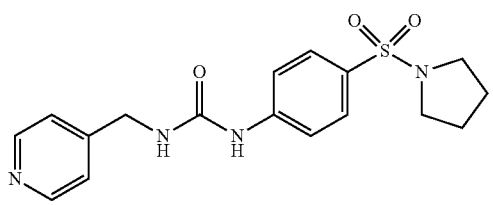 [SMILES: O=C(NCc1ccncc1)Nc1ccc(S(=O)(=O)N2CCCC2)cc1]

The title compound was prepared as described in example N-cyclohexyl-4-(3-pyridin-4-ylmethyl-ureido)-benzene-sulfonamide. $^1$H NMR (400 MHz, DMSO-d$_6$): δ=9.27 (brs, 1H), 8.50 (dd, J=4.4, 1.6 Hz, 2H), 7.69-7.60 (m, 4H), 7.29 (d, J=6.0 Hz, 2H), 6.95 (t, J=6.0 Hz, 1H), 4.34 (d, J=6.4 Hz, 2H), 3.13-3.04 (m, 4H), 1.66-1.58 (m, 4H). MS: m/z 360.9 (M+H$^+$).

Example 228: Synthesis of 1-[4-(Piperidine-1-sulfonyl)-phenyl]-3-pyridin-4-ylmethyl-urea

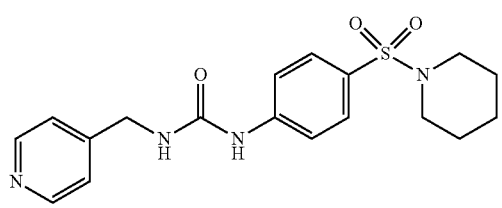 [SMILES: O=C(NCc1ccncc1)Nc1ccc(S(=O)(=O)N2CCCCC2)cc1]

The title compound was prepared as described in example N-cyclohexyl-4-(3-pyridin-4-ylmethyl-ureido)-benzene-sulfonamide. $^1$H NMR (400 MHz, DMSO-d$_6$): δ=9.33 (brs, 1H), 8.50 (dd, J=4.8, 1.6 Hz, 2H), 7.64 (d, J=8.8 Hz, 2H), 7.57 (d, J=8.4 Hz, 2H), 7.29 (d, J=6.0 Hz, 2H), 6.99 (t, J=5.6 Hz, 1H), 4.35 (d, J=6.0 Hz, 2H), 2.88-2.76 (m, 4H), 1.57-1.47 (m, 4H), 1.40-1.29 (m, 2H). MS: m/z 375.0 (M+H$^+$).

Example 229: Synthesis of 1-[4-(Morpholine-4-sulfonyl)-phenyl]-3-pyridin-4-ylmethyl-urea

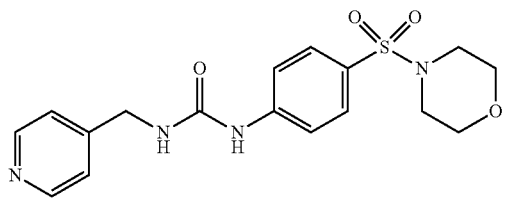 [SMILES: O=C(NCc1ccncc1)Nc1ccc(S(=O)(=O)N2CCOCC2)cc1]

The title compound was prepared as described in example N-cyclohexyl-4-(3-pyridin-4-ylmethyl-ureido)-benzene-sulfonamide. $^1$H NMR (400 MHz, DMSO-d$_6$): δ=9.34 (brs, 1H), 8.51 (dd, J=4.8, 1.6 Hz, 2H), 7.67 (d, J=9.2 Hz, 2H), 7.59 (d, J=8.8 Hz, 2H), 7.30 (d, J=6.0 Hz, 2H), 6.97 (t, J=6.0 Hz, 1H), 4.35 (d, J=6.0 Hz, 2H), 3.68-3.58 (m, 4H), 2.86-2.76 (m, 4H). MS: m/z 377.1 (M+H$^+$).

Example 230: Synthesis of 1-[4-(4-Methyl-piperazine-1-sulfonyl)-phenyl]-3-pyridin-4-ylmethyl-urea

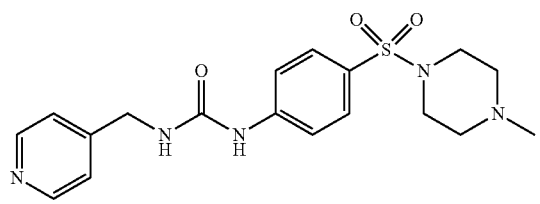 [SMILES: CN1CCN(S(=O)(=O)c2ccc(NC(=O)NCc3ccncc3)cc2)CC1]

The title compound was prepared as described in example N-cyclohexyl-4-(3-pyridin-4-ylmethyl-ureido)-benzene-sulfonamide. $^1$H NMR (400 MHz, DMSO-d$_6$): δ=9.34 (brs, 1H), 8.51 (d, J=5.2 Hz, 2H), 7.67 (d, J=8.8 Hz, 2H), 7.59 (d, J=8.8 Hz, 2H), 7.30 (d, J=4.8 Hz, 2H), 6.99 (t, J=5.6 Hz, 1H), 4.35 (d, J=6.0 Hz, 2H), 2.92-2.73 (m, 4H), 2.41-2.27 (m, 4H), 2.13 (s, 3H). MS: m/z 390.0 (M+H$^+$).

Example 231: Synthesis of 1-[4-(1,3-Dihydro-isoindole-2-sulfonyl)-phenyl]-3-pyridin-4-ylmethyl-urea

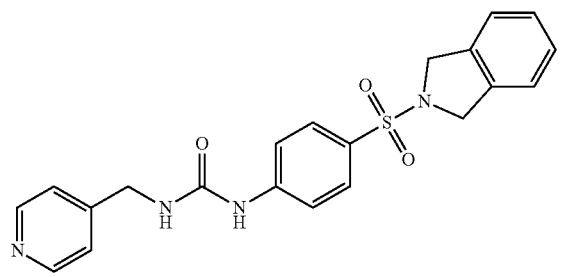 [SMILES: O=C(NCc1ccncc1)Nc1ccc(S(=O)(=O)N2Cc3ccccc3C2)cc1]

The title compound was prepared as described in example N-cyclohexyl-4-(3-pyridin-4-ylmethyl-ureido)-benzene-sulfonamide. $^1$H NMR (300 MHz, DMSO-d$_6$): δ=9.23 (s, 1H), 8.48 (d, J=6.0 Hz, 2H), 7.73 (d, J=8.7 Hz, 2H), 7.61 (d, J=8.4 Hz, 2H), 7.27-7.24 (m, 6H), 6.93-6.88 (m, 1H), 4.52 (s, 4H), 4.32 (d, J=6.3 Hz, 2H). MS: m/z 409.1 (M+H$^+$).

Example 232: Synthesis of 1-[4-(8-Oxa-3-aza-bicyclo[3.2.1]octane-3-sulfonyl)-phenyl]-3-pyridin-3-ylmethyl-urea

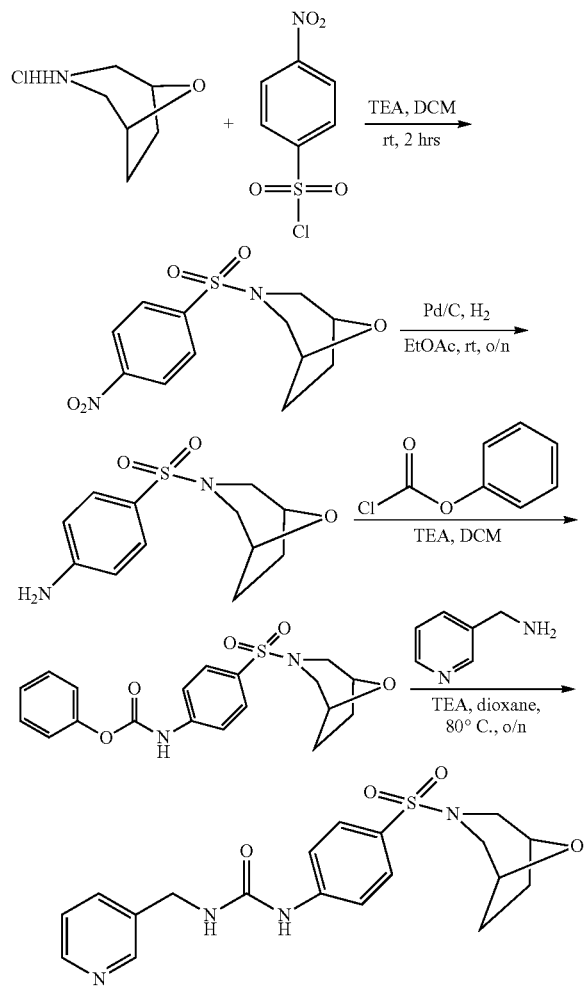

Step 1: To a solution of 8-oxa-3-aza-bicyclo[3.2.1]octane (100 mg, 0.668 mmol, HCl salt) in dry DCM (20 mL) was added 4-nitro-benzenesulfonyl chloride (296 mg, 1.34 mmol) and followed by TEA (202.8 mg, 2.00 mmol). The resulting mixture was stirred at room temperature for 2 hours. The reaction was monitored by TLC. Then the mixture was concentrated in vacuum to give a residue which was purified by a silica gel column eluting with DCM/MeOH (60:1) to afford 3-(4-nitro-benzenesulfonyl)-8-oxa-3-aza-bicyclo[3.2.1]octane (150 mg, yield: 75%) as a white solid. $^1$H NMR (400 MHz, CDCl$_3$): δ=8.39 (dd, J=7.2, 2.0 Hz, 2H), 7.92 (dd, J=6.8, 2.0 Hz, 2H), 4.39 (s, 2H), 3.45 (d, J=11.6 Hz, 2H), 2.27 (dd, J=11.2, 2.0 Hz, 2H), 2.05-1.95 (m, 4H).

Step 2: To a solution of 3-(4-nitro-benzenesulfonyl)-8-oxa-3-aza-bicyclo[3.2.1]octane (100 mg, 0.335 mmol) in EtOAc (20 mL) was added Pd/C (20 mg, 20% wt). The resulting suspension was stirred at room temperature overnight. The reaction was monitored by LC-MS. Then Pd/C was filtered off and the filtrate was concentrated in vacuum to afford 4-(8-oxa-3-aza-bicyclo[3.2.1]octane-3-sulfonyl)-phenylamine (83 mg, yield: 92%) as a white solid. $^1$H NMR (400 MHz, DMSO-d$_6$): δ=7.32 (d, J=8.8, 2H), 6.64 (d, J=8.8 Hz, 2H), 6.07 (brs, 2H), 4.31 (s, 2H), 3.15 (d, J=11.6 Hz, 2H), 2.37 (dd, J=11.6, 2.0 Hz, 2H), 1.82-1.74 (m, 4H).

Step 3: To a solution of 4-(8-oxa-3-aza-bicyclo[3.2.1]octane-3-sulfonyl)-phenylamine (100 mg, 0.373 mmol) in DCM (10 mL) was added phenyl carbonchloridate (117 mg, 0.745 mmol) and followed by TEA (113 mg, 55.4 mmol). The resulting mixture was stirred at room temperature overnight. The reaction was monitored by TLC. Then the mixture was concentrated in vacuum to give a residue which was purified by silica gel column eluting with DCM/MeOH (60:1) to afford [4-(8-oxa-3-aza-bicyclo[3.2.1]octane-3-sulfonyl)-phenyl]-carbamic acid phenyl ester (132 mg, yield: 92%) as a white solid. $^1$H NMR (400 MHz, CDCl$_3$): δ=7.71 (d, J=9.2 Hz, 2H), 6.64 (d, J=8.8 Hz, 2H), 7.42 (t, J=8.0 Hz, 2H), 7.27 (t, J=7.2 Hz, 1H), 7.22-7.18 (m, 2H), 4.36 (s, 2H), 3.38 (d, J=11.2 Hz, 2H), 2.63 (dd, J=7.2, 2.0 Hz, 2H), 2.06-1.90 (m, 4H).

Step 4: To a solution of [4-(8-oxa-3-aza-bicyclo[3.2.1]octane-3-sulfonyl)-phenyl]-carbamic acid phenyl ester (120 mg, 0.309 mmol) in dioxane (8 mL) was added c-Pyridin-3-yl-methylamine (40 mg, 0.371 mmol) and followed by TEA (94 mg, 0.927 mmol). The resulting mixture was stirred at 80° C. overnight. The reaction was monitored by LC-MS. Then the white solid precipitated from the reaction mixture was filtered. The cake was washed with dioxane (20 mL) and dried in air to afford 1-[4-(8-oxa-3-aza-bicyclo[3.2.1]octane-3-sulfonyl)-phenyl]-3-pyridin-3-ylmethyl-urea (76.4 mg, yield: 62%) as a white solid. $^1$H NMR (400 MHz, DMSO-d$_6$): δ=9.19 (brs, 1H), 8.53 (d, J=1.6 Hz, 1H), 8.46 (d, J=5.2 Hz, 1H), 7.71 (d, J=8.0 Hz, 1H), 7.64 (d, J=8.8 Hz, 2H), 7.56 (d, J=8.8 Hz, 2H), 7.36 (dd, J=8.0, 4.8 Hz, 1H), 6.91 (t, J=6.0 Hz, 1H), 4.34 (d, J=6.4 Hz, 2H), 4.32 (s, 2H), 3.21 (d, J=10.8 Hz, 2H), 2.40 (d, J=10.0 Hz, 2H), 1.84-1.73 (m, 4H). MS: m/z 403.1 (M+H$^+$).

Example 233: Synthesis of 1-[4-(8-Oxa-3-aza-bicyclo[3.2.1]octane-3-sulfonyl)-phenyl]-3-pyridin-2-ylmethyl-urea

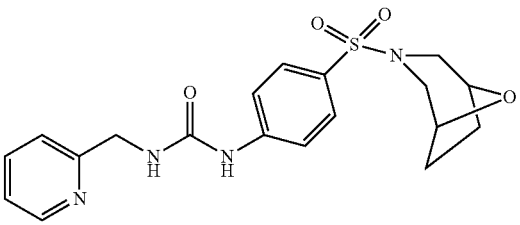 [SMILES: O=C(NCc1ccccn1)Nc1ccc(S(=O)(=O)N2CC3CCC(C2)O3)cc1]

The title compound was prepared as described in example 1-[4-(8-oxa-3-aza-bicyclo[3.2.1]octane-3-sulfonyl)-phenyl]-3-pyridin-3-ylmethyl-urea. $^1$H NMR (400 MHz, DMSO-d$_6$): δ=9.35 (brs, 1H), 8.53 (d, J=4.0 Hz, 1H), 7.78 (dt, J=8.0, 2.0 Hz, 1H), 7.65 (d, J=8.8 Hz, 1H), 7.64 (d, J=8.8 Hz, 2H), 7.56 (d, J=8.4 Hz, 2H), 7.35 (d, J=7.6 Hz, 1H), 6.96 (t, J=5.6 Hz, 1H), 4.43 (d, J=6.0 Hz, 2H), 4.32 (s, 2H), 3.21 (d, J=10.8 Hz, 2H), 2.41 (dd, J=11.2, 2.0 Hz, 2H), 1.83-1.74 (m, 4H). MS: m/z 403.1 (M+H$^+$).

Example 234: Synthesis of 1-[4-(8-Oxa-3-aza-bicyclo[3.2.1]octane-3-sulfonyl)-phenyl]-3-pyridin-4-ylmethyl-urea

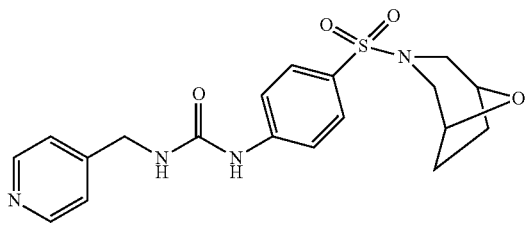 [SMILES: O=C(NCc1ccncc1)Nc1ccc(S(=O)(=O)N2CC3CCC(C2)O3)cc1]

The title compound was prepared as described in example 1-[4-(8-oxa-3-aza-bicyclo[3.2.1]octane-3-sulfonyl)-phenyl]-3-pyridin-3-ylmethyl-urea. ¹H NMR (400 MHz, DMSO-d₆): δ=9.51 (brs, 1H), 8.74 (d, J=6.0 Hz, 2H), 7.73 (d, J=6.4 Hz, 2H), 7.65 (d, J=9.2 Hz, 2H), 7.57 (d, J=8.8 Hz, 2H), 7.17 (t, J=5.6 Hz, 1H), 4.52 (d, J=6.4 Hz, 2H), 4.32 (s, 2H), 3.21 (d, J=11.2 Hz, 2H), 2.40 (dd, J=11.2, 2.0 Hz, 2H), 1.84-1.73 (m, 4H). MS: m/z 403.1 (M+H⁺).

Example 235: Synthesis of 1-[4-(3,4-Dihydro-1H-isoquinoline-2-sulfonyl)-phenyl]-3-pyridin-4-ylmethyl-urea

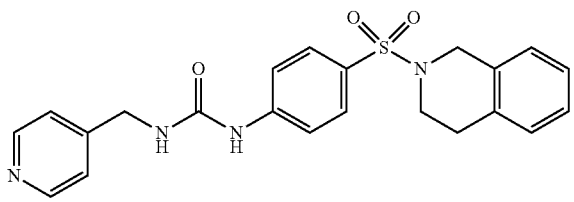 [SMILES: O=C(NCc1ccncc1)Nc1ccc(S(=O)(=O)N2CCc3ccccc3C2)cc1]

The title compound was prepared as described in example N-cyclohexyl-4-(3-pyridin-4-ylmethyl-ureido)-benzenesulfonamide. ¹H NMR (400 MHz, DMSO-d₆): δ=9.34 (brs, 1H), 8.49 (dd, J=4.8, 1.2 Hz, 2H), 7.72-7.60 (m, 4H), 7.28 (d, J=6.0 Hz, 2H), 7.17-7.08 (m, 4H), 6.98 (t, J=6.0 Hz, 1H), 4.34 (d, J=6.0 Hz, 2H), 4.13 (s, 2H), 3.23 (t, J=6.0 Hz, 2H), 2.85 (t, J=6.0 Hz, 2H). MS: m/z 423.0 (M+H⁺).

Example 236: Synthesis of 1-[4-(8-Chloro-3,4-dihydro-1H-isoquinoline-2-sulfonyl)-phenyl]-3-pyridin-4-ylmethyl-urea

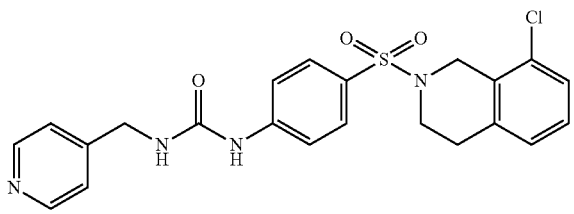 [SMILES: O=C(NCc1ccncc1)Nc1ccc(S(=O)(=O)N2CCc3cccc(Cl)c3C2)cc1]

The title compound was prepared as described in example N-cyclohexyl-4-(3-pyridin-4-ylmethyl-ureido)-benzenesulfonamide. ¹H NMR (400 MHz, DMSO-d₆): δ=9.27 (s, 1H), 8.50 (d, J=5.2 Hz, 2H), 7.70-7.63 (m, 4H), 7.31-7.27 (m, 3H), 7.21 (t, J=8.0 Hz, 1H), 7.13 (d, J=7.9 Hz, 1H), 6.94 (t, J=5.2 Hz, 1H), 4.34 (d, J=5.2 Hz, 2H), 4.12 (s, 2H), 3.28 (t, J=6.0 Hz, 2H), 2.89 (t, J=5.2 Hz, 2H). MS: m/z 456.9 (M+H⁺).

Example 237: Synthesis of Pyridin-4-ylmethyl-3-[4-(8-trifluoromethyl-3,4-dihydro-1H-isoquinoline-2-sulfonyl)-phenyl]-urea

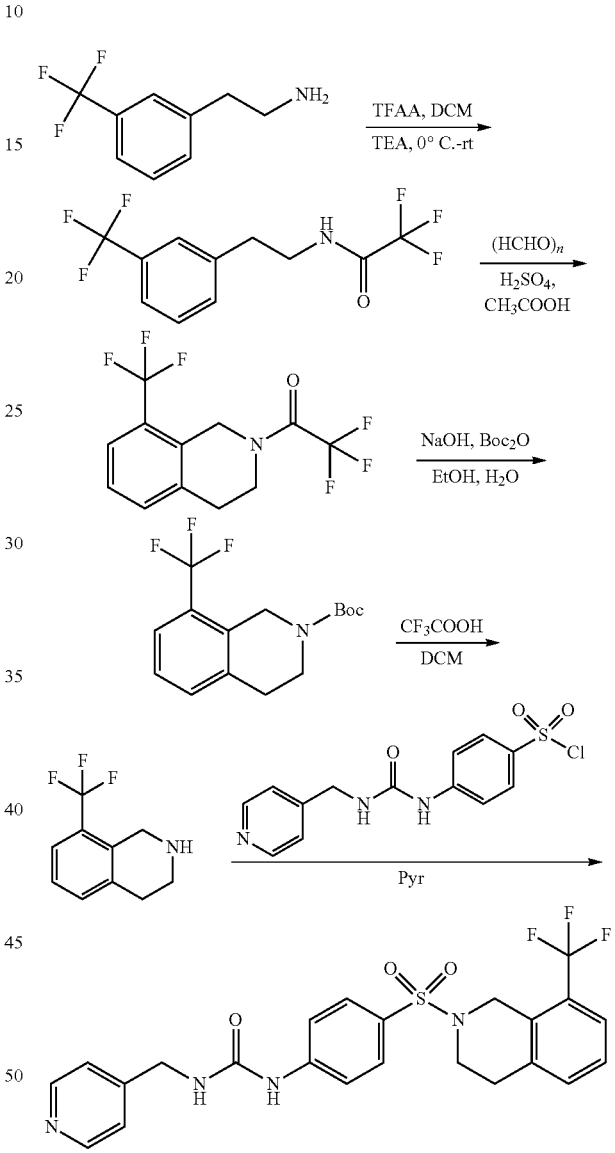

Step 1: To the solution of 2-(3-trifluoromethyl-phenyl)-ethylamine (1.7 g, 9.0 mmol) in DCM (10 mL) was added TEA (1.4 g, 9.9 mmol) at 0° ° C. under N₂. Then a solution of TFAA (2.1 g, 9.9 mmol) in DCM (10 mL) was added dropwise. The mixture was stirred at room temperature for 2 hrs. The reaction mixture was diluted with DCM (10 mL), washed with H₂O (10 mL), dried over sodium sulfate and concentrated under reduced pressure. The residue was purified by silica gel column eluting with PE/EtOAc (8:1) to give the 2,2,2-trifluoro-N-[2-(3-trifluoromethyl-phenyl)-ethyl]-acetamide (1.3 g, yield: 52%) as a yellow solid. ¹H NMR (400 MHz, DMSO-d₆): δ=9.476 (brs, 1H), 7.59-7.52 (m, 4H), 3.49-3.44 (m, 2H), 2.92 (t, J=6.8 Hz, 2H).

Step 2: (CH₂O)ₙ was added to 2,2,2-trifluoro-N-[2-(3-trifluoromethyl-phenyl)-ethyl]-acetamide (1.3 g, 4.6 mmol) in a 100 mL round-bottomed before a solution of CH₃COOH (15 mL) and H₂SO₄ (20 mL) was added. The mixture was stirred at room temperature for 2 hrs under N₂. The reaction mixture was extracted with EtOAc (40 mL*2). The combined organic layer was washed with ice water (30 mL) and aq.NaHCO₃, dried over Na₂SO₄ and concentrated under reduced pressure. The residue was purified by flash (8% EtOAc in PE) to give the 2,2,2-trifluoro-1-(8-trifluoromethyl-3,4-dihydro-1H-isoquinolin-2-yl)-ethanone (0.9 g, yield: 64%) as a white solid. MS: m/z 298.4 (M+H⁺).

Step 3: To a solution of 2,2,2-trifluoro-1-(8-trifluoromethyl-3,4-dihydro-1H-isoquinolin-2-yl)-ethanone (315 mg, 4.6 mmol) in EtOH (10 mL) was added a solution of NaOH (440 mg, 11.0 mmol) in H₂O (10 mL). The mixture was refluxed at 90° ° C. for 2 hrs. Then Boc₂O (36 mg, 1.65 mmol) was added and the reaction mixture was stirred for another 1 h at room temperature. After that, the reaction mixture was concentrated under reduced pressure to dryness and extracted with DCM (20 mL). The organic layer was washed with H₂O (20 mL), dried over Na₂SO₄ and concentrated under reduced pressure to give the 8-trifluoromethyl-3,4-dihydro-1H-isoquinoline-2-carboxylic acid tert-butyl ester (350 mg, yield: quantitative) as a white solid.

Step 4: The mixture of 8-trifluoromethyl-3,4-dihydro-1H-isoquinoline-2-carboxylic acid tert-butyl ester (350 mg, 1.1 mol) in TFA/DCM (1.3 g/3 mL) was stirred at room temperature for 1 hrs. The reaction was concentrated to dryness in vacuum to afford 8-trifluoromethyl-1,2,3,4-tetrahydro-isoquinoline (400 mg, yield: quantitative) as a white solid.

Step 5: This step is similar to general procedure for 4-(3-pyridin-4-ylmethyl-ureido)-N-(3-chloro-phenyl)-benzenesulfonamide. ¹H NMR (400 MHz, DMSO-d₆): δ=9.27 (s, 1H), 8.50 (dd, J=2.8, 1.6 Hz, 2H), 7.67-7.63 (m, 4H), 7.56 (d, J=8.0 Hz, 1H), 7.43 (d, J=7.2 Hz, 1H), 7.39 (t, J=7.9 Hz, 1H), 7.30 (d, J=6.0 Hz, 2H), 6.94 (t, J=6.0 Hz, 1H), 4.35-4.30 (m, 4H), 3.37-3.32 (m, 2H), 2.95 (t, J=6.0 Hz, 2H). MS: m/z 490.9 (M+H⁺).

Example 238: Synthesis of Pyridin-4-ylmethyl-3-[4-(6-trifluoromethyl-3,4-dihydro-1H-isoquinoline-2-sulfonyl)-phenyl]-urea

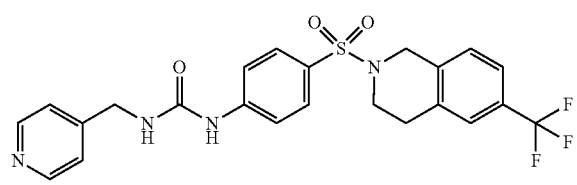 [SMILES: O=C(NCc1ccncc1)Nc1ccc(S(=O)(=O)N2CCc3cc(C(F)(F)F)ccc3C2)cc1]

The title compound was prepared as described in example 1-Pyridin-4-ylmethyl-3-[4-(8-trifluoromethyl-3,4-dihydro-1H-isoquinoline-2-sulfonyl)-phenyl]-urea. H NMR (400 MHz, DMSO-d₆): δ=9.28 (s, 1H), 8.50 (dd, J=1.6, 3.2 Hz, 2H), 7.69 (d, J=8.8 Hz, 2H), 7.63 (d, J=9.2 Hz, 2H), 7.50 (d, J=6.4 Hz, 2H), 7.39 (d, J=8.8 Hz, 1H), 7.28 (d, J=6.0 Hz, 2H), 6.94 (t, J=6.0 Hz, 1H), 4.34 (d, J=6.0 Hz, 2H), 4.23 (s, 2H), 3.27 (overlap, 2H), 2.94 (t, J=6.0 Hz, 2H). MS: m/z 490.9 (M+H⁺).

Example 239: Synthesis of 1-[4-(8-Fluoro-3,4-dihydro-1H-isoquinoline-2-sulfonyl)-phenyl]-3-pyridin-4-ylmethyl-urea

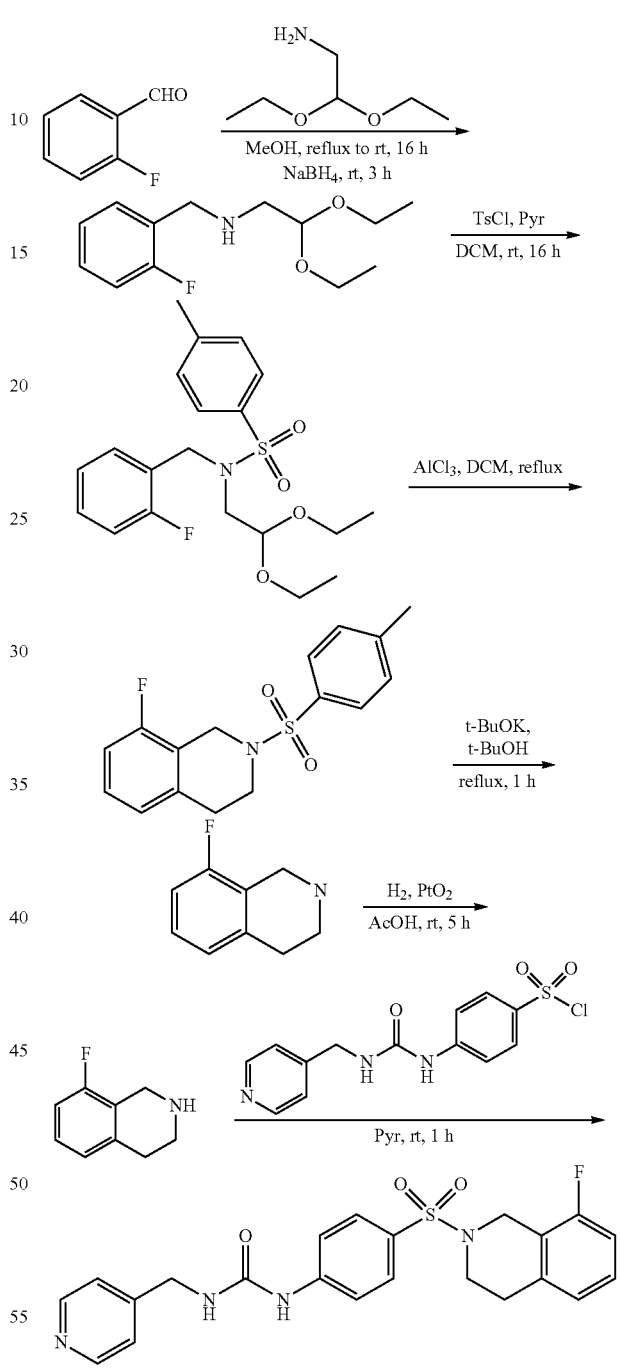

Step 1: To a solution of 2-fluoro-benzaldehyde (5.0 g, 40.3 mmol) in MeOH (80 mL) was added 2,2-diethoxy-ethylamine (5.4 g, 40.3 mmol). The mixture was stirred at 70° C. for 2 hrs and at room temperature for 16 hrs. Then NaBH₄ (1.5 g, 40.3 mmol) was added portionwise. After stirring at room temperature for 3 hrs, the reaction mixture was diluted with H₂O (50 mL), concentrated to 50 mL and extracted with EtOAc (50 mL*3). The combined organic layer was washed with brine, dried over Na₂SO₄ and concentrated to give (2,2-diethoxy-ethyl)-(2-fluoro-benzyl)-amine (crude) as colorless oil which was used to the next step without further purification.

Step 2: To a solution of (2,2-diethoxy-ethyl)-(2-fluoro-benzyl)-amine (5.0 g, crude) and pyridine (4.4 g, 56.0 mmol) in DCM (100 mL) was added TsCl (5.1 g, 27.0 mmol) portion wise at 0° C. After stirring at room temperature for 16 hrs, the reaction mixture was washed with aq.HCl (2N, 30 mL), sat.NaHCO₃ (30 mL) and brine (30 mL). The DCM solution was dried over Na₂SO₄ and concentrated. The residue was purified by silica gel column eluting with PE/EtOAc (30:1) to give N-(2,2-diethoxy-ethyl)-N-(2-fluoro-benzyl)-4-methyl-benzenesulfonamide (5.7 g, yield: 71% for two steps) as a white solid. ¹H NMR (400 MHz, CDCl₃): δ=7.67 (d, J=8.4 Hz, 2H), 7.37 (td, J=7.6, 1.2 Hz, 1H), 7.28-7.18 (m, 3H), 7.07 (td, J=7.6, 1.2 Hz, 1H), 6.94 (td, J=8.4, 0.8 Hz, 1H), 4.59-4.55 (m, 3H), 3.66-3.57 (m, 2H), 3.43-3.34 (m, 2H), 3.27 (d, J=5.2 Hz, 2H), 2.42 (s, 3H), 1.11 (t, J=7.2 Hz, 6H).

Step 3: To a stirring solution of N-(2,2-diethoxy-ethyl)-N-(2-fluoro-benzyl)-4-methyl-benzenesulfonamide (4.4 g, 11.1 mmol) in DCM (100 mL) was added AlCl₃ (5.9 g, 44.4 mmol). After stirring at 45° C. for 1.5 hrs, the reaction mixture was poured to ice-water (100 mL) and extracted with DCM (100 mL*2). The combined organic layer was washed with sat.NaHCO₃ (100 mL), dried over Na₂SO₄ and concentrated. The residue was purified by silica gel column eluting with PE/EtOAc (40:1) to give 8-fluoro-2-(toluene-4-sulfonyl)-1,2-dihydro-isoquinoline (880 mg, yield: 26%) as a white solid. ¹H NMR (300 MHz, CDCl₃): δ=7.73 (d, J=8.4 Hz, 2H), 7.35-7.27 (m, 2H), 7.10 (dd, J=13.8, 7.8 Hz, 1H), 6.86-6.79 (m, 2H), 6.72 (d, J=7.2 Hz, 1H), 5.82 (dd, J=7.8, 1.8 Hz, 1H), 4.68 (s, 2H), 2.41 (s, 3H).

Step 4: t-BuOK (1.5 g, 13.2 mmol) was dissolved in t-BuOH (30 mL) and then 8-fluoro-2-(toluene-4-sulfonyl)-1,2-dihydro-isoquinoline (800 mg, 2.6 mmol) was added. After stirring at 85° C. for 1 h, the reaction mixture was poured to water (100 mL) and extracted with EtOAc (50 mL*2). The combined organic layer was washed with brine (30 mL), dried over Na₂SO₄ and concentrated. The residue was purified by silica gel column eluting with PE/EtOAc (30:1) to give 8-fluoro-isoquinoline (230 mg, yield: 59%) as yellow oil. ¹H NMR (400 MHz, CDCl₃): δ=9.55 (s, 1H), 8.60 (d, J=5.6 Hz, 1H), 7.68-7.60 (m, 3H), 7.27-7.21 (m, 1H).

Step 5: A mixture of 8-fluoro-isoquinoline (100 mg, 0.7 mmol) and PtO₂ (30 mg) in AcOH (4 mL) was stirred at room temperature for 5 hrs under H₂ atmosphere (50 psi). The reaction mixture was filtered to remove the catalyst. The filtrate was concentrated and co-evaporated with toluene (15 mL*3) to give 8-fluoro-1,2,3,4-tetrahydro-isoquinoline (crude) as pale yellow oil which was used to the next step without further purification.

Step 6: This step was similar to general procedure of N-(2-methoxy-benzyl)-N-methyl-4-(3-pyridin-4-ylmethyl-ureido)-benzenesulfonamide. ¹H NMR (400 MHz, DMSO-d₆): δ=9.28 (s, 1H), 8.50 (d, J=6.0 Hz, 2H), 7.70 (d, J=8.8 Hz, 2H), 7.64 (d, J=8.8 Hz, 2H), 7.28 (d, J=5.2 Hz, 2H), 7.21 (dd, J=13.4, 7.8 Hz, 1H), 7.05-6.97 (m, 2H), 6.93 (t, J=5.6 Hz, 1H), 4.34 (d, J=5.6 Hz, 2H), 4.13 (s, 2H), 3.27 (t, J=5.6 Hz, 2H), 2.88 (t, J=5.6 Hz, 2H). MS: m/z 440.9 (M+H⁺).

Example 240: Synthesis of 1-[4-(8-Methyl-3,4-dihydro-1H-isoquinoline-2-sulfonyl)-phenyl]-3-pyridin-4-ylmethyl-urea

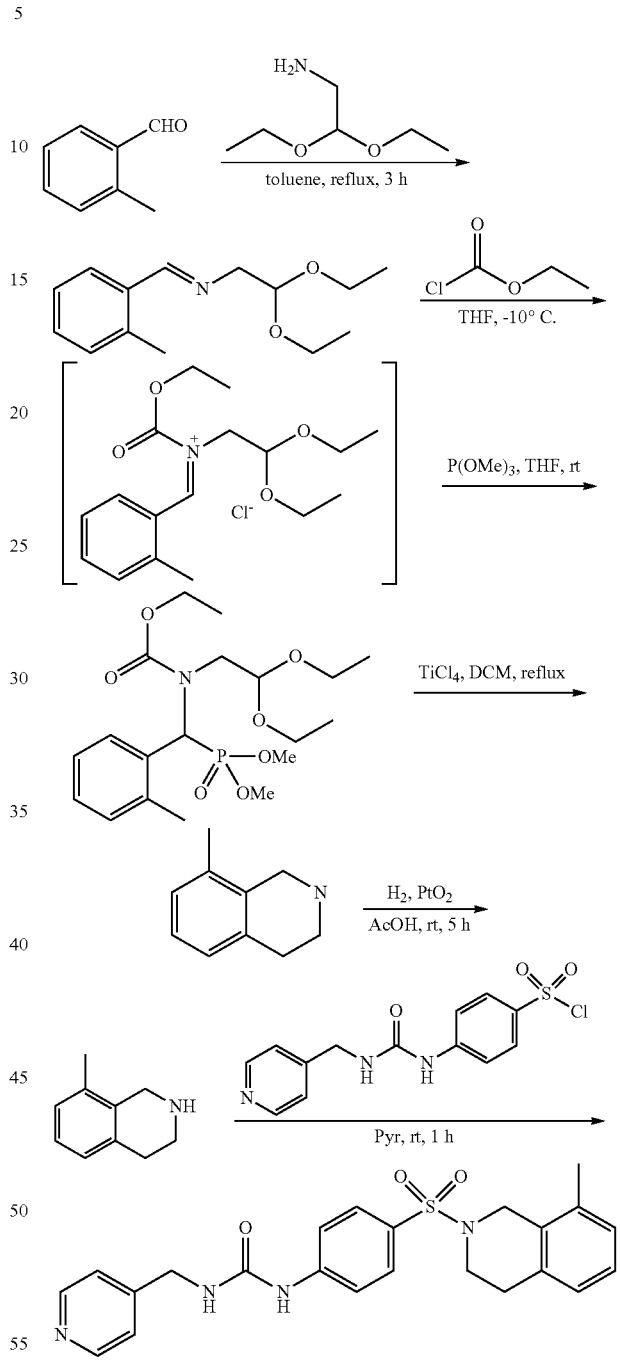

Step 1: A mixture of 2-methyl-benzaldehyde (5.0 g, 41.7 mmol) and 2,2-diethoxy-ethylamine (5.5 g, 41.7 mmol) in toluene (50 mL) was refluxed for 3 hrs with a Dean-Stark trap. The reaction mixture was concentrated to give (2,2-diethoxy-ethyl)-(2-methyl-benzylidene)-amine (crude) as colorless oil which was used to the next step without further purification.

Step 2&3: To a solution of (2,2-diethoxy-ethyl)-(2-methyl-benzylidene)-amine (crude) in THF (50 mL) was added ethyl chloroformate (4.6 g, 41.7 mmol) at −10° C.

After stirring at −10° C. for 5 min, the cooling bath was removed and P(OMe)₃ (6.6 g, 53.2 mmol) was added at room temperature. The reaction was stirred at room temperature for 20 hrs and then concentrated to removed traces of P(OMe)₃. The residue was co-evaporated with toluene (20 mL*2) to give {[(2,2-diethoxy-ethyl)-ethoxycarbonyl-amino]-o-tolyl-methyl}-phosphonic acid dimethyl ester (crude) as colorless oil which was used to the next step without further purification.

Step 4: To a solution of {[(2,2-diethoxy-ethyl)-ethoxycarbonyl-amino]-o-tolyl-methyl}-phosphonic acid dimethyl ester (crude) in DCM (60 mL) was added TiCl₄ (27.5 mL, 250 mmol). After stirring at 45° C. for 24 hrs, the reaction mixture was poured to ice (100 g)/NH₄OH (100 mL). The mixture was filtered to remove TiO₂ and the filtrate was washed with aq.HCl (1 N, 50 mL*2). The acidic layer was washed with DCM (20 mL) and then basified with NH₄OH to adjust pH=9. The suspension was extracted with DCM (50 mL*3). The combined organic layer was dried over Na₂SO₄ and concentrated. The residue was purified by silica gel column eluting with PE/EtOAc (10:1) to give 8-methyl-isoquinoline (2.0 g, yield: 34% for four steps) as colorless oil. ¹H NMR (400 MHz, CDCl₃): δ=9.46 (s, 1H), 8.55 (d, J=5.6 Hz, 1H), 7.68-7.54 (m, 3H), 7.39 (d, J=6.4 Hz, 1H), 2.79 (s, 3H).

Step 5: A mixture of 8-methyl-isoquinoline (100 mg, 0.7 mmol) and PtO₂ (30 mg) in AcOH (3 mL) was stirred at room temperature for 5 hrs under H₂ atmosphere (50 psi). The reaction mixture was filtered to remove the catalyst. The filtrate was concentrated and co-evaporated with toluene (15 mL*3) to give 8-methyl-1,2,3,4-tetrahydro-isoquinoline (crude) as colorless oil which was used to the next step without further purification.

Step 6: This step was similar to general procedure of N-(2-methoxy-benzyl)-N-methyl-4-(3-pyridin-4-ylmethyl-ureido)-benzenesulfonamide. ¹H NMR (400 MHz, DMSO-d₆): δ=9.26 (s, 1H), 8.49 (dd, J=4.4, 1.6 Hz, 2H), 7.71 (d, J=8.8 Hz, 2H), 7.64 (d, J=8.8 Hz, 2H), 7.28 (d, J=5.6 Hz, 2H), 7.08-6.91 (m, 4H), 4.34 (d, J=6.0 Hz, 2H), 4.03 (s, 2H), 3.22 (t, J=5.6 Hz, 2H), 2.84 (t, J=5.6 Hz, 2H), 2.15 (s, 3H). MS: m/z 436.9 (M+H⁺).

Example 241: Synthesis of 1-[4-(3-Methyl-3,4-dihydro-1H-isoquinoline-2-sulfonyl)-phenyl]-3-pyridin-4-ylmethyl-urea

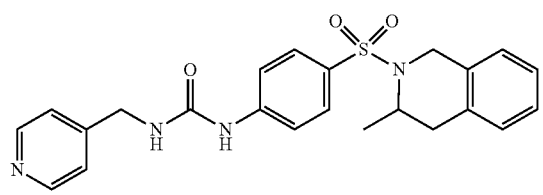 [SMILES: CC1Cc2ccccc2CN1S(=O)(=O)c1ccc(NC(=O)NCc2ccncc2)cc1]

The title compound was prepared as described in example N-cyclohexyl-4-(3-pyridin-4-ylmethyl-ureido)-benzenesulfonamide. ¹H NMR (400 MHz, DMSO-d₆): δ=9.17 (s, 1H), 8.51 (d, J=6.0 Hz, 2H), 7.63 (d, J=8.8 Hz, 2H), 7.50 (d, J=8.8 Hz, 2H), 7.32 (d, J=5.6 Hz, 2H), 7.16-7.08 (m, 3H), 7.01 (d, J=7.2 Hz, 1H), 6.90 (t, J=6.0 Hz, 1H), 4.99 (q, J=2.8 Hz, 1H), 4.33 (d, J=6.0 Hz, 2H), 3.75-3.68 (m, 1H), 3.39 (overlap, 1H), 2.64-2.62 (m, 2H), 1.34 (d, J=6.8 Hz, 3H). MS: m/z 436.9 (M+H⁺).

Example 242: Synthesis of N-Phenyl-4-(3-pyridin-4-ylmethyl-ureido)-benzenesulfonamide

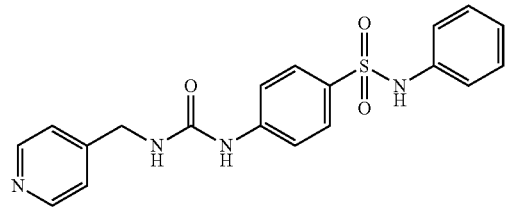 [SMILES: O=C(NCc1ccncc1)Nc1ccc(S(=O)(=O)Nc2ccccc2)cc1]

The title compound was prepared as described in example N-cyclohexyl-4-(3-pyridin-4-ylmethyl-ureido)-benzenesulfonamide. ¹H NMR (400 MHz, CD₃OD): 8.51 (s, 2H), 7.63 (d, J=8.8 Hz, 2H), 7.49 (d, J=9.2 Hz, 2H), 7.40 (s, 2H), 7.21-7.17 (t, J=8 Hz, 2H), 7.08-7.04 (m, 3H), 4.43 (s, 2H). MS: m/z 382.9 (M+H⁺)

Example 243: Synthesis of N-(2-Methoxy-phenyl)-4-(3-pyridin-4-ylmethyl-ureido)-benzenesulfonamide

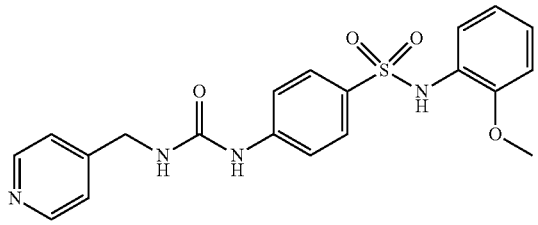 [SMILES: COc1ccccc1NS(=O)(=O)c1ccc(NC(=O)NCc2ccncc2)cc1]

The title compound was prepared as described in example N-cyclohexyl-4-(3-pyridin-4-ylmethyl-ureido)-benzenesulfonamide. ¹H NMR (400 MHz, DMSO-d₆): δ=9.45 (brs, 1H), 8.49 (dd, J=4.4, 1.6 Hz, 2H), 7.58-7.47 (m, 4H), 7.27 (d, J=6.0 Hz, 2H), 7.24-7.16 (m, 2H), 7.09-7.03 (m, 1H), 6.91-6.87 (m, 1H), 6.86-6.81 (m, 1H), 4.32 (d, J=6.0 Hz, 2H), 3.34 (s, 3H). MS: m/z 412.9 (M+H⁺).

Example 244: Synthesis of N-(3-Methoxy-phenyl)-4-(3-pyridin-4-ylmethyl-ureido)-benzenesulfonamide

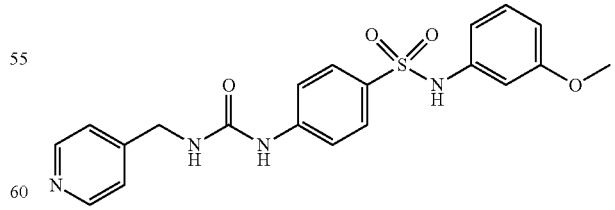

The title compound was prepared as described in example N-cyclohexyl-4-(3-pyridin-4-ylmethyl-ureido)-benzenesulfonamide. ¹H NMR (400 MHz, DMSO-d₆): δ=10.13 (brs, 1H), 9.21 (brs, 1H), 8.49 (d, J=5.6 Hz, 2H), 7.63 (d, J=8.8 Hz, 2H), 7.53 (d, J=9.2 Hz, 2H), 7.27 (d, J=5.6 Hz, 2H), 7.11

(t, J=4.0 Hz, 1H), 6.93 (t, J=5.6 Hz, 1H), 6.67-6.62 (m, 2H), 6.59-6.54 (m, 1H), 4.32 (d, J=6.0 Hz, 2H), 3.65 (s, 3H). MS: m/z 412.9 (M+H⁺).

Example 245: Synthesis of N-(4-Methoxy-phenyl)-4-(3-pyridin-4-ylmethyl-ureido)-benzenesulfonamide

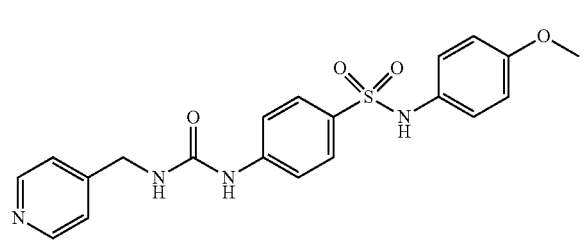 [SMILES: COc1ccc(NS(=O)(=O)c2ccc(NC(=O)NCc3ccncc3)cc2)cc1]

The title compound was prepared as described in example N-cyclohexyl-4-(3-pyridin-4-ylmethyl-ureido)-benzenesulfonamide. ¹H NMR (300 MHz, DMSO-d₆): δ=9.72 (brs, 1H), 9.24 (brs, 1H), 8.49 (d, J=5.4 Hz, 2H), 7.58-7.46 (m, 4H), 7.27 (d, J=5.1 Hz, 2H), 7.02-6.90 (m, 3H), 6.84-6.75 (m, 2H), 4.32 (d, J=5.7 Hz, 2H), 3.66 (s, 3H). MS: m/z 412.9 (M+H⁺).

Example 246: Synthesis of 4-(3-Pyridin-4-ylmethyl-ureido)-N-o-tolyl-benzenesulfonamide

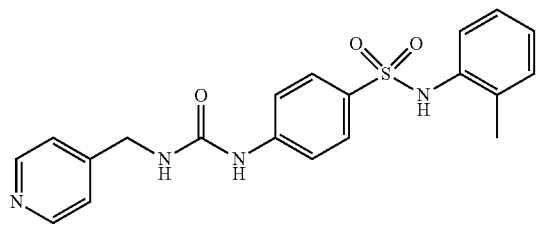 [SMILES: Cc1ccccc1NS(=O)(=O)c1ccc(NC(=O)NCc2ccncc2)cc1]

The title compound was prepared as described in example N-cyclohexyl-4-(3-pyridin-4-ylmethyl-ureido)-benzenesulfonamide. ¹H NMR (400 MHz, DMSO-d₆): δ=9.34 (brs, 1H), 9.26 (brs, 1H), 8.50 (d, J=6.0 Hz, 2H), 7.58-7.46 (m, 4H), 7.29 (d, J=5.6 Hz, 2H), 7.15-7.10 (m, 1H), 7.10-7.05 (m, 2H), 7.01-6.92 (m, 2H), 4.33 (d, J=5.6 Hz, 2H), 2.00 (s, 3H). MS: m/z 396.9 (M+H⁺).

Example 247: Synthesis of 4-(3-Pyridin-4-ylmethyl-ureido)-N-m-tolyl-benzenesulfonamide

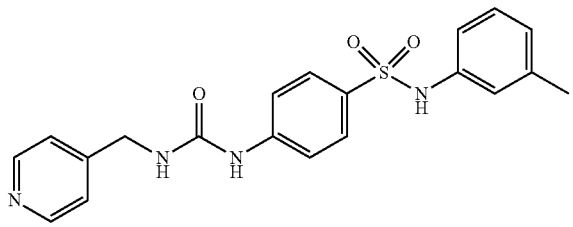 [SMILES: Cc1cccc(NS(=O)(=O)c2ccc(NC(=O)NCc3ccncc3)cc2)c1]

The title compound was prepared as described in example N-cyclohexyl-4-(3-pyridin-4-ylmethyl-ureido)-benzenesulfonamide. ¹H NMR (300 MHz, DMSO-d₆): δ=9.94 (brs, 1H), 9.32 (brs, 1H), 8.48 (d, J=4.8 Hz, 2H), 7.61 (d, J=8.7 Hz, 2H), 7.52 (d, J=9.0 Hz, 2H), 7.30-7.23 (m, 2H), 7.12-7.01 (m, 2H), 6.91-6.84 (m, 2H), 6.80 (d, J=7.5 Hz, 1H), 4.31 (d, J=5.7 Hz, 2H), 1.84 (s, 3H). MS: m/z 396.9 (M+H⁺).

Example 248: Synthesis of 4-(3-Pyridin-4-ylmethyl-ureido)-N-p-tolyl-benzenesulfonamide

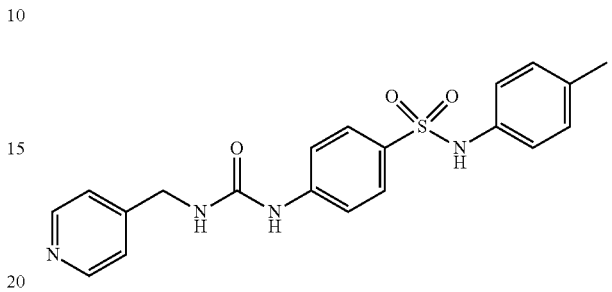

The title compound was prepared as described in example N-cyclohexyl-4-(3-pyridin-4-ylmethyl-ureido)-benzenesulfonamide. ¹H NMR (300 MHz, DMSO-d₆): δ=9.93 (brs, 1H), 9.19 (brs, 1H), 8.49 (d, J=4.8 Hz, 2H), 7.57 (d, J=8.7 Hz, 2H), 7.50 (d, J=9.3 Hz, 2H), 7.30-7.24 (m, 2H), 7.04-6.98 (m, 2H), 6.97-6.88 (m, 3H), 4.32 (d, J=5.4 Hz, 2H), 2.18 (s, 3H). MS: m/z 397.0 (M+H⁺).

Example 249: Synthesis of 4-(3-Pyridin-4-ylmethyl-ureido)-N-thiazol-2-yl-benzenesulfonamide

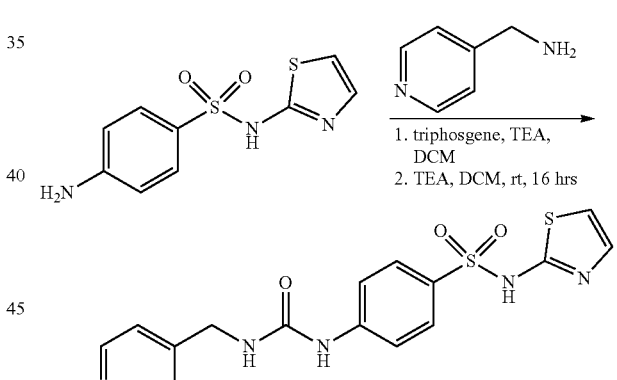

Triphosgen (70 mg, 0.235 mmol) was dissolved in DCM (10 mL) and cooled to −10° C. under N₂ atmosphere. To this cooled solution was added dropwise a mixture of 4-amino-N-thiazol-2-yl-benzenesulfonamide (200 mg, 0.783 mmol) and TEA (238 mg, 2.35 mmol) in DCM (10 mL). The mixture was stirred at −10° C. for 5 min and allowed to warm up to room temperature for 1 hour. Then a solution of c-pyridin-4-yl-methylamine (85 mg, 0.861 mmol) and TEA (238 mg, 2.35 mmol) in DCM (10 mL) was added. The resulting mixture was stirred at room temperature for 16 hours. The reaction was monitored by LC-MS. Then the mixture was diluted with DCM (20 mL) and washed with brine (20 mL). The organic layer was concentrated in vacuum to give a residue which was purified by prep-HPLC with NH₄Ac as additive to afford 4-(3-pyridin-4-ylmethyl-ureido)-N-thiazol-2-yl-benzenesulfonamide (151.6 mg, yield: 50%) as a yellow solid. ¹H NMR (400 MHz, DMSO-d$_6$): δ=9.17 (brs, 1H), 8.49 (dd, J=4.8, 1.6 Hz, 2H), 7.61 (d, J=8.8 Hz, 2H), 7.47 (d, J=8.8 Hz, 2H), 7.28 (d, J=5.6 Hz, 2H), 7.09 (d, J=4.0 Hz, 1H), 7.05 (t, J=6.0 Hz, 1H), 6.62 (d, J=4.4 Hz, 1H), 4.33 (d, J=5.6 Hz, 2H). MS: m/z 389.9 (M+H$^+$).

Example 250: Synthesis of N-(4,5-Dimethyl-oxazol-2-yl)-4-(3-pyridin-4-ylmethyl-ureido)-benzenesulfonamide

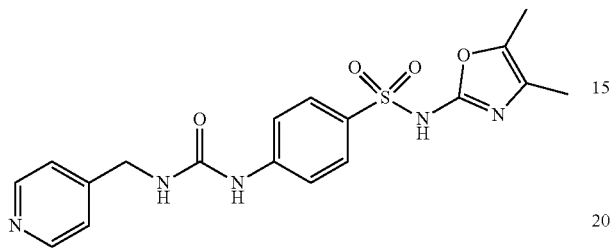

The title compound was prepared as described in example 4-(3-pyridin-4-ylmethyl-ureido)-N-thiazol-2-yl-benzenesulfonamide. $^1$H NMR (400 MHz, DMSO-d$_6$): δ=9.32 (brs, 1H), 8.51 (dd, J=4.8, 1.6 Hz, 2H), 7.65-7.54 (m, 4H), 7.30 (d, J=6.0 Hz, 2H), 7.01 (t, J=5.6 Hz, 1H), 4.34 (d, J=6.0 Hz, 2H), 2.04 (s, 3H), 1.61 (s, 3H). MS: m/z 402.0 (M+H$^+$).

Example 251: Synthesis of N-(5-Methyl-isoxazol-3-yl)-4-(3-pyridin-4-ylmethyl-ureido)-benzenesulfonamide

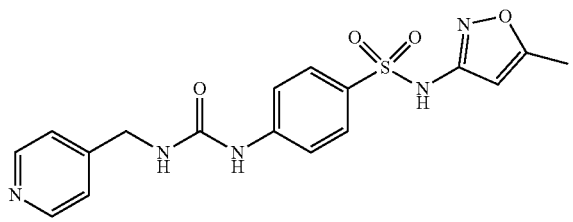 [SMILES: Cc1cc(NS(=O)(=O)c2ccc(NC(=O)NCc3ccncc3)cc2)no1]

The title compound was prepared as described in example 4-(3-pyridin-4-ylmethyl-ureido)-N-thiazol-2-yl-benzenesulfonamide. $^1$H NMR (400 MHz, DMSO-d$_6$): δ=9.24 (brs, 1H), 8.49 (d, J=6.0 Hz, 2H), 7.64 (d, J=8.8 Hz, 2H), 7.51 (d, J=8.8 Hz, 2H), 7.28 (d, J=6.0 Hz, 2H), 7.02 (t, J=6.4 Hz, 1H), 5.99 (s, 1H), 4.33 (d, J=6.0 Hz, 2H), 2.22 (s, 3H). MS: m/z 387.9 (M+H$^+$).

Example 252: Synthesis of 4-(3-Pyridin-4-ylmethyl-ureido)-N-pyrimidin-2-yl-benzenesulfonamide

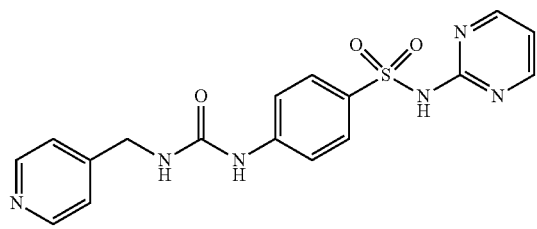 [SMILES: O=C(NCc1ccncc1)Nc1ccc(S(=O)(=O)Nc2ncccn2)cc1]

The title compound was prepared as described in example 4-(3-pyridin-4-ylmethyl-ureido)-N-thiazol-2-yl-benzenesulfonamide. $^1$H NMR (400 MHz, DMSO-d$_6$): δ=9.30 (brs, 1H), 8.49 (dd, J=4.8, 1.6 Hz, 2H), 8.39 (d, J=4.4 Hz, 2H), 7.78 (d, J=8.8 Hz, 2H), 7.51 (d, J=8.8 Hz, 2H), 7.28 (d, J=5.6 Hz, 2H), 7.08 (t, J=6.0 Hz, 1H), 6.86 (s, 1H), 4.33 (d, J=6.4 Hz, 2H). MS: m/z 384.9 (M+H$^+$).

Example 253: Synthesis of N-(4-Methyl-pyrimidin-2-yl)-4-(3-pyridin-4-ylmethyl-ureido)-benzenesulfonamide

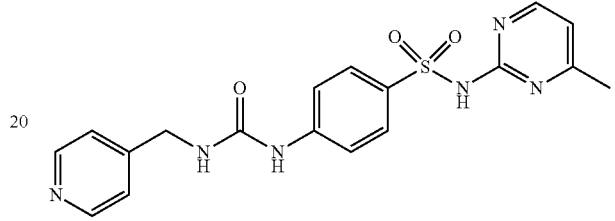

The title compound was prepared as described in example 4-(3-pyridin-4-ylmethyl-ureido)-N-thiazol-2-yl-benzenesulfonamide. $^1$H NMR (400 MHz, DMSO-d$_6$): δ=9.25 (brs, 1H), 8.48 (dd, J=4.8, 1.6 Hz, 2H), 8.22 (d, J=4.8 Hz, 1H), 7.80 (d, J=8.8 Hz, 2H), 7.51 (d, J=8.8 Hz, 2H), 7.28 (d, J=6.0 Hz, 2H), 7.09 (t, J=5.6 Hz, 1H), 6.76 (d, J=4.4 Hz, 1H), 4.33 (d, J=5.6 Hz, 2H), 2.26 (s, 3H). MS: m/z 398.9 (M+H$^+$).

Example 254: Synthesis of N-Pyridin-2-yl-4-(3-pyridin-4-ylmethyl-ureido)-benzenesulfonamide

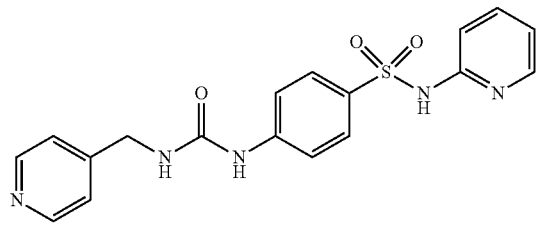 [SMILES: O=C(NCc1ccncc1)Nc1ccc(S(=O)(=O)Nc2ccccn2)cc1]

The title compound was prepared as described in example 4-(3-pyridin-4-ylmethyl-ureido)-N-thiazol-2-yl-benzenesulfonamide. $^1$H NMR (400 MHz, DMSO-d$_6$): δ=11.55 (brs, 1H), 9.14 (brs, 1H), 8.49 (d, J=2.0 Hz, 2H), 8.04 (d, J=4.8 Hz, 1H), 7.74 (d, J=9.2 Hz, 2H), 7.71-7.65 (m, 1H), 7.53 (d, J=8.8 Hz, 2H), 7.27 (d, J=5.2 Hz, 2H), 7.11 (d, J=8.4 Hz, 1H), 6.93-6.84 (m, 2H), 4.32 (d, J=6.0 Hz, 2H). MS: m/z 383.9 (M+H$^+$).

Example 255: Synthesis of 4-[3-(1H-Pyrazol-4-ylmethyl)-ureido]-N-pyridin-2-yl-benzenesulfonamide

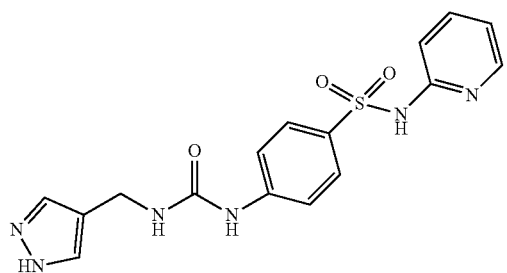 [SMILES: O=C(NCc1cn[nH]c1)Nc1ccc(S(=O)(=O)Nc2ccccn2)cc1]

The title compound was prepared as described in example 4-(3-pyridin-4-ylmethyl-ureido)-N-thiazol-2-yl-benzenesulfonamide. ¹H NMR (400 MHz, DMSO-$d_6$): δ=12.52 (brs, 1H), 9.04 (brs, 1H), 8.04 (d, J=4.8 Hz, 1H), 7.72 (d, J=8.8 Hz, 2H), 7.70-7.64 (m, 1H), 7.59-7.44 (m, 4H), 7.10 (d, J=8.8 Hz, 1H), 6.87 (t, J=6.4 Hz, 1H), 6.61 (t, J=5.6 Hz, 1H), 4.14 (d, J=5.2 Hz, 2H). MS: m/z 372.9 (M+H⁺).

Example 256: Synthesis of N-Benzyl-4-[3-(1H-pyrazol-4-ylmethyl)-ureido]-benzenesulfonamide

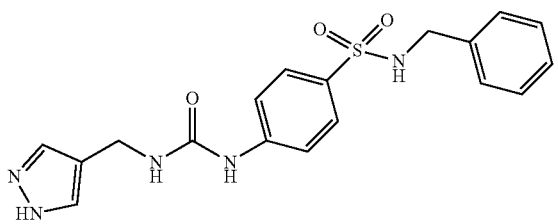 [SMILES: O=C(NCc1cn[nH]c1)Nc1ccc(S(=O)(=O)NCc2ccccc2)cc1]

The title compound was prepared as described in example 4-(3-pyridin-4-ylmethyl-ureido)-N-thiazol-2-yl-benzenesulfonamide. ¹H NMR (400 MHz, DMSO-$d_6$): δ=12.64 (brs, 1H), 9.05 (s, 1H), 7.90 (s, 1H), 7.70-7.42 (m, 6H), 7.33-7.19 (m, 5H), 6.68 (t, J=5.2 Hz, 1H), 4.16 (d, J=5.2 Hz, 2H), 3.92 (s, 2H). MS: m/z 385.9 (M+H⁺).

Example 257: Synthesis of 1-[4-(3,4-Dihydro-1H-isoquinoline-2-sulfonyl)-phenyl]-3-(1H-pyrazol-4-ylmethyl)-urea

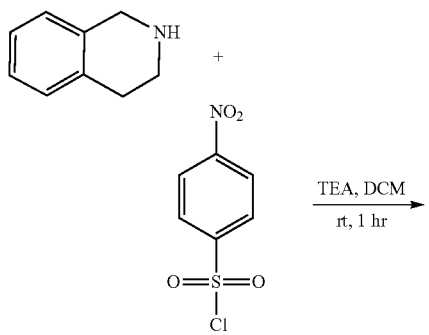

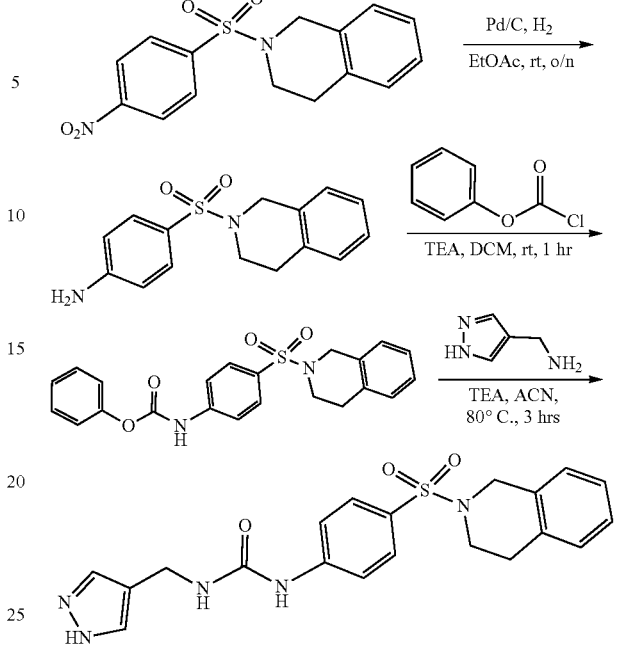

Step 1: To a solution of 1,2,3,4-tetrahydro-isoquinoline (266.4 mg, 2.0 mmol) in dry DCM (20 mL) was added 4-nitro-benzenesulfonyl chloride (665 mg, 3.0 mmol) and followed by TEA (607.2 mg, 6.0 mmol). The resulting mixture was stirred at room temperature for 1 hour. The reaction was monitored by TLC. Then the mixture was concentrated in vacuum to give a residue which was purified by silica gel column (DCM as eluent) to afford 2-(4-nitro-benzenesulfonyl)-1,2,3,4-tetrahydro-isoquinoline (612 mg, yield: 96%) as a yellow solid. ¹H NMR (400 MHz, DMSO-$d_6$): δ=8.42 (dd, J=6.8, 2.0 Hz, 2H), 8.10 (dd, J=6.8, 2.0 Hz, 2H), 7.19-7.18 (m, 4H), 4.29 (s, 2H), 3.40 (t, J=6.4 Hz, 2H), 2.86 (d, J=6.0 Hz, 2H).

Step 2: To a solution of 2-(4-nitro-benzenesulfonyl)-1,2,3,4-tetrahydro-isoquinoline (612 mg, 1.92 mmol) in MeOH (20 mL) was added Pd/C (122 mg, 20% wt). The resulting suspension was stirred at room temperature overnight. The reaction was monitored by LC-MS. Then Pd/C was filtered off and the filtrate was concentrated in vacuum to afford 4-(3,4-dihydro-1H-isoquinoline-2-sulfonyl)-phenylamine (510 mg, yield: 92%) as a white solid. ¹H NMR (400 MHz, DMSO-$d_6$): δ=7.44 (dd, J=7.2, 1.6 Hz, 2H), 7.17-7.08 (m, 4H), 6.64 (dd, J=6.8, 2.0 Hz, 2H), 6.08 (s, 2H), 4.06 (s, 2H), 3.16 (t, J=6.0 Hz, 2H), 2.84 (t, J=5.6 Hz, 2H).

Step 3: To a solution of 4-(3,4-dihydro-1H-isoquinoline-2-sulfonyl)-phenylamine (144 mg, 0.50 mmol) in DCM (20 mL) was added phenyl carbonchloridate (94 mg, 0.60 mmol) and followed by TEA (152 mg, 1.50 mmol). The resulting mixture was stirred at room temperature for 1 hour. The reaction was monitored by TLC. Then the mixture was concentrated in vacuum to give a residue which was purified by silica gel column eluting with PE/EtOAc (10:1 to 4:1) to afford [4-(3,4-dihydro-1H-isoquinoline-2-sulfonyl)-phenyl]-carbamic acid phenyl ester (176 mg, yield: 86%) as a white solid.

Step 4: To a solution of [4-(3,4-dihydro-1H-isoquinoline-2-sulfonyl)-phenyl]-carbamic acid phenyl ester (100 mg, 0.245 mmol) in ACN (20 mL) was added c-(1H-pyrazol-4-yl)-methylamine (100 mg, 80% purity) and followed by TEA (74.4 mg, 0.735 mmol). The resulting mixture was stirred at 80° C. for 3 hours. The reaction was monitored by LC-MS. Then the mixture was concentrated in vacuum to give a residue which was purified by prep-HPLC with NH₄OH as additive to afford 1-[4-(3,4-dihydro-1H-isoquinoline-2-sulfonyl)-phenyl]-3-(1H-pyrazol-4-ylmethyl)-urea (50.0 mg, yield: 50%) as a white solid. ¹H NMR (400 MHz, DMSO-d₆): δ=12.66 (brs, 1H), 9.04 (brs, 1H), 7.74-7.55 (m, 5H), 7.44 (brs, 1H), 7.20-7.06 (m, 4H), 6.58 (t, J=5.2 Hz, 1H), 4.16 (d, J=5.6 Hz, 2H), 4.13 (s, 2H), 3.23 (t, J=5.6 Hz, 2H), 2.84 (t, J=6.0 Hz, 2H). MS: m/z 412.0 (M+H⁺).

Example 258: Synthesis of 1-[4-(8-Oxa-3-aza-bicyclo[3.2.1]octane-3-sulfonyl)-phenyl]-3-(1H-pyrazol-4-ylmethyl)-urea

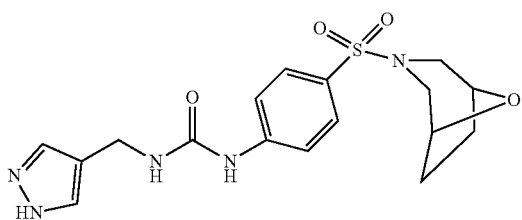 [SMILES: O=C(NCc1cn[nH]c1)Nc1ccc(S(=O)(=O)N2CC3CCC(C2)O3)cc1]

The title compound was prepared as described in example 1-[4-(3,4-dihydro-1H-isoquinoline-2-sulfonyl)-phenyl]-3-(1H-pyrazol-4-ylmethyl)-urea. ¹H NMR (400 MHz, DMSO-d₆): δ=12.65 (brs, 1H), 9.00 (s, 1H), 7.62 (d, J=8.8 Hz, 2H), 7.55 (d, J=8.8 Hz, 2H), 7.45 (brs, 1H), 6.56 (t, J=5.2 Hz, 1H), 4.32 (s, 2H), 4.17 (d, J=5.6 Hz, 2H), 3.21 (d, J=10.8 Hz, 2H), 2.41 (dd, J=11.2, 1.6 Hz, 2H), 1.85-1.72 (m, 4H). MS: m/z 391.9 (M+H⁺).

Example 259: Synthesis of N-Cyclobutylmethyl-4-[3-(1H-pyrazol-4-ylmethyl)-ureido]-benzenesulfonamide

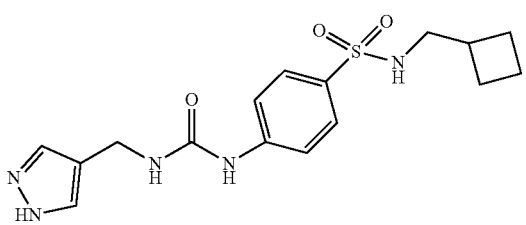 [SMILES: O=C(NCc1cn[nH]c1)Nc1ccc(S(=O)(=O)NCC2CCC2)cc1]

The title compound was prepared as described in example 1-[4-(3,4-dihydro-1H-isoquinoline-2-sulfonyl)-phenyl]-3-(1H-pyrazol-4-ylmethyl)-urea. ¹H NMR (400 MHz, DMSO-d₆): δ=12.58 (brs, 1H), 8.86 (s, 1H), 7.67-7.46 (m, 6H), 7.34 (t, J=6.0 Hz, 1H), 6.51 (d, J=5.2 Hz, 1H), 4.16 (d, J=5.6 Hz, 2H), 2.70 (t, J=6.8 Hz, 2H), 2.35-2.25 (m, 1H), 1.94-1.84 (m, 2H), 1.80-1.68 (m, 2H), 1.62-1.52 (m, 2H). MS: m/z 364.0 (M+H⁺).

Example 260: Synthesis of N-Phenyl-4-[3-(1H-pyrazol-4-ylmethyl)-ureido]-benzenesulfonamide

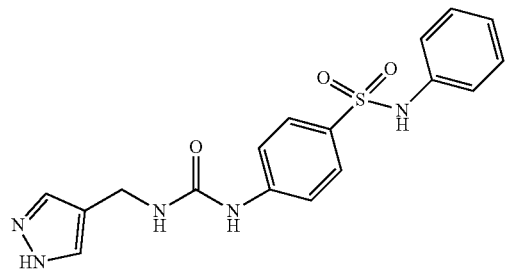 [SMILES: O=C(NCc1cn[nH]c1)Nc1ccc(S(=O)(=O)Nc2ccccc2)cc1]

The title compound was prepared as described in example 1-[4-(3,4-dihydro-1H-isoquinoline-2-sulfonyl)-phenyl]-3-(1H-pyrazol-4-ylmethyl)-urea. ¹H NMR (400 MHz, DMSO-d₆): δ=12.66 (brs, 1H), 8.88 (s, 1H), 7.66-7.42 (m, 6H), 7.18 (t, J=7.6 Hz, 2H), 7.04 (d, J=8.0 Hz, 2H), 6.95 (t, J=7.2 Hz, 1H), 6.54 (t, J=5.2 Hz, 1H), 4.14 (d, J=5.2 Hz, 2H). MS: m/z 371.9 (M+H⁺).

Example 261: Synthesis of 1-[4-(8-Oxa-3-aza-bicyclo[3.2.1]octane-3-sulfonyl)-phenyl]-3-(1H-pyrazol-4-ylmethyl)-urea

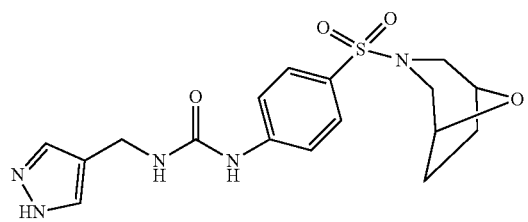 [SMILES: O=C(NCc1cn[nH]c1)Nc1ccc(S(=O)(=O)N2CC3CCC(C2)O3)cc1]

The title compound was prepared as described in example 1-[4-(3,4-dihydro-1H-isoquinoline-2-sulfonyl)-phenyl]-3-(1H-pyrazol-4-ylmethyl)-urea. ¹H NMR (400 MHz, DMSO-d₆): δ=12.65 (brs, 1H), 9.00 (s, 1H), 7.62 (d, J=8.8 Hz, 2H), 7.55 (d, J=8.8 Hz, 2H), 7.45 (brs, 1H), 6.56 (t, J=5.2 Hz, 1H), 4.32 (s, 2H), 4.17 (d, J=5.6 Hz, 2H), 3.21 (d, J=10.8 Hz, 2H), 2.41 (dd, J=11.2, 1.6 Hz, 2H), 1.85-1.72 (m, 4H). MS: m/z 391.9 (M+H⁺).

Example 262: Synthesis of 4-[3-(1H-Pyrazol-4-ylmethyl)-ureido]-N-pyridin-2-yl-benzenesulfonamide

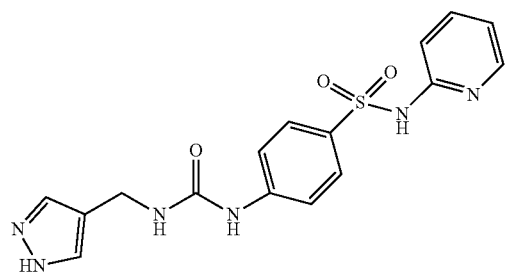

The title compound was prepared as described in example 1-[4-(3,4-dihydro-1H-isoquinoline-2-sulfonyl)-phenyl]-3-(1H-pyrazol-4-ylmethyl)-urea. $^1$H NMR (400 MHz, DMSO-$d_6$): δ=12.52 (brs, 1H), 9.04 (brs, 1H), 8.04 (d, J=4.8 Hz, 1H), 7.72 (d, J=8.8 Hz, 2H), 7.70-7.64 (m, 1H), 7.59-7.44 (m, 4H), 7.10 (d, J=8.8 Hz, 1H), 6.87 (t, J=6.4 Hz, 1H), 6.61 (t, J=5.6 Hz, 1H), 4.14 (d, J=5.2 Hz, 2H). MS: m/z 372.9 (M+H$^+$).

Example 263: Synthesis of N-Phenyl-4-[3-(1H-pyrazol-4-ylmethyl)-ureido]-benzenesulfonamide

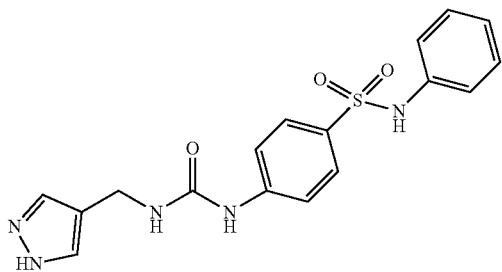

The title compound was prepared as described in example 1-[4-(3,4-dihydro-1H-isoquinoline-2-sulfonyl)-phenyl]-3-(1H-pyrazol-4-ylmethyl)-urea. $^1$H NMR (400 MHz, DMSO-$d_6$): δ=12.66 (brs, 1H), 8.88 (s, 1H), 7.66-7.42 (m, 6H), 7.18 (t, J=7.6 Hz, 2H), 7.04 (d, J=8.0 Hz, 2H), 6.95 (t, J=7.2 Hz, 1H), 6.54 (t, J=5.2 Hz, 1H), 4.14 (d, J=5.2 Hz, 2H). MS: m/z 371.9 (M+H$^+$).

Example 264: Synthesis of N-Benzyl-4-[3-(1H-pyrazol-4-ylmethyl)-ureido]-benzenesulfonamide

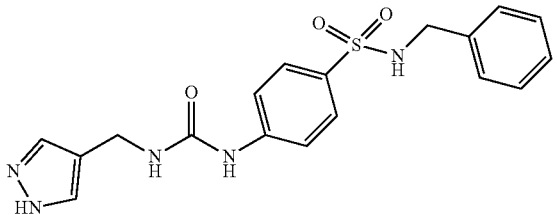 [SMILES: O=C(NCc1cn[nH]c1)Nc1ccc(S(=O)(=O)NCc2ccccc2)cc1]

The title compound was prepared as described in example 1-[4-(3,4-dihydro-1H-isoquinoline-2-sulfonyl)-phenyl]-3-(1H-pyrazol-4-ylmethyl)-urea. $^1$H NMR (400 MHz, DMSO-$d_6$): δ=12.64 (brs, 1H), 9.05 (s, 1H), 7.90 (s, 1H), 7.70-7.42 (m, 6H), 7.33-7.19 (m, 5H), 6.68 (t, J=5.2 Hz, 1H), 4.16 (d, J=5.2 Hz, 2H), 3.92 (s, 2H). MS: m/z 385.9 (M+H$^+$).

Example 265: Synthesis of N-Cyclobutylmethyl-4-[3-(1H-pyrazol-4-ylmethyl)-ureido]-benzenesulfonamide

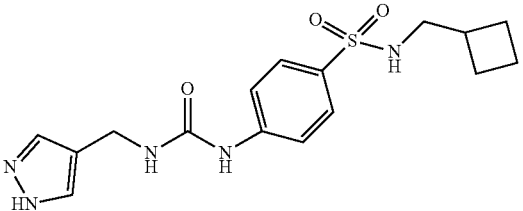 [SMILES: O=C(NCc1cn[nH]c1)Nc1ccc(S(=O)(=O)NCC2CCC2)cc1]

The title compound was prepared as described in example 1-[4-(3,4-dihydro-1H-isoquinoline-2-sulfonyl)-phenyl]-3-(1H-pyrazol-4-ylmethyl)-urea. $^1$H NMR (400 MHz, DMSO-$d_6$): δ=12.58 (brs, 1H), 8.86 (s, 1H), 7.67-7.46 (m, 6H), 7.34 (t, J=6.0 Hz, 1H), 6.51 (d, J=5.2 Hz, 1H), 4.16 (d, J=5.6 Hz, 2H), 2.70 (t, J=6.8 Hz, 2H), 2.35-2.25 (m, 1H), 1.94-1.84 (m, 2H), 1.80-1.68 (m, 2H), 1.62-1.52 (m, 2H). MS: m/z 364.0 (M+H$^+$).

Example 266: Synthesis of N-Cyclopentyl-N-methyl-4-[3-(1H-pyrazol-4-ylmethyl)-ureido]-benzenesulfonamide

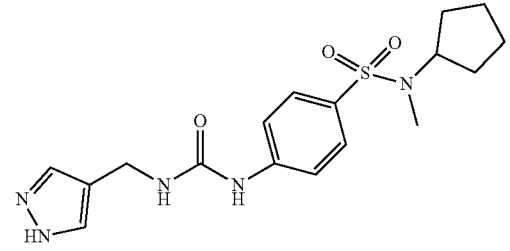 [SMILES: CN(C1CCCC1)S(=O)(=O)c1ccc(NC(=O)NCc2cn[nH]c2)cc1]

The title compound was prepared as described in example 1-[4-(3,4-dihydro-1H-isoquinoline-2-sulfonyl)-phenyl]-3-(1H-pyrazol-4-ylmethyl)-urea. $^1$H NMR (400 MHz, DMSO-$d_6$): δ=12.64 (brs, 1H), 8.92 (s, 1H), 7.67-7.46 (m, 6H), 6.52 (t, J=5.6 Hz, 1H), 4.22-4.10 (m, 3H), 2.59 (s, 3H), 1.55-1.44 (m, 4H), 1.43-1.34 (m, 2H), 1.32-1.25 (m, 2H). MS: m/z 378.0 (M+H$^+$).

Example 267: Synthesis of N-Benzyl-N-isopropyl-4-(3-oxazol-5-ylmethyl-ureido)-benzenesulfonamide

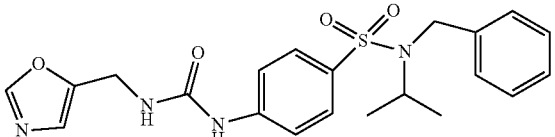

The title compound was prepared as described in example 1-[4-(3,4-dihydro-1H-isoquinoline-2-sulfonyl)-phenyl]-3-(1H-pyrazol-4-ylmethyl)-urea. $^1$H NMR (400 MHz, DMSO-$d_6$): δ=9.09 (s, 1H), 8.29 (s, 1H), 7.70 (d, J=8.0 Hz, 2H), 7.59 (d, J=8.0 Hz, 2H), 7.41 (d, J=7.2 Hz, 2H), 7.34 (t, J=7.2 Hz, 2H), 7.24 (d, J=7.6 Hz, 1H), 7.02 (s, 1H), 6.82 (t, J=5.6

Hz, 1H), 4.39 (d, J=6.4 Hz, 2H), 4.34 (s, 2H), 4.06-3.96 (m, 1H), 0.83 (d, J=6.4 Hz, 6H). MS: m/z 429.0 (M+H⁺).

Example 268: Synthesis of N-Benzyl-N-isopropyl-4-(3-thiazol-5-ylmethyl-ureido)-benzenesulfonamide

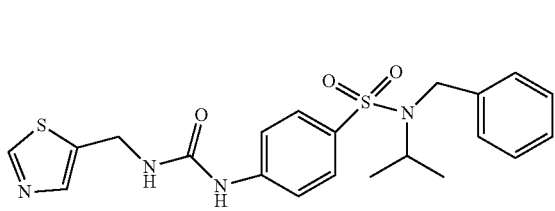 [SMILES: CC(C)N(Cc1ccccc1)S(=O)(=O)c1ccc(NC(=O)NCc2cnco2)cc1]

The title compound was prepared as described in example 1-[4-(3,4-dihydro-1H-isoquinoline-2-sulfonyl)-phenyl]-3-(1H-pyrazol-4-ylmethyl)-urea. ¹H NMR (400 MHz, DMSO-d₆): δ=9.14 (s, 1H), 8.98 (s, 1H), 7.91-7.54 (m, 5H), 7.50-7.17 (m, 5H), 7.03-6.28 (m, 1H), 4.68-4.46 (m, 2H), 4.35 (s, 2H), 4.12-3.91 (m, 1H), 0.99-0.62 (m, 6H). MS: m/z 444.9 (M+H⁺).

Example 269: Synthesis of N-Benzyl-N-isopropyl-4-(3-thiazol-2-ylmethyl-ureido)-benzenesulfonamide

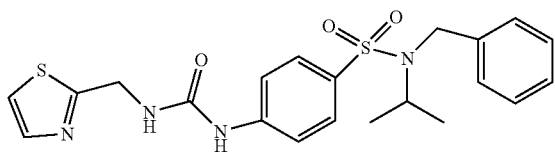 [SMILES: CC(C)N(Cc1ccccc1)S(=O)(=O)c1ccc(NC(=O)NCc2nccs2)cc1]

The title compound was prepared as described in example 1-[4-(3,4-dihydro-1H-isoquinoline-2-sulfonyl)-phenyl]-3-(1H-pyrazol-4-ylmethyl)-urea. ¹H NMR (400 MHz, DMSO-d₆): δ=9.32 (s, 1H), 7.79-7.69 (m, 3H), 7.68-7.60 (m, 3H), 7.42 (d, J=7.2 Hz, 2H), 7.34 (t, J=7.2 Hz, 2H), 7.25 (t, J=7.2 Hz, 1H), 7.15 (t, J=5.6 Hz, 1H), 4.63 (d, J=5.6 Hz, 2H), 4.35 (s, 2H), 4.08-3.97 (m, 1H), 0.84 (d, J=6.4 Hz, 6H). MS: m/z 444.9 (M+H⁺).

Example 270: Synthesis of N-Benzyl-N-isopropyl-4-[3-(1H-pyrazol-4-ylmethyl)-ureido]-benzenesulfonamide

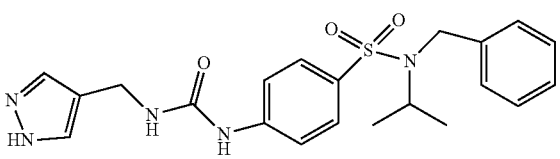 [SMILES: CC(C)N(Cc1ccccc1)S(=O)(=O)c1ccc(NC(=O)NCc2cn[nH]c2)cc1]

The title compound was prepared as described in example 1-[4-(3,4-dihydro-1H-isoquinoline-2-sulfonyl)-phenyl]-3-(1H-pyrazol-4-ylmethyl)-urea. ¹H NMR (400 MHz, DMSO-d₆): δ=12.60 (brs, 1H), 8.93 (s, 1H), 7.69 (dd, J=6.8, 1.6 Hz, 2H), 7.63-7.49 (m, 4H), 7.41 (d, J=6.8 Hz, 2H), 7.33 (t, J=7.6 Hz, 2H), 7.24 (t, J=7.6 Hz, 1H), 6.53 (t, J=5.2 Hz, 1H), 4.34 (s, 2H), 4.17 (d, J=5.2 Hz, 2H), 4.05-3.96 (m, 1H), 0.83 (d, J=6.8 Hz, 6H). MS: m/z 428.0 (M+H⁺).

Example 271: Synthesis of 1-[4-(3,4-Dihydro-1H-isoquinoline-2-sulfonyl)-phenyl]-3-oxazol-5-ylmethyl-urea

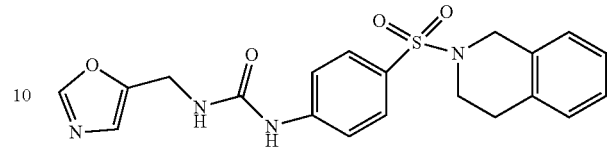

The title compound was prepared as described in example 1-[4-(3,4-dihydro-1H-isoquinoline-2-sulfonyl)-phenyl]-3-(1H-pyrazol-4-ylmethyl)-urea. ¹H NMR (400 MHz, DMSO-d₆): δ=9.12 (s, 1H), 8.27 (s, 1H), 7.68 (d, J=8.8 Hz, 2H), 7.62 (d, J=8.8 Hz, 2H), 7.17-7.08 (m, 4H), 7.01 (s, 1H), 6.82 (t, J=5.6 Hz, 1H), 4.38 (d, J=6.0 Hz, 2H), 4.14 (s, 2H), 3.24 (t, J=6.4 Hz, 2H), 2.84 (t, J=5.6 Hz, 2H). MS: m/z 412.9 (M+H⁺).

Example 272: Synthesis of N-(3-Methoxy-benzyl)-4-[3-(1H-pyrazol-4-ylmethyl)-ureido]-benzenesulfonamide

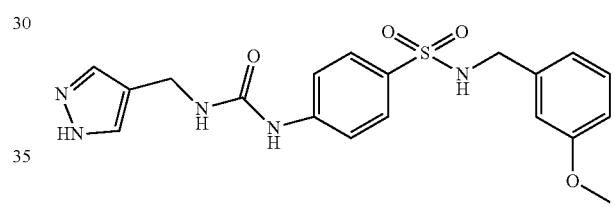

The title compound was prepared as described in example 1-[4-(3,4-dihydro-1H-isoquinoline-2-sulfonyl)-phenyl]-3-(1H-pyrazol-4-ylmethyl)-urea. ¹H NMR (400 MHz, DMSO-d₆): δ=12.60 (brs, 1H), 8.86 (s, 1H), 7.89 (t, J=6.4 Hz, 1H), 7.67-7.48 (m, 6H), 7.21-7.15 (m, 1H), 6.83-6.75 (m, 3H), 6.50 (t, J=5.6 Hz, 1H), 4.16 (d, J=5.2 Hz, 2H), 3.91 (d, J=6.4 Hz, 2H), 3.69 (s, 3H). MS: m/z 415.9 (M+H⁺).

Example 273: Synthesis of N-(2-Chloro-benzyl)-4-[3-(1H-pyrazol-4-ylmethyl)-ureido]-benzenesulfonamide

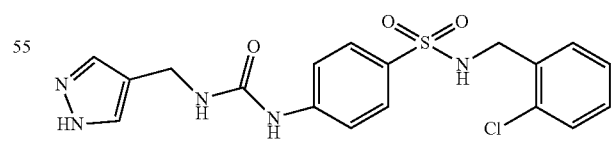

The title compound was prepared as described in example 1-[4-(3,4-dihydro-1H-isoquinoline-2-sulfonyl)-phenyl]-3-(1H-pyrazol-4-ylmethyl)-urea. ¹H NMR (400 MHz, DMSO-d₆): δ=12.60 (brs, 1H), 8.89 (s, 1H), 7.98 (t, J=6.0 Hz, 1H), 7.71-7.48 (m, 6H), 7.46-7.36 (m, 2H), 7.33-7.24 (m, 2H), 6.52 (t, J=5.6 Hz, 1H), 4.17 (d, J=5.6 Hz, 2H), 4.01 (d, J=6.4 Hz, 2H). MS: m/z 419.9 (M+H⁺).

Example 274: Synthesis of N-(2-Methoxy-benzyl)-4-[3-(1H-pyrazol-4-ylmethyl)-ureido]-benzenesulfonamide

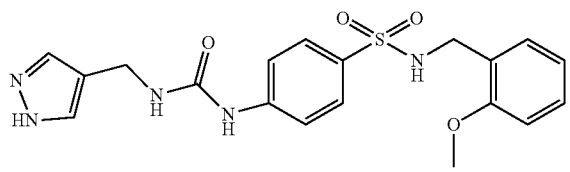 [SMILES: COc1ccccc1CNS(=O)(=O)c1ccc(NC(=O)NCc2cn[nH]c2)cc1]

The title compound was prepared as described in example 1-[4-(3,4-dihydro-1H-isoquinoline-2-sulfonyl)-phenyl]-3-(1H-pyrazol-4-ylmethyl)-urea. $^1$H NMR (400 MHz, DMSO-$d_6$): δ=12.62 (brs, 1H), 8.86 (s, 1H), 7.70 (t, J=6.4 Hz, 1H), 7.67-7.49 (m, 6H), 7.27-7.18 (m, 2H), 6.93-6.85 (m, 2H), 6.51 (t, J=5.6 Hz, 1H), 4.17 (d, J=5.6 Hz, 2H), 3.89 (d, J=5.6 Hz, 2H), 3.70 (s, 3H). MS: m/z 415.9 (M+H$^+$).

Example 275: Synthesis of N-(4-Methoxy-benzyl)-4-[3-(1H-pyrazol-4-ylmethyl)-ureido]-benzenesulfonamide

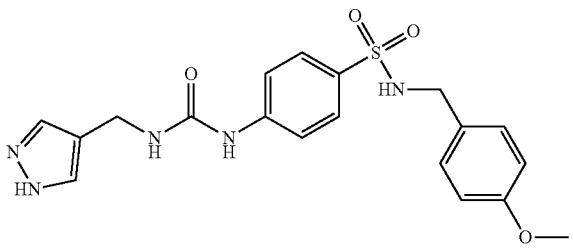 [SMILES: COc1ccc(CNS(=O)(=O)c2ccc(NC(=O)NCc3cn[nH]c3)cc2)cc1]

The title compound was prepared as described in example 1-[4-(3,4-dihydro-1H-isoquinoline-2-sulfonyl)-phenyl]-3-(1H-pyrazol-4-ylmethyl)-urea. $^1$H NMR (400 MHz, DMSO-$d_6$): δ=12.56 (brs, 1H), 8.87 (s, 1H), 7.80 (t, J=6.4 Hz, 1H), 7.68-7.48 (m, 6H), 7.14 (d, J=8.8 Hz, 2H), 6.83 (d, J=8.4 Hz, 2H), 6.51 (t, J=5.6 Hz, 1H), 4.16 (d, J=5.6 Hz, 2H), 3.85 (d, J=6.0 Hz, 2H), 3.71 (s, 3H). MS: m/z 415.9 (M+H$^+$).

Example 276: Synthesis of N-(4-Chloro-benzyl)-4-[3-(1H-pyrazol-4-ylmethyl)-ureido]-benzenesulfonamide

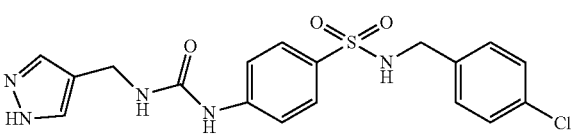 [SMILES: O=C(NCc1cn[nH]c1)Nc1ccc(S(=O)(=O)NCc2ccc(Cl)cc2)cc1]

The title compound was prepared as described in example 1-[4-(3,4-dihydro-1H-isoquinoline-2-sulfonyl)-phenyl]-3-(1H-pyrazol-4-ylmethyl)-urea. $^1$H NMR (400 MHz, DMSO-$d_6$): δ=12.59 (brs, 1H), 8.88 (s, 1H), 7.99 (t, J=6.4 Hz, 1H), 7.67-7.46 (m, 6H), 7.34-7.25 (m, 3H), 7.20 (d, J=7.2 Hz, 1H), 6.51 (t, J=5.6 Hz, 1H), 4.16 (d, J=5.6 Hz, 2H), 3.96 (d, J=6.4 Hz, 2H). MS: m/z 419.9 (M+H$^+$).

Example 277: Synthesis of N-cyclopentyl-3-(3-(pyridin-4-ylmethyl)ureido)benzenesulfonamide

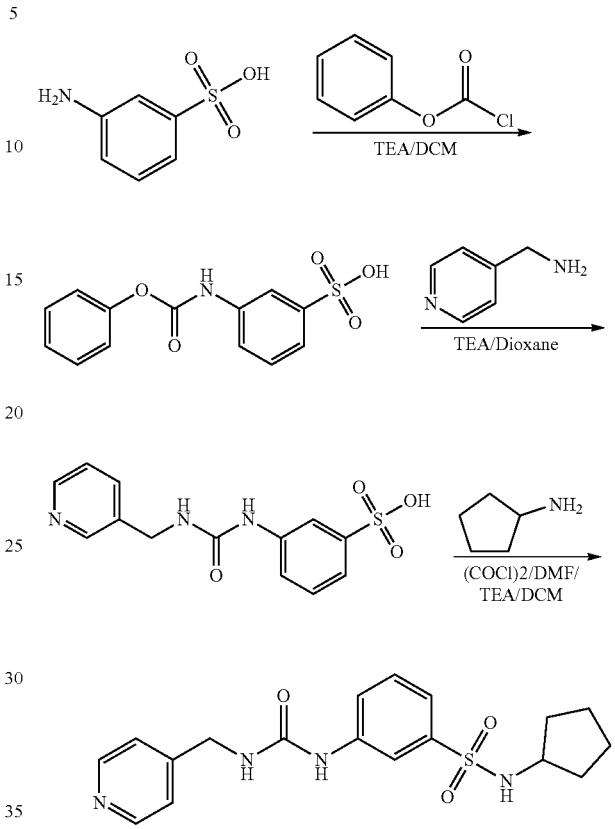

Step 1: A mixture of 3-aminobenzenesulfonic acid (34.6 g, 200 mmol), phenyl carbonochoridate (35 g, 220 mmol) and TEA (41 g, 400 mmol) in DCM (500 mL) was stirred at room temperature for 2 hrs. The mixture was concentrated in vacuum to remove most of DCM and then filtered. The filter cake was dried in vacuum to give the crude product (82 g, >100%), which was used in next step without further purification.

Step 2: A mixture of 3-((phenoxycarbonyl)amino)benzenesulfonic acid (41 g, 200 mmol), pyridin-4-ylmethanamine (35 g, 220 mmol) and TEA (41 g, 400 mmol) in dioxane (500 mL) was stirred at room temperature for 12 hrs. The mixture was concentrated in vacuum. The residue was purified by column chromatography on silica gel eluting with DMC/MeH (10:1) to give product as a yellow solid.

Step 3: A mixture of 3-(3-(pyridin-3-ylmethyl)ureido) benzenesulfonic acid (200 mg, 065 mmol), (COCl)$_2$ (100 mg, 0.78 mmol) and DMF in DCM (5 mL) was stirred at room temperature for 30 minutes. The mixture was concentrated in vacuum. The residue was added to a mixture of cyclopentanamine (70 mg, 0.78 mmol) and TEA (140 mg, 1.3 mmol) in DCM (5 mL) at room temperature. The mixture was stirred at room temperature for 12 hours and concentrated in vacuum. The residue was purified by pre-HPLC to give the title product (40 mg, 24) as a white solid. $^1$H NMR (400 MHz, CD$_3$OD): δ=8.47 (s, 2H), 8.01 (s, 1H), 7.57-7.55 (m, 1H), 7.47-7.391 (m, 4H), 4.46 (s, 2H), 3.53-3.51 (m, 1H), 1.69-1.44 (m, 8H). MS: m/z 375.0 (M+H$^+$).

Example 278: Synthesis of N-benzyl-3-(3-(pyridin-4-ylmethyl)ureido)benzenesulfonamide

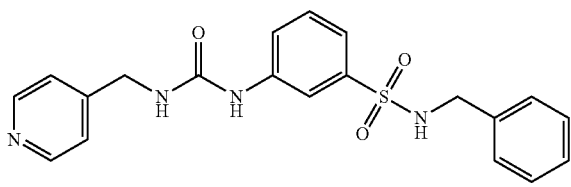 [SMILES: O=C(NCc1ccncc1)Nc1cccc(S(=O)(=O)NCc2ccccc2)c1]

The title compound was prepared as described in example N-cyclopentyl-3-(3-(pyridin-4-ylmethyl)ureido)benzenesulfonamide. $^1$H NMR (400 MHz, CD$_3$OD): δ=8.47-8.46 (s, 2H), 7.98 (s, 1H), 7.56-7.54 (m, 1H), 7.42-7.40 (m, 4H), 7.21 (m, 5H) 4.46 (s, 2H), 4.05 (s, 2H). MS: m/z 397.0 (M+H$^+$).

Example 279: Synthesis of 1-(3-(morpholinosulfonyl)phenyl)-3-(pyridin-4-ylmethyl)urea

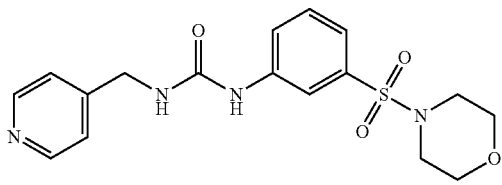 [SMILES: O=C(NCc1ccncc1)Nc1cccc(S(=O)(=O)N2CCOCC2)c1]

The title compound was prepared as described in example N-cyclopentyl-3-(3-(pyridin-4-ylmethyl)ureido)benzenesulfonamide. $^1$H NMR (400 MHz, CD$_3$OD): δ=8.47-8.46 (m, 2H), 7.99-7.98 (s, 1H), 7.61-7.58 (m, 1H), 7.49-7.40 (m, 1H), 7.39-7.35 (m, 3H), 4.46 (s, 2H), 3.69-3.67 (m, 4H), 2.98-2.95 (m, 4H). MS: m/z 377.0 (M+H$^+$).

Example 280: Synthesis of N-(cyclobutylmethyl)-3-(3-(pyridin-4-ylmethyl)ureido)benzenesulfonamide

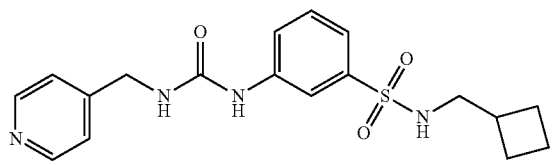 [SMILES: O=C(NCc1ccncc1)Nc1cccc(S(=O)(=O)NCC2CCC2)c1]

The title compound was prepared as described in example N-cyclopentyl-3-(3-(pyridin-4-ylmethyl)ureido)benzenesulfonamide. $^1$H NMR (400 MHz, CD$_3$OD): δ=8.47-8.46 (m, 2H), 7.99 (s, 1H), 7.56 (s, 1H), 7.44-7.39 (m, 4H), 4.46 (s, 2H), 2.87-2.85 (m, 2H), 2.40-2.36 (m, 1H), 1.98-1.29 (m, 6H). MS: m/z 377.0 (M+H$^+$).

Example 281: Synthesis of N-phenethyl-3-(3-(pyridin-4-ylmethyl)ureido)benzenesulfonamide

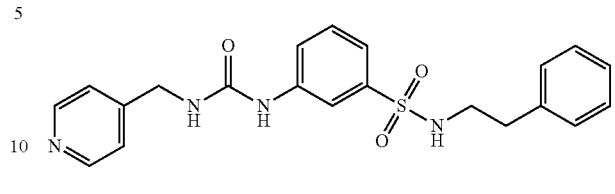

The title compound was prepared as described in example N-cyclopentyl-3-(3-(pyridin-4-ylmethyl)ureido)benzenesulfonamide. $^1$H NMR (400 MHz, CD$_3$OD): δ=8.47-8.46 (s, 2H), 7.98 (s, 1H), 7.56-7.54 (m, 1H), 7.42-7.39 (m, 4H), 7.223-7.09 (m, 5H), 4.46 (s, 2H), 3.10-3.07 (m, 2H), 2.72-2.69 (m, 2H). MS: m/z 411.0 (M+H$^+$).

Example 282: Synthesis of 4-(3-Pyridin-4-ylmethyl-ureido)-N-(2-chloro-phenyl)-benzenesulfonamide

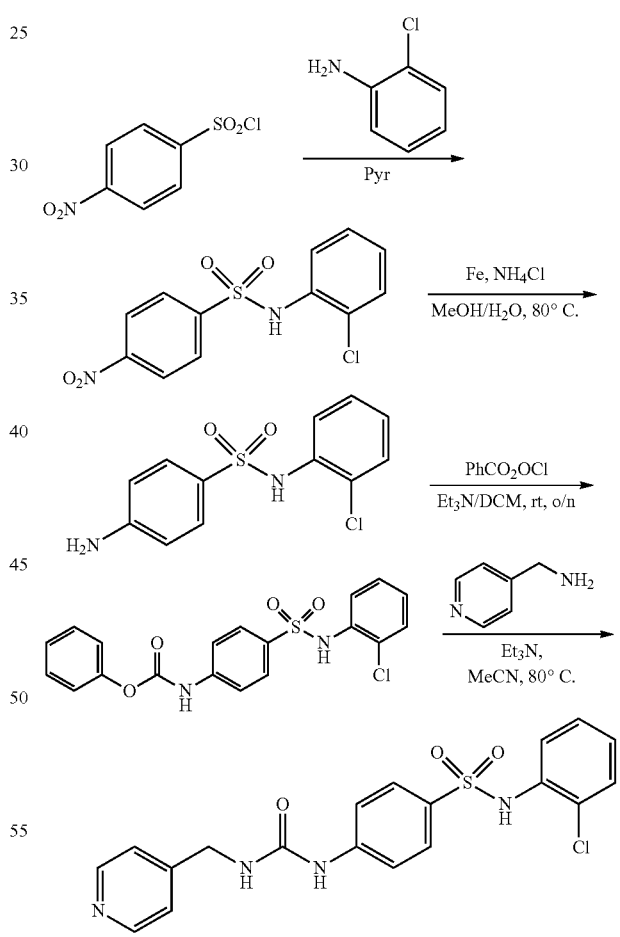

Step 1: To a solution of 4-nitro-benzenesulfonyl chloride (2.1 g, 9.5 mmol) in Pyr (15 mL) was added 2-chlorophenylamine (1.0 g, 7.9 mmol) and then was stirred at room temperature for 2 hrs. The reaction was concentrated under reduced pressure and the residue was purified by silica gel column eluting with PE/EtOAc (5:1) to give N-(2-chloro-phenyl)-4-nitro-benzenesulfonamide (0.8 g, yield: 28%) as a yellow solid. $^1$H NMR (400 MHz, DMSO-$d_6$): δ=10.46 (s, 1H), 8.40 (d, J=8.8 Hz, 2H), 7.95 (d, J=8.8 Hz, 2H), 7.44 (d, J=7.6 Hz, 1H), 7.32-7.24 (m, 3H).

Step 2: To a solution of N-(2-chloro-phenyl)-4-nitro-benzenesulfonamide (320 mg, 1.1 mmol) and Fe (616 mg, 11.0 mmol) in MeOH (5 mL) was a solution of NH$_4$Cl (1.2 g, 22.0 mmol) in water (10 mL). The reaction was stirred at 80° C. for 4 hrs. Then the reaction mixture was filtered. The filtrate was added to water (10 ml) and then extracted with EtOAc (20 mL*2). The combined organic layer was washed with brine (40 mL), dried over Na$_2$SO$_4$ and concentrated under reduced pressure. The residue was purified by silica gel column eluting with PE/EtOAc (2:1) to give 4-amino-N-(2-chloro-phenyl)-benzenesulfonamide (305 mg, yield: 98%) as a white solid.

Step 3 & 4: Step 3 to Step 4 was prepared as described in example 1-(4-benzenesulfonyl-phenyl)-3-pyridin-4-ylmethyl-urea. $^1$H NMR (300 MHz, DMSO-$d_6$): δ=9.69 (s, 1H), 9.19 (s, 1H), 8.51-8.49 (m, 2H), 7.58-7.54 (m, 4H), 7.40-7.34 (m, 1H), 7.29-7.25 (m, 4H), 7.20-7.17 (m, 1H), 6.92 (brs, 1H), 4.34-4.32 (m, 2H), MS: m/z 416.9 (M+H$^+$).

Example 283: Synthesis of 4-(3-Pyridin-4-ylmethyl-ureido)-N-(3-chloro-phenyl)-benzenesulfonamide

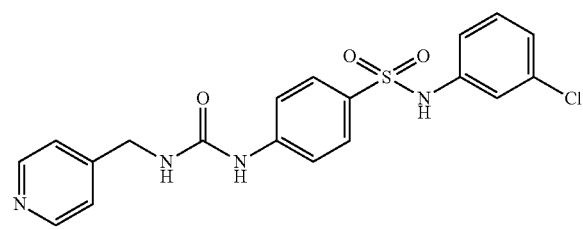 [SMILES: O=C(NCc1ccncc1)Nc1ccc(S(=O)(=O)Nc2cccc(Cl)c2)cc1]

The title compound was prepared as described in example 4-(3-benzyl-ureido)-N-(2-chloro-phenyl)-benzenesulfonamide. $^1$H NMR (300 MHz, DMSO-$d_6$): δ=10.39 (s, 1H), 9.21 (s, 1H), 8.48 (d, J=5.7 Hz, 2H), 7.65-7.53 (m, 4H), 7.28-7.22 (m, 3H), 7.10-7.03 (m, 3H), 6.93 (t, J=1.2 Hz, 1H), 4.32 (d, J=2.1 Hz, 2H), MS: m/z 416.9 (M+H$^+$).

Example 284: Synthesis of 4-(3-pyridin-4-ylmethyl-ureido)-N-(4-chloro-phenyl)-benzenesulfonamide

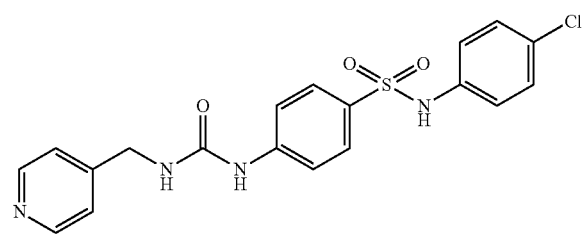 [SMILES: O=C(NCc1ccncc1)Nc1ccc(S(=O)(=O)Nc2ccc(Cl)cc2)cc1]

The title compound was prepared as described in example 4-(3-pyridin-4-ylmethyl-ureido)-N-(2-chloro-phenyl)-benzenesulfonamide. $^1$H NMR (400 MHz, DMSO-$d_6$): δ=10.26 (s, 1H), 9.19 (s, 1H), 8.49 (d, J=6.0 Hz, 2H), 7.60 (d, J=8.8 Hz, 2H), 7.53 (d, J=8.4 Hz, 2H), 7.28-7.25 (m, 4H), 7.07 (d, J=8.8 Hz, 2H), 6.93 (t, J=6.0 Hz, 1H), 4.32 (d, J=6.0 Hz, 2H). MS: m/z 416.9 (M+H$^+$).

Example 285: Synthesis of N-Benzyl-4-(3-oxazol-5-ylmethyl-ureido)-benzenesulfonamide

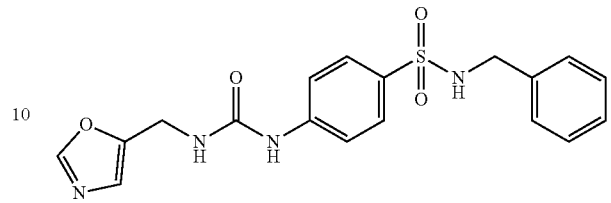

The title compound was prepared as described in example 4-(3-pyridin-4-ylmethyl-ureido)-N-(2-chloro-phenyl)-benzenesulfonamide. $^1$H NMR (400 MHz, DMSO-$d_6$): δ=9.05 (s, 1H), 8.29 (s, 1H), 7.92 (t, J=6.0 Hz, 1H), 7.66 (d, J=8.4 Hz, 2H), 7.56 (d, J=8.8 Hz, 2H), 7.28-7.22 (m, 5H), 7.02 (s, 1H), 6.81 (t, J=5.6 Hz, 1H), 4.39 (d, J=5.6 Hz, 2H), 3.92 (d, J=6.4 Hz, 2H). MS: m/z 386.9 (M+H$^+$).

Example 286: Synthesis of 1-[4-(3,4-Dihydro-1H-isoquinoline-2-sulfonyl)-phenyl]-3-thiazol-5-ylmethyl-urea

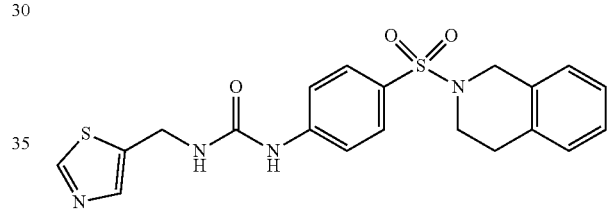

The title compound was prepared as described in example 4-(3-pyridin-4-ylmethyl-ureido)-N-(2-chloro-phenyl)-benzenesulfonamide. $^1$H NMR (400 MHz, DMSO-$d_6$): δ=9.17 (s, 1H), 8.96 (s, 1H), 7.78 (s, 1H), 7.68 (d, J=9.2 Hz, 2H), 7.63 (d, J=9.2 Hz, 2H), 7.13-7.11 (m, 4H), 6.94 (t, J=5.6 Hz, 1H), 4.52 (d, J=5.6 Hz, 2H), 4.14 (s, 2H), 3.24 (t, J=6.0 Hz, 2H), 2.84 (t, J=5.6 Hz, 2H). MS: m/z 428.9 (M+H$^+$).

Example 287: Synthesis of 1-[4-(3,4-Dihydro-1H-isoquinoline-2-sulfonyl)-phenyl]-3-(3,5-dimethyl-isoxazol-4-ylmethyl)-urea

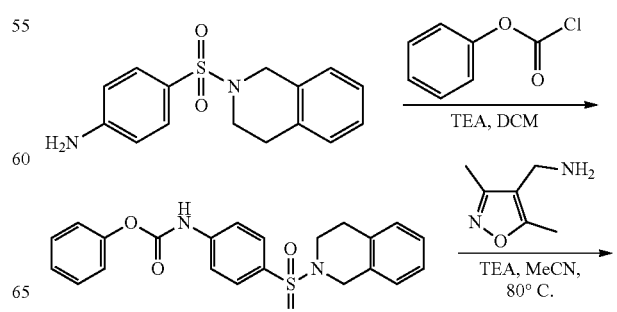

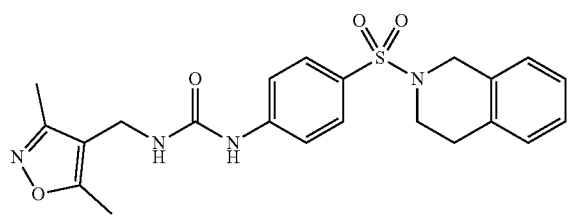

Step 1: To a solution of 4-(3,4-dihydro-1H-isoquinoline-2-sulfonyl)-phenylamine (300 mg, 1.04 mmoL) and Et₃N (0.3 mL, 2.1 mmoL) in DCM (10 mL) was added phenyl chroloformate (290 mg, 1.85 mmoL) at 0° C. and stirred at room temperature for 2 hrs.

The reaction mixture was concentrated to dryness in vacuum and the residue was purified by silica gel column eluting with PE/EtOAc (6:1) to give [4-(3,4-dihydro-1H-isoquinoline-2-sulfonyl)-phenyl]-carbamic acid phenyl ester (370 mg, yield: 87%) as a white solid. MS: m/z 409.1 (M+H⁺).

Step 2: To a solution of [4-(3,4-dihydro-1H-isoquinoline-2-sulfonyl)-phenyl]-carbamic acid phenyl ester (370 mg, 0.9 mmoL), C-(3,5-dimethyl-isoxazol-4-yl)-methylamine (115 mg, 0.9 mmoL) and Et₃N (0.3 mL, 2.1 mmoL) in MeCN (12 mL) at room temperature and stirred for 1 h at 80° C. The reaction mixture was concentrated to dryness in vacuum and part of the residue (260 mg) was purified by Prep-HPLC to give 1-[4-(3,4-dihydro-1H-isoquinoline-2-sulfonyl)-phenyl]-3-(3,5-dimethyl-isoxazol-4-ylmethyl)-urea (41 mg, yield: 10%) as a white solid. ¹H NMR (300 MHz, DMSO-d₆): δ=8.95 (s, 1H), 7.68 (d, J=8.7 Hz, 2H), 7.59 (d, J=9.0 Hz, 2H), 7.15-7.11 (m, 4H), 6.67 (t, J=5.7 Hz, 1H), 4.13 (s, 2H), 4.05 (d, J=5.1 Hz, 2H), 3.23 (t, J=5.7 Hz, 2H), 2.84 (t, J=4.8 Hz, 2H), 2.37 (s, 3H), 2.20 (s, 3H). MS: m/z 441.0 (M+H⁺).

Example 288: Synthesis of 1-[4-(3-Chloro-benzenesulfonyl)-phenyl]-3-pyridin-4-ylmethyl-urea

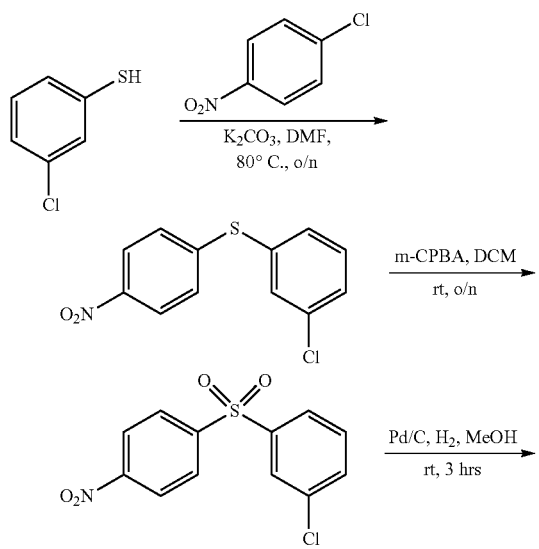

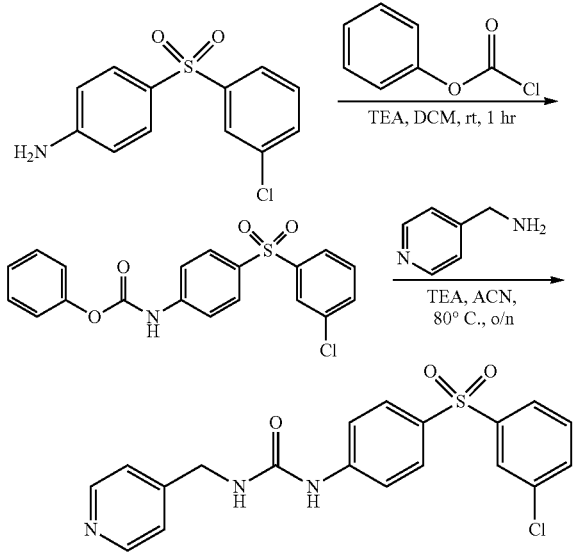

Step 1: To a solution of 3-chloro-benzenethiol (433.86 mg, 3.0 mmol) in DMF (20 mL) was added 1-chloro-4-nitro-benzene (709 mg, 4.5 mmol) and followed by K₂CO₃ (1.24 g, 9.0 mmol). The resulting mixture was stirred at 80° C. overnight. The reaction was monitored by TLC. Then the mixture was diluted with H₂O (40 mL) and extracted with DCM (20 mL×2). The combined organic layers were concentrated in vacuum to give a residue, which was purified by a silica gel column (PE/EA=100:1) to afford 4-(3-chloro-phenylthio)-1-nitrobenzene (726 mg, yield: 91%) as a yellow solid. ¹H NMR (400 MHz, CDCl₃): δ=8.11 (dd, J=6.8, 2.0 Hz, 2H), 7.51 (t, J=1.6 Hz, 1H), 7.44-7.36 (m, 3H), 7.25 (dd, J=6.8, 2.0 Hz, 2H).

Step 2: To a solution of 4-(3-chlorophenylthio)-1-nitrobenzene (726 mg, 2.73 mmol) in DCM (40 mL) was added 3-chloro-benzenecarboperoxoic acid (2.02 g, 8.20 mmol, 30% H₂O contained). The resulting mixture was stirred at room temperature overnight. The reaction was monitored by TLC. Then the mixture was mixed with saturated Na₂SO₃ (30 mL), and extracted with DCM (20 mL×2). The combined organic layers were concentrated in vacuum to give a residue, which was purified by a silica gel column (PE/EA=10:1) to afford 4-[(3-chlorophenyl)sulfonyl]-1-nitrobenzene (705 mg, yield: 88%) as yellow solid. ¹H NMR (400 MHz, CDCl₃): δ=8.36 (dd, J=9.2, 2.0 Hz, 2H), 8.14 (dd, J=8.8, 2.0 Hz, 2H), 7.95 (t, J=1.6 Hz, 1H), 7.86 (dd, J=8.0, 0.8 Hz, 1H), 7.62-7.58 (m, 1H), 7.50 (t, J=8.0 Hz, 1H).

Step 3: To a solution of 4-[(3-chlorophenyl)sulfonyl]-1-nitrobenzene (705 mg, 2.40 mmol) in EtOH/H₂O (v/v=40 mL/10 mL) was added powder iron (673 mg, 12.0 mmol), followed by NH₄Cl (643 mg, 12.0 mmol). The resulting mixture was stirred at 80° C. overnight. The reaction was monitored by LC-MS. Then powder iron was filtered off, and the filtrate was concentrated in vacuum to give a residue, which was purified by a reverse-phase column (5~95% ACN in H₂O) to afford 4-(3-chloro-benzenesulfonyl)-phenylamine (586 mg, yield: 92%) as a white solid. ¹H NMR (400 MHz, DMSO-d₆): δ=7.84 (t, J=2.0 Hz, 1H), 7.81-7.77 (m, 1H), 7.72-7.66 (m, 1H), 7.63-7.55 (m, 3H), 6.66-6.60 (m, 2H), 6.24 (s, 2H).

Step 4: To a solution of 4-(3-chloro-benzenesulfonyl)-phenylamine (586 mg, 2.19 mmol) in DCM (40 mL) was added phenyl carbonchloridate (514 mg, 3.28 mmol), followed by TEA (664.5 mg, 6.57 mmol). The resulting mixture was stirred at room temperature for 1 hour. The reaction was monitored by TLC. Then the mixture was concentrated in vacuum to give a residue, which was purified by a silica gel column eluting with PE/EA=10/1 to 4/1 to afford [4-(3-chloro-benzenesulfonyl)-phenyl]-carbamic acid phenyl ester (662 mg, yield: 78%) as a white solid.

Step 5: To a solution of [4-(3-Chloro-benzenesulfonyl)-phenyl]-carbamic acid phenyl ester (200 mg, 0.516 mmol) in ACN (40 mL) was added c-pyridin-4-yl-methylamine (67 mg, 0.619 mmol), followed by TEA (156 mg, 1.548 mmol). The resulting mixture was stirred at 80° C. for 2 hours. The reaction was monitored by LC-MS. Then the mixture was concentrated in vacuum to give a residue, which was purified by a prep-HPLC with NH$_4$OH as additive to afford 1-[4-(3-chloro-benzenesulfonyl)-phenyl]-3-pyridin-4-ylmethyl-urea (88.4 mg, yield: 43%) as a white solid. $^1$H NMR (400 MHz, DMSO-d$_6$): δ=9.33 (s, 1H), 8.50 (dd, J=4.8, 1.6 Hz, 2H), 7.93 (t, J=2.0 Hz, 1H), 7.89-7.83 (m, 3H), 7.76-7.72 (m, 1H), 7.67-7.60 (m, 3H), 7.28 (d, J=5.6 Hz, 2H), 6.96 (d, J=6.4 Hz, 1H), 4.33 (d, J=5.6 Hz, 2H). MS: m/z 401.9 (M+H$^+$).

Example 289: Synthesis of 1-[4-(4-Chloro-benzenesulfonyl)-phenyl]-3-pyridin-4-ylmethyl-urea

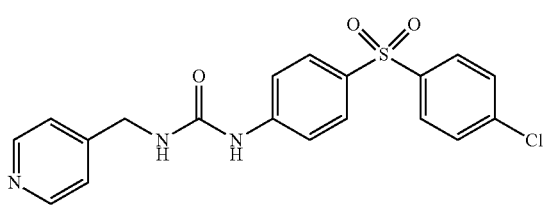 [SMILES: O=C(NCc1ccncc1)Nc1ccc(S(=O)(=O)c2ccc(Cl)cc2)cc1]

The title compound was prepared as described in example 1-[4-(3-chloro-benzenesulfonyl)-phenyl]-3-pyridin-4-ylmethyl-urea. $^1$H NMR (400 MHz, DMSO-d$_6$): δ=9.32 (s, 1H), 8.49 (dd, J=4.4, 1.6 Hz, 2H), 7.90 (dd, J=6.4, 2.0 Hz, 2H), 7.81 (dd, J=7.2, 1.6 Hz, 2H), 7.71-7.59 (m, 4H), 7.27 (dd, J=4.4, 1.6 Hz, 2H), 6.95 (t, J=6.0 Hz, 1H), 4.33 (d, J=5.6 Hz, 2H). MS: m/z 401.9 (M+H$^+$).

Example 290: Synthesis of 1-[4-(2-Chloro-benzenesulfonyl)-phenyl]-3-pyridin-4-ylmethyl-urea

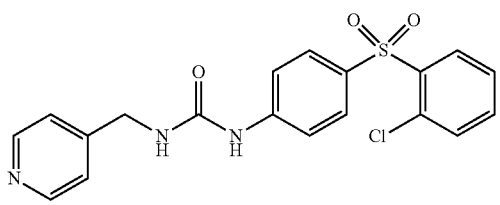 [SMILES: O=C(NCc1ccncc1)Nc1ccc(S(=O)(=O)c2ccccc2Cl)cc1]

The title compound was prepared as described in example 1-[4-(3-chloro-benzenesulfonyl)-phenyl]-3-pyridin-4-ylmethyl-urea. $^1$H NMR (400 MHz, DMSO-d$_6$): δ=9.34 (s, 1H), 8.50 (dd, J=4.4, 1.2 Hz, 2H), 8.23 (dd, J=8.0, 2.0 Hz, 1H), 7.78 (dd, J=7.2, 2.0 Hz, 2H), 7.73-7.59 (m, 5H), 7.28 (d, J=2.0 Hz, 2H), 6.96 (t, J=5.6 Hz, 1H), 4.34 (d, J=6.4 Hz, 2H). MS: m/z 401.9 (M+H$^+$).

Example 291: Synthesis of 1-[4-(3-Chloro-benzenesulfonyl)-phenyl]-3-(1H-pyrazol-4-ylmethyl)-urea

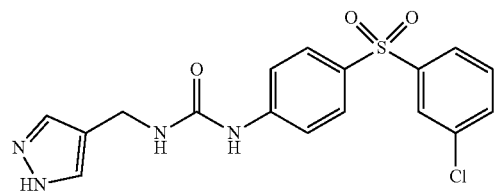

The title compound was prepared as described in example 1-[4-(3-chloro-benzenesulfonyl)-phenyl]-3-pyridin-4-ylmethyl-urea. $^1$H NMR (400 MHz, DMSO-d$_6$): δ=12.63 (brs, 1H), 9.04 (s, 1H), 7.93 (t, J=2.0 Hz, 1H), 7.90-7.82 (m, 3H), 7.77-7.71 (m, 1H), 7.67-7.59 (m, 3H), 7.58-7.45 (m, 2H), 6.57 (t, J=5.6 Hz, 1H), 4.16 (d, J=5.2 Hz, 2H). MS: m/z 390.9 (M+H$^+$).

Example 292: Synthesis of 1-[4-(2-Chloro-benzenesulfonyl)-phenyl]-3-(1H-pyrazol-4-ylmethyl)-urea

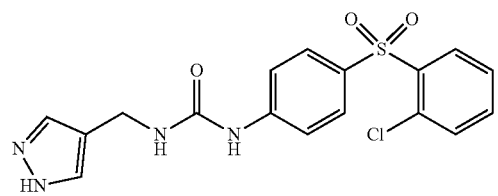

The title compound was prepared as described in example 1-[4-(3-chloro-benzenesulfonyl)-phenyl]-3-pyridin-4-ylmethyl-urea. $^1$H NMR (400 MHz, DMSO-d$_6$): δ=12.63 (brs, 1H), 9.04 (s, 1H), 8.23 (dd, J=7.6, 1.6 Hz, 1H), 7.79-7.74 (m, 2H), 7.72-7.63 (m, 2H), 7.63-7.46 (m, 5H), 6.56 (t, J=5.6 Hz, 1H), 4.16 (d, J=5.2 Hz, 2H). MS: m/z 390.9 (M+H$^+$).

Example 293: Synthesis of 1-[4-(4-Chloro-benzenesulfonyl)-phenyl]-3-(1H-pyrazol-4-ylmethyl)-urea

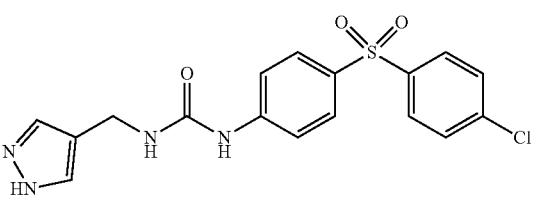 [SMILES: O=C(NCc1cn[nH]c1)Nc1ccc(S(=O)(=O)c2ccc(Cl)cc2)cc1]

The title compound was prepared as described in example 1-[4-(3-chloro-benzenesulfonyl)-phenyl]-3-pyridin-4-ylmethyl-urea. $^1$H NMR (400 MHz, DMSO-d$_6$): δ=12.61 (brs, 1H), 9.04 (s, 1H), 7.90 (dd, J=6.4, 2.0 Hz, 2H), 7.80 (dd, J=7.2, 2.0 Hz, 2H), 7.66 (dd, J=6.4, 2.0 Hz, 2H), 7.60 (dd, J=7.2, 2.0 Hz, 2H), 7.57-7.48 (m, 2H), 6.57 (t, J=5.2 Hz, 1H), 4.15 (d, J=5.2 Hz, 2H). MS: m/z 390.9 (M+H$^+$).

Example 294: Synthesis of 1-[4-(2-Methoxy-benzenesulfonyl)-phenyl]-3-pyridin-4-ylmethyl-urea

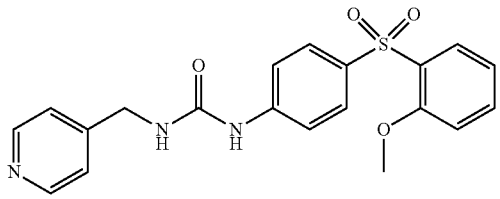

The title compound was prepared as described in example 1-[4-(3-chloro-benzenesulfonyl)-phenyl]-3-pyridin-4-ylmethyl-urea. $^1$H NMR (400 MHz, DMSO-d$_6$): δ=9.25 (s, 1H), 8.50 (dd, J=5.6, 1.6 Hz, 2H), 7.96 (dd, J=8.0, 1.6 Hz, 1H), 7.75 (d, J=8.8 Hz, 2H), 7.68-7.55 (m, 3H), 7.28 (d, J=6.0 Hz, 2H), 7.20-7.11 (m, 2H), 6.93 (t, J=6.0 Hz, 1H), 4.34 (d, J=6.0 Hz, 2H), 3.75 (s, 3H). MS: m/z 397.9 (M+H$^+$).

Example 295: Synthesis of 1-[4-(3-Methoxy-benzenesulfonyl)-phenyl]-3-pyridin-4-ylmethyl-urea

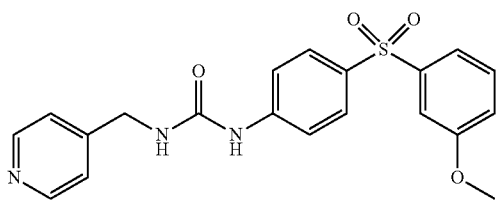 [SMILES: COc1cccc(S(=O)(=O)c2ccc(NC(=O)NCc3ccncc3)cc2)c1]

The title compound was prepared as described in example 1-[4-(3-chloro-benzenesulfonyl)-phenyl]-3-pyridin-4-ylmethyl-urea. $^1$H NMR (400 MHz, DMSO-d$_6$): δ=9.30 (s, 1H), 8.50 (dd, J=4.4, 1.6 Hz, 2H), 7.82 (dd, J=6.8, 2.0 Hz, 2H), 7.62 (dd, J=7.2, 2.0 Hz, 2H), 7.51 (t, J=8.0 Hz, 1H), 7.47-7.42 (m, 1H), 7.37 (t, J=2.0 Hz, 1H), 7.28 (dd, J=4.4, 1.6 Hz, 2H), 7.24-7.19 (m, 1H), 6.95 (t, J=6.0 Hz, 1H), 4.33 (d, J=5.6 Hz, 2H), 3.82 (s, 3H). MS: m/z 397.9 (M+H$^+$).

Example 296: Synthesis of 1-[4-(2-Methoxy-benzenesulfonyl)-phenyl]-3-(1H-pyrazol-4-ylmethyl)-urea

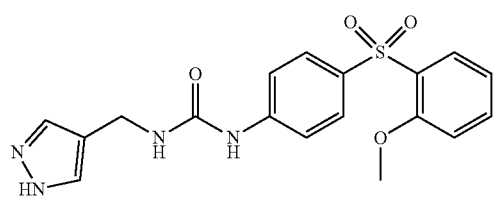 [SMILES: COc1ccccc1S(=O)(=O)c1ccc(NC(=O)NCc2cn[nH]c2)cc1]

The title compound was prepared as described in example 1-[4-(3-chloro-benzenesulfonyl)-phenyl]-3-pyridin-4-ylmethyl-urea. $^1$H NMR (400 MHz, DMSO-d6): δ=12.59 (brs, 1H), 8.94 (s, 1H), 7.95 (dd, J=8.0, 2.0 Hz, 1H), 7.96 (dd, J=6.8, 1.6 Hz, 2H), 7.66-7.60 (m, 1H), 7.59-7.44 (m, 4H), 7.19-7.11 (m, 2H), 6.52 (t, J=5.6 Hz, 1H), 4.15 (d, J=5.2 Hz, 2H), 3.74 (s, 3H). MS: m/z 386.9 (M+H$^+$).

Example 297: Synthesis of 1-[4-(3-Methoxy-benzenesulfonyl)-phenyl]-3-(1H-pyrazol-4-ylmethyl)-urea

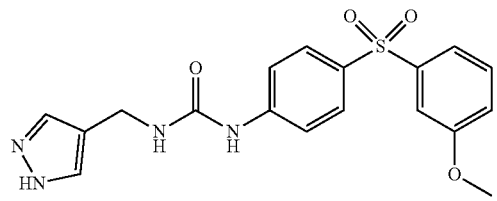 [SMILES: COc1cccc(S(=O)(=O)c2ccc(NC(=O)NCc3cn[nH]c3)cc2)c1]

The title compound was prepared as described in example 1-[4-(3-chloro-benzenesulfonyl)-phenyl]-3-pyridin-4-ylmethyl-urea. $^1$H NMR (400 MHz, DMSO-d$_6$): δ=12.62 (brs, 1H), 8.99 (s, 1H), 7.81 (dd, J=7.2, 1.6 Hz, 2H), 7.64-7.48 (m, 5H), 7.47-7.42 (m, 1H), 7.39-7.35 (m, 1H), 7.24-7.18 (m, 1H), 6.54 (t, J=5.6 Hz, 1H), 4.15 (d, J=5.6 Hz, 2H), 3.82 (s, 3H). MS: m/z 386.9 (M+H$^+$).

Example 298: Synthesis of 1-(4-Benzenesulfonyl-phenyl)-3-oxazol-5-ylmethyl-urea

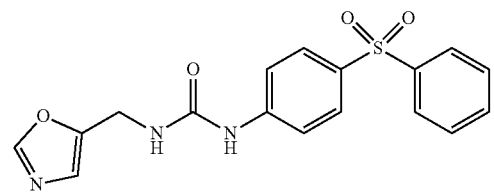

The title compound was prepared as described in example 1-[4-(3-chloro-benzenesulfonyl)-phenyl]-3-pyridin-4-ylmethyl-urea. $^1$H NMR (400 MHz, DMSO-d$_6$): δ=9.16 (brs, 1H), 8.27 (s, 1H), 7.89 (d, J=8.0 Hz, 2H), 81 (d, J=8.0 Hz, 2H), 7.70-7.55 (m, 5H), 7.00 (s, 1H), 6.83 (t, J=5.2 Hz, 1H), 4.36 (d, J=5.6 Hz, 2H). MS: m/z 357.9 (M+H$^+$).

Example 299: Synthesis of 1-(4-Benzenesulfonyl-phenyl)-3-(1H-pyrazol-4-ylmethyl)-urea

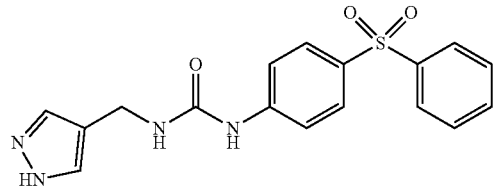

The title compound was prepared as described in example 1-[4-(3-chloro-benzenesulfonyl)-phenyl]-3-pyridin-4-ylmethyl-urea. $^1$H NMR (400 MHz, DMSO-d$_6$): δ=12.60 (brs, 1H), 8.99 (s, 1H), 7.89 (dd, J=7.2, 1.6 Hz, 2H), 7.79 (dd, J=7.2, 1.6 Hz, 2H), 7.68-7.63 (m, 1H), 7.62-7.46 (m, 6H), 6.54 (t, J=5.6 Hz, 1H), 4.14 (d, J=5.6 Hz, 2H). MS: m/z 356.9 (M+H$^+$).

Example 300: Synthesis of 1-(4-Benzenesulfonyl-phenyl)-3-pyridin-4-ylmethyl-urea

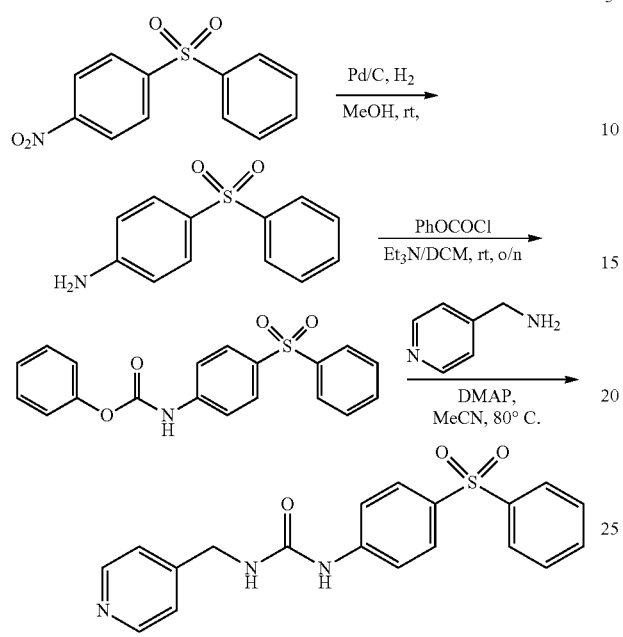

Example 301: Synthesis of 1-(4-Phenylmethane-sulfonyl-phenyl)-3-pyridin-4-ylmethyl-urea

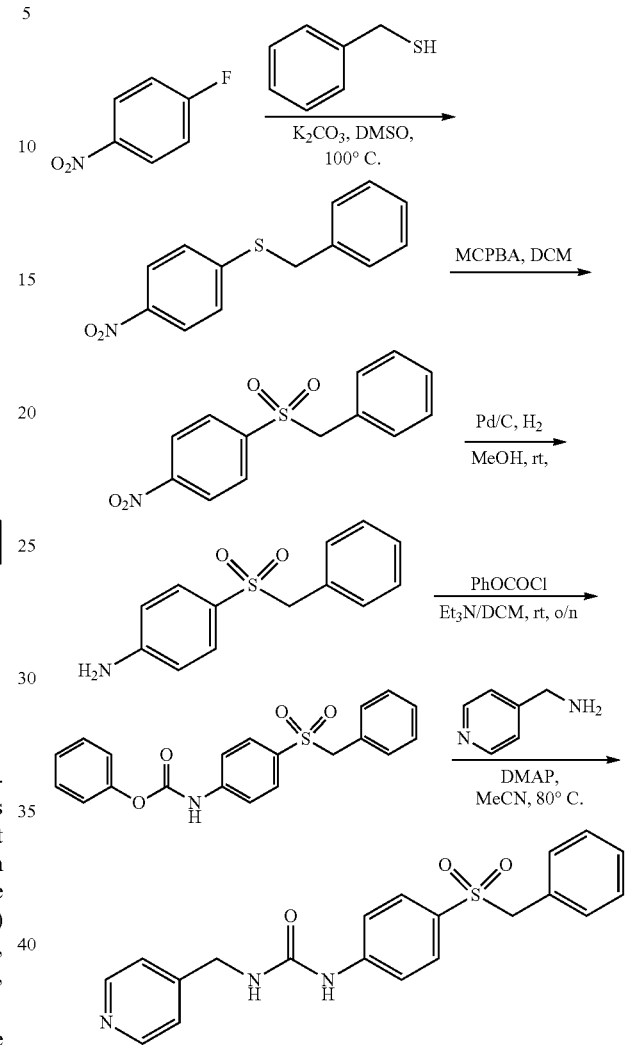

Step 1: To a solution of 1-benzenesulfonyl-4-nitro-benzene (0.92 g, 3.5 mmol) in MeOH/DCM (10 ml/10 ml) was added Pd/C (50% w/w, 0.31 g). The reaction was stirred at room temperature under $H_2$ overnight. Then the reaction mixture was filtered. The filtrate was concentrated to give 4-benzenesulfonyl-phenylamine (0.84 g, yield: quantitative) as a yellow solid. $^1$H NMR (400 MHz, CDCl$_3$): δ=7.88 (d, J=8.0 Hz, 2H), 7.70 (d, J=8.4 Hz, 2H), 7.51-7.43 (m, 3H), 6.65 (d, J=8.8 Hz, 2H), 4.14 (s, 2H).

Step 2: The solution of 4-benzenesulfonyl-phenylamine (300 mg, 1.3 mmol) and TEA (0.2 mL, 1.7 mmol) in DCM (20 mL) was degassed and purged with $N_2$. The mixture was stirred at 0° C. for a while. Then phenyl chroloformate (250 mg, 1.6 mmol) was added and the mixture was stirred at room temperature for overnight. After that, the solution was concentrated under reduced pressure. The residue was purified by silica gel column (PE/EA=3/1) to give the (4-benzenesulfonyl-phenyl)-carbamic acid phenyl ester (340 mg, 74%) as a white solid.

Step 3: To a solution of (4-benzenesulfonyl-phenyl)-carbamic acid phenyl ester (200 mg, 0.57 mmol) in MeCN (5 mL) was added DMAP (83 mg, 0.68 mmol) and 2-(aminomethyl)pyridine (62 mg, 0.57 mmol). The mixture was refluxed at 80° C. for overnight. After that, the solution was concentrated under reduced pressure. The residue was purified by prep-HPLC to give 1-(4-benzenesulfonyl-phenyl)-3-pyridin-4-ylmethyl-urea (24.7 mg, yield: 11%) as a white solid. $^1$H NMR (300 MHz, DMSO-d$_6$): δ=9.30 (s, 1H), 8.49 (d, J=6.0 Hz, 2H), 7.89 (d, J=6.9 Hz, 2H), 7.81 (d, J=8.7 Hz, 2H), 7.66-7.57 (m, 5H), 7.27 (d, J=5.7 Hz, 2H), 6.93 (t, J=5.1 Hz, 1H), 4.33 (d, J=6.4 Hz, 2H). MS: m/z 367.9 (M+H$^+$).

Step 1: The solution of 1-fluoro-4-nitro-benzene (1.0 g, 7.1 mmol) and $K_2CO_3$ (2.0 g, 14.21 mmol) in DMSO (20 mL) was added phenylmethanethiol (0.88 g, 7.1 mmol) and the reaction was stirred at 100° C. overnight. After that, water (80 mL) was added to the mixture. The aqueous phase was extracted with EA (80 mL×3). The organic layer was washed with brine (80 mL), dried over $Na_2SO_4$, and concentrated under reduced pressure. The residue was purified by silica gel column (PE/EA=100/1) to give the 1-benzylsulfanyl-4-nitro-benzene (0.95 g, yield: 56%) as a yellow solid. $^1$H NMR (400 MHz, CDCl$_3$): δ=8.08 (d, J=8.8 Hz, 2H), 7.39-7.26 (m, 7H), 4.25 (s, 2H).

Step 2: To the solution of 1-benzylsulfanyl-4-nitro-benzene (0.95 g, 3.9 mmol) in DCM (15 mL) was added m-CPBA (2.3 g, 9.7 mmol) and the reaction was stirred at room temperature overnight. The reaction was concentrated under reduced pressure. The residue was purified by silica gel column (PE/EA=5/1) to give the 1-nitro-4-phenylmethanesulfonyl-benzene (790 mg, yield: 72%) as a white solid. MS: m/z 295.4 (M+18).

Step 3 to Step 5: Step 3 to Step 5 was similar to general procedure of 1-[4-(4-Methoxy-benzenesulfonyl)-phenyl]-3- pyridin-4-ylmethyl-urea. ¹H NMR (400 MHz, DMSO-d₆): δ=9.28 (s, 1H), 8.51 (d, J=6.0 Hz, 2H), 7.58-7.50 (m, 4H), 7.31-7.28 (m, 5H), 7.13-7.11 (m, 2H), 7.97 (t, J=6.0 Hz, 1H), 4.56 (s, 2H), 4.34 (d, J=5.6 Hz, 2H), MS: m/z 381.9 (M+H⁺).

Example 302: Synthesis of 1-[4-(4-Methoxy-benzenesulfonyl)-phenyl]-3-pyridin-4-ylmethyl-urea

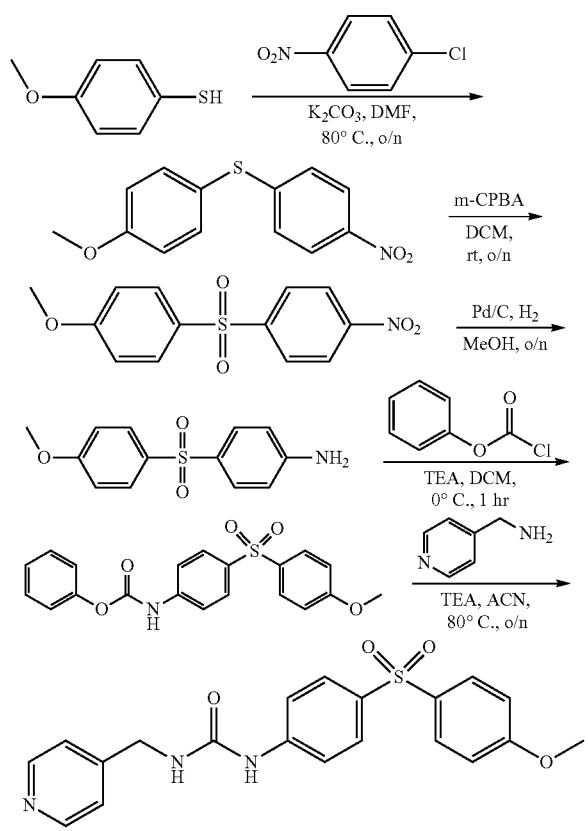

Step 1: To a solution of 4-methoxy-benzenethiol (420.6 mg, 3.0 mmol) in DMF (20 ml) was added 1-chloro-4-nitrobenzene (709 mg, 4.5 mmol) and K₂CO₃ (1.24 g, 9.1 mmol), the mixture was stirred at 80° C. overnight. The reaction was monitored by LCMS. Then the mixture was concentrated in vacuum to give a residue, which was purified by a silica gel column (PE/EA=100/1) to afford (4-methoxyphenyl)(4-nitrophenyl)sulfane (1.0 g, crude yield: >100%) as a yellow solid.

Step 2: To a solution of (4-methoxyphenyl)(4-nitrophenyl)sulfane (1.0 g, 3.82 mmol) in DCM (50 ml) was added m-CPBA (1.97 g, 11.46 mmol), the mixture was stirred at room temperature overnight. The reaction was monitored by TLC. Then the mixture was mixed with saturated aqueous sodium bicarbonate, the organic layer was concentrated in vacuum to give a residue, which was purified by a silica gel column (PE:EA=4:1) to afford 1-methoxy-4-((4-nitrophenyl)sulfonyl)benzene (1.09 g, 97.3%) as a white solid. ¹H NMR (400 MHz, DMSO-d₆): δ=8.32 (d, J=8.0 Hz, 2H), 8.09 (d, J=8.0 Hz, 2H), 7.89 (d, J=8.0 Hz, 2H), 7.00 (d, J=8.0 Hz, 2H), 3.86 (s, 3H).

Step 3: To a solution of 1-methoxy-4-((4-nitrophenyl)sulfonyl)benzene (1.09 g, 3.71 mmol) in MeOH (50 mL), was added Pd/C (10% wet, 393 mg). The reaction mixture was stirred at room temperature under H₂ (1 atm) overnight. Pd/C was filtered off and the filtrate was concentrated to dryness in vacuum. The residue was purified by flash to give 4-(4-methoxy-benzenesulfonyl)-phenylamine (0.97 g, yield: 100%) as a yellow solid.

Step 4: To a solution of 4-(4-methoxy-benzenesulfonyl)-phenylamine (483 mg, 1.83 mmol) in DCM (50 ml) was added phenyl chloroformate (573 mg, 3.66 mmol) and TEA (364 mg, 3.66 mmol), the mixture was stirred at 0° C. for 1 hr. The reaction was monitored by TLC. The mixture was concentrated in vacuum to give a residue, which was purified by a silica gel column (PE/EA=2/1) to afford [4-(4-methoxy-benzenesulfonyl)-phenyl]-carbamic acid phenyl ester (0.52 g, 75%) as a white solid.

Step 5: To a solution of [4-(4-methoxy-benzenesulfonyl)-phenyl]-carbamic acid phenyl ester (300 mg, 0.78 mmol) in MeCN (25 mL) was added pyridin-4-ylmethanamine (168.6 mg, 1.56 mmol) and TEA (157.8 mg, 1.56 mmol), the mixture was stirred at 80° C. overnight. The reaction was monitored by LCMS, then the mixture was concentrated in vacuum to give residue, which was purified by prep-HPLC to give 1-[4-(4-methoxy-benzenesulfonyl)-phenyl]-3-pyridin-4-ylmethyl-urea (74.6 mg, yield: 24%) as a white solid. ¹H NMR (400 MHz, DMSO-d₆): δ=9.26 (s, 1H), 8.49 (d, J=8.0 Hz, 2H), 7.82 (d, J=8.0 Hz, 2H), 7.76 (d, J=8.0 Hz, 2H), 7.59 (d, J=8.0 Hz, 2H), 7.27 (d, J=8.0 Hz, 2H), 7.10 (d, J=8.0 Hz, 2H), 6.93 (t, J=6.0 Hz, 1H), 4.32 (d, J=6.0 Hz, 2H), 3.81 (s, 3H). MS: m/z 397.9 (M+H⁺).

Example 303: Synthesis of 1-[4-(4-Methoxy-benzenesulfonyl)-phenyl]-3-(1H-pyrazol-4-ylmethyl)-urea

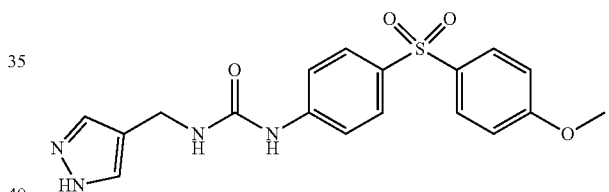

The title compound was prepared as described in example 1-[4-(4-methoxy-benzenesulfonyl)-phenyl]-3-pyridin-4-yl-methyl-urea. ¹H NMR (400 MHz, DMSO-d₆): δ=8.98 (s, 1H), 7.82 (d, J=8.0 Hz, 2H), 7.75 (d, J=8.0 Hz, 2H), 7.60-7.46 (m, 4H), 7.10 (d, J=8.0 Hz, 2H), 6.54 (t, J=8.0 Hz, 2H), 4.14 (d, J=8.0 Hz, 2H), 3.81 (s, 3H). MS: m/z 386.9 (M+H⁺).

Example 304: Synthesis of Ethyl 6-(3-(pyridin-4-ylmethyl)ureido)nicotinate

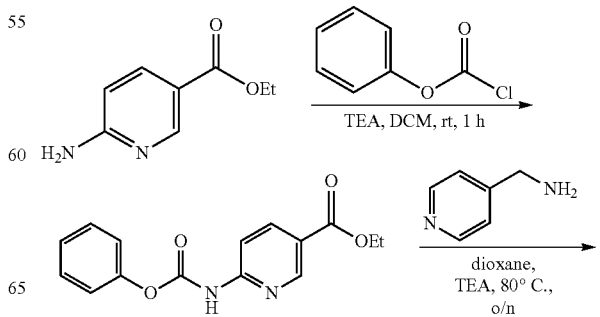

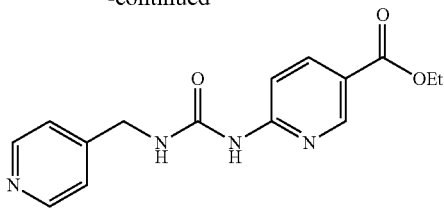

Step 1: To a solution of 6-amino-nicotinic acid ethylester (200 mg, 1.20 mmol) in DCM (40 mL) was added phenyl chloroformate (227 mg, 1.45 mmol) and TEA (366 mg, 3.62 mmol). The mixture was stirred at room temperature for 1 hr. The reaction was monitored by TLC. Then the reaction mixture was concentrated in vacuum to give a residue, which was purified by prep-TLC (PE/EA=10/1) to afford 6-phenoxycarbonylamino-nicotinic acid ethylester (280 mg, yield: 81%) as a white solid.

Step 2: To a solution of 6-phenoxycarbonylamino-nicotinic acid ethyl ester (280 mg, 0.98 mmol) in dioxane (40 mL) was added 4-(aminomethyl)pyridine (158 mg, 1.46 mmol) and TEA (297 mg, 2.92 mmol). The mixture was stirred at 80° C. overnight. The reaction was monitored by TLC. Then the reaction mixture was concentrated in vacuum to give a residue, which was purified by prep-TLC (DCM/MeOH=20/1) to afford 6-3-pyridin-4-ylmethyl-ureido-nicotinic acid ethyl ester (215 mg, yield: 73%) as a white solid. $^1$H NMR (400 MHz, DMSO-d6): δ=9.88 (brs, 1H), 8.76 (brs, 1H), 8.52-8.49 (m, 3H), 8.17 (dd, J=8.8, 2.4 Hz, 1H), 7.56 (d, J=8.8 Hz, 1H), 7.30 (d, J=6.0 Hz, 2H), 4.45 (d, J=6.0 Hz, 2H), 4.25 (q, J=7.2 Hz, 2H), 1.30 (t, J=7.2 Hz, 3H). MS: m/z 301.1 (M+H$^+$).

Example 305: Synthesis of 1-[4-(3-Chloro-benzenesulfonyl)-phenyl]-3-pyridin-4-ylmethyl-urea

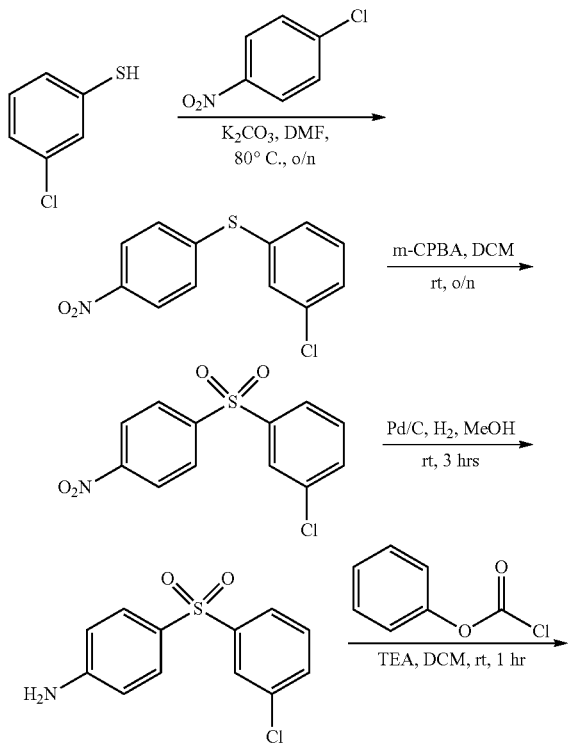

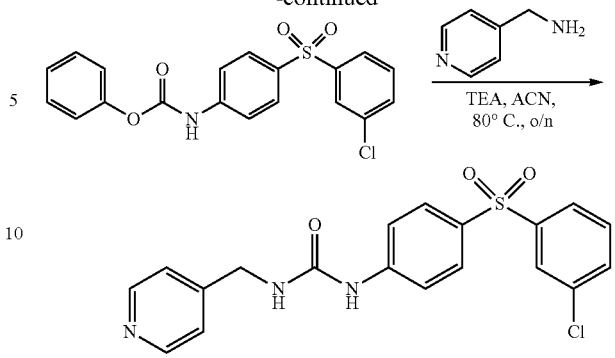

Step 1: To a solution of 3-chloro-benzenethiol (433.86 mg, 3.0 mmol) in DMF (20 mL) was added 1-chloro-4-nitro-benzene (709 mg, 4.5 mmol) and followed by K$_2$CO$_3$ (1.24 g, 9.0 mmol). The resulting mixture was stirred at 80° C. overnight. The reaction was monitored by TLC. Then the mixture was diluted with H$_2$O (40 mL) and extracted with DCM (20 mL×2). The combined organic layers were concentrated in vacuum to give a residue, which was purified by a silica gel column (PE/EA=100:1) to afford 4-(3-chlorophenylthio)-1-nitrobenzene (726 mg, yield: 91%) as a yellow solid. $^1$H NMR (400 MHz, CDCl$_3$): δ=8.11 (dd, J=6.8, 2.0 Hz, 2H), 7.51 (t, J=1.6 Hz, 1H), 7.44-7.36 (m, 3H), 7.25 (dd, J=6.8, 2.0 Hz, 2H).

Step 2: To a solution of 4-(3-chlorophenylthio)-1-nitrobenzene (726 mg, 2.73 mmol) in DCM (40 mL) was added 3-chloro-benzenecarboperoxoic acid (2.02 g, 8.20 mmol, 30% H$_2$O contained). The resulting mixture was stirred at room temperature overnight. The reaction was monitored by TLC. Then the mixture was mixed with saturated Na$_2$SO$_3$ (30 mL), and extracted with DCM (20 mL×2). The combined organic layers were concentrated in vacuum to give a residue, which was purified by a silica gel column (PE/EA=10:1) to afford 4-[(3-chlorophenyl)sulfonyl]-1-nitrobenzene (705 mg, yield: 88%) as yellow solid. $^1$H NMR (400 MHz, CDCl$_3$): δ=8.36 (dd, J=9.2, 2.0 Hz, 2H), 8.14 (dd, J=8.8, 2.0 Hz, 2H), 7.95 (t, J=1.6 Hz, 1H), 7.86 (dd, J=8.0, 0.8 Hz, 1H), 7.62-7.58 (m, 1H), 7.50 (t, J=8.0 Hz, 1H).

Step 3: To a solution of 4-[(3-chlorophenyl)sulfonyl]-1-nitrobenzene (705 mg, 2.40 mmol) in EtOH/H$_2$O (v/v=40 mL/10 mL) was added powder iron (673 mg, 12.0 mmol), followed by NH$_4$Cl (643 mg, 12.0 mmol). The resulting mixture was stirred at 80° C. overnight. The reaction was monitored by LC-MS. Then powder iron was filtered off, and the filtrate was concentrated in vacuum to give a residue, which was purified by a reverse-phase column (5~95% ACN in H$_2$O) to afford 4-(3-chloro-benzenesulfonyl)-phenylamine (586 mg, yield: 92%) as a white solid. $^1$H NMR (400 MHz, DMSO-d$_6$): δ=7.84 (t, J=2.0 Hz, 1H), 7.81-7.77 (m, 1H), 7.72-7.66 (m, 1H), 7.63-7.55 (m, 3H), 6.66-6.60 (m, 2H), 6.24 (s, 2H).

Step 4: To a solution of 4-(3-chloro-benzenesulfonyl)-phenylamine (586 mg, 2.19 mmol) in DCM (40 mL) was added phenyl carbonchloridate (514 mg, 3.28 mmol), followed by TEA (664.5 mg, 6.57 mmol). The resulting mixture was stirred at room temperature for 1 hour. The reaction was monitored by TLC. Then the mixture was concentrated in vacuum to give a residue, which was purified by a silica gel column eluting with PE/EA=10/1 to 4/1 to afford [4-(3-chloro-benzenesulfonyl)-phenyl]-carbamic acid phenyl ester (662 mg, yield: 78%) as a white solid.

Step 5: To a solution of [4-(3-Chloro-benzenesulfonyl)-phenyl]-carbamic acid phenyl ester (200 mg, 0.516 mmol) in ACN (40 mL) was added c-pyridin-4-yl-methylamine (67 mg, 0.619 mmol), followed by TEA (156 mg, 1.548 mmol). The resulting mixture was stirred at 80° C. for 2 hours. The reaction was monitored by LC-MS. Then the mixture was concentrated in vacuum to give a residue, which was purified by a prep-HPLC with NH$_4$OH as additive to afford 1-[4-(3-chloro-benzenesulfonyl)-phenyl]-3-pyridin-4-ylmethyl-urea (88.4 mg, yield: 43%) as a white solid. $^1$H NMR (400 MHz, DMSO-d$_6$): δ=9.33 (s, 1H), 8.50 (dd, J=4.8, 1.6 Hz, 2H), 7.93 (t, J=2.0 Hz, 1H), 7.89-7.83 (m, 3H), 7.76-7.72 (m, 1H), 7.67-7.60 (m, 3H), 7.28 (d, J=5.6 Hz, 2H), 6.96 (d, J=6.4 Hz, 1H), 4.33 (d, J=5.6 Hz, 2H). MS: m/z 401.9 (M+H$^+$).

Example 306: Synthesis of 1-[4-(4-Chloro-benzenesulfonyl)-phenyl]-3-pyridin-4-ylmethyl-urea

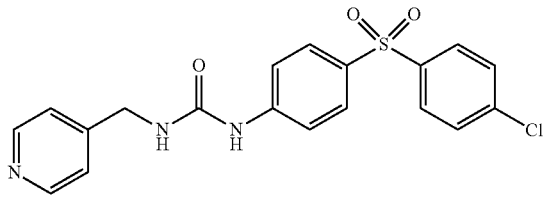

The title compound was prepared as described in example 1-[4-(3-chloro-benzenesulfonyl)-phenyl]-3-pyridin-4-ylmethyl-urea. $^1$H NMR (400 MHz, DMSO-d$_6$): δ=9.32 (s, 1H), 8.49 (dd, J=4.4, 1.6 Hz, 2H), 7.90 (dd, J=6.4, 2.0 Hz, 2H), 7.81 (dd, J=7.2, 1.6 Hz, 2H), 7.71-7.59 (m, 4H), 7.27 (dd, J=4.4, 1.6 Hz, 2H), 6.95 (t, J=6.0 Hz, 1H), 4.33 (d, J=5.6 Hz, 2H). MS: m/z 401.9 (M+H$^+$).

Example 307: Synthesis of 1-[4-(2-Chloro-benzenesulfonyl)-phenyl]-3-pyridin-4-ylmethyl-urea

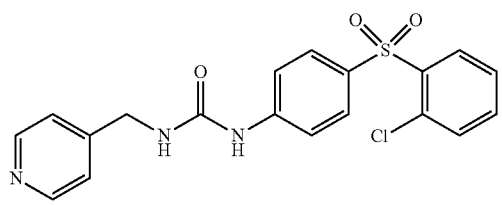 [SMILES: O=C(NCc1ccncc1)Nc1ccc(S(=O)(=O)c2ccccc2Cl)cc1]

The title compound was prepared as described in example 1-[4-(3-chloro-benzenesulfonyl)-phenyl]-3-pyridin-4-ylmethyl-urea. $^1$H NMR (400 MHz, DMSO-d$_6$): δ=9.34 (s, 1H), 8.50 (dd, J=4.4, 1.2 Hz, 2H), 8.23 (dd, J=8.0, 2.0 Hz, 1H), 7.78 (dd, J=7.2, 2.0 Hz, 2H), 7.73-7.59 (m, 5H), 7.28 (d, J=2.0 Hz, 2H), 6.96 (t, J=5.6 Hz, 1H), 4.34 (d, J=6.4 Hz, 2H). MS: m/z 401.9 (M+H$^+$).

Example 308: Synthesis of 1-[4-(3-Chloro-benzenesulfonyl)-phenyl]-3-(1H-pyrazol-4-ylmethyl)-urea

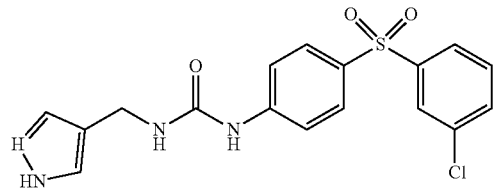

The title compound was prepared as described in example 1-[4-(3-chloro-benzenesulfonyl)-phenyl]-3-pyridin-4-ylmethyl-urea. $^1$H NMR (400 MHz, DMSO-d$_6$): δ=12.63 (brs, 1H), 9.04 (s, 1H), 7.93 (t, J=2.0 Hz, 1H), 7.90-7.82 (m, 3H), 7.77-7.71 (m, 1H), 7.67-7.59 (m, 3H), 7.58-7.45 (m, 2H), 6.57 (t, J=5.6 Hz, 1H), 4.16 (d, J=5.2 Hz, 2H). MS: m/z 390.9 (M+H$^+$).

Example 309: Synthesis of 1-[4-(2-Chloro-benzenesulfonyl)-phenyl]-3-(1H-pyrazol-4-ylmethyl)-urea

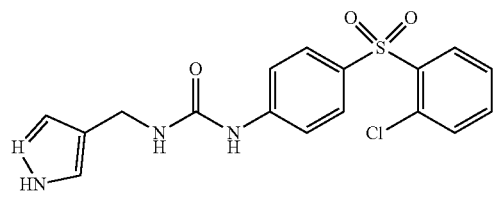

The title compound was prepared as described in example 1-[4-(3-chloro-benzenesulfonyl)-phenyl]-3-pyridin-4-ylmethyl-urea. $^1$H NMR (400 MHz, DMSO-d$_6$): δ=12.63 (brs, 1H), 9.04 (s, 1H), 8.23 (dd, J=7.6, 1.6 Hz, 1H), 7.79-7.74 (m, 2H), 7.72-7.63 (m, 2H), 7.63-7.46 (m, 5H), 6.56 (t, J=5.6 Hz, 1H), 4.16 (d, J=5.2 Hz, 2H). MS: m/z 390.9 (M+H$^+$).

Example 310: Synthesis of 1-[4-(4-Chloro-benzenesulfonyl)-phenyl]-3-(1H-pyrazol-4-ylmethyl)-urea

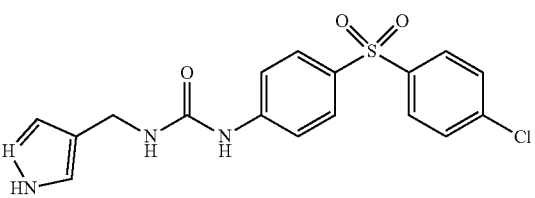

The title compound was prepared as described in example 1-[4-(3-chloro-benzenesulfonyl)-phenyl]-3-pyridin-4-ylmethyl-urea. $^1$H NMR (400 MHz, DMSO-d$_6$): δ=12.61 (brs, 1H), 9.04 (s, 1H), 7.90 (dd, J=6.4, 2.0 Hz, 2H), 7.80 (dd, J=7.2, 2.0 Hz, 2H), 7.66 (dd, J=6.4, 2.0 Hz, 2H), 7.60 (dd, J=7.2, 2.0 Hz, 2H), 7.57-7.48 (m, 2H), 6.57 (t, J=5.2 Hz, 1H), 4.15 (d, J=5.2 Hz, 2H). MS: m/z 390.9 (M+H$^+$).

Example 311: Synthesis of 1-[4-(2-Methoxy-benzenesulfonyl)-phenyl]-3-pyridin-4-ylmethyl-urea

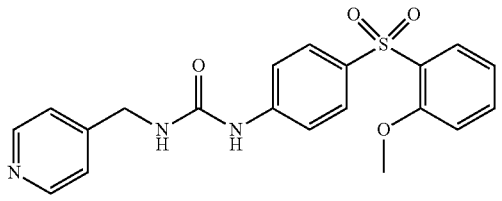 [SMILES: COc1ccccc1S(=O)(=O)c1ccc(NC(=O)NCc2ccncc2)cc1]

The title compound was prepared as described in example 1-[4-(3-chloro-benzenesulfonyl)-phenyl]-3-pyridin-4-ylmethyl-urea. $^1$H NMR (400 MHz, DMSO-d$_6$): δ=9.25 (s, 1H), 8.50 (dd, J=5.6, 1.6 Hz, 2H), 7.96 (dd, J=8.0, 1.6 Hz, 1H), 7.75 (d, J=8.8 Hz, 2H), 7.68-7.55 (m, 3H), 7.28 (d, J=6.0 Hz, 2H), 7.20-7.11 (m, 2H), 6.93 (t, J=6.0 Hz, 1H), 4.34 (d, J=6.0 Hz, 2H), 3.75 (s, 3H). MS: m/z 397.9 (M+H$^+$).

Example 312: Synthesis of 1-[4-(3-Methoxy-benzenesulfonyl)-phenyl]-3-pyridin-4-ylmethyl-urea

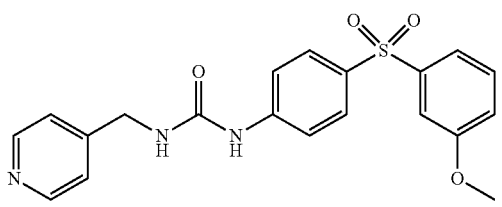 [SMILES: COc1cccc(S(=O)(=O)c2ccc(NC(=O)NCc3ccncc3)cc2)c1]

The title compound was prepared as described in example 1-[4-(3-chloro-benzenesulfonyl)-phenyl]-3-pyridin-4-ylmethyl-urea. $^1$H NMR (400 MHz, DMSO-d$_6$): δ=9.30 (s, 1H), 8.50 (dd, J=4.4, 1.6 Hz, 2H), 7.82 (dd, J=6.8, 2.0 Hz, 2H), 7.62 (dd, J=7.2, 2.0 Hz, 2H), 7.51 (t, J=8.0 Hz, 1H), 7.47-7.42 (m, 1H), 7.37 (t, J=2.0 Hz, 1H), 7.28 (dd, J=4.4, 1.6 Hz, 2H), 7.24-7.19 (m, 1H), 6.95 (t, J=6.0 Hz, 1H), 4.33 (d, J=5.6 Hz, 2H), 3.82 (s, 3H). MS: m/z 397.9 (M+H$^+$).

Example 313: Synthesis of 1-[4-(2-Methoxy-benzenesulfonyl)-phenyl]-3-(1H-pyrazol-4-ylmethyl)-urea

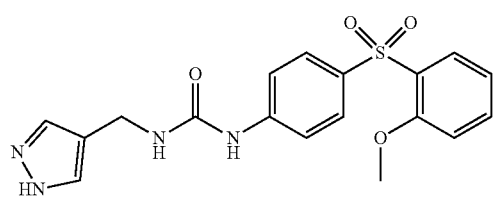 [SMILES: COc1ccccc1S(=O)(=O)c1ccc(NC(=O)NCc2cn[nH]c2)cc1]

The title compound was prepared as described in example 1-[4-(3-chloro-benzenesulfonyl)-phenyl]-3-pyridin-4-ylmethyl-urea. $^1$H NMR (400 MHz, DMSO-d6): δ=12.59 (brs, 1H), 8.94 (s, 1H), 7.95 (dd, J=8.0, 2.0 Hz, 1H), 7.96 (dd, J=6.8, 1.6 Hz, 2H), 7.66-7.60 (m, 1H), 7.59-7.44 (m, 4H), 7.19-7.11 (m, 2H), 6.52 (t, J=5.6 Hz, 1H), 4.15 (d, J=5.2 Hz, 2H), 3.74 (s, 3H). MS: m/z 386.9 (M+H$^+$).

Example 314: Synthesis of 1-[4-(3-Methoxy-benzenesulfonyl)-phenyl]-3-(1H-pyrazol-4-ylmethyl)-urea

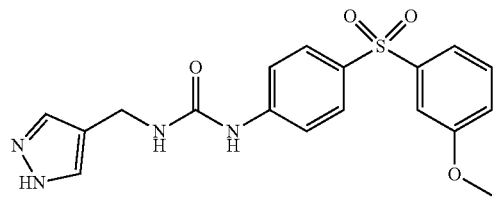 [SMILES: COc1cccc(S(=O)(=O)c2ccc(NC(=O)NCc3cn[nH]c3)cc2)c1]

The title compound was prepared as described in example 1-[4-(3-chloro-benzenesulfonyl)-phenyl]-3-pyridin-4-ylmethyl-urea. $^1$H NMR (400 MHz, DMSO-d$_6$): δ=12.62 (brs, 1H), 8.99 (s, 1H), 7.81 (dd, J=7.2, 1.6 Hz, 2H), 7.64-7.48 (m, 5H), 7.47-7.42 (m, 1H), 7.39-7.35 (m, 1H), 7.24-7.18 (m, 1H), 6.54 (t, J=5.6 Hz, 1H), 4.15 (d, J=5.6 Hz, 2H), 3.82 (s, 3H). MS: m/z 386.9 (M+H$^+$).

Example 315: Synthesis of 1-(4-Benzenesulfonyl-phenyl)-3-oxazol-5-ylmethyl-urea

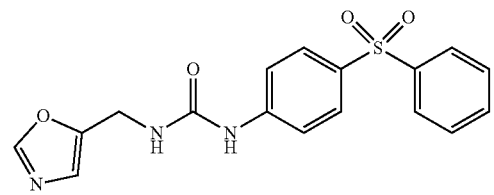

The title compound was prepared as described in example 1-[4-(3-chloro-benzenesulfonyl)-phenyl]-3-pyridin-4-ylmethyl-urea. $^1$H NMR (400 MHz, DMSO-d$_6$): δ=9.16 (brs, 1H), 8.27 (s, 1H), 7.89 (d, J=8.0 Hz, 2H), 81 (d, J=8.0 Hz, 2H), 7.70-7.55 (m, 5H), 7.00 (s, 1H), 6.83 (t, J=5.2 Hz, 1H), 4.36 (d, J=5.6 Hz, 2H). MS: m/z 357.9 (M+H$^+$).

Example 316: Synthesis of 1-(4-Benzenesulfonyl-phenyl)-3-(1H-pyrazol-4-ylmethyl)-urea

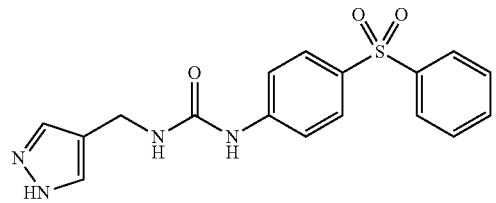 [SMILES: O=C(NCc1cn[nH]c1)Nc1ccc(S(=O)(=O)c2ccccc2)cc1]

The title compound was prepared as described in example 1-[4-(3-chloro-benzenesulfonyl)-phenyl]-3-pyridin-4-ylmethyl-urea. $^1$H NMR (400 MHz, DMSO-d$_6$): δ=12.60 (brs, 1H), 8.99 (s, 1H), 7.89 (dd, J=7.2, 1.6 Hz, 2H), 7.79 (dd, J=7.2, 1.6 Hz, 2H), 7.68-7.63 (m, 1H), 7.62-7.46 (m, 6H), 6.54 (t, J=5.6 Hz, 1H), 4.14 (d, J=5.6 Hz, 2H). MS: m/z 356.9 (M+H$^+$).

Example 317: Synthesis of 1-(4-Benzenesulfonyl-phenyl)-3-pyridin-4-ylmethyl-urea

Example 318: Synthesis of 1-(4-Phenylmethane-sulfonyl-phenyl)-3-pyridin-4-ylmethyl-urea

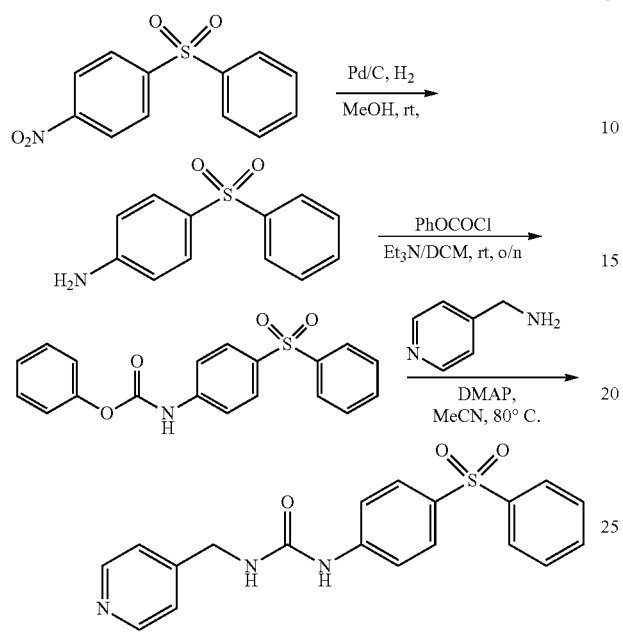

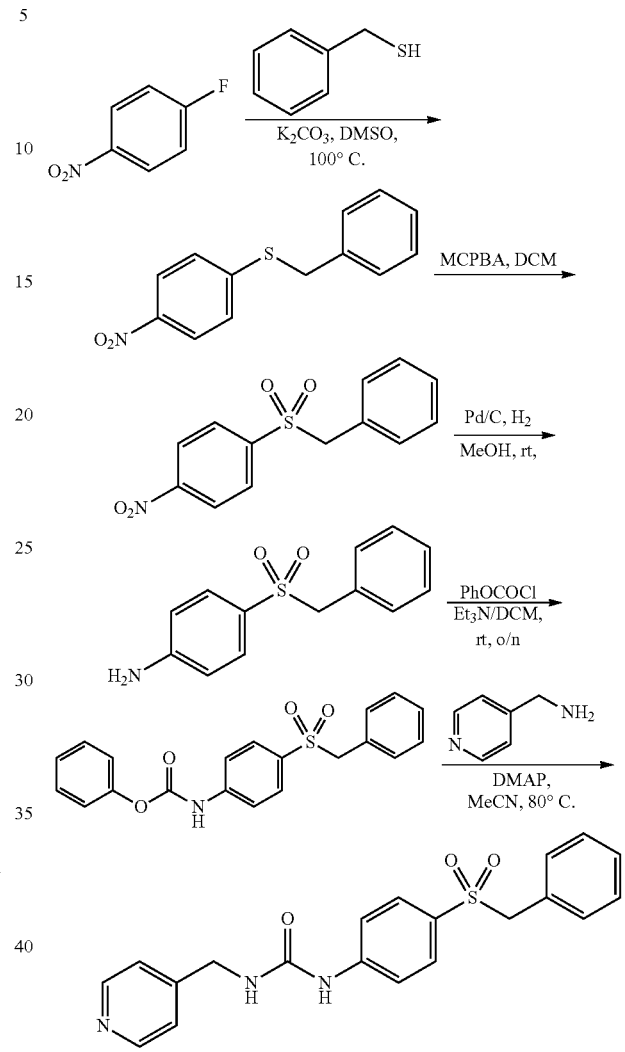

Step 1: To a solution of 1-benzenesulfonyl-4-nitro-benzene (0.92 g, 3.5 mmol) in MeOH/DCM (10 ml/10 ml) was added Pd/C (50% w/w, 0.31 g). The reaction was stirred at room temperature under $H_2$ overnight. Then the reaction mixture was filtered. The filtrate was concentrated to give 4-benzenesulfonyl-phenylamine (0.84 g, yield: quantitative) as a yellow solid. $^1$H NMR (400 MHz, CDCl$_3$): δ=7.88 (d, J=8.0 Hz, 2H), 7.70 (d, J=8.4 Hz, 2H), 7.51-7.43 (m, 3H), 6.65 (d, J=8.8 Hz, 2H), 4.14 (s, 2H).

Step 2: The solution of 4-benzenesulfonyl-phenylamine (300 mg, 1.3 mmol) and TEA (0.2 mL, 1.7 mmol) in DCM (20 mL) was degassed and purged with $N_2$. The mixture was stirred at 0° C. for a while. Then phenyl chroloformate (250 mg, 1.6 mmol) was added and the mixture was stirred at room temperature for overnight. After that, the solution was concentrated under reduced pressure. The residue was purified by silica gel column (PE/EA=3/1) to give the (4-benzenesulfonyl-phenyl)-carbamic acid phenyl ester (340 mg, 74%) as a white solid.

Step 3: To a solution of (4-benzenesulfonyl-phenyl)-carbamic acid phenyl ester (200 mg, 0.57 mmol) in MeCN (5 mL) was added DMAP (83 mg, 0.68 mmol) and 2-(aminomethyl)pyridine (62 mg, 0.57 mmol). The mixture was refluxed at 80° C. for overnight. After that, the solution was concentrated under reduced pressure. The residue was purified by prep-HPLC to give 1-(4-benzenesulfonyl-phenyl)-3-pyridin-4-ylmethyl-urea (24.7 mg, yield: 11%) as a white solid. $^1$H NMR (300 MHz, DMSO-d$_6$): δ=9.30 (s, 1H), 8.49 (d, J=6.0 Hz, 2H), 7.89 (d, J=6.9 Hz, 2H), 7.81 (d, J=8.7 Hz, 2H), 7.66-7.57 (m, 5H), 7.27 (d, J=5.7 Hz, 2H), 6.93 (t, J=5.1 Hz, 1H), 4.33 (d, J=6.4 Hz, 2H). MS: m/z 367.9 (M+H$^+$).

Step 1: The solution of 1-fluoro-4-nitro-benzene (1.0 g, 7.1 mmol) and K$_2$CO$_3$ (2.0 g, 14.21 mmol) in DMSO (20 mL) was added phenylmethanethiol (0.88 g, 7.1 mmol) and the reaction was stirred at 100° C. overnight. After that, water (80 mL) was added to the mixture. The aqueous phase was extracted with EA (80 mL×3). The organic layer was washed with brine (80 mL), dried over Na$_2$SO$_4$, and concentrated under reduced pressure. The residue was purified by silica gel column (PE/EA=100/1) to give the 1-benzylsulfanyl-4-nitro-benzene (0.95 g, yield: 56%) as a yellow solid. $^1$H NMR (400 MHz, CDCl$_3$): δ=8.08 (d, J=8.8 Hz, 2H), 7.39-7.26 (m, 7H), 4.25 (s, 2H).

Step 2: To the solution of 1-benzylsulfanyl-4-nitro-benzene (0.95 g, 3.9 mmol) in DCM (15 mL) was added m-CPBA (2.3 g, 9.7 mmol) and the reaction was stirred at room temperature overnight. The reaction was concentrated under reduced pressure. The residue was purified by silica gel column (PE/EA=5/1) to give the 1-nitro-4-phenylmethanesulfonyl-benzene (790 mg, yield: 72%) as a white solid. MS: m/z 295.4 (M+18).

Step 3 to Step 5: Step 3 to Step 5 was similar to general procedure of 1-[4-(4-Methoxy-benzenesulfonyl)-phenyl]-3- pyridin-4-ylmethyl-urea. ¹H NMR (400 MHz, DMSO-d₆): δ=9.28 (s, 1H), 8.51 (d, J=6.0 Hz, 2H), 7.58-7.50 (m, 4H), 7.31-7.28 (m, 5H), 7.13-7.11 (m, 2H), 7.97 (t, J=6.0 Hz, 1H), 4.56 (s, 2H), 4.34 (d, J=5.6 Hz, 2H), MS: m/z 381.9 (M+H⁺).

Example 319: Synthesis of 1-[4-(4-Methoxy-benzenesulfonyl)-phenyl]-3-pyridin-4-ylmethyl-urea

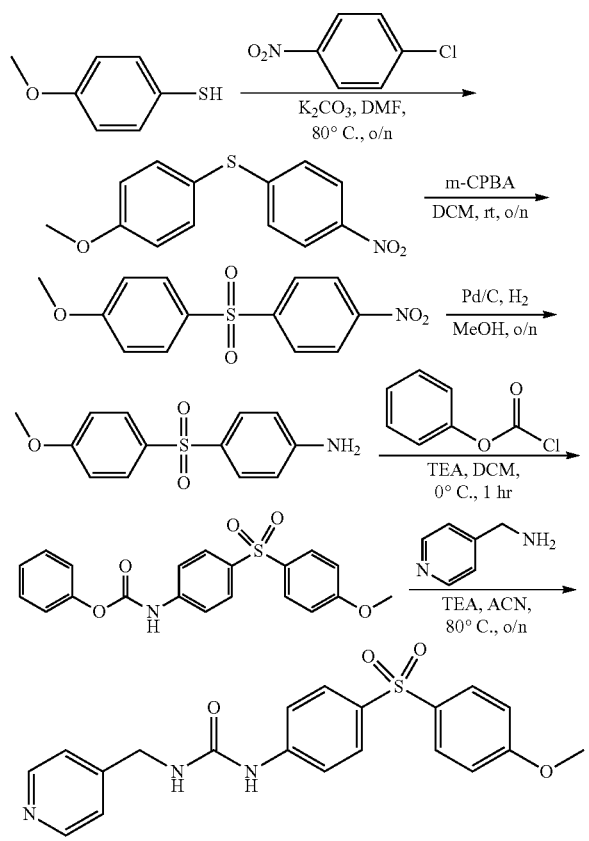

Step 1: To a solution of 4-methoxy-benzenethiol (420.6 mg, 3.0 mmol) in DMF (20 ml) was added 1-chloro-4-nitrobenzene (709 mg, 4.5 mmol) and K₂CO₃ (1.24 g, 9.1 mmol), the mixture was stirred at 80° C. overnight. The reaction was monitored by LCMS. Then the mixture was concentrated in vacuum to give a residue, which was purified by a silica gel column (PE/EA=100/1) to afford (4-methoxyphenyl)(4-nitrophenyl)sulfane (1.0 g, crude yield: >100%) as a yellow solid.

Step 2: To a solution of (4-methoxyphenyl)(4-nitrophenyl)sulfane (1.0 g, 3.82 mmol) in DCM (50 ml) was added m-CPBA (1.97 g, 11.46 mmol), the mixture was stirred at room temperature overnight. The reaction was monitored by TLC. Then the mixture was mixed with saturated aqueous sodium bicarbonate, the organic layer was concentrated in vacuum to give a residue, which was purified by a silica gel column (PE:EA=4:1) to afford 1-methoxy-4-((4-nitrophenyl)sulfonyl)benzene (1.09 g, 97.3%) as a white solid. ¹H NMR (400 MHz, DMSO-d₆): δ=8.32 (d, J=8.0 Hz, 2H), 8.09 (d, J=8.0 Hz, 2H), 7.89 (d, J=8.0 Hz, 2H), 7.00 (d, J=8.0 Hz, 2H), 3.86 (s, 3H).

Step 3: To a solution of 1-methoxy-4-((4-nitrophenyl)sulfonyl)benzene (1.09 g, 3.71 mmol) in MeOH (50 mL), was added Pd/C (10% wet, 393 mg). The reaction mixture was stirred at room temperature under H₂ (1 atm) overnight. Pd/C was filtered off and the filtrate was concentrated to dryness in vacuum. The residue was purified by flash to give 4-(4-methoxy-benzenesulfonyl)-phenylamine (0.97 g, yield: 100%) as a yellow solid.

Step 4: To a solution of 4-(4-methoxy-benzenesulfonyl)-phenylamine (483 mg, 1.83 mmol) in DCM (50 ml) was added phenyl chloroformate (573 mg, 3.66 mmol) and TEA (364 mg, 3.66 mmol), the mixture was stirred at 0° C. for 1 hr. The reaction was monitored by TLC. The mixture was concentrated in vacuum to give a residue, which was purified by a silica gel column (PE/EA=2/1) to afford [4-(4-methoxy-benzenesulfonyl)-phenyl]-carbamic acid phenyl ester (0.52 g, 75%) as a white solid.

Step 5: To a solution of [4-(4-methoxy-benzenesulfonyl)-phenyl]-carbamic acid phenyl ester (300 mg, 0.78 mmol) in MeCN (25 mL) was added pyridin-4-ylmethanamine (168.6 mg, 1.56 mmol) and TEA (157.8 mg, 1.56 mmol), the mixture was stirred at 80° C. overnight. The reaction was monitored by LCMS, then the mixture was concentrated in vacuum to give residue, which was purified by prep-HPLC to give 1-[4-(4-methoxy-benzenesulfonyl)-phenyl]-3-pyridin-4-ylmethyl-urea (74.6 mg, yield: 24%) as a white solid. ¹H NMR (400 MHz, DMSO-d₆): δ=9.26 (s, 1H), 8.49 (d, J=8.0 Hz, 2H), 7.82 (d, J=8.0 Hz, 2H), 7.76 (d, J=8.0 Hz, 2H), 7.59 (d, J=8.0 Hz, 2H), 7.27 (d, J=8.0 Hz, 2H), 7.10 (d, J=8.0 Hz, 2H), 6.93 (t, J=6.0 Hz, 1H), 4.32 (d, J=6.0 Hz, 2H), 3.81 (s, 3H). MS: m/z 397.9 (M+H⁺).

Example 320: Synthesis of 1-[4-(4-Methoxy-benzenesulfonyl)-phenyl]-3-(1H-pyrazol-4-ylmethyl)-urea

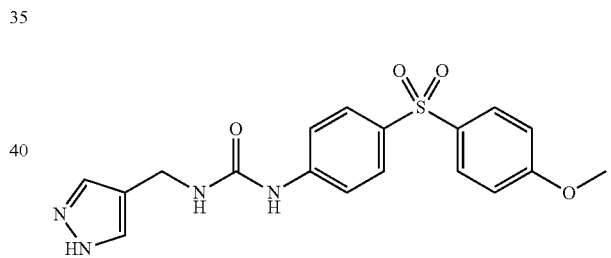

The title compound was prepared as described in example 1-[4-(4-methoxy-benzenesulfonyl)-phenyl]-3-pyridin-4-ylmethyl-urea. ¹H NMR (400 MHz, DMSO-d₆): δ=8.98 (s, 1H), 7.82 (d, J=8.0 Hz, 2H), 7.75 (d, J=8.0 Hz, 2H), 7.60-7.46 (m, 4H), 7.10 (d, J=8.0 Hz, 2H), 6.54 (t, J=8.0 Hz, 2H), 4.14 (d, J=8.0 Hz, 2H), 3.81 (s, 3H). MS: m/z 386.9 (M+H⁺).

Example 321: Synthesis of 4-(3-Benzyl-3-methyl-ureido)-benzoic acid ethyl ester

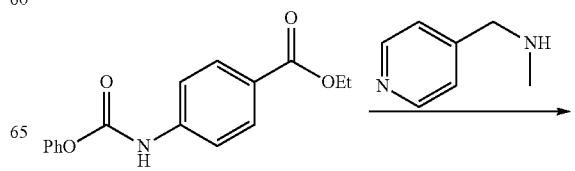

-continued

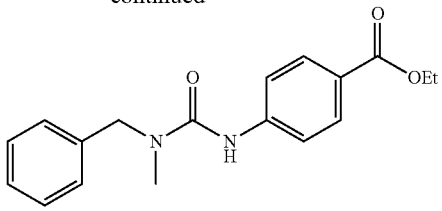

A solution of 4-phenoxycarbonylamino-benzoic acid ethyl ester (50 mg, 0.175 mmol), methyl-pyridin-4-ylmethyl-amine (23.5 mg, 0.193 mmol) and Et$_3$N (53.15 mg, 0.526 mmol) in 1,4-dioxane (2 ml) was stirred at 90° C. overnight. The mixture was concentrated and purified by prep-HPLC to give 4-(3-benzyl-3-methyl-ureido)-benzoic acid ethyl ester (14 mg, yield: 25.5%) as a white solid. $^1$H NMR (400 MHz, CD$_3$OD): δ=8.81 (brs, 2H), 8.01 (brs, 2H), 7.92 (d, J=6.8 Hz, 2H), 7.58 (d, J=6.8 Hz, 2H), 4.91 (s, 2H), 4.33 (q, J=7.2 Hz, 2H), 3.23 (s, 3H), 1.37 (t, J=7.2 Hz, 3H). MS: m/z 314.0 (M+H$^+$).

Example 322: Synthesis of 1-[(Pyridin-4-ylmethyl)-carbamoyl]-1H-indazole-5-carboxylic acid ethyl ester

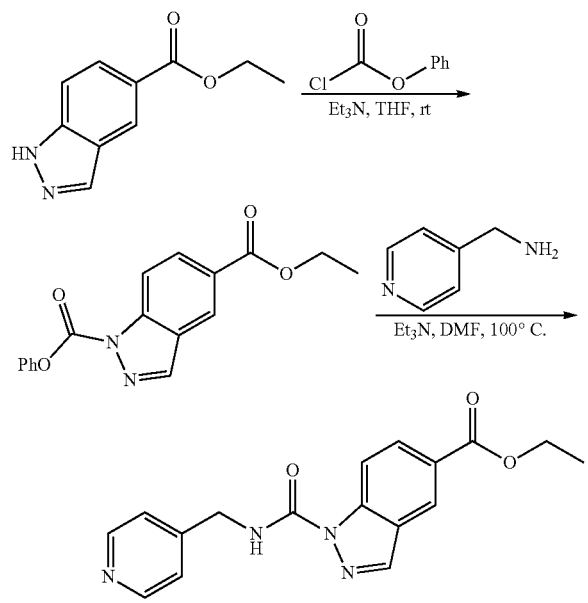

Step 1: A solution of 1H-indazole-5-carboxylic acid ethyl ester (175 mg, 0.92 mmol), phenyl chloroformate (217 mg, 1.39 mmol) and Et$_3$N (0.3 mL) in THF (2 ml) was stirred at 80° C. for 6 hrs. The mixture was concentrated to give crude indazole-1,5-dicarboxylic acid 5-ethyl ester 1-phenyl ester, which was used for next step directly without further purification. MS: m/z 311.6 (M+H)$^+$.

Step 2: A solution of indazole-1,5-dicarboxylic acid 5-ethyl ester 1-phenyl ester (280 mg, crude), pyridin-4-ylmethanamine (97.5 mg, 0.903 mmol) and Et$_3$N (273 mg, 2.7 mmol) in [1,4]dioxane (3 mL) was stirred at 100° C. for 2 hrs under MW irradiation. The mixture was concentrated and the brown oil was purified by prep-HPLC to give 1-[(pyridin-4-ylmethyl)-carbamoyl]-1H-indazole-5-carboxylic acid ethyl ester (96.5 mg, yield: 33%) as a white solid.

$^1$H NMR (400 MHz, DMSO-d6): δ=9.27 (t, J=6.2 Hz, 1H), 8.61 (t, J=2.0 Hz, 1H), 8.58-8.55 (m, 1H), 8.52 (dd, J=4.4, 1.6 Hz, 2H), 8.34 (d, J=8.8 Hz, 1H), 8.13 (dd, J=8.8, 1.6 Hz, 1H), 7.37 (d, J=6.0 Hz, 2H), 4.53 (d, J=6.4 Hz, 2H), 4.36 (d, J=7.2 Hz, 2H), 1.36 (t, J=7.2 Hz, 3H). MS: m/z 325.0 (M+H$^+$).

Example 323: Synthesis of 4-(2-Oxo-3-pyridin-4-ylmethyl-imidazolidin-1-yl)-benzoic acid ethyl ester and 4-(2-oxo-3-pyridin-4-ylmethyl-imidazolidin-1-yl)-benzoic acid

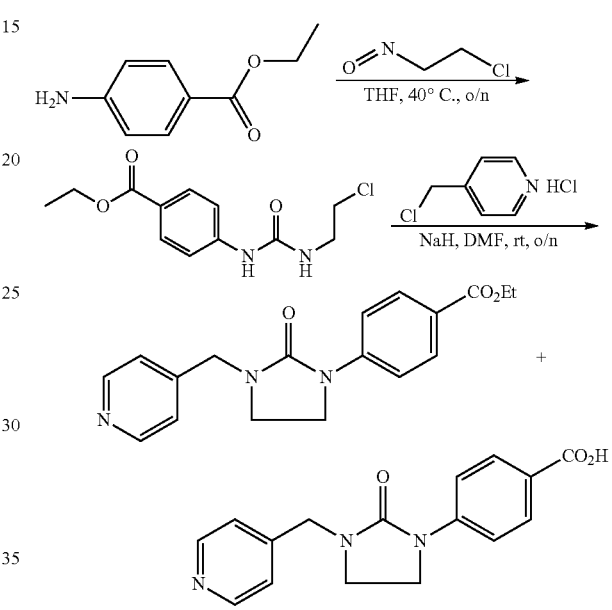

Step 1: To a solution of 4-amino-benzoic acid ethyl ester (446 mg, 2.7 mmol) in THF (5 mL), was added 1-chloro-2-isocyanato-ethane (0.27 mL, 2.9 mmol). The mixture was stirred at 40° C. overnight. After that, water (20 mL) and EA (20 mL) was added. The mixture was extracted with EA ((20 mL×2). The extracts were dried over Na$_2$SO$_4$ and concentrated to give 4-[3-(2-chloro-ethyl)-ureido]-benzoic acid ethyl ester (673 mg, yield: 92%) as a yellow solid.

Step 2: To a solution of 4-[3-(2-chloro-ethyl)-ureido]-benzoic acid ethyl ester (269 mg, 1.00 mmol) in DMF (5 mL), was added NaH (197 mg, 4.9 mmol). The suspension was stirred for half an hour at room temperature under N$_2$, followed by the addition of 4-chloromethyl-pyridine (183 mg, 1.12 mmol). The mixture was stirred overnight at room temperature. After that, NH$_4$Cl (40 mL) and EA (20 mL) was added. The aqueous phase was extracted with EA (20 mL×2). The extracts were washed with brine (20 mL×2), dried over Na$_2$SO$_4$ and concentrated. The residue was purified by silica gel column chromatography (EA) and recrystallized from MeCN to give 4-(2-oxo-3-pyridin-4-ylmethyl-imidazolidin-1-yl)-benzoic acid ethyl ester (100 mg, yield: 31%) as a yellow solid. The aqueous phase was purified by reverse phase column chromatography (MeCN/H$_2$O=5~95%) to afford 4-(2-oxo-3-pyridin-4-ylmethyl-imidazolidin-1-yl)-benzoic acid (20 mg, yield: 7%) as a white solid.

4-(2-Oxo-3-pyridin-4-ylmethyl-imidazolidin-1-yl)-benzoic acid ethyl ester: $^1$H NMR (400 MHz, DMSO-d$_6$): δ=8.54 (d, J=6.0 Hz, 2H), 7.93 (d, J=9.2 Hz, 2H), 7.74 (d, J=8.8 Hz, 2H), 7.33 (d, J=6.0 Hz, 2H), 4.46 (s, 2H), 4.28 (q, J=7.2 Hz, 2H), 3.92 (t, J=8.0 Hz, 2H), 3.46 (t, J=8.0 Hz, 2H), 1.31 (t, J=7.2 Hz, 3H). MS: m/z 325.9 (M+H⁺).

4-(2-oxo-3-pyridin-4-ylmethyl-imidazolidin-1-yl)-benzoic acid: ¹H NMR (400 MHz, DMSO-d₆): δ=8.55 (d, J=5.2 Hz, 2H), 7.91 (d, J=8.8 Hz, 2H), 7.72 (d, J=8.8 Hz, 2H), 7.33 (d, J=5.2 Hz, 2H), 4.46 (s, 2H), 3.92 (t, J=8.0 Hz, 2H), 3.46 (t, J=8.0 Hz, 2H). MS: m/z 297.9 (M+H⁺).

Example 324: Synthesis of N-[4-(3-Pyridin-4-ylmethyl-ureido)-phenyl]-benzenesulfonamide

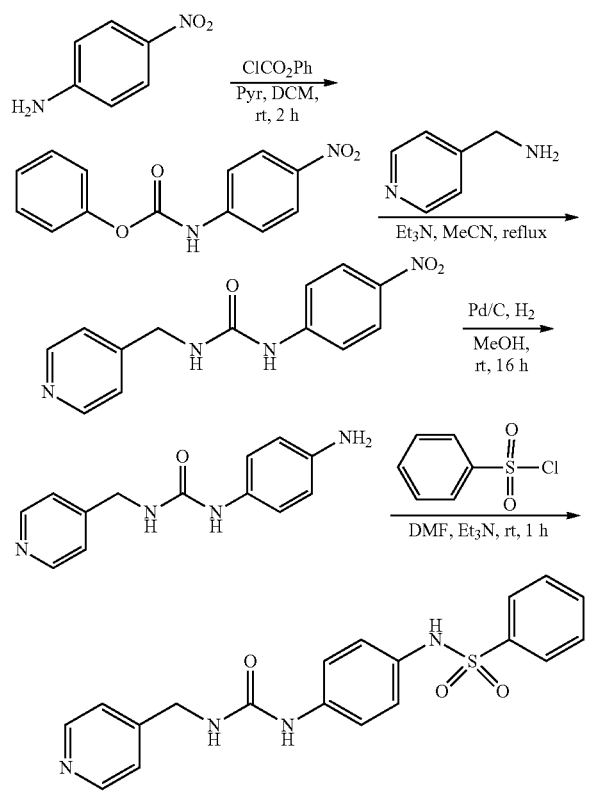

Step 1: To a solution of 4-nitro-phenylamine (2.0 g, 14.5 mmol) and pyridine (3 mL, 39.1 mmol) in DCM (100 mL) was added phenyl chloroformate (2.5 mL, 20.3 mmol) dropwise at 0° C. After stirring at room temperature for 2 hrs, the reaction mixture was diluted with DCM (50 mL), washed with water (50 mL). The DCM solution was dried over Na₂SO₄ and concentrated. The residue was washed with (PE/EA=8/1) to give (4-nitro-phenyl)-carbamic acid phenyl ester (2.4 g, yield: 64%) as a white solid. ¹H NMR (400 MHz, CDCl₃): δ=8.19 (d, J=8.8 Hz, 2H), 7.59 (d, J=8.8 Hz, 2H), 7.47-7.39 (m, 3H), 7.28 (t, J=8.0 Hz, 1H), 7.19 (d, J=7.6 Hz, 2H).

Step 2: To a solution of (4-nitro-phenyl)-carbamic acid phenyl ester (200 mg, 0.8 mmol) and TEA (0.2 mL, 1.5 mmol) in MeCN (5 mL) was added Pyridin-4-ylmethanamine (90 mg, 0.8 mmol). After stirring at 80° C. for 16 hrs, the precipitation was collected and washed with MeCN (2 mL) to give 1-(4-nitro-phenyl)-3-pyridin-4-ylmethyl-urea (200 mg, yield: 95%) as a white solid.

Step 3: A mixture of 1-(4-nitro-phenyl)-3-pyridin-4-ylmethyl-urea (200 mg, 0.7 mmol) and 10% Pd/C (50% w/w, 70 mg) in MeOH (25 mL) was stirred at room temperature for 16 hrs under H₂ atmosphere (balloon). The reaction mixture was filtered to remove catalyst. The filtrate was concentrated to give 1-(4-amino-phenyl)-3-pyridin-4-ylmethyl-urea (160 mg, crude) as a pale yellow solid.

Step 4: To a stirring solution of 1-(4-amino-phenyl)-3-pyridin-4-ylmethyl-urea (160 mg, 0.7 mmol) and TEA (0.3 mL, 2.0 mmol) in DMF (4 mL) was added benzenesulfonyl chloride (180 mg, 1.0 mmol). After stirring at room temperature for 1 h, the reaction mixture was diluted with H₂O (20 mL) and extracted with EA (20 mL×4). The combined EA was washed with brine, dried over Na₂SO₄ and concentrated. The residue was purified by silica gel column (DCM/MeOH=30/1) and then washed with MeOH (5 mL) to give N-[4-(3-pyridin-4-ylmethyl-ureido)-phenyl]-benzenesulfonamide (50 mg, yield: 18%, two steps) as a white solid. ¹H NMR (400 MHz, DMSO-d₆): δ=9.91 (s, 1H), 8.61 (s, 1H), 8.48 (dd, J=4.4, 1.2 Hz, 2H), 7.69 (d, J=7.6 Hz, 2H), 7.61-7.50 (m, 3H), 7.26-7.23 (m, 4H), 6.92 (d, J=8.8 Hz, 2H), 6.67 (t, J=5.6 Hz, 1H), 4.29 (d, J=5.6 Hz, 2H). MS: m/z 382.9 (M+H⁺).

Example 325: Synthesis of 2-Methoxy-N-[4-(3-pyridin-4-ylmethyl-ureido)-phenyl]-benzenesulfonamide

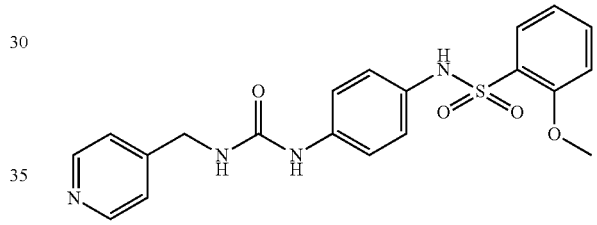

The title compound was prepared as described in example N-[4-(3-Pyridin-4-ylmethyl-ureido)-phenyl]-benzenesulfonamide. ¹H NMR (400 MHz, DMSO-d6): δ=9.59 (s, 1H), 8.54 (s, 1H), 8.47 (d, J=5.6 Hz, 2H), 7.66 (d, J=6.4 Hz, 1H), 7.53 (t, J=8.2 Hz, 1H), 7.24-7.16 (m, 5H), 7.00-6.92 (m, 3H), 6.64 (t, J=6.0 Hz, 1H), 4.27 (d, J=6.0 Hz, 2H), 3.91 (s, 3H). MS: m/z 412.9 (M+H⁺).

Example 326: Synthesis of 3-Methoxy-N-[4-(3-pyridin-4-ylmethyl-ureido)-phenyl]-benzenesulfonamide

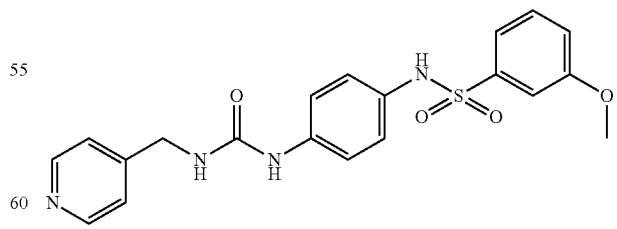

The title compound was prepared as described in example N-[4-(3-Pyridin-4-ylmethyl-ureido)-phenyl]-benzenesulfonamide. ¹H NMR (400 MHz, DMSO-d6): δ=9.89 (s, 1H), 8.61 (s, 1H), 8.48 (dd, J=1.6, 4.8 Hz, 2H), 7.43 (t, J=8.0 Hz, 1H), 7.26-7.23 (m, 5H), 7.20-7.13 (m, 2H), 6.93 (d, J=9.2

Hz, 2H), 6.67 (t, J=6.0 Hz, 1H), 4.29 (d, J=6.0 Hz, 2H), 3.91 (s, 3H). MS: m/z 412.9 (M+H⁺).

Example 327: Synthesis of 4-Methoxy-N-[4-(3-pyridin-4-ylmethyl-ureido)-phenyl]-benzenesulfonamide

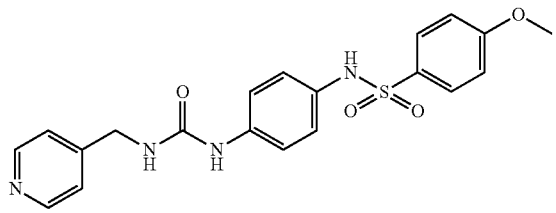 [SMILES: COc1ccc(S(=O)(=O)Nc2ccc(NC(=O)NCc3ccncc3)cc2)cc1]

The title compound was prepared as described in example N-[4-(3-Pyridin-4-ylmethyl-ureido)-phenyl]-benzenesulfonamide. ¹H NMR (400 MHz, DMSO-d6): δ=9.76 (s, 1H), 8.59 (s, 1H), 8.48 (d, J=6.0 Hz, 2H), 7.61 (d, J=9.2 Hz, 2H), 7.26-7.23 (m, 4H), 7.03 (d, J=8.8 Hz, 2H), 6.91 (d, J=8.8 Hz, 2H), 6.67 (t, J=6.0 Hz, 1H), 4.28 (t, J=6.8 Hz, 2H), 3.78 (s, 3H). MS: m/z 412.9 (M+H⁺).

Example 328: Synthesis of 2-Chloro-N-[4-(3-pyridin-4-ylmethyl-ureido)-phenyl]-benzenesulfonamide

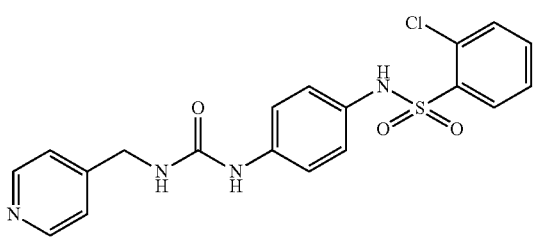 [SMILES: O=C(NCc1ccncc1)Nc1ccc(NS(=O)(=O)c2ccccc2Cl)cc1]

The title compound was prepared as described in example N-[4-(3-Pyridin-4-ylmethyl-ureido)-phenyl]-benzenesulfonamide. ¹H NMR (400 MHz, DMSO-d6): δ=10.23 (s, 1H), 8.60 (s, 1H), 8.47-8.48 (m, 2H), 7.93 (d, J=6.8 Hz, 1H), 7.62-7.60 (m, 2H), 7.48-7.47 (m, 1H), 7.23-7.25 (s, 4H), 6.96 (d, J=7.6 Hz, 2H), 6.67 (s, 1H), 4.28 (d, J=4.0 Hz, 2H). MS: m/z 416.9 (M+H⁺).

Example 329: Synthesis of 3-Chloro-N-[4-(3-pyridin-4-ylmethyl-ureido)-phenyl]-benzenesulfonamide

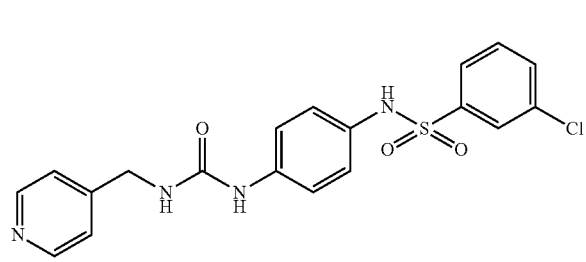 [SMILES: O=C(NCc1ccncc1)Nc1ccc(NS(=O)(=O)c2cccc(Cl)c2)cc1]

The title compound was prepared as described in example N-[4-(3-Pyridin-4-ylmethyl-ureido)-phenyl]-benzenesulfonamide. ¹H NMR (400 MHz, DMSO-d6): δ=10.03 (s, 1H), 8.67 (s, 1H), 8.51 (d, J=6.4 Hz, 2H), 7.69-7.68 (m, 2H), 7.62-7.54 (m, 2H), 7.30-7.27 (m, 4H), 6.92 (d, J=8.4 Hz, 2H), 6.70 (t, J=6.4 Hz, 1H), 4.31 (d, J=5.6 Hz, 2H). MS: m/z 416.9 (M+H⁺).

Example 330: Synthesis of 4-Chloro-N-[4-(3-pyridin-4-ylmethyl-ureido)-phenyl]-benzenesulfonamide

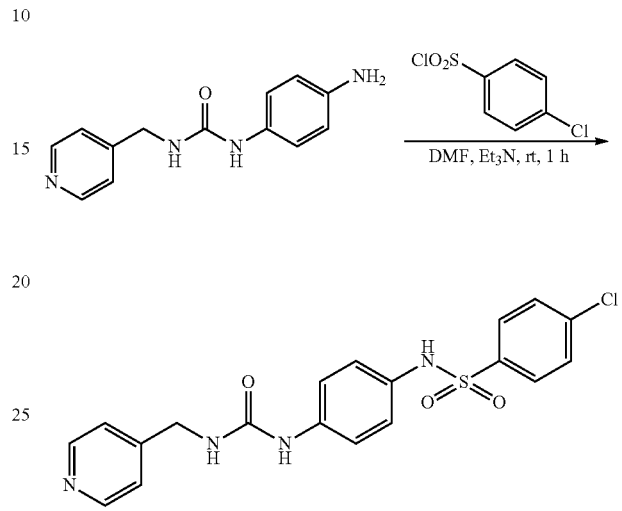

To a solution of 1-(4-amino-phenyl)-3-pyridin-4-ylmethyl-urea (200 mg, 0.8 mmoL) and Et₃N (0.3 mL, 2.0 mmoL) in DMF (11 mL) was added 4-chloro-benzenesulfonyl chloride (210 mg, 1.0 mmoL) at 0° C. The mixture was stirred at room temperature for 1 hr. The reaction mixture was diluted with EA (35 mL) and washed with H₂O (40 mL), brine (40 mL), dried over Na₂SO₄ and concentrated to dryness in vacuum. The residue was washed with MeOH (4 mL) and CH₃CN (4 mL) to give 4-chloro-N-[4-(3-pyridin-4-ylmethyl-ureido)-phenyl]-benzenesulfonamide (60 mg, yield: 17%) as a white solid. ¹H NMR (400 MHz, DMSO-d6): δ=9.98 (s, 1H), 8.64 (s, 1H), 8.48 (d, J=6.0 Hz, 2H), 7.68-7.60 (m, 4H), 7.28-7.25 (m, 4H), 6.92 (d, J=8.4 Hz, 2H), 6.68 (t, J=6.0 Hz, 1H), 4.30 (d, J=6.0 Hz, 2H). MS: m/z 416.9 (M+H⁺).

Example 331: Synthesis of N-[4-(3-Benzyl-ureido)-phenyl]-C-phenyl-methanesulfonamide

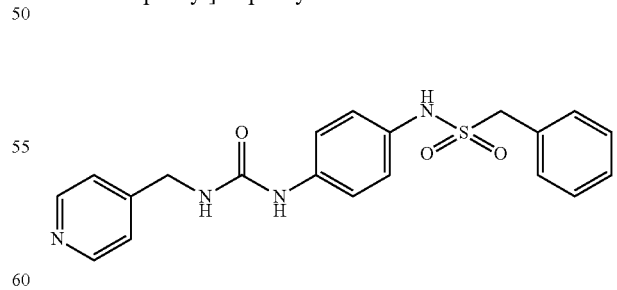

The title compound was prepared as described in example N-[4-(3-Pyridin-4-ylmethyl-ureido)-phenyl]-benzenesulfonamide. ¹H NMR (300 MHz, DMSO-d6): δ=9.56 (s, 1H), 8.70 (s, 1H), 8.50 (dd, J=1.2, 4.4 Hz, 2H), 7.38-7.35 (m, 5H), 7.29-7.25 (m, 4H), 7.09 (d, J=8.8 Hz, 2H), 6.71 (t, J=6.0 Hz, 1H), 4.35-4.32 (m, 4H), MS: m/z 397.0 (M+H⁺).

Example 332: Synthesis of 1-(2-chlorophenyl)-N-(4-(3-(pyridin-4-ylmethyl)ureido)phenyl)methanesulfonamide

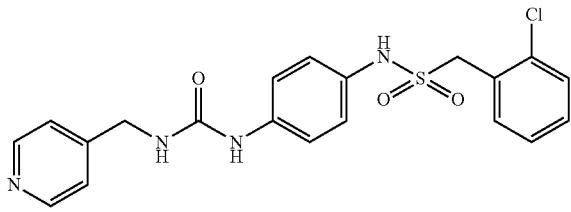 [SMILES: O=C(NCc1ccncc1)Nc1ccc(NS(=O)(=O)Cc2ccccc2Cl)cc1]

The title compound was prepared as described in example N-[4-(3-Pyridin-4-ylmethyl-ureido)-phenyl]-benzenesulfonamide. $^1$H NMR (400 MHz, DMSO-d6): δ=9.73 (s, 1H), 8.66 (s, 1H), 8.50 (d, J=5.6 Hz, 2H), 7.48 (d, J=6.8 Hz, 1H), 7.42-7.35 (m, 5H), 7.28 (d, J=5.6 Hz, 2H), 7.10 (d, J=8.8 Hz, 2H), 6.70 (t, J=6.0 Hz, 1H), 4.52 (s, 2H), 4.32 (d, J=6.0 Hz, 2H). MS: m/z 430.9 (M+H$^+$).

Example 333: Synthesis of 1-(3-chlorophenyl)-N-(4-(3-(pyridin-4-ylmethyl)ureido)phenyl)methanesulfonamide

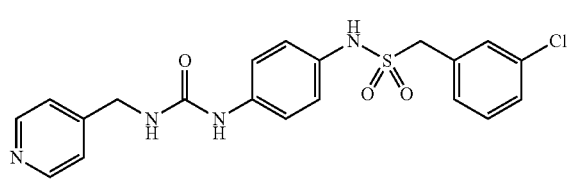 [SMILES: O=C(NCc1ccncc1)Nc1ccc(NS(=O)(=O)Cc2cccc(Cl)c2)cc1]

The title compound was prepared as described in example N-[4-(3-Pyridin-4-ylmethyl-ureido)-phenyl]-benzenesulfonamide. $^1$H NMR (400 MHz, DMSO-d6): δ=9.60 (s, 1H), 8.69 (s, 1H), 8.50 (d, J=6.0 Hz, 2H), 7.43-7.36 (m, 4H), 7.33 (s, 1H), 7.28 (d, J=5.6 Hz, 2H), 7.22 (d, J=6.8 Hz, 1H), 7.08 (d, J=8.8 Hz, 2H), 6.71 (t, J=6.0 Hz, 1H), 4.42 (s, 2H), 4.32 (d, J=6.0 Hz, 2H). MS: m/z 430.9 (M+H$^+$).

Example 334: Synthesis of 1-(4-chlorophenyl)-N-(4-(3-(pyridin-4-ylmethyl)ureido)phenyl)methanesulfonamide

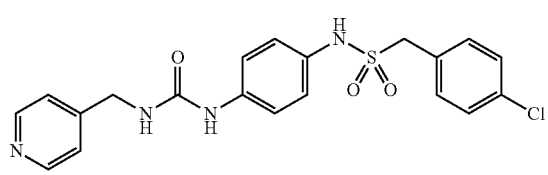 [SMILES: O=C(NCc1ccncc1)Nc1ccc(NS(=O)(=O)Cc2ccc(Cl)cc2)cc1]

The title compound was prepared as described in example N-[4-(3-Pyridin-4-ylmethyl-ureido)-phenyl]-benzenesulfonamide. $^1$H NMR (400 MHz, DMSO-d6): δ=9.55 (s, 1H), 8.68 (s, 1H), 8.50 (d, J=6.4 Hz, 2H), 7.43 (d, J=8.4 Hz, 2H), 7.37 (d, J=8.4 Hz, 2H), 7.29-7.27 (m, 4H), 7.07 (d, J=9.2 Hz, 2H), 6.7 (t, J=6 Hz, 1H), 4.38 (s, 2H), 4.32 (d, J=6 Hz, 2H). MS: m/z 430.9 (M+H$^+$).

Example 335: Synthesis of N-Methyl-C-phenyl-N-[4-(3-pyridin-4-ylmethyl-ureido)-phenyl]-methanesulfonamide

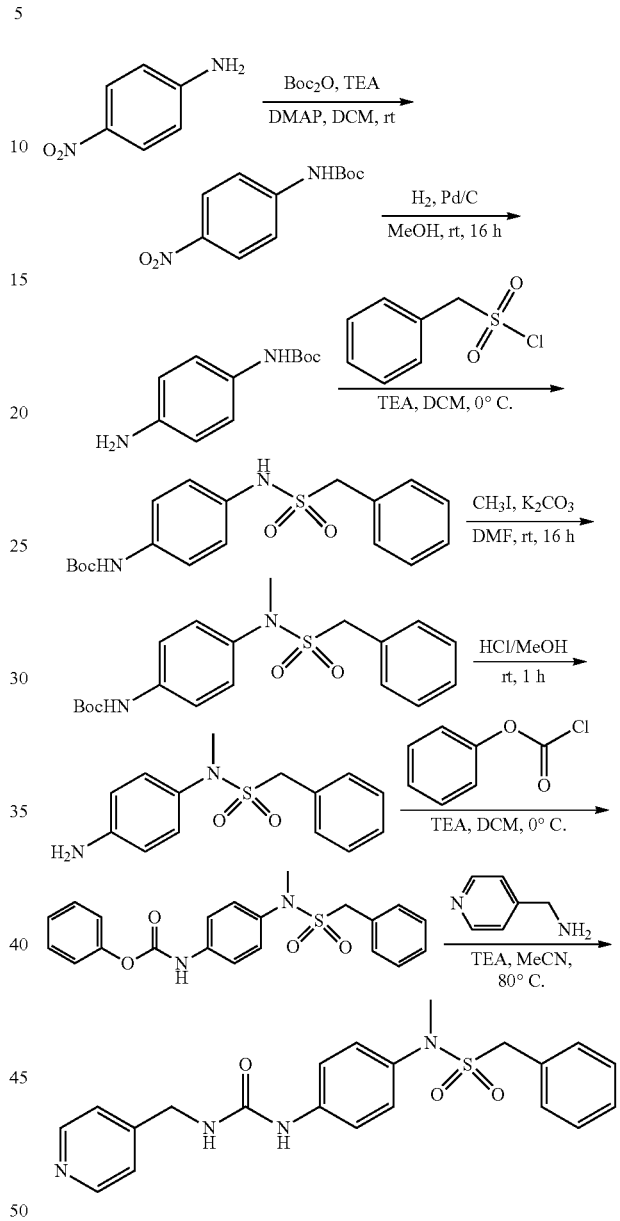

Step 1: To a solution of 4-nitro-phenylamine (5.0 g, 36.2 mmoL), TEA (10 mL, 69.3 mmoL) and DMAP (2.2 g, 18.0 mmoL) in DCM (100 mL) was added BOC$_2$O (9.5 g, 43.5 mmoL) at room temperature. After stirring at room temperature for 16 hrs, the precipitation was removed by filtration and the filtrate was washed with aq.HCl (1 N, 50 mL), Sat.NaHCO$_3$ (20 mL), dried and concentrated. The residue was purified by silica gel column (PE/EA=20/1) to give (4-nitro-phenyl)-carbamic acid tert-butyl ester (4.4 g, yield: 51%) as a yellow solid. $^1$H NM (400 MHz, CDCl$_3$): δ=8.17 (d, J=9.6 Hz, 2H), 7.54 (d, J=8.8 Hz, 2H), 7.08 (brs, 1H), 1.54 (s, 9H).

Step 2: A suspension of (4-nitro-phenyl)-carbamic acid tert-butyl ester (400 mg, 1.7 mmoL) and 10% Pd/C (50% w/w, 80 mg) in MeOH (6 mL) was stirred at room temperature for 16 hrs under H$_2$ atmosphere (balloon). The reaction mixture was filtered to remove catalyst and the filtrate was concentrated to give (4-amino-phenyl)-carbamic acid tert-butyl ester (300 mg, yield: 86%) as a red solid. MS: m/z 153.3 (M-55).

Step 3: To a solution of (4-amino-phenyl)-carbamic acid tert-butyl ester (200 mg, 1.0 mmoL) and Et₃N (0.3 mL, 2.0 mmoL) in DCM (6 mL) was added phenyl-methanesulfonyl chloride (200 mg, 1.1 mmoL) at 0°. After stirring at room temperature for 2 hrs, the reaction mixture was concentrated and the residue was purified by silica gel column (PE/EA=7/1) to give (4-phenylmethanesulfonylamino-phenyl)-carbamic acid tert-butyl ester (190 mg, yield: 54%) as a red solid.

Step 4: To a stirring solution of (4-phenylmethanesulfonylamino-phenyl)-carbamic acid tert-butyl ester (300 mg, 0.8 mmol) and K₂CO₃ (230 mg, 1.7 mmol) in DMF (6 mL) was added CH₃I (140 mg, 1.0 mmol). After stirring at room temperature for 16 hrs, the reaction mixture was diluted with H₂O (30 mL) and extracted with EA (30 mL×3). The combined EA was washed with brine, dried over Na₂SO₄ and concentrated. The residue was washed with (PE/EA=2/1) to give [4-(methyl-phenylmethanesulfonyl-amino)-phenyl]-carbamic acid tert-butyl ester (240 mg, yield: 77%) as a white solid. ¹H NMR (400 MHz, CDCl₃): δ=7.40-7.32 (m, 7H), 7.17 (d, J=9.2 Hz, 2H), 6.51 (s, 1H), 4.25 (s, 2H), 3.10 (s, 3H), 1.52 (s, 9H).

Step 5: To a solution of [4-(methyl-phenylmethanesulfonyl-amino)-phenyl]-carbamic acid tert-butyl ester (240 mg, 0.7 mmol) in DCM (5 mL) was added HCl/MeOH (4 M, 5 mL). After stirring at room temperature for 2 hrs, the reaction mixture was concentrated to give N-(4-amino-phenyl)-N-methyl-C-phenyl-methanesulfonamide (crude) as a white solid.

Step 6: To a solution of N-(4-amino-phenyl)-N-methyl-C-phenyl-methanesulfonamide (crude) and TEA (0.3 mL, 1.9 mmol) in DCM (10 mL) was added phenyl chloroformate (0.1 mL, 0.8 mmol) dropwise at 0° C. After stirring at this temperature for 20 min, the reaction mixture was diluted with DCM (30 mL), washed with aq.HCl (1 N, 20 mL) and Sat.NaHCO₃ (20 mL). The DCM solution was dried over Na₂SO₄ and concentrated to give [4-(methyl-phenylmethanesulfonyl-amino)-phenyl]-carbamic acid phenyl ester (crude) as a white solid.

Step 7: A mixture of [4-(methyl-phenylmethanesulfonyl-amino)-phenyl]-carbamic acid phenyl ester (crude), Pyridin-4-ylmethanamine (70 mg, 0.6 mmol) and TEA (0.2 mL, 1.3 mmol) in MeCN (10 mL) was stirred at 80° C. for 1 h and then concentrated. The residue was diluted by DCM (50 mL) and extracted by aq.HCl (1 N, 30 mL). The acidic layer was basified by Sat.NaHCO₃ to pH=8 and then extracted with DCM (30 mL×4). The combined DCM was dried over Na₂SO₄ and concentrated. The residue was washed with MeCN (10 mL) to give N-methyl-C-phenyl-N-[4-(3-pyridin-4-ylmethyl-ureido)-phenyl]-methanesulfonamide (90 mg, yield: 34%, three steps) as a white solid. ¹H NMR (400 MHz, DMSO-d₆): δ=8.81 (s, 1H), 8.50 (d, J=5.6 Hz, 2H), 7.41-7.35 (m, 7H), 7.29 (d, J=5.6 Hz, 2H), 7.14 (d, J=8.8 Hz, 2H), 6.76 (t, J=6.0 Hz, 1H), 4.45 (s, 2H), 4.33 (d, J=6.0 Hz, 2H), 3.15 (s, 3H). MS: m/z 410.9 (M+H⁺).

Example 336: Synthesis of N-Isopropyl-N-[4-(3-pyridin-4-ylmethyl-ureido)-phenyl]-benzenesulfonamide

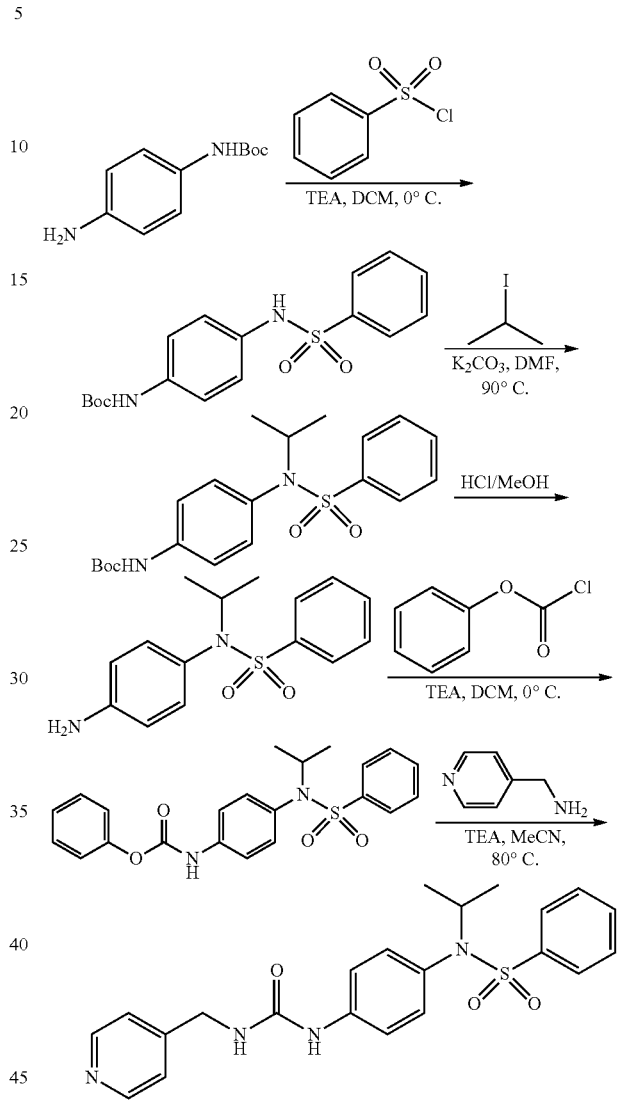

Step 1: This step was similar to general procedure of N-methyl-C-phenyl-N-[4-(3-pyridin-4-ylmethyl-ureido)-phenyl]-methanesulfonamide.

Step 2: To a stirring solution of (4-benzenesulfonylamino-phenyl)-carbamic acid tert-butyl ester (600 mg, 1.7 mmol) and K₂CO₃ (480 mg, 3.4 mmol) in DMF (10 mL) was added 2-iodo-propane (440 mg, 2.6 mmol). After stirring at 90° C. for 24 hrs, the reaction mixture was diluted with H₂O (30 mL) and extracted with EA (30 mL×3). The combined EA was washed with brine, dried over Na₂SO₄ and concentrated. The residue was purified by silica gel column (PE/EA=10/1) to give [4-(benzenesulfonyl-isopropyl-amino)-phenyl]-carbamic acid tert-butyl ester (530 mg, yield: 79%) as a white solid. ¹H NMR (300 MHz, CDCl₃): δ=7.76-7.73 (m, 2H), 7.59-7.53 (m, 1H), 7.50-7.43 (m, 2H), 7.34 (d, J=8.1 Hz, 2H), 6.95 (d, J=8.4 Hz, 2H), 6.54 (s, 1H), 4.67-4.57 (m, 1H), 1.53 (s, 9H), 1.04 (d, J=6.3 Hz, 6H).

Step 3-5: These three steps were similar to general procedure of N-methyl-C-phenyl-N-[4-(3-pyridin-4-ylmethyl-ureido)-phenyl]-methanesulfonamide. ¹H NMR (400 MHz, DMSO-d$_6$) δ=8.87 (s, 1H), 8.50 (dd, J=4.4, 1.6 Hz, 2H), 7.74-7.65 (m, 3H), 7.59 (td, J=6.4, 1.6 Hz, 2H), 7.42-7.38 (m, 2H), 7.28 (dd, J=4.4, 1.6 Hz, 2H), 6.87-6.84 (m, 2H), 6.79 (t, J=6.0 Hz, 1H), 4.46-4.41 (m, 1H), 4.33 (d, J=6.0 Hz, 2H), 0.94 (d, J=7.2 Hz, 6H). MS: m/z 424.9 (M+H$^+$).

Example 337: Synthesis of N-Methyl-N-[4-(3-pyridin-4-ylmethyl-ureido)-phenyl]-benzenesulfonamide

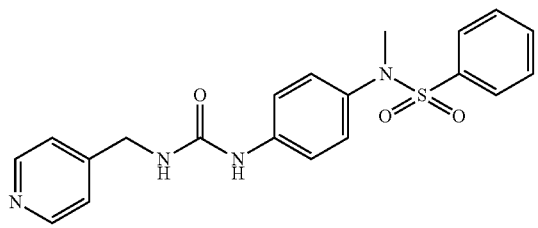 [SMILES: CN(c1ccc(NC(=O)NCc2ccncc2)cc1)S(=O)(=O)c1ccccc1]

The title compound was prepared as described in example N-methyl-C-phenyl-N-[4-(3-pyridin-4-ylmethyl-ureido)-phenyl]-methanesulfonamide. $^1$H NMR (300 MHz, DMSO-d6): δ=8.81 (s, 1H), 8.50 (d, J=5.7 Hz, 2H), 7.67 (t, J=5.4 Hz, 1H), 7.60-7.57 (m, 2H), 7.51-7.48 (m, 2H), 7.34 (d, J=9.0 Hz, 2H), 7.27 (d, J=5.1 Hz, 2H), 6.90 (d, J=9.0 Hz, 2H), 6.76 (t, J=5.4 Hz, 1H), 4.31 (d, J=5.7 Hz, 2H), 3.07 (s, 3H). MS: m/z 397.0 (M+H$^+$).

Example 338: Synthesis of N-Isopropyl-C-phenyl-N-[4-(3-pyridin-4-ylmethyl-ureido)-phenyl]-methanesulfonamide

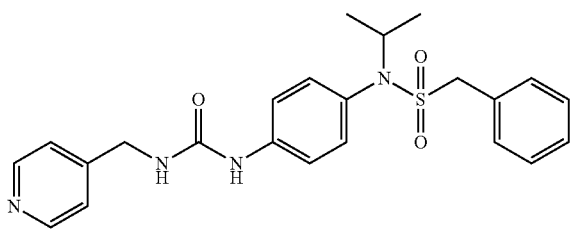 [SMILES: CC(C)N(c1ccc(NC(=O)NCc2ccncc2)cc1)S(=O)(=O)Cc1ccccc1]

The title compound was prepared as described in example N-[4-(3-Pyridin-4-ylmethyl-ureido)-phenyl]-benzenesulfonamide. $^1$H NMR (400 MHz, DMSO-d6): δ=8.86 (s, 1H), 8.50 (dd, J=2.0, 4.4 Hz, 2H), 7.46-7.36 (m, 7H), 7.28 (d, J=6.0 Hz, 2H), 6.90 (d, J=8.8 Hz, 2H), 6.78 (t, J=6.0 Hz, 1H), 4.46 (s, 2H), 4.33 (d, J=6.0 Hz, 2H), 4.16-4.12 (m, 1H), 0.96 (d, J=6.8 Hz, 6H). MS: m/z 439.0 (M+H$^+$).

Example 339: Synthesis of N-[4-(3-Oxazol-5-ylmethyl-ureido)-phenyl]-benzenesulfonamide

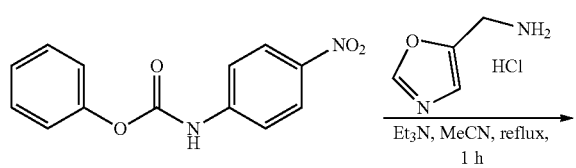

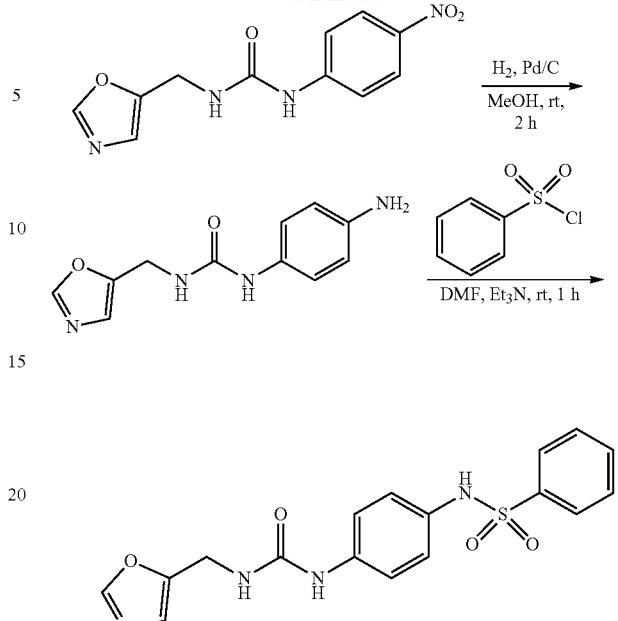

Step 1: To a solution of (4-nitro-phenyl)-carbamic acid phenyl ester (800 mg, 3.1 mmol) and TEA (1.4 mL, 9.3 mmol) in MeCN (20 mL) was added oxazol-5-ylmethanamine hydrochloride (420 mg, 3.1 mmol). After stirring at 80° C. for 1 hr, the reaction mixture was concentrated and purified by silica gel column (DCM/MeOH=20/1) to give 1-(4-nitro-phenyl)-3-oxazol-5-ylmethyl-urea (810 mg, yield: >100%) as a yellow solid.

Step 2-3: These two steps were similar to general procedure of N-[4-(3-pyridin-4-ylmethyl-ureido)-phenyl]-benzenesulfonamide. $^1$H NMR (400 MHz, DMSO-d$_6$): δ=9.91 (s, 1H), 8.48 (s, 1H), 8.26 (s, 1H), 7.70-7.67 (m, 2H), 7.61-7.50 (m, 3H), 7.22 (d, J=9.2 Hz, 2H), 6.97 (s, 1H), 6.91 (d, J=9.2 Hz, 2H), 6.55 (t, J=5.6 Hz, 1H), 4.32 (d, J=5.6 Hz, 2H). MS: m/z 372.9 (M+H$^+$).

Example 340: Synthesis of N-Oxazol-5-ylmethyl-2-(4-phenylmethanesulfonylamino-cyclohexa-1,5-dienyl)-acetamide

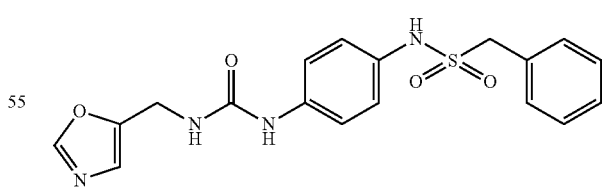

The title compound was prepared as described in example N-[4-(3-oxazol-5-ylmethyl-ureido)-phenyl]-C-phenyl-methanesulfonamide. $^1$H NMR (400 MHz, DMSO-d6): δ=9.54 (s, 1H), 8.54 (s, 1H), 8.28 (s, 1H), 7.36-7.34 (m, 5H), 7.27-7.26 (m, 2H), 7.08 (d, J=9.2 Hz, 2H), 7.00 (s, 1H), 6.57 (t, J=6.0 Hz, 1H), 4.36 (d, J=5.6 Hz, 4H). MS: m/z 386.9 (M+H$^+$).

Example 341: Synthesis of N-{4-[3-(1H-Pyrazol-4-ylmethyl)-ureido]-phenyl}-benzenesulfonamide

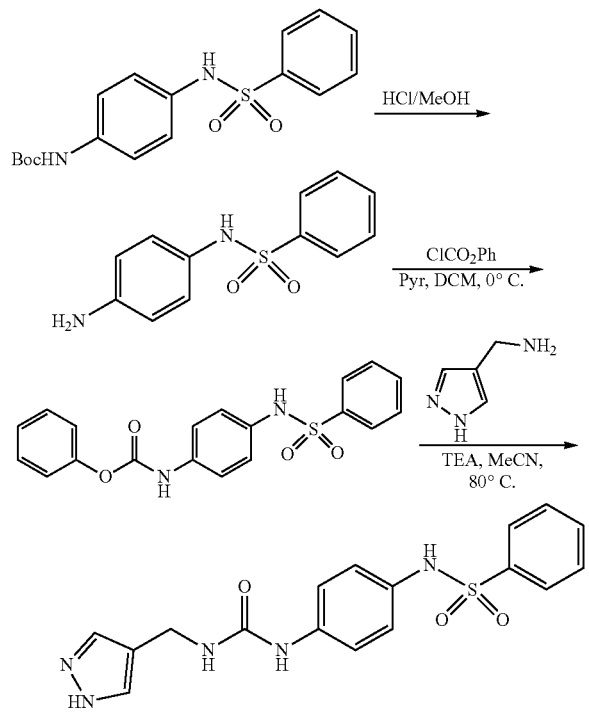

Step 1: To a solution of (4-benzenesulfonylamino-phenyl)-carbamic acid tert-butyl ester (1.0 g, 2.9 mmol) in DCM (10 mL) was added HCl/MeOH (4 M, 10 mL). After stirring at room temperature for 16 hrs, the reaction mixture was concentrated to dryness. The residue was diluted with Sat.NaHCO$_3$ (30 mL) and the aqueous phase was extracted with EA (40 mL×2). The combined organic layer was washed with brine (30 mL), dried over Na$_2$SO$_4$ and concentrated to give N-(4-amino-phenyl)-benzenesulfonamide (700 mg, yield: 98%) as a white solid.

Step 2: To a solution of N-(4-amino-phenyl)-benzenesulfonamide (200 mg, 0.8 mmol) and pyridine (200 mg, 2.4 mmol) in DCM (10 mL) was added phenyl chloroformate (160 mg, 1.0 mmol) dropwise at 0° C. After stirring at this temperature for 20 min, the reaction mixture was diluted with DCM (40 mL), washed with aq.HCl (1 N, 30 mL) and Sat.NaHCO$_3$ (20 mL). The DCM solution was dried over Na$_2$SO$_4$, concentrated and washed with (PE/EA=4/1) to give (4-benzenesulfonylamino-phenyl)-carbamic acid phenyl ester (280 mg, yield: 94%) as a white solid. $^1$H NMR (300 MHz, DMSO-d$_6$): δ=10.11 (s, 1H), 10.06 (s, 1H), 7.71 (d, J=6.9 Hz, 2H), 7.60-7.50 (m, 3H), 7.44-7.32 (m, 4H), 7.27-7.16 (m, 3H), 7.02 (d, J=9.0 Hz, 2H).

Step 3: A mixture of (4-benzenesulfonylamino-phenyl)-carbamic acid phenyl ester (130 mg, 0.4 mmol), (1H-pyrazol-4-yl)methanamine (120 mg, crude) and TEA (0.2 mL, 1.4 mmol) in MeCN (15 mL) was stirred at 80° C. for 16 hrs and then concentrated. The residue was purified by silica flash column (0% to 10% MeOH in DCM) to give N-{4-[3-(1H-pyrazol-4-ylmethyl)-ureido]-phenyl}-benzenesulfonamide (80 mg, yield: 61%) as a white solid. $^1$H NMR (400 MHz, DMSO-d$_6$): δ=12.59 (brs, 1H), 9.88 (s, 1H), 8.32 (s, 1H), 7.69-7.66 (m, 2H), 7.61-7.50 (m, 5H), 7.22 (dd, J=7.2, 2.0 Hz, 2H), 6.91 (dd, J=7.2, 2.0 Hz, 2H), 6.25 (t, J=5.6 Hz, 1H), 4.10 (d, J=5.6 Hz, 2H). MS: m/z 371.9 (M+H$^+$).

Example 342: Synthesis of N-(4-(3-((1H-pyrazol-4-yl)methyl)ureido)phenyl)-1-phenylmethanesulfonamide

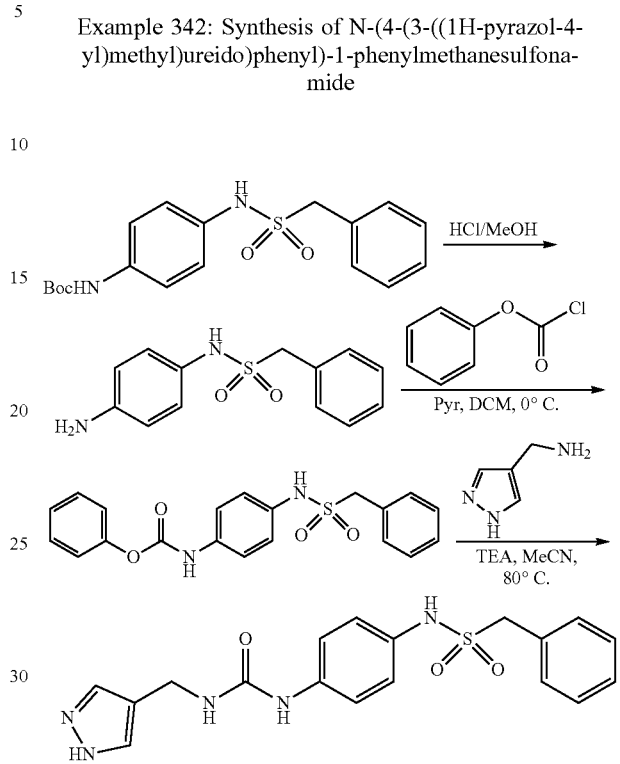

The title compound was prepared as described in example N-{4-[3-(1H-pyrazol-4-ylmethyl)-ureido]-phenyl}-benzenesulfonamide. H NMR (300 MHz, DMSO-d$_6$): δ=12.62 (brs, 1H), 9.51 (s, 1H), 8.38 (s, 1H), 7.53-7.51 (m, 2H), 7.37-7.24 (m, 7H), 7.10-7.06 (m, 2H), 6.28 (t, J=5.4 Hz, 1H), 4.34 (s, 2H), 4.14 (d, J=5.4 Hz, 2H). MS: m/z 385.9 (M+H$^+$).

Example 343: Synthesis of N-(4-{3-[1-(4-Methoxybenzyl)-1H-pyrazol-4-ylmethyl]-ureido}-phenyl)-benzenesulfonamide

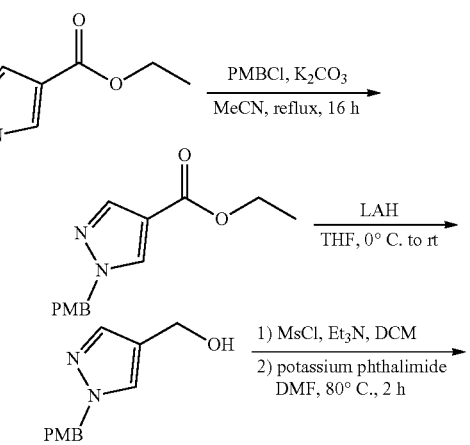

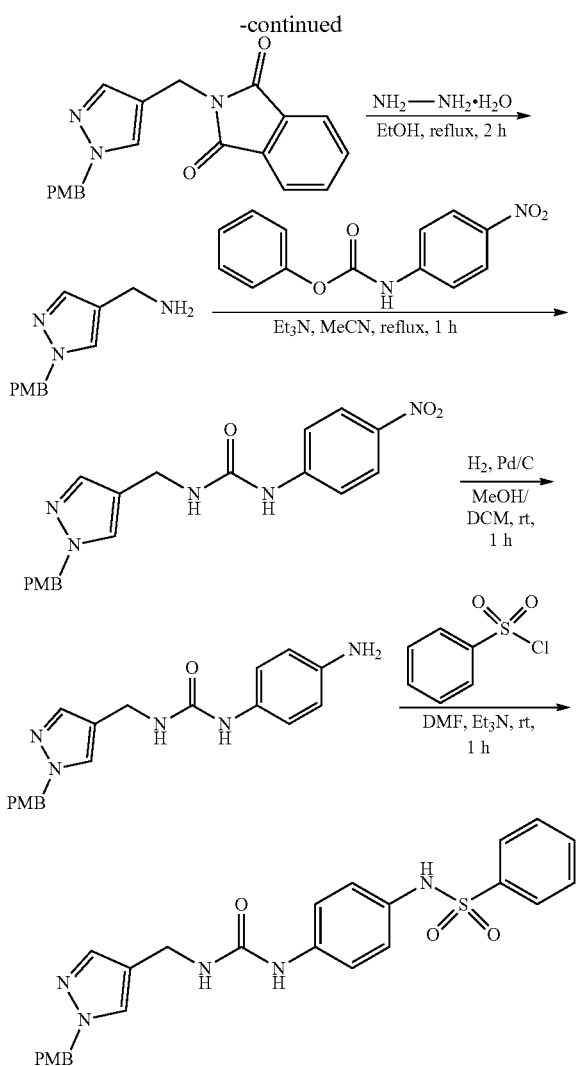

Step 1: A mixture of 1H-pyrazole-4-carboxylic acid ethyl ester (5.0 g, 35.7 mmol), PMBCl (6.2 g, 39.3 mmol) and K$_2$CO$_3$ (7.4 g, 53.6 mmol) in MeCN (100 mL) was refluxed for 16 hrs. Excessive K$_2$CO$_3$ was removed by filtration and the filtrate was concentrated to dryness. The residue was purified by silica gel column (PE/EA=5/1) to give 1-(4-methoxy-benzyl)-1H-pyrazole-4-carboxylic acid ethyl ester (9.5 g, yield: >100%) as a colorless oil.

Step 2: To a solution of 1-(4-methoxy-benzyl)-1H-pyrazole-4-carboxylic acid ethyl ester (1.0 g, 3.8 mmol) in THF (10 mL) was added LAH (300 mg, 7.7 mmol) portion wise at 0° C. After stirring at room temperature for 2 hrs, H$_2$O (0.3 mL), 15% NaOH (0.3 mL) and H$_2$O (0.9 mL) were then added dropwise at 0° C. The mixture was stirred at room temperature for another 20 min, dried over MgSO$_4$ and filtered. The filtrate was concentrated to give [1-(4-methoxy-benzyl)-1H-pyrazol-4-yl]-methanol (860 mg, yield: >100%) as a white solid.

Step 3: To a solution of [1-(4-methoxy-benzyl)-1H-pyrazol-4-yl]-methanol (860 mg, crude) and Et$_3$N (1.1 mL, 7.6 mmol) in DCM (20 mL) was added MsCl (500 mg, 4.3 mmol) dropwise at 0° C. After stirring at room temperature for 20 min, the reaction mixture was diluted with DCM (30 mL) and washed with water (30 mL). The DCM solution was dried over Na$_2$SO$_4$ and concentrated. The residue was dissolved in DMF (10 mL) and potassium phthalimide (870 mg, 4.7 mmol) was added. After stirring at 80° C. for 2 hrs, the reaction mixture was poured to water (50 mL) and extracted with EA (50 mL×3). The combined organic layer was washed with brine (40 mL×3), dried over Na$_2$SO$_4$ and concentrated. The residue was purified by silica gel column (PE/EA=2/1) to give 2-[1-(4-methoxy-benzyl)-1H-pyrazol-4-ylmethyl]-isoindole-1,3-dione (880 mg, yield: 64%) as a white solid.

Step 4: To a solution of 2-[1-(4-methoxy-benzyl)-1H-pyrazol-4-ylmethyl]-isoindole-1,3-dione (880 mg, 2.5 mmol) in EtOH (45 mL) was added hydrazine hydrate (98%, 260 mg, 5.1 mmol). After stirring at 80° C. for 2 hrs, the precipitation was removed by filtration and the filtrate was concentrated to dryness. The residue was purified by silica gel column (DCM/MeOH/NH$_3$.H$_2$O=10/1/0.03) to give C-[1-(4-methoxy-benzyl)-1H-pyrazol-4-yl]-methylamine (250 mg, yield: 45%) as a yellow oil. $^1$H NMR (300 MHz, CDCl$_3$): δ=7.47 (s, 1H), 7.28 (s, 1H), 7.20 (d, J=8.7 Hz, 2H), 6.88 (dd, J=6.6, 2.1 Hz, 2H), 5.21 (s, 2H), 3.80 (s, 3H), 3.75 (s, 2H).

Step 5: To a solution of C-[1-(4-methoxy-benzyl)-1H-pyrazol-4-yl]-methylamine (288 mg, 1.3 mmoL) and Et$_3$N (0.4 ml, 2.8 mmoL) in MeCN (10 mL) was added (4-nitro-phenyl)-carbamic acid phenyl ester (350 mg, 1.3 mmoL) at 0° C. Then the mixture was stirred at 80° C. for 30 min. The reaction mixture was purified with recrystallization to give 1-[1-(4-methoxy-benzyl)-1H-pyrazol-4-ylmethyl]-3-(4-nitro-phenyl)-urea (380 mg, yield: 74%) as a white solid.

Step 6: A suspension of 1-[1-(4-methoxy-benzyl)-1H-pyrazol-4-ylmethyl]-3-(4-nitro-phenyl)-urea (380 mg, 1 mmoL) and Pd/C (98 mg) in MeOH/DCM (9 mL/9 mL) under H$_2$ atmosphere (balloon) was stirred at room temperature for 2 hrs. The reaction mixture was filtered to remove catalyst and the filtrate was concentrated to give 1-(4-amino-phenyl)-3-[1-(4-methoxy-benzyl)-1H-pyrazol-4-ylmethyl]-urea (crude).

Step 7: To a solution of 1-(4-amino-phenyl)-3-[1-(4-methoxy-benzyl)-1H-pyrazol-4-ylmethyl]-urea (350 mg, 1 mmoL) and Et$_3$N (0.3 mL, 2.1 mmoL) in DMF (4 mL) was added benzenesulfonyl chloride (211 mg, 1.2 mmoL) at 0° C. Then the mixture was stirred at room temperature for 1 hr. The reaction mixture was diluted with H$_2$O (50 mL) and extracted with EA. The organic layers were dried over Na$_2$SO$_4$ and concentrated to dryness in vacuum. The residue was purified by silica flash column (4% MeOH in DCM) to give N-(4-{3-[1-(4-methoxy-benzyl)-1H-pyrazol-4-ylmethyl]-ureido}-phenyl)-benzenesulfonamide (320 mg, yield: 65%) as a white solid. $^1$H NMR (400 MHz, CD$_3$OD): δ=7.70 (d, J=7.6 Hz, 2H), 7.56-7.53 (m, 2H), 7.48-7.44 (m, 3H), 7.20-7.16 (m, 4H), 6.95 (d, J=8.8 Hz, 2H), 6.87 (d, J=8.8 Hz, 2H), 5.19 (s, 2H), 4.2 (s, 2H), 3.76 (s, 3H). MS: m/z 491.9 (M+H$^+$).

Example 344: Synthesis of N-Phenyl-C-[4-(3-pyridin-4-ylmethyl-ureido)-phenyl]-methanesulfonamide

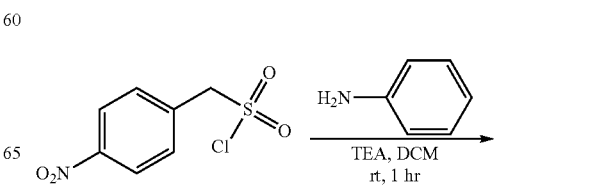

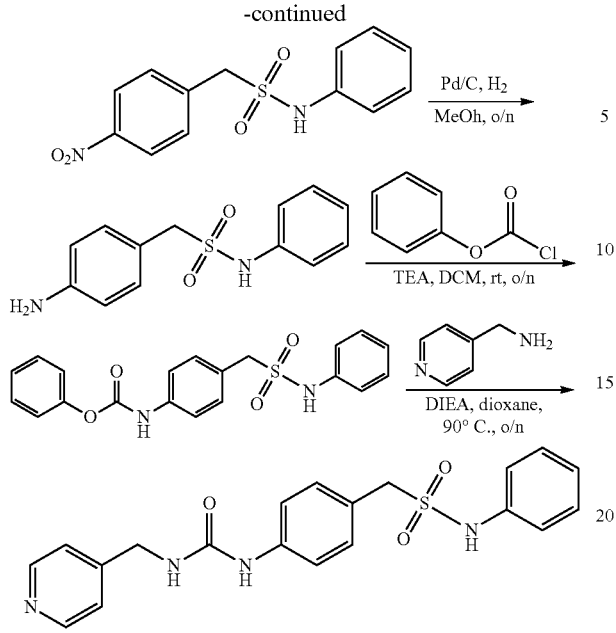

Step 1: To a solution of (4-nitro-phenyl)-methanesulfonyl chloride (300 mg, 1.3 mmol) in DCM (5 mL) was added aniline (145 mg, 1.56 mmol) and TEA (263.1 mg, 2.6 mmol), Then the mixture was stirred at rt for 1 hr. The reaction was monitored by TLC, The mixture was concentrated in vacuum to give residue, which was purified by a silica gel column (PE/EA=3:1) to give c-(4-nitro-phenyl)-n-phenyl-methanesulfonamide (151 mg, yield: 80%) as a yellow solid. $^1$H NMR (400 MHz, DMSO-d6): δ=9.92 (s, 1H), 8.21 (d, J=8.0 Hz, 2H), 7.55 (d, J=8.0 Hz, 2H), 7.32 (t, J=8.0 Hz, 2H), 7.19 (d, J=8.0 Hz, 2H), 7.09 (t, J=8.0 Hz, 1H), 4.68 (s, 2H).

Step 2: To a solution of c-(4-nitro-phenyl)-n-phenyl-methanesulfonamide (150 mg, 0.51 mmol) in MeOH (10 mL), was added Pd/C (10% wet, 54.06 mg). The reaction mixture was stirred at room temperature under H$_2$ (1 atm) for 1 hr. Pd/C was filtered off and the filtrate was concentrated to dryness in vacuum. The residue was purified by a silica gel column (PE/EA=3/1) to give c-(4-amino-phenyl)-N-phenyl-methanesulfonamide (130 mg, yield: 100%) as a yellow solid.

Step 3: To a solution of c-(4-Amino-phenyl)-n-phenyl-methanesulfonamide (130 mg, 0.49 mmol) in DCM 10 mL), was added phenyl chlorformate (153.4 mg. 0.98 mmol) and TEA (99.17 mg, 0.58 mmol). The mixture was stirred at room temperature overnight. Then the reaction was monitored by TLC. The mixture was concentrated in vacuum to give residue, which was purified by a silica gel column (PE/EA=3/1) to afford (4-phenylsulfamoylmethyl-phenyl)-carbamic acid phenyl ester (151 mg. 80%) as a yellow solid.

Step 4: To a solution of (4-phenylsulfamoylmethyl-phenyl)-carbamic acid phenyl ester (151 mg, 0.39 mmol) in dioxane 10 mL), was added pyridin-4-ylmethanamine (84.3 mg, 0.78 mmol) and DIEA (100.62 mg. 0.78 mmol). The mixture was stirred at 90° C. overnight. The reaction was monitored by LCMS. Then the mixture was concentrated in vacuum to give residue. The residue was purified by prep-HPLC to give n-phenyl-C-[4-(3-pyridin-4-ylmethyl-ureido)-phenyl]-methanesulfonamide (30 mg, yield: 15.8%) as a white solid. $^1$H NMR (400 MHz, DMSO-d6): δ=9.74 (s, 1H), 8.76 (s, 1H), 8.50 (d, J=8.0 Hz, 2H), 7.38 (d, J=8.0 Hz, 2H), 7.32 (t, J=8.0 Hz, 2H). 7.28 (d, J=8.0 Hz, 2H), 7.19 (d, J=8.0 Hz, 2H) 7.13-7.05 (m, 3H), 6.75 (t, J=8.0 Hz, 1H), 4.37-4.30 (m, 4H). MS: m/z 383.0 (M+H$^+$). MS: m/z 397.9 (M+H$^+$).

Example 345: Synthesis of N-Methyl-N-phenyl-C-[4-(3-pyridin-4-ylmethyl-ureido)-phenyl]-methanesulfonamide

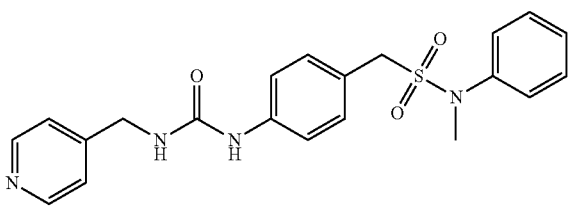 [SMILES: CN(c1ccccc1)S(=O)(=O)Cc1ccc(NC(=O)NCc2ccncc2)cc1]

The title compound was prepared as described in example n-methyl-n-phenyl-C-[4-(3-pyridin-4-ylmethyl-ureido)-phenyl]-methanesulfonamide. $^1$H NMR (400 MHz, DMSO-d6): δ=8.77 (s, 1H), 8.50 (d, J=8.0 Hz, 2H), 7.43-7.33 (m, 4H), 7.32-7.20 (m, 7H), 6.76 (t, J=8.0 Hz, 1H), 4.40 (s, 2H), 4.33 (d, J=8.0 Hz, 2H), 3.18 (s, 3H). MS: m/z 410.9 (M+H$^+$).

Example 346: Synthesis of Ethyl 4-(3-((1,2,3,4-tetrahydroquinolin-4-yl)methyl)ureido)benzoate

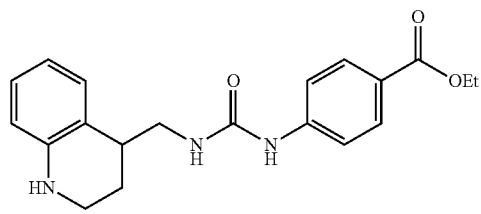 [SMILES: CCOC(=O)c1ccc(NC(=O)NCC2CCNc3ccccc32)cc1]

The title compound was prepared as described in example 4-(3 ethyl 4-(3-(pyridin-2-ylmethyl)ureido)benzoate. $^1$H NMR (400 MHz, DMSO-d$_6$): δ=8.97 (brs, 1H), 7.83 (d, J=8.8 Hz, 2H), 7.52 (d, J=8.8 Hz, 2H), 6.96 (d, J=7.6 Hz, 1H), 6.87 (t, J=8.0 Hz, 1H), 6.50-6.39 (m, 3H), 5.72 (s, 1H), 4.26 (q, J=7.2 Hz, 2H), 3.32-3.09 (m, 4H), 2.88-2.79 (m, 1H), 1.84-1.65 (m, 2H), 1.30 (t, J=7.2 Hz, 3H). MS: m/z 354.0 (M+H$^+$).

Example 347: Synthesis of Ethyl 4-(3-(quinolin-4-ylmethyl)ureido)benzoate

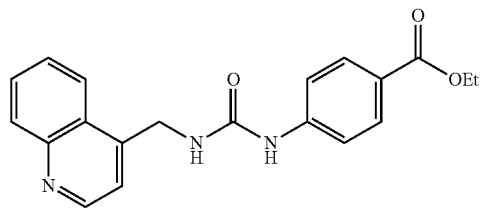 [SMILES: CCOC(=O)c1ccc(NC(=O)NCc2ccnc3ccccc23)cc1]

The title compound was prepared as described in example ethyl 4-(3-(pyridin-2-ylmethyl)ureido)benzoate. $^1$H NMR (400 MHz, DMSO-d$_6$): δ=9.21 (brs, 1H), 8.87 (d, J=4.4 Hz, 1H), 8.21 (d, J=8.0 Hz, 1H), 8.06 (d, J=8.0 Hz, 1H), 7.85 (d, J=8.8 Hz, 2H), 7.79 (t, J=7.2 Hz, 1H), 7.67 (t, J=7.2 Hz, 1H), 7.56 (d, J=8.4 Hz, 2H), 7.45 (d, J=4.0 Hz, 1H), 6.99 (d, J=6.0 Hz, 1H), 4.85 (d, J=5.6 Hz, 2H), 4.26 (q, J=6.8 Hz, 2H), 1.30 (t, J=7.2 Hz, 3H). MS: m/z 350.0 (M+H$^+$).

Example 348: Synthesis of Ethyl 4-(3-(isoquinolin-5-yl)ureido)benzoate

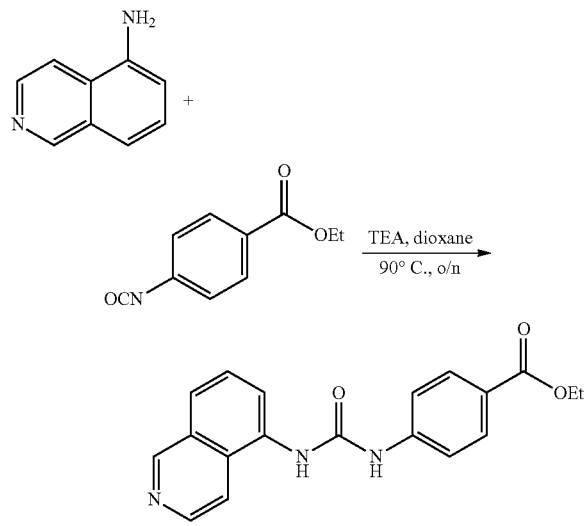

To a solution of 4-isocyanato-benzoic acid ethyl ester (100 mg, 0.523 mmol) in dioxane (20 mL) was added isoquinolin-5-ylamine (90.5 mg, 0.628 mmol), followed by TEA (158 mg, 1.57 mmol). The resulting mixture was stirred at 90° C. overnight. The reaction was monitored by LC-MS. Then the mixture was concentrated in vacuum to give a residue, which was purified by prep-TLC (DCM/MeOH=20/1) to afford ethyl 4-(3-(isoquinolin-5-yl)ureido)benzoate (167.2 mg, yield: 95%) as a brown solid. $^1$H NMR (400 MHz, DMSO-d$_6$): δ=9.49 (brs, 1H), 9.34 (s, 1H), 9.03 (s, 1H), 8.61 (d, J=6.0 Hz, 1H), 8.29 (d, J=7.6 Hz, 1H), 7.98 (d, J=5.6 Hz, 1H), 7.93 (d, J=8.4 Hz, 2H), 7.87 (d, J=8.4 Hz, 1H), 7.71-7.62 (m, 3H), 4.29 (q, J=7.2 Hz, 2H), 1.32 (t, J=7.2 Hz, 3H). MS: m/z 336.0 (M+H$^+$).

Example 349: Synthesis of Ethyl 4-(3-(1H-pyrrolo[2,3-c]pyridin-3-yl)ureido)benzoate

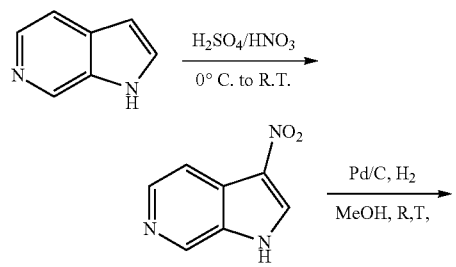

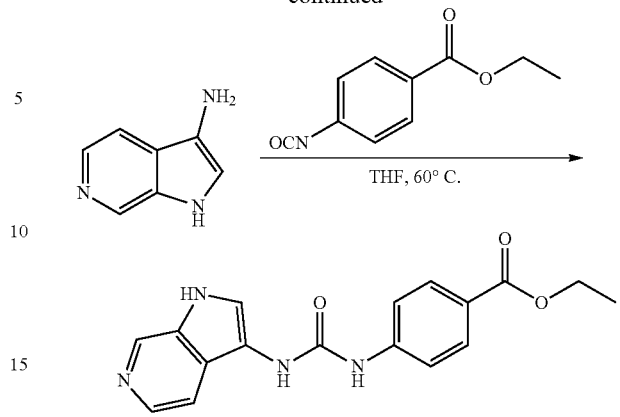

Step 1: To a solution of 1H-pyrrolo[2,3-c]pyridine (1 g, 8.47 mmol) in H$_2$SO$_4$ (5 mL) was added 69% HNO$_3$ (533 mg, 8.47 mmol) at 0° C. After stirred at 0° C. for 2 hrs, the reaction mixture was allowed to warm to room temperature and stirred overnight. The mixture was then poured into H$_2$O (100 mL) and basified by NaOH powder to pH>7. Then the mixture was extracted by EA (100 mL×3), dried over anhydrous Na$_2$SO$_4$, and evaporated in vacuum to afford 3-nitro-1H-pyrrolo[2,3-c]pyridine (690 mg, 50%) as a yellow solid. $^1$H NMR (400 MHz, DMSO-d$_6$): δ=8.94 (s, 1H), 8.85 (s, 1H), 8.44 (d, J=5.2 Hz, 1H), 8.02 (dd, J=5.6, 1.2 Hz, 1H). MS: m/z 164.0 (M+H)$^+$.

Step 2: To a solution of 3-nitro-1H-pyrrolo[2,3-c]pyridine (200 mg, 1.23 mmol) in MeOH (20 mL) was added 10% Pd/C (130 mg, 0.12 mmol). After stirred at balloon hydrogen atmosphere for 2 hrs, the mixture was filtered. The filtrate was evaporated in vacuum to give 1H-pyrrolo[2,3-c]pyridin-3-amineas a crude product which was used for next step without further purification.

Step 3: To a solution of 1H-pyrrolo[2,3-c]pyridin-3-amine (crude, 1.23 mmol) in THF (20 mL) was added 4-isocyanato-benzoic acid ethyl ester (235 mg, 1.23 mmol) and the mixture was heated to 60° C. for 3 hrs. Then the mixture was evaporated in vacuum to remove THF. The residue was partitioned in a mixture of H$_2$O (50 mL) and EA (50 mL). The aqueous phase was then extracted by EA (50 mL×2). Organic phase was combined, dried over anhydrous Na$_2$SO$_4$, and evaporated in vacuum. The residue was purified by pre-HPLC to afford ethyl 4-(3-(1H-pyrrolo[2,3-c]pyridin-3-yl)ureido)benzoate (120 mg, 30.1%) as a white solid. $^1$H NMR (400 MHz, DMSO-d$_6$): δ=11.36 (s, 1H), 9.10 (s, 1H), 8.75-8.72 (m, 2H), 8.11 (d, J=5.2 Hz, 1H), 7.90 (d, J=8.8 Hz, 2H), 7.76 (d, J=2.0 Hz, 1H), 7.62 (d, J=8.4 Hz, 2H), 7.51 (d, J=5.2 Hz, 1H), 4.28 (q, J=7.2 Hz, 2H), 1.32 (t, J=7.2 Hz, 3H). MS: m/z 324.9 (M+H)$^+$.

Example 350: Synthesis of Ethyl 4-(3-(1-methyl-1H-pyrrolo[2,3-c]pyridin-3-yl)ureido)benzoate

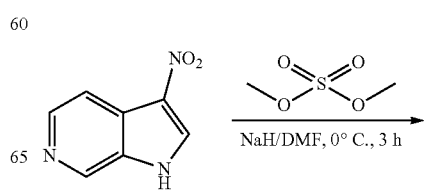

-continued

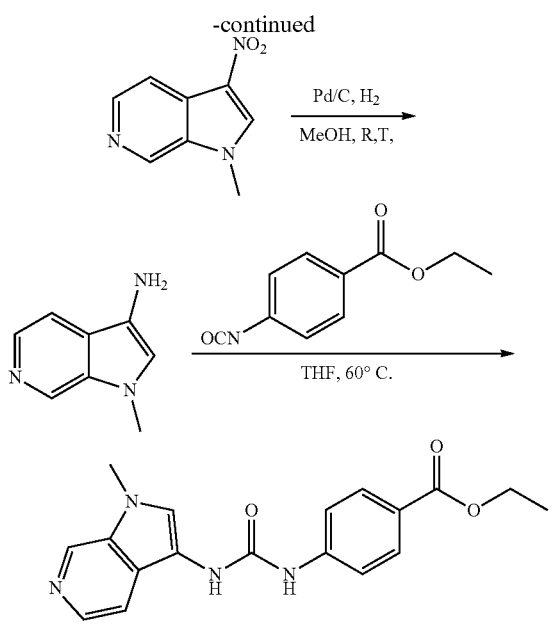

Example 351: Synthesis of Ethyl 4-(3-(6-methyl-6H-pyrrolo[2,3-c]pyridin-3-yl)ureido)benzoate

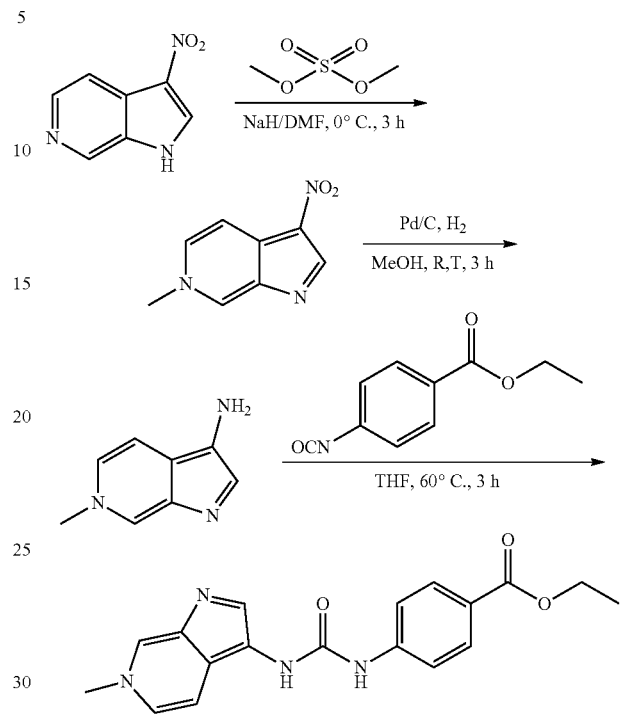

Step 1: To a solution of 3-nitro-1H-pyrrolo[2,3-c]pyridine (250 mg, 1.53 mmol in DMF (5 mL) was added NaH (60% dispersion in mineral oil, 61 mg, 1.53 mmol). After stirred at 0° C. for 10 min, dimethylsulfate (193 mg, 1.53 mmol) was added dropwise. After stirred at 0° C. for 3 hrs, the mixture was partitioned in a mixture of ethyl acetate (50 mL) and $H_2O$ (50 mL) and the aqueous phase was extracted by ethyl acetate (50 mL×2). Organic phase was combined, dried over anhydrous $Na_2SO_4$, and evaporated in vacuum. The residue was purified by flash column (ACN in water: 5% to 50%) to afford 1-methyl-3-nitro-1H-pyrrolo[2,3-c]pyridine (30 mg, 11%) as a white solid. $^1H$ NMR (400 MHz, $CD_3OD$): δ=8.94 (d, J=0.8 Hz, 1H), 8.61 (s, 1H), 8.43 (d, J=5.6 Hz, 1H), 8.12 (dd, J=5.2, 0.8 Hz, 1H), 4.06 (s, 3H). MS: m/z 178.0 $(M+H)^+$.

Step 2: To a solution of 1-methyl-3-nitro-1H-pyrrolo[2,3-c]pyridine (25 mg, 0.14 mmol) in MeOH (10 mL) was added 10% Pd/C (15 mg, 0.014 mmol). After stirred at balloon hydrogen atmosphere for 2 hrs, the mixture was filtered. The filtrate was evaporated in vacuum to give 1-methyl-1H-pyrrolo[2,3-c]pyridin-3-ylamine as a crude product which was used for next step without further purification.

Step 3: To a solution of 1-methyl-1H-pyrrolo[2,3-c]pyridin-3-ylamine (crude, 0.14 mmol) in THF (10 mL) was added 4-isocyanato-benzoic acid ethyl ester (26.8 mg, 0.14 mmol) and the mixture was stirred at room temperature overnight. Then the mixture was evaporated in vacuum. The residue was purified by pre-TLC (DCM/MeOH=10/1) to afford ethyl 4-(3-(1-methyl-1H-pyrrolo[2,3-c]pyridin-3-yl)ureido)benzoate (8 mg, 17%) as a yellow solid. $^1H$ NMR (400 MHz, $CD_3OD$): δ=9.02 (s, 1H), 8.16 (d, J=6.0 Hz, 1H), 8.12 (s, 1H), 7.96 (d, J=8.8 Hz, 2H), 7.90 (d, J=6.0 Hz, 1H), 7.60 (d, J=8.4 Hz, 2H), 4.35 (q, J=7.2 Hz, 2H), 4.04 (s, 3H), 1.38 (t, J=7.2 Hz, 3H). MS: m/z 339.0 $(M+H)^+$.

Step 1: To a solution of 3-nitro-1H-pyrrolo[2,3-c]pyridine (250 mg, 1.53 mmol) in DMF (5 mL) was added NaH (60% dispersion in mineral oil, 61 mg, 1.53 mmol). After stirred at 0° C. for 10 min, the mixture was added dimethylsulfate (193 mg, 1.53 mmol) dropwise. After stirred at 0° C. for 3 hrs, the mixture was partitioned in a mixture of $H_2O$ (50 mL) and EA (50 mL). The aqueous phase was then extracted by EA (50 mL×2). Organic phase was combined, dried over anhydrous $Na_2SO_4$, and evaporated in vacuum. The residue was washed with MeOH (5 mL) to afford 6-methyl-3-nitro-6H-pyrrolo[2,3-c]pyridine (70 mg, 26%) as a yellow solid. $^1H$ NMR (400 MHz, DMSO-$d_6$): δ=9.09 (s, 1H), 8.65 (s, 1H), 8.25 (dd, J=6.8, 1.2 Hz, 1H), 8.14 (d, J=6.8 Hz, 1H), 4.26 (s, 3H). MS: m/z 178.0 $(M+H)^+$.

Step 2: To a solution of 6-methyl-3-nitro-6H-pyrrolo[2,3-c]pyridine (70 mg, 0.4 mmol) in MeOH (15 mL) was added 10% Pd/C (42 mg, 0.04 mmol). After stirred at balloon hydrogen atmosphere for 3 hrs, the mixture was filtered. The filtrate was evaporated in vacuum to give 6-methyl-6H-pyrrolo[2,3-c]pyridin-3-ylamine as a crude product which was used for next step without further purification.

Step 3: To a solution of 6-methyl-6H-pyrrolo[2,3-c]pyridin-3-ylamine (crude, 0.4 mmol) in THF (15 mL) was added 4-isocyanato-benzoic acid ethyl ester (76.5 mg, 0.4 mmol) and the mixture was stirred at 60° C. for 3 hrs. Then the mixture was evaporated in vacuum to remove THF. The residue was partitioned in a mixture of $H_2O$ (30 mL) and EA (50 mL). The aqueous phase was then extracted by EA (50 mL×2). Organic phase was combined, dried over anhydrous $Na_2SO_4$, and evaporated in vacuum. The residue was purified by pre-HPLC to afford ethyl 4-(3-(6-methyl-6H-pyrrolo[2,3-c]pyridin-3-yl)ureido)benzoate (10 mg, 7.4%) as a yellow solid. $^1H$ NMR (400 MHz, $CD_3OD$): δ=9.08 (s, 1H), 8.38 (s, 1H), 8.19 (d, J=8.0 Hz, 1H), 8.12 (d, J=5.6 Hz, 1H), 7.96 (d, J=8.8 Hz, 2H), 7.62 (d, J=9.2 Hz, 2H), 4.40-4.32 (m, 5H), 1.38 (t, J=7.2 Hz, 3H). MS: m/z 339.0 (M+H)+.

Example 352: Synthesis of Ethyl 4-(furo[3,2-c]pyridine-2-carboxamido)benzoate

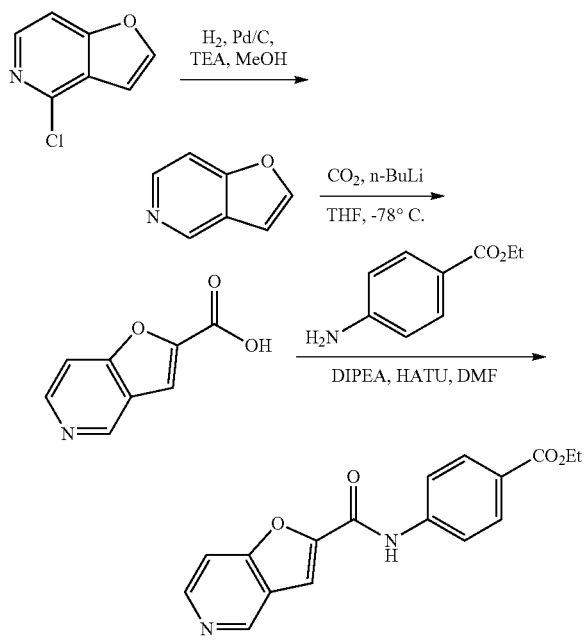

Step 1: To a solution of 4-chloro-furo[3,2-c]pyridine (700 mg, 39.65 mmoL), Pd/C (158 mg) and TEA (1 mL, 6.97 mmoL) in MeOH (16 mL) under H₂ atmosphere (balloon) at room temperature. Then the mixture was stirred at room temperature for 2 hrs. The reaction mixture was filtered to remove catalyst and the filtrate was concentrated to dryness in vacuum and the residue was purified by silica gel column (PE/EA=6/1) to give furo[3,2-c]pyridine (320 mg, yield: 59%) as a white oil. ¹H NMR (400 MHz, DMSO-d₆): δ=9.00 (s, 1H), 8.48 (d, J=6 Hz, 1H), 8.12 (d, J=2.4 Hz, 1H), 7.70 (d, J=6 Hz, 1H), 7.13 (dd, J=2.0, 0.8 Hz, 1H).

Step 2: To a solution of furo[3,2-c]pyridine (300 mg, 2.5 mmoL) in THF was added n-BuLi (1.5 mL, 3.75 mmoL) dropwisely at −70° C. and stirred at −70° C. for 1 hr. Then dry CO₂ is passed through the reaction mixture and the temperature is allowed to rise gradually in 2 hrs. The mixture was diluted with H₂O/LiOH (15 mL/100 mg) and extracted by EA (30 mL×1). Then the H₂O layer is acidified to pH 5 with HCl. Then the mixture was filtered to give furo[3,2-c]pyridine-2-carboxylic acid (172 mg, yield: 42%) as a white solid. ¹H NMR (400 MHz, DMSO-d₆): δ=13.83 (brs, 1H), 9.10 (s, 1H), 8.61 (d, J=5.6 Hz, 1H), 7.81-7.79 (m, 2H).

Step 3: To a solution of furo[3,2-c]pyridine-2-carboxylic acid (60 mg, 0.37 mmoL), 4-amino-benzoic acid ethyl ester (73 mg, 0.44 mmoL) and DIPEA (0.3 mL, 1.7 mmoL) in DMF (4 mL) was added HATU (210 mg, 0.55 mmoL) at room temperature. Then the mixture was stirred at room temperature for 3 hrs.

The reaction mixture was poured into H₂O (30 mL) and extracted with EA (20 mL×4). The combined EA extracts was washed with H₂O (60 mL), brine (60 mL), dried over Na₂SO₄ and concentrated to dryness in vacuum. The residue was purified by silica gel column (PE/EA=3/5) to give ethyl 4-(furo[3,2-c]pyridine-2-carboxamido)benzoate (50 mg, yield: 44%) as a white solid. ¹H NMR (300 MHz, CDCl₃): δ=9.10 (s, 1H), 8.68 (d, J=5.7 Hz, 1H), 8.47 (s, 1H), 8.12 (d, J=8.7 Hz, 2H), 7.82 (d, J=8.7 Hz, 2H), 7.72 (s, 1H), 7.55 (d, J=6.0 Hz, 1H), 4.39 (q, J=6.9 Hz, 2H), 1.42 (t, J=6.9 Hz, 3H). MS: m/z 311.1 (M+H+).

Example 353: Synthesis of Furo[3,2-c]pyridine-2-carboxylic acid [4-(3,4-dihydro-1H-isoquinoline-2-sulfonyl)-phenyl]-amide

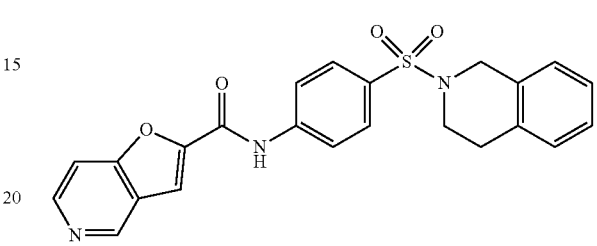

The title compound was prepared using general procedure of 4-[(furo[3,2-c]pyridine-2-carbonyl)-amino]-benzoic acid ethyl ester. ¹H NMR (400 MHz, DMSO-d₆): δ=11.03 (s, 1H), 9.17 (s, 1H), 8.64 (d, J=6.0 Hz, 1H), 8.08 (d, J=8.4 Hz, 2H), 7.97 (s, 1H), 7.87-7.82 (m, 3H), 7.16-7.13 (m, 4H), 4.20 (s, 2H), 3.32 (overlap, 2H), 2.87 (t, J=5.2 Hz, 2H). MS: m/z 433.9 (M+H+).

Example 354: Synthesis of Ethyl 6-(3-(pyridin-4-ylmethyl)ureido)nicotinate

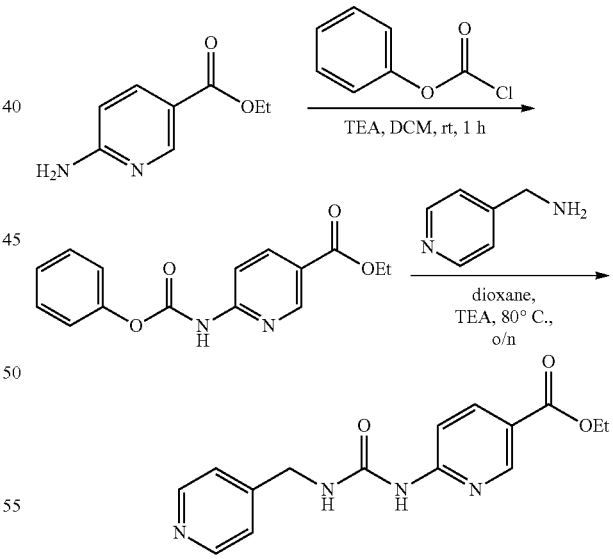

Step 1: To a solution of 6-amino-nicotinic acid ethylester (200 mg, 1.20 mmoL) in DCM (40 mL) was added phenyl chloroformate (227 mg, 1.45 mmoL) and TEA (366 mg, 3.62 mmoL). The mixture was stirred at room temperature for 1 hr. The reaction was monitored by TLC. Then the reaction mixture was concentrated in vacuum to give a residue, which was purified by prep-TLC (PE/EA=10/1) to afford 6-phenoxycarbonylamino-nicotinic acid ethylester (280 mg, yield: 81%) as a white solid.

Step 2: To a solution of 6-phenoxycarbonylamino-nicotinic acid ethyl ester (280 mg, 0.98 mmol) in dioxane (40 mL) was added 4-(aminomethyl)pyridine (158 mg, 1.46 mmol) and TEA (297 mg, 2.92 mmol). The mixture was stirred at 80° C. overnight. The reaction was monitored by TLC. Then the reaction mixture was concentrated in vacuum to give a residue, which was purified by prep-TLC (DCM/MeOH=20/1) to afford 6-3-pyridin-4-ylmethyi-ureido-nicotinic acid ethyl ester (215 mg, yield: 73%) as a white solid. $^1$H NMR (400 MHz, DMSO-d6): δ=9.88 (brs, 1H), 8.76 (brs, 1H), 8.52-8.49 (m, 3H), 8.17 (dd, J=8.8, 2.4 Hz, 1H), 7.56 (d, J=8.8 Hz, 1H), 7.30 (d, J=6.0 Hz, 2H), 4.45 (d, J=6.0 Hz, 2H), 4.25 (q, J=7.2 Hz, 2H), 1.30 (t, J=7.2 Hz, 3H). MS: m/z 301.1 (M+H$^+$).

Example 355: Synthesis of Ethyl 5-(3-(pyridin-4-ylmethyl)ureido)picolinate

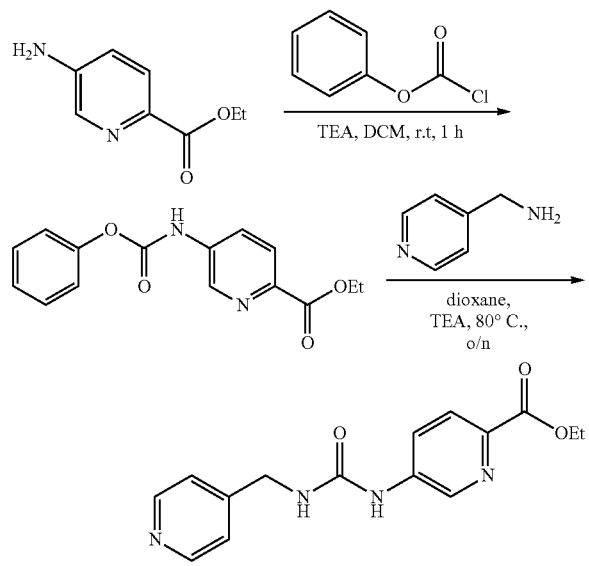

Step 1: To a solution of 5-amino-pyridine-2-carboxylic acid ethyl ester (220 mg, 1.33 PGP mmol) in DCM (40 mL) was added phenyl chloroformate (251 mg, 1.60 mmol) and TEA (395 mg, 3.90 mol). The mixture was stirred at room temperature for 1 hr. The reaction was monitored by TLC. Then the reaction mixture was concentrated in vacuum to give a residue, which was purified by prep-TLC (PE/EA=10/1) to afford 5-phenoxycarbonylamino-pyridine-2-carboxylic acid ethyl ester (150 mg, yield: 40%) as a white solid.

Step 2: To a solution of 5-phenoxycarbonylamino-pyridine-2-carboxylic acid ethyl ester (150 mg, 0.52 mmol) in dioxane (40 mL) was added 4-(aminomethyl) pyridine (85 mg, 0.79 mmol) and TEA (159 mg, 1.57 mmol). The mixture was stirred at 80° C. overnight. The reaction was monitored by TLC. Then the reaction mixture was concentrated in vacuum to give a residue, which was purified by prep-TLC (DCM/MeOH=20/1) to afford ethyl 5-(3-(pyridin-4-ylmethyl)ureido)picolinate (53 mg, yield: 34%) as a white solid. $^1$H NMR (400 MHz, DMSO-d$_6$): δ=9.46 (brs, 1H), 8.64 (d, J=2.4 Hz, 1H), 8.52 (d, J=5.6 Hz, 2H), 8.09 (dd, J=8.8, 2.0 Hz, 1H), 7.97 (d, J=8.4 Hz, 1H), 7.31 (d, J=5.6 Hz, 2H), 7.09 (brs, 1H), 4.36 (d, J=5.6 Hz, 2H), 4.28 (q, J=7.2 Hz, 2H). 1.31 (t, J=7.2 Hz, 3H). MS: m/z 301.1 (M+H$^+$).

Example 356: Synthesis of 6-(3-Pyridin-4-ylmethyl-ureido)-nicotinamide

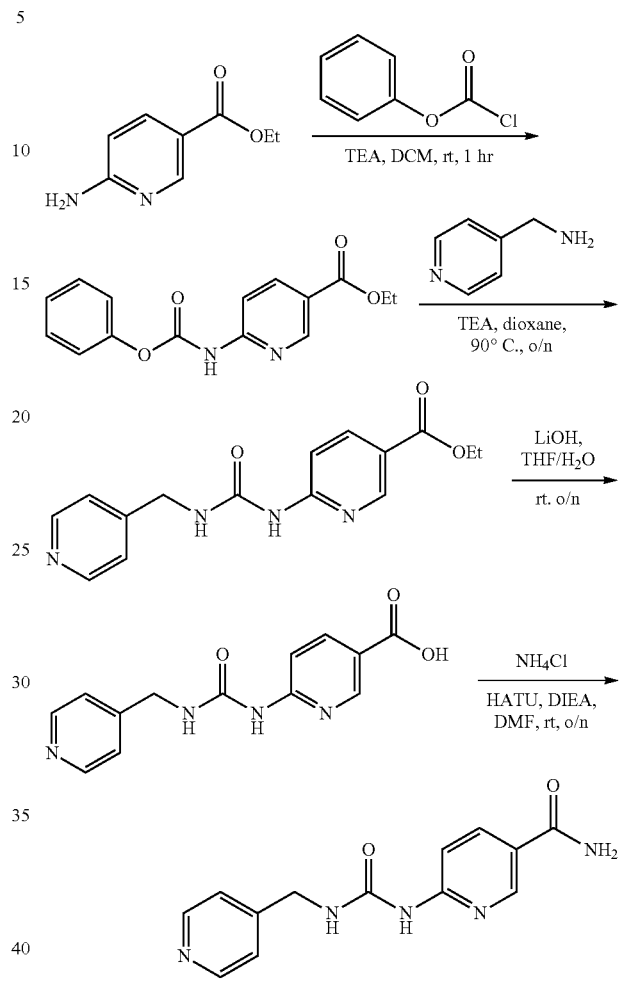

Step 1: To a solution of 6-amino-nicotinic acid ethyl ester (200 mg, 1.20 mmol) in DCM (20 mL) was added phenyl chloroformate (226 mg, 1.44 mmol), followed by TEA (365 mg, 3.60 mmol). The resulting mixture was stirred at room temperature for 1 hr. The reaction was monitored by TLC. Then the mixture was concentrated in vacuum to give a residue, which was purified by a silica gel column eluting with DCM to afford 6-phenoxycarbonylamino-nicotinic acid ethyl ester (322 mg, yield: 94%) as a white solid.

Step 2: To a solution of 6-phenoxycarbonylamino-nicotinic acid ethyl ester (322 mg, 1.12 mmol) in dioxane (40 mL) was added pyridin-4-ylmethanamine (146 mg, 1.35 mmol), followed by TEA (342 mg, 3.36 mmol). The resulting mixture was stirred at 90° C. overnight. The reaction was monitored by LC-MS. Then the mixture was concentrated in vacuum to give a residue, which was purified by a silica gel column (DCM/MeOH=50/1 as eluent) to afford 6-(3-pyridin-4-ylmethyl-ureido)-nicotinic acid ethyl ester (324 mg, yield: 96%) as a white solid.

Step 3: To a solution of 6-(3-pyridin-4-ylmethyl-ureido)-nicotinic acid ethyl ester (324 g, 1.08 mmol) in THF/H$_2$O (20 mL+5 mL) was added LiOH (136 mg, 3.24 mmol). The resulting mixture was stirred at room temperature overnight. The reaction was monitored by TLC. Then THF was removed in vacuum to give an aqueous residue, which was acidified to pH=45 with conc. HCl. The solid precipitated from the mixture was filtered. The cake was washed with H₂O (20 mL×2) and air dried to afford 6-(3-pyridin-4-ylmethyl-ureido)-nicotinic acid (480 g, crude) as a yellow solid.

Step 4: To a solution of 6-(3-pyridin-4-ylmethyl-ureido)-nicotinic acid (100 mg, 0.367 mmol) in DMF (10 mL) was added HATU (418 mg, 1.10 mmol) and DIEA (142 mg, 1.10 mmol). The mixture was stirred at room temperature for 30 mins. Then NH₄Cl (84 mg, 1.84 mmol) was added into the reaction mixture. The resulting reaction mixture was stirred at room temperature overnight. The reaction was monitored by LC-MS. Then the mixture was concentrated in vacuum to give a residue, which was purified by prep-HPLC with NH₄OH as additive to afford 6-(3-pyridin-4-ylmethyl-ureido)-nicotinamide (53.2 mg, yield: 53%) as a white solid. $^1$H NMR (400 MHz, DMSO-d₆): δ=9.70 (brs, 1H), 69 (d, J=1.2 Hz, 1H), 8.63-8.54 (m, 1H), 8.51 (d, J=4.8 Hz, 2H), 8.12 (dd, J=8.8, 2.0 Hz, 1H), 7.95 (brs, 1H), 7.45 (d, J=8.4 Hz, 1H), 7.39 (brs, 1H), 7.30 (d, J=5.2 Hz, 2H), 4.45 (d, J=6.0 Hz, 2H). MS: m/z 272.0 (M+H⁺).

Example 357: Synthesis of 5-(3-(pyridin-4-ylmethyl)ureido)picolinamide

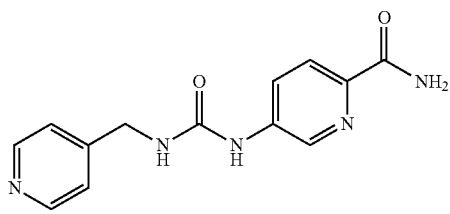 [SMILES: NC(=O)c1ccc(NC(=O)NCc2ccncc2)cn1]

The title compound was prepared as described in example 6-(3-pyridin-4-ylmethyl-ureido)-nicotinamide. $^1$H NMR (400 MHz, CD₃OD): δ=8.63 (s, 1H), 8.46 (d, J=6.0 Hz, 2H), 7.98-8.03 (m, 2H), 7.41 (d, J=6.0 Hz, 2H), 4.48 (s, 2H). MS: m/z 272.0 (M+H⁺).

Example 358: Synthesis of Ethyl 5-(3-(pyridin-4-ylmethyl)ureido)picolinate

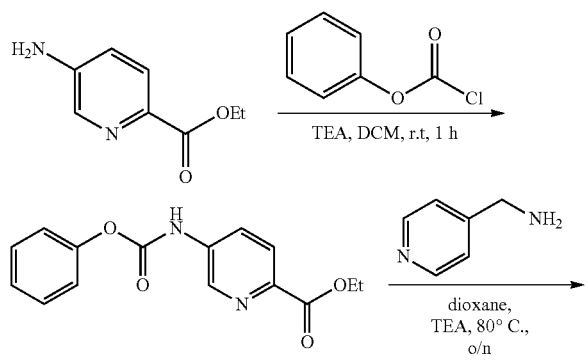

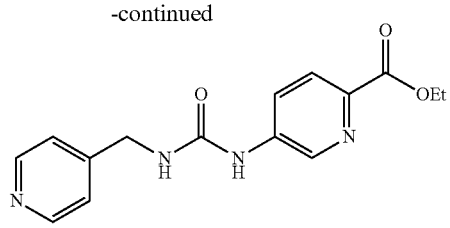

Step 1: To a solution of 5-amino-pyridine-2-carboxylic acid ethyl ester (220 mg, 1.33 mmol) in DCM (40 mL) was added phenyl chloroformate (251 mg, 1.60 mmol) and TEA (395 mg, 3.90 mol). The mixture was stirred at room temperature for 1 hr. The reaction was monitored by TLC. Then the reaction mixture was concentrated in vacuum to give a residue, which was purified by prep-TLC (PE/EA=10/1) to afford 5-phenoxycarbonylamino-pyridine-2-carboxylic acid ethyl ester (150 mg, yield: 40%) as a white solid.

Step 2: To a solution of 5-phenoxycarbonylamino-pyridine-2-carboxylic acid ethyl ester (150 mg, 0.52 mmol) in dioxane (40 mL) was added 4-(aminomethyl) pyridine (85 mg, 0.79 mmol) and TEA (159 mg, 1.57 mmol). The mixture was stirred at 80° C. overnight. The reaction was monitored by TLC. Then the reaction mixture was concentrated in vacuum to give a residue, which was purified by prep-TLC (DCM/MeOH=20/1) to afford ethyl 5-(3-(pyridin-4-ylmethyl)ureido)picolinate (53 mg, yield: 34%) as a white solid. $^1$H NMR (400 MHz, DMSO-d₆): δ=9.46 (brs, 1H), 8.64 (d, J=2.4 Hz, 1H), 8.52 (d, J=5.6 Hz, 2H), 8.09 (dd, J=8.8, 2.0 Hz, 1H), 7.97 (d, J=8.4 Hz, 1H), 7.31 (d, J=5.6 Hz, 2H), 7.09 (brs, 1H), 4.36 (d, J=5.6 Hz, 2H), 4.28 (q, J=7.2 Hz, 2H). 1.31 (t, J=7.2 Hz, 3H). MS: m/z 301.1 (M+H⁺).

Example 359: Synthesis of 6-(3-Pyridin-4-ylmethyl-ureido)-nicotinamide

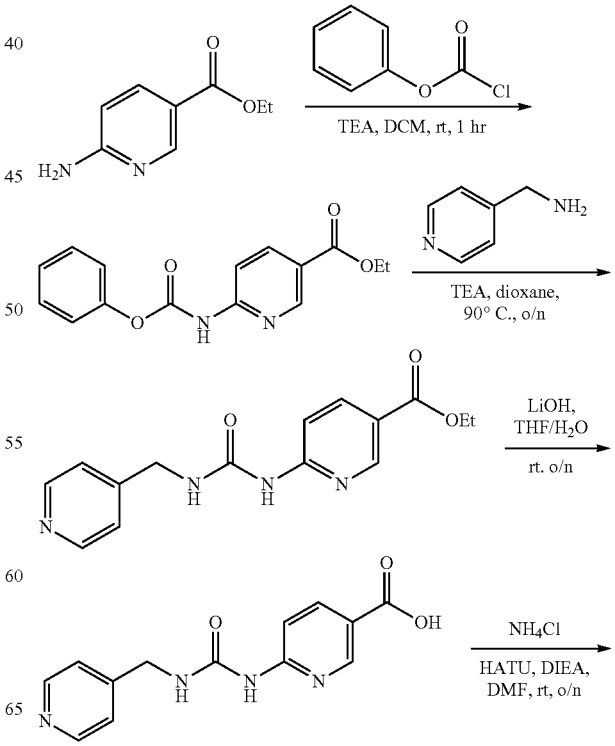

-continued

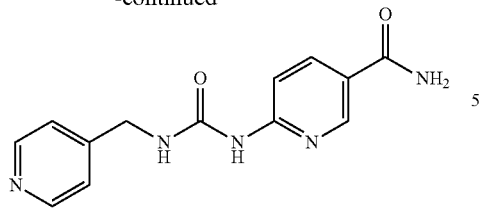

Step 1: To a solution of 6-amino-nicotinic acid ethyl ester (200 mg, 1.20 mmol) in DCM (20 mL) was added phenyl chloroformate (226 mg, 1.44 mmol), followed by TEA (365 mg, 3.60 mmol). The resulting mixture was stirred at room temperature for 1 hr. The reaction was monitored by TLC. Then the mixture was concentrated in vacuum to give a residue, which was purified by a silica gel column eluting with DCM to afford 6-phenoxycarbonylamino-nicotinic acid ethyl ester (322 mg, yield: 94%) as a white solid.

Step 2: To a solution of 6-phenoxycarbonylamino-nicotinic acid ethyl ester (322 mg, 1.12 mmol) in dioxane (40 mL) was added pyridin-4-ylmethanamine (146 mg, 1.35 mmol), followed by TEA (342 mg, 3.36 mmol). The resulting mixture was stirred at 90° C. overnight. The reaction was monitored by LC-MS. Then the mixture was concentrated in vacuum to give a residue, which was purified by a silica gel column (DCM/MeOH=50/1 as eluent) to afford 6-(3-pyridin-4-ylmethyl-ureido)-nicotinic acid ethyl ester (324 mg, yield: 96%) as a white solid.

Step 3: To a solution of 6-(3-pyridin-4-ylmethyl-ureido)-nicotinic acid ethyl ester (324 g, 1.08 mmol) in THF/H$_2$O (20 mL+5 mL) was added LiOH (136 mg, 3.24 mmol). The resulting mixture was stirred at room temperature overnight. The reaction was monitored by TLC. Then THF was removed in vacuum to give an aqueous residue, which was acidified to pH=45 with conc. HCl. The solid precipitated from the mixture was filtered. The cake was washed with H$_2$O (20 mL×2) and air dried to afford 6-(3-pyridin-4-ylmethyl-ureido)-nicotinic acid (480 g, crude) as a yellow solid.

Step 4: To a solution of 6-(3-pyridin-4-ylmethyl-ureido)-nicotinic acid (100 mg, 0.367 mmol) in DMF (10 mL) was added HATU (418 mg, 1.10 mmol) and DIEA (142 mg, 1.10 mmol). The mixture was stirred at room temperature for 30 mins. Then NH$_4$Cl (84 mg, 1.84 mmol) was added into the reaction mixture. The resulting reaction mixture was stirred at room temperature overnight. The reaction was monitored by LC-MS. Then the mixture was concentrated in vacuum to give a residue, which was purified by prep-HPLC with NH$_4$OH as additive to afford 6-(3-pyridin-4-ylmethyl-ureido)-nicotinamide (53.2 mg, yield: 53%) as a white solid. $^1$H NMR (400 MHz, DMSO-d$_6$): δ=9.70 (brs, 1H), 69 (d, J=1.2 Hz, 1H), 8.63-8.54 (m, 1H), 8.51 (d, J=4.8 Hz, 2H), 8.12 (dd, J=8.8, 2.0 Hz, 1H), 7.95 (brs, 1H), 7.45 (d, J=8.4 Hz, 1H), 7.39 (brs, 1H), 7.30 (d, J=5.2 Hz, 2H), 4.45 (d, J=6.0 Hz, 2H). MS: m/z 272.0 (M+H$^+$).

Example 360: Synthesis of 5-(3-(pyridin-4-ylmethyl)ureido)picolinamide

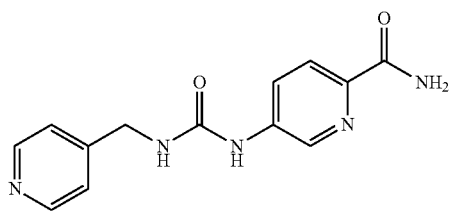 [SMILES: NC(=O)c1ccc(NC(=O)NCc2ccncc2)cn1]

The title compound was prepared as described in example 6-(3-pyridin-4-ylmethyl-ureido)-nicotinamide. $^1$H NMR (400 MHz, CD$_3$OD): δ=8.63 (s, 1H), 8.46 (d, J=6.0 Hz, 2H), 7.98-8.03 (m, 2H), 7.41 (d, J=6.0 Hz, 2H), 4.48 (s, 2H). MS: m/z 272.0 (M+H$^+$).

Example 361: Synthesis of 4-[2-(Pyridin-4-ylamino)-acetylamino]-benzoic acid ethyl ester

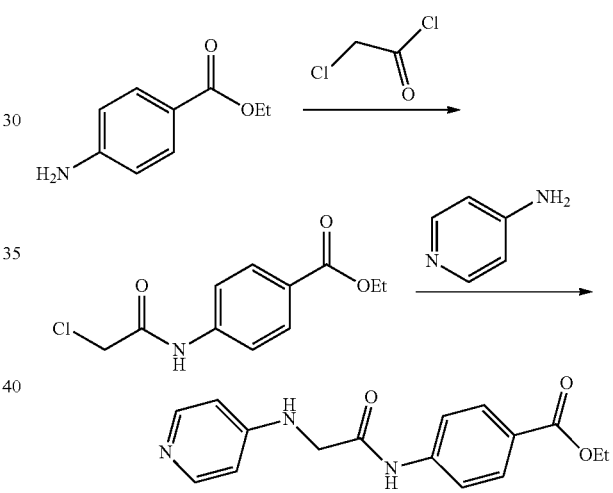

Step1: To a suspension of 4-amino-benzoic acid ethyl ester (200 mg, 1.2 mmol) and K$_2$CO$_3$ (501 mg, 3.6 mmol) in DCM (4 mL) at 0° C. was added 2-chloroacetyl chloride (164 mg, 1.45 mmol). The mixture was stirred at 40° C. overnight. The reactant was diluted with water (10 mL) and extracted with DCM (10 mL×3). The combined organic layers were concentrated and purified by prep-TLC to give 4-(2-chloro-acetylamino)-benzoic acid ethyl ester (200 mg, yield: 68.5%) as a white solid. $^1$H NMR (400 MHz, DMSO-d6): δ=10.66 (s, 1H), 7.94 (d, J=8.8 Hz, 2H), 7.73 (d, J=8.8 Hz, 2H), 4.40-4.14 (m, 4H), 1.31 (t, J=7.2 Hz, 3H).

Step 2: A solution of 4-(2-chloro-acetylamino)-benzoic acid ethyl ester (120 mg, 0.497 mmol), pyridin-4-ylamine (51.4 mg, 0.547 mmol) and DIEA (128.4 mg, 0.995 mmol) in DMF (4 mL) was stirred at 100° C. overnight. The mixture was evaporated and the residue was diluted with water. The resulting solid was filtered and purified by prep-TLC to give 4-[2-(pyridin-4-ylamino)-acetylamino]-benzoic acid ethyl ester (44 mg, yield: 29.6%) as a white solid. $^1$H NMR (400 MHz, DMSO-d6): δ=11.23 (s, 1H), 8.32 (s, 2H), 8.15 (d, J=7.3 Hz, 2H), 7.94 (d, J=8.8 Hz, 2H), 7.77 (d, J=8.8 Hz, 2H), 6.87 (d, J=7.2 Hz, 2H), 5.20 (s, 2H), 4.29 (q, J=7.1 Hz, 2H), 1.31 (t, J=7.2 Hz, 3H). MS: m/z 300.1 (M+H⁺).

Example 362: Synthesis of 4-[(Pyridin-4-ylcarbamoylmethyl)-amino]-benzoic acid ethyl ester

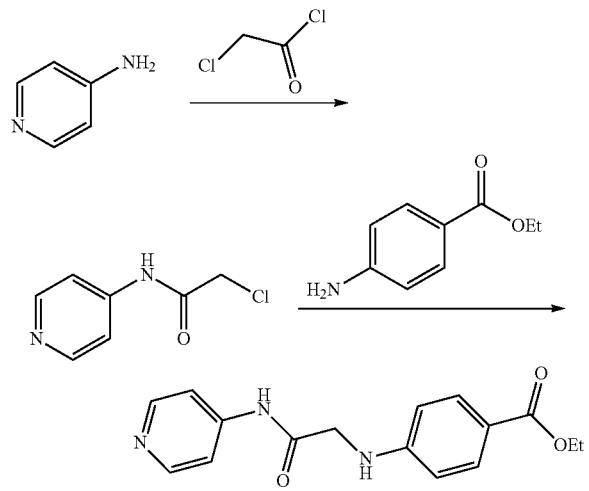

Step 1: To a solution of pyridin-4-ylamine (200 mg, 2.12 mmol) and DIEA (823 mg 0.6.38 mmol) in THF (3 mL) was added 2-chloroacetyl chloride (288 mg. 2.55 mmol), then the mixture was stirred at 30° C. for 2 hrs. The mixture was concentrated and the residue was purified by prep-TLC (DCM/MeOH=10/1) to give 4-amino-benzoic acid ethyl ester (200 mg, yield: 55.3%) as a white solid. ¹H NMR (400 MHz, DMSO-d6): δ=11.06 (s, 1H), 8.46 (dd, J=4.8, 1.4 Hz, 2H), 7.62 (dd, J=4.8, 1.4 Hz, 2H), 4.36 (s, 2H).

Step 2: A solution of 2-chloro-N-(pyridin-4-yl)acetamide (100 mg, 0.588 mmol), 4-amino-benzoic acid ethyl ester (106.7 mmol, 0.65 mmol) and DIEA (152 mg, 1.176 mmol) in DMF was stirred at 90° C. overnight. The mixture was filtered and the filtrate was purified by prep-HPLC to give 4-[(pyridin-4-ylcarbamoylmethyl)-amino]-benzoic acid ethyl ester (4 mg, 2.3%) as a yellow solid. ¹H NMR (400 MHz, CD₃OD): δ=8.05 (d, J=6.9 Hz, 2H), 7.98 (d, J=8.4 Hz, 2H), 7.71 (d, J=8.4 Hz, 2H), 6.87 (d, J=6.8 Hz, 2H), 5.12 (s, 2H), 4.34 (q, J=7.2 Hz, 2H), 1.37 (t, J=7.2 Hz, 3H). MS: m/z 300.0 (M+H⁺).

Example 363: Synthesis of 4-[3-Pyridin-4-yl-ureido)-methyl]-benzoic acid ethyl ester

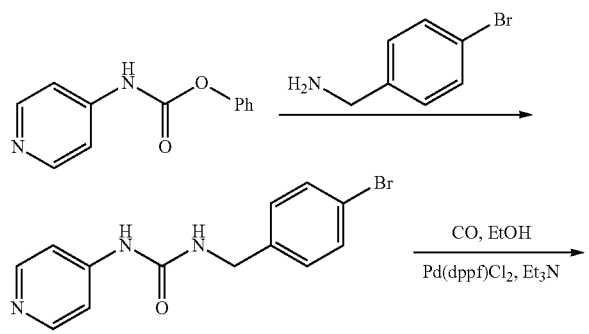

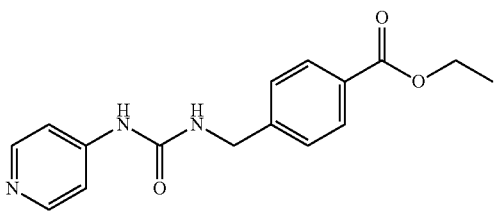

Step 1: A solution of pyridin-4-yl-carbamic acid phenyl ester (190 mg, 0.88 mmol), 4-bromo-benzylamine (182 mg, 0.968 mmol) and Et₃N (269 mg, 2.64 mmol) in 1,4-dioxane (2 mL) was stirred at 90° C. overnight. The mixture was concentrated and the residue was purified by prep-TLC to give 1-(4-bromo-benzyl)-3-pyridin-4-yl-urea (230 mg, yield: 84.6%) as a white solid. MS: m/z 308.1 (M+H)⁺.

Step 2: To a solution of 1-(4-bromo-benzyl)-3-pyridin-4-yl-urea (270 mg, 0.88 mmol) and Et₃N (178 mg, 1.76 mmol) in EtOH (5 mL), Pd(dppf)Cl₂ (60 mg, 0.088 mmol) was added, the mixture was stirred at 80° C. under CO balloon pressure for 3 days. The reaction was filtered, and the filtrate was concentrated to dryness. The residue was purified by prep-HPLC to give 4-[(3-pyridin-4-yl-ureido)-methyl]-benzoic acid ethyl ester (18.1 mg, yield: 6.68%). MS: m/z 300.0 (M+H)⁺. ¹H NMR (400 MHz, DMSO-d6): δ=9.16 (s, 1H), 8.29 (d, J=5.4 Hz, 2H), 7.93 (d, J=8.0 Hz, 2H), 7.43 (d, J=8.0 Hz, 2H), 7.38 (d, J=5.3 Hz, 2H), 6.99 (dd, J=8.4, 3.2 Hz, 1H), 4.39 (d, J=6.0 Hz, 2H), 4.30 (q, J=7.2 Hz, 2H), 1.31 (t, J=7.2 Hz, 3H). MS: m/z 300.0 (M+H⁺).

Example 364: Synthesis of 4-[(2-Pyridin-4-yl-cyclopropanecarbonyl)-amino]-benzoic acid ethyl ester

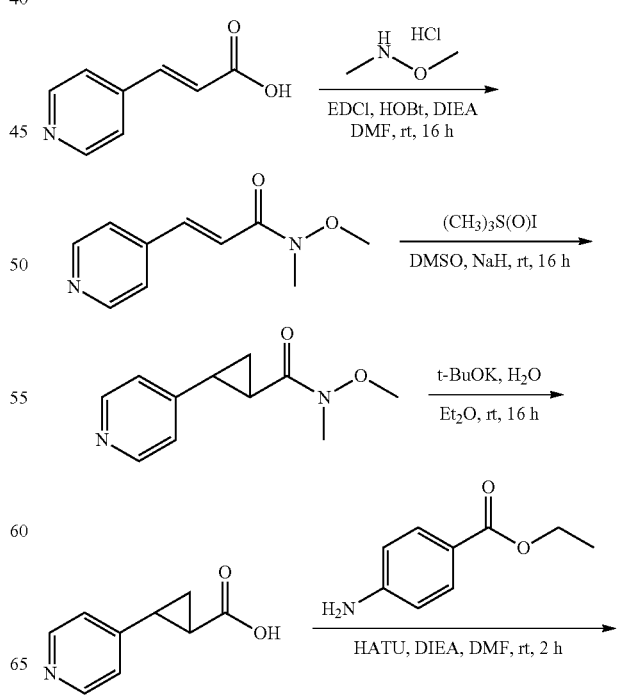

-continued

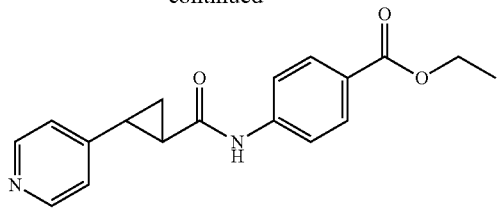

Step 1: A mixture of 3-pyridin-4-yl-acrylic acid (1.2 g, 8.1 mmol), EDCI (2.1 g, 10.5 mmol), HOBt (1.6 g, 10.5 mmol) and DIPEA (4.2 mL, 24.0 mmol) in DMF (30 mL) was stirred for 1 hr at room temperature, then O,N-dimethyl-hydroxylamine.HCl (950 mg, 9.7 mmol) was added. After stirring at room temperature for 16 hrs, the reaction mixture was diluted with H$_2$O (100 mL) and extracted with EA (40 mL×6). The combined EA was washed with brine, dried over Na$_2$SO$_4$ and concentrated. The residue was purified by silica flash column (50% to 100% EA in PE) to give N-methoxy-N-methyl-3-pyridin-4-yl-acrylamide (1.2 g, yield: 78%) as a yellow oil. $^1$H NMR (400 MHz, CDCl$_3$): δ=8.64 (d, J=6.0 Hz, 2H), 7.65 (d, J=15.6 Hz, 1H), 7.41 (d, J=6.0 Hz, 2H), 7.20 (d, J=15.6 Hz, 1H), 3.78 (s, 3H), 3.33 (s, 3H).

Step 2: To a suspension of trimethylsulfoxonium iodide (1.7 g, 7.6 mmol) in DMSO (10 mL) was added NaH (60%, 300 mg, 7.6 mmol) portionwise. After stirring at room temperature for 1 hr, a solution of N-methoxy-N-methyl-3-pyridin-4-yl-acrylamide (1.2 g, 6.3 mmol) in DMSO (5 mL) was added dropwise. The reaction mixture was stirred at room temperature for another 16 hrs. The reactant was diluted with H$_2$O (50 mL) and extracted with EA (30 mL×5). The combined EA was washed with brine, dried over Na$_2$SO$_4$ and concentrated. The residue was purified by silica flash column (30% to 100% EA in PE) to give 2-pyridin-4-yl-cyclopropanecarboxylic acid methoxy-methyl-amide (570 mg, yield: 44%) as a yellow oil. $^1$H NMR (400 MHz, CDCl$_3$): δ=8.48 (dd, J=4.4, 1.6 Hz, 2H), 7.02 (dd, J=4.4, 1.6 Hz, 2H), 3.70 (s, 3H), 3.24 (s, 3H), 2.50-2.43 (m, 2H), 1.75-1.68 (m, 1H), 1.38-1.32 (m, 1H).

Step 3: To a solution of 2-pyridin-4-yl-cyclopropanecarboxylic acid methoxy-methyl-amide (150 mg, 0.7 mmol) in Et$_2$O (4 mL) was added H$_2$O (0.03 mL, 1.5 mmol) and t-BuOK (490 mg, 4.4 mmol). After stirring at room temperature for 16 hrs, the reaction mixture was diluted with H$_2$O (5 mL) and acidified by aq.HCl (1 N) to pH=3. The solution was purified by reverse phase column (0% to 5% MeCN in H$_2$O) to give 2-pyridin-4-yl-cyclopropanecarboxylic acid (90 mg, yield: 62%) as a white solid. $^1$H NMR (400 MHz, D$_2$O): δ=8.48 (d, J=6.4 Hz, 2H), 7.64 (d, J=6.4 Hz, 2H), 2.60-2.50 (m, 1H), 2.07-2.00 (m, 1H), 1.75-1.66 (m, 1H), 1.52-1.47 (m, 1H).

Step 4: To a stirring solution of 2-pyridin-4-yl-cyclopropanecarboxylic acid (60 mg, 0.3 mmol), 4-amino-benzoic acid ethyl ester (60 mg, 0.4 mmol) and DIPEA (0.2 mL, 0.9 mmol) in DMF (2 mL) was added HATU (170 mg, 0.5 mmol). After stirring at room temperature for 2 hrs, the reaction mixture was diluted with H$_2$O (10 mL) and extracted with EA (10 mL×3). The combined EA was washed with brine, dried over Na$_2$SO$_4$ and concentrated. The residue was purified by silica gel column (PE/EA=1/2) to give 4-[(2-pyridin-4-yl-cyclopropanecarbonyl)-amino]-benzoic acid ethyl ester (24 mg, yield: 25%) as a white solid. $^1$H NMR (400 MHz, DMSO-d$_6$): δ=10.75 (s, 1H), 8.55 (dd, J=4.8, 1.2 Hz, 2H), 7.91 (d, J=8.8 Hz, 2H), 7.74 (d, J=8.8 Hz, 2H), 7.42 (dd, J=4.8, 1.2 Hz, 2H), 4.28 (q, J=7.2 Hz, 2H), 2.56-2.50 (m, 1H), 2.36-2.31 (m, 1H), 1.69-1.56 (m, 2H), 1.31 (t, J=7.2 Hz, 3H). MS: m/z 311.0 (M+H$^+$).

Example 365: Synthesis of Ethyl 4-((2,3-dioxo-4-((pyridin-4-ylmethyl)amino)cyclobutyl)amino)benzoate

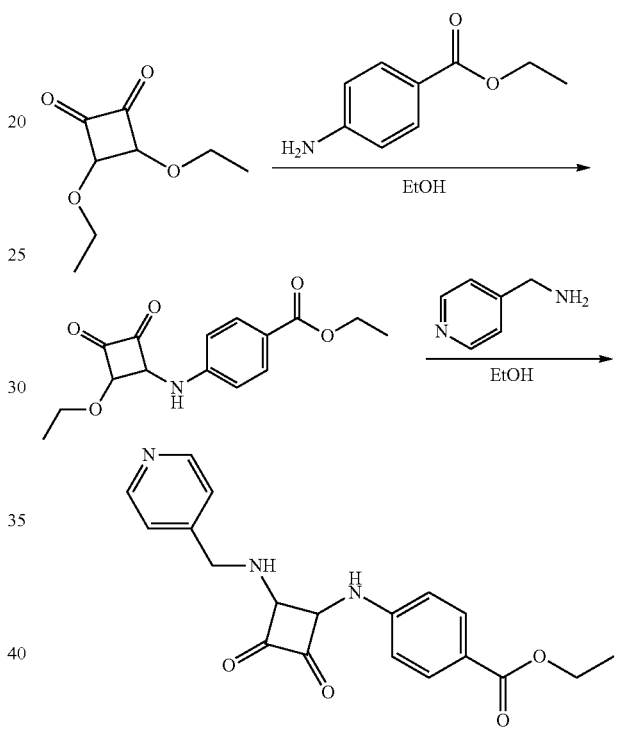

Step 1: A mixture of 3,4-diethoxycyclobutane-1,2-dione (183 mg, 1.1 mmol) and ethyl 4-aminobenzoate (177 mg, 1.1 mmol) in EtOH (5.0 mL) was stirred at 30° C. for 48 hrs. The mixture was concentrated in vacuum and the residue was washed with Et$_2$O to give ethyl 4-((2-ethoxy-3,4-dioxocyclobutyl)amino)benzoate (50 mg, 15%) as a yellow solid. $^1$H NMR (400 MHz, DMSO-d6): δ=11.0 (s, 1H), 7.93 (d, J=8.8 Hz, 2H), 7.50 (d, J=8.8 Hz, 2H), 4.79 (q, J=7.2 Hz, 2H), 4.29 (q, J=7.2 Hz, 2H), 1.42 (t, J=7.2 Hz, 3H), 1.31 (t, J=7.2 Hz, 3H).

Step 2: A mixture of ethyl 4-((2-ethoxy-3,4-dioxocyclobutyl)amino)benzoate (50 mg, 0.17 mmol) and pyridin-4-ylmethanamine (19 mg, 0.17 mmol) in EtOH (5.0 mL) was stirred at room temperature for 48 hrs. The mixture was concentrated in vacuum and the residue was purified by column chromatography on silica gel (DCM/MeOH=10/1) to give ethyl 4-((2,3-dioxo-4-((pyridin-4-ylmethyl)amino) cyclobutyl)amino)benzoate (25 mg, 42%) as a yellow solid. $^1$H NMR (400 MHz, DMSO-d6): δ=10.1 (s, 1H), 8.57 (d, J=4.4 Hz, 2H), 8.21 (brs, 1H), 7.92 (d, J=8.8 Hz, 2H), 7.54 (d, J=7.6 Hz, 2H), 7.40 (d, J=4.4 Hz, 2H), 4.87 (d, J=6.0 Hz, 2H), 4.28 (q, J=7.2 Hz, 2H), 1.31-1.29 (t, J=7.2 Hz, 3H). MS: m/z 351.9 (M+H$^+$).

Example 366: Synthesis of Ethyl 4-(2-amino-3-(pyridin-4-yl)propanamido)benzoate

Example 367: Synthesis of 4-{[(Pyridin-4-ylmethyl)-carbamoyl]-methyl}-benzoic acid ethyl ester

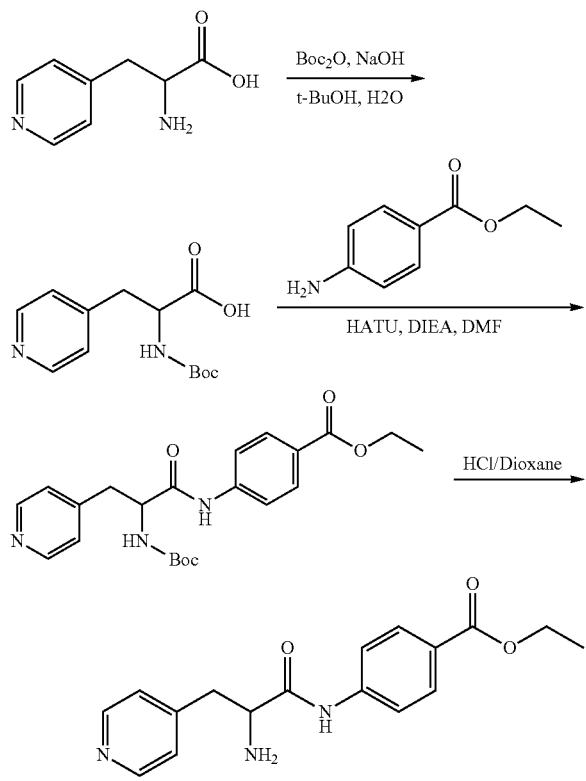

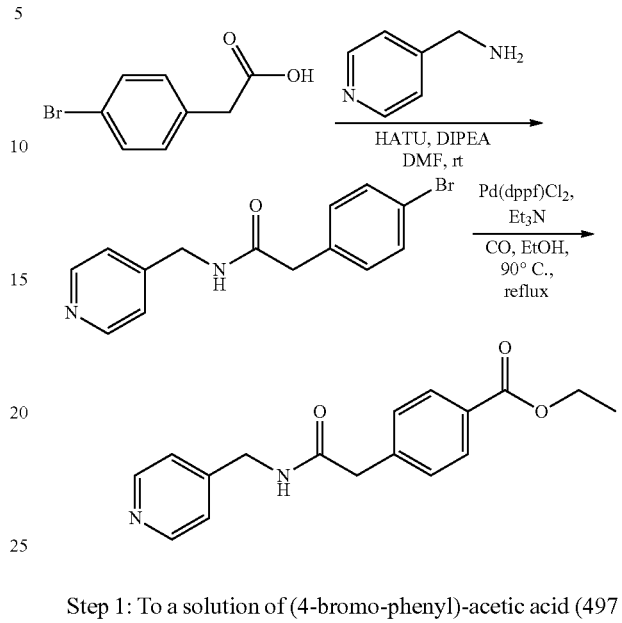

Step 1: A mixture of 2-amino-3-(pyridin-4-yl)propanoic acid (332 mg, 2.0 mmol), NaOH (160 mg, 4.0 mmol), Boc$_2$O (650 mg, 3.1 mmol) in t-BuOH (5 mL) and H$_2$O (5 mL) was stirred at room temperature for 16 hrs. The mixture was concentrated in vacuum and the residue was purified by flash chromatography to give 2-((tert-butoxycarbonyl)amino)-3-(pyridin-4-yl)propanoic acid (300 mg, 56%) as a white solid.

Step 2: A mixture of 2-((tert-butoxycarbonyl)amino)-3-(pyridin-4-yl)propanoic acid (150 mg, 0.56 mmol), HATU (350 mg, 0.86 mmol) and DIEA (220 mg, 1.71 mmol) in DMF (5 mL) was stirred at room temperature for 16 hrs. The mixture was concentrated in vacuum and the residue was purified by flash chromatography to give ethyl 4-(2-((tert-butoxycarbonyl)amino)-3-(pyridin-4-yl)propanamido)benzoate (60 mg, yield: 34%) as a white solid.

Step 3: A mixture of ethyl 4-(2-((tert-butoxycarbonyl)amino)-3-(pyridin-4-yl)propanamido)benzoate (60 mg, 0.14 mmol) and HCl/dioxane (4 mL) in dioxane (5 mL) was stirred at room temperature for 1 hr. The mixture was concentrated in vacuum and the residue was purified by prep-HPLC to give ethyl 4-(2-amino-3-(pyridin-4-yl)propanamido)benzoate (5 mg, yield: 11%) as a white solid. $^1$H NMR (400 MHz, DMSO-d6): δ=8.41 (d, J=6.0 Hz, 2H), 7.95 (d, J=8.8 Hz, 2H), 7.65 (d, J=8.8 Hz, 2H), 7.32 (d, J=6.0 Hz, 2H), 4.35 (q, J=7.2 Hz, 2H), 3.76 (t, J=6.8 Hz, 1H), 3.16-3.11 (m, 1H), 2.97-2.92 (m, 1H), 1.32 (t, J=7.2 Hz, 3H). MS: m/z 314.0 (M+H$^+$).

Step 1: To a solution of (4-bromo-phenyl)-acetic acid (497 mg, 2.31 mmol) in DMF (10 mL), was added 4-(aminomethyl)pyridine (293 mg, 2.72 mmol) and DIPEA (1.9 mL, 10.9 mmol), HATU (1.266 g, 3.33 mmol). The mixture was stirred 2 hrs at room temperature. After that, water (50 mL) and EA (50 mL) was added. The aqueous phase was extracted with EA (50 mL×2). The extracts were washed with brines (50 mL×2), dried over Na$_2$SO$_4$ and concentrated. The residue was purified by silica gel column chromatography (PE/EA=1/1) to give 2-(4-bromo-phenyl)-N-pyridin-4-ylmethyl-acetamide (290 mg, yield: 42%) as a white solid.

Step 2: To a solution of 2-(4-bromo-phenyl)-N-pyridin-4-ylmethyl-acetamide (290 mg, 0.95 mmol) in EtOH (10 mL), was added Pd(dppf)Cl$_2$ (145 mg, 0.198 mmol), and Et$_3$N (0.5 mL, 3.6 mmol). The suspension was degassed and purged with CO for several times. The mixture was refluxed overnight. After that, the mixture was filtered and the filtrate was purified by prep-HPLC to give 4-{[(pyridin-4-ylmethyl)-carbamoyl]-methyl}-benzoic acid ethyl ester (30 mg, yield: 10%) as a yellow solid. $^1$H NMR (400 MHz, CDCl$_3$): δ=8.52 (d, J=6.0 Hz, 2H), 8.05 (d, J=8.4 Hz, 2H), 7.39 (d, J=8.4 Hz, 2H), 7.09 (d, J=6.0 Hz, 2H), 5.79 (s, 1H), 4.42 (d, J=6.0 Hz, 2H), 4.38 (q, J=7.2 Hz, 2H), 3.72 (s, 2H), 1.40 (t, J=7.2 Hz, 3H). MS: m/z 298.9 (M+H$^+$).

Example 368: Synthesis of 4-(3-Pyridin-4-yl-propionylamino)-benzoic acid ethyl ester

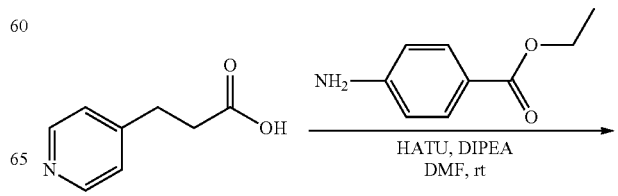

-continued

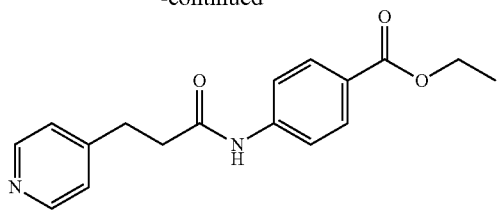

To a solution of 3-pyridin-4-yl-propionic acid (150 mg, 1.0 mmol) in DMF (5 mL), was added HATU (570.3 mg, 1.499 mmol) and DIPEA (1.0 mL, 5.7 mmol), the mixture was stirred for half an hour at room temperature, followed by the addition of 4-amino-benzoic acid ethyl ester (225 mg, 1.36 mmol). The mixture was stirred over night at room temperature. After that, water (20 mL×2) and EA (20 mL) was added. The aqueous phase was extracted with EA (20 mL). The extracts were washed with brines (30 mL×2), dried over $Na_2SO_4$ and concentrated to dryness. The residue was purified by silica gel column chromatography (EA) to give 4-(3-pyridin-4-yl-propionylamino)-benzoic acid ethyl ester (30 mg, yield: 10%) as a yellow solid. $^1$H NMR (400 MHz, DMSO-$d_6$) δ=10.30 (s, 1H), 8.46 (d, J=5.6 Hz, 2H), 7.90 (d, J=8.4 Hz, 2H), 7.70 (d, J=8.4 Hz, 2H), 7.28 (d, J=5.6 Hz, 2H), 4.28 (q, J=6.8 Hz, 2H), 2.93 (t, J=7.6 Hz, 2H), 2.72 (t, J=7.6 Hz, 2H), 1.30 (t, J=7.2 Hz, 3H). MS: m/z 299.1 (M+H$^+$).

Example 369: Synthesis of Ethyl 4-({(1E)-2-cyano-1-[(4-pyridylmethyl)amino]-2-azavinyl}amino)benzoate

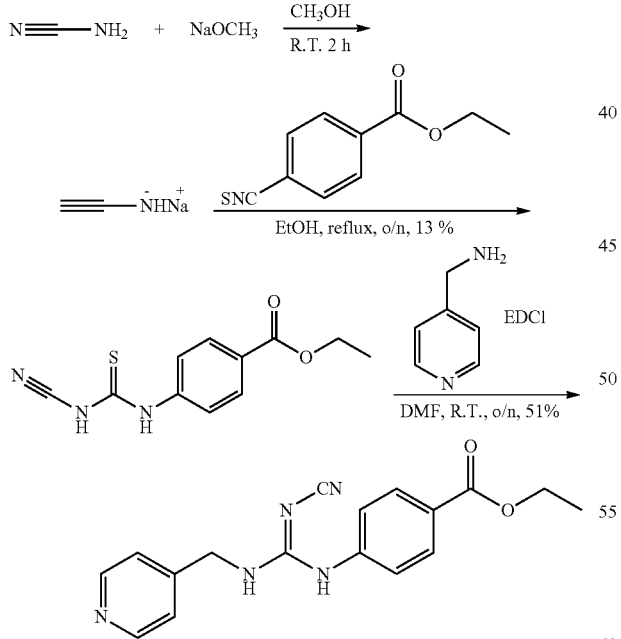

Step 1: To a solution of cyanamide (3 g, 71.4 mmol) in methanol (30 mL) was added sodium methoxide (3.9 g, 72.2 mmol) in portions. After stirred at room temperature for 2 hrs, the mixture was evaporated in vacuum to afford crude sodium cyanmide as a white solid which was used for next step without further purification.

Step 2: To a suspension of 4-isothiocyanato-benzoic acid ethyl ester (200 mg, 0.98 mmol) in EtOH (10 mL) was added sodium cyanmide (62 mg, 0.98 mmol). After heated to 70° C. overnight, the mixture was evaporated in vacuum. The residue was purified by flash column chromatograph (ACN in water: 5% to 95%) to afford ethyl 4-{[(cyanoamino)thioxomethyl]amino}benzoate (30 mg, 13%) as a white solid. $^1$H NMR (400 MHz, CD$_3$OD): δ=7.89 (d, J=8.4 Hz, 2H), 7.69 (d, J=8.4 Hz, 2H), 4.32 (q, J=7.0 Hz, 2H), 1.37 (t, J=7.0 Hz, 3H).

Step 3: To a solution of ethyl 4-{[(cyanoamino)thioxomethyl]amino}benzoate (30 mg, 0.12 mmol) in DMF (5 mL) was added 4-(aminomethyl)pyridine (15.7 mg, 0.14 mmol) and EDCI (27.8 mg, 0.14 mmol). After stirred at room temperature overnight, the reaction mixture was evaporated in vacuum. The residue was purified by prep-TLC (DCM/MeOH=10/1) to afford ethyl 4-({(1E)-2-cyano-1-[(4-pyridylmethyl)amino]-2-azavinyl}amino)benzoate (20 mg, 51%) as a yellow solid. $^1$H NMR (400 MHz, CD$_3$OD): δ=8.50 (d, J=5.6 Hz, 2H), 8.04 (d, J=8.4 Hz, 2H), 7.40-7.37 (m, 4H), 4.55 (s, 2H), 4.35 (q, J=7.0 Hz, 2H), 1.38 (t, J=7.0 Hz, 3H). MS: m/z 322.1 (M−H)$^−$.

Example 370: Synthesis of 4-{2-Nitro-1-[(pyridin-4-ylmethyl)-amino]-vinylamino}-benzoic acid ethyl ester

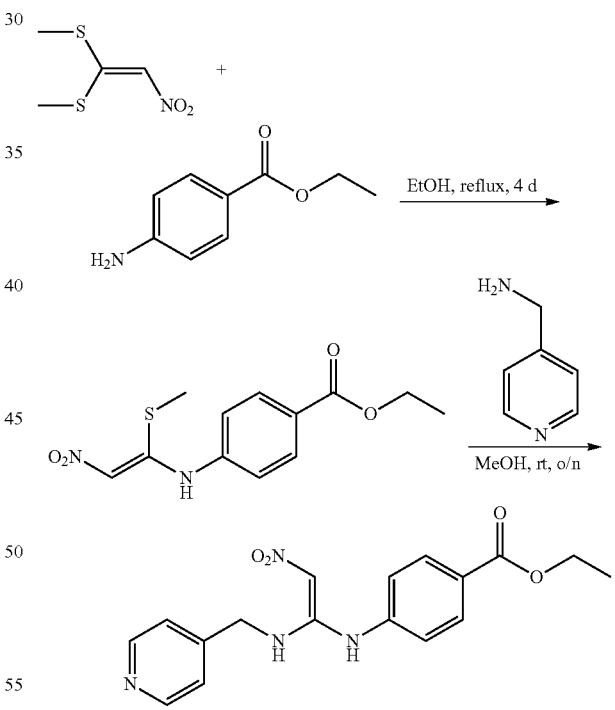

Step 1: To a solution of 4-amino-benzoic acid ethyl ester (2 g, 12.1 mmol) in ethanol (200 mL) was added 1,1-bis-methylsulfanyl-2-nitro-ethene (1.7 g, 12.1 mmol). After reflux for 4 days, the mixture was concentrated in vacuum. The residue was purified by flash column (ACN in water: 5% to 95%) to afford 4-(1-methylsulfanyl-2-nitro-vinylamino)-benzoic acid ethyl ester (270 mg, 8%) as a yellow solid. MS: m/z 280.9 (M−H)$^−$.

Step 2: To a solution of 4-(1-methylsulfanyl-2-nitro-vinylamino)-benzoic acid ethyl ester (60 mg, 0.21 mmol) in methanol (10 mL) was added Pyridin-4-ylmethanamine (230 mg, 2.1 mmol). After stirred at room temperature overnight, the mixture was concentrated in vacuum. The residue was purified by prep-TLC (DCM/MeOH=10/1) to afford 4-{2-nitro-1-[(pyridin-4-ylmethyl)-amino]-vinylamino}-benzoic acid ethyl ester (18.8 mg, 25.8%) as a yellow solid. $^1$H NMR (400 MHz, CD$_3$OD): δ=8.54 (d, J=6.4 Hz, 2H), 8.08 (d, J=8.0 Hz, 2H), 7.42 (d, J=6.4 Hz, 2H), 7.37 (d, J=8.0 Hz, 2H), 6.52 (s, 1H), 4.71 (s, 2H), 4.37 (q, J=7.2 Hz, 2H), 1.38 (t, J=7.2 Hz, 3H). MS: m/z 343.0 (M+H)$^+$.

Example 371: Synthesis of [6-(Morpholine-4-sulfonyl)-benzothiazol-2-yl]-pyridin-4-ylmethyl-amine

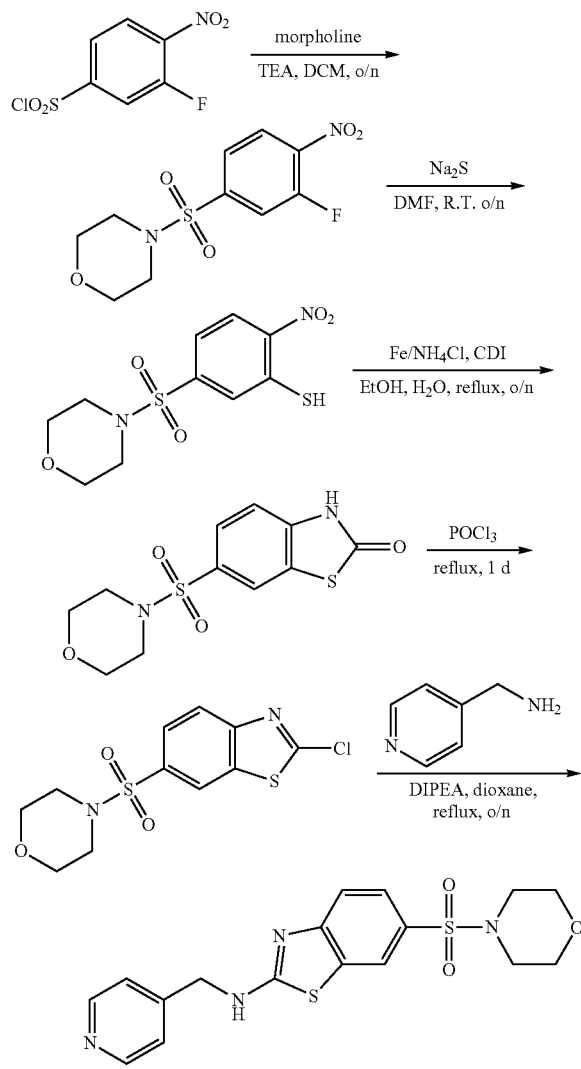

Step 1: To a solution of 3-fluoro-4-nitro-benzenesulfonyl chloride (1 g, 4.2 mmol) in dry DCM (15 mL) was added TEA (402.4 mg, 4.6 mmol). Then morpholine (468 mg, 4.6 mmol) was added dropwise and the reaction mixture was stirred at room temperature overnight. Then the mixture was concentrated in vacuum. The residue was purified by silica gel column chromatograph (PE:EA=2:1) to afford 4-(3-fluoro-4-nitro-benzenesulfonyl)-morpholine (617 mg, 51.4%) as a yellow solid.

Step 2: To a solution of 4-(3-fluoro-4-nitro-benzenesulfonyl)-morpholine (600 mg, 2.1 mmol) in DMF (10 mL) was added Na$_2$S (803 mg, 10.3 mmol). After stirred at room temperature overnight, the reaction mixture was added 1M HCl to pH=6. Then the mixture was diluted in H$_2$O (50 mL) and extracted by EA (50 mL×3). Organic phase was combined and evaporated in vacuum to afford 5-(morpholine-4-sulfonyl)-2-nitro-benzenethiol (600 mg, crude) as a yellow solid which was used for next step without further purification.

Step 3: To a solution of 5-(morpholine-4-sulfonyl)-2-nitro-benzenethiol (600 mg, crude) in a mixture of EtOH (80 mL) and H$_2$O (20 mL) was added Fe powder (560 mg, 10 mmol), NH$_4$Cl (1.1 g, 20 mmol), and CDI (973.2 mg, 6 mmol). After heated to reflux overnight, the reaction mixture was filtered. The filtrate was diluted in H$_2$O (100 mL) and extracted by EA (50 mL×3). Organic phase was combined and evaporated in vacuum. The residue was purified by flash column chromatograph (ACN in water: 10% to 95%) to afford 6-(morpholine-4-sulfonyl)-3H-benzothiazol-2-one (200 mg, 34%) as a yellow solid.

Step 4: 6-(Morpholine-4-sulfonyl)-3H-benzothiazol-2-one (40 mg, 0.13 mmol) was dissolved in POCl$_3$ (10 mL). After stirred at reflux overnight, the reaction mixture was concentrated in vacuum. The residue was partitioned in a mixture of EA (20 mL) and H$_2$O (20 mL). Then K$_2$CO$_3$ powder was added to pH>7. Then organic phase was collected and evaporated in vacuum. The residue was purified by flash column chromatograph (ACN in water: 10% to 95%) to afford 2-chloro-6-(morpholine-4-sulfonyl)-benzothiazole (40 mg, 94.1%) as a yellow solid.

Step 5: To a solution of 2-chloro-6-(morpholine-4-sulfonyl)-benzothiazole (20 mg, 0.063 mmol) in dioxane (10 mL) was added Pyridin-4-ylmethanamine (13.6 mg, 0.126 mmol) and DIPEA (16.3 mg, 0.126 mmol). After stirred at reflux overnight, the reaction mixture was evaporated in vacuum. The residue was purified by prep-HPLC to afford [6-(morpholine-4-sulfonyl)-benzothiazol-2-yl]-pyridin-4-ylmethyl-amine (5.4 mg, 22%) as a yellow solid. $^1$H NMR (400 MHz, CD$_3$OD): δ=8.49 (d, J=6.4 Hz, 2H), 8.08 (d, J=2.0 Hz, 1H), 7.64 (dd, J=8.4, 2.0 Hz, 1H), 7.54 (d, J=8.4 Hz, 1H), 7.45 (d, J=6.0 Hz, 2H), 4.78 (s, 2H), 3.71-3.68 (m, 4H), 2.96-2.94 (m, 4H). MS: m/z 390.9 (M+H)$^+$.

Example 372: Synthesis of 1-(1-Phenylmethanesulfonyl-piperidin-4-yl)-3-pyridin-4-ylmethyl-urea

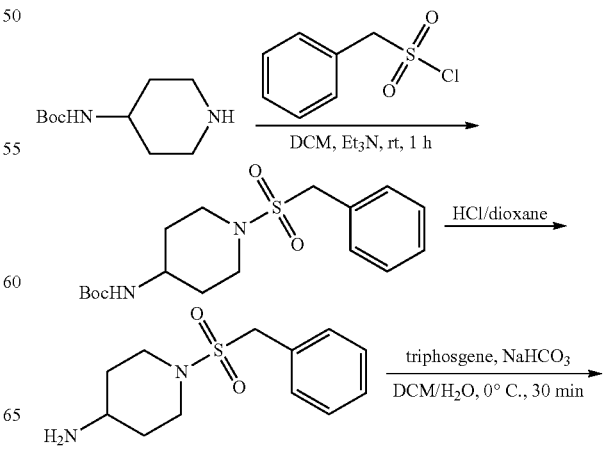

-continued

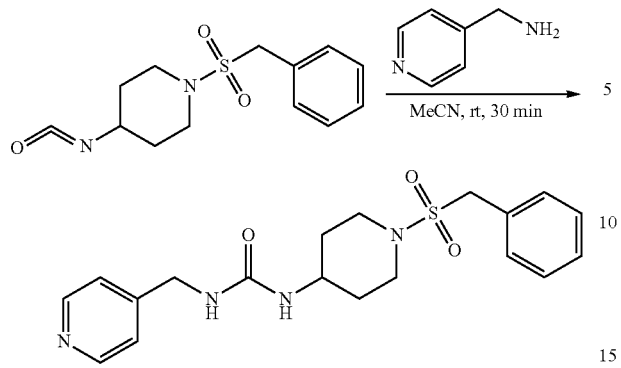

Step 1: To a solution of piperidin-4-yl-carbamic acid tert-butyl ester (1.0 g, 5.0 mmol) and Et₃N (1.1 mL, 7.5 mmol) in DCM (30 mL) was added phenyl-methanesulfonyl chloride (1.1 g, 6.0 mmol) at 0° C. After stirring at room temperature for 1 h, the reaction mixture was diluted with DCM (50 mL), washed with water (30 mL). The DCM solution was dried over Na₂SO₄ and concentrated. The residue was washed with (PE/EA=1/1) to give (1-phenyl-methanesulfonyl-piperidin-4-yl)-carbamic acid tert-butyl ester (1.0 g, yield: 56%) as a white solid. ¹H NMR (400 MHz, CDCl₃): δ=7.40-7.37 (m, 5H), 4.46-4.36 (m, 1H), 4.22 (s, 2H), 3.60 (d, J=12.4 Hz, 2H), 3.52-3.39 (m, 1H), 2.62 (t, J=11.6 Hz, 2H), 1.87 (d, J=12.4 Hz, 2H), 1.43 (s, 9H), 1.37-1.26 (m, 2H).

Step 2: To a solution of (1-phenylmethanesulfonyl-piperidin-4-yl)-carbamic acid tert-butyl ester (1.0 g, 2.8 mmol) in DCM/MeOH (10 mL/3 mL) was added HCl/dioxane (6 M, 10 mL). After stirring at room temperature for 2 hrs, the reaction mixture was concentrated. To the residue was added aq.NaOH (10%, 50 mL) and the mixture was extracted by EA (30 mL×4). The combined EA was washed with brine, dried over Na₂SO₄ and concentrated to give 1-phenylmethanesulfonyl-piperidin-4-ylamine (700 g, yield: 97%) as a white solid.

Step 3: To a solution of 1-phenylmethanesulfonyl-piperidin-4-ylamine (250 mg, 1.0 mmol) in DCM/H₂O (20 mL/20 mL) was added NaHCO₃ (340 mg, 4.0 mmol) and triphosgene (90 mg, 0.3 mmol) at 0° C. After stirring at 0° C. for 30 min, organic layer was separated, dried over Na₂SO₄ and concentrated to give 4-isocyanato-1-phenylmethanesulfonyl-piperidine (crude) as a white solid.

Step 4: To a solution of 4-isocyanato-1-phenylmethane-sulfonyl-piperidine (crude) in MeCN (10 mL) was added pyridin-4-ylmethanamine (110 mg, 1.0 mmol) at 0° C. After stirring at room temperature for 30 min, the precipitation was collected and washed with MeCN (10 mL) to give 1-(1-phenylmethanesulfonyl-piperidin-4-yl)-3-pyridin-4-yl-methyl-urea (300 mg, yield: 77%, two steps) as a white solid. ¹H NMR (400 MHz, DMSO-d₆): δ=8.60 (d, J=6.0 Hz, 2H), 7.42-7.33 (m, 5H), 7.21 (d, J=6.0 Hz, 2H), 6.38 (t, J=6.0 Hz, 1H), 6.14 (d, J=8.0 Hz, 1H), 4.39 (s, 2H), 4.22 (d, J=6.0 Hz, 2H), 3.51-3.45 (m, 3H), 2.80 (t, J=10.6 Hz, 2H), 1.79 (dd, J=12.8, 2.8 Hz, 2H), 1.35-1.24 (m, 2H). MS: m/z 389.0 (M+H⁺).

Example 373: Synthesis of 1-((1H-Pyrazol-4-yl)methyl)-3-(4-((2-fluorophenyl)sulfonyl)phenyl)urea

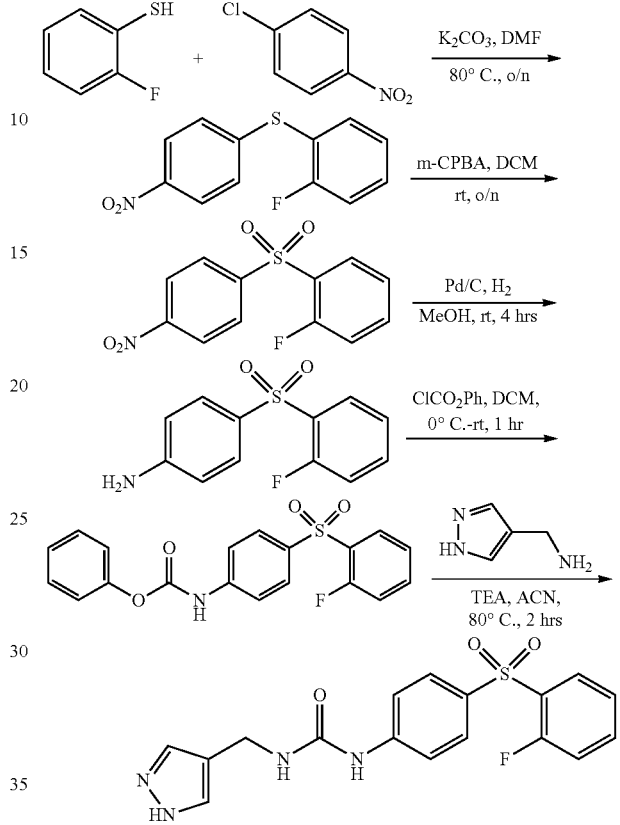

Step 1: To a solution of 2-fluorobenzenethiol (384.5 mg, 3.0 mmol) in DMF (20 mL) was added 1-chloro-4-nitrobenzene (709 mg, 4.5 mmol) and followed by K₂CO₃ (1.24 g, 9.0 mmol). The resulting mixture was stirred at 80° C. overnight. The reaction was monitored by TLC. Then K₂CO₃ was removed by filtration. The filtrate was concentrated in vacuum. The residue was purified by silica gel column (PE/EA=100/1 as eluent) to afford (2-fluorophenyl)(4-nitrophenyl)sulfane (596 mg, yield 80%) as a yellow solid. ¹H NMR (400 MHz, CDCl₃): δ=8.11-8.06 (m, 2H), 7.60-7.54 (m, 1H), 7.53-7.46 (m, 1H), 7.28-7.22 (m, 2H), 7.21-7.17 (m, 2H).

Step 2: To a solution of (2-fluorophenyl)(4-nitrophenyl)sulfane (596 mg, 2.39 mmol) in DCM (30 mL) was added m-CPBA (1.77 g, 7.17 mmol). The resulting mixture was stirred at room temperature overnight. The reaction was monitored by TLC. Then the mixture was mixture with saturated Na₂SO₃ and extracted with DCM (20 mL×2). The combined organic layer was concentrated in vacuum. The residue was purified by silica gel column (PE/EA=10/1) to afford 1-fluoro-2-((4-nitrophenyl)sulfonyl)benzene (608 mg, yield: 90%) as a white solid. ¹H NMR (400 MHz, CDCl₃): δ=8.40-8.33 (m, 2H), 8.24-8.17 (m, 2H), 8.16-8.11 (m, 1H), 7.69-7.62 (m, 1H), 7.41-7.35 (m, 1H), 7.18-7.11 (m, 1H).

Step 3: To a suspension of 1-fluoro-2-((4-nitrophenyl)sulfonyl)benzene (608 mg, 2.16 mmol) in MeOH (20 mL) was added Pd/C (60 mg, 10% wt). The resulting mixture was stirred under H₂ (balloon) atmosphere at room temperature for 4 hrs. The reaction was monitored by LC-MS and TLC. Then Pd/C was removed by filtration. The filtrate was concentrated in vacuum to give 4-((2-fluorophenyl)sulfonyl)aniline (412 mg, yield 76%) as a white solid. $^1$H NMR (400 MHz, DMSO-d$_6$): δ=7.93 (dt, J=8.0, 2.0 Hz, 1H), 7.73-7.65 (m, 1H), 7.55 (dd, J=8.8, 0.8 Hz, 2H), 7.41 (dt, J=8.8, 0.8 Hz, 1H), 7.39-7.32 (m, 1H), 6.67-6.60 (m, 2H), 6.26 (brs, 2H).

Step 4: To a solution of 4-((2-fluorophenyl)sulfonyl)aniline (250 mg, 1.0 mmol) in dry DCM (20 mL) was added phenyl chloroformate (236 mg, 1.50 mmol), followed by TEA (303.6 mg, 3.0 mmol). The resulting mixture was stirred at room temperature for 1 hr. The reaction was monitored by TLC. Then the mixture was concentrated in vacuum. The residue was purified by silica gel column (PE/EA=10/1) to afford phenyl (4-((2-fluorophenyl)sulfonyl)phenyl)carbamate (252.6 mg, yield 68%) as a white solid.

Step 5: To a solution of (4-((2-fluorophenyl)sulfonyl)phenyl)carbamate (252.6 mg, 0.68 mmol) in ACN (40 mL) was added (1H-pyrazol-4-yl)methanamine (200 mg, 2.06 mmol), followed by TEA (206 mg, 2.04 mmol). The resulting mixture was stirred at 80° C. for 2 hrs. The reaction was monitored by LC-MS. Then the mixture was concentrated in vacuum. The residue was purified by prep-HPLC with NH$_4$OH as additive to afford 1-((1H-pyrazol-4-yl)methyl)-3-(4-((2-fluorophenyl)sulfonyl)phenyl)urea (83.8 mg, yield 33%) as a white solid. $^1$H NMR (400 MHz, DMSO-d$_6$): δ=12.63 (br s, 1H), 9.07 (s, 1H), 8.04-7.96 (m, 1H), 7.83-7.49 (m, 7H), 7.46 (t, J=6.8 Hz, 1H), 7.39 (t, J=9.2 Hz, 1H), 6.57 (t, J=5.6 Hz, 1H), 4.15 (d, J=5.2 Hz, 2H). MS: m/z 374.9 (M+H$^+$).

Example 374: Synthesis of 1-(4-((2-Fluorophenyl)sulfonyl)phenyl)-3-(pyridin-4-ylmethyl)urea

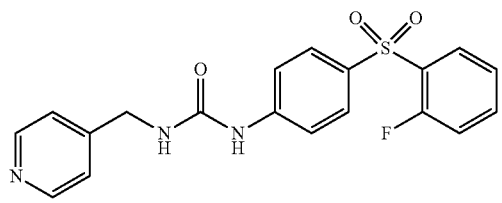

The title compound was prepared using general procedure of 1-((1H-pyrazol-4-yl)methyl)-3-(4-((2-fluorophenyl)sulfonyl)phenyl)urea. $^1$H NMR (400 MHz, DMSO-d$_6$): δ=9.41 (br s, 1H), 8.49 (d, J=5.6 Hz, 2H), 8.01 (dt, J=8.8, 1.6 Hz, 1H), 7.84-7.71 (m, 3H), 7.65 (d, J=8.8 Hz, 2H), 7.46 (t, J=7.6 Hz, 1H), 7.40 (t, J=9.2 Hz, 1H), 7.28 (d, J=6.0 Hz, 2H), 7.01 (t, J=6.0 Hz, 1H), 4.33 (d, J=6.0 Hz, 2H). MS: m/z 385.9 (M+H$^+$).

Example 375: Synthesis of 1-(4-((2-Fluorophenyl)sulfonyl)phenyl)-3-(oxazol-5-ylmethyl)urea

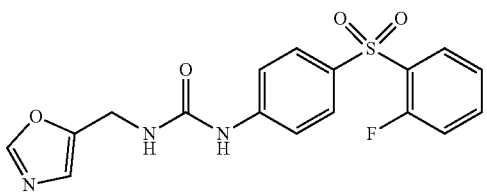 [SMILES: O=C(NCc1cnco1)Nc1ccc(S(=O)(=O)c2ccccc2F)cc1]

The title compound was prepare using genera procedure of 1-((1H-pyrazol-4-yl)methyl)-3-(4-((2-fluorophenyl)sulfonyl)phenyl)urea. $^1$H NMR (400 MHz, DMSO-d$_6$): δ=9.33 (br s, 1H), 8.28 (s, 1H), 8.00 (dt, J=8.0, 1.6 Hz, 1H), 7.80 (d, J=8.4 Hz, 2H), 7.79-7.71 (m, 1H), 7.64 (d, J=8.8 Hz, 2H), 7.46 (t, J=7.2 Hz, 1H), 7.40 (t, J=9.6 Hz, 1H), 7.01 (s, 1H), 6.97 (t, J=6.0 Hz, 1H), 4.36 (d, J=5.6 Hz, 2H). MS: m/z 375.9 (M+H$^+$).

Example 376: Synthesis of 1-(4-((3-Fluorophenyl)sulfonyl)phenyl)-3-(pyridin-4-ylmethyl)urea

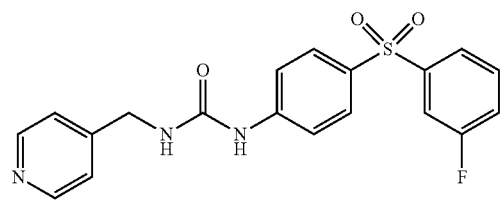

The title compound was prepared using general procedure of 1-((1H-pyrazol-4-yl)methyl)-3-(4-((2-fluorophenyl)sulfonyl)phenyl)urea. $^1$H NMR (400 MHz, DMSO-d$_6$): δ=9.39 (br s, 1H), 8.49 (dd, J=4.4, 1.6 Hz, 2H), 7.85 (d, J=9.2 Hz, 2H), 7.79-7.73 (m, 2H), 7.71-7.60 (m, 3H), 7.58-7.50 (m, 1H), 7.27 (d, J=5.6 Hz, 2H), 7.01 (t, J=6.0 Hz, 1H), 4.33 (d, J=6.0 Hz, 2H). MS: m/z 385.9 (M+H$^+$).

Example 377: Synthesis of 1-((1H-Pyrazol-4-yl)methyl)-3-(4-((3-fluorophenyl)sulfonyl)phenyl)urea

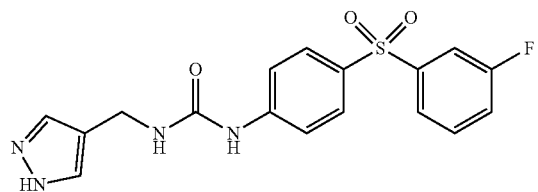 [SMILES: O=C(NCc1cn[nH]c1)Nc1ccc(S(=O)(=O)c2cccc(F)c2)cc1]

The title compound was prepared using general procedure of 1-((1H-pyrazol-4-yl)methyl)-3-(4-((2-fluorophenyl)sulfonyl)phenyl)urea. $^1$H NMR (400 MHz, DMSO-d$_6$): δ=12.63 (br s, 1H), 9.04 (s, 1H), 7.88-7.81 (m, 2H), 7.78-7.72 (m, 2H), 7.69-7.64 (m, 1H), 7.64-7.58 (m, 2H), 7.58-7.44 (m, 3H), 6.57 (t, J=5.6 Hz, 1H), 4.15 (d, J=5.6 Hz, 2H). MS: m/z 375.0 (M+H$^+$).

Example 378: Synthesis of 1-(4-((3-Fluorophenyl)sulfonyl)phenyl)-3-(oxazol-5-ylmethyl)urea

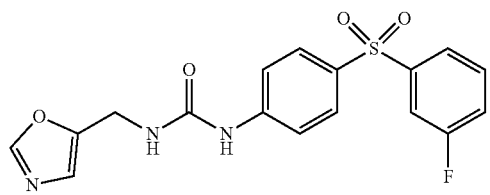

The title compound was prepared using general procedure of 1-((1H-pyrazol-4-yl)methyl)-3-(4-((2-fluorophenyl)sulfonyl)phenyl)urea. ¹H NMR (400 MHz, DMSO-d₆): δ=9.22 (br s, 1H), 8.29 (s, 1H), 7.85 (d, J=8.8 Hz, 2H), 7.80-7.73 (m, 2H), 7.71-7.59 (m, 3H), 7.58-7.51 (m, 1H), 7.01 (s, 1H), 6.87 (t, J=6.0 Hz, 1H), 4.36 (d, J=6.0 Hz, 2H). MS: m/z 375.9 (M+H⁺).

Example 379: Synthesis of 1-(4-((4-Fluorophenyl)sulfonyl)phenyl)-3-(pyridin-4-ylmethyl)urea

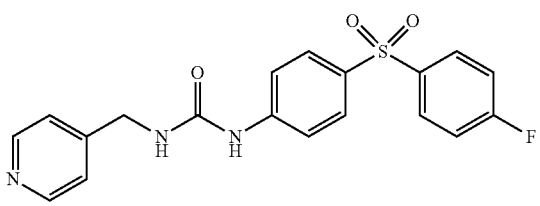 [SMILES: O=C(NCc1ccncc1)Nc1ccc(S(=O)(=O)c2ccc(F)cc2)cc1]

The title compound was prepared using general procedure of 1-((1H-pyrazol-4-yl)methyl)-3-(4-((2-fluorophenyl)sulfonyl)phenyl)urea. ¹H NMR (400 MHz, DMSO-d₆): δ=9.33 (br s, 1H), 8.49 (d, J=5.6 Hz, 2H), 7.98 (dd, J=8.8, 4.8 Hz, 2H), 7.82 (d, J=8.8 Hz, 2H), 7.63 (d, J=8.8 Hz, 2H), 7.44 (t, J=8.8 Hz, 2H), 7.27 (d, J=5.6 Hz, 2H), 6.96 (t, J=6.0 Hz, 1H), 4.33 (d, J=6.0 Hz, 2H). MS: m/z 385.9 (M+H⁺).

Example 380: Synthesis of 1-((1H-Pyrazol-4-yl)methyl)-3-(4-((4-fluorophenyl)sulfonyl)phenyl)urea

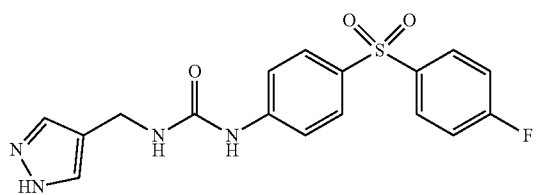 [SMILES: O=C(NCc1cn[nH]c1)Nc1ccc(S(=O)(=O)c2ccc(F)cc2)cc1]

The title compound was prepared using general procedure of 1-((1H-pyrazol-4-yl)methyl)-3-(4-((2-fluorophenyl)sulfonyl)phenyl)urea. ¹H NMR (400 MHz, DMSO-d₆): δ=12.63 (br s, 1H), 9.01 (s, 1H), 8.02-7.94 (m, 2H), 7.84-7.78 (m, 2H), 7.63-7.58 (m, 2H), 7.57-7.47 (m, 2H), 7.46-7.40 (m, 2H), 6.55 (t, J=5.6 Hz, 1H), 4.15 (d, J=5.6 Hz, 2H). MS: m/z 374.9 (M+H⁺).

Example 381: Synthesis of 1-(4-((4-Fluorophenyl)sulfonyl)phenyl)-3-(oxazol-5-ylmethyl)urea

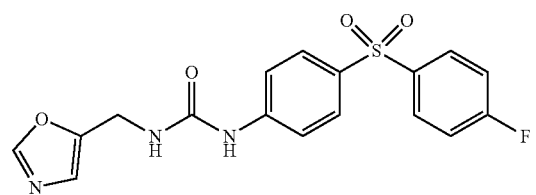 [SMILES: O=C(NCc1cnco1)Nc1ccc(S(=O)(=O)c2ccc(F)cc2)cc1]

The title compound was prepared using general procedure of 1-((1H-pyrazol-4-yl)methyl)-3-(4-((2-fluorophenyl)sulfonyl)phenyl)urea. ¹H NMR (400 MHz, DMSO-d₆): δ=9.18 (br s, 1H), 8.28 (s, 1H), 8.02-7.94 (m, 2H), 7.82 (d, J=8.8 Hz, 2H), 7.61 (d, J=9.2 Hz, 2H), 7.44 (t, J=8.8 Hz, 2H), 7.00 (s, 1H), 6.85 (t, J=6.0 Hz, 1H), 4.37 (d, J=6.0 Hz, 2H). MS: m/z 375.9 (M+H⁺).

Example 382: Synthesis of 1-[4-(2-Chloro-benzenesulfonyl)-phenyl]-3-oxazol-5-ylmethyl-urea

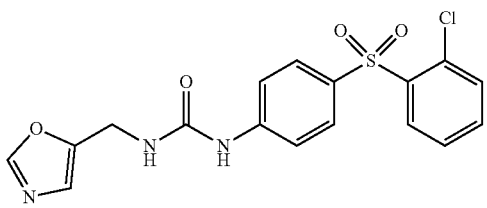 [SMILES: O=C(NCc1cnco1)Nc1ccc(S(=O)(=O)c2ccccc2Cl)cc1]

The title compound was prepared using general procedure of 1-((1H-pyrazol-4-yl)methyl)-3-(4-((2-fluorophenyl)sulfonyl)phenyl)urea. ¹H NMR (400 MHz, DMSO-d₆): δ=9.23 (s, 1H), 8.28 (s, 1H), 8.23 (d, J=7.6 Hz, 1H), 7.77 (d, J=8.8 Hz, 2H), 7.37-7.57 (m, 5H), 7.01 (s, 1H), 6.86 (t, J=6.0 Hz, 1H). MS: m/z 391.9 (M+H⁺).

Example 383: Synthesis of 1-(4-((3-Chlorophenyl)sulfonyl)phenyl)-3-(oxazol-5-ylmethyl)urea

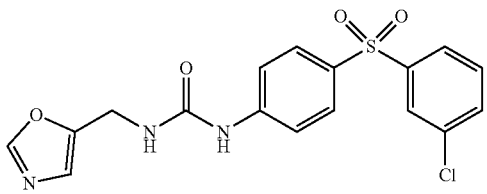

The title compound was prepared using general procedure of 1-((1H-pyrazol-4-yl)methyl)-3-(4-((2-fluorophenyl)sulfonyl)phenyl)urea. ¹H NMR (400 MHz, DMSO-d₆): δ=9.22 (brs, 1H), 8.28 (s, 1H), 7.94 (t, J=1.6 Hz, 1H), 7.89-7.83 (m, 3H), 7.77-7.72 (m, 1H), 7.66-7.58 (m, 3H), 7.01 (s, 1H), 6.87 (t, J=5.6 Hz, 1H), 4.37 (d, J=5.6 Hz, 2H). MS: m/z 391.9 (M+H⁺).

Example 384: Synthesis of 1-(4-((4-Chlorophenyl)sulfonyl)phenyl)-3-(oxazol-5-ylmethyl)urea

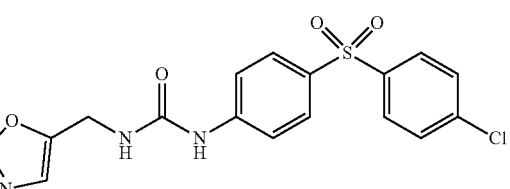

The title compound was prepared using general procedure of 1-((1H-pyrazol-4-yl)methyl)-3-(4-((2-fluorophenyl)sulfonyl)phenyl)urea. ¹H NMR (400 MHz, DMSO-d₆): δ=9.23 (brs, 1H), 8.28 (s, 1H), 7.94-7.88 (m, 2H), 7.82 (d, J=8.8 Hz, 2H), 7.70-7.65 (m, 2H), 7.64-7.58 (m, 2H), 7.01 (s, 1H), 6.88 (t, J=6.0 Hz, 1H), 4.37 (d, J=5.6 Hz, 2H). MS: m/z 391.9 (M+H$^+$).

Example 385: Synthesis of 1-[4-(3-Iodo-benzene-sulfonyl)-phenyl]-3-pyridin-4-ylmethyl-urea

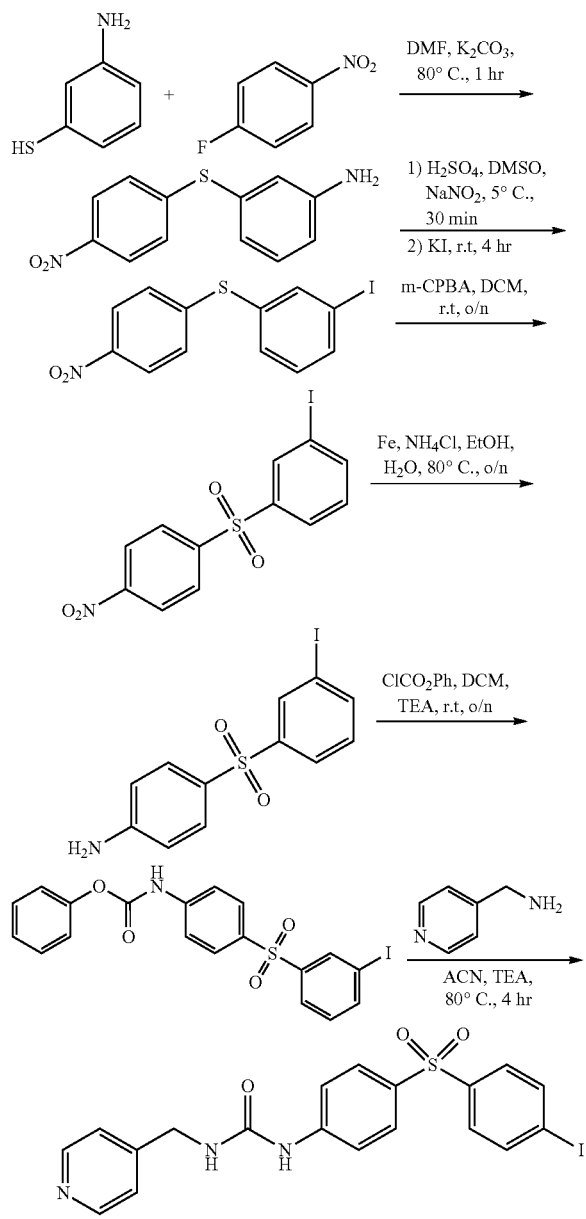

Step 1: To a solution of 3-amino-benzenethiol (1.25 g, 10 mmol) in DMF (30 mL) was added 1-fluoro-4-nitro-benzene (1.69 g, 12 mmol), followed by K$_2$CO$_3$ (2.76 g, 20 mmol). The resulting mixture was stirred at 80° C. overnight. The reaction was monitored by TLC and LC-MS. After completion, the reaction mixture was filtered. The cake was washed with MeOH (20 mL) and dried in vacuum to give a residue, which was purified by a silica gel column (PE/EA=5/1) to afford 3-(4-nitro-phenylsulfanyl)-phenylamine (1.95 g, yield: 81%) as an orange solid.

Step 2: To a solution of 3-(4-nitro-phenylsulfanyl)-phenylamine (1.0 g, 4.0 mmol) in a mixture solvents of aqueous 30% H$_2$SO$_4$ (10 mL) and DMSO (10 mL) was added aqueous NaNO$_2$ (828 mg, 12 mmol) in H$_2$O (2 mL). The resulting mixture was stirred at 5° C. for 0.5 hr. Then aqueous KI (3.98 g, 24 mmol) in H$_2$O (2 mL) was added into the reaction mixture, and the resulting mixture was stirred at room temperature for 5 hrs. The reaction was monitored by LC-MS and TLC. After completion, the mixture was poured into water (10 mL) and extracted with EA (5 mL×4). The combined organic layers were washed with saturated NaSO$_3$ (10 mL), dried over anhydrous sodium sulfate and concentrated in vacuum to give a residue, which was purified by a silica gel column (PE/EA=5/1) to afford (3-iodophenyl)(4-nitrophenyl)sulfane (1 g, yield: 72%) as a yellow solid.

Step 3: To a solution of (3-iodophenyl)(4-nitrophenyl)sulfane (1 g, 2.8 mmol) in DMF (20 mL) was added m-CPBA (963 mg, 5.6 mmol). The resulting mixture was stirred at room temperature overnight. The reaction was monitored by TLC and LC-MS. After completion, the mixture was poured into saturated NaSO$_3$ (10 mL) and extracted with EA (5 mL×4). The combined organic layers were dried over anhydrous sodium sulfate and concentrated in vacuum to give a residue, which was purified by a silica gel column eluting with PE/EA=6/1 to afford 1-iodo-3-((4-nitrophenyl)sulfonyl)benzene (630 mg, yield: 63%) as a brown solid.

Step 4: To a mixture of 1-iodo-3-((4-nitrophenyl)sulfonyl)benzene (630 mg, 1.6 mmol) in EtOH/H$_2$O (30 mL, 5/1) was added iron (454 mg, 8.1 mmol) and NH$_4$Cl (429 mg, 8.1 mmol). The resulting mixture was stirred at 80° C. overnight. The reaction was monitored by LC-MS. After completion, the reaction mixture was filtered and the cake was rinsed with DCM/MeOH (100 mL, 10/1). The combined filtrate was dried in vacuum to give a residue, which was purified by a silica gel column eluting with DCM to afford 4-((3-iodophenyl)sulfonyl)aniline (630 mg, yield: 70%) as white solid. $^1$H NMR (400 MHz, DMSO-d$_6$): δ=8.09 (s, 1H), 7.97 (d, J=8.4 Hz, 1H), 7.83 (d, J=8.4 Hz, 1H), 7.56 (d, J=8.8 Hz, 2H), 7.35 (t, J=8.0 Hz, 1H), 6.62 (d, J=8.8 Hz, 2H), 6.241 (brs, 2H).

Step 5: To a solution of 4-((3-iodophenyl)sulfonyl)aniline (100 mg, 0.28 mmol) in DCM (30 mL) was added phenyl chloroformate (87 mg, 0.58 mmol) and TEA (84 mg, 0.84 mmol). The resulting mixture was stirred at room temperature for 1 hr. The reaction was monitored by TLC. After completion, DCM was removed in vacuum to give a residue, which was purified by a silica gel column (PE/EA=6/1) to afford [4-(3-iodo-benzenesulfonyl)-phenyl]-carbamic acid phenyl ester (130 mg, yield: 97%) as a yellow solid.

Step 6: To a solution of [4-(3-iodo-benzenesulfonyl)-phenyl]-carbamic acid phenyl ester (130 mg, 0.27 mmol) in ACN (20 mL) was added C-pyridin-4-yl-methylamine (34 mg, 0.33 mmol) and TEA (0.5 ml). The resulting mixture was stirred at 80° C. for 4 hr. The reaction was monitored by TLC and LCMS. After completion, the reaction mixture was concentrated in vacuum to give a residue, which was purified by prep-TLC (DCM/MeOH=20/1) to afford 1-[4-(3-iodo-benzenesulfonyl)-phenyl]-3-pyridin-4-ylmethyl-urea (130 mg, yield: 98%) as yellow solid. $^1$H NMR (400 MHz, DMSO-d$_6$): δ=9.34 (d, 1H), 8.50-8.48 (m, 2H), 8.17 (t, J=1.6 Hz, 1H), 8.03-8.01 (m, 1H), 7.91-7.89 (m, 1H), 7.83 (d, J=9.2 Hz, 2H), 7.63 (d, J=6.8 Hz, 2H), 7.38 (t, J=8.0 Hz, 1H), 7.27 (d, J=6.0 Hz, 2H), 6.96 (t, J=6.0 Hz, 1H), 4.33 (d, J=6.0 Hz, 2H). MS: m/z 493.6 (M+H$^+$).

Example 386: Synthesis of 1-[4-(3-Iodo-benzene-sulfonyl)-phenyl]-3-(1H-pyrazol-4-ylmethyl)-urea

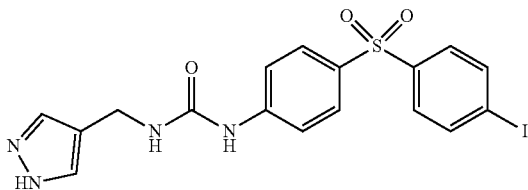 [SMILES: O=C(NCc1cn[nH]c1)Nc1ccc(S(=O)(=O)c2ccc(I)cc2)cc1]

The title compound was prepared using general procedure of 1-[4-(3-iodo-benzenesulfonyl)-phenyl]-3-pyridin-4-ylmethyl-urea. $^1$H NMR (400 MHz, DMSO-d$_6$): δ=12.63 (brs, 1H), 9.04 (brs, 1H), 8.18-8.17 (m, 1H), 8.02 (d, J=8.0 Hz, 1H), 7.91 (d, J=4.0 Hz, 1H), 7.83 (d, J=8.8 Hz, 2H), 7.61 (d, J=9.2 Hz, 2H), 7.53 (brs, 2H), 7.38 (t, J=8.0 Hz, 1H), 6.56 (t, J=5.6 Hz, 1H), 4.15 (d, J=5.2 Hz, 2H). MS: m/z 482.6 (M+H$^+$).

Example 387: Synthesis of 1-Pyridin-4-ylmethyl-3-[4-(toluene-2-sulfonyl)-phenyl]-urea

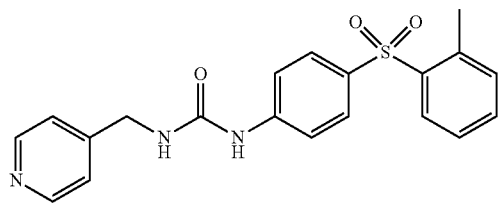 [SMILES: Cc1ccccc1S(=O)(=O)c1ccc(NC(=O)NCc2ccncc2)cc1]

The title compound was prepared using general procedure of 1-(1H-pyrazol-4-ylmethyl)-3-[4-(4-trifluoromethoxy-benzenesulfonyl)-phenyl]-urea. $^1$H NMR (400 MHz, CD$_3$OD): δ=8.46 (d, J=6.0 Hz, 2H), 8.13 (d, J=8.0 Hz, 1H), 7.45 (d, J=8.8 Hz, 2H), 7.61 (d, J=8.8 Hz, 2H) 7.55-7.50 (m, 1H), 7.45-7.41 (m, 1H), 7.38 (d, J=6.0 Hz, 2H), 7.31 (d, J=7.2 Hz, 1H), 4.45 (s, 2H), 2.42 (s, 3H), MS: m/z 381.8 (M+H$^+$).

Example 388: Synthesis of 1-(1H-Pyrazol-4-ylmethyl)-3-[4-(toluene-2-sulfonyl)-phenyl]-urea

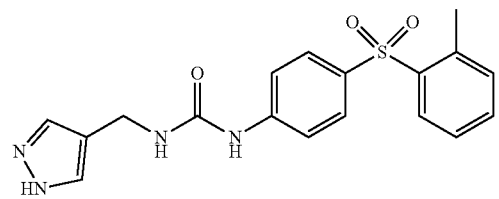 [SMILES: Cc1ccccc1S(=O)(=O)c1ccc(NC(=O)NCc2cn[nH]c2)cc1]

The title compound was prepared using general procedure of 1-(1H-pyrazol-4-ylmethyl)-3-[4-(4-trifluoromethoxy-benzenesulfonyl)-phenyl]-urea. $^1$H NMR (400 MHz, CD$_3$OD): δ=8.13 (d, J=7.6 Hz, 1H), 7.73 (d, J=8.4 Hz, 2H), 7.60-7.51 (m, 5H), 7.45-7.41 (m, 1H), 7.30 (d, J=7.2 Hz, 1H), 4.28 (s, 2H), 2.41 (s, 3H). MS: m/z 370.8 (M+H$^+$).

Example 389: Synthesis of 1-Oxazol-5-ylmethyl-3-[4-(toluene-2-sulfonyl)-phenyl]-urea

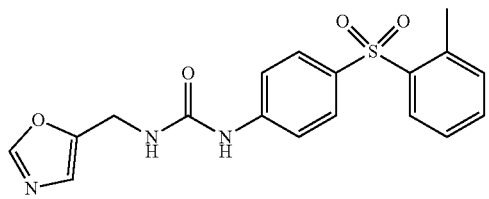 [SMILES: Cc1ccccc1S(=O)(=O)c1ccc(NC(=O)NCc2cnco2)cc1]

The title compound was prepared using general procedure of 1-(1H-pyrazol-4-ylmethyl)-3-[4-(4-trifluoromethoxy-benzenesulfonyl)-phenyl]-urea. $^1$H NMR (400 MHz, CD$_3$OD): δ=8.12-8.10 (m, 2H), 7.73 (d, J=8.8 Hz, 2H), 7.59 (d, J=8.8 Hz, 2H), 7.54-7.50 (m, 1H), 7.44-7.40 (m, 1H), 7.31 (d, J=7.6 Hz, 1H), 7.02 (s, 1H), 4.46 (s, 2H), 2.42 (s, 3H). MS: m/z 371.9 (M+H$^+$).

Example 390: Synthesis of 1-Pyridin-4-ylmethyl-3-[4-(toluene-3-sulfonyl)-phenyl]-urea

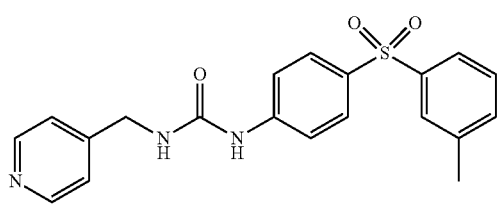 [SMILES: Cc1cccc(S(=O)(=O)c2ccc(NC(=O)NCc3ccncc3)cc2)c1]

The title compound was prepared using general procedure of 1-(1H-pyrazol-4-ylmethyl)-3-[4-(4-trifluoromethoxy-benzenesulfonyl)-phenyl]-urea. $^1$H NMR (400 MHz, DMSO-d$_6$): δ=9.85 (s, 1H), 8.49-8.47 (m, 2H), 7.81 (d, J=8.8 Hz, 2H), 7.71 (s, 2H), 7.63 (d, J=8.8 Hz, 2H), 7.48 (d, J=6.4 Hz, 2H), 7.28 (d, J=6.0 Hz, 2H), 4.34 (d, J=5.6 Hz, 2H), 2.31 (s, 3H). MS: m/z 382.0 (M+H$^+$).

Example 391: Synthesis of 1-(1H-Pyrazol-4-ylmethyl)-3-[4-(toluene-3-sulfonyl)-phenyl]-urea

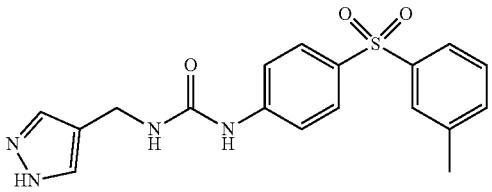 [SMILES: Cc1cccc(S(=O)(=O)c2ccc(NC(=O)NCc3cn[nH]c3)cc2)c1]

The title compound was prepared using general procedure of 1-(1H-pyrazol-4-ylmethyl)-3-[4-(4-trifluoromethoxy-benzenesulfonyl)-phenyl]-urea. $^1$H NMR (400 MHz, CD$_3$OD): δ=7.81 (d, J=9.2 Hz, 2H), 7.72 (d, J=6.8 Hz, 2H), 7.58-7.55 (m, 4H), 7.43 (d, J=4.8 Hz, 2H), 4.28 (s, 2H), 2.39 (s, 3H). MS: m/z 370.9 (M+H$^+$).

Example 392: Synthesis of 1-Oxazol-5-ylmethyl-3-[4-(toluene-3-sulfonyl)-phenyl]-urea

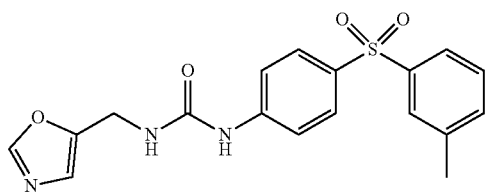 [SMILES: Cc1cccc(S(=O)(=O)c2ccc(NC(=O)NCc3cnco3)cc2)c1]

The title compound was prepared using general procedure of 1-(1H-pyrazol-4-ylmethyl)-3-[4-(4-trifluoromethoxy-benzenesulfonyl)-phenyl]-urea. $^1$H NMR (400 MHz, DMSO-d$_6$): δ=9.76 (br s, 1H), 8.28 (s, 1H), 7.80 (d, J=8.8 Hz, 2H), 7.71-7.67 (m, 2H), 7.62 (d, J=9.2 Hz, 2H), 7.48 (d, J=7.2 Hz, 2H), 7.19 (s, 1H), 7.00 (s, 1H), 4.37 (d, J=5.6 Hz, 2H), 2.37 (s, 3H). MS: m/z 371.9 (M+H$^+$).

Example 393: Synthesis of 1-Pyridin-4-ylmethyl-3-[4-(toluene-4-sulfonyl)-phenyl]-urea

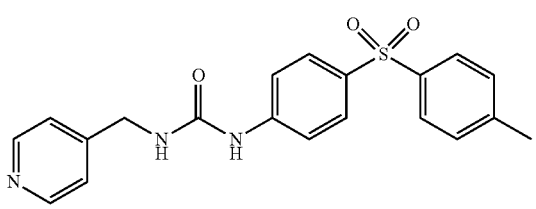 [SMILES: Cc1ccc(S(=O)(=O)c2ccc(NC(=O)NCc3ccncc3)cc2)cc1]

The title compound was prepared using general procedure of 1-(1H-pyrazol-4-ylmethyl)-3-[4-(4-trifluoromethoxy-benzenesulfonyl)-phenyl]-urea. $^1$H NMR (400 MHz, CD$_3$OD): δ=8.47-8.45 (m, 2H), 7.81-7.78 (m, 4H), 7.60-7.57 (m, 2H), 7.39-7.35 (m, 4H), 4.44 (s, 2H), 2.39 (s, 3H). MS: m/z 381.9 (M+H$^+$).

Example 394: Synthesis of 1-(1H-Pyrazol-4-ylmethyl)-3-[4-(toluene-4-sulfonyl)-phenyl]-urea

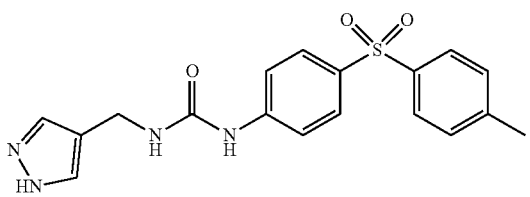 [SMILES: Cc1ccc(S(=O)(=O)c2ccc(NC(=O)NCc3cn[nH]c3)cc2)cc1]

The title compound was prepared using general procedure of 1-(1H-pyrazol-4-ylmethyl)-3-[4-(4-trifluoromethoxy-benzenesulfonyl)-phenyl]-urea. $^1$H NMR (400 MHz, CD$_3$OD): δ=7.80-7.78 (m, 4H), 7.65-7.50 (m, 4H), 7.36 (d, J=8.4 Hz, 2H), 4.28 (s, 2H), 2.39 (s, 3H). MS: m/z 371.0 (M+H$^+$).

Example 395: Synthesis of 1-Oxazol-5-ylmethyl-3-[4-(toluene-4-sulfonyl)-phenyl]-urea

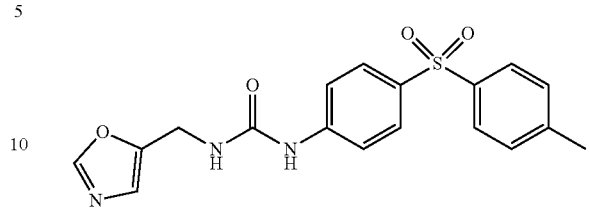

The title compound was prepared using general procedure of 1-(1H-pyrazol-4-ylmethyl)-3-[4-(4-trifluoromethoxy-benzenesulfonyl)-phenyl]-urea. $^1$H NMR (400 MHz, CD$_3$OD): δ=8.13 (s, 1H), 7.81-7.78 (m, 4H), 7.57 (d, J=8.8 Hz, 2H), 7.36 (d, J=8.0 Hz, 2H), 7.02 (s, 1H), 4.46 (s, 2H), 2.39 (s, 3H). MS: m/z 371.9 (M+H$^+$).

Example 396: Synthesis of 1-[4-(4-Cyano-benzenesulfonyl)-phenyl]-3-pyridin-4-ylmethyl-urea

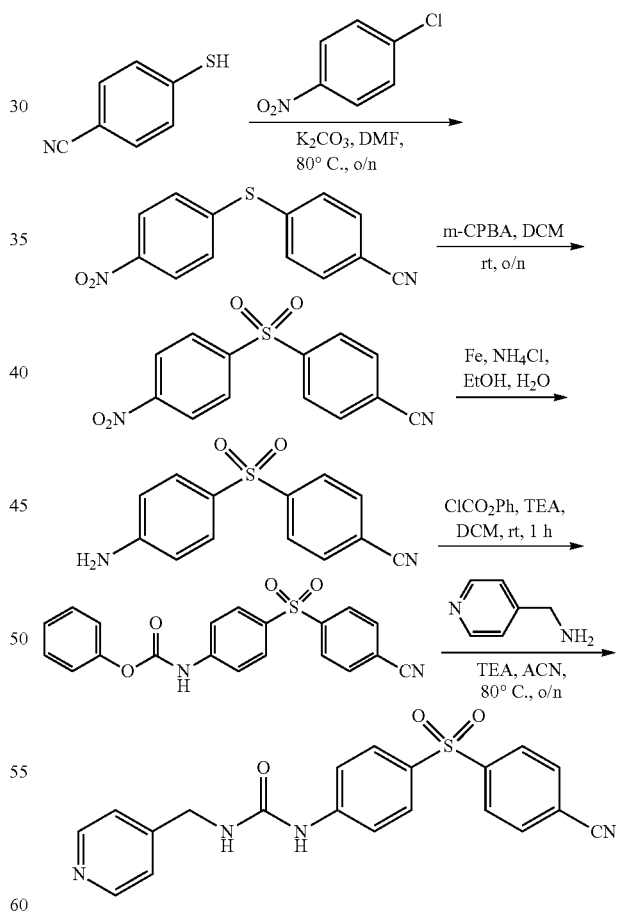

Step 1: To a solution of 4-mercapto-benzonitrile (900 mg, 6.65 mmol) in DMF (30 mL) was added 1-chloro-4-nitrobenzene (1.577 g, 9.9 mmol) and K$_2$CO$_3$ (4.6 g, 33.282 mmol). The reaction mixture was stirred at 80° C. under N$_2$ overnight. The reaction was completed detected by LC-MS. The reaction was quenched with water (40 mL) and extracted with EA (40 mL×3). The combined organic layer was dried over Na$_2$SO$_4$, filtered and concentrated. The crude product was purified by flash column (PE/EA=40/1) to give 4-(4-nitro-phenylsulfanyl)-benzonitrile (1.579 g, yield: 93%) as a yellow solid.

Step 2: To a solution of 4-(4-nitro-phenylsulfanyl)-benzonitrile (1 g, 3.9 mmol) in DCM (20 mL) was added m-CPBA (2.88 g, 11.7 mmol, 70% Wt) at room temperature. The solution was stirred at room temperature overnight. The reaction was completed detected by TLC. The reaction was quenched with Na$_2$SO$_3$ aqueous (10 mL) and extracted with DCM (20 mL×3). The combined organic layer was dried over Na$_2$SO$_4$, filtered and concentrated. The residue was purified by flash column (PE to PE/EA=50/1) to give 4-(4-nitro-benzenesulfonyl)-benzonitrile (1.15 g, yield: 100%) as a white solid.

Step 3: To a solution of 4-(4-nitro-benzenesulfonyl)-benzonitrile (1.15 g, 3.9 mmol) in EtOH (60 mL) and H$_2$O (15 mL) was added Fe (1.089 g, 19.5 mmol) and NH$_4$Cl (1.044 g, 19.5 mmol). The reaction mixture was stirred at 80° C. under N$_2$ overnight. The reaction was completed detected by LC-MS. After filtration via filter paper, the organic layer was concentrated under pressure to give 4-(4-amino-benzenesulfonyl)-benzonitrile (0.985 g, yield: 98%) as a yellow solid. $^1$H NMR (400 MHz, DMSO-d$_6$): δ=8.05-7.99 (m, 4H), 7.58 (d, J=8.8 Hz, 2H), 6.64 (d, J=8.8 Hz, 2H), 6.32 (s, 2H).

Step 4: To a solution of 4-(4-amino-benzenesulfonyl)-benzonitrile (0.985 g, 3.81 mmol) in DCM (60 mL) was added pyridine (1.54 g, 15.25 mmol) and phenyl chloroformate (1.193 g, 7.63 mmol) at 0° C. The reaction mixture was stirred at room temperature for 2 hrs. The reaction was completed detected by TLC. The reaction was concentrated and purified by flash column (PE/EA=2/1) to give [4-(4-cyano-benzenesulfonyl)-phenyl]-carbamic acid phenyl ester (0.826 g, yield: 57%) as a white solid. $^1$H NMR (400 MHz, CDCl$_3$): δ=8.10-8.06 (m, 4H), 7.82 (d, J=8.4 Hz, 2H), 7.64 (d, J=8.4 Hz, 2H), 7.37 (d, J=8.0 Hz, 3H), 7.11 (d, J=7.6 Hz, 3H).

Step 5: To a solution of [4-(4-cyano-benzenesulfonyl)-phenyl]-carbamic acid phenyl ester (150 mg, 0.397 mmol) in ACN (10 mL) was added TEA (120 mg, 0.595 mmol) and c-pyridin-4-yl-methylamine (64.3 mg, 0.595 mmol). The reaction mixture was stirred at 80° C. for 5 hrs. The reaction was completed detected by LC-MS. The reaction was concentrated and purified by prep-HPLC (5-95; NH$_4$HCO$_3$) to give 1-[4-(4-cyano-benzenesulfonyl)-phenyl]-3-pyridin-4-ylmethyl-urea (25 mg, yield: 16%) as a white solid. $^1$H NMR (400 MHz, DMSO-d$_6$): δ=9.39 (s, 1H), 8.50-8.49 (m, 2H), 8.08 (s, 4H), 7.86 (d, J=9.2 Hz, 2H), 7.64 (d, J=9.2 Hz, 2H), 7.27 (d, J=6.0 Hz, 2H), 6.99 (t, J=5.6 Hz, 1H), 4.33 (d, J=6.0 Hz, 2H). MS: m/z 392.9 (M+H$^+$).

Example 397: Synthesis of 1-[4-(4-Cyano-benzenesulfonyl)-phenyl]-3-(1H-pyrazol-4-ylmethyl)-urea

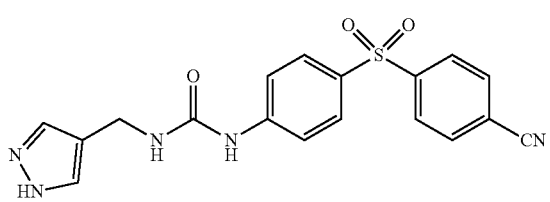 [SMILES: N#Cc1ccc(S(=O)(=O)c2ccc(NC(=O)NCc3cn[nH]c3)cc2)cc1]

The title compound was prepared using general procedure of 1-[4-(4-cyano-benzenesulfonyl)-phenyl]-3-pyridin-4-yl-methyl-urea. $^1$H NMR (400 MHz, CD$_3$OD): δ=7.99 (d, J=8.4 Hz, 2H), 7.82 (d, J=8.4 Hz, 2H), 7.76 (d, J=8.8 Hz, 2H), 7.51 (d, J=8.8 Hz, 4H), 4.18 (s, 2H). MS: m/z 381.9 (M+H$^+$).

Example 398: Synthesis of 1-[4-(4-Cyano-benzenesulfonyl)-phenyl]-3-oxazol-5-ylmethyl-urea

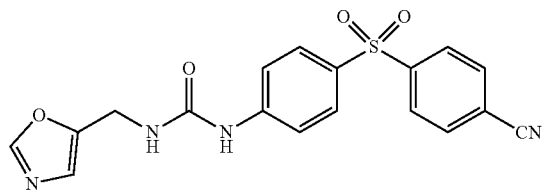 [SMILES: N#Cc1ccc(S(=O)(=O)c2ccc(NC(=O)NCc3cnco3)cc2)cc1]

The title compound was prepared using general procedure of 1-[4-(4-cyano-benzenesulfonyl)-phenyl]-3-pyridin-4-yl-methyl-urea. $^1$H NMR (400 MHz, DMSO-d$_6$): δ=9.78-9.74 (m, 1H), 8.28 (s, 1H), 8.07 (s, 4H), 7.85 (d, J=9.2 Hz, 2H), 7.64 (d, J=8.8 Hz, 2H), 7.17 (s, 1H), 7.00 (s, 1H), 4.37 (d, J=5.6 Hz, 2H). MS: m/z 382.9 (M+H$^+$).

Example 399: Synthesis of 1-Pyridin-4-ylmethyl-3-[4-(2-trifluoromethyl-benzenesulfonyl)-phenyl]-urea

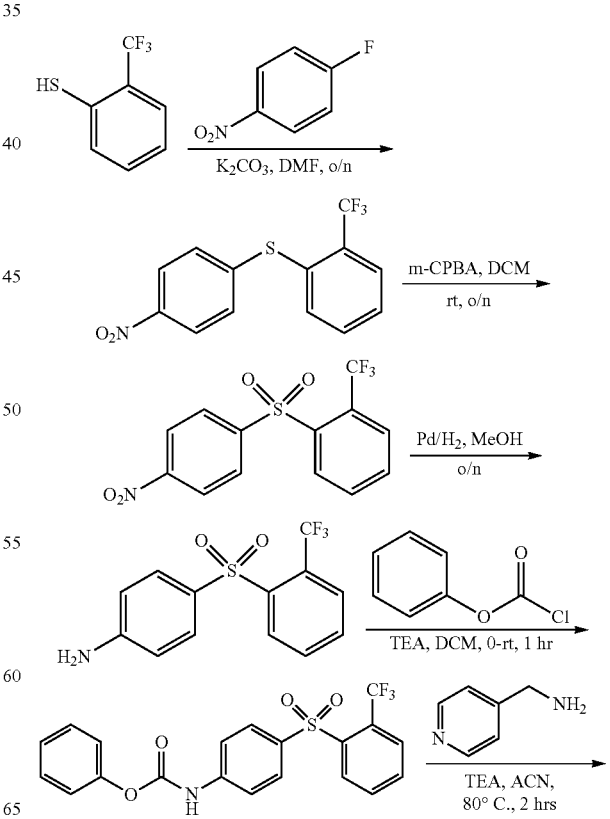

-continued

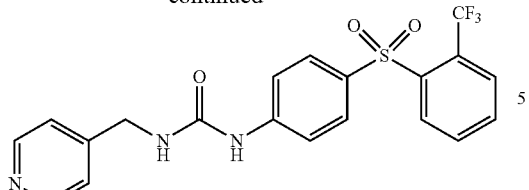

Step 1: To a solution of 2-trifluoromethyl-benzenethiol (534.51 mg, 3.0 mmol) in DMF (20 mL) was added 1-fluoro-4-nitro-benzene (635.0 mg, 4.5 mmol) and $K_2CO_3$ (1.24 g, 9.0 mmol), the mixture was stirred at 80° C. overnight. The reaction was monitored by TLC. After completion, the mixture was concentrated in vacuum to give a residue, which was purified by a silica gel column (PE/EA=50/1) to afford 3-(4-nitro-phenylsulfanyl)-2-trifluoromethyl-benzenee (940 mg, yield: >100%) as a yellow solid. $^1$H NMR (400 MHz, DMSO-d$_6$): δ=8.16 (d, J=9.2 Hz, 2H), 7.99 (d, J=7.6 Hz, 1H), 7.84-7.71 (m, 3H), 7.30 (d, J=8.8 Hz, 2H).

Step 2: To a solution of 3-(4-nitro-phenylsulfanyl)-2-trifluoromethyl-benzenee (940 mg, 3.14 mmol) in DCM (50 mL) was added m-CPBA (1625.5 mg, 9.42 mmol), the mixture was stirred at room temperature overnight. The reaction was monitored by TLC. After completion, the mixture was quenched with saturated aqueous sodium sulfite. The organic layer was concentrated in vacuum to give a residue, which was purified by a silica gel column (PE/EA=5/1) to afford 3-(4-nitro-benzenesulfonyl)-2-trifluoromethyl-benzene (810 mg, 78%) as a white solid.

Step 3: To a solution of 3-(4-nitro-benzenesulfonyl)-2-trifluoromethyl-benzene (810 mg, 2.4 mmol) in MeOH (30 mL) was added Pd/C (10% wet, 93.6 mg). The reaction mixture was stirred at room temperature under $H_2$ (1 atm) overnight. Pd/C was filtered off and the filtrate was concentrated to dryness in vacuum. The residue was purified by flash to give 4-(2-trifluoromethyl-benzenesulfonyl)-phenylamine (528.3 mg, yield: 71.1%) as a white solid.

Step 4: To a solution of 4-(2-trifluoromethyl-benzenesulfonyl)-phenylamine (170 mg, 0.56 mmol) in DCM (30 mL) was added phenyl chloroformate (175.35 mg, 1.12 mmol) and TEA (113.34 mg, 1.12 mmol), the mixture was stirred at 0° C. for 1 hr. The reaction was monitored by TLC. After completion, the mixture was concentrated in vacuum to give a residue, which was purified by a silica gel column (PE/EA=3/1) to afford [4-(2-trifluoromethyl-benzenesulfonyl)-phenyl]-carbamic acid phenyl ester (220 mg, 92.6%) as a white solid.

Step 5: To a solution of [4-(2-trifluoromethyl-benzenesulfonyl)-phenyl]-carbamic acid phenyl ester (50 mg, 0.12 mmol) in ACN (20 mL) was added c-pyridin-4-yl-methyl-amine (25.92 mg, 0.24 mmol) and TEA (24.29 mg, 0.24 mmol), the mixture was stirred at 80° C. for 3 hrs. The reaction was monitored by LCMS. After completion, the mixture was concentrated in vacuum to give a residue, which was purified by prep-HPLC to give 1-pyridin-4-ylmethyl-3-[4-(2-trifluoromethyl-benzenesulfonyl)-phenyl]-urea (16.1 mg, yield: 31.1%) as a white solid. $^1$H NMR (400 MHz, DMSO-d$_6$): δ=9.38 (s, 1H), 8.49 (d, J=6.0 Hz, 2H), 8.33 (d, J=7.2 Hz, 1H), 8.01-7.90 (m, 3H), 7.74 (d, J=8.8 Hz, 2H), 7.62 (d, J=9.2 Hz, 2H), 7.27 (d, J=6.0 Hz, 2H), 6.96 (t, J=5.6 Hz, 1H), 4.33 (d, J=6.4 Hz, 2H). MS: m/z 435.9 (M+H$^+$).

Example 400: Synthesis of 1-(1H-Pyrazol-4-ylmethyl)-3-[4-(2-trifluoromethyl-benzenesulfonyl)-phenyl]-urea

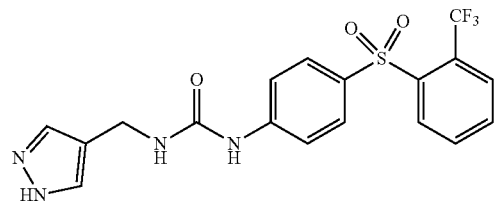 [SMILES: O=C(NCc1cn[nH]c1)Nc1ccc(S(=O)(=O)c2ccccc2C(F)(F)F)cc1]

The title compound was prepared using general procedure of 1-pyridin-4-ylmethyl-3-[4-(2-trifluoromethyl-benzenesulfonyl)-phenyl]-urea. $^1$H NMR (400 MHz, DMSO-d6): δ=12.62 (s, 1H), 9.06 (s, 1H), 8.32 (d, J=7.6 Hz, 1H), 8.02-7.86 (m, 3H), 7.73 (d, J=9.2 Hz, 2H), 7.60 (d, J=9.2 Hz, 2H), 7.58-7.42 (m, 2H), 6.58 (t, J=5.2 Hz, 1H), 4.15 (d, J=5.6 Hz, 2H). MS: m/z 424.9 (M+H$^+$).

Example 401: Synthesis of 1-Oxazol-5-ylmethyl-3-[4-(2-trifluoromethyl-benzenesulfonyl)-phenyl]-urea

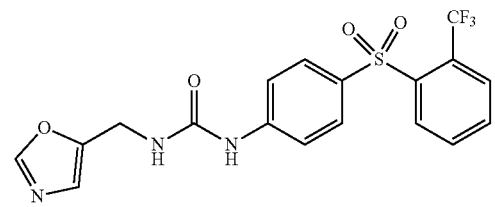 [SMILES: O=C(NCc1cnco1)Nc1ccc(S(=O)(=O)c2ccccc2C(F)(F)F)cc1]

The title compound was prepared using general procedure of 1-pyridin-4-ylmethyl-3-[4-(2-trifluoromethyl-benzenesulfonyl)-phenyl]-urea. $^1$H NMR (400 MHz, DMSO-d$_6$): δ=9.76 (s, 1H), 8.31 (d, J=7.6 Hz, 1H), 8.28 (s, 1H), 8.02-7.87 (m, 3H), 7.74 (d, J=8.8 Hz, 1H), 7.62 (d, J=8.8 Hz, 2H), 7.18 (t, J=5.2 Hz, 1H), 7.01 (s, 1H), 4.37 (d, J=5.6 Hz, 2H). MS: m/z 425.9 (M+H$^+$).

Example 402: Synthesis of 1-(Pyridin-4-ylmethyl)-3-(4-((3-(trifluoromethyl)phenyl)sulfonyl)phenyl) urea

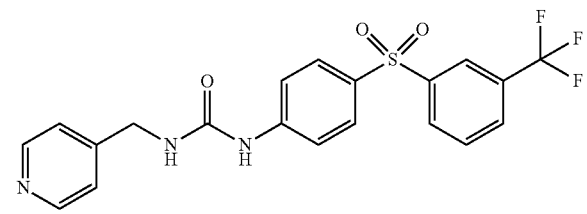 [SMILES: O=C(NCc1ccncc1)Nc1ccc(S(=O)(=O)c2cccc(C(F)(F)F)c2)cc1]

The title compound was prepared using general procedure of 1-pyridin-4-ylmethyl-3-[4-(2-trifluoromethyl-benzenesulfonyl)-phenyl]-urea. $^1$H NMR (400 MHz, DMSO-d$_6$): δ=9.37 (br s, 1H), 8.49 (d, J=5.6 Hz, 2H), 8.23 (d, J=8.0 Hz, 1H), 8.18 (s, 1H), 8.07 (d, J=7.6 Hz, 1H), 7.95-7.82 (m, 3H), 7.65 (d, J=8.8 Hz, 2H), 7.27 (d, J=6.0 Hz, 2H), 6.98 (t, J=5.6 Hz, 1H), 4.33 (d, J=6.0 Hz, 2H). MS: m/z 435.9 (M+H$^+$).

Example 403: Synthesis of 1-((1H-Pyrazol-4-yl)methyl)-3-(4-((3-(trifluoromethyl)phenyl)sulfonyl)phenyl)urea

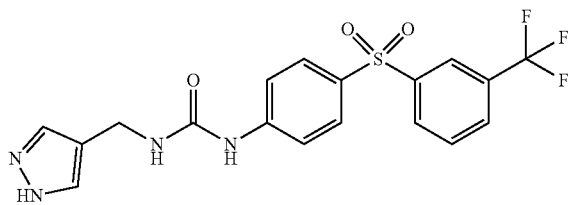 [SMILES: O=C(NCc1cn[nH]c1)Nc1ccc(S(=O)(=O)c2cccc(C(F)(F)F)c2)cc1]

The title compound was prepared using general procedure of 1-pyridin-4-ylmethyl-3-[4-(2-trifluoromethyl-benzenesulfonyl)-phenyl]-urea. $^1$H NMR (400 MHz, DMSO-d$_6$): δ=12.64 (br s, 1H), 9.06 (s, 1H), 8.23 (d, J=8.0 Hz, 1H), 8.18 (s, 1H), 8.07 (d, J=8.0 Hz, 1H), 7.93-7.83 (m, 3H), 7.62 (d, J=9.2 Hz, 2H), 7.60-7.41 (m, 2H), 6.58 (t, J=5.6 Hz, 1H), 4.15 (d, J=5.6 Hz, 2H). MS: m/z 424.9 (M+H$^+$).

Example 404: Synthesis of 1-(Oxazol-5-ylmethyl)-3-(4-((3-(trifluoromethyl)phenyl)sulfonyl)phenyl)urea

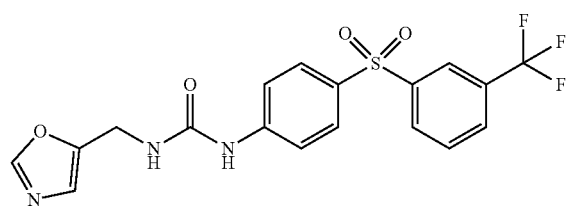 [SMILES: O=C(NCc1cnco1)Nc1ccc(S(=O)(=O)c2cccc(C(F)(F)F)c2)cc1]

The title compound was prepared using general procedure of 1-pyridin-4-ylmethyl-3-[4-(2-trifluoromethyl-benzenesulfonyl)-phenyl]-urea. $^1$H NMR (400 MHz, DMSO-d$_6$): δ=9.25 (br s, 1H), 8.28 (s, 1H), 8.23 (d, J=8.4 Hz, 1H), 8.18 (s, 1H), 8.07 (d, J=8.0 Hz, 1H), 7.95-7.83 (m, 3H), 7.63 (d, J=9.2 Hz, 2H), 7.01 (s, 1H), 6.90 (t, J=5.6 Hz, 1H), 4.37 (d, J=5.2 Hz, 2H). MS: m/z 425.9 (M+H$^+$).

Example 405: Synthesis of 1-(Pyridin-4-ylmethyl)-3-(4-((4-(trifluoromethyl)phenyl)sulfonyl)phenyl)urea

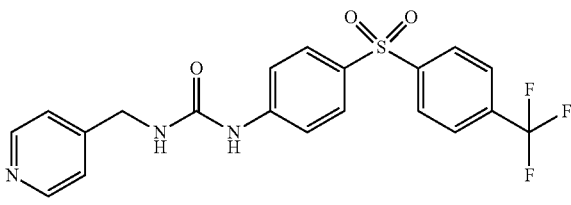 [SMILES: O=C(NCc1ccncc1)Nc1ccc(S(=O)(=O)c2ccc(C(F)(F)F)cc2)cc1]

The title compound was prepared using general procedure of 1-pyridin-4-ylmethyl-3-[4-(2-trifluoromethyl-benzenesulfonyl)-phenyl]-urea. $^1$H NMR (400 MHz, DMSO-d$_6$): δ=9.38 (br s, 1H), 8.50 (dd, J=4.8, 1.6 Hz, 2H), 8.12 (d, J=8.0 Hz, 2H), 7.98 (d, J=8.4 Hz, 2H), 7.86 (d, J=8.8 Hz, 2H), 7.65 (d, J=8.8 Hz, 2H), 7.27 (d, J=6.0 Hz, 2H), 6.98 (t, J=5.6 Hz, 1H), 4.33 (d, J=6.0 Hz, 2H). MS: m/z 435.9 (M+H$^+$).

Example 406: Synthesis of 1-((1H-Pyrazol-4-yl)methyl)-3-(4-((4-(trifluoromethyl)phenyl)sulfonyl)phenyl)urea

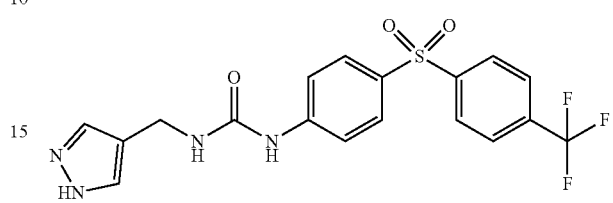

The title compound was prepared using general procedure of 1-pyridin-4-ylmethyl-3-[4-(2-trifluoromethyl-benzenesulfonyl)-phenyl]-urea. $^1$H NMR (400 MHz, DMSO-d$_6$): δ=12.62 (br s, 1H), 9.10 (s, 1H), 8.15 (d, J=8.4 Hz, 2H), 7.98 (d, J=8.8 Hz, 2H), 7.84 (d, J=9.2 Hz, 2H), 7.62 (d, J=9.2 Hz, 2H), 7.59-7.37 (m, 2H), 6.59 (t, J=5.6 Hz, 1H), 4.15 (d, J=5.6 Hz, 2H). MS: m/z 424.9 (M+H$^+$).

Example 407: Synthesis of 1-(Oxazol-5-ylmethyl)-3-(4-((4-(trifluoromethyl)phenyl)sulfonyl)phenyl)urea

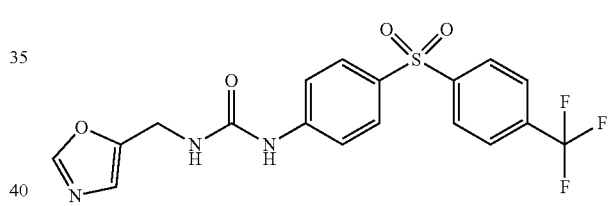

The title compound was prepared using general procedure of 1-pyridin-4-ylmethyl-3-[4-(2-trifluoromethyl-benzenesulfonyl)-phenyl]-urea. $^1$H NMR (400 MHz, DMSO-d$_6$): δ=9.24 (br s, 1H), 8.28 (s, 1H), 8.12 (d, J=8.4 Hz, 2H), 7.98 (d, J=8.4 Hz, 2H), 7.86 (d, J=8.8 Hz, 2H), 7.64 (d, J=8.8 Hz, 2H), 7.01 (s, 1H), 6.88 (t, J=5.6 Hz, 1H), 4.37 (d, J=5.6 Hz, 2H). MS: m/z 425.9 (M+H$^+$).

Example 408: Synthesis of 1-(4-((2-Methoxyphenyl)sulfonyl)phenyl)-3-(oxazol-5-ylmethyl)urea

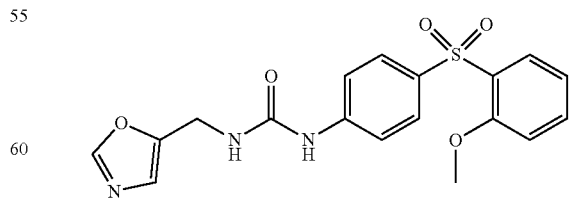

The title compound was prepared using general procedure of 1-pyridin-4-ylmethyl-3-[4-(2-trifluoromethyl-benzenesulfonyl)-phenyl]-urea. $^1$H NMR (400 MHz, DMSO-d$_6$): δ=9.14 (brs, 1H), 8.28 (s, 1H), 7.96 (dd, J=8.4, 1.6 Hz, 1H), 7.75 (d, J=8.8 Hz, 2H), 7.64 (t, J=8.4 Hz, 1H), 7.57 (d, J=8.8 Hz, 2H), 7.15 (t, J=8.0 Hz, 2H), 7.01 (s, 1H), 6.83 (t, J=5.6 Hz, 1H), 4.37 (d, J=5.6 Hz, 2H), 3.75 (s, 3H). MS: m/z 387.9 (M+H⁺).

Example 409: Synthesis of 1-[4-(3-Methoxy-benzenesulfonyl)-phenyl]-3-oxazol-5-ylmethyl-urea

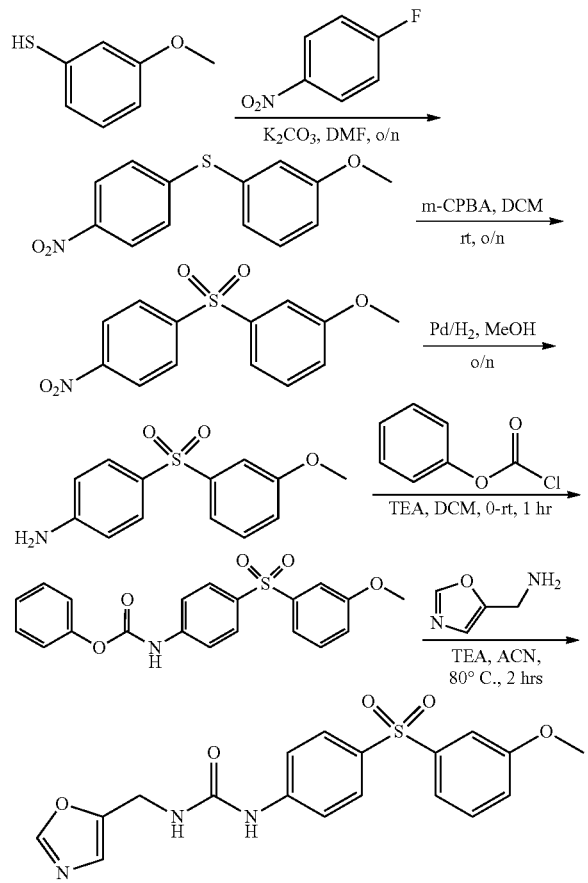

Step 1: To a solution of 3-methoxy-benzenethiol (420.6 mg, 3.0 mmol) in DMF (20 mL) was added 1-fluoro-4-nitro-benzene (635.0 mg, 4.5 mmol) and K₂CO₃ (1.24 g, 9.0 mmol), the mixture was stirred at 80° C. overnight. The reaction was monitored by TLC. After completion, the mixture was concentrated in vacuum to give a residue, which was purified by a silica gel column (PE/EA=30/1) to afford 1-methoxy-3-(4-nitro-phenylsulfanyl)-benzene (710 mg, yield: 90.5%) as a white solid. ¹H NMR (400 MHz, DMSO-d₆): δ=8.15 (d, J=9.2 Hz, 2H), 7.46 (t, J=8.0 Hz, 2H), 7.32 (d, J=9.2 Hz, 2H), 7.16-7.09 (m, 3H), 3.78 (s, 3H).

Step 2: To a solution of 1-methoxy-3-(4-nitro-phenylsulfanyl)-benzene (710 mg, 2.72 mmol) in DCM (50 mL) was added m-CPBA (1.41 mg, 8.16 mmol), the mixture was stirred at room temperature overnight. The reaction was monitored by TLC. After completion, the mixture was quenched with saturated aqueous sodium sulfite, the organic layer was concentrated in vacuum to give a residue, which was purified by a silica gel column (PE/EA=10/1) to afford 1-methoxy-3-(4-nitro-benzenesulfonyl)-benzene (0.71 g, 89.2%) as a white solid.

Step 3: To a solution of 1-methoxy-3-(4-nitro-benzenesulfonyl)-benzene (250 mg, 0.85 mmol) in MeOH (20 mL) was added Pd/C (10% wet, 30 mg), the reaction mixture was stirred at room temperature under H₂ (1 atm) overnight. Pd/C was filtered off and the filtrate was concentrated to dryness in vacuum. The residue was purified by flash to give 4-(3-methoxy-benzenesulfonyl)-phenylamine (210 mg, yield: 93.6%) as a white solid. ¹H NMR (400 MHz, DMSO-d₆): δ=7.55 (d, J=8.8 Hz, 2H), 7.47 (t, J=8.0 Hz, 1H), 7.40-7.35 (m, 1H), 7.31-7.28 (m, 1H), 7.19-7.14 (m, 1H), 6.60 (d, J=8.8 Hz, 2H), 6.19 (s, 2H), 3.80 (s, 3H).

Step 4: To a solution of 4-(3-methoxy-benzenesulfonyl)-phenylamine (210 mg, 0.79 mmol) in DCM (30 mL) was added phenyl chloroformate (247.38 mg, 1.58 mmol) and TEA (159.58 mg, 1.58 mmol), the mixture was stirred at 0° C. for 1 hr. The reaction was monitored by TLC. After completion, the mixture was concentrated in vacuum to give a residue, which was purified by a silica gel column (PE/EA=3/1) to afford [4-(3-methoxy-benzenesulfonyl)-phenyl]-carbamic acid phenyl ester (290 mg, 94%) as a white solid.

Step 5: To a solution of [4-(3-methoxy-benzenesulfonyl)-phenyl]-carbamic acid phenyl ester (80 mg, 0.21 mmol) in ACN (25 mL) was added c-oxazol-5-yl-methylamine (56.52 mg, 0.42 mmol) and TEA (42.5 mg, 0.42 mmol), the mixture was stirred at 80° C. overnight. The reaction was monitored by LCMS. After completion, the mixture was concentrated in vacuum to give a residue, the residue was purified by prep-HPLC to give 1-[4-(3-methoxy-benzenesulfonyl)-phenyl]-3-oxazol-5-ylmethyl-urea (12.1 mg, yield: 14.9%) as a white solid. ¹H NMR (400 MHz, DMSO-d₆): δ=9.19 (s, 1H), 8.28 (s, 1H), 7.82 (d, J=8.8 Hz, 2H), 7.59 (d, J=8.8 Hz, 2H), 7.51 (t, J=7.6 Hz, 1H), 7.46-7.41 (m, 1H), 7.39-7.35 (m, 1H), 7.24-7.19 (m, 1H), 7.00 (s, 1H), 6.86 (t, J=6.0 Hz, 1H), 4.36 (d, J=5.6 Hz, 2H), 3.81 (s, 3H). MS: m/z 388.1 (M+H⁺).

Example 410: Synthesis of 1-[4-(4-Methoxy-benzenesulfonyl)-phenyl]-3-oxazol-5-ylmethyl-urea

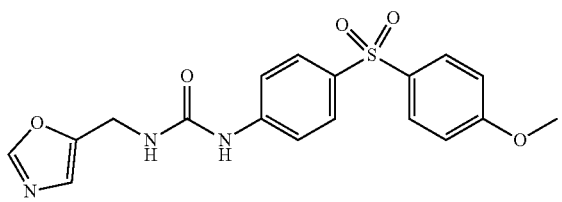 [SMILES: COc1ccc(S(=O)(=O)c2ccc(NC(=O)NCc3cnco3)cc2)cc1]

The title compound was prepared using general procedure of 1-pyridin-4-ylmethyl-3-[4-(2-trifluoromethyl-benzenesulfonyl)-phenyl]-urea. ¹H NMR (400 MHz, DMSO-d₆): δ=9.14 (s, 1H), 8.28 (s, 1H), 7.82 (d, J=8.8 Hz, 2H), 7.76 (d, J=8.8 Hz, 2H), 7.58 (d, J=8.8 Hz, 2H), 7.10 (d, J=9.2 Hz, 2H), 7.00 (s, 1H), 6.83 (t, J=6.0 Hz, 1H), 4.36 (d, J=5.6 Hz, 2H), 3.81 (s, 3H). MS: m/z 387.9 (M+H⁺).

Example 411: Synthesis of 1-Pyridin-4-ylmethyl-3-[4-(2-trifluoromethoxy-benzenesulfonyl)-phenyl]-urea

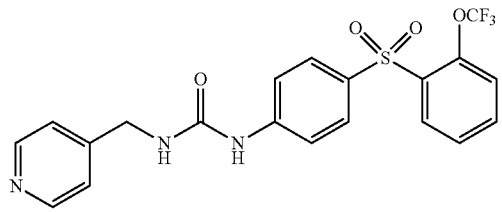 [SMILES: O=C(NCc1ccncc1)Nc1ccc(S(=O)(=O)c2ccccc2OC(F)(F)F)cc1]

The title compound was prepared using general procedure of 1-[4-(3-methoxy-benzenesulfonyl)-phenyl]-3-oxazol-5-ylmethyl-urea. $^1$H NMR (400 MHz, CD$_3$OD): δ=8.47-8.45 (m, 2H), 8.22 (d, J=1.2 Hz, 1H), 7.82-7.79 (m, 2H), 7.79-7.75 (m, 1H), 7.63-7.56 (m, 3H), 7.40-7.35 (m, 3H), 4.45 (s, 2H). MS: m/z 451.9 (M+H$^+$).

Example 412: Synthesis of 1-(1H-Pyrazol-4-ylmethyl)-3-[4-(2-trifluoromethoxy-benzenesulfonyl)-phenyl]-urea

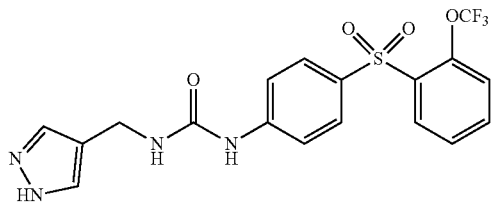 [SMILES: O=C(NCc1cn[nH]c1)Nc1ccc(S(=O)(=O)c2ccccc2OC(F)(F)F)cc1]

The title compound was prepared using general procedure of 1-[4-(3-methoxy-benzenesulfonyl)-phenyl]-3-oxazol-5-ylmethyl-urea. $^1$H NMR (400 MHz, CD$_3$OD): δ=8.24-8.22 (m, 1H), 7.80-7.67 (m, 5H), 7.60-7.54 (m, 3H), 7.43 (d, J=9.2 Hz, 1H), 4.29 (s, 2H). MS: m/z 440.9 (M+H$^+$).

Example 413: Synthesis of 1-Oxazol-5-ylmethyl-3-[4-(4-trifluoromethoxy-benzenesulfonyl)-phenyl]-urea

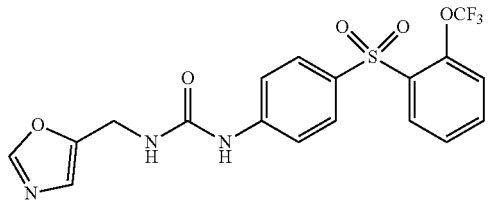

The title compound was prepared using general procedure of 1-[4-(3-methoxy-benzenesulfonyl)-phenyl]-3-oxazol-5-ylmethyl-urea. $^1$H NMR (400 MHz, CD$_3$OD): δ=8.23 (dd, J=8 Hz, 1.6 Hz, 1H), 8.13 (s, 1H), 7.81-7.79 (m, 2H), 7.75-7.71 (m, 1H), 7.63-7.57 (m, 2H), 7.57-7.53 (m, 1H), 7.42-7.40 (m, 1H), 7.04 (s, 1H), 4.47 (s, 2H). MS: m/z 441.9 (M+H$^+$).

Example 414: Synthesis of 1-Pyridin-4-ylmethyl-3-[4-(3-trifluoromethoxy-benzenesulfonyl)-phenyl]-urea

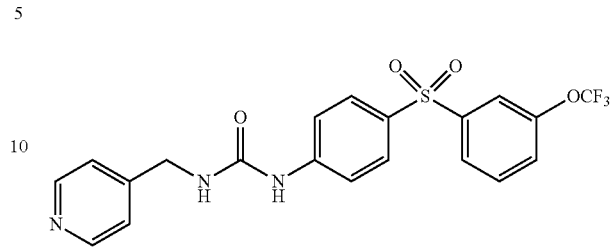

The title compound was prepared using general procedure of 1-[4-(3-methoxy-benzenesulfonyl)-phenyl]-3-oxazol-5-ylmethyl-urea. $^1$H NMR (400 MHz, CD$_3$OD): δ=8.46 (d, J=5.6 Hz, 2H), 7.93-7.81 (m, 4H), 7.69-7.61 (m, 3H), 7.55 (d, J=8.4 Hz, 1H), 7.38 (d, J=5.6 Hz, 2H), 4.44 (s, 2H). MS: m/z 451.9 (M+H$^+$).

Example 415: Synthesis of 1-(1H-Pyrazol-4-ylmethyl)-3-[4-(3-trifluoromethoxy-benzenesulfonyl)-phenyl]-urea

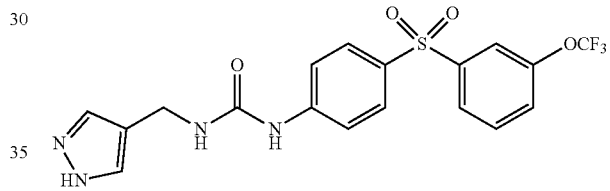

The title compound was prepared using general procedure of 1-[4-(3-methoxy-benzenesulfonyl)-phenyl]-3-oxazol-5-ylmethyl-urea. $^1$H NMR (400 MHz, CD$_3$OD): δ=7.93-7.90 (m, 1H), 7.87-7.80 (m, 5H), 7.69-7.65 (m, 1H), 7.62-7.55 (m, 2H), 7.54 (d, J=7.2 Hz, 1H), 4.31 (s, 2H). MS: m/z 440.9 (M+H$^+$).

Example 416: Synthesis of 1-Oxazol-5-ylmethyl-3-[4-(3-trifluoromethoxy-benzenesulfonyl)-phenyl]-urea

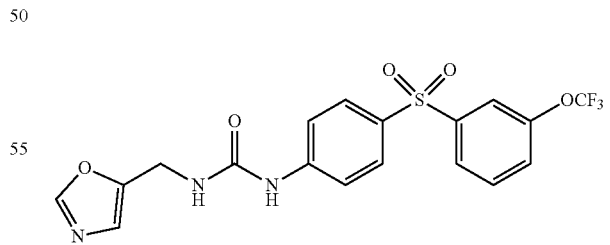

The title compound was prepared using general procedure of 1-[4-(3-methoxy-benzenesulfonyl)-phenyl]-3-oxazol-5-ylmethyl-urea. $^1$H NMR (400 MHz, CD$_3$OD): δ=8.13 (s, 1H), 7.93 (d, J=8.4 Hz, 1H), 7.86 (d, J=8.8 Hz, 2H), 7.81 (s, 1H), 7.69-7.65 (m, 1H), 7.62 (d, J=8.8 Hz, 2H), 7.55 (d, J=8.4 Hz, 1H), 7.02 (s, 1H), 4.46 (s, 2H). MS: m/z 441.9 (M+H$^+$).

Example 417: Synthesis of 1-Pyridin-4-ylmethyl-3-[4-(4-trifluoromethoxy-benzenesulfonyl)-phenyl]-urea

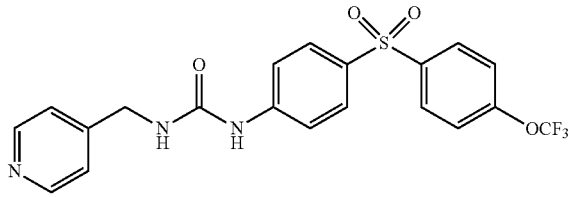 [SMILES: O=C(NCc1ccncc1)Nc1ccc(S(=O)(=O)c2ccc(OC(F)(F)F)cc2)cc1]

The title compound was prepared using general procedure of 1-[4-(3-methoxy-benzenesulfonyl)-phenyl]-3-oxazol-5-ylmethyl-urea. $^1$H NMR (400 MHz, CD$_3$OD): δ=8.46 (d, J=4.8 Hz, 2H), 8.04 (dd, J=6.8, 2.0 Hz, 2H), 7.84 (dd, J=6.8, 2.0 Hz, 2H), 7.62 (dd, J=7.2, 1.6 Hz, 2H), 7.46 (d, J=8.4 Hz, 2H), 7.38 (d, J=6.0 Hz, 2H) 4.44 (s, 2H). MS: m/z 451.7 (M+H$^+$).

Example 418: Synthesis of 1-(1H-Pyrazol-4-ylmethyl)-3-[4-(4-trifluoromethoxy-benzenesulfonyl)-phenyl]-urea

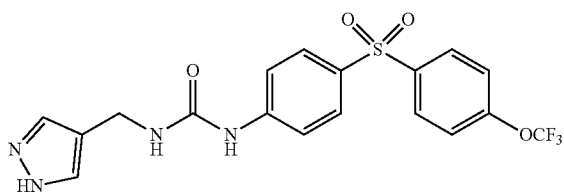 [SMILES: O=C(NCc1cn[nH]c1)Nc1ccc(S(=O)(=O)c2ccc(OC(F)(F)F)cc2)cc1]

The title compound was prepared using general procedure of 1-[4-(3-methoxy-benzenesulfonyl)-phenyl]-3-oxazol-5-ylmethyl-urea. $^1$H NMR (400 MHz, CD$_3$OD): δ=8.04 (d, J=8.4 Hz, 2H), 7.84 (d, J=8.8 Hz, 2H), 7.63-7.58 (m, 4H), 7.46 (d, J=8.4 Hz, 2H), 4.28 (s, 2H). MS: m/z 440.7 (M+H$^+$).

Example 419: Synthesis of 1-Oxazol-5-ylmethyl-3-[4-(4-trifluoromethoxy-benzenesulfonyl)-phenyl]-urea

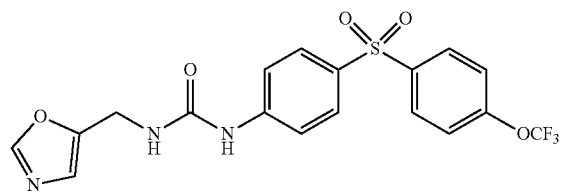 [SMILES: O=C(NCc1cnco1)Nc1ccc(S(=O)(=O)c2ccc(OC(F)(F)F)cc2)cc1]

The title compound was prepared using general procedure of 1-[4-(3-methoxy-benzenesulfonyl)-phenyl]-3-oxazol-5-ylmethyl-urea. $^1$H NMR (400 MHz, CD$_3$OD): δ=8.13 (s, 1H), 8.04 (d, J=8.8 Hz, 2H), 7.85 (d, J=9.2 Hz, 2H), 7.61 (d, J=8.8 Hz, 2H), 7.46 (d, J=8.0 Hz, 2H), 7.02 (s, 1H), 7.02 (s, 2H), 4.46 (s, 2H). MS: m/z 441.9 (M+H$^+$).

Example 420: Synthesis of 1-[4-(2,4-Difluoro-benzenesulfonyl)-phenyl]-3-pyridin-4-ylmethyl-urea

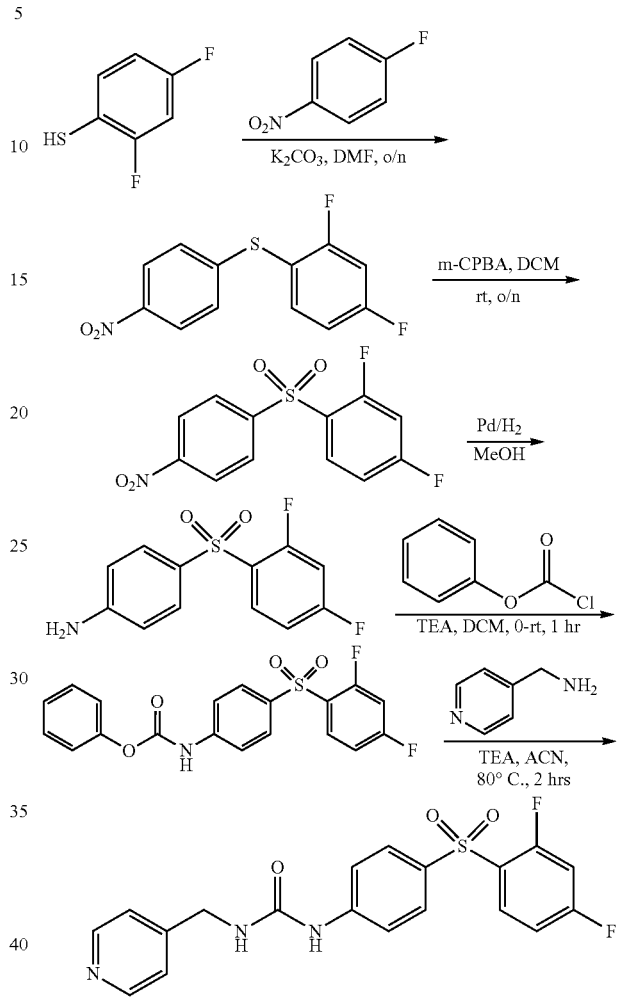

Step 1: To a solution of 2,4-difluoro-benzenethiol (584.6 mg, 4.0 mmol) in DMF (30 mL) was added 1-fluoro-4-nitrobenzene (846.59 mg, 6.0 mmol) and K$_2$CO$_3$ (1.66 g, 12.0 mmol), the mixture was stirred at 80° C. overnight. The reaction was monitored by TLC. After completion, the mixture was concentrated in vacuum to give a residue, which was purified by a silica gel column (PE/EA=50/1) to afford 2,4-difluoro-1-(4-nitro-phenylsulfanyl)-benzene (961 mg, yield: 91.3%) as a white solid. $^1$H NMR (400 MHz, CDCl$_3$): δ=8.09 (d, J=8.8 Hz, 2H), 7.67-7.55 (m, 1H), 7.16 (d, J=8.8 Hz, 2H), 7.05-6.96 (m, 2H).

Step 2: To a solution of 2,4-difluoro-1-(4-nitro-phenylsulfanyl)-benzene (961 mg, 3.59 mmol) in DCM (40 mL) was added m-CPBA (2186.4 mg, 10.77 mmol), the mixture was stirred at room temperature overnight. The reaction was monitored by TLC. After completion, the mixture was quenched with saturated aqueous sodium sulfite, the organic layer was concentrated in vacuum to give a residue, which was purified by a silica gel column (PE:EA=10:1) to afford 2,4-difluoro-1-(4-nitro-benzenesulfonyl)-benzene (961 mg, 89.3%) as a white solid. $^1$H NMR (400 MHz, CDCl$_3$): δ=8.38 (d, J=8.8 Hz, 2H), 8.19 (d, J=9.2 Hz, 2H), 8.18-8.10 (m, 1H), 7.15-7.07 (m, 1H), 6.94-6.86 (m, 1H).

Step 3: To a solution of 1,3-difluoro-5-(4-nitro-benzenesulfonyl)-benzene (300 mg, 1.0 mmol) in MeOH (30 mL), was added Pd/C (10% wet, 30 mg). The reaction mixture was stirred at room temperature under H$_2$ (1 atm) overnight. Pd/C was filtered off and the filtrate was concentrated to dryness in vacuum. The residue was purified by flash to give 4-(2,4-dfluoro-benzenesulfonyl)-phenylamine (215 mg, yield: 79.7%) as a white solid.

Step 4: To a solution of 4-(2,4-dfluoro-benzenesulfonyl)-phenylamine (215 mg, 0.79 mmol) in DCM (40 mL) was added phenyl chloroformate (247.4 mg, 1.58 mmol) and TEA (159.89 mg, 1.58 mmol), the mixture was stirred at 0° C. for 1 hr. The reaction was monitored by TLC. After completion, the mixture was concentrated in vacuum to give a residue, which was purified by a silica gel column (PE/EA=3/1) to afford [4-(2,4-difluoro-benzenesulfonyl)-phenyl]-carbamic acid phenyl ester (302 mg, yield: 97%) as a white solid.

Step 5: To a solution of [4-(2,4-difluoro-benzenesulfonyl)-phenyl]-carbamic acid phenyl ester (50 mg, 0.13 mmol) in ACN (30 mL) was added c-pyridin-4-yl-methylamine (28.12 mg, 0.26 mmol) and TEA (26.31 mg, 0.26 mmol), the mixture was stirred at 80° C. for 3 hrs. The reaction was monitored by LCMS. After completion, the mixture was concentrated in vacuum to give a residue, the residue was purified by prep-HPLC to give 1-[4-(2,4-difluoro-benzenesulfonyl)-phenyl]-3-pyridin-4-ylmethyl-urea (8 mg, yield: 1.5%) as a white solid. $^1$H NMR (400 MHz, DMSO-d$_6$) δ=10.23 (s, 1H), 8.49 (J=6.0 Hz, 2H), 8.12-8.03 (m, 1H), 8.79 (d, J=8.4 Hz, 2H), 7.66 (d, J=8.8 Hz, 2H), 7.62-7.46 (m, 2H), 7.40-7.33 (m, 1H), 7.28 (d, J=9.2 Hz, 2H), 4.34 (d, J=6.0 Hz, 2H). MS: m/z 403.9 (M+H$^+$).

Example 421: Synthesis of 1-[4-(2,4-Difluoro-benzenesulfonyl)-phenyl]-3-(1H-pyrazol-4-ylmethyl)-urea

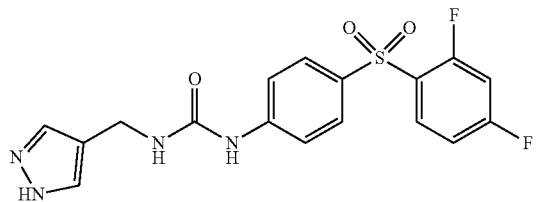 [SMILES: O=C(NCc1cn[nH]c1)Nc1ccc(S(=O)(=O)c2ccc(F)cc2F)cc1]

The title compound was prepared using general procedure of 1-[4-(2,4-difluoro-benzenesulfonyl)-phenyl]-3-pyridin-4-ylmethyl-urea. $^1$H NMR (400 MHz, DMSO-d$_6$): δ=12.60 (s, 1H), 9.09 (s, 1H), 8.11-8.04 (m, 1H), 7.78 (d, J=8.8 Hz, 2H), 7.62 (d, J=8.8 Hz, 2H), 7.59-7.45 (m, 3H), 7.40-7.33 (m, 1H), 6.59 (t, J=5.6 Hz, 1H), 4.15 (d, J=5.6 Hz, 2H). MS: m/z 392.9 (M+H$^+$).

Example 422: Synthesis of 1-[4-(2,4-Difluoro-benzenesulfonyl)-phenyl]-3-oxazol-5-ylmethyl-urea

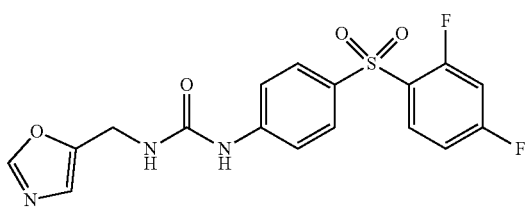 [SMILES: O=C(NCc1cnco1)Nc1ccc(S(=O)(=O)c2ccc(F)cc2F)cc1]

The title compound was prepared using general procedure of 1-[4-(2,4-difluoro-benzenesulfonyl)-phenyl]-3-pyridin-4-ylmethyl-urea. $^1$H NMR (400 MHz, DMSO-d$_6$): δ=9.26 (s, 1H), 8.29 (s, 1H), 8.12-8.04 (m, 1H), 8.09 (d, J=8.0 Hz, 2H), 7.63 (d, J=9.2 Hz, 2H), 7.56-7.49 (m, 1H), 7.41-7.33 (m, 1H), 7.01 (s, 1H), 6.89 (t, J=5.6 Hz, 1H), 4.37 (d, J=5.6 Hz, 2H). MS: m/z 393.9 (M+H$^+$).

Example 423: Synthesis of 1-[4-(2,4-Dichloro-benzenesulfonyl)-phenyl]-3-pyridin-4-ylmethyl-urea

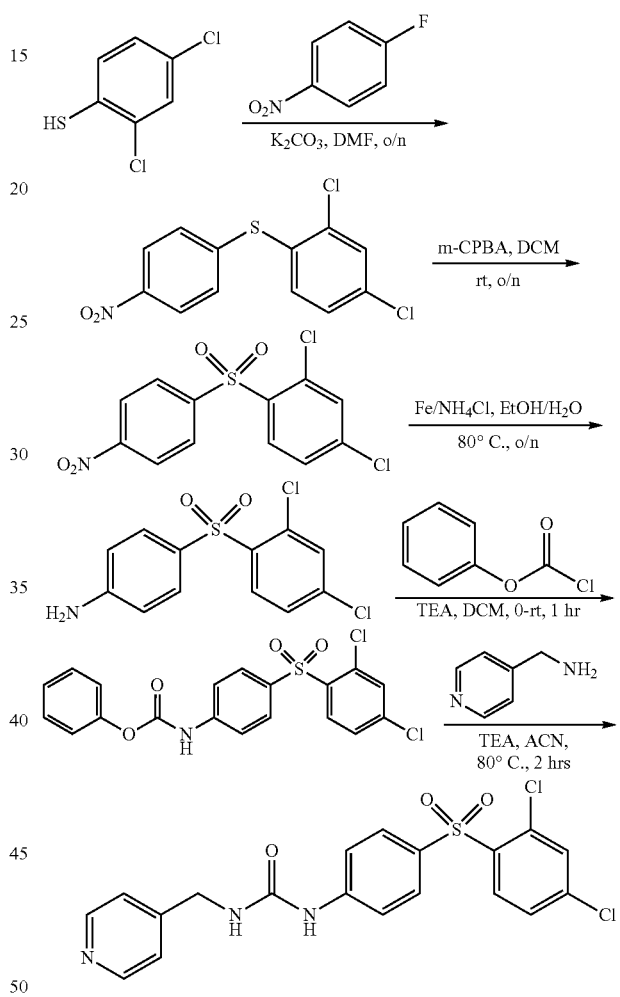

Step 1: To a solution of 2,4-dichloro-benzenethiol (895.35 mg, 5.0 mmol) in DMF (30 mL) was added 1-fluoro-4-nitrobenzene (1181.63 mg, 7.5 mmol) and K$_2$CO$_3$ (2.07 g, 15 mmol), the mixture was stirred at 80° C. overnight. The reaction was monitored by TLC. After completion, the mixture was concentrated in vacuum to give a residue, which was purified by a silica gel column (PE:EA=50:1) to afford 2,4-dichloro-1-(4-nitro-phenylsulfanyl)-benzene (1.85 g, yield 100%) as a white solid.

Step 2: To a solution of 2,4-dichloro-4-(4-nitro-phenylsulfanyl)-benzene (1.85 g, 6.16 mmol) in DCM (30 mL) was added m-CPBA (3188.9 mg, 18.48 mmol), the mixture was stirred at room temperature overnight. The reaction was monitored by TLC. After completion, the reaction was quenched with saturated aqueous sodium sulfite, the organic layer was concentrated in vacuum to give a residue, which was purified by a silica gel column (PE:EA=10:1) to afford 2,4-dichloro-4-(4-nitro-benzenesulfonyl)-benzene (1.89 g, 77.5%) as a white solid. $^1$H NMR (400 MHz, CDCl$_3$): δ=8.36 (d, J=8.8 Hz, 2H), 8.32 (d, J=8.8 Hz, 1H), 8.12 (d, J=8.8 Hz, 2H), 7.57-7.51 (dd, J=2.0, 2.0 Hz, 1H), 7.49 (d, J=1.6 Hz, 1H).

Step 3: To a solution of 2,4-dichloro-4-(4-nitro-benzenesulfonyl)-benzene (500 mg, 1.5 mmol) in EtOH (25 mL) and H$_2$O (5 mL) was added NH$_4$Cl (401.17 mg, 7.5 mmol), iron powder (418.8 mg, 7.5 mmol). The reaction mixture was stirred at 80° C. overnight. Iron powder was filtered off and the filtrate was concentrated in vacuum to give a residue, which was purified by flash to give 4-(2,4-dichloro-benzenesulfonyl)-phenylamine (370 mg, yield: 81.3%) as a white solid. $^1$H NMR (400 MHz, DMSO-d$_6$): δ=8.14 (d, J=8.8 Hz, 1H), 7.81 (s, 1H), 7.69 (d, J=8.0 Hz, 1H), 7.53 (d, J=8.4 Hz, 2H), 6.61 (d, J=8.0 Hz, 2H), 6.32 (s, 2H).

Step 4: To a solution of 4-(2,4-dichloro-benzenesulfonyl)-phenylamine (370 mg, 1.2 mmol) in DCM (30 mL) was added phenyl chloroformate (375.76 mg, 2.4 mmol) and TEA (242.8 mg, 2.4 mmol), the mixture was stirred at 0° C. for 1 hr. The reaction was monitored by TLC. After completion, the mixture was concentrated in vacuum to give a residue, which was purified by a silica gel column (PE/EA=3/1) to afford [4-(2,4-dichloro-benzenesulfonyl)-phenyl]-carbamic acid phenyl ester (380.0 mg, 73.5%) as a white solid.

Step 5: To a solution of [4-(2,4-dichloro-benzenesulfonyl)-phenyl]-carbamic acid phenyl ester (80 mg, 0.19 mmol) in ACN (30 mL) was added c-pyridin-4-yl-methylamine (41.09 mg, 0.38 mmol) and TEA (38.46 mg, 0.38 mmol), the mixture was stirred at 80° C. for 3 hrs. The reaction was monitored by LCMS. After completion, the mixture was concentrated in vacuum to give a residue, the residue was purified by prep-HPLC to give 1-[4-(2,4-dichloro-benzenesulfonyl)-phenyl]-3-pyridin-4-ylmethyl-urea (40.4 mg, yield: 66.2%) as a white solid. $^1$H NMR (400 MHz, DMSO-d$_6$): δ=9.39 (s, 1H), 8.49 (d, J=5.6 Hz, 2H), 8.22 (d, J=8.4 Hz, 1H), 7.85 (d, J=2.0 Hz, 1H), 7.78 (d, J=9.2 Hz, 2H), 7.76-7.71 (dd, J=1.6, 2.0 Hz, 1H), 7.63 (d, J=8.8 Hz, 2H), 7.27 (d, J=5.6 Hz, 2H), 6.98 (t, J=5.6 Hz, 1H), 4.33 (d, J=4.8 Hz, 2H). MS: m/z 435.9 (M+H$^+$).

Example 424: Synthesis of 1-[4-(2,4-Dichloro-benzenesulfonyl)-phenyl]-3-(1H-pyrazol-4-ylmethyl)-urea

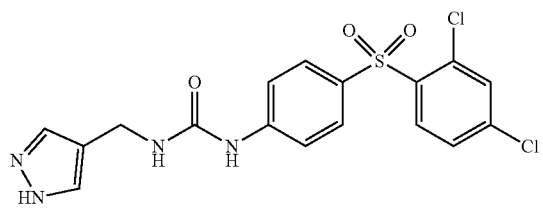 [SMILES: O=C(NCc1cn[nH]c1)Nc1ccc(S(=O)(=O)c2ccc(Cl)cc2Cl)cc1]

The title compound was prepared using general procedure of 1-[4-(2,4-Dichloro-benzenesulfonyl)-phenyl]-3-pyridin-4-ylmethyl-urea. $^1$H NMR (400 MHz, DMSO-d$_6$): δ=12.66 (s, 1H), 9.10 (s, 1H), 8.21 (d, J=8.4 Hz, 1H), 7.85 (d, J=2.0 Hz, 1H), 780-7.72 (m, 3H), 7.61 (d, J=8.8 Hz, 2H), 7.56-7.37 (m, 2H), 6.60 (t, J=5.6 Hz, 1H), 4.15 (d, J=5.2 Hz, 2H). MS: m/z 424.8 (M+H$^+$).

Example 425: Synthesis of 1-[4-(2,4-Dichloro-benzenesulfonyl)-phenyl]-3-oxazol-5-ylmethyl-urea

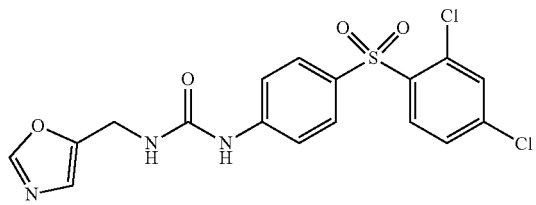 [SMILES: O=C(NCc1cnco1)Nc1ccc(S(=O)(=O)c2ccc(Cl)cc2Cl)cc1]

The title compound was prepared using general procedure of 1-[4-(2,4-Dichloro-benzenesulfonyl)-phenyl]-3-pyridin-4-ylmethyl-urea. $^1$H NMR (400 MHz, DMSO-d$_6$): δ=9.29 (s, 1H), 8.29 (s, 1H), 8.22 (d, J=8.8 Hz, 1H), 7.85 (d, J=2.0 Hz, 1H), 7.78 (d, J=9.2 Hz, 2H), 7.76-7.71 (dd, J=2.0, 2.0 Hz, 1H), 7.62 (d, J=8.8 Hz, 2H), 7.01 (s, 1H), 6.90 (t, J=5.6 Hz, 1H), 4.37 (d, J=5.6 Hz, 2H). MS: m/z 425.8 (M+H$^+$).

Example 426: Synthesis of 1-[4-(3,5-Difluoro-benzenesulfonyl)-phenyl]-3-pyridin-4-ylmethyl-urea

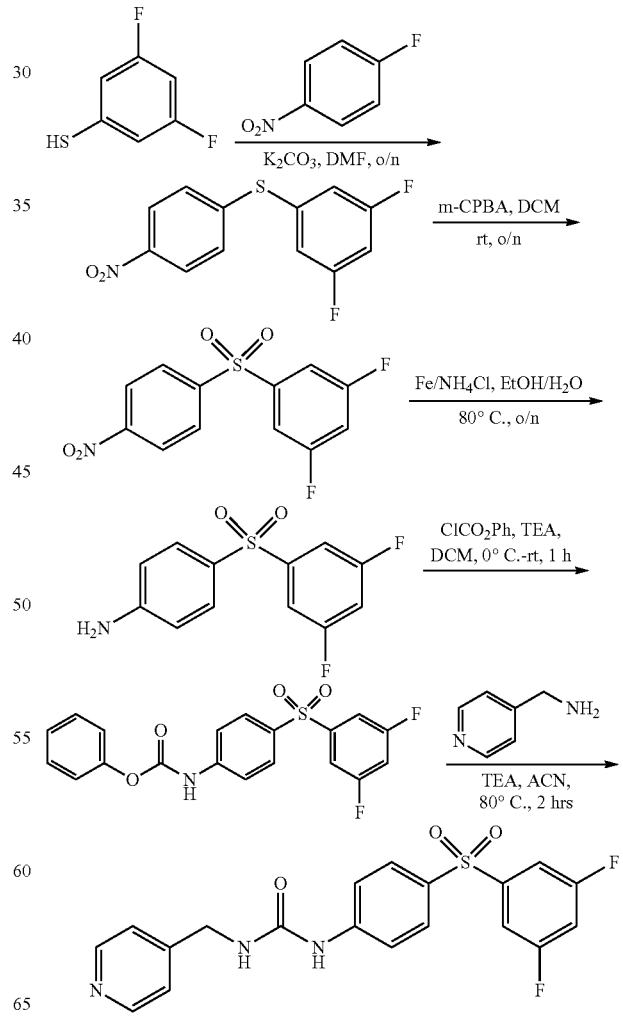

Step 1: To a solution of 3,5-difluoro-benzenethiol (584.6 mg, 4.0 mmol) in DMF (30 mL) was added 1-fluoro-4-nitrobenzene (846.59 mg, 6.0 mmol) and K₂CO₃ (1.66 g, 12.0 mmol), the mixture was stirred at 80° C. overnight. The reaction was monitored by TLC. After completion, the mixture was concentrated in vacuum to give a residue, which was purified by a silica gel column (PE/EA=50/1) to afford 1,3-difluoro-5-(4-nitro-phenylsulfanyl)-benzene (969 mg, yield: 90.6%) as a yellow solid. ¹H NMR (400 MHz, CDCl₃): δ=8.16 (d, J=8.8 Hz, 2H), 7.36 (d, J=8.8 Hz, 2H), 703-6.95 (m, 1H), 6.89-6.82 (m, 1H).

Step 2: To a solution of 1,3-difluoro-5-(4-nitro-phenylsulfanyl)-benzene (969 mg, 3.63 mmol) in DCM (50 mL) was added m-CPBA (2208.77 mg, 10.88 mmol), the mixture was stirred at room temperature overnight. The reaction was monitored by TLC. After completion, the mixture was quenched with saturated aqueous sodium sulfite, the organic layer was concentrated in vacuum to give a residue, which was purified by a silica gel column (PE:EA=10:1) to afford 1,3-difluoro-5-(4-nitro-benzenesulfonyl)-benzene (968 mg, 89.2%) as a white solid.

Step 3: To a solution of 1,3-difluoro-5-(4-nitro-benzenesulfonyl)-benzene (500 mg, 1.67 mmol) in MeOH (30 mL), was added Pd/C (10% wet, 50 mg). The reaction mixture was stirred at room temperature under H₂ (1 atm) overnight. Pd/C was filtered off and the filtrate was concentrated to dryness in vacuum. The residue was purified by flash to give 4-(3,5-difluoro-benzenesulfonyl)-phenylamine (447 mg, yield: 99.4%) as a white solid. ¹H NMR (400 MHz, DMSO-d₆): δ=7.66-7.55 (m, 5H), 6.63 (d, J=8.8 Hz, 2H), 6.33 (s, 2H).

Step 4: To a solution of 4-(3,5-difluoro-benzenesulfonyl)-phenylamine (447 mg, 1.66 mmol) in DCM (30 mL) was added phenyl chloroformate (519.8 mg, 3.32 mmol) and TEA (335.98 mg, 3.32 mmol), the mixture was stirred at 0° C. for 1 hr. The reaction was monitored by TLC. After completion, the mixture was concentrated in vacuum to give a residue, which was purified by a silica gel column (PE/EA=3/1) to afford [4-(3,5-difluoro-benzenesulfonyl)-phenyl]-carbamic acid phenyl ester (380 mg, yield: 58.7%) as a white solid.

Step 5: To a solution of [4-(3,5-difluoro-benzenesulfonyl)-phenyl]-carbamic acid phenyl ester (80 mg, 0.2 mmol) in ACN (20 mL) was added c-pyridin-4-yl-methylamine (433.2 mg, 0.4 mmol) and TEA (40.48 mg, 0.4 mmol), the mixture was stirred at 80° C. for 3 hrs. The reaction was monitored by LCMS. After completion, the mixture was concentrated in vacuum to give a residue, which was purified by prep-HPLC to give 1-[4-(3,5-difluoro-benzenesulfonyl)-phenyl]-3-pyridin-4-ylmethyl-urea (56 mg, yield: 62.8%) as a white solid. ¹H NMR (400 MHz, DMSO-d₆): δ=9.39 (s, 1H), 8.49 (J=6.4 Hz, 2H), 7.89 (d, J=8.8 Hz, 2H), 7.72-7.60 (m, 5H), 7.27 (d, J=6.0 Hz, 2H), 6.99 (t, J=6.0 Hz, 1H), 4.33 (d, J=5.6 Hz, 2H). MS: m/z 403.9 (M+H⁺).

Example 427: Synthesis of 1-[4-(3,5-Difluoro-benzenesulfonyl)-phenyl]-3-(1H-pyrazol-4-ylmethyl)-urea

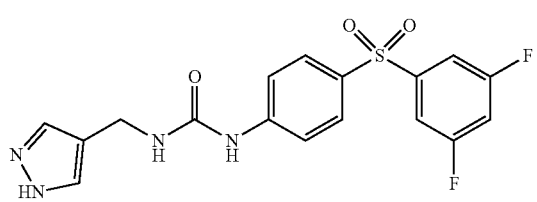 [SMILES: O=C(NCc1cn[nH]c1)Nc1ccc(S(=O)(=O)c2cc(F)cc(F)c2)cc1]

The title compound was prepared using general procedure of 1-[4-(3,5-difluoro-benzenesulfonyl)-phenyl]-3-pyridin-4-ylmethyl-urea. ¹H NMR (400 MHz, DMSO-d₆): δ=12.66 (s, 1H), 9.11 (s, 1H), 7.87 (d, J=8.8 Hz, 2H), 7.68 (d, J=6.0 Hz, 2H) 7.65-7.33 (m, 5H), 6.63 (t, J=5.6 Hz, 1H), 4.15 (d, J=5.6 Hz, 2H). MS: m/z 392.9 (M+H⁺).

Example 428: Synthesis of 1-[4-(3,5-Difluoro-benzenesulfonyl)-phenyl]-3-oxazol-5-ylmethyl-urea

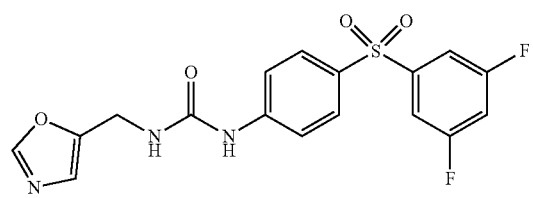 [SMILES: O=C(NCc1cnco1)Nc1ccc(S(=O)(=O)c2cc(F)cc(F)c2)cc1]

The title compound was prepared using general procedure of 1-[4-(3,5-difluoro-benzenesulfonyl)-phenyl]-3-pyridin-4-ylmethyl-urea. ¹H NMR (400 MHz, DMSO-d₆): δ=9.25 (s, 1H), 8.29 (s, 1H), 7.89 (d, J=9.2 Hz, 2H), 7.71-7.59 (m, 5H), 7.00 (s, 1H), 6.89 (t, J=4.8 Hz, 1H), 4.37 (d, J=5.6 Hz, 2H). MS: m/z 393.9 (M+H⁺).

Example 429: Synthesis of 1-(3-Cyano-4-((3,5-difluorophenyl)sulfonyl)phenyl)-3-(pyridin-4-ylmethyl)urea

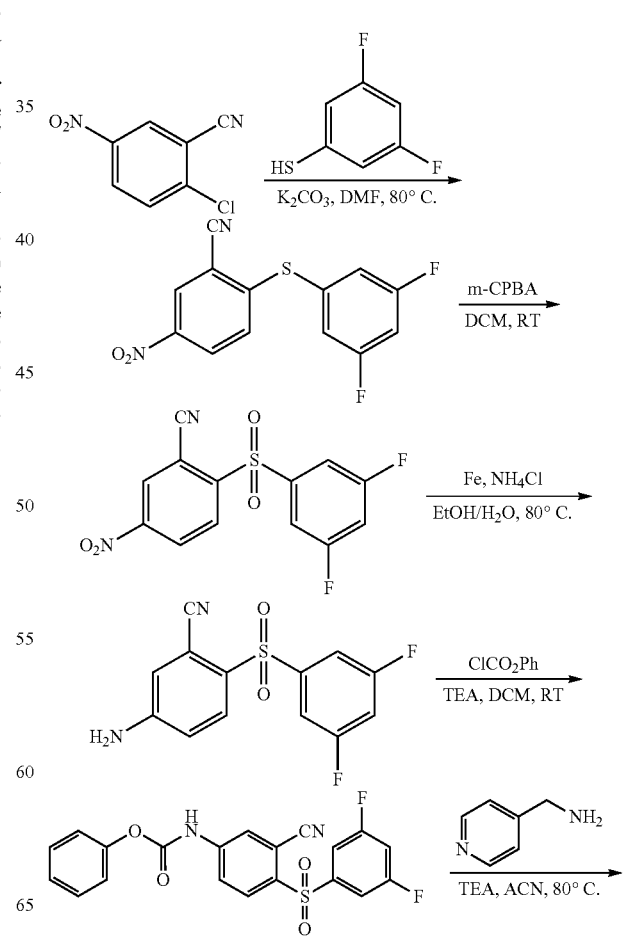

-continued

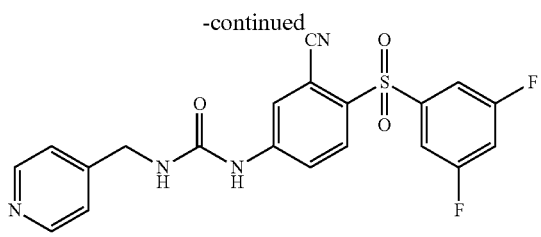

Step 1: To a solution of 2-chloro-5-nitrobenzonitrile (1 g, 5.49 mmol) and 3,5-difluorobenzenethiol (960 mg, 6.6 mmol) in DMF (20 mL) was added $K_2CO_3$ (2.3 g, 16 mmol). The reaction was stirred at 80° C. overnight. The residue was poured into $H_2O$ (20 mL) and the aqueous phase was extracted with EA (30 mL×2). The organic layer was washed with brine (20 mL), dried over $Na_2SO_4$ and concentrated. The residue was purified by silica gel column (PE/EA=10/1) to give 2-((3,5-difluorophenyl)thio)-5-nitrobenzonitrile (620 mg, yield: 39%) as a yellow solid.

Step 2: To a solution of 2-((3,5-difluorophenyl)thio)-5-nitrobenzonitrile (620 mg, 2.1 mmol) in DCM (20 mL), was added m-CPBA (815 mg, 4.7 mmol). The reaction was stirred at room temperature for 2 hrs. The mixture was concentrated and the residue was purified by silica gel column (PE/EA=5/1) to give 2-((3,5-difluorophenyl)sulfonyl)-5-nitrobenzonitrile (750 mg, crude) as a white solid.

Step 3: To a solution of 2-((3,5-difluorophenyl)sulfonyl)-5-nitrobenzonitrile (600 mg, 1.85 mmol) in $EtOH/H_2O$ (4/1, 25 mL), was added $NH_4Cl$ (980 mg, 18.5 mmol) and iron (725 mg, 13 mmol). The reaction was stirred at 80° C. for 2.5 hrs. The residue was poured into $H_2O$ (20 mL) and the aqueous phase was extracted with EA (20 mL). The organic layer was washed with brine (20 mL), dried over $Na_2SO_4$ and concentrated. The residue was purified by silica gel column (PE/EA=1/1) to give 5-amino-2-((3,5-difluorophenyl)sulfonyl)benzonitrile (300 mg, yield: 55%) as a yellow solid.

Step 4: To a solution of 5-amino-2-((3,5-difluorophenyl)sulfonyl)benzonitrile (150 mg, 0.51 mmol) in DCM (20 mL) was added TEA (153 mg, 1.53 mmol). When it was cooled to 0° C., to the above solution was added phenyl chloroformate (240 mg, 1.53 mmol) slowly. The reaction was stirred at room temperature for 3 hrs. The reaction was concentrated and the residue was purified by silica gel column (PE/EA=2/1) to give (3-cyano-4-((3,5-difluorophenyl)sulfonyl)phenyl) carbamate (80 mg, yield: 38%) as a white oil.

Step 5: To a solution of phenyl (3-cyano-4-((3,5-difluorophenyl)sulfonyl)phenyl)carbamate (80 mg, 0.19 mmol) and pyridin-4-ylmethanamine (25 mg, 0.23 mmol) in ACN (20 mL), was added TEA (58 mg, 0.57 mmol). The reaction was stirred at 80° C. for 3 hrs. The residue was poured into $H_2O$ (15 mL) and the aqueous phase was extracted with EA (15 mL). The organic layer was washed with brine (20 mL), dried over $Na_2SO_4$ and concentrated. The residue was purified by prep-HPLC ($NaHCO_3$) to give 1-(3-cyano-4-((3,5-difluorophenyl)sulfonyl)phenyl)-3-(pyridin-4-ylmethyl) urea (5.3 mg, yield: 6%) as a white solid. $^1H$ NMR (400 MHz, $CD_3OD$): δ=8.47 (d, J=6.0 Hz, 2H), 8.22 (d, J=8.8 Hz, 1H), 8.11 (d, J=2.4 Hz, 1H), 7.86 (dd, J=8.8 Hz, 1H), 7.65-7.63 (m, 2H), 7.42 (d, J=6.0 Hz, 3H), 4.46 (s, 2H). MS: m/z 429.0 ($M+H^+$).

Example 430: Synthesis of 1-(2-Cyano-4-((3,5-difluorophenyl)sulfonyl)phenyl)-3-(pyridin-4-ylmethyl)urea

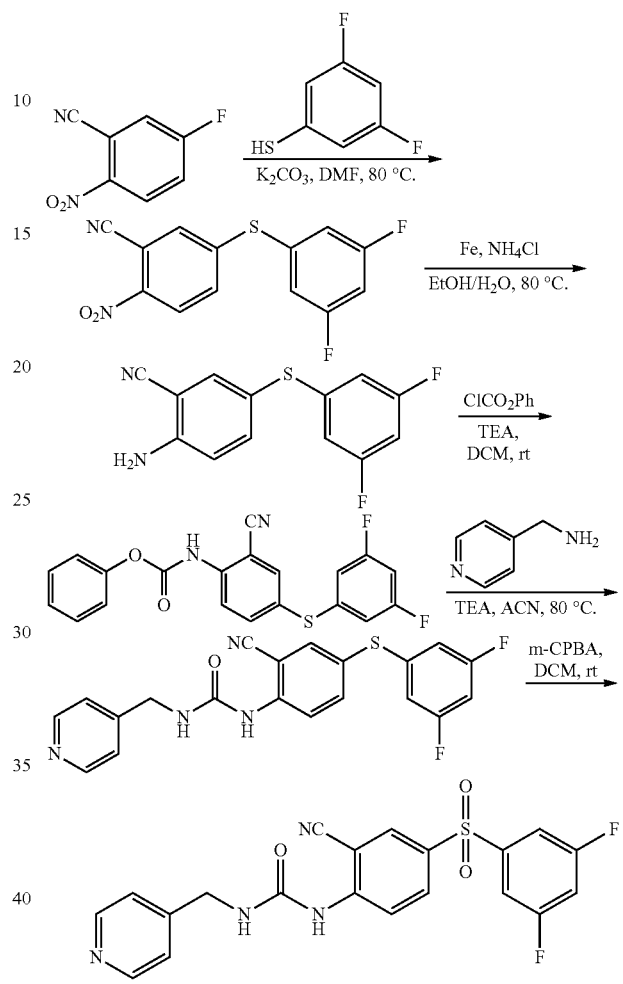

Step 1: To a solution of 5-fluoro-2-nitrobenzonitrile 1 g, 6 mmol) and 3,5-difluorobenzenethiol (1.03 g, 7.05 mmol) in DMF (20 mL), was added $K_2CO_3$ (2.5 g, 18 mmol). The reaction was stirred at 80° C. for 1.5 hrs. The residue was poured into $H_2O$ (20 mL) and the aqueous phase was extracted with EA (30 mL×2). The organic layer was washed with brine (25 mL), dried over $Na_2SO_4$ and concentrated. The residue was purified by silica gel column (PE/EA=3/1) to give 5-((3,5-difluorophenyl)thio)-2-nitrobenzonitrile (1.4 g, yield: 90%) as a yellow solid.

Step 2: To a solution of 5-((3,5-difluorophenyl)thio)-2-nitrobenzonitrile (1 g, 3.42 mmol) in $EtOH/H_2O$ (4/1, 25 mL), was added $NH_4Cl$ (1.8 g, 34.2 mmol) and iron (1.3 g, 24 mmol). The reaction was stirred at 80° C. for 2 hrs. The residue was poured into $H_2O$ (20 mL) and the aqueous phase was extracted with EA (20 mL). The organic layer was washed with brine (35 mL), dried over $Na_2SO_4$ and concentrated. The residue was purified by silica gel column (PE/EA=4/1) to give 2-amino-5-((3,5-difluorophenyl)thio) benzonitrile (800 mg, yield: 88%) as a yellow solid.

Step 3: To a solution of 2-amino-5-((3,5-difluorophenyl) thio)benzonitrile (800 mg, 3.05 mmol) in DCM (20 mL), was added TEA (920 mg, 9.15 mmol). When it was cooled to 0° C., to the above solution was added phenyl chloroformate (1.4 g, 9.15 mmol) slowly. The reaction was stirred at room temperature for 1 hr. The residue was concentrated and purified by silica gel column (PE/EA=8/1) to give phenyl (2-cyano-4-((3,5-difluorophenyl)thio)phenyl)carbamate (crude) as a yellow oil.

Step 4: To a solution of phenyl (2-cyano-4-((3,5-difluorophenyl)thio)phenyl)carbamate (crude, 3 mmol) and pyridin-4-ylmethanamine (388 mg, 3.6 mmol) in CAN (20 mL), was added TEA (909 mg, 9 mmol). The reaction was stirred at 80° C. for 1 hr. The residue was poured into H2O (20 mL) and the aqueous phase was extracted with EA (20 mL). The organic layer was washed with brine (25 mL), dried over $Na_2SO_4$ and concentrated. The residue was purified by silica gel column (PE/EA=3/1) to give 1-(2-cyano-4-((3,5-difluorophenyl)thio)phenyl)-3-(pyridin-4-ylmethyl)urea (500 mg, yield: 42%) as a white solid.

Step 5: To a solution of 1-(2-cyano-4-((3,5-difluorophenyl)thio)phenyl)-3-(pyridin-4-ylmethyl)urea (200 mg, 0.5 mmol) in DCM (20 mL), was added m-CPBA (175 mg, 1.0 mmol). The reaction was stirred at room temperature for 3 hrs. The residue was concentrated and purified by prep-HPLC ($NH_4HCO_3$) to give 1-(2-cyano-4-((3,5-difluorophenyl)sulfonyl)phenyl)-3-(pyridin-4-ylmethyl)urea (30.9 mg, yield: 14%) as a white solid. $^1H$ NMR (400 MHz, DMSO-$d_6$): δ=11.38 (s, 1H), 9.52 (s, 1H), 8.80 (s, 1H), 8.44 (d, J=5.6 Hz, 2H), 8.10 (d, J=7.2 Hz, 1H), 7.80 (s, 2H), 7.68-7.63 (m, 1H), 7.26-7.23 (m, 3H), 5.21 (s, 2H). MS: m/z 429.7 (M+H⁺).

Example 431: Synthesis of 1-[4-(3,4-Dichloro-benzenesulfonyl)-phenyl]-3-pyridin-4-ylmethyl-urea

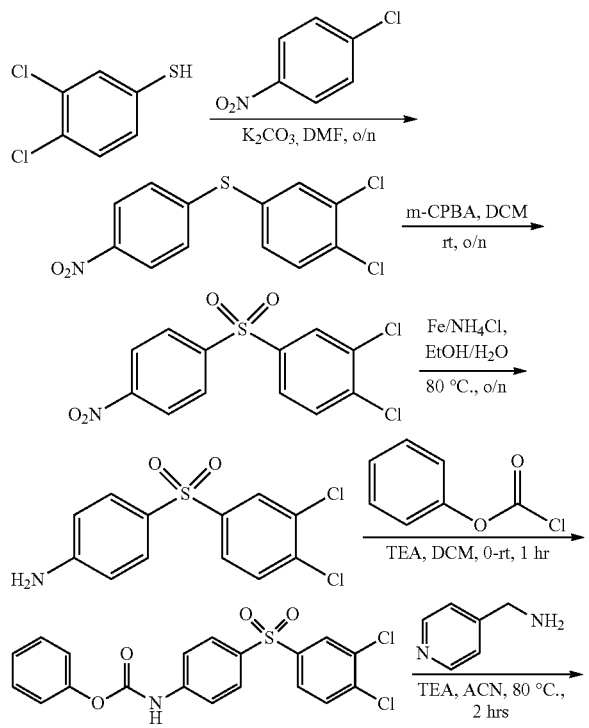

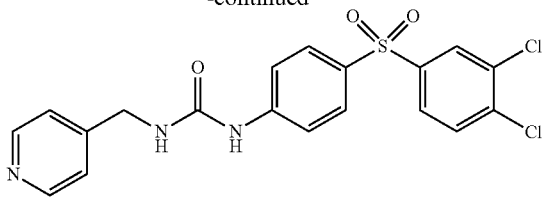

Step 1: To a solution of 3,4-dichloro-benzenethiol (537.21 mg, 3.0 mmol) in DMF (20 mL) was added 1-chloro-4-nitro-benzene (708.97 mg, 4.5 mmol) and $K_2CO_3$ (1.24 g, 9.0 mmol), the mixture was stirred at 80° C. overnight. The reaction was monitored by TLC. After completion, the mixture was concentrated in vacuum to give a residue, which was purified by a silica gel column (PE/EA=30/1) to afford 1,2-dichloro-4-(4-nitro-phenylsulfanyl)-benzene (851 mg, yield: 94%) as a yellow solid.

Step 2: To a solution of 1,2-dichloro-4-(4-nitro-phenylsulfanyl)-benzene (851 mg, 2.83 mmol) in DCM (30 mL) was added m-CPBA (1465.03 mg, 8.49 mmol), the mixture was stirred at room temperature overnight. The reaction was monitored by TLC. After completion, the mixture was quenched with saturated aqueous sodium sulfite. The organic layer was concentrated in vacuum to give a residue, which was purified by a silica gel column (PE:EA=10:1) to afford 1,2-dichloro-4-(4-nitro-benzenesulfonyl)-benzene (937 mg, 99.4%) as a white solid. $^1H$ NMR (400 MHz, $CDCl_3$): δ=8.38 (d, J=8.8 Hz, 2H), 8.13 (d, J=8.8 Hz, 2H), 8.047 (d, J=2.0 Hz, 1H), 7.81-7.77 (dd, J=1.6, 2.4 Hz, 1H), 7.64 (d, J=8.4 Hz, 1H).

Step 3: To a solution of 1,2-dichloro-4-(4-nitro-benzenesulfonyl)-benzene (937 mg, 2.82 mmol) in EtOH (15 mL) and $H_2O$ (5 mL) was added $NH_4Cl$ (754.21 mg, 14.1 mmol), iron powder (787.48 mg, 14.1 mmol). The reaction mixture was stirred at 80° C. overnight. Iron powder was filtered off and the filtrate was concentrated in vacuum to give a residue, which was purified by flash to give 4-(3,4-dichloro-benzenesulfonyl)-phenylamine (724.48 mg, yield: 85%) as a white solid. $^1H$ NMR (400 MHz, DMSO-$d_6$): δ=8.05 (d, J=2.0 Hz, 1H), 7.86-7.82 (m, 1H), 7.81-7.76 (dd, J=2.0, 2.0 Hz, 1H), 7.62-7.57 (dd, J=1.6, 2.0 Hz, 2H), 6.66-6.60 (dd, J=1.6, 2.0 Hz, 2H), 6.30 (s, 2H).

Step 4: To a solution of 4-(3,4-dichloro-benzenesulfonyl)-phenylamine (190 mg, 0.63 mmol) in DCM (30 mL) was added phenyl chloroformate (197.27 mg, 1.26 mmol) and TEA (127.51 mg, 1.26 mmol), the mixture was stirred at 0° C. for 1 hr. The reaction was monitored by TLC. After completion, the mixture was concentrated in vacuum to give a residue, which was purified by a silica gel column (PE/EA=3/1) to afford [4-(3,4-dichloro-benzenesulfonyl)-phenyl]-carbamic acid phenyl ester (240.0 mg, 86.3%) as a white solid.

Step 5: To a solution of [4-(3,4-dichloro-benzenesulfonyl)-phenyl]-carbamic acid phenyl ester (60 mg, 0.14 mmol) in ACN (20 mL) was added c-pyridin-4-yl-methylamine (30.27 mg, 0.28 mmol) and TEA (28.33 mg, 0.28 mmol), the mixture was stirred at 80° C. for 3 hrs. The reaction was monitored by LCMS. After completion, the mixture was concentrated in vacuum to give a residue, which was purified by prep-HPLC to give 1-[4-(3,4-dichloro-benzenesulfonyl)-phenyl]-3-pyridin-4-ylmethyl-urea (40.4 mg, yield: 66.2%) as a white solid. $^1H$ NMR (400 MHz, DMSO-$d_6$): δ=9.38 (s, 1H), 8.53-8.46 (dd, J=1.6, 1.2 Hz, 2H), 8.15 (d, J=1.6 Hz, 1H), 7.91-7.83 (m, 4H), 7.64 (d, J=9.2 Hz, 2H), 7.27 (d, J=6.0 Hz, 2H), 6.98 (t, J=6.0 Hz, 1H), 4.33 (d, J=6.0 Hz, 2H). MS: m/z 435.8 (M+H⁺).

Example 432: Synthesis of 1-[4-(3,4-Dichloro-benzenesulfonyl)-phenyl]-3-(1H-pyrazol-4-ylmethyl)-urea

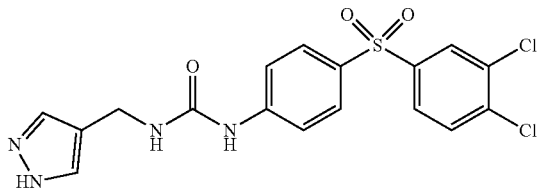 [SMILES: O=C(NCc1cn[nH]c1)Nc1ccc(S(=O)(=O)c2ccc(Cl)c(Cl)c2)cc1]

The title compound was prepared using general procedure of 1-[4-(3,4-Dichloro-benzenesulfonyl)-phenyl]-3-pyridin-4-ylmethyl-urea. ¹H NMR (400 MHz, DMSO-d₆): δ=12.63 (s, 1H), 9.14 (s, 1H), 8.14 (d, J=1.2 Hz, 1H), 7.90-7.84 (m, 4H), 7.61 (d, J=9.2 Hz, 2H), 7.54-7.45 (m, 2H), 6.62 (t, J=5.6 Hz, 1H), 4.15 (d, J=4.8 Hz, 2H). MS: m/z 424.8 (M+H⁺).

Example 433: Synthesis of 1-[4-(3,4-Dichloro-benzenesulfonyl)-phenyl]-3-oxazol-5-ylmethyl-urea

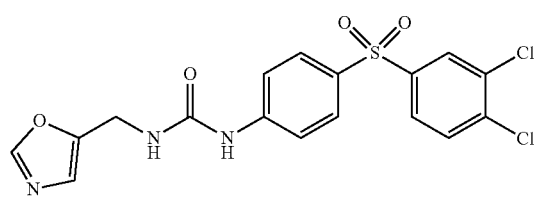 [SMILES: O=C(NCc1cnco1)Nc1ccc(S(=O)(=O)c2ccc(Cl)c(Cl)c2)cc1]

The title compound was prepared using general procedure of 1-[4-(3,4-Dichloro-benzenesulfonyl)-phenyl]-3-pyridin-4-ylmethyl-urea. ¹H NMR (400 MHz, DMSO-d₆): δ=9.22 (s, 1H), 8.28 (s, 1H), 8.14 (d, J=1.2 Hz, 1H), 7.89-7.85 (m, 4H), 7.62 (d, J=9.2 Hz, 2H), 7.00 (s, 1H), 6.86 (t, J=5.6 Hz, 1H), 4.37 (d, J=5.2 Hz, 2H). MS: m/z 425.8 (M+H⁺).

Example 434: Synthesis of 1-[4-(3,4-Difluoro-benzenesulfonyl)-phenyl]-3-pyridin-4-ylmethyl-urea

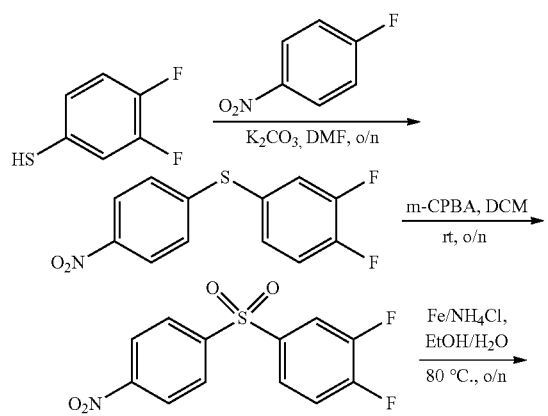

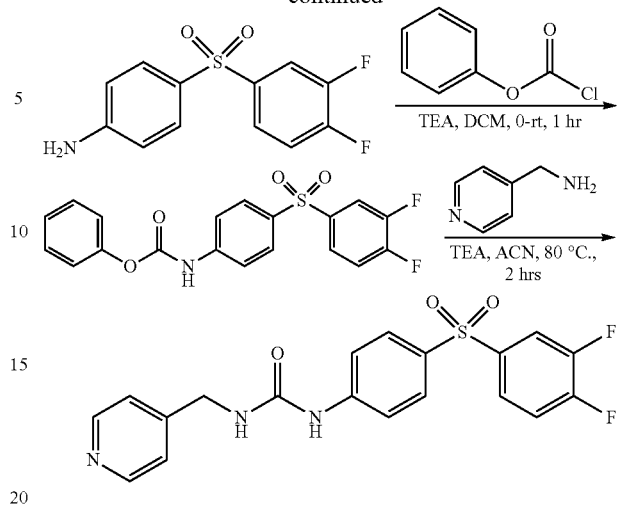

Step 1: To a solution of 3,4-difluoro-benzenethiol (584.6 mg, 4.0 mmol) in DMF (30 mL) was added 1-fluoro-4-nitrobenzene (846.59 mg, 6.0 mmol) and K₂CO₃ (1.66 g, 12.0 mmol), the mixture was stirred at 80° C. overnight. The reaction was monitored by TLC. After completion, the mixture was concentrated in vacuum to give a residue, which was purified by a silica gel column (PE/EA=50/1) to afford 1,2-difluoro-4-(4-nitro-phenylsulfanyl)-benzene (778 mg, yield: 77.6%) as a white solid. ¹H NMR (400 MHz, DMSO-d₆): δ=8.15 (d, J=9.2 Hz, 2H), 7.84-7.77 (m, 1H), 7.68-7.59 (m, 1H), 7.51-7.44 (m, 1H), 7.35 (d, J=8.8 Hz, 2H).

Step 2: To a solution of 1,2-difluoro-4-(4-nitro-phenylsulfanyl)-benzene (778 mg, 2.91 mmol) in DCM (30 mL) was added m-CPBA (1772.29 mg, 8.73 mmol), the mixture was stirred at room temperature overnight. The reaction was monitored by TLC. After completion, the mixture was quenched with saturated aqueous sodium sulfite, the organic layer was concentrated in vacuum to give a residue, which was purified by a silica gel column (PE:EA=10:1) to afford 1,2-difluoro-4-(4-nitro-benzenesulfonyl)-benzene (840 mg, 96.4%) as a white solid.

Step 3: To a solution of 1,2-difluoro-4-(4-nitro-benzenesulfonyl)-benzene (300 mg, 1.0 mmol) in MeOH (30 mL), was added Pd/C (10% wet, 30 mg). The reaction mixture was stirred at room temperature under H₂ (1 atm) overnight. Pd/C was filtered off and the filtrate was concentrated to dryness in vacuum. The residue was purified by flash to give 4-(3,4-difluoro-benzenesulfonyl)-phenylamine (209 mg, yield: 77.5%) as a white solid. ¹H NMR (400 MHz, DMSO-d₆): δ=8.00-7.92 (m, 1H), 7.75-7.69 (m, 1H), 7.68-7.62 (m, 1H), 7.58 (d, J=8.8 Hz, 2H), 6.62 (d, J=8.8 Hz, 2H), 6.27 (s, 2H).

Step 4: To a solution of 4-(3,4-difluoro-benzenesulfonyl)-phenylamine (209 mg, 0.78 mmol) in DCM (40 mL) was added phenyl chloroformate (244.2 mg, 1.56 mmol) and TEA (157.86 mg, 1.56 mmol), the mixture was stirred at 0° C. for 1 hr. The reaction was monitored by TLC. After completion, the mixture was concentrated in vacuum to give a residue, which was purified by a silica gel column (PE/EA=3/1) to afford [4-(3,4-difluoro-benzenesulfonyl)-phenyl]-carbamic acid phenyl ester (329 mg, yield: >1) as a white solid.

Step 5: To a solution of [4-(3,4-difluoro-benzenesulfonyl)-phenyl]-carbamic acid phenyl ester (50 mg, 0.13 mmol) in ACN (30 mL) was added c-pyridin-4-yl-methylamine (28.12 mg, 0.26 mmol) and TEA (28.31 mg, 0.26 mmol), the mixture was stirred at 80° C. for 3 hrs. The reaction was monitored by LCMS. After completion, the mixture was concentrated in vacuum to give a residue, the residue was purified by prep-HPLC to give 1-[4-(3,4-difluoro-benzenesulfonyl)-phenyl]-3-pyridin-4-ylmethyl-urea (8.2 mg, yield: 15.8%) as a white solid. $^1$H NMR (400 MHz, DMSO-$d_6$) δ=9.36 (s, 1H), 8.49 (J=6.0 Hz, 2H), 8.10-8.03 (m, 1H), 7.85 (d, J=8.8 Hz, 2H), 7.83-7.77 (m, 1H), 7.73-7.66 (m, 1H), 7.63 (d, J=8.8 Hz, 2H), 7.27 (d, J=6.0 Hz, 2H), 6.97 (t, J=6.0 Hz, 1H), 4.33 (d, J=6.0 Hz, 2H). MS: m/z 403.9 (M+H$^+$).

Example 435: Synthesis of 1-[4-(3,4-Difluoro-benzenesulfonyl)-phenyl]-3-(1H-pyrazol-4-ylmethyl)-urea

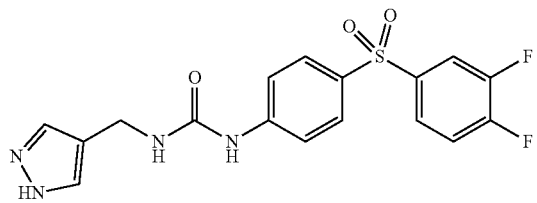 [SMILES: O=C(NCc1cn[nH]c1)Nc1ccc(S(=O)(=O)c2ccc(F)c(F)c2)cc1]

The title compound was prepared using general procedure of 1-[4-(3,4-difluoro-benzenesulfonyl)-phenyl]-3-pyridin-4-ylmethyl-urea. $^1$H NMR (400 MHz, DMSO-$d_6$): δ=12.64 (s, 1H), 9.04 (s, 1H), 8.09-8.02 (m, 1H), 7.84 (d, J=9.2 Hz, 2H), 7.82-7.76 (m, 1H), 7.72-7.64 (m, 1H), 7.60 (d, J=8.8 Hz, 2H), 7.56-7.45 (m, 2H), 6.57 (t, J=5.6 Hz, 1H), 4.14 (d, J=5.2 Hz, 2H). MS: m/z 392.9 (M+H$^+$).

Example 436: Synthesis of 1-[4-(3,4-Difluoro-benzenesulfonyl)-phenyl]-3-oxazol-5-ylmethyl-urea

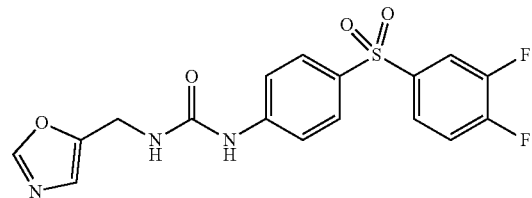 [SMILES: O=C(NCc1cnco1)Nc1ccc(S(=O)(=O)c2ccc(F)c(F)c2)cc1]

The title compound was prepared using general procedure of 1-[4-(3,4-difluoro-benzenesulfonyl)-phenyl]-3-pyridin-4-ylmethyl-urea. $^1$H NMR (400 MHz, DMSO-d6): δ=9.21 (s, 1H), 8.28 (s, 1H), 8.10-8.03 (m, 1H), 7.85 (d, J=8.4 Hz, 2H), 7.83-7.77 (m, 1H), 7.73-7.66 (m, 1H), 7.61 (d, J=9.2 Hz, 2H), 7.00 (s, 1H), 6.86 (t, J=6.0 Hz, 1H), 4.37 (d, J=5.6 Hz, 2H). MS: m/z 393.9 (M+H$^+$).

Example 437: Synthesis of Pyridin-4-ylmethyl-3-[4-(thiazole-2-sulfonyl)-phenyl]-urea

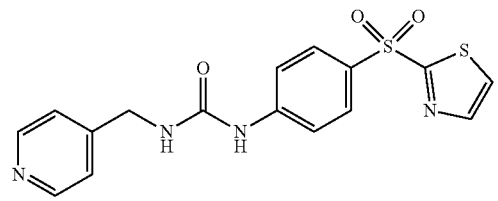 [SMILES: O=C(NCc1ccncc1)Nc1ccc(S(=O)(=O)c2nccs2)cc1]

The title compound was prepare using genera procedure of 1-(1H-pyrazol-4-ylmethyl)-3-[4-(thiazole-2-sulfonyl)-phenyl]-urea. $^1$H NMR (400 MHz, CD$_3$OD): δ=8.49-8.48 (m, 2H), 8.00 (s, 2H), 7.94 (d, J=9.2 Hz, 2H), 7.68 (d, J=8.8 Hz, 2H), 7.40 (d, J=6.0 Hz, 2H), 4.47 (s, 2H). MS: m/z 374.9 (M+H$^+$).

Example 438: Synthesis of 1-(1H-Pyrazol-4-ylmethyl)-3-[4-(thiazole-2-sulfonyl)-phenyl]-urea

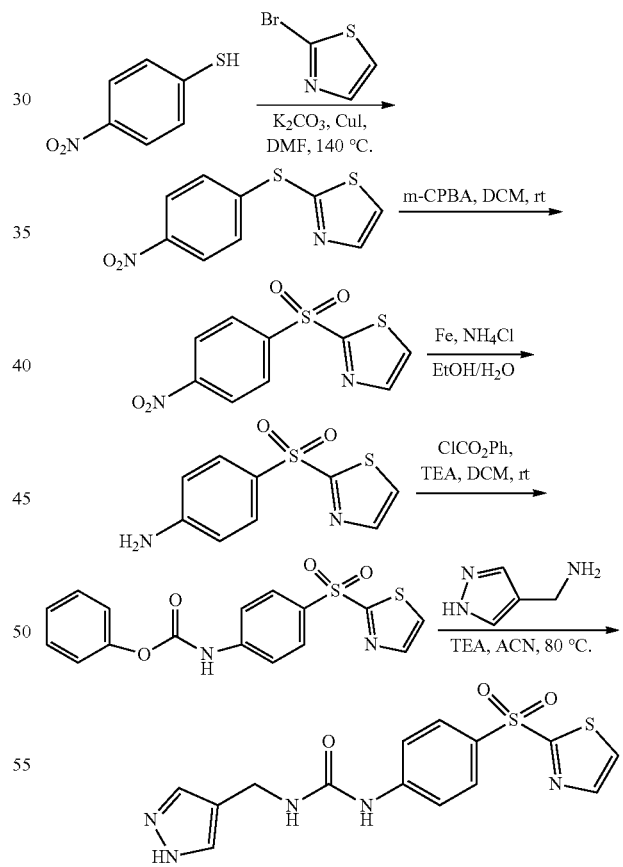

Step 1: A solution of 4-nitro-benzenethiol (3.0 g, 19 mmol), 2-bromo-thiazole (3.79 g, 23 mmol), K$_2$CO$_3$ (7.8 g, 57 mmol) and CuI (0.36 g, 1.9 mmol) in DMF (10 mL) was stirred at 140° C. overnight. The reaction solution was partitioned between EA (50 mL) and water (100 mL). The organic layer was washed with water (60 mL) and brine (60 mL), dried over Na$_2$SO$_4$ and concentrated in vacuum. The residue was purified by silica gel column (PE/EA=30/1) to give 2-(4-nitro-phenylsulfanyl)-thiazole (2.21 g, yield: 48%) as yellow solid. $^1$H NMR (300 MHz, DMSO-d$_6$): δ=9.48 (s, 1H), 8.29-8.16 (m, 3H), 7.36 (d, J=9.0 Hz, 2H). MS: m/z 239.0 (M+H$^+$).

Step 2: To a mixture of 2-(4-nitro-phenylsulfanyl)-thiazole (2.21 g, 9.0 mmol) in DCM (20 mL) was added m-CPBA (7.74 g, 45 mmol) at 0° C. slowly. Then the mixture was stirred at room temperature overnight. To the mixture was added Na$_2$SO$_3$, filtered and washed with NaHCO$_3$ and concentrated. The residue was purified with chromatography (PE/EA=3/1) to give 2-(4-nitro-benzenesulfonyl)-thiazole (1.8 g, yield: 74%) as a white solid. MS: m/z 271.0 (M+H$^+$).

Step 3: A mixture of 2-(4-nitro-benzenesulfonyl)-thiazole (1.5 g, 5.0 mmol), Fe (0.9 g, 15 mmol) and NH$_4$Cl (0.8 g, 15 mmol) in EtOH/H$_2$O (10 mL/3 mL) was stirred at 90° C. overnight. The reaction solution was filtered. The filtrate was concentrated to give 4-(thiazole-2-sulfonyl)-phenylamine (1 g, yield: 76%) as a white solid. MS: m/z 241.0 (M+H$^+$).

Step 4: To a solution of 4-(Thiazole-2-sulfonyl)-phenylamine (100 mg, 0.40 mmol) in DCM (20 mL) was added pyridine (66 mg, 0.80 mmol) and phenyl chloroformate (187 mg, 1.20 mmol) at 0° C. The reaction mixture was stirred at room temperature for 2 hrs. The reaction was completed detected by LC-MS. The reaction was quenched with water (10 mL), extracted with DCM (10 mL×3) and concentrated to give [4-(thiazole-2-sulfonyl)-phenyl]-carbamic acid phenyl ester (150 mg, yield: 79%) as a white solid. MS: m/z 361.0 (M+H$^+$).

Step 5: To a solution of [4-(Thiazole-2-sulfonyl)-phenyl]-carbamic acid phenyl ester (50 mg, 0.13 mmol) in ACN (10 mL) was added TEA (39 mg, 0.39 mmol) and C-(1H-pyrazol-4-yl)-methylamine (24 mg, 0.28 mmol). The reaction mixture was stirred at 80° C. for 3 hrs. The reaction was concentrated and purified by prep-HPLC to give 1-(1H-pyrazol-4-ylmethyl)-3-[4-(thiazole-2-sulfonyl)-phenyl]-urea (5 mg, yield: 10%) as a white solid. $^1$H NMR (400 MHz, CD$_3$OD): δ=7.98 (s, 2H), 7.92-7.90 (m, 4H), 7.64 (d, J=9.2 Hz, 2H), 4.32 (s, 2H). MS: m/z 363.9 (M+H$^+$).

Example 439: Synthesis of 1-Oxazol-5-ylmethyl-3-[4-(thiazole-2-sulfonyl)-phenyl]-urea

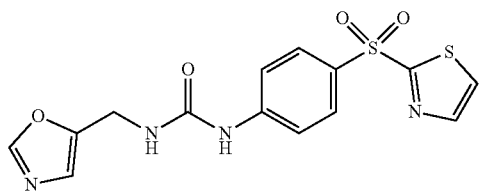 [SMILES: O=C(NCc1cnco1)Nc1ccc(S(=O)(=O)c2nccs2)cc1]

The title compound was prepared using general procedure of 1-(1H-pyrazol-4-ylmethyl)-3-[4-(thiazole-2-sulfonyl)-phenyl]-urea. $^1$H NMR (400 MHz, CD$_3$OD): δ=8.17 (s, 1H), 8.04 (s, 2H), 7.94 (d, J=9.2 Hz, 2H), 7.67 (d, J=9.2 Hz, 2H), 7.06 (s, 1H), 4.50 (s, 2H). MS: m/z 364.9 (M+H$^+$).

Example 440: Synthesis of 1-Pyridin-4-ylmethyl)-3-(4-(thiazol-5-ylsulfonyl)phenyl)urea

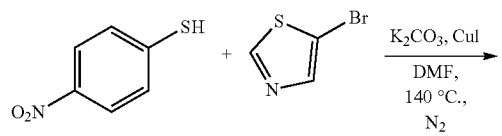

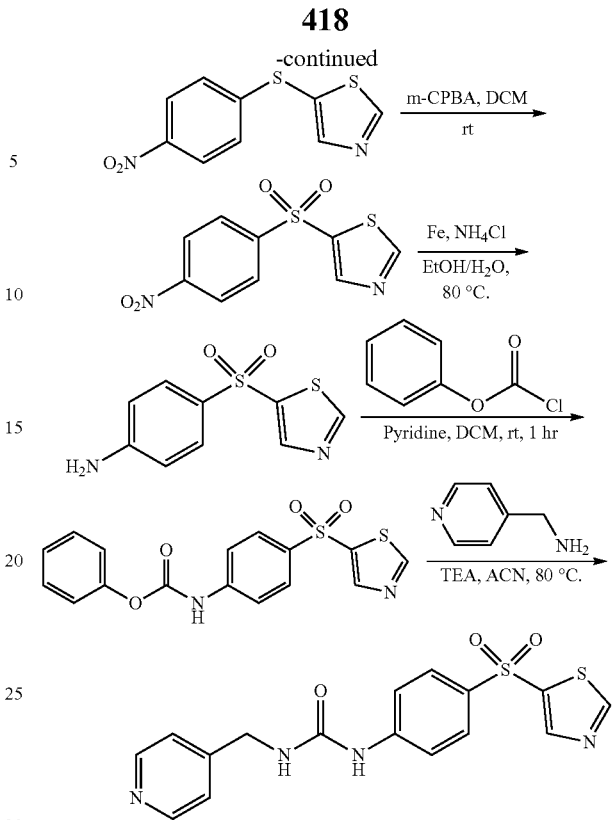

Step 1: To a solution of 4-Nitro-benzenethiol (50.0 mg, 0.32 mmol) in DMF (5 mL) was added 5-Bromo-thiazole (63.4 mg, 0.39 mmol), K$_2$CO$_3$ (132.7 mg, 0.96 mmol) and CuI (6.1 mg, 0.03 mmol). The reaction mixture was stirred at 140° C. under N$_2$ overnight. The reaction was completed detected by LC-MS. The reaction was quenched with water (5 mL) and extracted with DCM (10 mL×3). The combined organic layer was washed with brine (10 mL) and water (10 mL), dried over Na$_2$SO$_4$, filtered and concentrated. The residue was purified by silia gel chromatography (PE to PE/EA=20/1) to give 2-(4-Nitro-phenylsulfanyl)-thiazole (60.0 mg, yield: 78%) as a yellow solid. MS: m/z 239.0 (M+H$^+$).

Step 2: To a solution of 2-(4-Nitro-phenylsulfanyl)-thiazole (405.0 mg, 1.70 mmol) in DCM (30 mL) was added m-CPBA (1.73 g, 8.50 mmol, 85% Wt) at 0° C. The reaction mixture was allowed to warm to room temperature overnight. The reaction was completed detected by LC-MS. The reaction was quenched with Na$_2$SO$_3$ aqueous (10 mL) and extracted with DCM (20 mL×3). The combined organic layer was washed with NaHCO$_3$ aqueous (20 mL) and water (20 mL), dried over Na$_2$SO$_4$, filtered and concentrated. The residue was purified by silia gel chromatography (PE to PE/EA=20/1) to give 2-(4-Nitro-benzenesulfonyl)-thiazole (322.0 mg, yield: 70%) as a white solid. MS: m/z 271.0 (M+H$^+$).

Step 3: To a solution of 2-(4-Nitro-benzenesulfonyl)-thiazole (2.60 g, 9.6 mmol) in EtOH/H$_2$O (50/10 mL) was added Iron powder (2.68 g, 48.0 mmol) and NH$_4$Cl (2.57 g, 48.0 mmol) at room temperature. The reaction mixture was heated to 80° C. overnight. The reaction was completed detected by LC-MS. The reaction mixture was concentrated and then extracted with DCM (30 mL×3). The combined organic layer was washed with dilute HCl (1 mol/L, 30 mL) and water (30 mL), dried over Na$_2$SO$_4$, filtered and concentrated to give 4-(Thiazole-2-sulfonyl)-phenylamine (1.62 g, yield: 70%) as a yellow solid. ¹H NMR (400 MHz, DMSO-d₆): δ=8.14 (d, J=3.2 Hz, 1H), 8.03 (d, J=2.4 Hz, 1H), 7.61 (d, J=8.8 Hz, 2H), 6.67 (d, J=8.8 Hz, 2H), 6.08 (br s, 2H).

Step 4: To a solution of 4-(Thiazole-2-sulfonyl)-phenylamine (200.0 mg, 0.83 mmol) in DCM (20 mL) was added pyridine (197.0 mg, 2.49 mmol) and phenyl chloroformate (260.0 mg, 1.66 mmol) at 0° C. The reaction mixture was stirred at room temperature for 1 hr. The reaction was completed detected by LC-MS. The reaction was quenched with water (5 mL) and extracted with DCM (20 mL×3). The combined organic layer was washed with brine (20 mL) and water (20 mL), dried over Na₂SO₄, filtered and concentrated. The residue was purified by re-crystallization from ether absolute (10 mL) to give [4-(Thiazole-2-sulfonyl)-phenyl]-carbamic acid phenyl ester (264.0 g, yield: 88%) as a white solid. ¹H NMR (300 MHz, DMSO-d₆): δ=10.88 (s, 1H), 8.24 (d, J=2.4 Hz, 1H), 8.10 (d, J=3.0 Hz, 1H), 7.99 (d, J=8.7 Hz, 2H), 7.77 (d, J=8.7 Hz, 2H), 7.50-7.23 (m, 5H).

Step 5: To a solution of [4-(Thiazole-2-sulfonyl)-phenyl]-carbamic acid phenyl ester (80.0 mg, 0.22 mmol) in ACN (20 mL) was added TEA (111.3 mg, 1.1 mmol) and C-Pyridin-4-yl-methylamine (47.6 mg, 0.44 mmol). The reaction mixture was stirred at 80° C. for 2 hrs. The reaction was completed detected by LC-MS. The reaction was quenched with water (5 mL) and extracted with DCM (20 mL×3). The combined organic layer was washed with brine (20 mL) and water (20 mL), dried over Na₂SO₄, filtered and concentrated. The residue was purified by prep.HPLC to give 1-Pyridin-4-ylmethyl-3-[4-(thiazole-2-sulfonyl)-phenyl]-urea (17.0 mg, yield: 21%) as a white solid. ¹H NMR (400 MHz, DMSO-d₆): δ=9.47 (s, 1H), 8.50 (d, J=5.6 Hz, 2H), 8.22 (d, J=3.2 Hz, 1H), 8.08 (d, J=3.2 Hz, 1H), 7.87 (d, J=8.8 Hz, 2H), 7.68 (d, J=8.8 Hz, 2H), 7.28 (d, J=6.0 Hz, 2H), 7.02 (t, J=6.0 Hz, 1H), 4.34 (d, J=6.4 Hz, 2H). MS: m/z 374.9 (M+H⁺).

Example 441: Synthesis of 1-(1H-Pyrazol-4-ylmethyl)-3-[4-(thiazole-2-sulfonyl)-phenyl]-urea

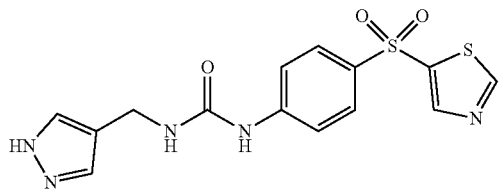 [SMILES: O=C(NCc1cn[nH]c1)Nc1ccc(S(=O)(=O)c2cncs2)cc1]

The title compound was prepared using general procedure of 1-pyridin-4-ylmethyl)-3-(4-(thiazol-5-ylsulfonyl)phenyl) urea. ¹H NMR (400 MHz, DMSO-d₆): δ=9.26 (s, 1H), 8.21 (d, J=3.2 Hz, 1H), 8.08 (d, J=2.8 Hz, 1H), 7.86 (d, J=8.8 Hz, 2H), 7.66 (d, J=9.2 Hz, 2H), 7.53 (s, 2H), 6.74 (t, J=5.4 Hz, 1H), 4.15 (d, J=5.6 Hz, 2H). MS: m/z 364.1 (M+H⁺).

Example 442: Synthesis of 1-Oxazol-5-ylmethyl-3-[4-(thiazole-2-sulfonyl)-phenyl]-urea

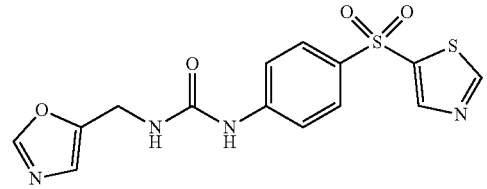 [SMILES: O=C(NCc1cnco1)Nc1ccc(S(=O)(=O)c2cncs2)cc1]

The title compound was prepared using general procedure of 1-pyridin-4-ylmethyl)-3-(4-(thiazol-5-ylsulfonyl)phenyl) urea. ¹H NMR (400 MHz, CD₃OD): δ=8.14 (s, 1H), 7.98 (s, 2H), 7.92 (d, J=8.8 Hz, 2H), 7.64 (d, J=8.8 Hz, 2H), 7.04 (s, 1H), 4.47 (s, 2H). MS: m/z 364.9 (M+H⁺).

Example 443: Synthesis of 1-(4-((1H-Pyrazol-4-yl)sulfonyl)phenyl)-3-(pyridin-4-ylmethyl)urea

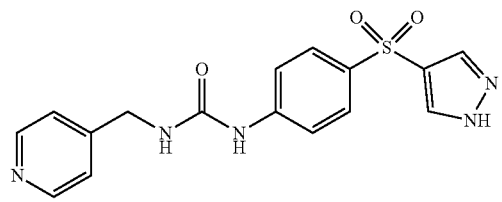 [SMILES: O=C(NCc1ccncc1)Nc1ccc(S(=O)(=O)c2cn[nH]c2)cc1]

The title compound was prepared using general procedure of 1-((1H-pyrazol-4-yl)methyl)-3-(4-((1H-pyrazol-4-yl) sulfonyl)phenyl)urea. ¹H NMR (400 MHz, CD₃OD): δ=8.75 (d, J=6.0 Hz, 2H), 8.04-7.98 (m, 4H), 7.85 (d, J=8.8 Hz, 2H), 7.62 (d, J=8.8 Hz, 2H), 4.67 (s, 2H). MS: m/z 358.0 (M+H⁺).

Example 444: Synthesis of 1-((1H-Pyrazol-4-yl)methyl)-3-(4-((1H-pyrazol-4-yl)sulfonyl)phenyl)urea

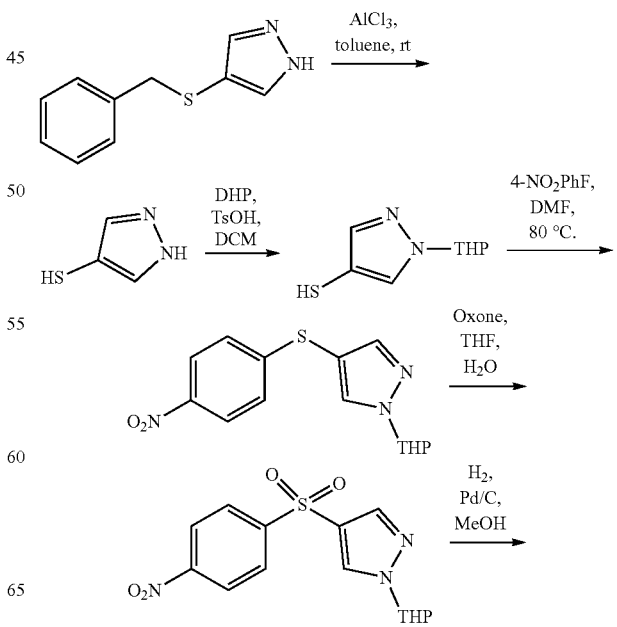

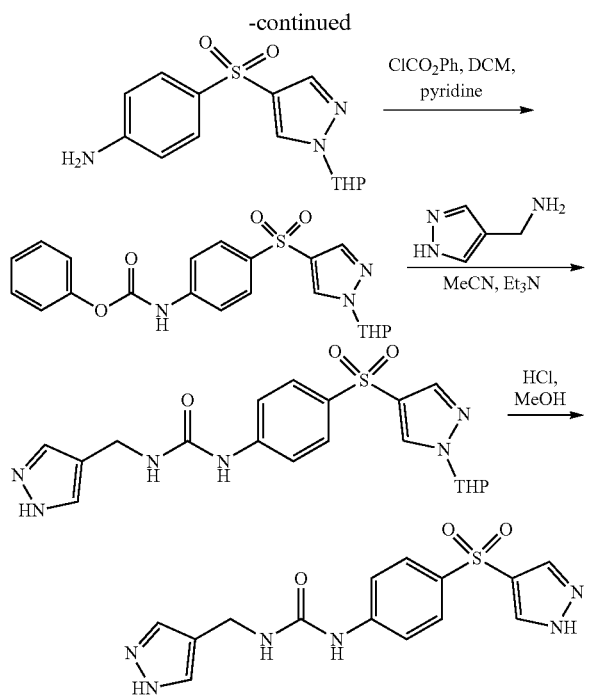

Step 1: To a solution of 4-Benzylsulfanyl-1-isopropyl-1H-pyrazole (1 g, 5.2 mmol) in toluene (10 mL) was added AlCl₃ (1.0 5 g, 7.8 mmol). The reaction was stirred at room temperature for 5 hrs. Then the reaction mixture was concentrated. The residue was purified by silica gel column chromatography (PE/EA=3/1) to give 1H-pyrazole-4-thiol (420 mg, yield: 81%) as red oil.

Step 2: To a solution of 1H-pyrazole-4-thiol (420 mg, 4.2 mmol) in DCM (5 mL) was added DHP (352 mg, 4.2 mmol) and TsOH (144 mg, 0.84 mmol). The reaction was stirred at room temperature for 3 hrs. The reaction mixture was concentrated and the residue was purified by silica gel column chromatography (PE/EA=3/1) to give 1-(tetrahydro-2H-pyran-2-yl)-1H-pyrazole-4-thiol (220 mg, yield: 29%) as yellow oil.

Step 3: To a solution of 1-(tetrahydro-2H-pyran-2-yl)-1H-pyrazole-4-thiol (220 mg, 1.19 mmol) in DMF (5 mL) was added Cs₂CO₃ (1.16 g, 3.57 mmol) and 1-Fluoro-4-nitrobenzene (252 mg, 1.79 mmol). The reaction was stirred at 80° C. for 3 hrs. Then the reaction was extracted with EA (10 mL×2). The combined organic layer was washed with brine (10 mL×2), dried over Na₂SO₄, filtered and concentrated. The residue was purified by silica gel column chromatography (PE/EA=3/1) to give 4-((4-nitrophenyl)thio)-1-(tetrahydro-2H-pyran-2-yl)-1H-pyrazole (290 mg, yield: 80%) as yellow oil.

Step 4: To a mixture of 4-((4-nitrophenyl)thio)-1-(tetrahydro-2H-pyran-2-yl)-1H-pyrazole (270 mg, 0.885 mmol) in THF (5 mL) and H₂O (5 mL) was added oxone (1.08 g, 1.77 mmol). The resulting mixture was stirred at room temperature for 3 hrs. Then the reaction mixture was filtered and the filtrate was concentrated to give 4-((4-nitrophenyl)sulfonyl)-1-(tetrahydro-2H-pyran-2-yl)-1H-pyrazole (270 mg, yield: 91%) as yellow oil. MS: m/z 338.3 (M+H⁺).

Step 5: To a mixture of 4-((4-nitrophenyl)sulfonyl)-1-(tetrahydro-2H-pyran-2-yl)-1H-pyrazole (270 mg, 0.801 mmol) in MeOH (10 mL) was added Pd/C (27 mg, 12.2 mmol). The resulting mixture was stirred at room temperature for 3 hrs. Then the reaction mixture was filtered and the filtrate was concentrated to give 4-((1-(tetrahydro-2H-pyran-2-yl)-1H-pyrazol-4-yl)sulfonyl)aniline (200 mg, yield: 82%) as colorless oil.

Step 6: To a mixture of 4-((1-(tetrahydro-2H-pyran-2-yl)-1H-pyrazol-4-yl)sulfonyl)aniline (200 mg, 0.65 mmol) in DCM (10 mL) was added phenyl chloroformate (203 mg, 1.3 mmol) and TEA (262 mg, 2.6 mmol). The resulting mixture was stirred at room temperature for 3 hrs. Then the reaction was extracted with DCM. The combined organic layer was washed with brine, dried over Na₂SO₄, filtered and concentrated to give phenyl (4-((1-(tetrahydro-2H-pyran-2-yl)-1H-pyrazol-4-yl)sulfonyl)phenyl)carbamate (120 mg, yield: 43%) as colorless oil.

Step 7: To a mixture of phenyl (4-((1-(tetrahydro-2H-pyran-2-yl)-1H-pyrazol-4-yl)sulfonyl)phenyl)carbamate (60 mg, 0.14 mmol) in ACN (10 mL) was added C-(1H-Pyrazol-4-yl)-methylamine (16 mg, 0.168 mmol) and TEA (42 mg, 0.42 mmol). The resulting mixture was stirred at 80° C. for 3 hrs. Then the reaction mixture was concentrated. The residue was extracted with EA. The combined organic layer was washed with brine, dried over Na₂SO₄, filtered and concentrated to give 1-((1H-pyrazol-4-yl)methyl)-3-(4-((1-(tetrahydro-2H-pyran-2-yl)-1H-pyrazol-4-yl)sulfonyl)phenyl)urea (70 mg, crude, yield: 100%) as yellow oil.

Step 8: A solution of 1-((1H-pyrazol-4-yl)methyl)-3-(4-((1-(tetrahydro-2H-pyran-2-yl)-1H-pyrazol-4-yl)sulfonyl)phenyl)urea (70 mg, crude, 0.14 mmol) in a solution of HCl in MeOH (4M, 5 mL) was stirred at room temperature for 3 hrs. Then the reaction mixture was concentrated and the residue was purified by HPLC to give 1-(1H-Pyrazol-4-ylmethyl)-3-[4-(2-trifluoromethoxy-benzenesulfonyl)-phenyl]-urea (12 mg, yield: 8%) as a white solid ¹H NMR (400 MHz, CD₃OD): δ=8.05 (s, 2H), 7.86 (d, J=7.2 Hz, 2H), 7.70 (s, 2H), 7.61 (d, J=7.2 Hz, 2H), 4.31 (s, 2H). MS: m/z 347.0 (M+H⁺).

Example 445: Synthesis of 1-(4-((1H-Pyrazol-4-yl)sulfonyl)phenyl)-3-(oxazol-5-ylmethyl)urea

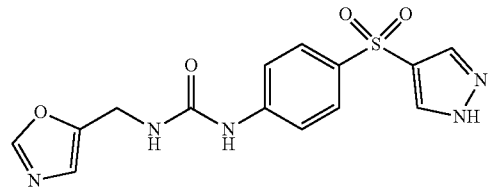 [SMILES: O=C(NCc1cnco1)Nc1ccc(S(=O)(=O)c2cn[nH]c2)cc1]

The title compound was prepared using general procedure of 1-((1H-pyrazol-4-yl)methyl)-3-(4-((1H-pyrazol-4-yl)sulfonyl)phenyl)urea. ¹H NMR (400 MHz, CD₃OD): δ=8.14 (s, 1H), 8.04 (s, 2H), 7.84 (d, J=7.0 Hz, 2H), 7.54 (d, J=7.2 Hz, 2H), 7.03 (s, 1H), 4.46 (s, 2H). MS: m/z 347.9 (M+H⁺).

Example 446: Synthesis of 1-[4-(1-Methyl-1H-pyrazole-4-sulfonyl)-phenyl]-3-pyridin-4-ylmethyl-urea

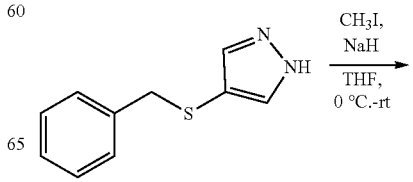

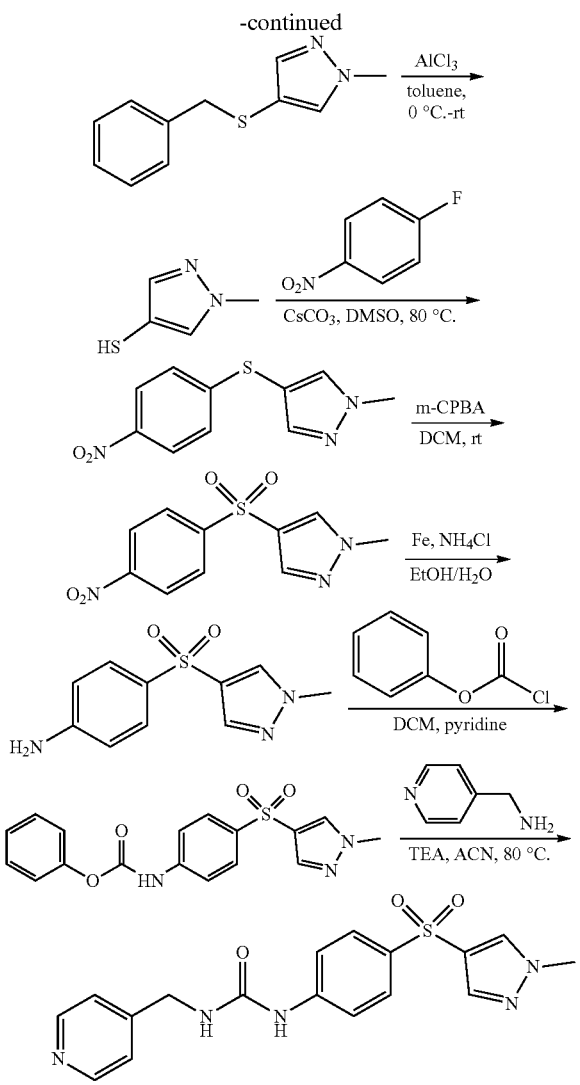

Step 1: To a solution of NaH (0.63 g, 15.76 mmol, 60%) in THF (20 mL) was added dropwise a solution of 4-Benzylsulfanyl-1H-pyrazole (3.0 g, 15.76 mmol) in THF (20 mL) at 0° C. The reaction mixture was stirred at 0° C. for 2 hrs. To the reaction mixture was added dropwise CH₃I (1.96 mL, 31.52 mmol) at 0° C. The reaction mixture was stirred at room temperature for another 2 hrs. The reaction was completed detected by LC-MS. The reaction was quenched with water (5 mL) and extracted with DCM (20 mL×3). The combined organic layer was washed with brine (20 mL) and water (20 mL) and concentrated under reduced pressure to give 4-Benzylsulfanyl-1-methyl-1H-pyrazole (3.60 g, yield: 100%) as yellow oil. ¹H NMR (400 MHz, DMSO-d₆): δ=7.63 (s, 1H), 7.30-7.18 (m, 6H), 3.86 (s, 2H), 3.76 (s, 3H).

Step 2: To a solution of 4-Benzylsulfanyl-1-methyl-1H-pyrazole (3.6 g, 17.6 mmol) in toluene (20 mL) was added AlCl₃ (3.5 g, 26.4 mmol) at 0° C. The reaction mixture was stirred at room temperature for 2 hrs. The reaction was completed detected by TLC (PE/EA=4/1). The reaction mixture was used to the next step without further purification.

Step 3: To a solution of Step 2 was added DMSO (20 mL), Cs₂CO₃ (28.7 g, 88.1 mmol) and 1-Fluoro-4-nitro-benzene (3.7 g, 26.4 mmol). The reaction mixture was stirred at 80° C. under N₂ for 10 hrs. The reaction was completed detected by LC-MS. The reaction was quenched with water (20 mL) and extracted with DCM (30 mL×3). The combined organic layer was washed with brine (30 mL) and water (30 mL), dried over Na₂SO₄, filtered and concentrated. The residue was purified by silia gel chromatography (PE to PE/EA=5/1) to give 1-Methyl-4-(4-nitro-phenylsulfanyl)-1H-pyrazole (2.05 g, yield: 50%) as a yellow solid. ¹H NMR (400 MHz, DMSO-d₆): δ=8.17 (s, 1H), 8.12 (d, J=9.2 Hz, 2H), 7.70 (s, 1H), 7.25 (d, J=8.8 Hz, 2H), 3.39 (s, 3H).

Step 4: To a solution of 1-Methyl-4-(4-nitro-phenylsulfanyl)-1H-pyrazole (1.00 g, 4.25 mmol) in DCM (20 mL) was added m-CPBA (2.20 g, 12.75 mmol, 85% Wt) at 0° C. The reaction mixture was allowed to warm to room temperature for 1 hr. The reaction was completed detected by LC-MS. The reaction was quenched with Na₂SO₃ aqueous (10 mL) and extracted with DCM (20 mL×3). The combined organic layer was washed with NaHCO₃ aqueous (20 mL) and water (20 mL) and concentrated. The residue was purified by silia gel chromatography (PE to PE/EA=10/1) to give 1-Methyl-4-(4-nitro-benzenesulfonyl)-1H-pyrazole (1.05 g, yield: 93%) as a white solid. ¹H NMR (400 MHz, DMSO-d₆): δ=8.59 (s, 1H), 8.41 (d, J=8.8 Hz, 2H), 8.19 (d, J=8.8 Hz, 2H), 8.04 (s, 1H), 3.88 (s, 3H).

Step 5: To a solution of 1-Methyl-4-(4-nitro-benzenesulfonyl)-1H-pyrazole (1.00 g, 3.74 mmol) in EtOH/H₂O (30 mL/10 mL) was added iron powder (1.04 g, 18.71 mmol) and NH₄Cl (1.00 g, 18.71 mmol) at room temperature. The reaction mixture was heated to 80° C. overnight. The reaction was completed detected by LC-MS. The reaction mixture was concentrated and then extracted with DCM (30 mL×3). The combined organic layer was washed with dilute HCl (1 mol/L, 30 mL) and water (30 mL) and concentrated under pressure to give 4-(1-Methyl-1H-pyrazole-4-sulfonyl)-phenylamine (0.79 g, yield: 89%) as a yellow solid. ¹H NMR (300 MHz, DMSO-d₆) δ=8.27 (s, 1H), 7.76 (s, 1H), 7.51 (d, J=8.4 Hz, 2H), 6.59 (d, J=8.4 Hz, 2H), 6.11 (br s, 2H), 3.82 (s, 3H).

Step 6: To a solution of 4-(1-Methyl-1H-pyrazole-4-sulfonyl)-phenylamine (750 mg, 3.16 mmol) in DCM (30 mL) was added pyridine (750 mg, 9.48 mmol) and phenyl chloroformate (742 mg, 4.74 mmol) at 0° C. The reaction mixture was stirred at room temperature for 2 hrs. The reaction was completed detected by LC-MS. The reaction was quenched with water (5 mL) and extracted with DCM (20 mL×3). The combined organic layer was washed with brine (20 mL) and water (20 mL) and concentrated. The residue was purified by silia gel chromatography (PE to PE/EA=5/1) to give [4-(1-Methyl-1H-pyrazole-4-sulfonyl)-phenyl]-carbamic acid phenyl ester (890 mg, yield: 79%) as a white solid. ¹H NMR (400 MHz, DMSO-d₆): δ=10.73 (s, 1H), 8.41 (s, 1H), 7.90-7.88 (m, 3H), 7.70 (d, J=8.8 Hz, 2H), 7.44 (t, J=7.8 Hz, 2H), 7.30-7.23 (m, 3H), 3.86 (s, 3H).

Step 7: To a solution of [4-(1-Methyl-1H-pyrazole-4-sulfonyl)-phenyl]-carbamic acid phenyl ester (90.0 mg, 0.25 mmol) in ACN (5 mL) was added TEA (76 mg, 0.75 mmol) and C-Pyridin-4-yl-methylamine (81 mg, 0.75 mmol). The reaction mixture was stirred at 80° C. for 2 hrs. The reaction was completed detected by LC-MS. The reaction was quenched with water (5 mL) and extracted with DCM (20 mL×3). The combined organic layer was washed with brine (20 mL) and water (20 mL), dried over Na₂SO₄, filtered and concentrated. The residue was purified by prep.HPLC to give 1-[4-(1-Methyl-1H-pyrazole-4-sulfonyl)-phenyl]-3-pyridin-4-ylmethyl-urea (65 mg, yield: 70%) as a yellow solid. ¹H NMR (400 MHz, DMSO-d₆): δ=9.36 (s, 1H), 8.51 (d, J=6.0 Hz, 2H), 8.38 (s, 1H), 7.85 (s, 1H), 7.76 (d, J=8.8

Hz, 2H), 7.60 (d, J=8.8 Hz, 2H), 7.30 (d, J=6.0 Hz, 2H), 7.00 (t, J=6.2 Hz, 1H), 4.34 (d, J=6.4 Hz, 2H), 3.85 (s, 3H). MS: m/z 372.0 (M+H$^+$).

Example 447: Synthesis of 1-[4-(1-Methyl-1H-pyrazole-4-sulfonyl)-phenyl]-3-(1H-pyrazol-4-ylm-ethyl)-urea

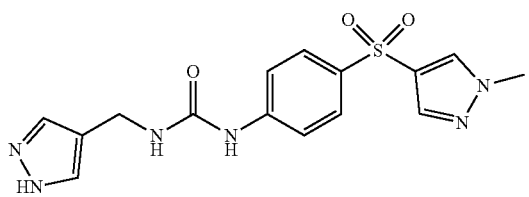 [SMILES: Cn1cc(S(=O)(=O)c2ccc(NC(=O)NCc3cn[nH]c3)cc2)cn1]

The title compound was prepare using genera procedure of 1-[4-(1-Methyl-1H-pyrazole-4-sulfonyl)-phenyl]-3-pyridin-4-ylmethyl-urea. $^1$H NMR (400 MHz, DMSO-d$_6$): δ=9.16 (s, 1H), 8.38 (s, 1H), 7.85 (s, 1H), 7.75 (d, J=8.8 Hz, 2H), 7.59-7.56 (m, 4H), 6.65 (s, 1H), 4.15 (d, J=4.0 Hz, 2H), 3.85 (s, 3H). MS: m/z 361.0 (M+H$^+$).

Example 448: Synthesis of 1-[4-(1-Methyl-1H-pyrazole-4-sulfonyl)-phenyl]-3-oxazol-5-ylmethyl-urea

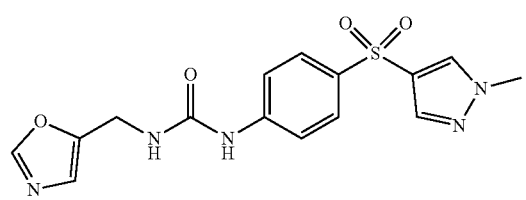 [SMILES: Cn1cc(S(=O)(=O)c2ccc(NC(=O)NCc3cnco3)cc2)cn1]

The title compound was prepared using general procedure of 1-[4-(1-Methyl-1H-pyrazole-4-sulfonyl)-phenyl]-3-pyridin-4-ylmethyl-urea. $^1$H NMR (400 MHz, DMSO-d$_6$): δ=9.63 (s, 1H), 8.38 (s, 1H), 8.29 (s, 1H), 7.85 (s, 1H), 7.76 (d, J=8.0 Hz, 2H), 7.60 (d, J=8.4 Hz, 2H), 7.12 (t, J=5.4 Hz, 1H), 7.01 (s, 1H), 4.37 (d, J=5.6 Hz, 2H), 3.82 (s, 3H). MS: m/z 361.9 (M+H$^+$).

Example 449: Synthesis of 1-[4-(1-Isopropyl-1H-pyrazole-4-sulfonyl)-phenyl]-3-pyridin-4-ylmethyl-urea

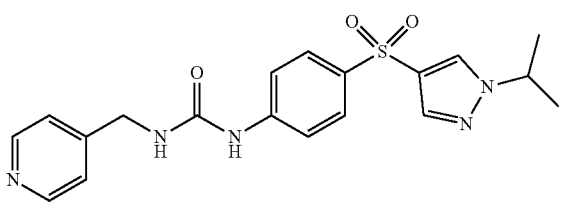 [SMILES: CC(C)n1cc(S(=O)(=O)c2ccc(NC(=O)NCc3ccncc3)cc2)cn1]

The title compound was prepared using general procedure of 1-[4-(1-Isopropyl-1H-pyrazole-4-sulfonyl)-phenyl]-3-(1H-pyrazol-4-ylmethyl)-urea. $^1$H NMR (400 MHz, CD$_3$OD): δ=8.47 (d, J=6.0 Hz, 2H), 8.24 (s, 1H), 7.84-7.80 (m, 3H), 7.60 (d, J=8.8 Hz, 2H), 7.40 (d, J=6.0 Hz, 2H), 4.57 (m, 1H), 4.45 (s, 2H), 1.47 (s, 6H). MS: m/z 400.0 (M+H$^+$).

Example 450: Synthesis of 1-[4-(1-Isopropyl-1H-pyrazole-4-sulfonyl)-phenyl]-3-(1H-pyrazol-4-ylm-ethyl)-urea

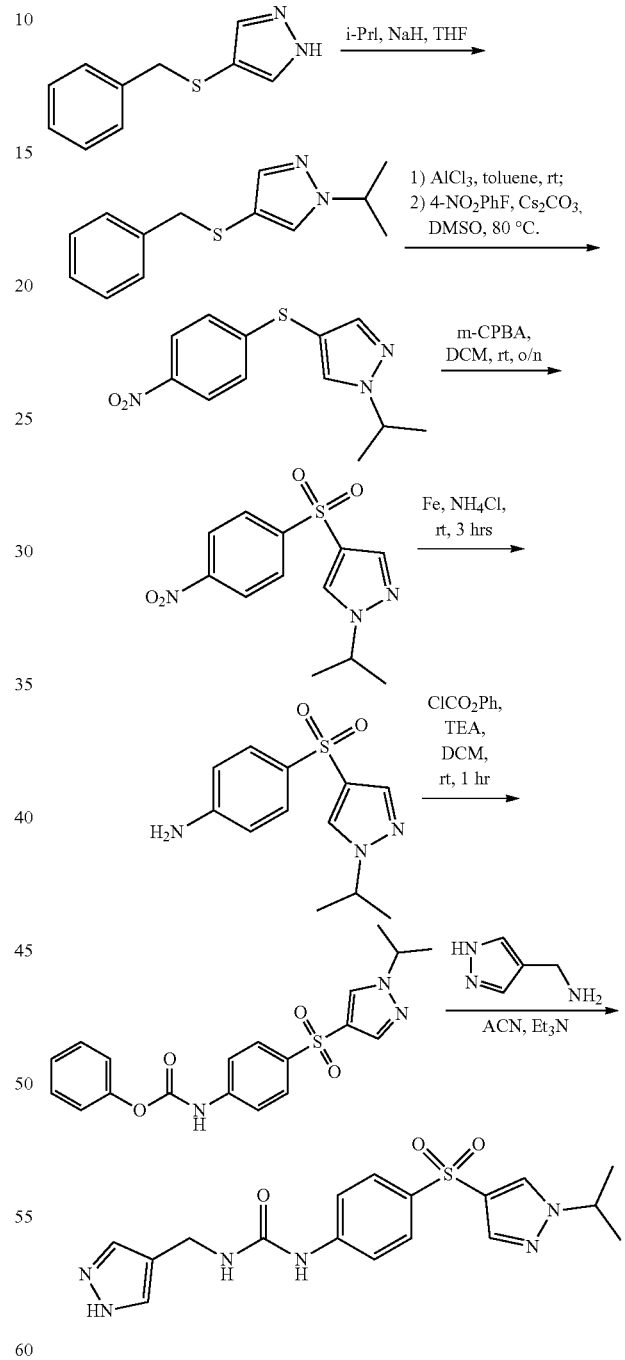

Step 1: To a solution of NaH (460 mg, 11.5 mmol) in THF (20 mL) was added 4-Benzylsulfanyl-1H-pyrazole (2 g, 10.5 mmol) at 0° C. The reaction mixture was stirred at 0° C. for 1 h. Then 2-Iodo-propane (2.67 g, 15.75 mmol) was added to the mixture. The reaction was stirred at room temperature for 3 hrs. Then the reaction mixture was quenched with NH$_4$Cl(aq) and extracted with EA (30 ml×2). The combined organic layer was washed with brine (30 ml×2), dried over Na₂SO₄, filtered and concentrated. The residue was purified by silica gel column chromatography (PE/EA=5/1) to give 4-Benzylsulfanyl-1-isopropyl-1H-pyrazole (2.4 g, yield: 98%) as colorless oil. MS: m/z 232.9 (M+H⁺).

Step 2: To a solution of 4-Benzylsulfanyl-1-isopropyl-1H-pyrazole (2.4 g, 10.3 mmol) in toluene (20 mL) was added AlCl₃ (2 g, 15.5 mmol). The reaction was stirred at room temperature for 5 hrs. Then DMSO (20 mL), Cs₂CO₃ (16.7 g, 51.5 mmol) and 1-Fluoro-4-nitro-benzene (2.18 g, 15.5 mmol) were added to the mixture and the reaction was stirred at 80° C. overnight. Then the reaction was extracted with EA (30 ml×2). The combined organic layer was washed with brine (30 mL×2), dried over Na₂SO₄, filtered and concentrated. The residue was purified by silica gel column chromatography (PE/EA=5/1) to give 1-Isopropyl-4-(4-nitro-phenylsulfanyl)-1H-pyrazole (760 mg, yield: 26%) as colorless oil. MS: m/z 264.0 (M+H⁺).

Step 3: To a mixture of 1-Isopropyl-4-(4-nitro-phenylsulfanyl)-1H-pyrazole (700 mg, 2.66 mmol) in DCM (20 mL) was added m-CPBA (2.2 g, 7.98 mmol). The resulting mixture was stirred at room temperature for 3 hrs. Then the reaction mixture was washed with Na₂SO₃ (aq), dried over Na₂SO₄, filtered and concentrated. The residue was purified by silica gel column chromatography (PE/EA=10/1) to give 1-Isopropyl-4-(4-nitro-benzenesulfonyl)-1H-pyrazole (780 mg, yield: 98%) as a yellow solid. MS: m/z 296.0 (M+H⁺).

Step 4: To a mixture of 1-Isopropyl-4-(4-nitro-benzenesulfonyl)-1H-pyrazole (720 mg, 2.44 mmol) in EtOH (10 mL) and H₂O (2 mL) was added Fe (683 mg, 12.2 mmol) and NH₄Cl (646 mg, 12.2 mmol). The resulting mixture was stirred at 80° C. for 3 hrs. Then the reaction mixture was filtered and the filtrate was concentrated to give 4-(1-Isopropyl-1H-pyrazole-4-sulfonyl)-phenylamine (560 mg, yield: 86%) as colorless oil. MS: m/z 266.0 (M+H⁺).

Step 5: To a mixture of 4-(1-Isopropyl-1H-pyrazole-4-sulfonyl)-phenylamine (540 mg, 2.03 mmol) in DCM (10 mL) was added phenyl chloroformate (475 mg, 5.7 mmol) and TEA (615 mg, 6.09 mmol). The resulting mixture was stirred at room temperature for 3 hrs. Then the reaction was extracted with DCM. The combined organic layer was washed with brine, dried over Na₂SO₄, filtered and concentrated. The residue was purified by silica gel column chromatography (PE/EA=1/1) to give [4-(1-Isopropyl-1H-pyrazole-4-sulfonyl)-phenyl]-carbamic acid phenyl ester (690 mg, yield: 85%) as a yellow solid. MS: m/z 386.1 (M+H⁺).

Step 6: To a mixture of [4-(1-Isopropyl-1H-pyrazole-4-sulfonyl)-phenyl]-carbamic acid phenyl ester (100 mg, 0.259 mmol) in CAN (10 mL) was added C-(1H-Pyrazol-4-yl)-methylamine (75.5 mg, 0.779 mmol) and TEA (78.6 mg, 0.779 mmol). The resulting mixture was stirred at 80° C. for 3 hrs. Then the reaction mixture was concentrated. The residue was extracted with EA. The combined organic layer was washed with brine, dried over Na₂SO₄, filtered and concentrated. The residue was purified by HPLC to give 1-[4-(1-Isopropyl-1H-pyrazole-4-sulfonyl)-phenyl]-3-(1H-pyrazol-4-ylmethyl)-urea (10 mg, yield: 9%) as a white solid ¹H NMR (400 MHz, CD₃OD): δ=8.23 (s, 1H), 7.83-7.80 (m, 3H), 7.70 (s, 2H), 7.58 (d, J=8.8 Hz, 2H), 4.57 (m, 1H), 4.29 (s, 2H), 1.50 (s, 6H). MS: m/z 389.0 (M+H⁺).

Example 451: Synthesis of 1-[4-(1-Isopropyl-1H-pyrazole-4-sulfonyl)-phenyl]-3-oxazol-5-ylmethyl-urea

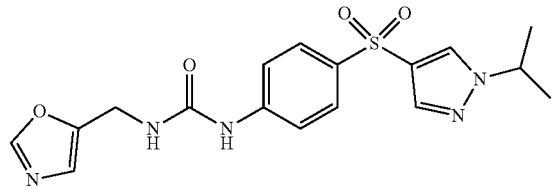 [SMILES: CC(C)n1cc(S(=O)(=O)c2ccc(NC(=O)NCc3cnco3)cc2)cn1]

The title compound was prepared using general procedure of 1-[4-(1-Isopropyl-1H-pyrazole-4-sulfonyl)-phenyl]-3-(1H-pyrazol-4-ylmethyl)-urea. ¹H NMR (400 MHz, CD₃OD): δ=8.24 (s, 1H), 8.14 (s, 1H), 7.84-7.80 (m, 3H), 7.59 (d, J=8.8 Hz, 2H), 7.02 (s, 1H), 4.57 (m, 1H), 4.46 (s, 2H), 1.47 (s, 6H). MS: m/z 390.0 (M+H⁺).

Example 452: Synthesis of 1-(4-(Pyridin-2-ylsulfonyl)phenyl)-3-(pyridin-4-ylmethyl)urea

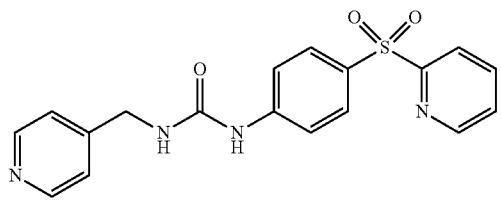

The title compound was prepared using general procedure of 1-((1H-pyrazol-4-yl)methyl)-3-(4-((2-fluorophenyl) sulfonyl)phenyl)urea. ¹H NMR (400 MHz, DMSO-d₆): δ=9.38 (brs, 1H), 8.68 (dd, J=8.0, 0.8 Hz, 1H), 8.50 (dd, J=4.4, 0.8 Hz, 1H), 8.19-8.08 (m, 2H), 7.82 (d, J=9.2 Hz, 2H), 7.70-7.59 (m, 3H), 7.29 (d, J=5.6 Hz, 2H), 6.99 (t, J=6.4 Hz, 1H), 4.34 (d, J=6.0 Hz, 2H). MS: m/z 369.0 (M+H⁺).

Example 453: Synthesis of 1-((1H-Pyrazol-4-yl)methyl)-3-(4-(Pyridin-2-ylsulfonyl)phenyl)urea

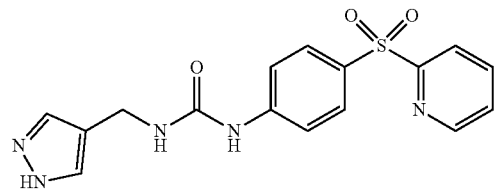 [SMILES: O=C(NCc1cn[nH]c1)Nc1ccc(S(=O)(=O)c2ccccn2)cc1]

The title compound was prepared using general procedure of 1-((1H-pyrazol-4-yl)methyl)-3-(4-((2-fluorophenyl) sulfonyl)phenyl)urea. ¹H NMR (400 MHz, DMSO-d₆): δ=12.63 (brs, 1H), 9.17 (s, 1H), 8.71-8.65 (m, 1H), 8.17-8.08 (m, 2H), 8.83-7.77 (m, 2H), 7.68-7.63 (m, 1H), 7.62-7.59 (m, 2H), 7.58-7.45 (m, 2H), 6.65 (t, J=5.6 Hz, 1H), 4.15 (d, J=5.6 Hz, 2H). MS: m/z 357.9 (M+H⁺).

Example 454: Synthesis of 1-(Oxazol-5-ylmethyl)-3-(4-(Pyridin-2-ylsulfonyl)phenyl)urea

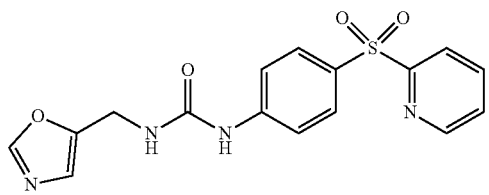 [SMILES: O=C(NCc1cnco1)Nc1ccc(S(=O)(=O)c2ccccn2)cc1]

The title compound was prepared using general procedure of 1-((1H-pyrazol-4-yl)methyl)-3-(4-((2-fluorophenyl)sulfonyl)phenyl)urea. $^1$H NMR (400 MHz, DMSO-d$_6$): δ=9.25 (brs, 1H), 8.70-8.66 (m, 1H), 8.29 (s, 1H), 8.17-8.09 (m, 2H), 7.82 (d, J=8.8 Hz, 2H), 7.69-7.59 (m, 3H), 7.01 (s, 1H), 6.89 (t, J=5.6 Hz, 1H), 4.37 (d, J=5.6 Hz, 2H). MS: m/z 358.9 (M+H$^+$).

Example 455: Synthesis of 1-[4-(Pyridine-3-sulfonyl)-phenyl]-3-pyridin-4-ylmethyl-urea

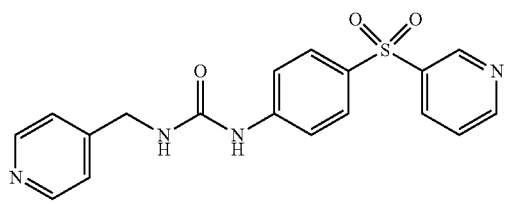 [SMILES: O=C(NCc1ccncc1)Nc1ccc(S(=O)(=O)c2cccnc2)cc1]

The title compound was prepared using general procedure of 1-oxazol-5-ylmethyl-3-[4-(pyridine-3-sulfonyl)-phenyl]-urea. $^1$H NMR (400 MHz, CD$_3$OD): δ=9.06 (d, J=0.8 Hz, 1H), 8.75 (d, J=4.0 Hz, 1H), 8.46 (d, J=4.4 Hz, 2H), 8.33-8.31 (m, 1H), 7.89 (d, J=8.8 Hz, 2H), 7.64 (d, J=9.2 Hz, 2H), 7.61-7.58 (m, 1H), 7.38 (d, J=5.6 Hz, 2H). MS: m/z 368.9 (M+H$^+$).

Example 456: Synthesis of 1-(1H-Pyrazol-4-ylmethyl)-3-[4-(Pyridine-3-sulfonyl)-phenyl]-urea

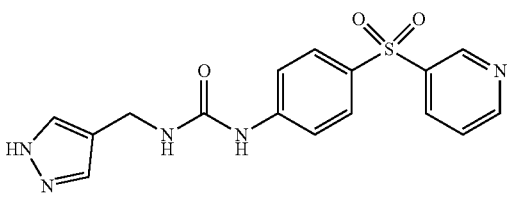 [SMILES: O=C(NCc1cn[nH]c1)Nc1ccc(S(=O)(=O)c2cccnc2)cc1]

The title compound was prepared using general procedure of 1-oxazol-5-ylmethyl-3-[4-(pyridine-3-sulfonyl)-phenyl]-urea. $^1$H NMR (400 MHz, CD$_3$OD): δ=9.33 (s, 1H), 8.95 (d, J=4.8 Hz, 1H), 8.80 (d, J=8.0 Hz, 1H), 8.25 (s, 2H), 8.10-7.98 (m, 1H), 7.94 (d, J=9.2 Hz, 2H), 7.69 (d, J=8.8 Hz, 2H), 4.37 (s, 2H). MS: m/z 358.0 (M+H$^+$).

Example 457: Synthesis of 1-Oxazol-5-ylmethyl-3-[4-(pyridine-3-sulfonyl)-phenyl]-urea

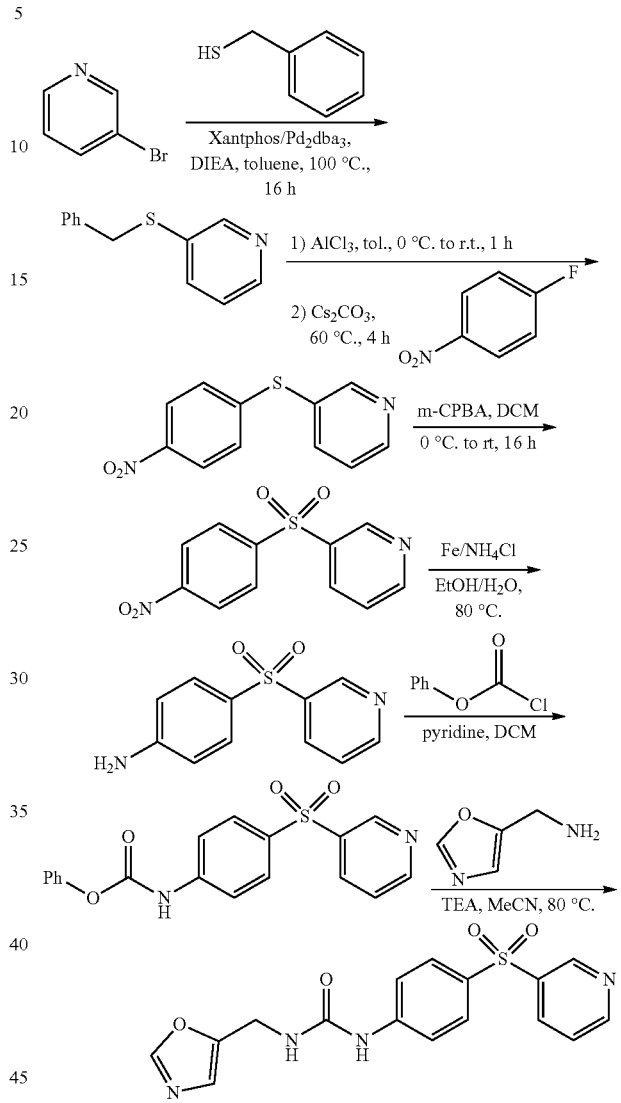

Step 1: To a solution of 3-bromo-pyridine (5.0 g, 32 mmol) and phenyl-methanethiol (4.37 g, 35 mmol) in toluene (50 mL) was added Xantphos (1.73 g, 3.0 mmol), Pd$_2$dba$_3$ (1.57 g, 1.50 mmol) and DIEA (7.80 g, 6 mmol). The reaction was stirred at 110° C. overnight. The resulting was filtered. The filtrate was concentrated and purified by silica gel column (PE/EA=10/1) to give 3-benzylsulfanyl-pyridine (5.8 g, 96%) as a yellow solid. MS: m/z 201.9 (M+H$^+$).

Step 2: To a mixture of 3-benzylsulfanyl-pyridine (1.0 g, 4.9 mmol) in toluene (5 mL) was added AlCl$_3$ (0.98 g, 7.4 mmol) at 0° C. The reaction was then stirred for 1 hrs, left the temperature slowly warmed to room temperature. The reaction mixture was diluted with DMSO (20 mL), 1-fluoro-4-nitro-benzene (1.9 g, 14 mmol) and CsCO$_3$ (29 g, 90 mmol) was added. The resulting mixture was then heated at 60° C. for 4 hrs. The mixture was filtered and the filtrate was diluted with water (40 mL), extracted with EA (30 mL×3) and concentrated. The residue was purified by silica gel column (PE/EA=5/1) to give 3-(4-nitro-phenylsulfanyl)- pyridine (0.40 g, 20%) as a yellow solid. ¹H NMR (300 MHz, DMSO-d₆): δ=8.74-8.71 (m, 2H), 8.17-8.14 (m, 2H), 8.04-8.02 (m, 1H), 7.59-7.54 (m, 1H), 7.36-7.32 (m, 2H). MS: m/z 232.8 (M+H⁺).

Step 3: To a mixture of 3-(4-nitro-phenylsulfanyl)-pyridine (0.40 g, 2.0 mmol) in DCM (20 mL) was added m-CPBA (5.16 g, 30 mmol) at 0° C. slowly. Then the mixture was stirred at room temperature overnight. To the mixture was added Na₂SO₃ and filtered and washed with NaHCO₃, dried over Na₂SO₄, filtered and concentrated. The residue was purified with chromatography (PE/EA=2/1) to give 3-(4-nitro-benzenesulfonyl)-pyridine (222 mg, yield: 42%) as a white solid. MS: m/z 265.0 (M+H⁺).

Step 4: A mixture of 3-(4-nitro-benzenesulfonyl)-pyridine (200 mg, 0.75 mmol), Fe (127 mg, 2.27 mmol) and NH₄Cl (121 mg, 2.27 mmol) in EtOH/H₂O (5 mL/2 mL) was stirred at 80° C. overnight. The reaction solution was filtered. The filtrate was concentrated to give 4-(pyridine-3-sulfonyl)-phenylamine (160 mg, yield: 91%) as a white solid. MS: m/z 235.0 (M+H⁺).

Step 5: To a solution of 4-(pyridine-3-sulfonyl)-phenylamine (170 mg, 0.73 mmol) in DCM (20 mL) was added pyridine (116 mg, 1.45 mmol) and phenyl chloroformate (227 mg, 1.45 mmol) at 0° C. The reaction mixture was stirred at room temperature for 2 hrs. The reaction was completed detected by LC-MS. The reaction was quenched with water (10 mL) and extracted with DCM (10 mL×3). The combined organic layer was dried over Na₂SO₄, filtered and concentrated.

The residue was purified by silica gel column (PE/EA=2/1) to give [4-(pyridine-3-sulfonyl)-phenyl]-carbamic acid phenyl ester (170 mg, yield: 79%) as a white solid. MS: m/z 355.0 (M+H⁺).

Step 6: To a solution of [4-(pyridine-3-sulfonyl)-phenyl]-carbamic acid phenyl ester (50 mg, 0.14 mmol) in ACN (5 mL), was added TEA (60.6 mg, 0.6 mmol) and C-Oxazol-5-yl-methylamine (37.9 mg, 0.28 mmol). The reaction mixture was stirred at 80° C. overnight. The reaction was quenched with water (10 mL) and extracted with DCM (10 mL×3). The combined organic layer was dried over Na₂SO₄, filtered and concentrated. The residue was purified by silica gel column (DCM/MEOH=10/1) and prep-HPLC to give 1-oxazol-5-ylmethyl-3-[4-(pyridine-3-sulfonyl)-phenyl]-urea (8.2 mg, yield: 16%) as a white solid. ¹H NMR (400 MHz, CD₃OD): δ=9.06 (d, J=2.0 Hz, 1H), 7.46 (dd, J=3.9 Hz, 1.6 Hz, 1H), 8.34-8.31 (m, 1H), 8.14 (s, 1H), 7.89 (d, J=8.8 Hz, 2H), 7.64-7.58 (m, 3H), 7.02 (s, 1H), 4.46 (s, 2H). MS: m/z 359.0 (M+H⁺).

Example 458: Synthesis of 1-(Pyridin-4-ylmethyl)-3-(4-(pyridin-4-ylsulfonyl)phenyl)urea

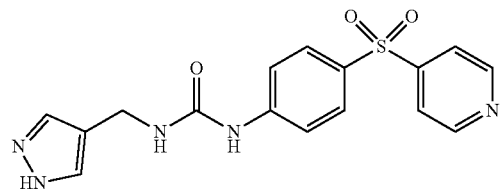 [SMILES: O=C(NCc1cn[nH]c1)Nc1ccc(S(=O)(=O)c2ccncc2)cc1]

The title compound was prepared using general procedure of 1-((1H-pyrazol-4-yl)methyl)-3-(4-((2-fluorophenyl)sulfonyl)phenyl)urea. ¹H NMR (400 MHz, DMSO-d₆): δ=9.55 (brs, 1H), 8.85 (d, J=6.0 Hz, 2H), 8.50 (d, J=5.6 Hz, 2H), 7.94-7.80 (m, 4H), 7.66 (d, J=8.8 Hz, 2H), 7.29 (d, J=5.6 Hz, 2H), 7.09 (t, J=6.0 Hz, 1H), 4.34 (d, J=5.6 Hz, 2H). MS: m/z 368.9 (M+H⁺).

Example 459: Synthesis of 1-((1H-Pyrazol-4-yl)methyl)-3-(4-(pyridin-4-ylsulfonyl)phenyl)urea

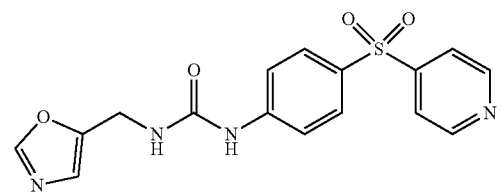 [SMILES: O=C(NCc1cnco1)Nc1ccc(S(=O)(=O)c2ccncc2)cc1]

The title compound was prepared using general procedure of 1-((1H-pyrazol-4-yl)methyl)-3-(4-((2-fluorophenyl)sulfonyl)phenyl)urea. ¹H NMR (400 MHz, DMSO-d₆): δ=12.64 (brs, 1H), 9.16 (s, 1H), 8.85 (dd, J=4.8, 1.6 Hz, 2H), 7.90-7.80 (m, 4H), 7.64 (d, J=9.2 Hz, 2H), 7.60-7.42 (m, 2H), 6.61 (t, J=5.6 Hz, 1H), 4.15 (d, J=5.2 Hz, 2H). MS: m/z 357.9 (M+H⁺).

Example 460: Synthesis of 1-(Oxazol-5-ylmethyl)-3-(4-(pyridin-4-ylsulfonyl)phenyl)urea

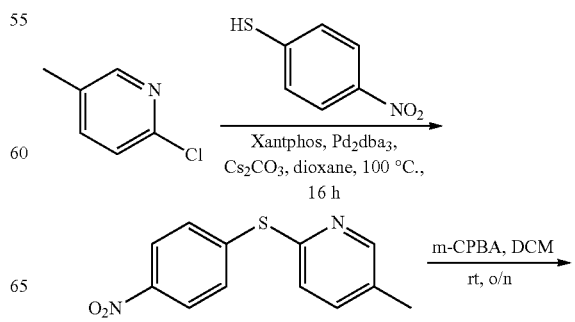

The title compound was prepared using general procedure of 1-((1H-pyrazol-4-yl)methyl)-3-(4-((2-fluorophenyl)sulfonyl)phenyl)urea. ¹H NMR (400 MHz, DMSO-d₆): δ=9.42 (brs, 1H), 8.85 (dd, J=4.8, 1.6 Hz, 2H), 8.28 (s, 1H), 7.90-7.81 (m, 4H), 7.65 (d, J=9.2 Hz, 2H), 7.01 (s, 1H), 6.98 (t, J=6.0 Hz, 1H), 4.37 (d, J=5.6 Hz, 2H). MS: m/z 358.9 (M+H⁺).

Example 461: Synthesis of 1-[4-(5-Methyl-pyridine-2-sulfonyl)-phenyl]-3-(1H-pyrazol-4-ylmethyl)-urea

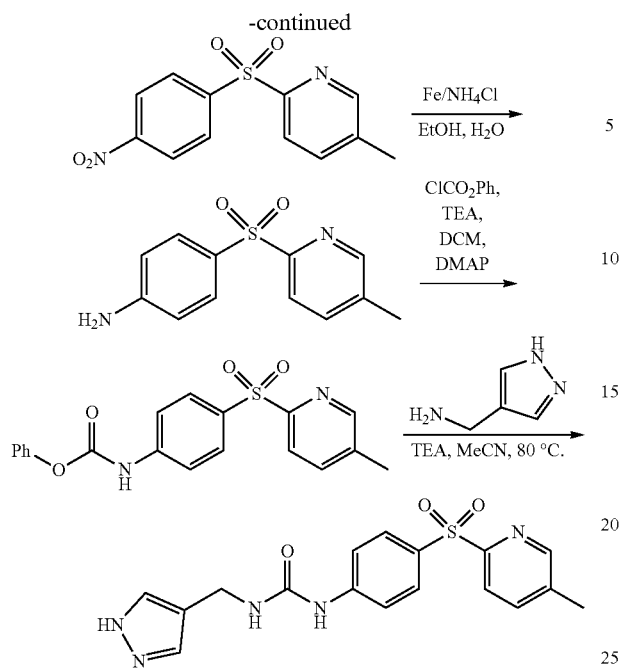

Step 1: A flask charged with 2-chloro-5-methyl-pyridine (1 g, 7.74 mmol), 4-nitro-benzenethiol (1 g, 6.45 mmol), Xantphos (370 mg, 0.64 mmol), Pd$_2$dba$_3$ (295 mg, 0.32 mmol) and Cs$_2$CO$_3$ (4.2 g, 12.9 mmol) in dioxane (40 mL) was degassed and filled with N$_2$. The resulting mixture was then heated to 100° C. for 16 hrs. The reaction mixture was concentrated. The residue was purified by silica gel column chromatography (PE to PE/EA=20/1 to 5/1) to give 5-methyl-2-(4-nitro-phenylsulfanyl)-pyridine (280 mg, yield: 15%) as a white solid. MS: m/z 246.7 (M+H$^+$).

Step 2: To a cooled mixture of 5-methyl-2-(4-nitro-phenylsulfanyl)-pyridine (280 mg, 1.13 mmol) in DCM (50 mL) at 0° C. was added m-CPBA (700 mg, 2.84 mmol) in portions. After addition, the resulting mixture was stirred at room temperature for 14 hrs. The mixture was then filtered and the filtrate was washed with aq. Na$_2$SO$_3$ (30 mL×2) and concentrated. The residue was purified by prep-TLC (PE/EA=2:1) to give 5-methyl-2-(4-nitro-benzenesulfonyl)-pyridine (125 mg, yield: 40%) as a yellow solid. $^1$H NMR (400 MHz, DMSO-d$_6$): δ=8.57 (s, 1H), 8.42 (d, J=8.9 Hz, 2H), 8.26-8.13 (m, 3H), 8.00 (d, J=6.8 Hz, 1H), 2.38 (s, 3H). MS: m/z 278.8 (M+H$^+$).

Step 3: A mixture of 5-methyl-2-(4-nitro-benzenesulfonyl)-pyridine (125 mg, 0.48 mmol), Fe (125 mg, 2.24 mmol) and NH$_4$Cl (120 mg, 2.24 mmol) in EtOH (20 mL) and water (4 mL) was stirred and heated to 80° C. for 16 hrs. The mixture was filtered and the filtrate was concentrated to give the crude 4-(5-methyl-pyridine-2-sulfonyl)-phenylamine (120 mg, yield: 100%) as a yellow solid. MS: m/z 248.8 (M+H$^+$).

Step 4: To a mixture of 4-(5-methyl-pyridine-2-sulfonyl)-phenylamine (120 mg, 0.48 mmol) and TEA (0.14 mL, 0.96 mmol) in DCM (12 mL) was added phenyl chloroformate (113 mg, 0.72 mmol) dropwise. After addition, the resulting mixture was stirred at room temperature for 16 hrs. The reaction mixture was concentrated. The residue was purified by prep-TLC (PE/EA=1/1) to give [4-(5-methyl-pyridine-2-sulfonyl)-phenyl]-carbamic acid phenyl ester (40 mg, yield: 23%) as a white solid. MS: m/z 368.8 (M+H$^+$).

Step 5: A mixture of [4-(5-methyl-pyridine-2-sulfonyl)-phenyl]-carbamic acid phenyl ester (40 mg, 0.11 mmol), C-(1H-pyrazol-4-yl)-methylamine (22 mg, 0.22 mmol) and TEA (33 mg, 0.33 mmol) in MeCN (5 mL) was heated to reflux for 16 hrs. The reaction mixture was concentrated. The residue was purified by prep-TLC (DCM/MeOH=10/1) and prep-HPLC (TFA system) to give 1-[4-(5-methyl-pyridine-2-sulfonyl)-phenyl]-3-(1H-pyrazol-4-ylmethyl)-urea (7 mg, yield: 17%) as a white solid. $^1$H NMR (400 MHz, CD$_3$OD): δ=8.47 (s, 1H), 8.05 (d, J=8.1 Hz, 1H), 7.92-7.80 (m, 3H), 7.68-7.49 (m, 4H), 4.28 (s, 2H), 2.40 (s, 3H). MS: m/z 372.0 (M+H$^+$).

Example 462: Synthesis of 1-[4-(6-Methyl-pyridine-3-sulfonyl)-phenyl]-3-pyridin-4-ylmethyl-urea

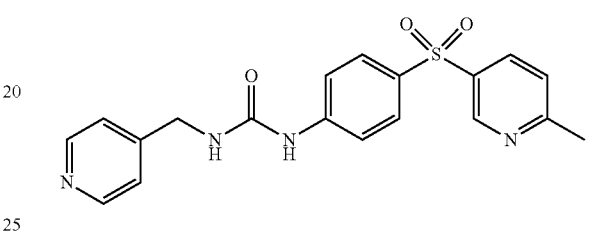

The title compound was prepared using general procedure of 1-[4-(6-methyl-pyridine-3-sulfonyl)-phenyl]-3-(1H-pyrazol-4-ylmethyl)-urea. $^1$H NMR (400 MHz, CD$_3$OD): δ=8.80 (d, J=2.1 Hz, 1H), 8.36 (d, J=6.1 Hz, 2H), 8.08 (dd, J=8.3, 2.4 Hz, 1H), 7.77 (d, J=8.9 Hz, 2H), 7.53 (d, J=8.9 Hz, 2H), 7.36 (d, J=8.3 Hz, 1H), 7.28 (d, J=5.9 Hz, 2H), 4.35 (s, 2H), 2.49 (s, 3H). MS: m/z 382.9 (M+H$^+$).

Example 463: Synthesis of 1-[4-(6-Methyl-pyridine-3-sulfonyl)-phenyl]-3-(1H-pyrazol-4-ylmethyl)-urea

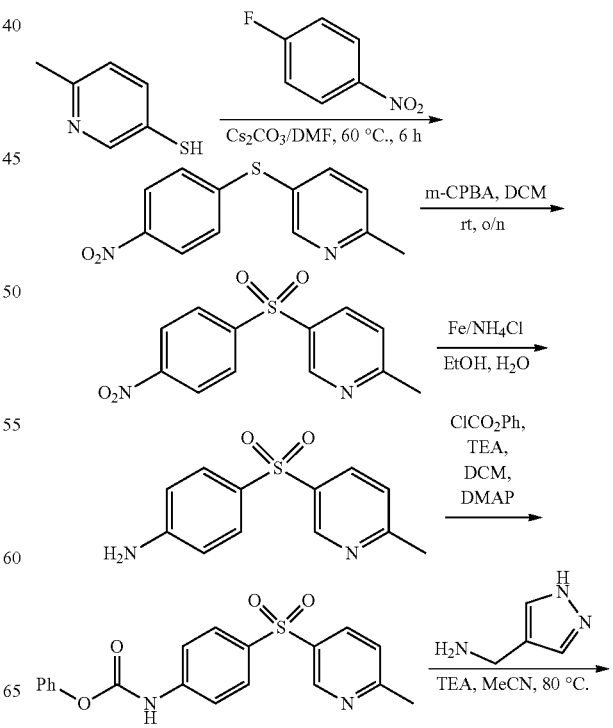

-continued

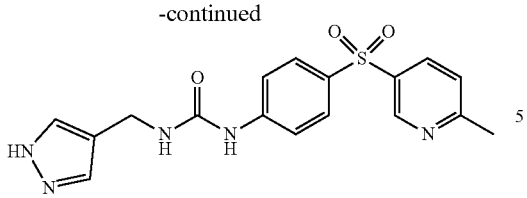

Step 1: To a mixture of 6-methyl-pyridine-3-thiol (580 mg, 4.63 mmol) and 1-fluoro-4-nitro-benzene (650 mg, 4.63 mmol) in DMF (15 mL) was added Cs₂CO₃ (3 g, 9.26 mmol). The resulting mixture was then heated to 60° C. for 6 hrs. The mixture was then poured into water (50 mL) and extracted with EA (30 mL×3). The combined organic layer was dried over Na₂SO₄, filtered and concentrated. The residue was purified by silica gel column chromatography (PE/EA=4/1) to give 2-methyl-5-(4-nitro-phenylsulfanyl)-pyridine (385 mg, yield: 34%) as a yellow solid. MS: m/z 246.8 (M+H⁺).

Step 2: To a cooled mixture of 2-methyl-5-(4-nitro-phenylsulfanyl)-pyridine (350 mg, 1.42 mmol) in DCM (50 mL) at 0° C. was added m-CPBA (880 mg, 3.54 mmol) in portions. After addition, the resulting mixture was stirred for 10 hrs at room temperature The mixture was then filtered and the filtrate was washed with aq. Na₂SO₃ (30 mL×2) and concentrated. The residue was purified column chromatography (PE/EA=4/1) to give 2-methyl-5-(4-nitro-benzenesulfonyl)-pyridine (170 mg, yield: 43%) as a yellow solid. ¹H NMR (400 MHz, CDCl₃): δ=9.05 (s, 1H), 8.37 (d, J=8.9 Hz, 2H), 8.23-8.01 (m, 3H), 7.34 (d, J=8.2 Hz, 1H), 2.65 (s, 3H). MS: m/z 279.0 (M+H⁺).

Step 3: A mixture of 2-methyl-5-(4-nitro-benzenesulfonyl)-pyridine (170 mg, 0.61 mmol), Fe (171 mg, 3.05 mmol) and NH₄Cl (162 mg, 3.05 mmol) in EtOH (25 mL) and water (5 mL) was stirred and heated to 80° C. for 16 hrs. The mixture was filtered and the filtrate was concentrated to give the crude 4-(6-methyl-pyridine-3-sulfonyl)-phenylamine (155 mg, yield: 100%) as a yellow solid. MS: m/z 248.9 (M+H⁺).

Step 4: To a mixture of 4-(6-methyl-pyridine-3-sulfonyl)-phenylamine (155 mg, 0.61 mmol) and pyridine (0.2 mL, 2.44 mmol) in DCM (20 mL) was added phenyl chloroformate (144 mg, 0.92 mmol) dropwise. After addition, the resulting mixture was stirred at room temperature for 16 hrs. The mixture was diluted with DCM (30 mL), washed with aq. NaHCO₃ and water, dried over Na₂SO₄, filtered and concentrated to give the crude [4-(6-methyl-pyridine-3-sulfonyl)-phenyl]-carbamic acid phenyl ester (220 mg, yield: 98%) as a white solid. MS: m/z 369.1 (M+H⁺).

Step 5: A mixture of [[4-(6-methyl-pyridine-3-sulfonyl)-phenyl]-carbamic acid phenyl ester (70 mg, 0.2 mmol), C-(1H-pyrazol-4-yl)-methylamine (37 mg, 0.4 mmol) and TEA (62 mg, 0.6 mmol) in MeCN (15 mL) was heated to reflux for 2 hrs. The reaction mixture was concentrated. The residue was purified by prep-TLC (DCM/MeOH=10/1) and prep-HPLC (TFA system) to give 1-[4-(6-methyl-pyridine-3-sulfonyl)-phenyl]-3-(1H-pyrazol-4-ylmethyl)-urea (12 mg, yield: 16%) as a white solid. ¹H NMR (400 MHz, CD₃OD): δ=8.95 (d, J=2.1 Hz, 1H), 8.25 (dd, J=8.3, 2.3 Hz, 1H), 7.87 (d, J=8.9 Hz, 2H), 7.72 (s, 2H), 7.61 (d, J=8.9 Hz, 2H), 7.52 (d, J=8.3 Hz, 1H), 4.30 (s, 2H), 2.61 (s, 3H). MS: m/z 371.9 (M+H⁺).

Example 464: Synthesis of 1-[4-(6-Methyl-pyridine-3-sulfonyl)-phenyl]-3-oxazol-5-ylmethyl-urea

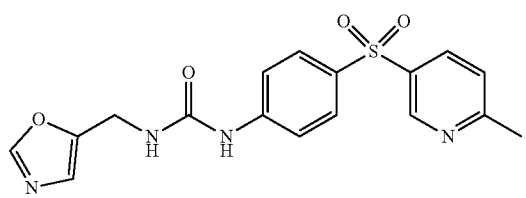 [SMILES: Cc1ccc(S(=O)(=O)c2ccc(NC(=O)NCc3cnco3)cc2)cn1]

The title compound was prepared using general procedure of 1-[4-(6-methyl-pyridine-3-sulfonyl)-phenyl]-3-(1H-pyrazol-4-ylmethyl)-urea. ¹H NMR (400 MHz, CD₃OD): δ=8.92 (d, J=2.0 Hz, 1H), 8.19 (dd, J=8.3, 2.4 Hz, 1H), 8.16 (s, 1H), 7.88 (d, J=8.9 Hz, 2H), 7.63 (d, J=8.9 Hz, 2H), 7.48 (d, J=8.2 Hz, 1H), 7.05 (s, 1H), 4.48 (s, 2H), 2.61 (s, 3H). MS: m/z 372.9 (M+H⁺).

Example 465: Synthesis of 1-[4-(6-Methoxy-pyridine-3-sulfonyl)-phenyl]-3-pyridin-4-ylmethyl-urea

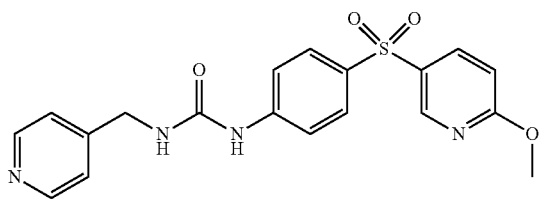 [SMILES: COc1ccc(S(=O)(=O)c2ccc(NC(=O)NCc3ccncc3)cc2)cn1]

The title compound was prepared using general procedure of 1-[4-(6-Methyl-pyridine-3-sulfonyl)-phenyl]-3-(1H-pyrazol-4-ylmethyl)-urea. ¹H NMR (400 MHz, CD₃OD): δ=8.69 (d, J=2.4 Hz, 1H), 8.46 (d, J=5.9 Hz, 2H), 8.06 (dd, J=8.8 Hz, 2.4 Hz, 1H), 7.83 (d, J=8.8 Hz, 2H), 7.61 (d, J=8.8 Hz, 2H), 7.38 (d, J=5.5 Hz, 2H), 6.88 (d, J=8.8 Hz, 1H), 4.45 (s, 2H), 3.96 (s, 3H). MS: m/z 399.0 (M+H⁺).

Example 466: Synthesis of 1-[4-(6-Methyl-pyridine-3-sulfonyl)-phenyl]-3-(1H-pyrazol-4-ylmethyl)-urea

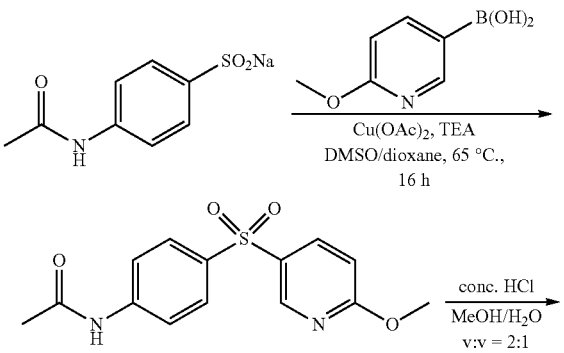

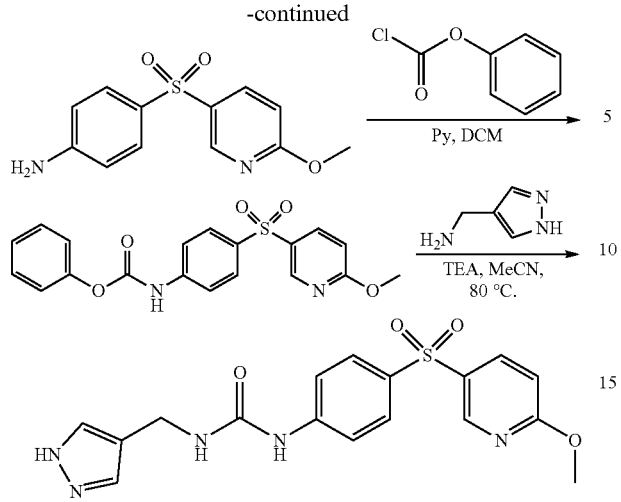

Step 1: A flask charged with 4-acetamidobenzenesulfinic acid sodium salt (2 g, 7.8 mmol), 2-methoxyl-5-pyridineboric acid (1.8 g, 11.7 mmol), TEA (4.4 mL, 31.2 mmol) and Cu(OAc)$_2$ (1.7 g, 9.36 mmol) in dioxane (50 mL) and DMSO (50 mL) was degassed and filled with N$_2$. The resulting mixture was then heated to 65° C. for 16 hrs. Dioxane was evaporated and the residue was diluted with water (150 mL) and NH$_3$.H$_2$O (20 mL), extracted with EA (50 mL×3) and concentrated. The residue was purified by silica gel column chromatography (PE/EA=5/1 to 1/1) to give N-[4-(6-methoxy-pyridine-3-sulfonyl)-phenyl]-acetamide (670 mg, yield: 28%) as a white solid. $^1$H NMR (300 MHz, CDCl$_3$): δ=8.73 (d, J=1.6 Hz, 1H), 8.01-7.94 (m, 1H), 7.88 (d, J=8.2 Hz, 2H), 7.67 (d, J=7.9 Hz, 2H), 7.50-7.45 (m, 1H), 6.80 (d, J=9.3 Hz, 1H), 3.98 (s, 3H), 2.22 (s, 3H). MS: m/z 307.1 (M+H$^+$).

Step 2: A mixture of N-[4-(6-methoxy-pyridine-3-sulfonyl)-phenyl]-acetamide (370 mg, 1.2 mmol) in HCl (conc., 2 mL) and MeOH (4 mL) was stirred at room temperature for 12 hrs. The mixture was diluted with EA (5 mL) and filtered to give 4-(6-methoxy-pyridine-3-sulfonyl)-phenylamine (200 mg, yield: 63%) as a white solid. MS: m/z 264.9 (M+H$^+$).

Step 3: To a mixture of 4-(6-methoxy-pyridine-3-sulfonyl)-phenylamine (200 mg, 0.75 mmol) and pyridine (0.24 mL, 3.0 mmol) in DCM (30 mL) was added phenyl chloroformate (178 mg, 1.13 mmol) dropwise. After addition, the resulting mixture was stirred at room temperature for 16 hrs. The mixture was diluted with DCM (30 mL), washed sequentially with sat. NaHCO$_3$, aq. CuSO$_4$ and water, dried over Na$_2$SO$_4$, filtered and concentrated to give the crude [[4-(6-methoxy-pyridine-3-sulfonyl)-phenyl]-carbamic acid phenyl ester (290 mg, yield: 100%) as a white solid. MS: m/z 385.0 (M+H$^+$).

Step 4: A mixture of [[4-(6-methoxy-pyridine-3-sulfonyl)-phenyl]-carbamic acid phenyl ester (290 mg, 0.75 mmol), C-(1H-pyrazol-4-yl)-methylamine (100 mg, 1.0 mmol) and TEA (0.32 mL, 2.25 mmol) in MeCN (40 mL) was heated to 80° C. for 4 hrs. The reaction mixture was concentrated. The residue was purified by prep-HPLC (NH$_3$.H$_2$O system) to give 1-[4-(6-methoxy-pyridine-3-sulfonyl)-phenyl]-3-(1H-pyrazol-4-ylmethyl)-urea (90 mg, yield: 31%) as a white solid. $^1$H NMR (400 MHz, CD$_3$OD): δ=8.69 (d, J=2.5 Hz, 1H), 8.06 (dd, J=8.8 Hz, 2.6 Hz, 1H), 7.82 (d, J=8.9 Hz, 2H), 7.64-7.48 (m, 4H), 6.88 (d, J=8.9 Hz, 1H), 4.28 (s, 2H), 3.97 (s, 3H). MS: m/z 388.1 (M+H$^+$).

Example 467: Synthesis of 1-[4-(6-Methoxy-pyridine-3-sulfonyl)-phenyl]-3-oxazol-5-ylmethyl-urea

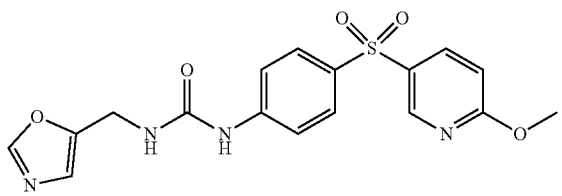 [SMILES: COc1ccc(S(=O)(=O)c2ccc(NC(=O)NCc3cnco3)cc2)cn1]

The title compound was prepared using general procedure of 1-[4-(6-Methyl-pyridine-3-sulfonyl)-phenyl]-3-(1H-pyrazol-4-ylmethyl)-urea. $^1$H NMR (400 MHz, DMSO-d$_6$): δ=9.19 (s, 1H), 8.72 (d, J=2.0 Hz, 1H), 8.28 (s, 1H), 8.12 (dd, J=8.8 Hz, 2.8 Hz, 1H), 7.83 (d, J=8.8 Hz, 2H), 7.60 (d, J=9.2 Hz, 2H), 7.00-6.97 (m, 2H), 6.85 (t, J=6.0 Hz, 1H), 4.36 (d, J=4.2 Hz, 2H), 3.92 (s, 3H). MS: m/z 388.9 (M+H$^+$).

Example 468: Synthesis of 1-[4-(6-Hydroxy-pyridine-3-sulfonyl)-phenyl]-3-pyridin-4-ylmethyl-urea

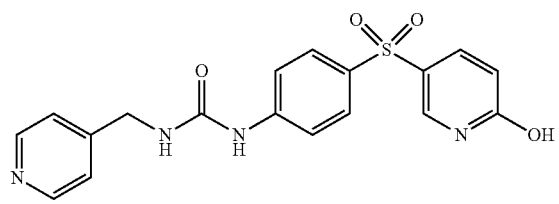 [SMILES: O=C(NCc1ccncc1)Nc1ccc(S(=O)(=O)c2ccc(O)nc2)cc1]

The title compound was prepared using general procedure of 1-[4-(6-hydroxy-pyridine-3-sulfonyl)-phenyl]-3-oxazol-5-ylmethyl-urea. $^1$H NMR (400 MHz, DMSO-d$_6$): δ=12.37 (s, 1H), 9.87 (s, 1H), 8.82 (d, J=6.0 Hz, 2H), 8.04 (d, J=2.4 Hz, 1H), 7.89 (d, J=6.4 Hz, 2H), 7.81 (d, J=8.4 Hz, 2H), 7.67-7.62 (m, 3H), 7.39 (t, J=6.0 Hz, 1H), 6.40 (d, J=10 Hz, 1H), 4.58 (d, J=6.0 Hz, 2H). MS: m/z 384.9 (M+H$^+$)

Example 469: Synthesis of 1-[4-(6-Hydroxy-pyridine-3-sulfonyl)-phenyl]-3-(1H-pyrazol-4-ylmethyl)-urea

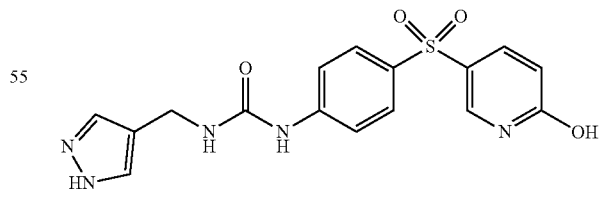

The title compound was prepared using general procedure of 1-[4-(6-hydroxy-pyridine-3-sulfonyl)-phenyl]-3-oxazol-5-ylmethyl-urea. $^1$H NMR (400 MHz, DMSO-d$_6$): δ=12.56-12.38 (m, 2H), 9.04 (s, 1H), 8.04 (s, 1H), 7.78 (d, J=8.0 Hz, 2H), 7.67-7.50 (m, 5H), 6.59-6.57 (m, 1H), 6.40 (d, J=10 Hz, 1H), 4.16-4.13 (m, 2H). MS: m/z 372.0 (M−H)

Example 470: Synthesis of 1-[4-(6-Hydroxy-pyridine-3-sulfonyl)-phenyl]-3-oxazol-5-ylmethyl-urea

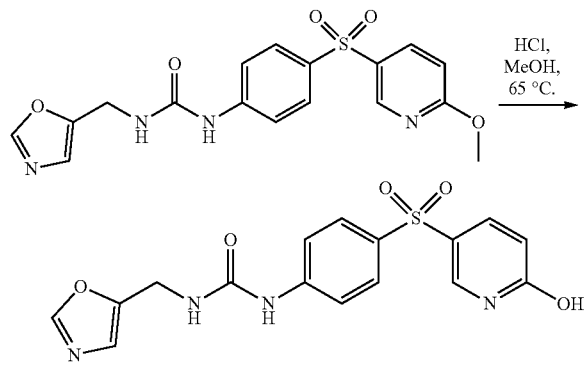

To a solution of 1-[4-(6-methoxy-pyridine-3-sulfonyl)-phenyl]-3-oxazol-5-ylmethyl-urea (105 mg, 0.28 mmol) in MeOH (2 mL) was added HCl (12 N, 1 mL). The reaction mixture was stirred at 65° C. overnight. The reaction was completed detected by LC-MS. The reaction was concentrated and purified by prep-HPLC (5-95%; NH$_4$HCO$_3$) to afford 1-[4-(6-hydroxy-pyridine-3-sulfonyl)-phenyl]-3-oxazol-5-ylmethyl-urea (80 mg, yield 80%) as a white solid. $^1$H NMR (400 MHz, DMSO-d$_6$): δ=9.30 (s, 1H), 8.28 (s, 1H), 8.05 (d, J=2.8 Hz, 1H), 7.79 (d, J=8.8 Hz, 2H), 7.66-7.60 (m, 3H), 7.01-6.98 (m, 2H), 6.39 (d, J=9.6 Hz, 1H), 4.37 (d, J=6.4 Hz, 2H). MS: m/z 375.1 (M+H$^+$).

Example 471: Synthesis of 1-[4-(6-Chloro-pyridine-3-sulfonyl)-phenyl]-3-pyridin-4-ylmethyl-urea

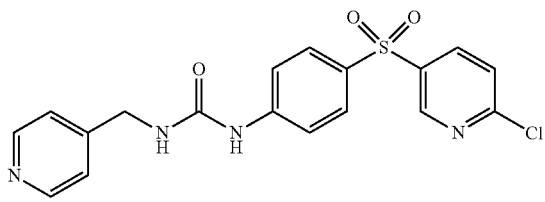 [SMILES: O=C(NCc1ccncc1)Nc1ccc(S(=O)(=O)c2ccc(Cl)nc2)cc1]

The title compound was prepared using general procedure of 1-[4-(6-chloro-pyridine-3-sulfonyl)-phenyl]-3-oxazol-5-ylmethyl-urea. $^1$H NMR (400 MHz, DMSO-d$_6$): δ=9.39 (s, 1H), 8.94 (d, J=2.0 Hz, 1H), 8.49 (d, J=6.0 Hz, 2H), 8.34-8.32 (m, 1H), 7.88 (d, J=8.8 Hz, 2H), 7.76 (d, J=8.4 Hz, 1H), 7.65 (d, J=8.4 Hz, 2H), 7.27 (d, J=6.0 Hz, 2H), 6.99 (t, J=6.0 Hz, 1H), 4.33 (d, J=6.4 Hz, 2H). MS: m/z 402.9 (M+H$^+$)

Example 472: Synthesis of 1-[4-(6-Chloro-pyridine-3-sulfonyl)-phenyl]-3-oxazol-5-ylmethyl-urea

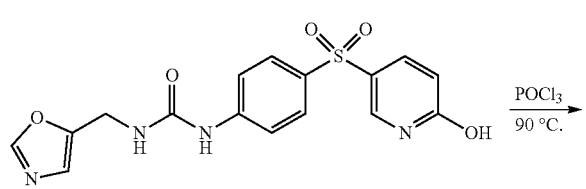

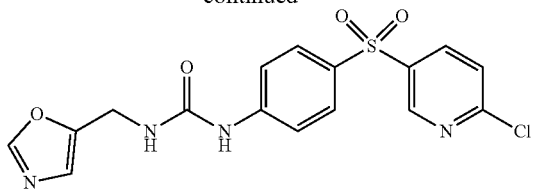

The solution of 1-[4-(6-hydroxy-pyridine-3-sulfonyl)-phenyl]-3-oxazol-5-ylmethyl-urea (80 mg, 0.267 mmol) and POCl$_3$ (3 mL) was stirred at 90° C. for 2 hrs. The reaction was cooled and concentrated. The residue was purified by prep-HPLC (5-95; NH$_4$HCO$_3$) to afford 1-[4-(6-chloro-pyridine-3-sulfonyl)-phenyl]-3-oxazol-5-ylmethyl-urea (30 mg, yield 29%) as a white solid $^1$H NMR (400 MHz, DMSO-d$_6$): δ=9.25 (s, 1H), 8.95 (d, J=2.0 Hz, 1H), 8.35-8.32 (m, 1H), 8.28 (s, 1H), 7.88 (d, J=8.8 Hz, 2H), 7.76 (d, J=8.4 Hz, 1H), 7.63 (d, J=8.8 Hz, 2H), 7.01 (s, 1H), 6.88 (t, J=5.8 Hz, 1H), 4.37 (d, J=5.2 Hz, 2H). MS: m/z 392.9 (M+H$^+$)

Example 473: Synthesis of 1-[4-(5-Chloro-pyridine-2-sulfonyl)-phenyl]-3-pyridin-4-ylmethyl-urea

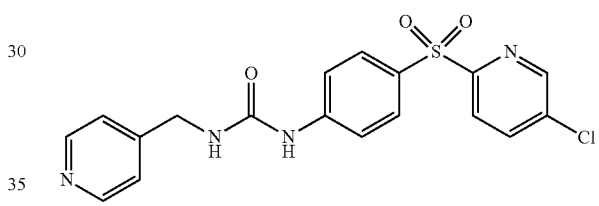

The title compound was prepared using general procedure of 1-[4-(5-chloro-pyridine-2-sulfonyl)-phenyl]-3-(1H-pyrazol-4-ylmethyl)-urea. $^1$H NMR (400 MHz, CD$_3$OD): δ=8.63-8.62 (m, 1H), 8.47-8.45 (m, 2H), 8.17-8.09 (m, 2H), 7.89-7.87 (m, 2H), 7.64-7.62 (m, 2H), 7.38 (d, J=6.0 Hz, 2H), 4.45 (s, 2H). MS: m/z 402.9 (M+H$^+$).

Example 474: Synthesis of 1-[4-(5-Chloro-pyridine-2-sulfonyl)-phenyl]-3-(1H-pyrazol-4-ylmethyl)-urea

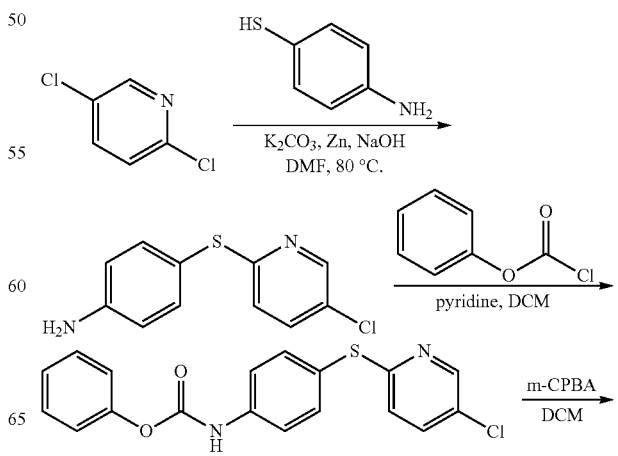

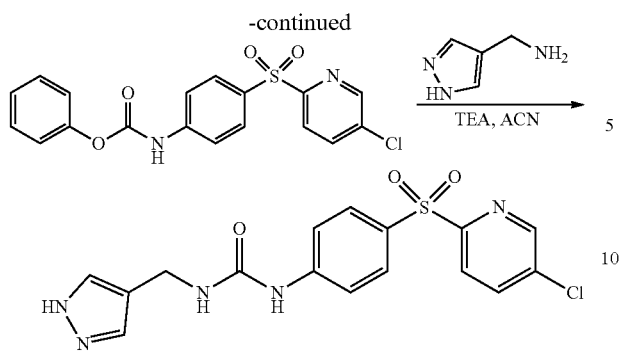

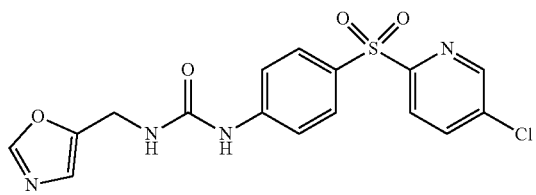 [SMILES: O=C(NCc1cnco1)Nc1ccc(S(=O)(=O)c2ccc(Cl)cn2)cc1]

Step 1: To a solution of 2, 5-dichloro-pyridine (1 g, 6.75 mmol) in DMF (10 mL) was added 4-amino-benzenethiol (0.845 g, 6.75 mmol), $K_2CO_3$ (1.87 g, 13.5 mmol), Zn (0.88 g, 13.5 mmol) and NaOH (aq) (2 mL). The reaction mixture was stirred at 80° C. under $N_2$ overnight. The reaction was completed detected by LC-MS. The reaction was quenched with water (40 mL) and extracted with EA (40 mL×3). The combined organic layer was dried over $Na_2SO_4$, filtered and concentrated. The residue was purified by flash column (PE/EA=5/1) to give 4-(5-chloro-pyridin-2-ylsulfanyl)-phenylamine (1.2 g, yield: 76%) as yellow oil. $^1$H NMR (400 MHz, $CDCl_3$): δ=8.35 (d, J=2.4 Hz, 1H), 7.39-7.36 (m, 3H), 6.74-6.71 (m, 3H). MS: m/z 237.1 (M+H$^+$)

Step 2: To a solution of 4-(5-chloro-pyridin-2-ylsulfanyl)-phenylamine (0.5 g, 2.1 mmol) in DCM (60 mL) was added pyridine (0.5 g, 6.3 mmol) and phenyl chloroformate (0.439 g, 3.1 mmol) at 0° C. The reaction mixture was stirred at room temperature for 2 hrs. The reaction was completed detected by TLC. The reaction was concentrated and purified by flash column (PE/EA=2/1) to give [4-(5-chloro-pyridin-2-ylsulfanyl)-phenyl]-carbamic acid phenyl ester (0.575 g, yield: 76%) as a white solid.

Step 3: To a solution of [4-(5-chloro-pyridin-2-ylsulfanyl)-phenyl]-carbamic acid phenyl ester (0.4 g, 1.12 mmol) in DCM (10 mL) was added m-CPBA (0.831 g, 3.37 mmol, 70% wt) at room temperature The solution was stirred at room temperature overnight. The reaction was completed detected by TLC. The reaction was quenched with $Na_2SO_3$ aqueous (10 mL) and extracted with DCM (20 mL×3). The combined organic layer was dried over $Na_2SO_4$, filtered and concentrated. The residue was purified by flash column (PE to PE/EA=2/1) to give [4-(5-chloro-pyridine-2-sulfonyl)-phenyl]-carbamic acid phenyl ester (0.371 g, yield: 85%) as a white solid. $^1$H NMR (400 MHz, $CDCl_3$): δ=8.59 (d, J=2.4 Hz, 1H), 8.14 (d, J=8.4 Hz, 1H), 8.03-8.00 (m, 2H), 7.88 (dd, $J_1$=8.4 Hz, 2.4 Hz, 1H), 7.63 (d, J=9.2 Hz, 2H), 7.43-7.39 (m, 2H), 7.29-7.25 (m, 1H), 7.18-7.16 (m, 2H).

Step 4: To a solution of [4-(5-chloro-pyridine-2-sulfonyl)-phenyl]-carbamic acid phenyl ester (170 mg, 0.438 mmol) in ACN (5 mL) was added TEA (133 mg, 1.31 mmol) and C-(1H-Pyrazol-4-yl)-methylamine (64 mg, 0.657 mmol). The reaction mixture was stirred at 80° C. under $N_2$ for 2 hrs. The reaction was completed detected by LC-MS. The reaction was concentrated and purified by prep-TLC (DCM/MeOH=10/1) and prep-HPLC (5-95; $NH_4HCO_3$) to afford 1-[4-(5-chloro-pyridine-2-sulfonyl)-phenyl]-3-(1H-pyrazol-4-ylmethyl)-urea (15 mg, yield: 9%) as a white solid. $^1$H NMR (400 MHz, DMSO-$d_6$): δ=12.56 (s, 1H), 8.77 (d, J=2.0 Hz, 1H), 8.26-8.24 (m, 1H), 8.16 (d, J=8.0 Hz, 1H), 7.81 (d, J=8.8 Hz, 2H), 7.62 (d, J=8.8 Hz, 2H), 7.53 (d, J=0.8 Hz, 2H), 6.59 (t, J=5.6 Hz, 1H), 4.15 (d, J=5.2 Hz, 2H). MS: m/z 391.9 (M+H$^+$).

Example 475: Synthesis of 1-[4-(5-Chloro-pyridine-2-sulfonyl)-phenyl]-3-oxazol-5-ylmethyl-urea The title compound was prepared using general procedure of 1-[4-(5-chloro-pyridine-2-sulfonyl)-phenyl]-3-(1H-pyrazol-4-ylmethyl)-urea. $^1$H NMR (400 MHz, $CD_3OD$): δ=8.64-8.63 (m, 1H), 8.17-8.14 (m, 2H), 8.11-8.09 (m, 1H), 7.89-7.87 (m, 2H), 7.62-7.60 (m, 2H), 7.03 (m, 1H), 4.47 (m, 2H). MS: m/z 392.9 (M+H$^+$).

Example 476: Synthesis of 1-[4-(Pyrazine-2-sulfonyl)-phenyl]-3-pyridin-4-ylmethyl-urea

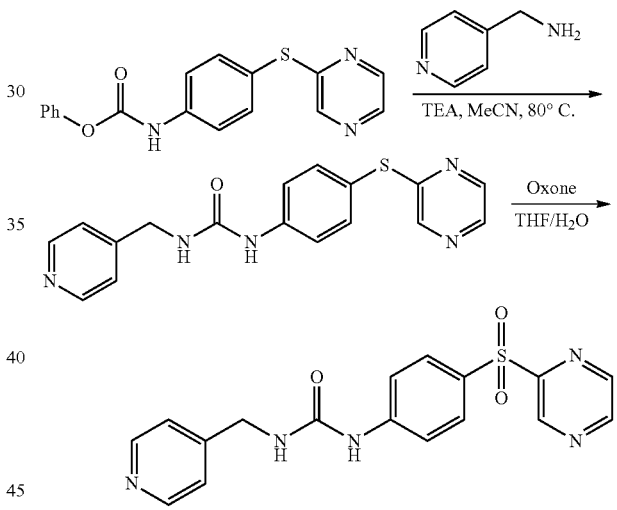

The title compound was prepared using general procedure of 1-[4-(pyrazine-2-sulfonyl)-phenyl]-3-(1H-pyrazol-4-ylmethyl)-urea. $^1$H NMR (400 MHz, $CD_3OD$): δ=9.326 (s, 1H), 8.821 (s, 1H), 8.69 (s, 1H), 8.48 (d, J=5.1 Hz, 2H), 7.942 (d, J=8.7 Hz, 2H), 7.675 (d, J=8.7 Hz, 2H), 7.405 (d, J=5.1 Hz, 2H), 4.46 (s, 2H). MS: m/z 369.9 (M+H$^+$).

Example 477: Synthesis of 1-[4-(Pyrazine-2-sulfonyl)-phenyl]-3-(1H-pyrazol-4-ylmethyl)-urea

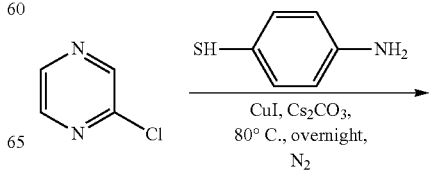

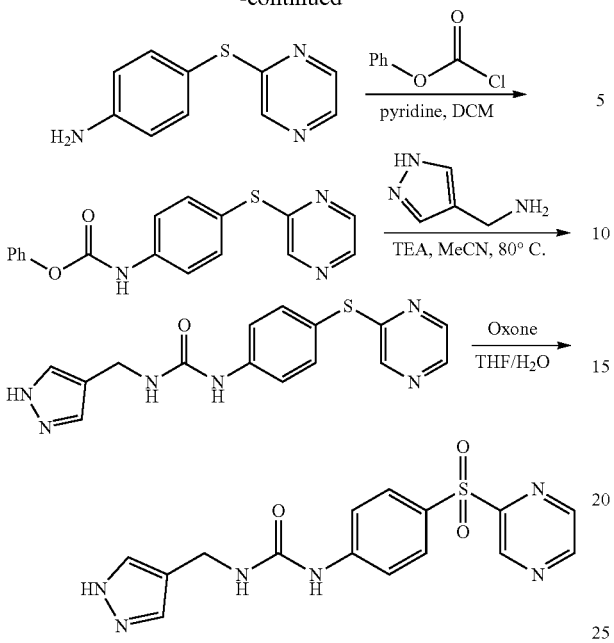

Step 1: To a mixture of 2-chloro-pyrazine (1 g, 8.8 mmol) and 4-Amino-benzenethiol (1.6 g, 13.2 mmol) in DMF (50 mL) was added Cs₂CO₃ (5.7 g, 17.6 mmol) and CuI (334 mg, 1.76 mmol). The resulting mixture was then heated to 80° C. and stirred overnight. The resultant was cooled to room temperature The reaction mixture was concentrated. The residue was diluted with water (10 mL) and EA (15 mL), separated and extracted with EA (20 ml×3). The combined organic layer was dried over Na₂SO₄, filtered and concentrated. The resultant was purified by silica gel column chromatography (PE/EA=2/1) to give 4-(pyrazin-2-ylsulfanyl)-phenylamine (1.02 g, yield: 56%) as a yellow solid. MS: m/s 204.0 (M+H⁺).

Step 2: To a solution of 4-(pyrazin-2-ylsulfanyl)-phenylamine (900 mg, 4.4 mmol) and pyridine (700 mg, 8.8 mmol) in DCM (10 mL) was added phenyl chloroformate (1 g, 6.6 mmol) dropwise at 0° C. The mixture was stirred at room temperature for 2 hrs. The mixture was washed with water and extracted with DCM (20 ml×3), The organic layers were dried with Na₂SO₄ and concentrated. The resultant was purified by silica gel column chromatography (PE:EA=5:1) to give [4-(pyrazin-2-ylsulfanyl)-phenyl]-carbamic acid phenyl ester (510 mg, yield: 37%) as white solid. MS: m/z 324.0 (M+H⁺).

Step 3: To a mixture of [4-(pyrazin-2-ylsulfanyl)-phenyl]-carbamic acid phenyl ester (100 mg, 0.31 mmol) in ACN (5 mL) was added c-(1-ethyl-pyrrolidin-2-yl)-methylamine (90 mg, 0.93 mmol), and TEA (156.6 mg, 1.55 mmol). The resulting mixture was then heated to 80° C. and stirred overnight. The resultant was cooled to room temperature The resulting mixture was concentrated and purified by prep-TLC (DCM/MeOH=10/1) to give 1-[4-(pyrazin-2-ylsulfanyl)-phenyl]-3-(1H-pyrazol-4-ylmethyl)-urea. (80 mg, yield: 79%) as a white solid.

Step 4: To a solution of 1-[4-(pyrazin-2-ylsulfanyl)-phenyl]-3-(1H-pyrazol-4-ylmethyl)-urea (80 mg, 0.245 mmol) in THF (2 mL) was added Oxone (300 mg in 2 ml water, 0.49 mmol). The mixture was stirred at room temperature for 4 hrs. To the mixture was added Na₂SO₃ (sat., aq., 2 mL) and continue to stir for 10 min and then filtered and extracted with EA (20 ml×3). The combined organic layer was dried over Na₂SO₄ and concentrated. The resultant was purified by prep-HPLC to give 1-[4-(pyrazine-2-sulfonyl)-phenyl]-3-(1H-pyrazol-4-ylmethyl)-urea (2.0 mg, yield: 2%) as a white solid. ¹H NMR (400 MHz, CD₃OD): δ=9.16 (s, 1H), 8.81 (s, 1H), 8.68 (s, 1H), 7.92 (d, J=8.8 Hz, 2H), 7.64 (d, J=8.8 Hz, 4H), 4.28 (s, 2H). MS: m/z 359.0 (M+H⁺).

Example 478: Synthesis of 1-Oxazol-5-ylmethyl-3-[4-(pyrazine-2-sulfonyl)-phenyl]-urea

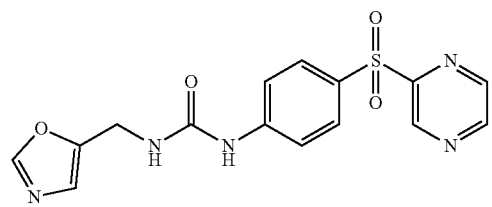 [SMILES: O=C(NCc1cnco1)Nc1ccc(S(=O)(=O)c2cnccn2)cc1]

The title compound was prepared using general procedure of 1-[4-(pyrazine-2-sulfonyl)-phenyl]-3-(1H-pyrazol-4-ylmethyl)-urea. ¹H NMR (400 MHz, CD₃OD): δ=9.32 (s, 1H), 8.81 (s, 1H), 8.68 (s, 1H), 8.14 (s, 1H), 7.93 (d, J=8.8 Hz, 2H), 7.64 (d, J=8.8 Hz, 2H), 7.03 (s, 1H), 4.47 (s, 2H). MS: m/z 359.9 (M+H⁺).

Example 479: Synthesis of 1-Pyridin-4-ylmethyl-3-[4-(pyrimidine-2-sulfonyl)-phenyl]-urea

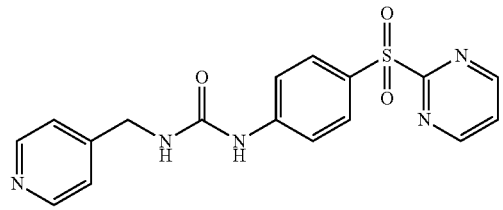 [SMILES: O=C(NCc1ccncc1)Nc1ccc(S(=O)(=O)c2ncccn2)cc1]

The title compound was prepare using general procedure of 1-[4 (pyrazine-2-sulfonyl)-phenyl]-3-(1H-pyrazol-4-ylmethyl)-urea. ¹H NMR (400 MHz, CD₃OD): δ=8.93 (d, J=4.8 Hz, 2H), 8.78 (d, J=6.4 Hz, 2H), 8.05 (d, J=6.4 Hz, 2H), 7.93 (d, J=8.4 Hz, 2H), 7.68-7.64 (m, 3H), 4.697 (s, 2H). MS: m/z 370.0 (M+H⁺).

Example 480: Synthesis of 1-(1H-Pyrazol-4-ylmethyl)-3-[4-(pyrimidine-2-sulfonyl)-phenyl]-urea

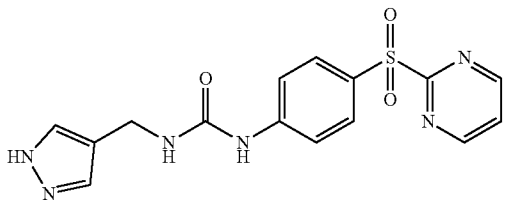 [SMILES: O=C(NCc1cn[nH]c1)Nc1ccc(S(=O)(=O)c2ncccn2)cc1]

The title compound was prepared using general procedure of 1-[4-(pyrazine-2-sulfonyl)-phenyl]-3-(1H-pyrazol-4-ylmethyl)-urea. ¹H NMR (400 MHz, CD₃OD): δ=9.93 (d, J=5.2 Hz, 2H), 7.92 (d, J=8.8 Hz, 2H), 7.68 (s, 2H), 7.65 (t, J=5.2 Hz, 3H), 4.30 (s, 2H). MS: m/z 358.9 (M+H⁺).

Example 481: Synthesis of 1-Oxazol-5-ylmethyl-3-[4-(pyrimidine-2-sulfonyl)-phenyl]-urea

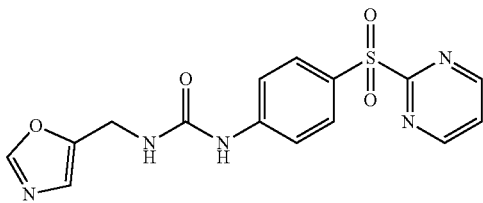 [SMILES: O=C(NCc1cnco1)Nc1ccc(S(=O)(=O)c2ncccn2)cc1]

The title compound was prepared using general procedure of 1-[4-(pyrazine-2-sulfonyl)-phenyl]-3-(1H-pyrazol-4-yl-methyl)-urea. ¹H NMR (400 MHz, CD₃OD): δ=9.93 (d, J=5.2 Hz, 1H), 8.14 (s, 1H), 7.93 (d, J=9.2 Hz, 2H), 7.65 (t, J=7.6 Hz, 3H), 7.03 (s, 2H), 4.47 (s, 2H). MS: m/z 359.9 (M+H⁺).

Example 482: Synthesis of 1-((1H-Pyrazol-4-yl)methyl)-3-(4-(pyrimidin-5-ylsulfonyl)phenyl)urea

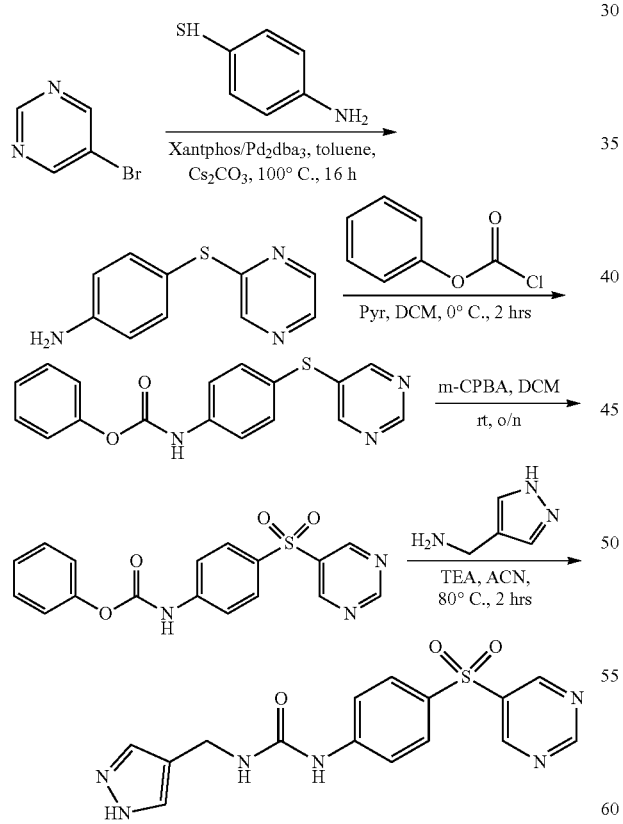

Step 1: To a solution of 5-bromopyrimidine (2.0 g, 12.6 mmol), Pd₂(dba)₃ (577 mg, 0.6 mmol), Xantphos (364 mg, 0.6 mmol) and Cs₂CO₃ (8.2 g, 25.2 mmol) in toluene (20 mL) was added 4-aminobenzenethiol (1.7 g, 13.2 mmol), and the mixture was stirred at 100° C. under N₂ for 16 hrs. The reaction mixture was then filtered and the filtrate was concentrated to dryness. The residue was purified by reverse flash (ACN/H₂O=5%-95%) to give 4-(pyrimidin-5-ylthio)aniline (640 mg, yield: 25%) as a white solid. ¹H NMR (300 MHz, DMSO-d6): δ=8.92 (s, 1H), 8.44 (brs, 2H), 7.26 (d, J=8.7 Hz, 2H), 6.64 (d, J=8.7 Hz, 2H), 5.65 (s, 2H).

Step 2: To a solution of 4-(pyrimidin-5-ylthio)aniline (500 mg, 2.5 mmol) in pyridine (10 mL) was added phenyl chloroformate (577 mg, 3.7 mmol) at 0° C. under N₂, and the mixture was stirred at room temperature for 2 hrs. The reaction mixture was concentrated to dryness and the residue was purified by flash (PE/EA=5%-40%) to give phenyl (4-(pyrimidin-5-ylthio)phenyl)carbamate (680 mg, yield: 86%) as a white solid. MS: m/z 324.1 (M+H⁺).

Step 3: To a solution of phenyl (4-(pyrimidin-5-ylthio)phenyl)carbamate (500 mg, 1.5 mmol) in DCM (10 mL) was added m-CPBA (800 mg, 3.0 mmol) and the mixture was stirred at room temperature for 16 hrs. The reaction mixture was diluted with DCM (20 mL) and then washed by saturated Na₂SO₃ (20 mL), saturated NaHCO₃ (20 mL) and then concentrated to dryness. The residue was purified by flash (PE/EA=5%-40%) to give phenyl (4-(pyrimidin-5-ylsulfonyl)phenyl)carbamate (230 mg, yield: 42%) as a white solid.

Step 4: To a solution of phenyl (4-(pyrimidin-5-ylsulfonyl)phenyl)carbamate (130 mg, 0.4 mmol) in ACN (10 mL) was added (1H-pyrazol-4-yl)methanamine (109 mg, 1.1 mmol) and TEA (75 mg, 0.7 mmol) and the mixture was stirred at 80° C. for 16 hrs. The reaction solution was concentrated to dryness and the residue was purified by prep-HPLC (NH₃.H₂O) to give 1-((H-pyrazol-4-yl)methyl)-3-(4-(pyrimidin-5-ylsulfonyl)phenyl)urea (48 mg, yield: 36%) as a white solid. ¹H NMR (400 MHz, DMSO-d6): δ=9.45 (s, 1H), 9.34 (d, J=4.4 Hz, 2H), 9.14 (s, 1H), 7.94 (d, J=8.8 Hz, 2H), 7.65 (d, J=8.8 Hz, 2H), 7.56 (d, J=4.4 Hz, 2H), 6.64 (t, J=4.8 Hz, 1H), 4.14 (d, J=4.8 Hz, 2H). MS: m/z 358.9 (M+H⁺).

Example 483: Synthesis of 1-(4-Cyclohexanesulfonyl-phenyl)-3-pyridin-4-ylmethyl-urea

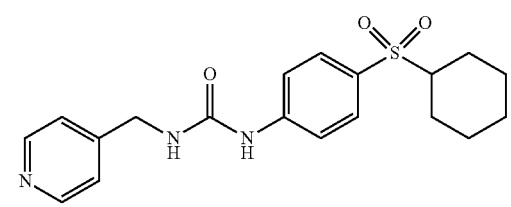 [SMILES: O=C(NCc1ccncc1)Nc1ccc(S(=O)(=O)C2CCCCC2)cc1]

The title compound was prepared using general procedure of 1-(4-cyclohexanesulfonyl-phenyl)-3-oxazol-5-ylmethyl-urea. ¹H NMR (400 MHz, DMSO-d₆): δ=9.55 (s, 1H), 8.53 (s, 2H), 7.66 (s, 4H), 7.35 (d, J=4.4 Hz, 2H), 7.22 (t, J=5.8 Hz, 1H), 4.37 (d, J=6.0 Hz, 2H), 3.06-3.03 (m, 1H), 1.88-1.86 (m, 2H), 1.74-1.73 (m, 2H), 1.57 (d, J=12.0 Hz, 1H), 1.26-1.15 (m, 4H), 1.08-1.03 (m, 1H). MS: m/z 374.0 (M+H⁺).

Example 484: Synthesis of 1-(4-Cyclohexanesulfonyl-phenyl)-3-(1H-pyrazol-4-ylmethyl)-urea

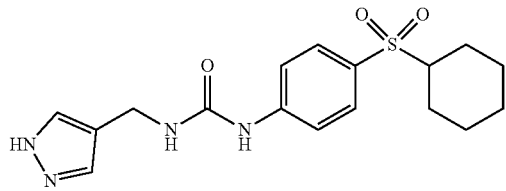 [SMILES: O=C(NCc1cn[nH]c1)Nc1ccc(S(=O)(=O)C2CCCCC2)cc1]

The title compound was prepared using general procedure of 1-(4-yclohexanesulfonyl-phenyl)-3-oxazol-5-ylmethyl-urea. $^1$H NMR (400 MHz, CD$_3$OD): δ=8.30 (s, 2H), 7.69 (dd, J=18.8, 8.8 Hz, 4H), 4.41 (s, 2H), 3.03-2.97 (m, 1H), 2.02-1.98 (m, 2H), 1.84-1.82 (m, 2H), 1.67 (d, J=12.4 Hz, 1H), 1.38-1.22 (m, 4H), 1.17-1.10 (m, 1H). MS: m/z 363.0 (M+H$^+$).

Example 485: Synthesis of 1-(4-Cyclohexanesulfonyl-phenyl)-3-oxazol-5-ylmethyl-urea

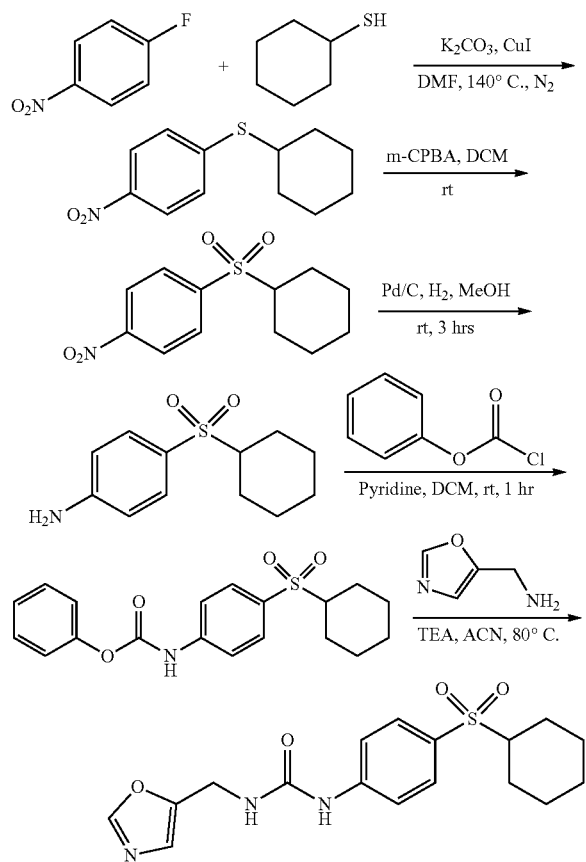

Step 1: To a solution of 1-fluoro-4-nitro-benzene (1.00 g, 7.09 mmol) in DMF (20 mL) was added cyclohexanethiol (0.99 g, 8.50 mmol), K$_2$CO$_3$ (2.94 g, 21.27 mmol) and CuI (0.14 g, 0.71 mmol). The reaction mixture was stirred at 140° C. under N$_2$ for 4 hrs. The reaction was completed detected by LC-MS. The reaction was quenched with water (5 mL) and extracted with DCM (20 mL×3). The combined organic layer was washed with brine (20 mL) and water (20 mL), dried over Na$_2$SO$_4$, filtered and concentrated. The residue was purified by silia gel chromatography (PE to PE/EA=20/1) to give 1-Cyclohexylsulfanyl-4-nitro-benzene (1.60 g, yield 95%) as a yellow solid. $^1$H NMR (400 MHz, DMSO-d$_6$): δ=8.15-8.12 (m, 2H), 7.54-7.50 (m, 2H), 3.63-3.57 (m, 1H), 2.01-1.97 (m, 2H), 1.74-1.71 (m, 2H), 1.63-1.58 (m, 1H), 1.47-1.34 (m, 4H), 1.31-1.26 (m, 1H).

Step 2: To a solution of 1-cyclohexylsulfanyl-4-nitro-benzene (1.60 g, 6.74 mmol) in DCM (30 mL) was added m-CPBA (5.46 g, 26.9 mmol, 85% Wt) at 0° C. The reaction mixture was allowed to warm to room temperature for 4 hrs. The reaction was completed detected by LC-MS. The reaction was quenched with Na$_2$SO$_3$ aqueous (10 mL) and extracted with DCM (20 mL×3). The combined organic layer was washed with NaHCO$_3$ aqueous (20 mL) and water (20 mL), dried over Na$_2$SO$_4$, filtered and concentrated. The residue was purified by silia gel chromatography (PE to PE/EA=10/1) to give 1-cyclohexanesulfonyl-4-nitro-benzene (1.50 g, yield: 82%) as a white solid. MS: m/z 270.1 (M+H$^+$).

Step 3: To a solution of 1-cyclohexanesulfonyl-4-nitro-benzene (1.50 g, 5.57 mmol) in MeOH (30 mL) was added Pd/C (0.15 g, 10% Wt). The reaction mixture was stirred at room temperature under H$_2$ overnight. The reaction was completed detected by LC-MS. After filtration via filter paper, the organic layer was concentrated under pressure to give 4-cyclohexanesulfonyl-phenylamine (1.26 g, yield: 95%) as a gray solid. $^1$H NMR (300 MHz, DMSO-d$_6$): δ=7.13-7.39 (m, 2H), 6.72-6.68 (m, 2H), 6.29 (br s, 2H), 2.95-2.86 (m, 1H), 1.88-1.85 (m, 2H), 1.84-1.83 (m, 2H), 1.74-1.72 (m, 1H), 1.22-1.14 (m, 5H).

Step 4: To a solution of 4-cyclohexanesulfonyl-phenylamine (1.25 g, 5.20 mmol) in DCM (30 mL) was added pyridine (1.23 g, 15.60 mmol) and phenyl chloroformate (1.63 g, 10.40 mmol) at 0° C. The reaction mixture was stirred at room temperature for 1 hr. The reaction was completed detected by LC-MS. The reaction was quenched with water (5 mL) and extracted with DCM (20 mL×3). The combined organic layer was washed with brine (20 mL) and water (20 mL), dried over Na$_2$SO$_4$, filtered and concentrated. The residue was purified by re-crystallization from ether absolute (10 mL) to give (4-cyclohexanesulfonyl-phenyl)-carbamic acid phenyl ester (0.79 g, yield: 44%) as a white solid. $^1$H NMR (400 MHz, DMSO-d$_6$): δ=10.78 (s, 1H), 7.80-7.74 (m, 4H), 7.49-7.43 (m, 2H), 7.31-7.25 (m, 3H), 3.13-3.08 (m, 1H), 1.88-1.84 (m, 2H), 1.79-1.74 (m, 2H), 1.58 (d, J=11.2 Hz, 1H), 1.28-1.16 (m, 4H), 1.07-1.02 (m, 1H).

Step 5: To a solution of (4-cyclohexanesulfonyl-phenyl)-carbamic acid phenyl ester (30.0 mg, 0.08 mmol) in ACN (20 mL) was added TEA (40.5 mg, 0.40 mmol) and c-oxazol-5-yl-methylamine (21.5 mg, 0.16 mmol). The reaction mixture was stirred at 80° C. for 4 hrs. The reaction was completed detected by LC-MS. The reaction was quenched with water (5 mL) and extracted with DCM (20 mL×3). The combined organic layers were washed with brine (20 mL) and water (20 mL), dried over Na$_2$SO$_4$, filtered and concentrated. The residue was purified by prep.HPLC to give 1-(4-cyclohexanesulfonyl-phenyl)-3-oxazol-5-ylmethyl-urea (20.9 mg, yield 69%) as a white solid. $^1$H NMR (400 MHz, DMSO-d$_6$): δ=9.84 (s, 1H), 9.30 (s, 1H), 7.65 (s, 4H), 7.24 (t, J=11.6 Hz, 1H), 7.03 (s, 1H), 4.39 (d, J=5.6 Hz, 2H), 3.06-3.03 (m, 1H), 1.88-1.83 (m, 2H), 1.78-1.69 (m, 2H), 1.58 (d, J=12.0 Hz, 1H), 1.26-1.15 (m, 4H), 1.09-1.02 (m, 1H). MS: m/z 364.0 (M+H⁺).

Example 486: Synthesis of 1-[4-(1-Methyl-piperidine-4-sulfonyl)-phenyl]-3-pyridin-4-ylmethyl-urea

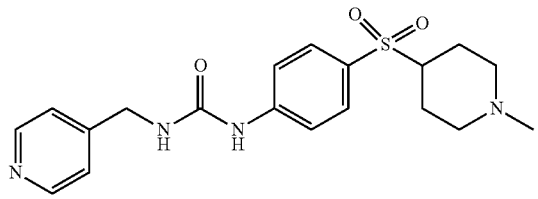 [SMILES: CN1CCC(S(=O)(=O)c2ccc(NC(=O)NCc3ccncc3)cc2)CC1]

The title compound was prepared using general procedure of 1-[4-(1-methyl-piperidine-4-sulfonyl)-phenyl]-3-oxazol-5-ylmethyl-urea. ¹H NMR (400 MHz, DMSO-d₆): δ=9.35 (s, 1H), 8.51-8.50 (m, 2H), 7.67 (s, 4H), 7.29 (d, J=5.6 Hz, 2H), 6.98 (s, 1H), 4.35 (d, J=5.6 Hz, 2H), 3.07-3.01 (m, 1H), 2.81-2.78 (m, 2H), 2.11 (s, 3H), 1.84-1.75 (m, 4H), 1.48-1.45 (m, 2H). MS: m/z 389.0 (M+H⁺).

Example 487: Synthesis of 1-[4-(1-Methyl-piperidine-4-sulfonyl)-phenyl]-3-(1H-pyrazol-4-ylmethyl)-urea

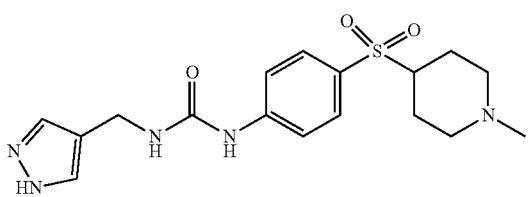 [SMILES: CN1CCC(S(=O)(=O)c2ccc(NC(=O)NCc3cn[nH]c3)cc2)CC1]

The title compound was prepared using general procedure of 1-[4-(1-methyl-piperidine-4-sulfonyl)-phenyl]-3-oxazol-5-ylmethyl-urea. ¹H NMR (400 MHz, CD₃OD): δ=8.26 (s, 2H), 7.78-7.71 (m, 4H), 4.39 (s, 2H), 3.60 (d, J=11.6 Hz, 2H), 3.48-3.41 (m, 1H), 3.05-2.99 (m, 2H), 2.84 (s, 3H), 2.22-2.20 (m, 2H), 1.96-1.93 (m, 2H). MS: m/z 378.0 (M+H⁺).

Example 488: Synthesis of 1-[4-(1-Methyl-piperidine-4-sulfonyl)-phenyl]-3-oxazol-5-ylmethyl-urea

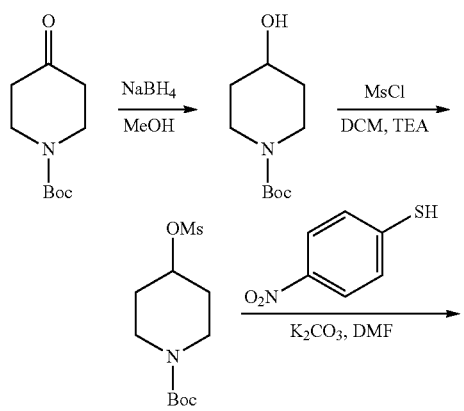

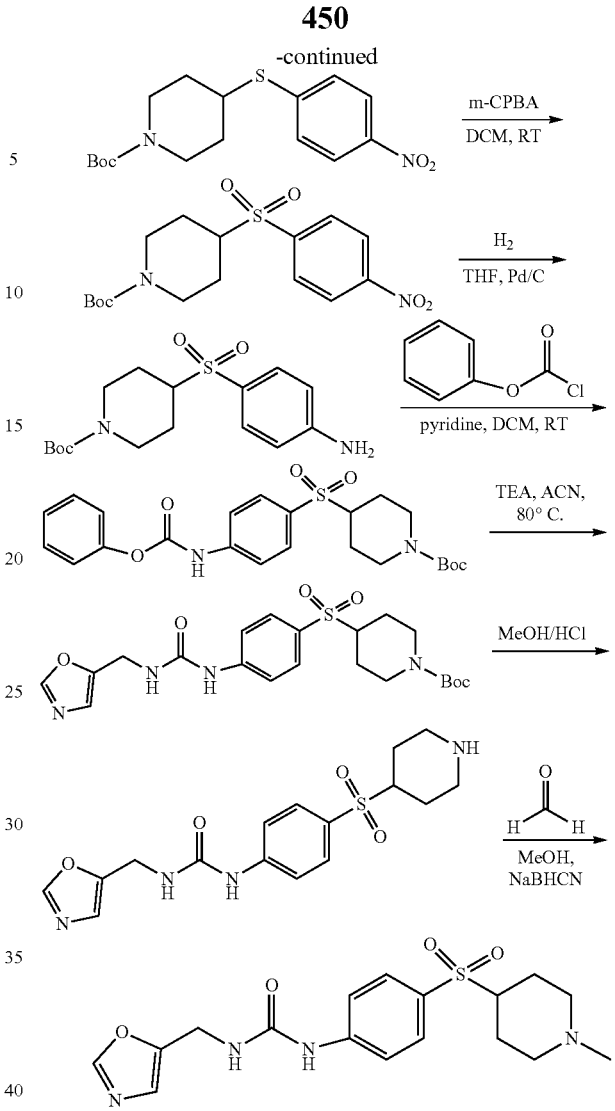

Step 1: To a mixture of 4-oxo-piperidine-1-carboxylic acid tert-butyl ester (20 g, 0.15 mol) in MeOH (100 mL) was added NaBH₄ (14.25 g, 0.75 mol) at 0° C. slowly. The reaction mixture was allowed to warm to room temperature overnight. The mixture was quenched with NH₄Cl (100 mL) and extracted with DCM (200 mL). The organic layer was washed with brine, dried over Na₂SO₄, filtered and concentrated to give 4-hydroxy-piperidine-1-carboxylic acid tert-butyl ester (19 g, yield 95%) as yellow solid. MS: m/z 202.0 (M+H⁺).

Step 2: To a mixture of 4-hydroxy-piperidine-1-carboxylic acid tert-butyl ester (19.0 g, 0.095 mol) in DCM (200 mL) was added TEA (19.19 g, 0.19 mol) and MsCl (21 g, 0.19 mol) at 0° C. slowly. The reaction mixture was allowed to warm to room temperature overnight. The mixture was washed with H₂O (100 mL×3) and extracted with DCM (200 mL×3). The combined organic layer was washed with brine, dried over Na₂SO₄, filtered and concentrated to give 4-methanesulfonyloxy-piperidine-1-carboxylic acid tert-butyl ester (20 g, yield 76%) as a yellow solid. ¹H NMR (400 MHz, CDCl₃): δ=4.89-4.88 (m, 1H), 3.72-3.67 (m, 2H), 3.33-3.29 (m, 2H), 3.27 (s, 3H), 1.97-1.94 (m, 2H), 1.84-1.79 (m, 2H), 1.46 (s, 9H).

Step 3: To a mixture of 4-methanesulfonyloxy-piperidine-1-carboxylic acid tert-butyl ester (5 g, 32 mmol) in DMF (25 mL) was added 4-nitro-benzenethiol (13.4 g, 48 mmol) and K$_2$CO$_3$ (8.8 g, 64 mmol). The mixture was stirred at 100° C. overnight. The mixture was washed H$_2$O (100 mL×5) and extracted with EA (100 mL×5). The combined organic layer was washed with brine, dried over Na$_2$SO$_4$, filtered and concentrated. The residue was purified by chromatography (PE/EA=20/1) to give 4-(4-nitro-phenylsulfanyl)-piperidine-1-carboxylic acid tert-butyl ester (3.38 g, yield 31%) as a yellow liquid. MS: m/z 339.0 (M+H$^+$).

Step 4: To a mixture of 4-(4-nitro-phenylsulfanyl)-piperidine-1-carboxylic acid tert-butyl ester (3.38 g, 10 mmol) in DCM (50 mL) was added m-CPBA (5.16 g, 30 mmol) at 0° C. slowly. Then the mixture was stirred at room temperature overnight. To the mixture was added Na$_2$SO$_3$ and filtered and washed with NaHCO$_3$. The combined organic layer was washed with brine, dried over Na$_2$SO$_4$, filtered and concentrated. The residue was purified with chromatography (PE/EA=3/1) to give 4-(4-nitro-benzenesulfonyl)-piperidine-1-carboxylic acid tert-butyl ester (2.58 g, yield 70%) as a white solid. MS: m/z 371.0 (M+H$^+$).

Step 5: A mixture of 4-(4-nitro-benzenesulfonyl)-piperidine-1-carboxylic acid tert-butyl ester (2.58 g, 6.90 mmol) and Pd/C (10% wet, 200 mg) in MeOH (50 mL) was stirred at room temperature under H$_2$ (1 atm) overnight. The reaction solution was filtered. The filtrate was concentrated to give 4-(4-amino-benzenesulfonyl)-piperidine-1-carboxylic acid tert-butyl ester (2.1 g, yield 91%) as a white solid. MS: m/z 341.0 (M+H$^+$).

Step 6: To a solution of 4-(4-amino-benzenesulfonyl)-piperidine-1-carboxylic acid tert-butyl ester (2.1 g, 6.0 mmol) in DCM (20 mL) was added pyridine (0.96 g, 12 mmol) and phenyl chloroformate (1.93 g, 12 mmol) at 0° C. The reaction mixture was stirred at room temperature for 2 hrs. The reaction was completed detected by LC-MS. The reaction was quenched with water (10 mL) and extracted with DCM (10 mL×3). The combined organic layer was washed with brine, dried over Na$_2$SO$_4$, filtered and concentrated. The residue was purified by silica gel column (PE/EA=10/1) to give 4-(4-phenoxycarbonylamino-benzenesulfonyl)-piperidine-1-carboxylic acid tert-butyl ester (0.46 g, yield 17%) as a white solid. MS: m/z 461.0 (M+H$^+$).

Step 7: A mixture of 4-(4-phenoxycarbonylamino-benzenesulfonyl)-piperidine-1-carboxylic acid tert-butyl ester (0.15 g, 0.3 mmol) in ACN (15 mL) was added TEA (60.6 mg, 0.6 mmol) and C-Oxazol-5-yl-methylamine (80 mg, 0.6 mmol). The reaction mixture was stirred at 80° C. overnight. The reaction was quenched with water (10 mL) and extracted with DCM (10 mL×3). The combined organic layer was washed with brine, dried over Na$_2$SO$_4$, filtered and concentrated. The residue was purified by silica gel column (DCM/MeOH=20/1) to give 4-[4-(3-oxazol-5-ylmethyl-ureido)-benzenesulfonyl]-piperidine-1-carboxylic acid tert-butyl ester (120 mg, yield 87%) as a white solid.

Step 8: A solution of 4-[4-(3-oxazol-5-ylmethyl-ureido)-benzenesulfonyl]-piperidine-1-carboxylic acid tert-butyl ester (120 mg, 0.25 mmol) in HCl/MeOH (3 mL) was stirred at room temperature for 1 hr. The reaction was completed detected by TLC. The mixture was concentrated to give 1-oxazol-5-ylmethyl-3-[4-(piperidine-4-sulfonyl)-phenyl]-urea (90 mg, yield 90%) as a white solid.

Step 9: To a mixture of 1-oxazol-5-ylmethyl-3-[4-(piperidine-4-sulfonyl)-phenyl]-urea (90 mg, 0.25 mmol) and formaldehyde (15 mg, 0.50 mol) in MeOH (10 mL) was stirred at room temperature for 1 hr. Then to the mixture was added NaBH$_3$CN (47 mg, 0.75 mol) and stirred at room temperature overnight. The mixture was purified by prep-HPLC to give 1-[4-(1-methyl-piperidine-4-sulfonyl)-phenyl]-3-oxazol-5-ylmethyl-urea (10 mg, yield 11%) as white solid. $^1$H NMR (400 MHz, DMSO-d$_6$): δ=9.54 (s, 1H), 8.29 (s, 1H), 7.72-7.67 (m, 4H), 7.142-7.14 (m, 1H), 7.02 (s, 1H), 4.39 (d, J=5.2 Hz, 2H), 3.32 (s, 1H), 3.09-3.06 (m, 2H), 2.81-2.75 (m, 2H), 2.62 (s, 3H), 1.99-1.82 (m, 4H). MS: m/z 379.2 (M+H$^+$).

Example 489: Synthesis of 1-[4-(1-Isopropyl-piperidine-4-sulfonyl)-phenyl]-3-pyridin-4-ylmethyl-urea

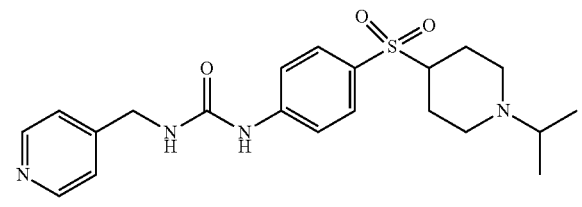 [SMILES: CC(C)N1CCC(S(=O)(=O)c2ccc(NC(=O)NCc3ccncc3)cc2)CC1]

The title compound was prepared using general procedure of 1-[4-(1-methyl-piperidine-4-sulfonyl)-phenyl]-3-oxazol-5-ylmethyl-urea. $^1$H NMR (400 MHz, DMSO-d$_6$): δ=9.47 (s, 1H), 8.50 (d, J=6.0 Hz, 2H), 7.66 (s, 4H), 7.29 (d, J=5.6 Hz, 2H), 7.11 (s, 1H), 4.33 (d, J=6.0 Hz, 2H), 3.06-2.99 (m, 1H), 2.81-2.78 (m, 2H), 2.67-2.54 (m, 1H), 2.05-2.03 (m, 2H), 1.81-1.79 (m, 2H), 1.39-1.35 (m, 2H), 0.89 (d, J=6.0 Hz, 6H). MS: m/z 417.0 (M+H$^+$).

Example 490: Synthesis of 1-[4-(1-Isopropyl-piperidine-4-sulfonyl)-phenyl]-3-(1H-pyrazol-4-ylmethyl)-urea

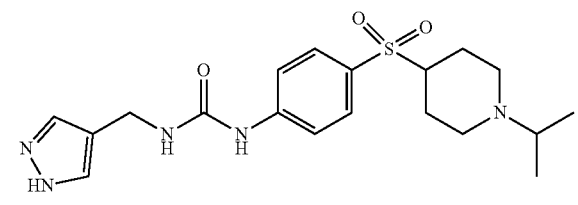 [SMILES: CC(C)N1CCC(S(=O)(=O)c2ccc(NC(=O)NCc3cn[nH]c3)cc2)CC1]

The title compound was prepared using general procedure of 1-[4-(1-methyl-piperidine-4-sulfonyl)-phenyl]-3-oxazol-5-ylmethyl-urea. $^1$H NMR (400 MHz, CD$_3$OD): δ=7.73 (d, J=8.8 Hz, 2H), 7.66-7.64 (m, 4H), 4.30 (s, 2H), 3.09-2.98 (m, 3H), 2.76-2.70 (m, 1H), 2.23-2.21 (m, 2H), 1.98-1.96 (m, 2H), 1.72-1.62 (m, 2H), 1.04 (d, J=6.4 Hz, 6H). MS: m/z 406.1 (M+H$^+$).

Example 491: Synthesis of 1-[4-(1-Isopropyl-piperidine-4-sulfonyl)-phenyl]-3-oxazol-5-ylmethyl-urea

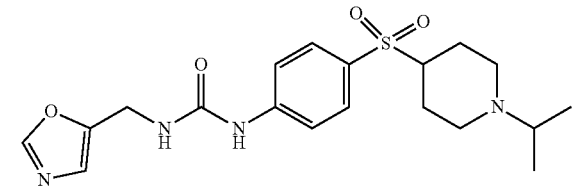 [SMILES: CC(C)N1CCC(S(=O)(=O)c2ccc(NC(=O)NCc3cnco3)cc2)CC1]

The title compound was prepared using general procedure of 1-[4-(1-methyl-piperidine-4-sulfonyl)-phenyl]-3-oxazol-5-ylmethyl-urea. ¹H NMR (300 MHz, DMSO-d₆): δ=9.24 (s, 1H), 8.29 (s, 1H), 7.64 (s, 4H), 7.01 (s, 1H), 6.91 (s, 1H), 4.38 (d, J=5.7 Hz, 2H), 3.34-3.32 (m, 1H), 2.82-2.76 (m, 2H), 2.68-2.60 (m, 1H), 2.08-1.99 (m, 2H), 1.81-1.76 (m, 2H), 1.39-1.34 (m, 2H), 0.89 (s, 6H). MS: m/z 407.1 (M+H⁺).

Example 492: Synthesis of 1-[4-(1-Isobutyl-piperidine-4-sulfonyl)-phenyl]-3-pyridin-4-ylmethyl-urea

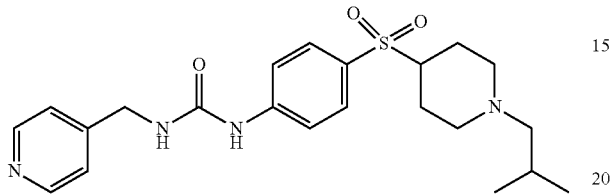

The title compound was prepared using general procedure of 1-[4-(1-methyl-piperidine-4-sulfonyl)-phenyl]-3-oxazol-5-ylmethyl-urea. ¹H NMR (400 MHz, CD₃OD): δ=8.48-8.46 (m, 2H), 7.76-7.66 (m, 4H), 7.40 (d, J=6.0 Hz, 2H), 4.47 (s, 2H), 3.31-3.30 (m, 3H), 2.11-1.94 (m, 9H), 0.88 (d, J=6.4 Hz, 6H). MS: m/z 431.0 (M+H⁺).

Example 493: Synthesis of 1-[4-(1-Isobutyl-piperidine-4-sulfonyl)-phenyl]-3-(1H-pyrazol-4-ylmethyl)-urea

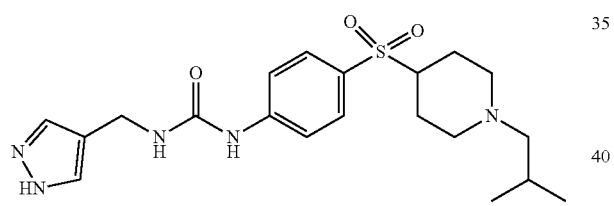

The title compound was prepared using general procedure of 1-[4-(1-methyl-piperidine-4-sulfonyl)-phenyl]-3-oxazol-5-ylmethyl-urea. ¹H NMR (400 MHz, CD₃OD): δ=7.71-7.69 (m, 2H), 7.63-7.61 (m, 2H), 7.57 (s, 2H), 4.28 (s, 2H), 3.03-2.92 (m, 3H), 2.04-2.02 (m, 2H), 1.89-1.83 (m, 4H), 1.78-1.63 (m, 3H), 0.84 (d, J=6.4 Hz, 6H). MS: m/z 420.0 (M+H⁺).

Example 494: Synthesis of 1-[4-(1-Isobutyl-piperidine-4-sulfonyl)-phenyl]-3-oxazol-5-ylmethyl-urea The title compound was prepared using general procedure of 1-[4-(1-methyl-piperidine-4-sulfonyl)-phenyl]-3-oxazol-5-ylmethyl-urea. ¹H NMR (300 MHz, DMSO-d₆): δ=9.25 (s, 1H), 8.29 (s, 1H), 7.65 (s, 4H), 7.01 (s, 1H), 6.90-6.89 (m, 1H), 4.38-4.36 (m, 2H), 3.13-2.77 (m, 3H), 1.79-1.74 (m, 9H), 0.79 (d, J=4.2 Hz, 6H). MS: m/z 421.0 (M+H⁺).

Example 495: Synthesis of 1-(1H-Pyrazol-4-ylmethyl)-3-{4-[1-(tetrahydro-pyran-4-yl)-piperidine-4-sulfonyl]-phenyl}-urea

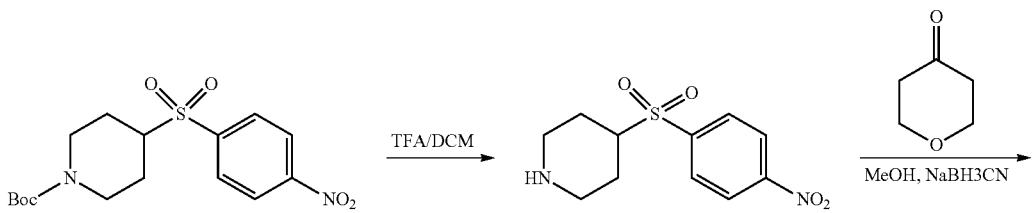

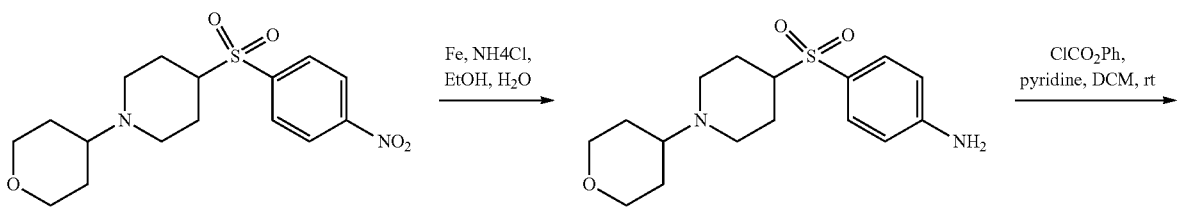

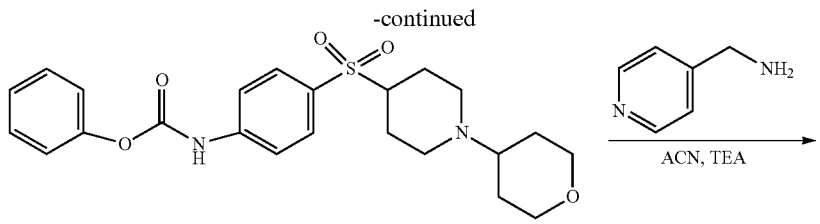

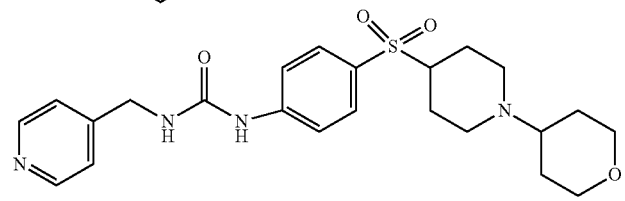

Step 1: A mixture of 4-(4-nitro-benzenesulfonyl)-piperidine-1-carboxylic acid tert-butyl ester (1.8 g, 4.8 mmol) in DCM/TFA (30 mL/6 mL) was stirred at room temperature overnight. The mixture was concentrated to give 4-(4-nitro-benzenesulfonyl)-piperidine (1.8 g, yield 1000%) as a white solid. MS: m/z 271.0 (M+H$^+$).

Step 2: A mixture of 4-(4-nitro-benzenesulfonyl)-piperidine (1.80 g, 67 mmol) and tetrahydro-pyran-4-one (1.3 g, 13 mmol) in MeOH (30 mL) was stirred at room temperature for 1 hr. Then NaBH$_3$CN (1.26 g, 0.02 mol) was added and the mixture was stirred at room temperature overnight. The mixture was purified by silica gel chromatography (PE/EA=20/1) to give 4-(4-nitro-benzenesulfonyl)-1-(tetrahydro-pyran-4-yl)-piperidine (200 mg, yield 8%) as a white solid. MS: m/z 355.0 (M+H$^+$).

Step 3: A mixture of 4-(4-nitro-benzenesulfonyl)-1-(tetrahydro-pyran-4-yl)-piperidine (200 mg, 0.56 mmol), iron (94.92 mg, 1.69 mmol) and NH$_4$Cl (90.39 mg, 1.69 mol) in EtOH/H$_2$O (5 mL/2 mL) was stirred at 90° C. overnight. The reaction was completed detected by LC-MS. The mixture was filtered and extracted with EA (30 mL×3). The organic layer was washed with brined (30 mL), dried over Na$_2$SO$_4$, filtered and concentrated to give the crude 4-[1-(tetrahydro-pyran-4-yl)-piperidine-4-sulfonyl]-phenylamine (100 mg, yield 55%) as a yellow solid. MS: m/z 325.0 (M+H$^+$).

Step 4: To a mixture of 4-[1-(tetrahydro-pyran-4-yl)-piperidine-4-sulfonyl]-phenylamine (100 mg, 0.3 mmol) and pyridine (48 mg, 0.6 mmol) in DCM (5 mL) was added phenyl chloroformate (93 mg, 0.6 mmol) dropwise at 0° C. The reaction mixture was allowed to warm to room temperature for 1 hr. The reaction was completed detected by LC-MS. The combined organic layer was washed with brine (5 mL), dried over Na$_2$SO$_4$, filtered and concentrated. The residue was was purified by prep-TLC (DCM/MeOH=20/1) to give {4-[1-(tetrahydro-pyran-4-yl)-piperidine-4-sulfonyl]-phenyl}-carbamic acid phenyl ester (50 mg, yield 37%) as a white solid. MS: m/z 445.0 (M+H$^+$).

Step 5: To a solution of {4-[1-(tetrahydro-pyran-4-yl)-piperidine-4-sulfonyl]-phenyl}-carbamic acid phenyl ester (50 mg, 0.112 mmol) and TEA (34 mg g, 0.337 mmol) in ACN (10 mL) was added c-pyridin-4-yl-methylamine (36.45 mg, 0.337 mmol). The reaction was stirred at 0° C. for 1 h. Then the reaction mixture was concentrated in vacuum. The residue was purified by prep-HPLC to give 1-pyridin-4-ylmethyl-3-{4-[1-(tetrahydro-pyran-4-yl)-piperidine-4-sulfonyl]-phenyl}-urea (3.5 mg, yield: 7%) as a white solid. $^1$H NMR (400 MHz, CD$_3$OD): δ=8.47 (d, J=5.2 Hz, 2H), 7.76-7.66 (m, 4H), 7.4 (d, J=5.6 Hz, 2H), 4.47 (s, 2H), 3.98-3.95 (m, 2H), 3.39-3.36 (m, 2H), 3.17-3.14 (m, 3H), 2.60 (s, 1H), 2.28 (s, 2H), 2.03-2.0 (m, 2H), 1.79-1.68 (m, 6H). MS: m/z 459.0 (M+H$^+$)

Example 496: Synthesis of 1-(1H-Pyrazol-4-ylmethyl)-3-{4-[1-(tetrahydro-pyran-4-yl)-piperidine-4-sulfonyl]-phenyl}-urea

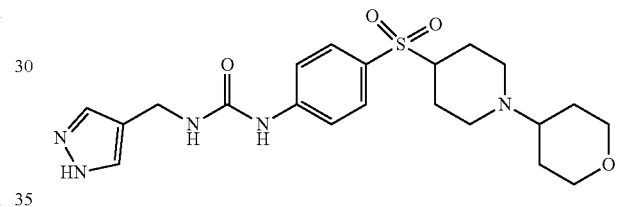

The title compound was prepared using general procedure of 1-(h-pyrazol-4-ylmethyl)-3-{4-[1-(tetrahydro-pyran-4-yl)-piperidine-4-sulfonyl]-phenyl}-urea. H NMR (400 MHz, CD$_3$OD): δ=7.73 (d, J=8.8 Hz, 2H), 7.66-7.60 (m, 4H), 4.30 (s, 2H), 3.96-3.93 (m, 2H), 3.38-3.31 (m, 2H), 3.08-3.06 (m, 3H), 2.49-2.45 (m, 1H), 2.19-2.13 (m, 2H), 1.75-1.48 (m, 8H). MS: m/z 448.0 (M+H$^+$).

Example 497: Synthesis of 1-Oxazol-5-ylmethyl-3-{4-[1-(tetrahydro-pyran-4-yl)-piperidine-4-sulfonyl]-phenyl}-urea

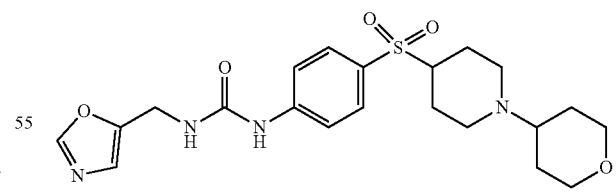

The title compound was prepared using general procedure of 1-(1H-pyrazol-4-ylmethyl)-3-{4-[1-(tetrahydro-pyran-4-yl)-piperidine-4-sulfonyl]-phenyl}-urea. $^1$H NMR (400 MHz, CD$_3$OD): δ=8.16 (s, 1H), 7.70 (d, J=9.2 Hz, 2H), 7.67-7.64 (m, 2H), 7.04 (s, 1H), 4.48 (s, 2H), 3.96-3.93 (m, 2H), 3.35-3.30 (m, 2H), 3.09-3.06 (m, 3H), 2.51-2.43 (m, 1H), 2.21-2.14 (m, 2H), 1.99-1.95 (m, 2H), 1.77-1.49 (m, 6H). MS: m/z 449.0 (M+H$^+$).

Example 498: Synthesis of 1-(4-([1,1'-Biphenyl]-2-ylsulfonyl)phenyl)-3-(pyridin-4-ylmethyl)urea

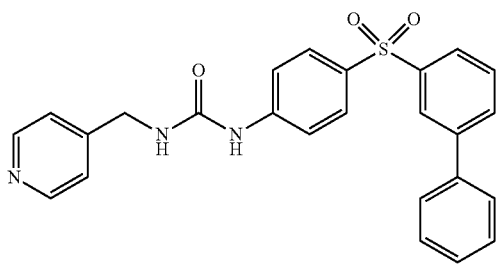 [SMILES: O=C(NCc1ccncc1)Nc1ccc(S(=O)(=O)c2cccc(-c3ccccc3)c2)cc1]

The title compound was prepared using general procedure of 1-(4-([1,1'-biphenyl]-2-ylsulfonyl) phenyl)-3-(pyridin-4-ylmethyl)urea. $^1$H NMR (400 MHz, DMSO-$d_6$): δ=9.31 (s, 1H), 8.48 (d, J=6 Hz, 2H), 8.11 (s, 1H), 7.95 (d, J=7.6 Hz, 1H), 7.89 (d, J=8.4 Hz, 3H), 7.71-7.67 (m, 3H), 7.62 (d, J=8.8 Hz, 2H), 7.51 (t, J=7.6 Hz, 2H), 7.44 (t, J=7.6 Hz, 1H), 7.26 (d, J=5.6 Hz, 2H), 6.96-6.93 (m, 1H), 4.32 (d, J=6.0 Hz, 2H). MS: m/z 444.0 (M+H$^+$).

Example 499: Synthesis of 1-((1H-Pyrazol-4-yl)methyl)-3-(4-([1,1'-biphenyl]-3-ylsulfonyl)phenyl)urea

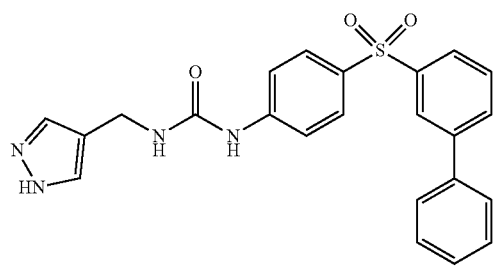 [SMILES: O=C(NCc1cn[nH]c1)Nc1ccc(S(=O)(=O)c2cccc(-c3ccccc3)c2)cc1]

The title compound was prepared using general procedure of 1-(4-([1,1'-biphenyl]-2-ylsulfonyl) phenyl)-3-(pyridin-4-ylmethyl)urea. $^1$H NMR (400 MHz, DMSO-$d_6$): δ=12.59 (s, 1H), 9.17 (s, 1H), 8.10 (s, 1H), 7.94 (d, J=7.6 Hz, 1H), 7.88-7.87 (m, 3H), 7.71-7.67 (m, 3H), 7.61-7.49 (m, 6H), 7.44 (t, J=7.2 Hz, 1H), 6.63 (t, J=5.6 Hz, 1H), 4.14 (d, J=5.6 Hz, 2H). MS: m/z 433.0 (M+H$^+$).

Example 500: Synthesis of 1-(4-([1,1'-Biphenyl]-3-ylsulfonyl)phenyl)-3-(oxazol-5-ylmethyl)urea

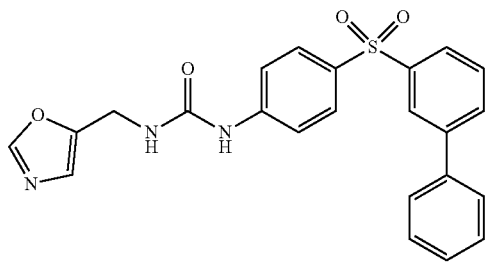 [SMILES: O=C(NCc1cnco1)Nc1ccc(S(=O)(=O)c2cccc(-c3ccccc3)c2)cc1]

The title compound was prepared using general procedure of 1-(4-([1,1'-biphenyl]-2-ylsulfonyl) phenyl)-3-(pyridin-4-ylmethyl)urea. $^1$H NMR (400 MHz, DMSO-$d_6$): δ=9.19 (s, 1H), 8.27 (s, 1H), 8.10 (s, 1H), 7.95 (d, J=7.2 Hz, 1H), 7.89-7.87 (m, 3H), 7.71-7.67 (m, 3H), 7.60 (d, J=8.8 Hz, 2H), 7.53-7.49 (m, 2H), 7.46-7.44 (m, 1H), 6.99 (s, 1H), 6.85-6.82 (m, 1H), 4.36 (d, J=5.2 Hz, 2H). MS: m/z 434.0 (M+H$^+$).

Example 501: Synthesis of 1-(4-([1,1'-Biphenyl]-2-ylsulfonyl)phenyl)-3-(pyridin-4-ylmethyl)urea

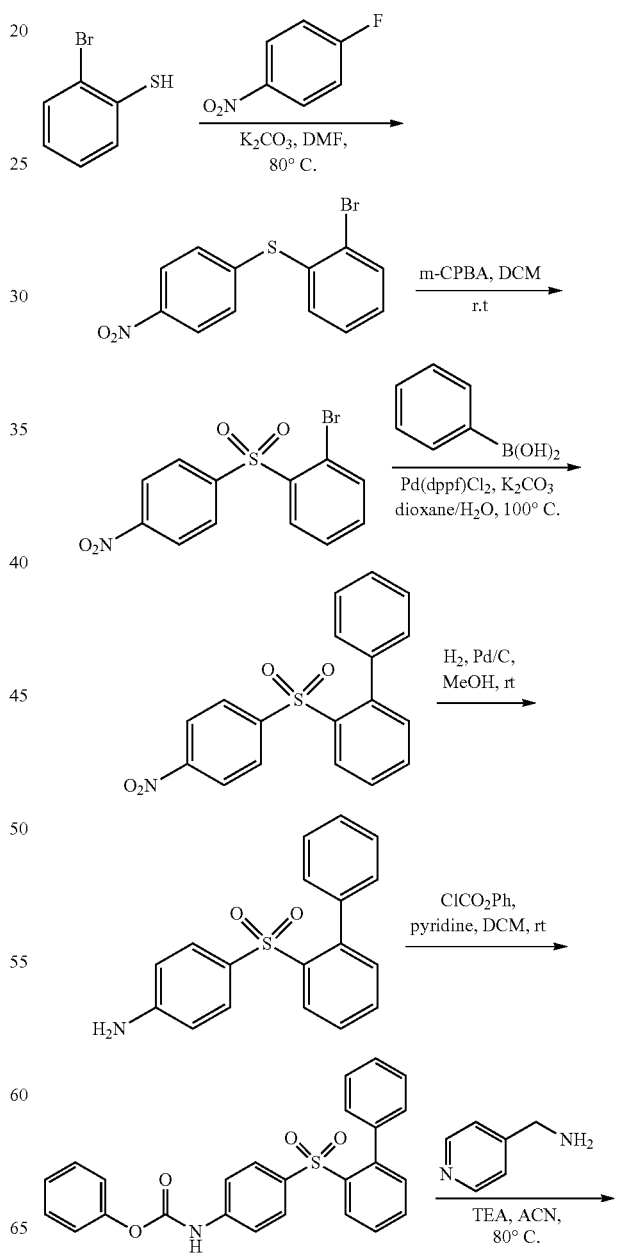

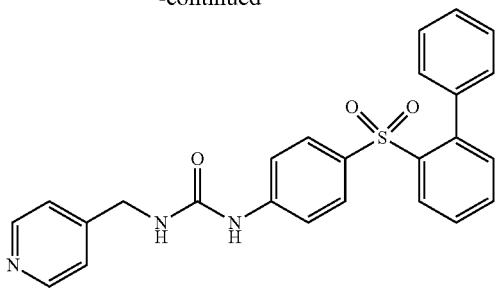

Step 1: To a solution of 2-bromobenzenethiol (1 g, 5.32 mmol) and 1-fluoro-4-nitrobenzene (1.12 g, 7.98 mmol) in DMF (10 mL) was added $K_2CO_3$ (2.2 g, 15.96 mmol). The reaction was stirred at 80° C. overnight. Then DMF was removed in vacuum. The residue was purified by flash column (PE) to give (2-bromophenyl) (4-nitrophenyl) sulfane as a white solid (1.6 g, yield: 97.5%). $^1$H NMR (300 MHz, $CDCl_3$): δ=8.16-8.11 (m, 2H), 7.77-7.74 (m, 1H), 7.60-7.56 (m, 1H), 7.42-7.35 (m, 2H), 7.42-7.35 (m, 2H).

Step 2: To a solution of (2-bromophenyl)(4-nitrophenyl) sulfane (1.6 g, 5.17 mmol) in DCM (30 mL) was added m-CPBA (3.15 g, 15.5 mmol) slowly at 0° C. The reaction was stirred at room temperature overnight. The reaction mixture was quenched with $Na_2SO_3$ (aq). Then the mixture was concentrated in vacuum and purified by flash column (PE/EA=10:1) to give 1-bromo-2-((4-nitrophenyl) sulfonyl) benzene (1.67 g, yield: 94.6%).

Step 3: To a solution of 1-bromo-2-((4-nitrophenyl)sulfonyl)benzene (2.42 g, 7.09 mmol), phenylboronic acid (1.30 g, 10.6 mmol) and $K_2CO_3$ (2.94 g, 21.2 mmol) in 1,4-dioxane (50 mL) and water (10 mL) was added Pd(dppf)$Cl_2$ (259 mg 0.354 mmol). The reaction was stirred at 90° C. under $N_2$ for 4 hrs. Then 1, 4-dioxane and water was removed in vacuum. The residue was purified by silica gel column (PE/EA=5/1) to give 2-((4-nitrophenyl)sulfonyl)-1, 1'-biphenyl (1.463 mg, yield: 60%). $^1$H NMR (300 MHz, $CDCl_3$): δ=8.50-8.46 (m, 1H), 8.01 (d, J=8.7 Hz, 2H), 7.68-7.65 (m, 2H), 7.40-7.33 (m, 3H), 7.26-7.19 (m, 3H), 6.97 (d, J=7.5 Hz, 2H).

Step 4: To a solution of 2-((4-nitrophenyl) sulfonyl)-1,1'-biphenyl (500 mg, 1.47 mmol) in MeOH (5 mL) was added Pd/C (10% wet, 100 mg). The reaction was stirred at room temperature under $H_2$ (3 atm) overnight. The Pd/C was filtered. The organic layers were concentrated in vacuum to give 4-([1,1'-biphenyl]-2-ylsulfonyl)aniline as a yellow oil (455 mg, crude), which was used for next step without further purification. MS: m/z 310.1. (M+H$^+$).

Step 5: To a solution of 4-([1,1'-biphenyl]-2-ylsulfonyl) aniline (455 mg, 0.767 mmol) in DCM (10 mL) was added pyridine (349 mg, 4.4 mmol) and phenyl chloroformate (224 mg, 1.6 mmol) dropwise at 0° C. The reaction was stirred at room temperature for 2 hrs. The mixture was washed with water (10 mL×2). The combined organic layers were dried over $Na_2SO_4$ and concentrated in vacuum. The residue was purified by flash column (PE/EA=10/1) to give phenyl (4-([1,1'-biphenyl]-2-ylsulfonyl)phenyl)carbamate as a colorless oil (473 mg, yield: 74.8%).

Step 6: To a solution of phenyl (4-([1,1'-biphenyl]-2-ylsulfonyl)phenyl)carbamate (150 mg, 0.35 mmol) in ACN (5 mL) was added pyridin-4-ylmethanamine (56.7 mg, 0.52 mmol) and TEA (106 mg, 1.048 mmol). The reaction was stirred at 80° C. for 1.5 hrs. The ACN was removed in vacuum. The residue was purified by prep-TLC (DCM/MeOH=10/1) to give 1-(4-([1,1'-Biphenyl]-2-ylsulfonyl)phenyl)-3-(pyridin-4-ylmethyl)urea (50.4 mg, yield: 36%). $^1$H NMR (400 MHz, DMSO-$d_6$): δ=9.21 (s, 1H), 8.50 (d, J=5.6 Hz, 2H), 8.23-8.21 (m, 1H), 7.71-7.67 (m, 2H), 7.38-7.34 (m, 3H), 7.29-7.25 (m, 5H), 7.05 (d, J=9.2 Hz, 2H), 6.97 (d, J=7.8 Hz, 2H), 6.91 (t, J=6.0 Hz, 1H), 4.32 (d, J=6.0 Hz, 2H). MS: m/z 444.0 (M+H$^+$).

Example 502: Synthesis of 1-((1H-Pyrazol-4-yl)methyl)-3-(4-([1,1'-biphenyl]-2-ylsulfonyl)phenyl)urea

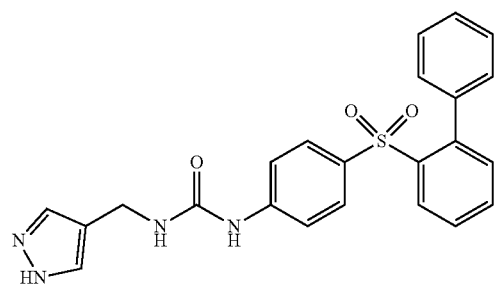 [SMILES: O=C(NCc1cn[nH]c1)Nc1ccc(S(=O)(=O)c2ccccc2-c2ccccc2)cc1]

The title compound was prepared using general procedure of 1-(4-([1,1'-biphenyl]-2-ylsulfonyl) phenyl)-3-(pyridin-4-ylmethyl)urea. $^1$H NMR (400 MHz, DMSO-$d_6$): δ=12.67 (s, 1H), 9.35 (s, 1H), 8.24-8.21 (m, 1H), 7.71-7.67 (m, 2H), 7.53 (s, 2H), 7.38-7.33 (m, 3H), 7.30-7.24 (m, 3H), 7.03 (t, J=8.8 Hz, 2H), 6.97 (d, J=7.2 Hz, 2H), 6.78 (t, J=5.2 Hz, 1H), 4.15 (d, J=5.2 Hz, 2H). MS: m/z 433.1 (M+H$^+$).

Example 503: Synthesis of 1-(4-([1,1'-Biphenyl]-2-ylsulfonyl)phenyl)-3-(oxazol-5-ylmethyl)urea

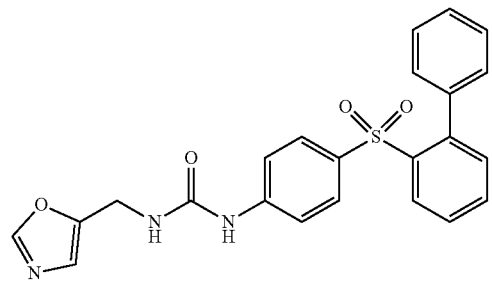 [SMILES: O=C(NCc1cnco1)Nc1ccc(S(=O)(=O)c2ccccc2-c2ccccc2)cc1]

The title compound was prepared using general procedure of 1-(4-([1,1'-biphenyl]-2-ylsulfonyl)phenyl)-3-(pyridin-4-ylmethyl)urea. $^1$H NMR (400 MHz, DMSO-$d_6$): δ=9.15 (s, 1H), 8.28 (s, 1H), 8.24-8.21 (m, 1H), 7.71-7.67 (m, 2H), 7.36-7.33 (m, 3H), 7.29-7.24 (m, 3H), 7.06-7.01 (m, 3H), 6.98-6.95 (m, 2H), 6.84 (t, J=6 Hz, 1H), 4.36 (d, J=5.6 Hz, 2H). MS: m/z 434.0 (M+H$^+$).

Example 504: Synthesis of 1-(4-((2'-Methyl-[1,1'-biphenyl]-2-yl)sulfonyl)phenyl)-3-(pyridin-4-ylmethyl)urea

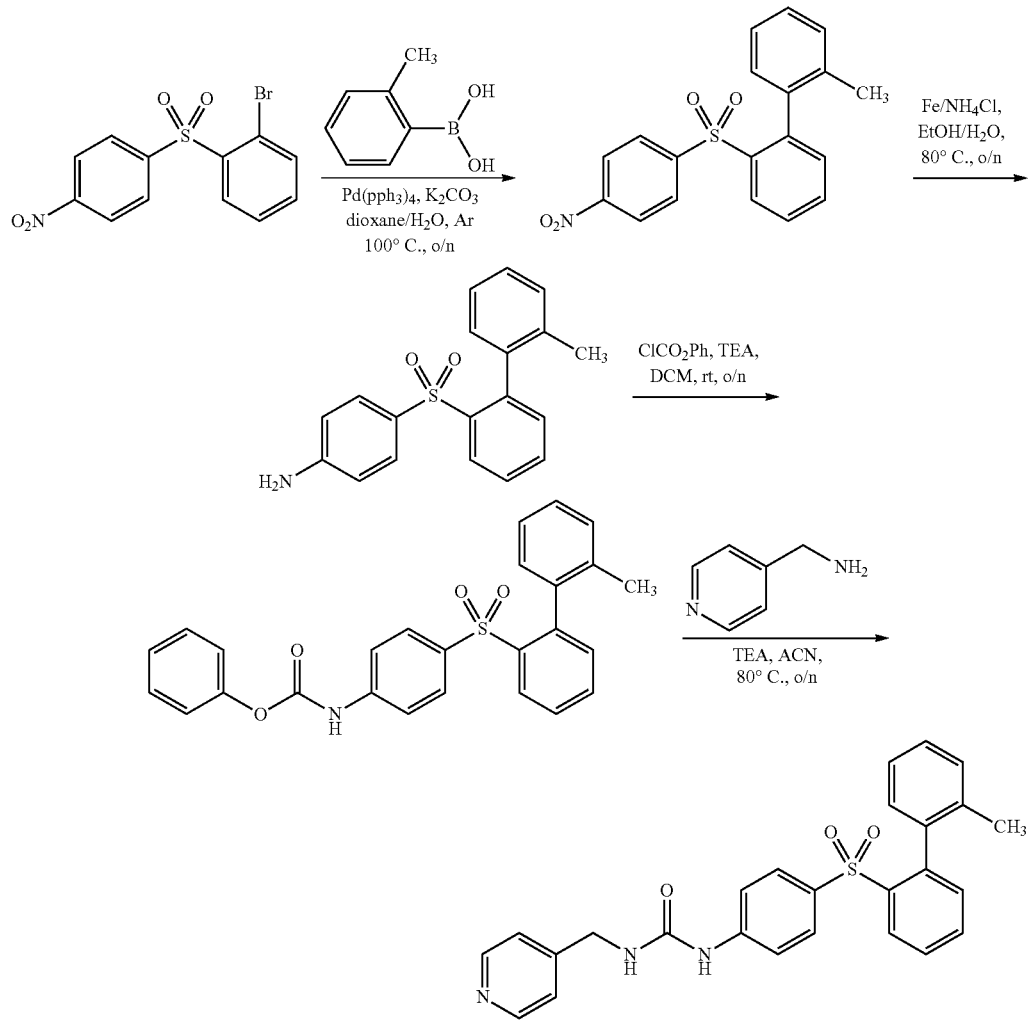

Step 1: To a solution of 1-bromo-2-((4-nitrophenyl)sulfonyl)benzene (400 mg, 1.16 mmol) in dioxane/H$_2$O (48 mL) (v/v, 5:1) was added 2-methylphenylboronic acid (477 mg, 3.50 mmol), Pd(PPh$_3$)$_4$ (135 mg, 0.12 mmol) and potassium carbonate (480 mg, 3.48 mmol). After stirred at 100° C. overnight under balloon Ar atmosphere, the reaction was filtered and the filtrate was concentrated in vacuum to give a crude product which was purified by silica gel column (PE/EA=4/1) to give 2-methyl-2'-((4-nitrophenyl)sulfonyl)-1,1'-biphenyl (180 mg, 44%) as a yellow solid. $^1$H NMR (400 MHz, DMSO-d$_6$): δ=8.41-8.39 (m, 1H), 8.19-8.15 (m, 2H), 7.83-7.78 (m, 2H), 7.47-7.44 (m, 2H), 7.30-7.25 (m, 2H), 7.08-7.02 (m, 2H), 6.68 (d, J=6.8 Hz, 1H), 1.56 (s, 3H).

Step 2: To a solution of 2-methyl-2'-((4-nitrophenyl)sulfonyl)-1,1'-biphenyl (180 mg, 0.51 mmol) in EtOH/H$_2$O (30 mL) (v/v, 5:1) was added iron (143 mg, 2.55 mmol) and NH$_4$Cl (135 mg, 2.55 mmol). The reaction mixture was stirred at 80° C. overnight. The reaction was monitored by LCMS and TLC. After completion, the reaction mixture was filtrated and the cake was washed with EtOH. The solvent was concentrated in vacuum to give a crude product, which was purified by silica gel column (PE/EA=2/1) to give 4-((2'-methyl-[1,1'-biphenyl]-2-yl)sulfonyl)aniline (140 mg, 85%) as a white solid. $^1$H NMR (400 MHz, DMSO-d$_6$): δ=8.22-8.20 (m, 1H), 7.66-7.62 (m, 2H), 7.27-7.25 (m, 1H), 7.17-7.08 (m, 3H), 6.87-6.85 (m, 1H), 6.78-6.75 (m, 2H), 6.38-6.36 (m, 2H), 6.08 (s, 2H), 1.51 (s, 3H).

Step 3: To a solution of 4-((2'-methyl-[1,1'-biphenyl]-2-yl)sulfonyl)aniline (140 mg, 0.43 mmol) in DCM (15 mL) was added phenyl chloroformate (312 mg, 2.0 mmol) and TEA (0.5 mL). Then the mixture was stirred at room temperature overnight. The reaction was monitored by TLC and LCMS. After completion, the mixture was concentrated in vacuum to give a crude product which was purified by a silica gel column (PE/EA=2/1) to afford phenyl (4-((2'-methyl-[1,1'-biphenyl]-2-yl)sulfonyl)phenyl)carbamate (160 mg, 84%) as a white solid.

Step 4: To a solution of phenyl (4-((2'-methyl-[1,1'-biphenyl]-2-yl)sulfonyl)phenyl)carbamate (80 mg, 0.18 mmol) in ACN (15 mL) was added Pyridin-4-ylmethanamine (25 mg, 0.23 mmol) and TEA (0.5 mL). Then the mixture was stirred at 80° C. overnight. The reaction was monitored by TLC and LCMS. After completion, the mixture was concentrated in vacuum to give a residue which was purified by pre-HPLC to afford 1-(4-((2'-methyl-[1,1'-biphenyl]-2-yl)sulfonyl)phenyl)-3-(pyridin-4-ylmethyl)urea (34.3 mg, 44%) as a white solid. $^1$H NMR (400 MHz, DMSO-d$_6$): δ=9.24 (s, 1H), 8.50 (d, J=6.0 Hz, 2H), 8.29-8.27 (m, 1H), 7.71-7.68 (m, 2H), 7.38 (d, J=8.0 Hz, 2H), 7.29-7.25 (m, 3H), 7.21-7.19 (m, 1H), 7.10 (t, J=8.0 Hz, 2H), 7.02 (d, J=8.8 Hz, 2H), 6.93 (t, J=6.0 Hz, 1H), 6.80 (d, J=7.0 Hz, 1H), 4.33 (d, J=5.6 Hz, 2H), 1.57 (s, 3H). MS: m/z 458.1 (M+H$^+$).

Example 505: Synthesis of 1-((1H-Pyrazol-4-yl)methyl)-3-(4-((2'-methyl-[1,1'-biphenyl]-2-yl)sulfonyl)phenyl)urea

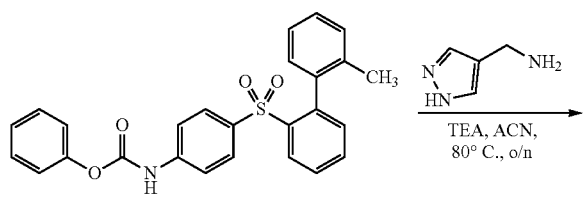

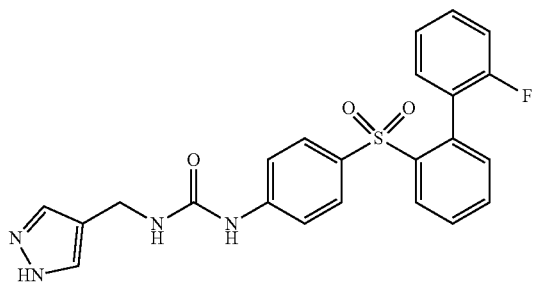 [SMILES: O=C(NCc1cn[nH]c1)Nc1ccc(S(=O)(=O)c2ccccc2-c2ccccc2F)cc1]

To a solution of [4-(3'-methyl-biphenyl-2-sulfonyl)-phenyl]-carbamic acid phenyl ester (80 mg, 0.18 mmol) in ACN (15 mL) was added (1H-pyrazol-4-yl)methanamine (23 mg, 0.23 mmol) and TEA (0.5 mL). The mixture was stirred at 80° C. overnight. The reaction was monitored by TLC and LCMS. After completion, the mixture was concentrated in vacuum to give a crude product which was purified by prep-TLC (DCM/MeOH=10/1) to afford 1-((1H-pyrazol-4-yl)methyl)-3-(4-((2'-methyl-[1,1'-biphenyl]-2-yl)sulfonyl)phenyl)urea (33.8 mg, 15%) as a white solid. $^1$H NMR (400 MHz, DMSO-d$_6$): δ=12.56 (s, 1H), 8.93 (s, 1H), 8.29-8.27 (m, 1H), 7.71-7.67 (m, 2H), 7.53 (s, 2H), 7.35 (d, J=8.8 Hz, 2H), 7.29-7.25 (m, 1H), 7.20-7.18 (m, 1H), 7.12-7.08 (m, 2H), 7.01 (d, J=8.8 Hz, 2H), 6.80 (d, J=7.6 Hz, 1H), 6.51 (s, 1H), 4.15 (d, J=6.0 Hz, 2H), 1.49 (s, 3H). MS: m/z 447.1 (M+H$^+$).

Example 506: Synthesis of 1-[4-(2'-Fluoro-biphenyl-2-sulfonyl)-phenyl]-3-pyridin-4-ylmethyl-urea

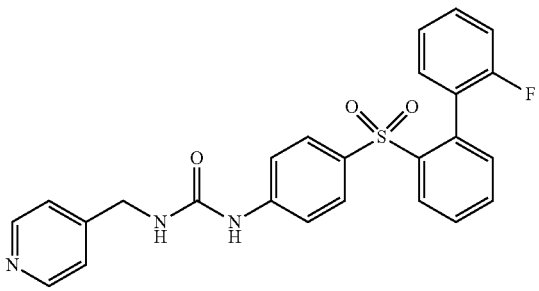 [SMILES: O=C(NCc1ccncc1)Nc1ccc(S(=O)(=O)c2ccccc2-c2ccccc2F)cc1]

The title compound was prepared using general procedure of 1-(4-([1,1'-biphenyl]-2-ylsulfonyl)phenyl)-3-(pyridin-4-ylmethyl)urea. $^1$H NMR (400 MHz, DMSO-d$_6$): δ=9.25 (s, 1H), 8.51-8.49 (m, 2H), 8.26-8.24 (m, 1H), 7.74-7.71 (m, 2H), 7.45-7.41 (m, 3H), 7.33-7.28 (m, 3H), 7.18-7.07 (m, 4H), 7.03-6.98 (m, 1H), 6.95-6.92 (m, 1H), 4.33 (d, J=6.0 Hz, 2H). MS: m/z 461.7 (M+H$^+$).

Example 507: Synthesis of 1-[4-(2'-Fluoro-biphenyl-2-sulfonyl)-phenyl]-3-(1H-pyrazol-4-ylmethyl)-urea

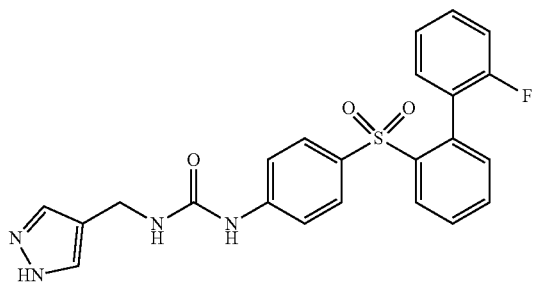 [SMILES: O=C(NCc1cn[nH]c1)Nc1ccc(S(=O)(=O)c2ccccc2-c2ccccc2F)cc1]

The title compound was prepare using genera procedure of 1-(4-([1,1'-biphenyl]-2-ylsulfonyl)phenyl)-3-(pyridin-4-ylmethyl)urea. $^1$H NMR (400 MHz, DMSO-d$_6$): δ=12.58 (s, 1H), 8.94 (s, 1H), 8.26-8.24 (m, 1H), 7.75-7.70 (m, 2H), 7.55-7.38 (m, 5H), 7.32-7.30 (m, 1H), 7.17-7.08 (m, 4H), 7.02-6.98 (m, 1H), 6.52 (t, J=5.6 Hz, 1H), 4.15 (d, J=5.2 Hz, 2H). MS: m/z 450.7 (M+H$^+$).

Example 508: Synthesis of 1-[4-(3'-Fluoro-biphenyl-2-sulfonyl)-phenyl]-3-pyridin-4-ylmethyl-urea

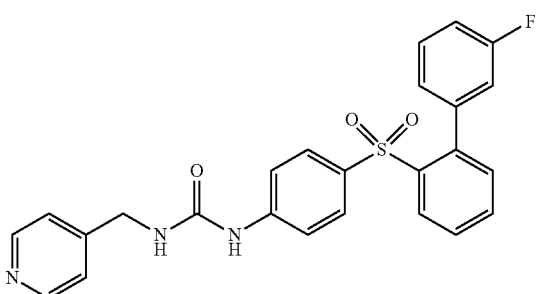

The title compound was prepared using general procedure of 1-(4-([1,1'-biphenyl]-2-ylsulfonyl)phenyl)-3-(pyridin-4-ylmethyl)urea. $^1$H NMR (400 MHz, DMSO-d$_6$): δ=9.25 (s, 1H), 8.52-8.50 (m, 2H), 8.23-8.21 (m, 1H), 7.73-7.70 (m, 2H), 7.40 (d, J=8.4 Hz, 2H), 7.36-7.28 (m, 4H), 7.23-7.18 (m, 1H), 7.12 (d, J=8.8 Hz, 2H), 6.92 (t, J=6 Hz, 1H), 6.82 (d, J=7.6 Hz, 1H), 6.75-6.72 (m, 1H), 4.33 (d, J=5.6 Hz, 2H). MS: m/z 462.1 (M+H$^+$).

Example 509: Synthesis of 1-[4-(3'-Fluoro-biphenyl-2-sulfonyl)-phenyl]-3-(1H-pyrazol-4-ylmethyl)-urea

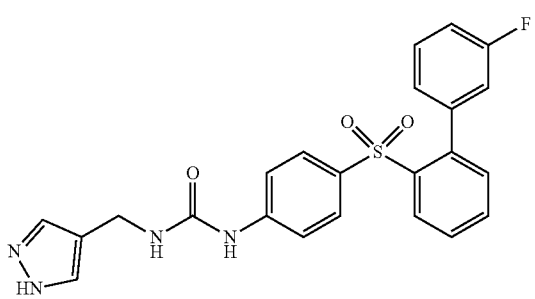 [SMILES: O=C(NCc1cn[nH]c1)Nc1ccc(S(=O)(=O)c2ccccc2-c2cccc(F)c2)cc1]

The title compound was prepared using general procedure of 1-(4-([1,1'-biphenyl]-2-ylsulfonyl)phenyl)-3-(pyridin-4-ylmethyl)urea. $^1$H NMR (400 MHz, DMSO-d$_6$): δ=12.62 (s, 1H), 8.96 (s, 1H), 8.22 (d, J=7.2 Hz, 1H), 7.74-7.68 (m, 2H), 7.56-7.37 (m, 4H), 7.35-7.28 (m, 2H), 7.23-7.18 (m, 1H), 7.10 (d, J=8.8 Hz, 2H), 6.81 (d, J=6.8 Hz, 1H), 6.73 (d, J=9.2 Hz, 1H), 6.53 (t, J=5.2 Hz, 1H), 4.14 (d, J=4.8 Hz, 2H). MS: m/z 450.8 (M+H$^+$).

Example 510: Synthesis of 1-[4-(4'-Fluoro-biphenyl-2-sulfonyl)-phenyl]-3-pyridin-4-ylmethyl-urea

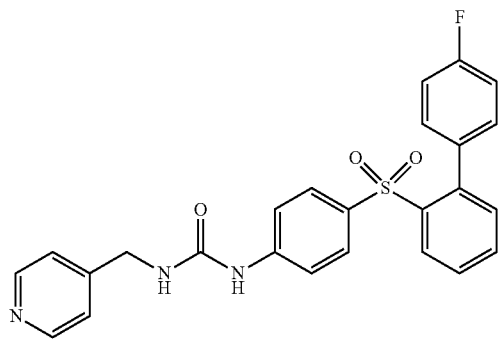 [SMILES: O=C(NCc1ccncc1)Nc1ccc(S(=O)(=O)c2ccccc2-c2ccc(F)cc2)cc1]

The title compound was prepared using general procedure of 1-(4-([1,1'-biphenyl]-2-ylsulfonyl)phenyl)-3-(pyridin-4-ylmethyl)urea. $^1$H NMR (400 MHz, DMSO-d$_6$): δ=9.23 (s, 1H), 8.51-8.49 (m, 2H), 8.23-8.21 (m, 1H), 7.72-7.68 (m, 2H), 7.39 (d, J=8.8 Hz, 2H), 7.29-7.25 (m, 3H), 7.13-7.08 (m, 4H), 7.02-6.98 (m, 2H), 6.91 (t, J=6.0 Hz, 1H), 4.32 (d, J=6.0 Hz, 2H). MS: m/z 461.8 (M+H$^+$).

Example 511: Synthesis of 1-[4-(4'-Fluoro-biphenyl-2-sulfonyl)-phenyl]-3-(1H-pyrazol-4-ylmethyl)-urea

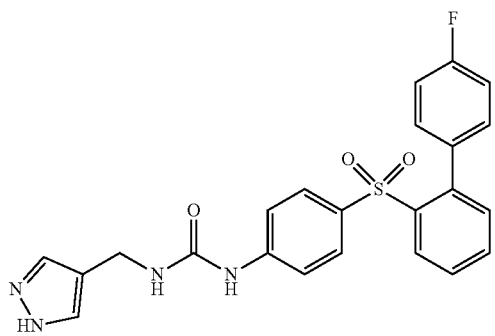 [SMILES: O=C(NCc1cn[nH]c1)Nc1ccc(S(=O)(=O)c2ccccc2-c2ccc(F)cc2)cc1]

The title compound was prepared using general procedure of 1-(4-([1,1'-biphenyl]-2-ylsulfonyl)phenyl)-3-(pyridin-4-ylmethyl)urea. $^1$H NMR (400 MHz, DMSO-d$_6$): δ=12.49 (s, 1H), 8.95 (s, 1H), 8.23-8.21 (m, 1H), 7.73-7.68 (m, 2H), 7.53 (s, 2H), 7.36 (d, J=8.8 Hz, 2H), 7.27-7.25 (m, 1H), 7.13-7.06 (m, 4H), 7.01-6.98 (m, 2H), 6.53 (t, J=5.6 Hz, 1H), 4.14 (d, J=5.6 Hz, 2H). MS: m/z 450.7 (M+H$^+$).

Example 512: Synthesis of 1-[4-(3'-Methyl-biphenyl-2-sulfonyl)-phenyl]-3-pyridin-4-ylmethyl-urea

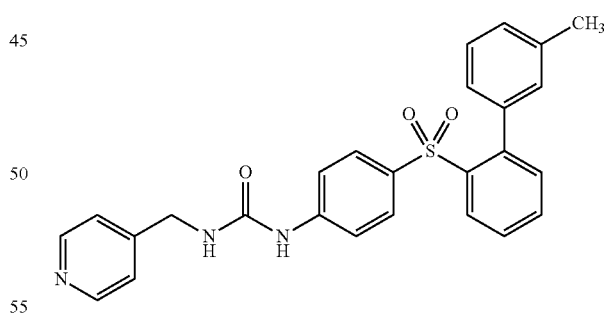

The title compound was prepared using general procedure of 1-(4-([1,1'-biphenyl]-2-ylsulfonyl)phenyl)-3-(pyridin-4-ylmethyl)urea. $^1$H NMR (400 MHz, DMSO-d$_6$): δ=9.22 (s, 1H), 8.50 (d, J=5.2 Hz, 2H), 8.24 (d, J=7.2 Hz, 1H), 7.71-7.65 (m, 2H), 7.36 (d, J=8.8 Hz, 2H), 7.28 (d, J=4.8 Hz, 2H), 7.24-7.14 (m, 3H), 7.03 (d, J=8.4 Hz, 2H), 6.91 (t, J=5.6 Hz, 1H), 6.85 (d, J=7.2 Hz, 1H), 6.50 (s, 1H), 4.33 (d, J=5.2 Hz, 2H), 2.18 (s, 3H). MS: m/z 457.8 (M+H$^+$).

Example 513: Synthesis of 1-[4-(3'-Methyl-biphenyl-2-sulfonyl)-phenyl]-3-(1H-pyrazol-4-ylmethyl)-urea

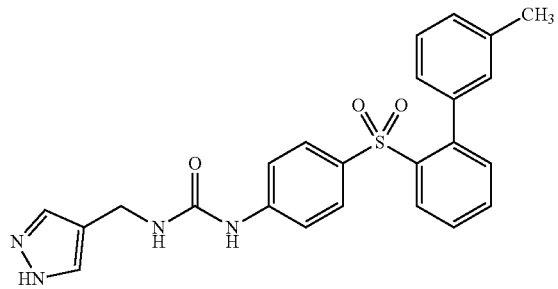 [SMILES: Cc1cccc(-c2ccccc2S(=O)(=O)c2ccc(NC(=O)NCc3cn[nH]c3)cc2)c1]

The title compound was prepared using general procedure of 1-(4-([1,1'-biphenyl]-2-ylsulfonyl)phenyl)-3-(pyridin-4-ylmethyl)urea. $^1$H NMR (400 MHz, DMSO-d$_6$): δ=12.64 (s, 1H), 8.98 (s, 1H), 8.25-8.22 (m, 1H), 7.69-7.66 (m, 2H), 7.52 (br s, 2H), 7.34 (d, J=8.8 Hz, 2H), 7.24-7.16 (m, 3H), 7.03 (d, J=8.8 Hz, 2H), 6.84 (d, J=7.2 Hz, 1H), 6.55 (d, J=5.6 Hz, 1H), 6.51 (s, 1H), 4.15 (d, J=6.0 Hz, 2H), 2.18 (s, 3H). MS: m/z 446.8 (M+H$^+$).

Example 515: Synthesis of 1-[4-(4'-Methyl-biphenyl-2-sulfonyl)-phenyl]-3-(1H-pyrazol-4-ylmethyl)-urea

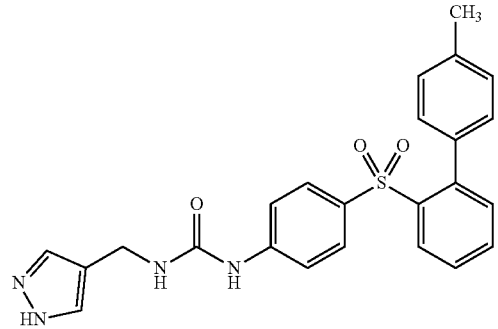

The title compound was prepared using general procedure of 1-(4-([1,1'-biphenyl]-2-ylsulfonyl)phenyl)-3-(pyridin-4-ylmethyl)urea. 1H NMR (400 MHz, DMSO-d6): δ=12.66 (s, 1H), 8.91 (s, 1H), 8.21-8.19 (m, 1H), 7.69-7.64 (m, 2H), 7.54 (br s, 2H), 7.33 (d, J=5.2 Hz, 2H), 7.24-7.21 (m, 1H), 7.09-7.05 (m, 4H), 6.85 (d, J=8.0 Hz, 2H), 6.51 (t, J=5.2 Hz, 1H), 4.15 (d, J=5.2 Hz, 2H), 2.36 (s, 3H). MS: m/z 466.8 (M+H$^+$).

Example 514: Synthesis of 1-[4-(4'-Methyl-biphenyl-2-sulfonyl)-phenyl]-3-pyridin-4-ylmethyl-urea

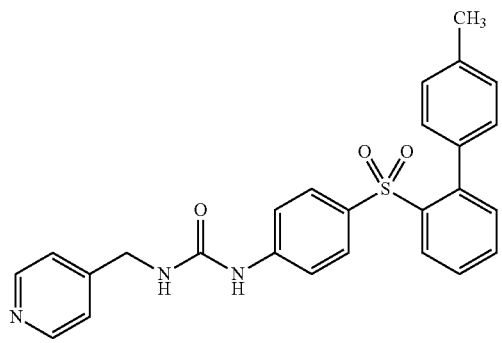

The title compound was prepared using general procedure of 1-(4-([1,1'-biphenyl]-2-ylsulfonyl)phenyl)-3-(pyridin-4-ylmethyl)urea. $^1$H NMR (400 MHz, DMSO-d$_6$): δ=9.21 (s, 1H), 8.51-8.50 (m, 2H), 8.18 (d, J=1.6 Hz, 1H), 7.69-7.64 (m, 2H), 7.36 (d, J=9.2 Hz, 2H), 7.28 (d, J=5.6 Hz, 2H), 7.23 (t, J=5.6 Hz, 1H), 7.07 (d, J=9.2 Hz, 4H), 6.91 (t, J=6.0 Hz, 1H), 6.85 (d, J=8.0 Hz, 2H), 4.32 (d, J=6.0 Hz, 2H), 1.98 (s, 3H). MS: m/z 458.1 (M+H$^+$).

Example 516: Synthesis of 1-[4-(2'-Chloro-biphenyl-2-sulfonyl)-phenyl]-3-pyridin-4-ylmethyl-urea

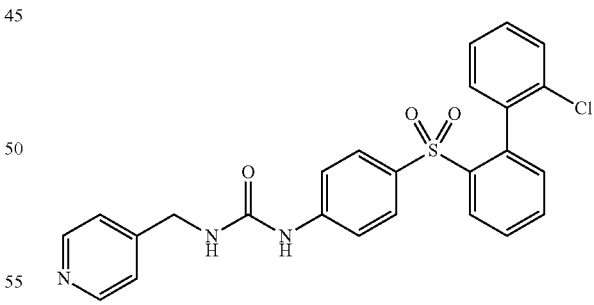

The title compound was prepared using general procedure of 1-(4-([1,1'-biphenyl]-2-ylsulfonyl)phenyl)-3-(pyridin-4-ylmethyl)urea. $^1$H NMR (400 MHz, DMSO-d$_6$): δ=9.25 (s, 1H), 8.51-8.50 (m, 2H), 8.26-8.24 (m, 1H), 7.74-7.71 (m, 2H), 7.43-7.40 (m, 3H), 7.36-7.25 (m, 5H), 7.13-7.08 (m, 3H), 6.93 (t, J=6.0 Hz, 1H), 4.33 (d, J=6.0 Hz, 2H). MS: m/z 477.7 (M+H$^+$).

Example 517: Synthesis of 1-[4-(2'-Chloro-biphenyl-2-sulfonyl)-phenyl]-3-(1H-pyrazol-4-ylmethyl)-urea

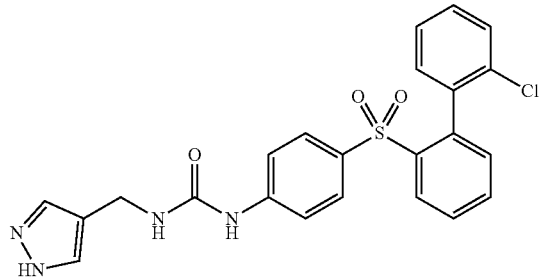 [SMILES: O=C(NCc1cn[nH]c1)Nc1ccc(S(=O)(=O)c2ccccc2-c2ccccc2Cl)cc1]

The title compound was prepared using general procedure of 1-(4-([1,1'-biphenyl]-2-ylsulfonyl)phenyl)-3-(pyridin-4-ylmethyl)urea. $^1$H NMR (400 MHz, DMSO-d$_6$): δ=12.64 (s, 1H), 9.39 (s, 1H), 8.26-8.24 (m, 1H), 7.75-7.71 (m, 2H), 7.53 (s, 2H), 7.44-7.40 (m, 3H), 7.36-7.31 (m, 2H), 7.27-7.24 (m, 1H), 7.09 (d, J=8.8 Hz, 3H), 6.80 (t, J=5.2 Hz, 1H), 4.15 (d, J=5.2 Hz, 2H). MS: m/z 466.7 (M+H$^+$).

Example 519: Synthesis of 1-[4-(3'-Chloro-biphenyl-2-sulfonyl)-phenyl]-3-(1H-pyrazol-4-ylmethyl)-urea

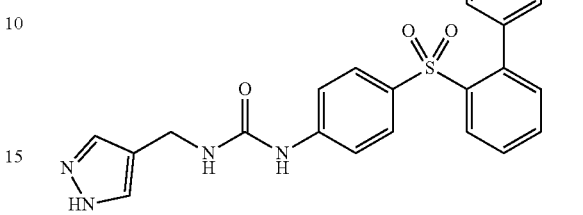

The title compound was prepared using general procedure of 1-(4-([1,1'-biphenyl]-2-ylsulfonyl)phenyl)-3-(pyridin-4-ylmethyl)urea. $^1$H NMR (400 MHz, DMSO-d$_6$): δ=12.72 (s, 1H), 10.05 (s, 1H), 8.23-8.20 (m, 1H), 7.73-7.70 (m, 2H), 7.44-7.42 (m, 5H), 7.34-7.28 (m, 2H), 7.25 (t, J=5.2 Hz, 1H), 7.09 (d, J=8.8 Hz, 2H), 6.96-6.92 (m, 2H), 4.10 (d, J=5.2 Hz, 2H). MS: m/z 466.7 (M+H$^+$).

Example 518: Synthesis of 1-[4-(3'-Chloro-biphenyl-2-sulfonyl)-phenyl]-3-pyridin-4-ylmethyl-urea

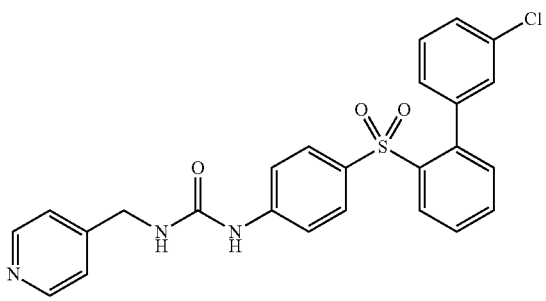 [SMILES: O=C(NCc1ccncc1)Nc1ccc(S(=O)(=O)c2ccccc2-c2cccc(Cl)c2)cc1]

The title compound was prepare using genera procedure of 1-(4-([1,1'-biphenyl]-2-ylsulfonyl)phenyl)-3-(pyridin-4-ylmethyl)urea. $^1$H NMR (400 MHz, DMSO-d$_6$): δ=9.26 (s, 1H), 8.51-8.49 (m, 2H), 8.24-8.22 (m, 1H), 7.73-7.70 (m, 2H), 7.42 (d, J=8.8 Hz, 3H), 7.35-7.27 (m, 4H), 7.11 (d, J=8.4 Hz, 2H), 7.00-6.97 (m, 1H), 6.92 (t, J=6.0 Hz, 1H), 6.84 (t, J=2.0 Hz, 1H), 4.33 (d, J=6.0 Hz, 2H). MS: m/z 477.7 (M+H$^+$).

Example 520: Synthesis of 1-[4-(4'-Chloro-biphenyl-2-sulfonyl)-phenyl]-3-pyridin-4-ylmethyl-urea

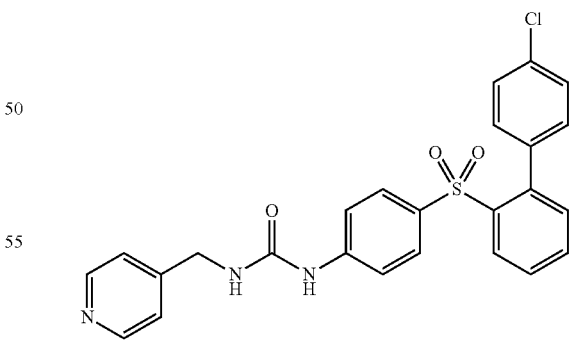

The title compound was prepared using general procedure of 1-(4-([1,1'-biphenyl]-2-ylsulfonyl)phenyl)-3-(pyridin-4-ylmethyl)urea. $^1$H NMR (400 MHz, DMSO-d$_6$): δ=9.25 (s, 1H), 8.51-8.49 (m, 2H), 8.21-8.19 (m, 2H), 7.72-7.68 (m, 2H), 7.41 (d, J=8.4 Hz, 2H), 7.35 (d, J=8.4 Hz, 2H), 7.29-7.28 (m, 3H), 7.13 (d, J=8.8 Hz, 2H), 7.01 (d, J=8.4 Hz, 2H), 4.33 (d, J=5.6 Hz, 2H). MS: m/z 477.7 (M+H$^+$).

Example 521: Synthesis of 1-[4-(4'-Chloro-biphenyl-2-sulfonyl)-phenyl]-3-(1H-pyrazol-4-ylmethyl)-urea

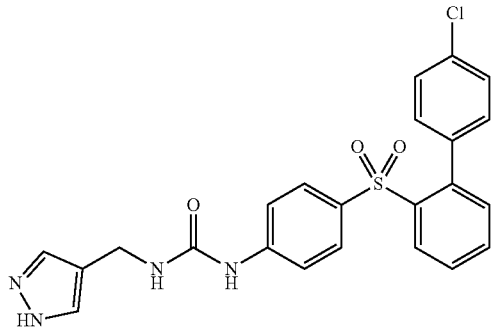 [SMILES: O=C(NCc1cn[nH]c1)Nc1ccc(S(=O)(=O)c2ccccc2-c2ccc(Cl)cc2)cc1]

The title compound was prepared using general procedure of 1-(4-([1,1'-biphenyl]-2-ylsulfonyl)phenyl)-3-(pyridin-4-ylmethyl)urea. $^1$H NMR (400 MHz, DMSO-d$_6$): δ=12.69 (s, 1H), 9.73 (s, 1H), 8.19 (d, J=6.4 Hz, 1H), 7.73-7.67 (m, 2H), 7.53 (br s, 2H), 7.40 (d, J=8.4 Hz, 2H), 7.35 (d, J=8.0 Hz, 2H), 7.26 (d, J=7.6 Hz, 1H), 7.10 (d, J=8.4 Hz, 2H), 7.00 (d, J=8.4 Hz, 3H), 4.15 (d, J=5.2 Hz, 2H). MS: m/z 467.0 (M+H$^+$).

Example 522: Synthesis of 1-[4-(2'-Methoxy-biphenyl-2-sulfonyl)-phenyl]-3-pyridin-4-ylmethyl-urea

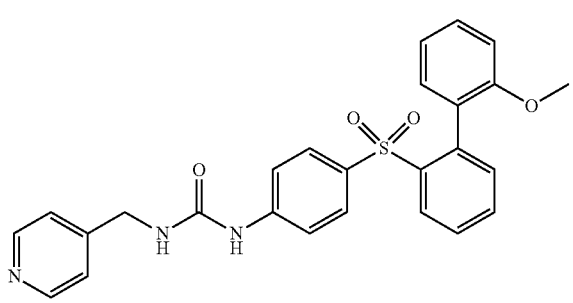 [SMILES: COc1ccccc1-c1ccccc1S(=O)(=O)c1ccc(NC(=O)NCc2ccncc2)cc1]

The title compound was prepared using general procedure of 1-(4-([1,1'-biphenyl]-2-ylsulfonyl)phenyl)-3-(pyridin-4-ylmethyl)urea. $^1$H NMR (400 MHz, DMSO-d$_6$): δ=9.20 (s, 1H), 8.50 (dd, J=4.8, 2.0 Hz, 2H), 8.24-8.22 (m, 1H), 7.66-7.62 (m, 2H), 7.37-7.32 (m, 3H), 7.27 (d, J=6.0 Hz, 2H), 7.19-7.17 (m, 1H), 7.04 (d, J=8.8 Hz, 2H), 6.92-6.89 (m, 3H), 6.79 (d, J=8.4 Hz, 1H), 4.33 (d, J=6.0 Hz, 2H), 3.29 (s, 3H). MS: m/z 473.8 (M+H$^+$).

Example 523: Synthesis of 1-[4-(2'-Methoxy-biphenyl-2-sulfonyl)-phenyl]-3-(1H-pyrazol-4-ylmethyl)-urea

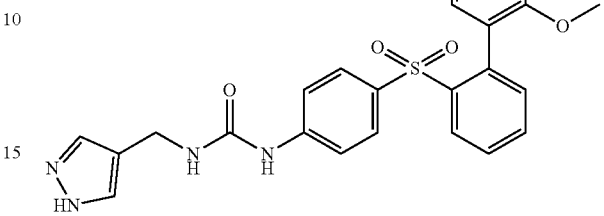

The title compound was prepared using general procedure of 1-(4-([1,1'-biphenyl]-2-ylsulfonyl)phenyl)-3-(pyridin-4-ylmethyl)urea. $^1$H NMR (400 MHz, DMSO-d$_6$): δ=12.58 (s, 1H), 9.07 (s, 1H), 8.29-8.27 (m, 1H), 7.70-7.67 (m, 2H), 7.58 (s, 2H), 7.41-7.37 (m, 3H), 7.23 (dd, J=5.6, 2.0 Hz, 1H), 7.07 (d, J=8.8 Hz, 2H), 6.98-6.96 (m, 2H), 6.84 (d, J=8.4 Hz, 1H), 6.63-6.61 (m, 1H), 4.19 (d, J=5.6 Hz, 2H), 3.3 (s, 3H). MS: m/z 463.1 (M+H$^+$).

Example 524: Synthesis of 1-[4-(3'-Methoxy-biphenyl-2-sulfonyl)-phenyl]-3-pyridin-4-ylmethyl-urea

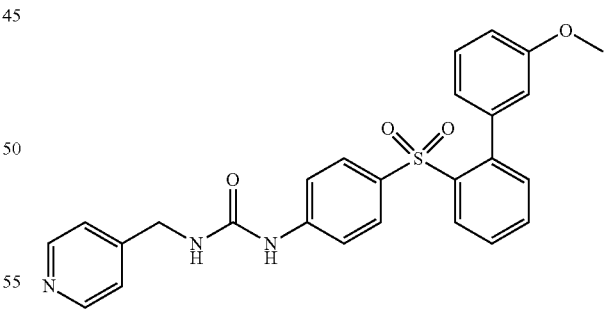

The title compound was prepared using general procedure of 1-(4-([1,1'-biphenyl]-2-ylsulfonyl)phenyl)-3-(pyridin-4-ylmethyl)urea. $^1$H NMR (400 MHz, DMSO-d$_6$): δ=9.21 (s, 1H), 8.50 (dd, J=4.4, 1.6 Hz, 2H), 8.22 (d, J=7.2 Hz, 1H), 7.70-7.67 (m, 2H), 7.36 (d, J=9.2 Hz, 2H), 7.29-7.25 (m, 3H), 7.19 (t, J=8.0 Hz, 1H), 7.07 (d, J=9.2 Hz, 2H), 6.91-6.89 (m, 2H), 6.59 (d, J=7.6 Hz, 1H), 6.36 (t, J=2.0 Hz, 1H), 4.33 (d, J=6.0 Hz, 2H), 3.62 (s, 3H). MS: m/z 474.1 (M+H$^+$).

Example 525: Synthesis of 1-[4-(3'-Methoxy-biphenyl-2-sulfonyl)-phenyl]-3-(1H-pyrazol-4-ylmethyl)-urea

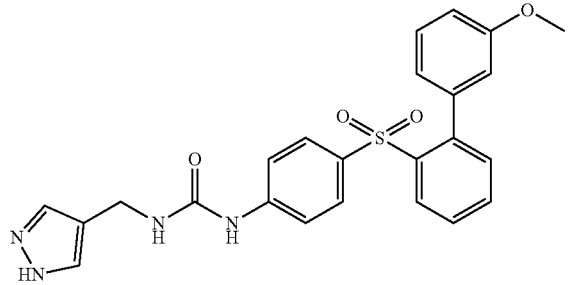 [SMILES: COc1cccc(-c2ccccc2S(=O)(=O)c2ccc(NC(=O)NCc3cn[nH]c3)cc2)c1]

The title compound was prepared using general procedure of 1-(4-([1,1'-biphenyl]-2-ylsulfonyl)phenyl)-3-(pyridin-4-ylmethyl)urea. $^1$H NMR (400 MHz, DMSO-$d_6$): δ=12.57 (s, 1H), 8.91 (s, 1H), 8.23-8.21 (m, 1H), 7.70-7.67 (m, 2H), 7.53 (d, J=2.8 Hz, 2H), 7.33 (d, J=8.8 Hz, 2H), 7.27-7.25 (m, 1H), 7.19 (t, J=8.0 Hz, 1H), 7.05 (d, J=9.2 Hz, 2H), 6.92-6.89 (m, 1H), 6.59-6.51 (m, 2H), 6.37-6.36 (m, 1H), 4.15 (d, J=5.2 Hz, 2H), 3.62 (s, 3H). MS: m/z 462.8 (M+H$^+$).

Example 526: Synthesis of 1-[4-(4'-Methoxy-biphenyl-2-sulfonyl)-phenyl]-3-pyridin-4-ylmethyl-urea

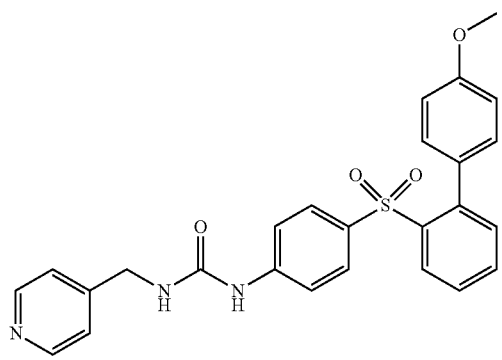 [SMILES: COc1ccc(-c2ccccc2S(=O)(=O)c2ccc(NC(=O)NCc3ccncc3)cc2)cc1]

The title compound was prepared using general procedure of 1-(4-([1,1'-biphenyl]-2-ylsulfonyl)phenyl)-3-(pyridin-4-ylmethyl)urea. $^1$H NMR (400 MHz, DMSO-$d_6$): δ=9.20 (s, 1H), 8.50 (dd, J=4.4, 1.6 Hz, 2H), 8.20 (dd, J=7.6, 1.6 Hz, 1H), 7.69-7.64 (m, 2H), 7.36 (d, J=9.2 Hz, 2H), 7.28 (d, J=6.0 Hz, 2H), 7.23 (dd, J=8.8, 1.6 Hz, 1H), 7.06 (d, J=8.4 Hz, 2H), 6.90-6.87 (m, 3H), 6.83-6.81 (m, 2H), 4.32 (d, J=6.0 Hz, 2H), 3.79 (s, 3H). MS: m/z 474.1 (M+H$^+$).

Example 527: Synthesis of 1-[4-(4'-Methoxy-biphenyl-2-sulfonyl)-phenyl]-3-(1H-pyrazol-4-ylmethyl)-urea

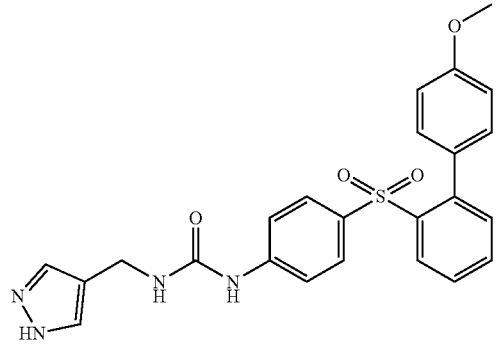 [SMILES: COc1ccc(-c2ccccc2S(=O)(=O)c2ccc(NC(=O)NCc3cn[nH]c3)cc2)cc1]

The title compound was prepared using general procedure of 1-(4-([1,1'-biphenyl]-2-ylsulfonyl)phenyl)-3-(pyridin-4-ylmethyl)urea. $^1$H NMR (400 MHz, DMSO-$d_6$): δ=12.63 (s, 1H), 8.93 (s, 1H), 8.22-8.19 (m, 1H), 7.68-7.63 (m, 4H), 7.33 (d, J=9.2 Hz, 2H), 7.24-7.22 (m, 1H), 7.05 (d, J=8.8 Hz, 2H), 6.88 (dd, J=6.8, 2.4 Hz, 2H), 6.83-6.81 (m, 2H), 6.51 (s, 1H), 4.14 (d, J=5.6 Hz, 2H), 3.80 (s, 3H). MS: m/z 462.8 (M+H$^+$).

Example 528: Synthesis of 1-(4-((3'-Cyano-[1,1'-biphenyl]-2-yl)sulfonyl)phenyl)-3-(pyridin-4-ylmethyl)urea -continued

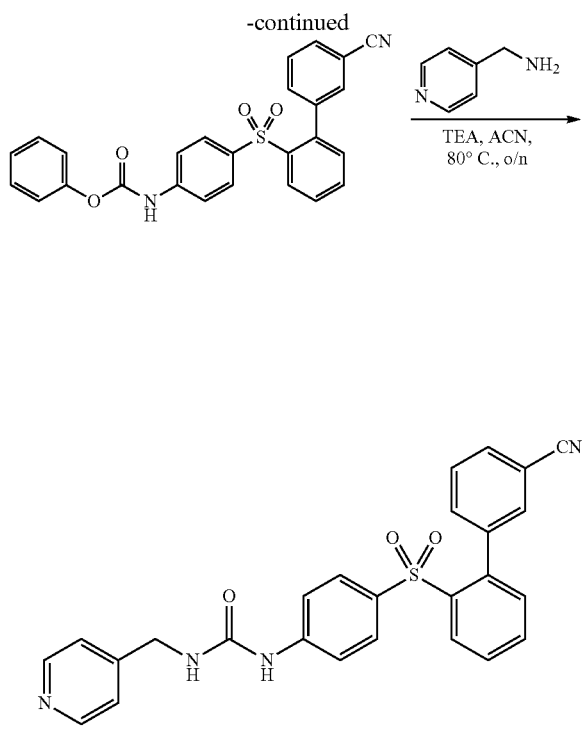

Step 1: To a solution of 1-bromo-2-((4-nitrophenyl)sulfonyl)benzene (400 mg, 1.16 mmol) in dioxane/H₂O. (60 mL) (v/v, 5:1) was added (3-cyanophenyl)boronic acid (204 mg, 1.40 mmol), Pd(dppf)Cl₂ (84 mg, 0.12 mmol) and potassium carbonate (480 mg, 3.48 mmol). After stirred at 80° C. overnight under Ar balloon atmosphere, the reaction was filtrated and the filtrate was concentrated in vacuum to give a crude product which was purified by silica gel column (PE/EA=3/1) to give 2'-((4-nitrophenyl)sulfonyl)-[1,1'-biphenyl]-3-carbonitrile (300 mg, 71%) as a yellow solid. $^1$H NMR (400 MHz, DMSO-d₆): δ=8.39-8.37 (m, 1H), 8.22 (d, J=8.8 Hz, 2H), 7.86-7.81 (m, 3H), 7.52-7.47 (m, 3H), 7.40-7.38 (m, 1H), 7.31-7.29 (m, 1H), 7.22 (s, 1H).

Step 2: To a solution of 2'-((4-nitrophenyl)sulfonyl)-[1,1'-biphenyl]-3-carbonitrile (300 mg, 0.82 mmol) in EtOH/H₂O (60 mL) (v/v, 5:1) was added iron (230 mg, 4.1 mmol) and NH₄Cl (217 mg, 4.1 mmol). The reaction mixture was stirred at 80° C. overnight. The reaction was monitored by LCMS and TLC. After completion, the reaction mixture was filtrated and the cake was washed with EtOH. Then the combined solvent was concentrated in vacuum to give a crude product which was purified by silica gel column (PE/EA=4/1) to give 2'-((4-aminophenyl)sulfonyl)-[1,1'-biphenyl]-3-carbonitrile (250 mg, 91%) as a brown solid. $^1$H NMR (400 MHz, DMSO-d₆): δ=8.17-8.15 (m, 1H), 7.84 (d, J=7.6 Hz, 1H), 7.72-7.68 (m, 2H), 7.54 (t, J=8.0 Hz, 1H), 7.40 (d, J=8.0 Hz, 1H), 7.32 (s, 1H), 7.29-7.27 (m, 1H), 6.85 (d, J=8.8 Hz, 2H), 6.41 (d, J=8.8 Hz, 2H), 6.16 (s, 2H).

Step 3: To a solution of 2'-((4-aminophenyl)sulfonyl)-[1,1'-biphenyl]-3-carbonitrile (250 mg, 0.75 mmol) in DCM (20 mL) was added phenyl chloroformate (312 mg, 2.0 mmol) and TEA (0.5 mL). The mixture was stirred at room temperature overnight. The reaction was monitored by TLC and LCMS. After completion, the mixture was concentrated in vacuum to give a crude product which was purified by a silica gel column (PE/EA=3/1) to afford phenyl (4-((3'-cyano-[1,1'-biphenyl]-2-yl)sulfonyl)phenyl)carbamate (300 mg, 88%) as a white solid. $^1$H NMR (400 MHz, DMSO-d₆):

δ=10.73 (s, 1H), 8.29-8.26 (m, 1H), 7.83-7.81 (m, 1H), 7.78-7.75 (m, 2H), 7.52-7.50 (m, 1H), 7.46-7.43 (m, 1H), 7.39-7.37 (m, 3H), 7.34-7.30 (m, 1H), 7.28-7.22 (m, 2H), 7.19 (s, 2H), 7.17 (s, 3H).

Step 4: To a solution of phenyl (4-((3'-cyano-[1,1'-biphenyl]-2-yl)sulfonyl)phenyl)carbamate (100 mg, 0.22 mmol) in ACN (20 mL) was added Pyridin-4-ylmethanamine (31 mg, 0.25 mmol) and TEA (0.5 mL). Then the mixture was stirred at 80° C. overnight. The reaction was monitored by TLC and LCMS. After completion, the mixture was concentrated in vacuum to give a crude product which was purified by pre-HPLC to afford 1-(4-((3'-cyano-[1,1'-biphenyl]-2-yl)sulfonyl)phenyl)-3-(pyridin-4-ylmethyl)urea (60.5 mg, 59%) as a white solid. $^1$H NMR (400 MHz, DMSO-d₆): δ=9.29 (s, 1H), 8.50 (d, J=6.0 Hz, 2H), 8.25-8.23 (m, 1H), 7.84 (s, 1H), 7.76-7.73 (m, 2H), 7.53 (t, J=8.0 Hz, 1H), 7.42 (d, J=8.8 Hz, 2H), 7.37 (d, J=4.8 Hz, 1H), 7.32 (d, J=2.0 Hz, 3H), 7.29 (d, J=5.2 Hz, 1H), 7.08 (d, J=8.8 Hz, 2H), 6.92 (d, J=5.6 Hz, 2H), 4.33 (d, J=5.6 Hz, 2H). MS: m/z 468.7 (M+H⁺).

Example 529: Synthesis of 1-((1H-Pyrazol-4-yl)methyl)-3-(4-((3'-cyano-[1,1'-biphenyl]-2-yl)sulfonyl)phenyl)urea

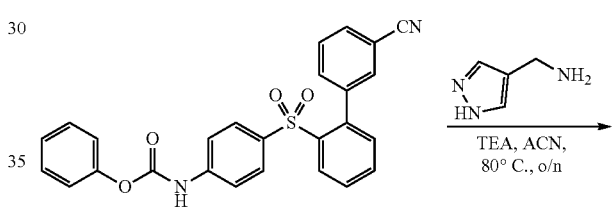

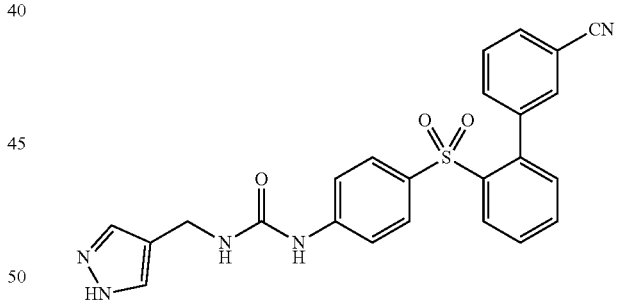

To a solution of (4-((3'-cyano-[1,1'-biphenyl]-2-yl)sulfonyl)phenyl)carbamate (150 mg, 0.33 mmol) in ACN (20 mL) was added (1H-pyrazol-4-yl)methanamine (35 mg, 0.36 mmol) and TEA (0.5 mL). The mixture was stirred at 80° C. overnight. The reaction was monitored by TLC and LCMS. After completion, the mixture was concentrated in vacuum to give a residue which was purified by prep-TLC (DCM/MeOH=10/1) to afford (4-((3'-cyano-[1,1'-biphenyl]-2-yl)sulfonyl)phenyl)carbamate (30.1 mg, 20%) as a white solid. $^1$H NMR (400 MHz, DMSO-d₆) δ=12.66 (s, 1H), 8.98 (s, 1H), 8.23 (d, J=5.6 Hz, 1H), 7.84 (d, J=8.0 Hz, 1H), 7.74 (s, 2H), 7.62-7.50 (m, 2H), 7.41-7.28 (m, 6H), 7.08 (d, J=8.0 Hz, 2H), 6.52 (s, 1H), 4.15 (d, J=5.6 Hz, 2H). MS: m/z 457.8 (M+H⁺).

Example 530: Synthesis of 1-[4-(4'-Cyano-biphenyl-2-sulfonyl)-phenyl]-3-pyridin-4-ylmethyl-urea

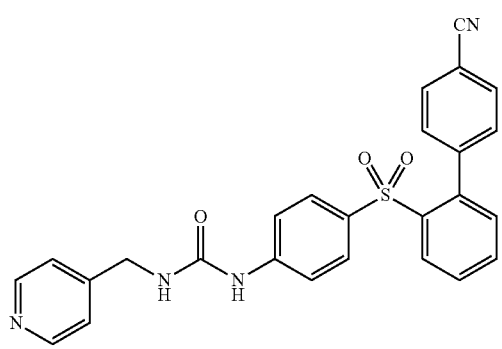

The title compound was prepared using general procedure of 1-(4-([1,1'-biphenyl]-2-ylsulfonyl)phenyl)-3-(pyridin-4-ylmethyl)urea. $^1$H NMR (400 MHz, DMSO-d$_6$): δ=9.36 (s, 1H), 8.54 (d, J=3.6 Hz, 2H), 8.21 (d, J=6.4 Hz, 1H), 7.77-7.71 (m, 4H), 7.42 (d, J=8.4 Hz, 2H), 7.35 (d, J=4.4 Hz, 2H), 7.29 (d, J=6.4 Hz, 1H), 7.20-7.11 (m, 4H), 7.04-6.98 (m, 1H), 4.36 (d, J=6.0 Hz, 2H). MS: m/z 468.8 (M+H$^+$).

Example 531: Synthesis of 1-[4-(4'-Cyano-biphenyl-2-sulfonyl)-phenyl]-3-(1H-pyrazol-4-ylmethyl)-urea

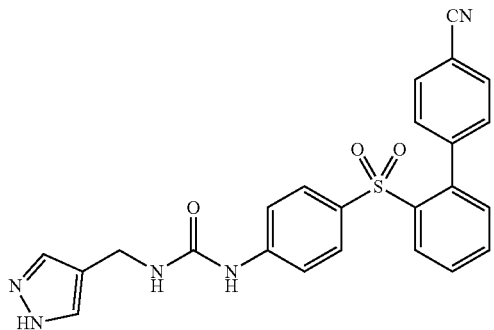 [SMILES: N#Cc1ccc(-c2ccccc2S(=O)(=O)c2ccc(NC(=O)NCc3cn[nH]c3)cc2)cc1]

The title compound was prepared using general procedure of 1-(4-([1,1'-biphenyl]-2-ylsulfonyl)phenyl)-3-(pyridin-4-ylmethyl)urea. $^1$H NMR (400 MHz, DMSO-d$_6$): δ=12.63 (s, 1H), 9.00 (s, 1H), 8.23-8.21 (m, 1H), 7.77-7.72 (m, 4H), 7.53 (br s, 2H), 7.39 (d, J=8.8 Hz, 2H), 7.30-7.28 (m, 1H), 7.18 (d, J=8.8 Hz, 2H), 7.12 (d, J=8.8 Hz, 2H), 6.55 (s, 1H), 4.15 (d, J=5.6 Hz, 2H). MS: m/z 457.8 (M+H$^+$).

Example 532: Synthesis of 1-[4-(2-Pyridin-3-yl-benzenesulfonyl)-phenyl]-3-pyridin-4-ylmethyl-urea

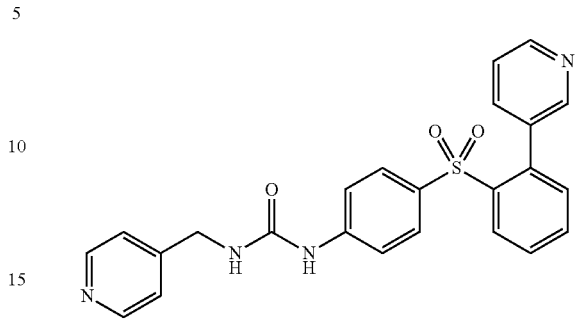

The title compound was prepared using general procedure of 1-(4-([1,1'-biphenyl]-2-ylsulfonyl)phenyl)-3-(pyridin-4-ylmethyl)urea. $^1$H NMR (400 MHz, CD$_3$OD): δ=8.48-8.44 (m, 3H), 8.34 (d, J=6.8 Hz, 1H), 8.06 (s, 1H), 7.68 (s, 2H), 7.50 (d, J=7.6 Hz, 1H), 7.37-7.36 (m, 5H), 7.25 (d, J=6.4 Hz, 1H), 7.08 (d, J=7.6 Hz, 2H), 4.43 (s, 2H). MS: m/z 445.1 (M+H$^+$).

Example 533: Synthesis of 1-{4-[2-(6-Methoxy-pyridin-3-yl)-benzenesulfonyl]-phenyl}-3-pyridin-4-ylmethyl-urea

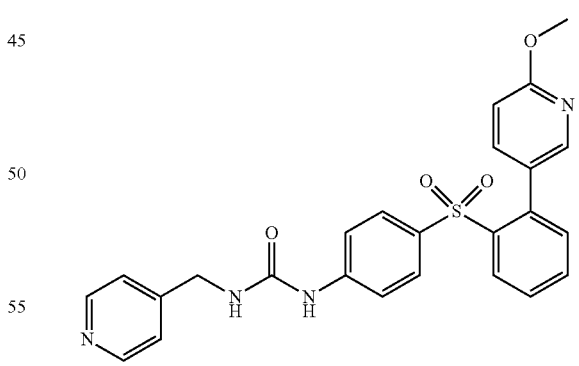

The title compound was prepared using general procedure of 1-(4-([1,1'-biphenyl]-2-ylsulfonyl)phenyl)-3-(pyridin-4-ylmethyl)urea. $^1$H NMR (400 MHz, DMSO-d$_6$): δ=9.20 (s, 1H), 8.50 (dd, J=4.4, 1.6 Hz, 2H), 8.23 (dd, J=7.6, 1.6 Hz, 1H), 7.75-7.68 (m, 2H), 7.62 (d, J=2.0 Hz, 1H), 7.41-7.36 (m, 3H), 7.32-7.27 (m, 3H), 7.09 (d, J=9.2 Hz, 2H), 6.93-6.77 (m, 1H), 6.75 (d, J=0.8 Hz, 1H), 4.32 (d, J=6.0 Hz, 2H), 3.87 (s, 3H). MS: m/z 474.8 (M+H$^+$).

Example 534: Synthesis of 1-{4-[2-(6-Methoxy-pyridin-3-yl)-benzenesulfonyl]-phenyl}-3-(1H-pyrazol-4-ylmethyl)-urea

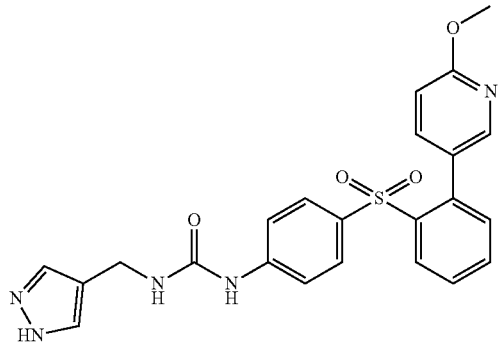 [SMILES: COc1ccc(-c2ccccc2S(=O)(=O)c2ccc(NC(=O)NCc3cn[nH]c3)cc2)cn1]

The title compound was prepared using general procedure of 1-(4-([1,1'-biphenyl]-2-ylsulfonyl)phenyl)-3-(pyridin-4-ylmethyl)urea. $^1$H NMR (400 MHz, DMSO-d$_6$): δ=12.60 (s, 1H), 8.94 (s, 1H), 8.23 (dd, J=7.6, 1.6 Hz, 1H), 7.75-7.67 (m, 2H), 7.63 (d, J=2.0 Hz, 1H), 7.53 (s, 2H), 7.39-7.35 (m, 3H), 7.31-7.29 (m, 1H), 7.08 (d, J=4.8 Hz, 2H), 6.77-6.75 (m, 1H), 6.52 (t, J=5.2 Hz, 1H), 4.14 (d, J=5.2 Hz, 2H), 3.88 (s, 3H). MS: m/z 463.8 (M+H$^+$).

Example 535: Synthesis of 1-(1H-Pyrazol-4-ylmethyl)-3-[4-(2-pyridin-3-yl-benzenesulfonyl)-phenyl]-urea

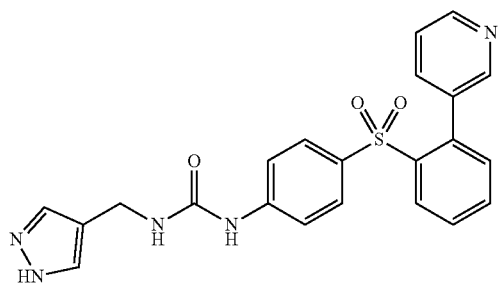 [SMILES: O=C(NCc1cn[nH]c1)Nc1ccc(S(=O)(=O)c2ccccc2-c2cccnc2)cc1]

The title compound was prepared using general procedure of 1-(4-([1,1'-biphenyl]-2-ylsulfonyl)phenyl)-3-(pyridin-4-ylmethyl)urea. $^1$H NMR (400 MHz, CD$_3$OD): δ=8.50-8.49 (m, 1H), 8.38-8.36 (m, 1H), 8.07 (d, J=1.2 Hz, 1H), 7.74-7.71 (m, 2H), 7.58-7.52 (m, 3H), 7.39-7.28 (m, 4H), 7.09 (d, J=9.2 Hz, 2H), 4.28 (s, 2H). MS: m/z 433.8 (M+H)$^+$.

Example 536: Synthesis of 1-[4-(2-Pyridin-4-yl-benzenesulfonyl)-phenyl]-3-pyridin-4-ylmethyl-urea

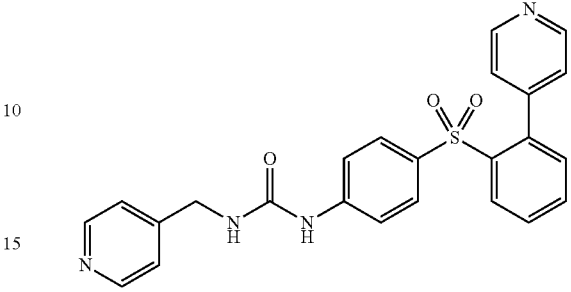

The title compound was prepared using general procedure of 1-(4-([1,1'-biphenyl]-2-ylsulfonyl)phenyl)-3-(pyridin-4-ylmethyl)urea. $^1$H NMR (400 MHz, DMSO-d$_6$): δ=9.76 (s, 1H), 8.84 (d, J=6.4 Hz, 2H), 8.73 (d, J=6.8 Hz, 2H), 8.20-8.18 (m, 1H), 7.90 (d, J=6.8 Hz, 2H), 7.81-7.77 (m, 2H), 7.51-7.46 (m, 5H), 7.38-7.36 (m, 1H), 7.30 (d, J=9.2 Hz, 2H), 4.57 (s, 2H). MS: m/z 445.1 (M+H)$^+$.

Example 537: Synthesis of 1-(1H-Pyrazol-4-ylmethyl)-3-[4-(2-pyridin-4-yl-benzenesulfonyl)-phenyl]-urea

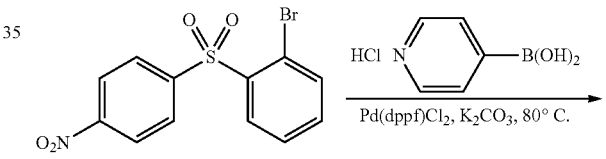

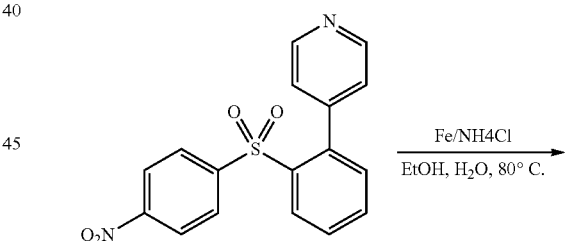

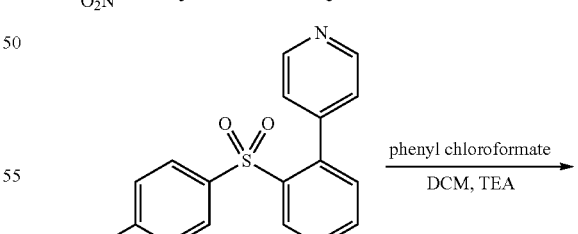

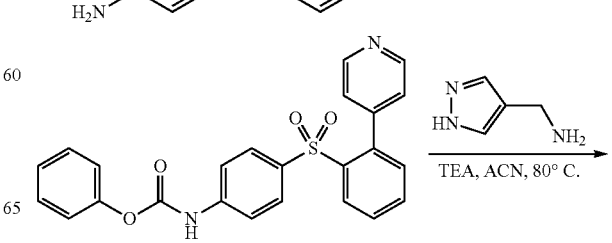

-continued

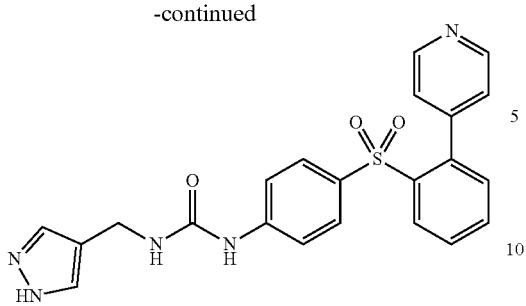

Step 1: To a solution of 4-[(2-bromophenyl)sulfonyl]-1-nitrobenzene (400 mg, 1.17 mmol) in a mixture of dioxane (10 mL) and H$_2$O (1 mL) was added K$_2$CO$_3$ (324 mg, 2.34 mmol), Pd(dppf)Cl$_2$ (103 mg, 0.12 mmol) and pyridine-4-boronic acid (173 mg, 1.4 mmol). Then the mixture was stirred at 80° C. for 6 hrs. This reaction was monitored by LC-MS. The reaction mixture was then diluted with H$_2$O (10 mL) and extracted with EA (10 mL×3). The combined organic layer was dried over anhydrous Na$_2$SO$_4$, filtered and evaporated in vacuum to give the crude product which was used to the next step without further purification.

Step 2: To a solution of 4-[2-(4-nitro-benzenesulfonyl)-phenyl]-pyridine (486 mg, 1.43 mmol) in a mixture of EtOH (10 mL) and H$_2$O (1 mL) was added iron (320 mg, 5.6 mmol) and NH$_4$Cl (306 mg, 5.6 mmol). Then the mixture was stirred at 80° C. overnight. This reaction was monitored by TLC (PE/EA=1/4). The reaction mixture was then diluted with H$_2$O (10 mL) and extracted with EA (10 mL×3). The combined organic layer was dried over anhydrous Na$_2$SO$_4$, and evaporated in vacuum. The residue was purified by silica gel chromatography column (PE/EA=1/4) to give 4-(2-pyridin-4-yl-benzenesulfonyl)-phenylamine (324 mg, 73.1%) as yellow oil. $^1$H NMR (400 MHz, DMSO-d$_6$): δ=8.51-8.50 (m, 2H), 7.96 (s, 2H), 7.06-7.04 (m, 2H), 6.92 (d, J=8.8 Hz, 2H), 6.41 (d, J=8.8 Hz, 2H), 6.15 (s, 2H).

Step 3: To a solution of 4-(2-pyridin-4-yl-benzenesulfonyl)-phenylamine (324 mg, 1.05 mmol) in DCM (10 mL) was added phenyl chloroformate (196.3 mg, 1.26 mmol) and TEA (211.5 mg, 2.1 mmol). Then the mixture was stirred at room temperature overnight. This reaction was monitored by LC-MS. The solvent was removed by vacuo. The residue was purificated by silica gel column chromatography (PE/EA=4/1) to give [4-(2-pyridin-4-yl-benzenesulfonyl)-phenyl]-carbamic acid phenyl ester (364 mg, 81%) as yellow oil which was used to the next step without further purification.

Step 4: To a solution of [4-(2-pyridin-4-yl-benzenesulfonyl)-phenyl]-carbamic acid phenyl ester (100 mg, 0.23 mmol) in ACN (10 mL) was added (1H-pyrazol-3-yl)methanamine (27.1 mg, 0.28 mmol) and TEA (47.1 mg, 0.47 mmol). Then the mixture was stirred at 80° C. for 2 hrs. This reaction was monitored by LCMS. The reaction mixture was then diluted with H$_2$O (10 mL) and extracted with EA (10 mL×3). The combined organic layer was dried over anhydrous Na$_2$SO$_4$, and evaporated in vacuum. The residue was purified by prep-HPLC to give 1-(1H-pyrazol-4-ylmethyl)-3-[4-(2-pyridin-4-yl-benzenesulfonyl)-phenyl]-urea (21.3 mg, 21%) as a yellow solid. $^1$H NMR (400 MHz, DMSO-d$_6$): δ=8.43-8.41 (m, 2H), 8.34-8.32 (m, 1H), 7.72-7.69 (m, 2H), 7.58 (s, 2H), 7.36-7.34 (m, 2H), 7.27-7.25 (m, 1H), 7.18-7.15 (m, 2H), 7.08-7.07 (m, 2H), 4.28 (s, 2H). MS: m/z 433.8 (M+H)$^+$.

Example 538: Synthesis of 1-(4-(Benzo[d]thiazol-2-yl)phenyl)-3-(pyridin-4-ylmethyl)urea

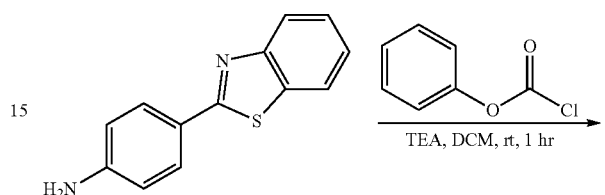

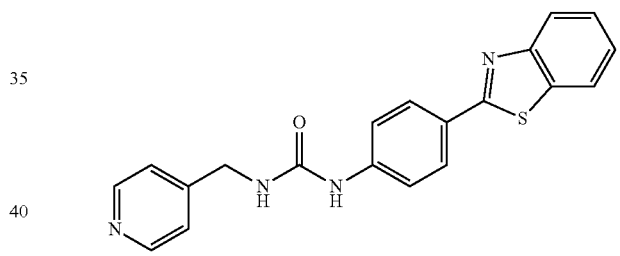

Step 1: To a solution of 4-(benzo[d]thiazol-2-yl)aniline (226 mg, 1.0 mmol) in DCM (20 mL) was added phenyl carbonchloridate (235 mg, 1.50 mmol) and followed by TEA (304 mg, 3.0 mmol). The resulting mixture was stirred at room temperature for 1 hr. Then the mixture was concentrated in vacuum. The residue was purified by silica gel column (PE/EA=10/1 to 3/1) to afford phenyl (4-(benzo[d]thiazol-2-yl)phenyl)carbamate (326 mg, yield 94%) as a white solid.

Step 2: To a solution of phenyl (4-(benzo[d]thiazol-2-yl)phenyl)carbamate (100 mg, 0.29 mmol) in ACN (20 mL) was added c-pyridin-4-yl-methylamine (37 mg, 0.35 mmol) and followed by TEA (88 mg, 0.87 mmol). The resulting mixture was stirred at 80° C. for 2 hrs. Then the mixture was concentrated in vacuum. The residue was purified by a prep-HPLC with NH$_4$HCO$_3$ as additive to afford 1-(4-(benzo[d]thiazol-2-yl)phenyl)-3-(pyridin-4-ylmethyl)urea (52.4 mg, yield 50%) as a white solid. $^1$H NMR (400 MHz, DMSO-d$_6$): δ=9.16 (br s, 1H), 8.52 (d, J=6.0 Hz, 2H), 8.10 (d, J=8.0 Hz, 1H), 8.03-7.94 (m, 3H), 7.62 (d, J=8.8 Hz, 2H), 7.52 (t, J=8.4 Hz, 1H), 7.42 (t, J=8.0 Hz, 1H), 7.31 (d, J=6.0 Hz, 2H), 6.91 (d, J=6.0 Hz, 1H), 4.36 (d, J=6.0 Hz, 2H). MS: m/z 361.0 (M+H$^+$).

Example 539: Synthesis of 1-(4-(Benzo[d]thiazol-2-yl)phenyl)-3-(oxazol-5-ylmethyl)urea

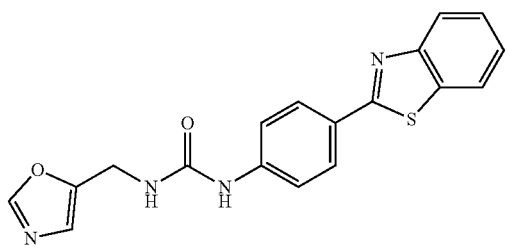 [SMILES: O=C(NCc1cnco1)Nc1ccc(-c2nc3ccccc3s2)cc1]

The title compound was prepared as described in example phenyl (4-(benzo[d]thiazol-2-yl)phenyl)carbamate. $^1$H NMR (400 MHz, DMSO-d$_6$): δ=9.02 (br s, 1H), 8.31 (s, 1H), 8.11 (d, J=7.6 Hz, 1H), 8.04-7.93 (m, 3H), 7.61 (d, J=8.8 Hz, 2H), 7.52 (t, J=7.2 Hz, 1H), 7.42 (t, J=7.2 Hz, 1H), 7.04 (s, 1H), 6.80 (t, J=6.0 Hz, 1H), 4.40 (d, J=5.6 Hz, 2H). MS: m/z 350.9 (M+H$^+$).

Example 540: Synthesis of 1-((1H-Pyrazol-4-yl)methyl)-3-(4-(benzo[d]thiazol-2-yl)phenyl)urea

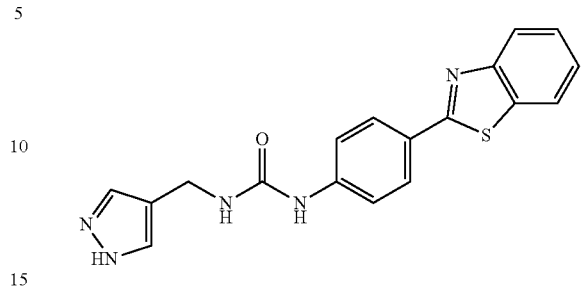

The title compound was prepared as described in example phenyl (4-(benzo[d]thiazol-2-yl)phenyl)carbamate. $^1$H NMR (400 MHz, DMSO-d$_6$): δ=12.67 (br s, 1H), 8.99 (s, 1H), 8.10 (d, J=8.0 Hz, 1H), 8.04-7.90 (m, 3H), 7.74-7.46 (m, 5H), 7.42 (t, J=7.6 Hz, 1H), 6.58 (t, J=4.8 Hz, 1H), 4.18 (d, J=4.4 Hz, 2H). MS: m/z 350.0 (M+H$^+$).

Example 541: Synthesis of 1-(4-(5-Phenylthiazol-2-yl)phenyl)-3-(pyridin-4-ylmethyl)urea

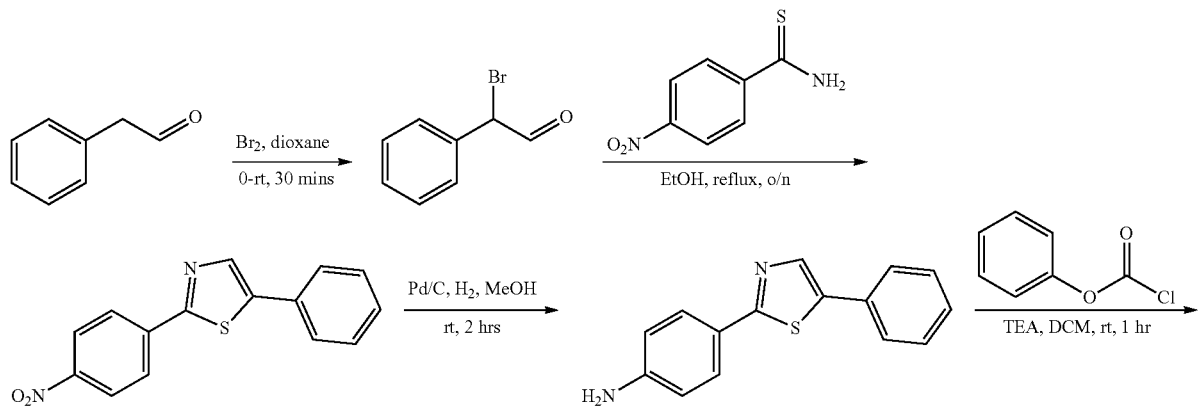

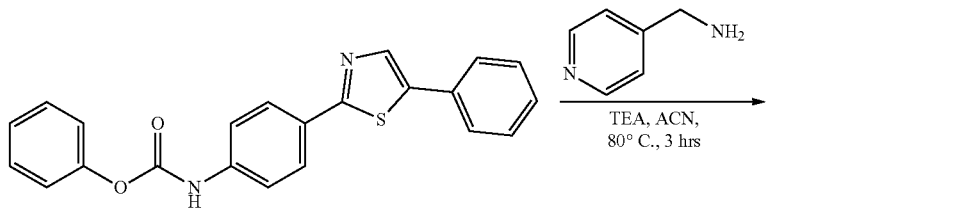

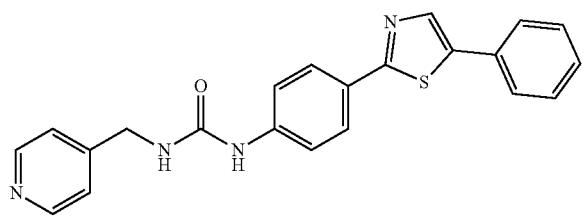

Step 1 to Step 2: To a solution of 2-phenylacetaldehyde (3.6 g, 30.0 mmol) in dioxane (40 mL) was added Br$_2$ (5.27 g, 33.0 mmol) dropwise at 0° C. over 10 min. The resulting mixture was stirred at 0° C. for 10 min and allowed to warm to room temperature for 10 min. The reaction mixture was concentrated in vacuum. The residue was dissolved in EtOH (60 mL) and 4-nitrobenzothioamide (4.35 g, 23.9 mmol) was added. The resulting mixture was stirred at 80° C. overnight. The mixture was concentrated in vacuum. The residue was purified by silica gel column (PE/EA=10/1 to 3/1) to afford 2-(4-nitrophenyl)-5-phenylthiazole (3.76 g, yield 44%) as a yellow solid. $^1$H NMR (400 MHz, DMSO-d$_6$): δ=8.32 (d, J=9.2 Hz, 2H), 8.18-8.19 (m, 3H), 7.63 (d, J=8.4 Hz, 2H), 7.46 (t, J=7.2 Hz, 2H), 7.39 (t, J=7.2 Hz, 1H).

Step 3: To a solution of 2-(4-nitrophenyl)-5-phenylthiazole (3.76 g, 13.32) mmol) in MeOH (60 mL) was added Pd/C (376 mg, 10% wt). The resulting mixture was stirred at room temperature under H$_2$ (50 psi) atmosphere overnight. Then Pd/C was removed by filtration. The filtrate was concentrated in vacuum. The residue was purified by reverse-phase column (ACN in H$_2$O from 10% to 80%, 60 mins) to afford 4-(5-phenylthiazol-2-yl)aniline (762 mg, yield 16%) as a pale-yellow solid. $^1$H NMR (400 MHz, DMSO-d$_6$): δ=8.12 (br s, 1H), 7.65 (t, J=8.0 Hz, 4H), 7.44 (d, J=7.6 Hz, 2H), 7.33 (d, J=7.6 Hz, 1H), 6.64 (t, J=8.4 Hz, 2H), 5.72 (br s, 2H).

Step 4: To a solution of 4-(5-phenylthiazol-2-yl)aniline (300 mg, 1.19 mmol) in dry DCM (30 mL) was added phenyl carbonochloridate (410 mg, 2.62 mmol) and followed by TEA (361 mg, 3.57 mmol). The resulting mixture was stirred at room temperature for 1 hour. Then the mixture was concentrated in vacuum. The residue was purified by silica gel column (PE/EA=100/1 to 10/1) to afford phenyl (4-(5-phenylthiazol-2-yl)phenyl)carbamate (445 mg, yield 76%) as a white solid.

Step 5:
To a solution of phenyl (4-(5-phenylthiazol-2-yl)phenyl) carbamate (120 mg, 0.24 mmol) in ACN (20 mL) was added pyridin-4-ylmethanamine (53 mg, 0.48 mmol) and followed by TEA (74 mg, 0.72 mmol). The resulting mixture was stirred at 80° C. overnight. Then the mixture was concentrated in vacuum. The residue was purified by prep-HPLC with NH$_4$OH as additive to afford 1-(4-(5-phenylthiazol-2-yl)phenyl)-3-(pyridin-4-ylmethyl)urea (38.7 mg, yield 41%) as a white solid. $^1$H NMR (400 MHz, DMSO-d$_6$): δ=9.05 (br s, 1H), 8.51 (d, J=6.0 Hz, 2H), 8.24 (s, 1H), 7.85 (d, J=8.8 Hz, 2H), 7.70 (d, J=7.6 Hz, 2H), 7.57 (d, J=8.8 Hz, 2H), 7.46 (t, J=7.2 Hz, 2H), 7.37 (t, J=7.6 Hz, 1H), 7.31 (d, J=5.6 Hz, 2H), 6.86 (t, J=6.0 Hz, 1H), 4.35 (d, J=6.0 Hz, 2H). MS: m/z 387.0 (M+H$^+$).

Example 542: Synthesis of 1-(Oxazol-5-ylmethyl)-3-(4-(5-phenylthiazol-2-yl)phenyl)urea

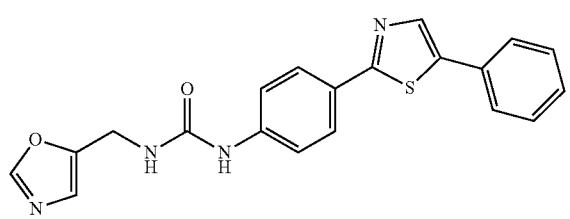 [SMILES: O=C(NCc1cnco1)Nc1ccc(-c2ncc(-c3ccccc3)s2)cc1]

The title compound was prepared as described in example 1-(4-(5-phenylthiazol-2-yl)phenyl)-3-(pyridin-4-ylmethyl) urea. $^1$H NMR (400 MHz, DMSO-d$_6$): δ=8.96 (br s, 1H), 8.29 (s, 1H), 8.24 (s, 1H), 7.85 (d, J=8.8 Hz, 2H), 7.70 (d, J=7.6 Hz, 2H), 7.55 (d, J=8.8 Hz, 2H), 7.46 (t, J=7.6 Hz, 2H), 7.37 (t, J=7.6 Hz, 1H), 7.03 (s, 1H), 6.77 (t, J=5.6 Hz, 1H), 4.39 (d, J=5.2 Hz, 2H). MS: m/z 377.1 (M+H$^+$).

Example 543: Synthesis of 1-((1H-Pyrazol-4-yl)methyl)-3-(4-(5-phenylthiazol-2-yl)phenyl)urea

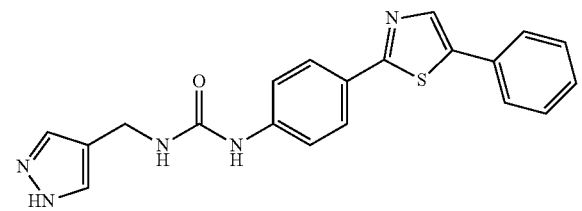 [SMILES: O=C(NCc1cn[nH]c1)Nc1ccc(-c2ncc(-c3ccccc3)s2)cc1]

The title compound was prepared as described in example 1-(4-(5-phenylthiazol-2-yl)phenyl)-3-(pyridin-4-ylmethyl) urea. $^1$H NMR (400 MHz, DMSO-d$_6$): δ=12.58 (br s, 1H), 8.77 (s, 1H), 8.24 (s, 1H), 7.84 (d, J=8.4 Hz, 2H), 7.70 (d, J=6.8 Hz, 2H), 7.63-7.51 (m, 4H), 7.46 (t, J=7.2 Hz, 2H), 7.36 (t, J=7.6 Hz, 1H), 6.46 (t, J=5.6 Hz, 1H), 4.17 (d, J=5.2 Hz, 2H). MS: m/z 376.1 (M+H$^+$).

Example 544: Synthesis of 1-(4-(5-Benzylthiazol-2-yl)phenyl)-3-(pyridin-4-ylmethyl)urea

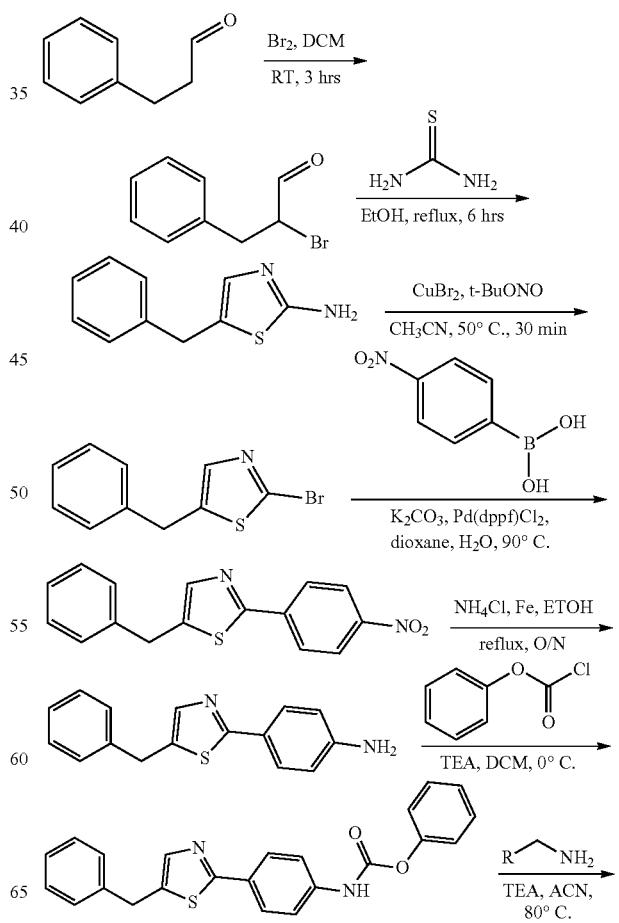

-continued

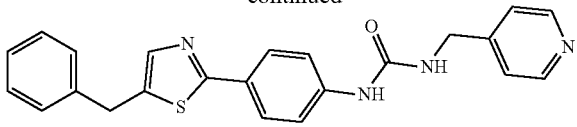

Step 1: To a solution of 3-phenylpropanal (500 mg, 3.7 mmol) in DCM (50 mL) was added Br$_2$ (566 mg, 3.5 mmol) at 0° C. The reaction mixture was stirred at room temperature for 3 hrs. To the reaction mixture was added sat..NaHCO$_3$ solution (10 mL) with stirring. The organic layer was washed with brine (15 mL), dried over Na$_2$SO$_4$, filtered and concentrated. The residue was purified by silica gel column (PE/EA=10/1) to give 2-bromo-3-phenylpropanal (crude 1.1 g, yield quantitative) as yellow oil.

Step 2: To a solution of 2-bromo-3-phenylpropanal (1.1 g, 3.7 mmol) in EtOH (100 mL) was added thiourea (340 mg, 4.4 mmol). The reaction was stirred at 80° C. for 6 hrs. The reaction mixture was cooled to room temperature and poured into sat.NaHCO$_3$ solution (15 mL). The aqueous phase was extracted with EA (20 mL). The organic layer was washed with brine (15 mL), dried over Na$_2$SO$_4$, filtered and concentrated. The residue was purified by silica gel column (PE/EA=1/1) to give 5-benzylthiazol-2-amine (350 mg, yield 50%) as a yellow solid.

Step 3: To a solution of 5-benzylthiazol-2-amine (350 mg, 1.84 mmol) in ACN (30 mL) was added CuBr$_2$ (821 mg, 3.68 mmol) and BuONO (431 mg, 3.68 mmol). The reaction was stirred at 50° C. for 0.5 hrs. The reaction mixture was cooled to room temperature and poured into H$_2$O (15 mL). The aqueous phase was extracted with EA (30 mL). The organic layer was washed with brine (20 mL), dried over Na$_2$SO$_4$, filtered and concentrated. The residue was purified by silica gel column (PE/EA=4/1) to give 5-benzyl-2-bromothiazole (300 mg, yield 64%) as yellow oil.

Step 4: To a solution of 5-benzyl-2-bromothiazole (300 mg, 1.19 mmol) and (4-nitrophenyl)boronic acid (400 mg, 2.37 mmol) in dioxane/H$_2$O (4/1, 25 mL) was added Pd(dppf)Cl$_2$ (175 mg, 0.24 mmol) and K$_2$CO$_3$ (500 mg, 3.6 mmol). The reaction was stirred at 90° C. overnight. The reaction mixture was cooled to room temperature and poured into H$_2$O (10 mL). The aqueous phase was extracted with EA (20 mL). The organic layer was washed with brine (20 mL), dried over Na$_2$SO$_4$, filtered and concentrated. The residue was purified by silica gel column (PE/EA=5/1) to give 5-benzyl-2-(4-nitrophenyl)thiazole (250 mg, yield 71%) as a yellow solid.

Step 5: To a solution of 5-benzyl-2-(4-nitrophenyl)thiazole (250 mg, 0.84 mmol) in EtOH/H$_2$O (4/1, 25 mL) was added NH$_4$Cl (445 mg, 8.4 mmol) and Fe (330 mg, 6 mmol). The reaction was stirred at 90° C. overnight. The reaction mixture was cooled to room temperature and poured into H$_2$O (20 mL). The aqueous phase was extracted with EA (25 mL). The organic layer was washed with brine (20 mL), dried over Na$_2$SO$_4$, filtered and concentrated. The residue was purified by silica gel column (PE/EA=2/1) to give 4-(5-benzylthiazol-2-yl)aniline (100 mg, yield 49%) as yellow oil.

Step 6: To a solution of 4-(5-benzylthiazol-2-yl)aniline (100 mg, 0.38 mmol) and phenyl carbonochloridate (70 mg, 0.45 mmol) in DCM was added TEA (120 mg, 1.14 mmol). The reaction was stirred at 0° C. for 1 hr. The organic layer was washed with brine (20 mL), dried over Na$_2$SO$_4$, filtered and concentrated. The residue was purified by silica gel column (PE/EA=2/1) to give phenyl (4-(5-benzylthiazol-2-yl)phenyl)carbamate (80 mg, yield 53%) as a white solid.

Step 7: To a solution of phenyl (4-(5-benzylthiazol-2-yl)phenyl)carbamate (40 mg, 0.1 mmol) and pyridin-4-ylmethanamine (14 mg, 0.12 mmol) in ACN was added TEA (31 mg, 0.3 mmol). The reaction was stirred at 80° C. for 3 hrs. The reaction mixture was cooled to room temperature and poured into H$_2$O (20 mL). The aqueous phase was extracted with EA (20 mL). The organic layer was washed with brine (20 mL), dried over Na$_2$SO$_4$, filtered and concentrated. The residue was purified by prep-HPLC (NH$_4$HCO$_3$) to give 1-(4-(5-benzylthiazol-2-yl)phenyl)-3-(pyridin-4-ylmethyl)urea (18.6 mg, yield 50%) as a white solid. $^1$H NMR (400 MHz, CDCl$_3$+CD$_3$OD): δ 8.50 (d, J=6.0 Hz, 2H), 7.77 (d, J=8.4 Hz, 2H), 7.71 (s, 1H), 7.51 (d, J=8.8 Hz, 3H), 7.41 (d, J=5.6 Hz, 2H), 7.36-7.24 (m, 5H), 4.49 (s, 2H), 4.20 (s, 2H). MS: m/z 401.0 (M+H$^+$).

Example 545: Synthesis of 1-(4-(5-Benzylthiazol-2-yl)phenyl)-3-(oxazol-5-ylmethyl)urea

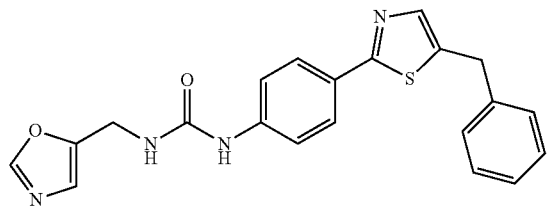 [SMILES: O=C(NCc1cnco1)Nc1ccc(-c2ncc(Cc3ccccc3)s2)cc1]

The title compound was prepared using general procedure of 1-(4-(5-benzylthiazol-2-yl)phenyl)-3-(pyridin-4-ylmethyl)urea. $^1$H NMR (400 MHz, CDCl$_3$+CD$_3$OD): δ=7.97 (s, 1H), 7.78 (d, J=8.8 Hz, 2H), 7.50 (dd, J=6.4 Hz, 4H), 7.39-7.28 (m, 5H), 7.04 (s, 1H), 4.58 (s, 3H), 4.21 (s, 2H). MS: m/z 391.0 (M+H$^+$).

Example 546: Synthesis of 1-((1H-Pyrazol-4-yl)methyl)-3-(4-(5-benzylthiazol-2-yl)phenyl)urea

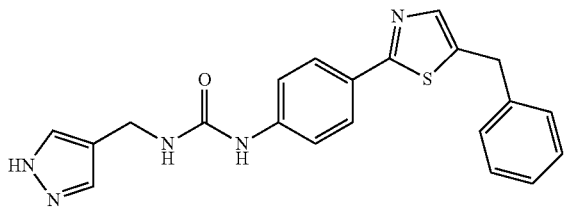 [SMILES: O=C(NCc1cn[nH]c1)Nc1ccc(-c2ncc(Cc3ccccc3)s2)cc1]

The title compound was prepared using general procedure of 1-(4-(5-benzylthiazol-2-yl)phenyl)-3-(pyridin-4-ylmethyl)urea. $^1$H NMR (400 MHz, DMSO-d$_6$): δ=12.66 (s, 1H), 8.70 (s, 1H), 7.72 (d, J=8.8 Hz, 2H), 7.62 (s, 2H), 7.48 (d, J=8.8 Hz, 3H), 7.35-7.23 (m, 5H), 6.44 (t, J=5.6 Hz, 1H), 4.19 (s, 2H), 4.16 (d, J=5.2 Hz, 2H). MS: m/z 390.0 (M+H$^+$).

Example 547: Synthesis of 1-(4-Benzothiazol-4-yl-phenyl)-3-pyridin-4-ylmethyl-urea

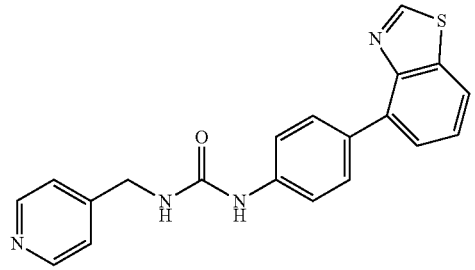 [SMILES: O=C(NCc1ccncc1)Nc1ccc(-c2cccc3scnc23)cc1]

The title compound was prepared using general procedure of 1-(4-benzothiazol-4-yl-phenyl)-3-oxazol-5-ylmethyl-urea. $^1$H NMR (400 MHz, DMSO-$d_6$): δ=9.41 (s, 1H), 8.87 (s, 1H), 8.52-8.51 (m, 2H), 8.13-8.10 (m, 1H), 7.78 (d, J=8.4 Hz, 2H), 7.63-7.61 (m, 1H), 7.56-7.52 (m, 3H), 7.31 (d, J=6.0 Hz, 2H), 6.80 (t, J=6.0 Hz, 1H), 4.36 (d, J=5.6 Hz, 2H). MS: m/z 361.0 (M+H$^+$).

Example 548: Synthesis of 1-(4-Benzothiazol-4-yl-phenyl)-3-(1H-pyrazol-4-ylmethyl)-urea

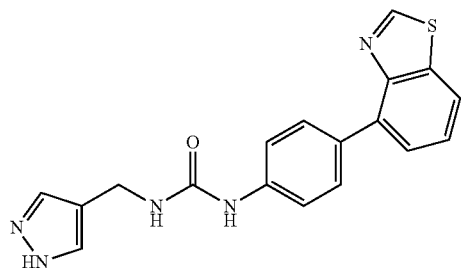 [SMILES: O=C(NCc1cn[nH]c1)Nc1ccc(-c2cccc3scnc23)cc1]

The title compound was prepared using general procedure of 1-(4-benzothiazol-4-yl-phenyl)-3-oxazol-5-ylmethyl-urea. $^1$H NMR (400 MHz, DMSO-$d_6$): δ=12.60 (s, 1H), 9.41 (s, 1H), 8.58 (s, 1H), 8.12-8.11 (m, 1H), 7.78-7.76 (m, 2H), 7.62-7.51 (m, 6H), 6.38 (s, 1H), 4.17 (s, 2H). MS: m/z 350.1 (M+H$^+$).

Example 549: Synthesis of 1-(4-Benzothiazol-4-yl-phenyl)-3-oxazol-5-ylmethyl-urea

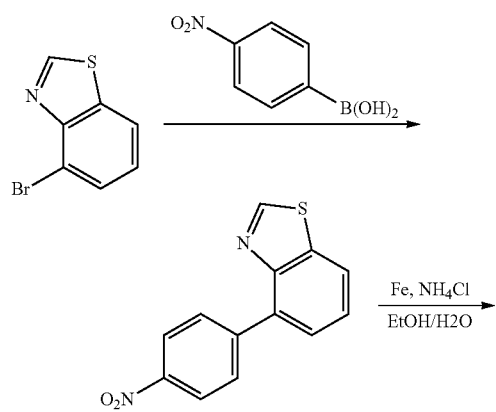

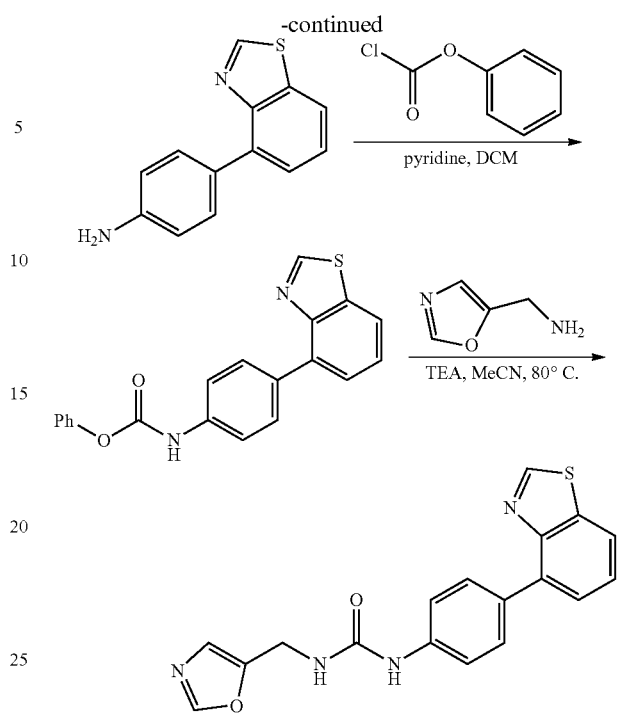

Step 1: To a mixture of 4-bromo-benzothiazole (500 mg, 2.3 mmol), 4-nitrophenylboronic acid (576 mg, 3.45 mmol) and $K_2CO_3$ (952.2 mg, 6.9 mmol) in dioxane/$H_2O$ (20 mL/10 mL) was added Pd(PPh$_3$)$_4$ (132 mg, 0.115 mmol). The mixture was stirred at 95° C. under $N_2$ overnight. The mixture was concentrated. The residue was purified with flash to give 4-(4-nitro-phenyl)-benzothiazole (288 mg, yield 49%) as a yellow solid. $^1$H NMR (300 MHz, DMSO-$d_6$) δ=9.51 (s, 1H), 8.38-8.30 (m, 3H), 8.17 (d, J=8.7 Hz, 2H), 7.79 (d, J=7.5 Hz, 1H), 7.651 (t, J=7.5 Hz, 1H). MS: m/z 257.0 (M+H$^+$).

Step 2: To a mixture of 4-(4-nitro-phenyl)-benzothiazole (288 mg, 1.125 mmol), Fe (75.6 mg, 1.35 mmol) and $NH_4Cl$ (135 mg, 2.25 mol) in EtOH/$H_2O$ (10 mL/4 mL) was stirred at 80° C. for 1 hr. The reaction was completed detected by LC-MS. The mixture was filtered and extracted with EA. The organic layer was concentrated to give the crude 4-benzothiazol-4-yl-phenylamine (151 mg, yield 59%) as a white solid. MS: m/z 227.0 (M+H$^+$).

Step 3: To a mixture of 4-benzothiazol-4-yl-phenylamine (131 mg, 0.58 mmol) and pyridine (92.8 mg, 0.16 mmol) in DCM (5 mL) was added phenyl chloroformate (108 mg, 0.696 mmol) at 0° C. dropwise. The reaction mixture was allowed to warm to room temperature for 1 hr. The reaction was completed detected by LC-MS. The organic layer was washed with brine (5 mL), dried over $Na_2SO_4$, filtered and concentrated to the crude give (4-benzothiazol-4-yl-phenyl)-carbamic acid phenyl ester (150 mg, yield 75%) as a yellow solid. MS: m/z 347.0 (M+H$^+$).

Step 4: To a mixture of (4-benzothiazol-4-yl-phenyl)-carbamic acid phenyl ester (51 mg, 0.15 mmol) and c-oxazol-5-yl-methylamine (25 mg, 0.19 mmol) in ACN (5 mL) was added TEA (30.3 mg, 0.3 mmol). The mixture was stirred at 80° C. for 4 hrs. The reaction was completed detected by LC-MS. The mixture was washed with $H_2O$, filtered and purified by Prep-HPLC to give 1-(4-benzothiazol-4-yl-phenyl)-3-oxazol-5-ylmethyl-urea (21.7 mg, yield 41%) as a white solid. $^1$H NMR (400 MHz, DMSO-$d_6$):

δ=9.40 (s, 1H), 8.73 (s, 1H), 8.29 (s, 1H), 8.12-8.09 (m, 1H), 7.77 (d, J=8.8 Hz, 2H), 7.61-7.60 (m, 1H), 7.55-7.50 (m, 3H), 7.02 (s, 1H), 6.68 (t, J=5.6 Hz, 1H), 4.39 (d, J=6.0 Hz, 2H). MS: m/z 351.1 (M+H$^+$).

Example 550: Synthesis of 1-[4-(1H-Benzoimidazol-4-yl)-phenyl]-3-pyridin-4-ylmethyl-urea

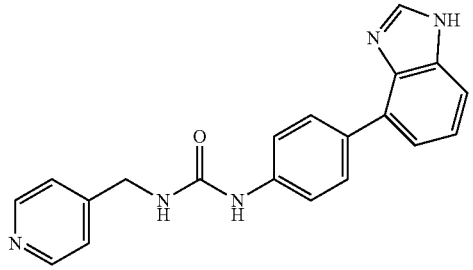 [SMILES: O=C(NCc1ccncc1)Nc1ccc(-c2cccc3[nH]cnc23)cc1]

The title compound was prepared using general procedure of 1-[4-(1H-benzoimidazol-4-yl)-phenyl]-3-oxazol-5-ylmethyl-urea. $^1$H NMR (400 MHz, DMSO-d$_6$): δ=12.5 (s, 1H), 8.85-8.84 (m, 1H), 8.52 (d, J=5.6 Hz, 2H), 8.244 (s, 1H), 8.05 (d, J=5.6 Hz, 1H), 7.57-7.36 (m, 5H), 7.32 (d, J=5.2 Hz, 2H), 7.26 (t, J=6.8 Hz, 1H), 6.82-6.81 (m, 1H), 4.36 (d, J=5.6 Hz, 1H). MS: m/z 344.1 (M+H$^+$).

Example 551: Synthesis of 1-[4-(1H-Benzoimidazol-4-yl)-phenyl]-3-(1H-pyrazol-4-ylmethyl)-urea

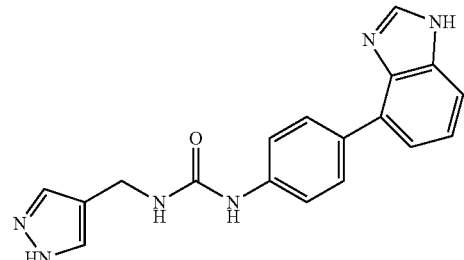

The title compound was prepared using general procedure of 1-[4-(h-benzoimidazol-4-yl)-phenyl]-3-oxazol-5-ylmethyl-urea. $^1$H NMR (400 MHz, DMSO-d$_6$): δ=12.62 (s, 2H), 8.56 (s, 1H), 8.25 (s, 1H), 7.88 (s, 2H), 7.56-7.50 (m, 5H), 7.33 (d, J=7.2 Hz, 1H), 7.26 (t, J=7.6 Hz, 1H), 6.37 (t, J=5.6 Hz, 1H), 4.18 (d, J=5.2 Hz, 2H). MS: m/z 333.1 (M+H$^+$).

Example 552: Synthesis of 1-[4-(1H-Benzoimidazol-4-yl)-phenyl]-3-oxazol-5-ylmethyl-urea

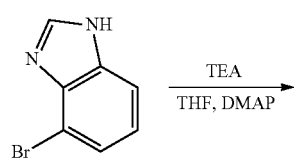

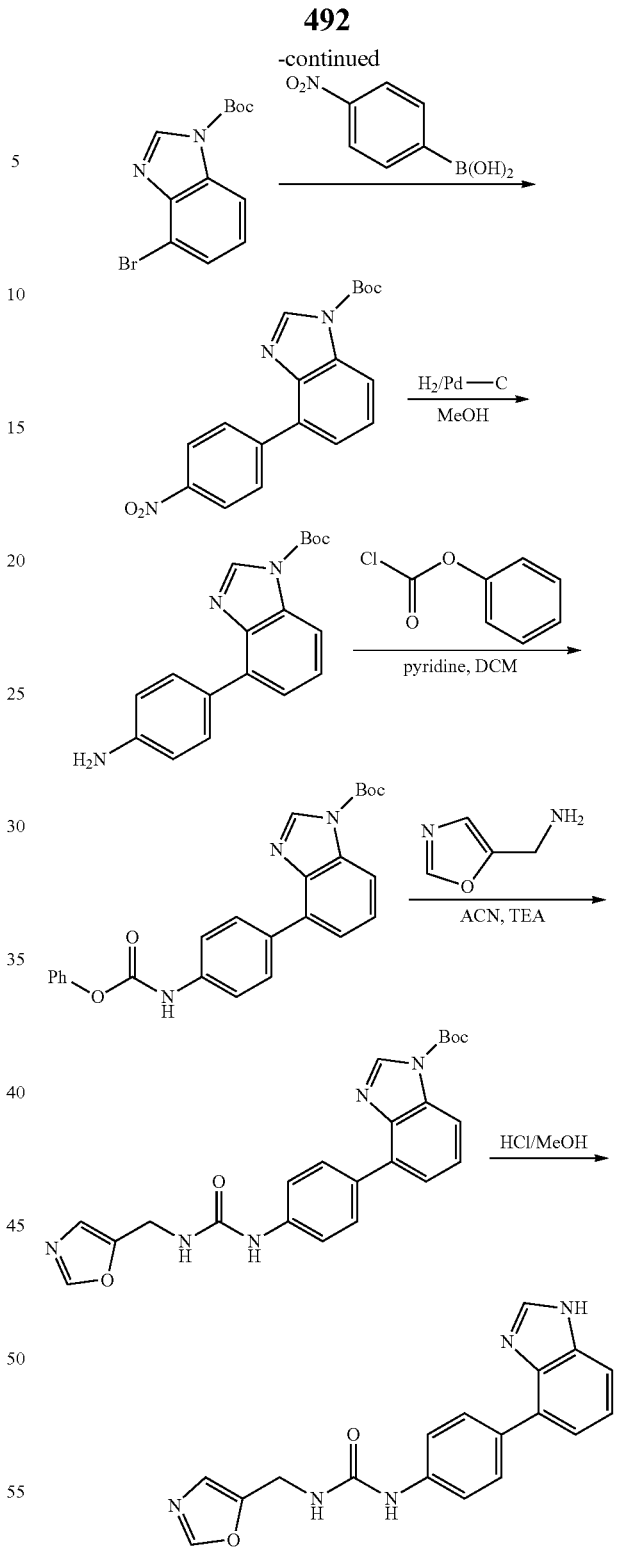

Step 1: To a mixture of 4-bromo-1H-benzoimidazole (500 mg, 2.5 mmol) and TEA (757.5 mg, 7.5 mmol) in THF (10 mL) was added Boc$_2$O (834 mg, 3.8 mmol) and DMAP (151 mg, 1.25 mmol). The mixture was stirred at room temperature overnight. The mixture was concentrated and purified by silia gel chromatography (PE/EA=5/1) to give 4-bromo-benzoimidazole-1-carboxylic acid tert-butyl ester (700 mg, yield 95%) as yellow liquid. $^1$H NMR (300 MHz, CDCl$_3$):

δ=8.48 (s, 1H), 7.97 (d, J=8.1 Hz, 1H), 7.56 (d, J=7.8 Hz, 1H), 7.30-7.25 (m, 1H), 1.26 (t, J=7.2 Hz, 9H). MS: m/z 296.0 (M+H⁺).

Step 2: To a mixture of 4-bromo-benzoimidazole-1-carboxylic acid tert-butyl ester (625 mg, 2.1 mmol), 4-nitrophenylboronic acid (423 mg, 2.5 mmol) and K₂CO₃ (869 mg, 6.3 mmol) in dioxane/H₂O (20 mL/10 mL), was added Pd(PPh₃)₄ (111.5 mg, 0.21 mmol). The mixture was stirred at 95° C. under N₂ overnight. The mixture was concentrated and purified by flash to give 4-(4-nitro-phenyl)-benzoimidazole-1-carboxylic acid tert-butyl ester (383 mg, yield 44%) as a yellow solid. MS: m/z 240.0 (M−100+H1).

Step 3: To a mixture of 4-(4-nitro-phenyl)-benzoimidazole-1-carboxylic acid tert-butyl ester (333 mg, 1.12 mmol) in MeOH/THF (5 mL/1 mL) was added Pd/C (33 mg, wet 10%). The reaction mixture was stirred at room temperature under H₂ (1 atm) overnight. Pd/C was filtered and the filtrate was concentrated in vacuum to give the crude 4-(4-amino-phenyl)-benzoimidazole-1-carboxylic acid tert-butyl ester (300 mg, yield 86%) as a yellow solid. MS: m/z 310.0 (M+H⁺).

Step 4: To a mixture of 4-(4-amino-phenyl)-benzoimidazole-1-carboxylic acid tert-butyl ester (300 mg, 0.96 mmol) and pyridine (153 mg, 1.92 mmol) in DCM (5 mL) was added phenyl chloroformate (165 mg, 1.06 mmol) at 0° C. dropwise. The reaction mixture was allowed to warm to room temperature for 2 hrs. The reaction was completed detected by LC-MS. The organic layer was washed with brine (5 mL), dried over Na₂SO₄ filtered and concentrated to give the crude 4-(4-phenoxycarbonylamino-phenyl)-benzoimidazole-1-carboxylic acid tert-butyl ester (160 mg, yield 39%) as a yellow solid. MS: m/z 330.0 (M−100+H1).

Step 5: To a mixture of 4-(4-phenoxycarbonylamino-phenyl)-benzoimidazole-1-carboxylic acid tert-butyl ester (40 mg, 0.093 mmol) and C-Oxazol-5-yl-methylamine (15 mg, 0.011 mmol) in ACN (5 mL) was added TEA (28.1 mg, 0.27 mmol). The mixture was stirred at room temperature overnight. The reaction was completed detected by LC-MS. The mixture was washed with H₂O and filtered to give the crude 4-[4-(3-Oxazol-5-ylmethyl-ureido)-phenyl]-benzoimidazole-1-carboxylic acid tert-butyl ester (30 mg, yield 49%) as a brown solid. MS: m/z 334.0 (M−100+H⁺).

Step 6: A mixture of 4-[4-(3-oxazol-5-ylmethyl-ureido)-phenyl]-benzoimidazole-1-carboxylic acid tert-butyl ester (30 mg, 69 mmol) in MeOH/HCl (2 mL) was stirred at room temperature overnight. The reaction was completed detected by LC-MS. The mixture was purified with prep-HPLC to give 1-[4-(1H-benzoimidazol-4-yl)-phenyl]-3-oxazol-5-yl-methyl-urea (3 mg, yield 13%) as a white solid. ¹H NMR (400 MHz, DMSO-d₆): δ=12.53 (s, 1H), 8.69 (s, 1H), 8.3 (s, 1H), 8.24 (s, 1H), 8.05 (d, J=7.6 Hz, 1H), 7.55-7.45 (m, 4H), 7.37 (d, J=7.2 Hz, 1H), 7.25 (t, J=7.6 Hz, 1H), 7.03 (s, 1H), 6.66 (s, 1H), 4.40 (d, J=5.6 Hz, 2H). MS: m/z 334.1 (M+H⁺).

Example 553: Synthesis of 1-(4-((4-Phenylthiazol-2-yl)amino)phenyl)-3-(pyridin-4-ylmethyl)urea

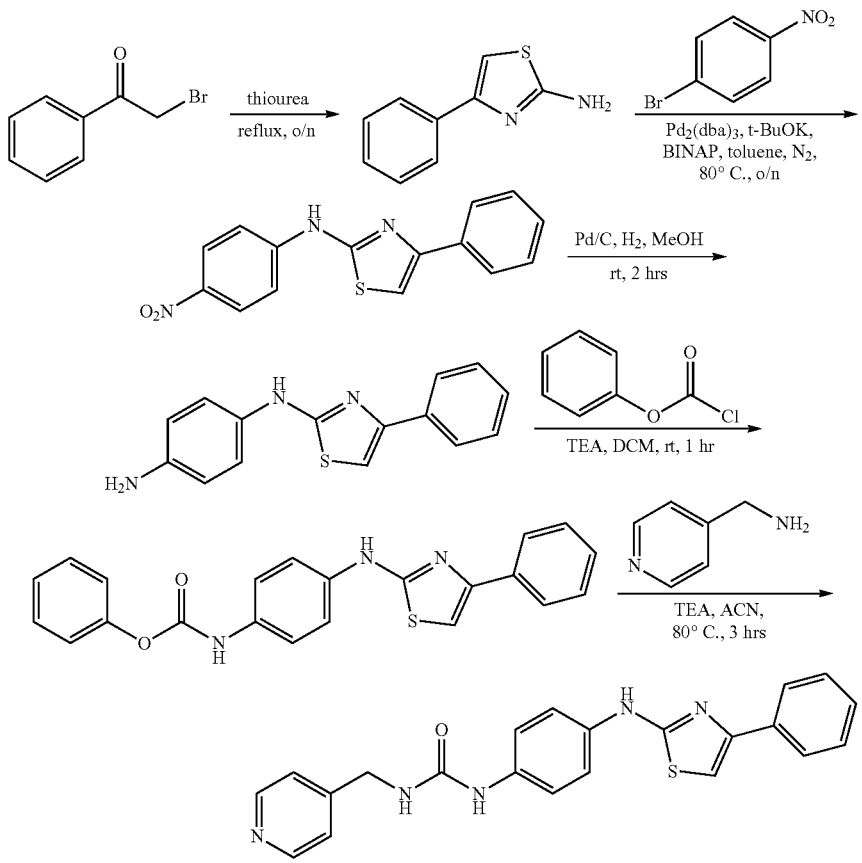

Step 1: To a solution of 2-bromo-1-phenylethanone (1.99 g, 10.0 mmol) in EtOH (40 mL) was added thiourea (0.84 g, 11.0 mmol). The resulting mixture was stirred at 80° C. overnight.

Then the mixture was concentrated in vacuum. The residue was purified by silica gel column (DCM/MeOH=60/1) to afford 4-phenylthiazol-2-amine (1.56 g, yield 89%) as a white solid. $^1$H NMR (400 MHz, DMSO-d$_6$): δ=8.27 (br s, 2H), 7.75 (d, J=7.2 Hz, 2H), 7.50-7.42 (m, 2H), 7.41-7.35 (m, 1H), 7.17 (s, 1H).

Step 2: To a solution of 4-phenylthiazol-2-amine (1.38 g, 7.83 mmol) and 1-bromo-4-nitrobenzene (1.90 g, 9.40 mmol) in toluene (40 mL) was added Pd$_2$(dba)$_3$ (358 mg, 0.39 mmol), BINAP (244 mg, 0.39 mmol) and t-BuOK (1.76 g, 15.6 mmol). The resulting mixture was stirred at 80° C. under N$_2$ atmosphere overnight. Then the mixture was filtered and concentrated in vacuum. The residue was purified by silica gel column (PE/EA=100/1 to 30/1) to afford N-(4-nitrophenyl)-4-phenylthiazol-2-amine (1.08 g, yield 46%) as a yellow solid. $^1$H NMR (400 MHz, DMSO-d$_6$): δ=11.09 (br s, 1H), 8.28 (d, J=9.2 Hz, 2H), 8.02-7.89 (m, 4H), 7.56 (s, 1H), 7.46 (t, J=7.6 Hz, 2H), 7.35 (t, J=7.2 Hz, 1H).

Step 3: To a solution of N-(4-nitrophenyl)-4-phenylthiazol-2-amine (1.08 g, 3.63 mmol) in MeOH (30 mL) was added Pd/C (216 mg, 20% wt). The resulting mixture was stirred at room temperature under H$_2$ atmosphere for 2 hours. Then Pd/C was filtered and the filtrate was concentrated in vacuum. The residue was purified by reverse-phase column (ACN in H$_2$O, 5-95%, 40 mins) to afford N$^1$-(4-phenylthiazol-2-yl)benzene-1,4-diamine (680 mg, yield 70%) as a white solid. $^1$H NMR (400 MHz, DMSO-d$_6$): δ=9.68 (br s, 1H), 7.87 (d, J=7.2 Hz, 2H), 7.40 (d, J=8.0 Hz, 2H), 7.33-7.23 (m, 3H), 7.15 (s, 1H), 6.57 (d, J=8.8 Hz, 2H), 4.85 (br s, 2H).

Step 4: To a solution of N$^1$-(4-phenylthiazol-2-yl)benzene-1,4-diamine (680 mg, 2.54 mmol) in dry DCM (20 mL) was added phenyl carbonochloridate (478 mg, 3.05 mmol) and followed by TEA (771 mg, 7.62 mmol). The resulting mixture was stirred at room temperature for 1 hour. Then the mixture was concentrated in vacuum. The residue was purified by silica gel column (PE/EA=10/1 to 4/1) to afford phenyl (4-((4-phenylthiazol-2-yl)amino)phenyl)carbamate (476 mg, yield 48%) as a white solid.

Step 5: To a solution of phenyl (4-((4-phenylthiazol-2-yl)amino)phenyl)carbamate (120 mg, 0.31 mmol) in ACN (20 mL) was added pyridin-4-ylmethanamine (40.4 mg, 0.37 mmol) and followed by TEA (94.0 mg, 0.93 mmol). The resulting mixture was stirred at 80° C. for 3 hours. Then the mixture was concentrated in vacuum. The residue was purified by prep-HPLC with NH$_4$OH as additive to afford 1-(4-((4-phenylthiazol-2-yl)amino)phenyl)-3-(pyridin-4-ylmethyl)urea (13.0 mg, yield 10%) as a brown solid. $^1$H NMR (400 MHz, DMSO-d$_6$): δ=10.09 (br s, 1H), 8.62 (br s, 1H), 8.52 (dd, J=4.8, 1.6 Hz, 2H), 7.91 (d, J=7.2 Hz, 2H), 7.58 (d, J=8.8 Hz, 2H), 7.42 (t, J=7.2 Hz, 2H), 7.39 (t, J=8.8 Hz, 2H), 7.34-7.29 (m, 3H), 7.28 (s, 1H), 6.72 (t, J=6.4 Hz, 1H), 4.34 (d, J=6.0 Hz, 2H). MS: m/z 402.0 (M+H$^+$).

Example 554: Synthesis of 1-((1H-Pyrazol-4-yl)methyl)-3-(4-((4-phenylthiazol-2-yl)amino)phenyl)urea

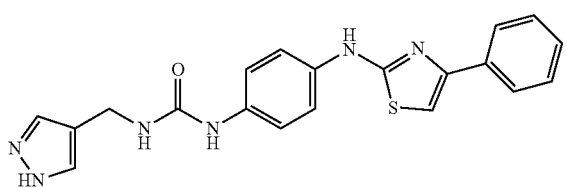 [SMILES: O=C(NCc1cn[nH]c1)Nc1ccc(Nc2nc(-c3ccccc3)cs2)cc1]

The title compound was prepared as described in example 1-(4-((4-Phenylthiazol-2-yl)amino)phenyl)-3-(pyridin-4-ylmethyl)urea. $^1$H NMR (400 MHz, DMSO-d$_6$): δ=12.58 (br s, 1H), 10.06 (br s, 1H), 8.31 (br s, 1H), 7.91 (d, J=7.2 Hz, 2H), 7.57 (d, J=8.8 Hz, 2H), 7.56-7.47 (m, 2H), 7.42 (t, J=7.6 Hz, 2H), 7.36 (d, J=8.8 Hz, 2H), 7.28 (d, J=7.2 Hz, 1H), 7.26 (s, 1H), 6.27 (t, J=5.6 Hz, 1H), 4.14 (d, J=5.6 Hz, 2H). MS: m/z 391.0 (M+H$^+$).

Example 555: Synthesis of 1-(Oxazol-5-ylmethyl)-3-(4-((4-phenylthiazol-2-yl)amino)phenyl)urea

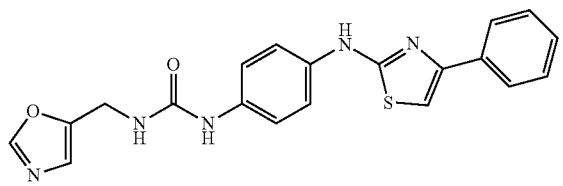 [SMILES: O=C(NCc1cnco1)Nc1ccc(Nc2nc(-c3ccccc3)cs2)cc1]

The title compound was prepared as described in example 1-(4-((4-phenylthiazol-2-yl)amino)phenyl)-3-(pyridin-4-ylmethyl)urea. $^1$H NMR (400 MHz, DMSO-d$_6$): δ=10.12 (br s, 1H), 8.62 (br s, 1H), 8.29 (s, 1H), 7.91 (d, J=7.6 Hz, 2H), 7.58 (d, J=8.8 Hz, 2H), 7.42 (t, J=7.6 Hz, 2H), 7.37 (d, J=8.8 Hz, 2H), 7.30 (d, J=7.6 Hz, 1H), 7.27 (s, 1H), 7.01 (s, 1H), 6.67 (t, J=6.0 Hz, 1H), 4.36 (d, J=5.6 Hz, 2H). MS: m/z 392.0 (M+H$^+$).

Example 556: Synthesis of 1-(4-((4-Phenylthiazol-2-yl)amino)phenyl)urea

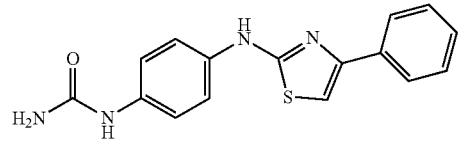 [SMILES: NC(=O)Nc1ccc(Nc2nc(-c3ccccc3)cs2)cc1]

The title compound was prepared as described in example 1-(4-((4-phenylthiazol-2-yl)amino)phenyl)-3-(pyridin-4-ylmethyl)urea. $^1$H NMR (400 MHz, DMSO-d$_6$): δ=10.07 (br s, 1H), 8.46 (br s, 1H), 7.91 (d, J=7.6 Hz, 2H), 7.57 (d, J=8.8 Hz, 2H), 7.42 (t, J=7.6 Hz, 2H), 7.36 (d, J=9.2 Hz, 2H), 7.30 (d, J=7.2 Hz, 1H), 7.26 (s, 1H), 5.78 (br s, 2H). MS: m/z 311.0 (M+H$^+$).

Example 557: Synthesis of 1-(4-(Benzo[d]thiazol-2-ylamino)phenyl)-3-(oxazol-5-ylmethyl)urea

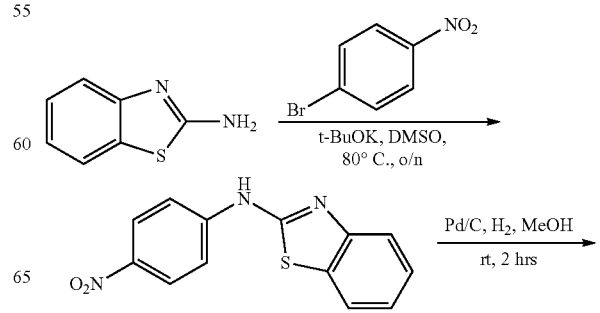

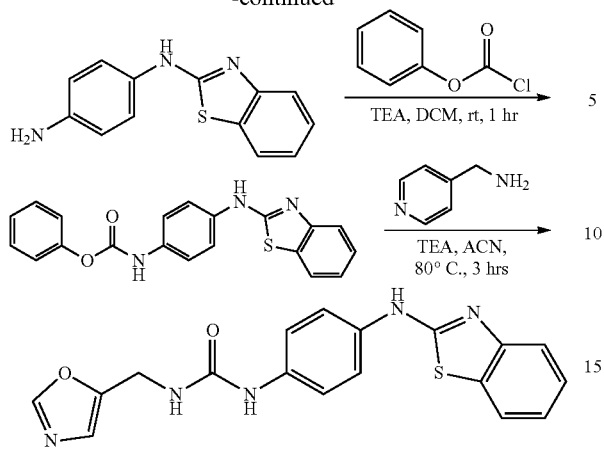

Step 1: To a solution of benzo[d]thiazol-2-amine (2.0 g, 13.3 mmol) and 1-bromo-4-nitrobenzene (4.03 g, 20.0 mmol) in DMSO (20 mL) was added t-BuOK (2.24 g, 20.0 mmol). The resulting mixture was stirred at 80° C. overnight. Then to the reaction mixture was added $H_2O$ (40 mL) and extracted with EA (40 mL×2). The combined organic layer was washed with brine (40 mL×2) and concentrated in vacuum. The residue was purified by silica gel column (PE/EA=100/1 to 30/1) to afford N-(4-nitrophenyl)benzo[d]thiazol-2-amine (1.96 g, yield 54%) as a yellow solid.

Step 2: To a solution of N-(4-nitrophenyl)benzo[d]thiazol-2-amine (1.96 g, 7.20 mmol) in MeOH (40 mL) was added Pd/C (392 mg, 20% wt). The resulting mixture was stirred at room temperature under $H_2$ atmosphere overnight. Then Pd/C was filtered and the filtrate was concentrated in vacuum. The residue was purified by silica gel column (DCM/MeOH=200/1 to 40/1) to afford $N^1$-(benzo[d]thiazol-2-yl)benzene-1,4-diamine (976 mg, yield 56%) as a yellow solid. $^1H$ NMR (300 MHz, DMSO-$d_6$): δ=7.42 (d, J=7.8 Hz, 1H), 7.08 (t, J=7.5 Hz, 1H), 7.02-6.92 (m, 3H), 6.70 (d, J=8.4 Hz, 2H), 6.38 (dt, J=7.8 Hz, 1H), 5.41 (br s, 2H).

Step 3: To a solution of $N^1$-(benzo[d]thiazol-2-yl)benzene-1,4-diamine (100 mg, 0.42 mmol) in dry DCM (20 mL) was added phenyl carbonochloridate (78 mg, 0.50 mmol) and followed by TEA (126 mg, 1.24 mmol). The resulting mixture was stirred at room temperature for 1 hour. The reaction was monitored by TLC. Then the mixture was concentrated in vacuum. The residue was purified by silica gel column (PE/EA=200/1 to 30/1) to afford phenyl (4-(benzo[d]thiazol-2-ylamino)phenyl)carbamate (126 mg, yield 84%) as a white solid.

Step 4: To a solution of phenyl (4-(benzo[d]thiazol-2-ylamino)phenyl)carbamate (126 mg, 0.35 mmol) in ACN (20 mL) was added oxazol-5-ylmethanamine (56.3 mg, 0.42 mmol, HCl salt) and followed by TEA (106 mg, 1.05 mmol). The resulting mixture was stirred at 80° C. for 3 hours. The reaction was monitored by LC-MS. Then the mixture was concentrated in vacuum. The residue was purified by prep-HPLC with $NH_4OH$ as additive to afford 1-(4-(benzo[d]thiazol-2-ylamino)phenyl)-3-(oxazol-5-ylmethyl)urea (61.0 mg, yield 48%) as a white solid. $^1H$ NMR (400 MHz, DMSO-$d_6$): δ=8.99 (br s, 1H), 8.30 (br s, 1H), 7.59 (d, J=8.8 Hz, 2H), 7.45 (d, J=7.6 Hz, 1H), 7.25 (d, J=8.4 Hz, 2H), 7.09 (t, J=7.6 Hz, 1H), 7.03 (s, 1H), 6.99 (t, J=7.6 Hz, 1H), 6.81 (t, J=5.6 Hz, 1H), 6.42 (d, J=8.0 Hz, 1H), 4.40 (d, J=5.6 Hz, 2H). MS: m/z 366.0 (M+H$^+$).

Example 558: Synthesis of 1-((1H-Pyrazol-4-yl)methyl)-3-(4-(benzo[d]thiazol-2-ylamino)phenyl)urea

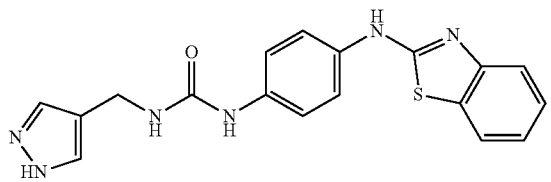

The title compound was prepared as described in example 1-(4-(benzo[d]thiazol-2-ylamino)phenyl)-3-(oxazol-5-ylmethyl)urea. $^1H$ NMR (400 MHz, DMSO-$d_6$): δ=12.62 (br s, 1H), 8.82 (br s, 1H), 8.16 (br s, 1H), 7.59 (d, J=8.8 Hz, 2H), 7.57-7.50 (m, 2H), 7.47 (d, J=7.6 Hz, 1H), 7.25 (d, J=8.8 Hz, 2H), 7.11 (t, J=8.0 Hz, 1H), 7.01 (t, J=8.0 Hz, 1H), 6.50 (t, J=5.2 Hz, 1H), 6.43 (d, J=8.0 Hz, 1H), 6.18 (d, J=5.6 Hz, 2H). MS: m/z 365.1 (M+H$^+$).

Example 559: Synthesis of 1-(4-(Benzo[d]thiazol-2-ylamino)phenyl)urea

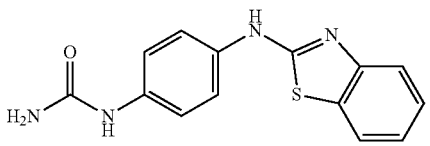 [SMILES: NC(=O)Nc1ccc(Nc2nc3ccccc3s2)cc1]

The title compound was prepared as described in example 1-(4-(benzo[d]thiazol-2-ylamino)phenyl)-3-(oxazol-5-ylmethyl)urea. $^1H$ NMR (400 MHz, DMSO-$d_6$): δ=8.87 (br s, 1H), 8.18 (br s, 1H), 7.59 (d, J=8.4 Hz, 2H), 7.47 (d, J=8.0 Hz, 1H), 7.24 (d, J=8.4 Hz, 2H), 7.11 (t, J=8.4 Hz, 1H), 7.01 (t, J=7.2 Hz, 1H), 6.43 (d, J=8.4 Hz, 1H), 5.97 (brs, 2H). MS: m/z 285.0 (M+H$^+$).

Example 560: Synthesis of 1-(4-((5-Phenylthiazol-2-yl)amino)phenyl)-3-(pyridin-4-ylmethyl)urea

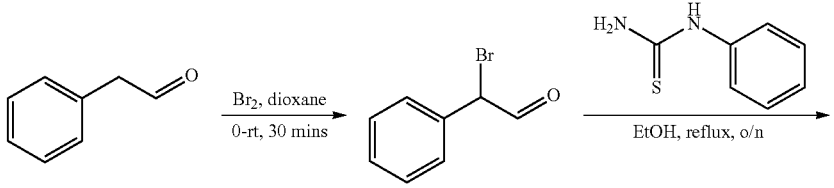

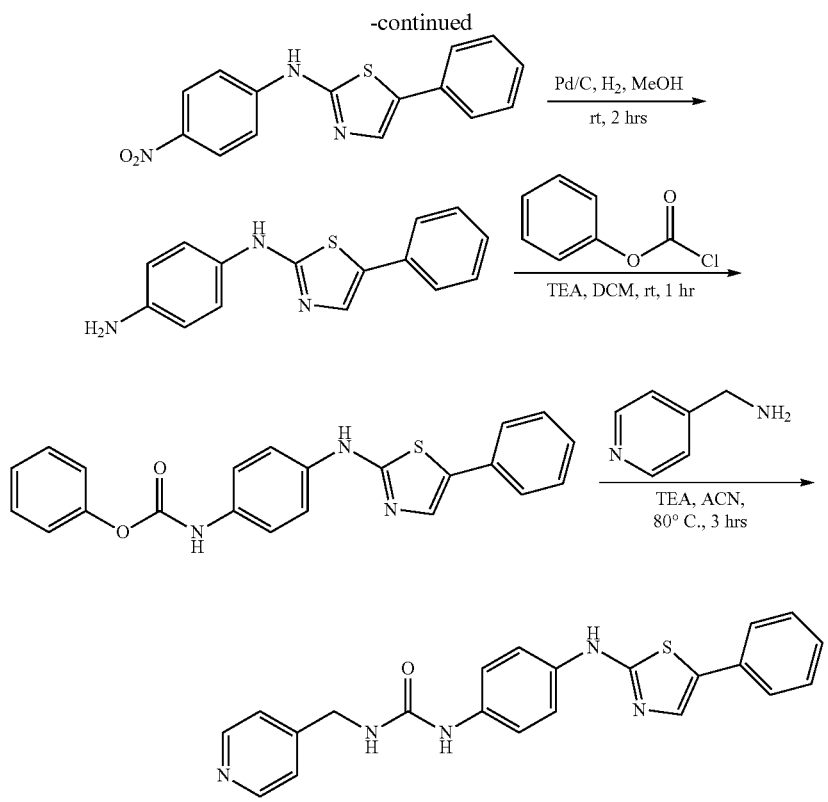

Step 1 to 2: To a solution of 2-phenylacetaldehyde (120 mg, 1.0 mmol) in dioxane (10 mL) was added Br$_2$ (176 mg, 1.1 mmol) at 0° C. The resulting mixture was stirred at 0° C. for 10 min and then at room temperature for another 10 min. Then the mixture was concentrated in vacuum. The residue was dissolved in EtOH (20 mL) and 1-phenylthiourea (197 mg, 1.0 mmol) was added. The resulting mixture was stirred at 80° C. overnight. The reaction was monitored by TLC and LC-MS. The mixture was concentrated in vacuum. The residue was purified by silica gel column (PE/EA=100/1 to 30/1) to afford N-(4-nitrophenyl)-5-phenylthiazol-2-amine (126 mg, yield 42%) as a yellow solid.

Step 3: To a solution of N-(4-nitrophenyl)-5-phenylthiazol-2-amine (126 mg, 0.42 mmol) in MeOH (20 mL) was added Pd/C (25 mg, 20% wt). The resulting mixture was stirred at room temperature under H$_2$ atmosphere overnight. The reaction was monitored by LC-MS. Then Pd/C was filtered and the filtrate was concentrated in vacuum to afford N$^1$-(5-phenylthiazol-2-yl)benzene-1,4-diamine (92 mg, yield 81%) as a yellow solid. $^1$H NMR (400 MHz, DMSO-d$_6$): δ=9.74 (br s, 1H), 7.58 (br s, 1H), 7.46 (d, J=7.2 Hz, 2H), 7.35 (t, J=8.0 Hz, 2H), 7.28-7.14 (m, 3H), 6.56 (d, J=8.8 Hz, 2H), 4.94 (br s, 2H).

Step 4: To a solution of N$^1$-(5-phenylthiazol-2-yl)benzene-1,4-diamine (300 mg, 1.12 mmol) in dry DCM (20 mL) was added phenyl carbonochloridate (351 mg, 2.24 mmol) and followed by TEA (341 mg, 3.36 mmol). The resulting mixture was stirred at room temperature for 1 hour. The reaction was monitored by TLC. Then the mixture was concentrated in vacuum. The residue was purified by silica gel column (DCM/MeOH=50/1) to afford phenyl (4-((5-phenylthiazol-2-yl)amino)phenyl)carbamate (342 mg, yield 79%) as a white solid.

Step 5: To a solution of phenyl (4-((5-phenylthiazol-2-yl)amino)phenyl)carbamate (100 mg, 0.26 mmol) in ACN (20 mL) was added pyridin-4-ylmethanamine (56 mg, 0.52 mmol) and TEA (78 mg, 0.77 mmol). The resulting mixture was stirred at 80° C. for 3 hrs. The reaction was monitored by LC-MS. Then the mixture was concentrated in vacuum. The residue was purified by prep-HPLC with NH$_4$HCO$_3$ as additive to afford 1-(4-((5-phenylthiazol-2-yl)amino)phenyl)-3-(pyridin-4-ylmethyl)urea (42.9 mg, yield 41%) as a white solid. $^1$H NMR (400 MHz, DMSO-d$_6$): δ=10.12 (br s, 1H), 8.59 (br s, 1H), 8.51 (d, J=6.0 Hz, 2H), 7.64 (s, 1H), 7.56-7.46 (m, 4H), 7.43-7.33 (m, 4H), 7.29 (d, J=6.0 Hz, 2H), 7.23 (t, J=7.6 Hz, 1H), 6.66 (t, J=6.0 Hz, 1H), 4.33 (d, J=6.0 Hz, 2H). MS: m/z 402.1 (M+H$^+$).

Example 561: Synthesis of 1-(Oxazol-5-ylmethyl)-3-(4-((5-phenylthiazol-2-yl)amino)phenyl)urea

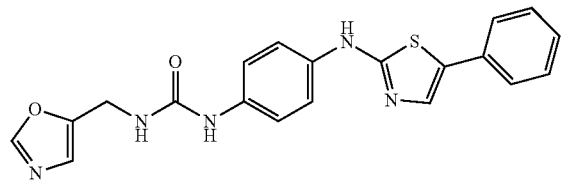 [SMILES: O=C(NCc1cnco1)Nc1ccc(Nc2ncc(-c3ccccc3)s2)cc1]

The title compound was prepared as described in example 1-(4-((5-phenylthiazol-2-yl)amino)phenyl)-3-(pyridin-4-ylmethyl)urea. $^1$H NMR (400 MHz, DMSO-d$_6$): δ=10.12 (br s, 1H), 8.46 (br s, 1H), 8.28 (s, 1H), 7.64 (s, 1H), 7.55-7.46 (m, 4H), 7.42-7.30 (m, 4H), 7.24 (d, J=7.6 Hz, 1H), 7.00 (s, 1H), 6.54 (t, J=5.6 Hz, 1H), 4.36 (d, J=6.0 Hz, 2H). MS: m/z 392.1 (M+H$^+$).

Example 562: Synthesis of 1-((1H-Pyrazol-4-yl)methyl)-3-(4-((5-phenylthiazol-2-yl)amino)phenyl) urea

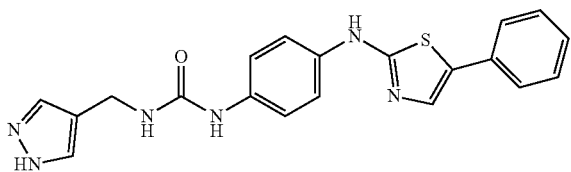 [SMILES: O=C(NCc1cn[nH]c1)Nc1ccc(Nc2ncc(-c3ccccc3)s2)cc1]

The title compound was prepared as described in example 1-(4-((5-phenylthiazol-2-yl)amino)phenyl)-3-(pyridin-4-yl-methyl)urea. $^1$H NMR (400 MHz, DMSO-d$_6$): δ=12.61 (br s, 1H), 10.11 (br s, 1H), 8.31 (s, 1H), 7.64 (s, 1H), 7.60-7.43 (m, 6H), 7.42-7.28 (m, 4H), 7.23 (d, J=7.2 Hz, 1H), 6.24 (t, J=5.6 Hz, 1H), 4.14 (d, J=4.8 Hz, 2H). MS: m/z 391.0 (M+H$^+$).

Example 563: Synthesis of 1-(1H-Pyrazol-4-ylmethyl)-3-[4-(4-o-tolyl-thiazol-2-ylamino)-phenyl]-urea

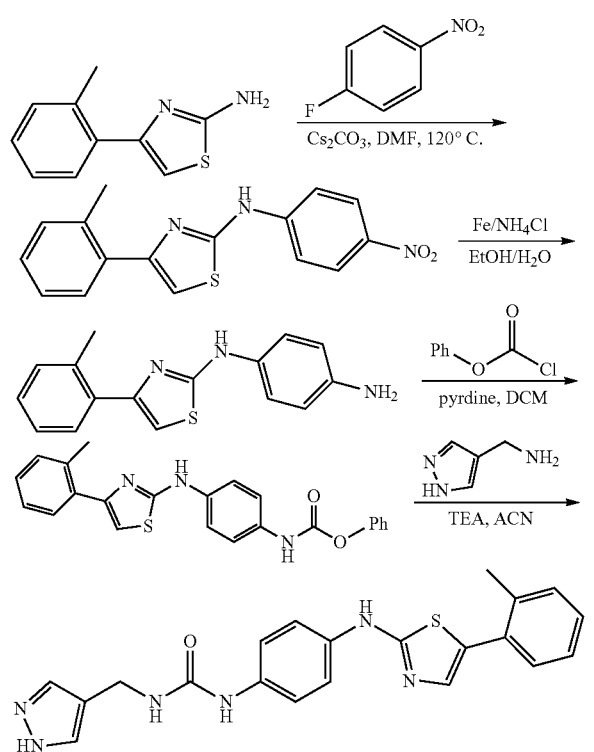

Step 1: To a solution of 4-o-tolyl-thiazol-2-ylamine (460 mg, 2.42 mmol) in DMF (5 mL) was added 1-Fluoro-4-nitro-benzene (375.5 mg, 2.66 mmol) and CsCO$_3$ (2.36 g, 7.26 mmol). The reaction mixture was stirred at 120° C. under N$_2$ for 2 hrs. The reaction was quenched with water (40 mL) and extracted with EA (40 mL×3). The combined organic layer was concentrated. The residue was purified by flash column (PE/EA=4/1) to give (4-nitro-phenyl)-(4-o-tolyl-thiazol-2-yl)-amine (477 mg, yield 63%) as a yellow solid. MS: m/z 312.3 (M+H$^+$)

Step 2: To a solution of (4-nitro-phenyl)-(4-o-tolyl-thiazol-2-yl)-amine (300 mg, 0.96 mmol) in EtOH (20 mL) and H$_2$O (5 mL) was added Fe (269 mg, 4.82 mmol) and NH$_4$Cl (258 mg, 4.82 mmol). The reaction mixture was stirred at 80° C. under N$_2$ for 1 hr. The reaction was completed detected by LC-MS. The reaction was filtered. The filterate was concentrated and purified by flash column to give n-(4-o-tolyl-thiazol-2-yl)-benzene-1,4-diamine (0.172 g, yield 63%) as a gray solid. MS: m/z 282.5 (M+H$^+$)

Step 3: To a solution of n-(4-o-tolyl-thiazol-2-yl)-benzene-1,4-diamine (98 mg, 0.348 mmol) in DCM (5 mL) was added pyridine (82.6 mg, 1.046 mmol) and phenyl chloroformate (48.2 mg, 0.348 mmol) at 0° C. The reaction mixture was stirred at 0° C. for 30 min. The reaction was completed detected by LC-MS. The reaction was concentrated to give the crude [4-(4-o-tolyl-thiazol-2-ylamino)-phenyl]-carbamic acid phenyl ester. MS: m/z 402.4 (M+H$^+$).

Step 4: To a solution of [4-(4-o-tolyl-thiazol-2-ylamino)-phenyl]-carbamic acid phenyl ester (140 mg, 0.348 mmol) in ACN (5 mL) was added TEA (105.5 mg, 1.044 mmol) and c-(1 h-pyrazol-4-yl)-methylamine (40 mg, 0.418 mmol). The reaction mixture was stirred at 80° C. under N$_2$ for 1.5 hrs. The reaction was completed detected by LC-MS. The reaction was concentrated and purified by prep-HPLC (NH$_3$.H$_2$O system) to afford 1-(1 h-pyrazol-4-ylmethyl)-3-[4-(4-o-tolyl-thiazol-2-ylamino)-phenyl]-urea (24.2 mg, yield 17%) as a white solid. $^1$H NMR (400 MHz, DMSO-d$_6$): δ=12.59 (s, 1H), 10.01 (s, 1H), 8.26 (s, 1H), 7.62-7.50 (m, 5H), 7.33-7.23 (m, 5H), 6.88 (s, 1H), 6.23 (t, J=5.6 Hz, 1H), 4.13 (d, J=5.2 Hz, 2H), 2.46 (s, 3H). MS: m/z 405.1 (M+H$^+$).

Example 564: Synthesis of 1-(1H-Pyrazol-4-ylmethyl)-3-[4-(4-m-tolyl-thiazol-2-ylamino)-phenyl]-urea

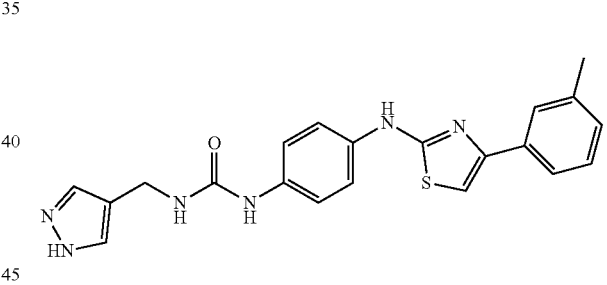

The title compound was prepared using general procedure of 1-(h-pyrazol-4-ylmethyl)-3-[4-(4-o-tolyl-thiazol-2-ylamino)-phenyl]-urea. $^1$H NMR (400 MHz, DMSO-d$_6$): δ=12.62 (s, 1H), 10.04 (s, 1H), 8.29 (s, 1H), 7.70 (d, J=8.4 Hz, 2H), 7.56-7.30 (m, 7H), 7.22 (s, 1H), 7.12 (d, J=7.2 Hz, 1H), 6.26 (s, 1H), 4.14 (d, J=5.2 Hz, 2H), 2.37 (s, 3H). MS: m/z 405.1 (M+H$^+$)

Example 565: Synthesis of 1-(1H-Pyrazol-4-ylmethyl)-3-[4-(4-p-tolyl-thiazol-2-ylamino)-phenyl]-urea

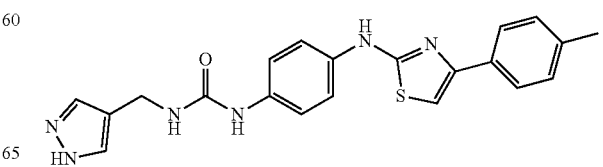

The title compound was prepared using general procedure of 1-(h-pyrazol-4-ylmethyl)-3-[4-(4-o-tolyl-thiazol-2-ylamino)-phenyl]-urea. $^1$H NMR (400 MHz, DMSO-d$_6$): δ=12.62 (s, 1H), 10.02 (s, 1H), 8.28 (s, 1H), 7.79 (d, J=8 Hz, 2H), 7.60-7.46 (m, 4H), 7.35 (d, J=8.4 Hz, 2H), 7.22 (d, J=7.6 Hz, 2H), 7.18 (s, 1H), 6.25 (t, J=5.2 Hz, 1H), 4.14 (d, J=5.2 Hz, 2H), 2.33 (s, 3H). MS: m/z 405.1 (M+H$^+$).

Example 566: Synthesis of 1-((1H-Pyrazol-4-yl)methyl)-3-(4-((4-(2-methoxyphenyl)thiazol-2-yl)amino)phenyl)urea

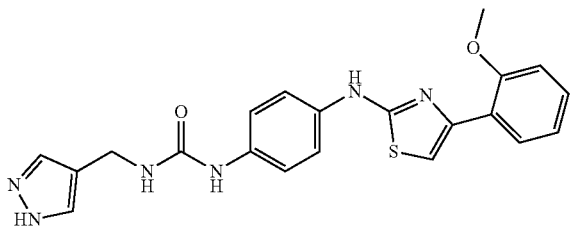 [SMILES: COc1ccccc1-c1csc(Nc2ccc(NC(=O)NCc3cn[nH]c3)cc2)n1]

The title compound was prepared using general procedure of 1-(h-pyrazol-4-ylmethyl)-3-[4-(4-o-tolyl-thiazol-2-ylamino)-phenyl]-urea. $^1$H NMR (400 MHz, DMSO-d$_6$): δ=9.99 (s, 1H), 8.29 (s, 1H), 8.14 (d, J=8.0 Hz, 1H), 7.56-7.53 (m, 4H), 7.36-7.29 (m, 4H), 7.12-7.05 (m, 2H), 6.28 (brs, 1H), 4.14 (2H), 3.91 (s, 3H). MS: m/z 421.1 (M+H$^+$).

Example 567: Synthesis of 1-((1H-Pyrazol-4-yl)methyl)-3-(4-((4-(3-methoxyphenyl)thiazol-2-yl)amino)phenyl)urea

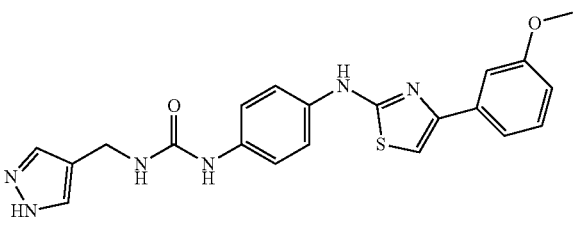 [SMILES: COc1cccc(-c2csc(Nc3ccc(NC(=O)NCc4cn[nH]c4)cc3)n2)c1]

The title compound was prepared using general procedure of 1-((1H-pyrazol-4-yl)methyl)-3-(4-((4-(2-methoxyphenyl)thiazol-2-yl)amino)phenyl)urea. $^1$H NMR (400 MHz, DMSO-d$_6$): δ=10.05 (s, 1H), 8.29 (s, 1H), 7.55-7.44 (m, 6H), 7.36-7.28 (m, 4H), 6.90-6.86 (m, 1H), 6.35-6.25 (m, 1H), 4.14 (s, 2H), 3.81 (s, 3H). MS: m/z 421.1 (M+H$^+$).

Example 568: Synthesis of 1-((1H-Pyrazol-4-yl)methyl)-3-(4-((4-(4-methoxyphenyl)thiazol-2-yl)amino)phenyl)urea

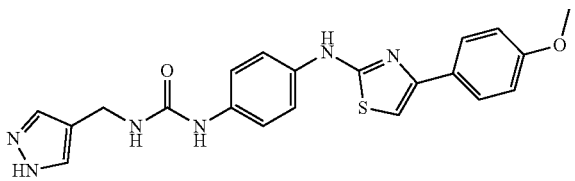 [SMILES: COc1ccc(-c2csc(Nc3ccc(NC(=O)NCc4cn[nH]c4)cc3)n2)cc1]

The title compound was prepared using general procedure of 1-((1H-pyrazol-4-yl)methyl)-3-(4-((4-(2-methoxyphenyl)thiazol-2-yl)amino)phenyl)urea. $^1$H NMR (400 MHz, DMSO-d$_6$): δ=10.05 (s, 1H), 8.29 (s, 1H), 7.55-7.53 (m, 4H), 7.50-7.48 (m, 1H), 7.45-7.43 (m, 1H), 7.36-7.33 (m, 3H), 7.31-7.28 (m, 1H), 6.90-6.88 (m, 1H), 6.30-6.20 (m, 1H), 4.14 (s, 2H), 3.81 (s, 3H). m/z 421.1 (M+H$^+$).

Example 569: Synthesis of 1-[4-(Benzothiazol-2-ylamino)-phenyl]-3-pyridin-4-ylmethyl-urea

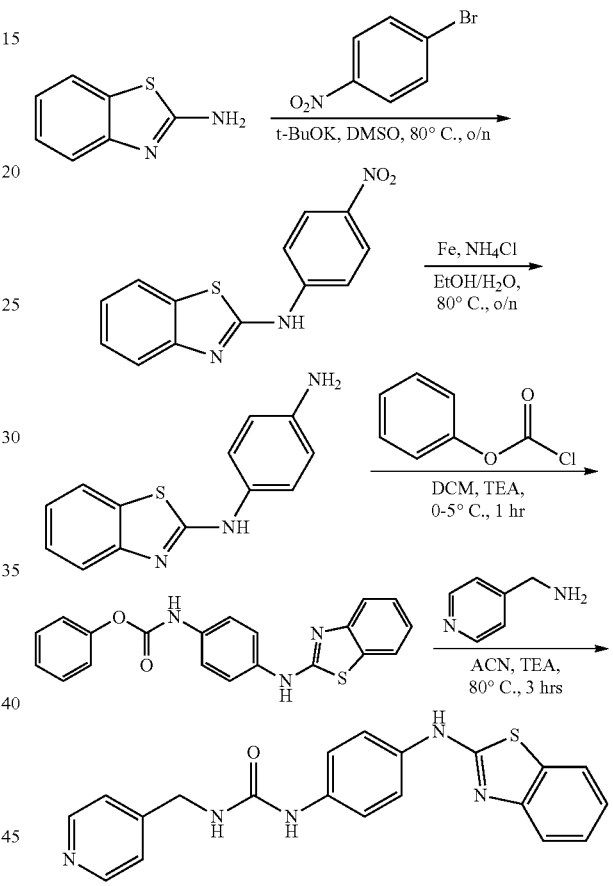

Step 1: To a solution of benzothiazol-2-ylamine (901 mg, 6.0 mmol) in DMSO (30 mL) was added 1-bromo-4-nitrobenzene (1.3 g, 6.6 mmol) and t-BuOK (740.5 mg, 6.6 mmol). The mixture was stirred at 80° C. overnight. The reaction was monitored by LCMS. After cooling and addition of water (30 mL), a suspension was generated which was extracted with EA (100 mL). The combined organic layer was dried over sodium sulfate anhydrous, filtered and concentrated in vacuum. The residue was purified by flash column to afford benzothiazol-2-yl-(4-nitro-phenyl)-amine (804 mg, yield 49%) as a brown solid. $^1$H NMR (400 MHz, DMSO-d$_6$): δ=8.65 (s, 1H), 8.41 (d, J=8.8 Hz, 2H), 7.79 (d, J=8.8 Hz, 2H), 7.51 (d, J=6.8 Hz, 1H), 7.12 (t, J=7.6 Hz, 1H), 7.08 (t, J=7.2 Hz, 1H), 6.64 (d, J=7.6 Hz, 1H).

Step 2: To a solution of benzothiazol-2-yl-(4-nitro-phenyl)-amine (404 mg, 1.48 mmol) in EtOH (25 mL) and H$_2$O (5 mL) was added NH$_4$Cl (395.83 mg, 7.4 mmol) and iron powder (13.29 mg, 7.4 mmol). The reaction mixture was stirred at 80° C. overnight. Iron powder was filtered off and the filtrate was concentrated in vacuum. The residue was purified by flash to give n-benzothiazol-2-yl-benzene-1,4-diamine (134 mg, yield 39%) as a yellow solid.

Step 3: To a solution of n-benzothiazol-2-yl-benzene-1,4-diamine (134 mg, 0.55 mmol) in DCM (30 mL) was added phenyl chloroformate (87.05 mg, 0.55 mmol) and TEA (111.31 mg, 1.1 mmol). The mixture was stirred at 0° C. for 1 hr. The reaction was monitored by TLC. After completion, the mixture was concentrated in vacuum. The residue was purified by a silica gel column (PE/EA=3/1) to afford [4-(benzothiazol-2-ylamino)-phenyl]-carbamic acid phenyl ester (80.3 mg, yield 41%) as a yellow solid.

Step 4: To a solution of [4-(benzothiazol-2-ylamino)-phenyl]-carbamic acid phenyl ester (80 mg, 0.22 mmol) in ACN (20 mL) was added c-pyridin-4-yl-methylamine (30.27 mg, 0.28 mmol) and TEA (44.53 mg, 0.44 mmol). The mixture was stirred at 80° C. for 3 hrs. The reaction was monitored by LCMS. After completion, the mixture was concentrated in vacuum. The residue was purified by prep-HPLC to give 1-[4-(1 h-Indazol-3-yl)-phenyl]-3-pyridin-4-ylmethyl-urea (6.7 mg, yield 3%) as a white solid. $^1$H NMR (400 MHz, DMSO-$d_6$): δ=9.62 (s, 1H), 8.51 (d, J=5.2 Hz, 2H), 7.62 (d, J=8.8 Hz, 2H), 7.46 (d, J=8.0 Hz, 1H), 7.32 (d, J=5.6 Hz, 3H), 7.24 (d, J=8.8 Hz, 3H), 7.10 (t, J=7.6 Hz, 1H), 6.99 (t, J=6.4 Hz, 1H), 6.42 (d, J=7.6 Hz, 1H), 4.36 (d, J=6.0 Hz, 2H). MS: m/z 376.0 (M+H$^+$).

Example 570: Synthesis of 1-{4-[4-(4-Fluoro-phenyl)-thiazol-2-ylamino]-phenyl}-3-(1H-pyrazol-4-ylmethyl)-urea purified by slurry in EA to give 4-(4-fluoro-phenyl)-thiazol-2-ylamine (1 g, crude, yield: quantitative) as a white solid. MS: m/z 195.3 (M+H$^+$).

Step 2: To a solution of 4-(4-fluoro-phenyl)-thiazol-2-ylamine (1.0 g, 5.2 mmol) in DMF (10 mL) was added 1-fluoro-4-nitro-benzene (806.5 mg, 5.7 mmol) and CsCO$_3$ (5.07 g, 15.6 mmol). The reaction was stirred at 80° C. under N$_2$ for 2 hrs. The reaction was quenched with water (40 mL) and extracted with EA (40 mL×3). The combined organic layer was dried over Na$_2$SO$_4$, filtered and concentrated in vacuum. The residue was purified by silica gel column (PE/EA=10/1) to give [4-(4-fluoro-phenyl)-thiazol-2-yl]-(4-nitro-phenyl)-amine (990 mg, yield 60%) as a yellow solid. MS: m/z 316.4 (M+H$^+$).

Step 3: To a solution of [4-(4-fluoro-phenyl)-thiazol-2-yl]-(4-nitro-phenyl)-amine (990 mg, 3.14 mmol) in EtOH (30 mL) and water (6 mL) was added iron powder (880 mg, 15.7 mmol) and NH$_4$Cl (840 mg, 15.7 mmol). The reaction mixture was stirred at 80° C. under nitrogen for 1 hr. The iron powder was filtered. The organic layer was concentrated in vacuum. The mixture was extracted with ethyl acetate (50 mL×2). The combined organic layer was washed with water and brine, dried over Na$_2$SO$_4$, filtered and concentrated in vacuum. The residue was purified by silica gel column (PE/EA=10/1) to give N-[4-(4-fluoro-phenyl)-thiazol-2-yl]-benzene-1, 4-diamine (550 mg, yield 62%) as a brown solid. MS: m/z 286.4 (M+H$^+$).

Step 4: To a solution of N-[4-(4-fluoro-phenyl)-thiazol-2-yl]-benzene-1, 4-diamine (200 mg, 0.7 mmol) in DCM (7

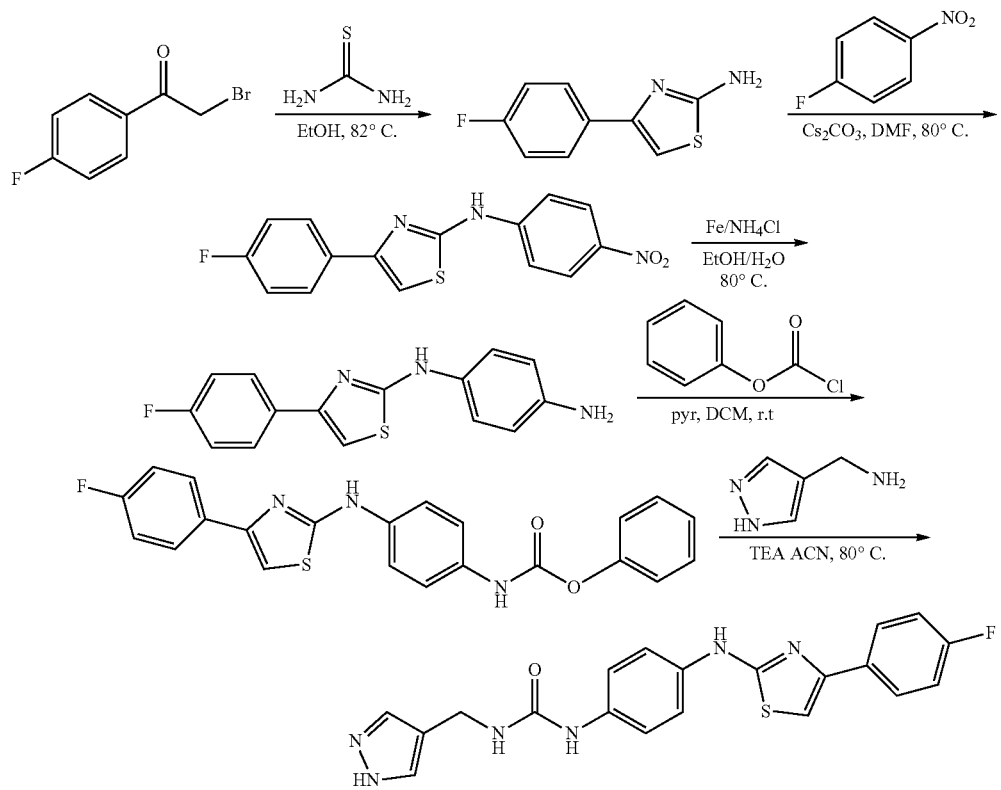

Step 1: To a solution of 2-bromo-1-(4-fluoro-phenyl)-ethanone (1.5 g, 6.9 mmol) and thiourea (524 mg, 6.9 mmol) in EtOH (10 mL) was stirred at 82° C. under N$_2$ for 3 hrs. The reaction was concentrated in vacuum. The residue was mL) was added pyridine (165.9 mg, 2.1 mmol). The mixture was cooled to 0° C. and added phenyl chloroformate (120.6 mg, 0.77 mmol) dropwise. The reaction was stirred at room temperature for 0.5 hr. The mixture was washed with water (50 mL×2). The combined organic layer was dried over Na₂SO₄, filtered and concentrated in vacuum. The residue was purified by silica gel column (PE/EA=10/1) to give {4-[4-(4-Fluoro-phenyl)-thiazol-2-ylamino]-phenyl}-carbamic acid phenyl ester (94 mg, yield 33%) as a brown solid. MS: m/z 406.4 (M+H⁺).

Step 5: To a solution of {4-[4-(4-Fluoro-phenyl)-thiazol-2-ylamino]-phenyl}-carbamic acid phenyl ester (94 mg, 0.23 mmol) and C-(1H-Pyrazol-4-yl)-methylamine (26.8 mg, 0.276 mmol) in acetonitrile (5 mL) was added TEA (69.7 mg, 0.69 mmol). The reaction was stirred at 80° C. for 1.5 hrs. The acetonitrile was removed in vacuum. The mixture was washed with DCM (2 mL) and filtered. The solid was purified by prep-HPLC to give 1-{4-[4-(4-fluoro-phenyl)-thiazol-2-ylamino]-phenyl}-3-(1H-pyrazol-4-ylmethyl)-urea (19.2 mg, yield 21%) as a yellow solid. ¹H NMR (400 MHz, DMSO-d₆): δ=12.57 (s, 1H), 10.07 (s, 1H), 8.29 (s, 1H), 7.95 (dd, J=8.8, 5.6 Hz, 2H), 7.57-7.52 (m, 4H), 7.35 (d, J=8.8 Hz, 2H), 7.27-7.23 (m, 3H), 6.26 (t, J=5.2 Hz, 1H), 4.14 (d, J=5.2 Hz, 2H). MS: m/z 409.1 (M+H⁺).

Example 571: Synthesis of 1-{4-[4-(2-Fluoro-phenyl)-thiazol-2-ylamino]-phenyl}-3-(1H-pyrazol-4-ylmethyl)-urea

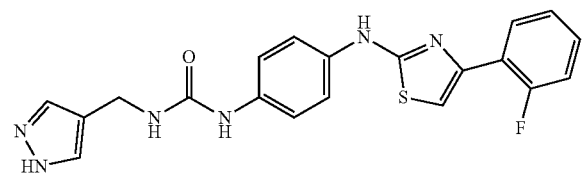 [SMILES: O=C(NCc1cn[nH]c1)Nc1ccc(Nc2nc(-c3ccccc3F)cs2)cc1]

The title compound was prepared using general procedure of 1-{4-[4-(4-fluoro-phenyl)-thiazol-2-ylamino]-phenyl}-3-(1H-pyrazol-4-ylmethyl)-urea. ¹H NMR (400 MHz, DMSO-d₆): δ=12.62 (s, 1H), 10.10 (s, 1H), 8.30 (s, 1H), 8.13-8.10 (m, 1H), 7.57-7.29 (m, 9H), 7.19 (d, J=2.4 Hz, 1H), 6.27-6.24 (m, 1H), 4.14 (d, J=5.2 Hz, 2H). MS: m/z 409.1 (M+H⁺).

Example 572: Synthesis of 1-{4-[4-(3-Fluoro-phenyl)-thiazol-2-ylamino]-phenyl}-3-(1H-pyrazol-4-ylmethyl)-urea

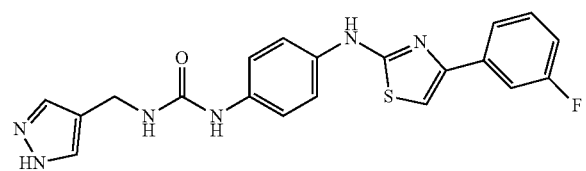 [SMILES: O=C(NCc1cn[nH]c1)Nc1ccc(Nc2nc(-c3cccc(F)c3)cs2)cc1]

The title compound was prepared using general procedure of 1-{4-[4-(4-fluoro-phenyl)-thiazol-2-ylamino]-phenyl}-3-(1H-pyrazol-4-ylmethyl)-urea. ¹H NMR (400 MHz, DMSO-d₆) δ=12.56 (s, 1H), 10.09 (s, 1H), 8.29 (s, 1H), 7.76 (d, J=8.0 Hz, 1H), 7.71-7.68 (m, 1H), 7.56-7.45 (m, 5H), 7.40-7.35 (m, 3H), 7.13 (d, J=2.0 Hz, 1H), 6.26 (s, 1H), 4.14 (d, J=5.6 Hz, 2H). MS: m/z 409.0 (M+H⁺).

Example 573: Synthesis of 1-{4-[4-(2-Chloro-phenyl)-thiazol-2-ylamino]-phenyl}-3-(1H-pyrazol-4-ylmethyl)-urea

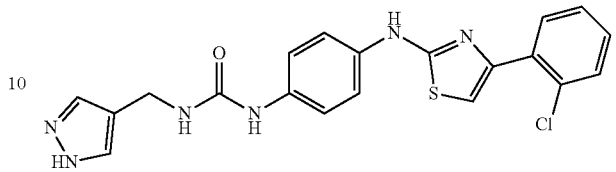

The title compound was prepared using general procedure of 1-{4-[4-(4-fluoro-phenyl)-thiazol-2-ylamino]-phenyl}-3-(1H-pyrazol-4-ylmethyl)-urea. ¹H NMR (400 MHz, DMSO-d₆): δ=12.60 (s, 1H), 10.11 (s, 1H), 8.50 (s, 1H), 7.93 (dd, J=7.6, 2.0 Hz, 1H), 7.54-7.44 (m, 6H), 7.37-7.33 (m, 3H), 7.28 (s, 1H), 6.39 (s, 1H), 4.14 (d, J=5.2 Hz, 2H). MS: m/z 425.0 (M+H⁺).

Example 574: Synthesis of 1-{4-[4-(3-Chloro-phenyl)-thiazol-2-ylamino]-phenyl}-3-(1H-pyrazol-4-ylmethyl)-urea

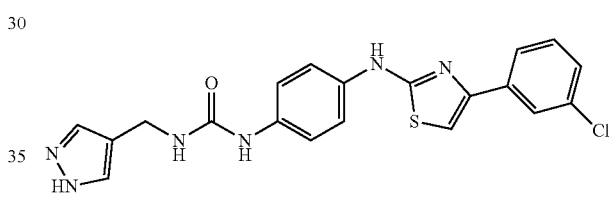

The title compound was prepared using general procedure of 1-{4-[4-(4-fluoro-phenyl)-thiazol-2-ylamino]-phenyl}-3-(1H-pyrazol-4-ylmethyl)-urea. ¹H NMR (400 MHz, DMSO-d₆): δ=10.10 (s, 1H), 8.31 (s, 1H), 7.93 (d, J=1.6 Hz, 1H), 7.88 (d, J=8.0 Hz, 1H), 7.56-7.53 (m, 4H), 7.48-7.43 (m, 2H), 7.38-7.35 (m, 3H), 6.28 (s, 1H), 4.15 (s, 2H). MS: m/z 425.0 (M+H⁺).

Example 575: Synthesis of 1-{4-[4-(4-Chloro-phenyl)-thiazol-2-ylamino]-phenyl}-3-(1H-pyrazol-4-ylmethyl)-urea

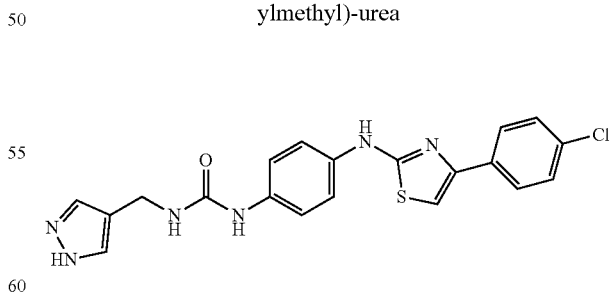

The title compound was prepared using general procedure of 1-{4-[4-(4-fluoro-phenyl)-thiazol-2-ylamino]-phenyl}-3-(1H-pyrazol-4-ylmethyl)-urea. ¹H NMR (400 MHz, DMSO-d₆): δ=10.08 (s, 1H), 8.30 (s, 1H), 7.93 (d, J=8.4 Hz, 2H), 7.56-7.54 (m, 4H), 7.48 (d, J=8.4 Hz, 2H), 7.37-7.33 (m, 3H), 6.27 (s, 1H), 4.15 (s, 2H). MS: m/z 425.0 (M+H⁺).

Example 576: Synthesis of N-[4-(3-Pyridin-4-ylmethyl-ureido)-phenyl]-C-p-tolyl-methanesulfonamide

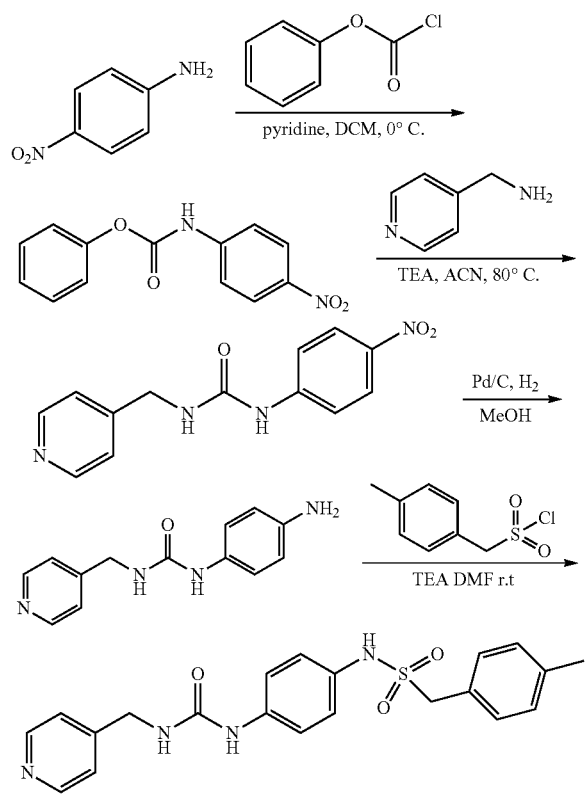

Step 1: To a solution of 4-nitro-phenylamine (10 g, 72.4 mmol) and pyridine (15.4 g, 195.5 mmol) in DCM (400 mL) was added phenyl chloroformate (15.8 g, 101.36 mmol) slowly under 0° C. The reaction mixture was stirred at room temperature for 2 hrs. The reaction mixture was filtered. The filtrate was concentrated and purified by flash column (PE/EA=10/1) to give (4-nitro-phenyl)-carbamic acid phenyl ester (16.06 g, yield 86%) as a white solid. $^1$H NMR (400 MHz, CDCl$_3$): δ=8.19 (d, J=9.2 Hz, 2H), 7.59 (d, J=8.8 Hz, 2H), 7.47 (s, 1H), 7.43-7.39 (m, 2H), 7.29-7.25 (m, 1H), 7.19 (d, J=7.6 Hz, 2H).

Step 2: A mixture of (4-Nitro-phenyl)-carbamic acid phenyl ester (10.0 g, 38.75 mmol), C-Pyridin-4-yl-methylamine (4.188 g, 38.75 mmol) and TEA (7.82 g, 77.5 mmol) in ACN (100 mL) was stirred at 80° C. under N$_2$ overnight. The reaction solution was filtered. The filter cake was washed with ACN (50 mL) to give 1-(4-nitro-phenyl)-3-pyridin-4-ylmethyl-urea (10.22 g, yield 95%) as a white solid. MS: m/z 273.1 (M+H$^+$).

Step 3: To a solution of 1-(4-nitro-phenyl)-3-pyridin-4-ylmethyl-urea (5.0 g, 18.4 mmol) in MeOH (50 mL) was added Pd/C (10% wet, 1 g). The reaction mixture was stirred at room temperature under H$_2$ (3 atm) overnight. The reaction solution was filtered. The filtrate was concentrated to give the crude 1-(4-amino-phenyl)-3-pyridin-4-ylmethyl-urea (4.42 g, yield 99.5%) as a yellow solid. MS: m/z 243.0 (M+H$^+$)

Step 4: A solution of 1-(4-Amino-phenyl)-3-pyridin-4-ylmethyl-urea (80 mg, 0.33 mmol) in DMF (3 mL) was added p-Tolyl-methanesulfonyl chloride (94.7 mg, 0.46 mmol) and TEA (168.4 mg, 1.65 mmol). The reaction mixture was stirred at room temperature overnight. The mixture was washed with H$_2$O (10 mL) and extracted with EA (50 mL). The combined organic phase was dried over Na$_2$SO$_4$, filtered and concentrated. The residue was purified by prep-HPLC (5-95; NH$_4$HCO$_3$) to give n-[4-(3-pyridin-4-ylmethyl-ureido)-phenyl]-c-p-tolyl-methanesulfonamide (35 mg, yield 26%) as a white solid. $^1$H NMR (400 MHz, DMSO-d$_6$): δ=9.49 (s, 1H), 8.68 (s, 1H), 8.51-8.49 (m, 2H), 7.37 (d, J=8.8 Hz, 2H), 7.28 (d, J=5.6 Hz, 2H), 7.18-7.13 (m, 4H), 7.08 (d, J=8.8 Hz, 2H), 6.71 (t, J=5.6 Hz, 1H), 4.32 (d, J=5.6 Hz, 2H), 4.29 (s, 2H), 2.29 (s, 3H). MS: m/z 410.9 (M+H$^+$).

Example 577: Synthesis of N-[4-(3-Pyridin-4-ylmethyl-ureido)-phenyl]-C-m-tolyl-methanesulfonamide

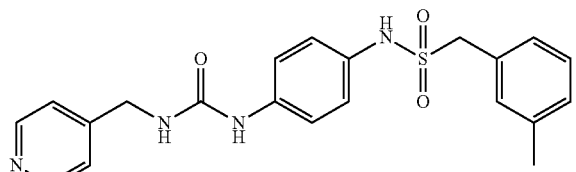

The title compound was prepared using general procedure of N-[4-(3-Pyridin-4-ylmethyl-ureido)-phenyl]-C-p-tolyl-methanesulfonamide. $^1$H NMR (400 MHz, DMSO-d$_6$): δ=9.52 (s, 1H), 8.69 (s, 1H), 8.50 (d, J=6.0 Hz, 2H), 7.41-7.33 (m, 2H), 7.31-7.26 (m, 2H), 7.25-7.21 (m, 1H), 7.15 (d, J=8.0 Hz, 1H), 7.10-7.03 (m, 4H), 6.72 (t, J=5.6 Hz, 1H), 4.32 (d, J=6.0 Hz, 2H), 4.30 (s, 2H), 2.28 (s, 3H). MS: m/z 411.0 (M+H$^+$).

Example 578: Synthesis of 1-[4-(2-Methyl-benzylsulfanylamino)-phenyl]-3-pyridin-4-ylmethyl-urea

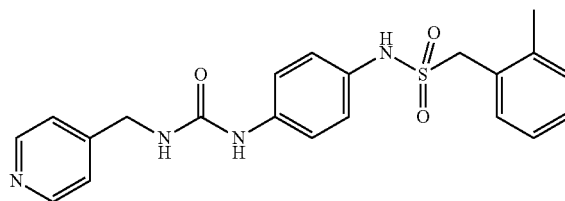

The title compound was prepared using general procedure of N-[4-(3-Pyridin-4-ylmethyl-ureido)-phenyl]-C-p-tolyl-methanesulfonamide. $^1$H NMR (400 MHz, CD$_3$OD): δ=8.48-8.46 (m, 2H), 7.40 (d, J=6.4 Hz, 2H), 7.35 (d, J=6.8 Hz, 2H), 7.21-7.12 (m, 6H), 4.45 (s, 2H), 4.39 (s, 2H), 2.33 (s, 3H). MS: m/z 410.8 (M+H$^+$).

Example 579: Synthesis of C-(4-Bromo-phenyl)-N-[4-(3-pyridin-4-ylmethyl-ureido)-phenyl]-methanesulfonamide

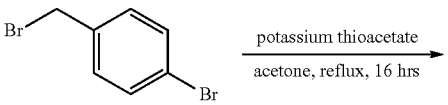

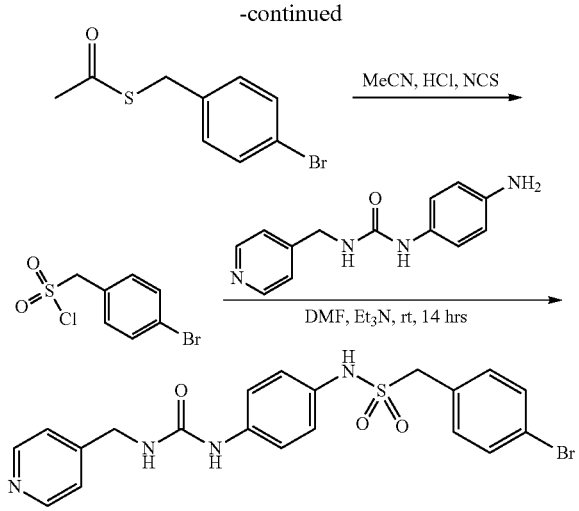

Step 1: A mixture of 1-bromo-4-bromomethyl-benzene (2.0 g, 8.0 mmol) and thioacetic acid S-(4-bromo-benzyl) ester (1.37 g, 12 mmol) in acetone (50 mL) was heated to reflux for 16 hrs. The mixture was cooled and filtered. The filtrate was concentrated and the residue was purified by silica gel column chromatography (PE/EA=10/1) to give (4-bromo-phenyl)-methanesulfonyl chloride (1.7 g, yield 87%) as brown oil. $^1$H NMR (400 MHz, CDCl$_3$): δ=7.41 (d, J=8.4 Hz, 2H), 7.16 (d, J=8.4 Hz, 2H), 4.05 (s, 2H), 2.35 (s, 3H).

Step 2: To a solution of HCl (2M, 1.547 mL) in MeCN (30 mL) was added NCS (3.3 g, 24.6 mmol) at 0° C. in portions. The resulting mixture was stirred for 5 min at 0° C. Then to this mixture was added a solution of (4-bromo-phenyl)-methanesulfonyl chloride (1.5 g, 6.15 mmol) in MeCN (3 mL) dropwise at 0° C. during 1 min. The reaction mixture was stirred for 10 min. Na$_2$SO$_4$ (about 5 g) was added and the mixture was filtered. The filtrate was concentrated. The residue was purified by silica gel column chromatography (PE/EA=10/1) to give (4-bromo-phenyl)-methanesulfonyl chloride (1.2 g, yield 73%) as a white solid. $^1$H NMR (300 MHz, CDCl$_3$): δ=7.62 (d, J=8.4 Hz, 2H), 7.37 (d, J=8.4 Hz, 2H), 4.83 (s, 2H).

Step 3: A mixture of (4-bromo-phenyl)-methanesulfonyl chloride (470 mg, 1.73 mmol), 1-(4-amino-phenyl)-3-pyridin-4-ylmethyl-urea (300 mg, 1.24 mmol) and TEA (0.9 mL, 6.2 mmol) in DMF (10 mL) was stirred at 80° C. for 14 hrs. The mixture was diluted with water (30 mL) and extracted with EA (30 mL×3). The combined organic layer was dried over Na$_2$SO$_4$, filtered and concentrated. The residue was purified by silica gel column chromatography (DCM/MeOH=30/1 to 15/1) to give C-(4-bromo-phenyl)-N-[4-(3-pyridin-4-ylmethyl-ureido)-phenyl]-methanesulfonamide (270 mg, yield 46%) as a white solid. $^1$H NMR (400 MHz, CD$_3$OD): δ=8.47 (d, J=6.1 Hz, 2H), 7.48 (d, J=8.4 Hz, 2H), 7.40 (d, J=5.9 Hz, 2H), 7.37-7.30 (m, 2H), 7.21 (d, J=8.4 Hz, 2H), 7.15-7.08 (m, 2H), 4.45 (s, 2H), 4.32 (s, 2H). MS: m/z 475.1 (M+H$^+$).

Example 580: Synthesis of C-(4-Methoxy-phenyl)-N-[4-(3-pyridin-4-ylmethyl-ureido)-phenyl]-methanesulfonamide

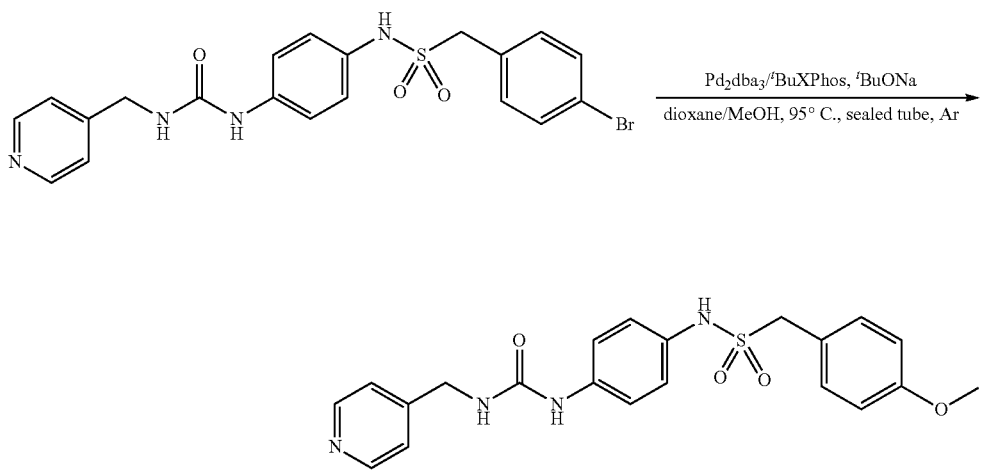

A mixture of C-(4-bromo-phenyl)-N-[4-(3-pyridin-4-ylmethyl-ureido)-phenyl]-methanesulfonamide (24 mg, 0.05 mmol), Pd$_2$dba$_3$ (8 mg, 0.008 mmol), $^t$BuXPhos (8 mg, 0.019 mmol) and $^t$BuONa (24 mg, 0.25 mmol) in dioxane (1.5 mL) and dry MeOH (0.5 mL) was heated at 95° C. for 16 hrs under Ar. The reaction mixture was concentrated. The residue was purified by prep-TLC (DCM/MeOH=10/1) to give C-(4-methoxy-phenyl)-N-[4-(3-pyridin-4-ylmethyl-ureido)-phenyl]-methanesulfonamide (10 mg, yield 9%) as a white solid. $^1$H NMR (400 MHz, CD$_3$OD): δ=8.47 (d, J=5.6 Hz, 2H), 7.40 (d, J=5.3 Hz, 2H), 7.33 (d, J=8.6 Hz, 2H), 7.19 (d, J=8.5 Hz, 2H), 7.11 (d, J=8.6 Hz, 2H), 6.87 (d, J=8.5 Hz, 2H), 4.45 (s, 2H), 4.27 (s, 2H), 3.77 (s, 3H). MS: m/z 427.1 (M+H$^+$).

Example 581: Synthesis of C-(4-Cyclopropyl-phenyl)-N-[4-(3-pyridin-4-ylmethyl-ureido)-phenyl]-methanesulfonamide

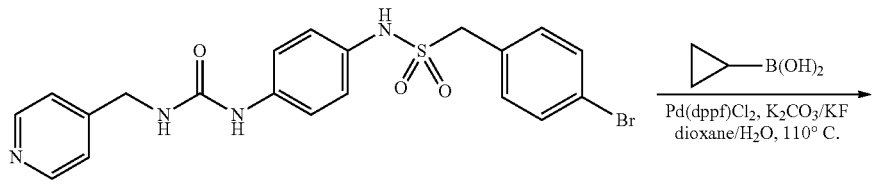

A mixture of C-(4-bromo-phenyl)-N-[4-(3-pyridin-4-yl-methyl-ureido)-phenyl]-methanesulfonamide (47 mg, 0.1 mmol), cyclopropylboronic acid (26 mg, 0.3 mmol), Pd(dppf)Cl$_2$ (8 mg, 0.01 mmol), K$_2$CO$_3$ (42 mg, 0.3 mmol) and KF.2H$_2$O (28 mg, 0.3 mmol) in dioxane (3 mL) and water (0.5 mL) was heated to 110° C. for 16 hrs under N$_2$. The resulting mixture was concentrated. The residue was purified by prep-TLC (DCM/MeOH=10/1) to give C-(4-cyclopropyl-phenyl)-N-[4-(3-pyridin-4-ylmethyl-ureido)-phenyl]-methanesulfonamide (5.5 mg, yield 13%) as a yellow solid. $^1$H NMR (400 MHz, CD$_3$OD): δ=8.47 (d, J=6.2 Hz, 2H), 7.40 (d, J=6.1 Hz, 2H), 7.33 (d, J=8.9 Hz, 2H), 7.15 (d, J=8.1 Hz, 2H), 7.10 (d, J=8.9 Hz, 2H), 7.03 (d, J=8.2 Hz, 2H), 4.45 (s, 2H), 4.28 (s, 2H), 1.95-1.83 (m, 1H), 0.99-0.92 (m, 2H), 0.68-0.62 (m, 2H). MS: m/z 437.2 (M+H$^+$).

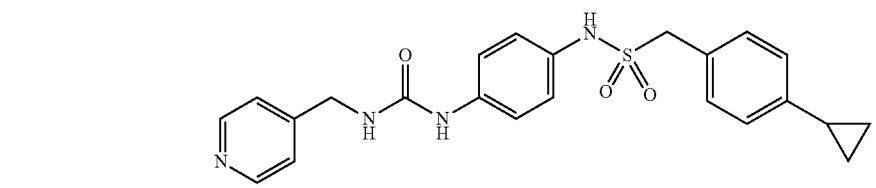

Example 582: Synthesis of C-Biphenyl-4-yl-N-[4-(3-pyridin-4-ylmethyl-ureido)-phenyl]-methanesulfonamide

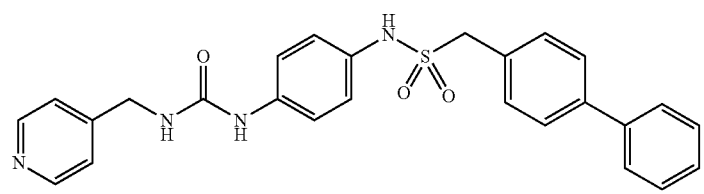

To a solution of C-(4-Bromo-phenyl)-N-[4-(3-pyridin-4-ylmethyl-ureido)-phenyl]-methanesulfonamide (50 mg, 0.105 mmol) in dioxane (4 mL) and H₂O (0.7 mL) was added phenylboronic acid (25 mg, 0.21 mmol), K₂CO₃ (72 mg, 0.525 mmol) and Pd (dppf) Cl₂ (7.6 mg, 0.0105 mmol). The mixture was stirred at 110° C. overnight. The reaction was concentrated and the residue was purified by TLC (DCM/MEOH=10/1) to give C-Biphenyl-4-yl-N-[4-(3-pyridin-4-ylmethyl-ureido)-phenyl]-methanesulfonamide (52 mg, yield 81%) as a white solid. ¹H NMR (400 MHz, CD₃OD): δ=8.47 (d, J=4.4 Hz, 2H), 7.60-7.56 (m, 4H) 7.44-7.32 (m, 9H), 7.14 (t, J=6.8 Hz, 2H), 4.45 (s, 2H), 4.39 (s, 2H). MS: m/z 472.8 (M+H⁺).

Example 583: Synthesis of C-(4-Cyano-phenyl)-N-[4-(3-pyridin-4-ylmethyl-ureido)-phenyl]-methanesulfonamide

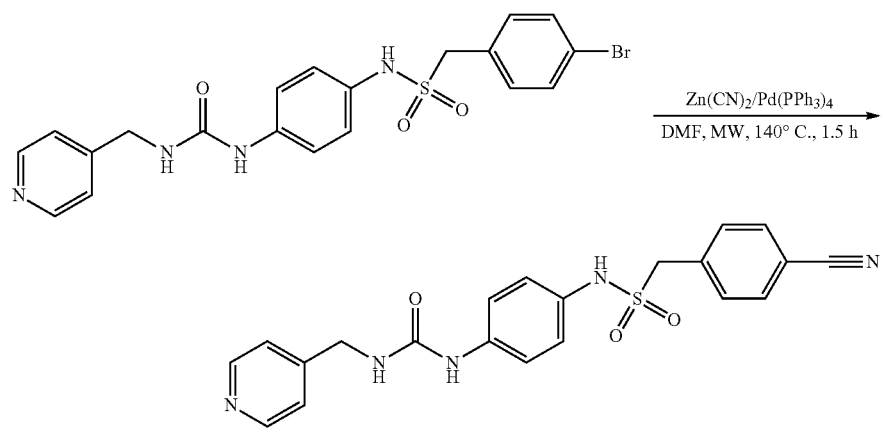

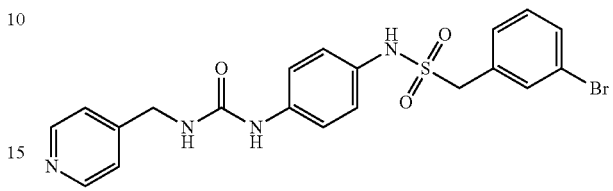

A mixture of C-(4-bromo-phenyl)-N-[4-(3-pyridin-4-ylmethyl-ureido)-phenyl]-methanesulfonamide (60 mg, 0.126 mmol), Zn(CN)₂ (74 mg, 0.63 mmol) and Pd(PPh₃)₄ (15 mg, 0.013 mmol) in DMF (2 mL) was stirred at 150° C. for 1.5 hrs in a sealed microwave under N₂. The mixture was diluted with water (20 mL) and extracted with EA (15 mL×3). The combined organic layer was concentrated. The residue was purified by prep-TLC (DCM/MeOH=10/1) to give C-(4-cyano-phenyl)-N-[4-(3-pyridin-4-ylmethyl-ureido)-phenyl]-methanesulfonamide (15 mg, yield 28%) as a white solid. ¹H NMR (400 MHz, CD₃OD): δ=8.47 (d, J=6.1 Hz, 2H), 7.69 (d, J=8.3 Hz, 2H), 7.48 (d, J=8.3 Hz, 2H), 7.40 (d, J=6.0 Hz, 2H), 7.34 (d, J=8.9 Hz, 2H), 7.11 (d, J=8.8 Hz, 2H), 4.50-4.40 (m, 4H). MS: m/z 421.9 (M+H⁺).

Example 584: Synthesis of 1-[4-(3-Bromo-benzylsulfanylamino)-phenyl]-3-pyridin-4-ylmethyl-urea The title compound was prepared using general procedure of C-(4-bromo-phenyl)-N-[4-(3-pyridin-4-ylmethyl-ureido)-phenyl]-methanesulfonamide. ¹H NMR (400 MHz, CD₃OD): δ=8.47 (d, J=6.4 Hz, 2H), 7.49 (m, 2H), 7.40 (d, J=5.6 Hz, 2H), 7.35 (d, J=8.8 Hz, 2H), 7.27-7.22 (m, 2H), 7.12 (d, J=8.8 Hz, 2H), 4.45 (s, 2H), 4.34 (s, 2H). MS: m/z 474.7 (M+H⁺).

Example 585: Synthesis of C-(3-Methoxy-phenyl)-N-[4-(3-pyridin-4-ylmethyl-ureido)-phenyl]-methanesulfonamide

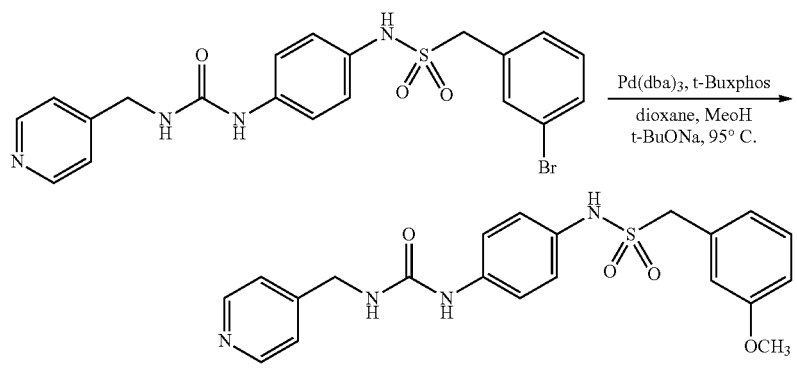

A mixture of C-(3-bromo-phenyl)-N-[4-(3-pyridin-4-yl-methyl-ureido)-phenyl]-methanesulfonamide (50 mg, 0.105 mmol), Pd₂(dba)₃ (19 mg 0.021 mmol), t-Buxphos (18 mg 0.042 mmol) and t-BuONa (50 mg 0.525 mmol) in dioxane (1.5 mL) and MeOH (0.5 mL) was stirred at 95° C. in microwave tube overnight. The reaction mixture was cooled to r.t and concentrated. The residue was purified by prep-HPLC to get C-(3-Methoxy-phenyl)-N-[4-(3-pyridin-4-yl-methyl-ureido)-phenyl]-methanesulfonamide (14 mg, yield 31%) as a white solid. ¹H NMR (400 MHz, CD₃OD): δ=8.45 (d, J=4.4 Hz, 2H), 7.40 (d, J=6.0 Hz, 2H), 7.34 (d, J=6.8 Hz, 2H), 7.25-7.21 (m, 1H), 7.12 (d, J=6.8 Hz, 2H), 6.89-6.83 (m, 3H), 4.45 (s, 2H) 4.31 (s, 2H), 3.74 (s, 3H). MS: m/z 426.9 (M+H⁺).

Example 586: Synthesis of C-(2-Bromo-phenyl)-N-[4-(3-pyridin-4-ylmethyl-ureido)-phenyl]-methanesulfonamide

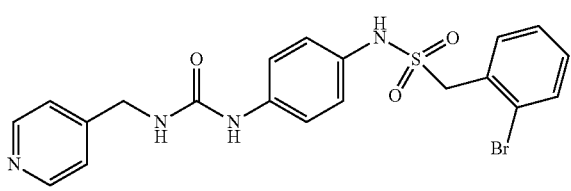 [SMILES: O=C(NCc1ccncc1)Nc1ccc(NS(=O)(=O)Cc2ccccc2Br)cc1]

The title compound was prepared using general procedure of C-(4-bromo-phenyl)-N-[4-(3-pyridin-4-ylmethyl-ureido)-phenyl]-methanesulfonamide. ¹H NMR (400 MHz, DMSO-d₆) δ=9.76 (s, 1H), 8.68 (s, 1H), 8.50 (d, J=5.2 Hz, 2H), 7.65 (d, J=7.6 Hz, 1H), 7.41 (d, J=4 Hz, 2H), 7.36 (d, J=8.8 Hz, 2H), 7.31-7.27 (m, 3H), 7.11 (d, J=9.2 Hz, 2H), 6.71 (t, J=5.6 Hz, 1H), 4.54 (s, 2H), 4.32 (d, J=5.6 Hz, 2H). MS: m/z 475.0 (M+H⁺).

Example 587: Synthesis of C-(2-Methoxy-phenyl)-N-[4-(3-pyridin-4-ylmethyl-ureido)-phenyl]-methanesulfonamide

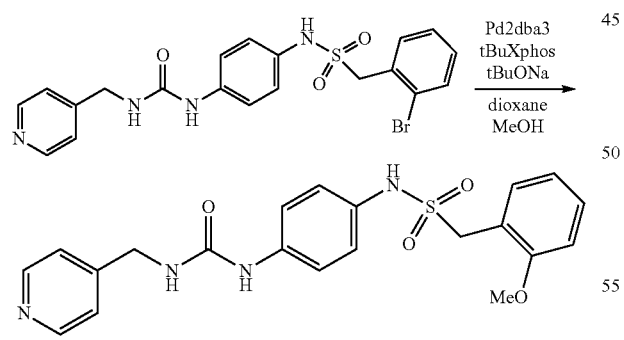

A mixture of C-(2-bromo-phenyl)-n-[4-(3-pyridin-4-ylm-ethyl-ureido)-phenyl]-methanesulfonamide (24 mg, 0.05 mmol), Pd₂dba₃ (8 mg, 0.008 mmol), tBuxphos (8 mg, 0.019 mmol) and tBuONa (24 mg, 0.25 mmol) in 1,4-dioxane (1.5 mL) and MeOH (0.5 mL) was stirred at 95° C. under Ar overnight. The reaction was repeated five times. All of the solution was concentrated and purified by prep-TLC (DCM/MeOH=10/1) and prep-HPLC (5-95; NH₄HCO₃) to afford C-(2-methoxy-phenyl)-n-[4-(3-pyridin-4-ylmethyl-ureido)-phenyl]-methanesulfonamide (1.3 mg, yield 1%) as a yellow solid. ¹H NMR (800 MHz, CD₃OD): 8.38 (d, J=6.0 Hz, 2H), 7.31 (d, J=6.0 Hz, 2H), 7.22-7.18 (m, 4H), 7.00-6.97 (m, 2H), 6.82-6.80 (m, 2H), 4.35 (s, 4H), 3.55 (s, 3H). MS: m/z 427.0 (M+H⁺).

Example 588: Synthesis of 1-[4-(4-Fluoro-phenyl-methanesulfonyl)-phenyl]-3-(1H-pyrazol-4-yl)-urea

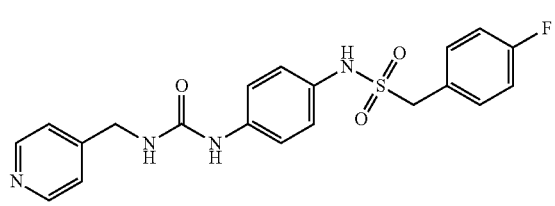 [SMILES: O=C(NCc1ccncc1)Nc1ccc(NS(=O)(=O)Cc2ccc(F)cc2)cc1]

The title compound was prepared using general procedure of C-(4-bromo-phenyl)-N-[4-(3-pyridin-4-ylmethyl-ureido)-phenyl]-methanesulfonamide. ¹H NMR (400 MHz, DMSO-d₆) δ=9.56 (s, 1H), 8.72 (s, 1H), 8.51 (d, J=5.6 Hz, 2H), 7.38-7.27 (m, 6H), 7.22-7.18 (m, 2H), 7.08-7.06 (m, 2H), 6.74-6.71 (m, 1H), 4.38 (s, 2H), 4.32 (d, J=6.0 Hz, 2H). MS: m/z 414.9 (M+H⁺).

Example 589: Synthesis of C-(3-Fluoro-phenyl)-N-[4-(3-pyridin-4-ylmethyl-ureido)-phenyl]-methanesulfonamide

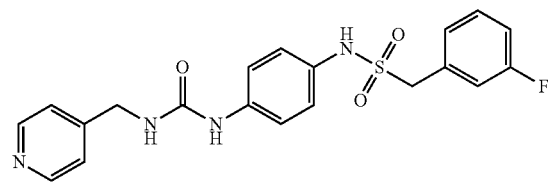 [SMILES: O=C(NCc1ccncc1)Nc1ccc(NS(=O)(=O)Cc2cccc(F)c2)cc1]

The title compound was prepared using general procedure of C-(4-bromo-phenyl)-N-[4-(3-pyridin-4-ylmethyl-ureido)-phenyl]-methanesulfonamide. ¹H NMR (400 MHz, DMSO-d₆) δ=9.60 (s, 1H), 8.69 (s, 1H), 8.51-8.49 (m, 2H), 7.43-7.35 (m, 3H), 7.29-7.28 (m, 2H), 7.22-7.17 (m, 1H), 7.11-7.07 (m, 4H), 6.71-6.69 (m, 1H), 4.42 (s, 2H), 4.32 (d, J=6.0 Hz, 2H). MS: m/z 415.1 (M+H⁺).

Example 590: Synthesis of C-(2-Fluoro-phenyl)-N-[4-(3-pyridin-4-ylmethyl-ureido)-phenyl]-methanesulfonamide

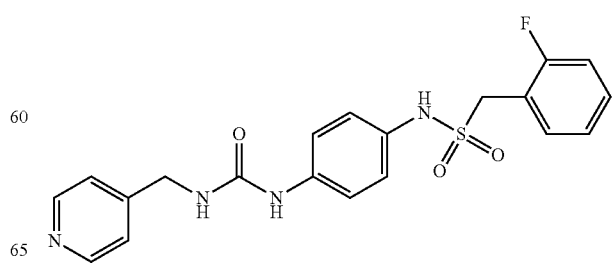

The title compound was prepared using general procedure of C-(4-bromo-phenyl)-N-[4-(3-pyridin-4-ylmethyl-ureido)-phenyl]-methanesulfonamide. $^1$H NMR (400 MHz, CD$_3$OD): δ=8.47 (d, J=6.2 Hz, 2H), 7.45-7.27 (m, 6H), 7.18-7.05 (m, 4H), 4.48-4.38 (m, 4H). MS: m/z 414.9 (M+H$^+$).

Example 591: Synthesis of 1-(3-Chlorophenyl)-N-(4-(3-(oxazol-5-ylmethyl)ureido)phenyl)methane-sulfonamide

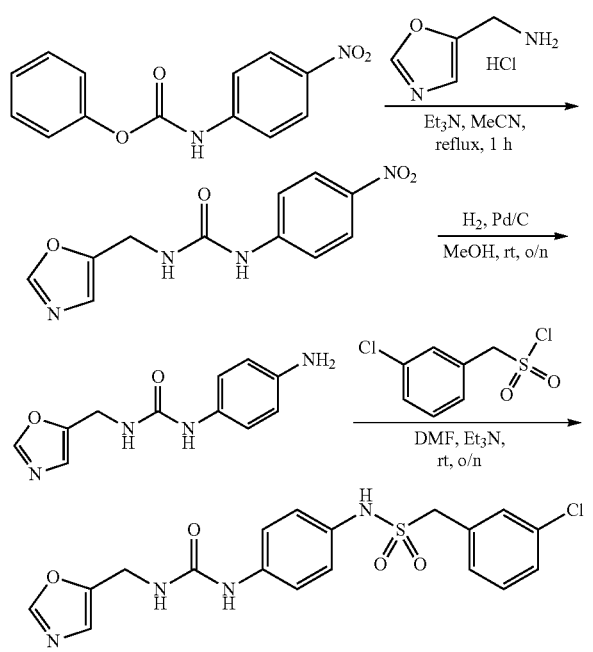

Step 1: A solution of phenyl (4-nitrophenyl)carbamate (500 mg, 1.94 mmoL), oxazol-5-ylmethanamine hydrochloride (261 mg, 1.94 mmoL) and Et$_3$N (1 mL, 6.93 mmoL) in MeCN (16 mL) was refluxed for 1 hr. The reaction mixture was concentrated to dryness in vacuum and the residue was purified by silica gel column (DCM/MeOH=40/1) to give 1-(4-nitro-phenyl)-3-oxazol-5-ylmethyl-urea (480 mg, yield: 94%) as a white solid.

Step 2: A suspension of 1-(4-nitro-phenyl)-3-oxazol-5-ylmethyl-urea (900 mg, 3.44 mmoL) and 10% Pd/C (190 mg) in MeOH (25 mL) was stirred for 19 hrs at room temperature under H$_2$ atmosphere (balloon). The reaction mixture was filtered to remove catalyst and the filtrate was concentrated to dryness in vacuum to give 1-(4-amino-phenyl)-3-oxazol-5-ylmethyl-urea (670 mg, yield 84%) as a red solid. MS: m/z 233.0 (M+H$^+$).

Step 3: To a solution of 1-(4-amino-phenyl)-3-oxazol-5-ylmethyl-urea (100 mg, 0.43 mmoL) and Et$_3$N (0.1 mL, 0.69 mmoL) in DMF (2.5 mL) was added (3-chloro-phenyl)-methanesulfonyl chloride (97 mg, 0.43 mmoL) at 0° C. and the mixture was stirred for 19 hrs at room temperature. The reaction mixture was poured into H$_2$O (18 mL) and extracted with EA (20 mL×3). The combined organic layer was washed with H$_2$O (50 mL) and brine (50 mL), dried over Na$_2$SO$_4$, filtered and concentrated to dryness in vacuum. The residue was purified by silica flash column (4% MeOH in DCM) and triturated with MeCN (2 mL) to give 1-(3-chlorophenyl)-N-(4-(3-(oxazol-5-ylmethyl)ureido) phenyl)methanesulfonamide (71 mg, yield 39%) as a yellow solid. $^1$H NMR (400 MHz, DMSO-d$_6$): δ=9.62 (s, 1H), 8.57 (s, 1H), 8.29 (s, 1H), 7.44-7.33 (m, 5H), 7.22 (d, J=7.2 Hz, 1H), 7.07 (d, J=8.8 Hz, 2H), 7.00 (s, 1H), 6.59 (t, J=5.6 Hz, 1H), 4.42 (s, 2H), 4.36 (d, J=5.6 Hz, 2H). MS: m/z 420.9 (M+H$^+$).

Example 592: Synthesis of 1-(4-Chlorophenyl)-N-(4-(3-(oxazol-5-ylmethyl)ureido)phenyl)methane-sulfonamide

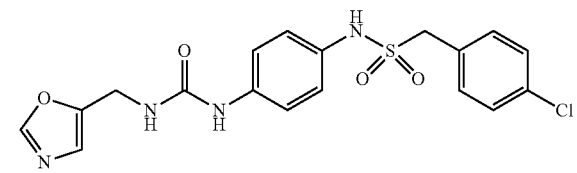 [SMILES: O=C(NCc1cnco1)Nc1ccc(NS(=O)(=O)Cc2ccc(Cl)cc2)cc1]

The title compound was prepared using general procedure of 1-(3-chlorophenyl)-N-(4-(3-(oxazol-5-ylmethyl)ureido) phenyl)methanesulfonamide. $^1$H NMR (400 MHz, DMSO-d$_6$): δ=9.56 (s, 1H), 8.57 (s, 1H), 8.29 (s, 1H), 7.43 (d, J=8.4 Hz, 2H), 7.35 (d, J=8.8 Hz, 2H), 7.28 (d, J=8.8 Hz, 2H), 7.07 (d, J=8.8 Hz, 2H), 7.00 (s, 1H), 6.59 (t, J=6.0 Hz, 1H), 4.39-4.35 (m, 4H). MS: m/z 420.9 (M+H$^+$).

Example 593: Synthesis of 1-(2-Chlorophenyl)-N-(4-(3-(oxazol-5-ylmethyl)ureido)phenyl)methane-sulfonamide

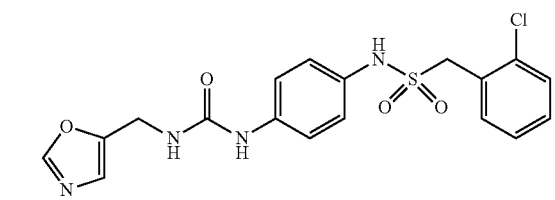 [SMILES: O=C(NCc1cnco1)Nc1ccc(NS(=O)(=O)Cc2ccccc2Cl)cc1]

The title compound was prepared using general procedure of 1-(3-chlorophenyl)-N-(4-(3-(oxazol-5-ylmethyl)ureido) phenyl)methanesulfonamide. $^1$H NMR (400 MHz, DMSO-d$_6$): δ=9.76 (s, 1H), 8.55 (s, 1H), 8.28 (s, 1H), 7.49-7.47 (m, 1H), 7.42-7.32 (m, 5H), 7.10 (d, J=9.2 Hz, 2H), 7.00 (s, 1H), 6.59 (t, J=6.0 Hz, 1H), 4.53 (s, 2H), 4.36 (d, J=5.6 Hz, 2H). MS: m/z 420.9 (M+H$^+$).

Example 594: Synthesis of 1-(3,4-Dichlorophenyl)-N-(4-(3-(oxazol-5-ylmethyl)ureido)phenyl)methane-sulfonamide

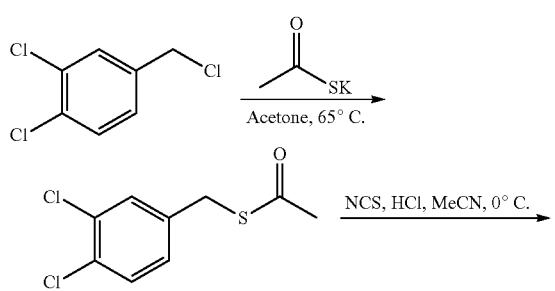

-continued

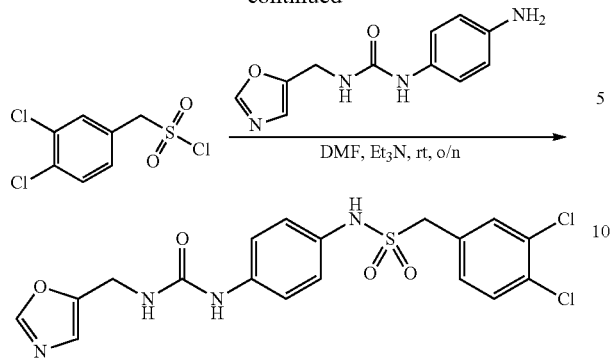

Step 1: A solution of 1,2-dichloro-4-chloromethyl-benzene (1.0 g, 5.1 mmoL) and potassium thioacetate (0.87 g, 7.6 mmoL) in acetone (25 mL) was stirred at 65° C. for 19 hrs. The reaction mixture was filtered and the filtrate was concentrated to dryness in vacuum. The residue was purified by silica gel column (PE/EA=25/1) to give thioacetic acid S-(3,4-dichloro-benzyl) ester (1.25 g, crude) as brown oil. $^1$H NMR (400 MHz, CDCl$_3$): δ=7.38 (d, J=2.0 Hz, 1H), 7.35 (d, J=8.4 Hz, 1H), 7.12 (dd, J=8.0, 3.0 Hz, 1H), 4.04 (s, 2H), 2.36 (s, 3H).

Step 2: To a solution of concentrated HCl (0.5 mL) in MeCN (10 mL) was added NCS (1.14 g, 8.51 mmoL) at 0° C. The reaction mixture was stirred for 15 min. Then a solution of thioacetic acid S-(3,4-dichloro-benzyl) ester (500 mg, 2.13 mmoL) in MeCN (1 mL) was added to the reaction mixture dropwise. Then the mixture was stirred at 0° C. for 30 min. The reaction mixture was concentrated to dryness in vacuum and the residue was purified by silica gel column (PE/EA=20/1) to give (3,4-dichloro-phenyl)-methanesulfonyl chloride (248 mg, yield 45%) as a yellow solid. $^1$H NMR (300 MHz, CDCl$_3$): δ=7.60-7.55 (m, 2H), 7.35 (dd, J=8.1, 1.2 Hz, 1H), 4.82 (s, 2H).

Step 3: To a solution of 1-(4-amino-phenyl)-3-oxazol-5-ylmethyl-urea (100 mg, 0.43 mmoL) and Et$_3$N (0.1 mL, 0.69 mmoL) in DMF (3 mL) was added (3,4-dichloro-phenyl)-methanesulfonyl chloride (123 mg, 0.47 mmoL) at 0° C. The mixture was stirred at 35° C. for 7 hrs. The reaction mixture was poured into H$_2$O (20 mL) and extracted with EA (20 mL×5). The combined organic layer was washed with H$_2$O (50 mL) and brine (60 mL×3), dried over Na$_2$SO$_4$, filtered and concentrated to dryness in vacuum. The residue was purified by silica flash column (5% MeOH in DCM) and triturated with MeCN (2.5 mL) to give C-(3,4-dichloro-phenyl)-N-[4-(3-oxazol-5-ylmethyl-ureido)-phenyl]-methanesulfonamide (41 mg, yield 21%) as a white solid. $^1$H NMR (400 MHz, DMSO-d$_6$): δ=9.62 (s, 1H), 8.58 (s, 1H), 8.29 (s, 1H), 7.64 (d, J=8.4 Hz, 1H), 7.50 (d, J=2.0 Hz, 1H), 7.35 (dd, J=6.8, 1.6 Hz, 2H), 7.25 (dd, J=8.4, 2.0 Hz, 1H), 7.06 (d, J=8.8 Hz, 2H), 7.00 (s, 1H), 6.59 (t, J=6.0 Hz, 1H), 4.45 (s, 2H), 4.36 (d, J=5.6 Hz, 2H). MS: m/z 454.8 (M+H$^+$).

Example 595: Synthesis of C-(3-Chloro-phenyl)-N-{4-[3-(1H-pyrazol-4-ylmethyl)-ureido]-phenyl}-methanesulfonamide

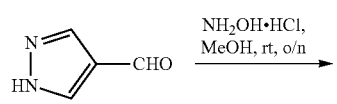

-continued

Step 1: A solution of 1H-pyrazole-4-carbaldehyde (2.05 g, 21.4 mmoL) and hydroxylamine hydrochloride (1.63 g, 23.5 mmoL) in MeOH (50 mL) was stirred at room temperature for 19 hrs. The reaction mixture was concentrated to give 1H-pyrazole-4-carbaldehyde oxime (3.3 g, crude) as a yellow solid.

Step 2: To a solution of 1H-pyrazole-4-carbaldehyde oxime (300 mg, 2.7 mmol) in MeOH (25 mL) was added NH$_3$·H$_2$O (2 mL) and Raney-Ni (50 mg). The suspension was stirred at room temperature for 24 hrs under H$_2$ atmosphere (balloon). The reaction mixture was filtered to remove most of catalyst and the filtrate was concentrated to dryness in vacuum. Then the residue was diluted with MeOH (15 mL) and the mixture was filtered again. The filtrate was concentrated to give c-(1H-pyrazol-4-yl)-methylamine (123 mg, yield 47%) as a green solid.

Step 3: To a solution of (4-amino-phenyl)-carbamic acid tert-butyl ester (150 mg, 0.72 mmol) and Et$_3$N (0.2 mL, 1.4 mmoL) in DCM (5 mL) was added (3-chloro-phenyl)-methanesulfonyl chloride (178 mg, 0.79 mmoL) at 0° C. The reaction mixture was stirred at room temperature for 19 hrs. The reaction mixture was concentrated to dryness in vacuum. Then the residue was purified by silica gel column (PE/EA=5/1) to give [4-(3-chloro-phenylmethanesulfonylamino)-phenyl]-carbamic acid tert-butyl ester (128 mg, yield 45%) as a red solid.

Step 4: A solution of [4-(3-chloro-phenylmethanesulfonylamino)-phenyl]-carbamic acid tert-butyl ester (128 mg, 0.32 mmol) in HCl/MeOH (5 M, 5 mL, 25 mmol) was stirred at room temperature for 19 hrs. The reaction mixture was concentrated to dryness in vacuum and the residue was dissolved in EA (20 mL). The organic layer was washed with saturated aqueous NaHCO₃ (40 mL), dried over Na₂SO₄, filtered and concentrated to give N-(4-amino-phenyl)-C-(3-chloro-phenyl)-methanesulfonamide (95 mg, yield 99%) as a white solid.

Step 5: To a solution of N-(4-amino-phenyl)-C-(3-chloro-phenyl)-methanesulfonamide (95 mg, 0.32 mmol) and pyridine (101 mg, 1.28 mmol) in DCM (5 mL) was added phenyl chloroformate (65 mg, 0.42 mmol) at 0° C. The reaction mixture was stirred for 30 min at 0° C. The reaction mixture was diluted with DCM (25 mL), washed with 1 M HCl (20 mL) and saturated aqueous NaHCO₃ (20 mL), dried over Na₂SO₄, filtered and concentrated to dryness in vacuum. Then the residue was purified by silica flash column (19% EA in PE) to give [4-(3-chloro-phenylmethanesulfonylamino)-phenyl]-carbamic acid phenyl ester (98 mg, yield 74%) as a white solid.

Step 6: A solution of [4-(3-chloro-phenylmethanesulfonylamino)-phenyl]-carbamic acid phenyl ester (100 mg, 0.24 mmol), C-(1H-pyrazol-4-yl)-methylamine (103 mg, 1.06 mmol) and Et₃N (0.5 mL, 3.5 mmol) in MeCN (10 mL) was stirred at 80° C. for 1 hr. The reaction mixture was concentrated to dryness in vacuum. The residue was dissolved in DMF (2 mL). H₂O (1 mL) was added into the mixture and the resulting solid was collected by filtration. Then the pad was dissolved in DMF (1.5 mL) again and H₂O was added into the mixture. The mixture was filtered and the pad was rinsed with H₂O to give C-(3-chloro-phenyl)-N-{4-[3-(1H-pyrazol-4-ylmethyl)-ureido]-phenyl}-methanesulfonamide (19 mg, yield 19%) as a white solid. ¹H NMR (400 MHz, DMSO-d₆): δ=9.60 (s, 1H), 8.42 (s, 1H), 7.53 (s, 2H), 7.43-7.34 (m, 5H), 7.22 (d, J=7.2 Hz, 1H), 7.06 (d, J=8.4 Hz, 2H), 6.30 (t, J=5.60 Hz, 1H), 4.42 (s, 2H), 4.14 (d, J=5.2 Hz, 2H). MS: m/z 419.9 (M+H⁺).

Example 596: Synthesis of C-(2-Chloro-phenyl)-N-{4-[3-(1H-pyrazol-4-ylmethyl)-ureido]-phenyl}-methanesulfonamide

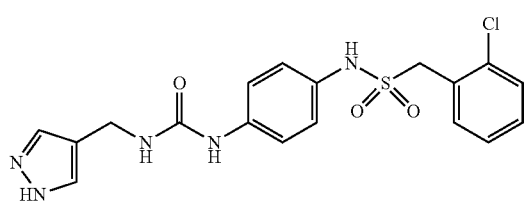 [SMILES: O=C(NCc1cn[nH]c1)Nc1ccc(NS(=O)(=O)Cc2ccccc2Cl)cc1]

The title compound was prepared using general procedure of C-(3-chloro-phenyl)-N-{4-[3-(1H-pyrazol-4-ylmethyl)-ureido]-phenyl}-methanesulfonamide. ¹H NMR (400 MHz, CD₃OD): δ=7.60 (s, 2H), 7.45 (dd, J=7.2, 2.4 Hz, 1H), 7.39 (dd, J=8.0, 2.4 Hz, 1H), 7.31-7.28 (m, 4H), 7.12 (dd, J=6.8, 2.0 Hz, 2H), 4.57 (s, 2H), 4.28 (s, 2H). MS: m/z 419.9 (M+H⁺).

Example 597: Synthesis of C-(4-Chloro-phenyl)-N-{4-[3-(1H-pyrazol-4-ylmethyl)-ureido]-phenyl}-methanesulfonamide

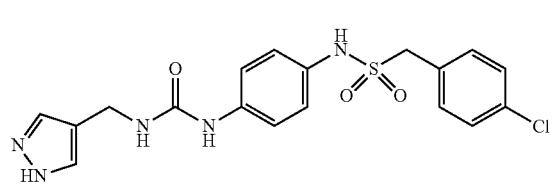 [SMILES: O=C(NCc1cn[nH]c1)Nc1ccc(NS(=O)(=O)Cc2ccc(Cl)cc2)cc1]

The title compound was prepared using general procedure of C-(3-chloro-phenyl)-N-{4-[3-(1H-pyrazol-4-ylmethyl)-ureido]-phenyl}-methanesulfonamide. ¹H NMR (400 MHz, DMSO-d₆): δ=9.55 (s, 1H), 8.45 (s, 1H), 7.55 (s, 2H), 7.43 (d, J=8.4 Hz, 2H), 7.35 (d, J=8.4 Hz, 2H), 7.28 (d, J=8.4 Hz, 2H), 7.06 (d, J=9.2 Hz, 2H), 6.33 (s, 1H), 4.38 (s, 2H), 4.14 (d, J=2.4 Hz, 2H). MS: m/z 419.9 (M+H⁺).

Example 598: Synthesis of C-(3,4-Dichloro-phenyl)-N-{4-[3-(1H-pyrazol-4-ylmethyl)-ureido]-phenyl}-methanesulfonamide

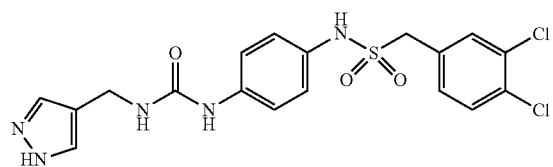 [SMILES: O=C(NCc1cn[nH]c1)Nc1ccc(NS(=O)(=O)Cc2ccc(Cl)c(Cl)c2)cc1]

The title compound was prepared using general procedure of C-(3-chloro-phenyl)-N-{4-[3-(1H-pyrazol-4-ylmethyl)-ureido]-phenyl}-methanesulfonamide. ¹H NMR (400 MHz, DMSO-d₆): δ=9.60 (s, 1H), 8.45 (s, 1H), 7.65 (d, J=8.4 Hz, 1H), 7.55-7.51 (m, 3H), 7.35 (d, J=8.8 Hz, 2H), 7.25 (dd, J=8.4, 2.0 Hz, 1H), 7.06 (d, J=8.8 Hz, 2H), 6.32 (s, 1H), 4.45 (s, 2H), 4.14 (s, 2H). MS: m/z 453.9 (M+H⁺).

Example 599: Synthesis of N-(3-Fluoro-benzyl)-4-[3-(1H-pyrazol-4-ylmethyl)-ureido]-benzenesulfonamide

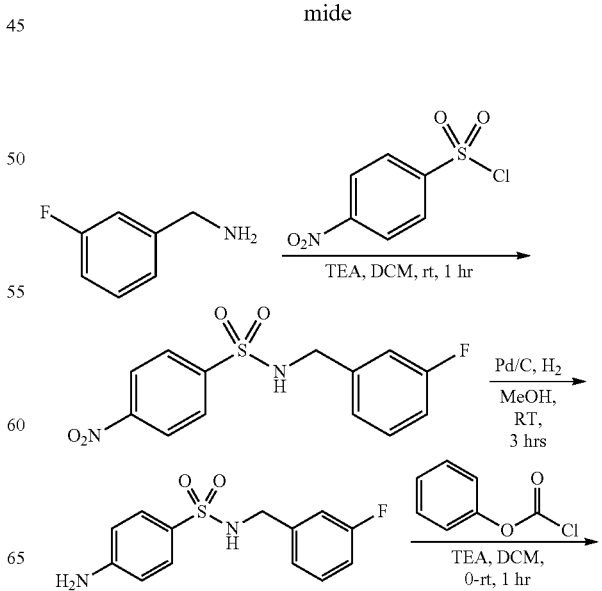

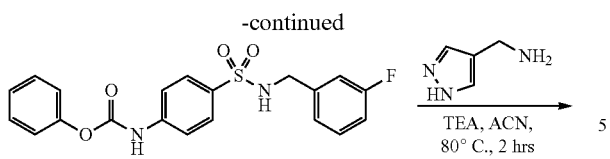

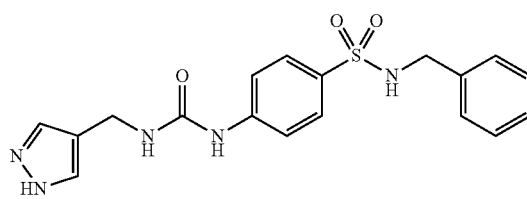

Step 1: To a solution of 3-fluoro-benzylamine (282.8 mg, 2.26 mmol) in DCM (20 mL) was added 4-nitro-benzenesulfonyl chloride (500.8 mg, 2.26 mmol) and TEA (228.3 mg, 2.26 mmol). The mixture was stirred at room temperature for 1 hr. The mixture was concentrated in vacuum. The residue was purified by a silica gel column (DCM) to afford n-(3-fluoro-benzyl)-4-nitro-benzenesulfonamide (636.4 mg, yield 91%) as a yellow solid. $^1$H NMR (400 MHz, DMSO-$d_6$) δ=8.62 (t, J=6.0 Hz, 1H), 8.36 (d, J=8.8 Hz, 2H), 8.00 (d, J=9.2 Hz, 2H), 7.33-7.27 (m, 1H), 7.07-7.00 (m, 3H), 4.10 (d, J=6.4 Hz, 2H).

Step 2: To a solution of n-(3-fluoro-benzyl)-4-nitro-benzenesulfonamide (636.4 mg, 2.1 mmol) in MeOH (30 mL) was added Pd/C (10% wet, 93.3 mg). The reaction mixture was stirred at room temperature under $H_2$ (1 atm) for 3 hrs. Pd/C was filtered off and the filtrate was concentrated to dryness in vacuum. The residue was purified by flash to give 4-amino-n-(3-fluoro-benzyl)-benzenesulfonamide (474 mg, yield 81%) as a white solid.

Step 3: To a solution of 4-amino-n-(3-fluoro-benzyl)-benzenesulfonamide (300 mg, 1.07 mmol) in DCM (30 mL) was added phenyl chloroformate (502.59 mg, 3.21 mmol) and TEA (324.85 mg, 3.21 mmol). The mixture was stirred at 0° C. for 1 hr. The reaction mixture was concentrated in vacuum. The residue was purified by a silica gel column (PE/EA=3/1) to afford [4-(3-fluoro-benzylsulfamoyl)-phenyl]-carbamic acid phenyl ester (256.7 mg, yield 60%) as a white solid.

Step 4: To a solution of [4-(3-fluoro-benzylsulfamoyl)-phenyl]-carbamic acid phenyl ester (256.7 mg, 0.64 mmol) in ACN (40 mL) was added C-(1 h-pyrazol-4-yl)-methylamine (124.31 mg, 1.28 mmol) and TEA (129.54 mg, 1.28 mmol). The reaction mixture was stirred at 80° C. overnight. The mixture was concentrated in vacuum. The residue was purified by prep-HPLC to give N-(3-fluoro-benzyl)-4-[3-(1H-pyrazol-4-ylmethyl)-ureido]-benzenesulfonamide (11 mg, yield 4%) as a white solid. $^1$H NMR (400 MHz, DMSO-$d_6$): δ=9.60 (s, 1H), 8.04 (t, J=6.4 Hz, 1H), 7.64 (d, J=9.2 Hz, 2H), 7.60-7.49 (m, 4H), 7.37-7.28 (m, 1H), 7.12-7.00 (m, 3H), 6.93 (t, J=4.8 Hz, 1H), 4.16 (d, J=4.8 Hz, 2H), 3.95 (d, J=6.4 Hz, 2H). MS: m/z 403.9 (M+H$^+$).

Example 600: Synthesis of N-(4-Methyl-benzyl)-4-[3-(1H-pyrazol-4-ylmethyl)-ureido]-benzenesulfonamide

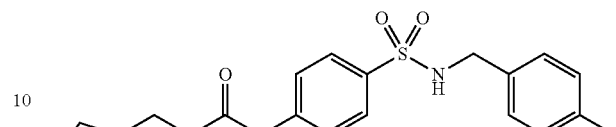

The title compound was prepared using general procedure of N-(3-Fluoro-benzyl)-4-[3-(1H-pyrazol-4-ylmethyl)-ureido]-benzenesulfonamide. $^1$H NMR (400 MHz, CD$_3$OD): δ=7.68 (d, J=8.8 Hz, 2H), 7.60 (s, 2H), 7.53 (d, J=8.8 Hz, 2H), 7.09-7.02 (m, 4H), 4.30 (s, 2H), 3.96 (s, 2H), 2.26 (s, 3H). MS: m/z 400.0 (M+H$^+$).

Example 601: Synthesis of 1-[4-(1,6-Dimethyl-1H-indazol-3-yl)-phenyl]-3-pyridin-4-ylmethyl-urea

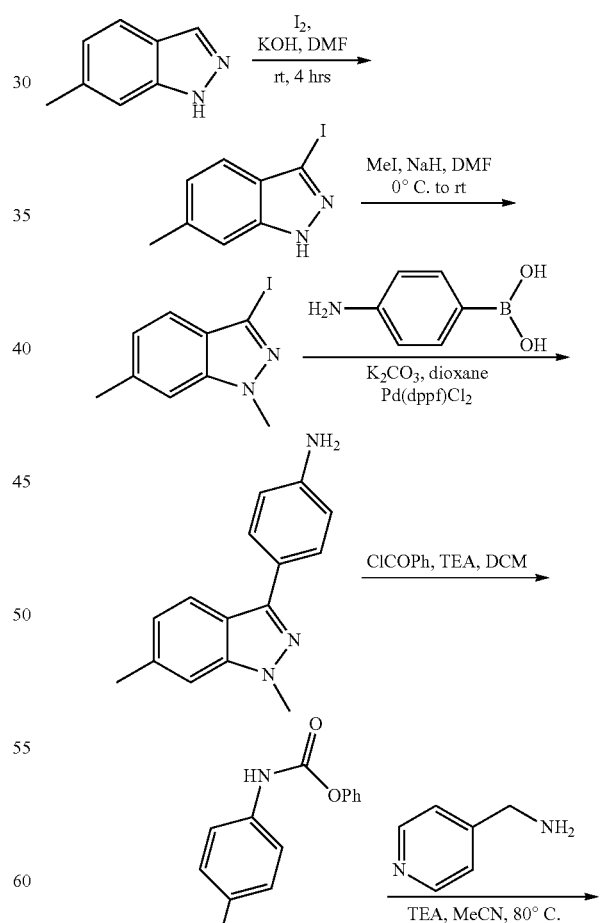

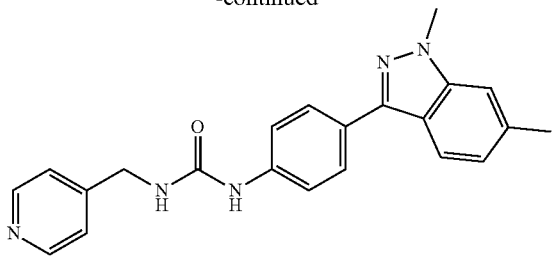

Step 1: A solution of 6-methyl-1H-indazole (1.5 g, 11.4 mmoL), KOH (1.6 g, 28.6 mmoL) and I₂ (5.77 g, 22.7 mmoL) in DMF (40 mL) was stirred at room temperature for 4 hrs. The reaction mixture was poured into H₂O (200 mL) and extracted with EA (200 mL). The EA layer was washed with saturated aqueous NaSO₃ (100 mL), H₂O (200 mL), brine (200 mL), dried over Na₂SO₄ and concentrated to give 3-iodo-6-methyl-1H-indazole (2.25 g, yield: 78%) as a yellow solid.

Step 2: To a solution of 3-iodo-6-methyl-1H-indazole (2.25 g, 8.7 mmoL) in DMF (15 mL) was added NaH (420 mg, 10.5 mmoL) at 0° C. and the mixture was stirred at room temperature for 40 min under N₂ atmosphere (balloon). Then MeI (0.65 mL, 10.4 mmoL) was added into the reaction mixture and the mixture was stirred at room temperature for 1 hr. The reaction mixture was poured into H₂O (100 mL) and extracted with EA (100 mL). The EA layer was washed with H₂O (100 mL), brine (100 mL), dried over Na₂SO₄ and concentrated to dryness in vacuum. The residue was purified by silica flash column (9% EA in PE) to give 3-iodo-1,6-dimethyl-1H-indazole (1.62 g, yield: 68%) as a yellow solid. ¹H NMR (400 MHz, CDCl₃): δ=7.33 (d, J=8.4 Hz, 1H), 7.13 (s, 1H), 7.03 (d, J=8.0 Hz, 1H), 4.05 (s, 3H), 2.51 (s, 3H). MS: m/z 273.2 (M+H⁺).

Step 3: A suspension of 3-iodo-1,6-dimethyl-1H-indazole (1.1 g, 4.04 mmoL), HCl salt of 4-aminobenzeneboronic acid (0.84 g, 4.84 mmoL), K₂CO₃ (1.4 g, 10.14 mmoL) and Pd(dppf)Cl₂ (296 mg, 0.4 mmoL) in dioxane/H₂O (15 mL/2 mL) was stirred at 80° C. for 19 hrs under N₂ atmosphere (balloon). The reaction mixture was poured into H₂O (200 mL) and extracted with EA (150 mL). The EA layer was washed with brine (150 mL), dried over Na₂SO₄ and concentrated to dryness in vacuum. The residue was purified by silica gel column (PE/EA=5/1) to give 4-(1,6-dimethyl-1H-indazol-3-yl)-phenylamine (670 mg, yield: 48%) as a yellow solid. MS: m/z 238.4 (M+H⁺).

Step 4: To a solution of 4-(1,6-dimethyl-1H-indazol-3-yl)-phenylamine (670 mg, 2.8 mmoL) and TEA (1.2 mL, 8.3 mmoL) in DCM (8 mL) was added chloro-formicaciphenyl-lester (575 mg, 3.7 mmoL) at 0° C. and the mixture was stirred at room temperature for 1 hr. The reaction mixture was poured into H₂O (50 mL) and extracted with EA (50 mL). The EA layer was washed with brine (50 mL), dried over Na₂SO₄ and concentrated to dryness in vacuum. The residue was purified by silica flash column (21% EA in PE) to give [4-(1,6-dimethyl-1H-indazol-3-yl)-phenyl]-carbamic acid phenyl ester (490 mg, yield: 49%) as a white solid. MS: m/z 358.5 (M+H⁺).

Step 5: A solution of [4-(1,6-dimethyl-1H-indazol-3-yl)-phenyl]-carbamic acid phenyl ester (100 mg, 0.28 mmoL), c-pyridin-4-yl-methylamine (45 mg, 0.42 mmoL) and TEA (0.2 mL, 1.39 mmoL) in MeCN (4 mL) was stirred at 80° C. for 3 hrs. H₂O (20 mL) was added into the mixture and the resulting solid was collected by filtration. Then the pad was dissolved in DMSO/MeOH (0.5 mL/1 mL) and standing there overnight. Then the mixture was filtered and the pad was rinsed with MeOH to give 1-[4-(1,6-dimethyl-1H-indazol-3-yl)-phenyl]-3-pyridin-4-ylmethyl-urea (6.8 mg, yield: 7%) as a white solid. ¹H NMR (400 MHz, DMSO-d₆): δ=8.84 (s, 1H), 8.51 (d, J=5.6 Hz, 2H), 7.91 (d, J=8.0 Hz, 1H), 7.83 (d, J=8.4 Hz, 2H), 7.55 (d, J=8.8 Hz, 2H), 7.43 (s, 1H), 7.31 (d, J=6.0 Hz, 2H), 7.04 (d, J=8.4 Hz, 1H), 6.78 (t, J=5.6 Hz, 1H), 4.35 (d, J=6.0 Hz, 2H), 4.03 (s, 3H), 2.48 (s, 3H). MS: m/z 372.2 (M+H⁺).

Example 602: Synthesis of 1-[4-(1,6-Dimethyl-1H-indazol-3-yl)-phenyl]-3-(1H-pyrazol-4-ylmethyl)-urea

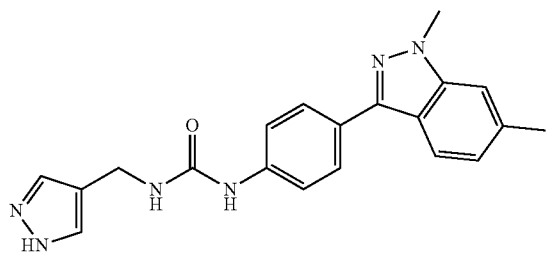 [SMILES: Cc1ccc2c(-c3ccc(NC(=O)NCc4cn[nH]c4)cc3)nn(C)c2c1]

The title compound was prepared using general procedure of 1-[4-(1,6-dimethyl-1H-indazol-3-yl)-phenyl]-3-pyridin-4-ylmethyl-urea. ¹H NMR (400 MHz, DMSO-d₆): δ=12.64 (brs, 1H), 8.66 (dd, J=10.8, 4.4 Hz, 1H), 7.92 (d, J=8.8 Hz, 1H), 7.82 (d, J=8.8 Hz, 2H), 7.59-7.50 (m, 4H), 7.43 (s, 1H), 7.03 (d, J=8.4 Hz, 1H), 6.43 (s, 1H), 4.17 (d, J=4.8 Hz, 2H), 4.03 (s, 3H), 2.47 (s, 3H). MS: m/z 361.1 (M+H⁺).

Example 603: Synthesis of 1-[4-(1,6-Dimethyl-1H-indazol-3-yl)-phenyl]-3-oxazol-5-ylmethyl-urea

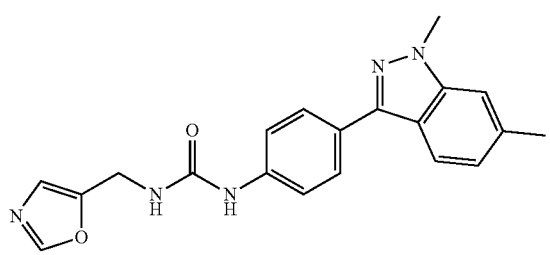 [SMILES: Cc1ccc2c(-c3ccc(NC(=O)NCc4cnco4)cc3)nn(C)c2c1]

The title compound was prepared using general procedure of 1-[4-(1,6-dimethyl-1H-indazol-3-yl)-phenyl]-3-pyridin-4-ylmethyl-urea. ¹H NMR (400 MHz, DMSO-d₆): δ=8.72 (s, 1H), 8.30 (s, 1H), 7.92 (d, J=8.4 Hz, 1H), 7.83 (d, J=4.8 Hz, 2H), 7.53 (d, J=8.4 Hz, 2H), 7.43 (s, 1H), 7.05-7.03 (m, 2H), 6.66 (t, J=5.6 Hz, 1H), 4.39 (d, J=5.6 Hz, 2H), 4.03 (s, 3H), 2.48 (s, 3H). MS: m/z 362.1 (M+H⁺).

Example 604: Synthesis of 1-[4-(1-Methyl-1H-pyrazolo[3,4-b]pyridin-3-yl)-phenyl]-3-oxazol-5-ylmethyl-urea

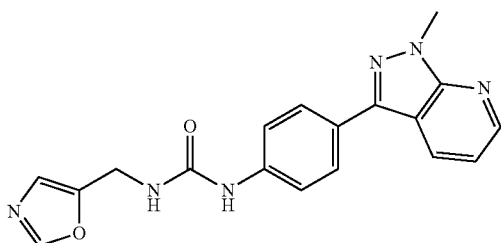

The title compound was prepared using general procedure of 1-[4-(1,6-dimethyl-1H-indazol-3-yl)-phenyl]-3-pyridin-4-ylmethyl-urea. $^1$H NMR (400 MHz, DMSO-d$_6$): δ=8.78 (s, 1H), 8.60-8.56 (m, 2H), 8.30 (s, 1H), 7.90 (d, J=8.8 Hz, 2H), 7.56 (d, J=8.8 Hz, 2H), 7.28 (dd, J=8.4, 4.4 Hz, 1H), 7.03 (s, 1H), 6.69 (t, J=5.6 Hz, 1H), 4.39 (d, J=6.0 Hz, 2H), 4.10 (s, 3H). MS: m/z 349.0 (M+H$^+$).

Example 605: Synthesis of 1-[4-(1-Methyl-1H-pyrazolo[3,4-b]pyridin-3-yl)-phenyl]-3-pyridin-4-ylmethyl-urea

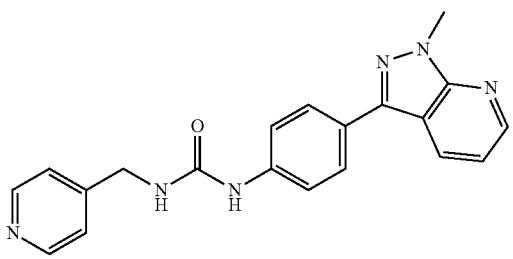 [SMILES: Cn1nc(-c2ccc(NC(=O)NCc3ccncc3)cc2)c2cccnc21]

The title compound was prepared using general procedure of 1-[4-(1,6-dimethyl-1H-indazol-3-yl)-phenyl]-3-pyridin-4-ylmethyl-urea. $^1$H NMR (400 MHz, DMSO-d$_6$): δ=8.92 (s, 1H), 8.60-8.56 (m, 2H), 8.52-8.51 (m, 2H), 7.90 (d, J=8.8 Hz, 2H), 7.58 (d, J=8.8 Hz, 2H), 7.32-7.27 (m, 3H), 6.83-6.80 (m, 1H), 4.36 (d, J=6.0 Hz, 2H), 4.10 (s, 3H). MS: m/z 359.1 (M+H$^+$).

Example 606: Synthesis of 1-[4-(1-Methyl-1H-pyrazolo[3,4-b]pyridin-3-yl)-phenyl]-3-(1H-pyrazol-4-ylmethyl)-urea

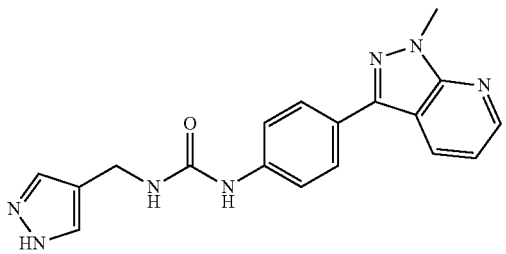 [SMILES: Cn1nc(-c2ccc(NC(=O)NCc3cn[nH]c3)cc2)c2cccnc21]

The title compound was prepared using general procedure of 1-[4-(1,6-dimethyl-1H-indazol-3-yl)-phenyl]-3-pyridin-4-ylmethyl-urea. $^1$H NMR (400 MHz, DMSO-d$_6$): δ=12.57 (brs, 1H), 8.62-8.56 (m, 3H), 7.89 (d, J=8.4 Hz, 2H), 7.57-7.55 (m, 4H), 7.28 (dd, J=8.0, 4.8 Hz, 1H), 6.39 (t, J=5.6 Hz, 1H), 4.17 (d, J=5.2 Hz, 2H), 4.10 (s, 3H). MS: m/z 348.1 (M+H$^+$).

Example 607: Synthesis of 1-[4-(1-Methyl-1H-pyrazolo[4,3-b]pyridin-3-yl)-phenyl]-3-oxazol-5-ylmethyl-urea

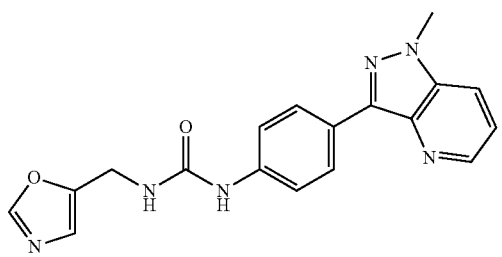 [SMILES: Cn1nc(-c2ccc(NC(=O)NCc3cnco3)cc2)c2ncccc21]

The title compound was prepared using general procedure of 1-[4-(1,6-dimethyl-1H-indazol-3-yl)-phenyl]-3-pyridin-4-ylmethyl-urea. $^1$H NMR (400 MHz, DMSO-d$_6$): δ=8.73 (s, 1H), 8.60 (dd, J=4.4, 1.2 Hz, 1H), 8.35 (d, J=8.4 Hz, 2H), 8.29 (s, 1H), 8.16 (dd, J=8.8, 1.2 Hz, 1H), 7.53 (d, J=8.8 Hz, 2H), 7.45 (dd, J=8.8, 4.4 Hz, 1H), 7.03 (s, 1H), 6.67 (t, J=5.6 Hz, 1H), 4.39 (d, J=6.0 Hz, 2H), 4.11 (s, 3H). MS: m/z 349.1 (M+H$^+$).

Example 608: Synthesis of 1-[4-(1-Methyl-1H-pyrazolo[4,3-b]pyridin-3-yl)-phenyl]-3-pyridin-4-ylmethyl-urea

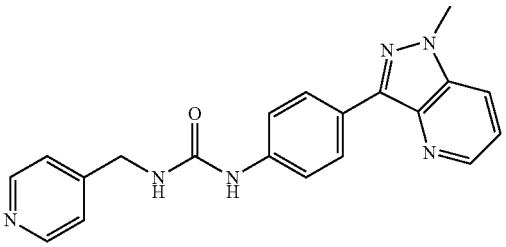 [SMILES: Cn1nc(-c2ccc(NC(=O)NCc3ccncc3)cc2)c2ncccc21]

The title compound was prepared using general procedure of 1-[4-(1,6-dimethyl-1H-indazol-3-yl)-phenyl]-3-pyridin-4-ylmethyl-urea. $^1$H NMR (400 MHz, DMSO-d$_6$): δ=8.87 (s, 1H), 8.60 (dd, J=4.4, 1.6 Hz, 1H), 8.51 (d, J=4.8 Hz, 2H), 8.36 (d, J=8.8 Hz, 2H), 8.16 (dd, J=8.4, 0.8 Hz, 1H), 7.55 (d, J=8.4 Hz, 2H), 7.45 (dd, J=8.4, 4.4 Hz, 1H), 7.31 (d, J=6.0 Hz, 2H), 6.79 (t, J=6.0 Hz, 1H), 4.35 (d, J=6.0 Hz, 2H), 4.11 (s, 3H). MS: m/z 359.1 (M+H$^+$).

Example 609: Synthesis of 1-[4-(1-Methyl-1H-pyrazolo[4,3-b]pyridin-3-yl)-phenyl]-3-(1H-pyrazol-4-ylmethyl)-urea

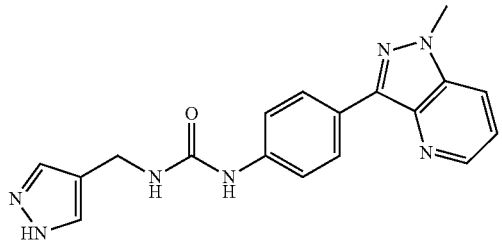 [SMILES: Cn1nc(-c2ccc(NC(=O)NCc3cn[nH]c3)cc2)c2ncccc21]

The title compound was prepared using general procedure of 1-[4-(1,6-dimethyl-1H-indazol-3-yl)-phenyl]-3-pyridin-4-ylmethyl-urea. $^1$H NMR (400 MHz, DMSO-d$_6$): δ=12.62 (brs, 1H), 8.61-8.57 (m, 2H), 8.35 (d, J=8.4 Hz, 2H), 8.16 (dd, J=8.8, 1.6 Hz, 1H), 7.53 (d, J=8.8 Hz, 4H), 7.45 (dd, J=8.8, 4.4 Hz, 1H), 6.37 (t, J=5.6 Hz, 1H), 4.17 (d, J=4.2 Hz, 2H), 4.11 (s, 3H). MS: m/z 348.1 (M+H$^+$).

Example 610: Synthesis of 1-[4-(1H-Indazol-3-yl)-phenyl]-3-pyridin-4-ylmethyl-urea

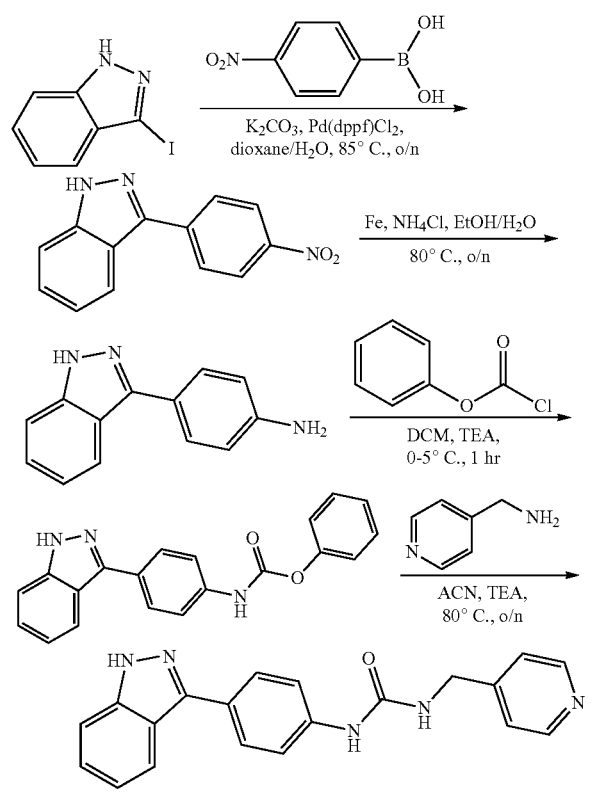

Step 1: To a solution of 3-iodo-1H-indazole (2.4 g, 10.0 mmol) in dioxane (30 mL) and H$_2$O (10 mL) was added 4-nitrophenylboronic acid (2.5 g, 15.0 mmol) and K$_2$CO$_3$ (4.14 g, 30 mmol), Pd(dppf)Cl2 (731.7 mg, 1.0 mmol), the mixture was stirred at 80° C. overnight. The reaction was monitored by TLC. After completion, the mixture was filtered, the filtrate was concentrated in vacuum to give a residue, which was purified by a silica gel column (PE/EA=3/1) to afford 3-(4-nitro-phenyl)-1H-indazole (1.69 g, yield: 70.7%) as a yellow solid.

Step 2: To a solution of 3-(4-nitro-phenyl)-1H-indazole (600 mg, 2.5 mmol) in EtOH (35 mL) and H$_2$O (5 mL) was added NH$_4$Cl (671.29 mg, 12.5 mmol), iron powder (700.9 mg, 12.5 mmol). The reaction mixture was stirred at 80° C. overnight. Iron powder was filtered off and the filtrate was concentrated in vacuum to give a residue, which was purified by flash to give 4-(1 h-indazol-3-yl)-phenylamine (465 mg, yield: 88.7%) as a Brown solid. $^1$H NMR (400 MHz, DMSO-d$_6$): δ=12.89 (s, 1H), 7.97 (d, J=8.0 Hz, 1H), 7.65 (d, J=8.4 Hz, 2H), 7.51 (d, J=8.4 Hz, 1H), 7.35 (t, J=6.8 Hz, 1H), 7.13 (d, J=7.2 Hz, 1H), 6.69 (t, J=8.4 Hz, 2H), 5.32 (s, 2H).

Step 3: To a solution of 4-(h-Indazol-3-yl)-phenylamine (465 mg, 2.2 mmol) in DCM (30 mL) was added phenyl chloroformate (688.9 mg, 4.4 mmol) and TEA (455.2 mg, 4.4 mmol), the mixture was stirred at 0° C. for 1 hr. The reaction was monitored by TLC. After completion, the mixture was concentrated in vacuum to give a residue, which was purified by a silica gel column (PE/EA=3/1) to afford [4-(1 h-indazol-3-yl)-phenyl]-carbamic acid phenyl ester (625.3 mg, yield: 85.4%) as a white solid.

Step 4: To a solution of [4-(h-indazol-3-yl)-phenyl]-carbamic acid phenyl ester (200 mg, 0.61 mmol) in ACN (30 mL) was added c-pyridin-4-yl-methylamine (197.89 mg, 1.83 mmol) and TEA (185.2 mg, 1.83 mmol), the mixture was stirred at 80° C. for 3 hrs. The reaction was monitored by LCMS. After completion, the mixture was concentrated in vacuum to give a residue, the residue was purified by prep-HPLC to give 1-[4-(h-Indazol-3-yl)-phenyl]-3-pyridin-4-ylmethyl-urea (6.7 mg, yield: 3.2%) as a white solid. $^1$H NMR (400 MHz, DMSO-d$_6$): δ=13.09 (s, 1H), 8.88 (s, 1H), 8.52 (d, J=6.0 Hz, 1H), 8.04 (d, J=8.4 Hz, 1H), 7.87 (d, J=8.4 Hz, 2H), 7.60-7.51 (m, 3H), 7.38 (t, J=7.6 Hz, 1H), 7.31 (d, J=5.6 Hz, 2H), 7.18 (t, J=7.6 Hz, 1H), 6.79 (t, J=6.0 Hz, 1H) 4.36 (d, J=6.0 Hz, 2H). MS: m/z 344.0 (M+H$^+$).

Example 611: Synthesis of 1-[4-(1H-Indazol-3-yl)-phenyl]-3-oxazol-5-ylmethyl-urea

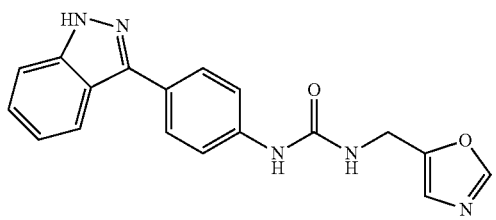 [SMILES: O=C(NCc1cnco1)Nc1ccc(-c2n[nH]c3ccccc23)cc1]

The title compound was prepared using general procedure of 1-[4-(1H-Indazol-3-yl)-phenyl]-3-pyridin-4-ylmethyl-urea. $^1$H NMR (400 MHz, DMSO-d$_6$): δ=13.09 (s, 1H), 8.83 (s, 1H), 8.30 (s, 1H), 8.04 (d, J=8.0 Hz, 1H), 7.86 (d, J=8.4 Hz, 2H), 7.55 (d, J=8.8 Hz, 3H), 7.38 (t, J=6.8 Hz, 1H), 7.17 (t, J=7.2 Hz, 1H), 7.03 (s, 1H), 6.76 (t, J=6.0 Hz, 1H), 4.39 (d, J=5.2 Hz, 2H). MS: m/z 334.0 (M+H$^+$).

Example 612: Synthesis of 1-[4-(1H-Indazol-3-yl)-phenyl]-3-(1H-pyrazol-4-ylmethyl)-urea

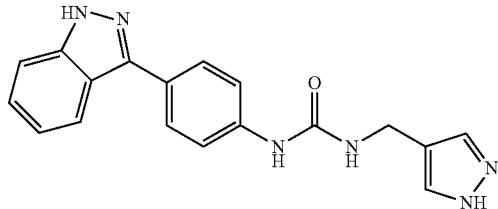 [SMILES: O=C(NCc1cn[nH]c1)Nc1ccc(-c2n[nH]c3ccccc23)cc1]

The title compound was prepared using general procedure of 1-[4-(1H-Indazol-3-yl)-phenyl]-3-pyridin-4-ylmethyl-urea. ¹H NMR (400 MHz, DMSO-d₆): δ=13.08 (s, 1H), 12.55 (s, 1H), 8.59 (s, 1H), 8.04 (d, J=8.4 Hz, 1H), 7.85 (d, J=8.4 Hz, 2H), 7.63-7.48 (m, 5H), 7.38 (t, J=6.8 Hz, 1H), 7.17 (t, J=7.2 Hz, 1H), 6.38 (t, J=5.6 Hz, 1H), 4.17 (d, J=4.8 Hz, 2H). MS: m/z 333.0 (M+H⁺).

Example 613: Synthesis of 1-[4-(1-Methyl-1H-indazol-3-yl)-phenyl]-3-pyridin-4-ylmethyl-urea

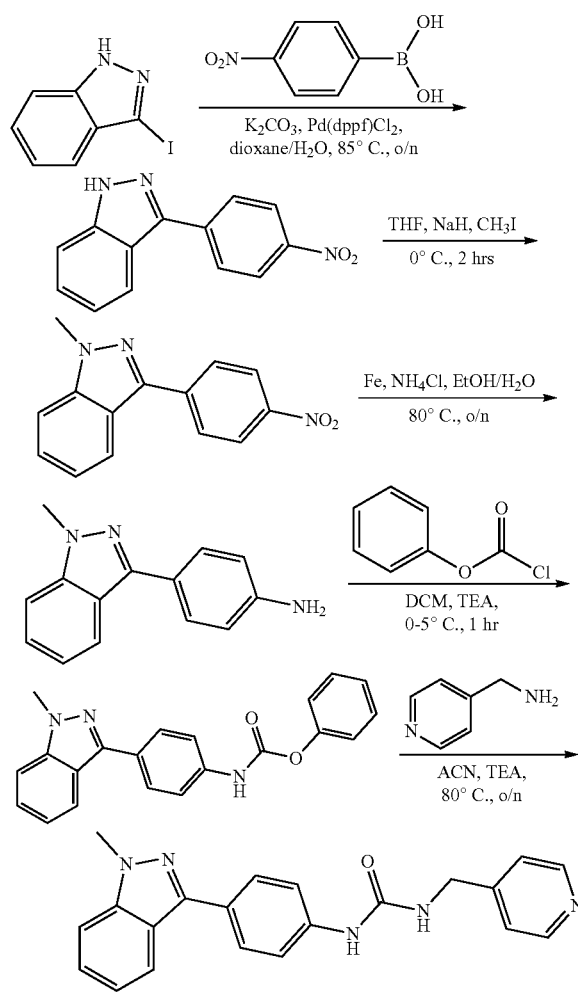

Step 1: To a solution of 3-iodo-1H-indazole (2.4 g, 10.0 mmol) in dioxane (30 mL) and H₂O (10 mL) was added 4-nitrophenylboronic acid (2.5 g, 15.0 mmol) and K₂CO₃ (4.14 g, 30 mmol), Pd(dppf)Cl₂ (731.7 mg, 1.0 mmol), the mixture was stirred at 80° C. overnight. The reaction was monitored by TLC. After completion, the mixture was filtered, the filtrate was concentrated in vacuum to give a residue, which was purified by a silica gel column (PE/EA=3/1) to afford 3-(4-nitro-phenyl)-1H-indazole (1.69 g, yield: 70.7%) as a yellow solid.

Step 2: To a solution of 3-(4-nitro-phenyl)-1H-indazole (500 mg, 2.1 mmol) in THF (20 mL) was added NaH (75.6 mg, 3.15 mmol), MeI (387.49 mg, 2.73 mmol). The reaction mixture was stirred at 0° C., for 1 hr. The mixture was added MeOH and concentrated in vacuum to give a residue, which was purified by a silica gel column (PE/EA=3/1) to give 1-methyl-3-(4-nitro-phenyl)-1H-indazole (408 mg, yield: 77.08%) as a white solid. ¹H NMR (400 MHz, DMSO-d₆): δ=8.36 (d, J=9.2 Hz, 2H), 8.29 (d, J=8.8 Hz, 2H), 8.19 (d, J=8.4 Hz, 1H), 7.78 (d, J=8.4 Hz, 1H), 7.53 (t, J=7.6 Hz, 1H), 7.34 (t, J=8.0 Hz, 1H), 4.18 (s, 3H).

Step 3: To a solution of 1-methyl-3-(4-nitro-phenyl)-1H-indazole (408 mg, 1.6 mmol) in EtOH (25 mL) and H₂O (5 mL) was added NH₄Cl (430.59 mg, 8.05 mmol), iron powder (449.59 mg, 8.0 mmol). The reaction mixture was stirred at 80° C. overnight. Iron powder was filtered off and the filtrate was concentrated in vacuum to give a residue, which was purified by flash to give 4-(1-methyl-1H-indazol-3-yl)-phenylamine (360 mg, yield: 100%) as a Brown solid. ¹H NMR (400 MHz, DMSO-d₆): δ=7.98 (d, J=8.0 Hz, 1H), 7.65-7.58 (m, 3H), 7.40 (t, J=7.2 Hz, 1H), 7.16 (t, J=7.6 Hz, 1H), 6.68 (d, J=8.4 Hz, 2H), 5.31 (s, 2H), 4.04 (s, 3H).

Step 4: To a solution of 4-(1-methyl-1H-indazol-3-yl)-phenylamine (360 mg, 1.6 mmol) in DCM (30 mL) was added phenyl chloroformate (501 mg, 3.2 mmol) and TEA (328.8 mg, 3.2 mmol), the mixture was stirred at 0° C. for 1 hr. The reaction was monitored by TLC. After completion, the mixture was concentrated in vacuum to give a residue, which was purified by a silica gel column (PE/EA=3/1) to afford [4-(1-methyl-1H-indazol-3-yl)-phenyl]-carbamic acid phenyl ester (527 mg, yield: 95.3%) as a white solid.

Step 5: To a solution of [4-(1-methyl-1H-indazol-3-yl)-phenyl]-carbamic acid phenyl ester (100 mg, 0.29 mmol) in ACN (30 mL) was added c-pyridin-4-yl-methylamine (67.27 mg, 0.58 mmol) and TEA (58.09 mg, 0.58 mmol), the mixture was stirred at 80° C. for 3 hrs. The reaction was monitored by LCMS. After completion, the mixture was concentrated in vacuum to give a residue, the residue was purified by prep-HPLC to give 1-[4-(1-methyl-1H-indazol-3-yl)-phenyl]-3-pyridin-4-ylmethyl-urea (50.2 mg, yield: 51.8%) as a white solid. ¹H NMR (400 MHz, DMSO-d₆): δ=8.91 (s, 1H), 8.51 (d, J=5.6 Hz, 2H), 8.05 (d, J=8.0 Hz, 1H), 7.85 (d, J=8.4 Hz, 2H), 7.66 (d, J=8.0 Hz, 1H), 7.56 (d, J=8.8 Hz, 2H), 7.44 (t, J=7.2 Hz, 1H), 7.31 (d, J=6.0 Hz, 2H), 7.21 (t, J=7.2 Hz, 1H), 6.82 (t, J=5.6 Hz, 1H), 4.35 (d, J=6.0 Hz, 2H), 4.08 (s, 3H). MS: m/z 358.0 (M+H⁺).

Example 614: Synthesis of 1-[4-(1-Methyl-1H-indazol-3-yl)-phenyl]-3-oxazol-5-ylmethyl-urea

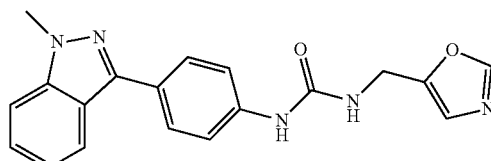

The title compound was prepared using general procedure of 1-[4-(1-methyl-1H-indazol-3-yl)-phenyl]-3-pyridin-4-yl-methyl-urea. ¹H NMR (400 MHz, DMSO-d₆): δ=8.76 (s, 1H), 8.31 (s, 1H), 8.05 (d, J=8.4 Hz, 1H), 7.85 (d, J=8.8 Hz, 2H), 7.66 (d, J=8.4 Hz, 1H), 7.54 (d, J=8.8 Hz, 2H), 7.44 (t, J=7.2 Hz, 1H), 7.21 (t, J=7.2 Hz, 1H), 7.03 (s, 1H), 6.68 (t, J=6.0 Hz, 1H), 4.39 (d, J=5.6 Hz, 2H), 4.08 (s, 3H). MS: m/z 348.0 (M+H⁺).

Example 615: Synthesis of 1-[4-(1-Methyl-1H-indazol-3-yl)-phenyl]-3-(1H-pyrazol-4-ylmethyl)-urea

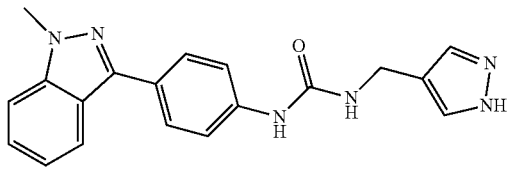 [SMILES: Cn1nc(-c2ccc(NC(=O)NCc3cn[nH]c3)cc2)c2ccccc21]

The title compound was prepared using general procedure of 1-[4-(1-methyl-1H-indazol-3-yl)-phenyl]-3-pyridin-4-yl-methyl-urea. ¹H NMR (400 MHz, DMSO-d₆): δ=12.65 (s, 1H), 8.59 (s, 1H), 8.04 (d, J=8.4 Hz, 1H), 7.83 (d, J=8.8 Hz, 2H), 7.65 (d, J=8.0 Hz, 1H), 7.54 (d, J=8.8 Hz, 4H), 7.44 (t, J=7.6 Hz, 1H), 7.21 (t, J=7.6 Hz, 1H), 6.38 (t, J=5.2 Hz, 1H), 4.17 (d, J=5.2 Hz, 2H), 4.08 (s, 3H). MS: m/z 347.1 (M+H⁺).

Example 616: Synthesis of 1-[4-(5-Fluoro-1-methyl-1H-indazol-3-yl)-phenyl]-3-pyridin-4-ylmethyl-urea

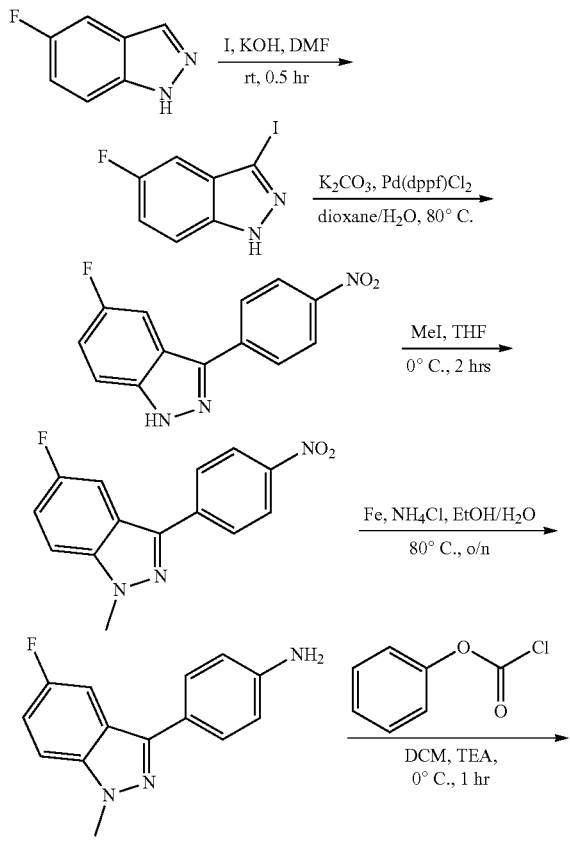

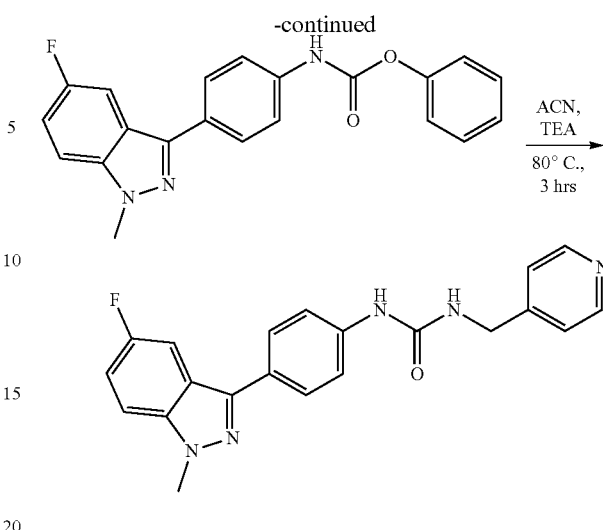

Step 1: To a solution of 5-fluoro-1H-indazole (2.0 g, 14.0 mmol) in DMF (50 mL) was added I₂ (7.46 g, 28.0 mmol) and KOH (2.4 g, 42 mmol), the mixture was stirred at room temperature for 0.5 hr. The reaction was monitored by TLC. After completion, the mixture was filtered, the filtrate was concentrated in vacuum to give a residue, which was purified by a silica gel column (PE/EA=3/1) to afford 5-fluoro-3-iodo-1H-indazole (3.7 g, yield: 96.1%) as a white solid. ¹H NMR (400 MHz, DMSO-d₆): δ=13.64 (s, 1H), 7.63 (dd, J=4.8, 4.4 Hz, 1H), 7.38-7.30 (m, 1H), 7.20 (dd, J=6.4, 2.4 Hz, 1H).

Step 2: To a solution of 5-fluoro-3-iodo-1H-indazole (2.0 g, 7.6 mmol) in dioxane (40 mL) and H₂O (10 mL) was added 4-nitrophenylboronic acid (1.89 g, 11.4 mmol) and K₂CO₃ (2.09 g, 15.2 mmol), Pd(dppf)Cl₂ (555.56 mg, 0.76 mmol), the mixture was stirred at 80° C. overnight. The reaction was monitored by TLC. After completion, the mixture was filtered, the filtrate was concentrated in vacuum to give a residue, which was purified by a silica gel column (PE/EA=3/1) to afford 5-fluoro-3-(4-nitro-phenyl)-1H-indazole (1.87 g, yield: 95.4%) as a yellow solid. ¹H NMR (400 MHz, DMSO-d₆): δ=14.06 (s, 1H), 8.41-8.28 (m, 4H), 7.99 (dd, J=7.2, 2.0 Hz, 1H), 7.73 (dd, J=4.4, 4.8 Hz, 1H), 7.41-7.33 (m, 1H)

Step 3: To a solution of 5-fluoro-3-(4-nitro-phenyl)-1H-indazole (1.6 g, 6.0 mmol) in THF (20 mL) was added NaH (216 mg, 9.0 mmol), MeI (1.2 g, 9.0 mmol). The reaction mixture was stirred at 0° C., for 1 hr. The mixture was added MeOH and concentrated in vacuum to give a residue, which was purified by a silica gel column (PE/EA=3/1) to give 5-fluoro-1-methyl-3-(4-nitro-phenyl)-1H-indazole (1.1 g, yield: 65.4%) as a white solid.

Step 4: To a solution of 5-fluoro-1-methyl-3-(4-nitrophenyl)-1H-indazole (1.0 g, 3.7 mmol) in EtOH (45 mL) and H₂O (5 mL) was added NH₄Cl (980 mg, 18.5 mmol), iron powder (1017 mg, 8.5 mmol). The reaction mixture was stirred at 80° C. overnight. Iron powder was filtered off and the filtrate was concentrated in vacuum to give a residue, which was purified by flash to give 4-(5-fluoro-1-methyl-1H-indazol-3-yl)-phenylamine (1.1 g, yield: >1) as a white solid. ¹H NMR (400 MHz, DMSO-d₆): δ=7.23 (dd, J=7.2, 2.4 Hz, 1H), 7.69-7.58 (m, 3H), 7.35-7.26 (m, 1H), 6.70 (d, J=8.0 Hz, 2H), 5.29 (s, 2H), 5.31 (s, 2H), 4.05 (s, 3H).

Step 5: To a solution of 4-(5-fluoro-1-methyl-1H-indazol-3-yl)-phenylamine (500 mg, 2.0 mmol) in DCM (30 mL) was added phenyl chloroformate (343 mg, 2.2 mmol) and TEA (1 mL), the mixture was stirred at 0° C. for 1 hr. The reaction was monitored by TLC. After completion, the mixture was concentrated in vacuum to give a residue, which was purified by a silica gel column (PE/EA=3/1) to afford [4-(5-fluoro-1-methyl-1H-indazol-3-yl)-phenyl]-carbamic acid phenyl ester (800 mg, yield: >1) as a white solid.

Step 6: To a solution of [4-(5-fluoro-1-methyl-1H-indazol-3-yl)-phenyl]-carbamic acid phenyl ester (100 mg, 0.28 mmol) in ACN (30 mL) was added c-pyridin-4-yl-methylamine (29.8 mg, 0.28 mmol) and TEA (0.5 mL), the mixture was stirred at 80° C. for 3 hrs. The reaction was monitored by LCMS. After completion, the mixture was concentrated in vacuum to give a residue, the residue was purified by prep-HPLC to give 1-[4-(5-fluoro-1-methyl-1H-indazol-3-yl)-phenyl]-3-pyridin-4-ylmethyl-urea (41.0 mg, yield: 39.8%) as a white solid. $^1$H NMR (400 MHz, DMSO-d$_6$): δ=8.87 (s, 1H), 8.52 (d, J=5.6 Hz, 2H), 7.85-7.79 (m, 3H), 7.72 (dd, J=4.8, 4.0 Hz, 1H), 7.56 (d, J=8.8 Hz, 2H), 7.48-7.30 (m, 3H), 6.79 (t, J=6.0 Hz, 1H), 4.36 (d, J=6.0 Hz, 2H), 4.08 (s, 3H). MS: m/z 376.1 (M+H$^+$).

Example 617: Synthesis of 1-[4-(5-Fluoro-1-methyl-1H-indazol-3-yl)-phenyl]-3-(1H-pyrazol-4-ylmethyl)-urea

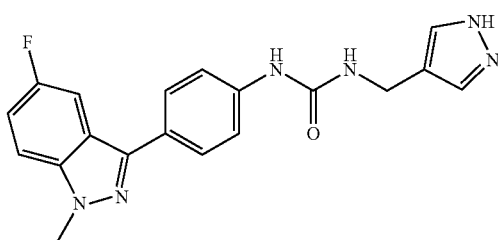 [SMILES: Cn1nc(-c2ccc(NC(=O)NCc3cn[nH]c3)cc2)c2cc(F)ccc21]

The title compound was prepared using general procedure of 1-[4-(5-Fluoro-1-methyl-1H-indazol-3-yl)-phenyl]-3-pyridin-4-ylmethyl-urea. $^1$H NMR (400 MHz, DMSO-d$_6$): δ=12.63 (s, 1H), 8.58 (s, 1H), 7.83-7.79 (m, 3H), 7.72 (dd, J=4.8, 4.0 Hz, 1H), 7.53 (d, J=8.8 Hz, 4H), 7.37-7.32 (m, 1H), 6.37 (t, J=6.0 Hz, 1H), 4.17 (d, J=5.6 Hz, 2H), 4.08 (s, 3H). MS: m/z 365.1 (M+H$^+$).

Example 618: Synthesis of 1-[4-(5-Fluoro-1-methyl-1H-indazol-3-yl)-phenyl]-3-oxazol-5-ylmethyl-urea

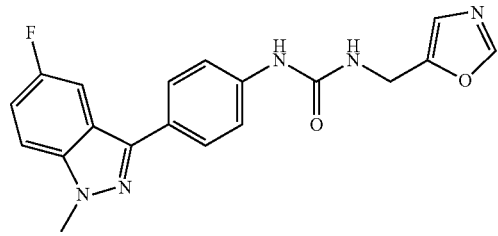 [SMILES: Cn1nc(-c2ccc(NC(=O)NCc3cnco3)cc2)c2cc(F)ccc21]

The title compound was prepared using general procedure of 1-[4-(5-Fluoro-1-methyl-1H-indazol-3-yl)-phenyl]-3-pyridin-4-ylmethyl-urea. $^1$H NMR (400 MHz, DMSO-d$_6$): δ=8.73 (s, 1H), 8.29 (s, 1H), 7.86-7.77 (m, 3H), 7.72 (dd, J=4.4, 4.8 Hz, 1H), 7.54 (d, J=9.2 Hz, 2H), 7.39-7.31 (m, 1H), 7.03 (s, 1H), 6.66 (t, J=6.0 Hz, 1H), 4.40 (d, J=5.6 Hz, 2H), 4.08 (s, 3H). MS: m/z 366.1 (M+H$^+$).

Example 619: Synthesis of 1-(4-(1,7-Dimethyl-1H-indazol-3-yl)phenyl)-3-(pyridin-4-ylmethyl)urea

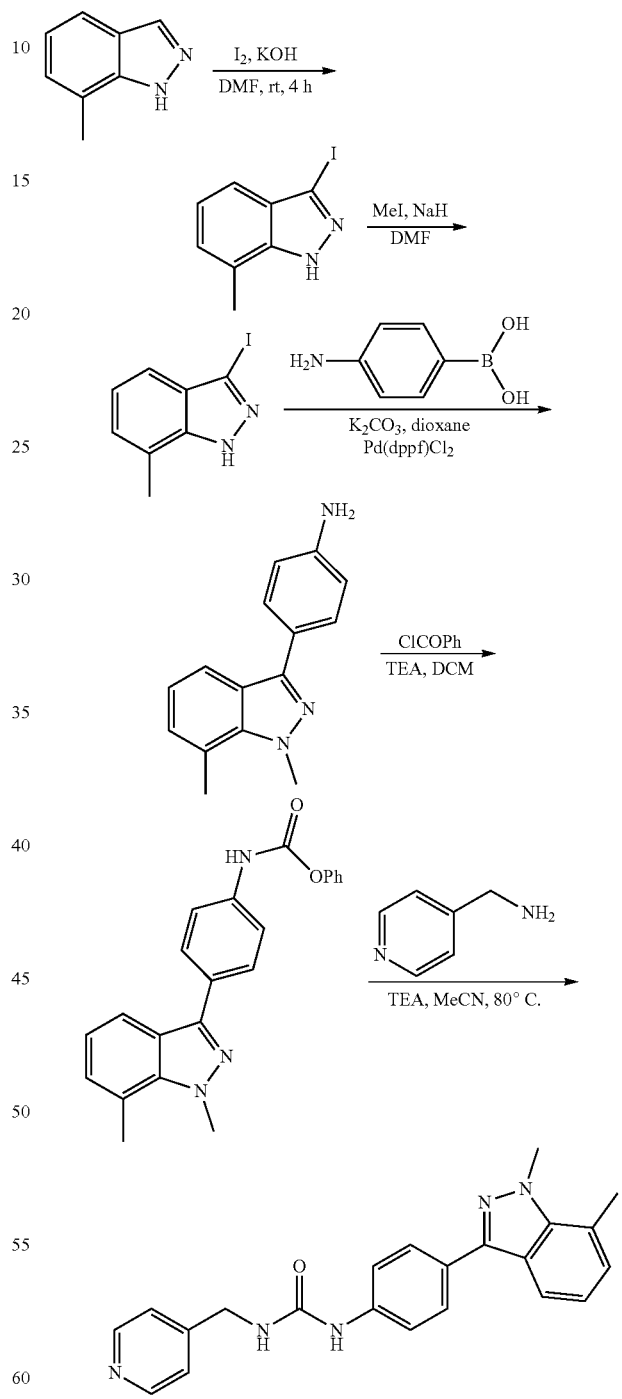

Step 1: A solution of 7-methyl-1H-indazole (2 g, 15.15 mmoL), KOH (2.12 g, 37.88 mmoL) and I$_2$ (7.7 g, 30.3 mmoL) in DMF (40 mL) was stirred at room temperature for 4 hrs. The reaction mixture was poured into H$_2$O (200 mL) and extracted with EA (200 mL). The EA layer was washed with saturated NaSO₃ (100 mL), H₂O (200 mL), brine (200 mL), dried over Na₂SO₄ and concentrated to give 3-iodo-7-methyl-1H-indazole (3.6 g, yield: 92%) as a yellow solid.

Step 2: To a solution of 3-iodo-7-methyl-1H-indazole (3.6 g, 13.9 mmoL) in DMF (20 mL) was added NaH (670 mg, 16.68 mmoL) at 0° C. and the mixture was stirred at room temperature for 40 mins under N₂ atmosphere (balloon). Then MeI (1.04 ml, 16.68 mmoL) was added into the reaction mixture and the mixture was stirred at room temperature for 1 hr. The reaction mixture was poured into H₂O (100 mL) and extracted with EA (100 mL). The EA layer was washed with H₂O (100 mL), brine (100 mL), dried over Na₂SO₄ and concentrated to dryness in vacuum. The residue was purified by silica flash column (9% EA in PE) to give 3-iodo-1,7-dimethyl-1H-indazole (2.663 g, yield: 70%) as a yellow solid. $^1$H NMR (400 MHz, CDCl₃): δ=7.28 (t, J=8.0 Hz, 1H), 7.13 (d, J=7.2 Hz, 1H), 7.06 (t, J=7.6 Hz, 1H), 4.32 (s, 3H), 2.74 (s, 3H). MS: m/z 273.1 (M+H⁺).

Step 3: A suspension of 3-iodo-1,7-dimethyl-1H-indazole (2.633 g, 9.68 mmoL), HCl salt of 4-aminobenzeneboronic acid (1.8 g, 10.65 mmoL), K₂CO₃ (3.34 g, 24.2 mmoL) and Pd(dppf)Cl₂ (0.7 mg, 0.9 mmoL) in dioxane/H₂O (20 mL/4 mL) was stirred at 80° C. for 19 hrs under N₂ atmosphere (balloon). The reaction mixture was poured into H₂O (200 mL) and extracted with EA (150 mL). The EA layer was washed with brine (150 mL), dried over Na₂SO₄ and concentrated to dryness in vacuum. The residue was purified by silica gel column (PE/EA=4/1) to give 4-(1,7-dimethyl-1H-indazol-3-yl)-phenylamine (1.396 g, yield: 60.8%) as a yellow solid. $^1$H NMR (300 MHz, CDCl₃): δ=7.80 (d, J=7.8 Hz, 1H), 7.72 (d, J=8.1 Hz, 2H), 7.12-7.02 (m, 2H), 6.82 (d, J=8.1 Hz, 2H), 4.36 (s, 3H), 3.82 (brs, 2H), 2.80 (s, 3H).

Step 4: To a solution of 4-(1,7-dimethyl-1H-indazol-3-yl)-phenylamine (1.39 mg, 5.86 mmoL) and TEA (2.5 mL, 17.595 mmoL) in DCM (10 mL) was added phenyl chloroformate (1.1 g, 7.038 mmoL) at 0° C. and the mixture was stirred at room temperature for 1 hr. The reaction mixture was poured into H₂O (50 mL) and extracted with EA (50 mL). The EA layer was washed with brine (50 mL), dried over Na₂SO₄ and concentrated to dryness in vacuum. The residue was purified by silica flash column (21% EA in PE) to give [4-(1,7-dimethyl-1H-indazol-3-yl)-phenyl]-carbamic acid phenyl ester (1.71 mg, yield: 81%) as a white solid. $^1$H NMR (400 MHz, CDCl₃): δ=7.88 (d, J=8.0 Hz, 2H), 7.80 (d, J=7.6 Hz, 1H), 7.57 (d, J=8.0 Hz, 2H), 7.42-7.38 (m, 2H), 7.26-7.22 (m, 4H), 7.12-7.04 (m, 3H), 4.36 (s, 3H), 2.79 (s, 3H).

Step 5: A solution of [4-(1,7-dimethyl-1H-indazol-3-yl)-phenyl]-carbamic acid phenyl ester (100 mg, 0.28 mmoL), c-pyridin-4-yl-methylamine (45 mg, 0.42 mmoL) and TEA (0.2 mL, 1.39 mmoL) in MeCN (4 mL) was stirred at 80° C. for 3 hrs. The reaction mixture was poured into H₂O (20 mL) and filtered. The pad was suspended in DMSO/MeOH (0.5 mL/1 mL) and standing there overnight. Then the mixture was filtered and rinsed with MeOH (5 mL) to give 1-[4-(1,7-dimethyl-1H-indazol-3-yl)-phenyl]-3-pyridin-4-ylmethyl-urea (68 mg, yield: 66%) as a white solid. $^1$H NMR (300 MHz, DMSO-d₆): δ=8.86 (s, 1H), 8.52-8.50 (d, J=6 Hz, 2H), 7.83-7.77 (q, 3H), 7.56-7.54 (t, 2H), 7.32-7.30 (d, J=6 Hz, 2H), 7.12-7.07 (q, 2H), 6.78 (s, 1H), 4.36-4.34 (d, J=6 Hz, 2H), 4.31 (s, 3H), 2.77 (s, 3H). MS: m/z 372.1 (M+H⁺).

Example 620: Synthesis of 1-(4-(1,7-Dimethyl-1H-indazol-3-yl)phenyl)-3-(oxazol-5-ylmethyl)urea

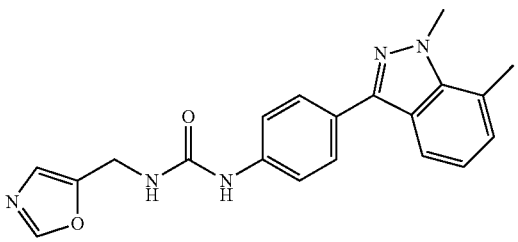 [SMILES: Cc1cccc2c(-c3ccc(NC(=O)NCc4cnco4)cc3)nn(C)c12]

The title compound was prepared using general procedure of 1-(4-(1,7-dimethyl-1H-indazol-3-yl)phenyl)-3-(pyridin-4-ylmethyl)urea. $^1$H NMR (300 MHz, DMSO-d₆): δ=8.73 (s, 1H), 8.29 (s, 1H), 7.83-7.77 (m, 3H), 7.53 (d, J=8.1 Hz, 2H), 7.13-7.12 (m, 1H), 7.05-7.02 (m, 2H), 6.66 (t, J=1.8 Hz, 1H), 4.39 (t, J=3.0 Hz, 2H), 4.31 (s, 3H), 2.77 (s, 3H). MS: m/z 362.1 (M+H⁺).

Example 621: Synthesis of 1-(4-(1,7-Dimethyl-1H-indazol-3-yl)phenyl)-3-(oxazol-5-ylmethyl)urea

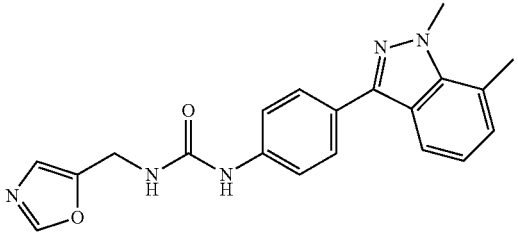 [SMILES: Cc1cccc2c(-c3ccc(NC(=O)NCc4cnco4)cc3)nn(C)c12]

The title compound was prepared using general procedure of 1-(4-(1,7-dimethyl-1H-indazol-3-yl)phenyl)-3-(pyridin-4-ylmethyl)urea. $^1$H NMR (300 MHz, DMSO-d₆): δ=9.19 (s, 1H), 8.77 (s, 1H), 8.32-8.28 (m, 2H), 8.04-8.02 (m, 1H), 7.90-7.88 (m, 2H), 7.58-7.56 (m, 2H), 7.02 (s, 1H), 7.68 (s, 1H), 4.39 (s, 2H), 4.21 (s, 3H). MS: m/z 349.1 (M+H⁺).

Example 622: Synthesis of 1-(4-(1-Methyl-1H-pyrazolo[3,4-c]pyridin-3-yl)phenyl)-3-(pyridin-4-ylmethyl)urea

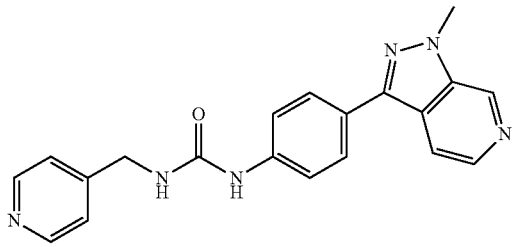 [SMILES: Cn1nc(-c2ccc(NC(=O)NCc3ccncc3)cc2)c2ccncc21]

The title compound was prepared using general procedure of 1-(4-(1,7-dimethyl-1H-indazol-3-yl)phenyl)-3-(pyridin-4-ylmethyl)urea. $^1$H NMR (300 MHz, DMSO-d₆): δ=9.19 (s, 1H), 8.91 (s, 1H), 8.52-8.50 (m, 2H), 8.31-8.29 (m, 1H), 8.04-8.02 (m, 1H), 7.90-7.88 (m, 2H), 7.59-7.57 (m, 2H), 7.32-7.30 (m, 2H), 6.80 (s, 1H), 4.35 (s, 2H), 4.20 (s, 3H). MS: m/z 359.1 (M+H⁺)

Example 633: Synthesis of 1-((1H-Pyrazol-4-yl)methyl)-3-(4-(1-methyl-1H-pyrazolo[3,4-c]pyridin-3-yl)phenyl)urea

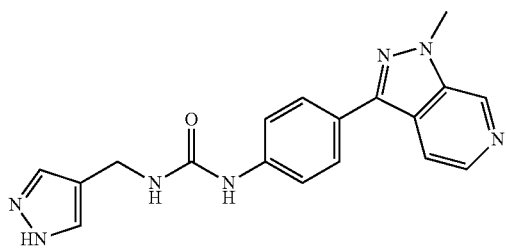 [SMILES: Cn1nc(-c2ccc(NC(=O)NCc3cn[nH]c3)cc2)c2ccncc21]

The title compound was prepared using general procedure of 1-(4-(1,7-dimethyl-1H-indazol-3-yl)phenyl)-3-(pyridin-4-ylmethyl)urea. ¹H NMR (300 MHz, DMSO-d₆): δ=12.62 (brs, 1H), 9.19 (s, 1H), 8.62 (s, 1H), 8.32-8.29 (m, 1H), 8.06-8.03 (m, 1H), 7.90-7.86 (m, 2H), 7.58-7.53 (m, 4H), 6.39 (s, 1H), 4.20 (s, 3H), 4.17 (s, 2H). MS: m/z 348.1 (M+H⁺)

Example 634: Synthesis of 1-((1H-Pyrazol-4-yl)methyl)-3-(4-(1,7-dimethyl-1H-indazol-3-yl)phenyl)urea

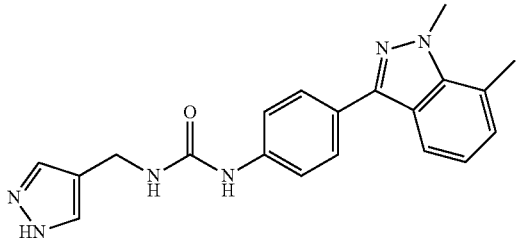 [SMILES: Cc1cccc2c(-c3ccc(NC(=O)NCc4cn[nH]c4)cc3)nn(C)c12]

The title compound was prepared using general procedure of 1-(4-(1,7-dimethyl-1H-indazol-3-yl)phenyl)-3-(pyridin-4-ylmethyl)urea. ¹H NMR (400 MHz, CDCl₃+CD₃OD): δ=7.78-7.75 (m, 3H), 7.66 (s, 2H), 7.58 (s, 2H), 7.521 (d, J=8.4 Hz, 2H), 7.14 (d, J=8.0 Hz, 1H), 7.04 (d, J=8.0 Hz, 1H), 4.35 (s, 3H), 4.33 (s, 2H), 2.80 (s, 3H). MS: m/z 361.1 (M+H⁺).

Example 635: Synthesis of 1-[4-(1-Methyl-1H-pyrazolo[4,3-c]pyridin-3-yl)-phenyl]-3-(1H-pyrazol-4-ylmethyl)-urea

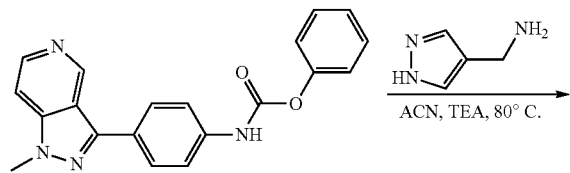

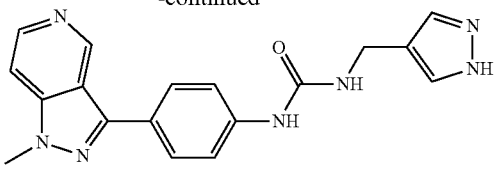

To a solution of [4-(1-methyl-1H-pyrazolo[4,3-c]pyridin-3-yl)-phenyl]-carbamic acid phenyl ester (120 mg, 0.35 mmol) in ACN (10 mL) was added (1H-pyrazol-3-yl)methanamine (55.7 mg, 0.42 mmol) and TEA (85 mg, 0.84 mmol). Then the mixture was stirred at 80° C. overnight. This reaction was monitored by LC-MS. The reaction mixture was then diluted with H₂O (10 mL) and extracted with EA (10 mL×3). The combined organic layer was dried over anhydrous Na₂SO₄, filtered and evaporated in vacuum. The residue was purified by pre-HPLC to give 1-[4-(1-methyl-1H-pyrazolo[4,3-c]pyridin-3-yl)-phenyl]-3-(1H-pyrazol-4-ylmethyl)-urea (3.8 mg, 3.1%) as a yellow solid. ¹H NMR (400 MHz, DMSO-d₆): δ=9.26 (d, J=0.8 Hz, 1H), 8.36 (d, J=6.0 Hz, 1H), 7.91 (d, J=9.2 Hz, 2H), 7.61-7.56 (m, 5H), 4.32 (s, 2H), 4.12 (s, 3H). MS: m/z 348.1 (M+H)⁺.

Example 636: Synthesis of 1-[4-(1-methyl-1H-pyrazolo[4,3-c]pyridin-3-yl)-phenyl]-3-oxazol-5-ylmethyl-urea

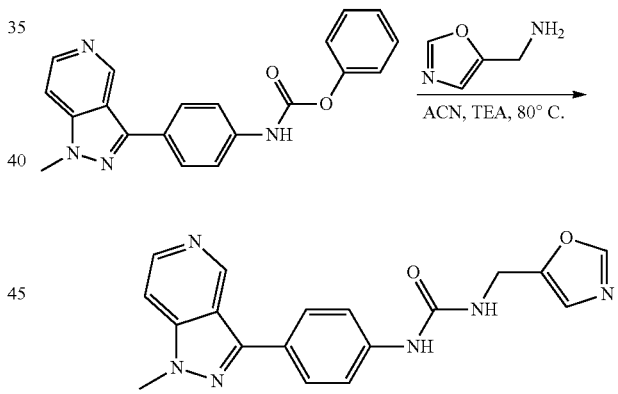

To a solution of [4-(1-methyl-1H-pyrazolo[4,3-c]pyridin-3-yl)-phenyl]-carbamic acid phenyl ester (120 mg, 0.35 mmol) in ACN (10 mL) was added C-oxazol-5-yl-methylamine (56.5 mg, 0.42 mmol) and TEA (85 mg, 0.84 mmol). Then, the mixture was stirred at 80° C. overnight. This reaction was monitored by LC-MS. The reaction mixture was then diluted with H₂O (10 mL) and extracted with EA (10 mL×3). The combined organic layer was dried over anhydrous Na₂SO₄, and evaporated in vacuum. The residue was purified by pre-HPLC to give 1-[4-(1-methyl-1H-pyrazolo[4,3-c]pyridin-3-yl)-phenyl]-3-oxazol-5-ylmethyl-urea (1.5 mg, 1.23%) as a yellow solid. ¹H NMR (400 MHz, DMSO-d₆): δ=7.97 (s, 1H), 7.07 (d, J=6.0 Hz, 1H), 6.86 (s, 1H), 6.63-6.60 (m, 2H), 6.32-6.26 (m, 3H), 5.76 (s, 1H), 3.21 (s, 2H), 2.82 (s, 3H). MS: m/z 349.1 (M+H)⁺.

Example 637: Synthesis of 1-[4-(1-methyl-1H-pyrazolo[4,3-c]pyridin-3-yl)-phenyl]-3-pyridin-4-ylmethyl-urea

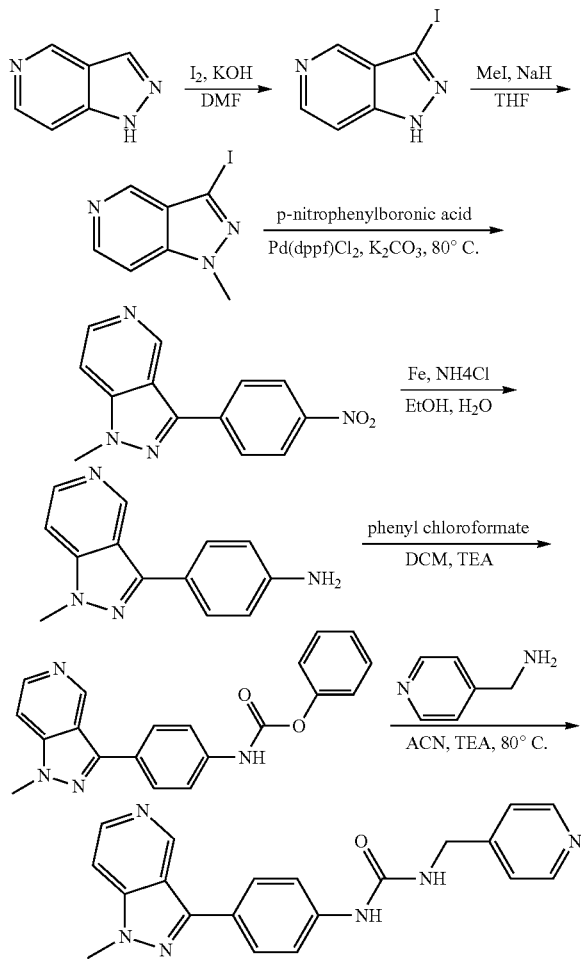

Step 1: To a solution of 1H-pyrazolo[4,3-c]pyridine (500 mg, 4.2 mmol) in DMF (10 mL) was added I$_2$ (1.6 g, 6.3 mmol) and KOH (705.6 mg, 12.6 mmol). Then the mixture was stirred at room temperature overnight. This reaction was monitored by LC-MS. The reaction mixture was then diluted with NaHSO$_3$ (aq, 10 mL) and extracted with EA (10 mL×3). The combined organic layer was dried over anhydrous Na$_2$SO$_4$, and evaporated in vacuum. The residue was purified by silica gel column chromatography (PE/EA=4/1) to give 3-iodo-1H-pyrazolo[4,3-c]pyridine (660 mg, 64%) as white oil.

Step 2: To a solution of 3-iodo-1H-pyrazolo[4,3-c]pyridine (660 mg, 2.69 mmol) in THF (10 mL) was added NaH (60%, 162 mg, 4.04 mmol) at 0° C. and this mixture was stirred at 0° C. for 0.5 hr. Then CH$_3$I (573 mg, 4.04 mmol) was added at 0° C. The reaction temperature was allowed to warm to room temperature slowly and stirred overnight. This reaction was monitored by LC-MS. The reaction mixture was quenched with H$_2$O (10 mL) extracted with EA (10 mL×3). The combined organic layer was dried over anhydrous Na$_2$SO$_4$, filtered and evaporated in vacuum. The residue was purified by silica gel column chromatography (PE/EA=4/1) to give {3-iodo-1-methyl-1H-pyrazolo[4,3-c]pyridine (221 mg, 31.7%) as white oil.

Step 3: To a solution of {3-iodo-1-methyl-1H-pyrazolo[4,3-c]pyridine (220 mg, 0.85 mmol) in a mixture of dioxane (10 mL) and H$_2$O (1 mL) was added K$_2$CO$_3$ (235 mg, 1.7 mmol), Pd(dppf)Cl$_2$ (62 mg, 0.08 mmol) and p-nitrophenylboronic acid (170 mg, 1.02 mmol). Then the mixture was stirred at 80° C. overnight. This reaction was monitored by LC-MS. The reaction mixture was then diluted with H$_2$O (10 mL) and extracted with EA (10 mL×3). The combined organic layer was dried over anhydrous Na$_2$SO$_4$, filtered and evaporated in vacuum. The residue was purified by silica gel column chromatography to give 1-methyl-3-(4-nitrophenyl)-1H-pyrazolo[4,3-c]pyridine (197 mg, 91.2%) as yellow oil.

Step 4: To a solution of 1-methyl-3-(4-nitro-phenyl)-1H-pyrazolo[4,3-c]pyridine (277 mg, 1.09 mmol) in a mixture of EtOH (10 mL) and H$_2$O (1 mL) was added Fe (244 mg, 4.36 mmol) and NH$_4$Cl (233 mg, 4.36 mmol). Then the mixture was stirred at 80° C. overnight. This reaction was monitored by TLC (PE/EA=1/4). The reaction mixture was then diluted with H$_2$O (10 mL) and extracted with EA (10 mL×3). The combined organic layer was dried over anhydrous Na$_2$SO$_4$, filtered and evaporated in vacuum. The residue was purified by silica gel chromatography column (PE/EA=1/4) to give 4-(1-methyl-1H-pyrazolo[4,3-c]pyridin-3-yl)-phenylamine (120 mg, 49.2%) as yellow oil. $^1$H NMR (400 MHz, DMSO-d$_6$): δ=9.31 (s, 1H), 8.37 (d, J=6.0 Hz, 1H), 7.72 (d, J=8.0 Hz, 2H), 7.63 (d, J=6.0 Hz, 1H), 6.70 (d, J=8.8 Hz, 1H), 5.42 (s, 2H), 4.04 (t, J=7.6 Hz, 3H).

Step 5: To a solution of 4-(1-methyl-1H-pyrazolo[4,3-c]pyridin-3-yl)-phenylamine (120 mg, 0.54 mmol) in DCM (10 mL) was added phenyl chloroformate (100.7 mg, 0.65 mmol) and TEA (65.1 mg, 0.65 mmol). Then the mixture was stirred at room temperature overnight. This reaction was monitored by LC-MS. The solvent was removed by vacuo. The residue was purificated by silica gel column chromatography (PE/EA=4/1) to give [4-(1-methyl-1H-pyrazolo[4,3-c]pyridin-3-yl)-phenyl]-carbamic acid phenyl ester (152 mg, 82%) as yellow oil which was used to the next step without further purification.

Step 6: To a solution of [4-(1-methyl-1H-pyrazolo[4,3-c]pyridin-3-yl)-phenyl]-carbamic acid phenyl ester (120 mg, 0.35 mmol) in ACN (5 mL) was added 4-pyridinemethanamine (45.2 mg, 0.42 mmol) and TEA (70.8 mg, 0.7 mmol). Then the mixture was stirred at 80° C. for 3 hrs. This reaction was monitored by LC-MS. The reaction mixture was then diluted with H$_2$O (10 mL) and extracted with EA (10 mL×3). The combined organic layer was dried over anhydrous Na$_2$SO$_4$, filtered and evaporated in vacuum. The residue was purified by pre-HPLC to give 1-[4-(1-methyl-1H-pyrazolo[4,3-c]pyridin-3-yl)-phenyl]-3-pyridin-4-ylmethyl-urea (25 mg, 20%) as a yellow solid. $^1$H NMR (400 MHz, CD$_3$OD): δ=9.25 (s, 1H), 8.48 (dd, J=8.8 Hz, J=1.6 Hz, 2H), 8.35 (d, J=6.0 Hz, 1H), 7.90 (dd, J=6.8 Hz, J=1.6 Hz, 2H), 7.60-7.57 (m, 3H), 7.42 (d, J=6.4 Hz, 2H), 4.48 (s, 2H), 4.11 (s, 3H). MS: m/z 359.1 (M+H)$^+$.

Example 638: Synthesis of 1-(4-(1,5-Dimethyl-1H-indazol-3-yl)phenyl)-3-(pyridin-4-ylmethyl)urea

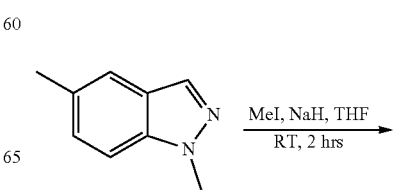

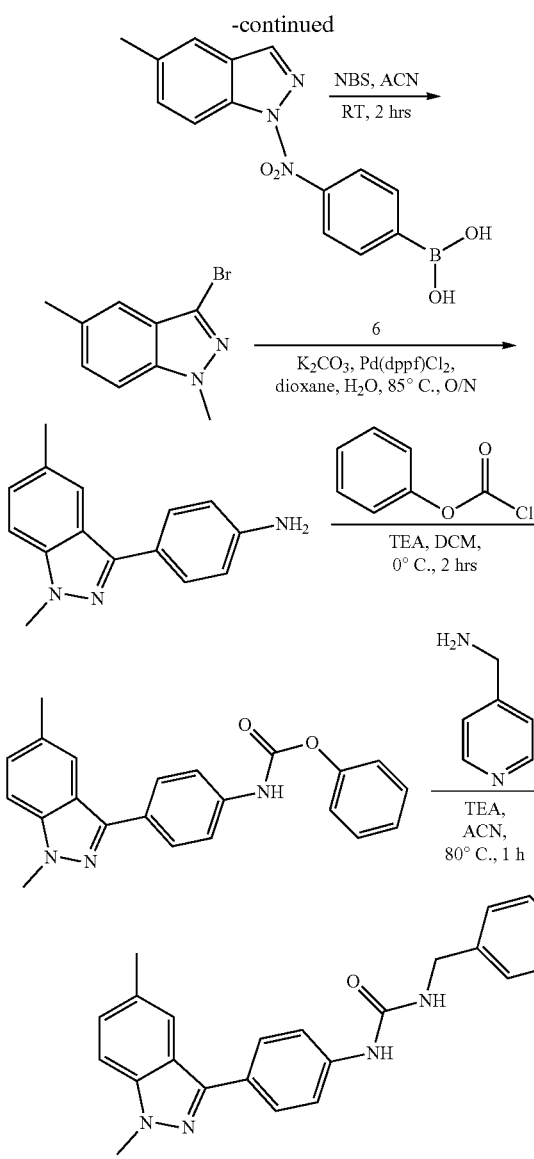

Step 1: To a solution of 1,5-dimethyl-1H-indazole (1 g, 7.58 mmol) and iodomethane (1.2 g, 8.33 mmol) in THF was added NaH (365 mg, 15.2 mmol) at 0° C. Then the reaction was stirred at room temperature for 2 hrs. The mixture was poured into H$_2$O (20 mL) and the aqueous phase was extracted with EA (20 mL). The organic layer was washed with brine (20 mL), dried over Na$_2$SO$_4$, filtered and concentrated. The residue was purified by silica gel column (PE/EA=4/1) to give 1,5-dimethyl-1H-indazole (490 mg, yield: 44%) as a white solid.

Step 2: To a solution of 1,5-dimethyl-1H-indazole (490 mg, 3.36 mmol) in ACN (15 mL) was added NBS (720 mg, 4.0 mmol). The reaction was stirred at room temperature for 2 hrs. The mixture was poured into sat.NaHCO$_3$ solution (10 mL) and the aqueous phase was extracted with EA (10 mL). The organic layer was washed with brine (15 mL), dried over Na$_2$SO$_4$, filtered and concentrated. The residue was purified by silica gel column (PE/EA=4/1) to give 3-bromo-1,5-dimethyl-1H-indazole (840 mg, crude) as yellow oil.

Step 3 to 5: The title compound was prepared using general procedure of 1-(4-(5-benzylthiazol-2-yl)phenyl)-3-(pyridin-4-ylmethyl)urea. $^1$H NMR (400 MHz, CDCl$_3$): δ=8.38 (d, J=6.0 Hz, 2H), 7.85 (s, 1H), 7.70 (d, J=8.4 Hz, 2H), 7.64 (s, 1H), 7.38 (d, J=8.8 Hz, 2H), 7.26-7.22 (m, 2H), 7.09 (d, J=6.0 Hz, 2H), 6.08 (t, J=6.0 Hz, 1H), 4.31 (d, J=6.0 Hz, 2H), 4.01 (s, 3H), 2.43 (s, 3H). MS: m/z 372.1 (M+H$^+$).

Example 639: Synthesis of 1-((1H-Pyrazol-4-yl)methyl)-3-(4-(1,5-dimethyl-1H-indazol-3-yl)phenyl)urea

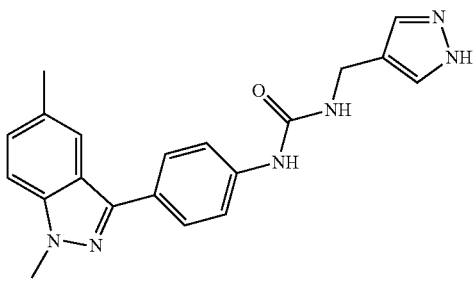 [SMILES: Cc1ccc2c(c1)c(-c1ccc(NC(=O)NCc3cn[nH]c3)cc1)nn2C]

The title compound was prepared using general procedure of 1-(4-(1,5-dimethyl-1H-indazol-3-yl)phenyl)-3-(pyridin-4-ylmethyl)urea. $^1$H NMR (400 MHz, DMSO-d$_6$): δ=12.61 (s, 1H), 8.56 (s, 1H), 7.83-7.81 (m, 3H), 7.55-7.51 (m, 5H), 7.27 (d, J=8.8 Hz, 1H), 6.35 (t, J=5.6 Hz, 1H), 4.18 (d, J=5.2 Hz, 2H), 4.04 (s, 3H), 2.45 (s, 3H). MS: m/z 361.1 (M+H$^+$).

Example 640: Synthesis of 1-(4-(1,5-Dimethyl-1H-indazol-3-yl)phenyl)-3-(oxazol-5-ylmethyl)urea

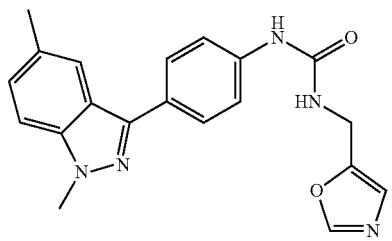 [SMILES: Cc1ccc2c(c1)c(-c1ccc(NC(=O)NCc3cnco3)cc1)nn2C]

The title compound was prepared using general procedure of 1-(4-(1,5-dimethyl-1H-indazol-3-yl)phenyl)-3-(pyridin-4-ylmethyl)urea. $^1$H NMR (400 MHz, CDCl$_3$): δ=7.91 (d, J=8.4 Hz, 2H), 7.82 (s, 1H), 7.73 (s, 1H), 7.41 (d, J=8.8 Hz, 2H), 7.32 (s, 1H), 7.27 (s, 1H), 7.01 (s, 1H), 6.58 (s, 1H), 5.19 (s, 1H), 4.53 (s, 2H), 4.08 (s, 3H), 2.49 (s, 3H). MS: m/z 362.1 (M+H$^+$).

Example 641: Synthesis of 1-(4-(5-Chloro-1-methyl-1H-indazol-3-yl)phenyl)-3-(oxazol-5-ylmethyl)urea

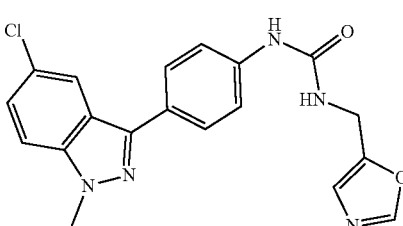

The title compound was prepared using general procedure of 1-(4-(1,5-dimethyl-1H-indazol-3-yl)phenyl)-3-(pyridin-4-ylmethyl)urea. ¹H NMR (400 MHz, CDCl₃+CD₃OD): δ=7.93 (d, J=2.4 Hz, 2H), 7.79 (d, J=8.4 Hz, 2H), 7.56 (d, J=8.8 Hz, 2H), 7.44 (s, 1H), 7.39 (s, 2H), 7.02 (s, 1H), 4.51 (s, 2H), 4.21 (s, 3H). MS: m/z 382.0 (M+H⁺).

Example 642: Synthesis of 1-(4-(5-Chloro-1-methyl-1H-indazol-3-yl)phenyl)-3-(pyridin-4-ylmethyl)urea

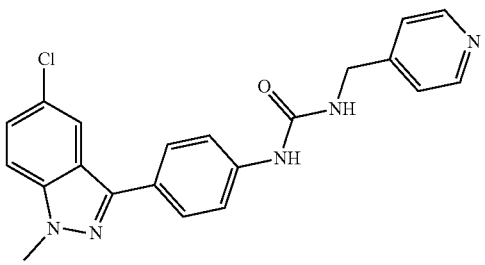

The title compound was prepared using general procedure of 1-(4-(1,5-dimethyl-1H-indazol-3-yl)phenyl)-3-(pyridin-4-ylmethyl)urea. ¹H NMR (400 MHz, CDCl₃): δ=8.42 (d, J=4.8 Hz, 2H), 7.76 (s, 2H), 7.72 (d, J=8.8 Hz, 2H), 7.37 (d, J=8.8 Hz, 2H), 7.30-7.25 (m, 2H), 7.12 (d, J=5.6 Hz, 2H), 6.04 (t, J=5.6 Hz, 1H), 4.33 (d, J=6.0 Hz, 2H), 4.02 (s, 3H). MS: m/z 392.1 (M+H⁺).

Example 643: Synthesis of 1-((1H-Pyrazol-4-yl)methyl)-3-(4-(5-chloro-1-methyl-1H-indazol-3-yl)phenyl)urea

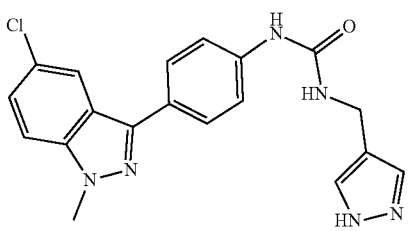 [SMILES: Cn1nc(-c2ccc(NC(=O)NCc3cn[nH]c3)cc2)c2cc(Cl)ccc21]

The title compound was prepared using general procedure of 1-(4-(1,5-dimethyl-1H-indazol-3-yl)phenyl)-3-(pyridin-4-ylmethyl)urea. ¹H NMR (400 MHz, DMSO-d₆): δ=8.59 (s, 1H), 8.07 (s, 1H), 7.83 (d, J=8.8 Hz, 2H), 7.73 (d, J=8.8 Hz, 1H), 7.55 (d, J=8.4 Hz, 3H), 7.46 (d, J=8.4 Hz, 1H), 6.37 (t, J=5.2 Hz, 1H), 4.18 (d, J=5.2 Hz, 2H), 4.08 (s, 3H). MS: m/z 381.1 (M+H⁺).

Example 644: Synthesis of 1-(4-(1,4-Dimethyl-1H-indazol-3-yl)phenyl)-3-(oxazol-5-ylmethyl)urea

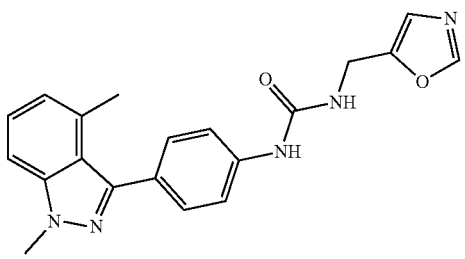 [SMILES: Cc1cccc2c1c(-c1ccc(NC(=O)NCc3cnco3)cc1)nn2C]

The title compound was prepared using general procedure of 1-(4-(1,5-dimethyl-1H-indazol-3-yl)phenyl)-3-(pyridin-4-ylmethyl)urea. ¹H NMR (400 MHz, CDCl₃+CD₃OD): δ=8.66 (s, 1H), 8.29 (s, 1H), 8.11 (s, 1H), 7.48 (d, J=4.8 Hz, 3H), 7.25-7.22 (m, 3H), 7.02 (s, 1H), 6.64 (t, J=5.6 Hz, 1H), 4.40 (d, J=6.0 Hz, 1H), 4.04 (s, 3H), 2.50 (d, J=1.6 Hz, 3H). MS: m/z 362.1 (M+H⁺).

Example 645: Synthesis of 1-(4-(1,4-Dimethyl-1H-indazol-3-yl)phenyl)-3-(pyridin-4-ylmethyl)urea

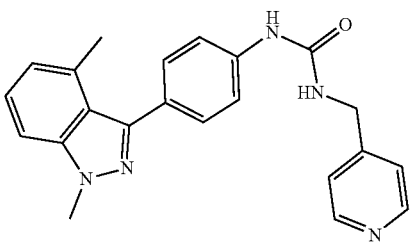 [SMILES: Cc1cccc2c1c(-c1ccc(NC(=O)NCc3ccncc3)cc1)nn2C]

The title compound was prepared using general procedure of 1-(4-(1,5-dimethyl-1H-indazol-3-yl)phenyl)-3-(pyridin-4-ylmethyl)urea. ¹H NMR (400 MHz, CD₃OD): δ=8.49 (d, J=4.8 Hz, 2H), 8.06 (s, 1H), 7.46-7.37 (m, 5H), 7.31-7.24 (m, 3H), 4.48 (s, 2H), 4.06 (s, 3H), 2.49 (s, 3H). MS: m/z 372.1 (M+H⁺).

Example 646: Synthesis of 1-((1H-Pyrazol-4-yl)methyl)-3-(4-(1,4-dimethyl-1H-indazol-3-yl)phenyl)urea

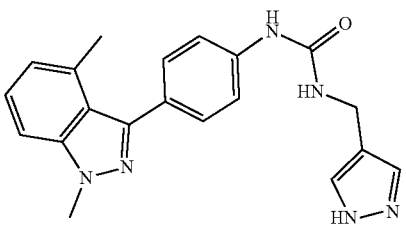 [SMILES: Cc1cccc2c1c(-c1ccc(NC(=O)NCc3cn[nH]c3)cc1)nn2C]

The title compound was prepared using general procedure of 1-(4-(1,5-dimethyl-1H-indazol-3-yl)phenyl)-3-(pyridin-4-ylmethyl)urea. ¹H NMR (400 MHz, CDCl₃+CD₃OD): δ=8.05 (s, 1H), 7.60 (d, J=12.4 Hz, 3H), 7.48 (d, J=8.4 Hz, 2H), 7.34 (s, 2H), 7.29 (d, J=8.8 Hz, 1H), 4.36 (s, 2H), 4.11 (s, 3H), 2.54 (s, 3H). MS: m/z 361.1 (M+H⁺).

Example 647: Synthesis of 1-[4-(5-Methoxy-1-methyl-1H-indazol-3-yl)-phenyl]-3-pyridin-4-ylmethyl-urea

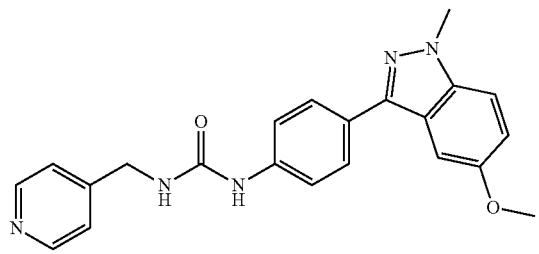 [SMILES: COc1ccc2c(c1)c(-c1ccc(NC(=O)NCc3ccncc3)cc1)nn2C]

The title compound was prepared using general procedure of 1-[4-(5-methoxy-1-methyl-1H-indazol-3-yl)-phenyl]-3-oxazol-5-ylmethyl-urea. ¹H NMR (300 MHz, DMSO-d₆): δ=8.89 (s, 1H), 8.51 (d, J=3.9 Hz, 2H), 7.82 (d, J=7.8 Hz, 2H), 7.58-7.54 (m, 3H), 7.36-7.31 (m, 3H), 7.09 (d, J=9.0 Hz, 1H), 6.82 (t, J=5.7 Hz, 1H), 4.36 (d, J=5.4 Hz, 2H), 4.04 (s, 3H), 3.84 (s, 3H). MS: m/z 388.1 (M+H⁺).

Example 648: Synthesis of 1-[4-(5-Methoxy-1-methyl-1H-indazol-3-yl)-phenyl]-3-(1H-pyrazol-4-ylmethyl)-urea

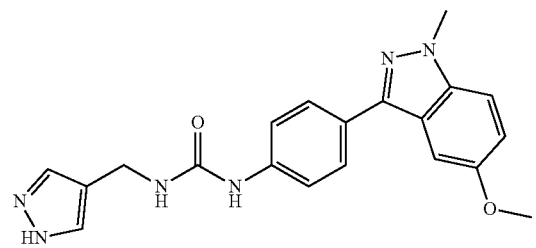 [SMILES: COc1ccc2c(c1)c(-c1ccc(NC(=O)NCc3cn[nH]c3)cc1)nn2C]

The title compound was prepared using general procedure of 1-[4-(5-Methoxy-1-methyl-1H-indazol-3-yl)-phenyl]-3-oxazol-5-ylmethyl-urea. ¹H NMR (300 MHz, DMSO-d₆): δ=12.63 (brs, 1H), 8.57 (s, 1H), 7.81 (d, J=8.4 Hz, 2H), 7.60-7.50 (m, 5H), 7.36 (s, 1H), 7.09 (d, J=8.7 Hz, 1H), 6.37 (t, J=5.4 Hz, 1H), 4.17 (d, J=5.1 Hz, 2H), 4.04 (s, 3H), 3.84 (s, 3H). MS: m/z 377.1 (M+H⁺).

Example 649: Synthesis of 1-[4-(5-Methoxy-1-methyl-1H-indazol-3-yl)-phenyl]-3-oxazol-5-ylmethyl-urea

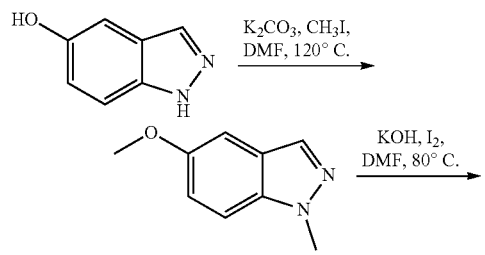

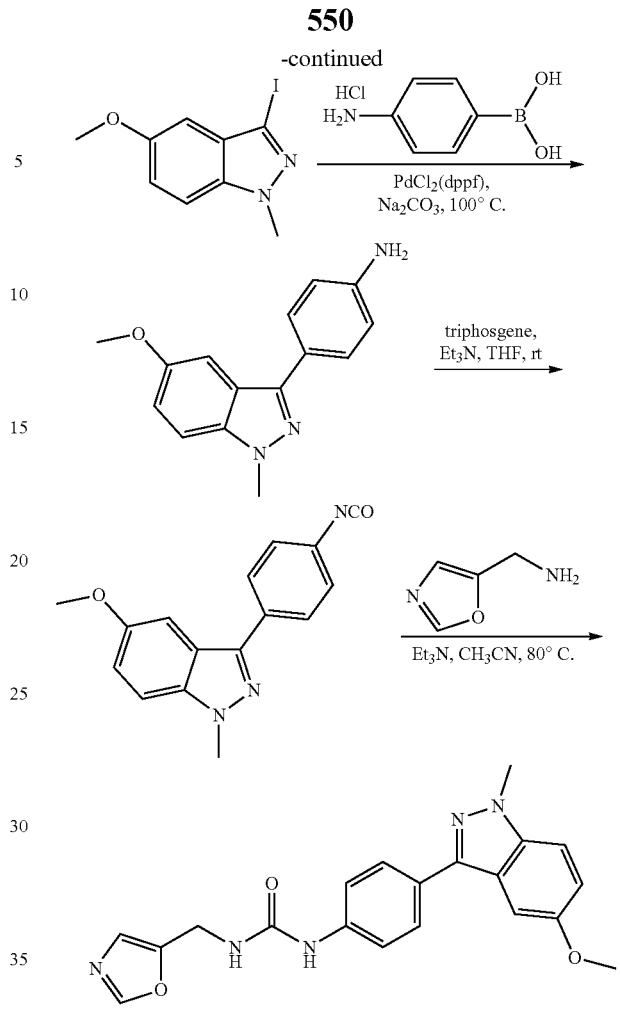

Step 1: To a solution of 1H-Indazol-5-ol (1.3 g, 10 mmol) in DMF (40 mL) was added K₂CO₃ (3.5 g, 25 mmol) and CH₃I (1.6 mL, 25 mmol) at room temperature, the resulting mixture was stirred at 120° C. for 18 hrs. After cooled to room temperature, the reaction was acidified with the addition of saturated aqueous NH₄Cl (10 ml). The solvent was removed under vacuum and the residue was diluted with water (200 mL). The aqueous phase was extracted with EA (50 mL×3). The combined organic layer was dried over anhydrous Na₂SO₄, filtered and concentrated to dryness under reduced pressure. The residue was purified by silica gel column (PE/EA=4/1) to give 5-methoxy-1-methyl-1H-indazole (876 mg, yield: 54%) as a white solid. ¹H NMR (300 MHz, CDCl₃): δ=7.87 (s, 1H), 7.28 (d, J=7.2 Hz, 1H), 7.08-7.05 (m, 2H), 4.04 (s, 3H), 3.84 (s, 3H). MS: m/z 163.0 (M+H⁺).

Step 2: To a solution of 5-methoxy-1-methyl-1H-indazole (476 mg, 2.9 mmol) in DMF (10 mL) was added KOH (195 mg, 3.5 mmol) and I₂ (889 mg, 3.5 mmol). The resultant mixture was stirred at 80° C. overnight. The reaction was quenched with the addition of saturated aqueous NaHSO₃ (100 mL). The mixture was extracted with EA (30 mL×3). The combined organic layer was dried over anhydrous Na₂SO₄, filtered and concentrated to dryness under reduced pressure. The residue was purified by silica gel column (PE/EA=8/1) to give 3-iodo-5-methoxy-1-methyl-1H-indazole (580 mg, yield: 69%) as a white solid.

Step 3: To a mixture of 3-iodo-5-methoxy-1-methyl-1H-indazole (540 mg, 1.88 mmol) and 4-aminophenylboronic acid (HCl salt, 461 mg, 2.7 mmol) in dioxane/$H_2O$ (5 mL/5 mL) was added $PdCl_2$(dppf) (69 mg, 0.09 mmol) and $Na_2CO_3$ (942 mg, 7.6 mmol). The resultant mixture was degassed and backfilled with N2 for three times. The it was stirred at 100° C. overnight. After cooled to room temperature, the reaction solution was poured into $H_2O$ (50 mL). The mixture was extracted with EA (30 mL×3). The combined organic layer was dried over anhydrous $NaSO_4$, filtered and concentrated to dryness under reduced pressure. The residue was purified by silica gel column (DCM/EA) to give 4-(5-methoxy-1-methyl-1H-indazol-3-yl)-phenylamine (370 mg, yield: 78%) as a tan solid. $^1$H NMR (300 MHz, $CDCl_3$): δ=7.72 (d, J=8.1 Hz, 2H), 7.32-7.26 (m, 2H), 7.10 (d, J=8.4 Hz, 1H), 6.83 (d, J=7.5 Hz, 2H), 4.07 (s, 3H), 3.88 (s, 3H), 3.79 (brs, 2H). MS: m/z 254.4 (M+H$^+$).

Steps 4 and 5: A solution of triphosgen (54 mg, 0.18 mmol) in THF (5 mL) was added to a mixture of 4-(5-methoxy-1-methyl-1H-indazol-3-yl)-phenylamine (127 mg, 0.5 mmol) and $Et_3N$ (0.17 mL, 1.25 mmol) in THF (10 mL) dropwise, the mixture was stirred at room temperature for 0.5 hr. The reactant was filtered and concentrated to dryness. MeCN (20 mL) was added, followed by 3-oxazol-5-yl-methylamine (60 mg, 0.6 mmol) and $Et_3N$ (0.17 mL, 1.25 mmol). The mixture was stirred at 80° C. for 2 hrs. The reaction solution was concentrated and the residue was purified by silica gel column (DCM/MeOH=15/1) to give 1-[4-(5-methoxy-1-methyl-1H-indazol-3-yl)-phenyl]-3-oxazol-5-ylmethyl-urea (130 mg, yield: 69%) as a white solid. $^1$H NMR (300 MHz, DMSO-$d_6$): δ=8.72 (s, 1H), 8.30 (s, 1H), 7.82 (d, J=8.4 Hz, 2H), 7.60-7.50 (m, 3H), 7.36 (s, 1H), 7.09 (d, J=9.6 Hz, 1H), 7.03 (s, 1H), 6.67 (t, J=6.3 Hz, 1H), 4.39 (d, J=6.3 Hz, 2H), 4.04 (s, 3H), 3.84 (s, 3H). MS: m/z 378.1 (M+H$^+$).

Pharmaceutical Compositions

Example A-1: Parenteral Composition

To prepare a parenteral pharmaceutical composition suitable for administration by injection, 100 mg of a water-soluble salt of a compound of Formula (I), (Ia), (II), (Ia), (III), (IIIa), (IV), (IVa), (V) or (Va), or pharmaceutically acceptable salt, N-oxide, racemate or stereoisomer thereof, is dissolved in 2% HPMC, 1% Tween 80 in DI water, pH 2.2 with MSA, q.s. to at least 20 mg/mL. The mixture is incorporated into a dosage unit form suitable for administration by injection.

Example A-2: Oral Composition

To prepare a pharmaceutical composition for oral delivery, 100 mg of a compound of Formula (I), (Ia), (II), (IIa), (III), (IIIa), (IV), (IVa), (V) or (Va), or pharmaceutically acceptable salt, N-oxide, racemate or stereoisomer thereof, is mixed with 750 mg of starch. The mixture is incorporated into an oral dosage unit for, such as a hard gelatin capsule, which is suitable for oral administration.

BIOLOGY EXAMPLES

Example B-1: Enzyme Assay and NMN Detection

NAMPT reaction was performed in 50 mM HEPES, pH 7.5, containing 5 mM $MgCl_2$, 0.1% Prionex, 0.005% Tween 20, and 1 mM TCEP at room temperature in Greiner 384-well black polypropylene plates. The concentration of substrates and enzymes in the final assay were as follows: ATP (120 uM), nicotinamide (5 uM), phosphoribosylpyrophosphate (6.25 uM), NAMPT enzyme (16 nM), pyrophosphatase (0.04 U/ml) in the final reaction volume 6 uL. Following 2 h incubation the reaction was stopped by addition 2.5 ul 20% acetophenone in dimethyl sulfoxide (DMSO) and 2.5 ul 2 MKOH. Plates were centrifuges and added with 10.5 ul 88% formic acid. The fluorescence (ex380/em460) was measured following another short incubation and 30 min incubation. The increased concentration of NMN was determined from a calibration curve obtained at the time of experiment.

Representative data for exemplary compounds disclosed in Table 1 is presented in the following table B-1.

TABLE B-1

| Compound | $EC_{50}$ |
|---|---|
| Ethyl 4-(3-((1H-pyrazol-4-yl)methyl)ureido)benzoate | B |
| Ethyl 4-(3-(oxazol-4-ylmethyl)ureido)benzoate | E |
| Ethyl 4-(3-((3,5-dimethylisoxazol-4-yl)methyl)ureido)benzoate | E |
| Ethyl 4-(3-((1-methyl-1H-pyrazol-4-yl)methyl)ureido)benzoate | E |
| N-(3-Chloro-phenyl)-4-[3-(1H-pyrazol-4-ylmethyl)-ureido]-benzamide | B |
| 4-(3-((1H-pyrazol-4-yl)methyl)ureido)-N-(2-methoxyphenyl)benzamide | B |
| 4-(3-((1H-pyrazol-4-yl)methyl)ureido)-N-(2-chlorophenyl)benzamide | B |
| 4-(3-((1H-pyrazol-4-yl)methyl)ureido)-N-(4-methoxyphenyl)benzamide | B |
| 4-(3-((1H-pyrazol-4-yl)methyl)ureido)-N-(4-chlorophenyl)benzamide | B |
| 4-(3-((1H-pyrazol-4-yl)methyl)ureido)-N-(3-methoxyphenyl)benzamide | B |
| Ethyl 4-(3-(oxazol-5-ylmethyl)ureido)benzoate | D |
| Ethyl 4-(3-((3-amino-1H-pyrazol-4-yl)methyl)ureido)benzoate | E |
| Ethyl 4-(3-((1H-imidazol-5-yl)methyl)ureido)benzoate | E |
| Ethyl 4-(3-((1-methyl-1H-pyrazol-5-yl)methyl)ureido)benzoate | E |
| Ethyl 4-(3-((1H-imidazol-4-yl)methyl)ureido)benzoate | E |
| Ethyl 4-(3-((1H-pyrazol-3-yl)methyl)ureido)benzoate | E |
| Ethyl 4-(3-((3-methyl-1H-pyrazol-4-yl)methyl)ureido)benzoate | E |
| Ethyl 4-(3-((1-(4-methoxybenzyl)-1H-1,2,3-triazol-4-yl)methyl)ureido)benzoate | E |
| Ethyl 4-(3-((1H-1,2,3-triazol-4-yl)methyl)ureido)benzoate | E |
| Ethyl 4-(3-((1-methyl-1H-imidazol-5-yl)methyl)ureido)benzoate | E |
| Ethyl 4-(3-((1-methyl-1H-imidazol-4-yl)methyl)ureido)benzoate | E |
| 4-[3-(1H-Pyrazol-4-ylmethyl)-ureido]-N-pyridin-2-yl-benzenesulfonamide | C |
| N-Benzyl-4-[3-(1H-pyrazol-4-ylmethyl)-ureido]-benzenesulfonamide | B |
| 1-[4-(3,4-Dihydro-1H-isoquinoline-2-sulfonyl)-phenyl]-3-(1H-pyrazol-4-ylmethyl)-urea | A |
| 1-[4-(8-Oxa-3-aza-bicyclo[3.2.1]octane-3-sulfonyl)-phenyl]-3-(1H-pyrazol-4-ylmethyl)-urea | B |
| N-Cyclobutylmethyl-4-[3-(1H-pyrazol-4-ylmethyl)-ureido]-benzenesulfonamide | B |

TABLE B-1-continued

| Compound | EC$_{50}$ |
|---|---|
| N-Phenyl-4-[3-(1H-pyrazol-4-ylmethyl)-ureido]-benzenesulfonamide | B |
| N-Cyclopentyl-N-methyl-4-[3-(1H-pyrazol-4-ylmethyl)-ureido]-benzenesulfonamide | B |
| N-Benzyl-N-isopropyl-4-(3-oxazol-5-ylmethyl-ureido)-benzenesulfonamide | A |
| N-Benzyl-N-isopropyl-4-(3-thiazol-5-ylmethyl-ureido)-benzenesulfonamide | A |
| N-Benzyl-N-isopropyl-4-(3-thiazol-2-ylmethyl-ureido)-benzenesulfonamide | E |
| N-Benzyl-N-isopropyl-4-[3-(1H-pyrazol-4-ylmethyl)-ureido]-benzenesulfonamide | A |
| 1-[4-(3,4-Dihydro-1H-isoquinoline-2-sulfonyl)-phenyl]-3-oxazol-5-ylmethyl-urea | B |
| N-(3-Methoxy-benzyl)-4-[3-(1H-pyrazol-4-ylmethyl)-ureido]-benzenesulfonamide | B |
| N-(2-Chloro-benzyl)-4-[3-(1H-pyrazol-4-ylmethyl)-ureido]-benzenesulfonamide | A |
| N-(2-Methoxy-benzyl)-4-[3-(1H-pyrazol-4-ylmethyl)-ureido]-benzenesulfonamide | A |
| N-(4-Methoxy-benzyl)-4-[3-(1H-pyrazol-4-ylmethyl)-ureido]-benzenesulfonamide | A |
| N-(4-Chloro-benzyl)-4-[3-(1H-pyrazol-4-ylmethyl)-ureido]-benzenesulfonamide | B |
| N-Benzyl-4-(3-oxazol-5-ylmethyl-ureido)-benzenesulfonamide | B |
| 1-[4-(3,4-Dihydro-1H-isoquinoline-2-sulfonyl)-phenyl]-3-thiazol-5-ylmethyl-urea | B |
| 1-[4-(3,4-Dihydro-1H-isoquinoline-2-sulfonyl)-phenyl]-3-(3,5-dimethyl-isoxazol-4-ylmethyl)-urea | E |
| 1-[4-(3-Chloro-benzenesulfonyl)-phenyl]-3-(1H-pyrazol-4-ylmethyl)-urea | A |
| 1-[4-(2-Chloro-benzenesulfonyl)-phenyl]-3-(1H-pyrazol-4-ylmethyl)-urea | A |
| 1-[4-(4-Chloro-benzenesulfonyl)-phenyl]-3-(1H-pyrazol-4-ylmethyl)-urea | A |
| 1-[4-(2-Methoxy-benzenesulfonyl)-phenyl]-3-(1H-pyrazol-4-ylmethyl)-urea | A |
| 1-[4-(3-Methoxy-benzenesulfonyl)-phenyl]-3-(1H-pyrazol-4-ylmethyl)-urea | A |
| 1-(4-Benzenesulfonyl-phenyl)-3-oxazol-5-ylmethyl-urea | A |
| 1-(4-Benzenesulfonyl-phenyl)-3-(1H-pyrazol-4-ylmethyl)-urea | A |
| 1-[4-(4-Methoxy-benzenesulfonyl)-phenyl]-3-(1H-pyrazol-4-ylmethyl)-urea | A |
| N-[4-(3-Oxazol-5-ylmethyl-ureido)-phenyl]-benzenesulfonamide | B |
| N-Oxazol-5-ylmethyl-2-(4-phenylmethanesulfonylamino-cyclohexa-1,5-dienyl)-acetamide | B |
| N-{4-[3-(1H-Pyrazol-4-ylmethyl)-ureido]-phenyl}-benzenesulfonamide | A |
| N-(4-(3-((1H-pyrazol-4-yl)methyl)ureido)phenyl)-1-phenylmethanesulfonamide | A |
| N-(4-{3-[1-(4-Methoxy-benzyl)-1H-pyrazol-4-ylmethyl]-ureido}-phenyl)-benzenesulfonamide | E |

Where A = <100 nM;
B = 100 nM-2 uM;
C = 2-5 uM;
D = 5-20 uM;
E = >20 uM

Representative data for exemplary compounds disclosed in Table 2 is presented in the following table B-2.

TABLE B-2

| Compound | EC$_{50}$ |
|---|---|
| 1-(4-Fluorophenyl)-3-(pyridin-4-ylmethyl)urea | E |
| 1-(4-Chlorophenyl)-3-(pyridin-4-ylmethyl)urea | D |
| 1-(Pyridin-4-ylmethyl)-3-(p-tolyl)urea | E |
| Ethyl 2-(3-(pyridin-4-ylmethyl)ureido)benzoate | E |
| Ethyl 3-(3-(pyridin-4-ylmethyl)ureido)benzoate | D |
| 1-(Pyridin-4-ylmethyl)-3-(4-(trifluoromethyl)phenyl)urea | D |
| 1-(Pyridin-4-ylmethyl)-3-(4-(trifluoromethoxy)phenyl)urea | E |
| 1-(4-Methoxyphenyl)-3-(pyridin-4-ylmethyl)urea | E |
| N,N-diethyl-4-(3-(pyridin-4-ylmethyl)ureido)benzamide | E |
| 4-(3-(Pyridin-4-ylmethyl)ureido)-N-(p-tolyl)benzamide | C |
| N-methyl-4-(3-(pyridin-4-ylmethyl)ureido)-N-(p-tolyl)benzamide | D |
| N-phenyl-4-(3-(pyridin-4-ylmethyl)ureido)benzamide | C |
| N-ethyl-N-methyl-4-(3-(pyridin-4-ylmethyl)ureido)benzamide | D |
| N-methyl-N-propyl-4-(3-(pyridin-4-ylmethyl)ureido)benzamide | D |
| N-(2-hydroxyethyl)-4-(3-(pyridin-4-ylmethyl)ureido)benzamide | E |
| N-butyl-4-(3-(pyridin-4-ylmethyl)ureido)benzamide | B |
| N-cyclopentyl-4-(3-(pyridin-4-ylmethyl)ureido)benzamide | D |
| Ethyl 4-(3-(pyridin-4-ylmethyl)ureido)benzoate | C |
| Ethyl 4-(3-((2-aminopyridin-4-yl)methyl)ureido)benzoate | E |
| Ethyl 4-(3-((2-methoxypyridin-4-yl)methyl)ureido)benzoate | E |
| Ethyl 4-(3-((3-methylpyridin-4-yl)methyl)ureido)benzoate | E |
| Ethyl 4-(3-((3-aminopyridin-4-yl)methyl)ureido)benzoate | E |
| Ethyl 4-(3-((2-methylpyridin-4-yl)methyl)ureido)benzoate | E |
| Ethyl 4-(3-((2-chloropyridin-4-yl)methyl)ureido)benzoate | E |
| Ethyl 4-(3-((3-chloropyridin-4-yl)methyl)ureido)benzoate | E |
| Ethyl 4-(3-((2-fluoropyridin-4-yl)methyl)ureido)benzoate | E |
| Ethyl 4-(3-((3-fluoropyridm-4-yl)methyl)ureido)benzoate | B |
| 4-(3-(Pyridin-4-ylmethyl)ureido)benzoic acid | E |
| 3-(3-(Pyridin-4-ylmethyl)ureido)benzoic acid | E |
| 4-(3-(Pyridin-4-ylmethyl)ureido)benzamide | D |
| N-propyl-4-(3-(pyridin-4-ylmethyl)ureido)benzamide | C |
| N-Isopropyl-4-(3-(pyridin-4-ylmethyl)ureido)benzamide | B |

TABLE B-2-continued

| Compound | EC$_{50}$ |
|---|---|
| N,N-dimethyl-4-(3-(pyridin-4-ylmethyl)ureido)benzamide | E |
| N-(2-morpholinoethyl)-4-(3-(pyridin-4-ylmethyl)ureido)benzamide | B |
| N-cyclohexyl-4-(3-(pyridin-4-ylmethyl)ureido)benzamide | C |
| N-(2-(piperidin-1-yl)ethyl)-4-(3-(pyridin-4-ylmethyl)ureido)benzamide | C |
| 4-(3-(Pyridin-4-ylmethyl)ureido)-N-(2-(pyrrolidin-1-yl)ethyl)benzamide | C |
| N-isobutyl-4-(3-(pyridin-4-ylmethyl)ureido)benzamide | B |
| N-cyclobutyl-4-(3-(pyridin-4-ylmethyl)ureido)benzamide | D |
| N-(cyclopropylmethyl)-4-(3-(pyridin-4-ylmethyl)ureido)benzamide | C |
| 4-(3-(pyridin-4-ylmethyl)ureido)-N-(tetrahydrofuran-3-yl)benzamide | D |
| N-(2-methoxyethyl)-4-(3-(pyridin-4-ylmethyl)ureido)benzamide | C |
| N-phenethyl-4-(3-(pyridin-4-ylmethyl)ureido)benzamide | B |
| 1-(4-(Morpholine-4-carbonyl)phenyl)-3-(pyridin-4-ylmethyl)urea | D |
| 1-(4-(4-Methylpiperazine-1-carbonyl)phenyl)-3-(pyridin-4-ylmethyl)urea | D |
| 1-(4-(Piperidine-1-carbonyl)phenyl)-3-(pyridin-4-ylmethyl)urea | D |
| 1-(Pyridin-4-ylmethyl)-3-(4-(pyrrolidine-1-carbonyl)phenyl)urea | D |
| N-cyclopentylmethyl)-4-(3-(pyridin-4-ylmethyl)ureido)benzamide | D |
| 1-(4-(8-Oxa-3-azabicyclo[3.2.1]octane-3-carbonyl)phenyl)-3-(pyridin-4-ylmethyl)urea | B |
| N-pyridin-4-ylmethyl)-4-(3-(pyridin-4-ylmethyl)ureido)benzamide | E |
| N-(4-methylphenethyl)-4-(3-(pyridin-4-ylmethyl)ureido)benzamide | B |
| N-(4-fluorophenethyl)-4-(3-(pyridin-4-ylmethyl)ureido)benzamide | B |
| N-(3-ethoxypropyl)-4-(3-(pyridin-4-ylmethyl)ureido)benzamide | B |
| N-(2-(dimethylamino)ethyl)-4-(3-(pyridin-4-ylmethyl)ureido)benzamide | D |
| N-(2-chlorobenzyl)-4-(3-(pyridin-4-ylmethyl)ureido)benzamide | E |
| N-(3-chlorobenzyl)-4-(3-(pyridin-4-ylmethyl)ureido)benzamide | E |
| N-(2-methoxybenzyl)-4-(3-(pyridin-4-ylmethyl)ureido)benzamide | E |
| N-(3-methoxybenzyl)-4-(3-(pyridin-4-ylmethyl)ureido)benzamide | E |
| N-(4-methoxybenzyl)-4-(3-(pyridin-4-ylmethyl)ureido)benzamide | E |
| N-(2-fluorobenzyl)-4-(3-(pyridin-4-ylmethyl)ureido)benzamide | C |
| N-(3-fluorobenzyl)-4-(3-(pyridin-4-ylmethyl)ureido)benzamide | E |
| N-(2-methylbenzyl)-4-(3-(pyridin-4-ylmethyl)ureido)benzamide | B |
| N-(4-methylbenzyl)-4-(3-(pyridin-4-ylmethyl)ureido)benzamide | E |
| N-(3-methylbenzyl)-4-(3-(pyridin-4-ylmethyl)ureido)benzamide | E |
| N-(4-chlorobenzyl)-4-(3-(pyridin-4-ylmethyl)ureido)benzamide | E |
| N-(4-fluorobenzyl)-4-(3-(pyridin-4-ylmethyl)ureido)benzamide | E |
| N-benzyl-N-methyl-4-(3-(pyridin-4-ylmethyl)ureido)benzamide | B |
| 1-(4-(Isoindoline-2-carbonyl)phenyl)-3-(pyridin-4-ylmethyl)urea | E |
| 1-(Pyridin-4-ylmethyl)-3-(4-(1,2,3,4-tetrahydroisoquinoline-2-carbonyl)phenyl)urea | B |
| N-(4-chlorophenyl)-4-(3-(pyridin-4-ylmethyl)ureido)benzamide | B |
| N-(2-chlorophenyl)-4-(3-(pyridin-4-ylmethyl)ureido)benzamide | B |
| N-(3-chlorophenyl)-4-(3-(pyridin-4-ylmethyl)ureido)benzamide | B |
| N-(2-fluorophenyl)-4-(3-(pyridin-4-ylmethyl)ureido)benzamide | B |
| N-(3-fluorophenyl)-4-(3-(pyridin-4-ylmethyl)ureido)benzamide | B |
| N-(4-fluorophenyl)-4-(3-(pyridin-4-ylmethyl)ureido)benzamide | B |
| 4-(3-(Pyridin-4-ylmethyl)ureido)-N-(o-tolyl)benzamide | B |
| 4-(3-(Pyridin-4-ylmethyl)ureido)-N-(m-tolyl)benzamide | B |
| N-(4-(methoxymethyl)phenyl)-4-(3-(pyridin-4-ylmethyl)ureido)benzamide | E |
| N-(2-methoxyphenyl)-4-(3-(pyridin-4-ylmethyl)ureido)benzamide | B |
| N-(3-methoxyphenyl)-4-(3-(pyridin-4-ylmethyl)ureido)benzamide | B |
| N-(4-methoxyphenyl)-4-(3-(pyridin-4-ylmethyl)ureido)benzamide | B |
| N-(2-(dimethylamino)phenyl)-4-(3-(pyridin-4-ylmethyl)ureido)benzamide | B |
| N-(3-(dimethylamino)phenyl)-4-(3-(pyridin-4-ylmethyl)ureido)benzamide | B |
| N-(4-(dimethylamino)phenyl)-4-(3-(pyridin-4-ylmethyl)ureido)benzamide | B |
| 4-(3-(Pyridin-4-ylmethyl)ureido)-N-(2-(trifluoromethoxy)phenyl)benzamide | B |
| 4-(3-(pyridin-4-ylmethyl)ureido)-N-(3-(trifluoromethoxy)phenyl)benzamide | C |
| 4-(3-(pyridin-4-ylmethyl)ureido)-N-(4-(trifluoromethoxy)phenyl)benzamide | B |
| N-(4-ethoxyphenyl)-4-(3-(pyridin-4-ylmethyl)ureido)benzamide | B |
| N-(4-isopropoxyphenyl)-4-(3-(pyridin-4-ylmethyl)ureido)benzamide | B |
| Methyl 4-(4-(3-(pyridin-4-ylmethyl)ureido)benzamido)benzoate | B |
| N-(4-cyanophenyl)-4-(3-(pyridin-4-ylmethyl)ureido)benzamide | B |
| N-(3,4-dimethylphenyl)-4-(3-(pyridin-4-ylmethyl)ureido)benzamide | B |
| N-(3,4-dimethoxyphenyl)-4-(3-(pyridin-4-ylmethyl)ureido)benzamide | B |
| N-(benzo[d][1,3]dioxol-5-yl)-4-(3-(pyridin-4-ylmethyl)ureido)benzamide | D |
| N-(4-methoxy-3-methylphenyl)-4-(3-(pyridin-4-ylmethyl)ureido)benzamide | B |
| N-(2,3-dihydrobenzo[b][1,4]dioxin-6-yl)-4-(3-(pyridin-4-ylmethyl)ureido)benzamide | B |
| N-(pyridin-2-yl)-4-(3-(pyridin-4-ylmethyl)ureido)benzamide | D |
| N-(pyridin-3-yl)-4-(3-(pyridin-4-ylmethyl)ureido)benzamide | E |
| 4-(3-(pyridin-4-ylmethyl)ureido)-N-(pyrimidin-5-yl)benzamide | B |
| N-(3-methylisoxazol-5-yl)-4-(3-(pyridin-4-ylmethyl)ureido)benzamide | C |
| 4-(3-(Pyridin-4-ylmethyl)ureido)-N-(thiophen-2-yl)benzamide | C |
| N-Cyclohexyl-4-(3-pyridin-4-ylmethyl-ureido)-benzenesulfonamide | B |
| N-4-(3-pyridin-4-ylmethyl-ureido)-benzenesulfonamide | D |
| N-Methyl-4-(3-pyridin-4-ylmethyl-ureido)-benzenesulfonamide | C |
| N-Propyl-4-(3-pyridin-4-ylmethyl-ureido)-benzenesulfonamide | B |
| N-Isopropyl-4-(3-pyridin-4-ylmethyl-ureido)-benzenesulfonamide | B |
| N-Cyclopropyl-4-(3-pyridin-4-ylmethyl-ureido)-benzenesulfonamide | C |
| N-Cyclobutyl-4-(3-pyridin-4-ylmethyl-ureido)-benzenesulfonamide | B |
| N-cyclopentyl-4-(3-pyridin-4-ylmethyl-ureido)-benzenesulfonamide | B |
| 4-(3-Pyridin-4-ylmethyl-ureido)-N-pyrrolidin-3-yl-benzenesulfonamide | D |

TABLE B-2-continued

| Compound | EC$_{50}$ |
|---|---|
| N-(1-Methyl-pyrrolidin-3-yl)-4-(3-pyridin-4-ylmethyl-ureido)-benzenesulfonamide | C |
| N-(tert-butyl)-4-(3-(pyridin-4-ylmethyl)ureido)benzenesulfonamide | B |
| N-(2-Dimethylamino-ethyl)-4-(3-pyridin-4-ylmethyl-ureido)-benzenesulfonamide | B |
| N-Cyclopropylmethyl-4-(3-pyridin-4-ylmethyl-ureido)-benzenesulfonamide | B |
| N-Cyclobutylmethyl-4-(3-pyridin-4-ylmethyl-ureido)-benzenesulfonamide | B |
| 4-Pyridin-4-ylmethyl-ureido)-N-(2-pyrrolidin-1-yl-ethyl)-benzensulfonamide | C |
| N-[2-(4-Methyl-piperazin-1-yl)-ethyl]-4-(3-pyridin-4-ylmethyl-ureido)-benzenesulfonamide | B |
| N-(2-Morpholin-4-yl-ethyl)-4-(3-pyridin-4-ylmethyl-ureido)-benzenesulfonamide | B |
| N-(2-Piperidin-1-yl-ethyl)-4-(3-pyridin-4-ylmethyl-ureido)-benzenesulfonamide | C |
| N-(2-Hydroxy-ethyl)-4-(3-pyridin-4-ylmethyl-ureido)-benzenesulfonamide | C |
| 4-(3-Pyridin-4-ylmethyl-ureido)-N-(tetrahydro-furan-3-yl)-benzenesulfonamide | B |
| N-(2-Methoxy-ethyl)-4-(3-pyridin-4-ylmethyl-ureido)-benzenesulfonamide | B |
| N-(3-Methoxy-propyl)-4-(3-pyridin-4-ylmethyl-ureido)-benzenesulfonamide | B |
| N-(1-Ethyl-pyrrolidin-2-ylmethyl)-4-(3-pyridin-4-ylmethyl-ureido)-benzenesulfonamide | B |
| N-neopentyl-4-(3-pyridin-4-ylmethyl-ureido)-benzenesulfonamide | B |
| N-(1-Cyclobutyl-ethyl)-4-(3-pyridin-4-ylmethyl-ureido)-benzenesulfonamide | B |
| N-Benzyl-4-(3-pyridin-4-ylmethyl-ureido)-benzenesulfonamide | B |
| N-(2-fluorobenzyl)-4-(3-(pyridin-4-ylmethyl)ureido)benzenesulfonamide | B |
| N-(3-fluorobenzyl)-4-(3-(pyridin-4-ylmethyl)ureido)benzenesulfonamide | B |
| N-(4-fluorobenzyl)-4-(3-(pyridin-4-ylmethyl)ureido)benzenesulfonamide | B |
| N-(2-Chloro-benzyl)-4-(3-pyridin-4-ylmethyl-ureido)-benzenesulfonamide | A |
| N-(3-Chloro-benzyl)-4-(3-pyridin-4-ylmethyl-ureido)-benzenesulfonamide | B |
| N-(4-chlorobenzyl)-4-(3-(pyridin-4-ylmethyl)ureido)benzenesulfonamide | B |
| N-(2-methoxybenzyl)-4-(3-(pyridin-4-ylmethyl)ureido)benzenesulfonamide | B |
| N-(3-Methoxy-benzyl)-4-(3-pyridin-4-ylmethyl-ureido)-benzenesulfonamide | B |
| N-(4-methoxybenzyl)-4-(3-(pyridin-4-ylmethyl)ureido)benzenesulfonamide | B |
| N-(2-Methyl-benzyl)-4-(3-pyridin-4-ylmethyl-ureido)-benzenesulfonamide | B |
| N-(3-Methyl-benzyl)-4-(3-pyridin-4-ylmethyl-ureido)-benzenesulfonamide | B |
| N-(4-methylbenzyl)-4-(3-(pyridin-4-ylmethyl)ureido)benzenesulfonamide | B |
| N-(2-Cyano-benzyl)-4-(3-pyridin-4-ylmethyl-ureido)-benzenesulfonamide | B |
| N-(3-Cyano-benzyl)-4-(3-pyridin-4-ylmethyl-ureido)-benzenesulfonamide | B |
| N-(4-cyanobenzyl)-4-(3-(pyridin-4-ylmethyl)ureido)benzenesulfonamide | B |
| 2-{[4-(3-Pyridin-4-ylmethyl-ureido)-benzenesulfonylamino]-methyl}-benzoic acid methyl ester | A |
| 3-{[4-(3-Pyridin-4-ylmethyl-ureido)-benzenesulfonylamino]-methyl}-benzoic acid methyl ester | B |
| 4-{[4-(3-Pyridin-4-ylmethyl-ureido)-benzenesulfonylamino]-methyl}-benzoic acid methyl ester | B |
| 4-(3-Pyridin-4-ylmethyl-ureido)-N-(3-trifluoromethyl-benzyl)-benzenesulfonamide | B |
| 4-(3-Pyridin-4-ylmethyl-ureido)-N-(2-trifluoromethyl-benzyl)-benzenesulfonamide | B |
| 4-(3-Pyridin-4-ylmethyl-ureido)-N-(4-trifluoromethyl-benzyl)-benzenesulfonamide | B |
| 4-(3-Pyridin-4-ylmethyl-ureido)-N-(2-trifluoromethoxy-benzyl)-benzenesulfonamide | A |
| 4-(3-Pyridin-4-ylmethyl-ureido)-N-(3-trifluoromethoxy-benzyl)-benzenesulfonamide | B |
| 4-(3-Pyridin-4-ylmethyl-ureido)-N-(4-trifluoromethoxy-benzyl)-benzenesulfonamide | B |
| N-(2-Dimethylamino-benzyl)-4-(3-pyridin-4-ylmethyl-ureido)-benzenesulfonamide | A |
| N-(3-Dimethylamino-benzyl)-4-(3-pyridin-4-ylmethyl-ureido)-benzenesulfonamide | B |
| N-(4-Dimethylamino-benzyl)-4-(3-pyridin-4-ylmethyl-ureido)-benzenesulfonamide | B |
| N-(4-Methanesulfonyl-benzyl)-4-(3-pyridin-4-ylmethyl-ureido)-benzenesulfonamide | B |
| N,N-dimethyl-4-((4-(3-(pyridin-4-ylmethyl)ureido)phenylsulfonamido)methyl)benzenesulfonamide | B |
| N-(4-((dimethylamino)methyl)benzyl)-4-(3-(pyridin-4-ylmethyl)ureido)benzenesulfonamide | A |
| N-(4-Methoxymethyl-benzyl)-4-(3-pyridin-4-ylmethyl-ureido)-benzenesulfonamide | B |
| N-(1-phenylethyl)-4-(3-(pyridin-4-ylmethyl)ureido)benzenesulfonamide | B |
| N-Pyridin-4-ylmethyl-4-(3-pyridin-4-ylmethyl-ureido)-benzenesulfonamide | B |
| 4-(3-Pyridin-4-ylmethyl-ureido)-N-(1,2,3,4-tetrahydro-naphthalen-1-yl)-benzenesulfonamide | A |
| N,N-Dimethyl-4-(3-pyridin-4-ylmethy-ureido)-benzenesulfonamide | C |
| N,N-Diethyl-4-(3-pyridin-4-ylmethyl-ureido)-benzenesulfonamide | B |
| N-(2-Hydroxy-ethyl)-N-methyl-4-(3-pyridin-4-ylmethyl-ureido)-benzenesulfonamide | B |
| N-Cyclopentyl-N-methyl-4-(3-pyridin-4-ylmethyl-ureido)-benzenesulfonamide | B |
| N-benzyl-N-methyl-4-(3-(pyridin-4-ylmethyl)ureido)benzenesulfonamide | A |
| N-(2-Fluoro-benzyl)-N-methyl-4-(3-pyridin-4-ylmethyl-ureido)-benzenesulfonamide | A |
| N-(2-Chloro-benzyl)-N-methyl-4-(3-pyridin-4-ylmethyl-ureido)-benzenesulfonamide | A |
| 1-[4-(Piperazine-1-sulfonyl)-phenyl}-3-pyridin-4-ylmethyl-urea | D |
| N-Cyclobutylmethyl-N-methyl-4-(3-pyridin-4-ylmethyl-ureido)-benzenesulfonamide | B |
| N-Cyclohexyl-N-methyl-4-(3-pyridin-4-ylmethyl-ureido)-benzenesulfonamide | B |
| N-Cyclopentyl-N-isobutyl-4-(3-pyridin-4-ylmethyl-ureido)-benzenesulfonamide | A |
| N-Cyclopentyl-N-ethyl-4-(3-pyridin-4-ylmethyl-ureido)-benzenesulfonamide | A |
| N-methyl-4-(3-(pyridin-4-ylmethyl)ureido)-N-(2-(trifluoromethyl)benzyl)benzenesulfonamide | A |
| N-Methyl-4-(3-pyridin-4-ylmethyl-ureido)-N-(2-trifluoromethoxy-benzyl)-benzenesulfonamide | A |
| N-(2-Methoxy-benzyl)-N-methyl-4-(3-pyridin-4-ylmethyl-ureido)-benzenesulfonamide | A |
| N-Benzyl-N-isopropyl-4-(3-pyridin-4-ylmethyl-ureido)-benzenesulfonamide | A |
| N-Benzyl-N-ethyl-4-(3-pyridin-4-ylmethyl-ureido)-benzenesulfonamide | A |
| N-Benzyl-N-cyclopropyl-4-(3-pyridin-4-ylmethyl-ureido)-benzenesulfonamide | A |

TABLE B-2-continued

| Compound | EC$_{50}$ |
|---|---|
| N-Benzyl-N-propyl-4-(3-pyridin-4-ylmethyl-ureido)-benzenesulfonamide | A |
| N,N-Dibenzyl-4-(3-pyridin-4-ylmethyl-ureido)-benzenesulfonamide | E |
| N-Methyl-N-(2-methyl-benzyl)-4-(3-pyridin-4-ylmethyl-ureido)-benzenesulfonamide | A |
| N-Benzyl-4-(3-pyridin-4-ylmethyl-ureido)-N-(2,2,2-trifluoro-ethyl)-benzenesulfonamide | A |
| N-Benzyl-N-phenyl-4-(3-pyridin-4-ylmethyl-ureido)-benzenesulfonamide | B |
| Pyridin-4-ylmethyl-3-[4-(pyrrolidine-1-sulfonyl)-phenyl]-urea | B |
| 1-[4-(Piperidine-1-sulfonyl)-phenyl]-3-pyridin-4-ylmethyl-urea | B |
| 1-[4-(Morpholine-4-sulfonyl)-phenyl]-3-pyridin-4-ylmethyl-urea | B |
| 1-[4-(4-Methyl-piperazine-1-sulfonyl)-phenyl]-3-pyridin-4-ylmethyl-urea | B |
| 1-[4-(1,3-Dihydro-isoindole-2-sulfonyl)-phenyl]-3-pyridin-4-ylmethyl-urea | B |
| 1-[4-(8-Oxa-3-aza-bicyclo[3.2.1]octane-3-sulfonyl)-phenyl]-3-pyridin-4-ylmethyl-urea | B |
| 1-[4-(3,4-Dihydro-1H-isoquinoline-2-sulfonyl)-phenyl]-3-pyridin-4-ylmethyl-urea | B |
| 1-[4-(8-Chloro-3,4-dihydro-1H-isoquinoline-2-sulfonyl)-phenyl]-3-pyridin-4-ylmethyl-urea | A |
| Pyridin-4-ylmethyl-3-[4-(8-trifluoromethyl-3,4-dihydro-1H-isoquinoline-2-sulfonyl)-phenyl]-urea | B |
| Pyridin-4-ylmethyl-3-[4-(6-trifluoromethyl-3,4-dihydro-1H-isoquinoline-2-sulfonyl)-phenyl]-urea | B |
| 1-[4-(8-Fluoro-3,4-dihydro-1H-isoquinoline-2-sulfonyl)-phenyl]-3-pyridin-4-ylmethyl-urea | A |
| 1-[4-(8-Methyl-3,4-dihydro-1H-isoquinoline-2-sulfonyl)-phenyl]-3-pyridin-4-ylmethyl-urea | A |
| 1-[4-(3-Methyl-3,4-dihydro-1H-isoquinoline-2-sulfonyl)-phenyl]-3-pyridin-4-ylmethyl-urea | B |
| N-Phenyl-4-(3-pyridin-4-ylmethyl-ureido)-benzenesulfonamide | B |
| N-(2-Methoxy-phenyl)-4-(3-pyridin-4-ylmethyl-ureido)-benzenesulfonamide | B |
| N-(3-Methoxy-phenyl)-4-(3-pyridin-4-ylmethyl-ureido)-benzenesulfonamide | B |
| N-(4-Methoxy-phenyl)-4-(3-pyridin-4-ylmethyl-ureido)-benzenesulfonamide | B |
| 4-(3-Pyridin-4-ylmethyl-ureido)-N-o-tolyl-benzenesulfonamide | B |
| 4-(3-Pyridin-4-ylmethyl-ureido)-N-m-tolyl-benzenesulfonamide | B |
| 4-(3-Pyridin-4-ylmethyl-ureido)-N-p-tolyl-benzenesulfonamide | B |
| 4-(3-Pyridin-4-ylmethyl-ureido)-N-thiazol-2-yl-benzenesulfonamide | B |
| N-(4,5-Dimethyl-oxazol-2-yl)-4-(3-pyridin-4-ylmethyl-ureido)-benzenesulfonamide | E |
| N-(5-Methyl-isoxazol-3-yl)-4-(3-pyridin-4-ylmethyl-ureido)-benzenesulfonamide | E |
| 4-(3-Pyridin-4-ylmethyl-ureido)-N-pyrimidin-2-yl-benzenesulfonamide | D |
| N-(4-Methyl-pyrimidin-2-yl)-4-(3-pyridin-4-ylmethyl-ureido)-benzenesulfonamide | B |
| N-Pyridin-2-yl-4-(3-pyridin-4-ylmethyl-ureido)-benzenesulfonamide | E |
| N-cyclopentyl-3-(3-(pyridin-4-ylmethyl)ureido)benzenesulfonamide | E |
| N-benzyl-3-(3-(pyridin-4-ylmethyl)ureido)benzenesulfonamide | D |
| 1-(3-(morpholinosulfonyl)phenyl)-3-(pyridin-4-ylmethyl)urea | E |
| N-(cyclobutylmethyl)-3-(3-(pyridin-4-ylmethyl)ureido)benzenesulfonamide | E |
| N-phenethyl-3-(3-(pyridin-4-ylmethyl)ureido)benzenesulfonamide | E |
| 4-(3-pyridin-4-ylmethyl-ureido)-N-(2-chloro-phenyl)-benzenesulfonamide | B |
| 4-(3-pyridin-4-ylmethyl-ureido)-N-(3-chloro-phenyl)-benzenesulfonamide | B |
| 4-(3-pyridin-4-ylmethyl-ureido)-N-(4-chloro-phenyl)-benzenesulfonamide | B |
| 1-[4-(3-Chloro-benzenesulfonyl)-phenyl]-3-pyridin-4-ylmethyl-urea | A |
| 1-[4-(4-Chloro-benzenesulfonyl)-phenyl]-3-pyridin-4-ylmethyl-urea | B |
| 1-[4-(2-Chloro-benzenesulfonyl)-phenyl]-3-pyridin-4-ylmethyl-urea | A |
| 1-[4-(2-Methoxy-benzenesulfonyl)-phenyl]-3-pyridin-4-ylmethyl-urea | A |
| 1-[4-(3-Methoxy-benzenesulfonyl)-phenyl]-3-pyridin-4-ylmethyl-urea | A |
| 1-(4-Benzenesulfonyl-phenyl)-3-pyridin-4-ylmethyl-urea | A |
| 1-(4-Phenylmethanesulfonyl-phenyl)-3-pyridin-4-ylmethyl-urea | C |
| 1-[4-(4-Methoxy-benzenesulfonyl)-phenyl]-3-pyridin-4-ylmethyl-urea | B |
| N-[4-(3-Pyridin-4-ylmethyl-ureido)-phenyl]-benzenesulfonamide | A |
| 2-Methoxy-N-[4-(3-pyridin-4-ylmethyl-ureido)-phenyl]-benzenesulfonamide | B |
| 3-Methoxy-N-[4-(3-pyridin-4-ylmethyl-ureido)-phenyl]-benzenesulfonamide | A |
| 4-Methoxy-N-[4-(3-pyridin-4-ylmethyl-ureido)-phenyl]-benzenesulfonamide | B |
| 2-Chloro-N-[4-(3-pyridin-4-ylmethyl-ureido)-phenyl]-benzenesulfonamide | A |
| 3-Chloro-N-[4-(3-pyridin-4-ylmethyl-ureido)-phenyl]-benzenesulfonamide | A |
| 4-Chloro-N-[4-(3-pyridin-4-ylmethyl-ureido)-phenyl]-benzenesulfonamide | A |
| N-[4-(3-Benzyl-ureido)-phenyl]-C-phenyl-methanesulfonamide | A |
| 1-(2-chlorophenyl)-N-(4-(3-(pyridin-4-ylmethyl)ureido)phenyl)methanesulfonamide | A |
| 1-(3-chlorophenyl)-N-(4-(3-(pyridin-4-ylmethyl)ureido)phenyl)methanesulfonamide | A |
| 1-(4-chlorophenyl)-N-(4-(3-(pyridin-4-ylmethyl)ureido)phenyl)methanesulfonamide | A |
| N-Methyl-C-phenyl-N-[4-(3-pyridin-4-ylmethyl-ureido)-phenyl]-methanesulfonamide | A |
| N-Isopropyl-N-[4-(3-pyridin-4-ylmethyl-ureido)-phenyl]-benzenesulfonamide | C |
| N-Methyl-N-[4-(3-pyridin-4-ylmethyl-ureido)-phenyl]-benzenesulfonamide | B |
| N-Isopropyl-C-phenyl-N-[4-(3-pyridin-4-ylmethyl-ureido)-phenyl]-methanesulfonamide | C |
| N-Phenyl-C-[4-(3-pyridin-4-ylmethyl-ureido)-phenyl]-methanesulfonamide | B |
| N-Methyl-N-phenyl-C-[4-(3-pyridin-4-ylmethyl-ureido)-phenyl]-methanesulfonamide | B |

Where A = <100 nM;
B = 100 nM-2 uM;
C = 2-5 uM;
D = 5-20 uM;
E = >20 uM

Representative data for exemplary compounds disclosed in Table 3 is presented in the following table B-3.

TABLE B-3

| Compound Name | EC$_{50}$ |
|---|---|
| 1-(4-Chlorophenyl)-3-(pyridin-3-ylmethyl)urea | E |
| 1-(4-Fluorophenyl)-3-(pyridin-2-ylmethyl)urea | E |
| 1-(4-Chlorophenyl)-3-(pyridin-2-ylmethyl)urea | E |
| 1-(Pyridin-3-ylmethyl)-3-(4-(trifluoromethoxy)phenyl)urea | E |
| 1-(Pyridin-2-ylmethyl)-3-(p-tolyl)urea | E |
| 1-(4-Fluorophenyl)-3-(pyridin-3-ylmethyl)urea | E |
| 1-(Pyridin-3-ylmethyl)-3-(p-tolyl)urea | E |
| 1-(Pyridin-3-ylmethyl)-3-(4-(trifluoromethyl)phenyl)urea | E |
| 1-(4-Methoxyphenyl)-3-(pyridin-3-ylmethyl)urea | E |
| 1-(Pyridin-2-ylmethyl)-3-(4-(trifluoromethyl)phenyl)urea | E |
| 1-(Pyridin-2-ylmethyl)-3-(4-(trifluoromethoxy)phenyl)urea | E |
| 1-(4-Methoxyphenyl)-3-(pyridin-2-ylmethyl)urea | E |
| Ethyl 4-(3-(pyridin-2-ylmethyl)ureido)benzoate | E |
| Ethyl 4-(3-(pyridin-3-ylmethyl)ureido)benzoate | E |
| Ethyl 4-(3-(pyridin-4-ylmethyl)thioureido)benzoate | E |
| Ethyl 4-(3-benzylureido)benzoate | E |
| Ethyl 4-(3-(pyrimidin-5-ylmethyl)ureido)benzoate | E |
| Ethyl 4-(3-((1,2,3,4-tetrahydroquinolin-4-yl)methyl)ureido)benzoate | E |
| Ethyl 4-(3-(quinolin-4-ylmethyl)ureido)benzoate | E |
| Ethyl 4-(3-((3-chloropyridin-4-yl)methyl)ureido)benzoate | E |
| Ethyl 4-(3-(pyridazin-4-ylmethyl)ureido)benzoate | E |
| 3-(3-Benzyl-ureido)-benzoic acid | E |
| Methyl 4-(1-methyl-3-(pyridin-4-ylmethyl)ureido)benzoate | E |
| N-Benzyl-4-(3-benzyl-ureido)-benzenesulfonamide | E |
| 1-[4-(8-Oxa-3-aza-bicyclo[3.2.1]octane-3-sulfonyl)-phenyl]-3-pyridin-3-ylmethyl-urea | E |
| 1-[4-(8-Oxa-3-aza-bicyclo[3.2.1]octane-3-sulfonyl)-phenyl]-3-pyridin-2-ylmethyl-urea | E |
| Ethyl 6-(3-(pyridin-4-ylmethyl)ureido)nicotinate | E |
| Ethyl 5-(3-(pyridin-4-ylmethyl)ureido)picolinate | E |
| 6-(3-Pyridin-4-ylmethyl-ureido)-nicotinamide | E |
| 5-(3-(pyridin-4-ylmethyl)ureido)picolinamide | C |
| 4-(3-Benzyl-3-methyl-ureido)-benzoic acid ethyl ester | E |
| 1-[(Pyridin-4-ylmethyl)-carbamoyl]-1H-indazole-5-carboxylic acid ethyl ester | E |
| 4-(2-Oxo-3-pyridin-4-ylmethyl-imidazolidin-1-yl)-benzoic acid ethyl ester | E |
| 4-(2-oxo-3-pyridin-4-ylmethyl-imidazolidin-1-yl)-benzoic acid | E |

Where A = <100 nM;
B = 100 nM-2 uM;
C = 2-5 uM;
D = 5-20 uM;
E = >20 uM

Representative data for exemplary compounds disclosed in Table 4 is presented in the following table B-4.

TABLE B-4

| Compound Name | EC$_{50}$ |
|---|---|
| 1-((1H-Pyrazol-4-yl)methyl)-3-(4-((4-(trifluoromethyl)phenyl)sulfonyl)phenyl)urea | B |
| 1-((1H-Pyrazol-4-yl)methyl)-3-(4-(pyridin-2-ylsulfonyl)phenyl)urea | B |
| 1-[4-(5-Methyl-pyridine-2-sulfonyl)-phenyl]-3-(1H-pyrazol-4-ylmethyl)-urea | B |
| 1-((1H-Pyrazol-4-yl)methyl)-3-(4-((2-fluorophenyl)sulfonyl)phenyl)urea | A |
| 1-((1H-Pyrazol-4-yl)methyl)-3-(4-((3-fluorophenyl)sulfonyl)phenyl)urea | A |
| 1-((1H-Pyrazol-4-yl)methyl)-3-(4-((4-fluorophenyl)sulfonyl)phenyl)urea | A |
| 1-((1H-Pyrazol-4-yl)methyl)-3-(4-((3-(trifluoromethyl)phenyl)sulfonyl)phenyl)urea | A |
| 1-((1H-Pyrazol-4-yl)methyl)-3-(4-(pyridin-4-ylsulfonyl)phenyl)urea | B |
| 1-(1H-Pyrazol-4-ylmethyl)-3-[4-(4-trifluoromethoxy-benzenesulfonyl)-phenyl]-urea | B |
| 1-(1H-Pyrazol-4-ylmethyl)-3-[4-(toluene-4-sulfonyl)-phenyl]-urea | B |
| 1-(1H-Pyrazol-4-ylmethyl)-3-[4-(toluene-3-sulfonyl)-phenyl]-urea | B |
| 1-(1H-Pyrazol-4-ylmethyl)-3-[4-(toluene-2-sulfonyl)-phenyl]-urea | A |
| 1-[4-(4-Cyano-benzenesulfonyl)-phenyl]-3-(1H-pyrazol-4-ylmethyl)-urea | B |
| 1-[4-(3,4-Dichloro-benzenesulfonyl)-phenyl]-3-(1H-pyrazol-4-ylmethyl)-urea | A |
| C-(3-Chloro-phenyl)-N-{4-[3-(1H-pyrazol-4-ylmethyl)-ureido]-phenyl}-methanesulfonamide | A |
| C-(2-Chloro-phenyl)-N-{4-[3-(1H-pyrazol-4-ylmethyl)-ureido]-phenyl}-methanesulfonamide | A |
| C-(4-Chloro-phenyl)-N-{4-[3-(1H-pyrazol-4-ylmethyl)-ureido]-phenyl}-methanesulfonamide | A |
| 1-[4-(5-Chloro-pyridine-2-sulfonyl)-phenyl]-3-(1H-pyrazol-4-ylmethyl)-urea | B |
| 1-(1H-Pyrazol-4-ylmethyl)-3-[4-(2-trifluoromethyl-benzenesulfonyl)-phenyl]-urea | B |
| C-(3,4-Dichloro-phenyl)-N-{4-[3-(1H-pyrazol-4-ylmethyl)-ureido]-phenyl}-methanesulfonamide | A |
| N-(3-Fluoro-benzyl)-4-[3-(1H-pyrazol-4-ylmethyl)-ureido]-benzenesulfonamide | B |

TABLE B-4-continued

| Compound Name | EC$_{50}$ |
|---|---|
| 1-[4-(6-Methyl-pyridine-3-sulfonyl)-phenyl]-3-(1H-pyrazol-4-ylmethyl)-urea | B |
| 1-((1H-Pyrazol-4-yl)methyl)-3-(4-(pyrimidin-5-ylsulfonyl)phenyl)urea | B |
| 1-(4-Cyclohexanesulfonyl-phenyl)-3-(1H-pyrazol-4-ylmethyl)-urea | B |
| 1-(1H-Pyrazol-4-ylmethyl)-3-[4-(2-trifluoromethoxy-benzenesulfonyl)-phenyl]-urea | A |
| 1-(1H-Pyrazol-4-ylmethyl)-3-[4-(3-trifluoromethoxy-benzenesulfonyl)-phenyl]-urea | A |
| 1-[4-(3,4-Difluoro-benzenesulfonyl)-phenyl]-3-(1H-pyrazol-4-ylmethyl)-urea | B |
| 1-(1H-Pyrazol-4-ylmethyl)-3-[4-(thiazole-2-sulfonyl)-phenyl]-urea | C |
| 1-[4-(3,4-Dichloro-benzenesulfonyl)-phenyl]-3-(1H-pyrazol-4-ylmethyl)-urea | D |
| N-(4-Methyl-benzyl)-4-[3-(1H-pyrazol-4-ylmethyl)-ureido]-benzenesulfonamide | B |
| 1-[4-(2,4-Dichloro-benzenesulfonyl)-phenyl]-3-(1H-pyrazol-4-ylmethyl)-urea | B |
| 1-(1H-Pyrazol-4-ylmethyl)-3-[4-(pyridine-3-sulfonyl)-phenyl]-urea | B |
| 1-(1H-Pyrazol-4-ylmethyl)-3-[4-(thiazole-2-sulfonyl)-phenyl]-urea | B |
| 1-[4-(3,5-Difluoro-benzenesulfonyl)-phenyl]-3-(1H-pyrazol-4-ylmethyl)-urea | A |
| of 1-[4-(1-Isopropyl-1H-pyrazole-4-sulfonyl)-phenyl]-3-(1H-pyrazol-4-ylmethyl)-urea | A |
| 1-[4-(Pyrazine-2-sulfonyl)-phenyl]-3-(1H-pyrazol-4-ylmethyl)-urea | B |
| 1-[4-(1-Methyl-piperidine-4-sulfonyl)-phenyl]-3-(1H-pyrazol-4-ylmethyl)-urea | C |
| 1-[4-(1-Isopropyl-piperidine-4-sulfonyl)-phenyl]-3-(1H-pyrazol-4-ylmethyl)-urea | C |
| 1-[4-(1-Isobutyl-piperidine-4-sulfonyl)-phenyl]-3-(1H-pyrazol-4-ylmethyl)-urea | C |
| of 1-[4-(2,4-Difluoro-benzenesulfonyl)-phenyl]-3-(1H-pyrazol-4-ylmethyl)-urea | A |
| 1-[4-(6-Methyl-pyridine-3-sulfonyl)-phenyl]-3-(1H-pyrazol-4-ylmethyl)-urea | B |
| 1-[4-(1-Methyl-1H-pyrazole-4-sulfonyl)-phenyl]-3-(1H-pyrazol-4-ylmethyl)-urea | B |
| 1-(1H-Pyrazol-4-ylmethyl)-3-[4-(pyrimidine-2-sulfonyl)-phenyl]-urea | C |
| 1-(1H-Pyrazol-4-ylmethyl)-3-{4-[1-(tetrahydro-pyran-4-yl)-piperidine-4-sulfonyl]-phenyl}-urea | B |
| 1-((1H-Pyrazol-4-yl)methyl)-3-(4-(benzo[d]thiazol-2-yl)phenyl)urea | D |
| 1-[4-(1H-Indazol-3-yl)-phenyl]-3-(1H-pyrazol-4-ylmethyl)-urea | B |
| 1-[4-(1-Methyl-1H-indazol-3-yl)-phenyl]-3-(1H-pyrazol-4-ylmethyl)-urea | B |
| 1-((1H-Pyrazol-4-yl)methyl)-3-(4-((4-phenylthiazol-2-yl)amino)phenyl)urea | B |
| 1-((1H-Pyrazol-4-yl)methyl)-3-(4-(5-benzylthiazol-2-yl)phenyl)urea | C |
| 1-((1H-Pyrazol-4-yl)methyl)-3-(4-((1H-pyrazol-4-yl)sulfonyl)phenyl)urea | B |
| 1-((1H-Pyrazol-4-yl)methyl)-3-(4-(benzo[d]thiazol-2-ylamino)phenyl)urea | E |
| 1-(1H-Pyrazol-4-ylmethyl)-3-[4-(4-o-tolyl-thiazol-2-ylamino)-phenyl]-urea | B |
| 1-(1H-Pyrazol-4-ylmethyl)-3-[4-(4-m-tolyl-thiazol-2-ylamino)-phenyl]-urea | B |
| 1-((1H-Pyrazol-4-yl)methyl)-3-[4-(4-p-tolyl-thiazol-2-ylamino)-phenyl]-urea | C |
| 1-{4-[4-(2-Fluoro-phenyl)-thiazol-2-ylamino]-phenyl}-3-(1H-pyrazol-4-ylmethyl)-urea | B |
| 1-((1H-Pyrazol-4-yl)methyl)-3-(4-(1,5-dimethyl-1H-indazol-3-yl)phenyl)urea | B |
| 1-[4-(1,6-Dimethyl-1H-indazol-3-yl)-phenyl]-3-(1H-pyrazol-4-ylmethyl)-urea | B |
| 1-{4-[4-(3-Fluoro-phenyl)-thiazol-2-ylamino]-phenyl}-3-(1H-pyrazol-4-ylmethyl)-urea | B |
| 1-{4-[4-(4-Fluoro-phenyl)-thiazol-2-ylamino]-phenyl}-3-(1H-pyrazol-4-ylmethyl)-urea | B |
| 1-((1H-Pyrazol-4-yl)methyl)-3-(4-((4-(2-methoxyphenyl)thiazol-2-yl)amino)phenyl)urea | B |
| 1-((1H-Pyrazol-4-yl)methyl)-3-(4-((4-(3-methoxyphenyl)thiazol-2-yl)amino)phenyl)urea | B |
| 1-(4-Benzothiazol-4-yl-phenyl)-3-(1H-pyrazol-4-ylmethyl)-urea | B |
| 1-((1H-Pyrazol-4-yl)methyl)-3-(4-(1,7-dimethyl-1H-indazol-3-yl)phenyl)urea | C |
| 1-[4-(5-Methoxy-1-methyl-1H-indazol-3-yl)-phenyl]-3-(1H-pyrazol-4-ylmethyl)-urea | B |
| 1-[4-(5-Fluoro-1-methyl-1H-indazol-3-yl)-phenyl]-3-(1H-pyrazol-4-ylmethyl)-urea | B |
| 1-{4-[4-(2-Chloro-phenyl)-thiazol-2-ylamino]-phenyl}-3-(1H-pyrazol-4-ylmethyl)-urea | D |
| 1-{4-[4-(3-Chloro-phenyl)-thiazol-2-ylamino]-phenyl}-3-(1H-pyrazol-4-ylmethyl)-urea | C |
| 1-{4-[4-(4-Chloro-phenyl)-thiazol-2-ylamino]-phenyl}-3-(1H-pyrazol-4-ylmethyl)-urea | B |
| 1-((1H-Pyrazol-4-yl)methyl)-3-(4-((4-(4-methoxyphenyl)thiazol-2-yl)amino)phenyl)urea | B |
| 1-(4-(1H-Benzoimidazol-4-yl)-phenyl)-3-(1H-pyrazol-4-ylmethyl)-urea | E |
| 1-((1H-Pyrazol-4-yl)methyl)-3-(4-([1,1'-biphenyl]-3-ylsulfonyl)phenyl)urea | B |
| 1-((1H-Pyrazol-4-yl)methyl)-3-(4-([1,1'-biphenyl]-2-ylsulfonyl)phenyl)urea | A |
| 1-[4-(1-Methyl-1H-pyrazolo[3,4-b]pyridin-3-yl)-phenyl]-3-(1H-pyrazol-4-ylmethyl)-urea | B |
| 1-((1H-Pyrazol-4-yl)methyl)-3-(4-(5-chloro-1-methyl-1H-indazol-3-yl)phenyl)urea | B |
| 1-((1H-Pyrazol-4-yl)methyl)-3-(4-((5-phenylthiazol-2-yl)amino)phenyl)urea | B |
| 1-(1H-Pyrazol-4-ylmethyl)-3-(4-(5-phenylthiazol-2-yl)phenyl)urea | D |
| 1-[4-(1-Methyl-1H-pyrazolo[4,3-b]pyridin-3-yl)-phenyl]-3-(1H-pyrazol-4-ylmethyl)-urea | B |
| 1-((1H-Pyrazol-4-yl)methyl)-3-(4-(1-methyl-1H-pyrazolo[3,4-c]pyridin-3-yl)phenyl)urea | C |
| 1-((1H-Pyrazol-4-yl)methyl)-3-(4-(1,4-dimethyl-1H-indazol-3-yl)phenyl)urea | B |
| 1-[4-(1-Methyl-1H-pyrazolo[4,3-c]pyridin-3-yl)-phenyl]-3-(1H-pyrazol-4-ylmethyl)-urea | C |
| 1-(1H-Pyrazol-4-ylmethyl)-3-[4-(2-pyridin-3-yl-benzenesulfonyl)-phenyl]-urea | B |
| 1-[4-(3-Iodo-benzenesulfonyl)-phenyl]-3-(1H-pyrazol-4-ylmethyl)-urea | A |
| 1-[4-(2'-Fluoro-biphenyl-2-sulfonyl)-phenyl]-3-(1H-pyrazol-4-ylmethyl)-urea | A |
| 1-[4-(3'-Fluoro-biphenyl-2-sulfonyl)-phenyl]-3-(1H-pyrazol-4-ylmethyl)-urea | A |
| 1-[4-(4'-Fluoro-biphenyl-2-sulfonyl)-phenyl]-3-(1H-pyrazol-4-ylmethyl)-urea | B |
| 1-[4-(2'-Methoxy-biphenyl-2-sulfonyl)-phenyl]-3-(1H-pyrazol-4-ylmethyl)-urea | D |
| 1-[4-(3'-Methoxy-biphenyl-2-sulfonyl)-phenyl]-3-(1H-pyrazol-4-ylmethyl)-urea | C |
| 1-(1H-Pyrazol-4-ylmethyl)-3-[4-(2-pyridin-4-yl-benzenesulfonyl)-phenyl]-urea | B |
| 1-[4-(3'-Chloro-biphenyl-2-sulfonyl)-phenyl]-3-(1H-pyrazol-4-ylmethyl)-urea | B |
| 1-[4-(4'-Methyl-biphenyl-2-sulfonyl)-phenyl]-3-(1H-pyrazol-4-ylmethyl)-urea | D |
| 1-[4-(3'-Methyl-biphenyl-2-sulfonyl)-phenyl]-3-(1H-pyrazol-4-ylmethyl)-urea | B |
| 1-[4-(4'-Methoxy-biphenyl-2-sulfonyl)-phenyl]-3-(1H-pyrazol-4-ylmethyl)-urea | D |
| 1-((1H-Pyrazol-4-yl)methyl)-3-(4-((2'-chloro-[1,1'-biphenyl]-2-yl)sulfonyl)phenyl)urea | B |

TABLE B-4-continued

| Compound Name | EC$_{50}$ |
|---|---|
| 1-((1H-Pyrazol-4-yl)methyl)-3-(4-((4'-cyano-[1,1'-biphenyl]-2-yl)sulfonyl)phenyl)urea | D |
| 1-((1H-Pyrazol-4-yl)methyl)-3-(4-((2-(6-methoxypyridin-3-yl)phenyl)sulfonyl)phenyl)urea | D |
| 1-((1H-Pyrazol-4-yl)methyl)-3-(4-((3'-cyano-[1,1'-biphenyl]-2-yl)sulfonyl)phenyl)urea | D |
| 1-((1H-Pyrazol-4-yl)methyl)-3-(4-((2'-methyl-[1,1'-biphenyl]-2-yl)sulfonyl)phenyl)urea | B |

Where A = <100 nM;
B = 100 nM-2 uM;
C = 2-5 uM;
D = 5-20 uM;
E = >20 uM

Representative data for exemplary compounds disclosed in Table 5 is presented in the following table B-5.

TABLE B-5

| Compound Name | EC$_{50}$ |
|---|---|
| 1-Oxazol-5-ylmethyl-3-[4-(4-trifluoromethoxy-benzenesulfonyl)-phenyl]-urea | B |
| 1-[4-(4-Cyano-benzenesulfonyl)-phenyl]-3-oxazol-5-ylmethyl-urea | B |
| 1-(3-Chlorophenyl)-N-(4-(3-(oxazol-5-ylmethyl)ureido)phenyl)methanesulfonamide | A |
| 1-(4-Chlorophenyl)-N-(4-(3-(oxazol-5-ylmethyl)ureido)phenyl)methanesulfonamide | A |
| 1-(3,4-Dichlorophenyl)-N-(4-(3-(oxazol-5-ylmethyl)ureido)phenyl)methanesulfonamide | A |
| 1-(2-Chlorophenyl)-N-(4-(3-(oxazol-5-ylmethyl)ureido)phenyl)methanesulfonamide | A |
| 1-Oxazol-5-ylmethyl-3-[4-(toluene-4-sulfonyl)-phenyl]-urea | C |
| 1-[4-(3,4-Dichloro-benzenesulfonyl)-phenyl]-3-oxazol-5-ylmethyl-urea | B |
| 1-(Oxazol-5-ylmethyl)-3-(4-(pyridin-2-ylsulfonyl)phenyl)urea | B |
| 1-(4-((3-Chlorophenyl)sulfonyl)phenyl)-3-(oxazol-5-ylmethyl)urea | A |
| 1-(Oxazol-5-ylmethyl)-3-(4-(pyridin-4-ylsulfonyl)phenyl)urea | B |
| 1-(4-((2-Methoxyphenyl)sulfonyl)phenyl)-3-(oxazol-5-ylmethyl)urea | B |
| 1-Oxazol-5-ylmethyl-3-[4-(toluene-3-sulfonyl)-phenyl]-urea | B |
| 1-Oxazol-5-ylmethyl-3-[4-(toluene-2-sulfonyl)-phenyl]-urea | B |
| 1-[4-(5-Chloro-pyridine-2-sulfonyl)-phenyl]-3-oxazol-5-ylmethyl-urea | C |
| 1-(4-((2-Fluorophenyl)sulfonyl)phenyl)-3-(oxazol-5-ylmethyl)urea | B |
| 1-(4-((3-Fluorophenyl)sulfonyl)phenyl)-3-(oxazol-5-ylmethyl)urea | B |
| 1-(4-((4-Fluorophenyl)sulfonyl)phenyl)-3-(oxazol-5-ylmethyl)urea | B |
| 1-[4-(2-Chloro-benzenesulfonyl)-phenyl]-3-oxazol-5-ylmethyl-urea | B |
| 1-Oxazol-5-ylmethyl-3-[4-(2-trifluoromethyl-benzenesulfonyl)-phenyl]-urea | B |
| 1-(Oxazol-5-ylmethyl)-3-(4-((3-(trifluoromethyl)phenyl)sulfonyl)phenyl)urea | B |
| 1-(Oxazol-5-ylmethyl)-3-(4-((4-(trifluoromethyl)phenyl)sulfonyl)phenyl)urea | B |
| 1-(4-Cyclohexanesulfonyl-phenyl)-3-oxazol-5-ylmethyl-urea | C |
| 1-Oxazol-5-ylmethyl-3-[4-(4-trifluoromethoxy-benzenesulfonyl)-phenyl]-urea | A |
| 1-[4-(6-Methyl-pyridine-3-sulfonyl)-phenyl]-3-oxazol-5-ylmethyl-urea | B |
| 1-(4-((4-Chlorophenyl)sulfonyl)phenyl)-3-(oxazol-5-ylmethyl)urea | B |
| 1-Oxazol-5-ylmethyl-3-[4-(thiazole-2-sulfonyl)-phenyl]-urea | B |
| 1-[4-(1-Methyl-piperidine-4-sulfonyl)-phenyl]-3-oxazol-5-ylmethyl-urea | C |
| 1-Oxazol-5-ylmethyl-3-[4-(3-trifluoromethoxy-benzenesulfonyl)-phenyl]-urea | A |
| 1-[4-(3-Methoxy-benzenesulfonyl)-phenyl]-3-oxazol-5-ylmethyl-urea | B |
| 1-[4-(3,4-Difluoro-benzenesulfonyl)-phenyl]-3-oxazol-5-ylmethyl-urea | B |
| 1-Oxazol-5-ylmethyl-3-[4-(thiazole-2-sulfonyl)-phenyl]-urea | B |
| 1-[4-(3,4-Dichloro-benzenesulfonyl)-phenyl]-3-oxazol-5-ylmethyl-urea | C |
| 1-Oxazol-5-ylmethyl-3-[4-(pyridine-3-sulfonyl)-phenyl]-urea | B |
| 1-[4-(3,5-Difluoro-benzenesulfonyl)-phenyl]-3-oxazol-5-ylmethyl-urea | B |
| 1-[4-(1-Isopropyl-1H-pyrazole-4-sulfonyl)-phenyl]-3-oxazol-5-ylmethyl-urea | B |
| 1-Oxazol-5-ylmethyl-3-[4-(pyrazine-2-sulfonyl)-phenyl]-urea | B |
| 1-[4-(2,4-Difluoro-benzenesulfonyl)-phenyl]-3-oxazol-5-ylmethyl-urea | B |
| 1-[4-(6-Methoxy-pyridine-3-sulfonyl)-phenyl]-3-oxazol-5-ylmethyl-urea | B |
| 1-[4-(4-Methoxy-benzenesulfonyl)-phenyl]-3-oxazol-5-ylmethyl-urea | B |
| 1-[4-(1-Methyl-1H-pyrazole-4-sulfonyl)-phenyl]-3-oxazol-5-ylmethyl-urea | C |
| 1-Oxazol-5-ylmethyl-3-[4-(pyrimidine-2-sulfonyl)-phenyl]-urea | D |
| 1-Oxazol-5-ylmethyl-3-{4-[1-(tetrahydro-pyran-4-yl)-piperidine-4-sulfonyl]-phenyl}-urea | B |
| 1-[4-(1H-Indazol-3-yl)-phenyl]-3-oxazol-5-ylmethyl-urea | B |
| 1-(4-(Benzo[d]thiazol-2-yl)phenyl)-3-(oxazol-5-ylmethyl)urea | D |
| 1-[4-(6-Hydroxy-pyridine-3-sulfonyl)-phenyl]-3-oxazol-5-ylmethyl-urea | B |
| 1-[4-(6-Chloro-pyridine-3-sulfonyl)-phenyl]-3-oxazol-5-ylmethyl-urea | C |
| 1-[4-(1-Methyl-1H-indazol-3-yl)-phenyl]-3-oxazol-5-ylmethyl-urea | C |
| 1-(Oxazol-5-ylmethyl)-3-(4-((4-phenylthiazol-2-yl)amino)phenyl)urea | C |
| 1-(4-(5-Benzylthiazol-2-yl)phenyl)-3-(oxazol-5-ylmethyl)urea | D |
| 1-(4-((1H-pyrazol-4-yl)sulfonyl)phenyl)-3-(oxazol-5-ylmethyl)urea | B |
| 1-(4-(Benzo[d]thiazol-2-ylamino)phenyl)-3-(oxazol-5-ylmethyl)urea | D |
| 1-(4-(1,5-Dimethyl-1H-indazol-3-yl)phenyl)-3-(oxazol-5-ylmethyl)urea | D |
| 1-(4-(1,6-Dimethyl-1H-indazol-3-yl)-phenyl)-3-(oxazol-5-ylmethyl)urea | B |
| 1-(4-(1,7-Dimethyl-1H-indazol-3-yl)phenyl)-3-(oxazol-5-ylmethyl)urea | C |
| 1-(4-Benzothiazol-4-yl-phenyl)-3-oxazol-5-ylmethyl-urea | B |
| 1-[4-(5-Methoxy-1-methyl-1H-indazol-3-yl)-phenyl]-3-oxazol-5-ylmethyl-urea | E |

TABLE B-5-continued

| Compound Name | EC$_{50}$ |
|---|---|
| 1-[4-(5-Fluoro-1-methyl-1H-indazol-3-yl)-phenyl]-3-oxazol-5-ylmethyl-urea | C |
| 1-[4-(1H-Benzoimidazol-4-yl)-phenyl]-3-oxazol-5-ylmethyl-urea | E |
| 1-(4-([1,1'-Biphenyl]-3-ylsulfonyl)phenyl)-3-(oxazol-5-ylmethyl)urea | B |
| 1-(4-([1,1'-Biphenyl]-2-ylsulfonyl)phenyl)-3-(oxazol-5-ylmethyl)urea | A |
| 1-[4-(1-Methyl-1H-pyrazolo[3,4-b]pyridin-3-yl)-phenyl]-3-oxazol-5-ylmethyl-urea | C |
| 1-(4-(5-Chloro-1-methyl-1H-indazol-3-yl)phenyl)-3-(oxazol-5-ylmethyl)urea | B |
| 1-(Oxazol-5-ylmethyl)-3-(4-((5-phenylthiazol-2-yl)amino)phenyl)urea | B |
| 1-(Oxazol-5-ylmethyl)-3-(4-(5-phenylthiazol-2-yl)phenyl)urea | D |
| 1-[4-(1-Methyl-1H-pyrazolo[4,3-b]pyridin-3-yl)-phenyl]-3-oxazol-5-ylmethyl-urea | C |
| 1-(4-(1,7-Dimethyl-1H-indazol-3-yl)phenyl)-3-(oxazol-5-ylmethyl)urea | C |
| 1-[4-(1-Methyl-1H-pyrazolo[4,3-c]pyridin-3-yl)-phenyl]-3-oxazol-5-ylmethyl-urea | D |

Where A = <100 nM;
B = 100 nM-2 uM;
C = 2-5 uM;
D = 5-20 uM;
E = >20 uM

Representative data for exemplary compounds disclosed in Table 6 is presented in the following table B-6.

TABLE B-6

| Compound Name | EC$_{50}$ |
|---|---|
| C-(4-Methoxy-phenyl)-N-[4-(3-pyridin-4-ylmethyl-ureido)-phenyl]-methanesulfonamide | A |
| C-(4-Bromo-phenyl)-N-[4-(3-pyridin-4-ylmethyl-ureido)-phenyl]-methanesulfonamide | A |
| C-(4-Cyclopropyl-phenyl)-N-[4-(3-pyridin-4-ylmethyl-ureido)-phenyl]-methanesulfonamide | A |
| C-Biphenyl-4-yl-N-[4-(3-pyridin-4-ylmethyl-ureido)-phenyl]-methanesulfonamide | A |
| C-(4-Cyano-phenyl)-N-[4-(3-pyridin-4-ylmethyl-ureido)-phenyl]-methanesulfonamide | B |
| 1-[4-(3-Bromo-benzylsulfanylamino)-phenyl]-3-pyridin-4-ylmethyl-urea | A |
| C-(2-Bromo-phenyl)-N-[4-(3-pyridin-4-ylmethyl-ureido)-phenyl]-methanesulfonamide | A |
| C-(3-Methoxy-phenyl)-N-[4-(3-pyridin-4-ylmethyl-ureido)-phenyl]-methanesulfonamide | A |
| N-[4-(3-Pyridin-4-ylmethyl-ureido)-phenyl]-C-m-tolyl-methanesulfonamide | A |
| C-(3-Fluoro-phenyl)-N-[4-(3-pyridin-4-ylmethyl-ureido)-phenyl]-methanesulfonamide | A |
| N-[4-(3-Pyridin-4-ylmethyl-ureido)-phenyl]-C-p-tolyl-methanesulfonamide | A |
| C-(2-Methoxy-phenyl)-N-[4-(3-pyridin-4-ylmethyl-ureido)-phenyl]-methanesulfonamide | B |
| 1-[4-(4-Fluoro-phenylmethanesulfonyl)-phenyl]-3-(1H-pyrazol-4-yl)-urea | B |
| 1-[4-(2-Methyl-benzylsulfanylamino)-phenyl]-3-pyridin-4-ylmethyl-urea | A |
| C-(2-Fluoro-phenyl)-N-[4-(3-pyridin-4-ylmethyl-ureido)-phenyl]-methanesulfonamide | A |
| 1-Pyridin-4-ylmethyl-3-[4-(4-trifluoromethoxy-benzenesulfonyl)-phenyl]-urea | B |
| 1-[4-(4-Cyano-benzenesulfonyl)-phenyl]-3-pyridin-4-ylmethyl-urea | B |
| 1-Pyridin-4-ylmethyl-3-[4-(toluene-4-sulfonyl)-phenyl]-urea | A |
| 1-[4-(3,4-Dichloro-benzenesulfonyl)-phenyl]-3-pyridin-4-ylmethyl-urea | B |
| 1-(4-(Pyridin-2-ylsulfonyl)phenyl)-3-(pyridin-4-ylmethyl)urea | B |
| 1-(Pyridin-4-ylmethyl)-3-(4-(pyridin-4-ylsulfonyl)phenyl)urea | B |
| 1-Pyridin-4-ylmethyl-3-[4-(toluene-3-sulfonyl)-phenyl]-urea | B |
| 1-Pyridin-4-ylmethyl-3-[4-(toluene-2-sulfonyl)-phenyl]-urea | B |
| 1-[4-(5-Chloro-pyridine-2-sulfonyl)-phenyl]-3-pyridin-4-ylmethyl-urea | B |
| 1-(4-((2-Fluorophenyl)sulfonyl)phenyl)-3-(pyridin-4-ylmethyl)urea | B |
| 1-(4-((3-Fluorophenyl)sulfonyl)phenyl)-3-(pyridin-4-ylmethyl)urea | A |
| 1-(4-((4-Fluorophenyl)sulfonyl)phenyl)-3-(pyridin-4-ylmethyl)urea | B |
| 1-Pyridin-4-ylmethyl-3-[4-(2-trifluoromethyl-benzenesulfonyl)-phenyl]-urea | B |
| 1-(Pyridin-4-ylmethyl)-3-(4-((3-(trifluoromethyl)phenyl)sulfonyl)phenyl)urea | A |
| 1-((1H-Pyrazol-4-yl)methyl)-3-(4-((3-(trifluoromethyl)phenyl)sulfonyl)phenyl)urea | B |
| 1-(4-Cyclohexanesulfonyl-phenyl)-3-pyridin-4-ylmethyl-urea | B |
| 1-Pyridin-4-ylmethyl-3-[4-(2-trifluoromethoxy-benzenesulfonyl)-phenyl]-urea | A |
| 1-[4-(6-Methyl-pyridine-3-sulfonyl)-phenyl]-3-pyridin-4-ylmethyl-urea | B |
| Pyridin-4-ylmethyl-3-[4-(thiazole-2-sulfonyl)-phenyl]-urea | B |
| 1-Pyridin-4-ylmethyl-3-[4-(3-trifluoromethoxy-benzenesulfonyl)-phenyl]-urea | A |
| 1-[4-(2,4-Dichloro-benzenesulfonyl)-phenyl]-3-pyridin-4-ylmethyl-urea | B |
| of 1-[4-(3,4-Difluoro-benzenesulfonyl)-phenyl]-3-pyridin-4-ylmethyl-urea | A |
| 1-Pyridin-4-ylmethyl)-3-(4-(thiazol-5-ylsulfonyl)phenyl)urea | B |
| 1-[4-(Pyridine-3-sulfonyl)-phenyl]-3-pyridin-4-ylmethyl-urea | B |
| 1-[4-(1-Methyl-piperidine-4-sulfonyl)-phenyl]-3-pyridin-4-ylmethyl-urea | C |
| 1-[4-(1-Isopropyl-piperidine-4-sulfonyl)-phenyl]-3-pyridin-4-ylmethyl-urea | B |
| 1-[4-(1-Isobutyl-piperidine-4-sulfonyl)-phenyl]-3-pyridin-4-ylmethyl-urea | C |
| 1-[4-(3,5-Difluoro-benzenesulfonyl)-phenyl]-3-pyridin-4-ylmethyl-urea | B |
| 1-[4-(1-Isopropyl-1H-pyrazole-4-sulfonyl)-phenyl]-3-pyridin-4-ylmethyl-urea | A |
| 1-[4-(Pyrazine-2-sulfonyl)-phenyl]-3-pyridin-4-ylmethyl-urea | B |
| 1-[4-(2,4-Difluoro-benzenesulfonyl)-phenyl]-3-pyridin-4-ylmethyl-urea | B |
| 1-[4-(6-Methoxy-pyridine-3-sulfonyl)-phenyl]-3-pyridin-4-ylmethyl-urea | B |
| 1-[4-(1-Methyl-1H-pyrazole-4-sulfonyl)-phenyl]-3-pyridin-4-ylmethyl-urea | B |
| 1-Pyridin-4-ylmethyl-3-[4-(pyrimidine-2-sulfonyl)-phenyl]-urea | C |

TABLE B-6-continued

| Compound Name | EC$_{50}$ |
|---|---|
| 1-(1H-Pyrazol-4-ylmethyl)-3-{4-[1-(tetrahydro-pyran-4-yl)-piperidine-4-sulfonyl]-phenyl}-urea | B |
| 1-[4-(6-Hydroxy-pyridine-3-sulfonyl)-phenyl]-3-pyridin-4-ylmethyl-urea | B |
| 1-[4-(6-Chloro-pyridine-3-sulfonyl)-phenyl]-3-pyridin-4-ylmethyl-urea | B |
| 1-[4-(1H-Indazol-3-yl)-phenyl]-3-pyridin-4-ylmethyl-urea | B |
| 1-(4-(Benzo[d]thiazol-2-yl)phenyl)-3-(pyridin-4-ylmethyl)urea | D |
| 1-[4-(1-Methyl-1H-indazol-3-yl)-phenyl]-3-pyridin-4-ylmethyl-urea | B |
| 1-(4-((4-Phenylthiazol-2-yl)amino)phenyl)-3-(pyridin-4-ylmethyl)urea | B |
| 1-(4-(5-Benzylthiazol-2-yl)phenyl)-3-(pyridin-4-ylmethyl)urea | D |
| 1-(4-((1H-pyrazol-4-yl)sulfonyl)phenyl)-3-(pyridin-4-ylmethyl)urea | B |
| 1-[4-(Benzothiazol-2-ylamino)-phenyl]-3-pyridin-4-ylmethyl-urea | D |
| 1-(4-(1,5-Dimethyl-1H-indazol-3-yl)phenyl)-3-(pyridin-4-ylmethyl)urea | B |
| 1-(4-(1,7-Dimethyl-1H-indazol-3-yl)phenyl)-3-(pyridin-4-ylmethyl)urea | B |
| 1-(4-Benzothiazol-4-yl-phenyl)-3-pyridin-4-ylmethyl-urea | B |
| 1-[4-(1,6-Dimethyl-1H-indazol-3-yl)-phenyl]-3-pyridin-4-ylmethyl-urea | B |
| 1-[4-(5-Methoxy-1-methyl-1H-indazol-3-yl)-phenyl]-3-pyridin-4-ylmethyl-urea | B |
| 1-[4-(5-Fluoro-1-methyl-1H-indazol-3-yl)-phenyl]-3-pyridin-4-ylmethyl-urea | B |
| 1-[4-(1H-Benzoimidazol-4-yl)-phenyl]-3-pyridin-4-ylmethyl-urea | E |
| 1-(4-([1,1'-Biphenyl]-2-ylsulfonyl)phenyl)-3-(pyridin-4-ylmethyl)urea | B |
| 1-(4-([1,1'-Biphenyl]-2-ylsulfonyl)phenyl)-3-(pyridin-4-ylmethyl)urea | A |
| 1-(4-(1-Methyl-1H-pyrazolo[3,4-b]pyridin-3-yl)-phenyl]-3-pyridin-4-ylmethyl-urea | D |
| 1-(4-(5-Chloro-1-methyl-1H-indazol-3-yl)phenyl)-3-(pyridin-4-ylmethyl)urea | C |
| 1-(4-((5-Phenylthiazol-2-yl)amino)phenyl)-3-(pyridin-4-ylmethyl)urea | D |
| 1-[4-(1-Methyl-1H-pyrazolo[4,3-b]pyridin-3-yl)-phenyl]-3-pyridin-4-ylmethyl-urea | B |
| 1-(4-(1-Methyl-1H-pyrazolo[3,4-c]pyridin-3-yl)phenyl)-3-(pyridin-4-ylmethyl)urea | B |
| 1-[4-(1H-Indazol-3-yl)-phenyl]-3-pyridin-4-ylmethyl-urea | B |
| 1-(4-(1,4-Dimethyl-1H-indazol-3-yl)phenyl)-3-(pyridin-4-ylmethyl)urea | B |
| 1-[4-(3-Iodo-benzenesulfonyl)-phenyl]-3-pyridin-4-ylmethyl-urea | A |
| 1-[4-(2'-Fluoro-biphenyl-2-sulfonyl)-phenyl]-3-pyridin-4-ylmethyl-urea | A |
| 1-[4-(3'-Fluoro-biphenyl-2-sulfonyl)-phenyl]-3-pyridin-4-ylmethyl-urea | A |
| 1-[4-(4'-Fluoro-biphenyl-2-sulfonyl)-phenyl]-3-pyridin-4-ylmethyl-urea | B |
| 1-[4-(3'-Methoxy-biphenyl-2-sulfonyl)-phenyl]-3-pyridin-4-ylmethyl-urea | B |
| 1-[4-(4'-Methoxy-biphenyl-2-sulfonyl)-phenyl]-3-pyridin-4-ylmethyl-urea | D |
| 1-[4-(2-Pyridin-3-yl-benzenesulfonyl)-phenyl]-3-pyridin-4-ylmethyl-urea | B |
| 1-[4-(2-Pyridin-4-yl-benzenesulfonyl)-phenyl]-3-pyridin-4-ylmethyl-urea | B |
| 1-[4-(4'-Chloro-biphenyl-2-sulfonyl)-phenyl]-3-pyridin-4-ylmethyl-urea | D |
| 1-[4-(3'-Chloro-biphenyl-2-sulfonyl)-phenyl]-3-pyridin-4-ylmethyl-urea | B |
| 1-[4-(4'-Methyl-biphenyl-2-sulfonyl)-phenyl]-3-pyridin-4-ylmethyl-urea | C |
| 1-[4-(1-Methyl-1H-pyrazolo[4,3-c]pyridin-3-yl)-phenyl]-3-pyridin-4-ylmethyl-urea | D |
| 1-[4-(2'-Methoxy-biphenyl-2-sulfonyl)-phenyl]-3-pyridin-4-ylmethyl-urea | D |
| 1-[4-(4'-Methoxy-biphenyl-2-sulfonyl)-phenyl]-3-pyridin-4-ylmethyl-urea | D |
| 1-[4-(3'-Methyl-biphenyl-2-sulfonyl)-phenyl]-3-pyridin-4-ylmethyl-urea | B |
| 1-(4-((2'-Chloro-[1,1'-biphenyl]-2-yl)sulfonyl)phenyl)-3-(pyridin-4-ylmethyl)urea | B |
| 1-(4-((4'-Cyano-[1,1'-biphenyl]-2-yl)sulfonyl)phenyl)-3-(pyridin-4-ylmethyl)urea | D |
| 1-(4-((2-(6-Methoxypyridin-3-yl)phenyl)sulfonyl)phenyl)-3-(pyridin-4-ylmethyl)urea | D |
| 1-(4-((3'-Cyano-[1,1'-biphenyl]-2-yl)sulfonyl)phenyl)-3-(pyridin-4-ylmethyl)urea | C |
| 1-(4-((2'-Methyl-[1,1'-biphenyl]-2-yl)sulfonyl)phenyl)-3-(pyridin-4-ylmethyl)urea | B |
| 1-(3-Cyano-4-((3,5-difluorophenyl)sulfonyl)phenyl)-3-(pyridin-4-ylmethyl)urea | B |

Where A = <100 nM;
B = 100 nM-2 uM;
C = 2-5 uM;
D = 5-20 uM;
E = >20 uM

The examples and embodiments described herein are for illustrative purposes only and various modifications or changes suggested to persons skilled in the art are to be included within the spirit and purview of this application and scope of the appended claims.

What is claimed is:

1. A compound of Formula (Ia), or a pharmaceutically acceptable salt, or solvate thereof:

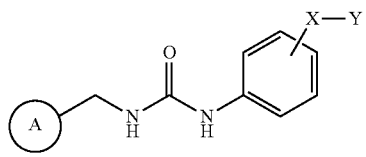

Formula (Ia)

wherein:

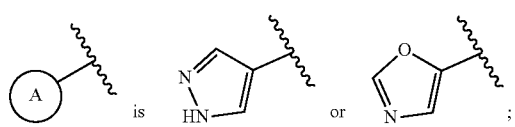

X is absent or -L$^1$-X$^1$-L$^2$-;

L$^1$ is absent or —CH$_2$—;

X$^1$ is selected from the group consisting of —SO$_2$—, —NR$^5$—, —SO$_2$NR$^5$—, —NR$^5$SO$_2$—, —C(=O)NR$^5$—, and —NR$^5$C(=O)—;

each R$^5$ is independently selected from the group consisting of H, D, substituted or unsubstituted C$_1$-C$_6$alkyl, substituted or unsubstituted C$_1$-C$_6$deuteroalkyl, substituted or unsubstituted C₁-C₆fluoroalkyl, substituted or unsubstituted C₃-C₆cycloalkyl, and substituted or unsubstituted benzyl;

L² is absent or substituted or unsubstituted C₁-C₄alkylene;

Y is selected from the group consisting of D, substituted or unsubstituted C₁-C₆deuteroalkyl, substituted or unsubstituted C₃-C₁₀cycloalkyl, substituted or unsubstituted C₂-C₁₀heterocycloalkyl, substituted or unsubstituted phenyl, substituted or unsubstituted benzyl, substituted or unsubstituted naphthyl, and substituted or unsubstituted heteroaryl, wherein if Y is substituted then Y is substituted with 1-4 R⁷ groups;

each R⁷ is independently selected from the group consisting of D, —CN, F, Cl, Br, I, —OH, —OR⁹, —SR⁹, —S(=O)R⁹, —S(=O)₂R⁹, —N(R⁸)S(=O)₂R⁹, —S(=O)₂NH₂, —S(=O)₂NR⁸R⁹, —C(=O)R⁹, —OC(=O)R⁹, —CO₂R⁸, —OCO₂R⁹, —NH₂, —NR⁸R⁹, —C(=O)NH₂, —C(=O)NR⁸R⁹, —OC(=O)NH₂, —OC(=O)NR⁸R⁹, —NR⁸C(=O)NH₂, —NR⁸C(=O)NR⁸R⁹, —NR⁸C(=O)R⁹, —NR⁸C(=O)OR⁹, substituted or unsubstituted C₁-C₆alkyl, substituted or unsubstituted C₁-C₆deuteroalkyl, substituted or unsubstituted C₁-C₆fluoroalkyl, a substituted or unsubstituted C₃-C₆cycloalkyl, a substituted or unsubstituted C₂-C₆heterocycloalkyl, a substituted or unsubstituted aryl, or a substituted or unsubstituted heteroaryl, a substituted or unsubstituted —C₁-C₄alkylene-C₃-C₁₀cycloalkyl, a substituted or unsubstituted —C₁-C₄alkylene-C₂-C₁₀heterocycloalkyl, a substituted or unsubstituted —C₁-C₄alkylene-aryl, and a substituted or unsubstituted —C₁-C₄alkylene-heteroaryl;

each R⁸ is independently selected from the group consisting of H, C₁-C₆alkyl, and C₁-C₆fluoroalkyl;

each R⁹ is independently selected from the group consisting of C₁-C₆alkyl, C₁-C₆fluoroalkyl, a substituted or unsubstituted C₃-C₆cycloalkyl, a substituted or unsubstituted C₂-C₆heterocycloalkyl, a substituted or unsubstituted aryl, a substituted or unsubstituted heteroaryl, a substituted or unsubstituted —C₁-C₄alkylene-C₃-C₁₀cycloalkyl, a substituted or unsubstituted —C₁-C₄alkylene-C₂-C₁₀heterocycloalkyl, a substituted or unsubstituted —C₁-C₄alkylene-aryl, and a substituted or unsubstituted —C₁-C₄alkylene-heteroaryl.

2. The compound of claim 1, or a pharmaceutically acceptable salt, or solvate thereof, wherein:
the groups

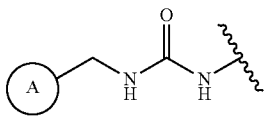

and —X—Y are in a 1,4-relationship on the phenyl or a 1,3-relationship on the phenyl.

3. The compound of claim 1, or a pharmaceutically acceptable salt, or solvate thereof, wherein:
X is absent or -L¹-X¹-L²-;
L¹ is absent or —CH₂—;
X¹ is selected from the group consisting of —SO₂—, —NR⁵—, —SO₂NR⁵—, —NR⁵SO₂—, —C(=O)NR⁵—, or —NR⁵C(=O)—;

each R⁵ is independently selected from the group consisting of H, C₁-C₄alkyl, and substituted or unsubstituted benzyl;
L² is absent or —CH₂—;
Y is selected from the group consisting of substituted or unsubstituted C₁-C₆deuteroalkyl, substituted or unsubstituted C₃-C₁₀cycloalkyl, substituted or unsubstituted C₂-C₁₀heterocycloalkyl, substituted or unsubstituted phenyl, substituted or unsubstituted benzyl, substituted or unsubstituted naphthyl, and substituted or unsubstituted heteroaryl, wherein if Y is substituted then Y is substituted with 1-2 R⁷ groups.

4. The compound of claim 1, wherein the compound of Formula (Ia) has the structure of Formula (IIa), or a pharmaceutically acceptable salt, or solvate thereof, wherein:

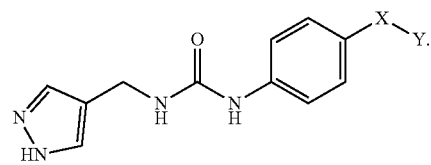

Formula (IIa)

5. The compound of claim 1, wherein the compound of Formula (Ia) has the structure of Formula (IIIa), or a pharmaceutically acceptable salt, or solvate thereof, wherein:

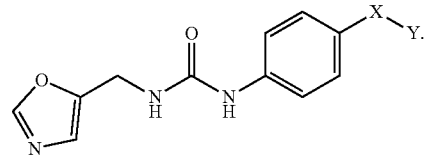

Formula (IIIa)

6. The compound of claim 1, or a pharmaceutically acceptable salt, or solvate thereof, wherein:
L¹ is absent;
R⁵ is independently selected from the group consisting of H, C₁-C₄alkyl, and substituted or unsubstituted benzyl; and
L² is absent or —CH₂—.

7. The compound of claim 1, or a pharmaceutically acceptable salt, or solvate thereof, wherein:
Y is selected from the group consisting of substituted or unsubstituted C₃-C₆cycloalkyl, substituted or unsubstituted C₂-C₆heterocycloalkyl, substituted or unsubstituted phenyl, substituted or unsubstituted benzyl, or substituted or unsubstituted monocyclic heteroaryl, and substituted or unsubstituted bicyclic heteroaryl, wherein if Y is substituted then Y is substituted with 1-2 R⁷ groups.

8. The compound of claim 1, or a pharmaceutically acceptable salt, or solvate thereof, wherein:
Y is a substituted or unsubstituted phenyl, wherein if Y is substituted then Y is substituted with 1-2 R⁷ groups.

9. The compound of claim 1, or a pharmaceutically acceptable salt, or solvate thereof, wherein:
Y is selected from the group consisting of substituted or unsubstituted cyclopropyl, substituted or unsubstituted cyclobutyl, substituted or unsubstituted cyclopentyl, and substituted or unsubstituted cyclohexyl, wherein if Y is substituted then Y is substituted with 1-2 $R^7$ groups.

10. The compound of claim 1, or a pharmaceutically acceptable salt, or solvate thereof, wherein:
   Y is a substituted or unsubstituted monocyclic 6-membered heteroaryl containing 1-2 N atoms, wherein if Y is substituted then Y is substituted with 1-2 $R^7$ groups;
   or Y is a substituted or unsubstituted monocyclic 5-membered $C_1$-$C_4$heteroaryl containing 1-4 N atoms and 0 or 1 S or O atom, or a substituted or unsubstituted monocyclic 5-membered $C_1$-$C_4$heteroaryl containing 0-4 N atoms and 1 S or O atom, wherein if Y is substituted then Y is substituted with 1-2 $R^7$ groups.

11. The compound of claim 1, or a pharmaceutically acceptable salt, or solvate thereof, wherein:
   Y is selected from the group consisting of substituted or unsubstituted furanyl, substituted or unsubstituted thienyl, substituted or unsubstituted pyrrolyl, substituted or unsubstituted oxazolyl, substituted or unsubstituted thiazolyl, substituted or unsubstituted imidazolyl, substituted or unsubstituted pyrazolyl, substituted or unsubstituted triazolyl, substituted or unsubstituted tetrazolyl, substituted or unsubstituted isoxazolyl, substituted or unsubstituted isothiazolyl, substituted or unsubstituted oxadiazolyl, substituted or unsubstituted thiadiazolyl, substituted or unsubstituted pyridinyl, substituted or unsubstituted pyrimidinyl, substituted or unsubstituted pyrazinyl, substituted or unsubstituted pyridazinyl, and substituted or unsubstituted triazinyl, wherein if Y is substituted then Y is substituted with 1-2 $R^7$ groups;
   or Y is selected from the group consisting of substituted or unsubstituted pyrrolidinyl, substituted or unsubstituted tetrahydrofuranyl, substituted or unsubstituted dihydrofuranyl, substituted or unsubstituted tetrahydrothienyl, substituted or unsubstituted oxazolidinonyl, substituted or unsubstituted tetrahydropyranyl, substituted or unsubstituted dihydropyranyl, substituted or unsubstituted tetrahydrothiopyranyl, substituted or unsubstituted piperidinyl, substituted or unsubstituted morpholinyl, substituted or unsubstituted thiomorpholinyl, substituted or unsubstituted thioxanyl, substituted or unsubstituted piperazinyl, substituted or unsubstituted aziridinyl, substituted or unsubstituted azetidinyl, substituted or unsubstituted oxetanyl, substituted or unsubstituted thietanyl, substituted or unsubstituted homopiperidinyl, substituted or unsubstituted oxepanyl, substituted or unsubstituted thiepanyl, substituted or unsubstituted oxazepinyl, substituted or unsubstituted diazepinyl, substituted or unsubstituted thiazepinyl, and substituted or unsubstituted 1,2,3,6-tetrahydropyridinyl, wherein if Y is substituted then Y is substituted with 1-2 $R^7$ groups;
   or Y is selected from the group consisting of substituted or unsubstituted indolizinyl, substituted or unsubstituted indolyl, substituted or unsubstituted benzofuranyl, substituted or unsubstituted benzothiophenyl, substituted or unsubstituted indazolyl, substituted or unsubstituted benzimidazolyl, substituted or unsubstituted purinyl, substituted or unsubstituted quinolizinyl, substituted or unsubstituted quinolinyl, substituted or unsubstituted isoquinolinyl, substituted or unsubstituted cinnolinyl, substituted or unsubstituted phthalazinyl, substituted or unsubstituted quinazolinyl, substituted or unsubstituted quinoxalinyl, substituted or unsubstituted 1,8-naphthyridinyl, and substituted or unsubstituted pteridinyl wherein if Y is substituted then Y is substituted with 1-2 $R^7$ groups.

12. The compound of claim 1, or a pharmaceutically acceptable salt, or solvate thereof, wherein:
   $L^1$ is absent or —$CH_2$—;
   $X^1$ is selected from the group consisting of —$NR^5$—, —$SO_2NR^5$—, and —C(=O)$NR^5$—;
   $R^5$ is independently selected from the group consisting of H, D, $C_1$-$C_4$alkyl, and substituted or unsubstituted benzyl; and
   $L^2$ is absent.

13. The compound of claim 1, or a pharmaceutically acceptable salt, or solvate thereof, wherein:
   each $R^7$ is independently selected from the group consisting of D, —CN, F, Cl, Br, I, —OH, —$OR^9$, —$SR^9$, —S(=O)$R^9$, —S(=O)$_2R^9$, —N($R^8$)S(=O)$_2R^9$, —S(=O)$_2NH_2$, —S(=O)$_2NR^8R^9$, —C(=O)$R^9$, —OC(=O)$R^9$, —$CO_2R^8$, —$OCO_2R^9$, —$NH_2$, —$NR^8R^9$, —C(=O)$NH_2$, —C(=O)$NR^8R^9$, —OC(=O)$NH_2$, —OC(=O)$NR^8R^9$, —$NR^8$C(=O)$NH_2$, —$NR^8$C(=O)$NR^8R^9$, —$NR^8$C(=O)$R^9$, —$NR^8$C(=O)$OR^9$, $C_1$-$C_6$alkyl, $C_1$-$C_6$deuteroalkyl, $C_1$-$C_6$fluoroalkyl, a unsubstituted $C_3$-$C_6$cycloalkyl, a unsubstituted $C_2$-$C_6$heterocycloalkyl, a unsubstituted phenyl, or a unsubstituted heteroaryl, a unsubstituted —$CH_2$—$C_3$-$C_6$cycloalkyl, a unsubstituted —$CH_2$—$C_2$-$C_6$heterocycloalkyl, a unsubstituted —$CH_2$-phenyl, and a unsubstituted —$CH_2$-heteroaryl;
   each $R^8$ is independently selected from the group consisting of H, $C_1$-$C_6$alkyl, and $C_1$-$C_6$fluoroalkyl;
   each $R^9$ is independently selected from the group consisting of $C_1$-$C_6$alkyl, $C_1$-$C_6$fluoroalkyl, a substituted or unsubstituted $C_3$-$C_6$cycloalkyl, a unsubstituted $C_2$-$C_6$heterocycloalkyl, a unsubstituted phenyl, a unsubstituted heteroaryl, a unsubstituted —$CH_2$—$C_3$-$C_{10}$cycloalkyl, a unsubstituted —$CH_2$—$C_2$-$C_{10}$heterocycloalkyl, a unsubstituted —$CH_2$-phenyl, and a unsubstituted —$CH_2$-heteroaryl.

14. A compound that is:
Ethyl 4-(3-((1H-pyrazol-4-yl)methyl)ureido)benzoate;
N-(3-Chloro-phenyl)-4-[3-(1H-pyrazol-4-ylmethyl)-ureido]-benzamide;
4-(3-((1H-pyrazol-4-yl)methyl)ureido)-N-(2-methoxyphenyl)benzamide;
4-(3-((1H-pyrazol-4-yl)methyl)ureido)-N-(2-chlorophenyl)benzamide;
4-(3-((1H-pyrazol-4-yl)methyl)ureido)-N-(4-methoxyphenyl)benzamide;
4-(3-((1H-pyrazol-4-yl)methyl)ureido)-N-(4-chlorophenyl)benzamide;
4-(3-((1H-pyrazol-4-yl)methyl)ureido)-N-(3-methoxyphenyl)benzamide;
4-[3-(1H-Pyrazol-4-ylmethyl)-ureido]-N-pyridin-2-yl-benzenesulfonamide;
N-Benzyl-4-[3-(1H-pyrazol-4-ylmethyl)-ureido]-benzenesulfonamide;
1-[4-(3,4-Dihydro-1H-isoquinoline-2-sulfonyl)-phenyl]-3-(1H-pyrazol-4-ylmethyl)-urea;
1-[4-(8-Oxa-3-aza-bicyclo[3.2.1]octane-3-sulfonyl)-phenyl]-3-(1H-pyrazol-4-ylmethyl)-urea;
N-Cyclobutylmethyl-4-[3-(1H-pyrazol-4-ylmethyl)-ureido]-benzenesulfonamide;
N-Phenyl-4-[3-(1H-pyrazol-4-ylmethyl)-ureido]-benzenesulfonamide;
N-Cyclopentyl-N-methyl-4-[3-(1H-pyrazol-4-ylmethyl)-ureido]-benzenesulfonamide;

N-Benzyl-N-isopropyl-4-[3-(1H-pyrazol-4-ylmethyl)-ureido]-benzenesulfonamide;
N-(3-Methoxy-benzyl)-4-[3-(1H-pyrazol-4-ylmethyl)-ureido]-benzenesulfonamide;
N-(2-Chloro-benzyl)-4-[3-(1H-pyrazol-4-ylmethyl)-ureido]-benzenesulfonamide;
N-(2-Methoxy-benzyl)-4-[3-(1H-pyrazol-4-ylmethyl)-ureido]-benzenesulfonamide;
N-(4-Methoxy-benzyl)-4-[3-(1H-pyrazol-4-ylmethyl)-ureido]-benzenesulfonamide;
N-(4-Chloro-benzyl)-4-[3-(1H-pyrazol-4-ylmethyl)-ureido]-benzenesulfonamide;
1-[4-(3-Chloro-benzenesulfonyl)-phenyl]-3-(1H-pyrazol-4-ylmethyl)-urea;
1-[4-(2-Chloro-benzenesulfonyl)-phenyl]-3-(1H-pyrazol-4-ylmethyl)-urea;
1-[4-(4-Chloro-benzenesulfonyl)-phenyl]-3-(1H-pyrazol-4-ylmethyl)-urea;
1-[4-(2-Methoxy-benzenesulfonyl)-phenyl]-3-(1H-pyrazol-4-ylmethyl)-urea;
1-[4-(3-Methoxy-benzenesulfonyl)-phenyl]-3-(1H-pyrazol-4-ylmethyl)-urea;
1-(4-Benzenesulfonyl-phenyl)-3-(1H-pyrazol-4-ylmethyl)-urea;
1-[4-(4-Methoxy-benzenesulfonyl)-phenyl]-3-(1H-pyrazol-4-ylmethyl)-urea;
N-{4-[3-(1H-Pyrazol-4-ylmethyl)-ureido]-phenyl}-benzenesulfonamide;
N-(4-(3-((1H-pyrazol-4-yl)methyl)ureido)phenyl)-1-phenylmethanesulfonamide;
1-((1H-Pyrazol-4-yl)methyl)-3-(4-((4-(trifluoromethyl)phenyl)sulfonyl)phenyl)urea;
1-((1H-Pyrazol-4-yl)methyl)-3-(4-(pyridin-2-ylsulfonyl)phenyl)urea;
1-[4-(5-Methyl-pyridine-2-sulfonyl)-phenyl]-3-(1H-pyrazol-4-ylmethyl)-urea;
1-((1H-Pyrazol-4-yl)methyl)-3-(4-((2-fluorophenyl)sulfonyl)phenyl)urea;
1-((1H-Pyrazol-4-yl)methyl)-3-(4-((3-fluorophenyl)sulfonyl)phenyl)urea;
1-((1H-Pyrazol-4-yl)methyl)-3-(4-((4-fluorophenyl)sulfonyl)phenyl)urea;
1-((1H-Pyrazol-4-yl)methyl)-3-(4-((3-(trifluoromethyl)phenyl)sulfonyl)phenyl)urea;
1-((1H-Pyrazol-4-yl)methyl)-3-(4-(pyridin-4-ylsulfonyl)phenyl)urea;
1-(1H-Pyrazol-4-ylmethyl)-3-[4-(4-trifluoromethoxy-benzenesulfonyl)-phenyl]-urea;
1-(1H-Pyrazol-4-ylmethyl)-3-[4-(toluene-4-sulfonyl)-phenyl]-urea;
1-(1H-Pyrazol-4-ylmethyl)-3-[4-(toluene-3-sulfonyl)-phenyl]-urea;
1-(1H-Pyrazol-4-ylmethyl)-3-[4-(toluene-2-sulfonyl)-phenyl]-urea;
1-[4-(4-Cyano-benzenesulfonyl)-phenyl]-3-(1H-pyrazol-4-ylmethyl)-urea;
1-[4-(3,4-Dichloro-benzenesulfonyl)-phenyl]-3-(1H-pyrazol-4-ylmethyl)-urea;
1-[4-(5-Chloro-pyridine-2-sulfonyl)-phenyl]-3-(1H-pyrazol-4-ylmethyl)-urea;
1-(1H-Pyrazol-4-ylmethyl)-3-[4-(2-trifluoromethyl-benzenesulfonyl)-phenyl]-urea;
N-(3-Fluoro-benzyl)-4-[3-(1H-pyrazol-4-ylmethyl)-ureido]-benzenesulfonamide;
1-[4-(6-Methyl-pyridine-3-sulfonyl)-phenyl]-3-(1H-pyrazol-4-ylmethyl)-urea;
1-((1H-Pyrazol-4-yl)methyl)-3-(4-(pyrimidin-5-ylsulfonyl)phenyl)urea;
1-(4-Cyclohexanesulfonyl-phenyl)-3-(1H-pyrazol-4-ylmethyl)-urea;
1-(1H-Pyrazol-4-ylmethyl)-3-[4-(2-trifluoromethoxy-benzenesulfonyl)-phenyl]-urea;
1-(1H-Pyrazol-4-ylmethyl)-3-[4-(3-trifluoromethoxy-benzenesulfonyl)-phenyl]-urea;
1-[4-(3,4-Difluoro-benzenesulfonyl)-phenyl]-3-(1H-pyrazol-4-ylmethyl)-urea;
1-(1H-Pyrazol-4-ylmethyl)-3-[4-(thiazole-2-sulfonyl)-phenyl]-urea;
1-[4-(3,4-Dichloro-benzenesulfonyl)-phenyl]-3-(1H-pyrazol-4-ylmethyl)-urea;
N-(4-Methyl-benzyl)-4-[3-(1H-pyrazol-4-ylmethyl)-ureido]-benzenesulfonamide;
1-[4-(2,4-Dichloro-benzenesulfonyl)-phenyl]-3-(1H-pyrazol-4-ylmethyl)-urea;
1-(1H-Pyrazol-4-ylmethyl)-3-[4-(pyridine-3-sulfonyl)-phenyl]-urea;
1-(1H-Pyrazol-4-ylmethyl)-3-[4-(thiazole-2-sulfonyl)-phenyl]-urea;
1-[4-(3,5-Difluoro-benzenesulfonyl)-phenyl]-3-(1H-pyrazol-4-ylmethyl)-urea;
of 1-[4-(1-Isopropyl-1H-pyrazole-4-sulfonyl)-phenyl]-3-(1H-pyrazol-4-ylmethyl)-urea;
1-[4-(Pyrazine-2-sulfonyl)-phenyl]-3-(1H-pyrazol-4-ylmethyl)-urea;
1-[4-(1-Methyl-piperidine-4-sulfonyl)-phenyl]-3-(1H-pyrazol-4-ylmethyl)-urea;
1-[4-(1-Isopropyl-piperidine-4-sulfonyl)-phenyl]-3-(1H-pyrazol-4-ylmethyl)-urea;
1-[4-(1-Isobutyl-piperidine-4-sulfonyl)-phenyl]-3-(1H-pyrazol-4-ylmethyl)-urea;
of 1-[4-(2,4-Difluoro-benzenesulfonyl)-phenyl]-3-(1H-pyrazol-4-ylmethyl)-urea;
1-[4-(6-Methyl-pyridine-3-sulfonyl)-phenyl]-3-(1H-pyrazol-4-ylmethyl)-urea;
1-[4-(1-Methyl-1H-pyrazole-4-sulfonyl)-phenyl]-3-(1H-pyrazol-4-ylmethyl)-urea;
1-(1H-Pyrazol-4-ylmethyl)-3-[4-(pyrimidine-2-sulfonyl)-phenyl]-urea;
1-(1H-Pyrazol-4-ylmethyl)-3-{4-[1-(tetrahydro-pyran-4-yl)-piperidine-4-sulfonyl]-phenyl}-urea;
1-((1H-Pyrazol-4-yl)methyl)-3-(4-(benzo[d]thiazol-2-yl)phenyl)urea;
1-[4-(1H-Indazol-3-yl)-phenyl]-3-(1H-pyrazol-4-ylmethyl)-urea;
1-[4-(1-Methyl-1H-indazol-3-yl)-phenyl]-3-(1H-pyrazol-4-ylmethyl)-urea;
1-((1H-Pyrazol-4-yl)methyl)-3-(4-((4-phenylthiazol-2-yl)amino)phenyl)urea;
1-((1H-Pyrazol-4-yl)methyl)-3-(4-(5-benzylthiazol-2-yl)phenyl)urea;
1-((1H-Pyrazol-4-yl)methyl)-3-(4-((1H-pyrazol-4-yl)sulfonyl)phenyl)urea;
1-((1H-Pyrazol-4-yl)methyl)-3-(4-(benzo[d]thiazol-2-ylamino)phenyl)urea;
1-(1H-Pyrazol-4-ylmethyl)-3-[4-(4-o-tolyl-thiazol-2-ylamino)-phenyl]-urea;
1-(1H-Pyrazol-4-ylmethyl)-3-[4-(4-m-tolyl-thiazol-2-ylamino)-phenyl]-urea;
1-(1H-Pyrazol-4-ylmethyl)-3-[4-(4-p-tolyl-thiazol-2-ylamino)-phenyl]-urea;
1-{4-[4-(2-Fluoro-phenyl)-thiazol-2-ylamino]-phenyl}-3-(1H-pyrazol-4-ylmethyl)-urea;

1-((1H-Pyrazol-4-yl)methyl)-3-(4-(1,5-dimethyl-1H-indazol-3-yl)phenyl)urea;
1-[4-(1,6-Dimethyl-1H-indazol-3-yl)-phenyl]-3-(1H-pyrazol-4-ylmethyl)-urea;
1-{4-[4-(3-Fluoro-phenyl)-thiazol-2-ylamino]-phenyl}-3-(1H-pyrazol-4-ylmethyl)-urea;
1-{4-[4-(4-Fluoro-phenyl)-thiazol-2-ylamino]-phenyl}-3-(1H-pyrazol-4-ylmethyl)-urea;
1-((1H-Pyrazol-4-yl)methyl)-3-(4-((4-(2-methoxyphenyl)thiazol-2-yl)amino)phenyl)urea;
1-((1H-Pyrazol-4-yl)methyl)-3-(4-((4-(3-methoxyphenyl)thiazol-2-yl)amino)phenyl)urea;
1-(4-Benzothiazol-4-yl-phenyl)-3-(1H-pyrazol-4-ylmethyl)-urea;
1-((1H-Pyrazol-4-yl)methyl)-3-(4-(1,7-dimethyl-1H-indazol-3-yl)phenyl)urea;
1-[4-(5-Methoxy-1-methyl-1H-indazol-3-yl)-phenyl]-3-(1H-pyrazol-4-ylmethyl)-urea;
1-[4-(5-Fluoro-1-methyl-1H-indazol-3-yl)-phenyl]-3-(1H-pyrazol-4-ylmethyl)-urea;
1-{4-[4-(2-Chloro-phenyl)-thiazol-2-ylamino]-phenyl}-3-(1H-pyrazol-4-ylmethyl)-urea;
1-{4-[4-(3-Chloro-phenyl)-thiazol-2-ylamino]-phenyl}-3-(1H-pyrazol-4-ylmethyl)-urea;
1-{4-[4-(4-Chloro-phenyl)-thiazol-2-ylamino]-phenyl}-3-(1H-pyrazol-4-ylmethyl)-urea;
1-((1H-Pyrazol-4-yl)methyl)-3-(4-((4-(4-methoxyphenyl)thiazol-2-yl)amino)phenyl)urea;
1-[4-(1H-Benzoimidazol-4-yl)-phenyl]-3-(1H-pyrazol-4-ylmethyl)-urea;
1-((1H-Pyrazol-4-yl) methyl)-3-(4-([1,1'-biphenyl]-3-ylsulfonyl)phenyl)urea;
1-((1H-Pyrazol-4-yl) methyl)-3-(4-([1,1'-biphenyl]-2-ylsulfonyl)phenyl)urea;
1-[4-(1-Methyl-1H-pyrazolo[3,4-b]pyridin-3-yl)-phenyl]-3-(1H-pyrazol-4-ylmethyl)-urea;
1-((1H-Pyrazol-4-yl)methyl)-3-(4-(5-chloro-1-methyl-1H-indazol-3-yl)phenyl)urea;
1-((1H-Pyrazol-4-yl)methyl)-3-(4-((5-phenylthiazol-2-yl)amino)phenyl)urea;
1-((1H-Pyrazol-4-yl)methyl)-3-(4-(5-phenylthiazol-2-yl)phenyl)urea;
1-[4-(1-Methyl-1H-pyrazolo[4,3-b]pyridin-3-yl)-phenyl]-3-(1H-pyrazol-4-ylmethyl)-urea;
1-((1H-Pyrazol-4-yl)methyl)-3-(4-(1-methyl-1H-pyrazolo[3,4-c]pyridin-3-yl)phenyl)urea;
1-((1H-Pyrazol-4-yl)methyl)-3-(4-(1,4-dimethyl-1H-indazol-3-yl)phenyl)urea;
1-[4-(1-Methyl-1H-pyrazolo[4,3-c]pyridin-3-yl)-phenyl]-3-(1H-pyrazol-4-ylmethyl)-urea;
1-(1H-Pyrazol-4-ylmethyl)-3-[4-(2-pyridin-3-yl-benzenesulfonyl)-phenyl]-urea;
1-[4-(3-Iodo-benzenesulfonyl)-phenyl]-3-(1H-pyrazol-4-ylmethyl)-urea;
1-[4-(2'-Fluoro-biphenyl-2-sulfonyl)-phenyl]-3-(1H-pyrazol-4-ylmethyl)-urea;
1-[4-(3'-Fluoro-biphenyl-2-sulfonyl)-phenyl]-3-(1H-pyrazol-4-ylmethyl)-urea;
1-[4-(4'-Fluoro-biphenyl-2-sulfonyl)-phenyl]-3-(1H-pyrazol-4-ylmethyl)-urea;
1-[4-(2'-Methoxy-biphenyl-2-sulfonyl)-phenyl]-3-(1H-pyrazol-4-ylmethyl)-urea;
1-[4-(3'-Methoxy-biphenyl-2-sulfonyl)-phenyl]-3-(1H-pyrazol-4-ylmethyl)-urea;
1-(1H-Pyrazol-4-ylmethyl)-3-[4-(2-pyridin-4-yl-benzenesulfonyl)-phenyl]-urea;
1-[4-(3'-Chloro-biphenyl-2-sulfonyl)-phenyl]-3-(1H-pyrazol-4-ylmethyl)-urea;
1-[4-(4'-Methyl-biphenyl-2-sulfonyl)-phenyl]-3-(1H-pyrazol-4-ylmethyl)-urea;
1-[4-(3'-Methyl-biphenyl-2-sulfonyl)-phenyl]-3-(1H-pyrazol-4-ylmethyl)-urea;
1-[4-(4'-Methoxy-biphenyl-2-sulfonyl)-phenyl]-3-(1H-pyrazol-4-ylmethyl)-urea;
1-((1H-Pyrazol-4-yl)methyl)-3-(4-((2'-chloro-[1,1'-biphenyl]-2-yl)sulfonyl)phenyl)urea;
1-((1H-Pyrazol-4-yl)methyl)-3-(4-((4'-cyano-[1,1'-biphenyl]-2-yl)sulfonyl)phenyl)urea;
1-((1H-Pyrazol-4-yl)methyl)-3-(4-((2-(6-methoxypyridin-3-yl)phenyl)sulfonyl)phenyl)urea;
1-((1H-Pyrazol-4-yl)methyl)-3-(4-((3'-cyano-[1,1'-biphenyl]-2-yl)sulfonyl)phenyl)urea;
1-((1H-Pyrazol-4-yl)methyl)-3-(4-((2'-methyl-[1,1'-biphenyl]-2-yl)sulfonyl)phenyl)urea;
1-[4-(6-Hydroxy-pyridine-3-sulfonyl)-phenyl]-3-(1H-pyrazol-4-ylmethyl)-urea;
or a pharmaceutically acceptable salt, or solvate thereof.

15. A compound that is:
Ethyl 4-(3-(oxazol-5-ylmethyl)ureido)benzoate;
N-Benzyl-N-isopropyl-4-(3-oxazol-5-ylmethyl-ureido)-benzenesulfonamide;
1-[4-(3,4-Dihydro-1H-isoquinoline-2-sulfonyl)-phenyl]-3-oxazol-5-ylmethyl-urea;
N-Benzyl-4-(3-oxazol-5-ylmethyl-ureido)-benzenesulfonamide;
1-(4-Benzenesulfonyl-phenyl)-3-oxazol-5-ylmethyl-urea;
N-[4-(3-Oxazol-5-ylmethyl-ureido)-phenyl]-benzenesulfonamide;
1-Oxazol-5-ylmethyl-3-[4-(4-trifluoromethoxy-benzenesulfonyl)-phenyl]-urea;
1-[4-(4-Cyano-benzenesulfonyl)-phenyl]-3-oxazol-5-ylmethyl-urea;
1-(3-Chlorophenyl)-N-(4-(3-(oxazol-5-ylmethyl)ureido)phenyl)methanesulfonamide;
1-(4-Chlorophenyl)-N-(4-(3-(oxazol-5-ylmethyl)ureido)phenyl)methanesulfonamide;
1-(3,4-Dichlorophenyl)-N-(4-(3-(oxazol-5-ylmethyl)ureido)phenyl)methanesulfonamide;
1-(2-Chlorophenyl)-N-(4-(3-(oxazol-5-ylmethyl)ureido)phenyl)methanesulfonamide;
1-Oxazol-5-ylmethyl-3-[4-(toluene-4-sulfonyl)-phenyl]-urea;
1-[4-(3,4-Dichloro-benzenesulfonyl)-phenyl]-3-oxazol-5-ylmethyl-urea;
1-(Oxazol-5-ylmethyl)-3-(4-(pyridin-2-ylsulfonyl)phenyl)urea;
1-(4-((3-Chlorophenyl)sulfonyl)phenyl)-3-(oxazol-5-ylmethyl)urea;
1-(Oxazol-5-ylmethyl)-3-(4-(pyridin-4-ylsulfonyl)phenyl)urea;
1-(4-((2-Methoxyphenyl)sulfonyl)phenyl)-3-(oxazol-5-ylmethyl)urea;
1-Oxazol-5-ylmethyl-3-[4-(toluene-3-sulfonyl)-phenyl]-urea;
1-Oxazol-5-ylmethyl-3-[4-(toluene-2-sulfonyl)-phenyl]-urea;
1-[4-(5-Chloro-pyridine-2-sulfonyl)-phenyl]-3-oxazol-5-ylmethyl-urea;
1-(4-((2-Fluorophenyl)sulfonyl)phenyl)-3-(oxazol-5-ylmethyl)urea;
1-(4-((3-Fluorophenyl)sulfonyl)phenyl)-3-(oxazol-5-ylmethyl)urea;

1-(4-((4-Fluorophenyl)sulfonyl)phenyl)-3-(oxazol-5-ylmethyl)urea;
1-[4-(2-Chloro-benzenesulfonyl)-phenyl]-3-oxazol-5-ylmethyl-urea;
1-Oxazol-5-ylmethyl-3-[4-(2-trifluoromethyl-benzenesulfonyl)-phenyl]-urea;
1-(Oxazol-5-ylmethyl)-3-(4-((3-(trifluoromethyl)phenyl)sulfonyl)phenyl)urea;
1-(Oxazol-5-ylmethyl)-3-(4-((4-(trifluoromethyl)phenyl)sulfonyl)phenyl)urea;
1-(4-Cyclohexanesulfonyl-phenyl)-3-oxazol-5-ylmethyl-urea;
1-Oxazol-5-ylmethyl-3-[4-(4-trifluoromethoxy-benzenesulfonyl)-phenyl]-urea;
1-[4-(6-Methyl-pyridine-3-sulfonyl)-phenyl]-3-oxazol-5-ylmethyl-urea;
1-(4-((4-Chlorophenyl)sulfonyl)phenyl)-3-(oxazol-5-ylmethyl)urea;
1-Oxazol-5-ylmethyl-3-[4-(thiazole-2-sulfonyl)-phenyl]-urea;
1-[4-(1-Methyl-piperidine-4-sulfonyl)-phenyl]-3-oxazol-5-ylmethyl-urea;
1-Oxazol-5-ylmethyl-3-[4-(3-trifluoromethoxy-benzenesulfonyl)-phenyl]-urea;
1-[4-(3-Methoxy-benzenesulfonyl)-phenyl]-3-oxazol-5-ylmethyl-urea;
1-[4-(3,4-Difluoro-benzenesulfonyl)-phenyl]-3-oxazol-5-ylmethyl-urea;
1-Oxazol-5-ylmethyl-3-[4-(thiazole-2-sulfonyl)-phenyl]-urea;
1-[4-(3,4-Dichloro-benzenesulfonyl)-phenyl]-3-oxazol-5-ylmethyl-urea;
1-Oxazol-5-ylmethyl-3-[4-(pyridine-3-sulfonyl)-phenyl]-urea;
1-[4-(3,5-Difluoro-benzenesulfonyl)-phenyl]-3-oxazol-5-ylmethyl-urea;
1-[4-(1-Isopropyl-1H-pyrazole-4-sulfonyl)-phenyl]-3-oxazol-5-ylmethyl-urea;
1-Oxazol-5-ylmethyl-3-[4-(pyrazine-2-sulfonyl)-phenyl]-urea;
1-[4-(2,4-Difluoro-benzenesulfonyl)-phenyl]-3-oxazol-5-ylmethyl-urea;
1-[4-(6-Methoxy-pyridine-3-sulfonyl)-phenyl]-3-oxazol-5-ylmethyl-urea;
1-[4-(4-Methoxy-benzenesulfonyl)-phenyl]-3-oxazol-5-ylmethyl-urea;
1-[4-(1-Methyl-1H-pyrazole-4-sulfonyl)-phenyl]-3-oxazol-5-ylmethyl-urea;
1-Oxazol-5-ylmethyl-3-[4-(pyrimidine-2-sulfonyl)-phenyl]-urea;
1-Oxazol-5-ylmethyl-3-{4-[1-(tetrahydro-pyran-4-yl)-piperidine-4-sulfonyl]-phenyl}-urea;
1-[4-(1H-Indazol-3-yl)-phenyl]-3-oxazol-5-ylmethyl-urea;
1-(4-(Benzo[d]thiazol-2-yl)phenyl)-3-(oxazol-5-ylmethyl)urea;
1-[4-(6-Hydroxy-pyridine-3-sulfonyl)-phenyl]-3-oxazol-5-ylmethyl-urea;
1-[4-(6-Chloro-pyridine-3-sulfonyl)-phenyl]-3-oxazol-5-ylmethyl-urea;
1-[4-(1-Methyl-1H-indazol-3-yl)-phenyl]-3-oxazol-5-ylmethyl-urea;
1-(Oxazol-5-ylmethyl)-3-(4-((4-phenylthiazol-2-yl)amino)phenyl)urea;
1-(4-(5-Benzylthiazol-2-yl)phenyl)-3-(oxazol-5-ylmethyl)urea;
1-(4-((1H-pyrazol-4-yl)sulfonyl)phenyl)-3-(oxazol-5-ylmethyl)urea;
1-(4-(Benzo[d]thiazol-2-ylamino)phenyl)-3-(oxazol-5-ylmethyl)urea;
1-(4-(1,5-Dimethyl-1H-indazol-3-yl)phenyl)-3-(oxazol-5-ylmethyl)urea;
1-[4-(1,6-Dimethyl-1H-indazol-3-yl)-phenyl]-3-oxazol-5-ylmethyl-urea;
1-(4-(1,7-Dimethyl-1H-indazol-3-yl)phenyl)-3-(oxazol-5-ylmethyl)urea;
1-(4-Benzothiazol-4-yl-phenyl)-3-oxazol-5-ylmethyl-urea;
1-[4-(5-Methoxy-1-methyl-1H-indazol-3-yl)-phenyl]-3-oxazol-5-ylmethyl-urea;
1-[4-(5-Fluoro-1-methyl-1H-indazol-3-yl)-phenyl]-3-oxazol-5-ylmethyl-urea;
1-[4-(1H-Benzoimidazol-4-yl)-phenyl]-3-oxazol-5-ylmethyl-urea;
1-(4-([1,1'-Biphenyl]-3-ylsulfonyl)phenyl)-3-(oxazol-5-ylmethyl)urea;
1-(4-([1,1'-Biphenyl]-2-ylsulfonyl)phenyl)-3-(oxazol-5-ylmethyl)urea;
1-[4-(1-Methyl-1H-pyrazolo[3,4-b]pyridin-3-yl)-phenyl]-3-oxazol-5-ylmethyl-urea;
1-(4-(5-Chloro-1-methyl-1H-indazol-3-yl)phenyl)-3-(oxazol-5-ylmethyl)urea;
1-(Oxazol-5-ylmethyl)-3-(4-((5-phenylthiazol-2-yl)amino)phenyl)urea;
1-(Oxazol-5-ylmethyl)-3-(4-(5-phenylthiazol-2-yl)phenyl)urea;
1-[4-(1-Methyl-1H-pyrazolo[4,3-b]pyridin-3-yl)-phenyl]-3-oxazol-5-ylmethyl-urea;
1-(4-(1,7-Dimethyl-1H-indazol-3-yl)phenyl)-3-(oxazol-5-ylmethyl)urea;
1-[4-(1-Methyl-1H-pyrazolo[4,3-c]pyridin-3-yl)-phenyl]-3-oxazol-5-ylmethyl-urea;

or a pharmaceutically acceptable salt, or solvate thereof.

16. A pharmaceutical composition comprising a compound of claim 1, or a pharmaceutically acceptable salt, or solvate thereof, and at least one pharmaceutically acceptable excipient.

17. A method of treating a disease or condition mediated by nicotinamide phosphoribosyltransferase (NAMPT) activity in a mammal comprising administering a compound of claim 1, or a pharmaceutically acceptable salt, or solvate thereof, to the mammal.

18. The method of claim 17, wherein the disease or condition is cancer, a hyperproliferative disease or condition, an inflammatory disease or condition, a metabolic disorder, a neurodegenerative disease or disorder, or a muscle wasting disease.

19. The compound of claim 1, wherein the compound is:

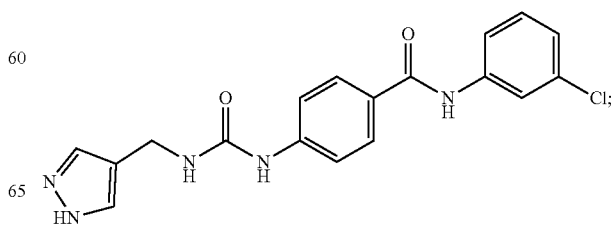

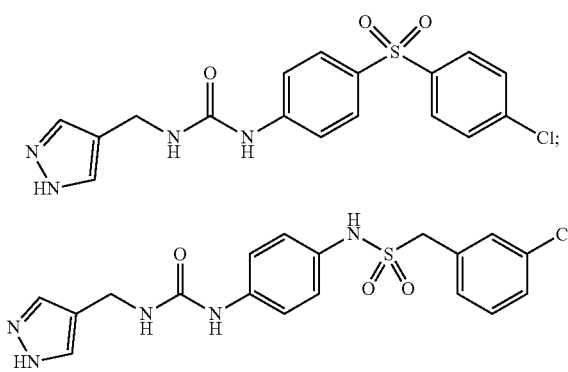

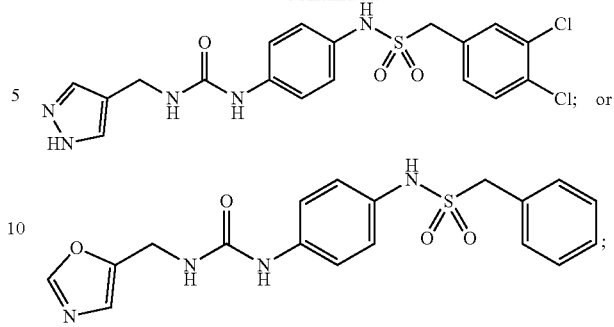

or a pharmaceutically acceptable salt, or solvate thereof.

20. The compound of claim 1, or a pharmaceutically acceptable salt, or solvate thereof, wherein:

$X^1$ is selected from the group consisting of —SO$_2$— and —C(=O)NR$^5$—;

$R^5$ is selected from the group consisting of H, and substituted or unsubstituted C$_1$-C$_6$alkyl;

$L^2$ is absent;

Y is selected from the group consisting substituted or unsubstituted phenyl, substituted or unsubstituted benzyl, and substituted or unsubstituted naphthyl, wherein if Y is substituted then Y is substituted with 1-2 R$^7$ groups; and each R$^7$ is independently selected from the group consisting of F, Cl, Br, unsubstituted C$_1$-C$_6$alkyl, and unsubstituted C$_3$-C$_6$cycloalkyl.

* * * * *

UNITED STATES PATENT AND TRADEMARK OFFICE
CERTIFICATE OF CORRECTION

PATENT NO. : 11,452,717 B2
APPLICATION NO. : 16/475635
DATED : September 27, 2022
INVENTOR(S) : Stephen Gardell et al.

It is certified that error appears in the above-identified patent and that said Letters Patent is hereby corrected as shown below:

In the Claims

Claim 1: Column 570, Line 64. Correct as follows:
'each' $R^5$ is independently selected from the group Claim 1: Column 571, Lines 35-36. Correct as follows:
each $R^8$ is independently selected from the group consisting of H, $C_1$-$C_6$alkyl, and $C_1$-$C_6$fluoroalkyl; and Claim 3: Column 572, Line 1. Correct as follows:
'each' $R^5$ is independently selected from the group Claim 3: Column 572, Line 4. Correct as follows:
$L^2$ is absent or -$CH_2$-; and Claim 13: Column 574, Lines 30-31. Correct as follows:
each $R^8$ is independently selected from the group consisting of H, $C_1$-$C_6$alkyl, and $C_1$-$C_6$fluoroalkyl; and Signed and Sealed this
Twenty-seventh Day of February, 2024

Katherine Kelly Vidal
*Director of the United States Patent and Trademark Office*